(12) United States Patent
Tsukada

(10) Patent No.: US 8,624,015 B2
(45) Date of Patent: Jan. 7, 2014

(54) PROBE SET AND METHOD FOR IDENTIFYING HLA ALLELE

(75) Inventor: Mamoru Tsukada, Fujisawa (JP)

(73) Assignee: Canon Kabushiki Kaisha, Tokyo (JP)

(*) Notice: Subject to any disclaimer, the term of this patent is extended or adjusted under 35 U.S.C. 154(b) by 0 days.

(21) Appl. No.: 13/467,972

(22) Filed: May 9, 2012

(65) Prior Publication Data

US 2012/0220485 A1    Aug. 30, 2012

Related U.S. Application Data

(62) Division of application No. 10/582,327, filed as application No. PCT/JP2004/019763 on Dec. 24, 2004, now Pat. No. 8,193,331.

(30) Foreign Application Priority Data

| Dec. 25, 2003 | (JP) | 2003-430553 |
|---|---|---|
| Dec. 25, 2003 | (JP) | 2003-430554 |
| Dec. 25, 2003 | (JP) | 2003-430555 |
| Dec. 25, 2003 | (JP) | 2003-430556 |
| Dec. 25, 2003 | (JP) | 2003-430557 |
| Dec. 25, 2003 | (JP) | 2003-430558 |
| Dec. 25, 2003 | (JP) | 2003-430559 |

(51) Int. Cl.
*C07H 21/04* (2006.01)
*C07H 21/02* (2006.01)
*C12Q 1/68* (2006.01)
*C12P 19/34* (2006.01)

(52) U.S. Cl.
USPC ...... 536/24.3; 536/23.1; 536/24.33; 435/6.1; 435/6.11; 435/6.12; 435/91.1; 435/91.2

(58) Field of Classification Search
USPC .......... 435/6.1, 6.11, 6.12, 91.1, 91.2, 91.51; 436/94, 501; 536/23.1, 24.3, 24.33, 536/25.3
See application file for complete search history.

(56) References Cited

U.S. PATENT DOCUMENTS

| 5,939,542 | A | 8/1999 | Kawai et al. |
|---|---|---|---|
| 5,976,789 | A | 11/1999 | Allibert et al. |
| 6,476,215 | B1 | 11/2002 | Okamoto et al. |
| 2003/0165884 | A1 | 9/2003 | Chow et al. |
| 2004/0241643 | A1 | 12/2004 | Yamamoto et al. |
| 2005/0143930 | A1 | 6/2005 | Tsukada |
| 2005/0239119 | A1 | 10/2005 | Tsukada |
| 2007/0099187 | A1 | 5/2007 | Tsukada |

FOREIGN PATENT DOCUMENTS

| EP | 0 540 997 | 5/1993 |
|---|---|---|
| EP | 0 575 845 | 12/1993 |
| EP | 1 291 440 | 3/2003 |
| JP | 6-78800 | 3/1994 |
| JP | 6-90757 A | 4/1994 |
| JP | 6-505625 A | 6/1994 |
| JP | 6-303998 A | 11/1994 |
| JP | 8-308596 A | 11/1996 |
| JP | 10-506541 A | 6/1998 |
| JP | 11-187900 | 7/1999 |
| JP | 11-216000 | 8/1999 |
| JP | 2000-511430 A | 9/2000 |
| WO | 92/10589 A1 | 6/1992 |
| WO | 00/79006 | 12/2000 |
| WO | 01/77372 | 10/2001 |
| WO | 03-027309 | 4/2003 |
| WO | 03/027390 | 4/2003 |
| WO | 03/034029 | 4/2003 |
| WO | 2005/001123 | 1/2005 |
| WO | 2005/052189 | 6/2005 |

OTHER PUBLICATIONS

The sequencing comparisons among SEQ ID No. 3320, human protocadherin beta 3 and beta 15 mRNAs, and human synaptotagmin XII transcript variants 1 and 2. Printed on Sep. 7, 2012.*

The sequencing comparisons among SEQ ID No. 3326, human KIAA1875 non-coding RNA and human ubiquitin specific peptidase 19 transcript variants 1-4. Printed on Sep. 7, 2012.*

Rafael Arguello, et al., "A novel method for simultaneous high resolution identification of HLA-A, HLA-B, and HLA-C w alleles", Proc. Natl. Acad. Sci., vol. 93, Oct. 1996,, pp. 10961-10965.

Dan Barouch, et al., "HLA-A2 Subtypes Are Functionally Distinct in Peptide Binding and Presentation", J. Exp. Med., vol. 182, No. 6, Dec. 1995, pp. 1847-1856.

Anthony S. Carter, et al., "Nested Polymerase Chain Reaction With Sequence-Specific Primers Typing for HLA-A, -B, and -C Alleles: Detection of Microchimerism in DR-Matched Individuals", Blood, vol. 94, No. 4, Aug. 15, 1999, pp. 1471-1477.

U. Shankarkumar, et al., "Novel HLA Class I Alleles Associated with Indian Leprosy Patients", Journal of Biomedicine and Biotechnology, vol. 2003, No. 3, 2003, pp. 208-211.

Chunxia Yan, et al., "HLA-A Gene Polymorphism Defined by High-Resolution Sequence-Based Typing in 161 Northern Chinese Han People", Geno., Prot. & Bioinfo., vol. 1, No. 4, Nov. 2003, pp. 304-309.

Mei Han, et al., "Multiplex Single Nucleotide Extension: A Robust and High Throughput Method for HLA-A Locus Typing", Human Immunology, vol. 64, 2003, pp. 1111-1122.

Peter Parham, et al., "Diversity and Diversification of HLA-A, B, C Alleles", Journal of Immunology, vol. 142, No. 11, 1989, pp. 3937-3950.

Erik Rozemuller, "Reference Panels for Sequence Based Typing: Selection Criteria for HLA-A and HLA-B", International Histocompatibility Workling Group, http://ihwg.org/manual/TMcontents.htm, retrieved Jul. 5, 2004.

(Continued)

*Primary Examiner* — Frank Lu
(74) *Attorney, Agent, or Firm* — Fitzpatrick, Cella, Harper & Scinto

(57) ABSTRACT

Provided is a probe set that is useful for identifying each allele of HLA individually, and a method of identification of an allele of HLA by the use thereof for each type.

The probe set is composed of probes that cover all of the partial sequences that contain a unique base to each allele. Using this probe set HLA contained in a specimen is identified.

1 Claim, No Drawings

(56) References Cited

OTHER PUBLICATIONS

Timothy A. Worrall, et al., "Allele-Specific HLA-DR Typing by Mass Spectrometry: An Alternative to Hybridization-Based Typing Methods", Anal. Chem., vol. 72, 2000, pp. 5233-5238.
European Search Report, dated Jan. 21, 2008 in European Application No. 04808113.
Result of Consultation dated Aug. 28, 2008 in European Application No. 04808113.7.
H. A. Erlich, et al., "HLA DNA Typing and Transplantation", Immunity, vol. 14, Apr. 2001, pp. 347-356.
J.-M. Tiercy, et al., "Molecular basis of HLA polymorphism" implications in clinical transplantation, Transplant Immunology, vol. 9, 2002, pp. 173-180.
European Office Action dated Jan. 3, 2012 in European Application No. 04 808 113.7.
Bodmer, et al., "Nomenclature for factors of the HLA system, 1995", Tissue Antigens, vol. 46, 1995, pp. 1-18.
Official Action dated Jan. 31, 2011 in European Application No. 04 808 113.7.
Bunce, et al., "Phototyping: comprehensive DNA typing for HLA-A, B, C, DRB1, DRB3, DRB4, DRB5 & DQB1 by PCR with 144 primer mixes utilizing sequence-specific primers (PCR-SSP)", Tissue Antigens, vol. 46, 1995, pp. 355-367.
Bodmer, et al., "Identification of HLA-DP polymorphism with DP alpha and DP bata probes and monoclonal antibodies: Correlation with primed lymphocyte typing", Proc. Natl. Acad. Sci. USA, vol. 84, 1987, pp. 4596-4600.
Holbeck, et al., "Exon-specific oligonucleotide probes localize HLA-DQ beta allelic polymorphisms", Immunogenetics, vol. 24, 1986, pp. 251-258.
Wordsworth, et al., "HLA-DR typing using DNA amplification by the polymerase chain reaction and sequential hybridization to sequence-specific oligonucleotide probes", Immunogenetics, vol. 32, 1990, pp. 413-418.
Tian, et al., "MICA genetic polymorphism and linkage disequilibrium with HLA-B in 29 African-American families", Immunogenetics, vol. 53, 2001, pp. 724-728.
The sequencing comparison between SEQ ID No. 251 and human Neurl1B mRNA. Printed on Jun. 21, 2010.
The sequencing comparison between SED ID No. 252 and human FLJ45422 mRNA. Printed on Jun. 21, 2010.
Duby, et al., "Using Synthetic Oligonucleotides as Probes", Current Protocol in Molecular Biology, supplement 2, 6.4.1 to 6.4.10, 1993.
European Office Action dated May 27, 2013 in European Application No. 04808113.7.
IMGT/HLA database release 2.3 excerpt, Oct. 2003, 6 pages.

* cited by examiner

PROBE SET AND METHOD FOR IDENTIFYING HLA ALLELE

This application is a divisional of application Ser. No. 10/582,327, filed Jun. 9, 2006, now U.S. Pat. No. 8,193,331, which is the National Stage of International Application No. PCT/JP2004/019763, filed Dec. 24, 2004. The contents of each of the foregoing applications are incorporated by reference herein.

REFERENCE TO SEQUENCE LISTING

A Sequence Listing has been submitted as a ASCII text file, which is incorporated by reference herein. The ASCII text file is named "Sequence_Listing.txt", was created on Sep. 25, 2009, and has a size of 1,547,033 bytes.

TECHNICAL FIELD

The present invention relates to a probe set and a method for identifying an allele of human HLA.

BACKGROUND ART

Human leukocyte antigen (HLA) is known to include multiple HLA types, such as HLA-A, HLA-B, HLA-C, HLA-DP, HLA-DQ, HLA-DR, and HLA-MICA. An HLA allele is designated with a four or more digit number by the WHO HLA Nomenclature Committee. The principle of the nomenclature is that the first two digits correspond to the serotypes; the third and fourth digits distinguish the alleles of different amino acid sequences (subtypes); and the fifth digit distinguishes the alleles of different base sequences but encoding the same amino acid sequence. Typing of these alleles has been conventionally conducted at the serological level. Although this serological method does not require special sample processing, and enables easy typing using antigen-antibody reaction, the serotypes are the roughest classification corresponding to the first two digits of the numbers according to the nomenclature described above.

Many of other commercially available kits of the type associated with genomic extraction do not have enough accuracy to identify each allele individually. It is the current state that such a kit distinguishes multiple alleles as a group. Moreover, even a kit based on the SBT (Sequencing Based Typing) method, which enables the most detailed polymorphic analysis, often fails to solve the problem of ambiguity by one analysis since most samples are heterozygotes requiring reexamination. Such problematic alleles are listed collectively in http://www.ihwg.org/protocols/sbt/ambiguities2.pdf by the International Histocompatibility Working Group (IHWG).

DISCLOSURE OF INVENTION

On the other hand, with the development of advanced medical treatment in recent years, detailed HLA typing is required in organ transplantation, etc. In addition, associations of HLA with diabetes, cancer, and other multifactorial diseases have been suggested. With such a background, a test method is desired that can identify each allele individually. Upon such demands it is an object of the present invention to provide a probe set that is useful for identifying each allele of HLA individually, and a method for identification of an HLA allele by the use thereof.

A probe set for identifying an allele of HLA according to the present invention is a probe set comprising multiple probes that can be used for identifying HLA allele contained in a specimen, characterized in that each of the multiple probes comprises a partial sequence containing a base represented by a capital letter in a sequence of each allele in an allele list in the description.

An embodiment of the present invention is a probe set comprising multiple probes that can be used for identification of an HLA-A allele in a specimen, characterized in that each of the multiple probes comprises a partial sequence containing a base represented by a capital letter in a sequence of each allele in an allele list in the description.

Another embodiment of the present invention is a method for identification of an HLA-A allele contained in a specimen using a probe set, characterized in that the probe set is the probe set described above.

Another embodiment of the present invention is a probe set comprising multiple probes that can be used for identification of an HLA-B allele in a specimen, characterized in that each of the multiple probes comprises a partial sequence containing a base represented by a capital letter in a sequence of each allele in an allele list in the description.

Another embodiment of the present invention is a method for identification of an HLA-B allele contained in a specimen using a probe set, characterized in that the probe set is the probe set described above.

Another embodiment of the present invention is a probe set comprising multiple probes that can be used for identification of an HLA-C allele in a specimen, characterized in that each of the multiple probes comprises a partial sequence containing a base represented by a capital letter in a sequence of each allele in an allele list in the description.

Another embodiment of the present invention is a method for identification of an HLA-C allele contained in a specimen using a probe set, characterized in that the probe set is the probe set described above.

Another embodiment of the present invention is a probe set comprising multiple probes that can be used for identification of an HLA-DP allele in a specimen, characterized in that each of the multiple probes comprises a partial sequence including a base represented by a capital letter in the sequence of each allele in the allele list in the description.

Another embodiment of the present invention is a method for identification of an HLA-DP allele contained in a specimen using a probe set, characterized in that the probe set is the probe set described above. Another embodiment according to the present invention is a probe set for identification of an HLA-DQ allele that is a probe set comprising multiple probes that can be used for identification of an HLA-DQ allele in a specimen, characterized in that each of the multiple probes comprises a partial sequence containing a base represented by a capital letter in a sequence of each allele in an allele list in the description.

Another embodiment of the present invention is a probe set comprising multiple probes that can be used for identification of an HLA-DQ allele in a specimen, characterized in that each of the multiple probes comprises a partial sequence containing a base represented by a capital letter in a sequence of each allele in an allele list in the description.

Another embodiment of the present invention is a method for identification of an HLA-DQ allele contained in a specimen using a probe set, characterized in that the probe set is the probe set described above.

Another embodiment of the present invention is a probe set comprising multiple probes that can be used for identification of an HLA-DR allele in a specimen, characterized in that each of the multiple probes comprises a partial sequence containing a base represented by a capital letter in a sequence of each allele in an allele list in the description.

Another embodiment of the present invention is a method for identification of an HLA-DR allele contained in a specimen using a probe set, characterized in that the probe set is the probe set described above.

Another embodiment of the present invention is a probe set comprising multiple probes that can be used for identification of an HLA-MICA allele in a specimen, characterized in that each of the multiple probes comprises a partial sequence containing a base represented by a capital letter in a sequence of each allele in an allele list in the description.

Another embodiment of the present invention is a method for identification of an HLA-MICA allele contained in a specimen using a probe set, characterized in that the probe set is the probe set described above.

The probe set according to the present invention, and identification of an allele of each HLA type by the use thereof can contribute to diathesis diagnoses and tailor-made medicines, which are required in organ transplantation, cancer, diabetes, and other multifactorial diseases.

Other features and advantages of the present invention will be apparent from the following description.

BEST MODE FOR CARRYING OUT THE INVENTION

Preferred embodiments of the present invention will now be described in detail. Each probe that constitutes the probe set of the present invention has a partial sequence including a base represented by a capital letter in each allele sequence in the allele lists described later. Preferably, segments consisting of 10 to 30 bases including a base represented by a capital letter are selected from each allele sequence, and the probe set is composed of probes having the obtained partial base sequences respectively. As specific examples, the following compositions can be employed:

1) A probe set for HLA-A allele identification consisting of respective probes listed in one of the probe list A1 shown in Tables 1-1 to 1-7 and the probe list A2 shown in Tables 2-1 to 2-6 shown later;

2) A probe set for HLA-B allele identification consisting of probes listed in one of the probe list B1 shown in Tables 5-1 to 5-9 and the probe list B2 shown in Tables 6-1 to 6-8 shown later;

3) A probe set for HLA-C allele identification consisting of probes listed in one of the probe list C1 shown in Tables 9 and the probe list C2 shown in Table 10 shown later;

4) A probe set for HLA-DP allele identification consisting of probes listed in one of the probe lists DP1-DP4 shown in Tables 13-1 to 16-5 respectively as shown later;

5) A probe set for HLA-DQ allele identification consisting of probes listed in one of the probe lists DQ1 to DQ 4 shown in Tables 17A, 17B-1, 17B-2, 18A, 18B-1 and 18B-2 respectively as shown later;

6) A probe set for HLA-DR allele identification consisting of probes listed in one of the probe lists DR1 and DR2 shown in Tables 21-1 to 21-8 and Tables 22-1 to 22-7 respectively, as shown later; and 7) A probe set for HLA-MICA allele identification consisting of probes listed in one of the probe lists MICA1 and MICA2 shown in Tables 25-1, 25-2 and Tables 26-1 to 26-2 respectively, as shown later.

For example, the No. 0 probe in the probe list A1 has a 16-base sequence of "gccccgcttcatcgcC", which is a segment containing the first capital lettered base C in A*010101, and the No. 0 probe in the probe list 2 has an 18-base sequence of "cttcatcgcCgtgggcta", which is a segment also containing the first capital lettered base C in the same allele.

In the allele list, each allele is assigned with a unique number such as "A*xxxx" in accordance with "allele nomenclature" by Japanese Society for Histocompatibility and Immunogenetics, HLA Standardization Committee.

To identify an allele using a probe set according to the present invention, two methods are possible: one is detection by hybridization; and the other is direct detection by PCR without hybridization. In either method, each probe is an oligonucleotide of preferably more than 10 and less than 30 nucleotides in length and designed to include the base represented by a capital letter, i.e., a base specific for the allele to be identified.

Moreover, the probe arrays provided in the present invention present groups of varied bases for identification of each allele individually by positions chosen for the probes. As a method for detection of such a varied base, the detection method by hybridization, and the method of direct detection by PCR without hybridization can also be preferably used. Also in these cases, the probes are designed as oligonucleotides of preferably more than 10 and less than 30 nucleotides in length each containing a base represented by a capital letter.

When a variation is detected by hybridization, probes are preferably designed to have a variant base represented by a capital letter near the center of the probes, which makes Tm difference between full-matched and mismatched pairs larger, enabling easier separation of them by adjusting the reaction temperature of hybridization.

On the other hand, when the variation is directly detected by PCR, the variant base is rather placed near the 3' end so that enzymatic recognition and elongation of annealed double strands will not occur. Also, some variation methods are possible, such as a method placing a variant base at the second from the 3' end an artificial variant base at the third from the 3' end as with Allele Specific Primer (Toyobo Co., Ltd.); a method circularizing probes by ligation with a mismatch placed near the 3' end (Amersham Biosciences Co., Ltd.); TaqMan-MGB (ABI Co.); and 3'-end mismatch using LNA (Proligo Japan Co., Ltd.).

For example, a segment including the fourth capital letter of A*2302 is "ggagcagTggagagC", and the corresponding segment of A*2303 of the same serotype is "ggagcagtTgagagc", differing at the ninth base. By using a probe with a sequence of one of these segments, one can be distinguished from the other by mismatching.

EXAMPLES

The present invention will be described further by way of examples in the following.

Example 1

Probes for Identification of HLA-A Allele

Extraction of DNA from 1 ml of human blood was performed using GFX Genomic Blood DNA Purification Kit from Amersham Biosciences. The protocol is as follows:
Blood 1 ml→
Add RBC Lysis Solution [hemolysate]→
Mix gently at room temperature for 5 minutes→
Centrifuge at 12,000-16,000×g for 20 seconds→
Discard the supernatant leaving 20-50 µl→
Resuspend the precipitation→
Add Extraction Solution and vortex vigorously→
Stand at room temperature for 5 minutes [extraction of DNA]→

Set a GFX Column in a Collection Tube→
Heat the elusion buffer to 70° C.→
Add the sample→
Centrifuge at 5,000×g for 1 minute (binding of DNA)→
Add Extraction Solution (washing)→
Centrifuge at 5,000×g for 1 minute→
Add Washing Solution (washing)→
Centrifuge at 12,000×g for 3 minutes→
Set a GFX Column in a centrifugal tube→
Eluate with pure water→
Stand at room temperature for 1 minute→
Centrifuge at 5,000-8,000×g for 1 minute→
Concentrate to 230 µl . . . solution (1).

Next, quantitative PCR was carried out using QuantiTect SYBR Green PCR Kit from QIAGEN and GeneAmp5700 from ABI. The reaction composition and the protocol are shown below.

1) Reaction Composition/Well (96 Well Microplate)
  QuantiTect SYBR Green 2×premix: 10 µl
  Solution (1): 1 µl
  Solution of one of the probes in the probe list
  A1 (10 µmol/µl): 1 µl
  Mixed primers (10 pmol/1 µl)*: 3 µl
  Ultra pure water: 5 µl
  (Total: 20 µl)
  *consisting of 1 µl each of the solutions respectively containing probes of the following sequences at 10 pmol/µl:

```
CCCATCTCAGGGTGAGGGGCT      (SEQ ID NO: 632)

GCGCTGCAGCGTCTCCTTCC       (SEQ ID NO: 633)

GCCCAGGTCTGGGTCAGGGCCAG    (SEQ ID NO: 634)
```

2) PCR Program
94° C.: 180 sec followed by 30 cycles of [94° C.: 10 sec→66° C.: 10 sec→72° C.: 20 sec.].

Referring to Amp Plot and Dissociation curves on a display of 5700 software, and to the allele-probe correspondence list A1 (Tables 3-1 to 3-9), it was identified as A*2402101.

Example 2

Extraction of DNA from 1 ml of human blood was performed in the same manner as in Example 1. PCR of human HLA-A was then performed using ABI 9700 PCR Instrument and Ex Taq from Takara Bio Inc. The reaction composition and the protocol are as follows:

1) Reaction Composition/Tube
  Ex Taq 2×premix: 20 µl
  Solution (1): 3 µl
  Cy-3 dUTP (1 mM): 2 µl
  Mix primer (10 pmol/µl)*: 3 µl
  Ultra pure water: 12 µl
  (Total: 40 µl)
  *consisting 1 µl each of the solutions respectively containing probes of the following sequences at 10 pmol/µl:

```
ATGGCTCCCCGAACCCTC     (SEQ ID NO: 635)

ATGGCGCCCCGAACCCTC     (SEQ ID NO: 636)

CATCTCAGGGTGAGGGGCT    (SEQ ID NO: 637)
```

2) PCR Program
94° C.: 180 sec followed by 30 cycles of [94° C.: 10 sec→66° C.: 10 sec→72° C.: 20 sec]

After the completion of the reaction, unreacted dNTPs, etc., were removed using a purification column (QIAGEN QIAquick PCR Purification Kit) to obtain a sample.

At the same time, a DNA microarray was prepared to identify the allele in the specimen described above. The method for the preparation was in accordance with examples in Japanese Patent Application Laid-Open No. H11-187900. SH group was used as the functional group for immobilization. A glass substrate was treated by a silane-coupling agent to bind the SH group of the probes via a divalent reagent EMCS (N-(6-maleimidocaproyloxy) succinimide). Each probe in the probe list A2 was used for each dot.

The DNA microarray was blocked in advance with PBS supplemented with 1 wt % of BSA (bovine serum albumin) for two hours. The sample was adjusted to have a salt concentration equal to that of the PBS, and to contain 0.1 wt % of SDS (sodium dodecyl sulfate) and 25% of formamide.

Then, hybridization was performed using the above sample (PCR product) and the prepared DNA microarray. 50 µl of the sample was reacted with the blocked DNA microarray at 60° C. for 2 hours. Unreacted substances were washed off by washing three times with 2×SSC solution (NaCl 300 mM, Sodium Citrate (trisodium citrate dihydrate, $C_6H_5Na_3.2H_2O$) 30 mM, pH 7.0), followed by washing twice with 0.1×SSC solution. The DNA microarray was air-dried and the fluorometry measurement was conducted using GenePix4000B made by Axon. Referring to the allele-probe list A2 (Tables 4-1 to 4-9), the sample was identified as A*2402101.

```
A*010101:
                                                              (SEQ ID NO: 1)
atggccgtcatggcgccccgaaccctcctcctgctactctcgggggccctggccctgacccagacctgggcgggct cccactccatgaggtatttcttcacatccgtgtcccggcccggccgcggggagccccgcttcatcgcCgtgggcta cgtggacgacacgcagttcgtgcggttcgacagcgacgccgcgagccagaagatggagccgcgggcgccgtggata gagcaggaggggccggagtattgggaccaggagacacggaatAtgaaggcccactcacagactgaccgagcgaacc tggggaccctgcgcggctactacaaccagagcgaggacggttctcacaccatccagataatgtatggctgcgacgt ggggccggacgggcgcttcctccgcgggtaccggcaggacgcctacgacggcaaggattacatcgccctgaacgag gacctgcgctcttggaccgcggcggacatggcagctcagatcaccaagcgcaagtgggaggcggtccatgcggcgg agcagcggagagTctacctggagggcCGgtgcgtggacgggctccgcagatacctggagaacgggaaggagacgct gcagcgcacggaccccccccaagacacatatgacccaccaccccatctctgaccatgaggccaccctgaggtgctgg
```

-continued gccctgGgcttctaccctgcggagatcacactgacctggcagcgggatggggaggaccagacccaggacacggagc tcgtggagaccaggcctgcaggggatggaaccttccagaagtgggcggctgtggtggtGccttctggaGaggagca gagatacacctgccatgtgcagcatgagggtctgcccaagcccctcaccctgagatgggag;

A*010102:
(SEQ ID NO: 2)
gctcccactccatgaggtatttcttcacatccgtgtcccggcccggccgcggggagccccgcttcatcgccgtggg ctacgtggacgacacgcagttcgtgcggttcgacagcgacgccgcgagccagaagatggagccgcgggcgccgtgg atagagcaggaggggccggagtattgggaccaggagacacggaatatgaaggcccactcacagactgaccgagcga acctggggaccctgcgcggctactacaaccagagcgaggacggttctcacaccatccagataatgtatggctgcga cgtggggccggacgggcgcttcctccgcgggtaccggcaggacgcctacgacggcaaggattacatcgccctgaac gaggacctgcgctcttggaccgcggcggacatggcagctcagatTaccaagcgcaagtgggaggcggtccatgcgg cggagcagcggagagtctacctggagggccggtgcgtggacgggctccgcagatacctggagaacgggaaggagac gctgcagcgcacgg;

A*0102:
(SEQ ID NO: 3)
atggccgtcatggcgccccgaaccctcctcctgctactctcgggggccctggccctgacccagacctgggcgggct cccactccatgaggtatttctCcacatccgtgtcccggcccggcagtggAgagccccgcttcatcgcagtgggcta cgtggacgacacgcagttcgtgcggttcgacagcgacgccgcgagccagaagatggagccgcgggcgccgtggata gagcaggaggggccggagtattgggaccaggagacacggaatatgaaggcccactcacagactgaccgagcgaacc tggggaccctgcgcggctactacaaccagagcgaggacggttctcacaccatccagataatgtatggctgcgacgt ggggccggacgggcgcttcctccgcgggtaccggcaggacgcctacgacggcaaggattacatcgccctgaacgag gacctgcgctcttggaccgcggcggacatggcagctcagatcaccaagcgcaagtgggaggcggtccatgcggcgg agcagcggagagtctacctggagggccggtgcgtggacgggctccgcagatacctggagaacgggaaggagacgct gcagcgcacggaccccccaagacacatatgacccaccaccccatctctgaccatgaggccaccctgaggtgctgg gccctgggcttctaccctgcggagatcacactgacctggcagcgggatggggaggaccagacccaggacacggagc tcgtggagaccaggcctgcaggggatggaaccttccagaagtgggcggctgtggtggtgccttctggagaggagca gagatacacctgccatgtgcagcatgagggtctgcccaagcccctcaccctgagatgggag A*0103:
(SEQ ID NO: 4)
gctcccactccatgaggtatttcttcacatccgtgtcccggcccggccgcggggagccccgcttcatcgccgtggg ctacgtggacgacacgcagttcgtgcggttcgacagcgacgccgcgagccagaagatggagccgcgggcgccgtgg atagagcaggaggggccggagtattgggaccaggagacacggaatatgaaggcccactcacagactgaccgagcga acctggggaccctgcgcggctactacaaccagagcgaggacggttctcacaccatccagatGatgtatggctgcga cgtggggccggacgggcgcttcctccgcgggtaccggcaggacgcctacgacggcaaggattacatcgccctgaac gaggacctgcgctcttggaccgcggcggacatggcagctcagatcaccaagcgcaagtgggaggcggtccatgcgg cggagcagcggagagtctacctggagggccggtgcgtggacgggctccgcagatacctggagaacgggaaggagac gctgcagcgcacgg;

A*0106:
(SEQ ID NO: 5)
gctcccactccatgaggtatttcttcacatccgtgtcccggcccggccgcggggagccccgcttcatcgccgtggg ctacgtggacgacacgcagttcgtgcggttcgacagcgacgccgcgagccagaagatggagccgcgggcgccgtgg atagagcaggaggggccggagtattgggaccaggagacacggaatatgaaggcccactcacagactgaccgagcga acctggggaccctgcgcggctactacaaccagagcgaggacggttctcacaccatccagataatgtatggctgcga cgtggggccggacgggcgcttcctccgcgggtaccggcaggacgcctacgacggcaaggattacatcgccctgaac -continued gaggacctgcgctcttggaccgcggcggacatggcagctcagatcaccaagcgcaagtgggaggcggtccatgcgg cggagcagTTgagagcctacctggagggccggtgcgtggacgggctccgcagatacctggagaacgggaaggagac gctgcagcgcacgg;

A*0107:

(SEQ ID NO: 6)
gctcccactccatgaggtatttcttcacatccgtgtcccggcccggccgcggggagccccgcttcatcgccgtggg ctacgtggacgacacgcagttcgtgcggttcgacagcgacgccgcgagccagaagatggagccgcgggcgccgtgg atagagcaggagaggccTgagtattgggaccaggagacacggaatgtgaaggcccactcacagactgaccgagAga acctggggaccctgcgcggctactacaaccagagcgaggCcggttctcacaccatccagataatgtatggctgcga cgtggggccggacgggcgcttcctccgcgggtaccggcaggacgcctacgacggcaaggattacatcgccctgaac gaggacctgcgctcttggaccgcggcggacatggcagctcagatcaccaagcgcaagtgggaggcggtccatgcgg cggagcagcggagagtctacctggagggccggtgcgtggacgggctccgcagatacctggagaacgggaaggagac gctgcagcgcacgg;

A*0108:

(SEQ ID NO: 7)
gctcccactccatgaggtatttcttcacatccgtgtcccggcccggccgcggggagccccgcttcatcgccgtggg ctacgtggacgacacgcagttcgtgcggttcgacagcgacgccgcgagccagaagatggagccgcgggcgccgtgg atagagcaggaggggccggagtattgggaccaggagacacggaatatgaaggcccactcacagactgaccgagcga acctggggaccctgcgcggctactacaaccagagcgaggacggttctcacaccatccagataatgtatggctgcga cgtggggccggacgggcgcttcctccgcgggtaccggcaggacgcctacgacggcaaggattacatcgccctgaac gaggacctgcgctcttggaccgcggcggacatggcagctcagatcaccaagcgcaagtgggaggcggtccatgcgg cggagcagcggagagtctacctggagggcTggtgcgtggacgggctccgcagatacctggagaacgggaaggagac gctgcagcgcacgg;

A*0109:

(SEQ ID NO: 8)
atggccgtcatggcgccccgaaccctcctcctgctactctcgggggccctggccctgacccagacctgggcgggct cccactccatgaggtatttcttcacatccgtgtcccggcccggccgcggggagccccgcttcatcgccgtgggcta cgtggacgacacgcagttAgtgcggttcgacagcgacgccgcgagccagaagatggagccgcgggcgccgtggata gagcaggaggggccggagtattgggaccaggagacacggaatatgaaggcccactcacagactgaccgagcgaacc tggggaccctgcgcggctactacaaccagagcgaggacggttctcacaccatccagataatgtatggctgcgacgt ggggccggacgggcgcttcctccgcgggtaccggcaggacgcctacgacggcaaggattacatcgccctgaacgag gacctgcgctcttggaccgcggcggacatggcagctcagatcaccaagcgcaagtgggaggcggtccatgcggcgg agcagcggagagtctacctggagggccggtgcgtggacgggctccgcagatacctggagaacgggaaggagacgct gcagcgcacggaccccccccaagacacatatgacccaccaccccatctctgaccatgaggccaccctgaggtgctgg gccctgggcttctaccctgcggagatcacactgacctggcagcgggatggggaggaccagacccaggacacggagc tcgtggagaccaggcctgcaggggatggaaccttccagaagtgggcggctgtggtggtgccttctggagaggagca gagatacacctgccatgtgcagcatgagggtctgcccaagcccctcaccctgagatgggag;

A*020101:

(SEQ ID NO: 9)
atggccgtcatggcgccccgaaccctcgtcctgctactctcgggggcTctggccctgacccagacctgggcgggct ctcactccatgaggtatttcttcacatccgtgtcccggcccggccgcggggagccccgcttcatcgcagtgggcta cgtggacgacacgcagttcgtgcggttcgacagcgacgccgcgagccagaggatggagccgcgggcgccgtggata gagcaggagggtccggagtattgggacggggagacacggaaAgtgaaggcccactcacagactCaccgagtggacc tggggaccctgcgcggctactacaaccagagcgaggCcggttctcacaccGtccagaGgatgtatggctgcgacgt ggggtcggacTggcgcttcctccgcgggtaccaccagtacgcctacgacggcaaggattacatcgccctgaaagag -continued gacctgcgctcttggaccgcggcggacatggcagctcagaccaccaagcacaagtgggaggcggcccatgTggcgg agcagtTgagagcctacctggagggcaCgtgcgtggagtggctccgcagatacctggagaacgggaaggagacgct gcagcgcacggacgcccccaaaacgcatatgactcaccacgctgtctctgaccatgaagccaccctgaggtgctgg gccctgagcttctaccctgcggagatcacactgacctggcagcgggatggggaggaccagacccaggacacggagc tcgtggagaccaggcctgcaggggatggaaccttccagaagtgggcggctgtggtggtgccttctggacaggagca gagatacacctgccatgtgcagcatgagggtTtgcccaagcccctcaccctgagatgggag;

A*020102:
(SEQ ID NO: 10)
gctcccactccatgaggtatttcttcacatccgtgtcccggcccggccgcggggagccccgcttcatcgcAgtggg ctacgtggacgacacgcagttcgtgcggttcgacagcgacgccgcgagccagaggatggagccgcgggcgccgtgg atagagcaggagggtccggagtattgggacgGggagacacggaaAgtgaaggcccactcacagactCaccgagtgg acctggggaccctgcgcggctactacaaccagagcgaggccggttctcacaccGtccagaGgatgtatggctgcga cgtggggtcggacTggcgcttcctccgcgggtaccaCcagTacgcctacgacggcaaggattacatcgccctgaaA gaggacctgcgctcttggaccgcggcggacatggcagctcagaCcaccaagcacaagtgggaggcggcccatgTgg cggagcagtTgagagcctacctggagggcaCgtgcgtggagTggctccgcagatacctggagaacgggaaggagac gctgcagcgcacgg;

A*020103:
(SEQ ID NO: 11)
aaccctcgtcctgctactctcgggggctctggccctgacccagacctgggcgggctctcactccatgaggtatttc ttcacatccgtgtcccggcccggccgcggggagccccgcttcatcgcagtgggctacgtggacgacacgcagttcg tgcggttcgacagcgacgccgcgagccagaggatggagccgcgggcgccgtggatagagcaggagggtccggagta ttgggacggggagacacggaaagtgaaggcccactcacagactcaTcgagtggacctggggaccctgcgcggctac tacaaccagagcgaggccggttctcacaccgtccagaggatgtatggctgcgacgtggggtcggactggcgcttcc tccgcgggtaccaccagtacgcctacgacggcaaggattacatcgccctgaaagaggacctgcgctcttggaccgc ggcggacatggcagctcagaccaccaagcacaagtgggaggcggcccatgtggcggagcagttgagagcctacctg gagggcacgtgcgtggagtggctccgcagatacctggagaacgggaaggagacgctgcagcgcacggacgcccca aaacgcatatgactcaccacgctgtctctgaccatgaagccaccctgaggtgctgggccctgagcttctaccctgc ggagatcacactgacctggcagcgggatggggaggaccagacccaggacacggagctcgtggagaccaggcctgca ggggatggaaccttccagaagtgggcggctgtggtggtgccttctggacaggagcagagatacacctgccatgtgc agcatgagggtttgcccaagcccctcaccctgagatggg;

A*020104:
(SEQ ID NO: 12)
gctctcactccatgaggtatttcttcacatccgtgtcccggcccggccgcggggagccccgcttcatcgcagtggg ctacgtggacgacacgcagttcgtgcggttcgacagcgacgccgcgagccagaggatggagccgcgggcgccgtgg atagagcaggagggtccggagtattgggacggggagacacggaaagtgaaggcccactcacagactcaccgagtgg acctggggaccctgcgcggctactacaaccagagcgaggccggttctcacaccgtccagaggatgtatggctgcga cgtggggtcggactggcgcttcctccgcgggtaccaccagtacgcctacgacggcaaggattacatcgccctgaaa gaggacctgcgctcttggaccgcAgcggacatggcagctcagaccaccaagcacaagtgggaggcggcccatgtgg cggagcagttgagagcctacctggagggcacgtgcgtggagtggctccgcagatacctggagaacgggaaggagac gctgcagcgcacgg A*020105:
(SEQ ID NO: 13)
gctctcactccatgaggtatttcttcacatccgtgtcccggcccggccgcggggagccccgcttcatcgcagtggg ctacgtggacgacacgcagttcgtgcggttcgacagcgacgccgcgagccagaggatggagccgcgggcgccgtgg -continued atagagcaggagggtccggagtattgggacggggagacacggaaagtgaaggcccactcacagactcaccgagtgg acctggggaccctgcgcggctactacaaccagagcgaggccggttctcacaccgtccagaggatgtatggctgcga cgtggggtcggactggcgcttcctccgcgggtaccaccagtacgcctacgacggcaaggattacatcgccctgaaa gaAgacctgcgctcttggaccgcggcggacatggcagctcagaccaccaagcacaagtgggaggcggcccatgtgg cggagcagttgagagcctacctggagggcacgtgcgtggagtggctccgcagatacctggagaacgggaaggagac gctgcagcgcacggacgcccccaaaacgcatatgactcaccacgctgtctctgaccatgaagccaccctgaggtgc tgggccctgagcttctaccctgcggagatcacactgacctggcagcgggatggggaggaccagacccaggacacgg agctcgtggagaccaggcctgcaggggatggaacttccagaagtgggcggctgtggtggtgccttctggacagga gcagagatacacctgccatgtgcagcatgagggtttgcccaagcccctcaccctgagatggg

A*020106:

(SEQ ID NO: 14)

gctctcactccatgaggtatttcttcacatccgtgtcccggcccggccgcggggagccccgcttcatcgcagtggg ctacgtggacgacacgcagttcgtgcggttcgacagcgacgccgcgagccagaggatggagccgcgggcgccgtgg atagagcaggagggtccggagtattgggacggggagacacggaaagtgaaggcccactcacagactcaccgagtgg acctggggaccctgcgcggctactacaaccagagcgaggccggttctcacaccgtccagaggatgtatggctgcga cgtggggtcggactggcgAttcctccgcgggtaccaccagtacgcctacgacggcaaggattacatcgccctgaaa gaggacctgcgctcttggaccgcggcggacatggcagctcagaccaccaagcacaagtgggaggcggcccatgtgg cggagcagttgagagcctacctggagggcacgtgcgtggagtggctccgcagatacctggagaacgggaaggagac gctgcagcgcacggacgcccccaaaacgcatatgactcaccacgctgtctctgaccatgaagccaccctgaggtgc tgggccctgagcttctaccctgcggagatcacactgacctggcagcgggatggggaggaccagacccaggacacgg agctcgtggagaccaggcctgcaggggatggaacttccagaagtgggcggctgtggtggtgccttctggacagga gcagagatacacctgccatgtgcagcatgagggtttgcccaagcccctcaccctgagatggg

A*020107:

(SEQ ID NO: 15)

gctctcactccatgaggtatttcttcacatccgtgtcccggcccggccgTggggagccccgcttcatcgcagtggg ctacgtggacgacacgcagttcgtgcggttcgacagcgacgccgcgagccagaggatggagccgcgggcgccgtgg atagagcaggagggtccggagtattgggacggggagacacggaaagtgaaggcccactcacagactcaccgagtgg acctggggaccctgcgcggctactacaaccagagcgaggccggttctcacaccgtccagaggatgtatggctgcga cgtggggtcggactggcgcttcctccgcgggtaccaccagtacgcctacgacggcaaggattacatcgccctgaaa gaggacctgcgctcttggaccgcggcggacatggcagctcagaccaccaagcacaagtgggaggcggcccatgtgg cggagcagttgagagcctacctggagggcacgtgcgtggagtggctccgcagatacctggagaacgggaaggagac gctgcagcgcacggacgcccccaaaacgcatatgactcaccacgctgtctctgaccatgaagccaccctgaggtgc tgggccctgagcttctaccctgcggagatcacactgacctggcagcgggatggggaggaccagacccaggacacgg agctcgtggagaccaggcctgcaggggatggaacttccagaagtgggcggctgtggtggtgccttctggacagga gcagagatacacctgccatgtgcagcatgagggtTtgcccaagcccctcaccctgagatggg

A*020108:

(SEQ ID NO: 16)

gctctcactccatgaggtatttcttcacatccgtgtcccggcccggccgcggggagccccgcttcatcgcagtggg ctacgtggacgacacgcagttcgtgcggttcgacagcgacgccgcgagccagaggatggagccgcgggcgccgtgg atagagcaggagggtccggagtattgggacggggagacacggaaagtgaaggcccactcacagactcaccgagtgg acctggggaccctgcgcggctactacaaccagagcgaggccggttctcacaccgtccagaggatgtatggctgcga cgtggggtcggactggcgcttcctccgcgggtaccaccagtacgcctacgacggcaaggattacatcgccctgaaa gaggacctgcgctcttggaccgcggcggacatggcagctcagaccaccaagcacaagtgggaggcggcccatgtgg cggagcagttgagagcctacctggagggcacgtgcgtggagtggctccgcagatacctggagaacgggaaggagac -continued gctgcagcgcacggacgcccccaaaacgcatatgactcaccacgctgtctctgaccatgaagccaccctgaggtgc tgggccctgagcttctaccctgcggagatcacactgacctggcagcgggatggggaggaccagacccaggacacAg agctcgtggagaccaggcctgcaggggatggaaccttccagaagtgggcggctgtggtggtgccttctggacagga gcagagatacacctgccatgtgcagcatgagggtttgcccaagcccctcaccctgagatggg

A*020109:

(SEQ ID NO: 17)

gctctcactccatgaggtatttcttcacatccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggagggtccggagtattgggacggggagacacggaaAgtgaaggcccactcacagactCaccgagtgg acctggggaccctgcgcggctactacaaccagagcgaggccggttctcacaccGtccagaGgatgtatggctgcga cgtggggtcggacTggcgcttcctccgcgggtaccaccagtacgcctacgacggcaaggattacatcgcccctgaaa gaggacctgcgctcttggaccgcggcggacatggcagctcagaccaccaagcacaagtgggaggcggcccatgTgg cggagcagTTgagagcctacctggagggcaCgtgcgtggagtggctccgcagatacctggagaacgggaaggagac gctgcagcgcacggacgcccccaaaacgcatatgactcaccacgctgtctctgaccatgaagccaccctgaggtgc tgggccctgagcttctaccctgcggagatcacactgacctggcagcgggatggggaggaccagacccaggacacgg agctcgtggagaccaggcctgcaggggatggaaccttccagaagtgggcggctgtggtggtgccttctggacagga gcagagatacacctgccatgtgcagcatgagggtTtgcccaagcccctcaccctgagatggg;

A*0202:

(SEQ ID NO: 18)

gctctcactccatgaggtatttcttcacatccgtgtcccggcccggccgcggggagccccgcttcatcgcagtggg ctacgtggacgacacgcagttcgtgcggttcgacagcgacgccgcgagccggaggatggagccgcgggcgccgtgg atagagcaggagggtccggagtattgggacggggagacacggaaagtgaaggcccactcacagactcaccgagtgg acctggggaccctgcgcggctactacaaccagagcgaggccggttctcacaccctccagaggatgtatggctgcga cgtggggtcggactggcgcttcctGcgcgggtaccaccagtacgcctacgacggcaaggattacatcgcccctgaaa gaggacctgcgctcttggaccgcggcggacatggcagctcagaccaccaagcacaagtgggaggcggcccatgtgg cggagcagtggagagcctacctggagggcacgtgcgtggagtggctccgcagatacctggagaacgggaaggagac gctgcagcgcacggacgcccccaaaacgcatatgactcaccacgctgtctctgaccatgaagccaccctgaggtgc tgggccctgagcttctaccctgcggagatcacactgacctggcagcgggatggggaggaccagacccaggacacgg agctcgtggagaccaggcctgcaggggatggaaccttccagaagtgggcggctgtggtggtgccttctggacagga gcagagatacacctgccatgtgcagcatgagggtTtgcccaagcccctcaccctgagatggg;

A*0203:

(SEQ ID NO: 19)

atggccgtcatggcgccccgaaccctcgtcctgctactctcgggggcTctggccctgacccagacctgggcgggct ctcactccatgaggtatttcttcacatccgtgtcccggcccggccgcggggagccccgcttcatcgcagtgggcta cgtggacgacacgcagttcgtgcggttcgacagcgacgccgcgagccagaggatggagccgcgggcgccgtggata gagcaggagggtccggagtattgggacggggagacacggaaagtgaaggcccactcacagactcaccgagtggacc tggggaccctgcgcggctactacaaccagagcgaggccggttctcacaccgtccagaggatgtatggctgcgacgt ggggtcggactggcgcttcctccgcgggtaccaccagtacgcctacgacggcaaggattacatcgcccctgaaagag gacctgcgctcttggaccgcggcggacatggcagctcagaccaccaagcacaagtgggagAcggcccatgAggcgg agcagTggagagcctacctggagggcaCgtgcgtggagtggctccgcagatacctggagaacgggaaggagacgct gcagcgcacggacgcccccaaaacgcatatgactcaccacgctgtctctgaccatgaagccaccctgaggtgctgg gccctgagcttctaccctgcggagatcacactgacctggcagcgggatggggaggaccagacccaggacacggagc -continued tcgtggagaccaggcctgcaggggatggaaccttccagaagtgggcggctgtggtggtgccttctggacaggagca gagatacacctgccatgtgcagcatgagggtTtgcccaagcccctcaccctgagatgggag;

A*0204:
(SEQ ID NO: 20)
atggccgtcatggcgccccgaaccctcgtcctgctactctcggggcTctggccctgacccagacctgggcgggct ctcactccatgaggtatttcttcacatccgtgtcccggcccggccgcggggagccccgcttcatcgcagtgggcta cgtggacgacacgcagttcgtgcggttcgacagcgacgccgcgagccagaggatggagccgcgggcgccgtggata gagcaggagggtccggagtattgggacggggagacacggaaAgtgaaggcccactcacagactCaccgagtggacc tggggaccctgcgcggctactacaaccagagcgaggccggttctcacaccGtccagatgatgtatggctgcgacgt ggggtcggacTggcgcttcctccgcgggtaccaccagtacgcctacgacggcaaggattacatcgccctgaaagag gacctgcgctcttggaccgcggcggacatggcagctcagaccaccaagcacaagtgggaggcggcccatgTggcgg agcagtTgagagcctacctggagggcaCgtgcgtggagtggctccgcagatacctggagaacgggaaggagacgct gcagcgcacggacgcccccaaaacgcatatgactcaccacgctgtctctgaccatgaagccaccctgaggtgctgg gccctgagcttctaccctgcggagatcacactgacctggcagcgggatggggaggaccagacccaggacacggagc tcgtggagaccaggcctgcaggggatggaaccttccagaagtgggcggctgtggtggtgccttctggacaggagca gagatacacctgccatgtgcagcatgagggtTtgcccaagcccctcaccctgagatgggag;

A*0205:
(SEQ ID NO: 21)
atggccgtcatggcgccccgaaccctcgtcctgctactctcggggctctggccctgacccagacctgggcgggct ctcactccatgaggtatttctacacCtccgtgtcccggcccggccgcggggagccccgcttcatcgcagtgggcta cgtggacgacacgcagttcgtgcggttcgacagcgacgccgcgagccggaggatggagccgcgggcgccgtggata gagcaggagggtccggagtattgggacggggagacacggaaagtgaaggcccactcacagactcaccgagtggacc tggggaccctgcgcggctactacaaccagagcgaggccggttctcacaccctccagaggatgtatggctgcgacgt ggggtcggactggcgcttcctGcgcgggtaccaccagtacgcctacgacggcaaggattacatcgccctgaaagag gacctgcgctcttggaccgcggcggacatggcagctcagaccaccaagcacaagtgggaggcggcccatgtggcgg agcagtggagagcctacctggagggcacgtgcgtggagtggctccgcagatacctggagaacgggaaggagacgct gcagcgcacggacgcccccaaaacgcatatgactcaccacgctgtctctgaccatgaagccaccctgaggtgctgg gccctgagcttctaccctgcggagatcacactgacctggcagcgggatggggaggaccagacccaggacacggagc tcgtggagaccaggcctgcaggggatggaaccttccagaagtgggcggctgtggtggtgccttctggacaggagca gagatacacctgccatgtgcagcatgagggtTtgcccaagcccctcaccctgagatgggag;

A*0206:
(SEQ ID NO: 22)
atggccgtcatggcgccccgaaccctcgtcctgctactctcggggcTctggccctgacccagacctgggcgggct ctcactccatgaggtatttctacacCtccgtgtcccggcccggccgcggggagccccgcttcatcgcagtgggcta cgtggacgacacgcagttcgtgcggttcgacagcgacgccgcgagccagaggatggagccgcgggcgccgtggata gagcaggagggtccggagtattgggacggggagacacggaaAgtgaaggcccactcacagactCaccgagtggacc tggggaccctgcgcggctactacaaccagagcgaggccggttctcacaccGtccagaGgatgtatggctgcgacgt ggggtcggacTggcgcttcctccgcgggtaccaccagtacgcctacgacggcaaggattacatcgccctgaaagag gacctgcgctcttggaccgcggcggacatggcagctcagaccaccaagcacaagtgggaggcggcccatgTggcgg agcagtTgagagcctacctggagggcaCgtgcgtggagtggctccgcagatacctggagaacgggaaggagacgct gcagcgcacggacgcccccaaaacgcatatgactcaccacgctgtctctgaccatgaagccaccctgaggtgctgg gccctgagcttctaccctgcggagatcacactgacctggcagcgggatggggaggaccagacccaggacacggagc -continued tcgtggagaccaggcctgcaggggatggaaccttccagaagtgggcggctgtggtggtgccttctggacaggagca gagatacacctgccatgtgcagcatgagggtTtgcccaagcccctcaccctgagatgggag A*0207:
(SEQ ID NO: 23)
atggccgtcatggcgccccgaaccctcgtcctgctactctcgggggctctggccctgacccagacctgggcgggct ctcactccatgaggtatttcttcacatccgtgtcccggcccggccgcggggagccccgcttcatcgcagtgggcta cgtggacgacacgcagttcgtgcggttcgacagcgacgccgcgagccagaggatggagccgcgggcgccgtggata gagcaggagggtccggagtattgggacggggagacacggaaagtgaaggcccactcacagactcaccgagtggacc tggggaccctgcgcggctactacaaccagagcgaggccggttctcacaccgtccagaggatgtGtggctgcgacgt ggggtcggactggcgcttcctccgcgggtaccaccagtacgcctacgacggcaaggattacatcgccctgaaagag gacctgcgctcttggaccgcggcggacatggcagctcagaccaccaagcacaagtgggaggcggcccatgtggcgg agcagttgagagcctacctggagggcacgtgcgtggagtggctccgcagatacctggagaacgggaaggagacgct gcagcgcacggacgcccccaaaacgcatatgactcaccacgctgtctctgaccatgaagccaccctgaggtgctgg gccctgagcttctaccctgcggagatcacactgacctggcagcgggatggggaggaccagacccaggacacggagc tcgtggagaccaggcctgcaggggatggaaccttccagaagtgggcggctgtggtggtgccttctggacaggagca gagatacacctgccatgtgcagcatgagggtttgcccaagcccctcaccctgagatgggag A*0208;
(SEQ ID NO: 24)
tgggcgggctctcactccatgaggtatttctacacCtccgtgtcccggcccggccgcggggagccccgcttcatcg cagtgggctacgtggacgacacgcagttcgtgcggttcgacagcgacgccgcgagccggaggatggagccgcgggc gccgtggatagagcaggagggtccggagtattgggacggggagacacggaatgtgaaggcccactcacagactcac cgagtggacctggggaccctgcgcggctactacaaccagagcgaggccggttctcacaccctccagaggatgtatg gctgcgacgtggggtcggactggcgcttcctGcgcgggtaccaccagtacgcctacgacggcaaggattacatcgc cctgaaagaggacctgcgctcttggaccgcggcggacatggcagctcagaccaccaagcacaagtgggaggcggcc catgtggcggagcagtggagagcctacctggagggcacgtgcgtggagtggctccgcagatacctggagaacggga aggagacgctgcagcgca;

A*0209:
(SEQ ID NO: 25)
atggccgtcatggcgccccgaaccctcgtcctgctactctcgggggctctggccctgacccagacctgggcgggct ctcactccatgaggtatttcttcacatccgtgtcccggcccggccgcggggagccccgcttcatcgcagtgggcta cgtggacgacacgcagttcgtgcggttcgacagcgacgccgcgagccagaggatggagccgcgggcgccgtggata gagcaggagggtccggagtattgggacggggagacacggaaagtgaaggcccactcacagactcaccgagtggacc tggggaccctgcgcggctactacaaccagagcgaggccggttctcacaccgtccagaggatgtatggctgcgacgt ggggtcggactggcgcttcctccgcgggtaccaccagtacgcctacgacggcaaggattacatcgccctgaaagag gacctgcgctcttggaccgcggcggacatggcagctcagaccaccaagcacaagtgggaggcggcccatgtggcgg agcagttgagagcctacctggagggcacgtgcgtggagtggctccgcagatacctggagaacgggaaggagacgct gcagcgcacggacgcccccaaaacgcatatgactcaccacgctgtctctgaccatgaagccaccctgaggtgctgg gccctgagcttctaccctgcggagatcacactgacctggcagcgggatggggaggaccagacccaggacacggagc tcgtggagaccaggcctgAaggggatggaaccttccagaagtgggcggctgtggtggtgccttctggacaggagca gagatacacctgccatgtgcagcatgagggtttgcccaagcccctcaccctgagatgggag;

A*0210:
(SEQ ID NO: 26)
atggccgtcatggcgccccgaaccctcgtcctgctactctcgggggcTctggccctgacccagacctgggcgggct ctcactccatgaggtatttctacacctccgtgtcccggcccggccgcggggagccccgcttcatcgcagtgggcta cgtggacgacacgcagttcgtgcggttcgacagcgacgccgcgagccagaggatggagccgcgggcgccgtggata gagcaggagggtccggagtattgggacggggagacacggaaagtgaaggcccactcacagactcaccgagtggacc tggggaccctgcgcggctactacaaccagagcgaggccggttctcacaccgtccagaGgatgtTtggctgcgacgt ggggtcggacgggcgcttcctccgcgggtaccaccagtacgcctacgacggcaaggattacatcgccctgaaagag gacctgcgctcttggaccgcggcggacatggcagctcagaccaccaagcacaagtgggaggcggcccatgTggcgg agcagtTgagagcctacctggagggcaCgtgcgtggagtggctccgcagatacctggagaacgggaaggagacgct gcagcgcacggacgcccccaaaacgcatatgactcaccacgctgtctctgaccatgaagccaccctgaggtgctgg gccctgagcttctaccctgcggagatcacactgacctggcagcgggatggggaggaccagacccaggacacggagc tcgtggagaccaggcctgcaggggatggaaccttccagaagtgggcggctgtggtggtgccttctggacaggagca gagatacacctgccatgtgcagcatgagggtTtgcccaagcccctcaccctgagatgggag;

A*0211:
(SEQ ID NO: 27)
atggccgtcatggcgccccgaaccctcgtcctgctactctcgggggctctggccctgacccagacctgggcgggct ctcactccatgaggtatttcttcacatccgtgtcccggcccggccgcggggagccccgcttcatcgcagtgggcta cgtggacgacacgcagttcgtgcggttcgacagcgacgccgcgagccagaggatggagccgcgggcgccgtggata gagcaggagggtccggagtattgggacggggagacacggaaagtgaaggcccactcacagaTtgaccgagtggacc tggggaccctgcgcggctactacaaccagagcgaggccggttctcacaccgtccagaggatgtatggctgcgacgt ggggtcggactggcgcttcctccgcgggtaccaccagtacgcctacgacggcaaggattacatcgccctgaaagag gacctgcgctcttggaccgcggcggacatggcagctcagaccaccaagcacaagtgggaggcggcccatgtggcgg agcagttgagagcctacctggagggcacgtgcgtggagtggctccgcagatacctggagaacgggaaggagacgct gcagcgcacggacgcccccaaaacgcatatgactcaccacgctgtctctgaccatgaagccaccctgaggtgctgg gccctgagcttctaccctgcggagatcacactgacctggcagcgggatggggaggaccagacccaggacacggagc tcgtggagaccaggcctgcaggggatggaaccttccagaagtgggcggctgtggtggtgccttctggacaggagca gagatacacctgccatgtgcagcatgagggtTtgcccaagcccctcaccctgagatgggag;

A*0212:
(SEQ ID NO: 28)
atggccgtcatggcgccccgaaccctcgtcctgctactctcgggggcTctggccctgacccagacctgggcgggct ctcactccatgaggtatttcttcacatccgtgtcccggcccggccgcggggagccccgcttcatcgcagtgggcta cgtggacgacacgcagttcgtgcggttcgacagcgacgccgcgagccagaggatggagccgcgggcgccgtggata gagcaggagggtccggagtattgggacggggagacacggaaagtgaaggcccactcacagactcaccgagtggacc tggggaccctgcgcggctactacaaccagagcgaggccggttctcacaccgtccagaggatgtatggctgcgacgt ggggtcggactggcgcttcctccgcgggtaccaccagtacgcctacgacggcaaggattacatcgccctgaaagag gacctgcgctcttggaccgcggcggacatggcagctcagaccaccaagcacaagtgggaggcggcccatgTggcgg agcagcAgagagcctacctggagggcaCgtgcgtggagtggctccgcagatacctggagaacgggaaggagacgct gcagcgcacggacgcccccaaaacgcatatgactcaccacgctgtctctgaccatgaagccaccctgaggtgctgg gccctgagcttctaccctgcggagatcacactgacctggcagcgggatggggaggaccagacccaggacacggagc tcgtggagaccaggcctgcaggggatggaaccttccagaagtgggcggctgtggtggtgccttctggacaggagca gagatacacctgccatgtgcagcatgagggtTtgcccaagcccctcaccctgagatgggag;

A*0213:
(SEQ ID NO: 29)
atggccgtcatggcgccccgaaccctcgtcctgctactctcgggggcTctggccctgacccagacctgggcgggct ctcactccatgaggtatttcttcacatccgtgtcccggcccggccgcggggagccccgcttcatcgcagtgggcta cgtggacgacacgcagttcgtgcggttcgacagcgacgccgcgagccagaggatggagccgcgggcgccgtggata gagcaggagggtccggagtattgggacggggagacacggaaagtgaaggcccactcacagactcaccgagtggacc tggggaccctgcgcggctactacaaccagagcgaggccggttctcacaccgtccagaggatgtatggctgcgacgt ggggtcggactggcgcttcctccgcgggtaccaccagtacgcctacgacggcaaggattacatcgccctgaaagag gacctgcgctcttggaccgcggcggacatggcagctcagaccaccaagcacaagtgggaggcggcccatgAggcgg agcagcAgagagcctacctggagggcaCgtgcgtggagtggctccgcagatacctggagaacgggaaggagacgct gcagcgcacggacgcccccaaaacgcatatgactcaccacgctgtctctgaccatgaagccaccctgaggtgctgg gccctgagcttctaccctgcggagatcacactgacctggcagcgggatggggaggaccagacccaggacacggagc tcgtggagaccaggcctgcaggggatggaaccttccagaagtgggcggctgtggtggtgccttctggacaggagca gagatacacctgccatgtgcagcatgagggtTtgcccaagcccctcaccctgagatgggag;

A*0214:  
(SEQ ID NO: 30)  
cgtcatggcgccccgaaccctcgtcctgctactctcgggggctctggccctgacccagacctgggcgggctctcac tccatgaggtatttctacacctccgtgtcccggcccggccgcggggagccccgcttcatcgcagtgggctacgtgg acgacacgcagttcgtgcggttcgacagcgacgccgcgagccggaggatggagccgcgggcgccgtggatagagca ggagggtccggagtattgggacggggagacacggaaagtgaaggcccactcacagactcaccgagtggacctgggg accctgcgcggctactacaaccagagcgaggccggttctcacaccctccagaggatgtatggctgcgacgtgggt cggactggcgcttcctGcgcgggtaccaccagtacgcctacgacggcaaggattacatcgccctgaaagaggacct gcgctcttggaccgcggcggacatggcagctcagaccaccaagcacaagtgggaggcggcccatgtggcggagcag tTgagagcctacctggagggcacgtgcgtggagtggctccgcagatacctggagaacgggaaggagacgctgcagc gcacggacgcccccaaaacgcatatgactcaccacgctgtctctgaccatgaagccaccctgaggtgctgggccct gagcttctaccctgcggagatcacactgacctggcagcgggatggggaggaccagacccaggacacggagctcgtg gagaccaggcctgcaggggatggaaccttccagaagtgggcggctgtggtggtgccttctggacaggagcagagat acacctgccatgtgcagcatgagggtTtgcccaagcccctcaccctgagatgggag;

A*0216:  
(SEQ ID NO: 31)  
atggccgtcatggcgccccgaaccctcgtcctgctactctcgggggctctggccctgacccagacctgggcgggct ctcactccatgaggtatttcttcacatccgtgtcccggcccggccgcggggagccccgcttcatcgcagtgggcta cgtggacgacacgcagttcgtgcgggttcgacagcgacgccgcgagccagaggatggagccgcgggcgccgtggata gagcaggagggtccggagtattgggacggggagacacggaaagtgaaggcccactcacagactcaccgagtggacc tggggaccctgcgcggctactacaaccagagcgaggccggttctcacaccgtccagaggatgtatggctgcgacgt ggggtcggactggcgcttcctccgcgggtaccaccagtacgcctacgacggcaaggattacatcgccctgaaagag gacctgcgctcttggaccgcggcggacatggcagctcagaccaccaagcacaagtgggaggcggcccatgtggcgg agcagttgagagcctacctggagggcgAgtgcgtggagtggctccgcagatacctggagaacgggaaggagacgct gcagcgcacggacgcccccaaaacgcatatgactcaccacgctgtctctgaccatgaagccaccctgaggtgctgg gccctgagcttctaccctgcggagatcacactgacctggcagcgggatggggaggaccagacccaggacacggagc tcgtggagaccaggcctgcaggggatggaaccttccagaagtgggcggctgtggtggtgccttctggacaggagca gagatacacctgccatgtgcagcatgagggtTtgcccaagcccctcaccctgagatgggag;

A*021701:  
(SEQ ID NO: 32)  
atggccgtcatggcTccccgaaccctcgtcctgctactctcgggggctctggccctgacccagacctgggcgggct ctcactccatgaggtatttcttcacatccgtgtcccggcccggccgcggggagccccgcttcatcgcagtgggcta cgtggacgacacgcagttcgtgcggttcgacagcgacgccgcgagccagaggatggagccgcgggcgccgtggata gagcaggagggtccggagtattgggacggggagacacggaaagtgaaggcccactcacagactcaccgagtggacc tggggaccctgcgcggctactacaaccagagcgaggccggttctcacaccctccagatgatgtttggctgcgacgt -continued ggggtcggactggcgcttcctccgcgggtaccaccagtacgcctacgacggcaaggattacatcgccctgaaagag gacctgcgctcttggaccgcggcggacatggcagctcagaccaccaagcacaagtgggaggcggcccatgtggcgg agcagttgagagcctacctggagggcacgtgcgtggagtggctccgcagatacctggagaacgggaaggagacgct gcagcgcacggacgcccccaaaacgcatatgactcaccacgctgtctctgaccatgaagccaccctgaggtgctgg gccctgagcttctaccctgcggagatcacactgacctggcagcgggatggggaggaccagacccaggacacggagc tcgtggagaccaggcctgcaggggatggaaccttccagaagtgggcggctgtggtggtgccttctggacaggagca gagatacacctgccatgtgcagcatgagggtttgcccaagcccctcaccctgagatgggag;

A*021702:
(SEQ ID NO: 33)
atggccgtcatggcgccccgaaccctcgtcctgctactctcgggggcTctggccctgacccagacctgggcgggct ctcactccatgaggtatttcttcacatccgtgtcccggcccggccgcggggagccccgcttcatcgcagtgggcta cgtggacgacacgcagttcgtgcggttcgacagcgacgccgcgagccagaggatggagccgcgggcgccgtggata gagcaggagggtccggagtattgggacggggagacacggaaagtgaaggcccactcacagactcaccgagtggacc tggggaccctgcgcggctactacaaccagagcgaggccggttctcacaccctccagatgatgtTtggctgcgacgt ggggtcggacTggcgcttcctccgcgggtaccaccagtacgcctacgacggcaaggattacatcgccctgaaagag gacctgcgctcttggaccgcggcggacatggcagctcagaccaccaagcacaagtgggaggcggcccatgTggcgg agcagtTgagagcctacctggagggcaCgtgcgtggagtggctccgcagatacctggagaacgggaaggagacgct gcagcgcacggacgcccccaaaacgcatatgactcaccacgctgtctctgaccatgaagccaccctgaggtgctgg gccctgAgcttctaccctgcggagatcacactgacctggcagcgggatggggaggaccagacccaggacacggagc tcgtggagaccaggcctgcag;

A*0218:
(SEQ ID NO: 34)
atggccgtcatggcgccccgaaccctcgtcctgctactctcgggggctctggccctgacccagacctgggcgggct ctcactccatgaggtatttcttcacatccgtgtcccggcccggccgcggggagccccgcttcatcgcagtgggcta cgtggacgacacgcagttcgtgcggttcgacagcgacgccgcgagccagaggatggagccgcgggcgccgtggata gagcaggagggtccggagtattgggacggggagacacggaaagtgaaggcccactcacagactcaccgagtggacc tggggaccctgcgcggctactacaaccagagcgaggccggttctcacaccgtccagaggatgtgtggctgcgacgt ggggtcggactggcgcttcctccgcgggtaccaccagtacgcctacgacggcaaggattacatcgccctgaaagag gacctgcgctcttggaccgcggcggacaAggcagctcagaccaccaagcacaagtgggaggcggcccatgtggcgg agcagttgagagcctacctggagggcacgtgcgtggagtggctccgcagatacctggagaacgggaaggagacgct gcagcgcacggacgcccccaaaacgcatatgactcaccacgctgtctctgaccatgaagccaccctgaggtgctgg gccctgagcttctaccctgcggagatcacactgacctggcagcgggatggggaggaccagacccaggacacggagc tcgtggagaccaggcctgcaggggatggaaccttccagaagtgggcggctgtggtggtgccttctggacaggagca gagatacacctgccatgtgcagcatgagggtttgcccaagcccctcaccctgagatgggag;

A*0219:
(SEQ ID NO: 35)
gctctcactccatgaggtatttcttcacatccgtgtcccggcccggccgcggggagccccgcttcatcgcagtggg ctacgtggacgacacgcagttcgtgcggttcgacagcgacgccgcgagccagaggatggagccgcgggcgccgtgg atagagcaggagggtccggagtattgggacggggagacacggaaagtgaaggcccactcacagactcaccgagtgG acctggggaccctgcgcggctactacaaccagagcgaggccggttctcacaccGtccagaggatgtatggctgcga cgtggggtcggactggcgcttcctccgcgggtaccaccagtacgcctacgacggcaaggattacatcgccctgaaa gaggacctgcgctcttggaccgcggcggacatggcGgctcagatcaccaagcgcaagtgggaggcggcccatgTgg cggagcagcAgagagcctacctggagggcaCgtgcgtggacgggctccgcagatacctggagaacgggaaggagac gctgcagcgcacgg;

A*022001:

(SEQ ID NO: 36)

gctctcactccatgaggtatttcttcacatccgtgtcccggcccggccgcggggagccccgcttcatcgcAgtggg ctacgtggacgacacgcagttcgtgcggttcgacagcgacgccgcgagccagaggatggagccgcgggcgccgtgg atagagcaggagggtccggagtattgggacGGggagacacggaatgtgaaggcccactcacagactCaccgagtgg acctggggaccctgcgcggctactacaaccagagcgaggccggttctcacaccGtccagaGgatgtatggctgcga cgtggggtcggacTggcgcttcctccgcgggtaccaCcagTacgcctacgacggcaaggattacatcgccctgaaA gaggacctgcgctcttggaccgcggcggacatggcagctcagaCcaccaagcacaagtgggaggcggcccatgTgg cggagcagtTgagagcctacctggagggcaCgtgcgtggagTggctccgcagatacctggagaacgggaaggagac gctgcagcgcacgg;

A*022002:

(SEQ ID NO: 37)

gctctcactccatgaggtatttcttcacatccgtgtcccggcccggccgcggggagccccgcttcatcgcagtggg ctacgtggacgacacgcagttcgtgcggttcgacagcgacgccgcgagccagaggatggagccgcgggcgccgtgg atagagcaggagggtccggagtattgggacggggagacacggaaCgtgaaggcccactcacagactcaccgagtgg acctggggaccctgcgcggctactacaaccagagcgaggccggttctcacaccgtccagaggatgtatggctgcga cgtggggtcggactggcgcttcctccgcgggtaccaccagtacgcctacgacggcaaggattacatcgccctgaaa gaggacctgcgctcttggaccgcggcggacatggcagctcagaccaccaagcacaagtgggaggcggcccatgtgg cggagcagttgagagcctacctggagggcacgtgcgtggagtggctccgcagatacctggagaacgggaaggagac gctgcagcgcacgg;

A*0221:

(SEQ ID NO: 38)

atggccgtcatggcgccccgaaccctcgtcctgctactctcgggggctctggccctgacccagacctgggcgggct ctcactccatgaggtatttctacacctccgtgtcccggcccggccgcggggagccccgcttcatcgcagtgggcta cgtggacAacacgcagttcgtgcggttcgacagcgacgccgcgagccagaggatggagccgcgggcgccgtggata gagcaggagggtccggagtattgggacggggagacacggaaagtgaaggcccactcacagactcaccgagtggacc tggggaccctgcgcggctactacaaccagagcgaggccggttctcacaccgtccagaggatgtatggctgcgacgt ggggtcggactggcgcttcctccgcgggtaccaccagtacgcctacgacggcaaggattacatcgccctgaaagag gacctgcgctcttggaccgcggcggacatggcagctcagaccaccaagcacaagtgggaggcggcccatgtggcgg agcagttgagagcctacctggagggcacgtgcgtggagtggctccgcagatacctggagaacgggaaggagacgct gcagcgcacggacgcccccaaaacgcatatgactcaccacgctgtctctgaccatgaagccaccctgaggtgctgg gccctgagcttctaccctgcggagatcacactgacctggcagcgggatggggaggaccagacccaggacacggagc tcgtggagaccaggcctgcaggggatggaaccttccagaagtgggcggctgtggtggtgccttctggacaggagca gagatacacctgccatgtgcagcatgagggtttgcccaagcccctcaccctgagatgggag;

A*0222:

(SEQ ID NO: 39)

atggccgtcatggcgccccgaaccctcgtcctgctactctcgggggcTctggccctgacccagacctgggcgggct ctcactccatgaggtatttcttcacatccgtgtcccggcccggccgcggggagccccgcttcatcgcagtgggcta cgtggacgacacgcagttcgtgcggttcgacagcgacgccgcgagccagaggatggagccgcgggcgccgtggata gagcaggagggtccggagtattgggacggggagacacggaaAgtgaaggcccactcacagactCaccgagtggacc tggggaccctgcgcggctactacaaccagagcgaggccggttctcacaccGtccagaGgatgtatggctgcgacgt ggggtcggacTggcgcttcctccgcgggtaccaccagtacgcctacgacggcaaggattacatcgccctgaaagag gacctgcgctcttggaccgcggcggacatggcagctcagaccaccaagcacaagtgggaggcggcccatgTggcgg agcagTggagagcctacctggagggcaCgtgcgtggagtggctccgcagatacctggagaacgggaaggagacgct gcagcgcacggacgcccccaaaacgcatatgactcaccacgctgtctctgaccatgaagccaccctgaggtgctgg gccctgagcttctaccctgcggagatcacactgacctggcagcgggatggggaggaccagacccaggacacggagc tcgtggagaccaggcctgcaggggatggaaccttccagaagtgggcggctgtggtggtgccttctggacaggagca gagatacacctgccatgtgcagcatgagggtTtgcccaagcccctcaccctgagatgggag;

A*0224:

(SEQ ID NO: 40)

gctctcactccatgaggtatttcttcacatccgtgtcccggcccggccgcggggagccccgcttcatcgcAgtggg ctacgtggacgacacgcagttcgtgcggttcgacagcgacgccgcgagccagaggatggagccgcgggcgccgtgg atagagcaggagggtccggagtattgggacgGggagacacggaaAgtgaaggcccactcacagactCaccgagtgg acctggggaccctgcgcggctactacaaccagagcgaggccggttctcacaccGtccagaGgatgtatggctgcga cgtggggtcggacTggcgcttcctccgcgggtaccaCcagTacgcctacgacggcaaggattacatcgccctgaac gaggacctgcgctcttggaccgcggcggacatggcagctcagaCcaccaagcacaagtgggaggcggcccatgTgg cggagcagtTgagagcctacctggagggcaCgtgcgtggagTggctccgcagatacctggagaacgggaaggagac gctgcagcgcacgg;

A*0225:

(SEQ ID NO: 41)

gctctcactccatgaggtatttcttcacatccgtgtcccggcccggccgcggggagccccgcttcatcgcagtggg ctacgtggacgacacgcagttcgtgcggttcgacagcgacgccgcgagccagaggatggagccgcgggcgccgtgg atagagcaggagggtccggagtattgggacggggagacacggaaagtgaaggcccactcacagactcaccgagtgg acctggggaccctgcgcggctactacaaccagagcgaggccggttctcacaccgtccagaggatgtatggctgcga cgtggggtcggactggcgcttcctccgcgggtaccaccagtacgcctacgacggcaaggattacatcgccctgaaa gaggacctgcgctcttggaccgcggcggacatggcagctcagaccaccaagcacaagtgggagAcggcccatgTgg cggagcagtTgagagcctacctggagggcaCgtgcgtggagtggctccgcagatacctggagaacgggaaggagac gctgcagcgcacgg;

A*0226:

(SEQ ID NO: 42)

gtcatggcgccccgaaccctcgtcctgctactctcggggcTctggccctgacccagacctgggcgggctctcact ccatgaggtatttcttcacatccgtgtcccggcccggccgcggggagccccgcttcatcgcagtgggctacgtgga cgacacgcagttcgtgcggttcgacagcgacgccgcgagccagaggatggagccgcgggcgccgtggatagagcag gagggtccggagtattgggacggggagacacggaaagtgaaggcccactcacagactcaccgagtggacctgggga ccctgcgcggctactacaaccagagcgaggccggttctcacaccgtccagaggatgtatggctgcgacgtggggtc ggactggcgcttcctccgcgggtaccaccagtacgcctacgacggcaaggattacatcgccctgaaagaggacctg cgctcttggaccgcggcggacatggcagctcagaccaccaagcacaagtgggaggcggcccatgAggcggagcagt TgagagcctacctggagggcaCgtgcgtggagtggctccgcagatacctggagaacgggaaggagacgctgcagcg cacggacgcccccaaaacgcatatgactcaccacgctgtctctgaccatgaagccaccctgaggtgctgggccctg agcttctaccctgcggagatcacactgacctggcagcgggatggggaggaccagacccaggacacggagctcgtgg agaccaggcctgcaggggatggaaccttccagaagtgggcggctgtggtggtgccttctggacaggagcagagata cacctgccatgtgcagcatgagggtTtgcccaagcccctcaccctgagatgggag;

A*0227:

(SEQ ID NO: 43)

gctctcactccatgaggtatttcttcacatccgtgtcccggcccggccgcggggagccccgcttcatcgcagtggg ctacgtggacgacacgcagttcgtgcggttcgacagcgacgccgcgagccagaggatggagccgcgggcgccgtgg atagagcaggagggtccggagtattgggacggggagacacggaaagtgaaggcccactcacagactcaccgagtgg acctggggaccctgcgcggctactacaaccagagcgaggccggttctcacaccGtccagaggatgtatggctgcga cgtggggtcggactggcgcttcctccgcgggtaccaccagtacgcctacgacggcaaggattacatcgccctgaaa -continued gaggacctgcgctcttggaccgcggcggacatggcagctcagaccaccaagcAcaagtgggaggcggcccatgcgg cggagcagcAgagagcctacctggagggcaCgtgcgtggagTggctccgcagatacctggagaacgggaaggagac gctgcagcgcacgg;

A*0228:

(SEQ ID NO: 44)

gctctcactccatgaggtatttctacacctccgtgtcccggcccggccgcggggagccccgcttcatcgcagtggg ctacgtggacgacacgcagttcgtgcggttcgacagcgacgccgcgagccagaggatggagccgcgggcgccgtgg atagagcaggagAgtccggagtattgggacggggagacacggaaagtgaaggcccactcacagactcaccgagtgg acctggggaccctgcgcggctactacaaccagagcgaggccggttctcacaccgtccagaggatgtatggctgcga cgtggggtcggactggcgcttcctccgcgggtaccaccagtacgcctacgacggcaaggattacatcgccctgaaa gaggacctgcgctcttggaccgcggcggacatggcagctcagaccaccaagcAcaagtgggaggcggcccatgTgg cggagcagtTgagagcctacctggagggcacgtgcgtggagTggctccgcagatacctggagaacgggaaggagac gctgcagcgcacgg;

A*0229:

(SEQ ID NO: 45)

gctctcactccatgaggtatttcttcacatccgtgtcccggcccggccgcggggagccccgcttcatcgcagtggg ctacgtggacgacacgcagttcgtgcggttcgacagcgacgccgcgagccagaggatggagccgcgggcgccgtgg atagagcaggagggtccggagtattgggacggggagacacggCaagtgaaggcccactcacagactcaccgagtgg acctggggaccctgcgcggctactacaaccagagcgaggccggttctcacaccgtccagaggatgtatggctgcga cgtggggtcggactggcgcttcctccgcgggtaccaccagtacgcctacgacggcaaggattacatcgccctgaaa gaggacctgcgctcttggaccgcggcggacatggcagctcagaccaccaagcAcaagtgggaggcggcccatgtgg cggagcagttgagagcctacctggagggcacgtgcgtggagtggctccgcagatacctggagaacgggaaggagac gctgcagcgcacgg;

A*0230:

(SEQ ID NO: 46)

atggccgtcatggcgccccgaaccctcgtcctgctactctcgggggctctggccctgacccagacctgggcgggct ctcaGtccatgaggtatttcttcacatccgtgtcccggcccggccgcggggagccccgcttcatcgcagtgggcta cgtggacgacacgcagttcgtgcggttcgacagcgacgccgcgagccagaggatggagccgcgggcgccgtggata gagcaggagggtccggagtattgggacggggagacacggaaagtgaaggcccactcacagactcaccgagtggacc tggggaccctgcgcggctactacaaccagagcgaggccggttctcacaccgtccagaggatgtatggctgcgacgt ggggtcggactggcgcttcctccgcgggtaccaccagtacgcctacgacggcaaggattacatcgccctgaaagag gacctgcgctcttggaccgcggcggacatggcagctcagaccaccaagcacaagtgggaggcggcccatgtggcgg agcagttgagagcctacctggagggcacgtgcgtggagtggctccgcagatacctggagaacgggaaggagacgct gcagcgcacggacgcccccaaaacgcatatgactcaccacgctgtctctgaccatgaagccaccctgaggtgctgg gccctgagcttctaccctgcggagatcacactgacctggcagcgggatggggaggaccagacccaggacacggagc tcgtggagaccaggcctgcaggggatggaaccttccagaagtgggcggctgtggtggtgccttctggacaggagca gagatacacctgccatgtgcagcatgagggtttgcccaagcccctcaccctgagatgggag;

A*0231:

(SEQ ID NO: 47)

gctctcactccatgaggtatttcttcacatccgtgtcccggcccggccgcggggagccccgcttcatcgcagtggg ctacgtggacgacacgcagttcgtgcggttcgacagcgacgccgGgagccagaggatggagccgcgggcgccgtgg atagagcaggagggtccggagtattgggacggggagacacggaaagtgaaggcccactcacagactcaccgagtgg acctggggaccctgcgcggctactacaaccagagcgaggccggttctcacaccgtccagaggatgtatggctgcga cgtggggtcggactggcgcttcctccgcgggtaccaccagtacgcctacgacggcaaggattacatcgccctgaaa -continued gaggacctgcgctcttggaccgcggcggacatggcagctcagaccaccaagcacaagtgggaggcggcccatgtgg cggagcagttgagagcctacctggagggcacgtgcgtggagtggctccgcagatacctggagaacgggaaggagac gctgcagcgcacgg;

A*0233:

(SEQ ID NO: 48)

atggccgtcatggcgccccgaaccctcgtcctgctactctcgggggctctggccctgacccagacctgggcgggct ctcactccatgaggtatttcttcacatccgtgtcccggcccggccgcggggagccccgcttcatcgcagtgggcta cgtggacgacacgcagttcgtgcggttcgacagcgacgccgcgagccagaggatggagcgcgggcgccgtggata gagcaggagggtccggagtattgggacggggagacacggaaagtgaaggcccactcacagactcaccgagtggacc tggggaccctgcgcggctactacaaccagagcgaggccggttctcacaccgtccagaggatgtCtggctgcgacgt ggggtcggactggcgcttcctccgcgggtaccaccagtacgcctacgacggcaaggattacatcgccctgaaagag gacctgcgctcttggaccgcggcggacatggcagctcagaccaccaagcacaagtgggaggcggcccatgtggcgg agcagttgagagcctacctggagggcacgtgcgtggagtggctccgcagatacctggagaacgggaaggagacgct gcagcgcacggacgcccccaaaacgcatatgactcaccacgctgtctctgaccatgaagccaccctgaggtgctgg gccctgagcttctaccctgcggagatcacactgacctggcagcgggatggggaggaccagacccaggacacggagc tcgtggagaccaggcctgcaggggatggaaccttccagaagtgggcggctgtggtggtgccttctggacaggagca gagatacacctgccatgtgcagcatgagggtttgcccaagcccctcaccctgagatgggag;

A*0234:

(SEQ ID NO: 49)

gctctcactccatgaggtatttcttcacatccgtgtcccggcccggccgcggggagccccgcttcatcgcagtggg ctacgtggacgacacgcagttcgtgcggttcgacagcgacgccgcgagccagaggatggagccgcgggcgccgtgg atagagcaggagggtccggagtattgggacggggagacacggaaAgtgaaggcccaGtcacagactCaccgagtgg acctggggaccctgcgcggctactacaaccagagcgaggccggttctcacaccGtccagaGgatgtatggctgcga cgtggggtcggacTggcgcttcctccgcgggtaccaccagtacgcctacgacggcaaggattacatcgccctgaaa gaggacctgcgctcttggaccgcggcggacatggcagctcagaccaccaagcacaagtgggaggcggcccatgTgg cggagcagTTgagagcctacctggagggcaCgtgcgtggagtggctccgcagatacctggagaacgggaaggagac gctgcagcgcacggacgcccccaaaacgcatatgactcaccacgctgtctctgaccatgaagccaccctgaggtgc tgggccctgagcttctaccctgcggagatcacactgacctggcagcgggatggggaggaccagacccaggacacgg agctcgtggagaccaggcctgcaggggatggaaccttccagaagtgggcggctgtggtggtgccttctggacagga gcagagatacacctgccatgtgcagcatgagggtTtgcccaagcccctcaccctgagatggg;

A*0235:

(SEQ ID NO: 50)

gctctcactccatgaggtatttcttcacatccgtgtcccggcccggccgcggggagccccgcttcatcgcagtggg ctacgtggacgacacgcagttcgtgcggttcgacagcgacgccgcgagccagaggatggagccgcgggcgccgtgg atagagcaggagggtccggagtattgggacggggagacacggaaAgtgaaggcccaGtcacagactgaccgagtgg acctggggaccctgcgcggctactacaaccagagcgaggccggttctcacaccGtccagaGgatgtatggctgcga cgtggggtcggacTggcgcttcctccgcgggtaccaCcagTacgcctacgacggcaaggattacatcgccctgaaA gaggacctgcgctcttggaccgcggcggacatggcagctcagaCcaccaagcacaagtgggaggcggcccatgTgg cggagcagtTgagagcctacctggagggcaCgtgcgtggagTggctccgcagatacctggagaacgggaaggagac gctgcagcgcacgg;

A*0236:

(SEQ ID NO: 51)

gctctcactccatgaggtatttcttcacatccgtgtcccggcccggccgcggggagccccgcttcatcgcAgtggg ctacgtggacgacacgcagttcgtgcggttcgacagcgacgccgcgagccagaggatggagccgcgggcgccgtgg atagagcaggagggtccggagtattgggacgGggagacacggaaAgtgaaggcccactcacagactCaccgagtgg -continued acctggggaccctgcgcggctactacaaccagagcgaggccggttctcacaccGtccagaGgatgtatggctgcga cgtggggtcggacTggcgcttcctccgcgggtaccaCcagTacgcctacgacggcaaggattacatcgccctgaaA gaggacctgcgctcttggaccgcggcggacatggcagctcagaCcaccaagcacaagtgggaggcggcccatgTgg cggagcagtTgagagcctacctggagggcaCgtgcgtggacgggctccgcagatacctggagaacgggaaggagac gctgcagcgcacgg;

A*0237:
(SEQ ID NO: 52)
gctctcactccatgaggtatttcttcacatccgtgtcccggcccggccgcggggagccccgcttcatcgcagtggg ctacgtggacgacacgcagttcgtgcggttcgacagcgacgccgcgagccagaggatggagccgcgggcgccgtgg atagagcaggagggtccggagtattgggacggggagacacggaaagtgaaggcccactcacagactcaccgagtgg acctggggaccctgcgcggctactacaaccagagcgaggccggttctcacaccGtccagaggatgtatggctgcga cgtggggtcggactggcgcttcctccgcgggtaccaccagtacgcctacgacggcaaggattacatcgccctgaaa gaggacctgcgctcttggaccgcggcggacatggcagctcagaccaccaagcAcaagtgggaggcggcccatgTgg cggagcagcAgagagcctacctggagggcaCgtgcgtggacgggctccgcagatacctggagaacgggaaggagac gctgcagcgcacgg;

A*0238:
(SEQ ID NO: 53)
gctctcactccatgaggtatttcttcacatccgtgtcccggcccggccgcggggagccccgcttcatcgcagtggg ctacgtggacgacacgcagttcgtgcggttcgacagcgacgccgcgagccagaggatggagccgcgggcgccgtgg atagagcaggagggtccggagtattgggacggggagacacggaaagtgaaggcccactcacagactcaccgagtgg acctggggaccctgcgcggctactacaaccagagcgaggccggttctcacaccgtccagaggatgtatggctgcga cgtggggtcggactggcgcttcctccgcgggtaccaccagtacgcctacgacggcaaggattacatcgccctgaaa gaggacctgcgctcttggaccgcggcggacatggcagctcagaccaccaagcAcaagtgggagAcggcccatgagg cggagcagcAgagagcctacctggagggccggtgcgtggagtggctccgcagatacctggagaacgggaaggagac gctgcagcgcacgg;

A*0239:
(SEQ ID NO: 54)
gctctcactccatgaggtatttcttcacatccgtgtcccggcccggccgcggggagccccgcttcatcgcagtggg ctacgtggacgacacgcagttcgtgcggttcgacagcgacgccgcgagccagaggatggagccgcgggcgccgtgg atagagcaggagggtccggagtattgggacggggagacacggaaagtgaaggcccactcacagactcaccgagtgg acctggggaccctgcgcggctactacaaccagagcgaggccggttctcacaccgtccagaggatgtTtggctgcga cgtggggtcggacgggcgcttcctccgcgggtaccaccagtacgcctacgacggcaaggattacatcgccctgaaa gaggacctgcgctcttggaccgcggcggacatggcGgctcagatcaccaagcAcaagtgggaggcggcccatgTgg cggagcagtTgagagCctacctggagggcaCgtgcgtggaGTggctccgcagatacctggagaacgggaaggagac gctgcagcgcacgg;

A*0240:
(SEQ ID NO: 55)
gctctcactccatgaggtatttcttcacatccgtgtcccggcccggccgcggggagccccgcttcatcgcagtggg ctacgtggacgacacgcagttcgtgcggttcgacagcgacgccgcgagccagaggatggagccgcgggcgccgtgg atagagcaggagggtccggagtattgggacggggagacacggaaagtgaaggcccactcacagactcaccgagtgg acctggggaccctgcgcggctactacaaccagagcgaggccggttctcacaccgtccagaggatgtatggctgcga cgtggggtcggactggcgcttcctccgcgggtaccaccagtacgcctacgacggcaaggattacatcgccctgaaa gaggacctgcgctcttggaccgcggcggacatggcagctcagaccaccaagcAcaagtgggaggcggcccGtgTgg cggagcagttgagagcctacctggagggcaCgtgcgtggagTggctccgcagatacctggagaacgggaaggagac gctgcagcgcacgg;

A*0241:

(SEQ ID NO: 56)

gctctcactccatgaggtatttctacacCtccgtgtcccggcccggccgcggggagccccgcttcatcgcAgtggg ctacgtggacgacacgcagttcgtgcggttcgacagcgacgccgcgagccagaggatggagccgcgggcgccgtgg atagagcaggagggtccggagtattgggacgGggagacacggaaAgtgaaggcccactcacagactCaccgagtgg acctggggaccctgcgcggctactacaaccagagcgaggccggttctcacaccGtccagaGgatgtatggctgcga cgtggggtcggacTggcgcttcctccgcgggtaccagcagTacgcctacgacggcaaggattacatcgccctgaaA gaggacctgcgctcttggaccgcggcggacatggcagctcagaCcaccaagcacaagtgggaggcggcccatgTgg cggagcagtTgagagcctacctggagggcaCgtgcgtggagTggctccgcagatacctggagaacgggaaggagac gctgcagcgcacgg;

A*0242:

(SEQ ID NO: 57)

gctctcactccatgaggtatttcttcacatccgtgtcccggcccggccgcggggagccccgcttcatcTcagtggg ctacgtggacgacacgcagttcgtgcggttcgacagcgacgccgcgagccagaggatggagccgcgggcgccgtgg atagagcaggagggtccggagtattgggacggggagacacggaaagtgaaggcccactcacagactcaccgagtgg acctggggaccctgcgcggctactacaaccagagcgaggccggttctcacaccgtccagaggatgtatggctgcga cgtggggtcggactggcgcttcctccgcgggtaccaccagtacgcctacgacggcaaggattacatcgccctgaaa gaggacctgcgctcttggaccgcggcggacatggcagctcagaccaccaagcacaagtgggaggcggcccatgtgg cggagcagttgagagcctacctggagggcacgtgcgtggagtggctccgcagatacctggagaacgggaaggagac gctgcagcgcacgg;

A*0244:

(SEQ ID NO: 58)

gctctcactccatgaggtatttctacacCtccgtgtcccggcccggccgcggggagccccgcttcatcgcagtggg ctacgtggacgacacgcagttcgtgcggttcgacagcgacgccgcgagccagaggatggagccgcgggcgccgtgg atagagcaggagggtccggagtattgggacggggagacacggaaagtgaaggcccactcacagactcaccgagtgg acctggggaccctgcgcggctactacaaccagagcgaggccggttctcacaccGtccagaggatgtatggctgcga cgtggggtcggactggcgcttcctccgcgggtaccaccagtacgcctacgacggcaaggattacatcgccctgaaa gaggacctgcgctcttggaccgcggcggacatggcagctcagatcaccaagcgcaagtgggaggcggcccatgTgg cggagcagcAgagagcctacctggagggcaCgtgcgtggagTggctccgcagatacctggagaacgggaaggagac gctgcagcgcacgg;

A*0245:

(SEQ ID NO: 59)

gctctcactccatgaggtatttcttcacatccgtgtcccggcccggccgcggggagccccgcttcatcgcAgtggg ctacgtggacgacacgcagttcgtgcggttcgacagcgacgccgcgagccagaggatggagccgcgggcgccgtgg atagagcaggagggtccggagtattgggaccaggagacacggaaAgtgaaggcccactcacagactCaccgagtgg acctggggaccctgcgcggctactacaaccagagcgaggccggttctcacaccGtccagaGgatgtatggctgcga cgtggggtcggacTggcgcttcctccgcgggtaccaCcagTacgcctacgacggcaaggattacatcgccctgaaA gaggacctgcgctcttggaccgcggcggacatggcagctcagaCcaccaagcacaagtgggaggcggcccatgTgg cggagcagtTgagagcctacctggagggcaCgtgcgtggagTggctccgcagatacctggagaacgggaaggagac gctgcagcgcacgg;

A*0246:

(SEQ ID NO: 60)

atggccgtcatggcgccccgaaccctcgtcctgctactctcgggggcTctggccctgacccagacctgggcgggct ctcactccatgaggtatttcttcacatccgtgtcccggcccggccgcggggagccccgcttcatcgcagtgggcta -continued cgtggacgacacgcagttcgtgcggttcgacagcgacgccgcgagccagaggatggagccgcgggcgccgtggata gagcaggagggtccggagtattgggacgaggagacaGggaaAgtgaaggcccactcacagactCaccgagtggacc tggggaccctgcgcggctactacaaccagagcgaggccggttctcacaccGtccagaGgatgtatggctgcgacgt ggggtcggacTggcgcttcctccgcgggtaccaccagtacgcctacgacggcaaggattacatcgccctgaaagag gacctgcgctcttggaccgcggcggacatggcagctcagaccaccaagcacaagtgggaggcggcccatgTggcgg agcagtTgagagcctacctggagggcaCgtgcgtggagtggctccgcagatacctggagaacgggaaggagacgct gcagcgcacgg;

A*0247:
(SEQ ID NO: 61)
gctctcactccatgaggtatttcttcacatccgtgtcccggcccggccgcggggagccccgcttcatcgcagtggg ctacgtggacgacacgcagttcgtgcggttcgacagcgacgccgcgagccggaggatggagccgcgggcgccgtgg atagagcaggagggtccggagtattgggacggggagacacggaaagtgaaggcccactcacagaGtcaccgagtgg acctggggaccctgcgcggctactacaaccagagcgaggccggttctcacaccctccagaggatgtatggctgcga cgtggggtcggactggcgcttcctgcgcgggtaccaccagtacgcctacgacggcaaggattacatcgccctgaaa gaggacctgcgctcttggaccgcggcggacatggcagctcagaccaccaagcacaagtgggaggcggcccatgtgg cggagcagtggagagcctacctggagggcacgtgcgtggagtggctccgcagatacctggagaacgggaaggagac gctgcagcgcacgg;

A*0248:
(SEQ ID NO: 62)
gctctcactccatgaggtatttcttcacatccgtgtcccggcccggccgcggggagccccgcttcatcgcagtggg ctacgtggacgacacgcagttcgtgcggttcgacagcgacgccgcgagccagaggatggagccgcgggcgccgtgg atagagcaggaggggccggagtattgggacgaggagacaGggaaagtgaaggcccactcacagactgaccgagtgg acctggggaccctgcgcggctactacaaccagagcgaggccggttctcacaccgtccagaggatgtatggctgcga cgtggggtcggactggcgcttcctccgcgggtaccaccagtacgcctacgacggcaaggattacatcgccctgaaa gaggacctgcgctcttggaccgcggcggacatggcagctcagaccaccaagcAcaagtgggaggcggcccatgTgg cggagcagtTgagagCctacctggagggcaCgtgcgtggaGTggctccgcagatacctggagaacgggaaggagac gctgcagcgcacgg;

A*0249:
(SEQ ID NO: 63)
gctctcactccatgaggtatttcttcacatccgtgtcccggcccggccgcggggagccccgcttcatcgcAgtggg ctacgtggacgacacgcagttcgtgcggttcgacagcgacgccgcgagccagaggatggagccgcgggcgccgtgg atagagcaggagggtccggagtattgggacgGggagacacggaaAgtgaaggcccactcacagactCaccgagtgg acctggggaccctgcgcggctactacaaccagagcgaggccggttctcacaccGtccagaGgatgtatggctgcga cgtggggtcggacTggcgcttcctccgcgggtaccaccagTacgcctacgacggcaaggattacatcgccctgaaA gaggacctgcgctcttggaccgcggcggacatggcagctcagaCcaccaagcAcaagtgggaggcggcccatgTgg cggagcagcggagagcctacctggagggcaCgtgcgtggagTggctccgcagatacctggagaacgggaaggagac gctgcagcgcacgg;

A*0250:
(SEQ ID NO: 64)
gctcccactccatgaggtatttcttcacatccAtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtattgggacggggagacacggaaAgtgaaggcccactcacagactCaccgagtgg acctggggaccctgcgcggctactacaaccagagcgaggccggttctcacaccatccagaggatgtatggctgcga cgtggggccggacgggcgcttcctccgcgggtaccaccagtacgcctacgacggcaaggattacatcgccctgaaa -continued gaggacctgcgctcttggaccgcggcggacatggcagctcagaccaccaagcacaagtgggaggcggcccatgtgg cggagcagtggagagcctacctggagggcacgtgcgtggagtggctccgcagatacctggagaacgggaaggagac gctgcagcgcacgg;

A*0251: (SEQ ID NO: 65)

gctctcactccatgaggtatttctacacCtccgtgtcccggcccggccgcggggagccccgcttcatcgcagtggg ctacgtggacgacacgcagttcgtgcggttcgacagcgacgccgcgagccagaggatggagccgcgggcgccgtgg atagagcaggagggtccggagtattgggacggggagacacggaaagtgaaggcccactcacagactcaccgagtgg acctggggaccctgcgcggctactacaaccagagcgaggccggttctcacaccgtccagaggatgtatggctgcga cgtggggtcggactggcgcttcctccgcgggtaccaccagtacgcctacgacggcaaggattacatcgccctgaaa gaggacctgcgctcttggaccgcggcggacatggcagctcagaccaccaagcAcaagtgggaggcggcccGtgTgg cggagcagttgagagcctacctggagggcaCgtgcgtggagTggctccgcagatacctggagaacgggaaggagac gctgcagcgcacgg;

A*0252: (SEQ ID NO: 66)

gctctcactccatgaggtatttcttcacatccgtgtcccggcccggccgcggggagccccgcttcatcgcagtggg ctacgtggacgacacgcagttcgtgcggttcgacagcgacgccgcgagccagaggatggagccgcgggcgccgtgg atagagcaggagggtccggagtattgggacggggagacacggaaagtgaaggcccactcacagactcaccgagtgg acctggggaccctgcgcggctactacaaccagagcgaggccggttctcacaccgtccagaggatgtatggctgcga cgtggggtcggacgggcgcttcctccgcgggtatgaAcagcacgcctacgacggcaaggattacatcgccctgaaa gaggacctgcgctcttggaccgcggcggacatggcagctcagaccaccaagcAcaagtgggaggcggcccatgTgg cggagcagtTgagagcctacctggagggcacgtgcgtggagtggctccgcagatacctggagaacgggaaggagac gctgcagcgcacgg;

A*0254: (SEQ ID NO: 67)

gctctcactccatgaggtatttctacacCtccgtgtcccggcccggccgcggggagccccgcttcatcgcagtggg ctacgtggacgacacgcagttcgtgcggttcgacagcgacgccgcgagccagaggatggagccgcgggcgccgtgg atagagcaggagggtccggagtattgggacggggagacacggaaagtgaaggcccactcacagactcaccgagtgg acctggggaccctgcgcggctactacaaccagagcgaggccggttctcacaccGtccagaggatgtatggctgcga cgtggggtcggactggcgcttcctccgcgggtaccaccagtacgcctacgacggcaaggattacatcgccctgaaa gaggacctgcgctcttggaccgcggcggacatggcagctcagaccaccaagcAcaagtgggaggcggcccatgTgg cggagcagcAgagagcctacctggagggcaCgtgcgtggacgggctccgcagatacctggagaacgggaaggagac gctgcagcgcacgg;

A*0255: (SEQ ID NO: 68)

gctctcactccatgaggtatttcttcacatccgtgtcccggcccggccgcggggagccccgcttcatcgcagtggg ctacgtggacgacacgcagttcgtgcggttcgacagcgacgccgcgagccagaggatggagccgcgggcgccgtgg atagagcaggaggggccggagtattgggaccggaaCacacggaatgtgaaggcccactcacagactCaccgagtgg acctggggaccctgcgcggctactacaaccagagcgaggccggttctcacaccGtccagaGgatgtatggctgcga cgtggggtcggacTggcgcttcctccgcgggtaccaCcagTacgcctacgacggcaaggattacatcgccctgaaA gaggacctgcgctcttggaccgcggcggacatggcagctcagaCcaccaagcacaagtgggaggcggcccatgTgg cggagcagtTgagagcctacctggagggcaCgtgcgtggagTggctccgcagatacctggagaacgggaaggagac gctgcagcgcacgg;

A*0256:

(SEQ ID NO: 69)
atggccgtcatggcgccccgaaccctcgtcctgctactctcgggggcTctggccctgacccagacctgggcgggct ctcactccatgaggtatttcttcacatccgtgtcccggcccggccgcggggagccccgcttcatcgcagtgggcta cgtggacgacacgcagttcgtgcggttcgacagcgacgccgcgagccagaggatggagccgcgggcgccgtggata gagcaggagggtccggagtattgggaccaggagacacggaatgtgaaggcccaGtcacagactCaccgagtggacc tggggaccctgcgcggctactacaaccagagcgaggccggttctcacaccGtccagaGgatgtatggctgcgacgt ggggtcggacTggcgcttcctccgcgggtaccaccagtacgcctacgacggcaaggattacatcgccctgaaagag gacctgcgctcttggaccgcggcggacatggcagctcagaccaccaagcacaagtgggaggcggcccatgTggcgg agcagtTgagagcctacctggagggcaCgtgcgtggagtggctccgcagatacctggagaacgggaaggagacgct gcagcgcacggacgcccccaaaacgcatatgactcaccacgctgtctctgaccatgaagccaccctgaggtgctgg gccctgagcttctaccctgcggagatcacactgacctggcagcgggatggggaggaccagacccaggacacggagc tcgtggagaccaggcctgcaggggatggaaccttccagaagtgggcggctgtggtggtgccttctggacaggagca gagatacacctgccatgtgcagcatgagggtTtgcccaagccccthecclgagatggg;

A*0257:

(SEQ ID NO: 70)
atggccgtcatggcgccccgaaccctcgtcctgctactctcgggggcTctggccctgacccagacctgggcgggct ctcactccatgaggtatttctacacCtccgtgtcccggcccggccgcggggagccccgcttcatcgcagtgggcta cgtggacgacacgcagttcgtgcggttcgacagcgacgccgcgagccagaggatggagccgcgggcgccgtggata gagcaggagggtccggagtattgggacggggagacacggaaagtgaaggcccactcacagactcaccgagtggacc tggggaccctgcgcggctactacaaccagagcgaggccggttctcacaccCtccagatgatgtatggctgcgacgt ggggtcggacTggcgcttcctccgcgggtaccaccagtacgcctacgacggcaaggattacatcgccctgaaagag gacctgcgctcttggaccgcggcggacatggcagctcagaccaccaagcacaagtgggaggcggcccatgTggcgg agcagtTgagagcctacctggagggcaCgtgcgtggagtggctccgcagatacctggagaacgggaaggagacgct gcagcgcacggacgcccccaaaacgcatatgactcaccacgctgtctctgaccatgaagccaccctgaggtgctgg gccctgagcttctaccctgcggagatcacactgacctggcagcgggatggggaggaccagacccaggacacggagc tcgtggagaccaggcctgcaggggatggaaccttccagaagtgggcggctgtggtggtgccttctggacaggagca gagatacacctgccatgtgcagcatgagggtTtgcccaagccccthecclgagatgggag;

A*0258:

(SEQ ID NO: 71)
gctctcactccatgaggtatttcttcacatccgtgtcccggcccggccgcggggagccccgcttcatcgcagtggg ctacgtggacgacacgcagttcgtgcggttcgacagcgacgccgcgagccagaggatggagccgcgggcgccgtgg atagagcaggagggtccggagtattgggacggggagacacggaaagtgaaggcccactcacagactcaccgagtgg acctggggaccctgcgcggctactacaaccagagcgaggccggttctcacaccCtccagaGgatgtatggctgcga cgtggggtcggactggcgcttcctccgcgggtaccaccagtacgcctacgacggcaaggattacatcgccctgaaa gaggacctgcgctcttggaccgcggcggacatggcagctcagaccaccaagcAcaagtgggaggcggcccatgTgg cggagcagtTgagagCctacctggagggcaCgtgcgtggaGTggctccgcagatacctggagaacgggaaggagac gctgcagcgcacgg;

A*0259:

(SEQ ID NO: 72)
gctctcactccatgaggtatttcttcacatccgtgtcccggcccggccgcgAggagccccgcttcatcgcagtggg ctacgtggacgacacgcagttcgtgcggttcgacagcgacgccgcgagccagaggatggagccgcgggcgccgtgg atagagcaggagggtccggagtattgggacggggagacacggaaagtgaaggcccactcacagactcaccgagtgg acctggggaccctgcgcggctactacaaccagagcgaggccggttctcacaccgtccagaggatgtatggctgcga -continued cgtggggtcggactggcgcttcctccgcgggtaccaccagtacgcctacgacggcaaggattacatcgccctgaaa gaggacctgcgctcttggaccgcggcggacatggcagctcagaccaccaagcacaagtgggaggcggcccatgtgg cggagcagttgagagcctacctggagggcacgtgcgtggagtggctccgcagatacctggagaacgggaaggagac gctgcagcgcacggacgcccccaaaacgcatatgactcaccacgctgtctctgaccatgaagccaccctgaggtgc tgggccctgagcttctaccctgcggagatcacactgacctggcagcgggatggggaggaccagacccaggacacgg agctcgtggagaccaggcctgcaggggatggaacctccagaagtgggcggctgtggtggccttctggacagga gcagagatacacctgccatgtgcagcatgagggtttgcccaagcccctcaccctgagatggg;

A*0260:

(SEQ ID NO: 73)

gctctcactccatgaggtatttcttcacatccgtgtcccggcccggccgcggggagccccgcttcatcgcagtggg ctacgtggacgacacgcagttcgtgcggttcgacagcgacgccgcgagccagaggatggagccgcgggcgccgtgg atagagcaggagggtccggagtattgggacggggagacacggaaagtgaaggcccactcacagactcaccgagtgg acctggggaccctgcgcggctactacaaccagagcgaggccggttctcacaccgtccagaggatgtatggctgcga cgtggggtcggactggcgcttcctccgcgggtaccaccagtTcgcctacgacggcaaggattacatcgccctgaaa gaggacctgcgctcttggaccgcggcggacatggcagctcagaccaccaagcacaagtgggaggcggcccatgtgg cggagcagtTgagagcctacctggagggcacgtgcgtggagtggctccgcagatacctggagaacgggaaggagac gctgcagcgcacgg;

A*030101:

(SEQ ID NO: 74)

atggccgtcatggcgccccgaaccctcctcctgctactctcgggggccctggccctgacccagacctgggcgggct cccactccatgaggtatttcttcacatccgtgtcccggcccggccgcggggagccccgcttcatcgccgtgggcta cgtggacgacacgcagttcgtgcggttcgacagcgacgccgcgagccagaggatggagccgcgggcgccgtggata gagcaggaggggccggagtattgggaccaggagacacggaatgtgaaggcccaGtcacagactgaccgagtgGacc tggggaccctgcgcggctactacaaccagagcgaggccggttctcacaccatccagataatgtatggctgcgacgt ggggtcggacgggcgcttcctccgcgggtaccggcaggacgcctacgacggcaaggattacatcgccctgaacgag gacctgcgctcttggaccgcggcggacatggcggctcagatcaccaagcgcaagtgggaggcggcccatgAggcgg agcagTTgagagcctacctggaTggcacgtgcgtggagtggctccgcagatacctggagaacgggaaggagacgct gcagcgcacggaccccccaagacacatatgacccaccacccatctctgaccatgaggccaccctgaggtgctgg gccctgggcttctaccctgcggagatcacactgacctggcagcgggatggggaggaccagacccaggacacggagc tcgtggagaccaggcctgcaggggatggaaccttccagaagtgggcggctgtggtggccttctggagaggagca gagatacacctgccatgtgcagcatgagggtctgcccaagcccctcaccctgagatgggag;

A*030102:

(SEQ ID NO: 75)

gctcccactccatgaggtatttcttcacatccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtattgggaccaggagacacggaatgtgaaggcccaGtcacagactgaccgagtgG acctggggaccctgcgcggctactacaaccagagcgaggccggttctcacaccatccagataatgtatggctgcga cgtggggtcggacgggcgcttcctccgcgggtaccggcaggacgcctacgacggcaaggattacatcgccctgaac gaggacctgcgctcttggaccgcggcggacatggcggctcagatcaccaagcgcaagtgggaggcggcccatgAgg cggagcagcTgagagcctacctggaTggcacgtgcgtggagtggctccgcagatacctggagaacgggaaggagac gctgcagcgcacgg;

A*030103:

(SEQ ID NO: 76)

gctcccactccatgaggtatttcttcacatccgtgtcccggcccggccgcggggagccccgcttcatcgccgtggg ctacgtggacgacacgcagttcgtgcggttcgacagcgacgccgcgagccagaggatggagccgcgggcgccgtgg -continued atagagcaggagggTccggagtattgggaccaggagacacggaatgtgaaggcccaGtcacagactgaccgagtgG acctggggaccctgcgcggctactacaaccagagcgaggccggttctcacaccatccagataatgtatggctgcga cgtggggtcggacgggcgcttcctccgcgggtaccggcaggacgcctacgacggcaaggattacatcgccctgaac gaggacctgcgctcttggaccgcggcggacatggcggctcagatcaccaagcgcaagtgggaggcggcccatgAgg cggagcagTTgagagcctacctggaTggcacgtgcgtggagtggctccgcagatacctggagaacgggaaggagac gctgcagcgcacgg;

A*0302:
(SEQ ID NO: 77)
atggccgtcatggcgccccgaaccctcctcctgctactctcgggggccctggccctgacccagacctgggcgggct cccactccatgaggtatttcttcacatccgtgtcccggcccggccgcggggagccccgcttcatcgccgtgggcta cgtggacgacacgcagttcgtgcggttcgacagcgacgccgcgagccagaggatggagccgcgggcgccgtggata gagcaggaggggccggagtattgggaccaggagacacggaatgtgaaggcccagtcacagactgaccgagtggacc tggggaccctgcgcggctactacaaccagagcgaggccggttctcacaccatccagataatgtatggctgcgacgt ggggtcggacgggcgcttcctccgcgggtaccggcaggacgcctacgacggcaaggattacatcgccctgaacgag gacctgcgctcttggaccgcggcggacatggcggctcagatcaccaagcgcaagtgggaggcggcccatgtggcgg agcagcAgagagcctacctggaTggcacgtgcgtggagtggctccgcagatacctggagaacgggaaggagacgct gcagcgcacggaccccccaagacacatatgacccaccaccccatctctgaccatgaggccaccctgaggtgctgg gccctgggcttctaccctgcggagatcacactgacctggcagcgggatggggaggaccagacccaggacacggagc tcgtggagaccaggcctgcaggggatggaaccttccagaagtgggcggctgtggtggtgccttctggagaggagca gagatacacctgccatgtgcagcatgagggtctgcccaagcccctcaccctgagatgggag;

A*0304:
(SEQ ID NO: 78)
atggccgtcatggcgccccgaaccctcctcctgctactctcgggggccctggccctgacccagacctgggcgggct cccactccatgaggtatttcttcacatccgtgtcccggcccggccgcggggagccccgcttcatcgccgtgggcta cgtggacgacacgcagttcgtgcggttcgacagcgacgccgcgagccagaggatggagccgcgggcgccgtggata gagcaggaggggccggagtattgggaccaggagacacggaatgtgaaggcccagtcacagactgaccgagtggacc tggggaccctgcgcggctactacaaccagagcgaggccggttctcacaccatccagataatgtatggctgcgacgt ggggtcggacgggcgcttcctccgcgggtaccggcaggacgcctacgacggcaaggattacatcgccctgaacgag gacctgcgctcttggaccgcggcggacatggcggctcagatcaccaagcgcaagtgggaggcggcccatgaggcgg agcagttgagagcctacctggaTggcacgtgcgtggagtggctccgcagatacctggagaacCggaaggagacgct gcagcgcacggaccccccaagacacatatgacccaccaccccatctctgaccatgaggccaccctgaggtgctgg gccctgggcttctaccctgcggagatcacactgacctggcagcgggatggggaggaccagacccaggacacggagc tcgtggagaccaggcctgcaggggatggaaccttccagaagtgggcggctgtggtggtgccttctggagaggagca gagatacacctgccatgtgcagcatgagggtctgcccaagcccctcaccctgagatgggag;

A*0305:
(SEQ ID NO: 79)
tctcgggggccctggccctgacccagacctgggcgggctcccactccatgaggtatttcttcacatccgtgtcccg gcccggccgcggggagccccgcttcatcgccgtgggctacgtggacgacacgcagttcgtgcggttcgacagcgac gccgcgagccagaggatggagccgcgggcgccgtggatagagcaggaggggccggagtattgggaccaggagacac ggaatgtgaaggcccaGtcacagactgaccgagtgGacctggggaccctgcgcggctactacaaccagagcgaggC cggttctcacaccatccagataatgtatggctgcgacgtggggtcggacgggcgcttcctccgcgggtaccggcag gacgcctacgacggcaaggattacatcgccctgaacgaggacctgcgctcttggaccgcggcggacatggcGgctc agatcaccaagcgcaagtgggaggcggcccatgAggcggagcagTTgagagcctacctggagggcaCgtgcgtgga -continued gtggctccgcagatacctggagaacgggaaggagacgctgcagcgcacggacccccccaagacacatatgacccac cacccatctctgaccatgaggccaccctgaggtgctgggccctgggcttctaccctgcggagatcacactgacct ggcagcgggatggggaggaccagacccaggacacggagctcgtggagaccaggcctgcaggggatggaaccttcca gaagtgggcggctgtggtggtgccttctggagaggagcagagatacacctgccatgtgcagcatgagggtctgccc aagcccctcaccctgagatggg;

A*0306:
(SEQ ID NO: 80)
gctcccactccatgaggtatttcttcacatccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtatgggaccaggagacacggaatgtgaaggcccagtcacagactgaccgagtgg acctggggaccctgcgcggctactacaaccagagcgaggccggttctcacaccatccagataatgtatggctgcga cgtggggtcggacgggcgcttcctccgcgggtaccggcaggacgcctacgacggcaaggattacatcgccctgaac gaggacctgcgctcttggaccgcggcggacatggcggctcagatcaccaagcgcaagtgggaggcggcccatgagg cggagcagttgagagcctacctggatgCcacgtgcgtggagtggctccgcagatacctggagaacgggaaggagac gctgcagcgcacgg;

A*0307:
(SEQ ID NO: 81)
gctcccactccatgaggtatttcttcacatccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtatgggaccaggagacacggaatgtgaaggcccagtcacagactgaccgagtgg acctggggaccctgcgcggctactacaaccagagcgaggccggttctcacaccatccagataatgtatggctgcga cgtggggtcggacgggcgcttcctccgcgggtaccggcaggacgcctacgacggcaaggattacatcgccctgaac gaggacctgcgctcttggaccgcggcggacatggcggctcagatcaccaagcgcaagtgggaggcggcccatgTgg cggagcagTTgagagcctacctggaTggcacgtgcgtggagtggctccgcagatacctggagaacgggaaggagac gctgcagcgcacgg;

A*0308:
(SEQ ID NO: 82)
gctcccactccatgaggtatttcttcacatccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtatgggaccaggagacacggaatgtgaaggcccactcacagactgaccgagtgG acctggggaccctgcgcggctactacaaccagagcgaggccggttctcacaccatccagataatgtatggctgcga cgtggggtcggacgggcgcttcctccgcgggtaccggcaggacgcctacgacggcaaggattacatcgccctgaac gaggacctgcgctcttggaccgcggcggacatggcggctcagatcaccaagcgcaagtgggaggcggcccatgAgg cggagcagTTgagagcctacctggaTggcacgtgcgtggagtggctccgcagatacctggagaacgggaaggagac gctgcagcgcacgg;

A*0309:
(SEQ ID NO: 83)
gctcccactccatgaggtatttcttcacatccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtatgggaccaggagacacggaatgtgaaggcccagtcacagactCaccgagtgG acctggggaccctgcgcggctactacaaccagagcgaggccggttctcacaccatccagataatgtatggctgcga cgtggggtcggacgggcgcttcctccgcgggtaccggcaggacgcctacgacggcaaggattacatcgccctgaac gaggacctgcgctcttggaccgcggcggacatggcggctcagatcaccaagcgcaagtgggaggcggcccatgAgg cggagcagTTgagagcctacctggaTggcacgtgcgtggagtggctccgcagatacctggagaacgggaaggagac gctgcagcgcacgg;

-continued

A*0310:
(SEQ ID NO: 84)
gctcccactccatgaggtatttcttcacatccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtattgggaccaggagacacggaatgtgaaggcccagtcacagactgaccgagtgG acctggggaccctgcgcggctactacaaccagagcgaggccggttctcacaccatccagataatgtatggctgcga cgtggggTcggacgggcgcttcctccgcgggtaccggcaggacgcctacgacggcaaggattacatcgccctgaac gaggacctgcgctcttggaccgcggcggacatggcGgctcagatcaccaagcgcaagtgggaggcggcccatgTgg cggagcagcAgagagcctacctggagggcaCgtgcgtggaGTggctccgcagatacctggagaacgggaaggagac gctgcagcgcacgg;

A*110101:
(SEQ ID NO: 85)
atggccgtcatggcgccccgaaccctcctcctgctactctcgggggccctggccctgacccagacctgggcgggct cccactccatgaggtatttctacacCtccgtgtcccggcccggccgcggggagccccgcttcatcgccgtgggcta cgtggacgacacgcagttcgtgcggttcgacagcgacgccgcgagccagaggatggagccgcgggcgccgtggata gagcaggaggggccggagtattgggaccaggagacacggaatgtgaaggcccaGtcacagactgaccgagtgGacc tggggaccctgcgcggctactacaaccagagcgaggacggttctcacaccatccagataatgtatggctgcgacgt ggggccggacgggcgcttcctccgcgggtaccggcaggacgcctacgacggcaaggattacatcgccctgaacgag gacctgcgctcttggaccgcggcggacatggcagctcagatcaccaagcgcaagtgggaggcggcccatgcggcgg agcagcAgagagcctacctggagggccggtgcgtggaGTggctccgcagatacctggagaacgggaaggagacgct gcagcgcacggaccccccaagacacatatgacccaccacccatctctgaccatgaggccaccctgaggtgctgg gccctgggcttctaccctgcggagatcacactgacctggcagcgggatggggaggaccagacccaggacacggagc tcgtggagaccaggcctgcaggggatggaaccttccagaagtgggcggctgtggtggtgccttctggagaggagca gagatacacctgccatgtgcagcatgagggtctgcccaagcccctcaccctgagatgggag;

A*110102:
(SEQ ID NO: 86)
gctcccactccatgaggtatttctacacctccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtattgggaccaggagacacggaatgtgaaggcccagtcacagactgaccgagtgg acctggggaccctgcgcggctactacaaccagagcgaggacggttctcacaccatccagataatgtatggctgcga cgtggggccggacgggcgcttcctccgcgggtaccggcaggacgcctacgacggcaaggattacatcgccctgaac gaggacctgcgctcttggaccgcggcAgacatggcagctcagatcaccaagcgcaagtgggaggcggcccatgcgg cggagcagcagagagcctacctggagggccggtgcgtggagtggctccgcagatacctggagaacgggaaggagac gctgcagcgcacggaccccccaagacacatatgacccaccacccatctctgaccatgaggccaccctgaggtgc tgggccctgggcttctaccctgcggagatcacactgacctggcagcgggatggggaggaccagacccaggacacgg agctcgtggagaccaggcctgcaggggatggaaccttccagaagtgggcggctgtggtggtgccttctggagagga gcagagatacacctgccatgtgcagcatgagggtctgcccaagcccctcaccctgagatggg;

A*1102:
(SEQ ID NO: 87)
atggccgtcatggcgccccgaaccctcctcctgctactctcgggggccctggccctgacccagacctgggcgggct cccactccatgaggtatttctacacctccgtgtcccggcccggccgcggggAagccccgcttcatcgccgtgggcta cgtggacgacacgcagttcgtgcggttcgacagcgacgccgcgagccagaggatggagccgcgggcgccgtggata gagcaggaggggccggagtattgggaccaggagacacggaatgtgaaggcccagtcacagactgaccgagtggacc tggggaccctgcgcggctactacaaccagagcgaggacggttctcacaccatccagataatgtatggctgcgacgt ggggccggacgggcgcttcctccgcgggtaccggcaggacgcctacgacggcaaggattacatcgccctgaacgag gacctgcgctcttggaccgcggcggacatggcagctcagatcaccaagcgcaagtgggaggcggcccatgcggcgg agcagcagagagcctacctggagggccggtgcgtggagtggctccgcagatacctggagaacgggaaggagacgct gcagcgcacggacccccccaagacacatatgacccaccaccccatctctgaccatgaggccaccctgaggtgctgg gccctgggcttctaccctgcggagatcacactgacctggcagcgggatggggaggaccagacccaggacacggagc tcgtggagaccaggcctgcaggggatggaaccttccagaagtgggcggctgtggtggtgccttctggagaggagca gagatacacctgccatgtgcagcatgagggtctgcccaagcccctcaccctgagatggg;

A*1103:
(SEQ ID NO: 88)
gctcccactccatgaggtatttctacacctccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtattgggaccaggagacacggaatgtgaaggcccagtcacagactgaccgagtgg acctggggaccctgcgcggctactacaaccagagcgaggacggttctcacaccatccagataatgtatggctgcga cgtggggccggacgggcgcttcctccgcgggtaccggcaggacgcctacgacggcaaggattacatcgccctgaac gaggacctgcgctcttggaccgcggcggacatggcagctcagatcaccaagcgcaagtgggaggcggcccGtgAgg cggagcagcAgagagcctacctggagggccggtgcgtggagtggctccgcagatacctggagaacgggaaggagac gctgcagcgcacgg;

A*1104:
(SEQ ID NO: 89)
atggccgtcatggcgccccgaaccctcctcctgctactctcgggggccctggccctgacccagacctgggcgggct cccactccatgaggtatttctacacCtccgtgtcccggcccggccgcggggagccccgcttcatcgccgtgggcta cgtggacgacacgcagttcgtgcggttcgacagcgacgccgcgagccagaggatggagccgcgggcgccgtggata gagcaggaggggccggagtattgggaccaggagacacggaatgtgaaggcccaGtcacagactgaccgagtgGacc tggggaccctgcgcggctactacaaccagagcgaggacggttctcacaccatccagataatgtatggctgcgacgt ggggccggacgggcgcttcctccgcgggtaccggcaggacgcctacgacggcaaggattacatcgccctgaacgag gacctgcgctcttggaccgcggcggacatggcagctcagatcaccaagcgcaagtgggaggcggcccatgcggcgg agcagcAgagagcctacctggagggcaCgtgcgtggaGTggctccgcagatacctggagaacgggaaggagacgct gcagcgcacggacccccccaagacacatatgacccaccaccccatctctgaccatgaggccaccctgaggtgctgg gccctgggcttctaccctgcggagatcacactgacctggcagcgggatggggaggaccagacccaggacacggagc tcgtggagaccaggcctgcaggggatggaaccttccagaagtgggcggctgtggtggtgccttctggagaggagca gagatacacctgccatgtgcagcatgagggtctgcccaagcccctcaccctgagatgggag;

A*1105:
(SEQ ID NO: 90)
atggccgtcatggcgccccgaaccctcctcctgctactctcgggggccctggccctgacccagacctgggcgggct cccactccatgaggtatttctacacctccgtgtcccggcccggccgcggggagccccgcttcatcgccgtgggcta cgtggacgacacgcagttcgtgcggttcgacagcgacgccgcgagccagaggatggagccgcgggcgccgtggata gagcaggaggggccggagtattgggaccaggagacacggaatgtgaaggcccagtcacagactgaccgagtggacc tggggaccctgcgcggctactacaaccagagcgaggacggttctcacaccatccagataatgtatggctgcgacgt ggggccggacgggcgcttcctccgcgggtaccggcaggacgcctacgacggcaaggattacatcgccctgaacgag gacctgcgctcttggaccgcggcggacatggcagctcagatcaccGagcgcaagtgggaggcggcccatgcggcgg agcagcagagagcctacctggagggccggtgcgtggagtggctccgcagatacctggagaacgggaaggagacgct gcagcgcacggacccccccaagacacatatgacccaccaccccatctctgaccatgaggccaccctgaggtgctgg gccctgggcttctaccctgcggagatcacactgacctggcagcgggatggggaggaccagacccaggacacggagc

A*1106:

(SEQ ID NO: 91)

gctcccactccatgaggtatttctacacctccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtattgggaccaggagacacggaatgtgaaggcccaGtcacagactCaccgagtgG acctggggaccctgcgcggctactacaaccagagcgaggacggttctcacaccatccagataatgtatggctgcga cgtggggccggacgggcgcttcctccgcgggtaccggcaggacgcctacgacggcaaggattacatcgccctgaac gaggacctgcgctcttggaccgcggcggacatggcagctcagatcaccaagcgcaagtgggaggcggcccatgcgg cggagcagcAgagagcctacctggagggccggtgcgtggaGTggctccgcagatacctggagaacgggaaggagac gctgcagcgcacgg;

A*1107:

(SEQ ID NO: 92)

atggccgtcatggcgccccgaaccctcctcctgctactctcgggggccctggccctgaccagacctgggcgggct cccactccatgaggtatttctacacctccgtgtcccggcccggccgcggggagccccgcttcatcgccgtgggcta cgtggacgacacgcagttcgtgcggttcgacagcgacgccgcgagccagaggatggagccgcgggcgccgtggata gagcaggaggggccggagtattgggaccaggagacacggaatgtgaaggcccagtcacagactgaccgagtggacc tggggaccctgcgcggctactacaaccagagcgaggacggttctcacaccatccagataatgtatggctgcgacgt ggggccggacgggcgcttActccgcgggtaccggcaggacgcctacgacggcaaggattacatcgccctgaacgag gacctgcgctcttggaccgcggcggacatggcagctcagatcaccaagcgcaagtgggaggcggcccatgcggcgg agcagcagagagcctacctggagggccggtgcgtggagtggctccgcagatacctggagaacgggaaggagacgct gcagcgcacggaccccccaagacacatatgacccaccacccatctctgaccatgaggccaccctgaggtgctgg gccctgggcttctaccctgcggagatcacactgacctggcagcgggatggggaggaccagacccaggacacggagc tcgtggagaccaggcctgcaggggatggaaccttccagaagtgggcggctgtggtggtgccttctggagaggagca gagatacacctgccatgtgcagcatgagggtctgcccaagcccctcaccctgagatgggag;

A*1108:

(SEQ ID NO: 93)

gctcccactccatgaggtatttctacacCtccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtattgggaccaggagacacggaatgtgaaggcccaGtcacagactgaccgagtgG acctggggaccctgcgcggctactacaaccagagcgaggacggttctcacaccatccagataatgtatggctgcga cgtggggccggacgggcgcttcctccgcgggtaccggcaggacgcctacgacggcaaggattacatcgccctgaac gaggacctgcgctcttggaccgcggcggacatggcagctcagatcaccaagcgcaagtgggaggcggcccatgAgg cggagcagcggagagcctacctggagggccggtgcgtggagtggctccgcagatacctggagaacgggaaggagac gctgcagcgcacgg;

A*1109:

(SEQ ID NO: 94)

gctcccactccatgaggtatttctacacctccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtattgggaccaggagacacggaatgtgaaggcccagtcacagactgaccgagtgg acctggggaccctgcgcggctactacaaccagagcgaggacggttctcacaccatccagataatgtatggctgcga cgtggggccggacgggcgcttcctccgcgggtaccggcaggacgcctacgacggcaaggattacatcgccctgaac gaggacctgcgctcttggaccgcggcggacatggcagctcagatcaccaagcgcaagtgggaggcggcccatgcgg -continued cggagcagcagagagcctacctgCagggccggtgcgtggagtggctccgcagatacctggagaacgggaaggagac gctgcagcgcacgg;

A*1110:

(SEQ ID NO: 95)
gctcccactccatgaggtatttctacacCtccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtattgggaccggaaCacacggaatgtgaaggcccagtcacagactgaccgagtgG acctggggaccctgcgcggctactacaaccagagcgaggacggttctcacaccatccagataatgtatggctgcga cgtggggccggacgggcgcttcctccgcgggtaccggcaggacgcctacgacggcaaggattacatcgccctgaac gaggacctgcgctcttggaccgcggcggacatggcagctcagatcaccaagcgcaagtgggaggcggcccatgcgg cggagcagcAgagagcctacctggagggccggtgcgtggagTggctccgcagatacctggagaacgggaaggagac gctgcagcgcacgg;

A*1111:

(SEQ ID NO: 96)
gctcccactccatgaggtatttctacacctccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtattgggaccTgcagacacggaatgtgaaggcccagtcacagactgaccgagtgG acctggggaccctgcgcggctactacaaccagagcgaggacggttctcacaccatccagataatgtatggctgcga cgtggggccggacgggcgcttcctccgcgggtaccggcaggacgcctacgacggcaaggattacatcgccctgaac gaggacctgcgctcttggaccgcggcggacatggcagctcagatcaccaagcgcaagtgggaggcggcccatgcgg cggagcagcAgagagcctacctggagggccggtgcgtggagTggctccgcagatacctggagaacgggaaggagac gctgcagcgcacgg;

A*1112:

(SEQ ID NO: 97)
ggctcccactccatgaggtatttctacacCtccgtgtcccggcccggccgcggggagccccgcttcatcgccgtgg gctacgtggacgacacgcagttcgtgcggttcgacagcgacgccgcgagccagaggatggagccgcgggcgccgtg gatagagcaggaggggccggagtattgggaccaggagacacggaatgtgaaggcccaGtcacagactgaccgagtg GacctggggaccctgcgcggctactacaaccagagcgaggCcggttctcacaccatccagataatgtatggctgcg acgtggggccggacgggcgcttcctccgcgggtaccggcaggacgcctacgacggcaaggattacatcgccctgaa cgaggacctgcgctcttggaccgcggcggacatggcagctcagatcaccaagcgcaagtgggaggcggcccatgcg gcggagcagcAgagagcctacctggagggccggtgcgtggaGTggctccgcagatacctggagaacgggaaggaga cgctgcagcgcacg;

A*1113:

(SEQ ID NO: 98)
gctcccactccatgaggtatttctacacctccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtattgggaccaggagacacggaatgtgaaggcccagtcacagactgaccgagtgg acctggggaccctgcgcggctactacaaccagagcgaggacggttctcacaccatccagataatgtatggctgcga cgtggggccggacgggcgcttcctccgcgggtaccggcaggacgcctacgacggcaaggattacatcgccctgaac gaggacctgcgctcttggaccgcggcggacatggcagctcagatcaccaGgcgcaagtgggaggcggcccatgcgg cggagcagcagagagcctacctggagggccggtgcgtggagtggctccgcagatacctggagaacgggaaggagac gctgcagcgcacgg;

A*1114:

(SEQ ID NO: 99)
ccctggccctgacccagacctgggcgggctcccactccatgaggtatttctacacctccgtgtcccggcccggccg cgggAagccccgcttcatcgccgtgggctacgtggacgacacgcagttcgtgcggttcgacagcgacgccgcgagc cagaggatggagccgcgggcgccgtggatagagcaggaggggccggagtattgggaccaggagacacggaatgtga aggcccagtcacagactgaccgagtggacctggggaccctgcgcggctactacaaccagagcgaggacggttctca caccatccagataatgtatggctgcgacgtggggccggacgggcgcttcctccgcgggtaccggcaggacgcctac gacggcaaggattacatcgccctgaacgaggacctgcgctcttggaccgcggcggacatggcagctcagatcacca agcgcaagtgggaggcggcccgtcGggcggagcagcagagagcctacctggagggccggtgcgtggagtggctccg cagatacctggagaacgggaaggagacgctgcagcgcacgg;

A*2301: (SEQ ID NO: 100)

atggccgtcatggcgccccgaaccctcgtcctgctactctcgggggccctggccctgacccagacctgggcaggct cccactccatgaggtatttctccacatccgtgtcccggcccggccgcggggagccccgcttcatcgccgtgggcta cgtggacgacacgcagttcgtgcggttcgacagcgacgccgcgagccagaggatggagccgcgggcgccgtggata gagcaggaggggccggagtatgggacgaggagacagggaaaGtgaaggcccactcacagactgaccgagagaacc tgcggatcgcgctccgctactacaaccagagcgaggccggttctcacaccctccagatgatgtttggctgcgacgt ggggtcggacgggcgcttcctccgcgggtaccaccagtacgcctacgacggcaaggattacatcgccctgaaagag gacctgcgctcttggaccgcggcggacatggcggctcagatcacccagcgcaagtgggaggcggcccgtgtggcgg agcagtTgagagCctacctggagggcacgtgcgtggacgggctccgcagatacctggagaacgggaaggagacgct gcagcgcacggaccccccaagacacatatgacccaccaccccatctctgaccatgaggccactctgagatgctgg gccctgggcttctaccctgcggagatcacactgacctggcagcgggatggggaggaccagacccaggacacggagc ttgtggagaccaggcctgcaggggatggaaccttccagaagtgggcAgctgtggtggtaccttctggagaggagca gagatacacctgccatgtgcagcatgagggtctgcccaagcccctcaccctgagatgggag;

A*2302: (SEQ ID NO: 101)
gctcccactccatgaggtatttctccacatccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtattgggacgaggagacaGggaaagtgaaggcccactcacagactgaccgagaga acctgcggatcgcgctccgctactacaaccagagcgaggccggttctcacaccctccagatgatgtttggctgcga cgtggggtcggacgggcgcttcctccgcgggtaccaccagtacgcctacgacggcaaggattacatcgccctgaaA gaggacctgcgctcttggaccgcggcggacatggcggctcagatcacccagcgcaagtgggaggcggcccGtgTgg cggagcagTggagagCctacctggagggcaCgtgcgtggacgggctccgcagatacctggagaacgggaaggagac gctgcagcgcacgg;

A*2303: (SEQ ID NO: 102)
gctcccactccatgaggtatttctccacatccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtattgggacgaggagacagggaaagtgaaggcccactcacagactgaccgagaga acctgcggatcgcgctccgctactacaaccagagcgaggccggttctcacaccctccagatgatgtttggctgcga cgtggggtcggacgggcgcttcctccgcgggtaccaccagTacgcctacgacggcaaggattacatcgccTtgaac gaggacctgcgctcttggaccgcggcggacatggcggctcagatcacccagcgcaagtgggaggcggcccGtgtgg cggagcagtTgagagcctacctggagggcacgtgcgtggacgggctccgcagatacctggagaacgggaaggagac gctgcagcgcacgg;

A*2304: (SEQ ID NO: 103)
gctcccactccatgaggtatttctccacatccgtgtcccggcccggccgcggggagccccgcttcatcgccgtggg ctacgtggacgacacgcagttcgtgcggttcgacagcgacgccgcgagccagaggatggagccgcgggcgccgtgg -continued atagagcaggaggggccggagtattgggacgaggagacaGggaaagtgaaggcccactcacagactgaccgagaga
acctgcggatcgcgctccgctactacaaccagagcgaggccggttctcacacccctccagatgatgtttggctgcga
cgtggggtcggacgggcgcttcctccgcgggtaccaccagtacgcctacgacggcaaggattacatcgccctgaaA
gaggacctgcgctcttggaccgcggcggacatggcggctcagatcacccagcgcaagtgggaggcggcccGtgTgg
cggagcagtTgagagCctacctggagggcaCgtgcgtggaGTggctccgcagatacctggagaacgggaaggagac
gctgcagcgcacgg;

A*2305:
(SEQ ID NO: 104)
gctcccactccatgaggtGtttctccacatccgtgtcccggcccggccgcggggagccccgcttcatcgccgtggg
ctacgtggacgacacgcagttcgtgcggttcgacagcgacgccgcgagccagaggatggagccgcgggcgccgtgg
atagagcaggaggggccggagtattgggacgaggagacagggaaagtgaaggcccactcacagactgaccgagaga
acctgcggatcgcgctccgctactacaaccagagcgaggccggttctcacacccctccagatgatgtttggctgcga
cgtggggtcggacgggcgcttcctccgcgggtaccaccagtacgcctacgacggcaaggattacatcgccctgaaa
gaggacctgcgctcttggaccgcggcggacatggcggctcagatcacccagcgcaagtgggaggcggcccgtgtgg
cggagcagtTgagagcctacctggagggcacgtgcgtggacgggctccgcagatacctggagaacgggaaggagac
gctgcagcgcacgg;

A*2306:
(SEQ ID NO: 105)
atggccgtcatggcgccccgaaccctcgtcctgctactctcgggggccctggccctgacccagacctgggcaggct
cccactccatgaggtatttctccacatccgtgtcccggcccggccgcggggagccccgcttcatcgccgtgggcta
cgtggacgacacgcagttcgtgcggttcgacagcgacgccgcgagccagaggatggagccgcgggcgccgtggata
gagcaggaggggccggagtattgggacgaggagacagggaaagtgaaggcccactcacagactgaccgagagaacc
tgcggatcgcgctccgctactacaacGagagcgaggccggttctcacacccctccagatgatgtttggctgcgacgt
ggggtcggacgggcgcttcctccgcgggtaccaccagtacgcctacgacggcaaggattacatcgccctgaaagag
gacctgcgctcttggaccgcggcggacatggcggctcagatcacccagcgcaagtgggaggcggcccgtgtggcgg
agcagttgagagcctacctggagggcacgtgcgtggacgggctccgcagatacctggagaacgggaaggagacgct
gcagcgcacggaccccccaagacacatatgacccaccacccatctctgaccatgaggccactctgagatgctgg
gccctgggcttctaccctgcggagatcacactgacctggcagcgggatggggaggaccagacccaggacacggagc
ttgtggagaccaggcctgcaggggatggaaccttccagaagtgggcagctgtggtggtaccttctggagaggagca
gagatacacctgccatgtgcagcatgagggtctgcccaagcccctcaccctgagatgggag;

A*2309:
(SEQ ID NO: 106)
atggccgtcatggcgccccgaaccctcgtcctgctactctcgggggccctggccctgacccagacctgggcaggct
cccactccatgaggtatttctccacatccgtgtcccggcccggccgcggggagccccgcttcatcgccgtgggcta
cgtggacgacacgcagttcgtgcggttcgacagcgacgccgcgagccagaggatggagccgcgggcgccgtggata
gagcaggaggggccggagtattgggaccaggagacacggaatatgaaggcccactcacagactgaccgagagaacc
tgcggatcgcgctccgctactacaaccagagcgaggccggttctcacacccctccagatgatgtttggctgcgacgt
ggggtcggacgggcgcttcctccgcgggtaccaccagtacgcctacgacggcaaggattacatcgccctgaaagag
gacctgcgctcttggaccgcggcggacatggcggctcagatcacccagcgcaagtgggaggcggcccgtgtggcgg
agcagtTgagagCctacctggagggcacgtgcgtggacgggctccgcagatacctggagaacgggaaggagacgct
gcagcgcacggaccccccaagacacatatgacccaccacccatctctgaccatgaggccactctgagatgctgg
gccctgggcttctaccctgcggagatcacactgacctggcagcgggatggggaggaccagacccaggacacggagc
ttgtggagaccaggcctgcaggggatggaaccttccagaagtgggcAgctgtggtggtaccttctggagaggagca
gagatacacctgccatgtgcagcatgagggtctgcccaagcccctcaccctgagatgggag;

A*240201:

(SEQ ID NO: 107)

atggccgtcatggcgccccgaaccctcgtcctgctactctcgggggccctggccctgacccagacctgggcaggct cccactccatgaggtatttctccacatccgtgtcccggcccggccgcggggagccccgcttcatcgccgtgggcta cgtggacgacacgcagttcgtgcggttcgacagcgacgccgcgagccagaggatggagccgcgggcgccgtggata gagcaggaggggccggagtattgggacgaggagacaGggaaagtgaaggcccactcacagactgaccgagagaacc tgcggatcgcgctcCgctactacaaccagagcgaggccggttctcacaccctccagatgatgtttggctgcgacgt ggggtcggacgggcgcttcctccgcgggtaccaccagtacgcctacgacggcaaggattacatcgccctgaaagag gacctgcgctcttggaccgcggcggacatggcggctcagatcaccaagcgcaagtgggaggcggcccatgtggcgg agcagcAgagagCctacctggagggcacgtgcgtggacgggctccgcagatacctggagaacgggaaggagacgct gcagcgcacggaccccccaagacacatatgacccaccacccatctctgaccatgaggccactctgagatgctgg gccctgggcttctaccctgcggagatcacactgacctggcagcgggatggggaggaccagacccaggacacggagc ttgtggagaccaggcctgcaggggatggaaccttccagaagtgggcAgctgtggtggtaccttctggagaggagca gagatacacctgccatgtgcagcatgagggtctgcccaagcccctcaccctgagatgggag;

A*240202:

(SEQ ID NO: 108)

gctcccactccatgaggtatttctccacatccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtattgggacgaggagacaGggaaagtgaaggcccactcacagactgaccgagaga acctgcggatcgcgctcCgctactacaaccagagcgaggCcggttctcacaccctccagatgatgtTtggctgcga cgtggggTcggacgggcgcttcctccgcgggtaccaccagTacgcctacgacggcaaggattacatcgccctgaaA gaggacctgcgctcttggaccgcggcggacatggcagctcagatcaccaagcgcaagtgggaggcggcccatgtgg cggagcagcAgagagCctacctggagggcaCgtgcgtggacgggctccgcagatacctggagaacgggaaggagac gctgcagcgcacgg;

A*240203:

(SEQ ID NO: 109)

atggccgtcatggcgccccgaaccctcgtcctgctactctcgggggccctggccctgacccagacctgggcaggct cccactccatgaggtatttctccacatccgtgtcccggcccggccgcggggagccccgcttcatcgccgtgggcta cgtggacgacacgcagttcgtgcggttcgacagcgacgccgcgagccagaggatggagccgcgggcgccgtggata gagcaggaggggccggagtattgggacgaggagacagggaaagtgaaggcccactcacagactgaccgagagaacc tgcggatcgcgctccgctactacaaccagagcgaggccggttctcacaccctccagatgatgtttggctgcgacgt ggggtcggacgggcgcttcctccgcgggtaccaccagtacgcctacgacggcaaggattacatcgccctgaaagag gacctgcgctcttggaccgcggcggacatggcggctcagatcaccaagcgcaagtgggaggcggcccatgtggcgg agcagcagagagcctacctggagggcacgtgcgtggacgggctccgcagatacctggagaacgggaaggagacgct gcagcgcacggaccccccaagacacatatgacccaccacccatctctgaccatgaggccactctgagatgctgg gccctgggcttctaccctgcAgagatcacactgacctggcagcgggatggggaggaccagacccaggacacggagc ttgtggagaccaggcctgcaggggatggaaccttccagaagtgggcagctgtggtggtaccttctggagaggagca gagatacacctgccatgtgcagcatgagggtctgcccaagcccctcaccctgagatgggag;

A*240204:

(SEQ ID NO: 110)

gctcccactccatgaggtatttctccacatccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtattgggacgaggagacagggaaagtgaaggcccactcacagactgaccgagaga acctgcggatcgcgctccgctactacaaccagagcgaggccggttctcacaccctccagatgatgtttggctgcga -continued cgtggggtcggacgggcgcttcctccgcgggtaccaccagtaTgcctacgacggcaaggattacatcgccctgaaa gaggacctgcgctcttggaccgcggcggacatggcggctcagatcaccaagcgcaagtgggaggcggcccatgtgg cggagcagcagagagcctacctggagggcacgtgcgtggacgggctccgcagatacctggagaacgggaaggagac gctgcagcgcacgg;

A*240301:

(SEQ ID NO: 111)
atggccgtcatggcgccccgaaccctcgtcctgctactctcgggggccctggccctgacccagacctgggcaggct cccactccatgaggtatttctccacatccgtgtcccggcccggccgcggggagccccgcttcatcgccgtgggcta cgtggacgacacgcagttcgtgcggttcgacagcgacgccgcgagccagaggatggagccgcgggcgccgtggata gagcaggaggggccggagtattgggacgaggagacagggaaagtgaaggcccactcacagactgaccgagagaacc tgcggatcgcgctccgctactacaaccagagcgaggccggttctcacaccctccagatgatgtttggctgcgacgt ggggtcggacgggcgcttcctccgcgggtaccaccagtacgcctacgacggcaaggattacatcgccctgaaagag gacctgcgctcttggaccgcggcggacatggcggctcagatcaccaagcgcaagtgggaggcggcccatgtggcgg agcagcagagagCctacctggagggcacgtgcgtggagTggctccgcagatacctggagaacgggaaggagacgct gcagcgcacggaccccccaagacacatatgacccaccacccatctctgaccatgaggccactctgagatgctgg gccctgggcttctaccctgcggagatcacactgacctggcagcgggatggggaggaccagacccaggacacggagc ttgtggagaccaggcctgcaggggatggaaccttccagaagtgggcAgctgtggtggtaccttctggagaggagca gagatacacctgccatgtgcagcatgagggtctgcccaagcccctcaccctgagatgggag;

A*240302:

(SEQ ID NO: 112)
gctcccactccatgaggtatttctccacatccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtattgggacgaggagacaGggaaagtgaaggcccactcacagactgaccgagaga acctgcggatcgcgctccgctactacaaccagagcgaggccggttctcacaccctccagatgatgtttggctgcga cgtggggtcggacgggcgcttcctccgcgggtaccaccagtacgcctacgacggcaaggattacatcgccctgaaa gaggacctgcgctcttggaccgcggcggacatggcggctcagatcaccaagcgcaagtgggaggcggcccatgtgg cggagcagcAgagagCctacctggagggcaCgtgcgtggaGTggctccgcagatacctggagaacgggaaggagac gctgcagcgcactg;

A*2404:

(SEQ ID NO: 113)
atggccgtcatggcgccccgaaccctcgtcctgctactctcgggggccctggccctgacccagacctgggcaggct cccactccatgaggtatttctccacatccgtgtcccggcccggccgcggggagccccgcttcatcgccgtgggcta cgtggacgacacgcagttcgtgcggttcgacagcgacgccgcgagccagaggatggagccgcgggcgccgtggata gagcaggaggggccggagtattgggacgaggagacaGggaaagtgaaggcccactcacagactgaccgagcgaacc tggggacctgcgcggctactacaaccagagcgaggccggttctcacaccctccagatgatgtttggctgcgacgt ggggtcggacgggcgcttcctccgcgggtaccaccagtacgcctacgacggcaaggattacatcgccctgaaagag gacctgcgctcttggaccgcggcggacatggcggctcagatcaccaagcgcaagtgggaggcggcccatgtggcgg agcagcAgagagCctacctggagggcacgtgcgtggacgggctccgcagatacctggagaacgggaaggagacgct gcagcgcacggaccccccaagacacatatgacccaccacccatctctgaccatgaggccactctgagatgctgg gccctgggcttctaccctgcggagatcacactgacctggcagcgggatggggaggaccagacccaggacacggagc ttgtggagaccaggcctgcaggggatggaaccttccagaagtgggcAgctgtggtggtaccttctggagaggagca gagatacacctgccatgtgcagcatgagggtctgcccaagcccctcaccctgagatgggag;

A*2405:

(SEQ ID NO: 114)

gctcccactccatgaggtatttctccacatccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtattgggacgaggagacaGggaaagtgaaggcccactcacagactgaccgagaga acctgcggatcgcgctccgctactacaaccagagcgaggccggttctcacaccctccagatgatgtttggctgcga cgtggggtcggacgggcgcttcctccgcgggtaccaccagtacgcctacgacggcaaggattacatcgccctgaaa gaggacctgcgctcttggaccgcggcggacatggcggctcagatcaccCagcgcaagtgggaggcggcccatgtgg cggagcagcAgagagCctacctggagggcaCgtgcgtggacgggctccgcagatacctggagaacgggaaggagac gctgcagcgcacgg;

A*2406:

(SEQ ID NO: 115)

gctcccactccatgaggtatttctccacatccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtattgggacgaggagacaGggaaagtgaaggcccactcacagactgaccgagaga acctgcggatcgcgctccgctactacaaccagagcgaggccggttctcacaccctccagatgatgtttggctgcga cgtggggtcggacgggcgcttcctccgcgggtaccaccagtacgcctacgacggcaaggattacatcgccctgaaA gaggacctgcgctcttggaccgcggcggacatggcGgctcagatcaccaagcgcaagtgggaggcggcccatgTgg cggagcagTggagagCctacctggagggcaCgtgcgtggacgggctccgcagatacctggagaacgggaaggagac gctgcagcgcacgg;

A*2407:

(SEQ ID NO: 116)

atggccgtcatggcgccccgaaccctcgtcctgctactctcgggggccctggccctgacccagacctgggcaggct cccactccatgaggtatttctccacatccgtgtcccggcccggccgcggggagccccgcttcatcgccgtgggcta cgtggacgacacgcagttcgtgcggttcgacagcgacgccgcgagccagaggatggagccgcgggcgccgtggata gagcaggaggggccggagtattgggacgaggagacagggaaagtgaaggcccaGtcacagactgaccgagagaacc tgcggatcgcgctcCgctactacaaccagagcgaggccggttctcacaccctccagatgatgtttggctgcgacgt ggggtcggacgggcgcttcctccgcgggtaccaccagtacgcctacgacggcaaggattacatcgccctgaaagag gacctgcgctcttggaccgcggcggacatggcggctcagatcaccaagcgcaagtgggaggcggcccatgtggcgg agcagcAgagagCctacctggagggcacgtgcgtggacgggctccgcagatacctggagaacgggaaggagacgct gcagcgcacggaccccccaagacacatatgacccaccaccccatctctgaccatgaggccactctgagatgctgg gccctgggcttctaccctgcggagatcacactgacctggcagcgggatggggaggaccagacccaggacacggagc ttgtggagaccaggcctgcaggggatggaaccttccagaagtgggcAgctgtggtggtaccttctggagaggagca gagatacacctgccatgtgcagcatgagggtctgcccaagccctcacccctgagatgggag;

A*2408:

(SEQ ID NO: 117)

atggccgtcatggcgccccgaaccctcgtcctgctactctcgggggccctggccctgacccagacctgggcaggct cccaAtccatgaggtatttctccacatccgtgtcccggcccggccgcggggagccccgcttcatcgccgtgggcta cgtggacgacacgcagttcgtgcggttcgacagcgacgccgcgagccagaggatggagccgcgggcgccgtggata gagcaggaggggccggagtattgggacggggagacacggaaagtgaaggcccactcacagactgaccgagagaacc tgcggatcgcgctccgctactacaaccagagcgaggccggttctcacaccctccagatgatgtttggctgcgacgt ggggtcggacgggcgcttcctccgcgggtaccaccagtacgcctacgacggcaaggattacatcgccctgaaagag gacctgcgctcttggaccgcggcggacatggcggctcagatcaccaagcgcaagtgggaggcggcccatgtggcgg agcagcagagagcctacctggagggcacgtgcgtggacgggctccgcagatacctggagaacgggaaggagacgct gcagcgcacggaccccccaagacacatatgacccaccacccccatctctgaccatgaggccactctgagatgctgg gccctgggcttctaccctgcggagatcacactgacctggcagcgggatggggaggaccagacccaggacacggagc ttgtggagaccaggcctgcaggggatggaaccttccagaagtgggcagctgtggtggtAccttctggagaggagca gagatacacctgccatgtgcagcatgagggtctgcccaagcccctcaccctgagatgggag;

A*2410:
(SEQ ID NO: 118)
gctcccactccatgaggtatttctccacatccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtattgggacgaggagacaGggaaagtgaaggcccactcacagactgaccgagaga acctgcggatcgcgctccgctactacaaccagagcgaggccggttctcacaccctccagatgatgtttggctgcga cgtggggtcggacgggcgcttcctccgcgggtaccaccagtacgcctacgacggcaaggattacatcgccctgaaa gaggacctgcgctcttggaccgcggcggacatggcggctcagatcaccaagcgcaagtgggaggcggcccatgtgg cggagcagcAgagagCctacctggagggccggtgcgtggaGTggctccgcagatacctggagaacgggaaggagac gctgcagcgcacgg;

A*2413:
(SEQ ID NO: 119)
gctcccactccatgaggtatttctccacatccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtattgggacgaggagacaGggaaagtgaaggcccactcacagactgaccgagaga acctgcggatcgcgctccgctactacaaccagagcgaggccggttctcacaccctccagatgatgtttggctgcga cgtggggtcggacgggcgcttcctccgcgggtaccaccagtacgcctacgacggcaaggattacatcgccctgaaA gaggacctgcgctcttggaccgcggcggacatggcGgctcagatcaccaagcgcaagtgggaggcggcccatgTgg cggagcagtTgagagCctacctggagggcaCgtgcgtggacgggctccgcagatacctggagaacgggaaggagac gctgcagcgcacgg;

A*2414:
(SEQ ID NO: 120)
gctcccactccatgaggtatttctccacatccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtattgggacgaggagacaGggaaagtgaaggcccactcacagactgaccgagaga acctgcggatcgcgctccgctactacaaccagagcgaggccggttctcacaccgtccagaggatgtatggctgcga cgtggggtcggacTggcgcttcctccgcgggtaccaccagTacgcctacgacggcaaggattacatcgccctgaaA gaggacctgcgctcttggaccgcggcggacatggcGgctcagatcaccaagcgcaagtgggaggcggcccatgtgg cggagcagcAgagagCctacctggagggcaCgtgcgtggacgggctccgcagatacctggagaacgggaaggagac gctgcagcgcacgg;

A*2415:
(SEQ ID NO: 121)
gctcccactccatgaggtatttctccacatccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtattgggacgaggagacaGggaaagtgaaggcccactcacagactgaccgagaga acctgcggatcgcgctcCgctactacaaccagagcgaggCcggttctcacaccCtccagatgatgtatggctgcga cgtggggccggacgggcgcttcctccgcgggtaccaccagTacgcctacgacggcaaggattacatcgccctgaaA gaggacctgcgctcttggaccgcggcggacatggcGgctcagatcaccaagcgcaagtgggaggcggcccatgtgg cggagcagcAgagagCctacctggagggcaCgtgcgtggacgggctccgcagatacctggagaacgggaaggagac gctgcagcgcacgg;

A*2417:
(SEQ ID NO: 122)
gctcccactccatgaggtatttctccacatccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtattgggacgaggagacaGggaaagtgaaggcccactcacagactgaccgagaga acctgcggatcgcgctcCgctactacaaccagagcgaggCcggttctcacaccctccagatgatgtTtggctgcga cgtggggTcggacgggcgcttcctccgcgggtaccggcaggacgcctacgacggcaaggattacatcgccctgaaA gaggacctgcgctcttggaccgcggcggacatggcGgctcagatcaccaagcgcaagtgggaggcggcccatgtgg cggagcagcAgagagCctacctggagggcaCgtgcgtggacgggctccgcagatacctggagaacgggaaggagac gctgcagcgcacgg;

A*2418:
(SEQ ID NO: 123)
gctcccactccatgaggtatttctccacatccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtattgggacgaggagacagggaaagtgaaggcccactcacagactgaccgagaga acctgcggatcgcgctccgctactacaaccagagcgaggccggttctcacaccctccagatgatgtttggctgcga cgtggggtcggacgggcgcttcctccgcgggtaccaccagtacgcctacgacggcaaggattacatcgccctgaaA gaggacctgcgctcttggaccgcggcggacatggcggctcagatcaccaagcgcaagtgggaggcggcccatgAgg cggagcagTTgagagcctacctggaTggcacgtgcgtggagtggctccgcagatacctggagaacgggaaggagac gctgcagcgcacgg;

A*2419:
(SEQ ID NO: 124)
gctcccactccatgaggtatttctccacatccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtattgggacgaggagacaGggaaagtgaaggcccaGtcacagactgaccgagtgG acctggggaccctgcgcggctactacaaccagagcgaggacggttctcacaccctccagatgatgtTtggctgcga cgtggggTcggacgggcgcttcctccgcgggtaccaccagTacgcctacgacggcaaggattacatcgccctgaaA gaggacctgcgctcttggaccgcggcggacatggcGgctcagatcaccaagcgcaagtgggaggcggcccatgtgg cggagcagcAgagagCctacctggagggcaCgtgcgtggacgggctccgcagatacctggagaacgggaaggagac gctgcagcgcacgg;

A*2420:
(SEQ ID NO: 125)
gctcccaatccatgaggtatttctccacatccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtattgggacgaggagacaGggaaagtgaaggcccactcacagactgaccgagaga acctgcggatcgcgctcCgctactacaaccagagcgaggCcggttctcacaccctccagatgatgtTtggctgcga cgtggggTcggacgggcgcttcctccgcgggtaccaccagTacgcctacgacggcaaggattacatcgccctgaaA gaggacctgcgctcttggaccgcggcggacatggcGgctcagatcaccaagcgcaagtgggaggcggcccatgtgg cggagcagcAgagagCctacctggagggcaCgtgcgtggacgggctccgcagatacctggagaacgggaaggagac gctgcagcgcacgg;

A*2421:
(SEQ ID NO: 126)
gctcccactccatgaggtatttctccacatccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtattgggacgaggagacaGggaaagtgaaggcccactcacagactgaccgagaga -continued acctgcggatcgcgctcCgctactacaaccagagcgaggCcggttctcacaccctccagatgatgtTtggctgcga
cgtggggTcggacgggcgcttcctccgcgggtaccaccagTacgcctacgacggcaaggattacatcgccctgaac
gaggacctgcgctcttggaccgcggcggacatggcGgctcagatcaccaagcgcaagtgggaggcggcccatgtgg
cggagcagcAgagagCctacctggagggcaCgtgcgtggacgggctccgcagatacctggagaacgggaaggagac
gctgcagcgcacgg;

A*2422:
(SEQ ID NO: 127)
atggccgtcatggcgccccgaaccctcgtcctgctactctcgggggccctggccctgacccagacctgggcaggct
cccactccatgaggtatttctccacatccgtgtcccggcccggccgcggggagccccgcttcatcgccgtgggcta
cgtggacgacacgcagttcgtgcggttcgacagcgacgccgcgagccagaggatggagccgcgggcgccgtggata
gagcaggaggggccggagtattgggacgaggagacagggaaagtgaaggcccactcacagactgaccgagagaacc
tgcggatcgcgctccgctactacaaccagagcgaggccggttctcacaccctccagatgatgtttggctgcgacgt
ggggtcggacgggcgcttcctccgcgggtaccaccagtacgcctacgacggcaaggattacatcgccctgaaagag
gacctgcgctcttggaccgcggcggacatggcggctcagatcaccaagcgcaagtgggaggcggcccatgtggcgg
agcagTggagagtctacctggagggcacgtgcgtggagTggctccgcagatacctggagaacgggaaggagacgct
gcagcgcacggaccccccaagacacatatgacccaccacccatctctgaccatgaggccactctgagatgctgg
gccctgggcttctaccctgcggagatcacactgacctggcagcgggatggggaggaccagacccaggacacggagc
ttgtggagaccaggcctgcaggggatggaaccttccagaagtgggcAgctgtggtggtaccttctggagaggagca
gagatacacctgccatgtgcagcatgagggtctgcccaagcccctcaccctgagatgggag;

A*2423:
(SEQ ID NO: 128)
gctcccactccatgaggtatttctccacatccgtgtcccggcccggccgcggggagccccgcttcatcgccgtggg
ctacgtggacgacacgcagttcgtgcggttcgacagcgacgccgcgagccagaggatggagccgcgggcgccgtgg
atagagcaggaggggccggagtattgggacgaggagacaGggaaagtgaaggcccactcacagactgaccgagaga
acctgcggatcgcgctccgctactacaaccagagcgaggccggttctcacaccctccagatgatgtttggctgcga
cgtggggtcggacgggcgcttcctccgcgggtaccaccagtacgcctacgacggcaaggattacatcgccctgaaa
gaggacctgcgctcttggaccgcggcggacatggcggctcagatcaccaagcgcaagtgggaggcggcccatgtgg
cggagcagcAgagagCctacctggagggcaCgtgcgtggacTggctccgcagatacctggagaacgggaaggagac
gctgcagcgcacgg;

A*2424:
(SEQ ID NO: 129)
gctcccactccatgaggtatttctccacatccgtgtcccggcccggccgcggggagccccgcttcatcgccgtggg
ctacgtggacgacacgcagttcgtgcggttcgacagcgacgccgcgagccagaggatggagccgcgggcgccgtgg
atagagcaggaggggccggagtattgggaccggaacacacgcgaatgtgaaggcccaGtcacagactgaccgagaga
acctgcggatcgcgctccgctactacaaccagagcgaggccggttctcacaccctccagatgatgtTtggctgcga
cgtggggtcggacgggcgcttcctccgcgggtaccaccagtacgcctacgacggcaaggattacatcgccctgaaA
gaggacctgcgctcttggaccgcggcggacatggcggctcagatcacccagcgcaagtgggaggcggcccGtgTgg
cggagcagtTgagagCctacctggagggcaCgtgcgtggacgggctccgcagatacctggagaacgggaaggagac
gctgcagcgcacgg;

A*2425:
(SEQ ID NO: 130)
gctcccactccatgaggtGtttctccacatccgtgtcccggcccggccgcggggagccccgcttcatcgccgtggg
ctacgtggacgacacgcagttcgtgcggttcgacagcgacgccgcgagccagaggatggagccgcgggcgccgtgg
atagagcaggaggggccggagtattgggacgaggagacagggaaagtgaaggcccactcacagactgaccgagaga
acctgcggatcgcgctccgctactacaaccagagcgaggccggttctcacaccctccagatgatgtttggctgcga cgtggggtcggacgggcgcttcctccgcgggtaccaccagtacgcctacgacggcaaggattacatcgccctgaaa gaggacctgcgctcttggaccgcggcggacatggcggctcagatcaccaagcgcaagtgggaggcggcccatgtgg cggagcagcAgagagcctacctggagggcacgtgcgtggacgggctccgcagatacctggagaacgggaaggagac gctgcagcgcacgg;

A*2426: (SEQ ID NO: 131)

aaccctcctcctgctactctcggggccctggccctgacccagacctgggcaggctcccactccatgaggtatttc tccacatccgtgtcccggcccggccgcggggagcccgcttcatcgccgtgggctacgtggacgacacgcagttcg tgcggttcgacagcgacgccgcgagccagaggatggagccgcgggcgccgtggatagagcaggagggccggagta ttgggacgaggagacagggaaagtgaaggcccactcacagactgaccgagagaacctgcggatcgcgctccgctac tacaaccagagcgaggccggttctcacaccctccagatgatgtttggctgcgacgtggggtcggacgggcgcttcc tccAcgggtaccaccagtacgcctacgacggcaaggattacatcgccctgaaagaggacctgcgctcttggaccgc ggcggacatggcggctcagatcaccaagcgcaagtgggaggcggcccatgtggcggagcagcagagagcctacctg gagggcacgtgcgtggacgggctccgcagatacctggagaacgggaaggagacgctgcagcgcacgg;

A*2427: (SEQ ID NO: 132)

atggccgtcatggcgccccgaaccctcgtcctgctactctcggggccctggccctgacccagacctgggcaggct cccactccatgaggtatttctccacatccgtgtcccggcccggccgcggggagcccgcttcatcgccgtgggcta cgtggacgacacgcagttcgtgcggttcgacagcgacgccgcgagccagaggatggagccgcgggcgccgtggata gagcaggagggccggagtattgggacgaggagacagggaaagtgaaggcccactcacagactgaccgagagaacc tgcggatcgcgctccgctactacaaccagagcgaggccggttctcacaccctccagatgatgtttggctgcgacgt ggggtcggacgggcgcttcctccgcgggtaccaccagtacgcctacgacggcaaggattacatcgccctgaaagag gacctgcgctcttggaccgcggcggacaGggcggctcagatcaccaagcgcaagtgggaggcggcccatgtggcgg agcagcagagagcctacctggagggcacgtgcgtggacgggctccgcagatacctggagaacgggaaggagacgct gcagcgcacgg;

A*2428: (SEQ ID NO: 133)

gctcccactccatgaggtatttctccacatccgtgtcccggcccggccgcggggagcccgcttcatcgccgtggg ctacgtggacgacacgcagttcgtgcggttcgacagcgacgccgcgagccagaggatggagccgcgggcgccgtgg atagagcaggagggccggagtattgggacgaggagacaGggaaagtgaaggcccactcacagactcaccgagtgG acctggggaccctgcgcggctactacaaccagagcgaggCcggttctcacaccctccagatgatgtTtggctgcga cgtggggTcggacgggcgcttcctccgcgggtaccaccagTacgcctacgacggcaaggattacatcgccctgaaA gaggacctgcgctcttggaccgcggcggacatggcGgctcagatcaccaagcgcaagtgggaggcggcccatgtgg cggagcagcAgagagCctacctggagggcaCgtgcgtggacgggctccgcagatacctggagaacgggaaggagac gctgcagcgcacgg;

A*2429: (SEQ ID NO: 134)

gctcccactccatgaggtatttctccacatccgtgtcccggcccggccgcggggagcccgcttcatcgccgtggg ctacgtggacgacacgcagttcgtgcggttcgacagcgacgccgcgagccagaggatggagccgcgggcgccgtgg atagagcaggagggccggagtattgggacgaggagacacggaaagtgaaggcccactcacagactgaccgagaga acctgcggatcgcgctcCgctactacaaccagagcgaggCcggttctcacaccctccagatgatgtTtggctgcga cgtggggtcggacgggcgcttcctccgcgggtaccaccagTacgcctacgacggcaaggattacatcgccctgaaA gaggacctgcgctcttggaccgcggcggacatggcGgctcagatcaccaagcgcaagtgggaggcggcccatgtgg -continued cggagcagcAgagagCctacctggagggcaCgtgcgtggacgggctccgcagatacctggagaacgggaaggagac gctgcagcgcacgg;

A*2430:

(SEQ ID NO: 135)

gctcccactccatgaggtatttctccacatccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtattgggacgaggagacaGggaaagtgaaggcccactcacagactCaccgagaga acctgcggatcgcgctcCgctactacaaccagagcgaggCcggttctcacaccctccagatgatgtTtggctgcga cgtggggTcggacgggcgcttcctccgcgggtaccaccagTacgcctacgacggcaaggattacatcgccctgaaA gaggacctgcgctcttggaccgcggcggacatggcGgctcagatcaccaagcgcaagtgggaggcggcccatgtgg cggagcagcAgagagCctacctggagggcaCgtgcgtggacgggctccgcagatacctggagaacgggaaggagac gctgcagcgcacgg;

A*2431:

(SEQ ID NO: 136)

gctcccactccatgaggtatttctccacatccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtattgggacgagCagacagggaaagtgaaggcccactcacagactgaccgagaga acctgcggatcgcgctccgctactacaaccagagcgaggccggttctcacaccctccagatgatgtttggctgcga cgtggggtcggacgggcgcttcctccgcgggtaccaccagtacgcctacgacggcaaggattacatcgccctgaaa gaggacctgcgctcttggaccgcggcggacatggcggctcagatcaccaagcgcaagtgggaggcggcccatgTgg cggagcagcAgagagcctacctggagggcaCgtgcgtggacgggctccgcagatacctggagaacgggaaggagac gctgcagcgcacgg;

A*2432:

(SEQ ID NO: 137)

gctcccactccatgaggtatttctccacatccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtattgggacgaggagacagggaaagtgaaggcccactcacagactgaccgagaga Gcctgcggatcgcgctccgctactacaaccagagcgaggccggttctcacaccctccagatgatgtttggctgcga cgtggggtcggacgggcgcttcctccgcgggtaccaccagtacgcctacgacggcaaggattacatcgccctgaaA gaggacctgcgctcttggaccgcggcggacatggcggctcagatcaccaagcgcaagtgggaggcggcccatgtgg cggagcagcAgagagcctacctggagggcaCgtgcgtggacgggctccgcagatacctggagaacgggaaggagac gctgcagcgcacgg;

A*2433:

(SEQ ID NO: 138)

gctcccactccatgaggtatttctccacatccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtattgggacgaggagacagggaaagtgaaggcccactcacagactgaccgagaga acctgcggatcgcgctccgctactacaaccagagcgaggccggttctcacaccctccagatgatgtttggctgcga cgtggggtcggacgggcgcttcctccgcgggtaccaccagtacgcctacgacggcaaggattacatcgccctgaaa gaggacctgcgctcttggaccgcggcggacatggcGgctcagatcaccaagcgcaagtgggaggcggcccatgTgg cggagcagcAgagagcctacctggagggcaCgtgcgtggagtggctccgcagatacctggagaacgggaaggagac gctgcagcgcacggacgcccccaaaacgcatatgactcaccacgctgtctctgaccatgaagccacccctgaggtgc tgggccctgagcttctaccctgcggagatcacactgacctggcagcgggatggggaggaccagacccaggacacgg agctcgtggagaccaggcctgcaggggatggaaccttccagaagtgggcggctgtggtggtgccttctggacagga gcagagatacacctgccatgtgcagcatgagggtTtgcccaagcccctcaccctgagatggg;

A*2434:
(SEQ ID NO: 139)
gctcccactccatgaggtatttctccacatccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtattgggacgaggagacagggaaagtgaaggcccactcacagaTtgaccgagaga acctgcggatcgcgctccgctactacaaccagagcgaggccggttctcacaccctccagatgatgtttggctgcga cgtggggtcggacgggcgcttcctccgcgggtaccaccagtacgcctacgacggcaaggattacatcgccctgaaa gaggacctgcgctcttggaccgcggcggacatggcggctcagatcaccaagcgcaagtgggaggcggcccatgtgg cggagcagcAgagagcctacctggagggcacgtgcgtggacgggctccgcagatacctggagaacgggaaggagac gctgcagcgcacgg;

A*2435:
(SEQ ID NO: 140)
gctcccactccatgaggtatttctccacatccgtgtcccggcccggccgcggggagccccgcttcatcgccgtggg ctacgtggacgacacgcagttcgtgcggttcgacagcgacgccgcgagccagaggatggagccgTgggcgccgtgg atagagcaggaggggccggagtattgggacgaggagacagggaaagtgaaggcccactcacagactgaccgagaga acctgcggatcgcgctccgctactacaaccagagcgaggccggttctcacaccctccagatgatgtttggctgcga cgtggggtcggacgggcgcttcctccgcgggtaccaccagtacgcctacgacggcaaggattacatcgccctgaaa gaggacctgcgctcttggaccgcggcggacatggcggctcagatcaccaagcgcaagtgggaggcggcccatgtgg cggagcagcagagagcctacctggagggcacgtgcgtggacgggctccgcagatacctggagaacgggaaggagac gctgcagcgcacgg;

A*2437:
(SEQ ID NO: 141)
gctcccactccatgaggtatttctccacatccgtgtcccggcccggccgcggggagccccgcttcatcgccgtggg ctacgtggacgacacgcagttcgtgcggttcgacagcgacgccgcgagccagaggatggagcTgcgggcgccgtgg atagagcaggaggggccggagtattgggacgaggagacagggaaagtgaaggcccactcacagactgaccgagaga acctgcggatcgcgctccgctactacaaccagagcgaggccggttctcacaccctccagatgatgtttggctgcga cgtggggtcggacgggcgcttcctccgcgggtaccaccagtacgcctacgacggcaaggattacatcgccctgaaa gaggacctgcgctcttggaccgcggcggacatggcggctcagatcaccaagcgcaagtgggaggcggcccatgtgg cggagcagcagagagcctacctggagggcacgtgcgtggacgggctccgcagatacctggagaacgggaaggagac gctgcagcgcacgg;

A*2438:
(SEQ ID NO: 142)
gctcccactccatgagCtatttctccacatccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtattgggacgaggagacagggaaagtgaaggcccactcacagactgaccgagaga acctgcggatcgcgctccgctactacaaccagagcgaggccggttctcacaccctccagatgatgtttggctgcga cgtggggtcggacgggcgcttcctccgcgggtaccaccagtacgcctacgacggcaaggattacatcgccctgaaa gaggacctgcgctcttggaccgcggcggacatggcggctcagatcaccaagcgcaagtgggaggcggcccatgtgg cggagcagcagagagcctacctggagggcacgtgcgtggacgggctccgcagatacctggagaacgggaaggagac gctgcagcgcacgg;

A*2501:

(SEQ ID NO: 143)
atggccgtcatggcgcccgaaccctcgtcctgctactctcgggggccctggccctgacccagacctgggcgggct cccactccatgaggtatttctacacctccgtgtcccggcccggccgcggggagccccgcttcatcgccgtgggcta cgtggacgacacgcagttcgtgcggttcgacagcgacgccgcgagccagaggatggagccgcgggcgccgtggata gagcaggaggggccggagtattgggaccggaacacacggaatgtgaaggcccactcacagactgaccgagagaGcc tgcggatcgcgctccgctactacaaccagagcgaggacggttctcacaccatccagaggatgtatggctgcgacgt ggggccggacgggcgcttcctccgcgggtaccagcaggacgcttacgacggcaaggattacatcgccctgaacgag gacctgcgctcttggaccgcggcggacatggcggctcagatcacccagcgcaagtgggagacggcccatgaggcgg agcagtggagagcctacctggagggccggtgcgtggagtggctccgcagatacctggagaacgggaaggagacgct gcagcgcacggacgcccccaagacgcatatgactcaccacgctgtctctgaccatgaggccaccctgagg tgctgg gccctgagcttctaccctgcggagatcacactgacctggcagcgggatggggaggaccagacccaggacacggagc tcgtggagaccaggcctgcaggggatggGaccttccagaagtgggcgtctgtggtggtgccttctggaCaggagca gagatacacctgccatgtgcagcatgagggtctgcccaagcccctcaccctgagatgggag;

A*2502:

(SEQ ID NO: 144)
atggccgtcatggcgcccgaaccctcgtcctgctactctcgggggccctggccctgacccagacctgggcgggct cccactccatgaggtatttctacacctccgtgtcccggcccggccgcggggagccccgcttcatcgccgtgggcta cgtggacgacacgcagttcgtgcggttcgacagcgacgccgcgagccagaggatggagccgcgggcgccgtggata gagcaggaggggccggagtattgggaccggaacacacggaatgtgaaggcccaGtcacagactgaccgagagaGcc tgcggatcgcgctccgctactacaaccagagcgaggacggttctcacaccatccagaggatgtatggctgcgacgt ggggccggacgggcgcttcctccgcgggtaccagcaggacgcttacgacggcaaggattacatcgccctgaacgag gacctgcgctcttggaccgcggcggacatggcggctcagatcacccagcgcaagtgggagacggcccatgaggcgg agcagtggagagcctacctggagggccggtgcgtggagtggctccgcagatacctggagaacgggaaggagacgct gcagcgcacggacgcccccaagacgcatatgactcaccacgctgtctctgaccatgaggccaccctgaggtgctgg gccctgagcttctaccctgcggagatcacactgacctggcagcgggatggggaggaccagacccaggacacggagc tcgtggagaccaggcctgcaggggatggGaccttccagaagtgggcgtctgtggtggtgccttctggaCaggagca gagatacacctgccatgtgcagcatgagggtctgcccaagcccctcaccctgagatgggag;

A*2503:

(SEQ ID NO: 145)
gctcccactccatgaggtatttcttcacatccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtattgggaccggaacacacggaatgtgaaggcccactcacagactgaccgagaga Gcctgcggatcgcgctccgctactacaaccagagcgaggacggttctcacaccatccagaggatgtatggctgcga cgtggggccggacgggcgcttcctccgcgggtaccagcaggacgcttacgacggcaaggattacatcgccctgaac gaggacctgcgctcttggaccgcggcggacatggcggctcagatcacccagcgcaagtgggagAcgcccatgAgg cggagcagTggagagcctacctggagggccggtgcgtggagTggctccgcagatacctggagaacgggaaggagac gctgcagcgcacgg;

A*2504:

(SEQ ID NO: 146)
gctcccactccatgaggtatttctacacctccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtattgggaccggaacacacggaatgtgaaggcccactcacagactgaccgagaga Gcctgcggatcgcgctccgctactacaaccagagcgaggacggttctcacaccatccagaggatgtatggctgcga -continued cgtggggccggacgggcgcttcctccgcgggtaccagcaggacgcttacgacggcaaggattacatcgccctgaac gaggacctgcgctcttggaccgcggcggacatggcggctcagatcacccagcgcaagtgggagacggcccatgAgg cggagcagcAgagagcctacctggagggccggtgcgtggagTggctccgcagatacctggagaacgggaaggagac gctgcagcgcacgg;

A*2601:

(SEQ ID NO: 147)
atggccgtcatggcgccccgaaccctcgtcctgctactctcgggggccctggccctgacccagacctgggcgggct cccactccatgaggtatttctacacctccgtgtcccggcccggccgcggggagccccgcttcatcgccgtgggcta cgtggacgacacgcagttcgtgcggttcgacagcgacgccgcgagccagaggatggagccgcgggcgccgtggata gagcaggaggggccggagtattgggaccggaaCacacggaatgtgaaggcccactcacagactgaccgagcgaacc tggggaccctgcgcggctactacaaccagagcgaggacggttctcacaccatccagaggatgtatggctgcgacgt ggggccggacgggcgcttcctccgcgggtaccagcaggacgcttacgacggcaaggattacatcgccctgaacgag gacctgcgctcttggaccgcggcggacatggcggctcagatcacccagcgcaagtgggagacggcccatgaggcgg agcagTggagagcctacctggagggccggtgcgtggagtggctccgcagatacctggagaacgggaaggagacgct gcagcgcacggacgcccccaagacgcatatgactcaccacgctgtctctgaccatgaggccaccctgaggtgctgg gccctgagcttctaccctgcggagatcacactgacctggcagcgggatggggaggaccagacccaggacacggagc tcgtggagaccaggcctgcaggggatggGaccttccagaagtgggcgtctgtggtggtgccttctggacaggagca gagatacacctgccatgtgcagcatgagggtctgcccaagcccctcaccctgagatgggag;

A*2602:

(SEQ ID NO: 148)
atggccgtcatggcgccccgaaccctcgtcctgctactctcgggggccctggccctgacccagacctgggcgggct cccactccatgaggtatttctacacctccgtgtcccggcccggccgcggggagccccgcttcatcgccgtgggcta cgtggacgacacgcagttcgtgcggttcgacagcgacgccgcgagccagaggatggagccgcgggcgccgtggata gagcaggaggggccggagtattgggaccggaacacacggaatgtgaaggcccactcacagactgaccgagcgaacc tggggaccctgcgcggctactacaaccagagcgaggacggttctcacaccatccagaggatgtatggctgcgacgt ggggccggacgggcgcttcctccgcgggtaccagcagAacgcttacgacggcaaggattacatcgccctgaacgag gacctgcgctcttggaccgcggcggacatggcggctcagatcacccagcgcaagtgggagacggcccatgaggcgg agcagtggagagcctacctggagggccggtgcgtggagtggctccgcagatacctggagaacgggaaggagacgct gcagcgcacggacgcccccaagacgcatatgactcaccacgctgtctctgaccatgaggccaccctgaggtgctgg gccctgagcttctaccctgcggagatcacactgacctggcagcgggatggggaggaccagacccaggacacggagc tcgtggagaccaggcctgcaggggatggaccttccagaagtgggcgtctgtggtggtgccttctggacaggagca gagatacacctgccatgtgcagcatgagggtctgcccaagcccctcaccctgagatgggag;

A*2603:

(SEQ ID NO: 149)
atggccgtcatggcgccccgaaccctcgtcctgctactctcgggggccctggccctgacccagacctgggcgggct cccactccatgaggtatttctacacctccgtgtcccggcccggccgcggggagccccgcttcatcgccgtgggcta cgtggacgacacgcagttcgtgcggttcgacagcgacgccgcgagccagaggatggagccgcgggcgccgtggata gagcaggaggggccggagtattgggaccggaacacacggaatgtgaaggcccactcacagactCaccgagtgGacc tggggaccctgcgcggctactacaaccagagcgaggacggttctcacaccatccagaggatgtatggctgcgacgt ggggccggacgggcgcttcctccgcgggtaccagcaggacgcttacgacggcaaggattacatcgccctgaacgag gacctgcgctcttggaccgcggcggacatggcggctcagatcacccagcgcaagtgggagacggcccatgaggcgg agcagTggagagcctacctggagggccggtgcgtggagtggctccgcagatacctggagaacgggaaggagacgct gcagcgcacggacgcccccaagacgcatatgactcaccacgctgtctctgaccatgaggccaccctgaggtgctgg gccctgagcttctaccctgcggagatcacactgacctggcagcgggatggggaggaccagacccaggacacggagc -continued tcgtggagaccaggcctgcaggggatggGaccttccagaagtgggcgtctgtggtggtgccttctggacaggagca gagatacacctgccatgtgcagcatgagggtctgcccaagcccctcaccctgagatgggag;

A*2604:

(SEQ ID NO: 150)
atggccgtcatggcgccccgaaccctcgtcctgctactctcgggggccctggccctgacccagacctgggcgggct cccactccatgaggtatttctacacctccgtgtcccggcccggccgcggggagccccgcttcatcgccgtgggcta cgtggacgacacgcagttcgtgcggttcgacagcgacgccgcgagccagaggatggagccgcgggcgccgtggata gagcaggaggggccggagtattgggaccggaacacacggaatgtgaaggcccactcacagactgaccgagcgaacc tggggaccctgcgcggctactacaaccagagcgaggacggttctcacaccatccagaggatgtatggctgcgacgt ggggccggacgggcgcttcctccgcgggtaccagcaggacgcttacgacggcaaggattacatcgccctgaacgag gacctgcgctcttggaccgcggcggacatggcggctcagatcacccagcgcaagtgggagacggcccatgaggcgg agcagtggagagcctacctggagggccTgtgcgtggagtggctccgcagatacctggagaacgggaaggagacgct gcagcgcacggacgcccccaagacgcatatgactcaccacgctgtctctgaccatgaggccaccctgaggtgctgg gccctgagcttctaccctgcggagatcacactgacctggcagcgggatggggaggaccagacccaggacacggagc tcgtggagaccaggcctgcaggggatgggaccttccagaagtgggcgtctgtggtggtgccttctggacaggagca gagatacacctgccatgtgcagcatgagggtctgcccaagcccctcaccctgagatgggag;

A*2605:

(SEQ ID NO: 151)
atggccgtcatggcgccccgaaccctcgtcctgctactctcgggggccctggccctgacccagacctgggcgggct cccactccatgaggtatttctacacctccgtgtcccggcccggccgcggggagccccgcttcatcgccgtgggcta cgtggacgacacgcagttcgtgcggttcgacagcgacgccgcgagccagaggatggagccgcgggcgccgtggata gagcaggaggggccggagtattgggaccggaacacacggaatgtgaaggcccactcacagactgaccgagAgaacc tggggaccctgcgcggctactacaaccagagcgaggacggttctcacaccatccagaggatgtatggctgcgacgt ggggccggacgggcgcttcctccgcgggtaccagcaggacgcttacgacggcaaggattacatcgccctgaacgag gacctgcgctcttggaccgcggcggacatggcggctcagatcacccagcgcaagtgggagacggcccatgaggcgg agcagTggagagcctacctggagggccggtgcgtggagtggctccgcagatacctggagaacgggaaggagacgct gcagcgcacggacgcccccaagacgcatatgactcaccacgctgtctctgaccatgaggccaccctgaggtgctgg gccctgagcttctaccctgcggagatcacactgacctggcagcgggatggggaggaccagacccaggacacggagc tcgtggagaccaggcctgcaggggatggGaccttccagaagtgggcgtctgtggtggtgccttctggacaggagca gagatacacctgccatgtgcagcatgagggtctgcccaagcccctcaccctgagatgggag;

A*2606:

(SEQ ID NO: 152)
gctcccactccatgaggtatttctacacctccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtattgggaccggaacacacggaatgtgaaggcccactcacagactcaccgagtgg acctggggaccctgcgcggctactacaaccagagcgaggacggttctcacaccatccagaggatgtatggctgcga cgtggggccggacgggcgcttcctccgcgggtaccagcGggacgcttacgacggcaaggattacatcgccctgaac gaggacctgcgctcttggaccgcggcggacatggcggctcagatcacccagcgcaagtgggagacggcccatgagg cggagcagtggagagcctacctggagggccggtgcgtggagtggctccgcagatacctggagaacgggaaggagac gctgcagcgcacgg;

A*2607:

(SEQ ID NO: 153)
atggccgtcatggcgccccgaaccctcgtcctgctactctcgggggccctggccctgacccagacctgggcgggct cccactccatgaggtatttctacacctccgtgtcccggcccggccgcggggagccccgcttcatcgccgtgggcta -continued cgtggacgacacgcagttcgtgcggttcgacagcgacgccgcgagccagaggatggagccgcgggcgccgtggata gagcaggaggggccggagtattgggacggggagacacggaaAgtgaaggcccactcacagactgaccgagcgaacc tggggaccctgcgcggctactacaaccagagcgaggacggttctcacaccatcagaggatgtatggctgcgacgt ggggccggacgggcgcttcctccgcgggtaccagcaggacgcttacgacggcaaggattacatcgccctgaacgag gacctgcgctcttggaccgcggcggacatggcggctcagatcacccagcgcaagtgggagacggcccatgaggcgg agcagTggagagcctacctggagggccggtgcgtggagtggctccgcagatacctggagaacgggaaggagacgct gcagcgcacggacgcccccaagacgcatatgactcaccacgctgtctctgaccatgaggccaccctgaggtgctgg gccctgagcttctaccctgcggagatcacactgacctggcagcgggatggggaggaccagacccaggacacggagc tcgtggagaccaggcctgcaggggatggGaccttcagaagtgggcgtctgtggtggtgccttctggacaggagca gagatacacctgccatgtgcagcatgagggtctgcccaagcccctcaccctgagatgggag;

A*2608:

(SEQ ID NO: 154)
atggccgtcatggcgccccgaaccctcgtcctgctactctcgggggccctggccctgacccagacctgggcgggct cccactccatgaggtatttctacacctccgtgtcccggcccggccgcggggagccccgcttcatcgccgtgggcta cgtggacgacacgcagttcgtgcggttcgacagcgacgccgcgagccagaggatggagccgcgggcgccgtggata gagcaggaggggccggagtattgggaccggaacacacggaatgtgaaggcccactcacagactgaccgagcgaacc tggggaccctgcgcggctactacaaccagagcgaggacggttctcacaccatccagaggatgtatggctgcgacgt ggggccggacgggcgcttcctccgcgggtaccagcaggacgcttacgacggcaaggattacatcgccctgaacgag gacctgcgctcttggaccgcggcggacatggcggctcagatcacccagcgcaagtgggagacggcccatgaggcgg agcagcAgagagcctacctggagggccggtgcgtggagtggctccgcagatacctggagaacgggaaggagacgct gcagcgcacggacgcccccaagacgcatatgactcaccacgctgtctctgaccatgaggccaccctgaggtgctgg gccctgagcttctaccctgcggagatcacactgacctggcagcgggatggggaggaccagacccaggacacggagc tcgtggagaccaggcctgcaggggatggGaccttcagaagtgggcgtctgtggtggtgccttctggacaggagca gagatacacctgccatgtgcagcatgagggtctgcccaagcccctcaccctgagatgggag;

A*2609:

(SEQ ID NO: 155)
gctcccactccatgaggtatttctacacctccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtattgggaccggaacacacggaatgtgaaggcccactcacagactgaccgagcga acctggggaccctgcgcggctactacaaccagagcgaggacggttctcacaccatccagaggatgtatggctgcga cgtggggccggacgggcgcttcctccgcgggtaccAgcaggacgcttacgacggcaaggattacatcgccctgaac gaggacctgcgctcttggaccgcggcggacatggcggctcagatcaccCagcgcaagtgggagAcggccatgAgg cggagcagtggagagcctacctggagggcaCgtgcgtggagtggctccgcagatacctggagaacgggaaggagac gctgcagcgcacgg;

A*2610:

(SEQ ID NO: 156)
gctcccactccatgaggtatttctacacctccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtattgggaccggaacacacggaatgtgaaggcccactcacagactgaccgagcga acctggggaccctgcgcggctactacaaccagagcgaggacggttctcacaccatccagaggatgtatggctgcga cgtggggccggacgggcgcttcctccgcgggtaccagcaggacgcttacgacggcaaggattacatcgccctgaaA gaggacctgcgctcttggaccgcggcggacatggcggctcagatcaccCagcgcaagtgggagAcggcccatgAgg cggagcagTggagagcctacctggagggccggtgcgtggagtggctccgcagatacctggagaacgggaaggagac gctgcagcgcacgg;

A*2612:

(SEQ ID NO: 157)
gctcccactccatgaggtatttctacacctccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtattgggaccggaacacacggaatgtgaaggcccactcacagactgaccgagcga acctggggaccctgcgcggctactacaaccagagcgaggacggttctcacaccatccagaggatgtatggctgcga cgtggggccggacgggcgcttcctccgcgggtaccagcaggacgcttacgacggcaaggattacatcgccctgaac gaggacctgcgctcttggaccgcggcggacatggcggctcagatcacccCagcgcaagtgggagAcggcccatgTgg cggagcagTggagagcctacctggagggccggtgcgtggagtggctccgcagatacctggagaacgggaaggagac gctgcagcgcacgg;

A*2613:

(SEQ ID NO: 158)
gctcccactccatgaggtatttctacacctccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtattgggaccggaacacacggaatgtgaaggcccaGtcacagactgaccgagcga acctggggaccctgcgcggctactacaaccagagcgaggacggttctcacaccatccagaggatgtatggctgcga cgtggggccggacgggcgcttcctccgcgggtaccAgcaggacgcttacgacggcaaggattacatcgccctgaac gaggacctgcgctcttggaccgcggcggacatggcggctcagatcacccCagcgcaagtgggagAcggcccatgAgg cggagcagTggagagcctacctggagggccggtgcgtggagtggctccgcagatacctggagaacgggaaggagac gctgcagcgcacgg;

A*2614:

(SEQ ID NO: 159)
gctcccactccatgaggtatttctacacCtccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtattgggaccggaaCacacggaatgtgaaggcccactcacagactgaccgagcga acctggggaccctgcgcggctactacaaccagagcgaggacggttctcacaccatccagaggatgtatggctgcga cgtggggccggacgggcgcttcctccgcgggtaccAgcaggacgcTtacgacggcaaggattacatcgccctgaac gaggacctgcgctcttggaccgcggcggacatggcggctcagatcacccagcgcaagtgggaggcggcccatgAgg cggagcagTggagagcctacctggagggccggtgcgtggagtggctccgcagatacctggagaacgggaaggagac gctgcagcgcacgg;

A*2615:

(SEQ ID NO: 160)
atggccgtcatggcgccccgaaccctcgtcctgctactctcgggggccctggccctgacccagacctgggcgggct cccactccatgaggtatttctacacctccgtgtcccggcccggccgcggggagccccgcttcatcgccgtgggcta cgtggacgacacgcagttcgtgcggttGgacagcgacgccgcgagccagaggatggagccgcgggcgccgtggata gagcaggaggggccggagtattgggaccggaacacacggaatgtgaaggcccactcacagactgaccgagcgaacc tggggaccctgcgcggctactacaaccagagcgaggacggttctcacaccatccagaggatgtatggctgcgacgt ggggccggacgggcgcttcctccgcgggtaccagcaggacgcttacgacggcaaggattacatcgccctgaacgag gacctgcgctcttggaccgcggcggacatggcggctcagatcacccagcgcaagtgggagacggcccatgaggcgg agcagtggagagcctacctggagggccggtgcgtggagtggctccgcagatacctggagaacgggaaggagacgct gcagcgcacggacgccccc aagacgcatatgactcaccacgctgtctctgaccatgaggccaccctgaggtgctgg gccctgagcttctaccctgcggagatcacactgacctggcagcgggatggggaggaccagacccaggacacggagc tcgtggagaccaggcctgcaggggatggaccttccagaagtgggcgtctgtggtggtgccttctggacaggagca gagatacacctgccatgtgcagcatgagggtctgcccaagcccctcaccctgagatgggag;

A*2616:
(SEQ ID NO: 161)
gctcccactccatgaggtatttctCcacatccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtattgggaccggaaCacacggaatgtgaaggcccactcacagactgaccgagcga acctggggaccctgcgcggctactacaaccagagcgaggacggttctcacaccatccagaggatgtatggctgcga cgtggggccggacgggcgcttcctccgcgggtaccAgcaggacgcttacgacggcaaggattacatcgccctgaac gaggacctgcgctcttggaccgcggcggacatggcggctcagatcacccAgcgcaagtgggagAcggcccatgAgg cggagcagTggagagcctacctggagggccggtgcgtggagtggctccgcagatacctggagaacgggaaggagac gctgcagcgcacgg;

A*2617:
(SEQ ID NO: 162)
gctcccactccatgaggtatttctacacctccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtattgggaccggaacacacggaatgtgaaggcccactcacagactgaccgagcga acctggggaccctgcgcggctactacaaccagagcgaggacggtActcacaccatccagaggatgtatggctgcga cgtggggccggacgggcgcttcctccgcgggtaccagcaggacgcttacgacggcaaggattacatcgccctgaac gaggacctgcgctcttggaccgcggcggacatggcggctcagatcacccagcgcaagtgggagacggcccatgagg cggagcagtggagagcctacctggagggccggtgcgtggagtggctccgcagatacctggagaacgggaaggagac gctgcagcgcacgg;

A*2618:
(SEQ ID NO: 163)
gctcccactccatgaggtatttctacacctccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtattgggaccggaacacacggaatgtgaaggcccactcacagactgaccgagcga acctggggaccctgcgcggctactacaaccagagcgaggacggttctcacaccatccagaggatgtatggctgcga cgtggggccggacgggcgcttcctccgcgggtaccAgcaggacgcTtacgacggcaaggattacatcgccctgaac gaggacctgcgctcttggaccgcggcggacatggcggctcagatcacccagcgcaagtgggaggcggcccGtgTgg cggagcagTggagagcctacctggagggccggtgcgtggagtggctccgcagatacctggagaacgggaaggagac gctgcagcgcacgg;

A*29010101:
(SEQ ID NO: 164)
atggccgtcatggcgccccgaaccctcctcctgctactcttgggggccctggccctgacccagacctgggcgggct cccactccatgaggtatttcaccacatccgtgtcccggcccggccgcggggagccccgcttcatcgccgtgggcta cgtggacgacacgcagttcgtgcggtttgacagcgacgccgcgagccagaggatggagccgcgggcaccgtggata gagcaggaggggccggagtattgggacctgcagacacggaatgtgaaggccagtcacagactgaccgagcgaacc tggggaccctgcgcggctactacaaccagagcgaggccggttctcacaccatccagatgatgtatggctgcCacgt ggggtcggacgggcgcttcctccgcgggtaccggcaggacgcctacgacggcaaggattacatcgccttgaacgag gacctgcgctcttggaccgcggcggacatggcggctcagatcacccagcgcaagtgggaggcggcccgtgtggcgg agcagttgagagcctacctggagggcacgtgcgtggagtggctccgcagatacctggagaacgggaaggagacgct gcagcgcacggacgcccccaagacgcatatgactcaccacgctgtctctgaccatgaggccacccctgaggtgctgg gccctgagcttctaccctgcggagatcacactgacctggcagcgggatgggaggaccagacccaggacacggagc ttgtggagaccaggcctgcaggggatggaaccttccagaagtgggcgtctgtggtggtgccttctggacaggagca gagatacacctgccatgtgcagcatgagggtctgcccaagcccctcacccctgagatgggag;

A*2902:

(SEQ ID NO: 165)
atggccgtcatggcgcccgaaccctcctcctgctactcttgggggccctggccctgacccagacctgggcgggct cccactccatgaggtatttcaccacatccgtgtcccggcccggccgcggggagccccgcttcatcgccgtgggcta cgtggacgacacgcagttcgtgcggtttgacagcgacgccgcgagccagaggatggagccgcgggcAccgtggata gagcaggaggggccggagtattgggacctgcagacacggaatgtgaaggcccagtcacagactgaccgagcgaacc tggggaccctgcgcggctactacaaccagagcgaggccggttctcacaccatccagatgatgtatggctgcgacgt ggggtcggacgggcgcttcctccgcgggtaccggcaggacgcctacgacggcaaggattacatcgccttgaacgag gacctgcgctcttggaccgcggcggacatggcggctcagatcacccagcgcaagtgggaggcggcccgtgtggcgg agcagttgagagcctacctggagggcacgtgcgtggagTggctccgcagatacctggagaacgggaaggagacgct gcagcgcacggacgcccccaagacgcatatgactcaccacgctgtctctgaccatgaggccaccctgaggtgctgg gccctgagcttctaccctgcggagatcacactgacctggcagcgggatggggaggaccagacccaggacacggagc ttgtggagaccaggcctgcaggggatggaaccttccagaagtgggcgtctgtggtggtgccttctggaCaggagca gagatacacctgccatgtgcagcatgagggtctgcccaagcccctcaccctgagatgggag;

A*2903:

(SEQ ID NO: 166)
atggccgtcatggcgcccgaaccctcctcctgctactcttgggggccctggccctgacccagacctgggcgggct cccactccatgaggtatttcaccacatccgtgtcccggcccggccgcggggagccccgcttcatcgccgtgggcta cgtggacgacacgcagttcgtgcggtttgacagcgacgccgcgagccagaggatggagccgcgggcAccgtggata gagcaggaggggccggagtattgggacctgcagacacggaatgtgaaggcccagtcacagactgaccgagcgaacc tggggaccctgcgcggctactacaaccagagcgaggccggttctcacaccatccagatgatgtatggctgcgacgt ggggtcggacgggcgcttcctccgcgggtaccggcaggacgcctacgacggcaaggattacatcgccttgaacgag gacctgcgctcttggaccgcggcggacatggcggctcagatcacccagcgcaagtgggaggcggcccgtgtggcgg agcagttgagagcctacctggagggcacgtgcgtggacgggctccgcagatacctggagaacgggaaggagacgct gcagcgcacggacgcccccaagacgcatatgactcaccacgctgtctctgaccatgaggccaccctgaggtgctgg gccctgagcttctaccctgcggagatcacactgacctggcagcgggatggggaggaccagacccaggacacggagc ttgtggagaccaggcctgcaggggatggaaccttccagaagtgggcgtctgtggtggtgccttctggaCaggagca gagatacacctgccatgtgcagcatgagggtctgcccaagcccctcaccctgagatgggag;

A*2904:

(SEQ ID NO: 167)
gctcccactccatgaggtatttcaccacatccgtgtcccggcccggccgcggggagccccgcttcatcgccgtggg ctacgtggacgacacgcagttcgtgcggtttgacagcgacgccgcgagccagaggatggagccgcgggcaccgtgg atagagcaggaggggccggagtattgggacctgcagacacggCatgtgaaggcccagtcacagactgaccgagcga acctggggaccctgcgcggctactacaaccagagcgaggccggttctcacaccatccagatgatgtatggctgcga cgtggggtcggacgggcgcttcctccgcgggtaccggcaggacgcctacgacggcaaggattacatcgccttgaac gaggacctgcgctcttggaccgcggcggacatggcggctcagatcacccagcgcaagtgggaggcggcccGtgtgg cggagcagttgagagcctacctggagggcacgtgcgtggagtggctccgcagatacctggagaacgggaaggagac gctgcagcgcacgg;

A*2905:

(SEQ ID NO: 168)
gctcccactccatgaggtatttcaccacatccgtgtcccggcccggccgcggggagccccgcttcatcgccgtggg ctacgtggacgacacgcagttcgtgcggtttgacagcgacgccgcgagccagaggatggagccgcgggcAccgtgg atagagcaggaggggccggagtattgggacctgcagacacggaatgtgaaggcccagtcacagactgaccgagcga acctggggaccctgcgcggctactacaaccagagcgaggccggttctcacaccatccagatgatgtatggctgcga -continued cgtggggtcggacgggcgcttcctccgcgggtaccggcaggacgcctacgacggcaaggattacatcgccttgaac gaggacctgcgctcttggaccgcggcggacatggcggctcagatcacccagcgcaagtgggaggcggcccatgagg cggagcagcAgagagcctacctggagggcacgtgcgtggagTggctccgcagatacctggagaacgggaaggagac gctgcagcgcacgg;

A*2906: (SEQ ID NO: 169)

gctcccactccatgaggtatttcaccacatccgtgtcccggcccggccgcggggagccccgcttcatcgccgtggg ctacgtggacgacacgcagttcgtgcggtttgacagcgacgccgcgagccagaggatggagccgcgggcAccgtgg atagagcaggaggggccggagtattgggacctgcagacacggaatgtgaaggcccagtcacagactgaccgagcga acctggggaccctgcgcggctactacaaccagagcgaggccggttctcacaccatccagatgatgtatggctgcga cgtggggtcggacgggcgcttcctccgcgggtaccggcaggacgcctacgacggcaaggattacatcgccttgaac gaggacctgcgctcttggaccgcggcggacatggcggctcagatcacccagcgcaagtgggaggcggcccgtgtgg cggagcagtTgagagcctacctggagggcacgtgcgtggagTggctccgcagatacctggagaacgggaaggagac gctgcagcgcgcgg;

A*2907: (SEQ ID NO: 170)

gctcccactccatgaggtatttcaccacatccgtgtcccggcccggccgcggggagccccgcttcatcgccgtggg ctacgtggacgacacgcagttcgtgcggtttgacagcgacgccgcgagccagaggatggagccgcgggcAccgtgg atagagcaggaggggccggagtattgggacctgcagacacggaatgtgaaggcccagtcacagactgaccgagcga acctggggaccctgcgcggctactacaaccagagcgaggccggttctcacaccctccagatgatgtTtggctgcga cgtggggtcggacgggcgcttcctccgcgggtaccggcaggacgcctacgacggcaaggattacatcgccttgaac gaggacctgcgctcttggaccgcggcggacatggcggctcagatcacccagcgcaagtgggaggcggcccgtgtgg cggagcagtTgagagcctacctggagggcacgtgcgtggagTggctccgcagatacctggagaacgggaaggagac gctgcagcgcacgg;

A*3001: (SEQ ID NO: 171)

atggccgtcatggcgccccgaaccctcctcctgctactctcgggggccctggccctgacccagacctgggcgggct cccactccatgaggtatttctCcacatccgtgtcccggcccggcagtggagagccccgcttcatcgcagtgggcta cgtggacgacacgcagttcgtgcggttcgacagcgacgccgcgagccagaggatggagccgcgggcgccgtggata gagcaggagaggccTgagtattgggaccaggagacacggaatgtgaaggcccagtcacagactgaccgagtggacc tggggaccctgcgcggctactacaaccagagcgaggccggttctcacaccatccagataatgtatggctgcgacgt ggggtcggacgggcgcttcctccgcgggtatgaacagcacgcctacgacggcaaggattacatcgccctgaacgag gacctgcgctcttggaccgcggcggacatggcggctcagatcacccagcgcaagtgggaggcggcccgtTgggcgg agcagttgagagcctacctggagggcacgtgcgtggagtggctccgcagatacctggagaacgggaaggagacgct gcagcgcacggaccccccaagacacatatgacccaccacccatctctgaccatgaggccaccctgaggtgctgg gccctgggcttctaccctgcggagatcacactgacctggcagcgggatgggaggaccagacccaggacacggagc tcgtggagaccaggcctgcaggggatggaaccttccagaagtgggcggctgtggtggtgccttctggagaggagca gagatacacctgccatgtgcagcatgagggtctgcccaagccctcaccctgagatgggag;

A*3002: (SEQ ID NO: 172)

atggccgtcatggcgccccgaaccctcctcctgctactctcgggggccctggccctgacccagacctgggcgggct cccactccatgaggtatttctccacatccgtgtcccggcccggcagtggAgagccccgcttcatcgcagtgggcta cgtggacgacacgcagttcgtgcggttcgacagcgacgccgcgagccagaggatggagccgcgggcgccgtggata gagcaggagaggccTgagtattgggaccaggagacacggaatgtgaaggcccactcacagactgaccgagagaacc tggggaccctgcgcggctactacaaccagagcgaggccggttctcacaccatccagataatgtatggctgcgacgt -continued ggggtcggacgggcgcttcctccgcgggtatgaacagcacgcctacgacggcaaggattacatcgccctgaacgag gacctgcgctcttggaccgcggcggacatggcggctcagatcacccagcgcaagtgggaggcggcccgtCgggcgg agcagttgagagcctacctggagggcaCgtgcgtggagTggctccgcagatacctggagaacgggaaggagacgct gcagcgcacggaccccccaagacacatatgacccaccaccccatctctgaccatgaggccaccctgaggtgctgg gccctgggcttctaccctgcggagatcacactgacctggcagcgggatggggaggaccagacccaggacacggagc tcgtggagaccaggcctgcaggggatggaaccttccagaagtgggcggctgtggtggtgccttctggagaggagca gagatacacctgccatgtgcagcatgagggtctgcccaagcccctcaccctgagatgggag;

A*3003:
(SEQ ID NO: 173)
ggctcccactccatgaggtatttctccacatccgtgtcccggcccggcagtggAgagccccgcttcatcgcagtgg gctacgtggacgacacgcagttcgtgcggttcgacagcgacgccgcgagccagaggatggagccgcgggcgccgtg gatagagcaggaggggccggagtattgggaccaggagacacggaatgtgaaggcccactcacagactgaccgagag aacctggggaccctgcgcggctactacaaccagagcgaggccggttctcacaccatccagataatgtatggctgcg acgtggggtcggacgggcgcttcctccgcgggtatgaacagcacgcctacgacggcaaggattacatcgccctgaa cgaggacctgcgctcttggaccgcggcggacatggcggctcagatcacccagcgcaagtgggaggcggcccgtCgg gcggagcagttgagagcctacctggagggcaCgtgcgtggagTggctccgcagatacctggagaacgggaaggaga cgctgcagcgcacggaccccccaagacacatatgacccaccaccccatctctgaccatgaggccaccctgaggtg ctgggccctgggcttctaccctgcggagatcacactgacctggcagcgggatggggaggaccagacccaggacacg gagctcgtggagaccaggcctgcaggggatggaaccttccagaagtgggcggctgtggtggtgccttctggagagg agcagag;

A*3004:
(SEQ ID NO: 174)
gctcccactccatgaggtatttctccacatccgtgtcccggcccggcagtggAgagccccgcttcatcgcagtggg ctacgtggacgacacgcagttcgtgcggttcgacagcgacgccgcgagccagaggatggagccgcgggcgccgtgg atagagcaggagaggcctgagtattgggaccaggagacacggaatgtgaaggcccactcacagactgaccgagaga acctggggaccctgcgcggctactacaaccagagcgaggccggttctcacaccatccagataatgtatggctgcga cgtggggtcggacgggcgcttcctccgcgggtatgaacagcacgcctacgacggcaaggattacatcgccctgaac gaggacctgcgctcttggaccgcggcggacatggcggctcagatcacccagcgcaagtgggaggcggcccatgTgg cggagcagtggagagcctacctggagggcacgtgcgtggagTggctccgcagatacctggagaacgggaaggagac gctgcagcgcacgg;

A*3006:
(SEQ ID NO: 175)
gctcccactccatgaggtatttctccacatccgtgtcccggcccggcagtggagagccccgcttcatcgcagtggg ctacgtggacgacGcgcagttcgtgcggttcgacagcgacgccgcgagccagaggatggagccgcgggcgccgtgg atagagcaggagaggcctgagtattgggaccaggagacacggaatgtgaaggcccactcacagactgaccgagaga acctggggaccctgcgcggctactacaaccagagcgaggccggttctcacaccatccagataatgtatggctgcga cgtggggtcggacgggcgcttcctccgcgggtatgaacagcacgcctacgacggcaaggattacatcgccctgaac gaggacctgcgctcttggaccgcggcggacatggcggctcagatcacccagcgcaagtgggaggcggcccatgtgg cggagcagtggagagcctacctggagggcacgtgcgtggagtggctccgcagatacctggagaacgggaaggagac gctgcagcgcacgg;

A*3007:
(SEQ ID NO: 176)
gctcccactccatgaggtatttctccacatccgtgtcccggcccggcagtggagagccccgcttcatcgcagtggg ctacgtggacgacacgcagttcgtgcggttcgacagcgacgccgcgagccagaggatggagccgcgggcgccgtgg -continued atagagcaggagaggcctgagtattgggacgaggagacagggaaAgtgaaggcccactcacagactgaccgagaga
acctggggaccctgcgcggctactacaaccagagcgaggccggttctcacaccatccagataatgtatggctgcga
cgtggggtcggacgggcgcttcctccgcgggtatgaacagcacgcctacgacggcaaggattacatcgccctgaac
gaggacctgcgctcttggaccgcggcggacatggcggctcagatcacccagcgcaagtgggaggcggcccgtCggg
cggagcagttgagagcctacctggagggcaCgtgcgtggagTggctccgcagatacctggagaacgggaaggagac
gctgcagcgcacgg;

A*3008:
(SEQ ID NO: 177)
atggccgtcatggcgccccgaaccctcctcctgctactctcgggggccctggccctgacccagacctgggcgggct
ctcactccatgaggtatttctacacCtccgtgtcccggcccggcagtggagagccccgcttcatcgcagtgggcta
cgtggacgacacgcagttcgtgcggttcgacagcgacgccgcgagccagaggatggagccgcgggcgccgtggata
gagcaggagaggccTgagtattgggaccaggagacacggaatgtgaaggcccagtcacagactgaccgagtggacc
tggggaccctgcgcggctactacaaccagagcgaggccggttctcacaccatccagataatgtatggctgcgacgt
ggggtcggacgggcgcttcctccgcgggtatgaacagcacgcctacgacggcaaggattacatcgccctgaacgag
gacctgcgctcttggaccgcggcggacatggcggctcagatcacccagcgcaagtgggaggcggcccgtTgggcgg
agcagttgagagcctacctggagggcacgtgcgtggagtggctccgcagatacctggagaacgggaaggagacgct
gcagcgcacggaccccccaagacacatatgacccaccacccatctctgaccatgaggccaccctgaggtgctgg
gccctgggcttctaccctgcggagatcacactgacctggcagcgggatggggaggaccagacccaggacacggagc
tcgtggagaccaggcctgcaggggatggaaccttccagaagtgggcggctgtggtggtgccttctggagaggagca
gagatacacctgccatgtgcagcatgagggtctgcccaagcccctcaccctgagatgggag;

A*3009:
(SEQ ID NO: 178)
gctcccactccatgaggtatttctccacatccgtgtcccggcccggcagtggAgagccccgcttcatcgcagtggg
ctacgtggacgacacgcagttcgtgcggttcgacagcgacgccgcgagccagaggatggagccgcgggcgccgtgg
atagagcaggagaggcctgagtattgggaccaggagacacggaatgtgaaggcccactcacagactgaccgagaga
acctggggaccctgcgcggctactacaaccagagcgaggccggttctcacaccatccagataatgtatggctgcga
cgtggggtcggacgggcgcttcctccgcgggtatgaacagcacgcctacgacggcaaggattacatcgccctgaac
gaggacctgcgctcttggaccgcggcggacatggcggctcagatcacccagcgcaagtgggaggcggcccgtgTgg
cggagcagtTgagagcctacctggagggcacgtgcgtggagTggctccgcagatacctggagaacgggaaggagac
gctgcagcgcacgg;

A*3010:
(SEQ ID NO: 179)
gctcccactccatgaggtatttctccacatccgtgtcccggcccggcagtggagagccccgcttcatcgcagtggg
ctacgtggacgacacgcagttcgtgcggttcgacagcgacgccgcgagccagaggatggagccgcgggcgccgtgg
atagagcaggagaggcctgagtattgggaccaggagacacggaatgtgaaggcccactcacagactgaccgagaga
acctggggaccctgcgcggctactacaaccagagcgaggccggttctcacaccatccagataatgCatggctgcga
cgtggggtcggacgggcgcttcctccgcgggtatgaacagcacgcctacgacggcaaggattacatcgccctgaac
gaggacctgcgctcttggaccgcggcggacatggcggctcagatcacccagcgcaagtgggaggcggcccgtcggg
cggagcagttgagagcctacctggagggcacgtgcgtggagtggctccgcagatacctggagaacgggaaggagac
gctgcagcgcacggacccccccaagacacatatgacccaccacccatctctgaccatgaggccaccctgaggtgc
tgggccctgggcttctaccctgcggagatcacactgacctggcagcgggatggggaggaccagacccaggacacgg
agctcgtggagaccaggcctgcaggggatggaaccttccagaagtgggcggctgtggtggtgccttctggagagga
gcagagatacacctgccatgtgcagcatgagggtctgcccaagcccctcaccctgagatggg;

A*3011:
(SEQ ID NO: 180)
gctcccactccatgaggtatttctCcacatccgtgtcccggcccggcagtggagagccccgcttcatcgcagtggg ctacgtggacgacacgcagttcgtgcggttcgacagcgacgccgcgagccagaggatggagccgcgggcgccgtgg atagagcaggaggggccggagtatgggaccaggagacacggaatgtgaaggcccagtcacagactgaccgagtgg acctggggaccctgcgcggctactacaaccagagcgaggccggttctcacaccatccagataatgtatggctgcga cgtggggtcggacgggcgcttcctccgcgggtatgaacagcacgcctacgacggcaaggattacatcgccctgaac gaggacctgcgctcttggaccgcggcggacatggcggctcagatcacccagcgcaagtgggaggcggcccgtTggg cggagcagttgagagcctacctggagggcacgtgcgtggagtggctccgcagatacctggagaacgggaaggagac gctgcagcgcacgg;

A*3012:
(SEQ ID NO: 181)
gctcccactccatgaggtatttctccacatccgtgtcccggcccggccgcggggagccccgcttcatcgcagtggg ctacgtggacgacacgcagttcgtgcggttcgacagcgacgccgcgagccagaggatggagccgcgggcgccgtgg atagagcaggagaggccTgagtattgggaccaggagacacggaatgtgaaggcccactcacagactgaccgagaga acctggggaccctgcgcggctactacaaccagagcgaggccggttctcacaccatccagataatgtatggctgcga cgtggggtcggacgggcgcttcctccgcgggtatgaacagcacgcctacgacggcaaggattacatcgccctgaac gaggacctgcgctcttggaccgcggcggacatggcggctcagatcacccagcgcaagtgggaggcggcccgtCggg cggagcagttgagagcctacctggagggcaCgtgcgtggagTggctccgcagatacctggagaacgggaaggagac gctgcagcgcacggaccccccccaagacacatatgacccaccaccccatctctgaccatgaggccaccctgaggtgc tgggccctgggcttctaccctgcggagatcacactgacctggcagcgggatggggaggaccagacccaggacacgg agctcgtggagaccaggcctgcaggggatggaaccttccagaagtgggcggctgtggtggtgccttctggagagga gcagagatacacctgccatgtgcagcatgagggtctgcccaagcccctcaccctgagatggg;

A*310102:
(SEQ ID NO: 182)
atggccgtcatggcgccccgaaccctcctcctgctactcttgggggccctggccctgacccagacctgggcgggct cccactccatgaggtatttcaccacatccgtgtcccggcccggccgcggggagccccgcttcatcgccgtgggcta cgtggacgacacgcagttcgtgcggttcgacagcgacgccgcgagccagaggatggagccgcgggcgccgtggata gagcaggagaggccTgagtattgggaccaggagacacggaatgtgaaggcccactcacagattgaccgagtggacc tggggaccctgcgcggctactacaaccagagcgaggccggttctcacaccatccagatgatgtatggctgcgacgt ggggtcggacgggcgcttcctccgcgggtaccagcaggacgcctacgacggcaaggattacatcgccTtgaacgag gacctgcgctcttggaccgcggcggacatggcggctcagatcacccagcgcaagtgggaggcggcccgtgtggcgg agcagttgagagcctacctggagggcacgtgcgtggagtggctccgcagatacctggagaacgggaaggagacgct gcagcgcacggaccccccccaagacgcatatgactcaccacgctgtctctgaccatgaggccaccctgaggtgctgg gccctgagcttctaccctgcggagatcacactgacctggcagcgggatggggaggaccagacccaggacacggagc tcgtggagaccaggcctgcaggggatggaaccttccagaagtgggcgtctgtggtggtgccttctggacaggagca gagatacacctgccatgtgcagcatgagggtctCcccaagcccctcaccctgagatgggag;

A*3102:
(SEQ ID NO: 183)
gctcccactccatgaggtatttcaccacatccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggagaggcctgagtattgggaccaggagacacggaaAgtgaaggcccactcacagaTtgaccgagtgg acctggggaccctgcgcggctactacaaccagagcgaggccggttctcacaccatccagatgatgtatggctgcga cgtggggTcggacgggcgcttcctccgcgggtaccAgcaggacgcctacgacggcaaggattacatcgccTtgaac -continued gaggacctgcgctcttggaccgcggcggacatggcggctcagatcacccagcgcaagtgggaggcggcccGtgtgg
cggagcagtTgagagcctacctggagggcacgtgcgtggagTggctccgcagatacctggagaacgggaaggagac
gctgcagcgcacgg;

A*3103:
(SEQ ID NO: 184)
gctcccactccatgaggtatttcaccacatccgtgtcccggcccggccgcggggagccccgcttcatcgccgtggg
ctacgtggacgacacgcagttcgtgcggttcgacagcgacgccgcgagccagaggatggagccgcgggcgccgtgg
atagagcaggagaggcctgagtattgggaccaggagacacggaatgtgaaggcccactcacagaTtgaccgagtgg
acctggggaccctgcgcggctactacaaccagagcgaggacggttctcacaccatccagataatgtatggctgcga
cgtggggtcggacgggcgcttcctccgcgggtaccggcaggacgcTtacgacggcaaggattacatcgccctgaac
gaggacctgcgctcttggaccgcggcggacatggcggctcagatcacccagcgcaagtgggaggcggcccGtgtgg
cggagcagtTgagagcctacctggagggcacgtgcgtggagTggctccgcagatacctggagaacgggaaggagac
gctgcagcgcacgg;

A*3104:
(SEQ ID NO: 185)
atggccgtcatggcgccccgaaccctcctcctgctactcttgggggccctggccctgacccagacctgggcgggct
cccactccatgaggtatttcaccacatccgtgtcccggcccggccgcggggagccccgcttcatcgccgtgggcta
cgtggacgacacgcagttcgtgcggttcgacagcgacgccgcgagccagaggatggagccgcgggcgccgtggata
gagcaggagaggcctgagtattgggaccaggagacacggaatgtgaaggcccactcacagattgaccgagtggacc
tggggaccctgcgcggctactacaaccagagcgaggccggttctcacaccatccagataatgtatggctgcgacgt
ggggtcggacgggcgcttcctccgcgggtaccggcaggacgcTtacgacggcaaggattacatcgccctgaacgag
gacctgcgctcttggaccgcggcggacatggcggctcagatcacccagcgcaagtgggaggcggcccgtgtggcgg
agcagttgagagcctacctggagggcacgtgcgtggagtggctccgcagatacctggagaacgggaaggagacgct
gcagcgcacggaccccccaagacgcatatgactcaccacgctgtctctgaccatgaggccaccctgaggtgctgg
gccctgagcttctaccctgcggagatcacactgacctggcagcgggatggggaggaccagacccaggacacggagc
tcgtggagaccaggcctgcaggggatggaaccttccagaagtgggcgtctgtggtggtgccttctggacaggagca
gagatacacctgccatgtgcagcatgagggtctCcccaagcccctcaccctgagatgggag;

A*3105:
(SEQ ID NO: 186)
gctcccactccatgaggtatttcaccacatccgtgtcccggcccggccgcggggagccccgcttcatcgccgtggg
ctacgtggacgacacgcagttcgtgcggttcgacagcgacgccgcgagccagaggatggagccgcgggcgccgtgg
atagagcaggagaggccTgagtattgggaccaggagacacggaatgtgaaggcccactcacagaTtgaccgagtgg
acctggggaccctgcgcggctactacaaccagagcgaggccggttctcacaccatccagatgatgtatggctgcga
cgtggggTcggacgggcgcttcctccgcgggtaccAgcaggacgcctacgacggcaaggattacatcgccTtgaac
gaggacctgcgctcttggaccgcggcggacatggcggctcagatcacccagcgcaagtgggaggcggcccGtgtgg
cggagcagtTgagagcctacctggagggcacgtgcgtggacgggctccgcagatacctggagaacgggaaggagac
gctgcagcgcacgg;

A*3106:
(SEQ ID NO: 187)
gctcccactccatgaggtatttcaccacatccgtgtcccggcccggccgcggggagccccgcttcatcgccgtggg
ctacgtggacgacacgcagttcgtgcggttcgacagcgacgccgcgagccagaggatggagccgcgggcgccgtgg
atagagcaggagaggccTgagtattgggaccaggagacacggaatgtgaaggcccactcacagaTtgaccgagtgg
acctggggaccctgcgcggctactacaaccagagcgaggccggttctcacaccatccagatgatgtatggctgcga
cgtggggTcggacgggcgcttcctccgcgggtaccggcaggacgcctacgacggcaaggattacatcgccTtgaac
gaggacctgcgctcttggaccgcggcggacatggcggctcagatcacccagcgcaagtgggaggcggcccGtgtgg -continued cggagcagtTgagagcctacctggagggcacgtgcgtggagTggctccgcagatacctggagaacgggaaggagac gctgcagcgcacgg;

A*3107: (SEQ ID NO: 188)

gctcccactccatgaggtatttcaccacatccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggagaggccTgagtattgggaccaggagacacggaaagtgaaggcccactcacagactgaccgagaga acctgcggatcgcgctcCgctactacaaccagagcgaggccggttctcacaccatccagatgatgtatggctgcga cgtggggtcggacgggcgcttcctccgcgggtaccAgcaggacgcctacgacggcaaggattacatcgccTtgaac gaggacctgcgctcttggaccgcggcggacatggcggctcagatcacccagcgcaagtgggaggcggcccgtgTgg cggagcagtTgagagcctacctggagggcacgtgcgtggagTggctccgcagatacctggagaacgggaaggagac gctgcagcgcacgg;

A*3108: (SEQ ID NO: 189)

gctcccactccatgaggtatttcAccacatccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtattgggacgaggagacaGggaaagtgaaggcccactcacagactgaccgagaga acctgcggatcgcgctcCgctactacaaccagagcgaggccggttctcacaccatccagatgatgtatggctgcga cgtggggtcggacgggcgcttcctccgcgggtaccAgcaggacgcctacgacggcaaggattacatcgccTtgaac gaggacctgcgctcttggaccgcggcggacatggcggctcagatcacccagcgcaagtgggaggcggcccgtgtgg cggagcagtTgagagcctacctggagggcacgtgcgtggagTggctccgcagatacctggagaacgggaaggagac gctgcagcgcacgg;

A*3109: (SEQ ID NO: 190)

gctcccactccatgaggtatttcaccacatccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggagaggcctgagtattgggaccaggagacacggaatgtgaaggGccactcacagattgaccgagtgg acctggggaccctgcgcggctactacaaccagagcgaggccggttctcacaccatccagatgatgtatggctgcga cgtggggtcggacgggcgcttcctccgcgggtaccagcaggacgcctacgacggcaaggattacatcgccttgaac gaggacctgcgctcttggaccgcggcggacatggcggctcagatcacccagcgcaagtgggaggcggcccgtgtgg cggagcagttgagagcctacctggagggcacgtgcgtggagtggctccgcagatacctggagaacgggaaggagac gctgcagcgcacgg;

A*3201: (SEQ ID NO: 191)

atggccgtcatggcgccccgaaccctcctcctgctactcttgggggccctggccctgacccagacctgggcgggct cccactccatgaggtatttcttcacatccgtgtcccggcccggccgcggggagccccgcttcatcgccgtgggcta cgtggacgacacgcagttcgtgcggtttgacagcgacgccgcgagccagaggatggagccgcgggcgccgtggata gagcaggaggggccggagtattgggaccaggagacacggaatgtgaaggcccactcacagactgaccgagagaGcc tgcggatcgcgctccgctactacaaccagagcgaggccggttctcacaccatccagatgatgtatggctgcgacgt ggggccggacgggcgcctcctccgcgggtaccagcaggacgcctacgacggcaaggattacatcgccttgaacgag gacctgcgctcttggaccgcggcggacatggcggctcagatcacccagcgcaagtgggaggcggcccgtgtggcgg agcagtTgagagcctacctggagggcacgtgcgtggagtggctccgcagatacctggagaacgggaaggagacgct gcagcgcacggacgcccccaagacgcatatgactcaccacgctgtctctgaccatgaggccaccctgaggtgctgg gccctgagcttctaccctgcggagatcacactgacctggcagcgggatggggaggaccagacccaggacacggagc -continued tTgtggagaccaggcctgcaggggatggaaccttccagaagtgggcgtctgtggtggtgccttctggaCaggagca gagatacacctgccatgtgcagcatgagggtctgcccaagcccctcaccctgagatgggag;

A*3202:

(SEQ ID NO: 192)
atggccgtcatggcgccccgaaccctcctcctgctactcttgggggccctggccctgacccagacctgggcgggct cccactccatgaggtatttcttcacatccgtgtcccggcccggccgcggggagcccgcttcatcgccgtgggcta cgtggacgacacgcagttcgtgcggtttgacagcgacgccgcgagccagaggatggagccgcgggcgccgtggata gagcaggaggggccggagtattgggaccaggagacacggaatgtgaaggcccactcacagactgaccgagagaGcc tgcggatcgcgctccgctactacaaccagagcgaggccggttctcacaccatccagatgatgtatggctgcgacgt ggggccggacgggcgcctcctccgcgggtaccagcaggacgcctacgacggcaaggattacatcgccttgaacgag gacctgcgctcttggaccgcggcggacatggcggctcagatcacccagcgcaagtgggaggcggcccatgtggcgg agcagcAgagagcctacctggagggcacgtgcgtggagtggctccgcagatacctggagaacgggaaggagacgct gcagcgcacggacgcccccaagacgcatatgactcaccacgctgtctctgaccatgaggccaccctgaggtgctgg gccctgagcttctaccctgcggagatcacactgacctggcagcgggatgggggaggaccagacccaggacacggagc tTgtggagaccaggcctgcaggggatggaaccttccagaagtgggcgtctgtggtggtgccttctggaCaggagca gagatacacctgccatgtgcagcatgagggtctgcccaagcccctcaccctgagatgggag;

A*3203:

(SEQ ID NO: 193)
gctcccactccatgaggtatttcttcacatccgtgtcccggcccggccgcggggagcccgcttcatcgccgtggg ctacgtggacgacacgcagttcgtgcggtttgacagcgacgccgcgagccagaggatggagccgcgggcgccgtgg atagagcaggaggggccggagtattgggaccaggagacacggaatgtgaaggcccactcacagactgaccgagaga acctgcggatcgcgctcCgctactacaaccagagcgaggccggttctcacaccatccagatgatgtatggctgcga cgtggggccggacgggcgcCtcctccgcgggtaccagcaggacgcctacgacggcaaggattacatcgccttgaac gaggacctgcgctcttggaccgcggcggacatggcggctcagatcacccagcgcaagtgggaggcggcccGtgtgg cggagcagtTgagagcctacctggagggcacgtgcgtggagtggctccgcagatacctggagaacgggaaggagac gctgcagcgcacgg;

A*3204:

(SEQ ID NO: 194)
gctcccactccatgaggtatttcttcacatccgtgtcccggcccggccgcggggagcccgcttcatcgccgtggg ctacgtggacgacacgcagttcgtgcggttcgacagcgacgccgcgagccagaggatggagccgcgggcgccgtgg atagagcaggaggggccggagtattgggaccaggagacacggaatgtgaaggcccactcacagactgaccgagaga Gcctgcggatcgcgctccgctactacaaccagagcgaggccggttctcacaccatccagataatgtatggctgcga cgtggggtcggacgggcgcttcctccgcgggtaccggcaggacgcctacgacggcaaggattacatcgccctgaac gaggacctgcgctcttggaccgcggcggacatggcggctcagatcaccaagcgcaagtgggaggcggcccatgagg cggagcagttgagagcctacctggaTggcaCgtgcgtggagTggctccgcagatacctggagaacgggaaggagac gctgcagcgcacgg;

A*3205:

(SEQ ID NO: 195)
atggccgtcatggcgccccgaaccctcctcctgctactcttgggggccctggccctgacccagacctgggcgggct cccactccatgaggtatttcttcacatccgtgtcccggcccggccgcggggagcccgcttcatcgccgtgggcta cgtggacgacacgcagttcgtgcggtttgacagcgacgccgcgagccagaggatggagccgcgggcgccgtggata gagcaggaggggccggagtattgggaccaggagacagggaaAgtgaaggcccactcacagactgaccgagagaGcc tgcggatcgcgctccgctactacaaccagagcgaggccggttctcacaccatccagatgatgtatggctgcgacgt ggggccggacgggcgcctcctccgcgggtaccagcaggacgcctacgacggcaaggattacatcgccttgaacgag gacctgcgctcttggaccgcggcggacatggcggctcagatcacccagcgcaagtgggaggcggccgtgtggcgg A*3206:
(SEQ ID NO: 196)
gctcccactccatgaggtatttcttcacatccgtgtcccggcccggccgcggggagccccgcttcatcgccgtggg ctacgtggacgacacgcagttcgtgcggtttgacagcgacgccgcgagccagaggatggagccgcgggcgccgtgg atagagcaggaggggccggagtattgggaccaggagacacggaatgtgaaggcccactcacagactgaccgagaga Gcctgcggatcgcgctccgctactacaaccagagcgaggccggttctcacaccatccagatgatgtatggctgcga cgtggggccggacgggcgcctcctccgcgggtaccagcaggacgcctacgacggcaaggattacatcgccttgaac gaggacctgcgctcttggaccgcggcggacatggcggctcagatcacccagcgcaagtgggaggcggcccatgTgg cggagcagtTgagagcctacctggagggcaCgtgcgtggagTggctccgcagatacctggagaacgggaaggagac gctgcagcgcacgg;

A*3207:
(SEQ ID NO: 197)
gctcccactccatgaggtatttctCcacatccgtgtcccggcccggccgcggggagccccgcttcatcgccgtggg ctacgtggacgacacgcagttcgtgcggtttgacagcgacgccgcgagccagaggatggagccgcgggcgccgtgg atagagcaggaggggccggagtattgggaccaggagacacggaatgtgaaggcccactcacagactgaccgagaga Gcctgcggatcgcgctccgctactacaaccagagcgaggccggttctcacaccatccagatgatgtatggctgcga cgtggggccggacgggcgcctcctccgcgggtaccagcaggacgcctacgacggcaaggattacatcgccttgaac gaggacctgcgctcttggaccgcggcggacatggcggctcagatcacccagcgcaagtgggaggcggcccGtgTgg cggagcagtTgagagcctacctggagggcaCgtgcgtggagTggctccgcagatacctggagaacgggaaggagac gctgcagcgcacgg;

A*3301:
(SEQ ID NO: 198)
atggccgtcatggcgccccgaaccctcctcctgctactcttgggggccctggccctgacccagacctgggcgggct cccactccatgaggtatttcaccacatccgtgtcccggcccggccgcggggagccccgcttcatcgccgtgggcta cgtggacgacacgcagttcgtgcggttcgacagcgacgccgcgagccagaggatggagccgcgggcgccgtggata gagcaggaggggccggagtattgggaccggaacacacggaatgtgaaggcccactcacagattgaccgagtggacc tggggaccctgcgcggctactacaaccagagcgaggccggttctcacaccatccagatgatgtatggctgcgacgt ggggtcggacgggcgcttcctccgcgggtaccagcaggacgcctacgacggcaaggattacatcgccttgaacgag gacctgcgctcttggaccgcggcggacatggcggctcagatcacccagcgcaagtgggaggcggcccgtgtggcgg agcagttgagagcctacctggagggcacgtgcgtggagtggctccgcagacacctggagaacgggaaggagacgct gcagcgcacggaccccccaGgacgcatatgactcaccacgctgtctctgaccatgaggccaccctgaggtgctgg gccctgagcttctaccctgcggagatcacactgacctggcagcgggatgggaggaccagacccaggacacggagc tcgtggagaccaggcctgcaggggatggaaccttccagaagtgggcgtctgtggtggtgccttctggacaggagca gagatacacctgccatgtgcagcatgagggtctccccaagcccctcaccctgagatgggag;

A*3303:
(SEQ ID NO: 199)
atggccgtcatggcgccccgaaccctcctcctgctactcttgggggccctggccctgacccagacctgggcgggct cccactccatgaggtatttcaccacatccgtgtcccggcccggccgcggggagccccgcttcatcgccgtgggcta cgtggacgacacgcagttcgtgcggttcgacagcgacgccgcgagccagaggatggagccgcgggcgccgtggata -continued gagcaggaggggccggagtattgggaccggaaCacacggaatgtgaaggcccactcacagattgaccgagtggacc tggggaccctgcgcggctactacaaccagagcgaggccggttctcacaccatccagatgatgtatggctgcgacgt ggggtcggacgggcgcttcctccgcgggtaccagcaggacgcctacgacggcaaggattacatcgccTtgaacgag gacctgcgctcttggaccgcggcggacatggcggctcagatcacccagcgcaagtgggaggcggcccgtgtggcgg agcagttgagagcctacctggagggcacgtgcgtggagtggctccgcagatacctggagaacgggaaggagacgct gcagcgcacggacccccccaagacgcatatgactcaccacgctgtctctgaccatgaggccaccctgaggtgctgg gccctgagcttctaccctgcggagatcacactgacctggcagcgggatggggaggaccagacccaggacacggagc tcgtggagaccaggcctgcaggggatggaaccttccagaagtgggcgtctgtggtggtgccttctggacaggagca gagatacacctgccatgtgcagcatgagggtctCcccaagcccctcaccctgagatgggag;

A*3304:

(SEQ ID NO: 200)
gctcccactccatgaggtatttcaccacatccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtattgggaccggaacacacggaatgtgaaggcccactcacagattgaccgagtgg acctggggaccctgcgcggctactacaaccagagcgaggccggttctcacaccatccagatgatgtatggctgcga cgtggggtcggacgggcgcttcctccgcgggtaccagcaggacgcctacgacggcaaggattacatcgccttgaac gaggacctgagctcCtggaccgcggcggacatggcggctcagatcacccagcgcaagtgggaggcggcccgtgtgg cggagcagttgagagcctacctggagggcacgtgcgtggagtggctccgcagacacctggagaacgggaaggagac gctgcagcgcacgg;

A*3305:

(SEQ ID NO: 201)
gctcccactccatgaggtatttcaccacatccgtgtcccggcccggccgcggggagccccgcttcatcgccgtggg ctacgtggacgacacgcagttcgtgcggttcgacagcgacgccgcgagccagaggatggagccgcgggcgccgtgg atagagcGggaggggccggagtattgggaccggaacacacggaatgtgaaggcccactcacagattgaccgagtgg acctggggaccctgcgcggctactacaaccagagcgaggccggttctcacaccatccagatgatgtatggctgcga cgtggggtcggacgggcgcttcctccgcgggtaccagcaggacgcctacgacggcaaggattacatcgccttgaac gaggacctgcgctcttggaccgcggcggacatggcggctcagatcacccagcgcaagtgggaggcggcccgtgtgg cggagcagttgagagcctacctggagggcacgtgcgtggagtggctccgcagacacctggagaacgggaaggagac gctgcagcgcacgg;

A*3306:

(SEQ ID NO: 202)
gctcccactccatgaggtatttcaccacatccgtgtcccggcccggccgcggggagccccgcttcatcgccgtggg ctacgtggacgacacgcagttcgtgcggttcgacagcgacgccgcgagccagaggatggagccgcgggcgccgtgg atGgagcaggaggggccggagtattgggaccggaacacacggaatgtgaaggcccactcacagattgaccgagtgg acctggggaccctgcgcggctactacaaccagagcgaggccggttctcacaccatccagatgatgtatggctgcga cgtggggtcggacgggcgcttcctccgcgggtaccagcaggacgcctacgacggcaaggattacatcgccttgaac gaggacctgcgctcttggaccgcggcggacatggcggctcagatcacccagcgcaagtgggaggcggcccgtgtgg cggagcagttgagagcctacctggagggcacgtgcgtggagtggctccgcagatacctggagaacgggaaggagac gctgcagcgcacggacccccccaagacgcatatgactcaccacgctgtctctgaccatgaggccaccctgaggtgc tgggccctgagcttctaccctgcggagatcacactgacctggcagcgggatggggaggaccagacccaggacacgg agctcgtggagaccaggcctgcaggggatggaaccttccagaagtgggcgtctgt;

A*3401:

(SEQ ID NO: 203)
atggccatcatggcgccccgaaccctcgtcctgctactctcgggggccctggccctgacccagacctgggcgggct cccactccatgaggtatttctacacctccgtgtcccggcccggccgcggggagccccgcttcatcgccgtgggcta cgtggacgacacgcagttcgtgcggttcgacagcgacgccgcgagccagaggatggagccgcgggcgccgtggata gagcaggaggggccggagtattgggaccggaacacacggaaagtgaaggcccagtcacagactgaccgagtggacc tggggaccctgcgcggctactacaaccagagcgaggacggttctcacaccatccagaggatgtatggctgcgacgt ggggccggacgggcgcttcctccgcgggtaccAgcaggacgcttacgacggcaaggattacatcgccctgaacgag gacctgcgctcttggaccgcggcggacatggcggctcagatcacccagcgcaagtgggagacggcccatgAggcgg agcagTggagagcctacctggagggcaCgtgcgtggagTggctccgcagatacctggagaacgggaaggagacgct gcagcgcacggacGcccccaagacacatatgactcaccacgctgtctctgaccatgaggccaccctgaggtgctgg gccctgagcttctaccctgcggagatcacactgacctggcagcgggatggggaggaccagacccaggacacggagc tcgtggagaccaggcctgcaggggatggaaccttccagaagtgggcgTctgtggtggtgccttctggaCaggagca gagatacacctgccatgtgcagcatgagggtctgcccaagcccctcaccctgagatgggag;

A*3402:

(SEQ ID NO: 204)
atggccgtcatggcgccccgaaccctcgtcctgctactctcgggggccctggccctgacccagacctgggcgggct cccactccatgaggtatttctacacctccgtgtcccggcccggccgcggggagccccgcttcatcgccgtgggcta cgtggacgacacgcagttcgtgcggttcgacagcgacgccgcgagccagaggatggagccgcgggcgccgtggata gagcaggaggggccggagtattgggaccggaacacacggaatgtgaaggcccagtcacagactgaccgagtggacc tggggaccctgcgcggctactacaaccagagcgaggacggttctcacaccatccagataatgtatggctgcgacgt ggggtcggacgggcgcttcctccgcgggtaccggcaggacgcttacgacggcaaggattacatcgccctgaacgag gacctgcgctcttggaccgcggcggacatggcggctcagatcacccagcgcaagtgggagacggcccatgAggcgg agcagtTgagagcctacctggagggcaCgtgcgtggagTggctccgcagatacctggagaacgggaaggagacgct gcagcgcacggacGcccccaagacGcatatgactcaccacgctgtctctgaccatgaggccaccctgaggtgctgg gccctgagcttctaccctgcggagatcacactgacctggcagcgggatggggaggaccagacccaggacacggagc tcgtggagaccaggcctgcaggggatggaaccttccagaagtgggcgTctgtggtggtgccttctggaCaggagca gagatacacctgccatgtgcagcatgagggtctgcccaagcccctcaccctgagatgggag;

A*3403:

(SEQ ID NO: 205)
gctcccactccatgaggtatttctacacctccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtattgggaccggaacacacggaatgtgaaggcccagtcacagactgaccgagtgg acctggggaccctgcgcggctactacaaccagagcgaggacggttctcacaccatccagataatgtatggctgcga cgtggggtcggacgggcgcttcctccgcgggtaccggcaggacgcTtacgacggcaaggattacatcgccctgaac gaggacctgcgctcttggaccgcggcggacatggcggctcagatcacccagcgcaagtgggaggcggcccatgAgg cggagcagtTgagagcctacctggagggcaCgtgcgtggagtggctccgcagatacctggagaacgggaaggagac gctgcagcgcacgg;

A*3404:

(SEQ ID NO: 206)
gctcccactccatgaggtatttctacacctccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggagAggccggagtattgggaccggaacacacggaatgtgaaggcccagtcacagactgaccgagtgg acctggggaccctgcgcggctactacaaccagagcgaggacggttctcacaccatccagataatgtatggctgcga cgtggggtcggacgggcgcttcctccgcgggtaccggcaggacgcttacgacggcaaggattacatcgccctgaac gaggacctgcgctcttggaccgcggcggacatggcggctcagatcacccagcgcaagtgggagacggcccatgAgg cggagcagtTgagagcctacctggagggcacgtgcgtggagTggctccgcagatacctggagaacgggaaggagac gctgcagcgcacgg;

A*3405:
(SEQ ID NO: 207)
gctcccactccatgaggtatttctacacctccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtattgggaccggaacacacggaaagtgaaggcccagtcacagactgaccgagtgg acctggggaccctgcgcggctactacaaccagagcgaggacggttctcacaccatccagaggatgtatggctgcga cgtggggccggacgggcgcttcctccgcgggtaccagcaggacgcttacgacggcaaggattacatcTccctgaac gaggacctgcgctcttggaccgcggcggacatggcggctcagatcacccagcgcaagtgggagacggcccatgagg cggagcagtggagagcctacctggagggcacgtgcgtggagtggctccgcagatacctggagaacgggaaggagac gctgcagcgcacgg;

A*3601:
(SEQ ID NO: 208)
atggccgtcatggcgccccgaaccctcctcctgctactctcgggggccctggccctgacccagacctgggcgggct cccactccatgaggtatttcttcacatccgtgtcccggcccggccgcggggagccccgcttcatcgccgtgggcta cgtggacgacacgcagttcgtgcggttcgacagcgacgccgcgagccagaagatggagccgcgggcgccgtggata gagcaggaggggccggagtattgggaccaggagacacggaatatgaaggcccactcacagactgaccgagcgaacc tggggaccctgcgcggctactacaaccagagcgaggacggttctcacaccatccagataatgtatggctgcgacgt ggggccggacgggcgcttcctccgcgggtaccggcaggacgcctacgacggcaaggattacatcgccctgaacgag gacctgcgctcttggaccgcggcggacatggcagctcagatcaccaagcgcaagtgggaggcggtccatgcggcgg agcagcggagagtctacctggagggcaCgtgcgtggaGtggctccgcagatacctggagaacgggaaggagacgct gcagcgcacggaccccccaagacacatatgacccaccacccccatctctgaccatgaggccaccctgaggtgctgg gccctgggcttctaccctgcggagatcacactgacctggcagcgggatgggggaggaccagacccaggacacggagc tcgtggagaccaggcctgcaggggatggaaccttccagaagtgggcggctgtggtggtgccttctggagaggagca gagatacacctgccatgtgcagcatgagggtctgcccaagcccctcaccctgagatgggag;

A*3602:
(SEQ ID NO: 209)
gctcccactccatgaggtatttcttcacatccgtgtcccggcccggccgcggggagccccgcttcatcgccgtggg ctacgtggacgacacgcagttcgtgcggttcgacagcgacgccgcgagccagaagatggagccgcgggcgccgtgg atagagcaggaggggccggagtattgggaccaggagacacggaatatgaaggcccactcacagactgaccgagcga acctggggaccctgcgcggctactacaaccagagcgaggacggttctcacaccatccagataatgtatggctgcga cgtggggccggacgggcgcttcctccgcgggtaccggcaggacgcctacgacggcaaggattacatcgccctgaac gaggacctgcgctcttggaccgcggcggacatggcagctcagatcaccaagcgcaagtgggaggcggtccatgcgg cggagcagcggagagcctacctggaTggcacgtgcgtggagtggctccgcagatacctggagaacgggaaggagac gctgcagcgcacgg;

A*3603:
(SEQ ID NO: 210)
atggccgtcatggcgccccgaaccctcctcctgctactctcgggggccctggccctgacccagacctgggcgggct cccactccatgaggtatttcttcacatccgtgtcccggcccggccgcggggagccccgcttcatcgccgtgggcta cgtggacgacacgcagttcgtgcggttcgacagcgacgccgcgagccagaagatggagccgcgggcgccgtggata gagcaggaggggccggagtattgggaccaggagacacggaatatgaaggcccactcacagactgaccgagcgaacc tggggaccctgcgcggctactacaaccagagcgaggacggttctcacaccCtccagatgatgtatggctgcgacgt ggggccggacgggcgcttcctccgcgggtaccggcaggacgcctacgacggcaaggattacatcgccctgaacgag -continued gacctgcgctcttggaccgcggcggacatggcagctcagatcaccaagcgcaagtgggaggcggtccatgcggcgg agcagcggagagtctacctggagggcaCgtgcgtggaGTggctccgcagatacctggagaacgggaaggagacgct gcagcgcacggaccccccaagacacatatgacccaccacccatctctgaccatgaggccaccctgaggtgctgg gccctgggcttctaccctgcggagatcacactgacctggcagcgggatggggaggaccagacccaggacacggagc tcgtggagaccaggcctgcaggggatggaaccttccagaagtgggcggctgtggtggtgccttctggagaggagca gagatacacctgccatgtgcagcatgagggtctgcccaagcccctcaccctgagatgggag;

A*3604: (SEQ ID NO: 211)

gctcccactccatgaggtatttcttcacatccgtgtcccggcccggccgcggggagccccgcttcatcgccgtggg ctacgtggacgacacgcagttcgtgcggttcgacagcgacgccgcgagccagaagatggagccgcgggcgccgtgg atagagcaggaggggccggagtattgggaccaggagacacggaatatgaaggcccactcacagactgaccgagcga acctggggaccctgcgcggctactacaaccagagcgaggacggttctcacaccatccagataatgtatggctgcga cgtggggccggacgggcgcttcctccgcgggtaccggcaggacgcctacgacggcaaggattacatcgccctgaac gaggacctgcgctcttggaccgcggcggacatggcagctcagatcaccaagcgcaagtgggaggcggtccatgcgg cggagcagcggagagtctacctggagggccggtgcgtggaGtggctccgcagatacctggagaacgggaaggagac gctgcagcgcacgg;

A*4301: (SEQ ID NO: 212)

atggccgtcatggcgccccgaaccctcgtcctgctactctcgggggccctggccctgacccagacctgggcgggct cccactccatgaggtatttctacacctccgtgtcccggcccggccgcggggagccccgcttcatcgccgtgggcta cgtggacgacacgcagttcgtgcggttcgacagcgacgccgcgagccagaggatggagccgcgggcgccgtggata gagcaggaggggccggagtattgggaccTgcagacacggaatgtgaaggcccactcacagactgaccgagcgaacc tggggaccctgcgcggctactacaaccagagcgaggacggttctcacaccatccagaggatgtatggctgcgacgt ggggccggacgggcgcttcctccgcgggtaccagcaggacgcttacgacggcaaggattacatcgccctgaacgag gacctgcgctcttggaccgcggcggacatggcggctcagatcacccagcgcaagtgggagacggcccatgaggcgg agcagtggagagcctacctggagggccggtgcgtggagtggctccgcagatacctggagaacgggaaggagacgct gcagcgcacggacgcccccaagacgcatatgactcaccacgctgtctctgaccatgaggccaccctgaggtgctgg gccctgagcttctaccctgcggagatcacactgacctggcagcgggatggggaggaccagacccaggacacggagc tcgtggagaccaggcctgcaggggatggGaccttccagaagtgggcgtctgtggtggtgccttctggaCaggagca gagatacacctgccatgtgcagcatgagggtctgcccaagcccctcaccctgagatgggag;

A*6601: (SEQ ID NO: 213)

atggccgtcatggcgccccgaaccctcgtcctgctactctcgggggccctggccctgacccagacctgggcgggct cccactccatgaggtatttctacacctccgtgtcccggcccggccgcggggagccccgcttcatcgccgtgggcta cgtggacgacacgcagttcgtgcggttcgacagcgacgccgcgagccagaggatggagccgcgggcgccgtggata gagcaggaggggccggagtattgggaccggaacacacggaatgtgaaggcccaGtcacagactgaccgagtgGacc tggggaccctgcgcggctactacaaccagagcgaggacggttctcacaccatccagaggatgtatggctgcgacgt ggggccggacgggcgcttcctccgcgggtaccagcaggacgcttacgacggcaaggattacatcgccctgaacgag gacctgcgctcttggaccgcggcggacatggcggctcagatcacccagcgcaagtgggagacggcccatgaggcgg agcagTggagagcctacctggagggccggtgcgtggagtggctccgcagatacctggagaacgggaaggagacgct gcagcgcacggacgcccccaagacgcatatgactcaccacgctgtctctgaccatgaggccaccctgaggtgctgg gccctgagcttctaccctgcggagatcacactgacctggcagcgggatggggaggaccagacccaggacacggagc tcgtggagaccaggcctgcaggggatggGaccttccagaagtgggcgtctgtggtggtgccttctggacaggagca gagatacacctgccatgtgcagcatgagggtctgcccaagcccctcaccctgagatgggag;

A*6602:
(SEQ ID NO: 214)
atggccgtcatggcgccccgaaccctcgtcctgctactctcgggggccctggccctgacccagacctgggcgggct cccactccatgaggtatttctacacctccgtgtcccggcccggccgcggggagccccgcttcatcgccgtgggcta cgtggacgacacgcagttcgtgcggttcgacagcgacgccgcgagccagaggatggagccgcgggcgccgtggata gagcaggaggggccggagtattgggaccggaacacacggaatgtgaaggcccagtcacagactgaccgagtggacc tggggaccctgcgcggctactacaaccagagcgaggccggttctcacaccatccagaggatgtatggctgcgacgt ggggccggacgggcgcttcctccgcgggtaccagcaggacgcttacgacggcaaggattacatcgccctgaacgag gacctgcgctcttggaccgcggcggacatggcggctcagatcacccagcgcaagtgggagacggcccatgaggcgg agcagtggagagcctacctggagggcgAgtgcgtggagtggctccgcagatacctggagaacgggaaggagacgct gcagcgcacggacgcccccaagacgcatatgactcaccacgctgtctctgaccatgaggccaccctgaggtgctgg gccctgagcttctaccctgcggagatcacactgacctggcagcgggatggggaggaccagacccaggacacggagc tcgtggagaccaggcctgcaggggatggaaccttccagaagtgggcgTctgtggtggtgccttctggaCaggagca gagatacacctgccatgtgcagcatgagggtctgcccaagcccctcaccctgagatgggag;

A*6603:
(SEQ ID NO: 215)
gctcccactccatgaggtatttctacacctccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtattgggaccggaacacacggaatgtgaaggcccactcacagactgaccgagtgg acctggggaccctgcgcggctactacaaccagagcgaggccggttctcacaccatccagaggatgtatggctgcga cgtggggccggacgggcgcttcctccgcgggtaccagcaggacgcttacgacggcaaggattacatcgccctgaac gaggacctgcgctcttggaccgcggcggacatggcggctcagatcacccagcgcaagtgggagacggcccatgAgg cggagcagtggagagcctacctggagggcgAgtgcgtggagTggctccgcagatacctggagaacgggaaggagac gctgcagcgcacgg;

A*6604:
(SEQ ID NO: 216)
gctcccactccatgaggtatttctacacctccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtattgggaccggaacacacggaatgtgaaggcccagtcacagactgaccgagtgg acctggggaccctgcgcggctactacaaccagagcgaggacggttctcacaccatccagaggatgtatggctgcga cgtggggccggacgggcgcttcctccgcgggtaccagcaggacgcttacgacggcaaggattacatcgccctgaac gaggacctgcgctcttggaccgcggcggacatggcggctcagatcacccagcgcaagtgggagacggcccatgAgg cggagcagtggagagcctacctggagggccggtgcgtggagtggctccgcagaCacctggagaacgggaaggagac gctgcagcgcacgg;

A*680101:
(SEQ ID NO: 217)
atggccgtcatggcgccccgaaccctcgtcctgctactctcgggggccctggccctgacccagacctgggcgggct cccactccatgaggtatttctacacCtccgtgtcccggcccggccgcggggagccccgcttcatcgccgtgggcta cgtggacgacacgcagttcgtgcggttcgacagcgacgccgcgagccagaggatggagccgcgggcgccgtggata gagcaggaggggccggagtattgggaccggaacacacggaatgtgaaggcccaGtcacagactgaccgagtggacc tggggaccctgcgcggctactacaaccagagcgaggccggttctcacaccatccagatgatgtatggctgcgacgt ggggTcggacgggcgcttcctccgcgggtaccggcaggacgcctacgacggcaaggattacatcgccctgaaagag gacctgcgctcttggaccgcggcggacatggcagctcagaccaccaagcacaagtgggaggcggcccatgtggcgg agcagTggagagcctacctggagggcacgtgcgtggagtggctccgcagatacctggagaacgggaaggagacgct -continued gcagcgcacggacgcccccaaaacgcatatgactcaccacgctgtctctgaccatgaagccaccctgaggtgctgg gccctgagcttctaccctgcggagatcacactgacctggcagcgggatggggaggaccagacccaggacacggagc tcgtggagaccaggcctgcaggggatggaaccttccagaagtgggTggctgtggtggtgccttctggacaggagca gagatacacctgccatgtgcagcatgagggtTtgcccaagcccctcaccctgagatgggag;

A*680102:
(SEQ ID NO: 218)
atggccgtcatggcgccccgaaccctcgtcctgctactctcgggggccctggccctgacccagacctgggcgggct cccactccatgaggtatttctacacTtccgtgtcccggcccggccgcggggagccccgcttcatcgccgtgggcta cgtggacgacacgcagttcgtgcggttcgacagcgacgccgcgagccagaggatggagccgcgggcgccgtggata gagcaggaggggccggagtattgggaccggaacacacggaatgtgaaggcccaGtcacagactgaccgagtggacc tggggaccctgcgcggctactacaaccagagcgaggccggttctcacaccatccagatgatgtatggctgcgacgt ggggTcggacgggcgcttcctccgcgggtaccggcaggacgcctacgacggcaaggattacatcgccctgaaagag gacctgcgctcttggaccgcggcggacatggcagctcagaccaccaagcacaagtgggaggcggcccatgtggcgg agcagTggagagcctacctggagggcacgtgcgtggagtggctccgcagatacctggagaacgggaaggagacgct gcagcgcacggacgcccccaaaacgcatatgactcaccacgctgtctctgaccatgaagccaccctgaggtgctgg gccctgagcttctaccctgcggagatcacactgacctggcagcgggatggggaggaccagacccaggacacggagc tcgtggagaccaggcctgcaggggatggaaccttccagaagtgggTggctgtggtggtgccttctggacaggagca gagatacacctgccatgtgcagcatgagggtTtgcccaagcccctcaccctgagatgggag;

A*6802:
(SEQ ID NO: 219)
atggccgtcatggcgccccgaaccctcgtcctgctactctcgggggccctggccctgacccagacctgggcgggct cccactccatgaggtatttctacacctccAtgtcccggcccggccgcggggagccccgcttcatcgccgtgggcta cgtggacgacacgcagttcgtgcggttcgacagcgacgccgcgagccagaggatggagccgcgggcgccgtggata gagcaggaggggccggagtattgggaccggaacacacggaatgtgaaggcccagtcacagactgaccgagtggacc tggggaccctgcgcggctactacaaccagagcgaggccggttctcacaccatccagaggatgtatggctgcgacgt ggggccggacgggcgcttcctccgcgggtaccaccagtacgcctacgacggcaaggattacatcgccctgaaagag gacctgcgctcttggaccgcggcggacatggcagctcagaccaccaagcacaagtgggaggcggcccatgtggcgg agcagtggagagcctacctggagggcacgtgcgtggagtggctccgcagatacctggagaacgggaaggagacgct gcagcgcacggacgcccccaaaacgcatatgactcaccacgctgtctctgaccatgaagccaccctgaggtgctgg gccctgagcttctaccctgcggagatcacactgacctggcagcgggatggggaggaccagacccaggacacggagc tcgtggagaccaggcctgcaggggatggaaccttccagaagtgggtggctgtggtggtgccttctggacaggagca gagatacacctgccatgtgcagcatgagggtTtgcccaagcccctcaccctgagatgggag;

A*680301:
(SEQ ID NO: 220)
atggccgtcatggcgccccgaaccctcgtcctgctactctcgggggccctggccctgacccagacctgggcgggct cccactccatgaggtatttctacacTtccgtgtcccggcccggccgcggggagccccgcttcatcgccgtgggcta cgtggacgacacgcagttcgtgcggttcgacagcgacgccgcgagccagaggatggagccgcgggcgccgtggata gagcaggaggggccggagtattgggaccggaacacacggaatgtgaaggcccactcacagactgaccgagtggacc tggggaccctgcgcggctactacaaccagagcgaggccggttctcacaccatccagatgatgtatggctgcgacgt ggggTcggacgggcgcttcctccgcgggtaccggcaggacgcctacgacggcaaggattacatcgccctgaaagag gacctgcgctcttggaccgcggcggacatggcagctcagaccaccaagcacaagtgggaggcggcccatgtggcgg agcagTggagagcctacctggagggcacgtgcgtggagtggctccgcagatacctggagaacgggaaggagacgct gcagcgcacggacgcccccaaaacgcatatgactcaccacgctgtctctgaccatgaagccaccctgaggtgctgg gccctgagcttctaccctgcggagatcacactgacctggcagcgggatgggggaggaccagacccaggacacggagc tcgtggagaccaggcctgcaggggatggaaccttccagaagtgggTggctgtggtggtgccttctggacaggagca gagatacacctgccatgtgcagcatgagggtTtgcccaagcccctcaccctgagatgggag;

A*680302:

(SEQ ID NO: 221)
gctctcactccatgaggtatttctacacTtccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtatgggaccggaacacacggaatgtgaaggcccactcacagactgaccgagtgg acctggggaccctgcgcggctactacaaccagagcgaggccggttctcacaccatccagatgatgtatggctgcga cgtggggtcggacgggcgcttcctccgcgggtaccggcaggacgcctacgacggcaaggattacatcgccctgaaa gaggacctgcgctcttggaccgcggcggacatggcagctcagaCcaccaagcacaagtgggaggcggcccatgtgg cggagcagTggagagcctacctggagggcacgtgcgtggagtggctccgcagatacctggagaacgggaaggagac gctgcagcgcacgg;

A*6804:

(SEQ ID NO: 222)
gctcccactccatgaggtatttctacacctccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtattgggaccggaaCacacggaatgtgaaggcccactcacagaTtgaccgagtgg acctggggaccctgcgcggctactacaaccagagcgaggccggttctcacaccatccagatgatgtatggctgcga cgtggggtcggacgggcgcttcctccgcgggtaccggcaggacgcctacgacggcaaggattacatcgccctgaaa gaggacctgcgctcttggaccgcggcggacatggcagctcagaccaccaagcAcaagtgggaggcggcccatgtgg cggagcagtggagagcctacctggagggcacgtgcgtggagTggctccgcagatacctggagaacgggaaggagac gctgcagcgcacgg;

A*6805:

(SEQ ID NO: 223)
gctcccactccatgaggtatttctacacTtccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtatgggaccggaacacacggaatgtgaaggcccactcacagactCaccgagtgg acctggggaccctgcgcggctactacaaccagagcgaggccggttctcacaccatccagatgatgtatggctgcga cgtggggtcggacgggcgcttcctccgcgggtaccggcaggacgcctacgacggcaaggattacatcgccctgaaa gaggacctgcgctcttggaccgcggcggacatggcagctcagaCcaccaagcacaagtgggaggcggcccatgtgg cggagcagTggagagcctacctggagggcacgtgcgtggagtggctccgcagatacctggagaacgggaaggagac gctgcagcgcacgg;

A*6806:

(SEQ ID NO: 224)
gctcccactccatgaggtatttctacacttccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtattgggaccggaacacacggaatgtgaaggcccaGtcacagactgaccgagtgg acctggggaccctgcgcggctactacaaccagagcgaggccggttctcacaccatccagatgatgtatggctgcga cgtggggtcggacgggcgcttcctccgcgggtatgaAcagcacgcctacgacggcaaggattacatcgccctgaaa gaggacctgcgctcttggaccgcggcggacatggcagctcagaccaccaagcAcaagtgggaggcggcccatgTgg cggagcagtggagagcctacctggagggcacgtgcgtggagtggctccgcagatacctggagaacgggaaggagac gctgcagcgcacgg;

A*6807:
(SEQ ID NO: 225)
gctcccactccatgaggtatttctacacttccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtattgggaccggaacacacggaatgtgaaggcccaGtcacagactgaccgagtgg acctggggaccctgcgcggctactacaaccagagcgaggccggttctcacaccatccagatgatgtatggctgcga cgtggggtcggacgggcgcttcctccgcgggtaccggcagCacgcctacgacggcaaggattacatcgccctgaaa gaggacctgcgctcttggaccgcggcggacatggcagctcagaccaccaagcAcaagtgggaggcggcccatgTgg cggagcagtggagagcctacctggagggcacgtgcgtggagtggctccgcagatacctggagaacgggaaggagac gctgcagcgcacgg;

A*6808:
(SEQ ID NO: 226)
atggccgtcatggcgccccgaaccctcgtcctgctactctcgggggccctggccctgacccagacctgggcgggct cccactccatgaggtatttctacacctccgtgtcccggcccggccgcggggagccccgcttcatcgccgtgggcta cgtggacgacacgcagttcgtgcggttcgacagcgacgccgcgagccagaggatggagccgcgggcgccgtggata gagcaggaggggccggagtattgggaccggaacacacggaatgtgaaggcccagtcacagactgaccgagtggacc tggggaccctgcgcggctactacaaccagagcgaggccggttctcacaccatccagatgatgtatggctgcgacgt ggggtcggacgggcgcttcctccgcgggtaccggcaggacgcctacgacggcaaggattacatcgccctgaaagag gacctgcgctcttggaccgcggcggacatggcagctcagaccaccaagcacaagtgggaggcggcccatgtggcgg agcagcTgagagcctacctggagggcacgtgcgtggagtggctccgcagatacctggagaacgggaaggagacgct gcagcgcacggacgcccccaaaacgcatatgactcaccacgctgtctctgaccatgaagccaccctgaggtgctgg gccctgagcttctaccctgcggagatcacactgacctggcagcgggatgggGaggaccagacccaggacacggagc tcgtggagaccaggcctgcaggggatggaaccttccagaagtgggTggctgtggtggtgccttctggacaggagca gagatacacctgccatgtgcagcatgagggtTtgcccaagcccctcaccctgagatgggag;

A*6809:
(SEQ ID NO: 227)
gctcccactccatgaggtatttctacacTtccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtattgggaccggaacacacggaatgtgaaggcccagtcacagactgaccgagtgg acctggggaccctgcgcggctactacaaccagagcgaggccggttctcacaccatccagatgatgtatggctgcga cgtggggtcggacgggcgcttcctccgcgggtaccggcaggacgcctacgacggcaaggattacatcgccctgaaa gaggacctgcgctcttggaccgcggcggacatggcagctcagaccaccaagcacaagtgggaggcggcccatgtgg cggagcagcAgagagcctacctggagggcacgtgcgtggagtggctccgcagatacctggagaacgggaaggagac gctgcagcgcacgg;

A*6810:
(SEQ ID NO: 228)
gctcccactccatgaggtatttctacacCtccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtattgggacGaggagacacggaatgtgaaggcccaGtcacagactgaccgagtgg acctggggaccctgcgcggctactacaaccagagcgaggccggttctcacaccatccagatgatgtatggctgcga cgtggggTcggacgggcgcttcctccgcgggtaccggcaggacgcctacgacggcaaggattacatcgccctgaaa gaggacctgcgctcttggaccgcggcggacatggcagctcagaccaccaagcacaagtgggaggcggcccatgTgg cggagcagTggagagcctacctggagggcaCgtgcgtggagTggctccgcagatacctggagaacgggaaggagac gctgcagcgcacgg;

A*6812:

(SEQ ID NO: 229)

accctcgtcctgctactctcggggggccctggccctgacccagacctgggcgggctcccactccatgaggtatttct acacTtccgtgtcccggcccggccgcggggagccccgcttcatcgccgtgggctacgtggacgacacgcagttcgt gcggttcgacagcgacgccgcgagccagaggatggagccgcgggcgccgtggatagagcaggaggggccggagtat tgggaccggaacacacggaatgtgaaggcccaGtcacagactgaccgagtggacctggggaccctgcgcggctact acaaccagagcgaggccggttctcacaccatccagatgatgtatggctgcgacgtggggtcggacgggcgcttcct ccgcgggtaccggcaggacgcctacgacggcaaggattacatcgccctgaaagaggacctgcgctcttggaccgcg gcggacatggcagctcagatcaccaagcacaagtgggaggcggcccatgtggcggagcagTggagagcctacctgg agggcacgtgcgtggagtggctccgcagatacctggagaacgggaag;

A*6813:

(SEQ ID NO: 230)

atggccgtcatggcgccccgaaccctcgtcctgctactctcggggggccctggccctgacccagacctgggcgggct cccactccatgaggtatttctacacCtccgtgtcccggcccggccgcggggagccccgcttcatcgccgtgggcta cgtggacgacacgcagttcgtgcggttcgacagcgacgccgcgagccagaggatggagccgcgggcgccgtggata gagcaggaggggccggagtattgggaccgggagacacggaatgtgaaggcccaGtcacagactgaccgagtggacc tggggaccctgcgcggctactacaaccagagcgaggccggttctcacaccatccagatgatgtatggctgcgacgt ggggTcggacgggcgcttcctccgcgggtaccggcaggacgcctacgacggcaaggattacatcgccctgaaagag gacctgcgctcttggaccgcggcggacatggcagctcagaccaccaagcacaagtgggaggcggcccatgtggcgg agcagTggagagcctacctggagggcacgtgcgtggagtggctccgcagatacctggagaacgggaaggagacgct gcagcgcacggacgcccccaaaacgcatatgactcaccacgctgtctctgaccatgaagccaccctgaggtgctgg gccctgagcttctaccctgcggagatcacactgacctggcagcgggatggggaggaccagacccaggacacggagc tcgtggagaccaggcctgcaggggatggaaccttccagaagtgggTggctgtggtggtgccttctggacaggagca gagatacacctgccatgtgcagcatgaggg;

A*6814:

(SEQ ID NO: 231)

gctcccactccatgaggtatttctacacCtccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtattgggacGaggagacacggaatgtgaaggcccaGtcacagactgaccgagtgg acctggggaccctgcgcggctactacaaccagagcgaggccggttctcacaccatccagatgatgtatggctgcga cgtggggTcggacgggcgcttcctccgcgggtaccggcaggacgcctacgacggcaaggattacatcgccctgaaa gaggacctgcgctcttggaccgcggcggacatggcagctcagaccaccaagcacaagtgggaggcggcccatgTgg cggagcagTggagagcctacctggagggcaCgtgcgtggagTggctccgcagatacctggagaacgggaaggagac gctgcagcgcgcgg;

A*6815:

(SEQ ID NO: 232)

gctcccactccatgaggtatttctacacctccAtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtattgggaccggaaCacacggaatgtgaaggcccactcacagactCaccgagtgg acctggggaccctgcgcggctactacaaccagagcgaggccggttctcacaccatccagaggatgtatggctgcga cgtggggccggacgggcgcttcctccgcgggtaccaccagtacgcctacgacggcaaggattacatcgccctgaaa gaggacctgcgctcttggaccgcggcggacatggcagctcagaccaccaagcacaagtgggaggcggcccatgtgg cggagcagtggagagcctacctggagggcacgtgcgtggagtggctccgcagatacctggagaacgggaaggagac gctgcagcgcacgg;

A*6816:

(SEQ ID NO: 233)

ccgtcatggcgccccgaaccctcgtcctgctactctcgggggccctggccctgacccagacctgggcgggctccca ctccatgaggtatttctacacttccgtgtcccggcccggccgcgggagccccgcttcatcgccgtgggctacgtg gacgacacgcagttcgtgcggttcgacagcgacgccgcgagccagaggatggagccgcgggcgccgtggatagagc aggaggggccggagtattgggaccggaacacacggaatgtgaaggcccagtcacagactgaccgagtggacctggg gaccctgcgcggctactacaaccagagcgaggccggttctcacaccatccagatgatgtatggctgcgacgtgggg tcggacgggcgcttcctccgcgggtaccggcaggacgcctacgacggcaaggattacatcgccctgaaagaggacc tgcgctcttggaccgcggcggacatggcagctcagaccaccaagcacaagtgggaggcggcccTtgtggcggagca gtggagagcctacctggagggcacgtgcgtggagtggctccgcagatacctggagaacgggaaggagacgctgcag cgcacgg;

A*6817:

(SEQ ID NO: 234)

atggccgtcatggcgccccgaaccctcgtcctgctactctcgggggccctggccctgacccagacctgggcgggct cccactccatgaggtatttctacacttccgtgtcccggcccggccgcgggagccccgcttcatcgccgtgggcta cgtggacgacacgcagttcgtgcggttcgacagcgacgccgcgagccagaggatggagccgcgggcgccgtggata gagcaggaggggccggagtattgggaccggaacacacggaatgtgaaggcccagtcacagactgaccgagtggacc tggggaccctgcgcggctactacaaccagagcgaggccggttctcacaccatccagatgatgtatggctgcgacgt ggggtcggacgggcgcttcctccgcgggtaccggcaggTcgcctacgacggcaaggattacatcgccctgaaagag gacctgcgctcttggaccgcggcggacatggcagctcagaccaccaagcacaagtgggaggcggcccatgtggcgg agcagtggagagcctacctggagggcacgtgcgtggagtggctccgcagatacctggagaacgggaaggagacgct gcagcgcacggacgcccccaaaacgcatatgactcaccacgctgtctctgaccatgaagccaccctgaggtgctgg gccctgagcttctaccctgcggagatcacactgacctggcagcgggatggggaggaccagacccaggacacggagc tcgtggagaccaggcctgcaggggatggaaccttccagaagtgggtggctgtggtggtgccttctggacaggagca gagatacacctgccatgtgcagcatgagggtTtgcccaagcccctcaccctgagatgggag;

A*6819:

(SEQ ID NO: 235)

gctcccactccatgaggtatttctacacttccgtgtcccggcccggccgcgggagccccgcttcatcgccgtggg ctacgtggacgacacgcagttcgtgcggttcgacagcgacgccgcgagccagaggatggagccgcgggcgccgtgg atagagcaggaggggccggagtattgggaccggaacacacggaatgtgaaggcccagtcacagactgaccgagtgg acctggggaccctgcgcggctactacaaccagagcgaggccggttctcacaccatccagatgatgtatggctgcga cgtggggtcggacgggcgcttcctccgcgggtaccggcaggacgcctacgacggcaaggattacatcgccctgaaa gaggacctgcgctcttggaccgcggcggacatggcagctcagaccaccaagcAcaagtgggaggcggcccatgTgg cggagcagTggagagcctacctggaTggcacgtgcgtggagtggctccgcagatacctggagaacgggaaggagac gctgcagcgcacgg;

A*6820:

(SEQ ID NO: 236)

gctcccactccatgaggtatttctacacttccgtgtcccggcccggccgcgggagccccgcttcatcgccgtggg ctacgtggacgacacgcagttcgtgcggttcgacagcgacgccgcgagccagaggatggagccgcgggcgccgtgg atagagcaggaggggccggagtattgggaccggaacacacggaatgtgaaggcccactcacagactcaccgagtgg acctggggaccctgcgcggctactacaaccagagcgaggccggttctcacaccatccagatgatgtatggctgcga cgtggggtcggacgggActtcctccgcgggtaccggcaggacgcctacgacggcaaggattacatcgccctgaaa gaggacctgcgctcttggaccgcggcggacatggcagctcagaccaccaagcacaagtgggaggcggcccatgtgg cggagcagtggagagcctacctggagggcacgtgcgtggagtggctccgcagatacctggagaacgggaaggagac gctgcagcgcacgg;

A*6821:
(SEQ ID NO: 237)
gctcccactccatgaggtatttctacacttccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtattgggaccggaacacacggaatgtgaaggcccagtcacagactgaccgagtgg acctggggaccctgcgcggctactacaaccagagcgaggccggttctcacaccatccagatgatgtatggctgcga cgtggggtcggacgggcgcttcctccgcgggtaccggcaggacgcctacgacggcaaggattacatcgccctgaaa gaggacctgcgctcttggaccgcggcggacatggcagctcagaccaccaagcacaagtgggaggcggcccatgTgg cggagcagtggagagcctacctggagggcacgtgcgtggagtggctccgcagatacctggagaacCggaaggagac gctgcagcgcacgg;

A*6822:
(SEQ ID NO: 238)
atggccgtcatggcgccccgaaccctcgtcctgctactctcgggggccctggccctgacccagacctgggcgggct cccactccatgaggtatttctacacctccgtgtcccggcccggccgcggggagccccgcttcatcgccgtgggcta cgtggacgacacgcagttcgtgcggttcgacagcgacgccgcgagccagaggatggagccgcgggcgccgtggata gagcaggaggggccggagtattgggaccggaacacacggaatgtgaaggcccagtcacagactgaccgagtggacc tggggaccctgcAcggctactacaaccagagcgaggccggttctcacaccatccagatgatgtatggctgcgacgt ggggtcggacgggcgcttcctccgcgggtaccggcaggacgcctacgacggcaaggattacatcgccctgaaagag gacctgcgctcttggaccgcggcggacatggcagctcagaccaccaagcacaagtgggaggcggcccatgtggcgg agcagtggagagcctacctggagggcacgtgcgtggagtggctccgcagatacctggagaacgggaaggagacgct gcagcgcacggacgcccccaaaacgcatatgactcaccacgctgtctctgaccatgaagccaccctgaggtgctgg gccctgagcttctaccctgcggagatcacactgacctggcagcgggatggggaggaccagacccaggacacggagc tcgtggagaccaggcctgcaggggatggaaccttccagaagtgggtggctgtggtggtgccttctggacaggagca gagatacacctgccatgtgcagcatgagggtttgcccaagcccctcaccctgagatgggag;

A*6823:
(SEQ ID NO: 239)
gctcccactccatgaggtatttctacacTtccgtgtcccggcccggccgcggggagccccgcttcatcgccgtggg ctacgtggacgacacgcagttcgtgcggttcgacagcgacgccgcgagccagaggatggagccgcgggcgccgtgg atagagcaggaggggccggagtattgggaccggaacacacggaatgtgaaggcccagtcacagactgaccgagtgg acctggggaccctgcgcggctactacaaccagagcgaggccggttctcacaccatccagaGgatgtatggctgcga cgtggggtcggacgggcgcttcctccgcgggtaccggcaggacgcctacgacggcaaggattacatcgccctgaaa gaggacctgcgctcttggaccgcggcggacatggcagctcagaCcaccaagcacaagtgggaggcggcccatgtgg cggagcagTggagagcctacctggagggcacgtgcgtggagtggctccgcagatacctggagaacgggaaggagac gctgcagcgcacgg;

A*6901:
(SEQ ID NO: 240)
atggccgtcatggcgccccgaaccctcgtcctgctactctcgggggccctggccctgacccagacctgggcgggct cccactccatgaggtatttctacacctccgtgtcccggcccggccgcggggagccccgcttcatcgccgtgggcta cgtggacgacacgcagttcgtgcggttcgacagcgacgccgcgagccagaggatggagccgcgggcgccgtggata gagcaggaggggccggagtattgggaccggaaCacacggaatgtgaaggcccaGtcacagactgaccgagtggacc tggggaccctgcgcggctactacaaccagagcgaggccggttctcacaccGtccagaGgatgtatggctgcgacgt ggggtcggacTggcgcttcctccgcgggtaccaccagtacgcctacgacggcaaggattacatcgccctgaaagag -continued gacctgcgctcttggaccgcggcggacatggcagctcagaccaccaagcacaagtgggaggcggcccatgTggcgg
agcagTTgagagcctacctggagggcaCgtgcgtggagtggctccgcagatacctggagaacgggaaggagacgct
gcagcgcacggacgcccccaaaacgcatatgactcaccacgctgtctctgaccatgaagccaccctgaggtgctgg
gccctgagcttctaccctgcggagatcacactgacctggcagcgggatggggaggaccagacccaggacacggagc
tcgtggagaccaggcctgcaggggatggaaccttccagaagtgggcggctgtggtggtgccttctggacaggagca
gagatacacctgccatgtgcagcatgagggtTtgcccaagcccctcaccctgagatgggag;

A*7401:
(SEQ ID NO: 241)
atggccgtcatggcgccccgaaccctcctcctgctactcttgggggccctggccctgacccagaccAgggcgggct
cccactccatgaggtatttcttcacatccgtgtcccggcccggccgcggggagccccgcttcatcgccgtgggcta
cgtggacgacacgcagttcgtgcggtttgacagcgacgccgcgagccagaggatggagccgcgggcgccgtggata
gagcaggaggggccggagtattgggaccaggagacacggaatgtgaaggcccactcacagactgaccgagtggacc
tggggaccctgcgcggctactacaaccagagcgaggccggttctcacaccatccagatgatgtatggctgcgacgt
ggggccggacgggcgcctcctccgcgggtaccagcaggacgcctacgacggcaaggattacatcgccttgaacgag
gacctgcgctcttggaccgcggcggacatggcggctcagatcacccagcgcaagtgggaggcggcccgtgtggcgg
agcagttgagagcctacctggagggcacgtgcgtggagtggctccgcagatacctggagaacgggaaggagacgct
gcagcgcacggacgcccccaagacgcatatgactcaccacgctgtctctgaccatgaggccaccctgaggtgctgg
gccctgagcttctaccctgcggagatcacactgacctggcagcgggatggggaggaccagacccaggacacggagc
ttgtggagaccaggcctgcaggggatggaaccttccagaagtgggcgtctgtggtggtgccttctggaCaggagca
gagatacacctgccatgtgcagcatgagggtctgcccaagcccctcaccctgagatgggag;

A*7402:
(SEQ ID NO: 242)
atggccgtcatggcgccccgaaccctcctcctgctactctTgggggccctggccctgacccagacctgggcgggct
cccactccatgaggtatttcttcacatccgtgtcccggcccggccgcggggagccccgcttcatcgccgtgggcta
cgtggacgacacgcagttcgtgcggtttgacagcgacgccgcgagccagaggatggagccgcgggcgccgtggata
gagcaggaggggccggagtattgggaccaggagacacggaatgtgaaggcccactcacagactgaccgagtgGacc
tggggaccctgcgcggctactacaaccagagcgaggccggttctcacaccatccagatgatgtatggctgcgacgt
ggggccggacgggcgcCtcctccgcgggtaccAgcaggacgcctacgacggcaaggattacatcgccTtgaacgag
gacctgcgctcttggaccgcggcggacatggcggctcagatcacccagcgcaagtgggaggcggcccgtgtggcgg
agcagtTgagagcctacctggagggcacgtgcgtggagTggctccgcagatacctggagaacgggaaggagacgct
gcagcgcacgg;

A*7403:
(SEQ ID NO: 243)
atggccgtcatggcgccccgaaccctcctcctgctactcttgggggccctggccctgacccagaccagggcgggct
cccactccatgaggtatttcttcacatccgtgtcccggcccggccgcggggagccccgcttcatcgccgtgggcta
cgtggacgacacgcagttcgtgcggtttgacagcgacgccgcgagccagaggatggagccgcgggcgccgtggata
gagcaggaggggccggagtattgggaccaggagacacggaatgtgaaggcccactcacagactgaccgagtggacc
tggCgaccctgcgcggctactacaaccagagcgaggccggttctcacaccatccagatgatgtatggctgcgacgt
ggggccggacgggcgcctcctccgcgggtaccagcaggacgcctacgacggcaaggattacatcgccttgaacgag
gacctgcgctcttggaccgcggcggacatggcggctcagatcacccagcgcaagtgggaggcggcccgtgtggcgg
agcagttgagagcctacctggagggcacgtgcgtggagtggctccgcagatacctggagaacgggaaggagacgct
gcagcgcacgg;

A*7404:
(SEQ ID NO: 244)
ggctcccactccatgaggtatttcttcacatccgtgtcccggcccggccgcggggagccccgcttcatcgccgtgg gctacgtggacgacacgcagttcgtgcggtttgacagcgacgccgcgagccagaggatggagccgcgggcgccgtg gatagagcaggaggggtccggagtattgggacggggagacacggaaAgtgaaggcccactcacagactgaccgagtg Gacctggggaccctgcgcggctactacaaccagagcgaggccggttctcacaccatccagatgatgtatggctgcg acgtggggccggacgggcgCtcctccgcgggtaccagcaggacgcctacgacggcaaggattacatcgccttgaa cgaggacctgcgctcttggaccgcggcggacatggcggctcagatcacccagcgcaagtgggaggcggcccGtgtg gcggagcagtTgagagcctacctggagggcacgtgcgtggagtggctccgcagatacctggagaacgggaaggaga cgctgcagcgcacgg;

A*7405:
(SEQ ID NO: 245)
gctcccactccatgaggtatttcttcacatccgtgtcccggcccggccgcggggagccccgcttcatcgccgtggg ctacgtggacgacacgcagttcgtgcggtttgacagcgacgccgcgagccagaggatggagccgcgggcgccgtgg atagagcaggaggggccggagtattgggaccaggagacacggaatgtgaaggcccactcacagGctgaccgagtgg acctggggaccctgcgcggctactacaaccagagcgaggccggttctcacaccatccagatgatgtatggctgcga cgtggggccggacgggcgcctcctccgcgggtaccagcaggacgcctacgacggcaaggattacatcgccttgaac gaggacctgcgctcttggaccgcggcggacatggcggctcagatcacccagcgcaagtgggaggcggcccgtgtgg cggagcagttgagagcctacctggagggcacgtgcgtggagtggctccgcagatacctggagaacgggaaggagac gctgcagcgcacgg;

A*7406:
(SEQ ID NO: 246)
gctcccactccatgaggtatttcttcacatccgtgtcccggcccggccgcggggagccccgcttcatcgccgtggg ctacgtggacgacacgcagttcgtgcggtttgacagcgacgccgcgagccagaggatggagccgcgggcgccgtgg atagagcaggaggggccggagtattgggaccaggagacacggaatgtgaaggcccactcacagactCaccgagtgG acctggggaccctgcgcggctactacaaccagagcgaggccggttctcacaccatccagatgatgtatggctgcga cgtggggccggacgggcgCtcctccgcgggtaccagcaggacgcctacgacggcaaggattacatcgccttgaac gaggacctgcgctcttggaccgcggcggacatggcggctcagatcacccagcgcaagtgggaggcggcccGtgtgg cggagcagtTgagagcctacctggagggcacgtgcgtggagtggctccgcagatacctggagaacgggaaggagac gctgcagcgcacg;

A*7407:
(SEQ ID NO: 247)
gctcccactccatgaggtatttcttcacatccgtgtcccggcccggccgcggggagccccgcttcatcgccgtggg ctacgtggacgacacgcagttcgtgcggtttgacagcgacgccgcgagccagaggatggagccgcgggcgccgtgg atagagcaggaggggccggagtattgggaccaggagacacggaatgtgaaggcccactcacagaTtgaccgagtgG acctggggaccctgcgcggctactacaaccagagcgaggccggttctcacaccatccagatgatgtatggctgcga cgtggggccggacgggcgCtcctccgcgggtaccagcaggacgcctacgacggcaaggattacatcgccttgaac gaggacctgcgctcttggaccgcggcggacatggcggctcagatcacccagcgcaagtgggaggcggcccGtgtgg cggagcagtTgagagcctacctggagggcacgtgcgtggagtggctccgcagatacctggagaacgggaaggagac gctgcagcgcacgg;

A*7408:
(SEQ ID NO: 248)
gctcccactccatgaggtatttcttcacatccgtgtcccggcccggccgcggggagccccgcttcatcgccgtggg ctacgtggacgacacgcagttcgtgcggtttgacagcgacgccgcgagccagaggatggagccgcgggcgccgtgg atagagcaggaggggccggagtattgggaccaggagacacggaatgtgaaggcccactcacagactgaccgagtgg -continued acctggggaccctgcgcggctactacaaccagagcgaggccggttctcacaccatccagatgatgtatggctgcga cgtggggccggacgggcgcctcctccgcgggtaccagcaggacgcctacgacggcaaggattacatcgccttgaac gaggacctgcgctcttggaccgcggcggacatggcggctcagatcacccagcgcaagtgggaggcggccAgtgtgg cggagcagttgagagcctacctggagggcacgtgcgtggagtggctccgcagatacctggagaacgggaaggagac gctgcagcgcacgg;

A*7409:
(SEQ ID NO: 249)
gctcccactccatgaggtatttcttcacatccgtgtcccCgcccggccgcggggagccccgcttcatcgccgtggg ctacgtggacgacacgcagttcgtgcggtttgacagcgacgccgcgagccagaggatggagccgcgggcgccgtgg atagagcaggaggggccggagtattgggaccaggagacacggaatgtgaaggcccactcacagactgaccgagtgg acctggggaccctgcgcggctactacaaccagagcgaggccggttctcacaccatccagatgatgtatggctgcga cgtggggccggacgggcgcctcctccgcgggtaccagcaggacgcctacgacggcaaggattacatcgccttgaac gaggacctgcgctcttggaccgcggcggacatggcggctcagatcacccagcgcaagtgggaggcggcccgtgtgg cggagcagttgagagcctacctggagggcacgtgcgtggagtggctccgcagatacctggagaacgggaaggagac gctgcagcgcacgg;

A*8001:
(SEQ ID NO: 250)
Atggccgtcatgccgccccgaaccctcctcctgctactctcgggggccctggccctgacccagacctgggcaggct cccactccatgaggtatttcttcacatccgtgtcccggcccggccgcggggagccccgcttcatcgcagtgggcta cgtggacgactcgcagttcgtgcagttcgacagcgacgccgcgagccagaggatggagccgcgggcgccgtggata gagcaggaggagccggagtattgggacgaggagacacggaatgtgaaggcccactcacagactaaccgagcgaacc tggggaccctgcgcggctactacaaccagagcgaggacggttctcacaccatccagataatgtatggctgcgacgt ggggtcggacgggcgcttcctccgcgggtaccggcaggacgcctacgacggcaaggattacatcgccctgaacgag gacctgcgctcttggaccgcggcggacatggcggctcagatcaccaagcgcaagtgggaggcggcccgtcgggcgg agcagctgagagcctacctggagggcgagtgcgtggacgggctccgcagatacctggagaacgggaaggagacgct gcagcgcacggacccccccaagacacatatgacccaccacccatctctgaccatgaggccactctgaggtgctgg gccctgagcttctaccctgcggagatcacactgacctggcagcgggatgggaggaccagacccaggacacggagc tcgtggagaccaggcctgcaggggatggaaccttccagaagtgggcggctgtggtggtaccttctggaaaggagaa gagatacacctgccatgtgcagcatgagggtctgcccGagcccctcaccctgagatgggag;

45

The probe list A1 is shown in Tables 1-1 to 1-7 and the probe list A2 is shown in Tables 2-1 to 2-6. The allele-probe lists are shown in Tables 3-1 to 3-9 and Tables 4-1 to 4-9.

TABLE 1-1

| Probe No. | Base Sequence | |
|---|---|---|
| 0 | g ccc cgc ttc atc gcC | (SEQ ID No: 251) |
| 1 | gac cag gag aca cgg aat A | (SEQ ID No: 252) |
| 2 | gcg gag cag cgg aga gT | (SEQ ID No: 253) |
| 3 | a gtc tac ctg gag ggc C | (SEQ ID No: 254) |
| 4 | gtc tac ctg gag ggc cG | (SEQ ID No: 255) |
| 5 | agg tgc tgg gcc ctg G | (SEQ ID No: 256) |
| 6 | g gtg gtg cct tct gga G | (SEQ ID No: 257) |
| 7 | c acc ctg aga tgg gag cT | (SEQ ID No: 258) |

TABLE 1-1-continued

| Probe No. | Base Sequence | |
|---|---|---|
| 8 | cc ctg aga tgg gag ctG | (SEQ ID No: 259) |
| 9 | g gac atg gca gct cag atT | (SEQ ID No: 260) |
| 10 | cac tcc atg agg tat ttc tC | (SEQ ID No: 261) |
| 11 | c cgg ccc ggc agt ggA | (SEQ ID No: 262) |
| 12 | t tct cac acc atc cag atG | (SEQ ID No: 263) |
| 13 | c cat gcg gcg gag cag T | (SEQ ID No: 264) |
| 14 | cat gcg gcg gag cag tT | (SEQ ID No: 265) |
| 15 | ata gag cag gag agg ccT | (SEQ ID No: 266) |
| 16 | c tca cag act gac cga gA | (SEQ ID No: 267) |
| 17 | c tac aac cag agc gag gC | (SEQ ID No: 268) |

TABLE 1-1-continued

| Probe No. | Base Sequence | |
|---|---|---|
| 18 | ga gtc tac ctg gag ggc T | (SEQ ID No: 269) |
| 19 | gtg gac gac acg cag ttA | (SEQ ID No: 270) |
| 20 | tg cta ctc tcg ggg gcT | (SEQ ID No: 271) |
| 21 | g gcc cac tca cag act C | (SEQ ID No: 272) |
| 22 | g gcc ggt tct cac acc G | (SEQ ID No: 273) |
| 23 | t tct cac acc gtc cag aG | (SEQ ID No: 274) |
| 24 | c gac gtg ggg tcg gac T | (SEQ ID No: 275) |
| 25 | gg gag gcg gcc cat gT | (SEQ ID No: 276) |
| 26 | c cat gtg gcg gag cag tT | (SEQ ID No: 277) |
| 27 | gcc tac ctg gag ggc aC | (SEQ ID No: 278) |
| 28 | ga gct gtg gtc gct gcT | (SEQ ID No: 279) |
| 29 | ag ccc cgc ttc atc gcA | (SEQ ID No: 280) |
| 30 | ccg gag tat tgg gac gG | (SEQ ID No: 281) |

TABLE 1-2

| Probe No. | Base Sequence | |
|---|---|---|
| 31 | gacggggaga cacggaaA | (SEQ ID No: 282) |
| 32 | cctccgcggg taccaC | (SEQ ID No: 283) |
| 33 | ccgcgggtac caccagT | (SEQ ID No: 284) |
| 34 | ggattacatc gccctgaaA | (SEQ ID No: 285) |
| 35 | ggacatggca gctcagaC | (SEQ ID No: 286) |
| 36 | gggcacgtgc gtggagT | (SEQ ID No: 287) |
| 37 | gcccactcac agactcaT | (SEQ ID No: 288) |
| 38 | tgcgctcttg gaccgcA | (SEQ ID No: 289) |
| 39 | attacatcgc cctgaaagaA | (SEQ ID No: 290) |
| 40 | ggggtcggac tggcgA | (SEQ ID No: 291) |
| 41 | tcccggcccg gccgT | (SEQ ID No: 292) |
| 42 | catgtgcagc atgagggtT | (SEQ ID No: 293) |
| 43 | gaccagaccc aggacacA | (SEQ ID No: 294) |
| 44 | ccatgtggcg gagcagT | (SEQ ID No: 295) |
| 45 | cggactggcg cttcctG | (SEQ ID No: 296) |
| 46 | ccaagcacaa gtgggagA | (SEQ ID No: 297) |
| 47 | tgggagacgg cccatgA | (SEQ ID No: 298) |
| 48 | ccatgaggcg gagcagT | (SEQ ID No: 299) |
| 49 | ccatgaggta tttctacacC | (SEQ ID No: 300) |
| 50 | caccgtccag aggatgtG | (SEQ ID No: 301) |
| 51 | gtggagacca ggcctgA | (SEQ ID No: 302) |
| 52 | caccgtccag aggatgtT | (SEQ ID No: 303) |

TABLE 1-2-continued

| Probe No. | Base Sequence | |
|---|---|---|
| 53 | gaaggcccac tcacagaT | (SEQ ID No: 304) |
| 54 | catgtggcgg agcagcA | (SEQ ID No: 305) |
| 55 | gggaggcggc ccatgA | (SEQ ID No: 306) |
| 56 | catgaggcgg agcagcA | (SEQ ID No: 307) |
| 57 | gcctacctgg agggcgA | (SEQ ID No: 308) |
| 58 | acaccctcca gatgatgtT | (SEQ ID No: 309) |
| 59 | gaggtgctgg gccctgA | (SEQ ID No: 310) |
| 60 | ggaccgcggc ggacaA | (SEQ ID No: 311) |

TABLE 1-3

| Probe No. | Base Sequence | |
|---|---|---|
| 61 | ca cag act cac cga gtg G | (SEQ ID No: 312) |
| 62 | c gcg gcg gac atg gcG | (SEQ ID No: 313) |
| 63 | gt ccg gag tat tgg gac G | (SEQ ID No: 314) |
| 64 | ac ggg gag aca cgg aaC | (SEQ ID No: 315) |
| 65 | ca gtg ggc tac gtg gac A | (SEQ ID No: 316) |
| 66 | tgg gag acg gcc cat gT | (SEQ ID No: 317) |
| 67 | c cat gag gcg gag cag tT | (SEQ ID No: 318) |
| 68 | a gct cag acc acc aag cA | (SEQ ID No: 319) |
| 69 | cat gcg gcg gag cag cA | (SEQ ID No: 320) |
| 70 | cg tgg ata gag cag gag A | (SEQ ID No: 321) |
| 71 | gac ggg gag aca cgg C | (SEQ ID No: 322) |
| 72 | c tgg gcg ggc tct caG | (SEQ ID No: 323) |
| 73 | tc gac agc gac gcc gG | (SEQ ID No: 324) |
| 74 | c acc gtc cag agg atg tC | (SEQ ID No: 325) |
| 75 | cgg aaa gtg aag gcc caG | (SEQ ID No: 326) |
| 76 | g gcc cag tca cag act C | (SEQ ID No: 327) |
| 77 | g gct cag atc acc aag cA | (SEQ ID No: 328) |
| 78 | gcg gag cag ttg aga gC | (SEQ ID No: 329) |
| 79 | g ggc acg tgc gtg gaG | (SEQ ID No: 330) |
| 80 | g tgg gag gcg gcc cG | (SEQ ID No: 331) |
| 81 | gg gag gcg gcc cgt gT | (SEQ ID No: 332) |
| 82 | c cgc ggg tac cag cag T | (SEQ ID No: 333) |
| 83 | g gag ccc cgc ttc atc T | (SEQ ID No: 334) |
| 84 | gac cag gag aca cgg aaA | (SEQ ID No: 335) |
| 85 | at tgg gac gag gag aca G | (SEQ ID No: 336) |
| 86 | gac gag gag aca ggg aaA | (SEQ ID No: 337) |
| 87 | g aag gcc cac tca cag aG | (SEQ ID No: 338) |

TABLE 1-3-continued

| Probe No. | Base Sequence | |
|---|---|---|
| 88 | g agg tat ttc ttc aca tcc A | (SEQ ID No: 339) |
| 89 | ttc ctc cgc ggg tat gaA | (SEQ ID No: 340) |
| 90 | gag tat tgg gac cgg aaC | (SEQ ID No: 341) |

TABLE 1-4

| Probe No. | Base Sequence | |
|---|---|---|
| 91 | cgg aat gtg aag gcc caG | (SEQ ID No: 342) |
| 92 | g gcc ggt tct cac acc C | (SEQ ID No: 343) |
| 93 | t tct cac acc ctc cag aG | (SEQ ID No: 344) |
| 94 | c cgg ccc ggc cgc gA | (SEQ ID No: 345) |
| 95 | cgc ggg tac cac cag tT | (SEQ ID No: 346) |
| 96 | ca cag act gac cga gtg G | (SEQ ID No: 347) |
| 97 | g ttg aga gcc tac ctg gaT | (SEQ ID No: 348) |
| 98 | cat gag gcg gag cag cT | (SEQ ID No: 349) |
| 99 | ctg aga gcc tac ctg gaT | (SEQ ID No: 350) |
| 100 | tgg ata gag cag gag ggT | (SEQ ID No: 351) |
| 101 | cag aga gcc tac ctg gaT | (SEQ ID No: 352) |
| 102 | ggc ctg gtt ctc ctt gC | (SEQ ID No: 353) |
| 103 | g aga gcc tac ctg gat gC | (SEQ ID No: 354) |
| 104 | ggc tgc gac gtg ggg T | (SEQ ID No: 355) |
| 105 | g ggc cgg tgc gtg gaG | (SEQ ID No: 356) |
| 106 | ggc cgg tgc gtg gag T | (SEQ ID No: 357) |
| 107 | gc tct tgg acc gcg gcA | (SEQ ID No: 358) |
| 108 | gg ccc ggc cgc ggg A | (SEQ ID No: 359) |
| 109 | gg gag gcg gcc cgt gA | (SEQ ID No: 360) |
| 110 | cgt gag gcg gag cag cA | (SEQ ID No: 361) |
| 111 | g gca gct cag atc acc G | (SEQ ID No: 362) |
| 112 | g ccg gac ggg cgc ttA | (SEQ ID No: 363) |
| 113 | g cag aga gcc tac ctg C | (SEQ ID No: 364) |
| 114 | g ccg gag tat tgg gac cT | (SEQ ID No: 365) |
| 115 | g gca gct cag atc acc aG | (SEQ ID No: 366) |
| 116 | g gag gcg gcc cgt cG | (SEQ ID No: 367) |
| 117 | ac gag gag aca ggg aaa G | (SEQ ID No: 368) |
| 118 | cc cag ccc acc gtc cA | (SEQ ID No: 369) |
| 119 | c cgt gtg gcg gag cag T | (SEQ ID No: 370) |
| 120 | gcg gag cag tgg aga gC | (SEQ ID No: 371) |

TABLE 1-5

| Probe No. | Base Sequence | |
|---|---|---|
| 121 | ggc aag gat tac atc gcc T | (SEQ ID No: 372) |
| 122 | cgt gtg gcg gag cag tT | (SEQ ID No: 373) |
| 123 | c tcc cac tcc atg agg tG | (SEQ ID No: 374) |
| 124 | cg ctc cgc tac tac aac G | (SEQ ID No: 375) |
| 125 | ctg cgg atc gcg ctc C | (SEQ ID No: 376) |
| 126 | gcg gag cag cag aga gC | (SEQ ID No: 377) |
| 127 | a tct tcc cag ccc acc G | (SEQ ID No: 378) |
| 128 | ctg ggc ttc tac cct gcA | (SEQ ID No: 379) |
| 129 | cgc ggg tac cac cag taT | (SEQ ID No: 380) |
| 130 | ag acg ctg cag cgc acT | (SEQ ID No: 381) |
| 131 | g gcg gct cag atc acc C | (SEQ ID No: 382) |
| 132 | ggg aaa gtg aag gcc caG | (SEQ ID No: 383) |
| 133 | cc tgg gca ggc tcc caA | (SEQ ID No: 384) |
| 134 | g ggc acg tgc gtg gac T | (SEQ ID No: 385) |
| 135 | gac ggg cgc ttc ctc cA | (SEQ ID No: 386) |
| 136 | gg acc gcg gcg gac aG | (SEQ ID No: 387) |
| 137 | cg gag tat tgg gac gag C | (SEQ ID No: 388) |
| 138 | a cag act gac cga gag aG | (SEQ ID No: 389) |
| 139 | c cag agg atg gag ccg T | (SEQ ID No: 390) |
| 140 | g agc cag agg atg gag cT | (SEQ ID No: 391) |
| 141 | gc tcc cac tcc atg agC | (SEQ ID No: 392) |
| 142 | g cct gca ggg gat ggG | (SEQ ID No: 393) |
| 143 | c cag cgc aag tgg gag A | (SEQ ID No: 394) |
| 144 | c cgc ggg tac cag cag A | (SEQ ID No: 395) |
| 145 | gcc tac ctg gag ggc cT | (SEQ ID No: 396) |
| 146 | tc cgc ggg tac cag cG | (SEQ ID No: 397) |
| 147 | ttc ctc cgc ggg tac cA | (SEQ ID No: 398) |
| 148 | gg tac cag cag gac gcT | (SEQ ID No: 399) |
| 149 | cg cag ttc gtg cgg ttG | (SEQ ID No: 400) |
| 150 | c cag agc gag gac ggt A | (SEQ ID No: 401) |

TABLE 1-6

| Probe No. | Base Sequence | |
|---|---|---|
| 151 | cag atg atg tat ggc tgc C | (SEQ ID No: 402) |
| 152 | g atg gag ccg cgg gcA | (SEQ ID No: 403) |
| 153 | g gac ctg cag aca cgg C | (SEQ ID No: 404) |
| 154 | gag acg ctg cag cgc G | (SEQ ID No: 405) |
| 155 | tgg gag gcg gcc cgt T | (SEQ ID No: 406) |

TABLE 1-6-continued

| Probe No. | Base Sequence | |
|---|---|---|
| 156 | gg gag gcg gcc cgt C | (SEQ ID No: 407) |
| 157 | g ggc tac gtg gac gac G | (SEQ ID No: 408) |
| 158 | cac acc atc cag ata atg C | (SEQ ID No: 409) |
| 159 | gtg cag cat gag ggt ctC | (SEQ ID No: 410) |
| 160 | gg tac cgg cag gac gcT | (SEQ ID No: 411) |
| 161 | c cac tcc atg agg tat ttc A | (SEQ ID No: 412) |
| 162 | g aca cgg aat gtg aag gG | (SEQ ID No: 413) |
| 163 | c cta gtt ctc ttt gga gct A | (SEQ ID No: 414) |
| 164 | gg ccg gac ggg cgc C | (SEQ ID No: 415) |
| 165 | gcc tac ctg gat ggc aC | (SEQ ID No: 416) |
| 166 | t ggc acg tgc gtg gag T | (SEQ ID No: 417) |
| 167 | gac cag gag aca ggg aaA | (SEQ ID No: 418) |
| 168 | gc acg gac ccc ccc aG | (SEQ ID No: 419) |
| 169 | ac gag gac ctg agc tcC | (SEQ ID No: 420) |
| 170 | gcg ccg tgg ata gag cG | (SEQ ID No: 421) |
| 171 | g cgg gcg ccg tgg atG | (SEQ ID No: 422) |
| 172 | c ccc atc gtg ggc atc C | (SEQ ID No: 423) |
| 173 | ctg cag cgc acg gac G | (SEQ ID No: 424) |
| 174 | g gac gcc ccc aag acG | (SEQ ID No: 425) |
| 175 | ctc ttt gga gct gtg atc G | (SEQ ID No: 426) |
| 176 | gac ggc aag gat tac atc T | (SEQ ID No: 427) |
| 177 | gtc tac ctg gag ggc aC | (SEQ ID No: 428) |
| 178 | cgg aga gcc tac ctg gaT | (SEQ ID No: 429) |
| 179 | g gac ggt tct cac acc C | (SEQ ID No: 430) |
| 180 | g ggc gag tgc gtg gag T | (SEQ ID No: 431) |

TABLE 1-7

| Probe No. | Base Sequence | |
|---|---|---|
| 181 | g gag tgg ctc cgc aga C | (SEQ ID No: 432) |
| 182 | ga acc ttc cag aag tgg gT | (SEQ ID No: 433) |
| 183 | cc atg agg tat ttc tac acT | (SEQ ID No: 434) |
| 184 | g agg tat ttc tac acc tcc A | (SEQ ID No: 435) |
| 185 | cgc ggg tac cgg cag C | (SEQ ID No: 436) |
| 186 | cat gtg gcg gag cag cT | (SEQ ID No: 437) |
| 187 | g ccg gag tat tgg gac G | (SEQ ID No: 438) |
| 188 | ag tgg gag gcg gcc cT | (SEQ ID No: 439) |
| 189 | gc ggg tac cgg cag gT | (SEQ ID No: 440) |

TABLE 1-7-continued

| Probe No. | Base Sequence | |
|---|---|---|
| 190 | tgg aga gcc tac ctg gaT | (SEQ ID No: 441) |
| 191 | tg ggg tcg gac ggg cA | (SEQ ID No: 442) |
| 192 | gc aga tac ctg gag aac C | (SEQ ID No: 443) |
| 193 | gac ctg ggg acc ctg cA | (SEQ ID No: 444) |
| 194 | gt tct cac acc atc cag aG | (SEQ ID No: 445) |
| 195 | g gcc ctg acc cag acc A | (SEQ ID No: 446) |
| 196 | c ctc ctc ctg cta ctc tT | (SEQ ID No: 447) |
| 197 | ctc ctc cgc ggg tac cA | (SEQ ID No: 448) |
| 198 | gac cga gtg gac ctg gC | (SEQ ID No: 449) |
| 199 | g aag gcc cac tca cag G | (SEQ ID No: 450) |
| 200 | ca cag att gac cga gtg G | (SEQ ID No: 451) |
| 201 | c aag tgg gag gcg gcc A | (SEQ ID No: 452) |
| 202 | c ttc aca tcc gtg tcc cC | (SEQ ID No: 453) |
| 203 | cag ccc acc atc ccc atT | (SEQ ID No: 454) |

TABLE 2-1

| Probe No. | Base Sequence | |
|---|---|---|
| 0 | cttcatcgcC gtgggcta | (SEQ ID No: 455) |
| 1 | acacggaatA tgaaggccc | (SEQ ID No: 456) |
| 2 | gcggagagTc tacctgg | (SEQ ID No: 457) |
| 3 | ggagggcCgg tgcgtg | (SEQ ID No: 458) |
| 4 | ggagggccGg tgcgtg | (SEQ ID No: 459) |
| 5 | gggccctgGg cttctac | (SEQ ID No: 460) |
| 6 | gtggtggtGc cttctgg | (SEQ ID No: 461) |
| 7 | ccttctggaG aggagcag | (SEQ ID No: 462) |
| 8 | agctcagatT accaagcgc | (SEQ ID No: 463) |
| 9 | ggtatttctC cacatccgt | (SEQ ID No: 464) |
| 10 | ggcagtggAg agcccc | (SEQ ID No: 465) |
| 11 | catccagatG atgtatggc | (SEQ ID No: 466) |
| 12 | cggagcagTt gagagcc | (SEQ ID No: 467) |
| 13 | cggagcagtT gagagcct | (SEQ ID No: 468) |
| 14 | ggagaggccT gagtattg | (SEQ ID No: 469) |
| 15 | ctgaccgagA gaacctgg | (SEQ ID No: 470) |
| 16 | gagcgaggCc ggttctc | (SEQ ID No: 471) |
| 17 | ggagggcTgg tgcgtg | (SEQ ID No: 472) |
| 18 | cacgcagttA gtgcggtt | (SEQ ID No: 473) |
| 19 | tcggggcTc tggccc | (SEQ ID No: 474) |
| 20 | gacacggaaA gtgaaggc | (SEQ ID No: 475) |

TABLE 2-1-continued

| Probe No. | Base Sequence | |
|---|---|---|
| 21 | tcacagactC accgagtg | (SEQ ID No: 476) |
| 22 | ctcacaccGt ccagagg | (SEQ ID No: 477) |
| 23 | ccgtccagaG gatgtatg | (SEQ ID No: 478) |
| 24 | ggtcggacTg gcgcttc | (SEQ ID No: 479) |
| 25 | ggcccatgTg gcggag | (SEQ ID No: 480) |
| 26 | ggagggcaCg tgcgtg | (SEQ ID No: 481) |
| 27 | catgagggtT tgcccaag | (SEQ ID No: 482) |
| 28 | cttcatcgcA gtgggcta | (SEQ ID No: 483) |
| 29 | ttgggacgGg gagacac | (SEQ ID No: 484) |
| 30 | gggtaccaCc agtacgc | (SEQ ID No: 485) |

TABLE 2-2

| Probe No. | Base Sequence | |
|---|---|---|
| 31 | taccaccagT acgcctac | (SEQ ID No: 486) |
| 32 | cgccctgaaA gaggacct | (SEQ ID No: 487) |
| 33 | cagctcagaC caccaagc | (SEQ ID No: 488) |
| 34 | cgtggagTgg ctccgc | (SEQ ID No: 489) |
| 35 | acagactcaT cgagtggac | (SEQ ID No: 490) |
| 36 | tggaccgcAg cggacat | (SEQ ID No: 491) |
| 37 | cctgaaagaA gacctgcg | (SEQ ID No: 492) |
| 38 | gactggcgAt tcctccg | (SEQ ID No: 493) |
| 39 | cccggccgTg gggag | (SEQ ID No: 494) |
| 40 | ccaggacacA gagctcgt | (SEQ ID No: 495) |
| 41 | cgcttcctGc gcgggt | (SEQ ID No: 496) |
| 42 | agtgggagAc ggcccat | (SEQ ID No: 497) |
| 43 | ggcccatgAg gcggag | (SEQ ID No: 498) |
| 44 | cggagcagTg gagagcc | (SEQ ID No: 499) |
| 45 | tctcacaccG tccagatg | (SEQ ID No: 500) |
| 46 | tttctacacC tccgtgtcc | (SEQ ID No: 501) |
| 47 | gaggatgtGt ggctgcg | (SEQ ID No: 502) |
| 48 | caggcctgAa ggggatg | (SEQ ID No: 503) |
| 49 | ccgtccagaG gatgtttg | (SEQ ID No: 504) |
| 50 | agaggatgtT tggctgcg | (SEQ ID No: 505) |
| 51 | actcacagaT tgaccgagt | (SEQ ID No: 506) |
| 52 | ggagcagcAg agagcct | (SEQ ID No: 507) |
| 53 | ggagggcgAg tgcgtg | (SEQ ID No: 508) |
| 54 | gtcatggcTc cccgaac | (SEQ ID No: 509) |
| 55 | agatgatgtT tggctgcga | (SEQ ID No: 510) |
| 56 | gggccctgAg cttctac | (SEQ ID No: 511) |

TABLE 2-2-continued

| Probe No. | Base Sequence | |
|---|---|---|
| 57 | ggcggacaAg gcagctc | (SEQ ID No: 512) |
| 58 | ccgagtgGac ctgggg | (SEQ ID No: 513) |
| 59 | ggacatggcG gctcagat | (SEQ ID No: 514) |
| 60 | tattgggacG gggagaca | (SEQ ID No: 515) |

TABLE 2-3

| Probe No. | Base Sequence | |
|---|---|---|
| 61 | g aca cgg aaC gtg aag gc | (SEQ ID No: 516) |
| 62 | tac gtg gac Aac acg cag | (SEQ ID No: 517) |
| 63 | cc acc aag cAc aag tgg g | (SEQ ID No: 518) |
| 64 | ag cag gag Agt ccg gag | (SEQ ID No: 519) |
| 65 | gag aca cgg Caa gtg aag | (SEQ ID No: 520) |
| 66 | g ggc tct caG tcc atg ag | (SEQ ID No: 521) |
| 67 | c gac gcc gGg agc cag | (SEQ ID No: 522) |
| 68 | g agg atg tCt ggc tgc g | (SEQ ID No: 523) |
| 69 | g aag gcc caG tca cag ac | (SEQ ID No: 524) |
| 70 | tc acc aag cAc aag tgg g | (SEQ ID No: 525) |
| 71 | ag ttg aga gCc tac ctg g | (SEQ ID No: 526) |
| 72 | tgc gtg gaG tgg ctc cg | (SEQ ID No: 527) |
| 73 | gcg gcc cGt gtg gcg | (SEQ ID No: 528) |
| 74 | g gcc cgt gTg gcg gag | (SEQ ID No: 529) |
| 75 | tac cag cag Tac gcc tac | (SEQ ID No: 530) |
| 76 | cgc ttc atc Tca gtg ggc | (SEQ ID No: 531) |
| 77 | gag gag aca Ggg aaa gtg | (SEQ ID No: 532) |
| 78 | g aca ggg aaA gtg aag gc | (SEQ ID No: 533) |
| 79 | ac tca cag aGt cac cga g | (SEQ ID No: 534) |
| 80 | ttc aca tcc Atg tcc cgg | (SEQ ID No: 535) |
| 81 | c ggg tat gaA cag cac gc | (SEQ ID No: 536) |
| 82 | g gac cgg aaC aca cgg aa | (SEQ ID No: 537) |
| 83 | tct cac acc Ctc cag atg | (SEQ ID No: 538) |
| 84 | ct cac acc Ctc cag agg | (SEQ ID No: 539) |
| 85 | cc ctc cag aGg atg tat g | (SEQ ID No: 540) |
| 86 | ggc cgc gAg gag ccc | (SEQ ID No: 541) |
| 87 | c cac cag tTc gcc tac g | (SEQ ID No: 542) |
| 88 | c tac ctg gaT ggc acg tg | (SEQ ID No: 543) |
| 89 | g gag cag cTg aga gcc t | (SEQ ID No: 544) |
| 90 | cag gag ggT ccg gag ta | (SEQ ID No: 545) |

TABLE 2-4

| Probe No. | Base Sequence | |
|---|---|---|
| 91 | ctg gag aac Cgg aag gag | (SEQ ID No: 546) |
| 92 | c ctg gat gCc acg tgc g | (SEQ ID No: 547) |
| 93 | c gtg ggg Tcg gac ggg | (SEQ ID No: 548) |
| 94 | acc gcg gcA gac atg gc | (SEQ ID No: 549) |
| 95 | c cgc ggg Aag ccc cg | (SEQ ID No: 550) |
| 96 | gcg gcc cGt gag gcg | (SEQ ID No: 551) |
| 97 | g gcc cgt gAg gcg gag | (SEQ ID No: 552) |
| 98 | cag atc acc Gag cgc aag | (SEQ ID No: 553) |
| 99 | ggg cgc ttA ctc cgc g | (SEQ ID No: 554) |
| 100 | c tac ctg Cag ggc cgg | (SEQ ID No: 555) |
| 101 | at tgg gac cTg cag aca c | (SEQ ID No: 556) |
| 102 | ag atc acc aGg cgc aag t | (SEQ ID No: 557) |
| 103 | gcc cgt cGg gcg gag | (SEQ ID No: 558) |
| 104 | aca ggg aaa Gtg aag gcc | (SEQ ID No: 559) |
| 105 | g aag tgg gcA gct gtg gt | (SEQ ID No: 560) |
| 106 | g tgg aga gCc tac ctg g | (SEQ ID No: 561) |
| 107 | tac atc gcc Ttg aac gag g | (SEQ ID No: 562) |
| 108 | cc atg agg tGt ttc tcc ac | (SEQ ID No: 563) |
| 109 | tac tac aac Gag agc gag g | (SEQ ID No: 564) |
| 110 | tc gcg ctc Cgc tac tac | (SEQ ID No: 565) |
| 111 | g cag aga gCc tac ctg g | (SEQ ID No: 566) |
| 112 | c tac cct gcA gag atc ac | (SEQ ID No: 567) |
| 113 | c cac cag taT gcc tac ga | (SEQ ID No: 568) |
| 114 | cag atc acc Cag cgc aag | (SEQ ID No: 569) |
| 115 | a ggc tcc caA tcc atg ag | (SEQ ID No: 570) |
| 116 | t gtg gtg gtA cct tct gg | (SEQ ID No: 571) |
| 117 | cg gag cag Tgg aga gtc | (SEQ ID No: 572) |
| 118 | c gtg gac Tgg ctc cgc | (SEQ ID No: 573) |
| 119 | c ttc ctc cAc ggg tac c | (SEQ ID No: 574) |
| 120 | g gcg gac aGg gcg gct | (SEQ ID No: 575) |

TABLE 2-5

| Probe No. | Base Sequence | |
|---|---|---|
| 121 | tca cag act Cac cga gag | (SEQ ID No: 576) |
| 122 | gg gac gag Cag aca ggg | (SEQ ID No: 577) |
| 123 | c cga gag aGc ctg cgg | (SEQ ID No: 578) |
| 124 | ac tca cag aTt gac cga ga | (SEQ ID No: 579) |
| 125 | g gag ccg Tgg gcg cc | (SEQ ID No: 580) |
| 126 | g atg gag cTg cgg gcg | (SEQ ID No: 581) |
| 127 | c tcc atg agC tat ttc tcc | (SEQ ID No: 582) |
| 128 | ggg gat ggG acc ttc ca | (SEQ ID No: 583) |
| 129 | cct tct gga Cag gag cag | (SEQ ID No: 584) |
| 130 | tac cag cag Aac gct tac g | (SEQ ID No: 585) |
| 131 | g gag ggc cTg tgc gtg | (SEQ ID No: 586) |
| 132 | g tac cag cGg gac gct t | (SEQ ID No: 587) |
| 133 | c ggg tac cAg cag gac g | (SEQ ID No: 588) |
| 134 | cag gac gcT tac gac gg | (SEQ ID No: 589) |
| 135 | gtg cgg ttG gac agc ga | (SEQ ID No: 590) |
| 136 | gag gac ggt Act cac acc | (SEQ ID No: 591) |
| 137 | t ggc tgc Cac gtg ggg | (SEQ ID No: 592) |
| 138 | ccg cgg gcA ccg tgg | (SEQ ID No: 593) |
| 139 | cag aca cgg Cat gtg aag | (SEQ ID No: 594) |
| 140 | g gcc cgt Tgg gcg gag | (SEQ ID No: 595) |
| 141 | g gcc cgt Cgg gcg ga | (SEQ ID No: 596) |
| 142 | tg gac gac Gcg cag ttc | (SEQ ID No: 597) |
| 143 | cag ata atg Cat ggc tgc g | (SEQ ID No: 598) |
| 144 | gag ggt ctC ccc aag cc | (SEQ ID No: 599) |
| 145 | agg tat ttc Acc aca tcc g | (SEQ ID No: 600) |
| 146 | at gtg aag gGc cac tca c | (SEQ ID No: 601) |
| 147 | c acg gag ctT gtg gag ac | (SEQ ID No: 602) |
| 148 | c ggg cgc Ctc ctc cg | (SEQ ID No: 603) |
| 149 | g gat ggc aCg tgc gtg g | (SEQ ID No: 604) |
| 150 | c ccc ccc aGg acg cat | (SEQ ID No: 605) |

TABLE 2-6

| Probe No. | Base Sequence | |
|---|---|---|
| 151 | ctg agc tcC tgg acc gc | (SEQ ID No: 606) |
| 152 | g ata gag cGg gag ggg c | (SEQ ID No: 607) |
| 153 | ccg tgg atG gag cag ga | (SEQ ID No: 608) |
| 154 | c acg gac Gcc ccc aag | (SEQ ID No: 609) |
| 155 | ag tgg gcg Tct gtg gtg | (SEQ ID No: 610) |
| 156 | c ccc aag acG cat atg ac | (SEQ ID No: 611) |
| 157 | g cag gag Agg ccg gag | (SEQ ID No: 612) |
| 158 | gat tac atc Tcc ctg aac g | (SEQ ID No: 613) |
| 159 | tc cgc aga Cac ctg gag | (SEQ ID No: 614) |

TABLE 2-6-continued

| Probe No. | Base Sequence | |
|---|---|---|
| 160 | g aag tgg gTg gct gtg g | (SEQ ID No: 615) |
| 161 | t ttc tac acT tcc gtg tcc | (SEQ ID No: 616) |
| 162 | ac acc tcc Atg tcc cgg | (SEQ ID No: 617) |
| 163 | c cgg cag Cac gcc tac | (SEQ ID No: 618) |
| 164 | tat tgg gac Gag gag aca c | (SEQ ID No: 619) |
| 165 | g gcg gcc cTt gtg gcg | (SEQ ID No: 620) |
| 166 | c cgg cag gTc gcc tac | (SEQ ID No: 621) |
| 167 | g gac ggg cAc ttc ctc c | (SEQ ID No: 622) |
| 168 | g acc ctg cAc ggc tac t | (SEQ ID No: 623) |
| 169 | cc atc cag aGg atg tat gg | (SEQ ID No: 624) |
| 170 | c cag acc Agg gcg ggc | (SEQ ID No: 625) |
| 171 | g cta ctc tTg ggg gcc c | (SEQ ID No: 626) |
| 172 | g gac ctg gCg acc ctg | (SEQ ID No: 627) |
| 173 | cac tca cag Gct gac cga | (SEQ ID No: 628) |
| 174 | g gcg gcc Agt gtg gcg | (SEQ ID No: 629) |
| 175 | gtg tcc cCg ccc ggc | (SEQ ID No: 630) |
| 176 | t ctg ccc Gag ccc ctc | (SEQ ID No: 631) |

TABLE 3-1

| Allele Number | Probe Number for Detection | | | | | | | | |
|---|---|---|---|---|---|---|---|---|---|
| A*010101 | 0 | 1 | 2 | 3 | 4 | 5 | 6 | 7 | 8 |
| A*010102 | 9 | | | | | | | | |
| A*0102 | 10 | 11 | | | | | | | |
| A*0103 | 12 | | | | | | | | |
| A*0106 | 13 | 14 | | | | | | | |
| A*0107 | 15 | 16 | 17 | | | | | | |
| A*0108 | 18 | | | | | | | | |
| A*0109 | 19 | | | | | | | | |
| A*020101 | 20 | 21 | 22 | 23 | 24 | 25 | 26 | 27 | 28 |
| A*020102 | 29 | 30 31 21 | 22 23 | 24 32 | 33 34 | 35 25 | 26 27 | 36 | |
| A*020103 | 37 | | | | | | | | |
| A*020104 | 38 | | | | | | | | |
| A*020105 | 39 | | | | | | | | |
| A*020106 | 40 | | | | | | | | |
| A*020107 | 41 | 42 | | | | | | | |
| A*020108 | 43 | | | | | | | | |
| A*020109 | 31 | 21 22 | 23 | 24 | 25 | 44 | 26 | 27 42 | |
| A*0202 | 45 | 42 | | | | | | | |
| A*0203 | 20 | 46 | 47 | 48 | 27 | 28 | | | |
| A*0204 | 20 | 21 | 22 | 24 | 25 | 26 | | 27 | 28 |
| A*0205 | 45 | 28 | | | | | | | |
| A*0206 | 20 | 49 21 | 22 | 23 | 24 | 25 | 26 | 27 28 | |
| A*0207 | 50 | | | | | | | | |
| A*0208 | 49 | 45 | | | | | | | |
| A*0209 | 51 | | | | | | | | |
| A*0210 | 20 | 23 | 52 | 25 | 26 | 27 | | 28 | |
| A*0211 | 53 | 42 | 28 | | | | | | |

TABLE 3-2

| Allele Number | Probe Number for Detection | | | | | | | |
|---|---|---|---|---|---|---|---|---|
| A*0212 | 20 | 25 | 54 | 27 | 28 | | | |
| A*0213 | 20 | 55 | 56 | 27 | 28 | | | |
| A*0214 | 45 | 26 | 28 | | | | | |
| A*0216 | 57 | 42 | 28 | | | | | |
| A*021701 | 20 | 58 | 24 | 25 | 26 | 27 | 28 | |
| A*021702 | 20 | 58 | 24 | 25 | 26 | 27 | 59 | |
| A*0218 | 60 | | | | | | | |
| A*0219 | 61 | 22 | 62 | 25 | 54 | 27 | | |
| A*022001 | 29 | 63 30 21 | 22 23 | 24 32 33 | 34 35 25 | 26 27 | 36 | |
| A*022002 | 64 | | | | | | | |
| A*0221 | 65 | | | | | | | |
| A*0222 | 20 | 21 | 22 | 23 24 | 25 | 44 | 27 | 28 |
| A*0224 | 29 | 30 31 21 | 22 23 | 24 32 33 | 35 25 26 | 27 36 | | |
| A*0225 | 46 | 66 | 26 | 27 | | | | |
| A*0226 | 20 | 55 | 67 | 27 | 28 | | | |
| A*0227 | 22 | 68 | 69 | 27 | 36 | | | |
| A*0228 | 70 | 68 | 25 | 26 | 36 | | | |
| A*0229 | 71 | 68 | | | | | | |
| A*0230 | 72 | | | | | | | |
| A*0231 | 73 | | | | | | | |
| A*0233 | 74 | | | | | | | |
| A*0234 | 31 | 75 76 | 22 23 | 24 25 | 44 26 | 27 42 | | |
| A*0235 | 31 | 75 22 | 23 24 | 32 33 | 34 35 | 25 26 | 27 36 | |
| A*0236 | 29 | 30 31 | 21 22 | 23 24 | 32 33 | 34 35 | 25 26 | 27 |
| A*0237 | 22 | 68 | 25 | 54 | 27 | | | |

TABLE 3-3

| Allele Number | Probe Number for Detection | | | | | | | | | | | |
|---|---|---|---|---|---|---|---|---|---|---|---|---|
| A*0238 | 68 | 46 | 56 | | | | | | | | | |
| A*0239 | 52 | 62 | 77 | 25 | | 26 | | 78 | | 27 | 79 | 36 |
| A*0240 | 68 | 80 | 81 | | 27 | | 36 | | | | | |
| A*0241 | 49 | 29 30 31 | 21 22 | 23 | 24 | 82 | 34 | 35 | 25 | 26 | 27 | 36 |
| A*0242 | 83 | | | | | | | | | | | |
| A*0244 | 49 | 22 | 25 | | 54 | | 27 | | | 36 | | |
| A*0245 | 29 | 84 21 22 | 23 24 | 32 | 33 | 34 | 35 | 25 | 26 | 27 | 36 | |
| A*0246 | 20 | 85 86 | 21 | | 22 | 23 | | 24 | | 25 | 26 | 27 |
| A*0247 | 87 | | | | | | | | | | | |
| A*0248 | 85 | 68 | 25 | | 26 | | 78 | | | 27 | 79 | 36 |
| A*0249 | 29 | 30 31 21 | 22 23 | 24 | 32 | 33 | 34 | 35 | 68 | 25 | 27 | 36 |
| A*0250 | 88 | 31 | 21 | | | | | | | | | |
| A*0251 | 49 | 68 | 80 | | 81 | | 27 | | | 36 | | |
| A*0252 | 89 | 68 | 25 | | 26 | | | | | | | |
| A*0254 | 49 | 22 | 68 | | 25 | | 54 | | | 27 | | |
| A*0255 | 90 | 21 22 23 | 24 32 | 33 | 34 | 35 | 25 | 26 | 27 | 36 | | |
| A*0256 | 20 | 91 76 | 22 23 | | 24 | 25 | 26 | | 27 | 42 | | |
| A*0257 | 20 | 49 | 92 | | 24 | | 25 | | | 26 | 27 | 28 |
| A*0258 | 92 | 93 | 68 | 25 | | 26 | | 78 | | 27 | 79 | 36 |
| A*0259 | 94 | | | | | | | | | | | |
| A*0260 | 95 | 26 | | | | | | | | | | |
| A*030101 | 91 | 96 | 55 | | 48 | | 67 | | | 97 | | |
| A*030102 | 91 | 96 | 55 | | 98 | | 99 | | | | | |
| A*030103 | 100 | 91 | 96 | | 55 | | 48 | | | 67 | 97 | |
| A*0302 | 54 | 101 | | | | | | | | | | |
| A*0304 | 102 | | | | | | | | | | | |
| A*0305 | 91 | 96 | 17 | | 62 | | 55 | | | 48 | 67 | 27 |
| A*0306 | 103 | | | | | | | | | | | |
| A*0307 | 25 | 44 | 25 | | 97 | | | | | | | |

TABLE 3-4

| Allele Number | Probe Number for Detection | | | | | |
|---|---|---|---|---|---|---|
| A*0308 | 96 | 55 | 48 | 67 | 97 | |
| A*0309 | 76 | 61 | 55 | 48 | 67 | 97 |

TABLE 3-4-continued

| Allele Number | Probe Number for Detection | | | | | | | | | |
|---|---|---|---|---|---|---|---|---|---|---|
| A*0310 | 96 | 104 | 62 | 25 | 54 | 27 | 79 | 36 | | |
| A*110101 | 49 | 91 | 96 | 69 | 105 | 106 | | | | |
| A*110102 | 107 | | | | | | | | | |
| A*1102 | 108 | | | | | | | | | |
| A*1103 | 80 | 109 | 110 | | | | | | | |
| A*1104 | 49 | 91 | 96 | 69 | 27 | 79 | 36 | | | |
| A*1105 | 111 | | | | | | | | | |
| A*1106 | 91 | 76 | 61 | 69 | 105 | 106 | | | | |
| A*1107 | 112 | | | | | | | | | |
| A*1108 | 49 | 91 | 96 | 55 | | | | | | |
| A*1109 | 113 | | | | | | | | | |
| A*1110 | 49 | 90 | 96 | 69 | 106 | | | | | |
| A*1111 | 114 | 96 | 69 | 106 | | | | | | |
| A*1112 | 49 | 91 | 96 | 17 | 69 | 105 | 106 | | | |
| A*1113 | 115 | | | | | | | | | |
| A*1114 | 108 | 116 | | | | | | | | |
| A*2301 | 117 | 118 | | | | | | | | |
| A*2302 | 85 | 34 | 80 | 81 | 119 | 120 | 27 | | | |
| A*2303 | 33 | 121 | 80 | 122 | | | | | | |
| A*2304 | 85 | 34 | 80 | 81 | 122 | 78 | 27 | 79 | 36 | |
| A*2305 | 123 | 122 | | | | | | | | |
| A*2306 | 124 | | | | | | | | | |
| A*2309 | 118 | | | | | | | | | |
| A*240201 | 85 | 125 | 54 | 126 | 127 | | | | | |
| A*240202 | 85 | 125 | 17 58 | 104 | 33 | 34 | 54 | 126 | 27 | |
| A*240203 | 128 | | | | | | | | | |
| A*240204 | 129 | | | | | | | | | |

TABLE 3-5

| Allele Number | Probe Number for Detection | | | | | | | | | | |
|---|---|---|---|---|---|---|---|---|---|---|---|
| A*240301 | 126 | 36 | 127 | | | | | | | | |
| A*240302 | 130 | | | | | | | | | | |
| A*2404 | 85 | 54 | 126 | 127 | | | | | | | |
| A*2405 | 85 | 131 | 54 | 126 | 27 | | | | | | |
| A*2406 | 85 | 34 | 62 | 25 | 44 | 120 | 27 | | | | |
| A*2407 | 132 | 125 | 54 | 126 | 127 | | | | | | |
| A*2408 | 133 | 28 | | | | | | | | | |
| A*2410 | 85 | 54 | 126 | 105 | 106 | | | | | | |
| A*2413 | 85 | 34 | 62 | 25 | 26 | 78 | 27 | | | | |
| A*2414 | 85 | 24 | 33 | 34 | 62 | 54 | 126 | 27 | | | |
| A*2415 | 85 | 125 | 17 | 92 | 33 | 34 | 62 | 54 | 126 | 27 | |
| A*2417 | 85 | 125 | 17 | 58 | 104 | 34 | 62 | 54 | 126 | 27 | |
| A*2418 | 34 | 55 | 48 | 67 | 97 | | | | | | |
| A*2419 | 85 | 132 | 96 | 58 | 104 | 33 | 34 | 62 | 54 | 126 | 27 |
| A*2420 | 85 | 125 | 17 | 58 | 104 | 33 | 34 | 62 | 54 | 126 | 27 |
| A*2421 | 85 | 125 | 17 | 58 | 104 | 33 | 62 | 54 | 126 | 27 | |
| A*2422 | 44 | 36 | 127 | | | | | | | | |
| A*2423 | 85 | 54 | 126 | 27 | 134 | | | | | | |
| A*2424 | 91 | 58 | 34 | 80 | 81 | 122 | 78 | 27 | | | |
| A*2425 | 123 | 54 | | | | | | | | | |
| A*2426 | 135 | | | | | | | | | | |
| A*2427 | 136 | | | | | | | | | | |
| A*2428 | 85 | 61 | 17 | 58 | 104 | 33 | 34 | 62 | 54 | 126 | 27 |
| A*2429 | 125 | 17 | 58 | 33 | 34 | 62 | 54 | 126 | 27 | | |
| A*2430 | 85 | 21 | 125 | 17 | 58 | 104 | 33 | 34 | 62 | 54 | 126 | 27 |
| A*2431 | 137 | 25 | 54 | 27 | | | | | | | |
| A*2432 | 138 | 34 | 54 | 27 | | | | | | | |
| A*2433 | 62 | 25 | 54 | 27 | 42 | | | | | | |
| A*2434 | 53 | 54 | | | | | | | | | |

TABLE 3-6

| Allele Number | Probe Number for Detection | | | | |
|---|---|---|---|---|---|
| A*2435 | 139 | | | | |
| A*2437 | 140 | | | | |
| A*2438 | 141 | | | | |
| A*2501 | 138 | 142 | 28 | | |
| A*2502 | 91 | 138 | 142 | 28 | |
| A*2503 | 138 | 143 | 47 | 48 | 106 |
| A*2504 | 138 | 47 | 56 | 106 | |
| A*2601 | 90 | 48 | 142 | | |
| A*2602 | 144 | | | | |
| A*2603 | 21 | 61 | 48 | 142 | |

TABLE 3-6-continued

| Allele Number | Probe Number for Detection | | | | | |
|---|---|---|---|---|---|---|
| A*2604 | 145 | | | | | |
| A*2605 | 16 | 48 | 142 | | | |
| A*2606 | 146 | | | | | |
| A*2607 | 31 | 48 | 142 | | | |
| A*2608 | 56 | 142 | | | | |
| A*2609 | 147 | 131 | 143 | 47 | 27 | |
| A*2610 | 34 | 131 | 143 | 47 | 48 | |
| A*2612 | 131 | 143 | 66 | 44 | | |
| A*2613 | 91 | 147 | 131 | 143 | 47 | 48 |
| A*2614 | 49 | 90 | 147 | 148 | 55 | 48 |
| A*2615 | 149 | | | | | |
| A*2616 | 10 | 90 | 147 | 131 | 143 | 47 | 48 |
| A*2617 | 150 | | | | | |
| A*2618 | 147 | 148 | 80 | 81 | 119 | |
| A*29010101 | 151 | | | | | |
| A*2902 | 152 | 36 | 28 | | | |
| A*2903 | 152 | 28 | | | | |
| A*2904 | 153 | 80 | | | | |
| A*2905 | 152 | 56 | 36 | | | |

TABLE 3-7

| Allele Number | Probe Number for Detection | | | | | | |
|---|---|---|---|---|---|---|---|
| A*2906 | 122 | 154 | | | | | |
| A*2907 | 152 | 58 | 122 | 36 | | | |
| A*3001 | 10 | 15 | 155 | | | | |
| A*3002 | 11 | 15 | 156 | 27 | 36 | | |
| A*3003 | 11 | 156 | 27 | 36 | | | |
| A*3004 | 11 | 25 | 36 | | | | |
| A*3006 | 157 | | | | | | |
| A*3007 | 86 | 156 | 27 | 36 | | | |
| A*3008 | 49 | 15 | 155 | | | | |
| A*3009 | 11 | 81 | 122 | 36 | | | |
| A*3010 | 158 | | | | | | |
| A*3011 | 10 | 155 | | | | | |
| A*3012 | 15 | 156 | 27 | 36 | | | |
| A*310102 | 15 | 121 | 159 | | | | |
| A*3102 | 84 | 53 | 104 | 147 | 121 | 80 | 122 | 36 |
| A*3103 | 53 | 160 | 80 | 122 | 36 | | |
| A*3104 | 160 | 159 | | | | | |
| A*3105 | 15 | 53 | 104 | 147 | 121 | 80 | 122 |
| A*3106 | 15 | 53 | 104 | 121 | 80 | 122 | 36 |
| A*3107 | 15 | 125 | 147 | 121 | 81 | 122 | 36 |
| A*3108 | 161 | 85 | 125 | 147 | 121 | 122 | 36 |
| A*3109 | 162 | | | | | | |
| A*3201 | 125 | 122 | 163 | | | | |
| A*3202 | 54 | 163 | | | | | |
| A*3203 | 125 | 164 | 80 | 122 | | | |
| A*3204 | 138 | 97 | 165 | 166 | | | |
| A*3205 | 167 | 125 | 122 | 163 | | | |
| A*3206 | 138 | 25 | 26 | 27 | 36 | | |
| A*3207 | 10 | 138 | 80 | 81 | 122 | 27 | 36 |

TABLE 3-8

| Allele Number | Probe Number for Detection | | | | | | |
|---|---|---|---|---|---|---|---|
| A*3301 | 168 | | | | | | |
| A*3303 | 90 | 121 | 159 | | | | |
| A*3304 | 169 | | | | | | |
| A*3305 | 170 | | | | | | |
| A*3306 | 171 | | | | | | |
| A*3401 | 172 | | | | | | |
| A*3402 | 47 | 67 | 27 | 36 | 173 | 174 | 175 | 28 |
| A*3403 | 160 | 55 | 67 | 27 | | | |
| A*3404 | 70 | 47 | 67 | 36 | | | |
| A*3405 | 176 | | | | | | |
| A*3601 | 177 | 79 | | | | | |
| A*3602 | 178 | | | | | | |
| A*3603 | 179 | 177 | 79 | 36 | | | |
| A*3604 | 105 | | | | | | |
| A*4301 | 114 | 142 | 28 | | | | |
| A*6601 | 91 | 96 | 48 | 142 | | | |
| A*6602 | 57 | 175 | 28 | | | | |
| A*6603 | 47 | 57 | 180 | | | | |
| A*6604 | 47 | 181 | | | | | |
| A*680101 | 49 | 91 | 104 | 44 | 182 | 28 | |
| A*680102 | 183 | 91 | 104 | 44 | 182 | 28 | |
| A*6802 | 184 | 28 | | | | | |
| A*680301 | 183 | 104 | 44 | 182 | 28 | | |
| A*680302 | 183 | 35 | 44 | | | | |
| A*6804 | 90 | 53 | 68 | 36 | | | |
| A*6805 | 183 | 21 | 35 | 44 | | | |
| A*6806 | 91 | 89 | 68 | 25 | | | |
| A*6807 | 91 | 185 | 68 | 25 | | | |

TABLE 3-9

| Allele Number | Probe Number for Detection | | | | | | | |
|---|---|---|---|---|---|---|---|---|
| A*6808 | 186 | 182 | 28 | | | | | |
| A*6809 | 183 | 54 | | | | | | |
| A*6810 | 49 | 187 | 91 | 104 | 25 | 44 | 27 | 36 |
| A*6812 | 183 | 91 | 44 | | | | | |
| A*6813 | 49 | 91 | 104 | 44 | 182 | | | |
| A*6814 | 68 | 154 | | | | | | |
| A*6815 | 184 | 90 | 21 | | | | | |
| A*6816 | 188 | | | | | | | |
| A*6817 | 189 | 28 | | | | | | |
| A*6819 | 68 | 25 | 44 | 190 | | | | |
| A*6820 | 191 | | | | | | | |
| A*6821 | 25 | 192 | | | | | | |
| A*6822 | 193 | | | | | | | |
| A*6823 | 183 | 194 | 35 | 44 | | | | |
| A*6901 | 91 | 22 | 23 | 24 | 25 | 44 | 26 | 27 | 42 | 28 |
| A*7401 | 195 | 28 | | | | | | |
| A*7402 | 196 | 96 | 164 | 197 | 121 | 122 | 36 | |
| A*7403 | 198 | | | | | | | |
| A*7404 | 31 | 96 | 164 | 80 | 122 | | | |
| A*7405 | 199 | | | | | | | |
| A*7406 | 21 | 61 | 164 | 80 | 122 | | | |
| A*7407 | 53 | 200 | 164 | 80 | 122 | | | |
| A*7408 | 201 | | | | | | | |
| A*7409 | 202 | | | | | | | |
| A*8001 | 203 | | | | | | | |

TABLE 4-1

| Allele Number | Probe Number for Detection | | | | | | | | | | | | | |
|---|---|---|---|---|---|---|---|---|---|---|---|---|---|---|
| A*010101 | 0 | 1 | 2 | 3 | 4 | 5 | 6 | 7 | | | | | | |
| A*010102 | 8 | | | | | | | | | | | | | |
| A*0102 | 9 | 10 | | | | | | | | | | | | |
| A*0103 | 11 | | | | | | | | | | | | | |
| A*0106 | 12 | 13 | | | | | | | | | | | | |
| A*0107 | 14 | 15 | 16 | | | | | | | | | | | |
| A*0108 | 17 | | | | | | | | | | | | | |
| A*0109 | 18 | | | | | | | | | | | | | |
| A*020101 | 19 | 20 | 21 | 22 | 23 | 24 | 25 | 13 | 26 | 27 | | | | |
| A*020102 | 28 | 29 | 20 | 21 | 22 | 23 | 24 | 30 | 31 | 32 | 33 | 25 | 13 | 26 | 34 |
| A*020103 | 35 | | | | | | | | | | | | | |
| A*020104 | 36 | | | | | | | | | | | | | |
| A*020105 | 37 | | | | | | | | | | | | | |
| A*020106 | 38 | | | | | | | | | | | | | |
| A*020107 | 39 | 27 | | | | | | | | | | | | |
| A*020108 | 40 | | | | | | | | | | | | | |
| A*020109 | 20 | 21 | 22 | 23 | 24 | 25 | 12 | 13 | 26 | 27 | | | | |
| A*0202 | 41 | 27 | | | | | | | | | | | | |
| A*0203 | 19 | 42 | 43 | 44 | 26 | 27 | | | | | | | | |
| A*0204 | 19 | 20 | 21 | 45 | 24 | 25 | 13 | 26 | 27 | | | | | |
| A*0205 | 46 | 41 | 27 | | | | | | | | | | | |
| A*0206 | 19 | 46 | 20 | 21 | 22 | 23 | 24 | 25 | 13 | 26 | 27 | | | |
| A*0207 | 47 | | | | | | | | | | | | | |
| A*0208 | 46 | 41 | | | | | | | | | | | | |
| A*0209 | 48 | | | | | | | | | | | | | |
| A*0210 | 19 | 49 | 50 | 25 | 13 | 26 | 27 | | | | | | | |
| A*0211 | 51 | 27 | | | | | | | | | | | | |
| A*0212 | 19 | 25 | 52 | 26 | 27 | | | | | | | | | |
| A*0213 | 19 | 43 | 52 | 26 | 27 | | | | | | | | | |

TABLE 4-2

| Allele Number | Probe Number for Detection | | | | | | | | | | | | | |
|---|---|---|---|---|---|---|---|---|---|---|---|---|---|---|
| A*0214 | 41 | 13 | 27 | | | | | | | | | | | |
| A*0216 | 53 | 27 | | | | | | | | | | | | |
| A*021701 | 54 | | | | | | | | | | | | | |
| A*021702 | 19 | 55 | 24 | 25 | 13 | 26 | 56 | | | | | | | |
| A*0218 | 57 | | | | | | | | | | | | | |
| A*0219 | 58 | 22 | 59 | 25 | 52 | 26 | | | | | | | | |
| A*022001 | 28 | 60 | 29 | 21 | 22 | 23 | 24 | 30 | 31 | 32 | 33 | 25 | 13 | 26 | 34 |
| A*022002 | 61 | | | | | | | | | | | | | |
| A*0221 | 62 | | | | | | | | | | | | | |
| A*0222 | 19 | 20 | 21 | 22 | 23 | 24 | 25 | 44 | 26 | 27 | | | | |
| A*0224 | 28 | 29 | 20 | 21 | 22 | 23 | 24 | 30 | 31 | 33 | 25 | 13 | 26 | 34 |
| A*0225 | 42 | 25 | 13 | 26 | | | | | | | | | | |
| A*0226 | 19 | 43 | 13 | 26 | 27 | | | | | | | | | |
| A*0227 | 22 | 63 | 52 | 26 | 34 | | | | | | | | | |
| A*0228 | 64 | 63 | 25 | 13 | 34 | | | | | | | | | |
| A*0229 | 65 | 63 | | | | | | | | | | | | |
| A*0230 | 66 | | | | | | | | | | | | | |
| A*0231 | 67 | | | | | | | | | | | | | |
| A*0233 | 68 | | | | | | | | | | | | | |
| A*0234 | 20 | 69 | 21 | 22 | 23 | 24 | 25 | 12 | 13 | 26 | 27 | | | |
| A*0235 | 20 | 69 | 22 | 23 | 24 | 30 | 31 | 32 | 33 | 25 | 13 | 26 | 34 | |
| A*0236 | 28 | 29 | 20 | 21 | 22 | 23 | 24 | 30 | 31 | 32 | 33 | 25 | 13 | 26 | |
| A*0237 | 22 | 63 | 25 | 52 | 26 | | | | | | | | | |
| A*0238 | 63 | 42 | 52 | | | | | | | | | | | |
| A*0239 | 50 | 59 | 70 | 25 | 13 | 71 | 26 | 72 | 34 | | | | | |
| A*0240 | 63 | 73 | 74 | 26 | 34 | | | | | | | | | |
| A*0241 | 46 | 28 | 29 | 20 | 21 | 22 | 23 | 24 | 75 | 32 | 33 | 25 | 13 | 26 | 34 |
| A*0242 | 76 | | | | | | | | | | | | | |
| A*0244 | 46 | 22 | 25 | 52 | 26 | 34 | | | | | | | | |

TABLE 4-3

| Allele Number | Probe Number for Detection | | | | | | | | | | | | | |
|---|---|---|---|---|---|---|---|---|---|---|---|---|---|---|
| A*0245 | 28 | 20 | 21 | 22 | 23 | 24 | 30 | 31 | 32 | 33 | 25 | 13 | 26 | 34 |
| A*0246 | 19 | 77 | 78 | 21 | 22 | 23 | 24 | 25 | 13 | 26 | | | | |
| A*0247 | 79 | | | | | | | | | | | | | |

TABLE 4-3-continued

| Allele Number | Probe Number for Detection | | | | | | | | | | | | |
|---|---|---|---|---|---|---|---|---|---|---|---|---|---|
| A*0248 | 77 | 63 | 25 | 13 | 71 | 26 | 72 | 34 | | | | | |
| A*0249 | 28 | 29 | 20 | 21 | 22 | 23 | 24 | 30 | 31 | 32 | 33 | 63 | 25 | 26 | 34 |
| A*0250 | 80 | 20 | 21 | | | | | | | | | | |
| A*0251 | 46 | 63 | 73 | 74 | 26 | 34 | | | | | | | |
| A*0252 | 81 | 63 | 25 | 13 | | | | | | | | | |
| A*0254 | 46 | 22 | 63 | 25 | 52 | 26 | | | | | | | |
| A*0255 | 82 | 21 | 22 | 23 | 24 | 30 | 31 | 32 | 33 | 25 | 13 | 26 | 34 |
| A*0256 | 19 | 69 | 21 | 22 | 23 | 24 | 25 | 13 | 26 | 27 | | | |
| A*0257 | 19 | 46 | 83 | 24 | 25 | 13 | 26 | 27 | | | | | |
| A*0258 | 84 | 85 | 63 | 25 | 13 | 71 | 26 | 72 | 34 | | | | |
| A*0259 | 86 | | | | | | | | | | | | |
| A*0260 | 87 | 13 | | | | | | | | | | | |
| A*030101 | 69 | 58 | 43 | 12 | 13 | 88 | | | | | | | |
| A*030102 | 69 | 58 | 43 | 89 | 88 | | | | | | | | |
| A*030103 | 90 | 69 | 58 | 43 | 12 | 13 | 88 | | | | | | |
| A*0302 | 52 | 88 | | | | | | | | | | | |
| A*0304 | 88 | 91 | | | | | | | | | | | |
| A*0305 | 69 | 58 | 16 | 59 | 43 | 12 | 13 | 26 | | | | | |
| A*0306 | 92 | | | | | | | | | | | | |
| A*0307 | 25 | 12 | 13 | 88 | | | | | | | | | |
| A*0308 | 58 | 43 | 12 | 13 | 88 | | | | | | | | |
| A*0309 | 21 | 58 | 43 | 12 | 13 | 88 | | | | | | | |
| A*0310 | 58 | 93 | 59 | 25 | 52 | 26 | 72 | 34 | | | | | |
| A*110101 | 46 | 69 | 58 | 52 | 72 | 34 | | | | | | | |
| A*110102 | 94 | | | | | | | | | | | | |
| A*1102 | 95 | | | | | | | | | | | | |

TABLE 4-4

| Allele Number | Probe Number for Detection | | | | | | | |
|---|---|---|---|---|---|---|---|---|
| A*1103 | 96 | 97 | 52 | | | | | |
| A*1104 | 46 | 69 | 58 | 52 | 26 | 72 | 34 | |
| A*1105 | 98 | | | | | | | |
| A*1106 | 69 | 21 | 58 | 52 | 72 | 34 | | |
| A*1107 | 99 | | | | | | | |
| A*1108 | 46 | 69 | 58 | 43 | | | | |
| A*1109 | 100 | | | | | | | |
| A*1110 | 46 | 82 | 58 | 52 | 34 | | | |
| A*1111 | 101 | 58 | 52 | 34 | | | | |
| A*1112 | 46 | 69 | 58 | 16 | 52 | 72 | 34 | |
| A*1113 | 102 | | | | | | | |
| A*1114 | 95 | 103 | | | | | | |
| A*2301 | 104 | 13 | 71 | 105 | | | | |
| A*2302 | 77 | 32 | 73 | 74 | 44 | 106 | 26 | |
| A*2303 | 31 | 107 | 73 | 13 | | | | |
| A*2304 | 77 | 32 | 73 | 74 | 13 | 71 | 26 | 72 | 34 |
| A*2305 | 108 | 13 | | | | | | |
| A*2306 | 109 | | | | | | | |
| A*2309 | 13 | 71 | 105 | | | | | |
| A*240201 | 77 | 110 | 52 | 111 | 105 | | | |
| A*240202 | 77 | 110 | 16 | 55 | 93 | 31 | 32 | 52 | 111 | 26 |
| A*240203 | 112 | | | | | | | |
| A*240204 | 113 | | | | | | | |
| A*240301 | 111 | 34 | 105 | | | | | |
| A*240302 | 77 | 52 | 111 | 26 | 72 | 34 | | |
| A*2404 | 77 | 52 | 111 | 105 | | | | |
| A*2405 | 77 | 114 | 52 | 111 | 26 | | | |
| A*2406 | 77 | 32 | 59 | 25 | 44 | 106 | 26 | |
| A*2407 | 69 | 110 | 52 | 111 | 105 | | | |

TABLE 4-5

| Allele Number | Probe Number for Detection | | | | | | | |
|---|---|---|---|---|---|---|---|---|
| A*2408 | 115 | 116 | | | | | | |
| A*2410 | 77 | 52 | 111 | 72 | 34 | | | |
| A*2413 | 77 | 32 | 59 | 25 | 13 | 71 | 26 | |
| A*2414 | 77 | 24 | 31 | 32 | 59 | 52 | 111 | 26 |

TABLE 4-5-continued

| Allele Number | Probe Number for Detection | | | | | | | | | |
|---|---|---|---|---|---|---|---|---|---|---|
| A*2415 | 77 | 110 | 16 | 83 | 31 | 32 | 59 | 52 | 111 | 26 |
| A*2417 | 77 | 110 | 16 | 55 | 93 | 32 | 59 | 52 | 111 | 26 |
| A*2418 | 32 | 43 | 12 | 13 | 88 | | | | | |
| A*2419 | 77 | 69 | 58 | 55 | 93 | 31 | 32 | 59 | 52 | 111 | 26 |
| A*2420 | 77 | 110 | 16 | 55 | 93 | 31 | 32 | 59 | 52 | 111 | 26 |
| A*2421 | 77 | 110 | 16 | 55 | 93 | 31 | 59 | 52 | 111 | 26 |
| A*2422 | 117 | 34 | 105 | | | | | | | |
| A*2423 | 77 | 52 | 111 | 26 | 118 | | | | | |
| A*2424 | 69 | 55 | 32 | 73 | 74 | 13 | 71 | 26 | | |
| A*2425 | 108 | 52 | | | | | | | | |
| A*2426 | 119 | | | | | | | | | |
| A*2427 | 120 | | | | | | | | | |
| A*2428 | 77 | 58 | 16 | 55 | 93 | 31 | 32 | 59 | 52 | 111 | 26 |
| A*2429 | 110 | 16 | 55 | 31 | 32 | 59 | 52 | 111 | 26 | |
| A*2430 | 77 | 121 | 110 | 16 | 55 | 93 | 31 | 32 | 59 | 52 | 111 | 26 |
| A*2431 | 122 | 25 | 52 | 26 | | | | | | |
| A*2432 | 123 | 32 | 52 | 26 | | | | | | |
| A*2433 | 59 | 25 | 52 | 26 | 27 | | | | | |
| A*2434 | 124 | 52 | | | | | | | | |
| A*2435 | 125 | | | | | | | | | |
| A*2437 | 126 | | | | | | | | | |
| A*2438 | 127 | | | | | | | | | |
| A*2501 | 123 | 128 | 129 | | | | | | | |
| A*2502 | 69 | 123 | 128 | 129 | | | | | | |
| A*2503 | 123 | 42 | 43 | 44 | 34 | | | | | |

TABLE 4-6

| Allele Number | Probe Number for Detection | | | | |
|---|---|---|---|---|---|
| A*2504 | 123 | 43 | 52 | 34 | |
| A*2601 | 82 | 44 | 128 | | |
| A*2602 | 130 | | | | |
| A*2603 | 21 | 58 | 44 | 128 | |
| A*2604 | 131 | | | | |
| A*2605 | 15 | 44 | 128 | | |
| A*2606 | 132 | | | | |
| A*2607 | 20 | 44 | 128 | | |
| A*2608 | 52 | 128 | | | |
| A*2609 | 133 | 114 | 42 | 43 | 26 |
| A*2610 | 32 | 114 | 42 | 43 | 44 |
| A*2612 | 114 | 42 | 25 | 44 | |
| A*2613 | 69 | 133 | 114 | 42 | 43 | 44 |
| A*2614 | 46 | 82 | 133 | 134 | 43 | 44 |
| A*2615 | 135 | | | | |
| A*2616 | 9 | 82 | 133 | 114 | 42 | 43 | 44 |
| A*2617 | 136 | | | | |
| A*2618 | 133 | 134 | 73 | 74 | 44 |
| A*29010101 | 137 | | | | |
| A*2902 | 138 | 34 | 129 | | |
| A*2903 | 138 | 129 | | | |
| A*2904 | 139 | 73 | | | |
| A*2905 | 138 | 52 | 34 | | |
| A*2906 | 138 | 13 | 34 | | |
| A*2907 | 138 | 55 | 13 | 34 | |
| A*3001 | 9 | 14 | 140 | | |
| A*3002 | 10 | 14 | 141 | 26 | 34 |
| A*3003 | 10 | 141 | 26 | 34 | |
| A*3004 | 10 | 25 | 34 | | |

TABLE 4-7

| Allele Number | Probe Number for Detection | | | | | | |
|---|---|---|---|---|---|---|---|
| A*3006 | 142 | | | | | | |
| A*3007 | 78 | 141 | 26 | 34 | | | |
| A*3008 | 46 | 14 | 140 | | | | |
| A*3009 | 10 | 74 | 13 | 34 | | | |
| A*3010 | 143 | | | | | | |
| A*3011 | 9 | 140 | | | | | |
| A*3012 | 14 | 141 | 26 | 34 | | | |
| A*310102 | 14 | 107 | 144 | | | | |
| A*3102 | 20 | 51 | 93 | 133 | 107 | 73 | 13 | 34 |

TABLE 4-7-continued

| Allele Number | Probe Number for Detection | | | | | | |
|---|---|---|---|---|---|---|---|
| A*3103 | 51 | 134 | 73 | 13 | 34 | | |
| A*3104 | 134 | 144 | | | | | |
| A*3105 | 14 | 51 | 93 | 133 | 107 | 73 | 13 |
| A*3106 | 14 | 51 | 93 | 107 | 73 | 13 | 34 |
| A*3107 | 14 | 110 | 133 | 107 | 74 | 13 | 34 |
| A*3108 | 145 | 77 | 110 | 133 | 107 | 13 | 34 |
| A*3109 | 146 | | | | | | |
| A*3201 | 123 | 13 | 147 | 129 | | | |
| A*3202 | 123 | 52 | 147 | 129 | | | |
| A*3203 | 110 | 148 | 73 | 13 | | | |
| A*3204 | 123 | 88 | 149 | 34 | | | |
| A*3205 | 78 | 123 | 13 | 147 | 129 | | |
| A*3206 | 123 | 25 | 13 | 26 | 34 | | |
| A*3207 | 9 | 123 | 73 | 74 | 13 | 26 | 34 |
| A*3301 | 150 | | | | | | |
| A*3303 | 82 | 107 | 144 | | | | |
| A*3304 | 151 | | | | | | |
| A*3305 | 152 | | | | | | |
| A*3306 | 153 | | | | | | |
| A*3401 | 133 | 43 | 44 | 26 | 34 | 154 | 155 | 129 |

TABLE 4-8

| Allele Number | Probe Number for Detection | | | | | | |
|---|---|---|---|---|---|---|---|
| A*3402 | 43 | 13 | 26 | 34 | 154 | 156 | 155 | 129 |
| A*3403 | 134 | 43 | 13 | 26 | | | |
| A*3404 | 157 | 43 | 13 | 34 | | | |
| A*3405 | 158 | | | | | | |
| A*3601 | 26 | 72 | | | | | |
| A*3602 | 88 | | | | | | |
| A*3603 | 83 | 26 | 72 | 34 | | | |
| A*3604 | 72 | | | | | | |
| A*4301 | 101 | 128 | 129 | | | | |
| A*6601 | 69 | 58 | 44 | 128 | | | |
| A*6602 | 53 | 155 | 129 | | | | |
| A*6603 | 43 | 53 | 34 | | | | |
| A*6604 | 43 | 159 | | | | | |
| A*680101 | 46 | 69 | 93 | 44 | 160 | 27 | |
| A*680102 | 161 | 69 | 93 | 44 | 160 | 27 | |
| A*6802 | 162 | 27 | | | | | |
| A*680301 | 161 | 93 | 44 | 160 | 27 | | |
| A*680302 | 161 | 33 | 44 | | | | |

TABLE 4-8-continued

| Allele Number | Probe Number for Detection | | | | | | | |
|---|---|---|---|---|---|---|---|---|
| A*6804 | 82 | 51 | 63 | 34 | | | | |
| A*6805 | 161 | 21 | 33 | 44 | | | | |
| A*6806 | 69 | 81 | 63 | 25 | | | | |
| A*6807 | 69 | 163 | 63 | 25 | | | | |
| A*6808 | 89 | 160 | 27 | | | | | |
| A*6809 | 161 | 52 | | | | | | |
| A*6810 | 46 | 164 | 69 | 93 | 25 | 44 | 26 | 34 |
| A*6812 | 161 | 69 | 44 | | | | | |
| A*6813 | 46 | 69 | 93 | 44 | 160 | | | |
| A*6814 | 46 | 164 | 69 | 93 | 25 | 44 | 26 | 34 |
| A*6815 | 162 | 82 | 21 | | | | | |

TABLE 4-9

| Allele Number | Probe Number for Detection | | | | | | | | | |
|---|---|---|---|---|---|---|---|---|---|---|
| A*6816 | 165 | | | | | | | | | |
| A*6817 | 166 | 27 | | | | | | | | |
| A*6819 | 63 | 25 | 44 | 88 | | | | | | |
| A*6820 | 167 | | | | | | | | | |
| A*6821 | 25 | 91 | | | | | | | | |
| A*6822 | 168 | | | | | | | | | |
| A*6823 | 161 | 169 | 33 | 44 | | | | | | |
| A*6901 | 82 | 69 | 22 | 23 | 24 | 25 | 12 | 13 | 26 | 27 |
| A*7401 | 170 | 129 | | | | | | | | |
| A*7402 | 171 | 58 | 148 | 133 | 107 | 13 | 34 | | | |
| A*7403 | 172 | | | | | | | | | |
| A*7404 | 20 | 58 | 148 | 73 | 13 | | | | | |
| A*7405 | 173 | | | | | | | | | |
| A*7406 | 21 | 58 | 148 | 73 | 13 | | | | | |
| A*7407 | 51 | 58 | 148 | 73 | 13 | | | | | |
| A*7408 | 174 | | | | | | | | | |
| A*7409 | 175 | | | | | | | | | |
| A*8001 | 176 | | | | | | | | | |

Example 3

Probes for Identification of HLA-B Allele

Extraction of DNA from 1 ml of human blood was performed using GFX Genomic Blood DNA Purification Kit from Amersham Biosciences in the same manner as in Example 1.

Next, quantitative PCR was carried out in the same manner as in Example 1 except that probes in the probe list B1 were used and 3 μl of the mixed primers consisting of 1 μl each of respective solutions of the following primers (10 pmol/μl):

```
CTGAGCTCTTCCTCCTACACA      (SEQ ID NO: 1155)

TCCTTCCCGTTCTCCAGGT        (SEQ ID NO: 1156)

AGGTCTCGGTCAGGGCCA         (SEQ ID NO: 1157)
```

After PCR amplification, the sample was identified being B*520101, referring to Amp Plot and Dissociation curves on a display of 5700 software and the allele-probe list B1 (described later).

Example 4

Extraction of DNA from 1 ml of human blood was performed in the same way as in Example 1. PCR of human HLA-B was then performed in the same manner as in Example 2 except that 2 μl of the mixed primer consisting of 1 μl each of the respective solutions of the following primers at 10 pmol/μl and 13 μl of ultra pure water used:

```
CTGAGCTCTTCCTCCTACACA      (SEQ ID NO: 1155)

GCTCCCACTCCATGAGGTATTTC.   (SEQ ID NO: 1158)
```

At the same time, a DNA microarray was prepared to identify the allele in the specimen described above in the same manner as in Example 2, except that probes in the probe list B2 were to form the probe dots respectively.

Then, hybridization was performed using the above specimen and the prepared DNA microarray in the same manner as in Example 2. Fluorometry measurement was conducted with GenePix4000B (Axon). Referring to the allele-probe list B2 (described later), the sample was identified as B*520101.

```
Allele list
B*070201
                                                          (SEQ ID NO: 1159)
atgctggtcatggcgccccgaaccgtcctcctgctgctctcggcggccctggccctgaccgagacctgggccggctccca ctccatgaggtatttctacacctccGtgtcccggcccggccgcggggagccccgcttcatctcagtgggctacgtggacg acacccagttcgtgaggttcgacagcgacgccgcgagtccgagagaggagccgcgggcgccgtggatagagcaggagggg ccggagtattgggaccggaacacacagatctacaaggcccaggcacagactgaccgagagagcctgcggaacctgcgcgg ctactacaaccagagcgaggccgggtctcacaccctccagagCatgtacggctgcgacgtggggccggacgggcgcctcc tccgcgggCatgaccagTacgcctacgacggcaaggattacatcgccctgaacgaggacctgcgctcctggaccgccgcg gacacggcggctcagatcacccagcgcaagtgggaggcggcccgtgaggcggagcagcGGagagcctacctggagggcgA gtgcgtggagtGgctccgcagatacctggagaacgggaaggacaagctgGagcgcgctgacccccaaagacacacgtga cccaccacccatctctgaccatgaggccaccctgaggtgctgggccctgggtttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccgtcttcccagtccaccgtccccatcgtgggcattgttgctggcctggctgtcctaNNNgca
```

B*070202

(SEQ ID NO: 1160)

atgctggtcatggcgccccgaaccgtcctcctgctgctctcggcggccctggccctgaccgagacctgggccggctccca ctccatgaggtatttctacacctccgtgtcccggcccggccgcggggagccccgcttcatctcagtgggctacgtggacg acacccagttcgtgaggttcgacagcgacgccgcgagtccgagagaggagccgcgggcgccgtggatagagcaggagggg ccggagtattgggaccggaacacacagatctacaaggcccaggcacagactgaccgagagagcctgcggaacctgcgcgg ctactacaaccagagcgaggccgggtctcacaccctccagagcatgtacggctgcgacgtggggccggacgggcgcctcc tccgcgggcatgaccagtacgcctacgacggcaaggattacatcgccctgaacgaggacctgcgctcctggaccgccgcg gacacggcggctcagatcacccagcgcaagtgggaggcggcccgtgaggcggagcagcggagagcctacctggagggcga gtgcgtggagtggctccgcagGtacctggagaacgggaaggacaagctggagcgcgctgaccccccaaagacacacgtga cccaccaccccatctctgaccatgaggccaccctgaggtgctgggccctgggtttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccgtcttcccagtccaccgtccccatcgtgggcattgttgctggcctggctgtccta...gca gttgtggtcatcggagctgtggtcgctgctgtgatgtgtaggaggaagagtt

B*070203

(SEQ ID NO: 1161)

gctcccactccatgaggtatttctacacctccgtgtcccggcccggccgcggggagccccgcttcatctcagtgggctac gtggacgacacGcagttcgtgaggttcgacagcgacgccgcgagtccgagagaggagccgcgggcgccgtggatagagca ggaggggccggagtattgggaccggaacacacagatctacaaggcccaggcacagactgaccgagagagcctgcggaacc tgcgcggctactacaaccagagcgaggccgggtctcacaccctccagagcatgtacggctgcgacgtggggccggacggg cgcctcctccgcgggcatgaccagtacgcctacgacggcaaggattacatcgccctgaacgaggacctgcgctcctggac cgccgcggacacggcggctcagatcacccagcgcaagtgggaggcggcccgtgaggcggagcagcggagagcctacctgg agggcgagtgcgtggagtggctccgcagatacctggagaacgggaaggacaagctggagcgcgctg

B*0703

(SEQ ID NO: 1162)

atgctggtcatggcgccccgaaccgtcctcctgctgctctcggcggccctggccctgaccgagacctgggccggctccca ctccatgaggtatttctacacctccgtgtcccggcccggccgcggggagccccgcttcatctcagtgggctacgtggacg acacccagttcgtgaggttcgacagcgacgccgcgagtccgagagaggagccgcgggcgccgtggatagagcaggagggg ccggagtattgggaccggaacacacagatctacaagaccaacAcacagactgaccgagagagcctgcggaacctgcgcgg ctactacaaccagagcgaggccgggtctcacaccctccagagcatgtacggctgcgacgtggggccggacgggcgcctcc tccgcgggcatgaccagtacgcctacgacggcaaggattacatcgccctgaacgaggacctgcgctcctggaccgccgcg gacacggcggctcagatcacccagcgcaagtgggaggcggcccgtgaggcggagcagcggagagcctacctggagggcga gtgcgtggagtggctccgcagatacctggagaacgggaaggacaagctggagcgcgctgaccccccaaagacacacgtga cccaccaccccatctctgaccatgaggccaccctgaggtgctgggccctgggtttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccgtcttcccagtccaccgtccccatcgtgggcattgttgctggcctggctgtccta...gca gttgtggtcatcggagctgtggtcgctgctgtgatgtgtaggaggaagagttcaggtgga

B*0704

(SEQ ID NO: 1163)

atgctggtcatggcgccccgaaccgtcctcctgctgctctcggcggccctggccctgaccgagacctgggccggctccca ctccatgaggtatttctacacctccgtgtcccggcccggccgcggggagccccgcttcatctcagtgggctacgtggacg -continued acacccagttcgtgaggttcgacagcgacgccgcgagtccgagagaggagccgcgggcgccgtggatagagcaggagggg ccggagtattgggaccggaacacacagatctacaaggcccaggcacagactgaccgagagagcctgcggaacctgcgcgg ctactacaaccagagcgaggccgggtctcacaccctccagagcatgtacggctgcgacgtggggccggacgggcgcctcc tccgcgggcatgaccagtacgcctacgacggcaaggattacatcgccctgaacgaggacctgcgctcctggaccgccgcg gacacggcggctcagatcacccagcgcaagtgggaggcggcccgtgaggcggagcaggaCagagcctacctggagggcga gtgcgtggagtggctccgcagatacctggagaacgggaaggacaagctggagcgcgctgaccccccaaagacacacgtga cccaccaccccatctctgaccatgaggccaccctgaggtgctgggccctgggtttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccgtcttcccagtccaccgtccccatcgtgggcattgttgctggcctggctgtccta...gca gttgtggtcatcggagctgtggtcgctgctgtgatgtgtaggaggaagagttcaggtgga

B*0705

(SEQ ID NO: 1164)

atgctggtcatggcgccccgaaccgtcctcctgctgctctcggcggccctggccctgaccgagacctgggccggctccca ctccatgaggtatttctacacctccgtgtcccggcccggccgcggggagccccgcttcatctcagtgggctacgtggacg acacccagttcgtgaggttcgacagcgacgccgcgagtccgagagaggagccgcgggcgccgtggatagagcaggagggg ccggagtattgggaccggaacacacagatctacaaggcccaggcacagactgaccgagagagcctgcggaacctgcgcgg ctactacaaccagagcgaggccgggtctcacaccctccagagcatgtacggctgcgacgtggggccggacgggcgcctcc tccgcgggcatAaccagtacgcctacgacggcaaggattacatcgccctgaacgaggacctgcgctcctggaccgccgcg gacacggcggctcagatcacccagcgcaagtgggaggcggcccgtgaggcggagcagcggagagcctacctggagggcga gtgcgtggagtggctccgcagatacctggagaacgggaaggacaagctggagcgcgctgaccccccaaagacacacgtga cccaccaccccatctctgaccatgaggccaccctgaggtgctgggccctgggtttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccgtcttcccagtccaccAtccccatcgtgggcattgttgctggcctggctgtccta...gca gttgtggtcatcggagctgtggtcgctgctgtgatgtgtaggaggaagagttcaggtgga

B*0706

(SEQ ID NO: 1165)

atgctggtcatggcgccccgaaccgtcctcctgctgctctcggcggccctggccctgaccgagacctgggccggctccca ctccatgaggtatttctacacctccgtgtcccggcccggccgcggggagccccgcttcatctcagtgggctacgtggacg acacccagttcgtgaggttcgacagcgacgccgcgagtccgagagaggagccgcgggcgccgtggatagagcaggagggg ccggagtattgggaccggaacacacagatctacaaggcccaggcacagactgaccgagagagcctgcggaacctgcgcgg ctactacaaccagagcgaggccgggtctcacaccctccagagcatgtacggctgcgacgtggggccggacgggcgcctcc tccgcgggcatAaccagtacgcctacgacggcaaggattacatcgccctgaacgaggacctgcgctcctggaccgccgcg gacacggcggctcagatcacccagcgcaagtgggaggcggcccgtgaggcggagcagcggagagcctacctggagggcga gtgcgtggagtggctccgcagatacctggagaacgggaaggacaagctggagcgcgctgaccccccaaagacacacgtga cccaccaccccatctctgaccatgaggccaccctgaggtgctgggccctgggtttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccgtcttcccagtccaccgtccccatcgtgggcattgttgctggcctggctgtccta...gca gttgtggtcatcggagctgtggtcgctgctgtgatgtgtaggaggaagagttcaggtgga

B*0707

(SEQ ID NO: 1166)

gctcccactccatgaggtatttctacacctccgtgtcccggcccggccgcggggagccccgcttcatctcagtgggctac gtggacgacacccagttcgtgaggttcgacagcgacgccgcgagtccgagagaggagccgcgggcgccgtggatagagca ggaggggccggagtattgggaccggaacacacagatctacaaggcccaggcacagactgaccgagagagcctgcggaacc tgcgcggctactacaaccagagcgaggccgggtctcacaccctccagagGatgtacggctgcgacgtggggccggacggg cgcctcctccgcgggcatgaccagtacgcctacgacggcaaggattacatcgccctgaacgaggacctgcgctcctggac cgccgcggacacggcggctcagatcacccagcgcaagtgggaggcggcccgtgaggcggagcagcggagagcctacctgg agggcgagtgcgtggagtggctccgcagatacctggagaacgggaaggacaagctggagcgcgctg

B*0708

(SEQ ID NO: 1167)

ggctcccactccatgaggtatttctacacctccgtgtcccggcccggccgcggggagccccgcttcatctcagtgggcta cgtggacgacacccagttcgtgaggttcgacagcgacgccgcgagtccgagagaggagccgcgggcgccgtggatagagc aggaggggccggagtattgggaccggaacacacagatctTcaagaccaacAcacagactgaccgagagagcctgcggaac ctgcgcggctactacaaccagagcgaggccgggtctcacaccctccagagcatgtacggctgcgacgtggggccggacgg gcgcctcctccgcgggcatgaccagtacgcctacgacggcaaggattacatcgccctgaacgaggacctgcgctcctgga ccgccgcggacacggcggctcagatcacccagcgcaagtgggaggcggcccgtgaggcggagcagcggagagcctacctg gagggcgagtgcgtggagtggctccgcagatacctggagaacgggaaggacaagctggagcgcgct

B*0709

(SEQ ID NO: 1168)

atgctggtcatggcgccccgaaccgtcctcctgctgctctcggcggccctggccctgaccgagacctgggccggctccca ctccatgaggtatttctacacctccgtgtcccggcccggccgcggggagccccgcttcatctcagtgggctacgtggacg acacccagttcgtgaggttcgacagcgacgccgcgagtccgagagaggagccgcgggcgccgtggatagagcaggagggg ccggagtattgggaccggaacacacagatctacaaggcccaggcacagactgaccgagagagcctgcggaacctgcgcgg ctactacaaccagagcgaggccgggtctcacaccctccagagcatgtacggctgcgacgtggggccggacgggcgcctcc tccgcgggcatgaccagtCcgcctacgacggcaaggattacatcgccctgaacgaggacctgcgctcctggaccgccgcg gacacggcggctcagatcacccagcgcaagtgggaggcggcccgtgaggcggagcagcggagagcctacctggagggcga gtgcgtggagtggctccgcagatacctggagaacgggaaggacaagctggagcgcgctg

B*0710

(SEQ ID NO: 1169)

gctcccactccatgaggtatttctacacctccgtgtcccggcccggccgcggggagccccgcttcatctcagtgggctac gtggacgacacccagttcgtgaggttcgacagcgacgccgcgagtccgagagaggagccgcgggcgccgtggatagagca ggaggggccggagtattgggaccggaacacacagatctGcaaggcccaggcacagactgaccgagagagcctgcggaacc tgcgcggctactacaaccagagcgaggccgggtctcacaccctccagagcatgtacggctgcgacgtggggccggacggg cgcctcctccgcgggcatgaccagtacgcctacgacggcaaggattacatcgccctgaacgaggacctgcgctcctggac cgccgcggacacggcggctcagatcacccagcgcaagtgggaggcggcccgtgaggcggagcagcggagagcctacctgg agggcgagtgcgtggagtggctccgcagatacctggagaacgggaaggacaagctggagcgcgctg

B*0711

(SEQ ID NO: 1170)

gctcccactccatgaggtatttctacacctccgtgtcccggcccggccgcggggagccccgcttcatctcagtgggctac gtggacgacacccagttcgtgaggttcgacagcgacgccgcgagtccgagagaggagccgcgggcgccgtggatagagca ggaggggccggagtattgggaccggaacacacagatctacaaggcccaggcacagactgaccgagagaActgcggaacc tgcgcggctactacaaccagagcgaggccgggtctcacaccctccagagcatgtacggctgcgacgtggggccggacggg cgcctcctccgcgggcatgaccagtCcgcctacgacggcaaggattacatcgccctgaacgaggacctgcgctcctggac -continued cgccgcggacacggcggctcagatcacccagcgcaagtgggaggcggcccgtgaggcggagcagcggagagcctacctgg agggcgagtgcgtggagtggctccgcagatacctggagaacgggaaggacaagctggagcgcgctg

B*0712

(SEQ ID NO: 1171)

gctcccactccatgaggtatttctacacctccgtgtcccggcccggccgcggggagccccgcttcatctcagtgggctac gtggacgacacccagttcgtgaggttcgacagcgacgccgcgagtccgagagaggagccgcgggcgccgtggatagagca ggaggggccggagtattgggaccggaacacacagatctacaaggcccaggcacagactgaccgagagagcctgcggaacc tgcgcggctactacaaccagagcgaggccgggtctcacatcAtccagaggatgtaTggctgcgacCtggggccCgacggg cgcctcctccgcgggcatgaccagtacgcctacgacggcaaggattacatcgccctgaacgaggacctgcgctcctggac cgccgcggacacggcggctcagatcacccagcgcaagtgggaggcggcccgtgaggcggagcagcggagagcctacctgg agggcgagtgcgtggagtggctccgcagatacctggagaacgggaaggacaagctggagcgcgctg

B*0713

(SEQ ID NO: 1172)

gctcccactccatgaggtatttctacacctccgtgtcccggcccggccgcggggagccccgcttcatctcagtgggctac gtggacgacacccagttcgtgaggttcgacagcgacgccgcgagtccgagaggggagccgcgggcgccgtgggtggagca ggaggggccggagtattgggaccgggagacacagaagtacaagGccaggcacagGctgaccgagTgagcctgcggaacc tgcgcggctactacaaccagagcgaggccgggtctcacaccctccagagcatgtacggctgcgacgtggggccggacggg cgcctcctccgcgggcatgaccagtacgcctacgacggcaaggattacatcgccctgaacgaggacctgcgctcctggac cgccgcggacacggcggctcagatcacccagcgcaagtgggaggcggcccgtgaggcggagcagcggagagcctacctgg agggcgagtgcgtggagtggctccgcagatacctggagaacgggaaggacaagctggagcgcgctg

B*0714

(SEQ ID NO: 1173)

gctcccactccatgaggtatttctacacctccgtgtcccggcccggccgcggggagccccgcttcatctcagtgggctac gtggacgacacccagttcgtgaggttcgacagcgacgccgcgagtccgagagaggagccgcgggcgccgtggatagagca ggaggggccggagtattgggaccggaacacacagatctacaaggcccaggcacagactgaccgagagagcctgcggaacc tgcgcggctactacaaccagagcgaggccgggtctcacaTcAtccagagGatgtacggctgcgacgtggggccggacggg cgcctcctccgcgggTatgaccagtacgcctacgacggcaaggattacatcgccctgaacgaggacctgcgctcctggac cgccgcggacacggcggctcagatcacccagcgcaagtgggaggcggcccgtgaggcggagcagcggagagcctacctgg agggcgagtgcgtggagtggctccgcagatacctggagaacgggaaggacaagctggagcgcgctg

B*0715

(SEQ ID NO: 1174)

gctcccactccatgaggtatttctacacctccgtgtcccggcccggccgcggggagccccgcttcatctcagtgggctac gtggacgacacccagttcgtgaggttcgacagcgacgccgcgagtccgagagaggagccgcgggcgccgtggatagagca ggaggggccggagtattgggaccggaacacacagatctacaaggcccaggcacagGctgaccgagTgagcctgcggaacc tgcgcggctactacaaccagagcgaggccgggtctcacaccctccagagcatgtacggctgcgacgtggggccggacggg cgcctcctccgcgggcatgaccagtacgcctacgacggcaaggattacatcgccctgaacgaggacctgcgctcctggac cgccgcggacacggcggctcagatcacccagcgcaagtgggaggcggcccgtgaggcggagcagcggagagcctacctgg agggcgagtgcgtggagtggctccgcagatacctggagaacgggaaggacaagctggagcgcgctg

B*0716

(SEQ ID NO: 1175)

gctcccactccatgaggtatttctacacctccgtgtcccggcccggccgcggggagccccgcttcatctcagtgggctac gtggacgacacccagttcgtgaggttcgacagcgacgccgcgagtccgagagaggagccgcgggcgccgtggatagagca ggaggggccggagtattgggaccggaacacacagatctacaagaccaacAcacagactTaccgagagagcctgcggaacc tgcgcggctactacaaccagagcgaggccgggtctcacaccctccagagcatgtacggctgcgacgtggggccggacggg cgcctcctccgcgggcatgaccagtacgcctacgacggcaaggattacatcgccctgaacgaggacctgcgctcctggac -continued cgccgcggacacggcggctcagatcacccagcgcaagtgggaggcggcccgtgaggcggagcagcggagagcctacctgg agggcgagtgcgtggagtggctccgcagatacctggagaacgggaaggacaagctggagcgcgctg B*0717 (SEQ ID NO: 1176)
gctcccactccatgaggtatttctacacctccgtgtcccggcccggccgcggggagccccgcttcatctcagtgggctac gtggacgacacccagttcgtgaggttcgacagcgacgccgcgagtccgagagaggagccgcgggcgccgtggatagagca ggaggggccggagtattgggaccggaacacacagatctacaaggcccaggcacagactgaccgagagagcctgcggaacc tgcgcggctactacaaccagagcgaggccgggtctcacaccctccagagcatgtacggctgcgacgtggggccggacggg cgcctcctccgcgggTatgaccagtCcgcctacgacggcaaggattacatcgccctgaacgaggacctgcgctcctggac cgccgcggacacggcggctcagatcacccagcgcaagtgggaggcggcccgtgaggcggagcagcggagagcctacctgg agggcgagtgcgtggagtggctccgcagatacctggagaacgggaaggacaagctggagcgcgctg B*0718 (SEQ ID NO: 1177)
atgctggtcatggcgccccgaaccgtcctcctgctgctctcggcggccctggccctgaccgagacctgggccggctccca ctccatgaggtatttctacacctccgtgtcccggcccggccgcggggagccccgcttcatctcagtgggctacgtggacg acacccagttcgtgaggttcgacagcgacgccgcgagtccgagagaggagccgcgggcgccgtggatagagcaggagggg ccggagtattgggaccggaacacacagatctacaaggcccaggcacagactgaccgagagagcctgcggaacctgcgcgg ctactacaaccagagcgaggccgggtctcacaTcatccagaggatgtaTggctgcgacgtggggccggacgggcgcctcc tccgcgggcatgaccagtacgcctacgacggcaaggattacatcgccctgaacgaggacctgcgctcctggaccgccgcg gacacggcggctcagatcacccagcgcaagtgggaggcggcccgtgaggcggagcagcggagagcctacctggagggcga gtgcgtggagtggctccgcagatacctggagaacgggaaggacaagctggagcgcgctgacccccaaagacacacgtga cccaccacccatctctgaccatgaggccaccctgaggtgctgggccctgggtttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgagggctgccgaagcccc tcaccctgagatgggagccgtcttcccagtccaccgtccccatcgtgggcattgttgctggcctggctgtccta...gca gttgtggtcatcggagctgtggtcgctgctgtgatgtgtaggaggaagagttcaggtgga B*0719 (SEQ ID NO: 1178)
gctcccactccatgaggtatttctacacctccgtgtcccggcccggccgcggggagccccgcttcatctcagtgggctac gtggacgacacccagttcgtgaggttcgacagcgacgccgcgagtccgagagaggagccgcgggcgccgtggatagagca ggaggggccggagtattgggaccggaacacacagatctacaaggcccaggcacagactgaccgagagagcctgcggaacc tgcgcggctactacaaccagagcgaggccgggtctcacaccctccagagcatgtacggctgcgacgtggggccggacggg cgcctcctccgcgggcatgaccagtacgcctacgacggcaaggattacatcgccctgaacgaggacctgcgctcctggac cgccgcggacacggcggctcagatcacccagcgcaagtgggaggcggcccgtgaggcggagcaggaCagagcctacctgg agggcaCgtgcgtggagtggctccgcagatacctggagaacgggaaggaDacgctggagcgcgcGg B*0720 (SEQ ID NO: 1179)
gctcccactccatgaggtatttctacacctccgtgtcccggcccggccgcggggagccccgcttcatctcagtgggctac gtggacgacacccagttcgtgaggttcgacagcgacgccgcgagtccgagagaggagccgcgggcgccgtggatagagca ggaggggccggagtattgggaccggaacacacagatctacaaggcccaggcacagactgaccgagagagcctgcggaacc tgcgcggctactacaaccagagcgaggccgggtctcacaccctccagagcatgtacggctgcgacgtggggccggacggg cgcctcctccgcgggcatgaccagtacgcctacgacggcaaggattacatcgccctgaacgaggacctgcgctcctggac cgccgcggacacggcggctcagatcacccagcgcaagtgggaggcggcccgtgaggcggagcagcggagagcctacctgg agggccTgtgcgtggagtCgctccgcagatacctggagaacgggaaggacaagctggagcgcgctg

B*0721

(SEQ ID NO: 1180)

gctcccactccatgaggtatttctacacctccgtgtcccggcccggccgcggggagcTccgcttcatctcagtgggctac gtggacgacacccagttcgtgaggttcgacagcgacgccgcgagtccgagagaggagccgcgggcgccgtggatagagca ggaggggccggagtattgggaccggaacacacagatctacaaggcccaggcacagactgaccgagagagcctgcggaacc tgcgcggctactacaaccagagcgaggcccgggtctcacaccctccagagcatgtacggctgcgacgtggggccggacggg cgcctcctccgcgggcatgaccagtacgcctacgacggcaaggattacatcgccctgaacgaggacctgcgctcctggac cgccgcggacacggcggctcagatcacccagcgcaagtgggaggcggcccgtgaggcggagcagcggagagcctacctgg agggcgagtgcgtggagtggctccgcagatacctggagaacgggaaggacaagctggagcgcgctg

B*0722

(SEQ ID NO: 1181)

gctcccactccatgaggtatttctacacctccgtgtcccggcccggccgcggggagccccgcttcatctcagtgggctac gtggacgacacccagttcgtgaggttcgacagcgacgccgcgagtccgagagaggagccgcgggcgccgtggatagagca ggaggggccggagtattgggaccggaacacacagatctacaaggcccaggcacagactgaccgagagagcctgcggaacc tgcgcggctactacaaccagagcgaggcccgggtctcacaccctccagagcatgtacggctgcgacgtggggccggacggg cgcctcctccgcgggcatgaccagtacgcctacgacggcaaggattacatcgccctgaacgaggacctgcgctcctggac cgccgcgAacacggcggctcagatcacccagcgcaagtgggaggcggcccgtgaggcggagcagcggagagcctacctgg agggcgagtgcgtggagtggctccgcagatacctggagaacgggaaggacaagctggagcgcgctg

B*0723

(SEQ ID NO: 1182)

gctcccactccatgaggtatttctacacctccgtgtcccggcccggccgcggggagccccgcttcatctcagtgggctac gtggacgacacccagttcgtgaggttcgacagcgacgccgcgagtccgagagaggagccgcgggcgccgtggatagagca ggaggggccggagtattgggaccggaacacacagatctacaaggcccaggcacagactgaccgagagagcctgcggaacc tgcgcggcCactacaaccagagcgaggcccgggtctcacaccctccagagcatgtacggctgcgacgtggggccggacggg cgcctcctccgcgggcatgaccagtacgcctacgacggcaaggattacatcgccctgaacgaggacctgcgctcctggac cgccgcggacacggcggctcagatcacccagcgcaagtgggaggcggcccgtgaggcggagcagcggagagcctacctgg agggcgagtgcgtggagtggctccgcagatacctggagaacgggaaggacaagctggagcgcgctg

B*0724

(SEQ ID NO: 1183)

gctcccactccatgaggtatttctacacctccgtgtcccggcccggccgcggggagccccgcttcatctcagtgggctac gtggacgacacccagttcgtgaggttcgacagcgacgccgcgagtccgagagaggagccgcgggcgccgtggatagagca ggaggggccggagtattgggaccggaacacacagatctacaaggcccaggcacagactgaccgagagagcctgcggaacc tgcgcggctactacaaccagagcgaggcccgggtctcacaccctccagagcatgtacggctgcgacgtggggccggacggg cgcctcctccgcgggcatgaccagtacgcctacgacggcaaggattacatcgccctgaacgaggacctgcgctcctggac cgccgcggacacggcggctcagatcacccagcgcaagtgggaggcggcccgtgaggcggagcagcggagagcctacctgg agggcCtgtgcgtggagtggctccgcagatacctggagaacgggaaggacaagctggagcgcgctg

B*0725

(SEQ ID NO: 1184)

gctcccactccatgaggtatttctacacctccgtgtcccggcccggccgcggggagccccgcttcatctcagtgggctac gtggacgacacccagttcgtgaggttcgacagcgacgccgcgagtccgagagaggagccgcgggcgccgtggatagagca ggaggggccggagtattgggaccggaacacacagatctacaaggcccaggcacagactgaccgagagagcctgcggaacc tgcgcggctactacaaccagagcgaggcccgggtctcacaccctccagagcatgtacggctgcgacgtggggccggacggg cgcctcctccgcgggcatgaccagtacgcctacgacggcaaggattacatcgccctgaacgaggacctgcgctcctggac cgccgcggacacggcggctcagatcacccagcgcaagtgggaggcggcccgtgTggcggagcaggaCagagcctacctgg agggcgagtgcgtggagtggctccgcagatacctggagaacgggaaggacaagctggagcgcgctg

B*0726

(SEQ ID NO: 1185)

gctcccactccatgaggtatttctacacctccgtgtcccggcccggccgcggggagccccgcttcatctcagtgggctac gtggacgacacccagttcgtgaggttcgacagcgacgccgcgagtccgagagaggagccgcgggcgccgtggatagagca ggaggggccggagtattgggaccggaacacacagatctacaaggcccaggcacagactgaccgagagagcctgcggaacc tgcgcggctactacaaccagagcgaggccgggtctcacaccctccagagcatgtacggctgcgacgtggggccggacggg cgcctcctccgcgggcatgaccagtacgcctacgacggcaaggattacatcgccctgaacgaggacctgcgctcctggac cgccgcggacacggcggctcagatcacccagcgcaagtgggaggcggcccgtgaggcggagcagcTgagagcctacctgg agggcgagtgcgtggagtggctccgcagatacctggagaacgggaaggacaagctggagcgcgctg

B*0727

(SEQ ID NO: 1186)

gctcccactccatgaggtatttctacacctccgtgtcccggcccggccgcggggagccccgcttcatctcagtgggctac gtggacgacacccagttcgtgaggttcgacagcgacgccgcgagtccgagagaggagccgcgggcgccgtggatagagca ggaggggccggagtattgggaccggaacacacagatctCcaagaccaacacacagactTaccgagagGacctgcggaccc tgctcCgctactacaaccagagcgaggccgggtctcacaccctccagagcatgtacggctgcgacgtggggccggacggg cgcctcctccgcgggcatgaccagtacgcctacgacggcaaggattacatcgccctgaacgaggacctgcgctcctggac cgccgcggacacggcggctcagatcacccagcgcaagtgggaggcggcccgtgaggcggagcagcggagagcctacctgg agggcgagtgcgtggagtggctccgcagatacctggagaacgggaaggacaagctggagcgcgctg

B*0728

(SEQ ID NO: 1187)

gctcccactccatgaggtatttctacacctccgtgtcccggcccggccgcggggagccccgcttcatctcagtgggctac gtggacgacacccagttcgtgaggttcgacagcgacgccgcgagtccgagagaggagccgcgggcgccgtggatagagca ggaggggccggagtattgggaccggaacacacagatctacaaggcccaggcacagactgaccgagagagcctgcggaacc tgcgcggctactacaaccagagcgaggccgggtctcacaccctccagagcatgtacggctgcgacgtggggccggacggg cgcctcctccgcgggTatgaccagGacgcctacgacggcaaggattacatcgccctgaacgaggacctgcgctcctggac cgccgcggacacggcggctcagatcacccagcgcaagtgggaggcggcccgtgaggcggagcagcggagagcctacctgg agggcgagtgcgtggagtggctccgcagatacctggagaacgggaaggacaagctggagcgcgctg

B*0729

(SEQ ID NO: 1188)

gctcccactccatgaggtatttcGacaccgccAtgtcccggcccggccgcggggagccccgcttcatctcagtgggctac gtggacgacacccagttcgtgaggttcgacagcgacgccgcgagtccgagagaggagccgcgggcgccgtggatagagca ggaggggccggagtattgggaccggaacacacagatctacaaggcccaggcacagactgaccgagagagcctgcggaacc tgcgcggctactacaaccagagcgaggccgggtctcacaccctccagagcatgtacggctgcgacgtggggccggacggg cgcctcctccgcgggcatgaccagtacgcctacgacggcaaggattacatcgccctgaacgaggacctgcgctcctggac cgccgcggacacggcggctcagatcacccagcgcaagtgggaggcggcccgtgaggcggagcagcggagagcctacctgg agggcgagtgcgtggagtggctccgcagatacctggagaacgggaaggacaagctggagcgcgctg

B*0730

(SEQ ID NO: 1189)

gctcccactccatgaggtatttctacacctccgtgtcccggcccggccgcggggagccccgcttcatctcagtgggctac gtggacgacacccagttcgtgaggttcgacagcgacgccgcgagtccgagagaggagccgcCggcgccgtggatagagca ggaggggccggagtattgggaccggaacacacagatctacaaggcccaggcacagactgaccgagagagcctgcggaacc tgcgcggctactacaaccagagcgaggccgggtctcacaccctccagagcatgtacggctgcgacgtggggccggacggg cgcctcctccgcgggcatgaccagtacgcctacgacggcaaggattacatcgccctgaacgaggacctgcgctcctggac cgccgcggacacggcggctcagatcacccagcgcaagtgggaggcggcccgtgaggcggagcagcggagagcctacctgg agggcgagtgcgtggagtggctccgcagatacctggagaacgggaaggacaagctggagcgcgctg

B*0731

(SEQ ID NO: 1190)

gctcccactccatgaggtatttctacacctccgtgtcccggcccggccgcggggagccccgcttcatctcagtgggctac gtggacgacacccagttcgtgaggttcgacagcgacgccgcgagtccgagagaggagccgcgggcgccgtggatagagca ggaggggccggagtattgggaccggaacacacagatctacaaggcccaggcacagactgaccgagagagcctgcggaacc tgcgcggctactacaaccagagcgaggccgggtctcacaccctccagagcatgtacggctgcgacgtggggccggacggg cgcctcctccgcgggcatgaccagtacgcctacgacggcaaggattacatcgccctgaacgaggacctgcgctcctggac cgccgcggacacggcggctcagatcacccagcgcaagtgggaggcggcccgtgaggcggagcagcggagagcctacctgg agggcACgtgcgtggagtggctccgcagatacctggagaacgggaaggacaagctggagcgcgctg

B*0801

(SEQ ID NO: 1191)

atgctggtcatggcgccccgaaccgtcctcctgctgctctcggcggccctggccctgaccgagacctgggccggctccca ctccatgaggtatttcGacaccgccatgtcccggcccggccgcggggagccccgcttcatctcagtgggctacgtggacg acacgcagttcgtgaggttcgacagcgacgccgcgagtccgagagaggagccgcgggcgccgtggatagagcaggagggg ccggagtattgggaccggaacacacagatcttcaagaccaacacacagactgaccgagagagcctgcggaacctgcgcgg ctactacaaccagagcgaggccgggtctcacaccctccagagcatgtacggctgcgacgtggggccggacgggcgcctcc tccgcgggcataaccagtacgcctacgacggcaaggattacatcgccctgaacgaggacctgcgctcctggaccgcggcg gacaccgcggctcagatcacccagcgcaagtgggaggcggcccgtgtggcggagcaggacagagcctacctggagggcac gtgcgtggagtggctccgcagatacctggagaacgggaaggacacgctggagcgcgcggaccccccaaagacacacgtga cccaccaccccatctctgaccatgaggccaccctgaggtgctgggccctgggcttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccgtcttcccagtccaccgtccccatcgtgggcattgttgctggcctggctgtccta...gca gttgtggtcatcggagctgtggtcgctgctgtgatgtgtaggaggaagagCtcaggtgga

B*0802

(SEQ ID NO: 1192)

atgctggtcatggcgccccgaaccgtcctcctgctgctctcggcggccctggccctgaccgagacctgggccggctccca ctccatgaggtatttcGacaccgccatgtcccggcccggccgcggggagccccgcttcatctcagtgggctacgtggacg acacgcagttcgtgaggttcgacagcgacgccgcgagtccgagagaggagccgcgggcgccgtggatagagcaggagggg ccggagtattgggaccggaacacacagatcttcaagaccaacacacagactgaccgagagaacctgcgcaccgcgctcCg ctactacaaccagagcgaggccgggtctcacaccctccagagcatgtacggctgcgacgtggggccggacgggcgcctcc tccgcgggcataaccagtacgcctacgacggcaaggattacatcgccctgaacgaggacctgcgctcctggaccgcggcg gacaccgcggctcagatcacccagcgcaagtgggaggcggcccgtgtggcggagcaggacagagcctacctggagggcac gtgcgtggagtggctccgcagatacctggagaacgggaaggacacgctggagcgcgcggaccccccaaagacacacgtga cccaccaccccatctctgaccatgaggccaccctgaggtgctgggccctgggcttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccgtcttcccagtccaccgtccccatcgtgggcattgttgctggcctggctgtccta...gca gttgtggtcatcggagctgtggtcgctgctgtgatgtgtaggaggaagagCtcaggtgga

B*0803

(SEQ ID NO: 1193)

ttcgacaccgccatgtcccggcccggccgcggggagccccgcttcatctcagtgggctacgtggacgacacgcagttcgt gaggttcgacagcgacgccgcgagtccgagagaggagccgcgggcgccgtggatagagcaggaggggccggagtattggg accggaacacacagatcttcaagaccaacacacagacttaccgagagaacctgcggaTcgCgctcCgctactacaaccag -continued agcgaggccgggtctcacaccctccagagcatgtacggctgcgacgtggggccggacgggcgcctcctccgcgggcatAa ccagtacgcctacgacggcaaggattacatcgccctgaacgaggacctgcgctcctggaccgcggcggacaccgcggctc agatcacccagcgcaagtgggaggcggcccgtgTggcggagcaggaCagagcctacctggagggcACgtgcgtggagtgg ctccgcagatacctggagaacgggaaggacacgctggagcgcgcGg

B*0804 (SEQ ID NO: 1194)

gctcccactccatgaggtatttcGacaccgccatgtcccggcccggccgcggggagccccgcttcatctcagtgggctac gtggacgacacgcagttcgtgaggttcgacagcgacgccgcgagtccgagagaggagccgcgggcgccgtggatagagca ggaggggccggagtattgggaccggaacacacagatctCcaagaccaacacacagactgaccgagagagcctgcggaacc tgcgcggctactacaaccagagcgaggccgggtctcacaccctccagagcatgtacggctgcgacgtggggccggacggg cgcctcctccgcgggcatAaccagtacgcctacgacggcaaggattacatcgccctgaacgaggacctgcgctcctggac cgcggcggacaccgcggctcagatcacccagcgcaagtgggaggcggcccgtgtggcggagcaggaCagagcctacctgg agggcAcgtgcgtggagtggctccgcagatacctggagaacgggaaggacacgctggagcgcgcGg

B*0805 (SEQ ID NO: 1195)

gctcccactccatgaggtatttcgacaccgccatgtcccggcccggccgcggggagccccgcttcatctcagtgggctac gtggacgacacgcagttcgtgaggttcgacagcgacgccgcgagtccgagagaggagccgcgggcgccgtggatagagca ggaggggccggagtattgggaccggaacacacagaCcttcaagaccaacacacagactgaccgagagagcctgcggaacc tgcgcggctactacaaccagagcgaggccgggtctcacaccctccagagcatgtacggctgcgacgtggggccggacggg cgcctcctccgcgggcataaccagtacgcctacgacggcaaggattacatcgccctgaacgaggacctgcgctcctggac cgcggcggacaccgcggctcagatcacccagcgcaagtgggaggcggcccgtgtggcggagcaggacagagcctacctgg agggcacgtgcgtggagtggctccgcagatacctggagaacgggaaggacacgctggagcgcgcgg

B*0806 (SEQ ID NO: 1196)

gctcccactccatgaggtatttcGacaccgccatgtcccggcccggccgcggggagccccgcttcatctcagtgggctac gtggacgacacgcagttcgtgaggttcgacagcgacgccgcgagtccgagagaggagccgcgggcgccgtggatagagca ggaggggccggagtattgggaccggaacacacagatctTcaagaccaacacacagactgaccgagagaActgcggaacc tgcgcggctactacaaccagagcgaggccgggtctcacaccctccagagcatgtacggctgcgacgtggggccggacggg cgcctcctccgcgggcatAaccagtacgcctacgacggcaaggattacatcgccctgaacgaggacctgcgctcctggac cgccgcggacaccgcggctcagatcacccagcgcaagtgggaggcggcccgtgaggcggagcagcgggagagcctacctgg agggcAcgtgcgtggagtggctccgcagatacctggagaacgggaaggacacgctggagcgcgcGg

B*0807 (SEQ ID NO: 1197)

gctcccactccatgaggtatttcGacaccgccatgtcccggcccggccgcggggagccccgcttcatctcagtgggctac gtggacgacacgcagttcgtgaggttcgacagcgacgccgcgagtccgagagaggagccgcgggcgccgtggatagagca ggaggggccggagtattgggaccggaacacacagatctTcaagaccaacacacagactgaccgagagagcctgcggaacc tgcgcggctactacaaccagagcgaggccgggtctcacaccctccagagcatgtacggctgcgacgtggggccggacggg cgcctcctccgcgggcatgaccagtacgcctacgacggcaaggattacatcgccctgaacgaggacctgcgctcctggac cgcggcggacaccgcggctcagatcacccagcgcaagtgggaggcggcccgtgtggcggagcaggaCagagcctacctgg agggcAcgtgcgtggagtggctccgcagatacctggagaacgggaaggacacgctggagcgcgcGg

B*0809 (SEQ ID NO: 1198)

gctcccactccatgaggtatttcGacaccgccatgtcccggcccggccgcggggagccccgcttcatctcagtgggctac gtggacgacacgcagttcgtgaggttcgacagcgacgccgcgagtccgagagaggagccgcgggcgccgtggatagagca ggaggggccggagtattgggaccggaacacacagatcttcaagaccaacacacagactgaccgagagagcctgcggaacc tgcgcggctactacaaccagagcgaggccgggtctcacacttggcagacgatgtaTggctgcgacgtggggccggacggg cgcctcctccgcgggcatAaccagtacgcctacgacggcaaggattacatcgccctgaacgaggacctgcgctcctggac cgcggcggacaccgcggctcagatcacccagcgcaagtgggaggcggcccgtgtggcggagcaggaCagagcctacctgg agggcAcgtgcgtggagtggctccgcagatacctggagaacgggaaggacacgctggagcgcgcGg

B*0810

(SEQ ID NO: 1199)
gctcccactccatgaggtatttcGacaccgccatgtcccggcccggccgcggggagccccgcttcatctcagtgggctac gtggacgacacgcagttcgtgaggttcgacagcgacgccgcgagtccgagagaggagccgcgggcgccgtggatagagca ggaggggccggagtattgggaccggGacacacagatctTcaagaccaacacacagactgaccgagagagcctgcggaacc tgcgcggctactacaaccagagcgaggcccgggtctcacaccctccagagcatgtacggctgcgacgtggggccggacggg cgcctcctccgcgggcatAaccagtacgcctacgacggcaaggattacatcgccctgaacgaggacctgcgctcctggac cgcggcggacaccgcggctcagatcacccagcgcaagtgggaggcggcccgtgtggcggagcaggaCagagcctacctgg agggcAcgtgcgtggagtggctccgcagatacctggagaacgggaaggacacgctggagcgcgcGg

B*0811

(SEQ ID NO: 1200)
gctcccactccatgaggtatttcGacaccgccatgtcccggcccggccgcggggagccccgcttcatctcagtgggctac gtggacgacacgcagttcgtgaggttcgacagcgacgccgcgagtccgagagaggagccgcgggcgccgtggatagagca ggaggggccggagtattgggaccggaacacacagatctTcaagaccaacacacagactgaccgagagagcctgcggaacc tgcgcggctactacaaccagagcgaggcccgggtctcacaccctccagagcatgtacggctgcgacgtggggccggacggg cgcctcctccgcgggcatAaccagtacgcctacgacggcaaggattacatcgccctgaacgaggacctgcgctcctggac cgcggcggacaccgcggctcagatcacccagcgcaagtgggaggcggcccgtgtggcggagcaggaCagagcctacctgg agggcgcgtgcgtggagtggctccgcagatacctggagaacgggaaggacacgctggagcgcgcGg

B*0812

(SEQ ID NO: 1201)
gctcccactccatgaggtatttcGacaccgccatgtcccggcccggccgcggggagccccgcttcatctcagtgggctac gtggacgacacgcagttcgtgaggttcgacagcgacgccgcgagtccgagagaggagccgcgggcgccgtggatagagca ggaggggccggagtattgggaccggaacacacagatcttcaagaccaacacacagactgaccgagagagcctgcggaacc tgcgcggctactacaaccagagcgaggcccgggtctcacaccctccagagGatgtacggctgcgacgtggggccggacggg cgcctcctccgcgggcatAaccagtacgcctacgacggcaaggattacatcgccctgaacgaggacctgcgctcctggac cgcggcggacaccgcggctcagatcacccagcgcaagtgggaggcggcccgtgtggcggagcaggaCagagcctacctgg agggcAcgtgcgtggagtggctccgcagatacctggagaacgggaaggacacgctggagcgcgcGg

B*0813

(SEQ ID NO: 1202)
gctcccactccatgaggtatttcGacaccgccatgtcccggcccggccgcggggagccccgcttcatctcagtgggctac gtggacgacacgcagttcgtgaggttcgacagcgacgccgcgagtccgagagaggagccgcgggcgccgtggatagagca ggaggggccggagtattgggaccggaacacacagatctTcaagaccaacacacagactgaccgagagagcctgcggaacc tgcgcggctactacaaccagagcgaggcccgggtctcacaccctccagagcatgtacggctgcgacgtggggccggacggg cgcctcctccgcgggcataaccagtacgcctacgacggcaaggattacatcgccctgaacgaggacctgcgctcctggac cgcggcggacaccgcggctcagatcacccagcgcaagtgggaggcggcccgtgtggcggagcagcTgagagcctacctgg agggcAcgtgcgtggagtggctccgcagatacctggagaacgggaaggacacgctggagcgcgcGg

B*0814

(SEQ ID NO: 1203)
gctcccactccatgaggtatttcGacaccgccatgtcccggcccggccgcggggagccccgcttcatctcagtgggctac gtggacgacacgcagttcgtgaggttcgacagcgacgccgcgagtccgagagaggagccgcgggcgccgtggatagagca ggaggggccggagtattgggaccggaacacacagatcttcaagaccaacacacagactgaccgagagagcctgcggaacc tgcgcggctactacaaccagagcgaggcccgggtctcacaccctccagagcatgtacggctgcgacgtggggccggacggg -continued cgcctcctccgcgggtaccaccagGacgcctacgacggcaaggattacatcgccctgaacgaggacctgcgctcctggac cgcggcggacaccgcggctcagatcacccagcgcaagtgggaggcggcccgtgtggcggagcaggaCagagcctacctgg agggcAcgtgcgtggagtggctccgcagatacctggagaacgggaaggacacgctggagcgcgcGg B*0815
(SEQ ID NO: 1204)
gctcccactccatgaggtatttcgacaccgccatgtcccggcccggccgcggggagccccgcttcatctcagtgggctac gtggacgacacgcagttcgtgaggttcgacagcgacgccgcgagtccgagagaggagccgcgggcgccgtggatagagca ggaggggccggagtattgggaccggaacacacagatcttcaagaccaacacacagactgaccgagTgagcctgcggaacc tgcgcggctactacaaccagagcgaggccgggtctcacaccctccagagcatgtacggctgcgacgtggggccggacggg cgcctcctccgcgggcataaccagtacgcctacgacggcaaggattacatcgccctgaacgaggacctgcgctcctggac cgcggcggacaccgcggctcagatcacccagcgcaagtgggaggcggcccgtgtggcggagcaggaCagagcctacctgg agggcaCgtgcgtggagtggctccgcagatacctggagaacgggaaggacacgctggagcgcgcGg B*0816
(SEQ ID NO: 1205)
gctcccactccatgaggtatttcgacaccgccatgtcccggcccggccgcggggagccccgcttcatctcagtgggctac gtggacgacacgcagttcgtgaggttcgacagcgacgccgcgagtccgagagaggagccgcgggcgccgtggatagagca ggaggggccggagtattgggaccggaacacacagatcttcaagaccaacacacagGctgaccgagagagcctgcggaacc tgcgcggctactacaaccagagcgaggccgggtctcacaccctccagaggatgtacggctgcgacgtggggccggacggg cgcctcctccgcgggcataaccagtacgcctacgacggcaaggattacatcgccctgaacgaggacctgcgctcctggac cgcggcggacaccgcggctcagatcacccagcgcaagtgggaggcggcccgtgtggcggagcaggaCagagcctacctgg agggcacgtgcgtggagtggctccgcagatacctggagaacgggaaggacacgctggagcgcgcGg B*0817
(SEQ ID NO: 1206)
gctcccactccatgaggtatttcGacaccgccatgtcccggcccggccgcggggagccccgcttcatctcagtgggctac gtggacgacacgcagttcgtgaggttcgacagcgacgccgcgagtccgagagaggagccgcgggcgccgtggatagagca ggaggggccggagtattgggaccgggagacacagatctCcaagaccaacacacagactgaccgagagaAcctgcggaacc tgcgcggctactacaaccagagcgaggccgggtctcacaccctccagagcatgtacggctgcgacgtggggccggacggg cgcctcctccgcgggcataaccagtacgcctacgacggcaaggattacatcgccctgaacgaggacctgcgctcctggac cgcggcggacaccgcggctcagatcacccagcgcaagtgggaggcggcccgtgtggcggagcaggacagagcctacctgg agggcacgtgcgtggagtggctccgcagatacctggagaacgggaaggacacgctggagcgcgcggaccccccaaagaca cacgtgacccaccacccatctctgaccatgaggccaccctgaggtgctgggccctgggCttctaccctgcggagatcac actgacctggcagcgggatggcgaggaccaaactcaggacactgagcttgtggagaccagaccagcaggagatagaacct tccagaagtgggcagctgtggtggtgccttctggagaagagcagagatacacatgccatgtacagcatgagggctgccg aagcccctcaccctgagatggg B*1301
(SEQ ID NO: 1207)
atgcgggtcacggcgccccgaaccctcctcctgctgctctggggggcagtggccctgaccgagacctgggccggctccca ctccatgaggtatttctacaccgccatgtcccggcccggccgcggggagccccgcttcatcaccgtgggctacgtggacg acacccagttcgtgaggttcgacagcgacgccacgagtccgaggatggcgcccgggcgccatggatagagcaggaggg ccggagtattgggaccgggagacacagatctccaagaccaacacacagacttaccgagagaacctgcgcaccgcgctccg ctactacaaccagagcgaggccgggtctcacatcAtccagaggatgtatggctgcgacctggggccggacgggcgcctcc tccgcgggcataaccagttagcctacgacggcaaggattacatcgccctgaacgaggacctgagctcctggaccgcggcg gacaccgcggctcagatcacccagcTcaagtgggaggcggcccgtgtggcggagcagctgagagcctacctggagggcga gtgcgtggagtggctccgcagatacctggagaacgggaaggagacgctgcagcgcgcggaccccccaaagacacacgtga cccaccacccatctctgaccatgaggccaccctgaggtgctgggccctgggcttctaccctgcggagatcacactgacc -continued tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccgtccccatcgtgggcattgttgctggcctggctgtccta...gca gttgtggtcatcggagctgtggtcgctgctgtgatgtgtaggaggaagagCtcaggtgga

B*1302 (SEQ ID NO: 1208)

atgcgggtcacggcgccccgaaccctcctcctgctgctctgggggcagtggccctgaccgagacctgggccggctccca ctccatgaggtatttctacaccgccatgtcccggcccggccgcggggagccccgcttcatcaccgtgggctacgtggacg acacccagttcgtgaggttcgacagcgacgccacgagtccgaggatggcgcccgggcgccatggatagagcaggagggg ccggagtattgggaccgggagacacagatctccaagaccaacacacagacttaccgagagaacctgcgcaccgcgctccg ctactacaaccagagcgaggccgggtctcacacttggcagaCgatgtatggctgcgacctggggccggacgggcgcctcc tccgcgggcataaccagttagcctacgacggcaaggattacatcgccctgaacgaggacctgagctcctggaccgcggcg gacaccgcggctcagatcacccagcTcaagtgggaggcggcccgtgtggcggagcagctgagagcctacctggagggcga gtgcgtggagtggctccgcagatacctggagaacgggaaggagacgctgcagcgcgcggaccccccaaagacacacgtga cccaccacccatctctgaccatgaggccaccctgaggtgctgggccctgggcttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccgtccccatcgtgggcattgttgctggcctggctgtccta...gca gttgtggtcatcggagctgtggtcgctgctgtgatgtgtaggaggaagagCtcaggtgga

B*1303 (SEQ ID NO: 1209)

atgcgggtcacggcgccccgaaccctcctcctgctgctctgggggcagtggccctgaccgagacctgggccggctccca ctccatgaggtatttctacaccgccatgtcccggcccggccgcggggagccccgcttcatcaccgtgggctacgtggacg acacccagttcgtgaggttcgacagcgacgccacgagtccgaggatggcgcccgggcgccatggatagagcaggagggg ccggagtattgggaccgggagacacagatctccaagaccaacacacagacttaccgagagaacctgcgcaccgcgctcCg ctactacaaccagagcgaggccgggtctcacacttggcagacgatgtaTggctgcgacctggggccggacgggcgcctcc tccgcgggcataaccagttAgcctacgacggcaaggattacatcgccctgaacgaggacctgagctcctggaccgcggcg gacaccgcggctcagatcacccagcgcaagtgggaggcggcccgtgTggcggagcagcTgagagcctacctggagggccT gtgcgtggagtggctccgcagatacctggagaacgggaaggagacgctgcagcgcgcggaccccccaaagacacacgtga cccaccacccatctctgaccatgaggccaccctgaggtgctgggccctgggcttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccgtccccatcgtgggcattgttgctggcctggctgtccta...gca gttgtggtcatcggagctgtggtcgctgctgtgatgtgtaggaggaagagCtcaggtgga

B*1304 (SEQ ID NO: 1210)

atgcgggtcacggcgccccgaaccctcctcctgctgctctgggggcagtggccctgaccgagacctgggccggctccca ctccatgaggtatttctacaccgccatgtcccggcccggccgcggggagccccgcttcatcaccgtgggctacgtggacg acacccagttcgtgaggttcgacagcgacgccacgagtccgaggatggcgcccgggcgccatggatagagcaggagggg ccggagtattgggaccgggagacacagatctccaagaccaacacacagacttaccgagagaacctgcgcaccgcgctccg ctactacaaccagagcgaggccgggtctcacacttggcagacgatgtatggctgcgacCtggggccggacgggcgcctcc tccgcgggcatgaccagtCgcctacgacggcaaggattacatcgccctgaacgaggacctgagctcctggaccgcggcg gacacggcggctcagatcacccagcgcaagtgggaggcggcccgtgtggcggagcagcTgagagcctacctggagggcct -continued

```
gtgcgtggagtggctccgcagatacctggagaacgggaaggagacgctgcagcgcgcggaccccccaaagacacatgtga cccaccacccatctctgaccatgaggccaccctgaggtgctgggccctgggcttctaccctgcggagatcacactgacc tggcagcgggatggcgaggaccaaactcaggacaccgagcttgtggagaccagaccagcaggagatagaaccttccagaa gtgggcagctgtggtggtgccttctggagaagagcagagatacacatgccatgtacagcatgaggggctgccaaagcccc tcaccctgagatgggagccatcttcccaAtccaccgtccccatcgtgggcattgttgctggcctggctgtccta...gca gttgtggtcatcggagctgtggtcgctgctgtgatgtgtaggaggaagagctcaggtgga
```

B*1306

(SEQ ID NO: 1211)
```
gctcccactccatgaggtatttctacaccgccatgtcccggcccggccgcggggagccccgcttcatcaccgtgggctac gtggacgacacccagttcgtgaggttcgacagcgacgccacgagtccgaggatggcgccccgggcgccatggatagagca ggaggggccggagtattgggaccgggagacacagatctccaagaccaacacacagacttaccgagagaacctgcgcaccg cgctccgctactacaaccagagcgaggccgggtctcacatcatccagaggatgtatggctgcgacctggggccggacggg cgcctcctccgcgggcataaccagttagcctacgacggcaaggattacatcgccctgaacgaggacctgagctcctggac cgcggcggacaccgcggctcagatcacccagcTcaagtgggaggcggcccgtgtggcggagcagctgagagcctacctgg agggcaCgtgcgtggagtggctccgcagatacctggagaacgggaaggagacgctgcagcgcgcgg
```

B*1308

(SEQ ID NO: 1212)
```
atgcgggtcacggcgccccgaaccctcctcctgctgctctgggggggcagtggccctgaccgagacctgggccggctccca ctccatgaggtatttctacaccgccatgtcccggcccggccgcggggagccccgcttcatcaccgtgggctacgtggacg acacccagttcgtgaggttcgacagcgacgccacgagtccgaggatggcgccccgggcgccatggatagagcaggagggg ccggagtattgggaccgggagacacagatctccaagaccaacacacagacttaccgagagaacctgcgcaccgcgctccg ctactacaaccagagcgaggccgggtctcacacttggcagacgatgtatggctgcgacctggggccggacgggcgcctcc tccgcgggcataaccagttagcctacgacggcaaggattacatcgccctgaacgaggacctgagctcctggaccgcggcg gacaccgcggctcagatcacccagctcaagtgggaggcggcccgtgtggcggagcagctgagagcctGcctggagggcga gtgcgtggagtggctccgcagatacctggagaacgggaaggagacgctgcagcgcgcggaccccccaaagacacacgtga cccaccacccatctctgaccatgaggccaccctgaggtgctgggccctgggcttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccgtccccatcgtgggcattgttgctggcctggctgtccta...gca gttgtggtcatcggagctgtggtcgctgctgtgatgtgtaggaggaagagctcaggtgga
```

B*1309

(SEQ ID NO: 1213)
```
gctcccactccatgaggtatttctacaccgccatgtcccggcccggccgcggggagccccgcttcatcaccgtgggctac gtggacgacacccagttcgtgaggttcgacagcgacgccacgagtccgaggatggcgccccgggcgccatggatagagca ggaggggccggagtattgggaccgggagacacagatctccaagaccaacacacagacttaccgagagagcctgcggaacc tgcgcggctactacaaccagagcgaggccgggtctcacacttggcagaCgtgtaTggctgcgacctggggccggacggg cgcctcctccgcgggcataaccagttAgcctacgacggcaaggattacatcgccctgaacgaggacctgagctcctggac cgcggcggacaccgcggctcagatcacccagcTcaagtgggaggcggcccgtgtggcggagcagctgagagcctacctgg agggcgagtgcgtggagtggctccgcagatacctggagaacgggaaggagacgctgcagcgcgcgg
```

B*1310

(SEQ ID NO: 1214)
```
gctcccactccatgaggtatttctacaccgccatgtcccggcccggccgcggggagccccgcttcatcaccgtgggctac gtggacgacacccagttcgtgaggttcgacagcgacgccacgagtccgaggatggcgccccgggcgccatggatagagca ggaggggccggagtattgggaccgggagacacagatctccaagaccaacacacagacttaccgagagaacctgcgcaccg cgctccgctactacaaccagagcgaggccgggtctcacaccctccagaggatgtacggctgcgacgtggggccggacggg
``` cgcctcctccgcgggtatgaccagtCcgcctacgacggcaaggattacatcgccctgaacgaggacctgagctcctggac cgcggcggacaccgcggctcagatcacccagcTcaagtgggaggcggcccgtgtggcggagcagctgagagcctacctgg agggcgagtgcgtggagtggctccgcagatacctggagaacgggaaggagacgctgcagcgcgcgg

B*1311

(SEQ ID NO: 1215)

gctcccactccatgaggtatttctacaccgccatgtcccggcccggccgcggggagccccgcttcatcaccgtgggctac gtggacgacacccagttcgtgcaggttcgacagcgacgccacgagtccgaggatggcgccccgggcgccatggatagagca ggaggggccggagtattgggaccgggagacacagatctccaagaccaacacacagacttaccgagagaacctgcgcaccg cgctccgctactacaaccagagcgaggccgggtctcacaccctccagaggatgtacggctgcgacctggggccggacggg cgcctcctccgcgggcataaccagttagcctacgacggcaaggattacatcgccctgaacgaggacctgagctcctggac cgcggcggacaccgcggctcagatcacccagcTcaagtgggaggcggcccgtgtggcggagcagctgagagcctacctgg agggcgagtgcgtggagtggctccgcagatacctggagaacgggaaggagacgctgcagcgcgcggaccccccaaagaca cacgtgacccaccaccccatctctgaccatgaggccaccctgaggtgctgggccctgggCttctaccctgcggagatcac actgacctggcagcgggatggcgaggaccaaactcaggacactgagcttgtggagaccagaccagcaggagatagaacct tccagaagtgggcagctgtggtggtgccttctggagaagagcagagatacacatgccatgtacagcatgaggggctgccg aagcccctcaccctgagatggg

B*1401

(SEQ ID NO: 1216)

atgctggtcatggcgccccgaaccgtcctcctgctgctctcggcggccctggccctgaccgagacctgggccggctccca ctccatgaggtatttctacacctccgtgtcccggcccggccgcggggagccccgcttcatctcagtgggctacgtggacg acacgcagttcgtgcaggttcgacagcgacgccgcgagtccgagagaggagccgcgggcgccgtggatagagcaggaggg ccggaatattgggaccggaacacacagatctgcaagaccaacacacagactgaccgagagagcctgcggaacctgcgcgg ctactacaaccagagcgaggccgggtctcacaccctccagTggatgtatggctgcgacgtggggccggacgggcgcctcc tccgcgggtataaccagttcgcctacgacggcaaggattacatcgccctgaacgaggacctgagctcctggaccgcggcg gacaccgcggctcagatcacccagcgcaagtgggaggcggcccgtgaggcggagcagctgagagcctacctggagggcac gtgcgtggagtggctccgcagacacctggagaacgggaaggagacgctgcagcgcgcggaccccccaaagacacatgtga cccaccaccccatctctgaccatgaggccaccctgaggtgctgggccctgggcttctaccctgcggagatcacactgacc tggcagcgggatggcgaggaccaaactcaggacaccgagcttgtggagaccagaccagcaggagaCagaaccttccagaa gtgggcagctgtggtggtgccttctggagaagagcagagatacacatgccatgtacagcatgaggggctgccgaagcccc tcaccctgagatgggagccAtcttcccagtccaccgtccccatcgtgggcattgttgctggcctggctgtccta...gca gttgtggtcatcggagctgtggtcgctgctgtgatgtgtaggaggaagagttcaggtgga

B*1402

(SEQ ID NO: 1217)

atgctggtcatggcgccccgaaccgtcctcctgctgctctcggcggccctggccctgaccgagacctgggccggctccca ctccatgaggtatttctacaccGccgtgtcccggcccggccgcggggagccccgcttcatctcagtgggctacgtggacg acacgcagttcgtgcaggttcgacagcgacgccgcgagtccgagagaggagccgcgggcgccgtggatagagcaggaggg ccggaatattgggaccggaacacacagatctgcaagaccaacacacagactgaccgagagagcctgcggaacctgcgcgg ctactacaaccagagcgaggccgggtctcacaccctccagTggatgtatggctgcgacgtggggccggacgggcgcctcc tccgcgggtataaccagttcgcctacgacggcaaggattacatcgccctgaacgaggacctgagctcctggaccgcggcg gacaccgcggctcagatcacccagcgcaagtgggaggcggcccgtgaggcggagcagctgagagcctacctggagggcac gtgcgtggagtggctccgcagacacctggagaacgggaaggagacgctgcagcgcgcggaccccccaaagacacatgtga cccaccaccccatctctgaccatgaggccaccctgaggtgctgggccctgggcttctaccctgcggagatcacactgacc tggcagcgggatggcgaggaccaaactcaggacaccgagcttgtggagaccagaccagcaggagaCagaaccttccagaa -continued gtgggcagctgtggtggtgccttctggagaagagcagagatacacatgccatgtacagcatgaggggctgccgaagcccc tcaccctgagatgggagccAtcttcccagtccaccgtccccatcgtgggcattgttgctggcctggctgtccta...gca gttgtggtcatcggagctgtggtcgctgctgtgatgtgtaggaggaagagttcaggtgga

B*1403

(SEQ ID NO: 1218)

gctcccactccatgaggtatttctacaccGccgtgtcccggcccggccgcggggagccccgcttcatctcagtgggctac gtggacgacacgcagttcgtgaggttcgacagcgacgccgcgagtccgagagaggagccgcgggcgccgtggatagagca ggaggggccggaatattgggaccggaacacacagatctgcaagaccaacacacagactgaccgagagagcctgcggaacc tgcgcggctactacaaccagagcgaggccgggtctcacaccctccagTggatgtatggctgcgacgtggggccggacggg cgcctcctccgcgggtataaccagttcgcctacgacggcaaggattacatcgccctgaacgaggacctgagctcctggac cgcggcggacaccgcggctcagatcacccagcgcaagtgggaggcggcccgtgaggcggagcagcggagagcctacctgg agggcacgtgcgtggagtggctccgcagacacctggagaacgggaaggagacgctgcagcgcgcggacccccaaagaca catgtgacccaccacccatctctgaccatgaggccaccctgaggtgctgggccctgggcttctaccctgcggagatcac actgacctggcagcgggatggcgaggaccaaactcaggacaccgagcttgtggagaccagaccagcaggagaCagaacct tccagaagtgggcagctgtggtggtgccttctggagaagagcagagatacacatgccatgtacagcatgaggggctgccg aagcccctcaccctgagatggg

B*1404

(SEQ ID NO: 1219)

gctcccactccatgaggCatttctacaccgccgtgtcccggcccggccgcggggagccccgcttcatctcagtgggctac gtggacgacacgcagttcgtgaggttcgacagcgacgccgcgagtccgagagaggagccgcgggcgccgtggatagagca ggaggggccggaatattgggaccggaacacacagaactgcaagaccaacacacagactgaccgagagagcctgcggaacc tgcgcggctactacaaccagagcgaggccgggtctcacaccctccagtggatgtatggctgcgacgtggggccggacggg cgcctcctccgcgggtataaccagttcgcctacgacggcaaggattacatcgccctgaacgaggacctgagctcctggac cgcggcggacaccgcggctcagatcacccagcgcaagtgggaggcggcccgtgaggcggagcagctgagagcctacctgg agggcacgtgcgtggagtggctccgcagacacctggagaacgggaaggagacgctgcagcgcgcgg

B*1405

(SEQ ID NO: 1220)

atgctggtcatggcgccccgaaccgtcctcctgctgctctcggcggccctggccctgaccgagacctgggccggctccca ctccatgaggtatttctacaccGccgtgtcccggcccggccgcggggagccccgcttcatctcagtgggctacgtggacg acacgcagttcgtgaggttcgacagcgacgccgcgagtccgagagaggagccgcgggcgccgtggatagagcaggagggg ccggaAtattgggaccggaacacacagatctgcaagaccaacacacagactgaccgagagagcctgcggaacctgcgcgg ctactacaaccagagcgaggccgggtctcacaccctccagagcatgtacggctgcgacgtggggccggacgggcgcctcc tccgcgggtataaccagttcgcctacgacggcaaggattacatcgccctgaacgaggacctgagctcctggaccgcggcg gacaccgcggctcagatcacccagcgcaagtgggaggcggcccgtgaggcggagcagcTgagagcctacctggagggcac gtgcgtggagtggctccgcagaCacctggagaacgggaaggagacgctgcagcgcgcGg

B*140601

(SEQ ID NO: 1221)

gctcccactccatgaggtatttctacaccGccgtgtcccggcccggccgcggggagccccgcttcatctcagtgggctac gtggacgacacgcagttcgtgaggttcgacagcgacgccgcgagtccgagagaggagccgcgggcgccgtggatagagca ggaggggccggaAtattgggaccggaacacacagatctgcaagaccaacacacagactgaccgagagagcctgcggaacc tgcgcggctactacaaccagagcgaggccgggtctcacaccctccagagGatgtacggctgcgacgtggggccggacggg cgcctcctccgcgggtataaccagttcgcctacgacggcaaggattacatcgccctgaacgaggacctgagctcctggac cgcggcggacaccgcggctcagatcacccagcgcaagtgggaggcggcccgtgaggcggagcagcTgagagcctacctgg agggcacgtgcgtggagtggctccgcagaCacctggagaacgggaaggagacgctgcagcgcgcGg -continued

B*140602

(SEQ ID NO: 1222)

gctcccactccatgaggtatttctacaccGccgtgtcccggcccggccgcggggagccccgcttcatctcagtgggctac gtggacgacacgcagttcgtgaggttcgacagcgacgccgcgagtccgagagaggagccgcgggcgccgtggatagagca ggaggggccggaAtattgggaccggaacacacagatctgcaagaccaacacacagactgaccgagagagcctgcggaacc tgcgcggctactacaaccagagcgaggccgggtctcacaccctccagaggatgtaTggctgcgacgtggggccggacggg cgcctcctccgcgggtataaccagttcgcctacgacggcaaggattacatcgccctgaacgaggacctgagctcctggac cgcggcggacaccgcggctcagatcacccagcgcaagtgggaggcggcccgtgaggcggagcagcTgagagcctacctgg agggcacgtgcgtggagtggctccgcagaCacctggagaacgggaaggagacgctgcagcgcgcGg

B*15010101

(SEQ ID NO: 1223)

atgcgggtcacggcgccccgaaccgtcctcctgctgctctcgggAgccctggccctgaccgagacctgggccggctccca ctccatgaggtatttctacaccgccatgtcccggcccggccgcggggagccccgcttcatcgcagtgggctacgtggacg acacccagttcgtgaggttcgacagcgacgccgcgagtccgaggatggcgccccgggcgccAtggatagagcaggagggg ccggagtattgggaccgggaGacacagatctCcaagaccaacacacagactTaccgagagagcctgcggaacctgcgcgg ctactacaaccagagcgaggccgggtctcacaccctccagaggatgtacggctgcgacgtggggccggacgggcgcctcc tccgcgggcatgaccagtccgcctacgacggcaaggattacatcgccctgaacgaggacctgagctcctggaccgcggcg gacacggcggctcagatcacccagcgcaagtgggaggcggcccgtgaggcggagcagTggagagcctacctggagggcct gtgcgtggagtggctccgcagatacctggagaacgggaaggagacgctgcagcgcgcggaccccccaaagacacatgtga cccaccaccccatctctgaccatgaggccacccctgaggtgctgggccctgggcttctaccctgcggagatcacactgacc tggcagcgggatggcgaggaccaaactcaggacacCgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccatccccatcgtgggcattgttgctggcctggctgtccta...gca gttgtggtcatcggagctgtggtcgctactgtgatgtgtaggaggaagagCtcaggtgga

B*150102

(SEQ ID NO: 1224)

gctcccactccatgaggtatttctacaccgccatgtcccggcccggccgcggggagccccgcttcatcgcagtgggctac gtggacgacacccagttcgtgaggttcgacagcgacgccgcgagtccgaggatggcgccccgggcgccatggatagagca ggaggggccggagtattgggaccgggagacacagatctccaagaccaacacacagacttaccgagagagcctgcggaacc tgcgcggctactacaaccagagcgaggccgggtctcacaccctccagaggatgtacggctgcgacgtggggccggacggg cgcctcctccgcgggcatgaccagtccgcctacgacggcaaAgattacatcgccctgaacgaggacctgagctcctggac cgcGgcggacacggcggctcagatcacccagcgcaagtgggaggcggcccgtgaggcggagcagTgagagcctacctgg agggccTgtgcgtggagtggctccgcagatacctggagaacgggaaggagacgctgcagcgcgcGg

B*150103

(SEQ ID NO: 1225)

gctcccactccatgaggtatttctacaccgccatgtcccggcccggccgcggggagccccgcttcatcgcagtgggctac gtggacgacacccagttcgtgaggttcgacagcgacgccgcgagtccgaggatggcgccccgggcgccatggatagagca ggaggggccggagtattgggaccgggagacacagatctccaagaccaacacacagacttaccgagagagcctgcggaacc tgcgcggctactacaaccagagcgaggccgggtctcacaccctccagaggatgtacggctgcgacgtggggccggacggg cgcctcctccgcgggcatgaccagtccgcctacgacggcaaggattacatcgccctgaaTgaggacctgagctcctggac cgcggcggacacggcggctcagatcacccagcgcaagtgggaggcggcccgtgaggcggagcagtggagagcctacctgg agggcctgtgcgtggagtggctccgcagatacctggagaacgggaaggagacgctgcagcgcgcgg

B*150104

(SEQ ID NO: 1226)

gctcccactccatgaggtatttctacaccgccatgtcccggcccggccgcggggagccccgcttcatcgcagtgggctac gtggacgacacgcagttcgtgCggttcgacagcgacgccgcgagtccgaggatggcgccccgggcgccatggatagagca ggaggggccggagtattgggaccgggagacacagatctccaagaccaacacacagacttaccgagagagcctgcggaacc tgcgcggctactacaaccagagcgaggccgggtctcacaccctccagaggatgtacggctgcgacgtggggccggacggg cgcctcctccgcgggcatgaccagtccgcctacgacggcaaggattacatcgccctgaacgaggacctgagctcctggac cgcggcggacacggcggctcagatcacccagcgcaagtgggaggcggcccgtgaggcggagcagtggagagcctacctgg agggccTgtgcgtggagtggctccgcagatacctggagaacgggaaggagacgctgcagcgcgcgg

B*1502

(SEQ ID NO: 1227)

atgcgggtcacggcgccccgaaccgtcctcctgctgctctcgggAgccctggccctgaccgagacctgggccggctccca ctccatgaggtatttctacaccgccatgtcccggcccggccgcggggagccccgcttcatcgcagtgggctacgtggacg acacccagttcgtgaggttcgacagcgacgccgcgagtccgaggatggcgccccgggcgccatggatagagcaggagggg ccggagtattgggaccggaacacacagatctCcaagaccaacacacagacttaccgagagagcctgcggaacctgcgcgg ctactacaaccagagcgaggccgggtctcacatcatccagaggatgtaTggctgcgacgtggggccggacgggcgcctcc tccgcgggTatgaccagtCcgcctacgacggcaaggattacatcgccctgaacgaggacctgagctcctggaccgcggcg gacacggcggctcagatcacccagcgcaagtgggaggcggcccgtgaggcggagcagcTgagagcctacctggagggcct gtgcgtggagtggctccgcagatacctggagaacgggaaggagacgctgcagcgcgcggaccccccaaagacacatgtga cccaccaccccatctctgaccatgaggccaccctgaggtgctgggccctgggcttctaccctgcggagatcacactgacc tggcagcgggatggcgaggaccaaactcaggacacCgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccatccccatcgtgggcattgttgctggcctggctgtcccta...gca gttgtggtcatcggagctgtggtcgctactgtgatgtgtaggaggaagagCtcaggtgga

B*1503

(SEQ ID NO: 1228)

atgcgggtcacggcgccccgaaccgtcctcctgctgctctcgggAgccctggccctgaccgagacctgggccggctccca ctccatgaggtatttctacaccgccatgtcccggcccggccgcggggagccccgcttcatctcagtgggctacgtggacg acacGcagttcgtgaggttcgacagcgacgccgcgagtccgagagaggagccgcgggcgccgtggatagagcaggagggg ccggagtattgggaccgggaGacacagatctCcaagaccaacAcacagacttaccgagagagcctgcggaacctgcgcgg ctactacaaccagagcgaggccgggtctcacaccctccagagGatgtacggctgcgacgtggggccggacgggcgcctcc tccgcgggcatgaccagtCcgcctacgacggcaaggattacatcgccctgaacgaggacctgagctcctggaccgcggcg gacacggcggctcagatcacccagcgcaagtgggaggcggcccgtgaggcggagcagcTgagagcctacctggagggcct gtgcgtggagtggctccgcagatacctggagaacgggaaggagacgctgcagcgcgcggaccccccaaagacacatgtga cccaccaccccatctctgaccatgaggccaccctgaggtgctgggccctgggcttctaccctgcggagatcacactgacc tggcagcgggatggcgaggaccaaactcaggacacCgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccatccccatcgtgggcattgttgctggcctggctgtcccta...gca gttgtggtcatcggagctgtggtcgctactgtgatgtgtaggaggaagagCtcaggtgga

B*1504

(SEQ ID NO: 1229)

atgcgggtcacggcgccccgaaccgtcctcctgctgctctcgggAgccctggccctgaccgagacctgggccggctccca ctccatgaggtatttctacaccgccatgtcccggcccggccgcggggagccccgcttcatcgcagtgggctacgtggacg acacccagttcgtgaggttcgacagcgacgccgcgagtccgaggatggcgccccgggcgccatggatagagcaggagggg -continued ccggagtattgggaccggagacacagatctccaagaccaacacacagacttaccgagagagcctgcggaacctgcgcgg ctactacaaccagagcgaggccgggtctcacacttggcagacgatgtaTggctgcgacgtggggccggacgggcgcctcc tccgcgggcatgaccagtccgcctacgacggcaaggattacatcgccctgaacgaggacctgagctcctggaccgcggcg gacacggcggctcagatcacccagcgcaagtgggaggcggcccgtgaggcggagcagTggagagcctacctggagggcct gtgcgtggagtggctccgcagatacctggagaacgggaaggagacgctgcagcgcgcggaccccccaaagacacatgtga cccaccacccatctctgaccatgaggccaccctgaggtgctgggccctgggcttctaccctgcggagatcacactgacc tggcagcgggatggcgaggaccaaactcaggacacCgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccatccccatcgtgggcattgttgctggcctggctgtccta...gca gttgtggtcatcggagctgtggtcgctactgtgatgtgtaggaggaagagCtcaggtgga

B*1505

(SEQ ID NO: 1230)

ggctcccactccatgaggtatttctacaccgccatgtcccggcccggccgcggggagccccgcttcatcgcagtgggcta cgtggacgacacccagttcgtgaggttcgacagcgacgccgcgagtccgaggatggcgcccgggcgccatggatagagc aggaggggccggagtattgggaccgggagacacagatctccaagaccaacacacagacttaccgagagagcctgcggaac ctgcgcggctactacaaccagagcgaggccgggtctcacaccctccagagGatgtacggctgcgacgtggggccggacgg gcgcctcctccgcgggcatgaccagtccgcctacgacggcaaggattacatcgccctgaacgaggacctgagctcctgga ccgcggcggacacggcggctcagatcacccagcgcaagtgggaggcggcccgtgTggcggagcagcTgagagcctacctg gagggccTgtgcgtggagtggctccgcagatacctggagaacgggaaggagacgctgcagcgcgcggaccccccaaagac acatgtgacccaccacccatctctgaccatgaggccaccctgaggtgctgggccctgggcttctaccctgcggagatca cactgacctggcagcgggatggcgaggaccaaactcaggacacCgagcttgtggagaccagaccagcaggagatagaacc ttccagaagtgggcagctgtggtggtgccttctggagaagagcagagatacacatgccatgtacagcatgaggggctgcc gaagcccctcaccctgagatgggagccatcttcccagtccaccatccccatcgtgggcattgttgctggcctggctgtcc ta...gcagttgtggtcatcggagctgtggtcgctActgtgatgtgtaggaggaagagctcaggtgga

B*1506

(SEQ ID NO: 1231)

ggctcccactccatgaggtatttctacaccgccatgtcccggcccggccgcggggagccccgcttcatcgcagtgggcta cgtggacgacacccagttcgtgaggttcgacagcgacgccgcgagtccgaggatggcgcccgggcgccatggatagagc aggaggggccggagtattgggaccgggagacacagatctccaagaccaacacacagacttaccgagagagcctgcggaac ctgcgcggctactacaaccagagcgaggccgggtctcacaccctccagaggatgtTtggctgcgacgtggggccggacgg gcgcctcctccgcgggtatgaccagtccgcctacgacggcaaggattacatcgccctgaacgaggacctgagctcctgga ccgcggcggacacggcggctcagatcacccagcgcaagtgggaggcggcccgtgaggcggagcagcTgagagcctacctg gagggcctgtgcgtggagtggctccgcagatacctggagaacgggaaggagacgctgcagcgcgcggaccccccaaagac acatgtgacccaccacccatctctgaccatgaggccaccctgaggtgctgggccctgggcttctaccctgcggagatca cactgacctggcagcgggatggcgaggaccaaactcaggacaccgagcttgtggagaccagaccagcaggagatagaacc ttccagaagtgggcagctgtggtggtgccttctggagaagagcagagatacacatgccatgtacagcatgaggggctgcc gaagcccctcaccctgagatgggagccatcttcccagtccaccatccccatcgtgggcattgttgctggcctggctgtcc ta...gcagttgtggtcatcggagctgtggtcgctActgtgatgtgtaggaggaagagCtcaggtgga

B*1507

(SEQ ID NO: 1232)

ggctcccactccatgaggtatttctacaccgccatgtcccggcccggccgcggggagccccgcttcatcgcagtgggcta cgtggacgacacccagttcgtgagGttcgacagcgacgccgcgagtccgaggatggcgccccgggcgccAtggatagagc aggaggggccggagtattgggaccgggaGacacagatctCcaagaccaacacacagactTaccgagagagcctgcggaac ctgcgcggctactacaaccagagcgaggccgggtctcacaccctccagagcatgtacggctgcgacgtggggccggacgg -continued gcgcctcctccgcgggcatgaccagtccgcctacgacggcaaggattacatcgccctgaacgaggacctgagctcctgga ccgcggcggacacggcggctcagatcacccagcgcaagtgggaggcggcccgtgaggcggagcagTggagagcctacctg gagggcctgtgcgtggagtggctccgcagatacctggagaacgggaaggagacgctgcagcgcgcggaccccccaaagac acatgtgacccaccaccccatctctgaccatgaggccaccctgaggtgctgggccctgggcttctaccctgcggagatca cactgacctggcagcgggatggcgaggaccaaactcaggacaccgagcttgtggagaccagaccagcaggagatagaacc ttccagaagtgggcagctgtggtggtgccttctggagaagagcagagatacacatgccatgtacagcatgaggggctgcc gaagcccctcaccctgagatgggagccatcttcccagtccaccatccccatcgtgggcattgttgctggcctggctgtcc ta...gcagttgtggtcatcggagctgtggtcgctactgtgatgtgtaggaggaagagCtcaggtgga

B*1508

(SEQ ID NO: 1233)
atgcgggtcacggcgccccgaaccgtcctcctgctgctctcgggAgccctggccctgaccgagacctgggccggctccca ctccatgaggtatttctacaccgccatgtcccggcccggccgcggggagccccgcttcatcgcagtgggctacgtggacg acacccagttcgtgaggttcgacagcgacgccgcgagtccgaggatggcgccccgggcgccatggatagagcaggagggg ccggagtattgggaccggaacacacagatctTcaagaccaacacacagactTaccgagagagcctgcggaacctgcgcgg ctactacaaccagagcgaggccgggtctcacaccctccagaggatgtacggctgcgacgtggggccggacgggcgcctcc tccgcgggcatgaccagtccgcctacgacggcaaggattacatcgccctgaacgaggacctgagctcctggaccgcggcg gacacggcggctcagatcacccagcgcaagtgggaggcggcccgtgaggcggagcagTgagagcctacctggagggcct gtgcgtggagtggctccgcagatacctggagaacgggaaggagacgctgcagcgcgcggaccccccaaagacacatgtga cccaccaccccatctctgaccatgaggccaccctgaggtgctgggccctgggcttctaccctgcggagatcacactgacc tggcagcgggatggcgaggaccaaactcaggacacCgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccatccccatcgtgggcattgttgctggcctggctgtcccta...gca gttgtggtcatcggagctgtggtcgctactgtgatgtgtaggaggaagagCtcaggtgga

B*1509

(SEQ ID NO: 1234)
atgcgggtcacggcgccccgaaccgtcctcctgctgctctcgggAgccctggccctgaccgagacctgggccggctccca ctccatgaggtatttctacaccgccatgtcccggcccggccgcggggagccccgcttcatctcagtgggctacgtggacg acacgcagttcgtgaggttcgacagcgacgccgcgagtccgagagaggagccgcgggcgccgtggatagagcaggagggg ccggagtattgggaccggaacacacagatctgcaagaccaacacacagacttaccgagagagcctgcggaacctgcgcgg ctactacaaccagagcgaggccgggtctcacaccctccagaggatgtacggctgcgacgtggggccggacgggcgcctcc tccgcgggcataaccagtacgcctacgacggcaaAgattacatcgccctgaacgaggacctgagctcctggaccgcggcg gacacggcggctcagatcacccagcgcaagtgggaggcggcccgtgaggcggagcagcTgagagcctacctggagggcct gtgcgtggagtggctccgcagatacctggagaacgggaaggagacgctgcagcgcgcggaccccccaaagacacatgtga cccaccaccccatctctgaccatgaggccaccctgaggtgctgggccctgggcttctaccctgcggagatcacactgacc tggcagcgggatggcgaggaccaaactcaggacacCgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccatccccatcgtgggcattgttgctggcctggctgtcccta...gca gttgtggtcatcggagctgtggtcgctactgtgatgtgtaggaggaagagCtcaggtgga

B*1510

(SEQ ID NO: 1235)
atgcgggtcacggcgccccgaaccgtcctcctgctgctctcgggAgccctggccctgaccgagacctgggccggctccca ctccatgaggtatttctacaccgccatgtcccggcccggccgcggggagccccgcttcatctcagtgggctacgtggacg acacGcagttcgtgaggttcgacagcgacgccgcgagtccgagagaggagccgcgggcgccgtggatagagcaggagggg -continued ccggagtattgggaccggaacacacagatctGcaagaccaacAcacagacttaccgagagagcctgcggaacctgcgcgg ctactacaaccagagcgaggccgggtctcacaccctccagagGatgtacggctgcgacgtggggccggacgggcgcctcc tccgcgggcatgaccagtacgcctacgacggcaaggattacatcgccctgaacgaggacctgagctcctggaccgcggcg gacacggcggctcagatcacccagcgcaagtgggaggcggcccgtgaggcggagcagTgagagcctacctggagggcct gtgcgtggagtggctccgcagatacctggagaacgggaaggagacgctgcagcgcgcggaccccccaaagacacatgtga cccaccacccatctctgaccatgaggccaccctgaggtgctgggccctgggcttctaccctgcggagatcacactgacc tggcagcgggatggcgaggaccaaactcaggacacCgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccatccccatcgtgggcattgttgctggcctggctgtcccta...gca gttgtggtcatcggagctgtggtcgctactgtgatgtgtaggaggaagagCtcaggtgga B*151101
(SEQ ID NO: 1236)
atgcgggtcacggcgccccgaaccgtcctcctgctgctctcgggAgccctggccctgaccgagacctgggccggctccca ctccatgaggtatttctacaccgccatgtcccggcccggccgcggggagccccgcttcatcgcagtgggctacgtggacg acacccagttcgtgaggttcgacagcgacgccgcgagtccgaggatggcgcccgggcgccAtggatagagcaggagggg ccggagtattgggaccggaacacacagatctacaagaccaacacacagactTaccgagagagcctgcggaacctgcgcgg ctactacaaccagagcgaggccgggtctcacaccctccagaggatgtacggctgcgacgtggggccggacgggcgcctcc tccgcgggcatgaccagtccgcctacgacggcaaggattacatcgccctgaacgaggacctgagctcctggaccgcggcg gacacggcggctcagatcacccagcgcaagtgggaggcggcccgtgaggcggagcagTggagagcctacctggagggcct gtgcgtggagtggctccgcagatacctggagaacgggaaggagacgctgcagcgcgcggaccccccaaagacacatgtga cccaccacccatctctgaccatgaggccaccctgaggtgctgggccctgggcttctaccctgcggagatcacactgacc tggcagcgggatggcgaggaccaaactcaggacacCgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccatccccatcgtgggcattgttgctggcctggctgtcccta...gca gttgtggtcatcggagctgtggtcgctactgtgatgtgtaggaggaagagCtcaggtgga B*151102
(SEQ ID NO: 1237)
gctcccactccatgaggtatttctacaccgccatgtcccggcccggccgcggggagccccgcttcatcgcagtgggctac gtggacgacacccagttcgtgaggttcgacagcgacgccgcgagtccgaggatggcTccccgggcgccatggatagagca ggaggggccggagtattgggaccggaacacacagatctacaagaccaacacacagacttaccgagagagcctgcggaacc tgcgcggctactacaaccagagcgaggccgggtctcacaccctccagaggatgtacggctgcgacgtggggccggacggg cgcctcctccgcgggcatgaccagtccgcctacgacggcaaggattacatcgccctgaacgaggacctgagctcctggac cgcggcggacacggcggctcagatcacccagcgcaagtgggaggcggcccgtgaggcggagcagtggagagcctacctgg agggcctgtgcgtggagtggctccgcagatacctggagaacgggaaggagacgctgcagcgcgcgg B*1512
(SEQ ID NO: 1238)
atgcgggtcacggcgccccgaaccgtcctcctgctgctctcgggagccctggccctgaccgagacctgggccggctccca ctccatgaggtatttctacaccgccatgtcccggcccggccgcggggagccccgcttcatcgcagtgggctacgtggacg acacccagttcgtgaggttcgacagcgacgccgcgagtccgaggatggcgcccgggcgccatggatagagcaggagggg ccggagtattgggacggagacacagatctccaagaccaacacacagacttaccgagagagcctgcggaacctgcgcgg ctactacaaccagagcgaggccgggtctcacaccctccagaggatgtacggctgcgacgtggggccggacgggcgcctcc tccgcgggcatgaccagtccgcctacgacggcaaggattacatcgccctgaacgaggacctgagctcctggaccgcggcg gacacggcggctcagatcacccagcgcaagtgggaggcggcccgtgaggcggagcagtggagagcctacctggagggcct gtgcgtggaCgggctccgcagatacctggagaacgggaaggagacgctgcagcgcgcggaccccccaaagacacatgtga -continued cccaccacccatctctgaccatgaggccaccctgaggtgctgggccctgggcttctaccctgcggagatcacactgacc tggcagcgggatggcgaggaccaaactcaggacaccgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccatccccatcgtgggcattgttgctggcctggctgtccta...gca gttgtggtcatcggagctgtggtcgctactgtgatgtgtaggaggaagagctcaggtgga B*1513
(SEQ ID NO: 1239)
atgcgggtcacggcgccccgaaccgtcctcctgctgctctcgggAgccctggccctgaccgagacctgggccggctccca ctccatgaggtatttctacaccgccatgtcccggcccggccgcggggagccccgcttcatcgcagtgggctacgtggacg acacccagttcgtgaggttcgacagcgacgccgcgagtccgaggatggcgccccgggcgccatggatagagcaggagggg ccggagtattgggaccggaacacacagatctccaagaccaacacacagacttaccgagagaacctgcggatcgcgctcCg ctactacaaccagagcgaggccgggtctcacatcatccagaggatgtaTggctgcgacgtggggccggacgggcgcctcc tccgcgggTatgaccagtCcgcctacgacggcaaggattacatcgccctgaacgaggacctgagctcctggaccgcggcg gacacggcggctcagatcacccagcgcaagtgggaggcggcccgtgaggcggagcagcTgagagcctacctggagggcct gtgcgtggagtggctccgcagatacctggagaacgggaaggagacgctgcagcgcgcggaccccccaaagacacatgtga cccaccacccatctctgaccatgaggccaccctgaggtgctgggccctgggcttctaccctgcggagatcacactgacc tggcagcgggatggcgaggaccaaactcaggacaCgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccatccccatcgtgggcattgttgctggcctggctgtccta...gca gttgtggtcatcggagctgtggtcgctactgtgatgtgtaggaggaagagCtcaggtgga B*1514
(SEQ ID NO: 1240)
atgcgggtcacggcgccccgaaccgtcctcctgctgctctcgggAgccctggccctgaccgagacctgggccggctccca ctccatgaggtatttctacaccgccatgtcccggcccggccgcggggagccccgcttcatcgcagtgggctacgtggacg acacccagttcgtgaggttcgacagcgacgccgcgagtccgaggatggcgccccgggcgccatggatagagcaggagggg ccggagtattgggaccggagacacagatctccaagaccaacacacagacttaccgagagagcctgcggaacctgcgcgg ctactacaaccagagcgaggccgggtctcacaccctccagaggatgtacggctgcgacgtggggccggacgggcgcctcc tccgcgggcatgaccagtccgcctacgacggcaaggattacatcgccctgaacgaggacctgagctcctggaccgcggcg gacacggcggctcagatcacccagcgcaagtgggaggcggcccgtgaggcggagcagtggagagcctacctggagggcct gtgcgtggagtCgctccgcagatacctggagaacgggaaggagacgctgcagcgcgcggaccccccaaagacacatgtga cccaccacccatctctgaccatgaggccaccctgaggtgctgggccctgggcttctaccctgcggagatcacactgacc tggcagcgggatggcgaggaccaaactcaggacaCgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccatccccatcgtgggcattgttgctggcctggctgtccta...gca gttgtggtcatcggagctgtggtcgctactgtgatgtgtaggaggaagagCtcaggtgga B*1515
(SEQ ID NO: 1241)
atgcgggtcacggcgccccgaaccgtcctcctgctgctctcgggAgccctggccctgaccgagacctgggccggctccca ctccatgaggtatttctacaccgccatgtcccggcccggccgcggggagccccgcttcatcgcagtgggctacgtggacg acacccagttcgtgaggttcgacagcgacgccgcgagtccgaggatggcgccccgggcgccAtggatagagcaggagggg ccggagtattgggaccggaacacacagatctCcaagaccaacacacagactTaccgagagagcctgcggaacctgcgcgg ctactacaaccagagcgaggccgggtctcacaccctccagaggatgtacggctgcgacgtggggccggacgggcgcctcc tccgcgggcatgaccagtccgcctacgacggcaaggattacatcgccctgaacgaggacctgagctcctggaccgcggcg -continued

```
gacacggcggctcagatcacccagcgcaagtgggaggcggcccgtgaggcggagcagTggagagcctacctggagggcct gtgcgtggagtggctccgcagatacctggagaacgggaaggagacgctgcagcgcgcggaccccccaaagacacatgtga cccaccaccccatctctgaccatgaggccaccctgaggtgctgggccctgggcttctaccctgcggagatcacactgacc tggcagcgggatggcgaggaccaaactcaggacacCgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccatccccatcgtgggcattgttgctggcctggctgtccta...gca gttgtggtcatcggagctgtggtcgctactgtgatgtgtaggaggaagagCtcaggtgga
```

B*1516
(SEQ ID NO: 1242)
```
atgcgggtcacggcgccccgaaccgtcctcctgctgctctcgggagccctggccctgaccgagacctgggccggctccca ctTcatgaggtatttctacaccgccatgtcccggcccggccgcggggagccccgcttcatcgcagtgggctacgtggacg acacgcagttcgtgaggttcgacagcgacgccgcgagtccgaggatggcgcccgggcgccatggatagagcaggagggg ccggagtattgggaccgggagacacggaacatgaaggcctccgcgcagacttaccgagagaacctgcggatcgcgctccg ctactacaaccagagcgaggccgggtctcacacttggcagaggatgtatggctgcgacctggggccggacgggcgcctcc tccgcgggcatgaccagtccgcctacgacggcaaggattacatcgccctgaacgaggacctgagctcctggaccgcggcg gacacggcggctcagatcacccagcgcaagtgggaggcggcccgtgaggcggagcagctgagagcctacctggagggcct gtgcgtggagtggctccgcagatacctggagaacgggaaggagacgctgcagcgcgcggaccccccaaagacacatgtga cccaccaccccatctctgaccatgaggccaccctgaggtgctgggccctgggcttctaccctgcggagatcacactgacc tggcagcgggatggcgaggaccaaactcaggacaccgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccatccccatcgtgggcattgttgctggcctggctgtccta...gca gttgtggtcatcggagctgtggtcgctactgtgatgtgtaggaggaagagCtcaggtgga
```

B*151701
(SEQ ID NO: 1243)
```
atgcgggtcacggcgccccgaaccgtcctcctgctgctctcgggagccctggccctgaccgagacctgggccggctccca ctccatgaggtatttctacaccgccatgtcccggcccggccgcggggagccccgcttcatcgcagtgggctacgtggacg acacccagttcgtgaggttcgacagcgacgccgcgagtccgaggatggcgcccgggcgccatggatagagcaggagggg ccggagtattgggaccgggagacacggaacatgaaggcctccgcGcagacttaccgagagaacctgcggatcgcgctccg ctactacaaccagagcgaggccgggtctcacacccctccagaggatgtacggctgcgacgtggggccggacgggcgcctcc tccgcgggtaccaccagDacgcctacgacggcaaggattacatcgccctgaacgaggacctgagctcctggaccgcggcg gacacggcggctcagatcacccagcgcaagtgggaggcggcccgtgaggcggagcagctgagagcctacctggagggcct gtgcgtggagtggctccgcagatacctggagaacgggaaggagacgctgcagcgcgcggaccccccaaagacacatgtga cccaccaccccatctctgaccatgaggccaccctgaggtgctgggccctgggcttctaccctgcggagatcacactgacc tggcagcgggatggcgaggaccaaactcaggacacCgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccatccccatcgtgggcattgttgctggcctggctgtccta...gca gttgtggtcatcggagctgtggtcgctActgtgatgtgtaggaggaagagCtcaggtgga
```

B*1518
(SEQ ID NO: 1244)
```
atgcgggtcacggcgccccgaaccgtcctcctgctgctctcgggAgccctggccctgaccgagacctgggccggctccca ctccatgaggtatttctacaccgccatgtcccggcccggccgcggggagccccgcttcatctcagtgggctacgtggacg acacGcagttcgtgaggttcgacagcgacgccgcgagtccgagagaggagccgcgggcgccgtggatagagcaggagggg ccggagtattgggaccggaacacacagatctGcaagaccaacAcacagacttaccgagagagcctgcggaacctgcgcgg ctactacaaccagagcgaggccgggtctcacacccctccagagGatgtacggctgcgacgtggggccggacgggcgcctcc
```

-continued tccgcgggcatgaccagtCcgcctacgacggcaaggattacatcgccctgaacgaggacctgagctcctggaccgcggcg gacacggcggctcagatcacccagcgcaagtgggaggcggcccgtgaggcggagcagcTgagagcctacctggagggcct gtgcgtggagtggctccgcagatacctggagaacgggaaggagacgctgcagcgcgcggaccccccaaagacacatgtga cccaccaccccatctctgaccatgaggccaccctgaggtgctgggccctgggcttctaccctgcggagatcacactgacc tggcagcgggatggcgaggaccaaactcaggacacCgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccatccccatcgtgggcattgttgctggcctggctgtccta...gca gttgtggtcatcggagctgtggtcgctactgtgatgtgtaggaggaagagCtcaggtgga

B*1519

(SEQ ID NO: 1245)

atgcgggtcacggcgccccgaaccgtcctcctgctgctctcgggagccctggccctgaccgagacctgggccggctccca ctccatgaggtatttctacaccgccatgtcccggcccggccgcggggagccccgcttcatcgcagtgggctacgtggacg acacccagttcgtgaggttcgacagcgacgccgcgagtccgaggatggcgccccgggcgccatggatagagcaggagggg ccggagtattgggaccgggagacacagatctccaagaccaacacacagacttaccgagagagcctgcggaacctgcgcgg ctactacaaccagagcgaggccgggtctcacaccctccagaggatgtacggctgcgacgtggggccggacgggcgcctcc tccgcgggcatgaccagtccgcctacgacggcaaggattacatcgccctgaacgaggacctgagctcctggaccgcggcg gacacggcggctcagatcacccagcgcaagtgggaggcggcccgtgaggcggagcagtggagagcctacctggagggcct gtgcgtggacgggctccgcagatacctggagaacgggaaggagacgctgcagcgcgcggaccccccaaagacacatgtga cccaccaccccatctctgaccatgaggccaccctgaggtgctgggccctgggcttctaccctgcggagatcacactgacc tggcagcgggatggcgaggaccaaactcaggacaccgagcttgtggagaccagaccagcaggagatagaaccttccagaa gtgggcagctgtggtggtgcTttctggagaagagcagagatacacatgccatgtacagcatgaggggctgccgaagcccc tcaccctgagatgggagccatcttcccagtccaccatccccatcgtgggcattgttgctggcctggctgtccta...gca gttgtggtcatcggagctgtggtcgctactgtgatgtgtaggaggaagagctcaggtgga

B*1520

(SEQ ID NO: 1246)

atgcgggtcacggcgccccgaaccgtcctcctgctgctctcgggAgccctggccctgaccgagacctgggccggctccca ctccatgaggtatttctacaccgccatgtcccggcccggccgcggggagccccgcttcatcgcagtgggctacgtggacg acacccagttcgtgaggttcgacagcgacgccgcgagtccgaggatggcgccccgggcgccatggatagagcaggagggg ccggagtattgggaccgggagacacagatctccaagaccaacacacagacttaccgagagagcctgcggaacctgcgcgg ctactacaaccagagcgaggccgggtctcacatcatccagaggatgtatggctgcgacctggggcccgacgggcgcctcc tccgcgggcatgaccagtccgcctacgacggcaaggattacatcgccctgaacgaggacctgagctcctggaccgcggcg gacaccgcggctcagatcacccagcgcaagtgggaggcggcccgtgtggcggagcagctgagagcctacctggagggcct gtgcgtggagtggctccgcagatacctggagaacgggaaggagacgctgcagcgcgcggaccccccaaagacacacgtga cccaccaccccGtctctgaccatgaggccaccctgaggtgctgggccctgggcttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccatccccatcgtgggcattgttgctggcctggctgtccta...gca gttgtggtcatcggagctgtggtcgctactgtgatgtgtaggaggaagagCtcaggtgga

B*1521

(SEQ ID NO: 1247)

atgcgggtcacggcgccccgaaccgtcctcctgctgctctcgggAgccctggccctgaccgagacctgggccggctccca ctccatgaggtatttctacaccgccatgtcccggcccggccgcggggagccccgcttcatcgcagtgggctacgtggacg acacccagttcgtgaggttcgacagcgacgccgcgagtccgaggatggcgccccgggcgccatggatagagcaggagggg -continued ccggagtattgggaccggaacacacagatctGcaagaccaacacacagacttaccgagagagcctgcggaacctgcgcgg ctactacaaccagagcgaggccgggtctcacatcatccagaggatgtaTggctgcgacgtggggccggacgggcgcctcc tccgcgggTatgaccagtCcgcctacgacggcaaggattacatcgccctgaacgaggacctgagctcctggaccgcggcg gacacggcggctcagatcacccagcgcaagtgggaggcggcccgtgaggcggagcagcTgagagcctacctggagggcct gtgcgtggagtggctccgcagatacctggagaacgggaaggagacgctgcagcgcgcggaccccccaaagacacatgtga cccaccacccatctctgaccatgaggccaccctgaggtgctgggccctgggcttctaccctgcggagatcacactgacc tggcagcgggatggcgaggaccaaactcaggacacCgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccatccccatcgtgggcattgttgctggcctggctgtccta...gca gttgtggtcatcggagctgtggtcgctactgtgatgtgtaggaggaagagCtcaggtgga

B*1523 (SEQ ID NO: 1248)

atgcgggtcacggcgccccgaaccgtcctcctgctgctctcgggAgccctggccctgaccgagacctgggccggctccca ctccatgaggtatttctacaccgccatgtcccggcccggccgcggggagccccgcttcatctcagtgggctacgtggacg acacgcagttcgtgaggttcgacagcgacgccgcgagtccgagagaggagccgcgggcgccgtggatagagcaggagggg ccggagtattgggaccggaacacacagatctGcaagaccaacAcacagacttaccgagagaacctgcggatcgcgctcCg ctactacaaccagagcgaggccgggtctcacaccctccagagGatgtacggctgcgacgtggggccggacgggcgcctcc tccgcgggcatgaccagtCcgcctacgacggcaaggattacatcgccctgaacgaggacctgagctcctggaccgcggcg gacacggcggctcagatcacccagcgcaagtgggaggcggcccgtgaggcggagcagcTgagagcctacctggagggcct gtgcgtggagtggctccgcagatacctggagaacgggaaggagacgctgcagcgcgcggaccccccaaagacacatgtga cccaccacccatctctgaccatgaggccaccctgaggtgctgggccctgggcttctaccctgcggagatcacactgacc tggcagcgggatggcgaggaccaaactcaggacacCgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccatccccatcgtgggcattgttgctggcctggctgtccta...gca gttgtggtcatcggagctgtggtcgctactgtgatgtgtaggaggaagagCtcaggtgga

B*1524 (SEQ ID NO: 1249)

gctcccactccatgaggtatttctacaccgccatgtcccggcccggccgcggggagccccgcttcatcgcagtgggctac gtggacgacacccagttcgtgaggttcgacagcgacgccgcgagtccgaggatggcgcccgggcgccatggatagagca ggaggggccggagtattgggaccgggagacacagatctccaagaccaacacacagacttaccgagagaacctgcggatcg CgctcCgctactacaaccagagcgaggccgggtctcacaccctccagagGatgtacggctgcgacgtggggccggacggg cgcctcctccgcgggcatgaccagtCcgcctacgacggcaaggattacatcgccctgaacgaggacctgagctcctggac cgcGgcggacacggcggctcagatcacccagcgcaagtgggaggcggcccgtgaggcggagcagTggagagcctacctgg agggccTgtgcgtggagtggctccgcagatacctggagaacgggaaggagacgctgcagcgcgcGg

B*1525 (SEQ ID NO: 1250)

atgcgggtcacggcgccccgaaccgtcctcctgctgctctcgggAgccctggccctgaccgagacctgggccggctccca ctccatgaggtatttctacaccgccatgtcccggcccggccgcggggagccccgcttcatcgcagtgggctacgtggacg acacccagttcgtgaggttcgacagcgacgccgcgagtccgaggatggcgcccgggcgccatggatagagcaggagggg ccggagtattgggacCgggaGacacagatctCcaagaccaacacacagacttaccgagagagcctgcggaacctgcgcgg ctactacaaccagagcgaggccgggtctcacatcatccagaggatgtaTggctgcgacgtggggccggacgggcgcctcc tccgcgggTatgaccagtCcgcctacgacggcaaggattacatcgccctgaacgaggacctgagctcctggaccgcggcg gacacggcggctcagatcacccagcgcaagtgggaggcggcccgtgaggcggagcagcTgagagcctacctggagggcct gtgcgtggagtggctccgcagatacctggagaacgggaaggagacgctgcagcgcgcggaccccccaaagacacatgtga -continued cccaccacccatctctgaccatgaggccaccctgaggtgctgggccctgggcttctaccctgcggagatcacactgacc tggcagcgggatggcgaggaccaaactcaggacacCgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccatccccatcgtgggcattgttgctggcctggctgtccta...gca gttgtggtcatcggagctgtggtcgctactgtgatgtgtaggaggaagagCtcaggtgga

B*1527

(SEQ ID NO: 1251)

gaggtatttctacaccgccatgtcccggcccggccgcggggagccccgcttcatcgcagtgggctacgtggacgacaccc agttcgtgaggttcgacagcgacgccgcgagtccgaggatggcgcccgggcgccatggatagagcaggaggggccggag tattgggaccgggagacacagatctccaagaccaacacacagacttaccgagagagcctgcggaacctgcgcggctacta caaccagagcgaggccgggtctcacaccctccagaggatgtTtggctgcgacgtggggccggacgggcgcctcctccgcg ggcatgaccagtccgcctacgacggcaaggattacatcgccctgaacgaggacctgagctcctggaccgcggcggacacg gcggctcagatcacccagcgcaagtgggaggcggcccgtgaggcggagcagTggagagcctacctggagggcCtgtgcgt ggagtggctccgcagatacctggagaacgggaaggagacgctgcagcgc

B*1528

(SEQ ID NO: 1252)

atgcgggtcacggcgccccgaaccgtcctcctgctgctctcgggagccctggccctgaccgagacctgggccggctccca ctccatgaggtatttctacaccgccatgtcccggcccggccgcggggagccccgcttcatcgcagtgggctacgtggacg acacccagttcgtgaggttcgacagcgacgccgcgagtccgaggatggcgccccgggcgccatggatagagcaggagggg ccggagtattgggaccgggagaTacagatctccaagaccaacacacagacttaccgagagagcctgcggaacctgcgcgg ctactacaaccagagcgaggccgggtctcacaccctccagaggatgtacggctgcgacgtggggccggacgggcgcctcc tccgcgggcatgaccagtccgcctacgacggcaaggattacatcgccctgaacgaggacctgagctcctggaccgcggcg gacacggcggctcagatcacccagcgcaagtgggaggcggcccgtgaggcggagcagtggagagcctacctggagggcct gtgcgtggagtggctccgcagatacctggagaacgggaaggagacgctgcagcgcgcggaccccccaaagacacatgtga cccaccaccccatctctgaccatgaggccaccctgaggtgctgggccctgggcttctaccctgcggagatcacactgacc tggcagcgggatggcgaggaccaaactcaggacaccgagcttgtggagaccagaccagcaggagatagaaccttccagaa gtgggcagctgtggtggtgccttctggagaagagcagagatacacatgccatgtacagcatgaggggctgccgaagcccc tcaccctgagatggg

B*1529

(SEQ ID NO: 1253)

atgcgggtcacggcgccccgaaccgtcctcctgctgctctcgggAgccctggccctgaccgagacctgggccggctccca ctccatgaggtatttctacaccgccatgtcccggcccggccgcggggagccccgcttcatctcagtgggctacgtggacg acacgcagttcgtgaggttcgacagcgacgccgcgagtccgagagaggagccgcgggcgccgtggatagagcaggagggg ccggagtattgggaccggaacacacagatctTcaagaccaacAcacagacttaccgagagagcctgcggaacctgcgcgg ctactacaaccagagcgaggccgggtctcacaccctccagagGatgtacggctgcgacgtggggccggacgggcgcctcc tccgcgggcatgaccagtCcgcctacgacggcaaggattacatcgccctgaacgaggacctgagctcctggaccgcggcg gacacggcggctcagatcacccagcgcaagtgggaggcggcccgtgaggcggagcagTgagagcctacctggagggcct gtgcgtggagtggctccgcagatacctggagaacgggaaggagacgctgcagcgcgcggaccccccaaagacacatgtga cccaccaccccatctctgaccatgaggccaccctgaggtgctgggccctgggcttctaccctgcggagatcacactgacc tggcagcgggatggcgaggaccaaactcaggacacCgagcttgtggagaccagaccagcaggagatagaaccttccagaa gtgggcagctgtggtggtgccttctggagaagagcagagatacacatgccatgtacagcatgaggggctgccgaagcccc tcaccctgagatggg

B*1530

(SEQ ID NO: 1254)

gaggtatttctacaccgccatgtcccggcccggccgcggggagccccgcttcatcgcagtgggctacgtggacgacaccc agttcgtgaggttcgacagcgacgccgcgagtccgaggatggcgccccgggcgccatggatagagcaggaggggccggag tattgggaccgggagacacagatctCcaagaccaacacacagacttaccgagagagcctgcggaacctgcgcggctacta caaccagagcgaggccgggtctcacaccctccagaggatgtacggctgcgacgtggggccggacgggcgcctcctccgcg ggcatAaccagtacgcctacgacggcaaggattacatcgccctgaacgaggacctgagctcctggaccgcGgcggacacg gcggctcagatcacccagcgcaagtgggaggcggcccgtgaggcggagcagTggagagcctacctggagggccTgtgcgt ggagtggctccgcagatacctggagaacgggaaggagacgctgcagcgc

B*1531

(SEQ ID NO: 1255)

gaggtatttctacaccgccatgtcccggcccggccgcggggagccccgcttcatcgcagtgggctacgtggacgacaccc agttcgtgaggttcgacagcgacgccgcgagtccgaggatggCgccccgggcgccatggatagagcaggaggggccggag tattgggaccggaacacacagatctccaagaccaacacacagacttaccgagagagcctgcggaacctgcgcggctacta caaccagagcgaggccgggtctcacaccctccagagGatgtacggctgcgacgtggggccggacgggcgcctcctccgcg ggTatgaccagtCcgcctacgacggcaaggattacatcgccctgaacgaggacctgagctcctggaccgcggcggacacg gcggctcagatcacccagcgcaagtgggaggcggcccgtgTggcggagcagcTgagagcctacctggagggccTgtgcgt ggagtggctccgcagatacctggagaacgggaaggagacgctgcagcgcgcGg

B*1532

(SEQ ID NO: 1256)

gctcccactccatgaggtatttctacaccgccatgtcccggcccggccgcggggagccccgcttcatcgcagtgggctac gtggacgacacccagttcgtgaggttcgacagcgacgccgcgagtccgaggatggcgccccgggcgccatggatagagca ggaggggccggagtattgggaccgggagacacagatctccaagaccaacacacagacttaccgagagagcctgcggaacc tgcgcggctactacaaccagagcgaggccgggtctcacaccctccagaggatgtCtggctgcgacgtggggccggacggg cgcctcctccgcgggcatgaccagtccgcctacgacggcaaggattacatcgccctgaacgaggacctgagctcctggac cgcggcggacacggcggctcagatcacccagcgcaagtgggaggcggcccgtgaggcggagcagTggagagcctacctgg agggccTgtgcgtggagtggctccgcagatacctggagaacgggaaggagacgctgcagcgcgcgg

B*1533

(SEQ ID NO: 1257)

gctcccactccatgaggtatttctacaccgccatgtcccggcccggccgcggggagccccgcttcatcgcagtgggctac gtggacgacacccagttcgtgaggttcgacagcgacgccgcgagtccgaggatggcgccccgggcgccatggatagagca ggaggggccggagtattgggaccgggagacacagatctccaagaccaacacacagacttaccgagagagcctgcggaacc tgcgcggctactacaaccagagcgaggccgggtctcacaccctccagaggatgtacggctgcgacgtggggccggacggg cgcctcctccgcgggcatgaccagtccgcctacgacggcaaggattacatcgccctgaacgaggacctgcgctcctggac cgccgcggacaAggcggctcagatcacccagcgcaagtgggaggcggcccgtgaggcggagcagtggagagcctacctgg agggcctgtgcgtggagtggctccgcagatacctggagaacgggaaggagacgctgcagcgcgcgg

B*1534

(SEQ ID NO: 1258)

gctcccactccatgaggtatttctacaccgccatgtcccggcccggccgcggggagccccgcttcatcgcagtgggctac gtggacgacacccagttcgtgaggttcgacagcgacgccgcgagtccgaggatggcgccccgggcgccatggatagagca ggaggggccggagtattgggaccgggagacacagatctCcaagaccaacacacagacttaccgagagagcctgcggaacc tgcgcggctactacaaccagagcgaggccgggtctcacaccctccagaggatgtacggctgcgacCtggggccggacggg cgcctcctccgcgggcatgaccagtCcgcctacgacggcaaggattacatcgccctgaacgaggacctgagctcctggac cgcGgcggacacggcggctcagatcacccagcgcaagtgggaggcggcccgtgaggcggagcagTggagagcctacctgg agggccTgtgcgtggagtggctccgcagatacctggagaacgggaaggagacgctgcagcgcgcGg -continued

B*1535

(SEQ ID NO: 1259)
gctcccactccatgaggtatttctacaccgccatgtcccggcccggccgcggggagccccgcttcatcgcagtgggctac gtggacgacacccagttcgtgaggttcgacagcgacgccgcgagtccgaggatggcgccccgggcgccatggatagagca ggaggggccggagtattgggaccgggagacacagatctccaagaccaacacacagacttaccgagagagcctgcggaacc tgcgcggctactacaaccagagcgaggcccggtctcacaccctccagaCGatgtacggctgcgacgtggggccggacggg cgcctcctccgcgggcatgaccagtCcgcctacgacggcaaggattacatcgccctgaacgaggacctgagctcctggac cgcGgcggacacggcggctcagatcacccagcgcaagtgggaggcggcccgtgaggcggagcagTggagagcctacctgg agggccTgtgcgtggagtggctccgcagatacctggagaacgggaaggagacgctgcagcgcgcGg

B*1536

(SEQ ID NO: 1260)
gctcccactccatgaggtatttctacaccgccatgtcccggcccggccgcggggagccccgcttcatcgcagtgggctac gtggacgacacccagttcgtgaggttcgacagcgacgccgcgagtccgaggatggcgccccgggcgccatggatagagca ggaggggccggagtattgggaccgggagacacagatctccaagaccaacacacagacttaccgagagaacctgcgCaccg cgctccgctactacaaccagagcgaggcccggtctcacatcatccagaggatgtatggctgcgacgtggggccggacggg cgcctcctccgcgggTatgaccagtCcgcctacgacggcaaggattacatcgccctgaacgaggacctgagctcctggac cgcggcggacacggcggctcagatcacccagcgcaagtgggaggcggcccgtgaggcggagcagcTgagagcctacctgg agggcCTgtgcgtggagtggctccgcagatacctggagaacgggaaggagacgctgCagcgcgcGg

B*1537

(SEQ ID NO: 1261)
gctcccactccatgaggtatttctacaccgccatgtcccggcccggccgcggggagccccgcttcatctcagtgggctac gtggacgacacGcagttcgtgaggttcgacagcgacgccgcgagtccgagagaggagccgcgggcgccgtggatagagca ggaggggccggagtattgggaccggaacacacagatctGcaagaccaacacacagactTaccgagagagcctgcggaacc tgcgcggctactacaaccagagcgaggcccggtctcacaccctccagaggatgtacggctgcgacgtggggccggacggg cgcctcctccgcgggcatgaccagtacgcctacgacggcaaggattacatcgccctgaacgaggacctgAgctcctggac cgcggcggacacggcggctcagatcacccagcgcaagtgggaggcggcccgtgaggcggagcagcTgagagcctacctgg agggccTgtgcgtggagtggctccgcagaCacctggagaacgggaaggagacgctgcagcgcgcgg

B*1538

(SEQ ID NO: 1262)
gctcccactccatgaggtatttctacaccgccatgtcccggcccggccgcggggagccccgcttcatcgcagtgggctac gtggacgacacccagttcgtgaggttcgacagcgacgccgcgagtccgaggatggcgccccgggcgccatggatagagca ggaggggccggagtattgggaccgggagacacagatctccaagaccaacacacagacttaccgagagagcctgcggaacc tgcgcggctactacaaccagagcgaggcccggtctcacaccctccagaggatgtacggctgcgacgtggggccggacggg cgcctcctccgcgggcatgaccagtccgcctacgacggcaaggattacatcgccctgaacgaggacctgagctcctggac cgcggcggacacggcggctcagatcacccagcgcaagtgggaggcggcccgtgaggcggagcagTggagagcctacctgg agggcctgtgcgtggagtggctccgcagaCacctggagaacgggaaggagacgctgcagcgcgcGg

B*1539

(SEQ ID NO: 1263)
gctcccactccatgaggtatttctacaccgccatgtcccggcccggccgcggggagccccgcttcatcGcagtgggctac gtggacgacacccagttcgtgaggttcgacagcgacgccgcgagtccgaggatggCgccccgggcgccatggatagagca ggaggggccggagtattgggacgggaGacacagatctCcaagaccaacAcacagacttaccgagagagcctgcggaacc tgcgcggctactacaaccagagcgaggcccggtctcacaccctccagagGatgtacggctgcgacgtggggccggacggg cgcctcctccgcgggcatgaccagtCcgcctacgacggcaaggattacatcgccctgaacgaggacctgagctcctggac cgcggcggacacggcggctcagatcacccagcgcaagtgggaggcggcccgtgaggcggagcagcTgagagcctacctgg agggccTgtgcgtggagtggctccgcagatacctggagaacgggaaggagacgctgcagcgcgcGg

B*1540

(SEQ ID NO: 1264)

gctcccactccatgaggtatttctacaccgccatgtcccggcccggccgcggggagccccgcttcatcGcagtgggctac gtggacgacacccagttcgtgaggttcgacagcgacgccgcgagtccgaggatggCgccccgggcgccatggatagagca ggaggggccggagtattgggacccgggaGacacagatctCcaagaccaacAcacagacttaccgagagagcctgcggaacc tgcgcggctactacaaccagagcgaggccgggtctcacaccctccagagGatgtacggctgcgacgtggggccggacggg cgcctcctccgcgggcatgaccagtCcgcctacgacggcaaggattacatcgccctgaacgaggacctgagctcctggac cgcggcggacacggcggctcagatcacccagcgcaagtgggaggcggcccgtgaggcggagcagcTgagagcctacctgg agggcgagtgcgtggagtggctccgcagatacctggagaacgggaaggagacgctgcagcgcgcGg

B*1542

(SEQ ID NO: 1265)

gctcccactccatgaggtatttctacaccgccatgtcccggcccggccgcggggagccccgcttcatcgcagtgggctac gtggacgacacccagttcgtgaggttcgacagcgacgccgcgagtccgaggatggcgccccgggcgccatggatagagca ggaggggccggagtattgggacccgggagacacagatctCcaagaccaacacacagactTaccgagagagcctgcggaacc tgcgcggctactacaaccagagcgaggccgggtctcacacttggcagaCgatgtaTggctgcgacCtggggccggacggg cgcctcctccgcgggcataaccagttAgcctacgacggcaaggattacatcgccctgaacgaggacctgagctcctggac cgcggcggacaccgcggctcagatcacccagcgcaagtgggaggcggcccgtgaggcggagcagctgagagcctacctgg agggcaCgtgcgtggagtggctccgcagatacctggagaacgggaaggagacgctgcagcgcgcGg

B*1543

(SEQ ID NO: 1266)

gctcccactccatgaggtatttctacaccgccatgtcccggcccggccgcggggagccccgcttcatcgcagtgggctac gtggacgacacccagttcgtgaggttcgacagcgacgccgcgagtccgaggatggcgccccgggcgccatggatagagca ggaggggccggagtattgggacccgggagacacagatctccaagaccaacacacagacttaccgagagGacctgcggaccc tgctccgctactacaaccagagcgaggccgggtctcacaccctccagaggatgtacggctgcgacgtggggccggacggg cgcctcctccgcgggcatgaccagtccgcctacgacggcaaggattacatcgccctgaacgaggacctgagctcctggac cgcggcggacacggcggctcagatcacccagcgcaagtgggaggcggcccgtgaggcggagcagTggagagcctacctgg agggccTgtgcgtggagtggctccgcagatacctggagaacgggaaggagacgctgcagcgcgcGg

B*1544

(SEQ ID NO: 1267)

gctcccactccatgaggtatttctacaccgccatgtcccggcccggccgcggggagccccgcttcatcgcagtgggctac gtggacgacacccagttcgtgaggttcgacagcgacgccgcgagtccgaggatggcgccccgggcgccatggatagagca ggaggggccggagtattgggaccggaacacacagatctGcaagaccaacacacagacttaccgagagagcctgcggaacc tgcgcggctactacaaccagagcgaggccgggtctcacatcatccagaggatgtatggctgcgacgtggggccggacggg cgcctcctccgcgggtatgaccagtCcgcctacgacggcaaggattacatcgccctgaacgaggacctgagctcctggac cgcGgcggacacggcggctcagatcacccagcgcaagtgggaggcggcccgtgaggcggagcagcTgagagcctacctgg agggcaCgtgcgtggagtggctccgcagatacctggagaacgggaaggagacgctgcagcgcgcGg

B*1545

(SEQ ID NO: 1268)

gctcccactccatgaggtatttctacaccgccAtgtcccggcccggccgcggggagccccgcttcatcgcagtgggctac gtggacgacacccagttcgtgaggttcgacagcgacgccgcgagtccgaggatggcgccCgggcgccAtggatagagca ggaggggccggagtattgggacccgggaGacacagatctCcaagaccaacacacagactTaccgagagagcctgcggaacc tgcgcggctactacaaccagagcgaggccgggtctcacaccctccagagcatgtacggctgcgacgtggggccggacggg cgcctcctccgcgggcatgaccagtacgcctacgacggcaaggattacatcgccctgaacgaggacctgagctcctggac cgcGgcggacacggcggctcagatcacccagcgcaagtgggaggcggcccgtgaggcggagcagTggagagcctacctgg agggccTgtgcgtggagtggctccgcagatacctggagaacgggaaggagacgctgcagcgcgcGg -continued

B*1546

(SEQ ID NO: 1269)
atgcgggtcacggcgccccgaaccgtcctcctgctgctctcgggAgccctggccctgaccgagacctgggccggctccca ctccatgaggtatttctacaccgccatgtcccggcccggccgcggggagccccgcttcatcGcagtgggctacgtggacg acacccagttcgtgaggttcgacagcgacgccAcgagtccgaggaaggagccgcgggcgccAtggatagagcaggagggg ccggagtattgggaccgggaGacacagatctCcaagaccaacacacagactTaccgagagagcctgcggaacctgcgcgg ctactacaaccagagcgaggccgggtctcacaccctccagaggatgtacggctgcgacgtggggccggacgggcgcctcc tccgcgggcatgaccagtCcgcctacgacggcaaggattacatcgccctgaacgaggacctgagctcctggaccgcggcg gacacgcggctcagatcacccagcgcaagtgggaggcggcccgtgaggcggagcagTggagagcctacctggagggccT gtgcgtggagtggctccgcagatacctggagaacgggaaggagacgctgcagcgcgcGg

B*1547

(SEQ ID NO: 1270)
gctcccactccatgaggtatttctacaccgccatgtcccggcccggccgcggggagccccgcttcatctcagtgggctac gtggacgacacGcagttcgtgaggttcgacagcgacgccgcgagtccgagagaggagccgcgggcgccgtggatagagca ggaggggccggagtattgggaccgggaGacacagatctCcaagaccaacAcacagactTaccgagagagcctgcggaacc tgcgcggctactacaaccagagcgaggccgggtctcacaccctccagagGatgtacggctgcgacgtggggccggacggg cgcctcctccgcgggcatgaccagtCcgcctacgacggcaaggattacatcgccctgaacgaggacctgAgctcctggac cgcGgcggacacggcggctcagatcacccagcgcaagtgggaggcggcccgtgaggcggagcagcggagagcctacctgg agggcgagtgcgtggagtggctccgcagatacctggagaacgggaaggagacgctgcagcgcgcGg

B*1548

(SEQ ID NO: 1271)
gctcccactccatgaggtatttctacaccgccatgtcccggcccggccgcggggagccccgcttcatcgcagtgggctac gtggacgacacccagttcgtgaggttcgacagcgacgccgcgagtccgaggatggcgccccgggcgccatggatagagca ggaggggccggagtattgggaccgggagacacagatctCcaagaccaacacacagacttaccgagagagcctgcggaacc tgcgcggctactacaaccagagcgaggccgggtctcacaccctccagaggatgtacggctgcgacgtggggccggacggg cgcctcctccgcgggcatAaccagtacgcctacgacggcaaggattacatcgccctgaacgaggacctgagctcctggac cgcggcggacaccgcggctcagatcacccagcgcaagtgggaggcggcccgtgtggcggagcagctgagaAcctacctgg agggcCTgtgcgtggagtggctccgcagatacctggagaacgggaaggagacgctgcagcgcgcGg

B*1549

(SEQ ID NO: 1272)
gctcccactccatgaggtatttctacaccgccatgtcccggcccggccgcggggagccccgcttcatctcagtgggctac gtggacgacacgcagttcgtgaggttcgacagcgacgccgcgagtccgagagaggagccgcgggcgccgtggatagagca ggaggggccggagtattgggaccgggagacacagatctccaagaccaacacacGgacttaccgagagagcctgcggaacc tgcgcggctactacaaccagagcgaggccgggtctcacaccctccagaggatgtacggctgcgacgtggggccggacggg cgcctcctccgcgggcatgaccagtccgcctacgacggcaaggattacatcgccctgaacgaggacctgagctcctggac cgcggcggacacggcggctcagatcacccagcgcaagtgggaggcggcccgtgaggcggagcagcggagagcctacctgg agggcgagtgcgtggagtggctccgcagatacctggagaacgggaaggagacgctgcagcgcgcgg

B*1550

(SEQ ID NO: 1273)
gctcccactccatgaggtatttctacaccgccatgtcccggcccggccgcggggagccccgcttcatcgcagtgggctac gtggacgacacccagttcgtgaggttcgacagcgacgccgcgagtccgaggatggcgccccgggcgccatggatagagca ggaggggccggagtattgggaccgggagacacagatctccaagaccaacacacagacttaccgagagagcctgcggaacc tgcgcggctactacaaccagagcgaggccgggtctcacaccctccagaggatgtacggctgcgacgtggggccggacggg cgcctcctccgcgggcatgaccagtCcgcctacgacggcaaggattacatcgccctgaacgaggacctgagctcctggac cgcggcggacacggcggctcagatcacccagcgcaagtgggaggcggcccgtgaggcggagcagTggagagcctacctgg agggcaCgtgcgtggagtggctccgcagatacctggagaacgggaaggagacgctgcagcgcgcGg

B*1551

(SEQ ID NO: 1274)

gctcccactccatgaggtatttctacaccgccatgtcccggcccggccgcggggagccccgcttcatctcagtgggctac gtggacgacacgcagttcgtgaggttcgacagcgacgccgcgagtccgagagaggagccgcgggcgccgtggatagagca ggaggggccggagtattgggaccggaacacacagatctGcaagaccaacacacagacttaccgagagagcctgcggaacc tgcgcggctactacaaccagagcgaggccgggtctcacaccctccagaggatgtacggctgcgacgtggggccggacggg cgcctcctccgcgggcatgaccagtCcgcctacgacggcaaggattacatcgccctgaacgaggacctgagctcctggac cgcggcggacacggcggctcagatcacccagcgcaagtgggaggcggcccgtgTggcggagcaggaCagagcctacctgg agggccTgtgcgtggagtggctccgcagatacctggagaacgggaaggaDacgctgCagcgcgcGg

B*1552

(SEQ ID NO: 1275)

atgcgggtcacggcgccccgaaccgtcctcctgctgctctcgggAgccctggccctgaccgagacctgggccggctccca ctccatgaggtatttctacaccgccatgtcccggcccggccgcggggagccccgcttcatctcagtgggctacgtggacg acacgcagttcgtgaggttcgacagcgacgccgcgagtccgagagaggagccgcgggcgccgtggatagagcaggagggg ccggagtattgggaccggaacacacagatctGcaagaccaacacacagacttaccgagagagcctgcggaacctgcgcgg ctactacaaccagagcgaggccgggtctcacaccctccagagGatgtacggctgcgacgtggggccggacgggcgcctcc tccgcgggcatgaccagtccgcctacgacggcaaggattacatcgccctgaacgaggacctgagctcctggaccgcggcg gacacggcggctcagatcacccagcgcaagtgggaggcggcccgtgTggcggagcagcTgagagcctacctggagggcga gtgcgtggagtggctccgcagatacctggagaacgggaaggagacgctgcagcgcgcGg

B*1553

(SEQ ID NO: 1276)

atgcgggtcacggcgccccgaaccgtcctcctgctgctctcgggAgccctggccctgaccgagacctgggccggctccca ctccatgaggtatttctacaccgccatgtcccggcccggccgcggggagccccgcttcatcaccgtgggctacgtggacg acacgcTgttcgtgaggttcgacagcgacgccAcgagtccgaggaaggagccgcgggcgccAtggatagagcaggagggg ccggagtattgggaccgggaGacacagatctCcaagaccaacacacagactTaccgagagagcctgcggaacctgcgcgg ctactacaaccagagcgaggccgggtctcacaccctccagaggatgtacggctgcgacgtggggccggacgggcgcctcc tccgcgggcatgaccagtCcgcctacgacggcaaggattacatcgccctgaacgaggacctgagctcctggaccgcggcg gacacggcggctcagatcacccagcgcaagtgggaggcggcccgtgaggcggagcagTggagagcctacctggagggccT gtgcgtggagtggctccgcagatacctggagaacgggaaggagacgctgcagcgcgcGg

B*1554

(SEQ ID NO: 1277)

atgcgggtcacggcgccccgaaccgtcctcctgctgctctcgggAgccctggccctgaccgagacctgggccggctccca ctccatgaggtatttctacaccgccatgtcccggcccggccgcggggagccccgcttcatctcagtgggctacgtggacg acacGcagttcgtgaggttcgacagcgacgccgcgagtccgagagaggagccgcgggcgccgtggatagagcaggagggg ccggagtattgggaccgggaGacacagatctCcaagaccaacacacagactTaccgagagagcctgcggaacctgcgcgg ctactacaaccagagcgaggccgggtctcacaccctccagaggatgtacggctgcgacgtggggccggacgggcgcctcc tccgcgggcatgaccagtccgcctacgacggcaaggattacatcgccctgaacgaggacctgagctcctggaccgcggcg gacacggcggctcagatcacccagcgcaagtgggaggcggcccgtgaggcggagcagTggagagcctacctggagggcct gtgcgtggagtggctccgcagatacctggagaacgggaaggagacgctgcagcgcgcggacccccaaagacacatgtga cccaccacccatctctgaccatgaggccaccctgaggtgctgggccctgggcttctaccctgcggagatcacactgacc tggcagcggatggcgaggaccaaactcaggacacCgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccatccccatcgtgggcattgttgctggcctggctgtcccta...gca gttgtggtcatcggagctgtggtcgctactgtgatgtgtaggaggaagagCtcaggtgga -continued

B*1555

(SEQ ID NO: 1278)

atgcgggtcacggcgccccgaaccgtcctcctgctgctctcgggAgccctggccctgaccgagacctgggccggctccca ctccatgaggtatttctacaccgccatgtcccggcccggccgcggggagccccgcttcatcgcagtgggctacgtggacg acacccagttcgtgaggttcgacagcgacgccgcgagtccgaggatggcgcccgggcgccatggatagagcaggagggg ccggagtattgggaccggaacacacagatctccaagaccaacacacagacttaccgagagagcctgcggaacctgcgcgg ctactacaaccagagcgaggccgggtctcacaccctccagagcatgtacggctgcgacgtggggccggacgggcgcctcc tccgcgggtatgaccagtccgcctacgacggcaaggattacatcgccctgaacgaggacctgagctcctggaccgcggcg gacacgcggctcagatcacccagcgcaagtgggaggcggcccgtgTggcggagcagcTgagagcctacctggagggcct gtgcgtggagtggctccgcagatacctggagaacgggaaggagacgctgcagcgcgcggacccccccaaagacacatgtga cccaccaccccatctctgaccatgaggccaccctgaggtgctgggccctgggcttctaccctgcggagatcacactgacc tggcagcgggatggcgaggaccaaactcaggacacCgagcttgtggagaccagaccagcaggagatagaaccttccagaa gtgggcagctgtggtggtgccttctggagaagagcagagatacacatgccatgtacagcatgagggggctgccgaagcccc tcaccctgagatgggagccatcttcccagtccaccatccccatcgtgggcattgttgctggcctggctgtccta...gca gttgtggtcatcggagctgtggtcgctactgtgatgtgtaggaggaagagCtcaggtgga

B*1556

(SEQ ID NO: 1279)

gctcccactccatgaggtatttctacaccgccatgtcccggcccggccgcggggagccccgcttcatcgcagtgggctac gtggacgacacccagttcgtgaggttcgacagcgacgccgcgagtccgaggatggcgcccgggcgccatggatagagca ggaggggccggagtattgggaccgggaGacacagatctTcaagaccaacacacagactTaccgagagagcctgcggaacc tgcgcggctactacaaccagagcgaggccgggtctcacaccctccagagGatgtacggctgcgacgtggggccggacggg cgcctcctccgcgggcatgaccagtCcgcctacgacggcaaggattacatcgccctgaacgaggacctgagctcctggac cgcGgcggacacgcggctcagatcacccagcgcaagtgggaggcggcccgtgaggcggagcagTgagagcctacctgg agggccTgtgcgtggagtggctccgcagatacctggagaacgggaaggagacgctgcagcgcgcGg

B*1557

(SEQ ID NO: 1280)

gggtcacggcgccccgaaccgtcctcctgctgctctcgggagccctggccctgaccgagacctgggccggctcccactcc atgaggtatttctacaccgccatgtcccggcccggccgcggggagccccgcttcatcgcagtgggctacgtggacgacac ccagttcgtgaggttcgacagcgacgccgcgagtccgaggatggcgcccgggcgccatggatagagcaggaggggccgg agtattgggaccgggagacacagatctccaagaccaacacacagacttaccgagTgaAcctgcggaacctgcgcggctac tacaaccagagcgaggccgggtctcacaccctccagaggatgtacggctgcgacgtggggccggacgggcgcctcctccg cgggcatgaccagtccgcctacgacggcaaggattacatcgccctgaacgaggacctgagctcctggaccgcggcggaca cggcggctcagatcacccagcgcaagtgggaggcggcccgtgaggcggagcagtggagagcctacctggagggccTgtgc gtggagtggctccgcagatacctggagaacgggaaggagacgctgCagcgcgcGg

B*1558

(SEQ ID NO: 1281)

atgcgggtcacggcgccccgaaccgtcctcctgctgctctcgggAgccctggccctgaccgagacctgggccggctccca ctccatgaggtatttctacaccgccatgtcccggcccggccgcggggagccccgcttcatcgcagtgggctacgtggacg acacccagttcgtgaggttcgacagcgacgccgcgagtccgaggatggcgcccgggcgccatggatagagcaggagggg ccggagtattgggaccgggagacacagatctccaagaccaacacacagacttaccgagagagcctgcggaacctgcgcgg ctactacaaccagagcgaggccgggtctcacaccctccagaggatgtacggctgcgacgtggggccggacgggcgcctcc tccgcgggcataaccagtTcgcctacgacggcaaggattacatcgccctgaacgaggacctgagctcctggaccgcggcg gacacgcggctcagatcacccagcgcaagtgggaggcggcccgtgaggcggagcagTgagagcctacctggagggccT gtgcgtggagtggctccgcagatacctggagaacgggaaggagacgctgcagcgcgcGg

B*1560

(SEQ ID NO: 1282)
gctcccactccatgaggtatttctacaccgccatgtcccggcccggccgcggggagccccgcttcatcgcagtgggctac gtggacgacacccagttcgtgaggttcAacagcgacgccgcgagtccgaggatggcgccccgggcgccatggatagagca ggaggggccggagtattgggacggggagacacagatctccaagaccaacacacagacttaccgagagagcctgcggaacc tgcgcggctactacaaccagagcgaggccgggtctcacaccctcagaggatgtacggctgcgacgtggggccggacggg cgcctcctccgcgggcatgaccagtccgcctacgacggcaaggattacatcgccctgaacgaggacctgagctcctggac cgcggcggacacggcggctcagatcacccagcgcaagtgggaggcggcccgtgaggcggagcagtggagagcctacctgg agggcctgtgcgtggagtggctccgcagatacctggagaacgggaaggagacgctgcagcgcgcgg

B*1561

(SEQ ID NO: 1283)
gctcccactccatgaggtatttctacaccgccatgtcccggcccggccgcggggagccccgcttcatctcagtgggctac gtggacgacacGcagttcgtgaggttcgacagcgacgccgcgagtccgagagaggagccgcgggcgccgtggatagagca ggaggggccggagtattgggacgggaGacacagatctCcaagaccaacAcacagactgaccgagagagcctgcggaacc tgcgcggctactacaaccagagcgaggccgggtctcacaccctcagagGatgtacggctgcgacgtggggccggacggg cgcctcctccgcgggcatgaccagtCcgcctacgacggcaaggattacatcgccctgaacgaggacctgAgctcctggac cgcggcggacacggcggctcagatcacccagcgcaagtgggaggcggcccgtgaggcggagcagcTgagagcctacctgg agggccTgtgcgtggagtggctccgcagatacctggagaacgggaaggagacgctgcagcgcgcGg

B*1562

(SEQ ID NO: 1284)
gctcccactccatgaggtatttctacaccgccatgtcccggcccggccgcggggagccccgcttcatctcagtgggctac gtggacgacacGcagttcgtgaggttcgacagcgacgccgcgagtccgagagaggagccgcgggcgccgtggatagagca ggaggggccggagtattgggacgggaGacacagatctCcaagaccaacAcacagactTaccgagagagcctgcggaacc tgcgcggctactacaaccagagcgaggccgggtctcacatcAtccagaggatgtaTggctgcgacCtggggccCgacggg cgcctcctccgcgggcatgaccagtCcgcctacgacggcaaggattacatcgccctgaacgaggacctgAgctcctggac cgcGgcggacacggcggctcagatcacccagcgcaagtgggaggcggcccgtgaggcggagcagcTgagagcctacctgg agggccTgtgcgtggagtggctccgcagatacctggagaacgggaaggagacgctgCagcgcgcGg

B*1563

(SEQ ID NO: 1285)
gctcccactccatgaggtatttctacaccgccAtgtcccggcccggccgcggggagccccgcttcatcgcagtgggctac gtggacgacacccagttcgtgaggttcgacagcgacgccgcgagtccgaggatggcgccCgggcgccAtggatagagca ggaggggccggagtattgggacgggaGacacagatctCcaagaccaacacacagactTaccgagagagcctgcggaacc tgcgcggctactacaaccagagcgaggccgggtctcacaccctcagagGatgtacggctgcgacgtggggccggacggg cgcctcctccgcgggcatgaccagtacgcctacgacggcaaggattacatcgccctgaacgaggacctgagctcctggac cgcGgcggacacggcggctcagatcacccagcgcaagtgggaggcggcccgtgaggcggagcagTggagagcctacctgg agggccTgtgcgtggagtggctccgcagatacctggagaacgggaaggagacgctgcagcgcgcGg

B*1564

(SEQ ID NO: 1286)
gctcccactccatgaggtatttctacaccgccatgtcccggcccggccgcggggagccccgcttcatctcagtgggctac gtggacgacacGcagttcgtgaggttcgacagcgacgccgcgagtccgagagaggagccgcgggcgccgtggatagagca ggaggggccggagtattgggaccggaacacacagatctCcaagaccaacAcacagactTaccgagagagcctgcggaacc tgcgcggctactacaaccagagcgaggccgggtctcacaccctcagagGatgtacggctgcgacgtggggccggacggg cgcctcctccgcgggcatgaccagtCcgcctacgacggcaaggattacatcgccctgaacgaggacctgAgctcctggac cgcggcggacacggcggctcagatcacccagcgcaagtgggaggcggcccgtgaggcggagcagcTgagagcctacctgg agggccTgtgcgtggagtggctccgcagatacctggagaacgggaaggagacgctgcagcgcgcGg -continued

B*1565

(SEQ ID NO: 1287)

gctcccactccatgaggtatttctacaccgccAtgtcccggcccggccgcggggagccccgcttcatcGcagtgggctac gtggacgacacccagttcgtgaggttcgacagcgacgccgcgagtccgaggatggCgccccgggcgccatggatagagca ggaggggccggagtattgggacccgggaGacacagatctCcaagaccaacAcacagactTaccgagagagcctgcggaacc tgcgcggctactacaaccagagcgaggccgggtctcacaccctccagagGatgtacggctgcgacgtggggccggacggg cgcctcctccgcgggcatgaccagtCcgcctacgacggcaaggattacatcgccctgaacgaggacctgagctcctggac cgcGgcggacacggcggctcagatcacccagcgcaagtgggaggcggcccgtgaggcggagcagcggagagcctacctgg agggccTgtgcgtggagtggctccgcagatacctggagaacgggaaggagacgctgcagcgcgcGg

B*1566

(SEQ ID NO: 1288)

atgcgggtcacggcgccccgaaccgtcctcctgctgctctcgggAgccctggccctgaccgagacctgggccggctccca ctccatgaggtatttctacaccgccatgtcccggcccggccgcggggagccccgcttcatcgcagtgggctacgtggacg acacccagttcgtgaggttcgacagcgacgccgcgagtccgaggatggCgccccgggcgccatggatagagcaggagggg ccggagtattgggaccgggagacacagatctGcaagaccaacacacagactTaccgagagagcctgcggaacctgcgcgg ctactacaaccagagcgaggccgggtctcacaccctccagaggatgtacggctgcgacgtggggccggacgggcgcctcc tccgcgggcatgaccagtccgcctacgacggcaaggattacatcgccctgaacgaggacctgagctcctggaccgcggcg gacacggcggctcagatcacccagcgcaagtgggaggcggcccgtgaggcggagcagTggagagcctacctggagggcct gtgcgtggagtggctccgcagatacctggagaacgggaaggagacgctgcagcgcgcggaccccccaaagacacatgtga cccaccacccatctctgaccatgaggccacccctgaggtgctgggccctgggcttctaccctgcggagatcacactgacc tggcagcgggatggcgaggaccaaactcaggacacCgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccatccccatcgtgggcattgttgctggcctggctgtcccta...gca gttgtggtcatcggagctgtggtcgctactgtgatgtgtaggaggaagagCtcaggtgga

B*1567

(SEQ ID NO: 1289)

gctcccacttcatgaggtatttctacaccgccatgtcccggcccggccgcggggagccccgcttcatcgcagtgggctac gtggacgacacgcagttcgtgaggttcgacagcgacgccgcgagtccgaggatggcgccccgggcgccatggatagagca ggaggggccggagtattgggaccgggagacacggaacatgaaggcctccgcgcagacttaccgagagaacctgcggatcg cgctccgctactacaaccagagcgaggccgggtctcacacttggcagaggatgtatggctgcgacctggggccggacggg cgcctcctccgcgggcatgaccagtccgcctacgacggcaaggattacatcgccctgaacgaggacctgagctcctggac cgcggcggacacggcggctcagatcacccagcAcaagtgggaggcggcccgtgaggcggagcagctgagagcctacctgg agggcctgtgcgtggagtggctccgcagatacctggagaacgggaaggagacgctgcagcgcgcgg

B*1568

(SEQ ID NO: 1290)

gctcccactccatgaggtatttctacacctccgtgtcccggcccggccgcggggagccccgcttcatctcagtgggctac gtggacgacacccagttcgtgaggttcgacagcgacgccgcgagtccgagagaggagccgcgggcgccgtggatagagca ggaggggccggagtattgggacccgggaGacacagatctCcaagaccaacacacagactTaccgagagagcctgcggaacc tgcgcggctactacaaccagagcgaggccgggtctcacaccctccagagcatgtacggctgcgacgtggggccggacggg cgcctcctccgcgggcatgaccagtccgcctacgacggcaaggattacatcgccctgaacgaggacctgagctcctggac cgcggcggacacggcggctcagatcacccagcgcaagtgggaggcggcccgtgaggcggagcagTggagagcctacctgg agggcctgtgcgtggagtggctccgcagatacctggagaacgggaaggagacgctgcagcgcgcggaccccccaaagaca catgtgacccaccacccatctctgaccatgaggccacccctgaggtgctgggccctgggcttctaccctgcggagatcac actgacctggcagcgggatggcgaggaccaaactcaggacacCgagcttgtggagaccagaccagcaggagatagaacct

B*1569

(SEQ ID NO: 1291)

gctcccactccatgaggtatttctacaccgccatgtcccggcccggccgcggggagccccgcttcatctcagtgggctac
gtggacgacacgcagttcgtgaggttcgacagcgacgccgcgagtccgagagaggagccgcgggcgccgtggatagagca
ggaggggccggagtattgggaccgggagacacagatctCcaagaccaacacacagacttaccgagagagcctgcggaacc
tgcgcggctactacaaccagagcgaggccgggtctcacaccctccagaggatgtacggctgcgacgtggggccggacggg
cgcctcctccgcgggcatgaccagtCcgcctacgacggcaaggattacatcgccctgaacgaggacctgagctcctggac
cgcggcggacacggcggctcagatcacccagcgcaagtgggaggcggcccgtgaggcggagcagTgagaAcctacctgg
agggcaCgtgcgtggagtggctccgcagatacctggagaacgggaaggagacgctgcagcgcgcGg

B*1570

(SEQ ID NO: 1292)

gctcccactccatgaggtatttctacaccgccAtgtcccggcccggccgcggggagccccgcttcatcgcagtgggctac
gtggacgacacccagttcgtgaggttcgacagcgacgccgcgagtccgaggatggcgccCcgggcgccAtggatagagca
ggaggggccggagtattgggacccgggaGacacagatctCcaagaccaacAcacagactgaccgagagagcctgcggaacc
tgcgcggctactacaaccagagcgaggccgggtctcacaccctccagagGatgtacggctgcgacgtggggccggacggg
cgcctcctccgcgggcatgaccagtCcgcctacgacggcaaggattacatcgccctgaacgaggacctgagctcctggac
cgcGgcggacacggcggctcagatcacccagcgcaagtgggaggcggcccgtgaggcggagcagTggagagcctacctgg
agggccTgtgcgtggagtggctccgcagatacctggagaacgggaaggagacgctgcagcgcgcGg

B*1571

(SEQ ID NO: 1293)

gctcccactccatgaggtatttcCacacctccgtgtcccggcccggccgcggggagccccgcttcatcgcagtgggctac
gtggacgacacccagttcgtgaggttcgacagcgacgccgcgagtccgaggatggcgccccgggcgccAtggatagagca
ggaggggccggagtattgggacccgggaGacacagatctCcaagaccaacacacagactTaccgagagagcctgcggaacc
tgcgcggctactacaaccagagcgaggccgggtctcacaccctccagagGatgtacggctgcgacgtggggccggacggg
cgcctcctccgcgggcatgaccagtccgcctacgacggcaaggattacatcgccctgaacgaggacctgagctcctggac
cgcggcggacacggcggctcagatcacccagcgcaagtgggaggcggcccgtgaggcggagcagTggagagcctacctgg
agggcctgtgcgtggagtggctccgcagatacctggagaacgggaaggagacgctgcagcgcgcggacccccccaaagaca
catgtgacccaccaccccatctctgaccatgaggccaccctgaggtgctgggccctgggcttctaccctgcggagatcac
actgacctggcagcgggatggcgaggaccaaactcaggacacCgagcttgtggagaccagaccagcaggagatagaacct
tccagaagtgggcagctgtggtggtgccttctggagaagagcagagatacacatgccatgtacagcatgaggggctgccg
aagcccctcaccctgagatggg

B*1572

(SEQ ID NO: 1294)

gctcccactccatgaggtatttctacaccgccatgtcccggcccggccgcggggagccccgcttcatctcagtgggctac
gtggacgacacGcagttcgtgaggttcgacagcgacgccgcgagtccgagagaggagccgcgggcgccgtggatagagca
ggaggggccggagtattgggaccggaacacacagatctGcaagaccaacacacagacttaccgagagagcctgcggaacc
tgcgcggctactacaaccagagcgaggccgggtctcacaccctccagaggatgtacggctgcgacgtggggccggacggg
cgcctcctccgcgggcatgaccagtCcgcctacgacggcaaggattacatcgccctgaacgaggacctgcgctcctggac
cgcggcggacacggcggctcagatcacccagcgcaagtgggaggcggcccgtgaggcggagcagTgagagcctacctgg
agggccTgtgcgtggagtggctccgcagatacctggagaacgggaaggagacgctgcagcgcgcggacccccccaaagaca
caTgtgacccaccaccccatctctgaccatgaggccaccctgaggtgctgggccctgggcttctaccctgcggagatcac
actgacctggcagcgggatggcgaggaccaaactcaggacacCgagcttgtggagaccagaccagcaggagatagaacct -continued tccagaagtgggcagctgtggtggtgccttctggagaagagcagagatacacatgccatgtacagcatgaggggctgccg aagcccctcaccctgagatggg

B*1573

(SEQ ID NO: 1295)

gctcccactccatgaggtatttctacaccgccatgtcccggcccggccgcggggagccccgcttcatcgcagtgggctac gtggacgacacccagttcgtgaggttcgacagcgacgccgcgagtccgaggatggcgccccgggcgccatggatagagca ggaggggccggagtattgggaccgggagacacagatctccaagaccaacacacagacttaccgagagagcctgcggaacc tgcgcggctactacaaccagagcgaggccgggtctcacaccctccagaggatgtacggctgcgacgtggggccggacggg cgcctcctccgcgggcataaccagttAgcctacgacggcaaggattacatcgccctgaacgaggacctgagctcctggac cgcggcggacacggcggctcagatcacccagcgcaagtgggaggcggcccgtgaggcggagcagTggagagcctacctgg agggccTgtgcgtggagtggctccgcagatacctggagaacgggaaggagacgctgcagcgcgcGg

B*1574

(SEQ ID NO: 1296)

gctcccactccatgaggtatttctacaccgccatgtcccggcccggccgcggggagccccgcttcatctcagtgggctac gtggacgacacgcagttcgtgaggttcgacagcgacgccgcgagtccgagagaggagccgcgggcgccgtggatagagca ggaggggccggagtattgggaccgggagacacagatctccaagaTcaacacacagacttaccgagagagcctgcggaacc tgcgcggctactacaaccagagcgaggccgggtctcacaccctccagaggatgtacggctgcgacgtggggccggacggg cgcctcctccgcgggcatgaccagtccgcctacgacggcaaggattacatcgccctgaacgaggacctgagctcctggac cgcggcggacacggcggctcagatcacccagcgcaagtgggaggcggcccgtgaggcggagcagctgagagcctacctgg agggcctgtgcgtggagtggctccgcagatacctggagaacgggaaggagacgctgcagcgcgcgg

B*1575

(SEQ ID NO: 1297)

gctcccactccatgaggtatttctacaccgccatgtcccggcccggccgcggggagccccgcttcatcgcagtgggctac gtggacgacacccagttcgtgaggttcgacagcgacgccgcgagtccgaggatggcgccccgggcgccatggatagagca ggaggggccggagtattgggaccgggagacacagatctccaagaccaacacacagacttaccgagagagcctgcggaacc tgcgcggctactacaaccagagcgaggccgggtctcacaccctccagaggatgtacggctgcgacgtggggccggacggg cgcctcctccgcgggcatgaccagtccgcctacgacggcaaggattacatcgccctgaacgaggacctgagctcctggac cgcggcggacacggcggctcagatcacccagcgcaagtgggaggcggcccgtCaggcggagcagtggagagcctacctgg agggcctgtgcgtggagtggctccgcagatacctggagaacgggaaggagacgctgcagcgcgcgg

B*180101

(SEQ ID NO: 1298)

atgcgggtcacggcgccccgaaccctcctcctgctgctctgggggggcagtggccctgaccgagacctgggctggctccca ctccatgaggtatttccacacctccgtgtcccggcccggccgcggggagccccgcttcatctcagtgggctacgtggacg gcacccagttcgtgaggttcgacagcgacgccgcgagtccgaggacggagccccgggcgccgtggatagagcaAgagggg ccggagtattgggaccggaacacacagatctccaagaccaacacacagactTaccgagagagcctgcggaacctgcgcgg ctactacaaccagagcgaggccgggtctcacaccctccagagGatgtacggctgcgacgtggggccggacgggcgcctcc tccgcgggcatgaccagtccgcctacgacggcaaggattacatcgccctgaacgaggacctgagctcctggaccgcggcg gacaccgcggctcagatcacccagcgcaagtgggaggcggcccgtgtggcggagcagctgagagcctacctggagggcac gtgcgtggagtggctccgcagacacctggagaacgggaaggagacgctgcagcgcgcggaccccccaaagacacatgtga cccaccacccatctctgaccatgaggccaccctgaggtgctgggccctgggcttctaccctgcggagatcacactgacc tggcagcgggatggcgaggaccaaactcaggacaccgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccatccccatcgtgggcattgttgctggcctggctgtccta...gca gttgtggtcatcggagctgtggtcgctactgtgatgtgtaggaggaagagCtcaggtgga

B*180102

(SEQ ID NO: 1299)

gctcccactccatgaggtatttccacacctccgtgtcccggcccggccgcggggagccccgcttcatctcagtgggctac gtggacggcacccagttcgtgaggttcgacagcgacgccgcgagtccgaggacggagccccgggcgccgtggatagagca agaggggccggagtattgggaccggaacacacagatctccaagaccaacacacagacttacAgagagagcctgcggaacc tgcgcggctactacaaccagagcgaggccgggtctcacaccctccagaggatgtacggctgcgacgtggggccggacggg cgcctcctccgcgggcatgaccagtccgcctacgacggcaaggattacatcgccctgaacgaggacctgagctcctggac cgcggcggacaccgcggctcagatcacccagcgcaagtgggaggcggcccgtgtggcggagcagctgagagcctacctgg agggcacgtgcgtggagtggctccgcagacacctggagaacgggaaggagacgctgcagcgcgcgg

B*1802

(SEQ ID NO: 1300)

atgcgggtcacggcgccccgaaccctcctcctgctgctctgggggggcagtggccctgaccgagacctgggctggctccca ctccatgaggtatttccacacctccgtgtcccggcccggccgcggggagccccgcttcatctcagtgggctacgtggacg gcacccagttcgtgaggttcgacagcgacgccgcgagtccgaggacggagccccgggcgccgtggatagagcaAgagggg ccggagtattgggaccggaacacacagatctccaagaccaacacacagacttaccgagagagcctgcggaacctgcgcgg ctactacaaccagagcgaggccgggtctcacaccctccagaatatgtaTggctgcgacgtggggccggacgggcgcctcc tccgcgggcatgaccagtccgcctacgacggcaaggattacatcgccctgaacgaggacctgagctcctggaccgcggcg gacaccgcggctcagatcacccagcgcaagtgggaggcggcccgtgtggcggagcagctgagagcctacctggagggcac gtgcgtggagtggctccgcagacacctggagaacgggaaggagacgctgcagcgcgcggaccccccaaagacacatgtga cccaccaccccatctctgaccatgaggccacccctgaggtgctgggccctgggcttctaccctgcggagatcacactgacc tggcagcgggatggcgaggaccaaactcaggacaccgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccatccccatcgtgggcattgttgctggcctggctgtccta...gca gttgtggtcatcggagctgtggtcgctactgtgatgtgtaggaggaagagCtcaggtgga

B*1803

(SEQ ID NO: 1301)

atgcgggtcacggcgccccgaaccctcctcctgctgctctgggggggcagtggccctgaccgagacctgggctggctccca ctccatgaggtatttccacacctccgtgtcccggcccggccgcggggagccccgcttcatctcagtgggctacgtggacg gcacccagttcgtgaggttcgacagcgacgccgcgagtccgaggacggagccccgggcgccgtggatagagcaAgagggg ccggagtattgggaccggaacacacagatctccaagaccaacacacagactgaccgagagagcctgcggaacctgcgcgg ctactacaaccagagcgaggccgggtctcacaccctccagagGatgtacggctgcgacgtggggccggacgggcgcctcc tccgcgggcatgaccagtccgcctacgacggcaaggattacatcgccctgaacgaggacctgagctcctggaccgcggcg gacaccgcggctcagatcacccagcgcaagtgggaggcggcccgtgtggcggagcagctgagagcctacctggagggcac gtgcgtggagtggctccgcagacacctggagaacgggaaggagacgctgcagcgcgcggaccccccaaagacacatgtga cccaccaccccatctctgaccatgaggccacccctgaggtgctgggccctgggcttctaccctgcggagatcacactgacc tggcagcgggatggcgaggaccaaactcaggacaccgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccatccccatcgtgggcattgttgctggcctggctgtccta...gca gttgtggtcatcggagctgtggtcgctactgtgatgtgtaggaggaagagCtcaggtgga

B*1804

(SEQ ID NO: 1302)

gctcccactccatgaggtatttctacaccgccatgtcccggcccggccgcggggagccccgcttcattGcagtgggctac gtggacggcacccagttcgtgaggttcgacagcgacgccgcgagtccgaggacggagccccgggcgccgtggatagagca AgaggggccggagtattgggaccggaacacacagatctCcaagaccaacacacagactTaccgagagagcctgcggaacc -continued tgcgcggctactacaaccagagcgaggccgggtctcacaccctccagagGatgtacggctgcgacgtggggccggacggg cgcctcctccgcgggcatgaccagtccgcctacgacggcaaggattacatcgccctgaacgaggacctgagctcctggac cgcggcggacaccgcggctcagatcacccagcgcaagtgggaggcggcccgtgTggcggagcagcTgagagcctacctgg agggcacgtgcgtggagtggctccgcagaCacctggagaacgggaaggagacgctgcagcgcgcgg

B*1805

(SEQ ID NO: 1303)

gctcccactccatgaggtatttccacacctccgtgtcccggcccggccgcggggagccccgcttcatctcagtgggctac gtggacggcacccagttcgtgaggttcgacagcgacgccgcgagtccgaggacggagccccgggcgccgtggatagagca agaggggccggagtattgggaccggaacacacagatctccaagaccaacacacagacttaccgagagagcctgcggaacc tgcgcggctactacaaccagagcgaggccgggtctcacaccctccagaggatgtacggctgcgacgtggggccggacggg cgcctcctccgcgggcatgaccagtccgcctacgacggcaaggattacatcgccctgaaGgaggacctgagctcctggac cgcggcggacaccgcggctcagatcacccagcgcaagtgggaggcggcccgtgtggcggagcagctgagagcctacctgg agggcacgtgcgtggagtggctccgcagacacctggagaacgggaaggagacgctgcagcgcgcgg

B*1806

(SEQ ID NO: 1304)

atgcgggtcacggcgccccgaaccctcctcctgctgctctggggggcagtggccctgaccgagacctgggctggctccca ctccatgaggtatttccacacctccgtgtcccggcccggccgcggggagccccgcttcatctcagtgggctacgtggacg gcacccagttcgtgaggttcgacagcgacgccgcgagtccgaggacggagccccgggcgccgtggatagagcaagagggg ccggagtattgggaccggaacacacagatctccaagaccaacacacagacttaccgagTgagcctgcggaacctgcgcgg ctactacaaccagagcgaggccgggtctcacaccctccagaggatgtacggctgcgacgtggggccggacgggcgcctcc tccgcgggcatgaccagtccgcctacgacggcaaggattacatcgccctgaacgaggacctgagctcctggaccgcggcg gacaccgcggctcagatcacccagcgcaagtgggaggcggcccgtgtggcggagcagctgagagcctacctggagggcac gtgcgtggagtggctccgcagaCacctggagaacgggaaggagacgctgcagcgcgcggaccccccaaagacacatgtga cccaccaccccatctctgaccatgaggccaccctgaggtgctgggccctgggcttctaccctgcggagatcacactgacc tggcagcgggatggcgaggaccaaactcaggacaccgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccatccccatcgtgggcattgttgctggcctggctgtccta...gca gttgtggtcatcggagctgtggtcgctActgtgatgtgtaggaggaagagCtcaggtgga

B*1807

(SEQ ID NO: 1305)

gctcccactccatgaggtatttccacacctccgtgtcccggcccggccgcggggagccccgcttcatctcagtgggctac gtggacggcacccagttcgtgaggttcgacagcgacgccgcgagtccgaggacggagccccgggcgccgtggatagagca AgaggggccggagtattgggaccggaacacacagatctTcaagaccaacacacagactTaccgagagagcctgcggaacc tgcgcggctactacaaccagagcgaggccgggtctcacaccctccagagGatgtacggctgcgacgtggggccggacggg cgcctcctccgcgggcatgaccagtccgcctacgacggcaaggattacatcgccctgaacgaggacctgagctcctggac cgcggcggacaccgcggctcagatcacccagcgcaagtgggaggcggcccgtgTggcggagcagcTgagagcctacctgg agggcacgtgcgtggagtggctccgcagaCacctggagaacgggaaggagacgctgcagcgcgcgg

B*1808

(SEQ ID NO: 1306)

gctcccactccatgaggtatttccacacctccgtgtcccggcccggccgcggggagccccgcttcatctcagtgggctac gtggacggcacccagttcgtgaggttcgacagcgacgccgcgagtccgaggacggagccccgggcgccgtggatagagca agaggggccggagtattgggaccggaacacacagatctccaagaccaacacacagacttaccgagagagcctgcggaacc tgcgcggctactacaaccagagcgaggccgggtctcacaccctccagaggatgtGcggctgcgacgtggggccggacggg cgcctcctccgcgggcatgaccagtccgcctacgacggcaaggattacatcgccctgaacgaggacctgagctcctggac -continued cgcggcggacaccgcggctcagatcacccagcgcaagtgggaggcggcccgtgtggcggagcagctgagagcctacctgg agggcacgtgcgtggagtggctccgcagacacctggagaacgggaaggagacgctgcagcgcgcgg B*1809
(SEQ ID NO: 1307)
gctcccactccatgaggtatttccacacctccgtgtcccggcccggccgcggggagccccgcttcatctcagtgggctac gtggacggcacccagttcgtgaggttcgacagcgacgccgcgagtccgaggacggagccccgggcgccgtggatagagca Agaggggccggagtattgggaccggaacacacagatctccaagaccaacacacagacttaccgagagaacctgcgcaccg cgctcCgctactacaaccagagcgaggccgggtctcacaccctccagagGatgtacggctgcgacgtggggccggacggg cgcctcctccgcgggcatgaccagtccgcctacgacggcaaggattacatcgccctgaacgaggacctgagctcctggac cgcggcggacaccgcggctcagatcacccagcgcaagtgggaggcggcccgtgTggcggagcagcTgagagcctacctgg agggcacgtgcgtggagtggctccgcagaCacctggagaacgggaaggagacgctgcagcgcgcgg B*1810
(SEQ ID NO: 1308)
gctcccactccatgaggtatttcCacacctccgtgtcccggcccggccgcggggagccccgcttcatctcagtgggctac gtggacggcacccagttcgtgaggttcgacagcgacgccgcgagtccgaggacggagccccgggcgccgtggatagagca AgaggggccggagtattgggaccggaacacacagatctCcaagaccaacacacagactTaccgagagagcctgcggaacc tgcgcggctactacaaccagagcgaggccgggtctcacaccctccagagGatgtacggctgcgacgtggggccggacggg cgcctcctccgcgggcatgaccagtccgcctacgacggcaaggattacatcgccctgaacgaggacctgagctcctggac cgcggcggacaccgcggctcagatcacccagcgcaagtgggaggcggcccgtgTggcggagcagcTgagagcctacctgg agggcgagtgcgtggagtggctccgcagatacctggagaacgggaaggagacgctgcagcgcgcgg B*1811
(SEQ ID NO: 1309)
gctcccactccatgaggtatttcCacacctccgtgtcccggcccggccgcggggagccccgcttcatctcagtgggctac gtggacggcacccagttcgtgaggttcgacagcgacgccgcgagtccgaggacggagccccgggcgccgtggatagagca AgaggggccggagtattgggaccggaacacacagatctCcaagaccaacacacagactTaccgagagagcctgcggaacc tgcgcggctactacaaccagagcgaggccgggtctcacaccctccagagGatgtacggctgcgacgtggggccggacggg cgcctcctccgcgggcatgaccagtccgcctacgacggcaaggattacatcgccctgaacgaggacctgagctcctggac cgcggcggacaccgcggctcagatcacccagcgcaagtgggaggcggcccgtgTggcggagcagcTgagagcctacctgg agggcaCgtgcgtggagtggctccgcagatacctggagaacgggaaggagacgctgcagcgcgcgg B*1812
(SEQ ID NO: 1310)
gctcccactccatgaggtatttccacacctccgtgtcccggcccggccgcggggagccccgcttcatctcagtgggctac gtggacggcacccagttcgtgaggttcgacagcgacgccgcgagtccgaggacggagccccgggcgccgtggatagagca AgaggggccggagtattgggaccgggaGacacagatctCcaagaccaacacacagactTaccgagagagcctgcggaacc tgcgcggctactacaaccagagcgaggccgggtctcacaccctccagagGatgtacggctgcgacgtggggccggacggg cgcctcctccgcgggcatgaccagtccgcctacgacggcaaggattacatcgccctgaacgaggacctgagctcctggac cgcggcggacaccgcggctcagatcacccagcgcaagtgggaggcggcccgtgTggcggagcagcTgagagcctacctgg agggcacgtgcgtggagtggctccgcagaCacctggagaacgggaaggagacgctgcagcgcgcgg B*1813
(SEQ ID NO: 1311)
gctcccactccatgaggtatttcCacacctccgtgtcccggcccggccgcggggagccccgcttcatctcagtgggctac gtggacggcacccagttcgtgaggttcgacagcgacgccgcgagtccgaggacggagccccgggcgccgtggatagagca AgaggggccggagtattgggaccggaacacacagatctCcaagaccaacacacagactTaccgagagagcctgcggaacc tgcgcggctactacaaccagagcgaggccgggtctcacaccctccagagGatgtacggctgcgacgtggggccggacggg cgcctcctccgcgggcatgaccagtccgcctacgacggcaaggattacatcgccctgaacgaggacctgagctcctggac -continued cgcggcggacaccgcggctcagatcacccagcgcaagtgggaggcggcccgtgTggcggagcagcggagagcctacctgg agggcacgtgcgtggagtggctccgcagaCacctggagaacgggaaggagacgctgcagcgcgcgg B*1814 (SEQ ID NO: 1312)
gctcccactccatgaggtatttcCacacctccgtgtcccggcccggccgcggggagccccgcttcatctcagtgggctac gtggacggcacccagttcgtgaggttcgacagcgacgccgcgagtccgaggacggagccccgggcgccgtggatagagca AgaggggccggagtattgggaccggaacacacagatctCcaagaccaacacacagactTaccgagagagcctgcggaacc tgcgcggctactacaaccagagcgaggccgggtctcacaccctccagagcatgtacggctgcgacgtggggccggacggg cgcctcctccgcgggcatgaccagtccgcctacgacggcaaggattacatcgccctgaacgaggacctgagctcctggac cgcggcggacaccgcggctcagatcacccagcgcaagtgggaggcggcccgtgTggcggagcagcTgagagcctacctgg agggcacgtgcgtggagtggctccgcagaCacctggagaacgggaaggagacgctgcagcgcgcgg B*1815 (SEQ ID NO: 1313)
gctcccactccatgaggtatttcCacacctccgtgtcccggcccggccgcggggagccccgcttcatctcagtgggctac gtggacggcacccagttcgtgaggttcgacagcgacgccgcgagtccgaggacggagccccgggcgccgtggatagagca AgaggggccggagtattgggaccggaacacacagatctCcaagaccaacacacagactTaccgagagagcctgcggaacc tgcgcggctactacaaccagagcgaggccgggtctcacaccctccagagGatgtacggctgcgacgtggggccggacggg cgcctcctccgcgggcatgaccagtccgcctacgacggcaaggattacatcgccctgaacgaggacctgagctcctggac cgcggcggacaccgcggctcagatcacccagcgcaagtgggaggcggcccgtgaggcggagcagcTgagagcctacctgg agggcacgtgcgtggagtggctccgcagaCacctggagaacgggaaggagacgctgcagcgcgcgg B*1818 (SEQ ID NO: 1314)
gctcccactccatgaggtatttccacacctccgtgtcccggcccggccgcggggagccccgcttcatctcagtgggctac gtggacggcacccagttcgtgaggttcgacagcgacgccgcgagtccgaggacggagccccgggcgccgtggatagagca agaggggccggagtattgggaccggaacacacagatctccaagaccaacacacagacttaccgagagagcctgcggaacc tgcgcggctactacaaccagagcgaggccgggtctcacaccctccagaggatgtCtggctgcgacgtggggccggacggg cgcctcctccgcgggcatgaccagtccgcctacgacggcaaggattacatcgccctgaacgaggacctgagctcctggac cgcggcggacaccgcggctcagatcacccagcgcaagtgggaggcggcccgtgtggcggagcagcTgagagcctacctgg agggcacgtgcgtggagtggctccgcagaCacctggagaacgggaaggagacgctgcagcgcgcgg B*2701 (SEQ ID NO: 1315)
gctcccactccatgaggtatttccacacctccgtgtcccggcccggccgcggggagccccgcttcatcaccgtgggctac gtggacgacacgctgttcgtgaggttcgacagcgacgccgcgagtccgagagaggagccgcgggcgccgtggatagagca ggaggggccggagtattgggaccgggagacacagatctGcaaggccaaggcacagacttaccgagagaacctgcgcaCcg CgctcCgctactacaaccagagcgaggccgggtctcacaccctccagaaTatgtatggctgcgacgtggggccggacggg cgcctcctccgcgggtaccaccagGacgcctacgacggcaaggattacatcgccctgaacgaggacctgagctcctggac cgccgcggacacggcggctcagatcacccagcgcaagtgggaggcggcccgtgTggcggagcagcTgagagcctacctgg agggcgagtgcgtggagtggctccgcagatacctggagaacgggaaggagacgctgcagcgcgcGg B*2702 (SEQ ID NO: 1316)
atgcgggtcacggcgccccgaaccctcctcctgctgctctgggggcagtggcccctgaccgagacctgggctggctccca ctccatgaggtatttccacacctccgtgtcccggcccggccgcggggagccccgcttcatcaccgtgggctacgtggacg acacgctgttcgtgaggttcgacagcgacgccgcgagtccgagagaggagccgcgggcgccgtggatagagcaggagggg ccggagtattgggaccgggagacacagatctgcaaggccaaggcacagactgaccgagagaacctgcggatcGcgctcCg ctactacaaccagagcgaggccgggtctcacaccctccagaaTatgtatggctgcgacgtggggccggacggggcgcctcc tccgcgggtaccaccagGacgcctacgacggcaaggattacatcgccctgaacgaggacctgagctcctggaccgccgcg -continued gacacggcggctcagatcacccagcgcaagtgggaggcggcccgtGtggcggagcagctgagagcctacctggagggcga gtgcgtggagtggctccgcagatacctggagaacgggaaggagacgctgcagcgcgcggaccccccaaagacacacgtga cccaccaccccatctctgaccatgaggccaccctgaggtgctgggccctgggcttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccgtcttcccagtccaccgtccccatcgtgggcattgttgctggcctggctgtccta...gca gttgtggtcatcggagctgtggtcgctgctgtgatgtgtaggaggaagagCtcaggtgga

B*2703 (SEQ ID NO: 1317)

atgcgggtcacggcgccccgaacccctcctcctgctgctctgggggcagtggccctgaccgagacctgggctggctccca ctccatgaggtatttccacacctccgtgtcccggcccggccgcggggagccccgcttcatcaccgtgggctacgtggacg acacgctgttcgtgaggttcgacagcgacgccgcgagtccgagagaggagccgcgggcgccgtggatagagcaggagggg ccggagCattgggaccgggagacacagatctgcaaggccaaggcacagactgaccgagaggacctgcggaccctgctccg ctactacaaccagagcgaggccgggtctcacaccctccagaatatgtatggctgcgacgtggggccggacgggcgcctcc tccgcgggtaccaccaggacgcctacgacggcaaggattacatcgccctgaacgaggacctgagctcctggaccgccgcg gacacggcggctcagatcacccagcgcaagtgggaggcggcccgtgtggcggagcagctgagagcctacctggagggcga gtgcgtggagtggctccgcagatacctggagaacgggaaggagacgctgcagcgcgcggaccccccaaagacacacgtga cccaccaccccatctctgaccatgaggccaccctgaggtgctgggccctgggcttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccgtcttcccagtccaccgtccccatcgtgggcattgttgctggcctggctgtccta...gca gttgtggtcatcggagctgtggtcgctgctgtgatgtgtaggaggaagagctcaggtgga

B*2704 (SEQ ID NO: 1318)

atgcgggtcacggcgccccgaacccctcctcctgctgctctgggggcagtggccctgaccgagacctgggctggctccca ctccatgaggtatttccacacctccgtgtcccggcccggccgcggggagccccgcttcatcaccgtgggctacgtggacg acacgctgttcgtgaggttcgacagcgacgccgcgagtccgagagaggagccgcgggcgccgtggatagagcaggagggg ccggagtattgggaccgggagacacagatctgcaaggccaaggcacagactgaccgagagagcctgcggaccctgctccg ctactacaaccagagcgaggccgggtctcacaccctccagaatatgtatggctgcgacgtggggccggacgggcgcctcc tccgcgggtaccaccagGacgcctacgacggcaaggattacatcgccctgaacgaggacctgagctcctggaccgccgcg gacacggcggctcagatcacccagcgcaagtgggaggcggcccgtgaggcggagcagctgagagcctacctggagggcga gtgcgtggagtggctccgcagatacctggagaacgggaaggagacgctgcagcgcgcggaccccccaaagacacacgtga cccaccaccccatctctgaccatgaggccaccctgaggtgctgggccctgggcttctaccctgGggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccgtcttcccagtccaccgtccccatcgtgggcattgttgctggcctggctgtccta...gca gttgtggtcatcggagctgtggtcgctgctgtgatgtgtaggaggaagagctcaggtgga

B*270502 (SEQ ID NO: 1319)

atgcgggtcacggcgccccgaacccctcctcctgctgctctgggggcagtggccctgaccgagacctgggctggctccca ctccatgaggtatttccacacctccgtgtcccggcccggccgcggggagccccgcttcatcaccgtgggctacgtggacg acacgctgttcgtgaggttcgacagcgacgccgcgagtccgagagaggagccgcgggcgccgtggatagagcaggagggg ccggagtattgggaccgggagacacagatctgCaaggccaaggcacagactgaccgagagGacctgcggaccctgctccg -continued ctactacaaccagagcgaggccgggtctcacaccctccagaaTatgtatggctgcgacgtggggccggacgggcgcctcc tccgcgggtaccaccagGacgcctacgacggcaaggattacatcgccctgaacgaggacctgAgctcctggaccgccgcg gacacggcggctcagatcacccagcgcaagtgggaggcggcccgtgtggcggagcagcTgagagcctacctggagggcga gtgcgtggagtggctccgcagatacctggagaacgggaaggagacgctgcagcgcgcggaccccccaaagacacacgtga cccaccaccccatctctgaccatgaggccaccctgaggtgctgggccctgggcttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccgtcttcccagtccaccgtccccatcgtgggcattgttgctggcctggctgtccta...gca gttgtggtcatcggagctgtggtcgctgctgtgatgtgtaggaggaagagCtcaggtgga B*270503
(SEQ ID NO: 1320)
gctacgtggacgacacgctgttcgtgaggttcgacagcgacgccgcgagtccgagagaggagccgcgggcgccgtggata gagcaggaggggccggagtattgggaccgggagacacagatctgcaaggccaaggcacagactgaccgagaggacctgcg gacccctgctccgctactacaaccagagcgaggccgggtctcacaccctccagaatatgtatggctgcgacgtggggccgg acgggcgcctcctccgcgggtaccaccaggacgcctacgacggcaaggattacatcgccctgaacgaggacctgagctcc tggaccgccgcggacacggcAgctcagatcacccagcgcaagtgggaggcggcccgtgtggcggagcagctgagagccta cctggagggcgagtgcgtggagtggct B*270504
(SEQ ID NO: 1321)
atgcgggtcacggcgccccgaaccctcctcctgctgctctgggggggcaGtggccctgaccgagacctgggccggctccca ctccatgaggtatttccacacctccgtgtcccggcccggccgcggggagccccgcttcatcaccgtgggctacgtggacg acacgctgttcgtgaggttcgacagcgacgccgcgagtccgagagaggagccgcgggcgccgtggatagagcaggagggg ccggagtattgggaccgggagacacagatctGcaaggccaaggcacagactgaccgagagGacctgcggaccctgctccg ctactacaaccagagcgaggccgggtctcacaccctccagaaTatgtaTggctgcgacgtggggccggacgggcgcctcc tccgcgggtaccaccagGacgcctacgacggcaaggattacatcgccctgaacgaggacctgAgctcctggaccgccgcg gacacggcggctcagatcacccagcgcaagtgggaggcggcccgtgTggcggagcagcTgagagcctacctggagggcga gtgcgtggagtggctccgcagatacctggagaacgggaaggagacgctgcagcgcgcGg B*270505
(SEQ ID NO: 1322)
atgcgggtcacggcgccccgaaccctcctcctgctgctctgggggcagtggccctgaccgagacctgggctggctccca ctccatgaggtatttccacacctccgtgtcccggcccggccgcggggagccccgcttcatcaccgtgggctacgtggacg acacgctgttcgtgaggttcgacagcgacgccgcgagtccgagagaggagccgcgggcgccgtggatagagcaggagggg ccggagtattgggaccgggagacacagatctgcaaggccaaggcacagactgaccgagaggacctgcggaccctgctccg ctactacaaccagagcgaggccggTtctcacaccctccagaatatgtatggctgcgacgtggggccggacgggcgcctcc tccgcgggtaccaccaggacgcctacgacggcaaggattacatcgccctgaacgaggacctgagctcctggaccgccgcg gacacggcggctcagatcacccagcgcaagtgggaggcggcccgtgtggcggagcagctgagagcctacctggagggcga gtgcgtggagtggctccgcagatacctggagaacgggaaggagacgctgcagcgcgcggaccccccaaagacacacgtga cccaccaccccatctctgaccatgaggccaccctgaggtgctgggccctgggcttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatggg B*270506
(SEQ ID NO: 1323)
gctcccactccatgaggtatttccacacctccgtgtcccggccTggccgcggggagccccgcttcatcaccgtgggctac gtggacgacacgctgttcgtgaggttcgacagcgacgccgcgagtccgagagaggagccgcgggcgccgtggatagagca -continued ggaggggccggagtattgggaccgggagacacagatctgcaaggccaaggcacagactgaccgagaggacctgcggaccc tgctccgctactacaaccagagcgaggccgggtctcacaccctccagaatatgtatggctgcgacgtggggccggacggg cgcctcctccgcgggtaccaccaggacgcctacgacggcaaggattacatcgccctgaacgaggacctgAgctcctggac cgccgcggacacggcggctcagatcacccagcgcaagtgggaggcggcccgtgtggcggagcagctgagagcctacctgg agggcgagtgcgtggagtggctccgcagatacctggagaacgggaaggagacgctgcagcgcgcgcgg

B*2706 (SEQ ID NO: 1324)

atgcgggtcacggcgccccgaaccctcctcctgctgctctgggggcagtggccctgaccgagacctgggctggctccca ctccatgaggtatttccacacctccgtgtcccggcccggccgcggggagcccgcttcatcaccgtgggctacgtggacg acacgctgttcgtgaggttcgacagcgacgccgcgagtccgagagaggagccgcgggcgccgtggatagagcaggaggg ccggagtattgggaccgggagacacagatctgcaaggccaaggcacagactgaccgagagagcctgcggaccctgctccg ctactacaaccagagcgaggccgggtctcacaccctccagaatatgtatggctgcgacgtggggccggacgggcgcctcc tccgcgggtatgaccagtacgcctacgacggcaaggattacatcgccctgaacgaggacctgagctcctggaccgccgcg gacacggcggctcagatcacccagcgcaagtgggaggcggcccgtgaggcggagcagctgagagcctacctggagggcga gtgcgtggagtggctccgcagatacctggagaacgggaaggagacgctgcagcgcgcggaccccccaaagacacacgtga cccaccaccccatctctgaccatgaggccaccctgaggtgctgggccctgggcttctaccctgGggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccgtcttcccagtccaccgtccccatcgtgggcattgttgctggcctggctgtccta...gca gttgtggtcatcggagctgtggtcgctgctgtgatgtgtaggaggaagagctcaggtgga

B*2707 (SEQ ID NO: 1325)

ggctcccactccatgaggtatttccacacctccgtgtcccggcccggccgcggggagcccgcttcatcaccgtgggcta cgtggacgacacgctgttcgtgaggttcgacagcgacgccgcgagtccgagagaggagccgcgggcgccgtggatagagc aggaggggccggagtattgggaccgggagacacagatctgcaaggccaaggcacagactgaccgagagGacctgcggacc ctgctcCgctactacaaccagagcgaggccgggtctcacaccctccagagcatgtacggctgcgacgtggggccggacgg gcgcctcctccgcgggcatAaccagtacgcctacgacggcaaggattacatcgccctgaacgaggacctgcgctcctgga ccgccgcggacacggcggctcagatcacccagcgcaagtgggaggcggcccgtgtggcggagcagcTgagagcctacctg gagggcgagtgcgtggagtggctccgcagatacctggagaacgggaaggagacgctgcagcgcgcggaccccccaaagac acacgtgacccaccaccccatctctgaccatgaggccaccctgaggtgctgggccctgggcttctaccctgcggagatca cactgacctggcagcgggatggcgaggaccaaactcaggacactgagcttgtggagaccagaccagcaggagatagaacc ttccagaagtgggcagctgtggtggtgccttctggagaagagcagagatacacatgccatgtacagcatgagggctgcc gaagcccctcaccctgagatgggagccgtcttcccagtccaccgtccccatcgtgggcattgttgctggcctggctgtcc ta...gcagttgtggtcatcggagctgtggtcgctgctgtgatgtgtaggaggaagagCtcaggtgga

B*2708 (SEQ ID NO: 1326)

atgcgggtcacggcgccccgaaccctcctcctgctgctctgggggcagtggccctgaccgagacctgggctggctccca ctccatgaggtatttccacacctccgtgtcccggcccggccgcggggagcccgcttcatcaccgtgggctacgtggacg acacgctgttcgtgaggttcgacagcgacgccgcgagtccgagagaggagccgcgggcgccgtggatagagcaggaggg ccggagtattgggaccgggagacacagatctGcaaggccaaggcacagactgaccgagagagcctgcggaacctgcgcgg ctactacaaccagagcgaggccgggtctcacaccctccagaaTatgtatggctgcgacgtggggccggacgggcgcctcc tccgcgggtaccaccagGacgcctacgacggcaaggattacatcgccctgaacgaggacctgagctcctggaccgccgcg gacacggcggctcagatcacccagcgcaagtgggaggcggcccgtgTggcggagcagctgagagcctacctggagggcga -continued gtgcgtggagtggctccgcagatacctggagaacgggaaggagacgctgcagcgcgcggaccccccaaagacacacgtga cccaccacccatctctgaccatgaggccaccctgaggtgctgggccctgggcttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccgtcttcccagtccaccgtccccatcgtgggcattgttgctggcctggctgtccta...gca gttgtggtcatcggagctgtggtcgctgctgtgatgtgtaggaggaagagCtcaggtgga

B*2709

(SEQ ID NO: 1327)

atgcgggtcacggcgccccgaaccctcctcctgctgctctgggggggcagtggccctgaccgagacctgggctggctccca ctccatgaggtatttccacacctccgtgtcccggcccggccgcggggagccccgcttcatcaccgtgggctacgtggacg acacgctgttcgtgaggttcgacagcgacgccgcgagtccgagagaggagccgcgggcgccgtggatagagcaggagggg ccggagtattgggaccgggagacacagatctgcaaggccaaggcacagactgaccgagaggacctgcggaccctgctccg ctactacaaccagagcgaggccgggtctcacaccctccagaatatgtatggctgcgacgtggggccggacgggcgcctcc tccgcgggtaccaccagCacgcctacgacggcaaggattacatcgccctgaacgaggacctgagctcctggaccgccgcg gacacggcggctcagatcacccagcgcaagtgggaggcggcccgtgtggcggagcagctgagagcctacctggagggcga gtgcgtggagtggctccgcagatacctggagaacgggaaggagacgctgcagcgcgcggaccccccaaagacacacgtga cccaccacccatctctgaccatgaggccaccctgaggtgctgggccctgggcttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccgtcttcccagtccaccgtccccatcgtgggcattgttgctggcctggctgtccta...gca gttgtggtcatcggagctgtggtcgctgctgtgatgtgtaggaggaagagctcaggtgga

B*2710

(SEQ ID NO: 1328)

gctcccactccatgaggtatttccacacctccgtgtcccggcccggccgcggggagccccgcttcatcaccgtgggctac gtggacgacacgctgttcgtgaggttcgacagcgacgccgcgagtccgagagaggagccgcgggcgccgtggatagagca ggaggggccggagtattgggaccgggagacacagatctGcaaggccaaggcacagactgaccgagagGacctgcggaccc tgctccgctactacaaccagagcgaggccgggtctcacaccctccagaaTatgtaTggctgcgacgtggggccggacggg cgcctcctccgcgggtaccaccagDacgcctacgacggcaaggattacatcgccctgaacgaggacctgAgctcctggac cgccgcggacacggcggctcagatcacccagcgcaagtgggaggcggcccgtgaggcggagcagcTgagagcctacctgg agggcgagtgcgtggagtggctccgcagatacctggagaacgggaaggagacgctgcagcgcgcGg

B*2711

(SEQ ID NO: 1329)

atgcgggtcacggcgccccgaaccctcctcctgctgctctgggggggcagtggccctgaccgagacctgggcTggctccca ctccatgaggtatttccacacctccgtgtcccggcccggccgcggggagccccgcttcatcaccgtgggctacgtggacg acacgctgttcgtgaggttcgacagcgacgccgcgagtccgagagaggagccgcgggcgccgtggatagagcaggagggg ccggagtattgggaccgggagacacagatctgcaaggccaaggcacagactgaccgagagagcctgcggaccctgctcCg ctactacaaccagagcgaggccgggtctcacaccctccagagcatgtacggctgcgacgtggggccggacgggcgcctcc tccgcgggcatAaccagtacgcctacgacggcaaggattacatcgccctgaacgaggacctgcgctcctggaccgccgcg gacacggcggctcagatcacccagcgcaagtgggaggcggcccgtgTggcggagcagcTgagagcctacctggagggcga gtgcgtggagtggctccgcagatacctggagaacgggaaggagacgctgcagcgcgcggaccccccaaagacacacgtga cccaccacccatctctgaccatgaggccaccctgaggtgctgggccctgggcttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc -continued tcaccctgagatgggagccgtcttcccagtccaccgtccccatcgtgggcattgttgctggcctggctgtccta...gca gttgtggtcatcggagctgtggtcgctgctgtgatgtgtaggaggaagagCtcaggtgga

B*2712

(SEQ ID NO: 1330)

atgcgggtcacggcgccccgaaccctcctcctgctgctctgggggcagtggccctgaccgagacctgggctggctccca ctccatgaggtatttccacacctccgtgtcccggcccggccgcggggagccccgcttcatcaccgtgggctacgtggacg acacgctgttcgtgaggttcgacagcgacgccgcgagtccgagagaggagccgcgggcgccgtggatagagcaggagggg ccggagtattgggaccgggagacacagatctGcaagaccaacAcacagactgaccgagagagcctgcggaacctgcgcgg ctactacaaccagagcgaggccgggtctcacaccctccagaaTatgtatggctgcgacgtggggccggacgggcgcctcc tccgcgggtaccaccagGacgcctacgacggcaaggattacatcgccctgaacgaggacctgagctcctggaccgccgcg gacacggcggctcagatcacccagcgcaagtgggaggcggcccgtgTggcggagcagctgagagcctacctggagggcga gtgcgtggagtggctccgcagataCctggagaacgggaaggagacgctgcagcgcgcggaccccccaaagacacacgtga cccaccacccatctctgaccatgaggccaccctgaggtgctgggccctgggcttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccgtcttcccagtccaccgtccccatcgtgggcattgttgctggcctggctgtccta...gca gttgtggtcatcggagctgtggtcgctgctgtgatgtgtaggaggaagagCtcaggtgga

B*2713

(SEQ ID NO: 1331)

atgcgggtcacggagccccgaaccctcctcctgctgctctgggggcagtggccctgaccgagacctgggctggctccca ctccatgaggtatttccacacctccgtgtcccggcccggccgcggggagccccgcttcatcaccgtgggctacgtggacg acacgctgttcgtgaggttcgacagcgacgccgcgagtccgagagaggagccgcgggcgccgtggatagagcaggagggg ccggagtattgggaccgggagacacagatctGcaaggccaaggcacagactgaccgagagGacctgcggaccctgctccg ctactacaaccagagcgaggccgggtctcacaccctccagaaTatgtatggctgcgacgtggggccggacgggcgcctcc tccgcgggtaccaccagGacgcctacgacggcaaggattacatcgccctgaacgaggacctgAgctcctggaccgccgcg gacacggcggctcagatcacccagcgcaagtgggaggcggcccgtgtggcggagcagcTgagagcctacctggagggcga gtgcgtggagtggctccgcagataCctggagaacgggaaggagacgctgcagcgcgcggaccccccaaagacacacgtga cccaccacccatctctgaccatgaggccaccctgaggtgctgggccctgggcttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccgtcttcccagtccaccgtccccatcgtgggcattgttgctggcctggctgtccta...gca gttgtggtcatcggagctgtggtcgctgctgtgatgtgtaggaggaagagCtcaggtgga

B*2714

(SEQ ID NO: 1332)

atgcgggtcacggcgccccgaaccctcctcctgctgctctgggggcagtggccctgaccgagacctgggctggctccca ctccatgaggtatttccacacctccgtgtcccggcccggccgcggggagccccgcttcatcaccgtgggctacgtggacg acacgctgttcgtgaggttcgacagcgacgccgcgagtccgagagaggagccgcgggcgccgtggatagagcaggagggg ccggagtattgggaccgggagacacagatctgcaaggccaaggcacagactgaccgagagGacctgcggaccctgctccg ctactacaaccagagcgaggccgggtctcacacttggcagacgatgtatggctgcgacCtggggccggacgggcgcctcc tccgcgggtaccaccagGacgcctacgacggcaaggattacatcgccctgaacgaggacctgAgctcctggaccgccgcg gacacggcggctcagatcacccagcgcaagtgggaggcggcccgtgTggcggagcagcTgagagcctacctggagggcga gtgcgtggagtggctccgcagataCctggagaacgggaaggagacgctgcagcgcgcGg -continued

B*2715

(SEQ ID NO: 1333)
gctcccactccatgaggtatttccacacctccgtgtcccggcccggccgcggggagccccgcttcatcaccgtgggctac gtggacgacacgctgttcgtgaggttcgacagcgacgccgcgagtccgagagaggagccgcgggcgccgtggatagagca ggaggggccggagtattgggaccgggagacacagatctgcaaggccaaggcacagactgaccgagagagcctgcggaccc tgctccgctactacaaccagagcgaggccgggtctcacaccctccagaaTatgtatggctgcgacgtggggccggacggg cgcctcctccgcgggtaccaccagGacgcctacgacggcaaggattacatcgccctgaacgaggacctgagctcctggac cgccgcggacacggcggctcagatcacccagcgcaagtgggaggcggcccgtgaggcggagcagctgagagcctacctgg agggcaCgtgcgtggagtggctccgcagatacctggagaacgggaaggagacgctgcagcgcgcGg

B*2716

(SEQ ID NO: 1334)
gctcccactccatgaggtatttccacacctccgtgtcccggcccggccgcggggagccccgcttcatcaccgtgggctac gtggacgacacgctgttcgtgaggttcgacagcgacgccgcgagtccgagagaggagccgcgggcgccgtggatagagca ggaggggccggagtattgggaccgggagacacagatctGcaagaccaacAcacagactgaccgagagGacctgcggaccc tgctccgctactacaaccagagcgaggccgggtctcacaccctccagaaTatgtaTggctgcgacgtggggccggacggg cgcctcctccgcgggtaccaccagGacgcctacgacggcaaggattacatcgccctgaacgaggacctgAgctcctggac cgccgcggacacggcggctcagatcacccagcgcaagtgggaggcggcccgtgTggcggagcagcTgagagcctacctgg agggcgagtgcgtggagtggctccgcagatacctggagaacgggaaggagacgctgcagcgcgcGg

B*2717

(SEQ ID NO: 1335)
gctcccactccatgaggtatttccacacctccgtgtcccggcccggccgcggggagccccgcttcatcaccgtgggctac gtggacgacacgctgttcgtgaggttcgacagcgacgccgcgagtccgagagaggagccgcgggcgccgtggatagagca ggaggggccggagtTttgggaccgggagacacagatctgcaaggccaaggcacagactgaccgagaggacctgcggaccc tgctccgctactacaaccagagcgaggccgggtctcacaccctccagaatatgtatggctgcgacgtggggccggacggg cgcctcctccgcgggtaccaccaggacgcctacgacggcaaggattacatcgccctgaacgaggacctgagctcctggac cgccgcggacacggcggctcagatcacccagcgcaagtgggaggcggcccgtgtggcggagcagctgagagcctacctgg agggcgagtgcgtggagtggctccgcagatacctggagaacgggaaggagacgctgcagcgcgcgg

B*2718

(SEQ ID NO: 1336)
atgcgggtcacggcgccccgaaccctcctcctgctgctctgggggggcagtggccctgaccgagacctgggctggctccca ctccatgaggtatttcCacacctccgtgtcccggcccggccgcggggagccccgcttcatcaccgtgggctacgtggacg acacgcTgttcgtgaggttcgacagcgacgccgcgagtccgagagaggagccgcgggcgccgtggatagagcaggagggg ccggagtattgggaccgggagacacagatctCcaagaccaacAcacagactTaccgagagagcctgcggaacctgcgcgg ctactacaaccagagcgaggccgggtctcacaccctccagaaTatgtatggctgcgacgtggggccggacgggcgcctcc tccgcgggtaccaccagGacgcctacgacggcaaggattacatcgccctgaacgaggacctgAgctcctggaccgccgcg gacacggcggctcagatcacccagcgcaagtgggaggcggcccgtgaggcggagcagcTgagagcctacctggagggcga gtgcgtggagtggctccgcagatacctggagaacgggaaggagacgctgcagcgcgcGg

B*2719

(SEQ ID NO: 1337)
gctcccactccatgaggtatttccacacctccgtgtcccggcccggccgcggggagccccgcttcatcaccgtgggctac gtggacgacacgctgttcgtgaggttcgacagcgacgccgcgagtccgagagaggagccgcgggcgccgtggatagagca ggaggggccggagtattgggaccgggagacacagatctgcaaggccaaggcacagactgaccgagagGacctgcggaccc tgctccgctactacaaccagagcgaggccgggtctcacatcAtccagagGatgtacggctgcgacgtggggccggacggg cgcctcctccgcgggtaccaccagGacgcctacgacggcaaggattacatcgccctgaacgaggacctgAgctcctggac -continued cgccgcggacacggcggctcagatcacccagcgcaagtgggaggcggcccgtgTggcggagcagcTgagagcctacctgg agggcgagtgcgtggagtggctccgcagatacctggagaacgggaaggagacgctgcagcgcgcGg

B*2720 (SEQ ID NO: 1338)

gctcccactccatgaggtatttccacacctccgtgtcccggcccggccgcggggagccccgcttcatcaccgtgggctac gtggacgacacgctgttcgtgaggttcgacagcgacgccgcgagtccgagagaggagccgcgggcgccgtggatagagca ggaggggccggagtattgggacccgggagacacagatctgcaaggccaaggcacagactgaccgagagagcctgcggaccc tgctccgctactacaaccagagcgaggccgggtctcacaccctccagaaTatgtacggctgcgacgtggggccggacggg cgcctcctccgcgggcatAaccagtacgcctacgacggcaaggattacatcgccctgaacgaggacctgcgctcctggac cgccgcggacacggcggctcagatcacccagcgcaagtgggaggcggcccgtgaggcggagcagcTgagagcctacctgg agggcgagtgcgtggagtggctccgcagatacctggagaacgggaaggagacgctgcagcgcgcGg

B*2721 (SEQ ID NO: 1339)

gctcccactccatgaggtatttccacacctccgtgtcccggcccggccgcggggagccccgcttcatcaccgtgggctac gtggacgacacgctgttcgtgaggttcgacagcgacgccgcgagtccgagagaggagccgcgggcgccgtggatagagca ggaggggccggagtattgggacccgggagacacagatctGcaaggccaaggcacagactgaccgagagagcctgcggaccc tgctcCgctactacaaccagagcgaggccgggtctcacaccctccagagGatgtacggctgcgacgtggggccggacggg cgcctcctccgcgggTatgaccagtacgcctacgacggcaaggattacatcgccctgaacgaggacctgAgctcctggac cgccgcggacacggcggctcagatcacccagcgcaagtgggaggcggcccgtgaggcggagcagcTgagagcctacctgg agggcgagtgcgtggagtggctccgcagatacctggagaacgggaaggagacgctgcagcgcgcGg

B*2723 (SEQ ID NO: 1340)

gctcccactccatgaggtatttccacacctccgtgtcccggcccggccgcggggagccccgcttcatcaccgtgggctac gtggacgacacgctgttcgtgaggttcgacagcgacgccgcgagtccgagagaggagccgcgggcgccgtggatagagca ggaggggccggagtattgggaccggaacacacagatctTcaagaccaacAcacagactTaccgagagagcctgcggaCcc tgctcCgctactacaaccagagcgaggccgggtctcacaccctccagaaTatgtatggctgcgacgtggggccggacggg cgcctcctccgcgggtaccaccagGacgcctacgacggcaaggattacatcgccctgaacgaggacctgagctcctggac cgccgcggacacggcggctcagatcacccagcgcaagtgggaggcggcccgtgTggcggagcagcTgagagcctacctgg agggcgagtgcgtggagtggctccgcagatacctggagaacgggaaggagacgctgcagcgcgcGg

B*2724 (SEQ ID NO: 1341)

gctcccactccatgaggtatttccacacctccgtgtcccggcccggccgcggggagccccgcttcatcaccgtgggctac gtggacgacacgctgttcgtgaggttcgacagcgacgccgcgagtccgagagaggagccgcgggcgccgtggatagagca ggaggggccggagtattgggacccgggagacacagatctgcaaggccaaggcacagactgaccgagagagcctgcggaccc tgctcCgctactacaaccagagcgaggccgggtctcacaccctccagagcatgtacggctgcgacgtggggccggacggg cgcctcctccgcgggcataaccagtacgcctacgacggcaaggattacatcgccctgaacgaggacctgcgctcctggac cgccgcggacacggcggctcagatcTcccagcgcaagtgggaggcggcccgtgaggcggagcagctgagagcctacctgg agggcgagtgcgtggagtggctccgcagatacctggagaacgggaaggagacgctgcagcgcgcGg

B*2725 (SEQ ID NO: 1342)

gctcccactccatgaggtatttccacacctccgtgtcccggcccggccgcggggagccccgcttcatcaccgtgggctac gtggacgacacgctgttcgtgaggttcgacagcgacgccgcgagtccgagagaggagccgcgggcgccgtggatagagca ggaggggccggagtattgggacccgggagacacagatctgcaaggccaaggcacagactgaccgagagagcctgcggaccc tgctccgctactacaaccagagcgaggccgggtctcacaccctccagaaTatgtatggctgcgacgtggggccggacggg cgcctcctccgcgggtaccaccaggacgcctacgacggcaaggattacatcgccctgaacgaggacctgagctcctggac -continued cgccgcggacacggcggctcagatcacccagcgcaagtgggaggcggcccgtgaggcggagcagtggagagcctacctgg agggccTgtgcgtggagtggctccgcagatacctggagaacgggaaggagacgctgcagcgcgcGg B*350101 (SEQ ID NO: 1343)
atgcgggtcacggcgccccgaaccgtcctcctgctgctctgggggcagtggccctgaccgagacctgggccggctccca ctccatgaggtatttctacaccgccatgtcccggcccggccgcggggagccccgcttcatcgcagtgggctacgtggacg acacccagttcgtgaggttcgacagcgacgccgcgagtccgaggacggagccccgggcgccatggatagagcaggagggg ccggagtattgggaccggaacacacagatctTcaagaccaacAcacagacttaccgagagagcctgcggaacctgcgcgg ctactacaaccagagcgaggccgggtctcacatcAtccagaggatgtaTggctgcgacctggggcccgacgggcgcctcc tccgcgggcatgaccagtCcgcctacgacggcaaggattacatcgccctgaacgaggacctgAgctcctggaccgcggcg gacaccgcggctcagatcacccagcgcaagtgggaggcggcccgtgTggcggagcagcTgagagcctacctggagggccT gtgcgtggagtggctccgcagatacctggagaacgggaaggagacgctgcagcgcgcggacccccccaaagacacacgtga cccaccaccccGtctctgaccatgaggccaccctgaggtgctgggccctgggcttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccatccccatcgtgggcattgttgctggcctggctgtccta...gca gttgtggtcatcggagctgtggtcgctactgtgatgtgtaggaggaagagCtcaggtgga B*350102 (SEQ ID NO: 1344)
gctcccactccatgaggtatttctacaccgccatgtcccggcccggccgcggggagccccgcttcatcgcagtgggctac gtggacgacacccagttcgtgaggttcgacagcgacgccgcgagtccgaggacggagccccgggcgccatggatagagca ggaggggccggagtattgggaccggaacacacagatcttcaagaccaacacacagacttaccgagagagcctgcggaacc tgcgcggctactacaaccagagcgaggccgggtctcacatcatccagaggatgtatggctgcgacctggggcccgacggg cgcctcctccgcgggcatgaccagtccgcctacgacggcaaggattacatcgccctgaacgaggacctgagctcctggac cgcggcggacaccgcggctcagatcacccagcgcaagtgggaggcggcccgtgtggcggagcagctgagagcTtacctgg agggcctgtgcgtggagtggctccgcagatacctggagaacgggaaggagacgctgcagcgcgcgg B*3502 (SEQ ID NO: 1345)
atgcgggtcacggcgccccgaaccgtcctcctgctgctctgggggcagtggccctgaccgagacctgggccggctccca ctccatgaggtatttctacaccgccatgtcccggcccggccgcggggagccccgcttcatcgcagtgggctacgtggacg acacccagttcgtgaggttcgacagcgacgccgcgagtccgaggacggagccccgggcgccatggatagagcaggagggg ccggagtattgggaccggaacacacagatcttcaagaccaacacacagacttaccgagagagcctgcggaacctgcgcgg ctactacaaccagagcgaggccgggtctcacatcatccagaggatgtatggctgcgacctggggcccgacgggcgcTtcc tccgcgggcataaccagtacgcctacgacggcaaggattacatcgccctgaacgaggacctgagctcctggaccgcggcg gacaccgcggctcagatcacccagcgcaagtgggaggcggcccgtgtggcggagcagctgagagcctacctggagggcct gtgcgtggagtggctccgcagatacctggagaacgggaaggagacgctgcagcgcgcggaccccccaaagacacacgtga cccaccaccccgtctctgaccatgaggccaccctgaggtgctgggccctgggcttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccatccccatcgtgggcattgttgctggcctggctgtccta...gca gttgtggtcatcggagctgtggtcgctactgtgatgtgtaggaggaagagctcaggtgga B*3503 (SEQ ID NO: 1346)
atgcgggtcacggcgccccgaaccgtcctcctgctgctctgggggcagtggccctgaccgagacctgggccggctccca ctccatgaggtatttctacaccgccatgtcccggcccggccgcggggagccccgcttcatcgcagtgggctacgtggacg

```
                                     -continued
acacccagttcgtgaggttcgacagcgacgccgcgagtccgaggacggagccccgggcgccatggatagagcaggagggg ccggagtattgggaccggaacacacagatcttcaagaccaacacacagacttaccgagagagcctgcggaacctgcgcgg ctactacaaccagagcgaggccgggtctcacatcatccagaggatgtatggctgcgacctggggcccgacgggcgcctcc tccgcgggcatgaccagtTcgcctacgacggcaaggattacatcgccctgaacgaggacctgAgctcctggaccgcggcg gacaccgcggctcagatcacccagcgcaagtgggaggcggcccgtgTggcggagcagcTgagagcctacctggagggccT gtgcgtggagtggctccgcagatacctggagaacgggaaggagacgctgcagcgcgcggaccccccaaagacacacgtga cccaccaccccGtctctgaccatgaggccaccctgaggtgctgggccctgggcttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccatccccatcgtgggcattgttgctggcctggctgtcccta...gca gttgtggtcatcggagctgtggtcgctactgtgatgtgtaggaggaagagCtcaggtgga B*3504
                                                                    (SEQ ID NO: 1347)
atgcgggtcacggcgccccgaaccgtcctcctgctgctctgggggcagtggccctgaccgagacctgggccggctccca ctccatgaggtatttctacaccgccatgtcccggcccggccgcggggagccccgcttcatcgcagtgggctacgtggacg acacccagttcgtgaggttcgacagcgacgccgcgagtccgaggacggagccccgggcgccatggatagagcaggagggg ccggagtattgggaccggaacacacagatcttcaagaccaacacacagacttaccgagagagcctgcggaacctgcgcgg ctactacaaccagagcgaggccgggtctcacatcatccagaggatgtatggctgcgacctggggccCgacgggcgcctcc tccgcgggcatAaccagtacgcctacgacggcaaggattacatcgccctgaacgaggacctgAgctcctggaccgcggcg gacaccgcggctcagatcacccagcgcaagtgggaggcggcccgtgTggcggagcagcTgagagcctacctggagggccT gtgcgtggagtggctccgcagatacctggagaacgggaaggagacgctgcagcgcgcggaccccccaaagacacacgtga cccaccaccccGtctctgaccatgaggccaccctgaggtgctgggccctgggcttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccatccccatcgtgggcattgttgctggcctggctgtcccta...gca gttgtggtcatcggagctgtggtcgctactgtgatgtgtaggaggaagagCtcaggtgga B*3505
                                                                    (SEQ ID NO: 1348)
atgcgggtcacggcgccccgaaccgtcctcctgctgctctgggggcagtggccctgaccgagacctgggccggctccca ctccatgaggtatttctacaccgccatgtcccggcccggccgcggggagccccgcttcatcgcagtgggctacgtggacg acacccagttcgtgaggttcgacagcgacgccgcgagtccgaggacggagccccgggcgccatggatagagcaggagggg ccggagtattgggaccggaacacacagatctTcaagaccaacAcacagacttaccgagagagcctgcggaacctgcgcgg ctactacaaccagagcgaggccgggtctcacaccctccagagcatgtacggctgcgacctggggcccgacgggcgcctcc tccgcgggcatgaccagtCcgcctacgacggcaaggattacatcgccctgaacgaggacctgAgctcctggaccgcggcg gacaccgcggctcagatcacccagcgcaagtgggaggcggcccgtgTggcggagcagcTgagagcctacctggagggccT gtgcgtggagtggctccgcagatacctggagaacgggaaggagacgctgcagcgcgcggaccccccaaagacacacgtga cccaccaccccGtctctgaccatgaggccaccctgaggtgctgggccctgggcttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccatccccatcgtgggcattgttgctggcctggctgtcccta...gca gttgtggtcatcggagctgtggtcgctactgtgatgtgtaggaggaagagCtcaggtgga
```

B*3506

(SEQ ID NO: 1349)
atgcgggtcacggcgccccgaaccgtcctcctgctgctctgggggcagtggccctgaccgagacctgggccggctccca ctccatgaggtatttctacaccgccatgtcccggcccggccgcggggagccccgcttcatcgcagtgggctacgtggacg acacccagttcgtgaggttcgacagcgacgccgcgagtccgaggacggagccccgggcgccatggatagagcaggagggg ccggagtattgggaccggaacacacagatcttcaagaccaacacacagacttaccgagagagcctgcggaacctgcgcgg ctactacaaccagagcgaggccgggtctcacatcatccagaggatgtatggctgcgacctggggcccgacgggcgcctcc tccgcgggcatAaccagtTcgcctacgacggcaaggattacatcgccctgaacgaggacctgAgctcctggaccgcggcg gacaccgcggctcagatcacccagcgcaagtgggaggcggcccgtgTggcggagcagcTgagagcctacctggagggccT gtgcgtggagtggctccgcagatacctggagaacgggaaggagacgctgcagcgcgcggaccccccaaagacacacgtga cccaccaccccGtctctgaccatgaggccaccctgaggtgctgggccctgggcttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccatccccatcgtgggcattgttgctggcctggctgtccta...gca gttgtggtcatcggagctgtggtcgctactgtgatgtgtaggaggaagagCtcaggtgga

B*3507

(SEQ ID NO: 1350)
atgcgggtcacggcgccccgaaccgtcctcctgctgctctgggggcagtggccctgaccgagacctgggccggctccca ctccatgaggtatttctacaccgccatgtcccggcccgTccgcggggagccccgcttcatcgcagtgggctacgtggacg acacccagttcgtgaggttcgacagcgacgccgcgagtccgaggacggagccccgggcgccatggatagagcaggagggg ccggagtattgggaccggaacacacagatcttcaagaccaacacacagacttaccgagagagcctgcggaacctgcgcgg ctactacaaccagagcgaggccgggtctcacatcatccagaggatgtatggctgcgacctggggcccgacgggcgcctcc tccgcgggcatgaccagtccgcctacgacggcaaggattacatcgccctgaacgaggacctgagctcctggaccgcggcg gacaccgcggctcagatcacccagcgcaagtgggaggcggcccgtgtggcggagcagctgagagcctacctggagggcct gtgcgtggagtggctccgcagatacctggagaacgggaaggagacgctgcagcgcgcggaccccccaaagacacacgtga cccaccaccccgtctctgaccatgaggccaccctgaggtgctgggccctgggcttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccatccccatcgtgggcattgttgctggcctggctgtccta...gca gttgtggtcatcggagctgtggtcgctactgtgatgtgtaggaggaagagctcaggtgga

B*3508

(SEQ ID NO: 1351)
atgcgggtcacggcgccccgaaccgtcctcctgctgctctgggggcagtggccctgaccgagacctgggccggctccca ctccatgaggtatttctacaccgccatgtcccggcccggccgcggggagccccgcttcatcgcagtgggctacgtggacg acacccagttcgtgaggttcgacagcgacgccgcgagtccgaggacggagccccgggcgccatggatagagcaggagggg ccggagtattgggaccggaacacacagatctTcaagaccaacAcacagacttaccgagagagcctgcggaacctgcgcgg ctactacaaccagagcgaggccgggtctcacatcAtccagaggatgtaTggctgcgacctggggcccgacgggcgcctcc tccgcgggcatgaccagtCcgcctacgacggcaaggattacatcgccctgaacgaggacctgAgctcctggaccgcggcg gacaccgcggctcagatcacccagcgcaagtgggaggcggcccgtgTggcggagcagcTgagagcctacctggagggccT gtgcgtggagtggctccgcagatacctggagaacgggaaggagacgctgcagcgcgcggaccccccaaagacacacgtga cccaccaccccGtctctgaccatgaggccaccctgaggtgctgggccctgggcttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc -continued tcaccctgagatgggagccatcttcccagtccaccatccccatcgtgggcattgttgctggcctggctgtccta...gca gttgtggtcatcggagctgtggtcgctactgtgatgtgtaggaggaagagCtcaggtgga

B*350901

(SEQ ID NO: 1352)

atgcgggtcacggcgccccgaaccgtcctcctgctgctctgggggcagtggccctgaccgagacctgggccggctccca ctccatgaggtatttctacaccgccatgtcccggcccggccgcggggagccccgcttcatcgcagtgggctacgtggacg acacccagttcgtgaggttcgacagcgacgccgcgagtccgaggacggagccccgggcgccatggatagagcaggagggg ccggagtattgggaccggaacacacagatcttcaagaccaacacacagacttaccgagagagcctgcggaacctgcgcgg ctactacaaccagagcgaggccgggtctcacatcatccagaggatgtatggctgcgacctggggccCgacgggcgcctcc tccgcgggcatAaccagtacgcctacgacggcaaggattacatcgccctgaacgaggacctgcgctcctggaccgcggcg gacaccgcggctcagatcacccagcgcaagtgggaggcggcccgtgTggcggagcagcTgagagcctacctggagggccT gtgcgtggagtggctccgcagatacctggagaacgggaaggagacgctgcagcgcgcggaccccccaaagacacacgtga cccaccaccccGtctctgaccatgaggccaccctgaggtgctgggccctgggcttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccatccccatcgtgggcattgttgctggcctggctgtccta...gca gttgtggtcatcggagctgtggtcgctactgtgatgtgtaggaggaagagCtcaggtgga

B*350902

(SEQ ID NO: 1353)

gctcccactccatgaggtatttctacaccgccatgtcccggcccggccgcggggagccccgcttcatcgcagtgggctac gtggacgacacccagttcgtgaggttcgacagcgacgccgcgagtccgaggacggagccccgggcgccatggatagagca ggaggggccggagtattgggaccggaacacacagatctTcaagaccaacacacagacttaccgagagagcctgcggaacc tgcgcggctactacaaccagagcgaggccgggtctcacatcatccagaggatgtatggctgcgacctggggccCgacggg cgcctcctccgcgggcatAaccagtacgcctacgacggcaaggattacatcgccctgaacgaggacctgcgctcctggac cgccgcggacacgcggctcagatcacccagcgcaagtgggaggcggcccgtgTggcggagcagcTgagagcctacctgg agggccTgtgcgtggagtggctccgcagatacctggagaacgggaaggagacgctgCagcgcgcGg

B*3510

(SEQ ID NO: 1354)

gctcccactccatgaggtatttctacaccgccatgtcccggcccggccgcggggagccccgcttcatcgcagtgggctac gtggacgacacccagttcgtgaggttcgacagcgacgccgcgagtccgaggacggagccccgggcgccatggatagagca ggaggggccggagtattgggaccgggaGacacagatctTcaagaccaacAcacagactTaccgagagagcctgcggaacc tgcgcggctactacaaccagagcgaggccgggtctcacatcAtccagaggatgtaTggctgcgacCtggggccCgacggg cgcctcctccgcgggcatgaccagtCcgcctacgacggcaaggattacatcgccctgaacgaggacctgAgctcctggac cgcggcggacacCgcggctcagatcacccagcgcaagtgggaggcggcccgtgTggcggagcagcTgagagcctacctgg agggccTgtgcgtggagtggctccgcagatacctggagaacggga

B*3511

(SEQ ID NO: 1355)

atgcgggtcacggcgccccgaaccgtcctcctgctgctctgggggcagtggccctgaccgagacctgggccggctccca ctccatgaggtatttctacaccgccatgtcccggcccggccgcggggagccccgcttcatcgcagtgggctacgtggacg acacccagttcgtgaggttcgacagcgacgccgcgagtccgaggacggagccccgggcgccatggatagagcaggagggg ccggagtattgggaccggaacacacagatctTcaagaccaacAcacagacttaccgagagagcctgcggaacctgcgcgg ctactacaaccagagcgaggccgggtctcacatcAtccagaggatgtaTggctgcgacctggggcccgacgggcgcctcc tccgcgggcatgaccagtCcgcctacgacggcaaggattacatcgccctgaacgaggacctgAgctcctggaccgcggcg gacaccgcggctcagatcacccagcgcaagtgggaggcggcccgtgaggcggagcagcTgagagcctacctggagggccT gtgcgtggagtggctccgcagatacctggagaacgggaaggagacgctgcagcgcgcggaccccccaaagacacacgtga -continued cccaccacccGtctctgaccatgaggccaccctgaggtgctgggccctgggcttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccatccccatcgtgggcattgttgctggcctggctgtccta...gca gttgtggtcatcggagctgtggtcgctactgtgatgtgtaggaggaagagCtcaggtgga

B*3512

(SEQ ID NO: 1356)

atgcgggtcacggcgccccgaaccgtcctcctgctgctctggggggcagtggccctgaccgagacctgggccggctccca ctccatgaggtatttctacaccgccatgtcccggcccggccgcggggagccccgcttcatcgcagtgggctacgtggacg acacccagttcgtgaggttcgacagcgacgccgcgagtccgaggacggagccccgggcgccatggatagagcaggagggg ccggagtattgggaccggaacacacagatcttcaagaccaacacacagacttaccgagagagcctgcggaacctgcgcgg ctactacaaccagagcgaggccgggtctcacatcatccagaggatgtacggctgcgacgtggggccggacgggcgcctcc tccgcgggcatAaccagtacgcctacgacggcaaggattacatcgccctgaacgaggacctgAgctcctggaccgcggcg gacaccgcggctcagatcacccagcgcaagtgggaggcggcccgtgTggcggagcagcTgagagcctacctggagggccT gtgcgtggagtggctccgcagataCctggagaacgggaaggagacgctgcagcgcgcggaccccccaaagacacacgtga cccaccacccGtctctgaccatgaggccaccctgaggtgctgggccctgggcttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccatccccatcgtgggcattgttgctggcctggctgtccta...gca gttgtggtcatcggagctgtggtcgctactgtgatgtgtaggaggaagagCtcaggtgga

B*3513

(SEQ ID NO: 1357)

gctcccactccatgaggtatttctacaccgccatgtcccggcccggccgcggggagccccgcttcatcgcagtgggctac gtggacgacacccagttcgtgaggttcgacagcgacgccgcgagtccgaggacggagccccgggcgccatggatagagca ggaggggccggagtattgggaccgggaGacacagatctTcaagaccaacacacagactTaccgagagagcctgcggaacc tgcgcggctactacaaccagagcgaggccgggtctcacatcatccagaggatgtatggctgcgacctggggccCgacggg cgcctcctccgcgggcatgaccagtTcgcctacgacggcaaggattacatcgccctgaacgaggacctgAgctcctggac cgcggcggacacCgcggctcagatcacccagcgcaagtgggaggcggcccgtgTggcggagcagcTgagagcctacctgg agggccTgtgcgtggagtggctccgcagataCctggagaacgggaaggagacgctgCagcgcgcGg

B*3514

(SEQ ID NO: 1358)

gctcccactccatgaggtatttctacaccgccatgtcccggcccggccgcggggagccccgcttcatcgcagtgggctac gtggacgacacccagttcgtgaggttcgacagcgacgccgcgagtccgaggacggagccccgggcgccatggatagagca ggaggggccggagtattgggaccgggacacacagatcttcaagaccaacacacagacttaccgagagagcctgcggaacc tgcgcggctactacaaccagagcgaggccgggtctcacatcatccagaggatgtatggctgcgacctggggcccgacggg cgcctcctccgcgggcatgaccagtccgcctacgacggcaaggattacatcgccctgaacgaggacctgagctcctggac cgcggcggacacCgcggctcagatcacccagcgcaagtgggaggcggcccgtgaggcggagcagTggagagcctacctgg agggccTgtgcgtggagtggctccgcagataCctggagaacgggaaggagacgctgcagcgcgcGg

B*3515

(SEQ ID NO: 1359)

atgcgggtcacggcgccccgaaccgtcctcctgctgctctggggggcagtggccctgaccgagacctgggccggctccca ctccatgaggtatttctacaccgccatgtcccggcccggccgcggggagccccgcttcatcgcagtgggctacgtggacg acacccagttcgtgaggttcgacagcgacgccgcgagtccgaggacggagccccgggcgccatggatagagcaggagggg ccggagtattgggaccggaacacacagatctTcaagaccaacAcacagacttaccgagagagcctgcggaacctgcgcgg -continued ctactacaaccagagcgaggccgggtctcacatcAtccagaggatgtaTggctgcgacctggggcccgacgggcgcctcc
tccgcgggcatgaccagtCcgcctacgacggcaaggattacatcgccctgaacgaggacctgAgctcctggaccgcggcg
gacaccgcggctcagatcacccagcgcaagtggggaggcggcccgtgTggcggagcagcTgagagcctacctggagggcga
gtgcgtggagtggctccgcagatacctggagaacgggaaggagacgctgcagcgcgcggaccccccaaagacacacgtga
cccaccaccccGtctctgaccatgaggccaccctgaggtgctgggccctgggcttctaccctgcggagatcacactgacc
tggcagcgggatggcgaggaccaaactcaggacactgagcttgtggagaccagaccagcaggagatagaaccttccagaa
gtgggcagctgtggtggtgccttctggagaagagcagagatacacatgccatgtacagcatgaggggctgccgaagcccc
tcaccctgagatgggagccatcttcccagtccaccatccccatcgtgggcattgttgctggcctggctgtccta...gca
gttgtggtcatcggagctgtggtcgctactgtgatgtgtaggaggaagagCtcaggtgga B*3516
(SEQ ID NO: 1360)
gctcccactccatgaggtatttctacaccgccatgtcccggcccggccgcggggagccccgcttcatcgcagtgggctac
gtggacgacacccagttcgtgaggttcgacagcgacgccgcgagtccgaggacggagccccgggcgccatggatagagca
ggaggggccggagtattgggaccgggaGacacagatctTcaagaccaacAcacagactTaccgagagagcctgcggaacc
tgcgcggctactacaaccagagcgaggccgggtctcacatcAtccagagcatgtacggctgcgacgtggggccCgacggg
cgcctcctccgcgggcatgaccagtCcgcctacgacggcaaggattacatcgccctgaacgaggacctgAgctcctggac
cgcggcggacacCgcggctcagatcacccagcgcaagtgggaggcggcccgtgTggcggagcagcTgagagcctacctgg
agggccTgtgcgtggagtggctccgcagatacctggagaacgggaaggagacgctgCagcgcgcGg B*3517
(SEQ ID NO: 1361)
gctcccactccatgaggtatttctacaccgccatgtcccggcccggccgcggggagccccgcttcatcgcagtgggctac
gtggacgacacccagttcgtgaggttcgacagcgacgccgcgagtccgaggacggagccCcgggcgccAtggatagagca
ggaggggccggagtattgggaccggaacacacagatctTcaagaccaacAcacagactTaccgagagagcctgcggaacc
tgcgcggctactacaaccagagcgaggccgggtctcacatcAtccagagcatgtacggctgcgacgtggggccCgacggg
cgcctcctccgcgggcatgaccagtCcgcctacgacggcaaggattacatcgccctgaacgaggacctgAgctcctggac
cgcggcggacacCgcggctcagatcacccagcgcaagtgggaggcggcccgtgTggcggagcagcTgagagcctacctgg
agggccTgtgcgtggagtggctccgcagatacctggagaacgggaaggagacgctgCagcgcgcGg B*3518
(SEQ ID NO: 1362)
gctcccactccatgaggtatttctacaccgccatgtcccggcccggccgcggggagccccgcttcatcgcagtgggctac
gtggacgacacccagttcgtgaggttcgacagcgacgccgcgagtccgaggacggagccccgggcgccatggatagagca
ggaggggccggagtattgggaccggaacacacagatctTcaagaccaacAcacagacttaccgagagagcctgcggaacc
tgcgcggctactacaaccagagcgaggccgggtctcacatcAtccagaggatgtatggctgcgacctggggccCgacggg
cgcctcctccgcgggcatAaccagtacgcctacgacggcaaggattacatcgccctgaacgaggacctgcgctcctggac
cgccgcggacacggcggctcagatcacccagcgcaagtgggaggcggcccgtgTggcggagcagcggagagcctacctgg
agggccTgtgcgtggagtggctccgcagatacctggagaacgggaaggagacgctgCagcgcgcGg B*3519
(SEQ ID NO: 1363)
gctcccactccatgaggtatttctacaccgccatgtcccggcccggccgcggggagccccgcttcatcgcagtgggctac
gtggacgacacccagttcgtgaggttcgacagcgacgccgcgagtccgaggaaggagccgcgggcgccAtggatagagca
ggaggggccggagtattgggaccggaacacacagatctTcaagaccaacAcacagactTaccgagagagcctgcggaacc
tgcgcggctactacaaccagagcgaggccgggtctcacatcAtccagaggatgtaTggctgcgacCtggggccCgacggg
cgcctcctccgcgggcatgaccagtCcgcctacgacggcaaggattacatcgccctgaacgaggacctgAgctcctggac
cgcggcggacacCgcggctcagatcacccagcgcaagtgggaggcggcccgtgTggcggagcagcTgagagcctacctgg
agggccTgtgcgtggagtggctccgcagatacctggagaacgggaaggagacgctgCagcgcgcGg

B*3520

(SEQ ID NO: 1364)
gctcccactccatgaggtatttctacaccgccatgtcccggcccggccgcggggagccccgcttcatcgcagtgggctac gtggacgacacccagttcgtgaggttcgacagcgacgccgcgagtccgaggaCggagccccgggcgccAtggatagagca ggaggggccggagtattgggaccggaacacacagatctCcaagaccaacAcacagactTaccgagagagcctgcggaacc tgcgcggctactacaaccagagcgaggccgggtctcacatcAtccagaggatgtaTggctgcgacCtggggccCgacggg cgcctcctccgcgggcatgaccagtCcgcctacgacggcaaggattacatcgccctgaacgaggacctgAgctcctggac cgcggcggacacCgcggctcagatcacccagcgcaagtgggaggcggcccgtgTggcggagcagcTgagagcctacctgg agggccTgtgcgtggagtggctccgcagatacctggagaacgggaaggagacgctgCagcgcgcGg

B*3521

(SEQ ID NO: 1365)
gctcccactccatgaggtatttctacaccgccatgtcccggcccggccgcggggagccccgcttcatcgcagtgggctac gtggacgacacccagttcgtgaggttcgacagcgacgccgcgagtccgaggacggagccccgggcgccatggatagagca ggaggggccggagtattgggaccggaacacacagatcttcaagaccaacacacagacttaccgagagagcctgcggaacc tgcgcggctactacaaccagagcgaggccgggtctcacatcatccagaggatgtatggctgcgacctggggcccgacggg cgcctcctccgcgggcatgaccagtCcgcctacgacggcaaggattacatcgccctgaacgaggacctgAgctcctggac cgcggcggacacCgcggctcagatcacccagcgcaagtgggaggcggcccgtgaggcggagcagcTgagagcctacctgg agggccTgtgcgtggagtggctccgcagaCacctggagaacgggaaggagacgctgcagcgcgcgg

B*3522

(SEQ ID NO: 1366)
gctcccactccatgaggtatttctacaccgccatgtcccggcccggccgcggggagccccgcttcatcgcagtgggctac gtggacgacacccagttcgtgaggttcgacagcgacgccgcgagtccgaggaCggagccccgggcgccatggatagagca ggaggggccggagtattgggaccggaacacacagatctTcaagaccaacacacagacttaccgagagagcctgcggaacc tgcgcggctactacaaccagagcgaggccgggtctcacaccctccagagcatgtacggctgcgacgtggggccggacggg cgcctcctccgcgggcatAaccagtacgcctacgacggcaaggattacatcgccctgaacgaggacctgAgctcctggac cgcggcggacacCgcggctcagatcacccagcgcaagtgggaggcggcccgtgTggcggagcagcTgagagcctacctgg agggccTgtgcgtggagtggctccgcagatacctggagaacgggaaggagacgctgcagcgcgcGg

B*3523

(SEQ ID NO: 1367)
gctcccactccatgaggtatttctacaccgccatgtcccggcccggccgcggggagccccgcttcatcgcagtgggctac gtggacgacacccagttcgtgaggttcgacagcgacgccgcgagtccgaggacggagccccgggcgccatggatagagca ggaggggccggagtattgggaccggaacacacagatcttcaagaccaacacacagacttaccgagagagcctgcggaacc tgcgcggctactacaaccagagcgaggccgggtctcacatcatccagaggatgtTggctgcgacctggggcccgacggg cgcctcctccgcgggcatgaccagtCcgcctacgacggcaaggattacatcgccctgaacgaggacctgagctcctggac cgcggcggacaccgcggctcagatcacccagcgcaagtgggaggcggcccgtgTggcggagcagcTgagagcctacctgg agggccTgtgcgtggagtggctccgcagatacctggagaacgggaaggagacgctgcagcgcgcGg

B*3524

(SEQ ID NO: 1368)
gctcccactccatgaggtatttctacaccgccatgtcccggcccggccgcggggagccccgcttcatcgcagtgggctac gtggacgacacccagttcgtgaggttcgacagcgacgccgcgagtccgaggacggagccccgggcgccatggatagagca ggaggggccggagtattgggaccggaacacacagatcttcaagaccaacacacagacttaccgagagagcctgcggaacc tgcgcggctactacaaccagagcgaggccgggtctcacatcatccagaggatgtatggctgcgacctggggcccgacggg cgcctcctccgcgggcatgaccagtCcgcctacgacggcaaggattacatcgccctgaacgaggacctgagctcctggac cgcggcggacaccgcggctcagatcacccagcgcaagtgggaggcggcccgtgTggcggagcagcTgagagcctacctgg agggccTgtgcgtggagtggctccgcagaCacctggagaacgggaaggagacgctgcagcgcgcgg -continued

B*3525

(SEQ ID NO: 1369)

gctcccactccatgaggtatttctacaccgccatgtcccggcccggccgcggggagccccgcttcatctcagtgggctac gtggacgacacGcagttcgtgaggttcgacagcgacgccgcgagtccgagagaggagccgcgggcgccgtggatagagca ggaggggccggagtattgggaccggaacacacagatctTcaagaccaacAcacagactTaccgagagagcctgcggaacc tgcgcggctactacaaccagagcgaggccgggtctcacatcAtccagaggatgtaTggctgcgacCtggggccCgacggg cgcctcctccgcgggcatgaccagtCcgcctacgacggcaaggattacatcgccctgaacgaggacctgAgctcctggac cgcggcggacacCgcggctcagatcacccagcgcaagtgggaggcggcccgtgTggcggagcagcTgagagcctacctgg agggccTgtgcgtggagtggctccgcagatacctggagaacgggaaggagacgctgCagcgcgcGg

B*3526

(SEQ ID NO: 1370)

gctcccactccatgaggtatttctacaccgccatgtcccggcccggccgcggggagccccgcttcatcgcagtgggctac gtggacgacacccagttcgtgaggttcgacagcgacgccgcgagtccgagagaggagccccgggcgccatggatagagca ggaggggccggaAtattgggaccggaacacacagatctgcaagaccaacacacagacttaccgagagagcctgcggaacc tgcgcggctactacaaccagagcgaggccgggtctcacatcatccagaggatgtatggctgcgacctggggcccgacggg cgcctcctccgcgggcatgaccagtccgcctacgacggcaaggattacatcgccctgaacgaggacctgagctcctggac cgcggcggacaccgcggctcagatcacccagcgcaagtgggaggcggcccgtgtggcggagcagctgagagcctacctgg agggcCTgtgcgtggagtggctccgcagatacctggagaacgggaaggagacgctgcagcgcgcGg

B*3527

(SEQ ID NO: 1371)

gctcccactccatgaggtatttctacaccgccatgtcccggcccggccgcggggagccccgcttcatcgcagtgggctac gtggacgacacccagttcgtgaggttcgacagcgacgccgcgagtccgaggacggagccccgggcgccatggatagagca ggaggggccggagtattgggaccggaacacacagatctTcaagaccaacAcacagacttaccgagagaAcctgcggaacc tgcgcggctactacaaccagagcgaggccgggtctcacatcAtccagaggatgtaTggctgcgacCtggggccCgacggg cgcctcctccgcgggcatgaccagtCcgcctacgacggcaaggattacatcgccctgaacgaggacctgAgctcctggac cgcggcggacacCgcggctcagatcacccagcgcaagtgggaggcggcccgtgTggcggagcagcTgagagcctacctgg agggccTgtgcgtggagtggctccgcagatacctggagaacgggaaggagacgctgCagcgcgcGg

B*3528

(SEQ ID NO: 1372)

atgcgggtcacggcgccccgaaccgtcctcctgctgctctgggggcagtggccctgaccgagacctgggccggctccca ctccatgaggtatttctacaccgccatgtcccggcccggccgcggggagccccgcttcatcgcagtgggctacgtggacg acacccagttcgtgaggttcgacagcgacgccgcgagtccgaggaCggagccccgggcgccAtggatagagcaggaggggg ccggagtattgggaccgggaGacacagatctCcaagaccaacAcacagactTaccgagagagcctgcggaacctgcgcgg ctactacaaccagagcgaggccgggtctcacatcAtccagaggatgtaTggctgcgacCtggggccCgacgggcgcctcc tccgcgggcatgaccagtCcgcctacgacggcaaggattacatcgccctgaacgaggacctgAgctcctggaccgcggcg gacacCgcggctcagatcacccagcgcaagtgggaggcggcccgtgTggcggagcagcTgagagcctacctggagggccT gtgcgtggagtggctccgcagatacctggagaacgggaaggagacgctgCagcgcgcGg

B*3529

(SEQ ID NO: 1373)

gctcccactccatgaggtatttctacaccgccatgtcccggcccggccgcggggagccccgcttcatcgcagtgggctac gtggacgacacccagttcgtgaggttcgacagcgacgccgcgagtccgaggacggagccCcgggcgccAtggatagagca ggaggggccggagtattgggaccggaacacacagatctTcaagaccaacAcacagactgaccgagagagcctgcggaacc tgcgcggctactacaaccagagcgaggccgggtctcacatcAtccagaggatgtaTggctgcgacCtggggccCgacggg cgcctcctccgcgggcatgaccagtCcgcctacgacggcaaggattacatcgccctgaacgaggacctgAgctcctggac cgcggcggacacCgcggctcagatcacccagcgcaagtgggaggcggcccgtgTggcggagcagcTgagagcctacctgg agggccTgtgcgtggagtggctccgcagatacctggagaacgggaaggagacgctgCagcgcgcGg

B*3530

(SEQ ID NO: 1374)

gctcccactccatgaggtatttctacaccgccatgtcccggcccggccgcggggagccccgcttcatcgcagtgggctac gtggacgacacccagttcgtgaggttcgacagcgacgccgcgagtccgaggacggagccCcgggcgccAtggatagagca ggaggggccggagtattgggaccggaacacacagatctTcaagaccaacAcacagactTaccgagagagcctgcggaacc tgcgcggctactacaaccagagcgaggccgggtctcacatcAtccagagcatgtacggctgcgacCtggggccCgacggg cgcctcctccgcgggcatgaccagtCcgcctacgacggcaaggattacatcgccctgaacgaggacctgAgctcctggac cgcggcggacacCgcggctcagatcacccagcgcaagtgggaggcggcccgtgTggcggagcagcTgagagcctacctgg agggcCTgtgcgtggagtggctccgcagatacctggagaacgggaaggagacgctgCagcgcgcGg

B*3531

(SEQ ID NO: 1375)

atgcgggtcacggcgccccgaaccgtcctcctgctgctctgggggcaGtggccctgaccgagacctgggccggctccca ctccatgaggtatttctacaccgccatgtcccggcccggccgcggggagccccgcttcatcgcagtgggctacgtggacg acacccagttcgtgaggttcgacagcgacgccgcgagtccgaggacggagccCcgggcgccatggatagagcaggagggg ccggagtattgggaccggaacacacagatctTcaagaccaacAcacagactTaccgagagagcctgcggaacctgcgcgg ctactacaaccagagcgaggccgggtctcacaccctccagagcatgtacggctgcgacgtggggccggacgggcgcctcc tccgcgggcatAaccagtacgcctacgacggcaaggattacatcgccctgaacgaggacctgcgctcctggaccgccgcg gacacggcggctcagatcacccagcgcaagtgggaggcggcccgtgTggcggagcagcTgagagcctacctggagggcga gtgcgtggagtggctccgcagatacctggagaacgggaaggagacgctgcagcgcgcggacccccccaaagacacacgtga cccaccacccatctctgaccatgaggccaccctgaggtgctgggccctgggcttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccgtcttcccagtccaccgtccccatcgtgggcattgttgctggcctggctgtccta...gca gttgtggtcatcggagctgtggtcgctgctgtgatgtgtaggaggaagagCtcaggtgga

B*3532

(SEQ ID NO: 1376)

gctcccactccatgaggtatttctacaccgccatgtcccggcccggccgcggggagccccgcttcatcgcagtgggctac gtggacgacacccagttcgtgaggttcgacagcgacgccgcgagtccgaggacggagccCcgggcgccAtggatagagca ggaggggccggagtattgggaccggaacacacagatctTcaagaccaacAcacagactTaccgagagagcctgcggaacc tgcgcggctactacaaccagagcgaggccgggtctcacaccctccagagGatgtacggctgcgacgtggggccCgacggg cgcctcctccgcgggcatgaccagtCcgcctacgacggcaaggattacatcgccctgaacgaggacctgAgctcctggac cgcggcggacacCgcggctcagatcacccagcgcaagtgggaggcggcccgtgTggcggagcagcTgagagcctacctgg agggcCTgtgcgtggagtggctccgcagatacctggagaacgggaaggagacgctgCagcgcgcGg

B*3533

(SEQ ID NO: 1377)

tgaccgagacctgggccggctcccactccatgaggtatttctacaccgccatgtcccggcccggccgcggggagcccgc ttcatcgcagtgggctacgtggacgacacccagttcgtgaggttcgacagcgacgccgcgagtccgaggacggagccccg ggcgccatggatagagcaggaggggccggagtattgggaccggaacacacagatctTcaagaccaacacacagactTacc gagagagcctgcggaacctgcgcggctactacaaccagagcgaggccgggtctcacatcatccagaggatgtatggctgc gacctggggccCgacgggcgcctcctccgcgggcatgaccagtTcgcctacgacggcaaggattacatcgccctgaacga ggacctgAgctcctggaccgcggcggacacCgcggctcagatcacccagcgcaagtgggaggcggcccgtgTggcggagc agcTgagagcctacctggagggcgagtgcgtggagtggctccgcagatacctggagaacgggaaggagacgctgCagcgc gcGg

B*3534

(SEQ ID NO: 1378)
gctcccactccatgaggtatttctacaccgccatgtcccggcccggccgcggggagccccgcttcatcgcagtgggctac gtggacgacacccagttcgtgaggttcgacagcgacgccgcgagtccgaggacggagccCcgggcgccAtggatagagca ggaggggccggagtattgggaccggaacacacagatctTcaagaccaacAcacagactTaccgagagagcctgcggaacc tgcgcggctactacaaccagagcgaggccgggtctcacatcAtccagaggatgtaTggctgcgacCtggggccCgacggg cgcctcctccgcgggcatgaccagtacgcctacgacggcaaggattacatcgccctgaacgaggacctgAgctcctggac cgcggcggacacCgcggctcagatcacccagcgcaagtgggaggcggcccgtgTggcggagcagcTgagagcctacctgg agggccTgtgcgtggagtggctccgcagatacctggagaacgggaaggagacgctgCagcgcgcGg

B*3535

(SEQ ID NO: 1379)
gctcccactccatgaggtatttctacaccgccatgtcccggcccggccgcggggagccccgcttcatcgcagtgggctac gtggacgacacccagttcgtgaggttcgacagcgacgccgcgagtccgaggacggagccccgggcgccatggatagagca ggaggggccggagtattgggaccggaacacacagatcttcaagaccaacacacagacttaccgagagagcctgcggaacc tgcgcggctactacaaccagagcgaggccgggtctcacatcatccagaggatgtatggctgcgacctggggcccgacggg cgcctcctccgcgggcatgaccagtCcgcctacgacggcaaggattacatcgccctgaacgaggacctgagctcctggac cgcggcggacaccgcggctcagatcacccagcgcaagtgggaggcggcccgtgTggcggagcagcTgagaAcctacctgg agggcaCgtgcgtggagtggctccgcagatacctggagaacgggaaggagacgctgcagcgcgcGg

B*3536

(SEQ ID NO: 1380)
gctcccactccatgaggtatttctacaccgccatgtcccggcccggccgcggggagccccgcttcatcgcagtgggctac gtggacgacacccagttcgtgaggttcgacagcgacgccgcgagtccgaggacggagccccgggcgccatggatagagca ggaggggccggagtattgggaccggaacacacagatcttcaagaccaacacacagacttaccgagagagcctgcggaacc tgcgcgActactacaaccagagcgaggccgggtctcacatcatccagaggatgtatggctgcgacctggggcccgacggg cgcctcctccgcgggcatgaccagttcgcctacgacggcaaggattacatcgccctgaacgaggacctgagctcctggac cgcggcggacaccgcggctcagatcacccagcgcaagtgggaggcggcccgtgtggcggagcagctgagagcctacctgg agggcctgtgcgtggagtggctccgcagatacctggagaacgggaaggagacgctgcagcgcgcgg

B*3537

(SEQ ID NO: 1381)
gctcccactccatgaggtatttctacaccgccatgtcccggcccggccgcggggagccccgcttcatcgcagtgggctac gtggacgacacccagttcgtgaggttcgacagcgacgccgcgagtccgaggacggagccccgggcgccatggatagagca ggaggggccggagtattgggaccggaacacacagatcttcaagaccaacacacagacttaccgagagagcctgcggaacc tgcgcggctactacaaccagagcgaggccgggtctcacacttggcagaCgatgtaTggctgcgacCtggggccCgacggg cgcctcctccgcgggcatgaccagtCcgcctacgacggcaaggattacatcgccctgaacgaggacctgAgctcctggac cgcggcggacacCgcggctcagatcacccagcgcaagtgggaggcggcccgtgTggcggagcagcTgagagcctacctgg agggccTgtgcgtggagtggctccgcagatacctggagaacgggaaggagacgctgCagcgcgcG

B*3538

(SEQ ID NO: 1382)
gctcccactccatgaggtatttctacaccgccatgtcccggcccggccgcggggagccccgcttcatcgcagtgggctac gtggacgacacccagttcgtgaggttcgacagcgacgccgcgagtccgaggacggagccccgggcgccatggatagagca ggaggggccggagtattgggaccggaacacacagatcttcaagaccaacacacagacttaccgagagagcctgcggaacc tgcgcggctactacaaccagagcgaggccgggtctcacatcAtccagaggatgtatggctgcgacctggggcccgacggg cgcctcctccgcgggcatgaccagtTcgcctacgacggcaaggattacatcgccctgaacgaggacctgagctcctggac cgcggcggacacCgcggctcagatcacccagcgcaagtgggaggcggcccgtgTggcggagcaggaCagagcctacctgg agggccTgtgcgtggagtggctccgcagatacctggagaacgggaaggaDacgctgCagcgcgcG -continued

B*3539

(SEQ ID NO: 1383)

gctcccactccatgaggtatttctacaccgccatgtcccggcccggccgcggggagccccgcttcatcgcagtgggctac gtggacgacacccagttcgtgaggttcgacagcgacgccgcgagtccgaggacggagccCcgggcgccAtggatagagca ggaggggccggagtattgggaccggaacacacagatctTcaagaccaacAcacagactTaccgagagagcctgcggaacc tgcgcggctactacaaccagagcgaggccgggtctcacaTcatccagagGatgtacggctgcgacgtggggccggacggg cgcctcctccgcgggcatgaccagtacgcctacgacggcaaggattacatcgccctgaacgaggacctgAgctcctggac cgcggcggacacCgcggctcagatcacccagcgcaagtgggaggcggcccgtgTggcggagcagcTgagagcctacctgg agggccTgtgcgtggagtggctccgcagatacctggagaacgggaaggagacgctgcagcgcgcGg

B*3541

(SEQ ID NO: 1384)

gggggcagtggccctgaccgagacctgggccggctcccactccatgaggtatttctacaccgccatgtcccggcccggcc gcggggagccccgcttcatcgcagtgggctacgtggacgacacccagttcgtgaggttcgacagcgacgccgcgagtccg aggacggagccccgggcgccatggatagagcaggaggggccggagtattgggaccggaacacacagatcttcaagaccaa cacacagacttaccgagagagcctgcggaacctgcgcggctactacaaccagagcgaggccgggtctcacatcatccaga ggatgtatggctgcgacctggggcccgacgggcgcctcctccgcgggcatgaccagtccgcctGcgacggcaaggattac atcgccctgaacgaggacctgagctcctggaccgcggcggacaccgcggctcagatcacccagcgcaagtgggaggcggc ccgtgtggcggagcagctgagagcctacctggagggcctgtgcgtggagtggctccgcagatacctggagaacgggaagg agacgctgcagcgcgcggaccccccaaagacacacgtgacccaccaccccgtctctgaccatgaggccaccctgaggtgc tgggccctgggcttctaccctgcggagatcacactgacctggcagcgggatggcgaggaccaaactcaggacactgagct tgtggagaccagaccagcaggagatagaaccttccagaagtgggcagctgtggtggtgccttctggagaagagcagagat acacatgccatgtacagcatgaggggctgccgaagcccctcaccctgagatgggagccatcttcccagtccaccatcccc atcgtgggcattgttgctggcctggctgtcct

B*3542

(SEQ ID NO: 1385)

atgcgggtcacggcgccccgaaccctcctcctgctgctctgggggcagtggccctgaccgagacctgggcTggctccca ctccatgaggtatttctacaccgccatgtcccggcccggccgcggggagccccgcttcatcgcagtgggctacgtggacg acacccagttcgtgaggttcgacagcgacgccgcgagtccgaggacggagccccgggcgccatggatagagcaggagggg ccggagtattgggaccggaacacacagatcttcaagaccaacacacagacttaccgagagagcctgcggaacctgcgcgg ctactacaaccagagcgaggccgggtctcacatcatccagaggatgtatggctgcgacctggggcccgacgggcgcctcc tccgcgggcatgaccagtccgcctacgacggcaaggattacatcgccctgaacgaggacctgagctcctggaccgcggcg gacaccgcggctcagatcacccagcgcaagtgggaggcggcccgtgtggcggagcagctgagagcctacctggagggcct gtgcgtggagtggctccgcagatacctggagaacgggaaggagacgctgcagcgcgcggaccccccaaagacacacgtga cccaccaccccGtctctgaccatgaggccaccctgaggtgctgggccctgggcttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccatccccatcgtgggcattgttgctggcctggctgtccta...gca gttgtggtcatcggagctgtggtcgctActgtgatgtgtaggaggaagagCtcag

B*3543

(SEQ ID NO: 1386)

atgcgggtcacggcgccccgaaccgtcctcctgctgctctgggggcagtggccctgaccgagacctgggccggctccca ctccatgaggtatttctacaccgccatgtcccggcccggccgcggggagccccgcttcatcgcagtgggctacgtggacg acacccagttcgtgaggttcgacagcgacgccgcgagtccgaggaCggagccccgggcgccatggatagagcaggagggg ccggagtattgggaccggaacacacagatctTcaagaccaacacacagactTaccgagagagcctgcggaacctgcgcgg ctactacaaccagagcgaggccgggtctcacaccctccagagGatgtacggctgcgacgtggggccggacgggcgcctcc

```
tccgcgggcatgaccagtccgcctacgacggcaaggattacatcgccctgaacgaggacctgagctcctggaccgcggcg
gacacggcggctcagatcacccagcgcaagtgggaggcggcccgtgaggcggagcagTggagagcctacctggagggcct
gtgcgtggagtggctccgcagatacctggagaacgggaaggagacgctgcagcgcgcggacccccaaagacacatgtga
cccaccacccatctctgaccatgaggccaccctgaggtgctgggccctgggcttctaccctgcggagatcacactgacc
tggcagcgggatggcgaggaccaaactcaggacaccgagcttgtggagaccagaccagcaggagatagaaccttccagaa
gtgggcagctgtggtggtgccttctggagaagagcagagatacacatgccatgtacagcatgaggggctgccgaagcccc
tcaccctgagatgggagccatcttcccagtccaccatccccatcgtgggcattgttgctggcctggctgtccta...gca
gttgtggtcatcggagctgtggtcgctactgtgatgtgtaggaggaagagCtcaggtgga
```

B*3544
(SEQ ID NO: 1387)
```
gctcccactccatgaggtatttctacaccgccatgtcccggcccggccgcggggagccccgcttcatcgcagtgggctac
gtggacgacacccagttcgtgaggttcgacagcgacgccgcgagtccgaggacggagcccgggcgccatggatagagca
ggaggggccggagtattgggaccggaacacacagatctTcaagaccaacacacagacttaccgagagagcctgcggaacc
tgcgcggctactacaaccagagcgaggccgggtctcacaccctccagaggatgtacggctgcgacgtggggccggacggg
cgcctcctccgcgggcatAaccagtacgcctacgacggcaaggattacatcgccctgaacgaggacctgagctcctggac
cgcGgcggacacggcggctcagatcacccagcgcaagtgggaggcggcccgtgaggcggagcagTggagagcctacctgg
agggccTgtgcgtggagtggctccgcagatacctggagaacgggaaggagacgctgcagcgcgcGg
```

B*3545
(SEQ ID NO: 1388)
```
gctcccactccatgaggtatttctacaccgccatgtcccggcccggccgcggggagccccgcttcatcgcagtgggctac
gtggacgacacccagttcgtgaggttcgacagcgacgccgcgagtccgaggacggagcccgggcgccatggatagagca
ggaggggccggagtattgggaccggaacacacagatcttcaagaccaacacacagacttaccgagagagcctgcggaacc
tgcgcggctactacaaccagagcgaggccgggtctcacatcAtccagaggatgtatggctgcgacctggggccCgacggg
cgcctcctccgcgggcatgaccagtCcgcctacgacggcaaggattacatcgccctgaacgaggacctgagctcctggac
cgcggcggacacCgcggctcagatcacccagcgcaagtgggaggcggcccgtgTggcggagcagcggagagcctacctgg
agggccTgtgcgtggagtCgctccgcagatacctggagaacgggaaggagacgctgcagcgcgcGg
```

B*3701
(SEQ ID NO: 1389)
```
atgcgggtcacggcgccccgaaccctcctcctgctgctctgggggggcagtggccctgaccgagacctgggctggctccca
ctccatgaggtatttccacacctccgtgtcccggcccggccgcggggagccccgcttcatctcagtgggctacgtggacg
acacccagttcgtgaggttcgacagcgacgccgcgagtccgaggacggagcccgggcgccgtggatagagcaggagggg
ccggagtattgggaccgggagacacagatctccaagaccaacacacagacttaccgagaggacctgcggaccctgctccg
ctactacaaccagagcgaggccgggtctcacaccatccagaggatgtCtggctgcgacgtggggccggacgggcgcctcc
tccgcgggtataaccagttcgcctacgacggcaaggattacatcgccctgaacgaggacctgagctcctggaccgcggcg
gacaccgcggctcagatcacccagcgcaagtgggaggcggcccgtgtggcggagcaggacagagcctacctggagggcac
gtgcgtggagtggctccgcagatacctggagaacgggaaggagacgctgcagcgcgcggacccccaaagacacatgtga
cccaccacccatctctgaccatgaggccaccctgaggtgctgggccctgggcttctaccctgcggagatcacactgacc
tggcagcgggatggcgaggaccaaactcaggacaccgagcttgtggagaccagaccagcaggagatagaaccttccagaa
gtgggcagctgtggtggtgccttctggagaagagcagagatacacatgccatgtacagcatgaggggctgccgaagcccc
tcaccctgagatgggagccatcttcccagtccaccatccccatcgtgggcattgttgctggcctggctgtccta...gca
gttgtggtcatcggagctgtggtcgctactgtgatgtgtaggaggaagagCtcaggtgga
```

-continued

B*3702

(SEQ ID NO: 1390)

atgcgggtcacggcgccccgaaccctcctcctgctgctctgggggcagtggccctgaccgagacctgggctggctccca ctccatgaggtatttccacacctccgtgtcccggcccggccgcggggagccccgcttcatctcagtgggctacgtggacg acacccagttcgtgaggttcgacagcgacgccgcgagtccgaggacggagccccgggcgccgtggatagagcaggagggg ccggagtattgggaccgggagacacagatctccaagaccaacacacagactTaccgagagGacctgcggaccctgctccg ctactacaaccagagcgaggccgggtctcacaccctccagaaTatgtatggctgcgacgtggggccggacgggcgcctcc tccgcgggtaccaccagGacgcctacgacggcaaggattacatcgccctgaacgaggacctgAgctcctggaccgccgcg gacacggcggctcagatcacccagcgcaagtgggaggcggcccgtgtggcggagcagcTgagagcctacctggagggcga gtgcgtggagtggctccgcagatacctggagaacgggaaggagacgctgcagcgcgcggaccccccaaagacacacgtga cccaccacccatctctgaccatgaggccaccctgaggtgctgggccctgggcttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccgtcttcccagtccaccgtccccatcgtgggcattgttgctggcctggctgtccta...gca gttgtggtcatcggagctgtggtcgctgctgtgatgtgtaggaggaagagCtcaggtgga

B*3704

(SEQ ID NO: 1391)

atgcgggtcacggcgccccgaaccctcctcctgctgctctgggggcagtggccctgaccgagacctgggctggctccca ctccatgaggtatttccacacctccgtgtcccggcccggccgcggggagccccgcttcatctcagtgggctacgtggacg acacccagttcgtgaggttcgacagcgacgccgcgagtccgaggacggagccccgggcgccgtggatagagcaggagggg ccggagtattgggaccgggagacacagatctccaagaccaacacacagacttaccgagaggacctgcggaccctgctccg ctactacaaccagagcgaggccgggtctcacaccatccagaggatgtCtggctgcgacgtggggccggacgggcgcctcc tccgcgggtataaccagttcgcctacgacggcaaggattacatcgccctgaacgaggacctgagctcctggaccgcggcg gacaccgcggctcagatcacccagcgcaagtgggaggcggcccgtgtggcggagcaggacagagcctacctggagggcac gtgcgtggagtggctccgcagaCacctggagaacgggaaggagacgctgcagcgcgcggaccccccaaagacacatgtga cccaccacccatctctgaccatgaggccaccctgaggtgctgggccctgggcttctaccctgcggagatcacactgacc tggcagcgggatggcgaggaccaaactcaggacaccgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccatccccatcgtgggcattgttgctggcctggctgtccta...gca gttgtggtcatcggagctgtggtcgctactgtgatgtgtaggaggaagagCtcaggtgga

B*3705

(SEQ ID NO: 1392)

atgcgggtcacggcgccccgaaccctcctcctgctgctctgggggcagtggccctgaccgagacctgggctggctccca ctccatgaggtatttccacacctccgtgtcccggcccggccgcggggagccccgcttcatctcagtgggctacgtggacg acacccagttcgtgaggttcgacagcgacgccgcgagtccgaggacggagccccgggcgccgtggatagagcaggagggg ccggagtattgggaccgggagacacagatctccaagaccaacacacagacttaccgagaggacctgcggaacctgcgcgg ctactacaaccagagcgaggccgggtctcacaccatccagaggatgtCtggctgcgacgtggggccggacgggcgcctcc tccgcgggtataaccagttcgcctacgacggcaaggattacatcgccctgaacgaggacctgagctcctggaccgcggcg gacaccgcggctcagatcacccagcgcaagtgggaggcggcccgtgtggcggagcaggaCagagcctacctggagggcaC gtgcgtggagtggctccgcagatacctggagaacgggaaggagacgctgcagcgcgcgg

B*3801

(SEQ ID NO: 1393)

atgctggtcatggcgccccgaaccgtcctcctgctgctctcggcggccctggccctgaccgagacctgggcccggctccca ctccatgaggtatttctacacctccgtgtcccggcccggccgcggggagccccgcttcatctcagtgggctacgtggacg -continued acacgcagttcgtgaggttcgacagcgacgccgcgagtccgagagaggagccgcgggcgccgtggatagagcaggagggg ccggaatatttgggaccggaacacacagatctgcaagaccaacacacagacttaccgagagaacctgcggaTcgcgctcCg ctactacaaccagagcgaggccgggtctcacaccctccagagGatgtacggctgcgacgtggggccggacgggcgcctcc tccgcgggcataaccagttcgcctacgacggcaaggattacatcgccctgaacgaggacctgagctcctggaccgcggcg gacaccgcggctcagatcacccagcgcaagtgggaggcggcccgtgtggcggagcagcTgagaAcctacctggagggcac gtgcgtggagtggctccgcagatacctggagaacgggaaggagacgctgcagcgcgcggaccccccaaagacacatgtga cccaccaccccatctctgaccatgaggccaccctgaggtgctgggccctgggcttctaccctgcggagatcacactgacc tggcagcgggatggcgaggaccaaactcaggacaccgagcttgtggagaccagaccagcaggagaCagaaccttccagaa gtgggcagctgtggtggtgccttctggagaagagcagagatacacatgccatgtacagcatgaggggctgccgaagcccc tcaccctgagatgggagccAtcttcccagtccaccgtccccatcgtgggcattgttgctggcctggctgtccta...gca gttgtggtcatcggagctgtggtcgctgctgtgatgtgtaggaggaagagttcaggtgga

B*380201

(SEQ ID NO: 1394)

atgctggtcatggcgccccgaaccgtcctcctgctgctctcggcggccctggccctgaccgagacctgggccggctccca ctccatgaggtatttctacacctccgtgtcccggcccggccgcggggagccccgcttcatctcagtgggctacgtggacg acacgcagttcgtgaggttcgacagcgacgccgcgagtccgagagaggagccgcgggcgccgtggatagagcaggagggg ccggaatatttgggaccggaacacacagatctgcaagaccaacacacagacttaccgagagaacctgcgcaCcgcgctcCg ctactacaaccagagcgaggccgggtctcacaccctccagagGatgtacggctgcgacgtggggccggacgggcgcctcc tccgcgggcataaccagttcgcctacgacggcaaggattacatcgccctgaacgaggacctgagctcctggaccgcggcg gacaccgcggctcagatcacccagcgcaagtgggaggcggcccgtgtggcggagcagcTgagaAcctacctggagggcac gtgcgtggagtggctccgcagatacctggagaacgggaaggagacgctgcagcgcgcggaccccccaaagacacatgtga cccaccaccccatctctgaccatgaggccaccctgaggtgctgggccctgggcttctaccctgcggagatcacactgacc tggcagcgggatggcgaggaccaaactcaggacaccgagcttgtggagaccagaccagcaggagaCagaaccttccagaa gtgggcagctgtggtggtgccttctggagaagagcagagatacacatgccatgtacagcatgaggggctgccgaagcccc tcaccctgagatgggagccAtcttcccagtccaccgtccccatcgtgggcattgttgctggcctggctgtccta...gca gttgtggtcatcggagctgtggtcgctgctgtgatgtgtaggaggaagagttcaggtgga

B*380202

(SEQ ID NO: 1395)

gctcccactccatgaggtatttctacacctccgtgtcccggcccggccgcggggagccccgcttcatctcagtgggctac gtggacgacacgcagttcgtgaggttcgacagcgacgccgcgagtccgagagaggagccgcgggcgccgtggatagagca ggagggggccggaatatttgggaccggaacacacagatctgcaagaccaacacacagacttaccgagagaacctgcgcaccg cgctccgctactacaaccagagcgaggccgggtctcacaccctccagaggatgtacggctgcgacgtggggccggacggg cgcctcctccgcgggcataaccagttcgcctacgacggcaaggattacatcgccctgaacgaggacctgagctcctggac Agcggcggacaccgcggctcagatcacccagcgcaagtgggaggcggcccgtgtggcggagcagctgagaacctacctgg agggcacgtgcgtggagtggctccgcagatacctggagaacgggaaggagacgctgcagcgcgcgg

B*3803

(SEQ ID NO: 1396)

gctcccactccatgaggtatttctacacctccgtgtcccggcccggccgcggggagccccgcttcatctcagtgggctac gtggacgacacgcagttcgtgaggttcgacagcgacgccgcgagtccgagagaggagccgcgggcgccgtggatagagca ggagggggccggaAtatttgggaccgggagacacagatctCcaagaccaacacacagactgaccgagagagcctgcgcaCcg cgctcCgctactacaaccagagcgaggccgggtctcacaccctccagagGatgtacggctgcgacgtggggccggacggg cgcctcctccgcgggcatAaccagtTcgcctacgacggcaaggattacatcgccctgaacgaggacctgagctcctggac cgcggcggacaccgcggctcagatcacccagcgcaagtgggaggcggcccgtgtggcggagcagcTgagaAcctacctgg agggcaCgtgcgtggagtggctccgcagatacctggagaacgggaaggagacgctgcagcgcgcGg

B*3804

(SEQ ID NO: 1397)
gctcccactccatgaggtatttctacacctccgtgtcccggcccggccgcggggagccccgcttcatctcagtgggctac
gtggacgacacgcagttcgtgaggttcgacagcgacgccgcgagtccgagagaggagccgcgggcgccgtggatagagca
ggaggggccggagtattgggacccgggaGacacagatctgcaagaccaacacacagacttaccgagagaAcctgcgcaCcg
cgctcCgctactacaaccagagcgaggccgggtctcacaccctccagagGatgtacggctgcgacgtggggccggacggg
cgcctcctccgcgggcatAaccagtTcgcctacgacggcaaggattacatcgccctgaacgaggacctgagctcctggac
cgcggcggacaccgcggctcagatcacccagcgcaagtgggaggcggcccgtgTggcggagcagcTgagaAcctacctgg
agggcaCgtgcgtggagtggctccgcagatacctggagaacgggaaggagacgctgcagcgcgcGg

B*3805

(SEQ ID NO: 1398)
gctcccactccatgaggtatttctacaccGccgtgtcccggcccggccgcggggagccccgcttcatctcagtgggctac
gtggacgacacgcagttcgtgaggttcgacagcgacgccgcgagtccgagagaggagccgcgggcgccgtggatagagca
ggaggggccggaatattgggaccggaacacacagatctgcaagaccaacacacagacttaccgagagaacctgcggaTcg
cgctcCgctactacaaccagagcgaggccgggtctcacaccctccagagGatgtacggctgcgacgtggggccggacggg
cgcctcctccgcgggcataaccagttcgcctacgacggcaaggattacatcgccctgaacgaggacctgagctcctggac
cgcggcggacaccgcggctcagatcacccagcgcaagtgggaggcggcccgtgtggcggagcagcTgagaAcctacctgg
agggcacgtgcgtggagtggctccgcagatacctggagaacgggaaggagacgctgcagcgcgcggaccccccaaagaca
catgtgacccaccacccatctctgaccatgaggccaccctgaggtgctgggccctgggcttctaccctgcggagatcac
actgacctggcagcgggatggcgaggaccaaactcaggacaccgagcttgtggagaccagaccagcaggagaCagaacct
tccagaagtgggcagctgtggtggtgccttctggagaagagcagagatacacatgccatgtacagcatgaggggctgccg
aagcccctcaccctgagatggg

B*3806

(SEQ ID NO: 1399)
gctcccactccatgaggtatttctacacctccgtgtcccggcccggccgcggggagccccgcttcatctcagtgggctac
gtggacgacacgcagttcgtgaggttcgacagcgacgccgcgagtccgaggacggagccccgggcgccatggatagagca
ggaggggccggagtattgggaccggaacacacagatctTcaagaccaacacacagacttaccgagagaacctgcggaTcg
cgctcCgctactacaaccagagcgaggccgggtctcacaccctccagagGatgtacggctgcgacgtggggccggacggg
cgcctcctccgcgggcatAaccagtTcgcctacgacggcaaggattacatcgccctgaacgaggacctgagctcctggac
cgcggcggacaccgcggctcagatcacccagcgcaagtgggaggcggcccgtgTggcggagcagcTgagaAcctacctgg
agggcaCgtgcgtggagtggctccgcagatacctggagaacgggaaggagacgctgcagcgcgcGg

B*3807

(SEQ ID NO: 1400)
gctcccactccatgaggtatttctacacctccgtgtcccggcccggccgcggggagccccgcttcatctcagtgggctac
gtggacgacacgcagttcgtgaggttcgacagcgacgccgcgagtccgaggacggagccccgggcgccatggatagagca
ggaggggccggGatattgggaccggaacacacagatcttcaagaccaacacacagacttaccgagagaacctgcggatcg
cgctccgctactacaaccagagcgaggccgggtctcacaccctccagaggatgtacggctgcgacgtggggccggacggg
cgcctcctccgcgggcataaccagttcgcctacgacggcaaggattacatcgccctgaacgaggacctgagctcctggac
cgcggcggacaccgcggctcagatcacccagcgcaagtgggaggcggcccgtgtggcggagcagctgagaacctacctgg
agggcacgtgcgtggagtggctccgcagatacctggagaacgggaaggagacgctgcagcgcgcgg

B*3808

(SEQ ID NO: 1401)
gctcccactccatgaggtatttctacacctccgtgtcccggcccggccgcggggagccccgcttcatctcagtgggctac
gtggacgacacgcagttcgtgaggttcgacagcgacgccgcgagtccgagagaggagccgcgggcgccgtggatagagca
ggaggggccggaAtattgggaccggaacacacagatctgcaagaccaacacacagacttaccgagagaacctgcgcaccg -continued cgctccgctactacaaccagagcgaggccgggtctcacaccctccagaggatgtacggctgcgacgtggggccggacggg cgcctcctccgcgggcataaccagttcgcctacgacggcaaggattacatcgccctgaacgaggacctgagctcctggac cgcggcggacaccgcggctcagatcacccagcgcaagtgggaggcggcccgtgtggcggagcagctgagaacctacctgg agggcATgtgcgtggagtggctccgcagatacctggagaacgggaaggagacgctgcagcgcgcGg

B*3809

(SEQ ID NO: 1402)
gctcccactccatgaggtatttctacacctccgtgtcccggcccggccgcggggagccccgcttcatctcagtgggctac gtggacgacacgcagttcgtgaggttcgacagcgacgccgcgagtccgagagaggagccgcgggcgccgtggatagagca ggaggggccggaatattgggaccggaacacacagatctgcaagaccaacacacagacttaccgagagaacctgcggatcg cgctccgctactacaaccagagcgaggccgggtctcacaccctccagaggatgtacggctgcgacgtggggccggacggg cgcctcctccgcgggcataaccagttcgcctacgacggcaaggattacatcgccctgaacgaggacctgagctcctggac cgcggcggaGaccgcggctcagatcacccagcgcaagtgggaggcggcccgtgtggcggagcagctgagaacctacctgg agggcacgtgcgtggagtggctccgcagatacctggagaacgggaaggagacgctgcagcgcgcg

B*390101

(SEQ ID NO: 1403)
atgctggtcatggcgccccgaaccgtcctcctgctgctctcggcggccctggccctgaccgagacctgggccggctccca ctccatgaggtatttctacacctccgtgtcccggcccggccgcggggagccccgcttcatctcagtgggctacgtggacg acacgcagttcgtgaggttcgacagcgacgccgcgagtccgagagaggagccgcgggcgccgtggatagagcaggagggg ccggaatattgggaccggaacacacagatctGcaagaccaacAcacagactgaccgagagagcctgcggaacctgcgcgg ctactacaaccagagcgaggccgggtctcacaccctccagagGatgtacggctgcgacgtggggccggacgggcgcctcc tccgcgggcataaccagttcgcctacgacggcaaggattacatcgccctgaacgaggacctgagctcctggaccgcggcg gacaccgcggctcagatcacccagcgcaagtgggaggcggcccgtgtggcggagcagcTgagaAcctacctggagggcac gtgcgtggagtggctccgcagatacctggagaacgggaaggagacgctgcagcgcgcggaccccccaaagacacatgtga cccaccaccccatctctgaccatgaggccaccctgaggtgctgggccctgggcttctaccctgcggagatcacactgacc tggcagcgggatggcgaggaccaaactcaggacaccgagcttgtggagaccagaccagcaggagaCagaaccttccagaa gtgggcagctgtggtggtgccttctggagaagagcagagatacacatgccatgtacagcatgaggggctgccgaagcccc tcaccctgagatgggagccAtcttcccagtccaccgtccccatcgtgggcattgttgctggcctggctgtccta...gca gttgtggtcatcggagctgtggtcgctgctgtgatgtgtaggaggaagagttcaggtgga

B*390103

(SEQ ID NO: 1404)
atgctggtcatggcgccccgaaccgtcctcctgctgctctcggcggccctggccctgaccgagacctgggccggctccca ctccatgaggtatttctacacctccgtgtcccggcccggccgcggggagccccgcttcatctcagtgggctacgtggacg acacgcagttcgtgaggttcgacagcgacgccgcgagtccgagagaggagccgcgggcgccgtggatagagcaggagggg ccggaatattgggaccggaacacacagatctGcaagaccaacacacagactgaccgagagagcctgcggaacctgcgcgg ctactacaaccagagcgaggccgggtctcacaccctccagaggatgtacggctgcgacgtggggccggacgggcgcctcc tccgcgggcataaccagttcgcctacgacggcaaggattacatcgccctgaacgaggacctgagctcctggaccgcggcg gacaccgcggctcagatcacccagcgcaagtgggaggcggcccgtgtggcggagcagctgagaacctacctggagggcac gtgcgtggagtggctccgcagatacctggagaacgggaaggagacgctgcagcgcgcggaccccccaaagacacatgtga cccaccaccccatctctgaccatgaggccaccctgaggtgctgggccctgggcttctaccctgcggagatcacactgacc tggcagcgggatggcgaggaccaaactcaggacaccgagcttgtggagaccagaccagcaggagaCagaaccttccagaa gtgggcagctgtggtggtgccttctggagaagagcagagatacacatgccatgtacagcatgaggggctgccgaagcccc tcaccctgagatgggagccatcttcccagtccaccgtccccatcgtgggcattgttgctggcctggctgtccta...gca gttgtggtcatcggagctgtggtcgctgctgtgatgtgtaggaggaagagCtcaggtgga

B*390104

(SEQ ID NO: 1405)

gctcccactccatgaggtatttctacacctccgtgtcccggcccggccgcggggagccccgcttcatctcagtgggctac gtggacgacacgcagttcgtgaggttcgacagcgacgccgcgagtccgagagaggagccgcgggcgccgtggatagagca ggaggggccAgaatattgggaccggaacacacagatctgcaagaccaacacacagactgaccgagagagcctgcggaacc tgcgcggctactacaaccagagcgaggccgggtctcacaccctccagaggatgtacggctgcgacgtggggccggacggg cgcctcctccgcgggcataaccagttcgcctacgacggcaaggattacatcgccctgaacgaggacctgagctcctggac cgcggcggacaccgcggctcagatcacccagcgcaagtgggaggcggcccgtgtggcggagcagctgagaacctacctgg agggcacgtgcgtggagtggctccgcagatacctggagaacgggaaggagacgctgcagcgcgcgg

B*390201

(SEQ ID NO: 1406)

atgctggtcatggcgccccgaaccgtcctcctgctgctctcggcggccctggccctgaccgagacctgggccggctccca ctccatgaggtatttctacacctccgtgtcccggcccggccgcggggagccccgcttcatctcagtgggctacgtggacg acacgcagttcgtgaggttcgacagcgacgccgcgagtccgagagaggagccgcgggcgccgtggatagagcaggagggg ccggaatattgggaccgggagacacagatctCcaagaccaacacacagactgaccgagagagcctgcggaacctgcgcgg ctactacaaccagagcgaggccgggtctcacaccctccagaggatgtacggctgcgacgtggggccggacgggcgcctcc tccgcgggcataaccagttcgcctacgacggcaaggattacatcgccctgaacgaggacctgagctcctggaccgcggcg gacaccgcggctcagatcacccagcgcaagtgggaggcggcccgtgtggcggagcagctgagaacctacctggagggcac gtgcgtggagtggctccgcagatacctggagaacgggaaggagacgctgcagcgcgcggaccccccaaagacacatgtga cccaccaccccatctctgaccatgaggccaccctgaggtgctgggccctgggcttctaccctgcggagatcacactgacc tggcagcgggatggcgaggaccaaactcaggacaccgagcttgtggagaccagaccagcaggagaCagaaccttccagaa gtgggcagctgtggtggtgccttctggagaagagcagagatacacatgccatgtacagcatgaggggctgccgaagcccc tcaccctgagatgggagccatcttcccagtccaccgtccccatcgtgggcattgttgctggcctggctgtccta...gca gttgtggtcatcggagctgtggtcgctgctgtgatgtgtaggaggaagagCtcaggtgga

B*390202

(SEQ ID NO: 1407)

atgctggtcatggcgccccgaaccgtcctcctgctgctctcggcggccctggccctgaccgagacctgggccggctccca ctccatgaggtatttctacacctccgtgtcccggcccggccgcggggagccccgcttcatctcagtgggctacgtggacg acacgcagttcgtgaggttcgacagcgacgccgcgagtccgagagaggagccgcgggcgccgtggatagagcaggagggg ccggagtattgggaccgggagacacagatctCcaagaccaacAcacagactgaccgagagagcctgcggaacctgcgcgg ctactacaaccagagcgaggccgggtctcacaccctccagagGatgtacggctgcgacgtggggccggacgggcgcctcc tccgcgggcataaccagttcgcctacgacggcaaggattacatcgccctgaacgaggacctgagctcctggaccgcggcg gacaccgcggctcagatcacccagcgcaagtgggaggcggcccgtgtggcggagcagcTgagaAcctacctggagggcac gtgcgtggagtggctccgcagatacctggagaacgggaaggagacgctgcagcgcgcggaccccccaaagacacatgtga cccaccaccccatctctgaccatgaggccaccctgaggtgctgggccctgggcttctaccctgcggagatcacactgacc tggcagcgggatggcgaggaccaaactcaggacaccgagcttgtggagaccagaccagcaggagaCagaaccttccagaa gtgggcagctgtggtggtgccttctggagaagagcagagatacacatgccatgtacagcatgaggggctgccgaagcccc tcaccctgagatgggagccAtcttcccagtccaccgtccccatcgtgggcattgttgctggcctggctgtccta...gca gttgtggtcatcggagctgtggtcgctgctgtgatgtgtaggaggaagagttcaggtgga

B*3903

(SEQ ID NO: 1408)

gtcctcctgctgctctcggcggccctggccctgaccgagacctgggccggctcccactccatgaggtatttctacacctc cgtgtcccggcccggccgcggggagccccgcttcatctcagtgggctacgtggacgacacgcagttcgtgaggttcgaca gcgacgccgcgagtccgagagaggagccgcgggcgccgtggatagagcaggaggggccggaatattgggaccggaacaca -continued cagatctGcaagaccaacAcacagactgaccgagagagcctgcggaacctgcgcggctactacaaccagagcgaggccgg gtctcacaccctccagagcatgtacggctgcgacgtggggccggacgggcgcctcctccgcgggcataaccagttcgcct acgacggcaaggattacatcgccctgaacgaggacctgagctcctggaccgcggcggacaccgcggctcagatcacccag cgcaagtgggaggcggcccgtgtggcggagcagcTgagaAcctacctggagggcacgtgcgtggagtggctccgcagata cctggagaacgggaaggagacgctgcagcgcgcggacccccccaaagacacatgtgacccaccaccccatctctgaccatg aggccaccctgaggtgctgggccctgggcttctaccctgcggagatcacactgacctggcagcgggatggcgaggaccaa actcaggacaccgagcttgtggagaccagaccagcaggagaCagaaccttccagaagtgggcagctgtggtggtgccttc tggagaagagcagagatacacatgccatgtacagcatgaggggctgccgaagcccctcaccctgagatgggagccAtctt cccagtccaccgtccccatcgtgggcattgttgctggcctggctgtccta...gcagttgtggtcatcggagctgtggtc gctgctgtgatgtgtaggaggaagagttcaggtgga B*3904
(SEQ ID NO: 1409)
atgctggtcatggcgccccgaaccgtcctcctgctgctctcggcggccctggccctgaccgagacctgggccggctccca ctccatgaggtatttctacaccgccAtgtcccggcccggccgcggggagcccgcttcatctcagtgggctacgtggacg acacgcagttcgtgaggttcgacagcgacgccgcgagtccgagagaggagccgcgggcgccgtggatagagcaggagggg ccggaatattgggaccggaacacacagatctGcaagaccaacAcacagactgaccgagagagcctgcggaacctgcgcgg ctactacaaccagagcgaggccgggtctcacaccctccagagGatgtacggctgcgacgtggggccggacgggcgcctcc tccgcgggcataaccagttcgcctacgacggcaaggattacatcgccctgaacgaggacctgagctcctggaccgcggcg gacaccgcggctcagatcacccagcgcaagtgggaggcggcccgtgtggcggagcagcTgagaAcctacctggagggcac gtgcgtggagtggctccgcagatacctggagaacgggaaggagacgctgcagcgcgcggacccccccaaagacacatgtga cccaccaccccatctctgaccatgaggccaccctgaggtgctgggccctgggcttctaccctgcggagatcacactgacc tggcagcgggatggcgaggaccaaactcaggacaccgagcttgtggagaccagaccagcaggagaCagaaccttccagaa gtgggcagctgtggtggtgccttctggagaagagcagagatacacatgccatgtacagcatgaggggctgccgaagcccc tcaccctgagatgggagccAtcttcccagtccaccgtccccatcgtgggcattgttgctggcctggctgtccta...gca gttgtggtcatcggagctgtggtcgctgctgtgatgtgtaggaggaagagttcaggtgga B*3905
(SEQ ID NO: 1410)
atgctggtcatggcgccccgaaccgtcctcctgctgctctcggcggccctggccctgaccgagacctgggccggctccca ctccatgaggtatttctacacctccgtgtcccggcccggccgcggggagcccgcttcatctcagtgggctacgtggacg acacgcagttcgtgaggttcgacagcgacgccgcgagtccgagagaggagccgcgggcgccgtggatagagcaggagggg ccggaatattgggaccggaacacacagatctgcaagaccaacacacagactTaccgagagagcctgcggaacctgcgcgg ctactacaaccagagcgaggccgggtctcacaccctccagagGatgtacggctgcgacgtggggccggacgggcgcctcc tccgcgggcataaccagttcgcctacgacggcaaggattacatcgccctgaacgaggacctgagctcctggaccgcggcg gacaccgcggctcagatcacccagcgcaagtgggaggcggcccgtgtggcggagcagcTgagaAcctacctggagggcac gtgcgtggagtggctccgcagatacctggagaacgggaaggagacgctgcagcgcgcggacccccccaaagacacatgtga cccaccaccccatctctgaccatgaggccaccctgaggtgctgggccctgggcttctaccctgcggagatcacactgacc tggcagcgggatggcgaggaccaaactcaggacaccgagcttgtggagaccagaccagcaggagaCagaaccttccagaa gtgggcagctgtggtggtgccttctggagaagagcagagatacacatgccatgtacagcatgaggggctgccgaagcccc tcaccctgagatgggagccAtcttcccagtccaccgtccccatcgtgggcattgttgctggcctggctgtccta...gca gttgtggtcatcggagctgtggtcgctgctgtgatgtgtaggaggaagagttcaggtgga B*390601
(SEQ ID NO: 1411)
atgctggtcatggcgccccgaaccgtcctcctgctgctctcggcggccctggccctgaccgagacctgggccggctccca ctccatgaggtatttctacacctccgtgtcccggcccggccgcggggagcccgcttcatctcagtgggctacgtggacg acacgcagttcgtgaggttcgacagcgacgccgcgagtccgagagaggagccgcgggcgccgtggatagagcaggagggg ccggaatattgggaccggaacacacagatctgcaagaccaacacacagactgaccgagagagcctgcggaacctgcgcgg ctactacaaccagagcgaggccgggtctcacacttggcagaCGatgtacggctgcgacgtggggccggacgggcgcctcc tccgcgggcataaccagttcgcctacgacggcaaggattacatcgccctgaacgaggacctgagctcctggaccgcggcg gacaccgcggctcagatcacccagcgcaagtgggaggcggcccgtgtggcggagcagcTgagaAcctacctggagggcac gtgcgtggagtggctccgcagatacctggagaacgggaaggagacgctgcagcgcgcggaccccccaaagacacatgtga cccaccaccccatctctgaccatgaggccaccctgaggtgctgggccctgggcttctaccctgcggagatcacactgacc tggcagcgggatggcgaggaccaaactcaggacaccgagcttgtggagaccagaccagcaggagaCagaaccttccagaa gtgggcagctgtggtggtgccttctggagaagagcagagatacacatgccatgtacagcatgaggggctgccgaagcccc tcaccctgagatgggagccAtcttcccagtccaccgtccccatcgtgggcattgttgctggcctggctgtccta...gca gttgtggtcatcggagctgtggtcgctgctgtgatgtgtaggaggaagagttcaggtgga

B*390602 (SEQ ID NO: 1412)

atgctggtcatggcgccccgaaccgtcctcctgctgctctcggcggccctggccctgaccgagacctgggccggctccca ctccatgaggtatttctacacctccgtgtcccggcccggccgcggggagccccgcttcatctcagtgggctacgtggacg acacgcagttcgtgaggttcgacagcgacgccgcgagtccgagagaggagccgcgggcgccgtggatagagcaggagggg ccggaatattgggaccggaacacacagatctgcaagaccaacacacagactgaccgagagagcctgcggaacctgcgcgg ctactacaaccagagcgaggccgggtctcacacttggcagaCgatgtaTggctgcgacgtggggccggacgggcgcctcc tccgcgggcataaccagttcgcctacgacggcaaggattacatcgccctgaacgaggacctgagctcctggaccgcggcg gacaccgcggctcagatcacccagcgcaagtgggaggcggcccgtgtggcggagcagcTgagaAcctacctggagggcac gtgcgtggagtggctccgcagatacctggagaacgggaaggagacgctgcagcgcgcggaccccccaaagacacatgtga cccaccaccccatctctgaccatgaggccaccctgaggtgctgggccctgggcttctaccctgcggagatcacactgacc tggcagcgggatggcgaggaccaaactcaggacaccgagcttgtggagaccagaccagcaggagaCagaaccttccagaa gtgggcagctgtggtggtgccttctggagaagagcagagatacacatgccatgtacagcatgaggggctgccgaagcccc tcaccctgagatgggagccAtcttcccagtccaccgtccccatcgtgggcattgttgctggcctggctgtccta...gca gttgtggtcatcggagctgtggtcgctgctgtgatgtgtaggaggaagagttcaggtgga

B*3907 (SEQ ID NO: 1413)

ggttcgacagcgacgccgcgagtccgagagaggagccgcgggcgccgtggatagagcaggagggggccggaAtattgggac cggaacacacagatctgcaagaccaacacacagacttaccgagagagcctgcggaacctgcgcggctactacaaccagag cgaggccgggtctcacaccctccagaggatgtacggctgcgacgtggggccggacgggcgcctcctccgcgggcatgacc agtCcgcctacgacggcaaggattacatcgccctgaacgaggacctgagctcctggaccgcggcggacaccgcggctcag atcacccagcgcaagtgggaggcggcccgtgtggcggagcagcTgagaAcctacctggagggcaCgtgcgtggagtggct ccgcagatacctg

B*3908 (SEQ ID NO: 1414)

atgctggtcatggcgccccgaaccgtcctcctgctgctctcggcggccctggccctgaccgagacctgggccggctccca ctccatgaggtatttctacacctccgtgtcccggcccggccgcggggagccccgcttcatctcagtgggctacgtggacg acacgcagttcgtgaggttcgacagcgacgccgcgagtccgagagaggagccgcgggcgccgtggatagagcaggagggg ccggaatattgggaccggagacacagatctCcaagaccaacacacagactTaccgagagagcctgcggaacctgcgcgg ctactacaaccagagcgaggccgggtctcacaccctccagagGatgtacggctgcgacgtggggccggacgggcgcctcc tccgcgggcataaccagttcgcctacgacggcaaggattacatcgccctgaacgaggacctgagctcctggaccgcggcg gacaccgcggctcagatcacccagcgcaagtgggaggcggcccgtgtggcggagcagcggagaAcctacctggagggcac -continued gtgcgtggagtggctccgcagatacctggagaacgggaaggagacgctgcagcgcgcggaccccccaaagacacatgtga cccaccaccccatctctgaccatgaggccaccctgaggtgctgggccctgggcttctaccctgcggagatcacactgacc tggcagcgggatggcgaggaccaaactcaggacaccgagcttgtggagaccagaccagcaggagaCagaaccttccagaa gtgggcagctgtggtggtgccttctggagaagagcagagatacacatgccatgtacagcatgagggctgccgaagcccc tcaccctgagatgggagccAtcttcccagtccaccgtccccatcgtgggcattgttgctggcctggctgtccta...gca gttgtggtcatcggagctgtggtcgctgctgtgatgtgtaggaggaagagttcaggtgga

B*3909

(SEQ ID NO: 1415)

atgctggtcatggcgccccgaaccgtcctcctgctgctctcggcggccctggccctgaccgagacctgggccggctccca ctccatgaggtatttctacacctccgtgtcccggcccggccgcggggagcccgcttcatctcagtgggctacgtggacg acacgcagttcgtgaggttcgacagcgacgccgcgagtccgagagaggagccgcgggcgccgtggatagagcaggaggg ccggaatatttgggaccggaacacacagatctgcaagaccaacacacagactgaccgagagagcctgcggaacctgcgcgg ctactacaaccagagcgaggccgggtctcacaccctccagaggatgtCtggctgcgacgtggggccggacgggcgcctcc tccgcgggcataaccagttcgcctacgacggcaaggattacatcgccctgaacgaggacctgagctcctggaccgcggcg gacaccgcggctcagatcacccagcgcaagtgggaggcggcccgtgtggcggagcagctgagaacctacctggagggcac gtgcgtggagtggctccgcagatacctggagaacgggaaggagacgctgcagcgcgcggaccccccaaagacacatgtga cccaccaccccatctctgaccatgaggccaccctgaggtgctgggccctgggcttctaccctgcggagatcacactgacc tggcagcgggatggcgaggaccaaactcaggacaccgagcttgtggagaccagaccagcaggagaCagaaccttccagaa gtgggcagctgtggtggtgccttctggagaagagcagagatacacatgccatgtacagcatgagggctgccgaagcccc tcaccctgagatgggagccAtcttcccagtccaccgtccccatcgtgggcattgttgctggcctggctgtccta...gca gttgtggtcatcggagctgtggtcgctgctgtgatgtgtaggaggaagagttcaggtgga

B*3910

(SEQ ID NO: 1416)

atgctggtcatggcgccccgaaccgtcctcctgctgctctcggcggccctggccctgaccgagacctgggccggctccca ctccatgaggtatttctacacctccgtgtcccggcccggccgcggggagcccgcttcatctcagtgggctacgtggacg acacgcagttcgtgaggttcgacagcgacgccgcgagtccgagagaggagccgcgggcgccgtggatagagcaggaggg ccggagtatttgggaccggaacacacagatctacaagaccaacAcacagactgaccgagagagcctgcggaacctgcgcgg ctactacaaccagagcgaggccgggtctcacaccctccagagGatgtacggctgcgacgtggggccggacgggcgcctcc tccgcgggcataaccagttcgcctacgacggcaaggattacatcgccctgaacgaggacctgagctcctggaccgcggcg gacaccgcggctcagatcacccagcgcaagtgggaggcggcccgtgtggcggagcagcTgagaAcctacctggagggcac gtgcgtggagtggctccgcagatacctggagaacgggaaggagacgctgcagcgcgcggaccccccaaagacacatgtga cccaccaccccatctctgaccatgaggccaccctgaggtgctgggccctgggcttctaccctgcggagatcacactgacc tggcagcgggatggcgaggaccaaactcaggacaccgagcttgtggagaccagaccagcaggagaCagaaccttccagaa gtgggcagctgtggtggtgccttctggagaagagcagagatacacatgccatgtacagcatgagggctgccgaagcccc tcaccctgagatgggagccAtcttcccagtccaccgtccccatcgtgggcattgttgctggcctggctgtccta...gca gttgtggtcatcggagctgtggtcgctgctgtgatgtgtaggaggaagagttcaggtgga

B*3911

(SEQ ID NO: 1417)

tacacctccgtgtcccggcccggccgcggggagcccgcttcatctcagtgggctacgtggacgacacgcagttcgtgag gttcgacagcgacgccgcgagtccgagagaggagccgcgggcgccgtggatagagcaggaggggccggaAtattgggacc ggaacacacagatctGcaagaccaacacacagactTaccgagagagcctgcggaacctgcgcggctactacaaccagagc gaggccgggtctcacaccctccagagGatgtacggctgcgacgtggggccggacgggcgcctcctccgcgggcataacca gttcgcctacgacggcaaggattacatcgccctgaacgaggacctgagctcctggaccgcggcggacaccgcggctcaga tcacccagcgcaagtgggaggcggcccgtgtggcggagcagcggagaAcctacctggagggcacgtgcgtggagtggctc -continued cgcagatacctggagaacgggaaggagacgctgcagcgcgcggaccccccaaagacacatgtgacccaccacccatctc tgaccatgaggccaccctgaggtgctgggccctgggcttctaccctgcggagatcacactgacctggcagcgggatggcg aggaccaaactcaggacacCgagcttgtggagaccag

B*3912

(SEQ ID NO: 1418)

gctcccactccatgaggtatttcgacaccgccgtgtcccggcccggccgcggAgagccccgcttcatctcagtgggctac gtggacgacacgcagttcgtgaggttcgacagcgacgccgcgagtccgagagaggagccgcgggcgccgtggatagagca ggaggggccggaatattgggaccggaacacacagatctgcaagaccaacacacagactgaccgagagagcctgcggaacc tgcgcggctactacaaccagagcgaggcgggtctcacaccctccagaggatgtacggctgcgacgtggggccggacggg cgcctcctccgcgggcataaccagttcgcctacgacggcaaggattacatcgccctgaacgaggacctgagctcctggac cgcggcggacaccgcggctcagatcacccagcgcaagtgggaggcggcccgtgtggcggagcagctgagaacctacctgg agggcacgtgcgtggagtggctccgcagatacctggagaacgggaaggagacgctgCagcgcgcgg

B*3913

(SEQ ID NO: 1419)

gctcccactccatgaggtatttctacacctccgtgtcccggcccggccgcggggagccccgcttcatctcagtgggctac gtggacgacacgcagttcgtgaggttcgacagcgacgccgcgagtccgagagaggagccgcgggcgccgtggatagagca ggaggggccggagtattgggaccgggagacacagatctCcaagaccaacacacagactTaccgagagagcctgcggaacc tgcgcggctactacaaccagagcgaggcgggtctcacaccctccagagGatgtacggctgcgacgtggggccggacggg cgcctcctccgcgggcatAaccagtTcgcctacgacggcaaggattacatcgccctgaacgaggacctgagctcctggac cgcggcggacaccgcggctcagatcacccagcgcaagtgggaggcggcccgtgTggcggagcagcTgagaAcctacctgg agggcaCgtgcgtggagtggctccgcagatacctggagaacgggaaggagacgctgcagcgcgcGg

B*3914

(SEQ ID NO: 1420)

gctcccactccatgaggtatttctacacctccgtgtcccggcccggccgcggggagccccgcttcatctcagtgggctac gtggacgacacgcagttcgtgaggttcgacagcgacgccgcgagtccgagagaggagccgcgggcgccgtggatagagca ggaggggccggaAtattgggaccggaacacacagatctGcaagaccaacAcacagactgaccgagagagcctgcggaacc tgcgcggctactacaaccagagcgaggccgggtctcacaccctccagagcatgtacggctgcgacgtggggccggacggg cgcctcctccgcgggcatAaccagtacgcctacgacggcaaggattacatcgccctgaacgaggacctgagctcctggac cgcggcggacaccgcggctcagatcacccagcgcaagtgggaggcggcccgtgtggcggagcagcTgagaAcctacctgg agggcaCgtgcgtggagtggctccgcagatacctggagaacgggaaggagacgctgcagcgcgcGg

B*3915

(SEQ ID NO: 1421)

gctcccactccatgaggtatttctacacctccgtgtcccggcccggccgcggggagccccgcttcatctcagtgggctac gtggacgacacgcagttcgtgaggttcgacagcgacgccgcgagtccgagagaggagccgcgggcgccgtggatagagca ggaggggccggaAtattgggaccggaacacacagatctGcaagaccaacAcacagactgaccgagagagcctgcggaacc tgcgcggctactacaaccagagcgaggccgggtctcacaccctccagagGatgtacggctgcgacgtggggccggacggg cgcctcctccgcgggcatgaccagtTcgcctacgacggcaaggattacatcgccctgaacgaggacctgagctcctggac cgcggcggacaccgcggctcagatcacccagcgcaagtgggaggcggcccgtgtggcggagcagcTgagaAcctacctgg agggcaCgtgcgtggagtggctccgcagatacctggagaacgggaaggagacgctgcagcgcgcGg

B*3916

(SEQ ID NO: 1422)

gctcccactccatgaggtatttctacacctccgtgtcccggcccggccgcggggagccccgcttcatctcagtgggctac gtggacgacacgcagttcgtgaggttcgacagcgacgccgcgagtccgagagaggagccgcgggcgccgtggatagagca ggaggggccggagtattgggaccggaacacacagatctacaagaccaacacacagactgaccgagagagcctgcggaacc tgcgcggctactacaaccagagcgaggccgggtctcacaccctccaCaggatgtacggctgcgacgtggggccggacggg cgcctcctccgcgggcataaccagttcgcctacgacggcaaggattacatcgccctgaacgaggacctgagctcctggac cgcggcggacaccgcggctcagatcacccagcgcaagtgggaggcggcccgtgtggcggagcagctgagaacctacctgg agggcacgtgcgtggagtggctccgcagatacctggagaacgggaaggagacgctgcagcgcgcgg B*3917 (SEQ ID NO: 1423)
atgctggtcatggcgcccgaaccgtcctcctgctgctctcggcggccctggccctgaccgagacctgggccggctccca ctccatgaggtatttctacacctccgtgtcccggcccggccgcggggagccccgcttcatctcagtgggctacgtggacg acacgcagttcgtgaggttcgacagcgacgccgcgagtccgagagaggagccgcgggcgccgtggatagagcaggagggg ccggagtattgggaccggaacacacagatctacaagaccaacacacagactgaccgagagagcctgcggaacctgcgcgg ctactacaaccagagcgaggccgggtctcacaccctccagaggatgtacggctgcgacgtggggccggacgggcgcctcc tccgcgggtataaccagttAgcctacgacggcaaggattacatcgccctgaacgaggacctgagctcctggaccgcggcg gacaccgcggctcagatcacccagcgcaagtgggaggcggcccgtgtggcggagcagctgagaAcctacctggagggcaC gtgcgtggagtggctccgcagatacctggagaacgggaaggagacgctgcagcgcgcgGg B*3918 (SEQ ID NO: 1424)
gctcccactccatgaggtatttctacacctccgtgtcccggcccggccgcggggagccccgcttcatctcagtgggctac gtggacgacacgcagttcgtgaggttcgacagcgacgccgcgagtccgagagaggagccgcgggcgccgtggatagagca ggaggggccggaAtattgggaccggaacacacagatctgcaagaccaacacacagactgaccgagagagcctgcggaacc tgcgcggctactacaaccagagcgaggccgggtctcacaccctccagaggatgtacggctgcgacgtggggccggacggg cgcctcctccgcgggcataaccagttcgcctacgacggcaaggattacatcgccctgaacgaggacctgagctcctggac cgcggcggacacgcggctcagatcacccagcgcaagtgggaggcggcccgtgaggcggagcagTggagaAcctacctgg agggcaCgtgcgtggagtggctccgcagatacctggagaacgggaaggagacgctgcagcgcgcgGg B*3919 (SEQ ID NO: 1425)
gctcccactccatgaggtatttctacacctccgtgtcccggcccggccgcggggagccccgcttcatctcagtgggctac gtggacgacacgcagttcgtgaggttcgacagcgacgccgcgagtccgaggacggagccccgggcgccAtggatagagca ggaggggccggagtattgggaccggaacacacagatctGcaagaccaacAcacagactgaccgagagagcctgcggaacc tgcgcggctactacaaccagagcgaggccgggtctcacaccctccagagGatgtacggctgcgacgtggggccggacggg cgcctcctccgcgggcatAaccagtTcgcctacgacggcaaggattacatcgccctgaacgaggacctgagctcctggac cgcggcggacaccgcggctcagatcacccagcgcaagtgggaggcggcccgtgTggcggagcagctgagaAcctacctgg agggcaCgtgcgtggagtggctccgcagatacctggagaacgggaaggagacgctgcagcgcgcgGg B*3920 (SEQ ID NO: 1426)
gctcccactccatgaggtatttctacacctccgtgtcccggcccggccgcggggagccccgcttcatctcagtgggctac gtggacgacacgcagttcgtgaggttcgacagcgacgccgcgagtccgagagaggagccgcgggcgccgtggatagagca ggaggggccggagtattgggaccggaacacacagatctacaagaccaacacacagacttaccgagagaAcctgcggaacc tgcgcggctactacaaccagagcgaggccgggtctcacaccctccagagGatgtacggctgcgacgtggggccggacggg cgcctcctccgcgggcatAaccagtTcgcctacgacggcaaggattacatcgccctgaacgaggacctgagctcctggac cgcggcggacaccgcggctcagatcacccagcgcaagtgggaggcggcccgtgTggcggagcagcTgagaAcctacctgg agggcaCgtgcgtggagtggctccgcagatacctggagaacgggaaggagacgctgcagcgcgcgGg B*3922 (SEQ ID NO: 1427)
gctcccactccatgaggtatttctacacctccgtgtcccggcccggccgcggggagccccgcttcatctcagtgggctac gtggacgacacgcagttcgtgaggttcgacagcgacgccgcgagtccgagagaggagccgcgggcgccgtggatagagca ggaggggccggaAtattgggaccgggaGacacagatctGcaagaccaacAcacagactgaccgagagagcctgcggaacc tgcgcggctactacaaccagagcgaggccgggtctcacaccctccagagGatgtacggctgcgacgtggggccggacggg

```
cgcctcctccgcgggcatAaccagtTcgcctacgacggcaaggattacatcgccctgaacgaggacctgagctcctggac cgcggcggacaccgcggctcagatcacccagcgcaagtgggaggcggcccgtgtggcggagcagcTgagaAcctacctgg agggcaCgtgcgtggagtggctccgcagatacctggagaacgggaaggagacgctgcagcgcgcGg
```

B*3923

(SEQ ID NO: 1428)
```
gctcccactccatgaggtatttctacacctccgtgtcccggcccggccgcggggagccccgcttcatctcagtgggctac gtggacgacacgcagttcgtgaggttcgacagcgacgccgcgagtccgagagaggagccgcgggcgccgtggatagagca ggaggggccggagtattgggaccgggagacacagatctccaagaccaacacacagactgaccgagagagcctgcggaacc tgcgcggctactacaaccagagcgaggccgggtctcacaccctccagaggatgtacggctgcgacgtggggccggacggg cgcctcctccgcgggcataaccagttcgcctacgacggcaaggattacatcgccctgaacgaggacctgagctcctggac cgcggcggacaccgcggctcagatcacccGgcgcaagtgggaggcggcccgtgtggcggagcagctgagaaacctacctgg agggcacgtgcgtggagtggctccgcagatacctggagaacgggaaggagacgctgcagcgcgcgg
```

B*3924

(SEQ ID NO: 1429)
```
atgctggtcatggcgccccgaaccgtcctcctgctgctctcggcggccctggccctgaccgagacctgggccggctccca ctccatgaggtatttctacacctccgtgtcccggcccggccgcggggagccccgcttcatctcagtgggctacgtggacg acacgcagttcgtgaggttcgacagcgacgccgcgagtccgagagaggagccgcgggcgccgtggatagagcaggagggg ccggaatattgggaccggaacacacagatctgcaagaccaacacacagactgaccgagagagcctgcggaacctgcgcgg ctactacaaccagagcgaggccgggtctcacaccctccagagcaCgtacggctgcgacgtggggccggacgggcgcctcc tccgcgggcataaccagttcgcctacgacggcaaggattacatcgccctgaacgaggacctgagctcctggaccgcggcg gacaccgcggctcagatcacccagcgcaagtgggaggcggcccgtgtggcggagcagctgagaaacctacctggagggcac gtgcgtggagtggctccgcagatacctggagaacgggaaggagacgctgcagcgcgcggaccccccaaagacacatgtga cccaccaccccatctctgaccatgaggccaccctgaggtgctgggccctgggcttctaccctgcggagatcacactgacc tggcagcgggatggcgaggaccaaactcaggacaccgagcttgtggagaccagaccagcaggagacagaaccttccagaa gtgggcagctgtggtggtgccttctggagaagagcagagatacacatgccatgtacagcatgaggggctgccgaagcccc tcaccctgagatgggagccatcttcccagtccaccgtccccatcgtgggcattgttgctggcctggctgtccta...gca gttgtggtcatcggagctgtggtcgctgctgtgatgtgtaggaggaagagttcaggtgga
```

B*3926

(SEQ ID NO: 1430)
```
gctcccactccatgaggtatttctacacctccgtgtcccggcccggccgcggggagccccgcttcatctcagtgggctac gtggacgacacgcagttcgtgaggttcgacagcgacgccgcgagtccgagagaggagccgcgggcgccgtggatagagca ggaggggccggaatattgggaccggaacacacagatctgcaagaccaacacacagactgaccgagagagcctgcggaacc tgcgcggctactacaaccagagcgaggccgggtctcacaccctccagaggatgtacggctgcgacgtggggccggacggg cgcctcctccgcgggcataaccagttcgcctacgacggcaaggattacatcgccctgaacgaggacctgagctcctggac cgcggcggacaccgcggctcagatcacccagcgcaagtgggaggcggcccTtgtggcggagcagctgagaaacctacctgg agggcacgtgcgtggagtggctccgcagatacctggagaacgggaaggagacgctgcagcgcgcgg
```

B*3927

(SEQ ID NO: 1431)
```
gctcccactccatgaggtatttctacacctccgtgtcccggcccggccgcggggagccccgcttcatctcagtgggctac gtggacgacacgcagttcgtgaggttcgacagcgacgccgcgagtccgagagaggagccgcgggcgccgtggatagagca ggaggggccggaatattgggaccggaacacacagatctgcaagaccaacAcacagactgaccgagTgagcctgcggaacc tgcgcggctactacaaccagagcgaggccgggtctcacaccctccagaggatgtacggctgcgacgtggggccggacggg cgcctcctccgcgggcataaccagttcgcctacgacggcaaggattacatcgccctgaacgaggacctgagctcctggac
```

-continued cgcggcggacaccgcggctcagatcacccagcgcaagtgggaggcggcccgtgtggcggagcagctgagaAcctacctgg agggcaCgtgcgtggagtggctccgcagatacctggagaacgggaaggagacgctgCagcgcgcGg

B*400101

(SEQ ID NO: 1432)

atgcgggtcacggcaccccgaaccgtcctcctgctgctctcggcggccctggccctgaccgagacctgggcGggctccca ctccatgaggtatttccacaccgccatgtcccggcccggccgcggggagccccgcttcatcaccgtgggctacgtggacg acacgctgttcgtgaggttcgacagcgacgccacgagtccgaggaaggagccgcgggcgccatggatagagcaggagggg ccggagtattgggaccgggagacacagatctccaagaccaacacacagacttaccgagagagcctgcggaacctgcgcgg ctactacaaccagagcgaggccgggtctcacaccctccagaggatgtacggctgcgacgtggggccggacgggcgcctcc tccgcgggcataaccagtacgcctacgacggcaaggattacatcgccctgaacgaggacctgcgctcctggaccgccgcg gacacggcggctcagatctcccagcgcaagttggaggcggcccgtgtggcggagcagctgagagcctacctggagggcga gtgcgtggagtggctccgcagatacctggagaacgggaaggacaagctggagcgcgctgacccccaaagacacacgtga cccaccaccccatctctgaccatgaggccaccctgaggtgctgggccctgggtttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccgtcttcccagtccaccgtccccatcgtgggcattgttgctggcctggctgtccta...gca gttgtggtcatcggagctgtggtcgctgctgtgatgtgtaggaggaagagttcaggtgga

B*400102

(SEQ ID NO: 1433)

atgcgggtcacggcaccccgaaccgtcctcctgctgctctcggcggccctggccctgaccgagacctgggccGgctccca ctccatgaggtatttcCacaccgccatgtcccggcccggccgcggggagccccgcttcatcaccgtgggctacgtggacg acacgcTgttcgtgaggttcgacagcgacgccAcgagtccgaggAaggagccgcgggcgccAtggatagagcaggagggg ccggagtattgggaccgggaGacacagatctCcaagaccaacacacagactTaccgagagagcctgcggaacctgcgcgg ctactacaaccagagcgaggccgggtctcacaccctccagagGatgtacggctgcgacgtggggccggacgggcgcctcc tccgcgggcatAaccagtacgcctacgacggcaaggattacatcgccctgaacgaggacctgcgctcctggaccgccgcg gacacggcggctcagatctcccagcgcaagtTggaggcggcccgtgTggcggagcagctgagagcctacctggagggcga gtgcgtggagtggctccgcagatacctggagaacgggaaggacaagctggagcgcgctgacccccaaagacacacgtga cccaccaccccatctctgaccatgaggccaccctgaggtgctgggccctgggtttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccgtcttcccagtccaccgtccccatcgtgggcattgttgctggcctggctgtccta...gca gttgtggtcatcggagctgtggtcgctgctgtgatgtgtaggaggaagagttcaggtgga

B*400103

(SEQ ID NO: 1434)

gctcccactccatgaggtatttcCacaccgccatgtcccggcccggccgcggggagccccgcttcatcaccgtgggctac gtggacgacacgcTgttcgtgaggttcgacagcgacgccAcgagtccgaggAaggagccgcgggcgccgtggatagagca ggaggggccggagtattgggaccgggaGacacagatctCcaagaccaacacacagactTaccgagagagcctgcggaacc tgcgcggctactacaaccagagcgaggccgggtctcacaccctccagagGatgtacggctgcgacgtggggccggacggg cgcctcctccgcgggcatAaccagtacgcctacgacggcaaggattacatcgccctgaacgaggacctgcgctcctggac cgccgcggacacggcggctcagatctcccagcgcaagtTggaggcggcccgtgTggcggagcagctgagagcctacctgg agggcgagtgcgtggagtggctccgcagatacctggagaacgggaaggacaagctggagcgcgctgacccccaaagaca cacgtgacccaccaccccatctctgaccatgaggccaccctgaggtgctgggccctgggtttctaccctgcggagatcac actgacctggcagcgggatggcgaggaccaaactcaggacactgagcttgtggagaccagaccagcaggagatagaacct -continued tccagaagtgggcagctgtggtggtgccttctggagaagagcagagatacacatgccatgtacagcatgaggggctgccg aagcccctcaccctgagatggg B*4002
(SEQ ID NO: 1435)
atgcgggtcacggcgccccgaaccctcctcctgctgctctgggggcagtggccctgaccgagacctgggcTggctccca ctccatgaggtatttccacacctccgtgtcccggcccggccgcggggagcccgcttcatcaccgtgggctacgtggacg acacgctgttcgtgaggttcgacagcgacgccacgagtccgaggaaggagccgcgggcgccatggatagagcaggagggg ccggagtattgggaccggggagacacagatctCcaagaccaacacacagactTaccgagagagcctgcggaacctgcgcgg ctactacaaccagagcgaggccgggtctcacaccctccagagcatgtacggctgcgacgtggggccggacgggcgcctcc tccgcgggcatAaccagtacgcctacgacggcaaggattacatcgccctgaacgaggacctgcgctcctggaccgccgcg gacacggcggctcagatcacccagcgcaagtgggaggcggcccgtgTggcggagcagcTgagagcctacctggagggcga gtgcgtggagtggctccgcagataccctggagaacgggaaggagacgctgcagcgcgcggaccccccaaagacacacgtga cccaccaccccatctctgaccatgaggccaccctgaggtgctgggccctgggcttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccgtcttcccagtccaccgtccccatcgtgggcattgttgctggcctggctgtccta...gca gttgtggtcatcggagctgtggtcgctgctgtgatgtgtaggaggaagagCtcaggtgga B*4003
(SEQ ID NO: 1436)
atgcgggtcacggcgccccgaaccctcctcctgctgctctgggggcagtggccctgaccgagacctgggcTggctccca ctccatgaggtatttccacacctccgtgtcccggcccggccgcggggagcccgcttcatcaccgtgggctacgtggacg acacgctgttcgtgaggttcgacagcgacgccacgagtccgaggaaggagccgcgggcgccatggatagagcaggagggg ccggagtattgggaccgggaGacacagatctCcaagaccaacacacagactTaccgagagagcctgcggaacctgcgcgg ctactacaaccagagcgaggccgggtctcacaccctccagagcatgtacggctgcgacgtggggccggacgggcgcctcc tccgcgggcatgaccagtCcgcctacgacggcaaggattacatcgccctgaacgaggacctgcgctcctggaccgccgcg gacacggcggctcagatcacccagcgcaagtgggaggcggcccgtgTggcggagcagcTgagagcctacctggagggcga gtgcgtggagtggctccgcagataccctggagaacgggaaggagacgctgcagcgcgcggaccccccaaagacacacgtga cccaccaccccatctctgaccatgaggccaccctgaggtgctgggccctgggcttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccgtcttcccagtccaccgtccccatcgtgggcattgttgctggcctggctgtccta...gca gttgtggtcatcggagctgtggtcgctgctgtgatgtgtaggaggaagagCtcaggtgga B*4004
(SEQ ID NO: 1437)
atgcgggtcacggcgccccgaaccctcctcctgctgctctgggggcagtggccctgaccgagacctgggcTggctccca ctccatgaggtatttccacacctccgtgtcccggcccggccgcggggagcccgcttcatcaccgtgggctacgtggacg acacgctgttcgtgaggttcgacagcgacgccacgagtccgaggaaggagccgcgggcgccatggatagagcaggagggg ccggagtattgggaccggggagacacagatctccaagaccaacacacagacttaccgagagagcctgcggaacctgcgcgg ctactacaaccagagcgaggccgggtctcacatcatccagaggatgtatggctgcgacCtggggccggacgggcgcctcc tccgcgggcatAaccagtacgcctacgacggcaaggattacatcgccctgaacgaggacctgcgctcctggaccgccgcg gacacggcggctcagatcacccagcgcaagtgggaggcggcccgtgTggcggagcagcTgagagcctacctggagggcga gtgcgtggagtggctccgcagataccctggagaacgggaaggagacgctgcagcgcgcggaccccccaaagacacacgtga cccaccaccccatctctgaccatgaggccaccctgaggtgctgggccctgggcttctaccctgcggagatcacactgacc tggcagcgggatggcgaggaccaaactcaggacactgagcttgtggagaccagaccagcaggagatagaaccttccagaa -continued gtgggcagctgtggtggtgccttctggagaagagcagagatacacatgccatgtacagcatgaggggctgccgaagcccc tcaccctgagatgggagccgtcttcccagtccaccgtccccatcgtgggcattgttgctggcctggctgtccta...gca gttgtggtcatcggagctgtggtcgctgctgtgatgtgtaggaggaagagCtcaggtgga

B*4005

(SEQ ID NO: 1438)

atgcgggtcacggcgccccgaaccctcctcctgctgctctgggggcagtggccctgaccgagacctgggcTggctccca ctccatgaggtatttccacacctccgtgtcccggcccggccgcggggagcccgcttcatcaccgtgggctacgtggacg acacgctgttcgtggaggttcgacagcgacgccacgagtccgaggaaggagccgcgggcgccatggatagagcaggaggg ccggagtattgggaccgggagacacagatctccaagaccaacacacagacttaccgagagagcctgcggaacctgcgcgg ctactacaaccagagcgaggccgggtctcacaccctccagagcatgtacggctgcgacgtggggccggacgggcgcctcc tccgcgggcatAaccagtacgcctacgacggcaaggattacatcgccctgaacgaggacctgcgctcctggaccgccgcg gacacggcggctcagatcacccagcgcaagtgggaggcggcccgtgaggcggagcagcTgagagcctacctggagggccT gtgcgtggagtggctccgcagatacctggagaacgggaaggagacgctgcagcgcgcggaccccccaaagacacacgtga cccaccacccatctctgaccatgaggccaccctgaggtgctgggccctgggcttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccgtcttcccagtccaccgtccccatcgtgggcattgttgctggcctggctgtccta...gca gttgtggtcatcggagctgtggtcgctgctgtgatgtgtaggaggaagagCtcaggtgga

B*400601

(SEQ ID NO: 1439)

atgcgggtcacggcgccccgaaccctcctcctgctgctctgggggcagtggccctgaccgagacctgggcTggctccca ctccatgaggtatttccacacctccgtgtcccggcccggccgcggggagcccgcttcatcaccgtgggctacgtggacg acacgctgttcgtggaggttcgacagcgacgccacgagtccgaggaaggagccgcgggcgccatggatagagcaggaggg ccggagtattgggaccgggagacacagatctccaagaccaacacacagacttaccgagagagcctgcggaacctgcgcgg ctactacaaccagagcgaggccgggtctcacacttggcagaCgatgtaTggctgcgacgtggggccggacgggcgcctcc tccgcgggcatAaccagtacgcctacgacggcaaggattacatcgccctgaacgaggacctgcgctcctggaccgccgcg gacacggcggctcagatcacccagcgcaagtgggaggcggcccgtgTggcggagcagcTgagagcctacctggagggcga gtgcgtggagtggctccgcagatacctggagaacgggaaggagacgctgcagcgcgcggaccccccaaagacacacgtga cccaccacccatctctgaccatgaggccaccctgaggtgctgggccctgggcttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccgtcttcccagtccaccgtccccatcgtgggcattgttgctggcctggctgtccta...gca gttgtggtcatcggagctgtggtcgctgctgtgatgtgtaggaggaagagCtcaggtgga

B*4007

(SEQ ID NO: 1440)

atgcgggtcacggcaccccgaaccgtcctcctgctgctctcggcggccctggccctgaccgagacctgggccggctccca ctccatgaggtatttccacaccgccatgtcccggcccggccgcggggagcccgcttcatcaccgtgggctacgtggacg acacgctgttcgtggaggttcgacagcgacgccacgagtccgaggaaggagccgcgggcgccatggatagagcaggaggg ccggagtattgggaccgggagacacagatctCaagaccaacacacagactTaccgagagagcctgcggaacctgcgcgg ctactacaaccagagcgaggccgggtctcacaccctccagagGatgtacggctgcgacgtggggccggacgggcgcctcc tccgcgggcatAaccagtacgcctacgacggcaaggattacatcgccctgaacgaggacctgcgctcctggaccgccgcg gacacggcggctcagatctcccagcgcaagtTggaggcggcccgtgTggcggagcagctgagagcctacctggagggcga gtgcgtggagtggctccgcagatacctggagaacgggaaggacaagctggagcgcgctgaccccccaaagacacacgtga -continued cccaccaccccatctctgaccatgaggccaccctgaggtgctgggccctgggtttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccgtcttcccagtccaccgtccccatcgtgggcattgttgctggcctggctgtccta...gca gttgtggtcatcggagctgtggtcgctgctgtgatgtgtaggaggaagagttcaggtgga B*4008
(SEQ ID NO: 1441)
atgcgggtcacggcgccccgaaccctcctcctgctgctctgggggcagtggccctgaccgagacctgggcTggctccca ctccatgaggtatttccacacctccgtgtcccggcccggccgcggggagccccgcttcatcaccgtgggctacgtggacg acacgctgttcgtgaggttcgacagcgacgccacgagtccgaggaaggagccgcgggcgccatggatagagcaggagggg ccggagtattgggaccggaacacacagatctTcaagaccaacacacagactTaccgagagagcctgcggaacctgcgcgg ctactaaccagagcgaggccgggtctcacaccctccagagcatgtacggctgcgacgtggggccggacgggcgcctcc tccgcgggcatAaccagtacgcctacgacggcaaggattacatcgccctgaacgaggacctgcgctcctggaccgccgcg gacacggcggctcagatcacccagcgcaagtgggaggcggcccgtgTggcggagcagcTgagagcctacctggagggcga gtgcgtggagtggctccgcagatacctggagaacgggaaggagacgctgcagcgcgcggacccccccaaagacacacgtga cccaccaccccatctctgaccatgaggccaccctgaggtgctgggccctgggcttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccgtcttcccagtccaccgtccccatcgtgggcattgttgctggcctggctgtccta...gca gttgtggtcatcggagctgtggtcgctgctgtgatgtgtaggaggaagagCtcaggtgga B*4009
(SEQ ID NO: 1442)
gctcccactccatgaggtatttcCacacctccgtgtcccggcccggccgcggggagccccgcttcatcaccgtgggctac gtggacgacacgcTgttcgtgaggttcgacagcgacgccAcgagtccgaggaaggagccgcgggcgccatggatagagca ggaggggccggagtattgggaccgggagacacagatctccaagaccaacacacagacttaccgagagagcctgcggaacc tgcgcggctactacaaccagagcgaggccgggtctcacaccctccagagcatgtacggctgcgacgtggggccggacggg cgcctcctccgcgggTatgaccagtacgcctacgacggcaaggattacatcgccctgaacgaggacctgcgctcctggac cgccgcggacacggcggctcagatcacccagcgcaagtgggaggcggcccgtgTggcggagcagcTgagagcctacctgg agggcgagtgcgtggagtggctccgcagatacctggagaacgggaaggaDacgctgCagcgcgcGg B*4010
(SEQ ID NO: 1443)
gctcccactccatgaggtatttctacaccgccatgtcccggcccggccgcggggagccccgcttcatcGcagtgggctac gtggacgacacgcagttcgtgaggttcgacagcgacgccAcgagtccgaggAaggagccgcgggcgccAtggatagagca ggaggggccggagtattgggaccgggaGacacagatctCcaagaccaacacacagactTaccgagagagcctgcggaacc tgcgcggctactacaaccagagcgaggccgggtctcacaccctccagagGatgtacggctgcgacgtggggccggacggg cgcctcctccgcgggcatAaccagtacgcctacgacggcaaggattacatcgccctgaacgaggacctgcgctcctggac cgccgcggacacggcggctcagatctcccagcgcaagtTggaggcggcccgtgTggcggagcagctgagagcctacctgg agggcgagtgcgtggagtggctccgcagatacctggagaacgggaaggacaagctggagcgcgctg B*4011
(SEQ ID NO: 1444)
gctcccactccatgaggtatttcCacacctccgtgtcccggcccggccgcggggagccccgcttcatcaccgtgggctac gtggacgacacgcTgttcgtgaggttcgacagcgacgccAcgagtccgaggaaggagccgcgggcgccatggatagagca ggaggggccggagtattgggaccgggagacacagatctccaagaccaacacacagacttaccgagagagcctgcggaacc tgcgcggctactacaaccagagcgaggccgggtctcacaccctccagagGatgtacggctgcgacgtggggccggacggg cgcctcctccgcgggcatAaccagtacgcctacgacggcaaggattacatcgccctgaacgaggacctgcgctcctggac -continued cgccgcggacacggcggctcagatcacccagcgcaagtgggaggcggcccgtgTggcggagcagcTgagagcctacctgg agggcgagtgcgtggagtggctccgcagatacctggagaacgggaaggaDacgctgCagcgcgcGg

B*4012

(SEQ ID NO: 1445)

atgcgggtcacggcgccccgaaccgtcctcctgctgctctcgggAgccctggccctgaccgagacctgggccggctccca ctccatgaggtatttctacaccgccatgtcccggcccggccgcggggagccccgcttcatctcagtgggctacgtggacg acacGcagttcgtgaggttcgacagcgacgccgcgagtccgagagaggagccgcgggcgccAtggatagagcaggaggg ccggagtattgggaccgggaDacacagatctCcaagaccaacacacagactTaccgagagagcctgcggaacctgcgcgg ctactacaaccagagcgaggccgggtctcacaccctccagagGatgtacggctgcgacgtggggccggacgggcgcctcc tccgcgggcatAaccagtacgcctacgacggcaaggattacatcgccctgaacgaggacctgcgctcctggaccgccgcg gacacggcggctcagatctcccagcgcaagtTggaggcggcccgtgTggcggagcagctgagagcctacctggagggcga gtgcgtggagtggctccgcagatacctggagaacgggaaggacaagctggagcgcgctg

B*4013

(SEQ ID NO: 1446)

atgcgggtcacggcgccccgaaccctcctcctgctgctctgggggcagtggccctgaccgagacctgggcTggctccca ctccatgaggtatttccacacctccgtgtcccggcccggccgcggggagccccgcttcatcaccgtgggctacgtggacg acacgctgttcgtgaggttcgacagcgacgccacgagtccgaggaaggagccgcgggcgccatggatagagcaggagggg ccggagtattgggaccgggagacacagatcttcaagaccaacacacagacttaccgagagaacctgcggatcGCgctcCg ctactacaaccagagcgaggccgggtctcacaccctccagagcatgtacggctgcgacgtggggccggacgggcgcctcc tccgcgggcatAaccagtacgcctacgacggcaaggattacatcgccctgaacgaggacctgcgctcctggaccgccgcg gacacggcggctcagatcacccagcgcaagtgggaggcggcccgtgTggcggagcagcTgagagcctacctggagggcga gtgcgtggagtggctccgcagatacctggagaacgggaaggagacgctgcagcgcgcgg

B*401401

(SEQ ID NO: 1447)

gctcccactccatgaggtatttcCacaccgccatgtcccggcccggccgcggggagccccgcttcatcaccgtgggctac gtggacgacacgcTgttcgtgaggttcgacagcgacgccAcgagtccgaggaaggagccgcgggcgccatggatagagca ggaggggccggagtattgggaccgggagacacagatctccaagaccaacacacagacttaccgagagagcctgcggaacc tgcgcggctactacaaccagagcgaggccgggtctcacaccctccagaggatgtacggctgcgacgtggggccggacggg cgcctcctccgcgggcatAaccagtacgcctacgacggcaaggattacatcgccctgaacgaggacctgcgctcctggac cgcggcggacacCgcggctcagatcacccagcgcaagtgggaggcggcccgtgTggcggagcagcTgagagcctacctgg agggcgagtgcgtggagtggctccgcagatacctggagaacgggaaggacaagctggagcgcgctg

B*401402

(SEQ ID NO: 1448)

gctcccactccatgaggtatttcCacaccgccatgtcccggcccggccgcggggagccccgcttcatcaccgtgggctac gtggacgacacgcTgttcgtgaggttcgacagcgacgccAcgagtccgaggaaggagccgcgggcgccatggatagagca ggaggggccggagtattgggaccgggagacacagatctccaagaccaacacacagacttaccgagagagcctgcggaacc tgcgcggctactacaaccagagcgaggccgggtctcacaccctccagaggatgtacggctgcgacgtggggccggacggg cgcctcctccgcgggcatAaccagtacgcctacgacggcaaggattacatcgccctgaacgaggacctgcgctcctggac cgcGgcggacacggcggctcagatcacccagcgcaagtgggaggcggcccgtgTggcggagcagcTgagagcctacctgg agggcgagtgcgtggagtggctccgcagatacctggagaacgggaaggacaagctggagcgcgctg

B*4015

(SEQ ID NO: 1449)

gctcccactccatgaggtatttccacaccgccatgtcccggcccggccgcggggagccccgcttcatcaccgtgggctac gtggacgacacgctgttcgtgaggttcgacagcgacgccacgagtccgaggaaggagccgcgggcgccatggatagagca ggaggggccggagtattgggaccgggagacacagatctccaagaccaacacacagacttaccgagagagcctgcggaacc

```
tgcgcggctactacaaccagagcgaggccgggtctcacaccctccagagcatgtacggctgcgacgtggggccggacggg cgcctcctccgcgggcataaccagtacgcctacgacggcaaggattacatcgccctgaacgaggacctgcgctcctggac cgccgcggacacggcggctcagatcacccagcgcaagtgggaggcggcccgtgaggcggagcagcggagagcctacctgg agggcgagtgcgtggaTtggctccgcagatacctggagaacgggaaggacaagctggagcgcgctg
```

B*4016
(SEQ ID NO: 1450)
```
atgcgggtcacggcaccccgaaccgtcctcctgctgctctcggcggccctggccctgaccgagacctgggccggctccca ctccatgaggtatttcCacaccgccAtgtcccggcccggccgcggggagcccgcttcatcaccgtgggctacgtggacg acacgcTgttcgtgaggttcgacagcgacgccAcgagtccgaggaaggagccgcgggcgccAtggatagagcaggagggg ccggagtattgggaccgggaGacacagatctCcaagaccaacacacagactTaccgagagagcctgcggaacctgcgcgg ctactacaaccagagcgaggccgggtctcacaccctccagagcatgtacggctgcgacgtggggccggacgggcgcctcc tccgcgggcatAaccagtacgcctacgacggcaaggattacatcgccctgaacgaggacctgcgctcctggaccgccgcg gacacggcggctcagatcacccagcgcaagtgggaggcggcccgtgaggcggagcagcggagagcctacctggagggcga gtgcgtggagtggctccgcagatacctggagaacgggaaggacaagctggagcgcgctg
```

B*4018
(SEQ ID NO: 1451)
```
gctcccactccatgaggtatttcCacacctccgtgtcccggcccggccgcggggagcccgcttcatcaccgtgggctac gtggacgacacgcTgttcgtgaggttcgacagcgacgccAcgagtccgaggaaggagccgcgggcgccatggatagagca ggaggggccggagtattgggaccgggagacacagatctCcaagaccaacacacagacttaccgagagagcctgcggaacc tgcgcggctactacaaccagagcgaggccgggtctcacaccctccagagcatgtacggctgcgacgtggggccggacggg cgcctcctccgcgggcatgaccagtacgcctacgacggcaaggattacatcgccctgaacgaggacctgcgctcctggac cgccgcggacacggcggctcagatcacccagcgcaagtgggaggcggcccgtgTggcggagcagcTgagagcctacctgg agggcgagtgcgtggagtggctccgcagatacctggagaacgggaaggaGacgctgCagcgcgcGg
```

B*4019
(SEQ ID NO: 1452)
```
gctcccactccatgaggtatttccacacctccgtgtcccggcccggccgcggggagcccgcttcatcaccgtgggctac gtggacgacacgctgttcgtgaggttcgacagcgacgccAcgagtccgaggaaggagccgcgggcgccatggatagagca ggaggggccggagtattgggaccgggagacacagatctCcaagaccaacAcacagacttaccgagagaacctgcggaTcg cgctccgctactacaaccagagcgaggccgggtctcacaccctccagagcatgtacggctgcgacgtggggccggacggg cgcctcctccgcgggcatAaccagtacgcctacgacggcaaggattacatcgccctgaacgaggacctgcgctcctggac cgccgcggacacggcggctcagatcacccagcgcaagtgggaggcggcccgtgTggcggagcagcTgagagcctacctgg agggcgagtgcgtggagtggctccgcagatacctggagaacgggaaggagacgctgCagcgcgcgg
```

B*4020
(SEQ ID NO: 1453)
```
atgcgggtcacggcgccccgaaccctcctcctgctgctctgggggggcagtggccctgaccgagacctgggcTggctccca ctccatgaggtatttccacacctccgtgtcccggcccggccgcggggagcccgcttcatcaccgtgggctacgtggacg acacgctgttcgtgaggttcgacagcgacgccacgagtccgaggaaggagccgcgggcgccatggatagagcaggagggg ccggagtattgggaccgggaGacacagatctCcaagaccaacacacagactTaccgagagagcctgcggaacctgcgcgg ctactacaaccagagcgaggccgggtctcacaccctccagagGatgtacggctgcgacgtggggccggacgggcgcctcc tccgcgggcatgaccagtCcgcctacgacggcaaggattacatcgccctgaacgaggacctgcgctcctggaccgccgcg gacacggcggctcagatcacccagcgcaagtgggaggcggcccgtgTggcggagcagcTgagagcctacctggagggcga gtgcgtggagtggctccgcagatacctggagaacgggaaggagacgctgcagcgcgcgg
```

B*4021
(SEQ ID NO: 1454)
```
gctcccactccatgaggtatttctacaccgccatgtcccggcccggccgcggggagcccgcttcatcgcagtgggctac gtggacgacacccagttcgtgaggttcgacagcgacgccgcgagtccgaggatggcgccCcgggcgccAtggatagagca
```

-continued ggaggggccggagtattgggaccgggaGacacagatctCcaagaccaacacacagactTaccgagagagcctgcggaacc tgcgcggctactacaaccagagcgaggccgggtctcacaccctccagagGatgtacggctgcgacgtggggccggacggg cgcctcctccgcgggcatAaccagtacgcctacgacggcaaggattacatcgccctgaacgaggacctgcgctcctggac cgccgcggacacggcggctcagatctcccagcgcaagtTggaggcggcccgtgTggcggagcagctgagagcctacctgg agggcgagtgcgtggagtggctccgcagatacctggagaacgggaaggacaagctggagcgcgctg B*4023 (SEQ ID NO: 1455)
atgcgggtcacggcaccccgaaccgtcctcctgctgctctcggcggccctggccctgaccgagacctgggccggctccca ctccatgaggtatttcCacaccgccatgtcccggcccggccgcggggagccccgcttcatcaccgtgggctacgtggacg acacgcTgttcgtgaggttcgacagcgacgccAcgagtccgaggAaggagccgcgggcgccAtggatagagcaggagggg ccggagtattgggaccgggaGacacagatctCcaagaccaacacacagactTaccgagagagcctgcggaacctgcgcgg ctactacaaccagagcgaggccgggtctcacaccctccagagGatgtacggctgcgacgtggggccggacgggcgcctcc tccgcgggcatAaccagtacgcctacgacggcaaggattacatcgccctgaacgaggacctgcgctcctggaccgccgcg gacacggcggctcagatcTcccagcgcaagtgggaggcggcccgtgaggcggagcagcggagagcctacctggagggcga gtgcgtggagtggctccgcagatacctggagaacgggaaggacaagctggagcgcgctg B*4024 (SEQ ID NO: 1456)
gctcccactccatgaggtatttcCacacctccgtgtcccggcccggccgcggggagccccgcttcatcaccgtgggctac gtggacgacacgctgttcgtgaggttcgacagcgacgccAcgagtccgaggaaggagccgcgggcgccAtggatagagca ggaggggccggagtattgggaccgggaGacacagatctCcaagaccaacAcacagactTaccgagagagcctgcggaacc tgcgcggctactacaaccagagcgaggccgggtctcacaccctccagagcatgtacggctgcgacCtggggccCgacggg cgcctcctccgcgggcatgaccagtacgcctacgacggcaaggattacatcgccctgaacgaggacctgcgctcctggac cgccgcggacacggcggctcagatcacccagcgcaagtgggaggcggcccgtgTggcggagcagcTgagagcctacctgg agggcgagtgcgtggagtggctccgcagatacctggagaacgggaaggagacgctgCagcgcgcGg B*4025 (SEQ ID NO: 1457)
gctcccactccatgaggtatttcCacaccgccatgtcccggcccggccgcggggagccccgcttcatcaccgtgggctac gtggacgacacgcTgttcgtgaggttcgacagcgacgccAcgagtccgaggAaggagccgcgggcgccAtggatagagca ggaggggccggagtattgggaccggaacacacagatctCcaagaccaacacacagactTaccgagagagcctgcggaacc tgcgcggctactacaaccagagcgaggccgggtctcacaccctccagagGatgtacggctgcgacgtggggccggacggg cgcctcctccgcgggcatAaccagtacgcctacgacggcaaggattacatcgccctgaacgaggacctgcgctcctggac cgccgcggacacggcggctcagatctcccagcgcaagtTggaggcggcccgtgTggcggagcagctgagagcctacctgg agggcgagtgcgtggagtggctccgcagatacctggagaacgggaaggacaagctggagcgcgctg B*4026 (SEQ ID NO: 1458)
gctcccactccatgaggtatttccacacctccgtgtcccggcccggccgcggggagccccgcttcatcaccgtgggctac gtggacgacacgctgttcgtgaggttcgacagcgacgccAcgagtccgaggaaggagccgcgggcgccatggatagagca ggaggggccggagtattgggaccgggaGacacagatctCcaagaccaacacacagactTaccgagagagcctgcggaacc tgcgcggctactacaaccagagcgaggccgggtctcacaccctccagaggatgtacggctgcgacgtggggccggacggg cgcctcctccgcgggcataaccagtacgcctacgacggcaaAgattacatcgccctgaacgaggacctgagctcctggac cgccgcggacacggcggctcagatcacccagcgcaagtgggaggcggcccgtgaggcggagcagcTgagagcctacctgg agggccTgtgcgtggagtggctccgcagatacctggagaacgggaaggagacgctgcagcgcgcgg

B*4027

(SEQ ID NO: 1459)

gctcccactccatgaggtatttccacacctccgtgtcccggcccggccgcggggagccccgcttcatcaccgtgggctac gtggacgacacgctgttcgtgaggttcgacagcgacgccacgagtccgaggaaggagccgcgggcgccatggatagagca ggaggggccggagtattgggaccgggagacacagatctccaagaccaacacacagacttaccgagagagcctgcggaacc tgcgcggctactacaaccagagcgaggcccgggtctcacaccctccagagcatgtacggctgcgacgtggggccggacggg cgcctcctccgcgggcataaccagAacgcctacgacggcaaggattacatcgccctgaacgaggacctgcgctcctggac cgccgcggacacggcggctcagatcacccagcgcaagtgggaggcggcccgtgtggcggagcagctgagagcctacctgg agggcgagtgcgtggagtggctccgcagatacctggagaacgggaaggagacgctgcagcgcgcgg

B*4028

(SEQ ID NO: 1460)

gctcccactccatgaggtatttccacacctccgtgtcccggcccggccgcggggagccccgcttcatcaccgtgggctac gtggacgacacgctgttcgtgaggttcgacagcgacgccacgagtccgaggaaggagccgcgggcgccatggatagagca ggaggggccggagtattgggaccgggagacacagatctccaagaccaacacacagacttaccgagagagcctgcggaacc tgcgcggctactacaaccagagcgaggcccgggtctcacatcatccagaggatgtatggctgcgacCtggggccggacggg cgcctcctccgcgggcataaccagtacgcctacgacggcaaAgattacatcgccctgaacgaggacctgagctcctggac cgcggcggacaccgcggctcagatcacccagcgcaagtgggaggcggcccgtgaggcggagcagcTgagagcctacctgg agggccTgtgcgtggagtggctccgcagaCacctggagaacgggaaggagacgctgcagcgcgcgg

B*4029

(SEQ ID NO: 1461)

gctcccactccatgaggtatttccacacctccgtgtcccggcccggccgcggggagccccgcttcatcaccgtgggctac gtggacgacacgctgttcgtgaggttcgacagcgacgccacgagtccgaggaaggagccgcgggcgccatggatagagca ggaggggccggagtattgggaccCggagacacagatctccaagaccaacacacagacttaccgagagagcctgcggaacc tgcgcggctactacaaccagagcgaggcccgggtctcacaccctccagagcatgtacggctgcgacgtggggccggacggg cgcctcctccgcgggcatAaccagtacgcctacgacggcaaggattacatcgccctgaacgaggacctgcgctcctggac cgccgcggacacggcggctcagatcacccagcgcaagtgggaggcggcccgtgtggcggagcagctgagagcctacctgg agggcgagtgcgtggagtggctccgcagatacctggagaacgggaaggagacgctgcagcgcgcgg

B*4030

(SEQ ID NO: 1462)

gctcccactccatgaggtatttccacaccgccatgtcccggcccggccgcggggagccccgcttcatcaccgtgggctac gtggacgacacgctgttcgtgaggttcgacagcgacgccacgagtccgaggaaggagccgcgggcgccatggatagagca ggaggggccggagtattgggaccgggagacacagatctccaagaccaacacacagacttaccgagagagcctgcggaacc tgcgcggctactacaaccagagcgaggcccgggtctcacatcatccagGtgatgtatggctgcgacgtggggccggacggg cgcctcctccgcgggcataaccagtacgcctacgacggcaaggattacatcgccctgaacgaggacctgcgctcctggac cgccgcggacacggcggctcagatctcccagcgcaagtTggaggcggcccgtgtggcggagcagcTgagagcctacctgg agggcgagtgcgtggagtggctccgcagatacctggagaacgggaaggacaagctggagcgcgctg

B*4031

(SEQ ID NO: 1463)

gctcccactccatgaggtatttcCacaccgccatgtcccggcccggccgcggggagccccgcttcatcaccgtgggctac gtggacgacacgcTgttcgtgaggttcgacagcgacgccAcgagtccgaggAaggagccgcgggcgccAtggatagagca ggaggggccggagtattgggaccgggaGacacagatctCcaagaccaacacacagactTaccgagagagcctgcggaacc tgcgcggctactacaaccagagcgaggcccgggtctcacaccctccagagcatgtacggctgcgacgtggggccggacggg cgcctcctccgcgggcatgaccagtacgcctacgacggcaaggattacatcgccctgaacgaggacctgcgctcctggac cgccgcggacacggcggctcagatctcccagcgcaagtTggaggcggcccgtgTggcggagcagctgagagcctacctgg agggcgagtgcgtggagtggctccgcagatacctggagaacgggaaggacaagctggagcgcgctg -continued

B*4032

(SEQ ID NO: 1464)

gctcccactccatgaggtatttcCacaccgccAtgtcccggcccggccgcggggagccccgcttcatcaccgtgggctac gtggacgacacgcTgttcgtgaggttcgacagcgacgccAcgagtccgaggaaggagccgcgggcgccAtggatagagca ggaggggccggagtattgggacccgggaGacacagatctCcaagaccaacacacagactTaccgagagagcctgcggaacc tgcgcggctactacaaccagagcgaggccgggtctcacaccctccagagcatgtacggctgcgacgtggggccggacggg cgcctcctccgcgggcatgaccagtacgcctacgacggcaaggattacatcgccctgaacgaggacctgcgctcctggac cgccgcggacacggcggctcagatcacccagcgcaagtgggaggcggcccgtgaggcggagcagctggagagcctacctgg agggcgagtgcgtggagtggctccgcagatacctggagaacgggaaggacaagctggagcgcgctg

B*4033

(SEQ ID NO: 1465)

gctcccactccatgaggtatttcCacaccgccatgtcccggcccggccgcggggagccccgcttcatcaccgtgggctac gtggacgacacgcTgttcgtgaggttcgacagcgacgccAcgagtccgaggAaggagccgcgggcgccAtggatagagca ggaggggccggagtattgggacccgggaGacacagatctCcaagaccaacacacagactTaccgagagagcctgcggaacc tgcgcggctactacaaccagagcgaggccgggtctcacaccctccagagGatgtacggctgcgacgtggggccggacggg cgcctcctccgcgggcatgaccagtacgcctacgacggcaaggattacatcgccctgaacgaggacctgcgctcctggac cgccgcggacacggcggctcagatctcccagcgcaagtTggaggcggcccgtgTggcggagcagctgagagcctacctgg agggcgagtgcgtggagtggctccgcagatacctggagaacgggaaggacaagctggagcgcgctg

B*4034

(SEQ ID NO: 1466)

gctcccactccatgaggtatttccacaccgccatgtcccggcccggccgcggggagccccgcttcatcaccgtgggctac gtggacgacacgctgttcgtgaggttcgacagcgacgccacgagtccgaggaaggagccgcgggcgccatggatagagca ggaggggccggagtattgggaccgggagacacagatctccaagaccaacacacagacttaccgagagagcctgcggaacc tgcgcggctactacaaccagagcgaggccgggtctcacatcatccaggtgatgtatggctgcgacgtggggccggacggg cgcctcctccgcgggcataaccagtacgcctacgacggcaagAattacatcgccctgaacgaggacctgcgctcctggac cgccgcggacacggcggctcagatctcccagcgcaagttggaggcggcccgtgtggcggagcagctgagagcctacctgg agggcgagtgcgtggagtggctccgcagatacctggagaacgggaaggacaagctggagcgcgctg

B*4035

(SEQ ID NO: 1467)

gctcccactccatgaggtatttcCacacctccgtgtcccggcccggccgcggggagccccgcttcatcaccgtgggctac gtggacgacacgcTgttcgtgaggttcgacagcgacgccAcgagtccgaggaaggagccgcgggcgccatggatagagca ggaggggccggagtattgggacccgggagacacagatctccaagaccaacacacagacttaccgagagagcctgcggaacc tgcgcggctactacaaccagagcgaggccgggtctcacaccctccagagcatgtacggctgcgacgtggggccggacggg cgcctcctccgcgggcatAaccagtacgcctacgacggcaaggattacatcgccctgaacgaggacctgAgctcctggac cgccgcggacacggcggctcagatcacccagcgcaagtgggaggcggcccgtgTggcggagcagctgagagcctacctgg agggcgagtgcgtggagtggctccgcagatacctggagaacgggaaggaDacgctgCagcgcgcGg

B*4036

(SEQ ID NO: 1468)

gctcccactccatgaggtatttccacaccgccatgtcccggcccggccgcggggagccccgcttcatcaccgtgggctac gtggacgacacgctgttcgtgaggttcgacagcgacgccacgagtccgaggaaggagccgcgggcgccatggatagagca ggaggggccggagtattgggacccgggagacacagatctccaagaccaacacacagacttaccgagagagcctgcggaacc tgcgcggctactacaaccagagcgaggccgggtctcacaccctccagagGatgtacggctgcgacgtggggccggacggg cgcctcctccgcgggcataaccagtTcgcctacgacggcaaggattacatcgccctgaacgaggacctgcgctcctggac cgccgcggacacggcggctcagatctcccagcgcaagtTggaggcggcccgtgTggcggagcagctgagagcctacctgg agggcgagtgcgtggagtggctccgcagatacctggagaacgggaaggacaagctggagcgcgctg -continued

B*4037

(SEQ ID NO: 1469)

gctcccactccatgaggtatttcCacacctccgtgtcccggcccggccgcggggagccccgcttcatcaccgtgggctac gtggacgacacgcTgttcgtgaggttcgacagcgacgccAcgagtccgaggaaggagccgcgggcgccatggatagagca ggaggggccggagtattgggaccgggagacacagatctCcaagaccaacacacagacttaccgagagaAcctgcggaacc tgcgcggctactacaaccagagcgaggccgggtctcacaccctccagagcatgtacggctgcgacgtggggccggacggg cgcctcctccgcgggcatAaccagtacgcctacgacggcaaggattacatcgccctgaacgaggacctgcgctcctggac cgccgcggacacggcggctcagatcacccagcgcaagtggggaggcggcccgtgTggcggagcagcTgagagcctacctgg agggcgagtgcgtggagtggctccgcagatacctggagaacgggaaggaDacgctgCagcgcgcGg

B*4038

(SEQ ID NO: 1470)

gctcccactccatgaggtatttccacacctccgtgtcccggcccggccgcggggagccccgcttcatcaccgtgggctac gtggacgacacgctgttcgtgaggttcgacagcgacgccacgagtccgaggaaggagccgcgggcgccatggatagagca ggaggggccggagtattgggaccgggagacacagatctccaagaccaacacacagacttaccgagagagcctgcggaacc tgcgcggctactacaaccagagcgaggccgggtctcacaccctccagaggatgtacggctgcgacgtggggccggacggg cgcctcctccgcgggcataaccagtCcgcctacgacggcaaggattacatcgccctgaacgaggacctgcgctcctggac cgccgcggacacggcggctcagatctcccagcgcaagtTggaggcggcccgtgTggcggagcagctgagagcctacctgg agggcgagtgcgtggagtggctccgcagatacctggagaacgggaaggacaagctggagcgcgctg

B*4039

(SEQ ID NO: 1471)

gggggcagtggccctgaccgagacctgggcTggctcccactccatgaggtatttccacacctccgtgtcccggcccggcc gcggggagccccgcttcatcaccgtgggctacgtggacgacacgctgttcgtgaggttcgacagcgacgccacgagtccg aggaaggagccgcgggcgccatggatagagcaggaggggccggagtattgggaccgggagacacagatctccaagaccaa cacacagacttaccgagagagcctgcggaacctgcgcggctactacaaccagagcgaggccgggtctcacaccctccaga gcatgtacggctgcgacgtggggccggacgggcgcctcctccgcgggcatAaccagtacgcctacgacggcaaggattac atcgccctgaacgaggacctgcgctcctggaccgccgcggacacggcggctcagatcacccagcgcaagtgggaggcggc ccgtgtggcggagcagcTgagagcctacctggagggcaCgtgcgtggagtggctccgcagatacctggagaacgggaagg agacgctgcagcgcgcggaccccccaaagacacacgtgacccaccacccatctctgaccatgaggccaccctgaggtgc tgggccctgggCttctaccctgcggagatcacactgacctggcagcgggatggcgaggaccaaactcaggacactgagct tgtggagaccagaccagcaggagatagaaccttccagaagtgggcagctgtggtggtgccttctggagaagagcagagat acacatgccatgtacagcatgaggggctgccgaagcccctcaccctgagatgggagccgtcttcccagtccaccgtcccc atcgtgggcattgttgctggcctggctgtcct

B*4040

(SEQ ID NO: 1472)

gctcccactccatgaggtatttctacacctccgtgtcccggcccggccgcggggagccccgcttcatcaccgtgggctac gtggacgacacgcTgttcgtgaggttcgacagcgacgccAcgagtccgaggaaggagccgcgggcgccatggatagagca ggaggggccggagtattgggaccgggagacacagatctCcaagaccaacacacagacttaccgagagagcctgcggaacc tgcgcggctactacaaccagagcgaggccgggtctcacaccctccagagcatgtacggctgcgacgtggggccggacggg cgcctcctccgcgggcatAaccagtacgcctacgacggcaaggattacatcgccctgaacgaggacctgcgctcctggac cgccgcggacacggcggctcagatcacccagcgcaagtgggaggcggcccgtgTggcggagcagcTgagagcctacctgg agggcgagtgcgtggagtggctccgcagatacctggagaacgggaaggaDacgctgCagcgcgcGg

B*4042

(SEQ ID NO: 1473)

gctcccactccatgaggtatttccacaccgccatgtcccggcccggccgcggggagccccgcttcatcaccgtgggctac gtggacgacacgctgttcgtgaggttcgacagcgacgccacgagtccgaggaaggagccgcgggcgccatggatagagca -continued ggaggggccggagtattgggaccgggagacacagatctccaagaccaacacacagacttaccgagagagcctgcggaacc tgcgcggctactacaaccagagcgaggccgggtctcacaccctccagaggatgtacggctgcgacgtggggccggacggg cgcctcctccgcgggTatgaccagtacgcctacgacggcaaggattacatcgccctgaacgaggacctgcgctcctggac cgccgcggacacggcggctcagatctcccagcgcaagtTggaggcggcccgtgTggcggagcagctgagagcctacctgg agggcgagtgcgtggagtggctccgcagatacctggagaacgggaaggacaagctggagcgcgctg B*4043 (SEQ ID NO: 1474)
gctcccactccatgaggtatttcCacaccgccatgtcccggcccggccgcggggagccccgcttcatcaccgtgggctac gtggacgacacgcTgttcgtgaggttcgacagcgacgccAcgagtccgaggAaggagccgcgggcgccAtggatagagca ggaggggccggagtattgggaccgggaDacacagatctCcaagaccaacacacagactgaccgagagagcctgcggaacc tgcgcggctactacaaccagagcgaggccgggtctcacaccctccagagGatgtacggctgcgacgtggggccggacggg cgcctcctccgcgggcatAaccagtacgcctacgacggcaaggattacatcgccctgaacgaggacctgcgctcctggac cgccgcggacacggcggctcagatctcccagcgcaagtTggaggcggcccgtgTggcggagcagctgagagcctacctgg agggcgagtgcgtggagtggctccgcagatacctggagaacgggaaggacaagctggagcgcgctg B*4044 (SEQ ID NO: 1475)
gctcccactccatgaggtatttccacacctccgtgtcccggcccggccgcggggagccccgcttcatcaccgtgggctac gtggacgacacgcTgttcgtgaggttcgacagcgacgccAcgagtccgaggaaggagccgcgggcgccatggatagagca ggaggggccggagtattgggaccgggagacacagatctCcaagaccaacacacagactTaccgagagagcctgcggaacc tgcgcggctactacaaccagagcgaggccgggtctcacacttggcagaCgatgtaTggctgcgacgtggggccggacggg cgcctcctccgcgggcatgaccagtacgcctacgacggcaaggattacatcgccctgaacgaggacctgcgctcctggac cgccgcggacacggcggctcagatcacccagcgcaagtgggaggcggcccgtgTggcggagcagcTgagagcctacctgg agggcgagtgcgtggagtggctccgcagatacctggagaacgggaaggagacgctgCagcgcgcgg B*4101 (SEQ ID NO: 1476)
atgcgggtcacggcaccccgaaccgtcctcctgctgctctcggcggccctggccctgaccgagacctgggccggctccca ctccatgaggtatttccacaccgccatgtcccggcccggccgcggggagccccgcttcatcaccgtgggctacgtggacg acacgctgttcgtgaggttcgacagcgacgccacgagtccgaggaaggagccgcgggcgccatggatagagcaggagggg ccggagtattgggaccgggagacacagatctccaagaccaacacacagacttaccgagagagcctgcggaacctgcgcgg ctactacaaccagagcgaggccgggtctcacacttgGcagaggatgtaTggctgcgacgtggggccggacgggcgcctcc tccgcgggcataaccagtacgcctacgacggcaaggattacatcgccctgaacgaggacctgcgctcctggaccgcggcg gacaccgcggctcagatcacccagcgcaagtgggaggcggcccgtgtggcggagcaggaCagagcctacctggagggcaC gtgcgtggagtggctccgcagatacctggagaacgggaaggacacgctggagcgcgcggaccccccaaagacacacgtga cccaccaccccatctctgaccatgaggccaccctgaggtgctgggccctgggcttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccgtcttcccagtccaccgtccccatcgtgggcattgttgctggcctggctgtcccta...gca gttgtggtcatcggagctgtggtcgctgctgtgatgtgtaggaggaagagCtcaggtgga B*4102 (SEQ ID NO: 1477)
atgcgggtcacggcaccccgaaccgtcctcctgctgctctcggcggccctggccctgaccgagacctgggccggctccca ctccatgaggtatttccacaccgccatgtcccggcccggccgcggggagccccgcttcatcaccgtgggctacgtggacg acacgctgttcgtgaggttcgacagcgacgccacgagtccgaggaaggagccgcgggcgccAtggatagagcaggagggg ccggagtattgggaccgggagacacagatctccaagaccaacacacagactTaccgagagagcctgcggaacctgcgcgg ctactacaaccagagcgaggccgggtctcacaccctccagagcatgtacggctgcgacgtggggccggacgggcgcctcc -continued tccgcgggcataaccagtacgcctacgacggcaaggattacatcgccctgaacgaggacctgcgctcctggaccgcggcg gacaccgcggctcagatcacccagcgcaagtgggaggcggcccgtgtggcggagcaggaCagagcctacctggagggcaC gtgcgtggagtggctccgcagatacctggagaacgggaaggacacgctggagcgcgcggaccccccaaagacacacgtga cccaccacccatctctgaccatgaggccaccctgaggtgctgggccctgggcttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccgtcttcccagtccaccgtccccatcgtgggcattgttgctggcctggctgtccta...gca gttgtggtcatcggagctgtggtcgctgctgtgatgtgtaggaggaagagCtcaggtgga

B*4103

(SEQ ID NO: 1478)

gctcccactccatgaggtatttccacaccgccatgtcccggcccggccgcggAgagccccgcttcatcaccgtgggctac gtggacgacacgctgttcgtgaggttcgacagcgacgccacgagtccgaggaaggagccgcgggcgccatggatagagca ggaggggccggagtattgggaccgggagacacagatctccaagaccaacacacagacttaccgagagagcctgcggaacc tgcgcggctactacaaccagagcgaggcccgggtctcacaccctccagaggatgtacggctgcgacgtggggccggacggg cgcctcctccgcgggcataaccagtacgcctacgacggcaaggattacatcgccctgaacgaggacctgcgctcctggac cgcggcggacaccgcggctcagatcacccagcgcaagtgggaggcggcccgtgtggcggagcaggaCagagcctacctgg agggcacgtgcgtggagtggctccgcagatacctggagaacgggaaggacacgctggagcgcgcgg

B*4104

(SEQ ID NO: 1479)

gctcccactccatgaggtatttccacaccgccatgtcccggcccggccgcggggagccccgcttcatcaccgtgggctac gtggacgacacgctgttcgtgaggttcgacagcgacgccacgagtccgaggaaggagccgcgggcgccatggatagagca ggaggggccggagtattgggaccgggagacacagatctccaagaccaacacacagacttaccgagagagcctgcggaacc tgcgcggctactacaaccagagcgaggcccgggtctcacaccctccagagcatgtacggctgcgacctggggccCgacggg cgcctcctccgcgggcatgaccagtacgcctacgacggcaaggattacatcgccctgaacgaggacctgcgctcctggac cgcggcggacaccgcggctcagatcacccagcgcaagtgggaggcggcccgtgTggcggagcaggaCagagcctacctgg agggcACgtgcgtggagtggctccgcagatacctggagaacgggaaggacacgctggagcgcgcGg

B*4105

(SEQ ID NO: 1480)

gctcccactccatgaggtatttccacaccgccatgtcccggcccggccgcggggagccccgcttcatcaccgtgggctac gtggacgacacgctgttcgtgaggttcgacagcgacgccacgagtccgaggaaggagccgcgggcgccatggatagagca ggaggggccggagtattgggaccgggagacacagatctccaagaccaacacacagacttaccgagagagcctgcggaaGc tgcgcggctactacaaccagagcgaggcccgggtctcacacttggcagaggatgtatggctgcgacgtggggccggacggg cgcctcctccgcgggcataaccagtacgcctacgacggcaaggattacatcgccctgaacgaggacctgcgctcctggac cgcggcggacaccgcggctcagatcacccagcgcaagtgggaggcggcccgtgtggcggagcaggacagagcctacctgg agggcacgtgcgtggagtggctccgcagatacctggagaacgggaaggacacgctggagcgcgcgg

B*4106

(SEQ ID NO: 1481)

gctcccactccatgaggtatttccacaccgccatgtcccggcccggccgcggggagccccgcttcatcaccgtgggctac gtggacgacacgctgttcgtgaggttcgacagcgacgccacgagtccgaggaaggagccgcgggcgccatggatagagca ggaggggccggagtattgggaccgggagacacagatctccaagaccaacacacagacttaccgagagagcctgcggaacc tgcgcggctactacaaccagagcgaggcccgggtctcacacttgGcagaggatgtatggctgcgacgtggggccggacggg cgcctcctccgcgggcataaccagtacgcctacgacggcaaggattacatcgccctgaacgaggacctgcgctcctggac cgcggcggacaccgcggctcagatcacccagcgcaagtgggaggcggcccgtgtggcggagcaggaCagagcctacctgg agggcaCgtgcgtggagtggctccgcagatacctggagaacgggaaggacacgctgCagcgcgcGg

B*4201

(SEQ ID NO: 1482)

atgctggtcatggcgccccgaaccgtcctcctgctgctctcggcggccctggccctgaccgagacctgggccggctccca ctccatgaggtatttctacacctccgtgtcccggcccggccgcggggagcccgcttcatctcagtgggctacgtggacg acacccagttcgtgaggttcgacagcgacgccgcgagtccgagagaggagccgcgggcgccgtggatagagcaggagggg ccggagtattgggaccggaacacacagatctacaaggcccaggcacagactgaccgagagagcctgcggaacctgcgcgg ctactacaaccagagcgaggccgggtctcacaccctccagagcatgtacggctgcgacgtggggccggacgggcgcctcc tccgcgggcataaccagtacgcctacgacggcaaggattacatcgccctgaacgaggacctgcgctcctggaccgcggcg gacaccgcggctcagatcacccagcgcaagtgggaggcggcccgtgtggcggagcaggaCagagcctacctggagggcaC gtgcgtggagtggctccgcagatacctggagaacgggaaggacacgctggagcgcgcggacccccaaagacacacgtga cccaccaccccatctctgaccatgaggccaccctgaggtgctgggccctgggcttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccgtcttcccagtccaccgtccccatcgtgggcattgttgctggcctggctgtccta...gca gttgtggtcatcggagctgtggtcgctgctgtgatgtgtaggaggaagagCtcaggtgga

B*4202

(SEQ ID NO: 1483)

ggctcccactccatgaggtatttcCacacctccgtgtcccggcccggccgcggggagcccgcttcatctcagtgggcta cgtggacgacacccagttcgtgaggttcgacagcgacgccgcgagtccgagagaggagccgcgggcgccgtggatagagc aggaggggccggagtattgggaccggaacacacagatctacaaggcccaggcacagactgaccgagagagcctgcggaac ctgcgcggctactacaaccagagcgaggccgggtctcacaccctccagagcatgtacggctgcgacgtggggccggacgg gcgcctcctccgcgggcatAaccagtacgcctacgacggcaaggattacatcgccctgaacgaggacctgcgctcctgga ccgcggcggacaccgcggctcagatcacccagcgcaagtgggaggcggcccgtgTggcggagcaggaCagagcctacctg gagggcACgtgcgtggagtggctccgcagatacctggagaacgggaaggacacgctggagcgcgcGg

B*4204

(SEQ ID NO: 1484)

gctcccactccatgaggtatttctacacctccgtgtcccggcccggccgcggggagcccgcttcatctcagtgggctac gtggacgacacccagttcgtgaggttcgacagcgacgccgcgagtccgagagaggagccgcgggcgccgtggatagagca ggaggggccggagtattgggaccggaacacacagatctacaaggcccaggcacagactgaccgagagagcctgcggaacc tgcgcggctactacaaccagagcgaggccgggtctcacacttggcagaCgatgtaTggctgcgacgtggggccggacggg cgcctcctccgcgggcatAaccagtacgcctacgacggcaaggattacatcgccctgaacgaggacctgcgctcctggac cgcggcggacaccgcggctcagatcacccagcgcaagtgggaggcggcccgtgTggcggagcaggaCagagcctacctgg agggcACgtgcgtggagtggctccgcagatacctggagaacgggaaggacacgctggagcgcgcGg

B*440201

(SEQ ID NO: 1485)

atgcgggtcacggcgccccgaaccctcctcctgctgctctgggggcagtggccctgaccgagacctgggccggctccca ctccatgaggtatttctacaccgccatgtcccggcccggccgcggggagcccgcttcatcaccgtgggctacgtggacg acacgctgttcgtgaggttcgacagcgacgccAcgagtccgaggaaggagccgcgggcgccatggatagagcaggaggg ccggagtattgggaccggagacacagatctccaagaccaacacacagacttaccgagagaacctgcgcaccgcgctcCg ctactacaaccagagcgaggccgggtctcacatcatccagaggatgtacggctgcgacgtggggccggacgggcgcctcc tccgcgggtatgaccaggacgcctacgacggcaaggattacatcgccctgaacgaggacctgagctcctggaccgcggcg gacaccgcggctcagatcacccagcgcaagtgggaggcggcccgtgtggcggagcaggaCagagcctacctggagggccT gtgcgtggagtcgctccgcagatacctggagaacgggaaggagacgctgcagcgcgcggacccccaaagacacatgtga cccaccaccccatctctgaccatgaggTcaccctgaggtgctgggccctgggcttctaccctgcggagatcacactgacc tggcagcgggatggcgaggaccaaactcaggacaccgagcttgtggagaccagaccagcaggagatagaaccttccagaa

```
gtgggcagctgtggtggtgccttctggagaagagcagagatacacatgccatgtacagcatgaggggctgccgaagcccc tcaccctgagatgggagccgtcttcccagtccaccgtccccatcgtgggcattgttgctggcctggctgtccta...gca gttgtggtcatcggagctgtggtcgctgctgtgatgtgtaggaggaagagCtcaggtgga ctgctgtgatgtgtaggaggaagagCtcaggtgga
```

B*440202

(SEQ ID NO: 1486)

```
gctcccactccatgaggtatttctacaccgccatgtcccggcccggccgcggggagccccgcttcatcaccgtgggctac gtggacgacacgctgttcgtgaggttcgacagcgacgccacgagtccgaggaaggagccgcgggcgccatggatagagca ggaggggccggagtattgggaccgggagacacagatctcGaagaccaacacacagacttaccgagagaacctgcgcaccg cgctcCgctactacaaccagagcgaggccgggtctcacatcatccagaggatgtacggctgcgacgtggggccggacggg cgcctcctccgcgggtatgaccaggacgcctacgacggcaaggattacatcgccctgaacgaggacctgagctcctggac cgcggcggacaccgcggctcagatcacccagcgcaagtgggaggcggcccgtgtggcggagcaggaCagagcctacctgg agggccTgtgcgtggagtcgctccgcagatacctggagaacgggaaggagacgctgcagcgcgcggaccccccaaagaca catgtgacccaccaccccatctctgaccatgaggTcaccctgaggtgctgggccctgggcttctaccctgcggagatcac actgacctggcagcgggatggcgaggaccaaactcaggacaccgagcttgtggagaccagaccagcaggagatagaacct tccagaagtgggcagctgtggtggtgccttctggagaagagcagagatacacatgccatgtacagcatgaggggctgccg aagcccctcaccctgagatggg
```

B*440203

(SEQ ID NO: 1487)

```
gctcccactccatgaggtatttctacaccgccatgtcccggcccggccgcggggagccccgcttcatcaccgtgggctac gtggacgacacgctgttcgtgaggttcgacagcgacgccacgagtccgaggaaggagccgcgggcgccatggatagagca ggaggggccggagtattgggaccgggagacacagatctccaagaccaacacacagacttaccgagagaacctgcgcaccg cgctccgctactacaaccagagcgaggccgggtctcacatcatccagaggatgtacggctgcgacgtggggccggacggg cgcctcctccgcgggtatgaccaggacgcctacgacggcaaggattacatcgccctgaacgaggacctgagctcctggac cgcggcggacaccgcggctcagatcacccagcgcaagtgggaggcggcccgtgtCgcggagcaggacagagcctacctgg agggcctgtgcgtggagtcgctccgcagatacctggagaacgggaaggagacgctgcagcgcgcgg
```

B*440301

(SEQ ID NO: 1488)

```
atgcgggtcacggcgccccgaaccctcctcctgctgctctgggggcagtggccctgaccgagacctgggccggctccca ctccatgaggtatttctacaccgccatgtcccggcccggccgcggggagccccgcttcatcaccgtgggctacgtggacg acacgctgttcgtgaggttcgacagcgacgccAcgagtccgaggaaggagccgcgggcgccatggatagagcaggagggg ccggagtattgggaccgggagacacagatctccaagaccaacacacagacttaccgagagaacctgcgcaccgcgctccg ctactacaaccagagcgaggccgggtctcacatcatccagaggatgtacggctgcgacgtggggccggacgggcgcctcc tccgcgggtatgaccaggacgcctacgacggcaaggattacatcgccctgaacgaggacctgagctcctggaccgcggcg gacaccgcggctcagatcacccagcgcaagtgggaggcggcccgtgtggcggagcagcTgagagcctacctggagggccT gtgcgtggagtcgctccgcagatacctggagaacgggaaggagacgctgcagcgcgcggaccccccaaagacacatgtga cccaccaccccatctctgaccatgaggTcaccctgaggtgctgggccctgggcttctaccctgcggagatcacactgacc tggcagcgggatggcgaggaccaaactcaggacaccgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccgtcttcccagtccaccgtccccatcgtgggcattgttgctggcctggctgtccta...gca gttgtggtcatcggagctgtggtcgctgctgtgatgtgtaggaggaagagCtcaggtgga
```

-continued

B*440302

(SEQ ID NO: 1489)
atgcgggtcacggcgccccgaaccctcctcctgctgctctgggggcagtggccctgaccgagacctgggccggctccca
ctccatgaggtatttctacaccgccatgtcccggcccggccgcggggagccccgcttcatcaccgtgggctacgtggacg
acacgctgttcgtgaggttcgacagcgacgccAcgagtccgaggaaggagccgcgggcgccatggatagagcaggagggg
ccggagtattgggaccgggagacacagatctccaagaccaacacacagacttaccgagagaacctgcgcaccgcgctccg
ctactacaaccagagcgaggccgggtctcacatcatccagaggatgtaTggctgcgacgtggggccggacgggcgcctcc
tccgcgggtatgaccaggacgcctacgacggcaaggattacatcgccctgaacgaggacctgagctcctggaccgcggcg
gacaccgcggctcagatcacccagcgcaagtgggaggcggcccgtgtggcggagcagcTgagagcctacctggagggccT
gtgcgtggagtcgctccgcagatacctggagaacgggaaggagacgctgcagcgcgcggacccccaaagacacatgtga
cccaccacccatctctgaccatgaggTcaccctgaggtgctgggccctgggcttctaccctgcggagatcacactgacc
tggcagcgggatggcgaggaccaaactcaggacaccgagcttgtggagaccagaccagcaggagatagaaccttccagaa
gtgggcagctgtggtggtgccttctggagaagagcagagatacacatgccatgtacagcatgaggggctgccgaagcccc
tcaccctgagatgggagccgtcttcccagtccaccgtccccatcgtgggcattgttgctggcctggctgtccta...gca
gttgtggtcatcggagctgtggtcgctgctgtgatgtgtaggaggaagagCtcaggtgga

B*4404

(SEQ ID NO: 1490)
atgcgggtcacggcgccccgaaccctcctcctgctgctctgggggcagtggccctgaccgagacctgggccggctccca
ctccatgaggtatttctacaccgccatgtcccggcccggccgcggggagccccgcttcatcaccgtgggctacgtggacg
acacgctgttcgtgaggttcgacagcgacgccacgagtccgaggaaggagccgcgggcgccatggatagagcaggagggg
ccggagtattgggaccgggagacacagatctccaagaccaacacacagacttaccgagagaacctgcgcaccgcgctccg
ctactacaaccagagcgaggccgggtctcacatcatccagaggatgtacggctgcgacgtggggccggacgggcgcctcc
tccgcgggtatgaccaggacgcctacgacggcaaggattacatcgccctgaacgaggacctgagctcctggaccgcggcg
gacaccgcggctcagatcacccagcgcaagtgggaggcggcccgtgtggcggagcagcggagagcctacctggagggcaC
gtgcgtggagtcgctccgcagatacctggagaacgggaaggagacgctgcagcgcgcggacccccaaagacacatgtga
cccaccacccatctctgaccatgaggTcaccctgaggtgctgggccctgggcttctaccctgcggagatcacactgacc
tggcagcgggatggcgaggaccaaactcaggacaccgagcttgtggagaccagaccagcaggagatagaaccttccagaa
gtgggcagctgtggtggtgccttctggagaagagcagagatacacatgccatgtacagcatgaggggctgccgaagcccc
tcaccctgagatgggagccgtcttcccagtccaccgtccccatcgtgggcattgttgctggcctggctgtccta...gca
gttgtggtcatcggagctgtggtcgctgctgtgatgtgtaggaggaagagCtcaggtgga

B*4405

(SEQ ID NO: 1491)
ggcgccatggatagagcaggaggggccggagtattgggaccgggaDacacagatctccaagaccaacacacagacttacc
gagagaacctgcgcaCcGcgctcCgctactacaaccagagcgaggccgggtctcacatcAtccagaggatgtacggctgc
gacgtggggccggacgggcgcctcctccgcgggTatgaccagtacgcctacgacggcaaggattacatcgccctgaacga
ggacctgagctcctggaccgcggcggacaccgcggctcagatcacccagcgcaagtgggaggcggcccgtgtggcggagc
aggaCagagcctacctggagggccTgtgcgtggagtCgctccgcagatacctggagaacgggaaggagacgctgcagcgc
gcGg

B*4406

(SEQ ID NO: 1492)
atgcgggtcacggcgccccgaaccctcctcctgctgctctgggggcagtggccctgaccgagacctgggccggctccca
ctccatgaggtatttctacaccgccatgtcccggcccggccgcggggagccccgcttcatTgcagtgggctacgtggacg
acacccagttcgtgaggttcgacagcgacgccgcgagtccgaggacggagccccgggcgccatggatagagcaggagggg
ccggagtattgggaccggaacacacagatcttcaagaccaacacacagacttaccgagagaacctgcggatcgcgctccg -continued ctactacaaccagagcgaggccgggtctcacatcatccagaggatgtacggctgcgacgtggggccggacgggcgcctcc tccgcgggtatgaccaggacgcctacgacggcaaggattacatcgccctgaacgaggacctgagctcctggaccgcggcg gacaccgcggctcagatcacccagcgcaagtgggaggcggcccgtgtggcggagcaggaCagagcctacctggagggcct gtgcgtggagtCgctccgcagatacctggagaacgggaaggagacgctgcagcgcgcgg

B*4407

(SEQ ID NO: 1493)

atgcgggtcacggcgccccgaaccctcctcctgctgctctgggggcagtggccctgaccgagacctgggccggctccca ctccatgaggtatttctacaccgccatgtcccggcccggccgcggggagccccgcttcatcaccgtgggctacgtggacg acacgctgttcgtggaggttcgacagcgacgccgcgagtccgaggaaggagccgcgggcgccatggatagagcaggagggg ccggagtattgggaccgggagacacagatctccaagaccaacacacagacttaccgagagaacctgcgcaccgcgctccg ctactacaaccagagcgaggccgggtctcacatcatccagaggatgtaTggctgcgacgtggggccggacgggcgcctcc tccgcgggtatgaccaggacgcctacgacggcaaggattacatcgccctgaacgaggacctgagctcctggaccgcggcg gacaccgcggctcagatcacccagcgcaagtgggaggcggcccgtgtggcggagcagcTgagagcctacctggagggccT gtgcgtggagtcgctccgcagatacctggagaacgggaaggagacgctgcagcgcgcggaccccccaaagacacatgtga cccaccaccccatctctgaccatgaggTcaccctgaggtgctgggccctgggcttctaccctgcggagatcacactgacc tggcagcgggatggcgaggaccaaactcaggacaccgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccgtcttcccagtccaccgtccccatcgtgggcattgttgctggcctggctgtccta...gca gttgtggtcatcggagctgtggtcgctgctgtgatgtgtaggaggaagagCtcaggtgga

B*4408

(SEQ ID NO: 1494)

atgcgggtcacggcgccccgaaccctcctcctgctgctctgggggcagtggccctgaccgagacctgggccggctccca ctccatgaggtatttctacaccgccatgtcccggcccggccgcggggagccccgcttcatcaccgtgggctacgtggacg acacgctgttcgtggaggttcgacagcgacgccgcgagtccgaggatggcgccCgggcgccatggatagagcaggagggg ccggagtattgggaccgggagacacagatctccaagaccaacacacagacttaccgagagaacctgcgcaccgcgctcCg ctactacaaccagagcgaggccgggtctcacatcatccagaggatgtacggctgcgacgtggggccggacgggcgcctcc tccgcgggtatgaccaggacgcctacgacggcaaggattacatcgccctgaacgaggacctgagctcctggaccgcggcg gacaccgcggctcagatcacccagcgcaagtgggaggcggcccgtgtggcggagcaggaCagagcctacctggagggccT gtgcgtggagtcgctccgcagatacctggagaacgggaaggagacgctgcagcgcgcggaccccccaaagacacatgtga cccaccaccccatctctgaccatgaggTcaccctgaggtgctgggccctgggcttctaccctgcggagatcacactgacc tggcagcgggatggcgaggaccaaactcaggacaccgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccgtcttcccagtccaccgtccccatcgtgggcattgttgctggcctggctgtccta...gca gttgtggtcatcggagctgtggtcgctgctgtgatgtgtaggaggaagagCtcaggtgga

B*4409

(SEQ ID NO: 1495)

atgcgggtcacggcgccccgaaccctcctcctgctgctctgggggcagtggccctgaccgagacctgggccggctccca ctccatgaggtatttctacaccgccatgtcccggcccggccgcggggagccccgcttcatcaccgtgggctacgtggacg acacgctgttcgtggaggttcgacagcgacgccAcgagtccgaggaaggagccgcgggcgccatggatagagcaggagggg ccggagtattgggaccgggagacacagatctccaagaccaacacacagacttaccgagagcctgcggaacctgcgcgg ctactacaaccagagcgaggccgggtctcacatcatccagaggatgtacggctgcgacgtggggccggacgggcgcctcc tccgcgggtatgaccaggacgcctacgacggcaaggattacatcgccctgaacgaggacctgagctcctggaccgcggcg gacaccgcggctcagatcacccagcgcaagtgggaggcggcccgtgtggcggagcaggaCagagcctacctggagggccT gtgcgtggagtcgctccgcagatacctggagaacgggaaggagacgctgcagcgcgcggaccccccaaagacacatgtga -continued cccaccaccccatctctgaccatgaggTcaccctgaggtgctgggccctgggcttctaccctgcggagatcacactgacc tggcagcgggatggcgaggaccaaactcaggacaccgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccgtcttcccagtccaccgtccccatcgtgggcattgttgctggcctggctgtccta...gca gttgtggtcatcggagctgtggtcgctgctgtgatgtgtaggaggaagagCtcaggtgga

B*4410

(SEQ ID NO: 1496)

gctcccactccatgaggtatttctacaccgccatgtcccggcccggccgcggggagccccgcttcatcaccgtgggctac gtggacgacacgctgttcgtgaggttcgacagcgacgccacgagtccgaggaaggagccgcgggcgccatggatagagca ggaggggccggagtattgggaccgggagacacagatctccaagaccaacacacagacttaccgagagaacctgcgcaccg cgctccgctactacaaccagagcgaggccgggtctcacatcatccagaggatgtTtggctgcgacctggggcccgacggg cgcctcctccgcgggcataaccagttagcctacgacggcaaggattacatcgccctgaacgaggacctgagctcctggac cgcggcggacaccgcggctcagatcacccagcgcaagtgggaggcggcccgtgtggcggagcagcTgagagcctacctgg agggcctgtgcgtggagtCgctccgcagatacctggagaacgggaaggagacgctgcagcgcgcGg

B*4411

(SEQ ID NO: 1497)

gctcccactccatgaggtatttctacaccgccAtgtcccggcccggccgcggggagccccgcttcatcaccgtgggctac gtggacgacacgctgttcgtgaggttcgacagcgacgccAcgagtccgaggaaggagccgcgggcgccAtggatagagca ggaggggccggagtattgggaccgggaGacacagatctccaagaccaacacacagacttaccgagagaacctgcgcaCcc cgctcCgctactacaaccagagcgaggccgggtctcacatcAtccagaggatgtacggctgcgacgtggggccggacggg cgcctcctccgcgggTatgaccagGacgcctacgacggcaaggattacatcgccctgaacgaggacctgagctcctggac cgcggcggacaccgcggctcagatcacccagcgcaagtgggaggcggcccgtgtggcggagcaggaCagagcctacctgg agggccTgtgcgtggagtCgctccgcagatacctggagaacgggaaggagacgctgcagcgcgcGg

B*4412

(SEQ ID NO: 1498)

gctcccactccatgaggtatttctacaccgccAtgtcccggcccggccgcggggagccccgcttcatcaccgtgggctac gtggacgacacgctgttcgtgaggttcgacagcgacgccAcgagtccgaggaaggagccgcgggcgccAtggatagagca ggaggggccggagtattgggaccggaacacacagatctccaagaccaacacacagacttaccgagagaacctgcgcaCcG cgctcCgctactacaaccagagcgaggccgggtctcacatcAtccagaggatgtacggctgcgacgtggggccggacggg cgcctcctccgcgggTatgaccagGacgcctacgacggcaaggattacatcgccctgaacgaggacctgagctcctggac cgcggcggacaccgcggctcagatcacccagcgcaagtgggaggcggcccgtgtggcggagcaggaCagagcctacctgg agggccTgtgcgtggagtCgctccgcagatacctggagaacgggaaggagacgctgcagcgcgcGg

B*4413

(SEQ ID NO: 1499)

atgcgggtcacggcgccccgaaccctcctcctgctgctctgggggggcagtggccctgaccgagacctgggccggctccca ctccatgaggtatttctacaccgccatgtcccggcccggccgcggggagccccgcttcatcaccgtgggctacgtggacg acacgctgttcgtgaggttcgacagcgacgccacgagtccgaggaaggagccgcgggcgccatggatagagcaggagggg ccggagtattgggaGcgggagacacagatctccaagaccaacacacagacttaccgagagaacctgcgcaccgcgctccg ctactacaaccagagcgaggccgggtctcacatcatccagaggatgtacggctgcgacgtggggccggacgggcgcctcc tccgcgggtatgaccaggacgcctacgacggcaaggattacatcgccctgaacgaggacctgagctcctggaccgcggcg gacaccgcggctcagatcacccagcgcaagtgggaggcggcccgtgtggcggagcagctgagagcctacctggagggcct gtgcgtggagtcgctccgcagatacctggagaacgggaaggagacgctgcagcgcgcggaccccccaaagacacatgtga cccaccaccccatctctgaccatgaggtcaccctgaggtgctgggccctgggcttctaccctgcggagatcacactgacc tggcagcgggatggcgaggaccaaactcaggacaccgagcttgtggagaccagaccagcaggagatagaaccttccagaa -continued gtgggcagctgtggtggtgccttctggagaagagcagagatacacatgccatgtacagcatgaggggctgccgaagcccc tcaccctgagatgggagccgtcttcccagtccaccgtccccatcgtgggcattgttgctggcctggctgtccta...gca gttgtggtcatcggagctgtggtcgctgctgtgatgtgtaggaggaagagctcaggtgga

B*4414

(SEQ ID NO: 1500)
gctcccactccatgaggtatttctacaccgccatgtcccggcccggccgcggggagccccgcttcatcaccgtgggctac gtggacgacacgctgttcgtgaggttcgacagcgacgccacgagtccgaggaaggagccgcgggcgccatggatagagca ggaggggccggagtattgggaccgggagacacagatctccaagaccaacacacagacttaccgagagaacctgcgcaccg cgctccgctactacaaccagagcgaggccgggtctcacatcatccagaggatgtacggctgcgacgtggggccggacggg cgcctcctccgcgggcatAaccagGacgcctacgacggcaaggattacatcgccctgaacgaggacctgagctcctggac cgcggcggacaccgcggctcagatcacccagcgcaagtgggaggcggcccgtgtggcggagcaggaCagagcctacctgg agggccTgtgcgtggagtCgctccgcagatacctggagaacgggaaggagacgctgcagcgcgcGg

B*4415

(SEQ ID NO: 1501)
gctcccactccatgaggtatttccacaccgccatgtcccggcccggccgcggggagccccgcttcatcaccgtgggctac gtggacgacacgctgttcgtgaggttcgacagcgacgccacgagtccgaggaaggagccgcgggcgccatggatagagca ggaggggccggagtattgggaccgggagacacagatctccaagaccaacacacagacttaccgagagagcctgcgcaCcg cgctcCgctactacaaccagagcgaggccgggtctcacacttggcagaggatgtatggctgcgacctggggcccgacggg cgcctcctccgcgggTataaccagttAgcctacgacggcaaggattacatcgccctgaacgaggacctgagctcctggac cgcggcggacaccgcggctcagatcacccagcgcaagtgggaggcggcccgtgtggcggagcaggaCagagcctacctgg agggcctgtgcgtggagtCgctccgcagatacctggagaacgggaaggagacgctgcagcgcgcGg

B*4416

(SEQ ID NO: 1502)
gctcccactccatgaggtatttctacaccgccAtgtcccggcccggccgcggggagccccgcttcatcaccgtgggctac gtggacgacacgctgttcgtgaggttcgacagcgacgccAcgagtccgaggaaggagccgcgggcgccAtggatagagca ggaggggccggagtattgggaccgggaGacacagatctccaagaccaacacacagacttaccgagagaacctgcgCaccG cgctccgctactacaaccagagcgaggccgggtctcacatcAtccagaggatgtacggctgcgacgtggggccggacggg cgcctcctccgcgggTatgaccagGacgcctacgacggcaaggattacatcgccctgaacgaggacctgagctcctggac cgcggcggacaccgcggctcagatcacccagcgcaagtgggaggcggcccgtgtggcggagcaggaCagagcctacctgg agggcgagtgcgtggagtggctccgcagatacctggagaacgggaaggagacgctgCagcgcgcGg

B*4417

(SEQ ID NO: 1503)
gctcccactccatgaggtatttctacaccgccatgtcccggcccggccgcggggagccccgcttcatcaccgtgggctac gtggacgacacgctgttcgtgaggttcgacagcgacgccacgagtccgaggaaggagccgcgggcgccatggatagagca ggaggggccggagtattgggaccgggagacacagatctccaagaccaacacacagacttaccgagagaacctgcgcaccg cgctccgctactacaaccagagcgaggccgggtctcacatcatccagaggatgtacggctgcgacgtggggccggacggg cgcctcctccgcgggcatgaccagtCcgcctacgacggcaaggattacatcgccctgaacgaggacctgagctcctggac cgcggcggacaccgcggctcagatcacccagcgcaagtgggaggcggcccgtgtggcggagcaggaCagagcctacctgg agggccTgtgcgtggagtCgctccgcagatacctggagaacgggaaggagacgctgcagcgcgcGg

B*4418

(SEQ ID NO: 1504)
atgcgggtcacggcaccccgaaccgtcctcctgctgctctcggcggccctggccctgaccgagacctgggccggctccca ctccatgaggtatttccacaccgccatgtcccggcccggccgcggggagccccgcttcatcaccgtgggctacgtggacg acacgctgttcgtgaggttcgacagcgacgccacgagtccgaggaaggagccgcgggcgccatggatagagcaggagggg ccggagtattgggaccgggagacacagatctccaagaccaacacacagacttaccgagagaacctgcggaTcgcgctcCg ctactacaaccagagcgaggccgggtctcacacttggcagaggatgtatggctgcgacctggggcccgacgggcgcctcc -continued tccgcgggTataaccagttAgcctacgacggcaaggattacatcgccctgaacgaggacctgagctcctggaccgcggcg gacaccgcggctcagatcacccagcgcaagtgggaggcggcccgtgtggcggagcaggaCagagcctacctggagggcct gtgcgtggagtCgctccgcagatacctggagaacgggaaggagacgctgcagcgcgcGg

B*4420

(SEQ ID NO: 1505)

gctcccactccatgaggtatttctacaccgccatgtcccggcccggccgcggggagccccgcttcatcaccgtgggctac gtggacgacacgctgttcgtgaggttcgacagcgacgccacgagtccgaggaaggagccgcgggcgccatggatagagca ggaggggccggagtattgggaccgggagacacagatctccaagaccaacacacagacttaccgagagaacctgcgcaccg cgctccgctactacaaccagagcgaggcccgggtctcacacttggcagacgatgtaTggctgcgacgtggggccggacggg cgcctcctccgcgggTatgaccagGacgcctacgacggcaaggattacatcgccctgaacgaggacctgagctcctggac cgcggcggacaccgcggctcagatcacccagcgcaagtgggaggcggcccgtgtggcggagcaggaCagagcctacctgg agggccTgtgcgtggagtCgctccgcagatacctggagaacgggaaggagacgctgcagcgcgcGg

B*4421

(SEQ ID NO: 1506)

gctcccactccatgaggtatttctacaccgccAtgtcccggcccggccgcggggagccccgcttcatcaccgtgggctac gtggacgacacgctgttcgtgaggttcgacagcgacgccAcgagtccgaggaaggagccgcgggcgccAtggatagagca ggaggggccggagtattgggaccgggaGacacagatctccaagaccaacacacagacttaccgagagaacctgcgcaCcG cgctcCgctactacaaccagagcgaggcccgggtctcacatcAtccagaggatgtacggctgcgacgtggggccggacggg cgcctcctccgcgggTatgaccagGacgcctacgacggcaaggattacatcgccctgaacgaggacctgagctcctggac cgcggcggacaccgcggctcagatcacccagcgcaagtgggaggcggcccgtgtggcggagcaggaCagagcctacctgg agggcgagtgcgtggagtCgctccgcagatacctggagaacgggaaggagacgctgcagcgcgcGg

B*4422

(SEQ ID NO: 1507)

gctcccactccatgaggtatttctacaccgccgtgtcccggcccggccgcggggagccccgcttcatcaccgtgggctac gtggacgacacgctgttcgtgaggttcgacagcgacgccAcgagtccgaggaaggagccgcgggcgccAtggatagagca ggaggggccggagtattgggaccgggaGacacagatctccaagaccaacacacagacttaccgagagaacctgcgcaCcG cgctcCgctactacaaccagagcgaggcccgggtctcacatcAtccagaggatgtacggctgcgacgtggggccggacggg cgcctcctccgcgggTatgaccagGacgcctacgacggcaaggattacatcgccctgaacgaggacctgagctcctggac cgcggcggacaccgcggctcagatcacccagcgcaagtgggaggcggcccgtgtggcggagcaggaCagagcctacctgg agggccTgtgcgtggagtCgctccgcagatacctggagaacgggaaggagacgctgcagcgcgcGg

B*4424

(SEQ ID NO: 1508)

gctcccactccatgaggtatttctacaccgccatgtcccggcccggccgcggggagccccgcttcatcaccgtgggctac gtggacgacacgctgttcgtgaggttcgacagcgacgccacgagtccgaggaaggagccgcgggcgccgtgggtGgagca ggaggggccggagtattgggaccgggagacacagatctccaagaccaacacacagacttaccgagagaacctgcgcaccg cgctccgctactacaaccagagcgaggcccgggtctcacatcatccagaggatgtacggctgcgacgtggggccggacggg cgcctcctccgcgggtatgaccaggacgcctacgacggcaaggattacatcgccctgaacgaggacctgagctcctggac cgcggcggacaccgcggctcagatcacccagcgcaagtgggaggcggcccgtgtggcggagcaggacagagcctacctgg agggcctgtgcgtggagtCgctccgcagatacctggagaacgggaaggagacgctgcagcgcgcGg

B*4425

(SEQ ID NO: 1509)

gctcccactccatgaggtatttctacaccgccatgtcccggcccggccgcggggagccccgcttcatcaccgtgggctac gtggacgacacgctgttcgtgaggttcgacagcgacgccacgagtccgaggaaggagccgcgggcgccatggatagagca ggaggggccggagtattgggaccgggagacacagatctCcaagaccaacacacagacttaccgagagaacctgcggaTcG cgctcCgctactacaaccagagcgaggcccgggtctcacatcAtccagaggatgtacggctgcgacgtggggccggacggg -continued cgcctcctccgcgggTatgaccagtacgcctacgacggcaaggattacatcgccctgaacgaggacctgagctcctggac cgcggcggacaccgcggctcagatcacccagcgcaagtgggaggcggcccgtgtggcggagcaggaCagagcctacctgg agggccTgtgcgtggagtCgctccgcagatacctggagaacgggaaggagacgctgcagcgcgcGg

B*4426

(SEQ ID NO: 1510)

gctcccactccatgaggtatttctacaccgccatgtcccggcccggccgcggggagccccgcttcatcaccgtgggctac gtggacgacacgctgttGgtgaggttcgacagcgacgccacgagtccgaggaaggagccgcgggcgccatggatagagca ggaggggccggagtattgggaccgggagacacagatctccaagaccaacacacagacttaccgagagaacctgcgcaccg cgctccgctactacaaccagagcgaggcccgggtctcacatcatccagaggatgtacggctgcgacgtggggccggacggg cgcctcctccgcgggtatgaccaggacgcctacgacggcaaggattacatcgccctgaacgaggacctgagctcctggac cgcggcggacaccgcggctcagatcacccagcgcaagtgggaggcggcccgtgtggcggagcagctgagagcctacctgg agggcctgtgcgtggagtcgctccgcagatacctggagaacgggaaggagacgctgcagcgcgcgg

B*4427

(SEQ ID NO: 1511)

gctcccactccatgaggtatttctacaccgccatgtcccggcccggccgcggggagccccgcttcatcaccgtgggctac gtggacgacacgctgttcgtgaggttcgacagcgacgccAcgagtccgaggaaggagccgcgggcgccatggatagagca ggaggggccggagtattgggaccgggagacacagatctccaagaccaacacacagacttaccgagagaacctgcgcaccg cgctcCgctactacaaccagagcgaggcccgggtctcacatcatccagaggatgtacggctgcgacgtggggccggacggg cgcctcctccgcgggtatgaccagGacgcctacgacggcaaggattacatcgccctgaacgaggacctgagctcctggac cgcggcggacaccgcggctcagatcacccagcgcaagtgggaggcggcccgtgtggcggagcaggaCagagcctacctgg agggccTgtgcgtggagtCgctccgcagatacctggagaacgggaaggagacgctgcagcgcgcggaccccccaaagaca catgtgacccaccaccccatctctgaccatgaggccaccctgaggtgctgggccctgggcttctaccctgcggagatcac actgacctggcagcgggatggcgaggaccaaactcaggacacCgagcttgtggagaccagaccagcaggagatagaacct tccagaagtgggcagctgtggtggtgccttctggagaagagcagagatacacatgccatgtacagcatgaggggctgccg aagcccctcaccctgagatggg

B*4428

(SEQ ID NO: 1512)

gctcccactccatgaggtatttctacaccgccatgtcccggcccggccgcggggagccccgcttcatcaccgtgggctac gtggacgacacgctgttcgtgaggttcgacagcgacgccAcgagtccgaggaaggagccgcgggcgccatggatagagca ggaggggccggagtattgggaccgggagacacagatctccaagaccaacacacagacttaccgagagaacctgcgcaccg cgctccgctactacaaccagagcgaggcccgggtctcacatcAtccagaggatgtaTggctgcgacgtggggccggacggg cgcctcctccgcgggTatgaccagGacgcctacgacggcaaggattacatcgccctgaacgaggacctgagctcctggac cgcggcggacacCgcggctcagatcacccagcgcaagtgggaggcggcccgtgTggcggagcagcggagagcctacctgg agggccTgtgcgtggagtCgctccgcagatacctggagaacgggaaggagacgctgcagcgcgcGg

B*4429

(SEQ ID NO: 1513)

gctcccactccatgaggtatttctacaccgccatgtcccggcccggccgcggggagccccgcttcatcaccgtgggctac gtggacgacacgctgttcgtgaggttcgacagcgacgccacgagtccgaggaaggagccgcgggcgccatggatagagca ggaggggccggagtattgggaccgggagacacagatctccaagaccaacacacagacttaccgagagaacctgcgcaccg cgctccgctactacaaccagagcgaggcccgggtctcacatcatccagaggatgtacggctgcgacgtggggccggacggg cgcctcctccgcgggtatgaccaggacgcctacgacggcaaggattacatcgccctgaacgaggacctgagctcctggac cgcggcggacaccgcggctcagatcacccagcgcaagtgggaggcggcccgtgtggcggagcagctgagaActacctgg agggcctgtgcgtggagtCgctccgcagatacctggagaacgggaaggagacgctgcagcgcgcGg

B*4430

(SEQ ID NO: 1514)

gctcccactccatgaggtatttctacaccgccatgtcccggcccggccgcggggagccccgcttcatcaccgtgggctac gtggacgacacgctgttcgtgaggttcgacagcgacgccacgagtccgaggaaggagccgcgggcgccatggatagagca ggaggggccggagtattgggaccgggagacacagatctccaagaccaacacacagacttaccgagagaacctgcgcaccg cgctccgctactacaaccagagcgaggccgggtctcacatcatccagaggatgtacggctgcgacgtggggccggacggg cgcctcctccgcgggtatgaccaggacgcctacgacggcaaggattacatcgccctgaacgaggacctgagctcctggac cgcggcggacaccgcggctcagatcacccagcgcaagtgggaggcggcccgtgtggcggagcagctgagagcctacctgg agggcctgtgcgCggagtcgctccgcagatacctggagaacgggaaggagacgctgcagcgcgcgg

B*4431

(SEQ ID NO: 1515)

atgcgggtcacggcgccccgaaccctcctcctgctgctctggggggcagtggccctgaccgagacctgggccggctccca ctccatgaggtatttctacaccgccatgtcccggcccggccgcggggagccccgcttcatcaccgtgggctacgtggacg acacgctgttcgtgaggttcgacagcgacgccacgagtccgaggaaggagccgcgggcgccatggatagagcaggagggg ccggagtattgggaccgggagacacagatctccaagaccaacacacagacttaccgagagaacctgcgcaccgcgctccg ctactacaaccagagcgaggccgggtctcacaccctccagaggatgtacggctgcgacgtggggccggacgggcgcctcc tccgcgggcataaccagtacgcctacgacggcaaggattacatcgccctgaacgaggacctgcgctcctggaccgccgcg gacacggcggctcagatctcccagcgcaagtTggaggcggcccgtgtggcggagcagctgagagcctacctggagggcga gtgcgtggagtCgctccgcagatacctggagaacgggaaggacaagctggagcgcgctgaccccccaaagacacacgtga cccaccaccccatctctgaccatgaggccaccctgaggtgctgggccctgggtttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatggg

B*4432

(SEQ ID NO: 1516)

gctcccactccatgaggtatttctacaccgccatgtcccggcccggccgcggggagccccgcttcatcaccgtgggctac gtggacgacacgctgttcgtgaggttcgacagcgacgccacgagtccgaggaaggagccgcgggcgccatggatagagca ggaggggccggagtattgggaccCggagacacagatctccaagaccaacacacagacttaccgagagaacctgcgcaccg cgctccgctactacaaccagagcgaggccgggtctcacatcatccagaggatgtacggctgcgacgtggggccggacggg cgcctcctccgcgggtatgaccaggacgcctacgacggcaaggattacatcgccctgaacgaggacctgagctcctggac cgcggcggacaccgcggctcagatcacccagcgcaagtgggaggcggcccgtgtggcggagcagctgagagcctacctgg agggcctgtgcgtggagtCgctccgcagatacctggagaacgggaaggagacgctgcagcgcgcgg

B*4433

(SEQ ID NO: 1517)

gctcccactccatgaggtatttctacaccgccatgtcccggcccggccgcggggagccccgcttcatcaccgtgggctac gtggacgacacgctgttcgtgaggttcgacagcgacgccacgagtccgaggaaggagccgcgggcgccatggatagagca ggaggggccggagtattgggaccgggagacacagatctccaagaccaacacacagacttaccgagagaacctgcgcaccg cgctccgctactacaaccagagcgaggccgggtctcacatcatccagaggatgtacggctgcgacgtggggccggacggg cgcctcctccgcgggtatgaccaggacgcctacgacggcaaggattacatcgccctgaacgaggacctgagctcctggac cgcggcggacaccgcggctcagatcacccagcgcaagtgggaggcggcccgtgtggcggagcaggacagagcctacctgg agggcctgtgcgtggagtcgctccgcagatacctggagaacgggaaggagacgctgcagcgcgcgg

B*4501

(SEQ ID NO: 1518)

atgcgggtcacggcgccccgaaccgtcctcctgctgctctcggcggccctggccctgaccgagacctgggccggctccca ctccatgaggtatttccacaccgccatgtcccggcccggccgcggggagccccgcttcatcaccgtgggctacgtggacg -continued acacgctgttcgtgaggttcgacagcgacgccacgagtccgaggaaggagccgcgggcgccatggatagagcaggagggg ccggagtattgggaccgggagacacagatctccaagaccaacacacagacttaccgagagagcctgcggaacctgcgcgg ctactacaaccagagcgaggccgggtctcacacttggcagaggatgtatggctgcgacctggggcccgacgggcgcctcc tccgcgggTataaccagttAgcctacgacggcaaggattacatcgccctgaacgaggacctgagctcctggaccgcggcg gacaccgcggctcagatcacccagcgcaagtgggaggcggcccgtgtggcggagcaggaCagagcctacctggagggcct gtgcgtggagtCgctccgcagatacctggagaacgggaaggagacgctgcagcgcgcggaccccccaaagacacatgtga cccaccacccatctctgaccatgaggccaccctgaggtgctgggccctggcttctaccctgcggagatcacactgacc tggcagcgggatggcgaggaccaaactcaggacacCgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccatccccatcgtgggcattgttgctggcctggctgtccta...gca gttgtggtcatcggagctgtggtcgctActgtgatgtgtaggaggaagagCtcaggtgga B*4502
(SEQ ID NO: 1519)
gctcccactccatgaggtatttccacaccgccatgtcccggcccggccgcggggagccccgcttcatcaccgtgggctac gtggacgacacgctgttcgtgaggttcgacagcgacgccacgagtccgaggaaggagccgcgggcgccatggatagagca ggaggggccggagtattgggaccgggagacacagatctccaagaccaacacacagactTaccgagagagcctgcggaacc tgcgcggctactacaaccagagcgaggccgggtctcacacttggcagaggatgtatggctgcgacctggggcccgacggg cgcctcctccgcgggTataaccagtTcgcctacgacggcaaggattacatcgccctgaacgaggacctgagctcctggac cgcggcggacaccgcggctcagatcacccagcgcaagtgggaggcggcccgtgtggcggagcaggaCagagcctacctgg agggccTgtgcgtggagtCgctccgcagatacctggagaacgggaaggagacgctgcagcgcgcGg B*4503
(SEQ ID NO: 1520)
gctcccactccatgaggtatttccacaccgccatgtcccggcccggccgcggggagccccgcttcatcaccgtgggctac gtggacgacacgctgttcgtgaggttcgacagcgacgccacgagtccgaggaaggagccgcgggcgccatggatagagca ggaggggccggagtattgggaccgggagacacagatctccaagaccaacacacagacttaccgagagagcctgcggaacc tgcgcggctactacaaccagagcgaggccgggtctcacacttggcagaggatgtatggctgcgacctggggcccgacggg cgcctcctccgcgggtataaccGgttagcctacgacggcaaggattacatcgccctgaacgaggacctgagctcctggac cgcggcggacaccgcggctcagatcacccagcgcaagtgggaggcggcccgtgtggcggagcaggacagagcctacctgg agggcctgtgcgtggagtcgctccgcagatacctggagaacgggaaggagacgctgcagcgcgcgg B*4504
(SEQ ID NO: 1521)
atgcgggtcacggcaccccgaaccgtcctcctgctgctctcggcggccctggccctgaccgagacctgggcggctccca ctccatgaggtatttccacaccgccatgtcccggcccggccgcggggagccccgcttcatcaccgtgggctacgtggacg acacgctgttcgtgaggttcgacagcgacgccacgagtccgaggaaggagccgcgggcgccatggatagagcaggagggg ccggagtattgggaccgggagacacagatctccaagaccaacacacagacttaccgagagagcctgcggaacctgcgcgg ctactacaaccagagcgaggccgggtctcacacttggcagaggatgtatggctgcgacctggggcccgacgggcgcctcc tccgcgggTataaccagttAgcctacgacggcaaggattacatcgccctgaacgaggacctgagctcctggaccgcggcg gacaccgcggctcagatcacccagcgcaagtgggaggcggcccgtgtggcggagcaggaCagagcctacctggagggcct gtgcgtggagtggctccgcagatacctggagaacgggaaggagacgctgcagcgcgcggaccccccaaagacacatgtga cccaccacccatctctgaccatgaggccaccctgaggtgctgggccctggcttctaccctgcggagatcacactgacc tggcagcgggatggcgaggaccaaactcaggacacCgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccatccccatcgtgggcattgttgctggcctggctgtccta...gca gttgtggtcatcggagctgtggtcgctActgtgatgtgtaggaggaagagCtcaggtgga

B*4505

(SEQ ID NO: 1522)

gctcccactccatgaggtatttccacaccgccatgtcccggcccggccgcggggagccccgcttcatcaccgtgggctac gtggacgacacgctgttcgtgaggttcgacagcgacgccacgagtccgaggaaggagccgcgggcgccatggatagagca ggaggggccggagtattgggaccgggagacacagatctccaagaccaacacacagacttaccgagagagcctgcggaacc tgcgcggctactacaaccagagcgaggccgggtctcacacttggcagaggatgtatggctgcgacctggggcccgacggg cgcctcctccgcgggtataaccagttagcctacgacggcaaggattacatcgccctgaacgaggacctgagctcctggac cgcggcggacaccgcggctcagatcacccagcgcaagtgggaggcggcccgtgtggcggagcaggacagagTctacctgg agggcctgtgcgtggagtcgctccgcagatacctggagaacgggaaggagacgctgcagcgcg

B*4506

(SEQ ID NO: 1523)

gctcccactccatgaggtatttccacaccgccatgtcccggcccggccgcggggagccccgcttcatcaccgtgggctac gtggacgacacgctgttcgtgaggttcgacagcgacgccacgagtccgaggaaggagccgcgggcgccatggatagagca ggaggggccggagtattgggaccgggagacacagatctacaaggcccaggcacagactgaccgagagagcctgcggaacc tgcgcggctactacaaccagagcgaggccgggtctcacacttggcagaggatgtatggctgcgacctggggcccgacggg cgcctcctccgcgggTataaccagttAgcctacgacggcaaggattacatcgccctgaacgaggacctgagctcctggac cgcggcggacaccgcggctcagatcacccagcgcaagtgggaggcggcccgtgtggcggagcaggaCagagcctacctgg agggcctgtgcgtggagtCgctccgcagatacctggagaacgggaaggagacgctgcagcgcgcGg

B*4601

(SEQ ID NO: 1524)

atgcgggtcacggcgccccgaaccgtcctcctgctgctctcgggagccctggccctgaccgagacctgggccggctccca ctccatgaggtatttctacaccgccatgtcccggcccggccgcggggagccccgcttcatcgcagtgggctacgtggacg acacccagttcgtgaggttcgacagcgacgccgcgagtccgaggatggcgccccgggcgccatggatagagcaggagggg ccggagtattgggaccgggagacacagaagtacaagCgccaggcacagactgaccgagtgagcctgcggaacctgcgcgg ctactacaaccagagcgaggccgggtctcacaccctccagaggatgtacggctgcgacgtggggccggacgggcgcctcc tccgcgggcatgaccagtccgcctacgacggcaaggattacatcgccctgaacgaggacctgagctcctggaccgcggcg gacacggcggctcagatcacccagcgcaagtgggaggcggcccgtgaggcggagcagtggagagcctacctggagggcct gtgcgtggagtggctccgcagatacctggagaacgggaaggagacgctgcagcgcgcggacccccccaaagacacatgtga cccaccacccatctctgaccatgaggccaccctgaggtgctgggccctgggcttctaccctgcggagatcacactgacc tggcagcgggatggcgaggaccaaactcaggacaccgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccatccccatcgtgggcattgttgctggcctggctgtccta...gca gttgtggtcatcggagctgtggtcgctactgtgatgtgtaggaggaagagCtcaggtgga

B*4602

(SEQ ID NO: 1525)

gctcccactccatgaggtatttctacaccgccatgtcccggcccggccgcggggagccccgcttcatcgcagtgggctac gtggacgacacccagttcgtgaggttcgacagcgacgccgcgagtccgaggatggcgccccgggcgccatggatagagca ggaggggccggagtattgggaccgggagacacagaagtacaagcgccaggcacagactgGccgagtgagcctgcggaacc tgcgcggctactacaaccagagcgaggccgggtctcacaccctccagaggatgtacggctgcgacgtggggccggacggg cgcctcctccgcgggcatgaccagtccgcctacgacggcaaggattacatcgccctgaacgaggacctgagctcctggac cgcggcggacacggcggctcagatcacccagcgcaagtgggaggcggcccgtgaggcggagcagtggagagcctacctgg agggcctgtgcgtggagtggctccgcagatacctggagaacgggaaggagacgctgcagcgcgcgg -continued

B*470101

(SEQ ID NO: 1526)
atgcgggtcacggcgccccgaaccctcctcctgctgctctgggggcagtggccctgaccgagacctgggctggctccca
ctccatgaggtatttctacaccgccatgtcccggcccggccgcggggagccccgcttcatcaccgtgggctacgtggacg
acacgctgttcgtgaggttcgacagcgacgccacgagtccgaggaaggagccgcgggcgccatggatagagcaggagggg
ccggagtattgggaccgggagacacagatctccaagaccaacacacagacttaccgagaggacctgcggaccctgctccg
ctactacaaccagagcgaggccgggtctcacaccctccagaggatgtttggctgcgacgtggggccggacgggcgcctcc
tccgcgggtaccaccaggacgcctacgacggcaaggattacatcgccctgaacgaggacctgagctcctggaccgccgcg
gacacggcggctcagatcacccagcgcaagtgggaggcggcccgtgtggcggagcagctgagagcctacctggagggcga
gtgcgtggagtggctccgcagatacctggagaacgggaaggagacgctgcagcgcgcggaccccccaaagacacacgtga
cccaccacccatctctgaccatgaggccaccctgaggtgctgggccctggcttctaccctgcggagatcacactgacc
tggcagcgggatggcgaggaccaaactcaggacactgagcttgtggagaccagaccagcaggagatagaaccttccagaa
gtgggcagctgtggtggtgccttctggagaagagcagagatacacatgccatgtacagcatgaggggctgccgaagcccc
tcaccctgagatgggagccgtcttcccagtccaccgtccccatcgtgggcattgttgctggcctggctgtccta...gca
gttgtggtcatcggagctgtggtcgctgctgtgGtgtgtaggaggaagagctcaggtgga

B*4702

(SEQ ID NO: 1527)
gcgggtcacggcgccccgaaccctcctcctgctgctctgggggcagtggccctgaccgagacctgggctggctcccact
ccatgaggtatttctacaccgccatgtcccggcccggccgcggggagccccgcttcatcaccgtgggctacgtggacgac
acgctgttcgtgaggttcgacagcgacgccacgagtccgaggaaggagccgcgggcgccatggatagagcaggaggggcc
ggagtattgggaccgggagacacagatctccaagaccaacacacagacttaccgagagagcctgcggaacctgcgcggct
actacaaccagagcgaggccgggtctcacaccctccagaggatgtTtggctgcgacgtggggccggacgggcgcctcctc
cgcgggtaccaccaggacgcctacgacggcaaggattacatcgccctgaacgaggacctgagctcctggaccgccgcgga
cacggcggctcagatcacccagcgcaagtgggaggcggcccgtgTggcggagcagcTgagagcctacctggagggcgagt
gcgtggagtggctccgcagatacctggagaacgggaaggagacgctgcagcgcgcggaccccccaaagacacacgtgacc
caccacccatctctgaccatgaggccaccctgaggtgctgggccctgggCttctaccctgcggagatcacactgacctg
gcagcgggatggcgaggaccaaactcaggacactgagcttgtggagaccagaccagcaggagatagaaccttccagaagt
gggcagctgtggtggtgccttctggagaagagcagagatacacatgccatgtacagcatgaggggctgccgaagcccctc
accctgagatgggagccgtcttcc

B*4703

(SEQ ID NO: 1528)
gctcccactccatgaggtatttctacaccgccatgtcccggcccggccgcggggagccccgcttcatcaccgtgggctac
gtggacgacacgctgttcgtgaggttcgacagcgacgccacgagtccgaggaaggagccgcgggcgccatggatagagca
ggaggggccggagtattgggaccgggagacacagatctccaagaccaacacacagacttaccgagagagcctgcggaacc
tgctcCgctactacaaccagagcgaggccgggtctcacaccctccagaggatgtTtggctgcgacgtggggccggacggg
cgcctcctccgcgggtaccaccagGacgcctacgacggcaaggattacatcgccctgaacgaggacctgagctcctggac
cgccgcggacacggcggctcagatcacccagcgcaagtgggaggcggcccgtgTggcggagcagcTgagagcctacctgg
agggcgagtgcgtggagtggctccgcagatacctggagaacgggaaggagacgctgcagcgcgcGg

B*4704

(SEQ ID NO: 1529)
gctcccactccatgaggtatttctacaccgccatgtcccggcccggccgcggggagccccgcttcatcaccgtgggctac
gtggacgacacgctgttcgtgaggttcgacagcgacgccacgagtccgaggaaggagccgcgggcgccatggatagagca
ggaggggccggagtattgggaccgggagacacagatctccaagaccaacAcacagacttaccgagagaacctgcgcaCcg
CgctcCgctactacaaccagagcgaggccgggtctcacaccctccagaaTatgtatggctgcgacgtggggccggacggg -continued cgcctcctccgcgggtaccaccagGacgcctacgacggcaaggattacatcgccctgaacgaggacctgagctcctggac cgccgcggacacggcggctcagatcacccagcgcaagtgggaggcggcccgtGTggcggagcagcTgagagcctacctgg agggcgagtgcgtggagtggctccgcagatacctggagaacgggaaggagacgctgcagcgcgcGg

B*4801

(SEQ ID NO: 1530)

atgctggtcatggcgcccgaaccgtcctcctgctgctctcggcggccctggccctgaccgagacctgggccggctccca ctccatgaggtatttctacacctccgtgtcccggcccggccgcggggagccccgcttcatctcagtgggctacgtggacg acacccagttcgtggaggttcgacagcgacgccgcgagtccgagagaggagccgcgggcgccgtggatagagcaggagggg ccggagtattgggaccgggagacacagatctccaagaccaacacacagactTaccgagagagcctgcggaacctgcgcgg ctactacaaccagagcgaggccgggtctcacaccctccagagcatgtacggctgcgacgtggggccggacgggcgcctcc tccgcgggcataaccagtacgcctacgacggcaaggattacatcgccctgaacgaggacctgcgctcctggaccgccgcg gacacggcggctcagatctcccagcgcaagttggaggcggcccgtgtggcggagcagctgagagcctacctggagggcga gtgcgtggagtggctccgcagatacctggagaacgggaaggacaagctggagcgcgctgaccccccaaagacacacgtga cccaccaccccatctctgaccatgaggccacccctgaggtgctgggccctgggtttctaccctgcggagatcacactgacc tggcagcgggatggcgaggaccaaactcaggacactgagcttgtggagaccagaccagcaggagatagaaccttccagaa gtggAcagctgtggtggtgccttctggagaagagcagagatacacatgccatgtacagcatgaggggctgccgaagcccc tcacCctgagatgggagccgtcttcccagtccaccgtccccatcgtgggcattgttgctggcctggctgtccta...gca gttgtggtcatcggagctgtggtcgctgctgtgatgtgtaggaggaagagttcaggtgga

B*4802

(SEQ ID NO: 1531)

gtcctcctgctgctctcggcggccctggccctgaccgagacctgggccggctcccactccatgaggtatttctacacctc cgtgtcccggcccggccgcggggagccccgcttcatctcagtgggctacgtggacgacacccagttcgtggaggttcgaca gcgacgccgcgagtccgagagaggagccgcgggcgccgtggatagagcaggaggggccggagtattgggaccgggagaca cagatctCcaagaccaacAcacagacttaccgagagagcctgcggaacctgcgcggctactacaaccagagcgaggccgg gtctcacatcAtccagaggatgtaTggctgcgacctggggcccgacgggcgcctcctccgcgggcatgaccagtCcgcct acgacggcaaggattacatcgccctgaacgaggacctgAgctcctggaccgcggcggacaccgcggctcagatcacccag cgcaagtgggaggcggcccgtgTggcggagcagcTgagagcctacctggagggccTgtgcgtggagtggctccgcagata cctggagaacgggaaggagacgctgcagcgcgcggacccccccaaagacacacgtgacccaccaccccGtctctgaccatg aggccaccctgaggtgctgggccctgggcttctaccctgcggagatcacactgacctggcagcgggatggcgaggaccaa actcaggacactgagcttgtggagaccagaccagcaggagatagaaccttccagaagtgggcagctgtggtggtgccttc tggagaagagcagagatacacatgccatgtacagcatgaggggctgccgaagcccctcaccctgagatgggagccatctt cccagtccaccatcccatcgtgggcattgttgctggcctggctgtccta...gcagttgtggtcatcggagctgtggtc gctactgtgatgtgtaggaggaagagCtcaggtgga

B*4803

(SEQ ID NO: 1532)

gctcccactccatgaggtatttctacacctccgtgtcccggcccggccgcggggagccccgcttcatctcagtgggctac gtggacgacacccagttcgtgaggttcgacagcgacgccgcgagtccgagagaggagccgcgggcgccgtggatagagca ggaggggccggagtattgggaccgggaGacacagatctCcaagaccaacacacagactTaccgagagagcctgcggaacc tgcgcggctactacaaccagagcgaggccgggtctcacaccctccagagGatgtacggctgcgacgtggggccggacggg cgcctcctccgcgggcatAaccagtacgcctacgacggcaaggattacatcgccctgaacgaggacctgcgctcctggac cgccgcggacacggcggctcagatctcccagcgcaagtTggaggcggcccgtgTggcggagcagctgagagcctacctgg agggcgagtgcgtggagtggctccgcagatacctggagaacgggaaggacaagctggagcgcgctg

B*4804

(SEQ ID NO: 1533)

gctcccactccatgaggtatttctacacctccgtgtcccggcccggccgcggggagccccgcttcatctcagtgggctac gtggacgacacccagttcgtgaggttcgacagcgacgccgcgagtccgagagaggagccgcgggcgccgtggatagagca ggaggggccggagtattgggaccgggagacacagatctccaagaccaacacacagacttaccgagagagcctgcggaacc tgcgcggctactacaaccagagcgaggccgggtctcacaccctccagagcatgtacggctgcgacgtggggccggacggg cgcctcctccgcgggcataaccagtacgcctacgacggcaaggattacatcgccctgaacgaggacctgcgctcctggac cgccgcggacacggcggctcagatctcccagcgcaagttggaggcggcccgtgtggcggagcagctgagagcctacctgg agggcgagtgcgtggagtggctccgcagataccggagaacgggaaggagacgctgcagcgcgcGgaccccccaaagaca cacgtgacccaccaccccatctctgaccatgaggccaccctgagtgctgggccctgggtttctaccctgcggagatcac actgacctggcagcgggatggcgaggaccaaactcaggacactgagcttgtggagaccagaccagcaggagatagaacct tccagaagtggAcagctgtggtggtgccttctggagaagagcagagatacacatgccatgtacagcatgaggggctgccg aagcccctcaccctgagatggg

B*4805

(SEQ ID NO: 1534)

atgctggtcatggcgccccgaaccgtcctcctgctgctctcggcggccctggccctgaccgagacctgggccggctccca ctccatgaggtatttctacacctccgtgtcccggcccggccgcggggagccccgcttcatctcCgtgggctacgtggacg acacccagttcgtgaggttcgacagcgacgccgcgagtccgagagaggagccgcgggcgccgtggatagagcaggagggg ccggagtattgggaccgggaGacacagatctCcaagaccaacacacagactTaccgagagagcctgcggaacctgcgcgg ctactacaaccagagcgaggccgggtctcacaccctccagagcatgtacggctgcgacgtggggccggacgggcgcctcc tccgcgggcatAaccagtacgcctacgacggcaaggattacatcgccctgaacgaggacctgcgctcctggaccgccgcg gacacggcggctcagatcacccagcgcaagtgggaggcggcccgtgaggcggagcagcggagagcctacctggagggcga gtgcgtggagtggctccgcagataccggagaacgggaaggacaagctggagcgcgctg

B*4806

(SEQ ID NO: 1535)

gctcccactccatgaggtatttctacacctccgtgtcccggcccggccgcggggagccccgcttcatctcagtgggctac gtggacgacacccagttcgtgaggttcgacagcgacgccgcgagtccgagagaggagccgcgggcgccgtggatagagca ggaggggccggagtattgggaccggaacacacagatctTcaagaccaacacacagactTaccgagagagcctgcggaacc tgcgcggctactacaaccagagcgaggccgggtctcacaccctccagagcatgtacggctgcgacgtggggccggacggg cgcctcctccgcgggcatAaccagtacgcctacgacggcaaggattacatcgccctgaacgaggacctgcgctcctggac cgccgcggacacggcggctcagatctcccagcgcaagtTggaggcggcccgtgTggcggagcagctgagagcctacctgg agggcgagtgcgtggagtggctccgcagataccggagaacgggaaggacaagctggagcgcgctg

B*4807

(SEQ ID NO: 1536)

gctcccactccatgaggtatttctacacctccgtgtcccggcccggccgcggggagccccgcttcatctcagtgggctac gtggacgacacccagttcgtgaggttcgacagcgacgccgcgagtccgagagaggagccgcgggcgccgtggatagagca ggaggggccggagtattgggaccgggagacacagatctccaagaccaacacacagacttaccgagagagcctgcggaacc tgcgcggctactacaaccagagcgaggccgggtctcacaccctccagagcatgtacggctgcgacgtggggccggacggg cgcctcctccgcgggcataaccagtTcgcctacgacggcaaggattacatcgccctgaacgaggacctgcgctcctggac cgccgcggacacggcggctcagatctcccagcgcaagtTggaggcggcccgtgTggcggagcagctgagagcctacctgg agggcgagtgcgtggagtggctccgcagataccggagaacgggaaggacaagctggagcgcgctg

B*4901

(SEQ ID NO: 1537)

atgcgggtcacggcaccccgaaccgtcctcctgctgctctcggcggccctggccctgaccgagacctgggccggctccca ctccatgaggtatttccacaccgccatgtcccggcccggccgcggggagccccgcttcatcaccgtgggctacgtggacg -continued acacgctgttcgtgaggttcgacagcgacgccacgagtccgaggaaggagccgcgggcgccatggatagagcaggagggg ccggagtattgggaccgggagacacagatctccaagaccaacacacagacttaccgagagaacctgcggatcgcgctcCg ctactacaaccagagcgaggccgggtctcacacttggcagaggatgtatggctgcgacctggggcccgacgggcgcctcc tccgcgggtataaccagttAgcctacgacggcaaggattacatcgccctgaacgaggacctgagctcctggaccgcggcg gacaccgcggctcagatcacccagcgcaagtgggaggcggcccgtgaggcggagcagcTgagagcctacctggagggcct gtgcgtggagtggctccgcagatacctggagaacgggaaggagacgctgcagcgcgcggacccccccaaagacacatgtga cccaccaccccatctctgaccatgaggccaccctgaggtgctgggccctggcttctaccctgcggagatcacactgacc tggcagcgggatggcgaggaccaaactcaggacacCgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccatccccatcgtgggcattgttgctggcctggctgtccta...gca gttgtggtcatcggagctgtggtcgctActgtgatgtgtaggaggaagagCtcaggtgga

B*4902

(SEQ ID NO: 1538)

tcccactccatgaggtatttccacaccgccatgtcccggcccggccgcggggagccccgcttcatcaccgtgggctacgt ggacgacacgctgttcgtgaggttcgacagcgacgccacgagtccgaggaaggagccgcgggcgccatggatagagcagg aggggccggagtattgggaccgggagacacagatctccaagaccaacacacagacttaccgagagaacctgcgcaCcgcg ctcCgctactacaaccagagcgaggccgggtctcacacttggcagaggatgtatggctgcgacctggggcccgacgggcg cctcctccgcgggtataaccagttAgcctacgacggcaaggattacatcgccctgaacgaggacctgagctcctggaccg cggcggacaccgcggctcagatcacccagcgcaagtgggaggcggcccgtgaggcggagcagcTgagagcctacctggag ggcctgtgcgtggagtggctccgcagatacctggagaacgggaaggagacgctgcagcgcgcggacccccccaaagacaca tgtgacccaccaccccatctctgaccatgaggccaccctgaggtgctgggccctggcttctaccctgcggagatcacac tgacctggcagcgggatggcgaggaccaaactcaggacacCgagcttgtggagaccagaccagcaggagatagaaccttc cagaagtgggcagctgtggtggtgccttctggagaagagcagagatacacatgccatgtacagcatgaggggctgccgaa gcccctcaccctgagatggg

B*4903

(SEQ ID NO: 1539)

gctcccactccatgaggtatttccacaccgccatgtcccggcccggccgcggggagccccgcttcattgcagtgggctac gtggacgacacccagttcgtgaggttcgacagcgacgccgcgagtccgaggacggagccCgggcgccatggatagagca ggaggggccggagtattgggaccgggagacacagatctccaagaccaacacacagacttaccgagagaacctgcggaTcg cgctcCgctactacaaccagagcgaggccgggtctcacacttggcagaggatgtatggctgcgacCtggggcccgacggg cgcctcctccgcgggTataaccagttAgcctacgacggcaaggattacatcgccctgaacgaggacctgagctcctggac cgcggcggacaccgcggctcagatcacccagcgcaagtgggaggcggcccgtgaggcggagcagcTgagagcctacctgg agggccTgtgcgtggagtggctccgcagatacctggagaacgggaaggagacgctgcagcgcgcGg

B*5001

(SEQ ID NO: 1540)

atgcgggtcacggcaccccgaaccgtcctcctgctgctctcggcggccctggccctgaccgagacctgggccggctccca ctccatgaggtatttccacaccgccatgtcccggcccggccgcggggagccccgcttcatcaccgtgggctacgtggacg acacgctgttcgtgaggttcgacagcgacgccacgagtccgaggaaggagccgcgggcgccatggatagagcaggagggg ccggagtattgggaccgggagacacagatctccaagaccaacacacagacttaccgagagagcctgcggaacctgcgcgg ctactacaaccagagcgaggccgggtctcacacttggcagaggatgtatggctgcgacctggggcccgacgggcgcctcc tccgcgggtataaccagttAgcctacgacggcaaggattacatcgccctgaacgaggacctgagctcctggaccgcggcg gacaccgcggctcagatcacccagcgcaagtgggaggcggcccgtgaggcggagcagcTgagagcctacctggagggcct gtgcgtggagtggctccgcagatacctggagaacgggaaggagacgctgcagcgcgcggacccccccaaagacacatgtga cccaccaccccatctctgaccatgaggccaccctgaggtgctgggccctggcttctaccctgcggagatcacactgacc -continued tggcagcgggatggcgaggaccaaactcaggacacCgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccatccccatcgtgggcattgttgctggcctggctgtccta...gca gttgtggtcatcggagctgtggtcgctActgtgatgtgtaggaggaagagCtcaggtgga

B*5002 (SEQ ID NO: 1541)

atgcgggtcacggcaccccgaaccgtcctcctgctgctctcggcggccctggccctgaccgagacctgggccggctccca ctccatgaggtatttccacaccgccatgtcccggcccggccgcggggagccccgcttcatcaccgtgggctacgtggacg acacgctgttcgtgaggttcgacagcgacgccacgagtccgaggaaggagccgcgggcgccatggatagagcaggagggg ccggagtattgggaccgggagacacagatctccaagaccaacacacagacttaccgagagagcctgcggaacctgcgcgg ctactacaaccagagcgaggccgggtctcacacttggcagaggatgtatggctgcgacctggggcccgacgggcgcctcc tccgcgggtataaccagttAgcctacgacggcaaggattacatcgccctgaacgaggacctgagctcctggaccgcggcg gacaccgcggctcagatcacccagcgcaagtgggaggcggcccgtgaggcggagcagcTgagagcctacctggagggcct gtgcgtggagtCgctccgcagatacctggagaacgggaaggagacgctgcagcgcgcggaccccccaaagacacatgtga cccaccaccccatctctgaccatgaggccacccctgaggtgctgggccctgggcttctaccctgcggagatcacactgacc tggcagcgggatggcgaggaccaaactcaggacacCgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccatccccatcgtgggcattgttgctggcctggctgtccta...gca gttgtggtcatcggagctgtggtcgctActgtgatgtgtaggaggaagagCtcaggtgga

B*5004 (SEQ ID NO: 1542)

gctcccactccatgaggtatttccacaccgccatgtcccggcccggccgcggggagccccgcttcatcaccgtgggctac gtggacgacacgctgttcgtgaggttcgacagcgacgccAcgagtccgaggaaggagccgcgggcgccatggatagagca ggaggggccggagtattgggaccgggagacacagatctccaagaccaacacacagacttaccgagagagcctgcggaacc tgcgcggctactacaaccagagcgaggccgggtctcacacttggcagaggatgtacggctgcgacgtggggcccgacggg cgcctcctccgcgggTataaccagttAgcctacgacggcaaggattacatcgccctgaacgaggacctgagctcctggac cgcggcggacaccgcggctcagatcacccagcgcaagtgggaggcggcccgtgaggcggagcagcTgagagcctacctgg agggccTgtgcgtggagtggctccgcagatacctggagaacgggaaggagacgctgcagcgcgcGg

B*510101 (SEQ ID NO: 1543)

atgcgggtcacggcgccccgaaccgtcctcctgctgctctgggggcagtggccctgaccgagacctgggccggctccca ctccatgaggtatttctacaccgccatgtcccggcccggccgcggggagccccgcttcatTgcagtgggctacgtggacg acacccagttcgtgaggttcgacagcgacgccgcgagtccgaggacggagccccgggcgccatggatagagcaggagggg ccggagtattgggaccggaacacacagatctTcaagaccaacacacagacttaccgagagaacctgcggatcgcgctcCg ctactacaaccagagcgaggccgggtctcacacttggcagaCgatgtatggctgcgacgtggggccggacgggcgcctcc tccgcgggcataaccagtacgcctacgacggcaaagattacatcgccctgaacgaggacctgagctcctggaccgcggcg gacaccgcggctcagatcacccagcgcaagtgggaggcggcccgtgaggcggagcagcTgagagcctacctggagggcct gtgcgtggagtggctccgcagaCacctggagaacgggaaggagacgctgcagcgcgcggaccccccaaagacacacgtga cccaccaccccGtctctgaccatgaggccacccctgaggtgctgggccctgggcttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccatccccatcgtgggcattgttgctggcctggctgtccta...gca gttgtggtcatcggagctgtggtcgctactgtgatgtgtaggaggaagagCtcaggtgga

B*510102 (SEQ ID NO: 1544)

atgcgggtcacggcgccccgaaccgtcctcctgctgctctgggggcagtggccctgaccgagacctgggccggctccca ctccatgaggtatttctacaccgccatgtcccggcccggccgcggggagccccgcttcatcgcagtgggctacgtggacg acacccagttcgtgaggttcgacagcgacgccgcgagtccgaggacggagccccgggcgccatggatagagcaggagggg ccggagtattgggaccggaacacacagatctTcaagaccaacacacagacttaccgagagaacctgcggatcgcgctcCg ctactacaaccagagcgaggccgggtctcacacttggcagaCgatgtatggctgcgacgtggggccggacgggcgcctcc tccgcgggcataaccagtacgcctacgacggcaaagattacatcgccctgaacgaggacctgagctcctggaccgcggcg gacaccgcggctcagatcacccagcgcaagtgggaggcggcccgtgaggcggagcagcTgagagcctacctggagggcct gtgcgtggagtggctccgcagaCacctggagaacgggaaggagacgctgcagcgcgcggaccccccaaagacacacgtga cccaccaccccGtctctgaccatgaggccaccctgaggtgctgggccctgggcttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacatgccatgtacagcatgaggggctgccgaagcccc tcaccctgagatgggagccatcttcccagtccaccatccccatcgtgggcattgttgctggcctggctgtccta...gca gttgtggtcatcggagctgtggtcgctactgtgatgtgtaggaggaagagCtcaggtgga

B*510103 (SEQ ID NO: 1545)

gctcccactccatgaggtatttctacaccgccatgtcccggcccggccgcggggagccccgcttcatTgcagtgggctac gtggacgacacccagttcgtgaggttcgacagcgacgccgcgagtccgaggacggagccccgggcgccgtggatagagca ggaggggccggagtattgggaccggaacacacagatctTcaagaccaacacacagacttaccgagagaacctgcggatcg cgctcCgctactacaaccagagcgaggccgggtctcacacttggcagaCgatgtaTggctgcgacgtggggccggacggg cgcctcctccgcgggcataaccagtacgcctacgacggcaaAgattacatcgccctgaacgaggacctgAgctcctggac cgcggcggacaccgcggctcagatcacccagcgcaagtgggaggcggcccgtgaggcggagcagcTgagagcctacctgg agggccTgtgcgtggagtggctccgcagaCacctggagaacgggaaggagacgctgcagcgcgcgg

B*510104 (SEQ ID NO: 1546)

gctcccactccatgaggtatttctacaccgccatgtcccggcccggccgcggggagccccgcttcatTgcagtgggctac gtggacgacacccagttcgtgaggttcgacagcgacgccgcgagtccgaggacggagccccgggcgccAtggatagagca ggaggggccggagtattgggaccggaacacacagatctTcaagaccaacacacagacttaccgagagaacctgcggatcg cgctcCgctactacaaccagagcgaggccgggtctcacacttggcagaCgatgtaTggctgcgacgtggggccggacggg cgcctcctccgcgggcatAaccagtacgcctacgacggcaaggattacatcgccctgaacgaggacctgAgctcctggac cgcggcggacaccgcggctcagatcacccagcgcaagtgggaggcggcccgtgaggcggagcagcTgagagcctacctgg agggccTgtgcgtggagtggctccgcagaCacctggagaacgggaaggagacgctgcagcgcgcgg

B*510105 (SEQ ID NO: 1547)

atgcgggtcacggcgccccgaaccgtcctcctgctgctctgggggcagtggccctgaccgagacctgggccggctccca ctccatgaggtatttctacaccgccatgtcccggcccggccgcggggagccccgcttcattgcagtgggctacgtggacg acacccagttcgtgaggttcgacagcgacgccgcgagtccgaggacggagccccgggcgccatggatagagcaggagggg ccggagtattgggaccggaacacacagatcttcaagaccaacacacagacttaccgagagaacctgcggatcgcgctccg ctactacaaccagagcgaggccgggtctcacacttggcagacgatgtatggctgcgacgtggggccggacgggcgcctcc tccgcgggcataaccagtacgcctacgacggcaaagattacatcgccctgaacgaggacctgagctcctggaccgcggcg gacaccgcggctcagatcacccagcgcaagtgggaggcggcccgtgaggcggagcagctgagagcctacctggagggcct gtgcgtggagtggctccgcagacacctggagaacgggaaggagacgctgcagcgcgcggaccccccaaagacacaTgtga cccaccaccccGtctctgaccatgaggccaccctgaggtgctgggccctgggcttctaccctgcggagatcacactgacc tggcagcgggatggcgaggaccaaactcaggacactgagcttgtggagaccagaccagcaggagatagaaccttccagaa -continued gtgggcagctgtggtggtgccttctggagaagagcagagatacacatgccatgtacagcatgaggggctgccgaagcccc tcaccctgagatgggagccatcttcccagtccaccatccccatcgtgggcattgttgctggcctggctgtccta...gca gttgtggtcatcggagctgtggtcgctactgtgatgtgtaggaggaagagCtcag

B*510201

(SEQ ID NO: 1548)

atgcgggtcacggcgccccgaaccgtcctcctgctgctctgggggcagtggccctgaccgagacctgggccggctccca ctccatgaggtatttctacaccgccatgtcccggcccggccgcggggagcccccgcttcatTgcagtgggctacgtggacg acacccagttcgtgaggttcgacagcgacgccgcgagtccgaggacggagcccccgggcgccatggatagagcaggagggg ccggagtattgggaccggaacacacagatctTcaagaccaacacacagacttaccgagagaacctgcggatcgcgctcCg ctactacaaccagagcgaggccgggtctcacacttggcagaCgatgtatggctgcgacgtggggccggacgggcgcctcc tccgcgggcataaccagtacgcctacgacggcaaAgattacatcgccctgaacgaggacctgAgctcctggaccgcggcg gacaccgcggctcagatcacccagcgcaagtgggaggcggcccgtgaggcggagcagcTgagagcctacctggagggccT gtgcgtggagtggctccgcagatacctggagaacgggaaggagacgctgcagcgcgcggaccccccaaagacacacgtga cccaccaccccGtctctgaccatgaggccaccctgaggtgctgggccctgggcttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccatccccatcgtgggcattgttgctggcctggctgtccta...gca gttgtggtcatcggagctgtggtcgctactgtgatgtgtaggaggaagagCtcaggtgga

B*510202

(SEQ ID NO: 1549)

atgcgggtcacggcgccccgaaccgtcctcctgctgctctgggggcagtggccctgaccgagacctgggccggctccca ctccatgaggtatttctacaccgccatgtcccggcccggccgcggggagcccccgcttcatcgcagtgggctacgtggacg acacccagttcgtgaggttcgacagcgacgccgcgagtccgaggacggagcccccgggcgccatggatagagcaggagggg ccggagtattgggaccggaacacacagatctTcaagaccaacacacagacttaccgagagaacctgcggatcgcgctcCg ctactacaaccagagcgaggccgggtctcacacttggcagaCgatgtatggctgcgacgtggggccggacgggcgcctcc tccgcgggcataaccagtacgcctacgacggcaaAgattacatcgccctgaacgaggacctgAgctcctggaccgcggcg gacaccgcggctcagatcacccagcgcaagtgggaggcggcccgtgaggcggagcagcTgagagcctacctggagggccT gtgcgtggagtggctccgcagatacctggagaacgggaaggagacgctgcagcgcgcggaccccccaaagacacacgtga cccaccaccccGtctctgaccatgaggccaccctgaggtgctgggccctgggcttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccatccccatcgtgggcattgttgctggcctggctgtccta...gca gttgtggtcatcggagctgtggtcgctactgtgatgtgtaggaggaagagCtcaggtgga

B*5103

(SEQ ID NO: 1550)

atgcgggtcacggcgccccgaaccgtcctcctgctgctctgggggcagtggccctgaccgagacctgggccggctccca ctccatgaggtatttctacaccgccatgtcccggcccggccgcggggagcccccgcttcattgcagtgggctacgtggacg acacccagttcgtgaggttcgacagcgacgccgcgagtccgaggacggagcccccgggcgccatggatagagcaggagggg ccggagtattgggaccggaacacacagatcttcaagaccaacacacagacttaccgagagaacctgcggatcgcgctccg ctactacaaccagagcgaggccgggtctcacacttggcagacgatgtatggctgcgacgtggggccggacgggcgcctcc tccgcgggcataaccagtacgcctacgacggcaaagattacatcgccctgaacgaggacctgagctcctggaccgcggcg gacaccgcggctcagatcacccagcgcaagtgggaggcggcccgtgaggcggagcagctgagagcctacctggagggcct gtgcgtggagGggctccgcagacacctggagaacgggaaggagacgctgcagcgcgcggaccccccaaagacacacgtga

```
cccaccaccccGtctctgaccatgaggccaccctgaggtgctgggccctgggcttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccatccccatcgtgggcattgttgctggcctggctgtccta...gca gttgtggtcatcggagctgtggtcgctactgtgatgtgtaggaggaagagctcaggtgga
```

B*5104 (SEQ ID NO: 1551)

```
atgcgggtcacggcgccccgaaccgtcctcctgctgctctgggggggcagtggccctgaccgagacctgggccggctccca ctccatgaggtatttctacaccgccatgtcccggcccggccgcggggagccccgcttcattgcagtgggctacgtggacg acacccagttcgtgaggttcgacagcgacgccgcgagtccgaggacggagccccgggcgccatggatagagcaggaggg ccggagtattgggaccggaacacacagatcttcaagaccaacacacagacttaccgagagaacctgcggatcgcgctccg ctactacaaccagagcgaggccgggtctcacatcAtccagaggatgtatggctgcgacgtggggccggacgggcgcctcc tccgcgggcataaccagtacgcctacgacggcaaagattacatcgccctgaacgaggacctgagctcctggaccgcggcg gacaccgcggctcagatcacccagcgcaagtgggaggcggcccgtgaggcggagcagcTgagagcctacctggagggcct gtgcgtggagtggctccgcagaCacctggagaacgggaaggagacgctgcagcgcgcggacccccaaagacacacgtga cccaccaccccGtctctgaccatgaggccaccctgaggtgctgggccctgggcttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccatccccatcgtgggcattgttgctggcctggctgtccta...gca gttgtggtcatcggagctgtggtcgctactgtgatgtgtaggaggaagagCtcaggtgga
```

B*5105 (SEQ ID NO: 1552)

```
gctcccactccatgaggtatttctacaccgccatgtcccggcccggccgcggggagccccgcttcatcgcagtgggctac gtggacgacacccagttcgtgaggttcgacagcgacgccgcgagtccgaggacggagccccgggcgccatggatagagca ggaggggccggagtattgggaccggaacacacagatcttcaagaccaacacacagacttaccgagagaacctgcggatcg cgctcCgctactacaaccagagcgaggccgggtctcacacttggcagacgatgtatggctgcgacgtggggccggacggg cgcctcctccgcgggcataaccagtacgcctacgacggcaaAgattacatcgccctgaacgaggacctgAgctcctggac cgcggcggacaccgcggctcagatcacccagcgcaagtgggaggcggcccgtgTggcggagcagcggagagcctacctgg agggccTgtgcgtggagtggctccgcagatacctggagaacgggaaggagacgctgcagcgcgcggacccccaaagaca cacgtgacccaccaccccGtctctgaccatgaggccaccctgaggtgctgggccctgggcttctaccctgcggagatcac actgacctggcagcgggatggcgaggaccaaactcaggacactgagcttgtggagaccagaccagcaggagatagaacct tccagaagtgggcagctgtggtggtgccttctggagaagagcagagatacacatgccatgtacagcatgaggggctgccg aagcccctcaccctgagatggg
```

B*5106 (SEQ ID NO: 1553)

```
gctcccactccatgaggtatttctacaccgccatgtcccggcccggccgcggggagccccgcttcatTgcagtgggctac gtggacgacacccagttcgtgaggttcgacagcgacgccgcgagtccgaggacggagccccgggcgccAtggatagagca ggaggggccggagtattgggaccggaacacacagatcTcaagaccaacacacagacttaccgagagaacctgcggatcg cgctcCgctactacaaccagagcgaggccgggtctcacaccctccagaggatgtacggctgcgacgtggggccggacggg cgcctcctccgcgggcataaccagtacgcctacgacggcaaAgattacatcgccctgaacgaggacctgAgctcctggac cgcggcggacaccgcggctcagatcacccagcgcaagtgggaggcggcccgtgaggcggagcagcTgagagcctacctgg agggccTgtgcgtggagtggctccgcagaCacctggagaacgggaaggagacgctgcagcgcgcgg
```

B*5107

(SEQ ID NO: 1554)

gctcccactccatgaggtatttctacaccgccatgtcccggcccggccgcggggagccccgcttcatTgcagtgggctac gtggacgacacccagttcgtgaggttcgacagcgacgccgcgagtccgaggaCggagccccgggcgccatggatagagca ggaggggccggagtattgggaccggaacacacagatctCcaagaccaacacacagacttaccgagagaacctgcggatcg cgctcCgctactacaaccagagcgaggccgggtctcacacttggcagaCgatgtaTggctgcgacgtggggccggacggg cgcctcctccgcgggcataaccagtacgcctacgacggcaaAgattacatcgccctgaacgaggacctgAgctcctggac cgcggcggacaccgcggctcagatcacccagcgcaagtgggaggcggcccgtgaggcggagcagcTgagagcctacctgg agggccTgtgcgtggagtggctccgcagaCacctggagaacgggaaggagacgctgcagcgcgcgg

B*5108

(SEQ ID NO: 1555)

atgcgggtcacggcgccccgaaccgtcctcctgctgctctgggggcagtggccctgaccgagacctgggccggctccca ctccatgaggtatttctacaccgccatgtcccggcccggccgcggggagccccgcttcattgcagtgggctacgtggacg acacccagttcgtgaggttcgacagcgacgccgcgagtccgaggacggagccccgggcgccatggatagagcaggagggg ccggagtattgggaccggaacacacagatcttcaagaccaacacacagacttaccgagagaacctgcggatcgcgctccg ctactacaaccagagcgaggccgggtctcacacttggcagacgatgtatggctgcgacgtggggccggacgggcgcctcc tccgcgggcataaccagtacgcctacgacggcaaagattacatcgccctgaacgaggacctgagctcctggaccgcggcg gacaccgcggctcagatcacccagcgcaagtgggaggcggcccgtgtggcggagcaggaCagagcctacctggagggcct gtgcgtggagtggctccgcagaCacctggagaacgggaaggagacgctgcagcgcgcggaccccccaaagacacacgtga cccaccaccccGtctctgaccatgaggccaccctgaggtgctgggccctgggcttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccatccccatcgtgggcattgttgctggcctggctgtcccta...gca gttgtggtcatcggagctgtggtcgctactgtgatgtgtaggaggaagagCtcaggtgga

B*5109

(SEQ ID NO: 1556)

gctcccactccatgaggtatttctacaccgccatgtcccggcccggccgcggggagccccgcttcatTgcagtgggctac gtggacgacacccagttcgtgaggttcgacagcgacgccgcgagtccgaggacggagccccgggcgccatggatagagca ggaggggccggagtattgggaccggaacacacagatcttcaagaccaacacacagacttaccgagagaacctgcggatcg cgctccgctactacaaccagagcgaggccgggtctcacacttggcagacgatgtatggctgcgacgtggggccggacggg cgcctcctccgcgggcataaccagtacgcctacgacggcaaagattacatcgccctgaacgaggacctgagctcctggac cgcggcggacaccgcggctcagatcacccagcgcaagtgggaggcggcccgtgTggcggagcagcTgagagcctacctgg agggccTgtgcgtggagtggctccgcagaCacctggagaacgggaaggagacgctgcagcgcgcgg

B*5110

(SEQ ID NO: 1557)

tacaccgccatgtcccggcccggccgcggggagccccgcttcattgcagtgggctacgtggacgacacccagttcgtgag gttcgacagcgacgccgcgagtccgaggacggagccccgggcgccatggatagagcaggaggggccggagtattgggacc ggaacacacagatcttcaagaccaacacacagacttaccgagagaacctgcggatcgcgctcCgctactacaaccagagc gaggccgggtctcacacttggcagaCgatgtaTggctgcgacgtggggccggacgggcgcctcctccgcgggcatAacca gtacgcctacgacggcaaggattacatcgccctgaacgaggacctgcgctcctggaccgccgcggacacggcggctcaga tcacccagcgcaagtgggaggcggcccgtgTggcggagcagcTgagagcctacctggagggcgagtgcgtggagtggctc cgcagatacctggagaacgggaaggagacgctgcagcgcgcggaccccccaaagacacacgtgacccaccaccccGtctc tgaccatgaggccaccctgaggtgctgggccctgggcttctaccctgcggagatcacactgacctggcagcgggatggcg aggaccaaactcaggacactgagcttgtggagaccag -continued

B*5112

(SEQ ID NO: 1558)
gctcccactccatgaggtatttctacaccgccatgtcccggcccggccgcggggagccccgcttcattgcagtgggctac gtggacgacacccagttcgtgaggttcgacagcgacgccgcgagtccgaggacggagccccgggcgccatggatagagca ggaggggccggagtattgggaccggaacacacagatcttcaagaccaacacacagacttaccgagagaacctgcggatcg cgctccgcGactacaaccagagcgaggccgggtctcacacttggcagacgatgtatggctgcgacgtggggccggacggg cgcctcctccgcgggcataaccagtacgcctacgacggcaaagattacatcgccctgaacgaggacctgagctcctggac cgcggcggacaccgcggctcagatcacccagcgcaagtgggaggcggcccgtgaggcggagcagctgagagcctacctgg agggcctgtgcgtggagtggctccgcagacacctggagaacgggaaggagacgctgcagcgcgcgg

B*511301

(SEQ ID NO: 1559)
gctcccactccatgaggtatttctacaccgccatgtcccggcccggccgcggggagccccgcttcatTgcagtgggctac gtggacgacacccagttcgtgaggttcgacagcgacgccgcgagtccgaggacggagccccgggcgccatggatagagca ggaggggccggagtattgggaccggaacacacagatcttcaagaccaacacacagacttaccgagagaacctgcggatcg cgctccgctactacaaccagagcgaggccgggtctcacacttggcagacgatgtatggctgcgacgtggggccggacggg cgcctcctccgcgggcataaccagtTcgcctacgacggcaaggattacatcgccctgaacgaggacctgAgctcctggac cgcggcggacaccgcggctcagatcacccagcgcaagtgggaggcggcccgtgaggcggagcagctgagagcctacctgg agggccTgtgcgtggagtggctccgcagaCacctggagaacgggaaggagacgctgcagcgcgcgg

B*511302

(SEQ ID NO: 1560)
gctcccactccatgaggtatttctacaccgccatgtcccggcccggccgcggggagccccgcttcatTgcagtgggctac gtggacgacacccagttcgtgaggttcgacagcgacgccgcgagtccgaggacggagccccgggcgccatggatagagca ggaggggccggagtattgggaccggaacacacagatcttcaagaccaacacacagacttaccgagagaacctgcggatcg cgctccgctactacaaccagagcgaggccgggtctcacacttggcagacgatgtatggctgcgacgtggggccggacggg cgcctcctccgcgggcataaccagtTcgcctacgacggcaaAgattacatcgccctgaacgaggacctgAgctcctggac cgcggcggacaccgcggctcagatcacccagcgcaagtgggaggcggcccgtgaggcggagcagctgagagcctacctgg agggccTgtgcgtggagtggctccgcagaCacctggagaacgggaaggagacgctgcagcgcgcgg

B*5114

(SEQ ID NO: 1561)
gctcccactccatgaggtatttctacaccgccatgtcccggcccggccgcggggagccccgcttcattgcagtgggctac gtggacgacacccagttcgtgaggttcgacagcgacgccgcgagtccgaggacggagccccgggcgccatggatagagca ggaggggccggagtattgggaccggaacacacagatcttcaagaccaacacacagacttaccgagagaacctgcggatcg cgctccgctactacaaccagagcgaggccgggtctcacacttggcagacgatgtatggctgcgacgtggggccggacggg cgcctcctccgcgggcataaAcagtacgcctacgacggcaaagattacatcgccctgaacgaggacctgagctcctggac cgcggcggacaccgcggctcagatcacccagcgcaagtgggaggcggcccgtgaggcggagcagctgagagcctacctgg agggcctgtgcgtggagtggctccgcagacacctggagaacgggaaggagacgctgcagcgcgcgg

B*5115

(SEQ ID NO: 1562)
gctcccactccatgaggtatttctacaccgccatgtcccggcccggccgcggggagccccgcttcatcgcagtgggctac gtggacgacacccagttcgtgaggttcgacagcgacgccgcgagtccgaggacggagccccgggcgccatggatagagca ggaggggccggagtattgggaccggaacacacagatcttcaagaccaacacacagacttaccgagagaacctgcggaTcg cgctcCgctactacaaccagagcgaggccgggtctcacacttggcagaCgatgtaTggctgcgacCtggggccggacggg cgcctcctccgcgggcataaccagttAgcctacgacggcaaggattacatcgccctgaacgaggacctgagctcctggac cgcggcggacaccgcggctcagatcacccagcgcaagtgggaggcggcccgtgTggcggagcagctgagagcctacctgg agggccTgtgcgtggagtggctccgcagatacctggagaacgggaaggagacgctgcagcgcgcGg

B*5116

(SEQ ID NO: 1563)
gctcccactccatgaggtatttctacaccgccatgtcccggcccggccgcggggagccccgcttcatTgcagtgggctac gtggacgacacccagttcgtgaggttcgacagcgacgccgcgagtccgaggacggagccccgggcgccAtggatagagca ggaggggccggagtattgggaccggaacacacagatctTcaagaccaacacacagacttaccgagagaacctgcggatcg cgctcCgctactacaaccagagcgaggccgggtctcacacttggcagaCgatgtaTggctgcgacgtggggccggacggg cgcctcctccgcgggcataaccagtacgcctacgacggcaaAgattacatcgccctgaacgaggacctgAgctcctggac cgcggcggacaccgcggctcagatcacccagcgcaagtgggaggcggcccgtgaggcggagcagcTgagagcctacctgg agggcgagtgcgtggagtggctccgcagaCacctggagaacgggaaggagacgctgcagcgcgcgg

B*5117

(SEQ ID NO: 1564)
gctcccactccatgaggtatttctacaccgccatgtcccggcccggccgcggggagccccgcttcattgcagtgggctac gtggacgacacccagttcgtgaggttcgacagcgacgccgcgagtccgaggacggagccccgggcgccatggatagagca ggaggggccggagtattgggaccggaacacacagatcttcaagaccaacacacagacttaccgagagaacctgcggatcg cgctccgctactacaaccagagcgaggccgggtctcacacttggcagacgatgtatggctgcgacgtggggccggacggg cgtctcctccgcggTtataaccagtacgcctacgacggcaaagattacatcgccctgaacgaggacctgagctcctggac cgcggcggacaccgcggctcagatcacccagcgcaagtgggaggcggcccgtgaggcggagcagctgagagcctacctgg agggcctgtgcgtggagtggctccgcagacacctggagaacgggaaggagacgctgcagcgcgcgg

B*5118

(SEQ ID NO: 1565)
gctcccactccatgaggtatttctacaccgccatgtcccggcccggccgcggggagccccgcttcattgcagtgggctac gtggacgacacccagttcgtgaggttcgacagcgacgccgcgagtccgaggacggagccccgggcgccatggatagagca ggaggggccggagtattgggaccggaacacacagatcttcaagaccaacacacagacttaccgagagaacctgcggatcg cgctccgctactacaaccagagcgaggccgggtctcacacttggcagacgatgtatggctgcgacgtggggccggacggg cgcctcctccCgggcataaccagtacgcctacgacggcaaagattacatcgccctgaacgaggacctgagctcctggac cgcggcggacaccgcggctcagatcacccagcgcaagtgggaggcggcccgtgaggcggagcagctgagagcctacctgg agggcctgtgcgtggagtggctccgcagacacctggagaacgggaaggagacgctgcagcgcgcgg

B*5119

(SEQ ID NO: 1566)
gctcccactccatgaggtatttctacaccgccatgtcccggcccggccgcggggagccccgcttcatTgcagtgggctac gtggacgacacccagttcgtgaggttcgacagcgacgccgcgagtccgaggacggagccccgggcgccatggatagagca ggaggggccggagtattgggaccggaacacacagatcttcaagaccaacacacagacttaccgagagaacctgcggatcg cgctccgctactacaaccagagcgaggccgggtctcacacttggcagacgatgtatggctgcgacgtggggccggacggg cgcctcctccgcgggcataaccagtacgcctacgacggcaaagattacatcgccctgaacgaggacctgagctcctggac cgcggcggacaccgcggctcagatcacccagcgcaagtgggaggcggcccgtgtggcggagcagctgagaAcctacctgg agggccTgtgcgtggagtggctccgcagaCacctggagaacgggaaggagacgctgcagcgcgcgg

B*5120

(SEQ ID NO: 1567)
gctcccactccatgaggtatttctacaccgccatgtcccggcccggccgcggggagccccgcttcatTgcagtgggctac gtggacgacacccagttcgtgaggttcgacagcgacgccgcgagtccgaggacggagccccgggcgccatggatagagca ggaggggccggagtattgggaccggaacacacagatcttcaagaccaacacacagactgaccgagagaacctgcggatcg cgctccgctactacaaccagagcgaggccgggtctcacacttggcagacgatgtatggctgcgacgtggggccggacggg cgcctcctccgcgggcataaccagtacgcctacgacggcaaagattacatcgccctgaacgaggacctgagctcctggac cgcggcggacaccgcggctcagatcacccagcgcaagtgggaggcggcccgtgtggcggagcaggaCagagcctacctgg agggccTgtgcgtggagtggctccgcagaCacctggagaacgggaaggagacgctgcagcgcgcgg -continued

B*5121

(SEQ ID NO: 1568)

gctcccactccatgaggtatttctacaccgccatgtcccggcccggccgcggggagccccgcttcatTgcagtgggctac
gtggacgacacccagttcgtgaggttcgacagcgacgccgcgagtccgaggacggagccccgggcgccatggatagagca
ggaggggccggagtattgggaccggaacacacagatcttcaagaccaacacacagacttaccgagagaacctgcggatcg
cgctccgctactacaaccagagcgaggccgggtctcacacttggcagacgatgtatggctgcgacgtggggccggacggg
cgcctcctccgcgggcataaccagtacgcctacgacggcaaAgattacatcgccctgaacgaggacctgagctcctggac
cgcggcggacaccgcggctcagatcacccagcgcaagtgggaggcggcccgtgaggcggagcagctgagagcctacctgg
agggcaCgtgcgtggagtggctccgcagaCacctggagaacgggaaggagacgctgcagcgcgcgg

B*5122

(SEQ ID NO: 1569)

gctcccactccatgaggtatttctacaccgccatgtcccggcccggccgcggggagccccgcttcatTgcagtgggctac
gtggacgacacccagttcgtgaggttcgacagcgacgccgcgagtccgaggacggagccccgggcgccatggatagagca
ggaggggccggagtattgggaccggaacacacagatctGcaagaccaacacacagacttaccgagagaacctgcggatcg
cgctcCgctactacaaccagagcgaggccgggtctcacacttggcagaCgatgtaTggctgcgacgtggggccggacggg
cgcctcctccgcgggcataaccagtacgcctacgacggcaaAgattacatcgccctgaacgaggacctgAgctcctggac
cgcggcggacaccgcggctcagatcacccagcgcaagtgggaggcggcccgtgaggcggagcagcTgagagcctacctgg
agggccTgtgcgtggagtggctccgcagaCacctggagaacgggaaggagacgctgcagcgcgcgg

B*5123

(SEQ ID NO: 1570)

gctcccactccatgaggtatttctacaccgccatgtcccggcccggccgcggggagccccgcttcatTgcagtgggctac
gtggacgacacccagttcgtgaggttcgacagcgacgccgcgagtccgaggacggagccccgggcgccatggatagagca
ggaggggccggagtattgggaccggaacacacagatcttcaagaccaacacacagacttaccgagagaacctgcggatcg
cgctccgctactacaaccagagcgaggccgggtctcacacttggcagacgatgtatggctgcgacgtggggccggacggg
cgcctcctccgcgggcataaccagtacgcctacgacggcaaagattacatcgccctgaacgaggacctgagctcctggac
cgcggcggacaccgcggctcagatcacccagcgcaagtgggaggcggcccgtgaggcggagcagcTgagagcctacctgg
agggcctgtgcgtggagtCgctccgcagatacctggagaacgggaaggagacgctgcagcgcgcgg

B*5124

(SEQ ID NO: 1571)

gctcccactccatgaggtatttctacaccgccatgtcccggcccggccgcggggagccccgcttcatTgcagtgggctac
gtggacgacacccagttcgtgaggttcgacagcgacgccgcgagtccgaggacggagccccgggcgccAtggatagagca
ggaggggccggagtattgggaccggaacacacagatctTcaagaccaacacacagacttaccgagagaacctgcggatcg
cgctcCgctactacaaccagagcgaggccgggtctcacacttggcagaCgatgtaTggctgcgacgtggggccggacggg
cgcctcctccgcgggcatAaccagtacgcctacgacggcaaggattacatcgccctgaacgaggacctgcgctcctggac
cgcggcggacaccgcggctcagatcacccagcgcaagtgggaggcggcccgtgaggcggagcagcTgagagcctacctgg
agggccTgtgcgtggagtggctccgcagaCacctggagaacgggaaggagacgctgcagcgcgcgg

B*5126

(SEQ ID NO: 1572)

gctcccactccatgaggtatttctacaccgccatgtcccggcccggccgcggggagccccgcttcattgcagtgggctac
gtggacgacacccagttcgtgaggttcgacagcgacgccgcgagtccgaggacggagAcccgggcgccatggatagagca
ggaggggccggagtattgggaccggaacacacagatcttcaagaccaacacacagacttaccgagagaacctgcggatcg
cgctccgctactacaaccagagcgaggccgggtctcacacttggcagacgatgtatggctgcgacgtggggccggacggg
cgcctcctccgcgggcataaccagtacgcctacgacggcaaagattacatcgccctgaacgaggacctgagctcctggac
cgcggcggacaccgcggctcagatcacccagcgcaagtgggaggcggcccgtgaggcggagcagctgagagcctacctgg
agggcctgtgcgtggagtggctccgcagacacctggagaacgggaaggagacgctgcagcgcgcgg -continued

B*5128

(SEQ ID NO: 1573)

```
gctcccactccatgaggtatttctacaccgccatgtcccggcccggccgcggggagccccgcttcattgcagtgggctac
gtggacgacacccagttcgtgaggttcgacagcgacgccgcgagtccgaggacggagccccgggcgccatggatagagca
ggaggggcGggagtattgggaccggaacacacagatcttcaagaccaacacacagacttaccgagagaacctgcggatcg
cgctccgctactacaaccagagcgaggccgggtctcacacttggcagacgatgtatggctgcgacgtggggccggacggg
cgcctcctccgcgggcataaccagtacgcctacgacggcaaagattacatcgccctgaacgaggacctgagctcctggac
cgcggcggacaccgcggctcagatcacccagcgcaagtgggaggcggcccgtgaggcggagcagctgagagcctacctgg
agggcctgtgcgtggagtggctccgcagacacctggagaacgggaaggagacgctgcagcgcgcgg
```

B*5129

(SEQ ID NO: 1574)

```
gctcccactccatgaggtatttctacaccgccatgtcccggcccggccgcggggagccccgcttcatTgcagtgggctac
gtggacgacacccagttcgtgaggttcgacagcgacgccgcgagtccgaggacggagccccgggcgccatggatagagca
ggaggggccggagtattgggaccggaacacacagatctTcaagaccaacacacagacttaccgagagaacctgcggatcg
cgctcCgctactacaaccagagcgaggccgggtctcacacttggcagaCgatgtatggctgcgacgtggggccggacggg
cgcctcctccgcgggcataaccagtacgcctacgacggcaaagattacatcgccctgaacgaggacctgagctcctggac
cgcggcggacaccgcggctcagatcacccagcgcaagtgggaggcggcccgtgaggcggagcagcggagagcctacctgg
agggcctgtgcgtggagtggctccgcagaCacctggagaacgggaaggagacgctgcagcgcgcggaccccccaaagaca
cacgtgacccaccaccccGtctctgaccatgaggccaccctgaggtgctgggcccctgggcttctaccctgcggagatcac
actgacctggcagcgggatggcgaggaccaaactcaggacactgagcttgtggagaccagaccagcaggagatagaacct
tccagaagtgggcagctgtggtggtgccttctggagaagagcagagatacacatgccatgtacagcatgaggggctgccg
aagcccctcaccctgagatggg
```

B*5130

(SEQ ID NO: 1575)

```
gctcccactccatgaggtatttctacaccgccatgtcccggcccggccgcggggagccccgcttcattgcagtgggctac
gtggacgacacccagttcgtgaggttcgacagcgacgccgcgagtccgaggacggagccccgggcgccatggatagagca
ggaggggccggagtattgggaccggaacacacagatcttcaagaccaacacacagacttaccgagagaacctgcggatcg
cgctccgctactacaaccagagcgaggccgggtctcacacttggcagacgatgtatggctgcgacgtggggccggacggg
cgcctcctccgcgggcataaccagtacgcctacgacggcaaagattacatcgccctgaacgaggacctgagctcctggac
cgcggcggacaccgcggctcagatcacccagcgcaagtgggaggcggcccgtgaggcggagcagctgagagcctacctgg
agggcctgtgcgtggagtggctccgcagacacctggagaacgggaaggagacgctgcagcgcgcggaccccccaaagaca
cacgtgacccaccaccccGtctctgaccatgaggccaccctgaggtgctgggcccctgggcttctaccctgcggagatcac
actgacctggcagcgggatggcgaggaccaaactcaggacactgagcttgtggagaccagaccagcaggagatGgaacct
tccagaagtgggcagctgtggtggtgccttctggagaagagcagagatacacatgccatgtacagcatgaggggctgccg
aagcccctcaccctgagatggg
```

B*5131

(SEQ ID NO: 1576)

```
gctcccactccatgaggtatttctacaccgccatgtcccggcccggccgcggggagccccgcttcatTgcagtgggctac
gtggacgacacccagttcgtgaggttcgacagcgacgccgcgagtccgaggacggagccccgggcgccatggatagagca
ggaggggccggagtattgggaccggaacacacagatcttcaagaccaacacacagacttaccgagagaacctgcggatcg
cgctccgctactacaaccagagcgaggccgggtctcacacttggcagacgatgtatggctgcgacgtggggccggacggg
cgcctcctccgcgggcataaccagtacgcctacgacggcaaAgattacatcgccctgaacgaggacctgagctcctggac
cgcggcggacaccgcggctcagatcacccagcgcaagtgggaggcggcccgtgTggcggagcagcTgagagcctacctgg
agggcgagtgcgtggagtggctccgcagaCacctggagaacgggaaggagacgctgcagcgcgcgg
```

B*5132

(SEQ ID NO: 1577)
gctcccactccatgaggtatttctacaccgccatgtcccggcccggccgcggggagccccgcttcattgcagtgggctac
gtggacgacacccagttcgtgaggttcgacagcgacgccgcgagtccgaggacggagccccgggcgccatggatagagca
ggaggggccggagtattgggaccggaacacacagatcttcaagaccaacacacagacttaccgagagaacctgcggatcg
cgctccgctactacaaccagagcgaggccgggtctcacacttggcagacgatgtatggctgcgacgtggggccggacggg
cgcctcctccgcgggcataaccagtacgcctacgacggcaaagattacatcgccctgaacgaggacctgagctcctggac
cgcggcggacaccgcggctcagatcacccagcgcaagtgggaggcggcccgtgaggcggagcagctgagagcctacctgg
agggcctgtgcgtggagtggctccgcagacacctggagaacgggaaggagacgctgcagcgcgcggaccccccaaagaca
cacgtgacccaccaccccgtctctgaccatgaggccaccctgaggtgctgggccctgggcttctaccctgcggagatcac
actgacctggcagcgggatggcgaggaccaaaactcaggacactgagcttgtggagaccagaccagcaggagatagaacct
tccagaagtgggcagctgtggtggtgccttctggagaagagcagagatacacatgccatgtacagcatgaggggctgcTg
aagcccctcaccctgagatggg

B*5133

(SEQ ID NO: 1578)
gctcccacttcatgaggtatttctacaccgccatgtcccggcccggccgcggggagccccgcttcatTgcagtgggctac
gtggacgacacccagttcgtgaggttcgacagcgacgccgcgagtccgaggacggagccccgggcgccAtggatagagca
ggaggggccggagtattgggaccggaacacacagatctTcaagaccaacacacagacttaccgagagaacctgcggatcg
cgctcCgctactacaaccagagcgaggccgggtctcacacttggcagaCgatgtaTggctgcgacgtggggccggacggg
cgcctcctccgcgggcataaccagtacgcctacgacggcaaAgattacatcgccctgaacgaggacctgAgctcctggac
cgcggcggacaccgcggctcagatcacccagcgcaagtgggaggcggcccgtgaggcggagcagcTgagagcctacctgg
agggccTgtgcgtggagtggctccgcagaCacctggagaacgggaaggagacgctgcagcgcgcgg

B*5134

(SEQ ID NO: 1579)
gctcccactccatgaggtatttctacaccgccatgtcccggcccggccgcggggagccccgcttcatTgcagtgggctac
gtggacgacacccagttcgtgaggttcgacagcgacgccgcgagtccgaggacggagccccgggcgccAtggatagagca
ggaggggccggagtattgggaccggaacacacagatctTcaagaccaacacacagacttaccgagagaacctgcggatcg
cgctcCgctactacaaccagagcgaggccgggtctcacacttggcagaCgatgtaTggctgcgacgtggggccggacggg
cgcctcctccgcgggcataaccagtacgcctacgacggcaaAgattacatcgccctgaacgaggacctgAgctcctggac
cgcggcggacacCgcggctcagatcacccagcgcaagtgggaggcggcccgtgaggcggagcagcTgagagcctacctgg
agggcgagtgcgtggagtggctccgcagatacctggagaacgggaaggagacgctgcagcgcgcgg

B*520101

(SEQ ID NO: 1580)
atgcgggtcacggcgccccgaaccgtcctcctgctgctctgggggggcagtggccctgaccgagacctgggccggctccca
ctccatgaggtatttctacaccgccatgtcccggcccggccgcggggagccccgcttcatcgcagtgggctacgtggacg
acacccagttcgtgaggttcgacagcgacgccgcgagtccgaggacggagccccgggcgccatggatagagcaggagggg
ccggagtattgggaccgggagacacagatctCcaagaccaacacacagacttaccgagagaacctgcggatcgcgctcCg
ctactacaaccagagcgaggccgggtctcacacttggcagaCgatgtatggctgcgacgtggggccggacgggcgcctcc
tccgcgggcataaccagtacgcctacgacggcaaagattacatcgccctgaacgaggacctgagctcctggaccgcggcg
gacaccgcggctcagatcacccagcgcaagtgggaggcggcccgtgaggcggagcagcTgagagcctacctggagggcct
gtgcgtggagtggctccgcagaCacctggagaacgggaaggagacgctgcagcgcgcggaccccccaaagacacacgtga
cccaccaccccGtctctgaccatgaggccaccctgaggtgctgggccctgggcttctaccctgcggagatcacactgacc
tggcagcgggatggcgaggaccaaaactcaggacactgagcttgtggagaccagaccagcaggagatagaaccttccagaa
gtgggcagctgtggtggtgccttctggagaagagcagagatacacatgccatgtacagcatgaggggctgccgaagcccc -continued tcaccctgagatgggagccatcttcccagtccaccatccccatcgtgggcattgttgctggcctggctgtccta...gca gttgtggtcatcggagctgtggtcgctactgtgatgtgtaggaggaagagCtcaggtgga

B*520102

(SEQ ID NO: 1581)

gtcctcctgctgctctgggggcagtggccctgaccgagacctgggccggctcccactccatgaggtatttctacaccgc catgtcccggcccggccgcggggagccccgcttcatTgcagtgggctacgtggacgacacccagttcgtgaggttcgaca gcgacgccgcgagtccgaggacggagcccgggcgccatggatagagcaggaggggccggagtattgggaccgggagaca cagatctCcaagaccaacacacagacttaccgagagaacctgcggatcgcgctcCgctactacaaccagagcgaggccgg gtctcacacttggcagaCgatgtatggctgcgacgtggggccggacgggcgcctcctccgcgggcataaccagtacgcct acgacggcaaagattacatcgccctgaacgaggacctgagctcctggaccgcggcggacaccgcggctcagatcacccag cgcaagtgggaggcggcccgtgaggcggagcagcTgagagcctacctggagggcctgtgcgtggagtggctccgcagaCa cctggagaacgggaaggagacgctgcagcgcgcggaccccccaaagacacacgtgacccaccaccccGtctctgaccatg aggccaccctgaggtgctgggccctgggcttctaccctgcggagatcacactgacctggcagcgggatggcgaggaccaa actcaggacactgagcttgtggagaccagaccagcaggagatagaaccttccagaagtgggcagctgtggtggtgccttc tggagaagagcagagatacacatgccatgtacagcatgaggggctgccgaagcccctcaccctgagatgggagccatctt cccagtccaccatccccatcgtgggcattgttgctggcctggctgtccta...gcagttgtggtcatcggagctgtggtc gctactgtgatgtgtaggaggaagagCtcaggtgga

B*520103

(SEQ ID NO: 1582)

gctcccactccatgaggtatttctacaccgccatgtcccggcccggccgcggggagccccgcttcatcgcagtgggctac gtggacgacacccagttcgtgaggttcgacagcgacgccgcgagtccgaggaCggagccgcgggcgccatggatagagca ggaggggccggagtattgggaccgggaGacacagatctCcaagaccaacacacagacttaccgagagaacctgcggatcg cgctcCgctactacaaccagagcgaggccgggtctcacacttggcagaCgatgtaTggctgcgacgtggggccggacggg cgcctcctccgcgggcataaccagtacgcctacgacggcaaAgattacatcgccctgaacgaggacctgagctcctggac cgcggcggacaccgcggctcagatcacccagcgcaagtgggaggcggcccgtgaggcggagcagcTgagagcctacctgg agggccTgtgcgtggagtggctccgcagaCacctggagaacgggaaggagacgctgcagcgcgcgg

B*520104

(SEQ ID NO: 1583)

gctcccactccatgaggtatttctacaccgccatgtcccggcccggccgcggggagccccgcttcattgcagtgggctac gtggacgacacccagttcgtgaggttcgacagcgacgccgcgagtccgaggacggagccccgggcgccatggatagagca ggaggggccggagtattgggaccgggagacacagatctccaagaccaacacacagacttaccgagagaacTtgcggatcg cgctccgctactacaaccagagcgaggccgggtctcacacttggcagacgatgtatggctgcgacgtggggccggacggg cgcctcctccgcgggcataaccagtacgcctacgacggcaaagattacatcgccctgaacgaggacctgagctcctggac cgcggcggacaccgcggctcagatcacccagcgcaagtgggaggcggcccgtgaggcggagcagctgagagcctacctgg agggcctgtgcgtggagtggctccgcagacacctggagaacgggaaggagacgctgcagcgcgcgg

B*5202

(SEQ ID NO: 1584)

gctcccactccatgaggtatttctacaccgccatgtcccggcccggccgcggggagccccgcttcatTgcagtgggctac gtggacgacacccagttcgtgaggttcgacagcgacgccgcgagtccgaggatggCgccccgggcgccatggatagagca ggaggggccggagtattgggaccgggaGacacagatctCcaagaccaacacacagacttaccgagagaacctgcggatcg cgctcCgctactacaaccagagcgaggccgggtctcacacttggcagaCgatgtaTggctgcgacgtggggccggacggg cgcctcctccgcgggcataaccagtacgcctacgacggcaaAgattacatcgccctgaacgaggacctgAgctcctggac cgcggcggacaccgcggctcagatcacccagcgcaagtgggaggcggcccgtgaggcggagcagcTgagagcctacctgg agggccTgtgcgtggagtggctccgcagaCacctggagaacgggaaggagacgctgcagcgcgcgg

B*5203

(SEQ ID NO: 1585)

gctcccactccatgaggtatttctacaccgccatgtcccggcccggccgcggggagccccgcttcatTgcagtgggctac
gtggacgacacccagttcgtgaggttcgacagcgacgccgcgagtccgaggacggagccccgggcgccatggatagagca
gtgacgacacccagttcgtgaggttcgacagcgacgccgcgagtccgaggacggagccccgggcgccatggatagagca
ggaggggccggagtattgggaccgggagacacagatctCcaagaccaacacacagacttaccgagagaacctgcggatcg
cgctccgctactacaaccagagcgaggccgggtctcacacttggcagacgatgtatggctgcgacgtggggccggacggg
cgcctcctccgcgggcataaccagtacgcctacgacggcaaagattacatcgccctgaacgaggacctgagctcctggac
cgcggcggacaccgcggctcagatcacccagcgcaagtgggaggcggcccgtgTggcggagcagcTgagagcctacctgg
agggccTgtgcgtggagtggctccgcagatacctggagaacgggaaggagacgctgcagcgcgcgg

B*5204

(SEQ ID NO: 1586)

atgcgggtcacggcgccccgaaccgtcctcctgctgctctgggggcagtggccctgaccgagacctgggccggctccca
ctccatgaggtatttctacaccgccatgtcccggcccggccgcggggagccccgcttcatcgcagtgggctacgtggacg
acacccagttcgtgaggttcgacagcgacgccgcgagtcAgaggacggagccccgggcgccatggatagagcaggagggg
ccggagtattgggaccgggagacacagatctccaagaccaacacacagacttaccgagagaacctgcggatcgcgctccg
ctactacaaccagagcgaggccgggtctcacacttggcagacgatgtatggctgcgacgtggggccggacgggcgcctcc
tccgcgggcataaccagtacgcctacgacggcaaagattacatcgccctgaacgaggacctgagctcctggaccgcggcg
gacaccgcggctcagatcacccagcgcaagtgggaggcggcccgtgaggcggagcagctgagagcctacctggagggcct
gtgcgtggagtggctccgcagacacctggagaacgggaaggagacgctgcagcgcgcggaccccccaaagacacacgtga
cccaccaccccgtctctgaccatgaggccaccctgaggtgctgggccctgggcttctaccctgcggagatcacactgacc
tggcagcgggatggcgaggaccaaactcaggacactgagcttgtggagaccagaccagcaggagatagaaccttccagaa
gtgggcagctgtggtggtgccttctggagaagagcagagatacatgccatgtacagcatgaggggctgccgaagcccc
tcaccctgagatgggagccatcttcccagtccaccatccccatcgtgggcattgttgctggcctggctgtccta...gca
gttgtggtcatcggagctgtggtcgctactgtgatgtgtaggaggaagagctcag

B*5205

(SEQ ID NO: 1587)

gctcccactccatgaggtatttctacaccgccatgtcccggcccggccgcggggagccccCcttcatcgcagtgggctac
gtggacgacacccagttcgtgaggttcgacagcgacgccgcgagtccgaggacggagccccgggcgccatggatagagca
ggaggggccggagtattgggaccgggagacacagatctccaagaccaacacacagacttaccgagagaacctgcggatcg
cgctccgctactacaaccagagcgaggccgggtctcacacttggcagacgatgtatggctgcgacgtggggccggacggg
cgcctcctccgcgggcataaccagtacgcctacgacggcaaagattacatcgccctgaacgaggacctgagctcctggac
cgcggcggacaccgcggctcagatcacccagcgcaagtgggaggcggcccgtgaggcggagcagctgagagcctacctgg
agggcctgtgcgtggagtggctccgcagacacctggagaacgggaaggagacgctgcagcgcgcgg

B*5301

(SEQ ID NO: 1588)

atgcgggtcacggcgccccgaaccgtcctcctgctgctctgggggcagtggccctgaccgagacctgggccggctccca
ctccatgaggtatttctacaccgccatgtcccggcccggccgcggggagccccgcttcatcgcagtgggctacgtggacg
acacccagttcgtgaggttcgacagcgacgccgcgagtccgaggacggagccccgggcgccatggatagagcaggagggg
ccggagtattgggaccggaacacacagatcttcaagaccaacAcacagacttaccgagagaacctgcggatcgcgctcCg
ctactacaaccagagcgaggccgggtctcacatcAtccagaggatgtaTggctgcgacctggggcccgacgggcgcctcc
tccgcgggcatgaccagtCcgcctacgacggcaaagattacatcgccctgaacgaggacctgAgctcctggaccgcggcg
gacaccgcggctcagatcacccagcgcaagtgggaggcggcccgtgTggcggagcagcTgagagcctacctggagggccT
gtgcgtggagtggctccgcagatacctggagaacgggaaggagacgctgcagcgcgcggaccccccaaagacacacgtga
cccaccaccccGtctctgaccatgaggccaccctgaggtgctgggccctgggcttctaccctgcggagatcacactgacc -continued

```
tggcagcgggatggcgaggaccaaactcaggacactgagcttgtggagaccagaccagcaggagatagaaccttccagaa
gtgggcagctgtggtggtgccttctggagaagagcagagatacacatgccatgtacagcatgaggggctgccgaagcccc
tcaccctgagatgggagccatcttcccagtccaccatccccatcgtgggcattgttgctggcctggctgtccta...gca
gttgtggtcatcggagctgtggtcgctactgtgatgtgtaggaggaagagCtcaggtgga
```

B*5302 (SEQ ID NO: 1589)
```
gctcccactccatgaggtatttctacaccgccatgtcccggcccggccgcggggagccccgcttcatcgcagtgggctac
gtggacgacacccagttcgtgaggttcgacagcgacgccgcgagtccgaggacggagccccgggcgccatggatagagca
ggaggggccggagtattgggaccggaacacacagatcttcaagaccaacacacagacttaccgagagaacctgcggatcg
cgctcCgctactacaaccagagcgaggccgggtctcacatcatccagaggatgtatggctgcgacctggggcccgacggg
cgcctcctccgcgggcatgaccagtCcgcctacgacggcaaggattacatcgccctgaacgaggacctgagctcctggac
cgcggcggacaccgcggctcagatcacccagcgcaagtgggaggcggcccgtgTggcggagcagcTgagagcctacctgg
agggccTgtgcgtggagtggctccgcagaCacctggagaacgggaaggagacgctgcagcgcgcgg
```

B*5303 (SEQ ID NO: 1590)
```
gctcccactccatgaggtatttctacaccgccatgtcccggcccggccgcggggagccccgcttcatcgcagtgggctac
gtggacgacacccagttcgtgaggttcgacagcgacgccgcgagtccgaggacggagccccgggcgccatggatagagca
ggaggggccggagtattgggaccggaacacacagatcttcaagaccaacacacagacttaccgagagGacctgcggaccc
tgctccgctactacaaccagagcgaggccgggtctcacatcatccagaggatgtatggctgcgacctggggcccgacggg
cgcctcctccgcgggcatgaccagtccgcctacgacggcaaggattacatcgccctgaacgaggacctgagctcctggac
cgcggcggacaccgcggctcagatcacccagcgcaagtgggaggcggcccgtgtggcggagcagcTgagagcctacctgg
agggccTgtgcgtggagtggctccgcagatacctggagaacgggaaggagacgctgcagcgcgcgGg
```

B*5304 (SEQ ID NO: 1591)
```
gctcccactccatgaggtatttctacaccgccatgtcccggcccggccgcggggagccccgcttcatcgcagtgggctac
gtggacgacacccagttcgtgaggttcgacagcgacgccgcgagtccgaggacggagccccgggcgccatggatagagca
ggaggggccggagtattgggaccggaacacacagatcttcaagaccaacacacagacttaccgagagaacctgcggaTcg
cgctcCgctactacaaccagagcgaggccgggtctcacatcatccagaggatgtatggctgcgacctggggccCgacggg
cgcctcctccgcgggcatgaccagtTcgcctacgacggcaaggattacatcgccctgaacgaggacctgAgctcctggac
cgcggcggacacCgcggctcagatcacccagcgcaagtgggaggcggcccgtgTggcggagcagcTgagagcctacctgg
agggccTgtgcgtggagtggctccgcagatacctggagaacgggaaggagacgctgCagcgcgcgGg
```

B*5305 (SEQ ID NO: 1592)
```
gctcccactccatgaggtatttctacaccgccatgtcccggcccggccgcggggagccccgcttcatcgcagtgggctac
gtggacgacacccagttcgtgaggttcgacagcgacgccgcgagtccgaggacggagccccgggcgccatggatagagca
ggaggggccggagtattgggaccggaacacacagatcttcaagaccaacAcacagacttaccgagagagcctgcggaTcg
CgctcCgctactacaaccagagcgaggccgggtctcacatcAtccagaggatgtaTggctgcgacCtggggccCgacggg
cgcctcctccgcgggcatgaccagtCcgcctacgacggcaaggattacatcgccctgaacgaggacctgAgctcctggac
cgcggcggacacCgcggctcagatcacccagcgcaagtgggaggcggcccgtgTggcggagcagcTgagagcctacctgg
agggccTgtgcgtggagtggctccgcagatacctggagaacgggaaggagacgctgCagcgcgcgGg
```

B*5306 (SEQ ID NO: 1593)
```
gctcccactccatgaggtatttctacaccgccatgtcccggcccggccgcggggagccccgcttcatTgcagtgggctac
gtggacgacacccagttcgtgaggttcgacagcgacgccgcgagtccgaggacggagccccgggcgccatggatagagca
ggaggggccggagtattgggaccggaacacacagatcttcaagaccaacacacagacttaccgagagaacctgcggatcg
cgctccgctactacaaccagagcgaggccgggtctcacatcatccagaggatgtatggctgcgacctggggcccgacggg
```

-continued cgcctcctccgcgggcatgaccagtCcgcctacgacggcaaggattacatcgccctgaacgaggacctgAgctcctggac cgcggcggacaccgcggctcagatcacccagcgcaagtgggaggcggcccgtgaggcggagcagcTgagagcctacctgg agggccTgtgcgtggagtggctccgcagaCacctggagaacgggaaggagacgctgcagcgcgcgg B*5307
(SEQ ID NO: 1594)
gctcccactccatgaggtatttctacaccgccatgtcccggcccggccgcggggagccccgcttcatcgcagtgggctac gtggacgacacccagttcgtgaggttcgacagcgacgccgcgagtccgaggacggagcccccgggcgccatggatagagca ggaggggccggagtattgggaccggaacacacagatcttcaagaccaacacacagacttaccgagagaacctgcggatcg cgctccgctactacaaccagagcgaggccgggtctcacaccatccagaggatgtCtggctgcgacgtggggccggacggg cgcctcctccgcgggtataaccagttcgcctacgacggcaaggattacatcgccctgaacgaggacctgagctcctggac cgcggcggacaccgcggctcagatcacccagcgcaagtgggaggcggcccgtgtggcggagcagcTgagagcctacctgg agggccTgtgcgtggagtggctccgcagatacctggagaacgggaaggagacgctgcagcgcgcgg B*5308
(SEQ ID NO: 1595)
gctcccactccatgaggtatttctacaccgccatgtcccggcccggccgcggggagccccgcttcatcgcagtgggctac gtggacgacacccagttcgtgaggttcgacagcgacgccgcgagtccgaggacggagcccccgggcgccatggatagagca ggaggggccggagtattgggaccggaacacacagatcttcaagaccaacAcacagacttaccgagagaAcctgcggaTcg CgctcCgctactacaaccagagcgaggccgggtctcacatcAtccagaggatgtaTggctgcgacCtggggccCgacggg cgcctcctccgcgggcatgaccagtCcgcctacgacggcaaggattacatcgccctgaacgaggacctgAgctcctggac cgcggcggacacCgcggctcagatcacccagcgcaagtgggaggcggcccgtgaggcggagcagcTgagagcctacctgg agggccTgtgcgtggagtggctccgcagatacctggagaacgggaaggagacgctgCagcgcgcGg B*5309
(SEQ ID NO: 1596)
gctcccactccatgaggtatttctacaccgccatgtcccggcccggccgcggggagccccgcttcatcgcagtgggctac gtggacgacacccagttcgtgaggttcgacagcgacgccgcgagtccgaggacggagcccccgggcgccatggatagagca ggaggggccggagtattgggaccggaacacacagatctccaagaccaacacacagacttaccgagagaacctgcgCaccg cgctccgctactacaaccagagcgaggccgggtctcacatcatccagaggatgtatggctgcgacctggggcccgacggg cgcctcctccgcgggcatgaccagtCcgcctacgacggcaaggattacatcgccctgaacgaggacctgagctcctggac cgcggcggacacCgcggctcagatcacccagcgcaagtgggaggcggcccgtgTggcggagcagcTgagagcctacctgg agggcCTgtgcgtggagtggctccgcagatacctggagaacgggaaggagacgctgCagcgcgcGg B*5401
(SEQ ID NO: 1597)
atgcgggtcacggcaccccgaaccctcctcctgctgctctgggggggccctggccctgaccgagacctgggccggctccca ctccatgaggtatttctacaccgccatgtcccggcccggccgcggggagccccgcttcatcgcagtgggctacgtggacg acacgcagttcgtgCggttcgacagcgacgccgcgagtccgagaggggagccgcgggcgccgtgggtggagcaggagggg ccggagtattgggaccggaacacacagatctacaaggcccaggcacagactgaccgagagagcctgcggaacctgcgcgg ctactacaaccagagcgaggccgggtctcacacttggcagacgatgtatggctgcgacctggggccggacggggcgcctcc tccgcgggcataaccagttagcctacgacggcaaggattacatcgccctgaacgaggacctgagctcctggaccgcggcg gacaccgcggctcagatcacccagcgcaagtgggaggcggcccgtgtggcggagcagctgagagcctacctggagggcac gtgcgtggagtggctccgcagatacctggagaacgggaaggagacgctgcagcgcgcggaccccccaaagacacacgtga cccaccaccccatctctgaccatgaggccaccctgaggtgctgggccctgggcttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc -continued tcaccctgagatgggagccatcttcccagtccaccatccccatcgtgggcattgttgctggcctggctgtccta...gca
gttgtggtcatcggagctgtggtcgctactgtgatgtgtaggaggaagagCtcaggtgga

B*5402

(SEQ ID NO: 1598)

gctcccactccatgaggtatttcCacacctccgtgtcccggcccggccgcggggagccccgcttcatcgcagtgggctac
gtggacgacacgcagttcgtgCggttcgacagcgacgccgcgagtccgagaggggagccgcgggcgccgtgggtggagca
ggaggggccggagtattgggaccggaacacacagatctacaaggcccaggcacagactgaccgagagagcctgcggaacc
tgcgcggctactacaaccagagcgaggccgggtctcacacttggcagacgatgtatggctgcgacctggggccggacggg
cgcctcctccgcgggcataaccagttagcctacgacggcaaggattacatcgccctgaacgaggacctgagctcctggac
cgcggcggacaccgcggctcagatcacccagcgcaagtgggaggcggcccgtgtggcggagcagctgagagcctacctgg
agggcaCgtgcgtggagtggctccgcagatacctggagaacgggaaggagacgctgcagcgcgcgg

B*5501

(SEQ ID NO: 1599)

atgcgggtcacggcaccccgaaccctcctcctgctgctctggggggccctggccctgaccgagacctgggccggctccca
ctccatgaggtatttctacaccgccatgtcccggcccggccgcggggagccccgcttcatcgcagtgggctacgtggacg
acacgcagttcgtgaggttcgacagcgacgccgcgagtccgagagaggagccgcgggcgccgtggatagagcaggagggg
ccggagtattgggaccggaacacacagatctacaaggcccaggcacagactgaccgagagagcctgcggaacctgcgcgg
ctactacaaccagagcgaggccgggtctcacacttggcagacgatgtatggctgcgacctggggccggacgggcgcctcc
tccgcgggcataaccagttAgcctacgacggcaaggattacatcgccctgaacgaggacctgagctcctggaccgcggcg
gacaccgcggctcagatcacccagcgcaagtgggaggcggcccgtgaggcggagcagctgagagcctacctggagggcaC
gtgcgtggagtggctccgcagatacctggagaacgggaaggagacgctgcagcgcgcggacccccccaaagacacacgtga
cccaccaccccatctctgaccatgaggccaccctgaggtgctgggccctgggcttctaccctgcggagatcacactgacc
tggcagcgggatggcgaggaccaaactcaggacactgagcttgtggagaccagaccagcaggagatagaaccttccagaa
gtgggcagctgtggtggtgccttctggagaagagcagagatacacatgccatgtacagcatgaggggctgccgaagcccc
tcaccctgagatgggagccatcttcccagtccaccatccccatcgtgggcattgttgctggcctggctgtccta...gca
gttgtggtcatcggagctgtggtcgctActgtgatgtgtaggaggaagagCtcaggtgga

B*5502

(SEQ ID NO: 1600)

atgcgggtcacggcaccccgaaccctcctcctgctgctctggggggccctggccctgaccgagacctgggccggctccca
ctccatgaggtatttctacaccgccatgtcccggcccggccgcggggagccccgcttcatcgcagtgggctacgtggacg
acacgcagttcgtgaggttcgacagcgacgccgcgagtccgagagaggagccgcgggcgccgtggatagagcaggagggg
ccggagtattgggaccggaacacacagatctacaaggcccaggcacagactgaccgagagagcctgcggaacctgcgcgg
ctactacaaccagagcgaggccgggtctcacacttggcagacgatgtatggctgcgacctggggccggacgggcgcctcc
tccgcgggcataaccagttAgcctacgacggcaaggattacatcgccctgaacgaggacctgagctcctggaccgcggcg
gacaccgcggctcagatcacccagcgcaagtgggaggcggcccgtgTggcggagcagctgagagcctacctggagggcaC
gtgcgtggagtggctccgcagatacctggagaacgggaaggagacgctgcagcgcgcggacccccccaaagacacacgtga
cccaccaccccatctctgaccatgaggccaccctgaggtgctgggccctgggcttctaccctgcggagatcacactgacc
tggcagcgggatggcgaggaccaaactcaggacactgagcttgtggagaccagaccagcaggagatagaaccttccagaa
gtgggcagctgtggtggtgccttctggagaagagcagagatacacatgccatgtacagcatgaggggctgccgaagcccc
tcaccctgagatgggagccatcttcccagtccaccatccccatcgtgggcattgttgctggcctggctgtccta...gca
gttgtggtcatcggagctgtggtcgctActgtgatgtgtaggaggaagagCtcaggtgga

B*5503

(SEQ ID NO: 1601)

gctcccactccatgaggtatttctacaccgccatgtcccggcccggccgcggggagccccgcttcatcgcagtgggctac gtggacgacacgcagttcgtgaggttcgacagcgacgccgcgagtccgagagaggagccgcgggcgccgtggatagagca ggaggggccggagtattgggaccggaacacacagatctacaaggcccaggcacagactgaccgagTgagcctgcggaacc tgcgcggctactacaaccagagcgaggccgggtctcacacttggcagacgatgtatggctgcgacctggggccggacggg cgcctcctccgcgggcataaccagttAgcctacgacggcaaggattacatcgccctgaacgaggacctgagctcctggac cgcggcggacaccgcggctcagatcacccagcgcaagtgggaggcggcccgtgaggcggagcagctgagagcctacctgg agggcaCgtgcgtggagtggctccgcagatacctggagaacgggaaggagacgctgCagcgcgcGg

B*5504

(SEQ ID NO: 1602)

gctcccactccatgaggtatttctacaccgccAtgtcccggcccggccgcggggagccccgcttcatcGcagtgggctac gtggacgacacGcagttcgtgaggttcgacagcgacgccgcgagtccgagagaggagccgcgggcgccgtggatagagca ggaggggccggagtattgggaccggaacacacagatctacaaggcccaggcacagactgaccgagagagcctgcggaacc tgcgcggctactacaaccagagcgaggccgggtctcacaccctccagagcatgtacggctgcgacgtggggccggacggg cgcctcctccgcgggcatAaccagtacgcctacgacggcaaggattacatcgccctgaacgaggacctgcgctcctggac cgccgcggacacCgcggctcagatcacccagcgcaagtgggaggcggcccgtgTggcggagcagcTgagagcctacctgg agggcaCgtgcgtggagtggctccgcagatacctggagaacgggaaggaDacgctgCagcgcgcGg

B*5505

(SEQ ID NO: 1603)

atgcgggtcacggcaccccgaaccctcctcctgctgctctggggggccctggccctgaccgagacctgggccggctccca ctccatgaggtatttctacaccgccatgtcccggcccggccgcggggagccccgcttcatcgcagtgggctacgtggacg acacgcagttcgtgaggttcgacagcgacgccgcgagtccgagagaggagccgcgggcgccgtggatagagcaggagggg ccggCgtattgggaccggaacacacagatctacaaggcccaggcacagactgaccgagagagcctgcggaacctgcgcgg ctactacaaccagagcgaggccgggtctcacacttggcagacgatgtatggctgcgacctggggccggacgggcgcctcc tccgcgggcataaccagttagcctacgacggcaaggattacatcgccctgaacgaggacctgagctcctggaccgcggcg gacaccgcggctcagatcacccagcgcaagtgggaggcggcccgtgaggcggagcagctgagagcctacctggagggcac gtgcgtggagtggctccgcagatacctggagaacgggaaggagacgctgcagcgcgcggaccccccaaagacacacgtga cccaccaccccatctctgaccatgaggccaccctgaggtgctgggccctgggcttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccatccccatcgtgggcattgttgctggcctggctgtccta...gca gttgtggtcatcggagctgtggtcgctactgtgatgtgtaggaggaagagctcaggtgga

B*5507

(SEQ ID NO: 1604)

gctcccactccatgaggtatttctacaccgccAtgtcccggcccggccgcggggagccccgcttcatcgcagtgggctac gtggacgacacgcagttcgtgaggttcgacagcgacgccgcgagtccgagagGgagccgcgggcgccgtggatagagca ggaggggccggagtattgggaccggaacacacagatctacaaggcccaggcacagactgaccgagagagcctgcggaacc tgcgcggctactacaaccagagcgaggccgggtctcacacttggcagacgatgtatggctgcgacctggggccggacggg cgcctcctccgcgggcataaccagttAgcctacgacggcaaggattacatcgccctgaacgaggacctgagctcctggac cgcggcggacaccgcggctcagatcacccagcgcaagtgggaggcggcccgtgtggcggagcagctgagagcctacctgg agggcacgtgcgtggagtggctccgcagatacctggagaacgggaaggagacgctgcagcgcgcGg

B*5508

(SEQ ID NO: 1605)

gctcccactccatgaggtatttctacaccgccatgtcccggcccggccgcggggagccccgcttcatcGcagtgggctac gtggacgacacGcagttcgtgaggttcgacagcgacgccgcgagtccgagagaggagccgcgggcgccgtggatagagca ggaggggccggagtattgggaccggaacacacagatctacaaggcccaggcacagactgaccgagagagcctgcggaacc tgcgcggctactacaaccagagcgaggccgggtctcacaccctccagagGatgtacggctgcgacgtggggccggacggg cgcctcctccgcgggcatAaccagtacgcctacgacggcaaggattacatcgccctgaacgaggacctgcgctcctggac cgccgcggacacCgcggctcagatcacccagcgcaagtgggaggcggcccgtgTggcggagcagcTgagagcctacctgg agggccTgtgcgtggagtggctccgcagatacctggagaacgggaaggagacgctgcagcgcgcGg

B*5509

(SEQ ID NO: 1606)

gctcccactccatgaggtatttctacaccgccAtgtcccggcccggccgcggggagccccgcttcatcGcagtgggctac gtggacgacacGcagttcgtgaggttcgacagcgacgccgcgagtccgagagaggagccgcgggcgccgtggatagagca ggaggggccggagtattgggaccggaacacacagatctacaaggcccaggcacagactgaccgagagagcctgcggaacc tgcgcggctactacaaccagagcgaggccgggtctcacacttggcagaCgatgtaTggctgcgacCtggggccggacggg cgcctcctccgcgggcataaccagttAgcctacgacggcaaggattacatcgccctgaacgaggacctgagctcctggac cgcggcggacacCgcggctcagatcacccagcgcaagtgggaggcggcccgtgaggcggagcagcggagagcctacctgg agggcgagtgcgtggagtggctccgcagatacctggagaacgggaaggagacgctgcagcgcgcGg

B*5510

(SEQ ID NO: 1607)

gctcccactccatgaggtatttctacacctccgtgtcccggcccggccgcggggagccccgcttcatctcagtgggctac gtggacgacacgcagttcgtgaggttcgacagcgacgccgcgagtccgagagaggagccgcgggcgccgtggatagagca ggaggggccggagtattgggaccggaacacacagatctacaaggcccaggcacagactgaccgagagagcctgcggaacc tgcgcggctactacaaccagagcgaggccgggtctcacacttggcagaCgatgtaTggctgcgacCtggggccggacggg cgcctcctccgcgggcataaccagttAgcctacgacggcaaggattacatcgccctgaacgaggacctgagctcctggac cgcggcggacaccgcggctcagatcacccagcgcaagtgggaggcggcccgtgTggcggagcagctgagagcctacctgg agggcaCgtgcgtggagtggctccgcagatacctggagaacgggaaggagacgctgcagcgcgcGg

B*5511

(SEQ ID NO: 1608)

gctcccactccatgaggtatttctacaccgccatgtcccggcccggccgcggggagccccgcttcatcgcagtgggctac gtggacgacacgcagttcgtgaggttcgacagcgacgccgcgagtccgagagaggagccgcgggcgccgtggatagagca ggaggggccggagtattgggaccggaacacacagatctacaaggcccaggcacagactgaccgagagagcctgcggaacc tgcgcggctactacaaccagagcgaggccgggtctcacacttggcagaTgatgtatggctgcgacctggggccggacggg cgcctcctccgcgggcataaccagttagcctacgacggcaaggattacatcgccctgaacgaggacctgagctcctggac cgcggcggacaccgcggctcagatcacccagcgcaagtgggaggcggcccgtgaggcggagcagctgagagcctacctgg agggcaCgtgcgtggagtggctccgcagatacctggagaacgggaaggagacgctgcagcgcgcGg

B*5512

(SEQ ID NO: 1609)

atgcgggtcacggcaccccgaaccctcctcctgctgctctgggggccctggcccctgaccgagacctgggccggctccca ctccatgaggtatttctacaccgccatgtcccggcccggccgcggggagccccgcttcatcgcagtgggctacgtggacg acacgcagttcgtgaggttcgacagcgacgccgcgagtccgagagaggagccgcgggcgccgtggatagagcaggagggg ccggagtattgggaccggaacacacagatctacaaggcccaggcacagactgaccgagagaActgcggaacctgcgcgg ctactacaaccagagcgaggccgggtctcacacttggcagacgatgtatggctgcgacctggggccggacgggcgcctcc tccgcgggcataaccagttAgcctacgacggcaaggattacatcgccctgaacgaggacctgagctcctggaccgcggcg gacaccgcggctcagatcacccagcgcaagtgggaggcggcccgtgTggcggagcagctgagagcctacctggagggcaC -continued gtgcgtggagtggctccgcagatacctggagaacgggaaggagacgctgcagcgcgcggaccccccaaagacacacgtga cccaccacccatctctgaccatgaggccaccctgaggtgctgggccctgggcttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccatccccatcgtgggcattgttgctggcctggctgtccta...gca gttgtggtcatcggagctgtggtcgctActgtgatgtgtaggaggaagagCtcaggtgga

B*5601

(SEQ ID NO: 1610)
atgcgggtcacggcaccccgaaccctcctcctgctgctctgggggccctggccctgaccgagacctgggccggctccca ctccatgaggtatttctacaccgccatgtcccggcccggccgcggggagccccgcttcatcgcagtgggctacgtggacg acacgcagttcgtgaggttcgacagcgacgccgcgagtccgagagaggagccgcgggcgccgtggatagagcaggagggg ccggagtattgggaccggaacacacagatctacaaggcccaggcacagactgaccgagagagcctgcggaacctgcgcgg ctactacaaccagagcgaggccgggtctcacacttggcagacgatgtaTggctgcgacctggggccggacgggcgcctcc tccgcgggcataaccagttAgcctacgacggcaaggattacatcgccctgaacgaggacctgagctcctggaccgcggcg gacaccgcggctcagatcacccagcgcaagtgggaggcggcccgtgTggcggagcagcTgagagcctacctggagggccT gtgcgtggagtggctccgcagatacctggagaacgggaaggagacgctgcagcgcgcggaccccccaaagacacacgtga cccaccacccatctctgaccatgaggccaccctgaggtgctgggccctgggcttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccatccccatcgtgggcattgttgctggcctggctgtccta...gca gttgtggtcatcggagctgtggtcgctActgtgatgtgtaggaggaagagCtcaggtgga

B*5602

(SEQ ID NO: 1611)
atgcgggtcacggcaccccgaaccctcctcctgctgctctgggggccctggccctgaccgagacctgggccggctccca ctccatgaggtatttctacaccgccatgtcccggcccggccgcggggagccccgcttcatcgcagtgggctacgtggacg acacgcagttcgtgaggttcgacagcgacgccgcgagtccgagagaggagccgcgggcgccgtggatagagcaggagggg ccggagtattgggaccggaacacacagatctacaaggcccaggcacagactgaccgagagagcctgcggaacctgcgcgg ctactacaaccagagcgaggccgggtctcacaccctccagaggatgtacggctgcgacctggggccggacgggcgcctcc tccgcgggcataaccagttAgcctacgacggcaaggattacatcgccctgaacgaggacctgagctcctggaccgcggcg gacaccgcggctcagatcacccagcgcaagtgggaggcggcccgtgTggcggagcagcTgagagcctacctggagggccT gtgcgtggagtggctccgcagatacctggagaacgggaaggagacgctgcagcgcgcggaccccccaaagacacacgtga cccaccacccatctctgaccatgaggccaccctgaggtgctgggccctgggcttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccatccccatcgtgggcattgttgctggcctggctgtccta...gca gttgtggtcatcggagctgtggtcgctActgtgatgtgtaggaggaagagCtcaggtgga

B*5603

(SEQ ID NO: 1612)
atgcgggtcacggcaccccgaaccCtcctcctgctgctctGggggccctggccctgaccgagacctgggccggctccca ctccatgaggtatttctacaccgccatgtcccggcccggccgcggggagccccgcttcatcGcagtgggctacgtggacg acacccagttcgtgaggttcgacagcgacgccgcgagtccgagagaggagccgcgggcgccgtggatagagcaggagggg ccggagtattgggaccggaacacacagatctacaaggcccaggcacagactgaccgagagagcctgcggaacctgcgcgg ctactacaaccagagcgaggccgggtctcacaccctccagagGatgtacggctgcgacgtggggccggacgggcgcctcc tccgcgggcatgaccagtccgcctacgacggcaaggattacatcgccctgaacgaggacctgagctcctggaccgcggcg -continued

```
gacacggcggctcagatcacccagcgcaagtgggaggcggcccgtgaggcggagcagTggagagcctacctggagggcct
gtgcgtggagtggctccgcagatacctggagaacgggaaggagacgctgcagcgcgcggacccccaaagacacatgtga
cccaccacccatctctgaccatgaggccaccctgaggtgctgggccctgggcttctaccctgcggagatcacactgacc
tggcagcgggatggcgaggaccaaactcaggacaccgagcttgtggagaccagaccagcaggagatagaaccttccagaa
gtgggcagctgtggtggtgccttctggagaagagcagagatacacatgccatgtacagcatgaggggctgccgaagcccc
tcacccctgagatgggagccatcttcccagtccaccatccccatcgtgggcattgttgctggcctggctgtcccta...gca
gttgtggtcatcggagctgtggtcgctactgtgatgtgtaggaggaagagCtcaggtgga
```

B*5604

(SEQ ID NO: 1613)
```
gctcccactccatgaggtatttctacaccgccatgtcccggcccggccgcggggagccccgcttcatcGcagtgggctac
gtggacgacacGcagttcgtgaggttcgacagcgacgccgcgagtccgagagaggagccgcgggcgccgtggatagagca
ggaggggccggagtattgggaccggaacacacagatctacaaggcccaggcacagactgaccgagagagcctgcggaacc
tgcgcggctactacaaccagagcgaggccgggtctcacaccctccagaggatgtacggctgcgacgtggggccggacggg
cgcctcctccgcgggcataaccagttAgcctacgacggcaaggattacatcgccctgaacgaggacctgagctcctggac
cgcggccggacaccgcggctcagatcacccagcgcaagtgggaggcggcccgtgTggcggagcagcTgagagcctacctgg
agggccTgtgcgtggagtggctccgcagatacctggagaacgggaaggagacgctgcagcgcgcGg
```

B*5605

(SEQ ID NO: 1614)
```
gctcccactccatgaggtatttctacaccgccatgtcccggcccggccgcggggagccccgcttcatTgcagtgggctac
gtggacgacacGcagttcgtgaggttcgacagcgacgccgcgagtccgagagaggagccgcgggcgccgtggatagagca
ggaggggccggagtattgggaccggaacacacagatctacaaggcccaggcacagactgaccgagagagcctgcggaacc
tgcgcggctactacaaccagagcgaggccgggtctcacacttggcagaCgatgtaTggctgcgacgtggggccggacggg
cgcctcctccgcgggcataaccagtacgcctacgacggcaaAgattacatcgccctgaacgaggacctgAgctcctggac
cgcggccggacaccgcggctcagatcacccagcgcaagtgggaggcggcccgtgaggcggagcagcTgagagcctacctgg
agggccTgtgcgtggagtggctccgcagaCacctggagaacgggaaggagacgctgcagcgcgcgg
```

B*5606

(SEQ ID NO: 1615)
```
gctcccactccatgaggtatttctacaccgccatgtcccggcccggccgcggggagccccgcttcatTgcagtgggctac
gtggacgacacccagttcgtgaggttcgacagcgacgccgcgagtccgaggaCggagcccgggcgccAtggatagagca
ggaggggccggagtattgggaccggaacacacagatctacaaggcccaggcacagactgaccgagagagcctgcggaacc
tgcgcggctactacaaccagagcgaggccgggtctcacacttggcagaCgatgtaTggctgcgacgtggggccggacggg
cgcctcctccgcgggcataaccagtacgcctacgacggcaaAgattacatcgccctgaacgaggacctgAgctcctggac
cgcggccggacaccgcggctcagatcacccagcgcaagtgggaggcggcccgtgaggcggagcagcTgagagcctacctgg
agggccTgtgcgtggagtggctccgcagaCacctggagaacgggaaggagacgctgcagcgcgcgg
```

B*5607

(SEQ ID NO: 1616)
```
gctcccactccatgaggtatttctacaccgccatgtcccggcccggccgcggggagccccgcttcatcgcagtgggctac
gtggacgacacGcagttcgtgaggttcgacagcgacgccgcgagtccgagagaggagccgcgggcgccgtggatagagca
ggaggggccggagtattgggaccggaacacacagatctacaaggcccaggcacagactgaccgagagaacctgcgcaCcg
cgctcCgctactacaaccagagcgaggccgggtctcacacttggcagaCgatgtaTggctgcgacCtggggccggacggg
cgcctcctccgcgggcataaccagttAgcctacgacggcaaggattacatcgccctgaacgaggacctgagctcctggac
cgcggccggacaccgcggctcagatcacccagcgcaagtgggaggcggcccgtgTggcggagcagcTgagagcctacctgg
agggccTgtgcgtggagtggctccgcagatacctggagaacgggaaggagacgctgcagcgcgcGg
```

-continued

B*5608

(SEQ ID NO: 1617)
gctcccactccatgaggtatttctacaccgccatgtcccggcccggccgcggggagccccgcttcatcgcagtgggctac gtggacgacacgcagttcgtgaggttcgacagcgacgccgcgagtccgagagaggagccgcgggcgccgtggatagagca ggaggggccggagtattgggaccgggagacacagaagtacaaggGccaggcacagactgaccgagagagcctgcggaacc tgcgcggctactacaaccagagcgaggccgggtctcacacttggcagacgatgtatggctgcgacctggggccggacggg cgcctcctccgcgggcataaccagttagcctacgacggcaaggattacatcgccctgaacgaggacctgagctcctggac cgcggcggacaccgcggctcagatcacccagcgcaagtgggaggcggcccgtgtggcggagcagcTgagagcctacctgg agggccTgtgcgtggagtggctccgcagatacctggagaacgggaaggagacgctgcagcgcgcGg

B*5609

(SEQ ID NO: 1618)
gctcccactccatgaggtatttctacaccgccatgtcccggcccggccgcggggagccccgcttcatcGcagtgggctac gtggacgacacGcagttcgtgaggttcgacagcgacgccgcgagtccgagagaggagccgcgggcgccgtggatagagca ggaggggccggagtattgggaccggaacacacagatctacaaggcccaggcacagactgaccgagagagcctgcggaacc tgcgcggctactacaaccagagcgaggccgggtctcacatcAtccagaggatgtaTggctgcgacCtggggccCgacggg cgcctcctccgcgggcatgaccagtCcgcctacgacggcaaggattacatcgccctgaacgaggacctgAgctcctggac cgcggcggacacCgcggctcagatcacccagcgcaagtgggaggcggcccgtgTggcggagcagcTgagagcctacctgg agggccTgtgcgtggagtggctccgcagatacctggagaacgggaaggagacgctgCagcgcgcGg

B*5610

(SEQ ID NO: 1619)
gctcccactccatgaggtatttctacaccgccAtgtcccggcccggccgcggggagccccgcttcatcGcagtgggctac gtggacgacacGcagttcgtgaggttcgacagcgacgccgcgagtccgagagaggagccgcgggcgccgtggatagagca ggaggggccggagtattgggaccggaacacacagatctacaaggcccaggcacagactgaccgagagagcctgcggaacc tgcgcggctactacaaccagagcgaggccgggtctcacaccctccagaggatgtacggctgcgacCtggggccggacggg cgcctcctccgcgggcataaccagttAgcctacgacggcaaggattacatcgccctgaacgaggacctgagctcctggac cgcggcggacaccgcggctcagatcacccagcgcaagtgggaggcggcccgtgTggcggagcagctgagagcctacctgg agggcaCgtgcgtggagtggctccgcagatacctggagaacgggaaggagacgctgcagcgcgcGg

B*5611

(SEQ ID NO: 1620)
atgcgggtcacggcaccccgaaccCtcctcctgctgctctgggggccctggccctgaccgagacctgggccggctccca ctccatgaggtatttctacaccgccatgtcccggcccggccgcggggagccccgcttcatcgcagtgggctacgtggacg acacgcagttcgtgaggttcgacagcgacgccgcgagtccgagagaggagccgcgggcgccgtggatagagcaggagggg ccggagtattgggaccggaacacacagatctacaaggcccaggcacagactgaccgagagagcctgcggaacctgcgcgg ctactacaaccagagcgaggccgggtctcacatcatccagaggatgtatggctgcgacctggggccCgacgggcgcctcc tccgcgggcatgaccagtTcgcctacgacggcaaggattacatcgccctgaacgaggacctgagctcctggaccgcggcg gacacCgcggctcagatcacccagcgcaagtgggaggcggcccgtgTggcggagcagcTgagagcctacctggagggccT gtgcgtggagtggctccgcagatacctggagaacgggaaggagacgctgcagcgcgcggacccccaaagacacacgtga cccaccaccccatctctgaccatgaggccaccctgaggtgctgggccctgggCttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatggg

B*570101

(SEQ ID NO: 1621)
atgcgggtcacggcaccccgaaccgtcctcctgctgctctgggggcagtggccctgaccgagacctgggccggctccca ctccatgaggtatttctacaccgccatgtcccggcccggccgcggggagccccgcttcatcgcagtgggctacgtggacg -continued acacccagttcgtgaggttcgacagcgacgccgcgagtccgaggatggcgccccgggcgccatggatagagcaggagggg ccggagtatttgggacggggagacacggaacatgaaggcctccgcgcagacttaccgagagaacctgcggatcgcgctccg ctactacaaccagagcgaggccgggtctcacatcatccaggTgatgtatggctgcgacgtggggccggacgggcgcctcc tccgcgggcatgaccagtCcgcctacgacggcaaggattacatcgccctgaacgaggacctgagctcctggaccgcggcg gacacggcggctcagatcacccagcgcaagtgggaggcggcccgtgtggcggagcagcTgagagcctacctggagggcct gtgcgtggagtggctccgcagatacctggagaacgggaaggagacgctgcagcgcgcggaccccccaaagacacatgtga cccaccaccccatctctgaccatgaggccaccctgaggtgctgggccctggcttctaccctgcggagatcacactgacc tggcagcgggatggcgaggaccaaactcaggacaccgagcttgtggagaccagaccagcaggagatagaaccttccagaa gtgggcagctgtggtggtgccttctggagaagagcagagatacacatgccatgtacagcatgaggggctgccaaagcccc tcaccctgagatgggagccatcttcccaAtccaccgtccccatcgtgggcattgttgctggcctggctgtccta...gca gttgtggtcatcggagctgtggtcgctgctgtgatgtgtaggaggaagagctcaggtgga

B*570102

(SEQ ID NO: 1622)

gctcccactccatgaggtatttctacaccgccatgtcccggcccggccgcggggagccccgcttcatcgcagtgggctac gtggacgacacccagttcgtgaggttcgacagcgacgccgcgagtccgaggatggcgccccgggcgccatggatagagca ggaggggccggagtatttgggacggggagacacggaacatgaaggcctccgcgcagacttaccgagagaacctgcggatcg cgctccgctactacaaccagagcgaggccgggtctcacatcatccaggtgatgtatggctgcgacgtggggccggacggg cgcctcctccgcgggcatgaccagtcTgcctacgacggcaaggattacatcgccctgaacgaggacctgagctcctggac cgcggcggacacggcggctcagatcacccagcgcaagtgggaggcggcccgtgtggcggagcagctgagagcctacctgg agggcctgtgcgtggagtggctccgcagatacctggagaacgggaaggagacgctgcagcgcgcgg

B*5702

(SEQ ID NO: 1623)

atgcgggtcacggcaccccgaaccgtcctcctgctgctctgggggcagtggcccctgaccgagacctgggccggctccca ctccatgaggtatttctacaccgccatgtcccggcccggccgcggggagccccgcttcatcgcagtgggctacgtggacg acacccagttcgtgaggttcgacagcgacgccgcgagtccgaggatggcgccccgggcgccatggatagagcaggagggg ccggagtatttgggacggggagacacggaacatgaaggcctccgcgcagacttaccgagagaacctgcggatcgcgctccg ctactacaaccagagcgaggccgggtctcacatcatccaggtgatgtatggctgcgacgtggggccggacgggcgcctcc tccgcgggcatAaccagtacgcctacgacggcaaggattacatcgccctgaacgaggacctgagctcctggaccgcggcg gacacggcggctcagatcacccagcgcaagtgggaggcggcccgtgtggcggagcagcggagagcctacctggagggcct gtgcgtggagtggctccgcagatacctggagaacgggaaggagacgctgcagcgcgcggaccccccaaagacacatgtga cccaccaccccatctctgaccatgaggccaccctgaggtgctgggccctggcttctaccctgcggagatcacactgacc tggcagcgggatggcgaggaccaaactcaggacaccgagcttgtggagaccagaccagcaggagatagaaccttccagaa gtgggcagctgtggtggtgccttctggagaagagcagagatacacatgccatgtacagcatgaggggctgccaaagcccc tcaccctgagatgggagccatcttcccaAtccaccgtccccatcgtgggcattgttgctggcctggctgtccta...gca gttgtggtcatcggagctgtggtcgctgctgtgatgtgtaggaggaagagctcaggtgga

B*570301

(SEQ ID NO: 1624)

atgcgggtcacggcaccccgaaccgtcctcctgctgctctgggggcagtggcccctgaccgagacctgggccggctccca ctccatgaggtatttctacaccgccatgtcccggcccggccgcggggagccccgcttcatcgcagtgggctacgtggacg acacccagttcgtgaggttcgacagcgacgccgcgagtccgaggatggcgccccgggcgccatggatagagcaggagggg ccggagtatttgggacggggagacacggaacatgaaggcctccgcgcagacttaccgagagaacctgcggatcgcgctccg ctactacaaccagagcgaggccgggtctcacatcatccaggtgatgtatggctgcgacgtggggccggacgggcgcctcc tccgcgggcatAaccagtacgcctacgacggcaaggattacatcgccctgaacgaggacctgagctcctggaccgcggcg gacacggcggctcagatcacccagcgcaagtgggaggcggcccgtgtggcggagcagcTgagagcctacctggagggcct gtgcgtggagtggctccgcagatacctggagaacgggaaggagacgctgcagcgcgcggaccccccaaagacacatgtga cccaccacccatctctgaccatgaggccaccctgaggtgctgggccctgggcttctaccctgcggagatcacactgacc tggcagcgggatggcgaggaccaaactcaggacaccgagcttgtggagaccagaccagcaggagatagaaccttccagaa gtgggcagctgtggtggtgccttctggagaagagcagagatacacatgccatgtacagcatgaggggctgccaaagcccc tcaccctgagatgggagccatcttcccaAtccaccgtccccatcgtgggcattgttgctggcctggctgtccta...gca gttgtggtcatcggagctgtggtcgctgctgtgatgtgtaggaggaagagctcaggtgga B*570302 (SEQ ID NO: 1625)
gctcccactccatgaggtatttctacaccgccatgtcccggcccggccgcggggagccccgcttcatcgcagtgggctac gtggacgacacccagttcgtgaggttcgacagcgacgccgcgagtccgaggatggcgccccgggcgccatggatagagca ggaggggccggagtattgggacggggagacacggaacatgaaggcctccgcgcagacttaccgagagaacctgcggatcg cgctccgctactacaaccagagcgaggccgggtctcacatcatccaggtgatgtatggctgcgacgtggggccggacggg cgcctcctccgcgggcataaccagtacgcctacgacggcaaggattacatcgccctgaacgaggacctgagctcctggac cgcggcggacacAgcggctcagatcacccagcgcaagtgggaggcggcccgtgtggcggagcagctgagagcctacctgg agggcctgtgcgtggagtggctccgcagatacctggagaacgggaaggagacgctgcagcgcgcggaccccccaaagaca catgtgacccaccacccatctctgaccatgaggccaccctgaggtgctgggccctgggcttctaccctgcggagatcac actgacctggcagcgggatggcgaggaccaaactcaggacaccgagcttgtggagaccagaccagcaggagatagaacct tccagaagtgggcagctgtggtggtgccttctggagaagagcagagatacacatgccatgtgcagcatgaggggctgcca aagcccctcaccctgagatggg B*5704 (SEQ ID NO: 1626)
gctcccactccatgaggtatttctacaccgccatgtcccggcccggccgcggggagccccgcttcatcgcagtgggctac gtggacgacacccagttcgtgaggttcgacagcgacgccgcgagtccgaggatggcgccccgggcgccatggatagagca ggaggggccggagtattgggacggggagacacggaacatgaaggcctccgcgcagacttaccgagagaacctgcggatcg cgctccgctactacaaccagagcgaggccgggtctcacatcatccagGtgatgtatggctgcgacgtggggccggacggg cgcctcctccgcgggtatgaccagGacgcctacgacggcaaggattacatcgccctgaacgaggacctgagctcctggac cgcggcggacacggcggctcagatcacccagcgcaagtgggaggcggcccgtgTggcggagcagcggagagcctacctgg agggcctgtgcgtggagtggctccgcagatacctggagaacgggaaggagacgctgcagcgcgcGg B*5705 (SEQ ID NO: 1627)
gctcccactccatgaggtatttctacaccgccatgtcccggcccggccgcggggagccccgcttcatcgcagtgggctac gtggacgacacccagttcgtgaggttcgacagcgacgccgcgagtccgaggatggcgccccgggcgccatggatagagca ggaggggccggagtattgggacGgggagacacggaacatgaaggcctccgcgcagacttaccgagagaacctgcggatcg cgctccgctactacaaccagagcgaggccgggtctcacatcatccagaggatgtatggctgcgacgtggggcccgacggg cgcctcctccgcgggTatAaccagtacgcctacgacggcaaggattacatcgccctgaacgaggacctgagctcctggac cgcggcggacacggcggctcagatcacccagcgcaagtgggaggcggcccgtgTggcggagcagcggagagcctacctgg agggccTgtgcgtggagtggctccgcagatacctggagaacgggaaggagacgctgcagcgcgcgg B*5706 (SEQ ID NO: 1628)
atgcgggtcacggcaccccgaaccgtcctcctgctgctctgggggcagtggccctgaccgagacctgggccggctccca ctccatgaggtatttctacaccgccatgtcccggcccggccgcggggagccccgcttcatcgcagtgggctacgtggacg acacccagttcgtgaggttcgacagcgacgccgcgagtccgaggatggcgccccgggcgccatggatagagcaggagggg ccggagtattgggacggggagacacggaacatgaaggcctccgcgcagacttaccgagagaacctgcggatcgcgctccg ctactacaaccagagcgaggccgggtctcacatcatccaggtgatgtatggctgcgacgtggggccggacgggcgcctcc -continued tccgcgggcatgaccagtccgcctacgacggcaaggattacatcgccctgaacgaggacctgagctcctggaccgcggcg gacacggcggctcagatcaTccagcgcaagtgggaggcggcccgtgtggcggagcagctgagagcctacctggagggcct gtgcgtggagtggctccgcagatacctggagaacgggaaggagacgctgcagcgcgcggaccccccaaagacacatgtga cccaccaccccatctctgaccatgaggccaccctgaggtgctgggcctgggcttctaccctgcggagatcacactgacc tggcagcgggatggcgaggaccaaactcaggacaccgagcttgtggagaccagaccagcaggagatagaaccttccagaa gtgggcagctgtggtggtgccttctggagaagagcagagatacacatgccatgtacagcatgaggggctgccaaagcccc tcaccctgagatgggagccatcttcccaatccaccgtccccatcgtgggcattgttgctggcctggctgtccta...gca gttgtggtcatcggagctgtggtcgctgctgtgatgtgtaggaggaagagctcaggtgga B*5707                                                        (SEQ ID NO: 1629)
gctcccactccatgaggtatttctacaccgccatgtcccggcccggccgcggggagccccgcttcatcgcagtgggctac gtggacgacacccagttcgtgaggttcgacagcgacgccgcgagtccgaggatggcgccccgggcgccatggatagagca ggaggggccggagtattgggacggggagacacggaacatgaaggcctccgcgcagacttaccgagagaacctgcggatcg cgctccgctactacaaccagagcgaggccgggtctcacatcatccagGtgatgtatggctgcgacgtggggccgacggg cgcctcctccgcgggcataaccagtacgcctacgacggcaaggattacatcgccctgaacgaggacctgagctcctggac cgcggcggacacggcggctcagatcacccagcgcaagtgggaggcggcccgtgtggcggagcagctgagagcctacctgg agggcctgtgcgtggagtCgctccgcagatacctggagaacgggaaggagacgctgcagcgcgcGg B*5708                                                        (SEQ ID NO: 1630)
gctcccactccatgaggtatttctacaccgccatgtcccggcccggccgcggggagccccgcttcatcgcagtgggctac gtggacgacacccagttcgtgaggttcgacagcgacgccgcgagtccgaggatggcgccccgggcgccatggatagagca ggaggggccggagtattgggacggggagacacggaacatgaaggcctccgcgcagacttaccgagagaacctgcggatcg cgctccCctactacaaccagagcgaggccgggtctcacatcatccaggtgatgtatggctgcgacgtggggccgacggg cgcctcctccgcgggcatgaccagtccgcctacgacggcaaggattacatcgccctgaacgaggacctgagctcctggac cgcggcggacacggcggctcagatcacccagcgcaagtgggaggcggcccgtgtggcggagcagctgagagcctacctgg agggcctgtgcgtggagtggctccgcagatacctggagaacgggaaggagacgctgcagcgcgcgg B*5709                                                        (SEQ ID NO: 1631)
gctcccactccatgaggtatttctacaccgccatgtcccggcccggccgcggggagccccgcttcatcgcagtgggctac gtggacgacacccagttcgtgaggttcgacagcgacgccgcgagtccgaggatggcgccccgggcgccatggatagagca ggaggggccggagtattgggacggggagacacggaacatgaaggcctccgcgcagacttaccgagagaacctgcggatcg cgctccgctactacaaccagagcgaggccgggtctcacatcatccagGtgatgtatggctgcgacgtggggccgacggg cgcctcctccgcgggcataaccagtacgcctacgacggcaaggattacatcgccctgaacgaggacctgagctcctggac cgcggcggacacggcggctcagatcacccagcgcaagtgggaggcggcccgtgaggcggagcaggaCagagcctacctgg agggcctgtgcgtggagtggctccgcagatacctggagaacgggaaggagacgctgcagcgcgcGg B*5801                                                        (SEQ ID NO: 1632)
atgcgggtcacggcgccccgaaccgtcctcctgctgctctgggggcagtggccctgaccgagacctgggccggctccca ctccatgaggtatttctacaccgccatgtcccggcccggccgcggggagccccgcttcatcgcagtgggctacgtggacg acacccagttcgtgaggttcgacagcgacgccgcgagtccgaggacggagccccgggcgccatggatagagcaggaggggg ccggagtattgggacGgggagacacggaacatgaaggcctccgcgcagacttaccgagagaacctgcggatcgcgctccg ctactacaaccagagcgaggccgggtctcacatcAtccagaggatgtatggctgcgacctggggcccgacgggcgcctcc tccgcgggcatgaccagtccgcctacgacggcaaggattacatcgccctgaacgaggacctgagctcctggaccgcggcg gacaccgcggctcagatcacccagcgcaagtgggaggcggcccgtgtggcggagcagctgagagcctacctggagggcct gtgcgtggagtggctccgcagatacctggagaacgggaaggagacgctgcagcgcgcggaccccccaaagacacacgtga -continued cccaccacccgtctctgaccatgaggccaccctgaggtgctgggccctgggcttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccatccccatcgtgggcattgttgctggcctggctgtccta...gca gttgtggtcatcggagctgtggtcgctActgtgatgtgtaggaggaagagCtcaggtgga

B*5802

(SEQ ID NO: 1633)

atgcgggtcacggcgcccgaaccgtcctcctgctgctctggggggcagtggccctgaccgagacctgggccggctccca ctccatgaggtatttctacaccgccatgtcccggcccggccgcggggagccccgcttcatcgcagtgggctacgtggacg acacccagttcgtgaggttcgacagcgacgccgcgagtccgaggacggagccccgggcgccatggatagagcaggagggg ccggagtattgggacggggagacacggaacatgaaggcctccgcgcagacttaccgagagaacctgcggatcgcgctccg ctactacaaccagagcgaggccgggtctcacaccctccagTggatgtatggctgcgacctggggcccgacgggcgcctcc tccgcgggcatgaccagtccgcctacgacggcaaggattacatcgccctgaacgaggacctgagctcctggaccgcggcg gacaccgcggctcagatcacccagcgcaagtgggaggcggcccgtgtggcggagcagctgagagcctacctggagggcct gtgcgtggagtggctccgcagatacctggagaacgggaaggagacgctgcagcgcgcggacccccaaagacacacgtga cccaccacccgtctctgaccatgaggccaccctgaggtgctgggccctgggcttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccatccccatcgtgggcattgttgctggcctggctgtccta...gca gttgtggtcatcggagctgtggtcgctactgtgatgtgtaggaggaagagCtcaggtgga

B*5804

(SEQ ID NO: 1634)

atgcgggtcacggcgcccgaaccgtcctcctgctgctctggggggcagtggccctgaccgagacctgggccggctccca ctccatgaggtatttctacaccgccatgtcccggcccggccgcggggagccccgcttcatcgcagtgggctacgtggacg acacccagttcgtgaggttcgacagcgacgccgcgagtccgaggacggagccccgggcgccatggatagagcaggagggg ccggagtattgggacgAggagacacggaacatgaaggcctccgcgcagacttaccgagagaacctgcggatcgcgctccg ctactacaaccagagcgaggccgggtctcacatcatccagaggatgtatggctgcgacctggggcccgacgggcgcctcc tccgcgggcatgaccagtccgcctacgacggcaaggattacatcgccctgaacgaggacctgagctcctggaccgcggcg gacaccgcggctcagatcacccagcgcaagtgggaggcggcccgtgtggcggagcagctgagagcctacctggagggcct gtgcgtggagtggctccgcagatacctggagaacgggaaggagacgctgcagcgcgcgg

B*5805

(SEQ ID NO: 1635)

gctcccactccatgaggtatttctacaccgccatgtcccggcccggccgcggggagccccgcttcatcgcagtgggctac gtggacgacacccagttcgtgaggttcgacagcgacgccgcgagtccgaggacggagccccgggcgccatggatagagca ggaggggccggagtattgggacggggagacacggaacatgaaggcctccgcgcagacttaccgagagaacctgcggatcg cgctccgctactacaaccagagcgaggccgggtctcacatcatccagaggatgtatggctgcgacctggggcccgacggg cgcctcctccgcgggcatgaccagtccgcctacgacggcaaggattacatcgccctgaacgaggacctgagctcctggac cgcggcggacaccgcggctcagatcacccagcgcaagttggaggcggcccgtgCggcggagcagctgagagcctacctgg agggcacgtgcgtggagtggctccgcagatacctggagaacgggaaggagacgctgcagcgcgcgg

B*5806

(SEQ ID NO: 1636)

gctcccactccatgaggtatttctacaccgccatgtcccggcccggccgcggggagccccgcttcatcgcagtgggctac gtggacgacacccagttcgtgaggttcgacagcgacgccgcgagtccgaggacggagccccgggcgccatggatagagca ggaggggccggagtattgggacggggagacacggaacatgaaggcctccgcgcagacttaccgagagaacctgcggatcg

```
cgctccgctactacaaccagagcgaggccgggtctcacaccctccagTggatgtatggctgcgacctggggcccgacggg
cgcctcctccgcgggcatgaccagtccgcctacgacggcaaggattacatcgccctgaacgaggacctgagctcctggac
cgcggcggacaccgcggctcagatcacccagcgcaagtgggaggcggcccgtgaggcggagcagctgagagcctacctgg
agggccTgtgcgtggagtggctccgcagatacctggagaacgggaaggagacgctgcagcgcgcgg
```

B*5807

(SEQ ID NO: 1637)
```
gctcccactccatgaggtatttctacaccgccatgtcccggcccggccgcggggagccccgcttcatcgcagtgggctac
gtggacgacacccagttcgtgaggttcgacagcgacgccgcgagtccgaggacggagccccgggcgccatggatagagca
ggaggggccggagtattgggacggggagacacggaacatgaaggcctccgcgcagacttaccgagagaacctgcggatcg
cgctccgctactacaaccagagcgaggccgggtctcacaccctccagTggatgtatggctgcgacctggggcccgacggg
cgcctcctccgcgggcatgaccagtccgcctacgacggcaaggattacatcgccctgaacgaggacctgagctcctggac
cgcggcggacaccgcggctcagatcacccagcgcaagtgggaggcggcccgtgtggcggagcagctgagagcctacctgg
agggcctgtgcgtggagtCgctccgcagatacctggagaacgggaaggagacgctgcagcgcgcgg
```

B*5901

(SEQ ID NO: 1638)
```
atgcgggtcacggcaccccgaaccctcctcctgctgctctgggggccctggccctgaccgagacctgggccggctccca
ctccatgaggtatttctacaccgccatgtcccggcccggccgcggggagccccgcttcatcgcagtgggctacgtggacg
acacgcagttcgtgaggttcgacagcgacgccgcgagtccgagagaggagccgcgggcgccgtggatagagcaggagggg
ccggagtattgggaccggaacacacagatcttcaagaccaacacacagacttaccgagagaacctgcggatcgcgctcCg
ctactacaaccagagcgaggccgggtctcacacttggcagacgatgtatggctgcgacctggggccggacgggcgcctcc
tccgcgggcataaccagttAgcctacgacggcaaggattacatcgccctgaacgaggacctgagctcctggaccgcggcg
gacaccgcggctcagatcacccagcgcaagtgggaggcggcccgtgTggcggagcagctgagagcctacctggagggcaC
gtgcgtggagtggctccgcagatacctggagaacgggaaggagacgctgcagcgcgcggacccccccaaagacacacgtga
cccaccaccccatctctgaccatgaggccaccctgaggtgctgggccctgggcttctaccctgcggagatcacactgacc
tggcagcgggatggcgaggaccaaactcaggacactgagcttgtggagaccagaccagcaggagatagaaccttccagaa
gtgggcagctgtggtggtgccttctggagaagagcagagatacacatgccatgtacagcatgagggctgccgaagcccc
tcaccctgagatgggagccatcttcccagtccaccatccccatcgtgggcattgttgctggcctggctgtccta...gca
gttgtggtcatcggagctgtggtcgctActgtgatgtgtaggaggaagagCtcaggtgga
```

B*670101

(SEQ ID NO: 1639)
```
atgctggtcatggcgccccgaaccgtcctcctgctgctctcggcggccctggccctgaccgagacctgggccggctccca
ctccatgaggtatttctacacctccgtgtcccggcccggccgcggggagccccgcttcatctcagtgggctacgtggacg
acacgcagttcgtgaggttcgacagcgacgccgcgagtccgagagaggagccgcgggcgccgtggatagagcaggagggg
ccggaAtattgggaccggaacacacagatctacaaggcccaggcacagactgaccgagagagcctgcggaacctgcgcgg
ctactacaaccagagcgaggccgggtctcacaccctccagagGatgtacggctgcgacgtggggccggacgggcgcctcc
tccgcgggcataaccagttcgcctacgacggcaaggattacatcgccctgaacgaggacctgagctcctggaccgcggcg
gacaccgcggctcagatcacccagcgcaagtgggaggcggcccgtgtggcggagcagcTgagaAcctacctggagggcac
gtgcgtggagtggctccgcagatacctggagaacgggaaggagacgctgcagcgcgcggacccccccaaagacacatgtga
cccaccaccccatctctgaccatgaggccaccctgaggtgctgggccctgggcttctaccctgcggagatcacactgacc
tggcagcgggatggcgaggaccaaactcaggacaccgagcttgtggagaccagaccagcaggagaCagaaccttccagaa
gtgggcagctgtggtggtgccttctggagaagagcagagatacacatgccatgtacagcatgagggctgccgaagcccc
tcaccctgagatgggagccAtcttcccagtccaccgtccccatcgtgggcattgttgctggcctggctgtccta...gca
gttgtggtcatcggagctgtggtcgctgctgtgatgtgtaggaggaagagttcaggtgga
```

B*670102

(SEQ ID NO: 1640)

gctcccactccatgaggtatttctacacctccgtgtcccggcccggccgcggggagccccgcttcatctcagtgggctac gtggacgacacgcagttcgtgaggttcgacagcgacgccgcgagtccgagagaggagccgcgggcgccgtggatagagca ggaggggccggagtattgggaccggaacacacagatctacaaggcccaggcacagactgaccgagagagcctgcggaacc tgcgcggctactacaaccagagcgaggccgggtctcacaccctccagagGatgtacggctgcgacgtggggccggacggg cgcctcctccgcgggcatAaccagtTcgcctacgacggcaaggattacatcgccctgaacgaggacctgagctcctggac cgcggcggacaccgcggctcagatcacccagcgcaagtgggaggcggcccgtgTggcggagcagcTgagaAcctacctgg agggcaCgtgcgtggagtggctccgcagatacctggagaacgggaaggagacgctgCagcg

B*6702

(SEQ ID NO: 1641)

atgctggtcatggcgccccgaaccgtcctcctgctgctctcggcggccctggccctgaccgagacctgggccggctccca ctccatgaggtatttctacacctccgtgtcccggcccggccgcggggagccccgcttcatctcagtgggctacgtggacg acacgcagttcgtgaggttcgacagcgacgccgcgagtccAagagggagccgcgggcgccgtgggtggagcaggagggg ccggagtattgggaccgggagacacagaagtacaagcgccaggcacaggctgaccgagtgagcctgcggaacctgcgcgg ctactacaaccagagcgaggccgggtctcacaccctccagaggatgtacggctgcgacgtggggccggacgggcgcctcc tccgcgggcataaccagttcgcctacgacggcaaggattacatcgccctgaacgaggacctgagctcctggaccgcggcg gacaccgcggctcagatcacccagcgcaagtgggaggcggcccgtgtggcggagcagctgagaacctacctggagggcac gtgcgtggagtggctccgcagatacctggagaacgggaaggagacgctgcagcgcgcggaccccccaaagacacatgtga cccaccaccccatctctgaccatgaggccaccctgaggtgctgggccctgggcttctaccctgcggagatcacactgacc tggcagcgggatggcgaggaccaaactcaggacaccgagcttgtggagaccagaccagcaggagacagaaccttccagaa gtgggcagctgtggtggtgccttctggagaagagcagagatacacatgccatgtacagcatgaggggctgccgaagcccc tcaccctgagatgggagccatcttcccagtccaccgtccccatcgtgggcattgttgctggcctggctgtcccta...gca gttgtggtcatcggagctgtggtcgctgctgtgatgtgtaggaggaagagttcaggtgga

B*7301

(SEQ ID NO: 1642)

atgctggtcatggcgccccgaaccgtcctcctgctgctctcggcggccctggccctgaccgagacctgggccggctccca ctccatgaggtatttccacacctccgtgtcccggcctggccgcggggagccccgcttcatcaccgtgggctacgtggacg acacccagttcgtgaggttcgacagcgacgccgcgagtccgagagaggagccgcgggcgccgtggatagagcaggagggg ccggagtattgggaccggaacacacagatctgcaaggccaaggcacagactgaccgagtgggcctgcggaacctgcgcgg ctactacaaccagagcgaggacgggtctcacacttggcagacgatgtatggctgcgacatggggccggacgggcgcctcc tccgcgggtataaccagttcgcctacgacggcaaggattacatcgccctgaacgaggacctgcgctcctggaccgccgcg gacacggcggctcagatcacccagcgcaagtgggaggcggcccgtgtggcggagcagctgagagcctacctggagggcga gtgcgtggagtggctccgcagacacctggagaacgggaaggagacgctgcagcgcgcggaccccccaaagacacacgtga cccaccaccccatctctgaccatgaggccaccctgaggtgctgggccctgggcttctaccctgcggagatcacactgacc tggcagcgggatggcgaggaccaaactcaggacaccgagcttgtggagaccaggccagcaggagatggaaccttccagaa gtgggcagctgtggtggtgccttctggacaagaacagagatacacgtgccatgtgcagcacgaggggctgcaggagccct gcaccctgagatggaagccatcttcccagtccaccatccccatcgtgggcattgttgctggcctggctgtccttgtggtc accgtagctgtggtCgctgtggtcgctgctgtgatgtgtaggaggaagagctcaggtgga

B*7801

(SEQ ID NO: 1643)

atgcgggtcacggcgccccgaaccgtcctcctgctgctctcgggggcagtggccctgaccgagacctgggccggctccca ctccatgaggtatttctacaccgccatgtcccggcccggccgcggggagccccgcttcatTgcagtgggctacgtggacg acacccagttcgtgaggttcgacagcgacgccgcgagtccgaggacggagcccccgggcgccatggatagagcaggagggg -continued
```
ccggagtattgggaccggaacacacagatctTcaagaccaacacacagactgaccgagagagcctgcggaacctgcgcgg ctactacaaccagagcgaggccgggtctcacacttggcagaCgatgtatggctgcgacgtggggccggacgggcgcctcc tccgcgggcataaccagtacgcctacgacggcaaagattacatcgccctgaacgaggacctgagctcctggaccgcggcg gacaccgcggctcagatcacccagcgcaagtgggaggcggcccgtgaggcggagcagcTgagagcctacctggagggcct gtgcgtggagtggctccgcagaCacctggagaacgggaaggagacgctgcagcgcgcggaccccccaaagacacacgtga cccaccaccccGtctctgaccatgaggccaccctgaggtgctgggccctgggcttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccatccccatcgtgggcattgttgctggcctggctgtcccta...gca gttgtggtcatcggagctgtggtcgctactgtgatgtgtaggaggaagagCtcaggtgga
```

B*780201
(SEQ ID NO: 1644)
```
atgcgggtcacggcgccccgaaccgtcctcctgctgctctgggggcagtggccctgaccgagacctgggccggctccca ctccatgaggtatttctacaccgccatgtcccggcccggccgcggggagccccgcttcatcgcagtgggctacgtggacg acacccagttcgtgaggttcgacagcgacgccgcgagtccgaggacggagccccgggcgccatggatagagcaggagggg ccggagtattgggaccggaacacacagatctTcaagaccaacacacagactTaccgagagagcctgcggaacctgcgcgg ctactacaaccagagcgaggccgggtctcacacttggcagaCgatgtatggctgcgacgtggggccggacgggcgcctcc tccgcgggcataaccagtacgcctacgacggcaaagattacatcgccctgaacgaggacctgagctcctggaccgcggcg gacaccgcggctcagatcacccagcgcaagtgggaggcggcccgtgaggcggagcagcTgagagcctacctggagggcct gtgcgtggagtggctccgcagaCacctggagaacgggaaggagacgctgcagcgcgcggaccccccaaagacacacgtga cccaccaccccGtctctgaccatgaggccaccctgaggtgctgggccctgggcttctaccctgcggagatcacactgacc tggcagcgggatggcgaggaccaaactcaggacactgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccatccccatcgtgggcattgttgctggcctggctgtcccta...gca gttgtggtcatcggagctgtggtcgctactgtgatgtgtaggaggaagagCtcaggtgga
```

B*780202
(SEQ ID NO: 1645)
```
gctcccactccatgaggtatttctacaccgccatgtcccggcccggccgcggggagccccgcttcatTgcagtgggctac gtggacgacacccagttcgtgaggttcgacagcgacgccgcgagtccgaggacggagccccgggcgccAtggatagagca ggaggggccggagtattgggaccggaacacacagatctTcaagaccaacacacagactTaccgagagagcctgcggaacc tgcgcggctactacaaccagagcgaggccgggtctcacacttggcagaCgatgtaTggctgcgacgtggggccggacggg cgcctcctccgcgggcataaccagtacgcctacgacggcaaAgattacatcgccctgaacgaggacctgAgctcctggac cgcggcggacaccgcggctcagatcacccagcgcaagtgggaggcggcccgtgaggcggagcagcTgagagcctacctgg agggccTgtgcgtggagtggctccgcagaCacctggagaacgggaaggagacgctgcagcgcgcgg
```

B*7803
(SEQ ID NO: 1646)
```
gctcccactccatgaggtatttctacaccgccatgtcccggcccggccgcggggagccccgcttcatTgcagtgggctac gtggacgacacccagttcgtgaggttcgacagcgacgccgcgagtccgaggacggagccccgggcgccatggatagagca ggaggggccggagtattgggaccggaacacacagatctGcaagaccaacAcacagactgaccgagagagcctgcggaacc tgcgcggctactacaaccagagcgaggccgggtctcacacttggcagaCgatgtaTggctgcgacgtggggccggacggg cgcctcctccgcgggcataaccagtacgcctacgacggcaaAgattacatcgccctgaacgaggacctgAgctcctggac cgcggcggacaccgcggctcagatcacccagcgcaagtgggaggcggcccgtgaggcggagcagcTgagagcctacctgg agggccTgtgcgtggagtggctccgcagaCacctggagaacgggaaggagacgctgcagcgcgcgg
```

B*7804

(SEQ ID NO: 1647)
gctcccactccatgaggtatttctacaccgccatgtcccggcccggccgcggggagccccgcttcatcgcagtgggctac gtggacgacacccagttcgtgaggttcgacagcgacgccgcgagtccgaggacggagccccgggcgccatggatagagca ggaggggccggagtattgggaccggaacacacagatcttcaagaccaacacacagacttaccgagagagcctgcggaacc tgcgcggctactacaaccagagcgaggccgggtctcacacttggcagacgatgtatggctgcgacgtggggccggacggg cgcctcctccgcgggcataaccagtacgcctacgacggcaaAgattacatcgccctgaacgaggacctgAgctcctggac cgcggcggacaccgcggctcagatcacccagcgcaagtgggaggcggcccgtgTggcggagcagcTgagagcctacctgg agggccTgtgcgtggagtggctccgcagatacctggagaacgggaaggagacgctgcagcgcgcggaccccccaaagaca cacgtgacccaccaccccGtctctgaccatgaggccaccctgaggtgctgggccctgggcttctaccctgcggagatcac actgacctggcagcgggatggcgaggaccaaactcaggacactgagcttgtggagaccagaccagcaggagatagaacct tccagaagtgggcagctgtggtggtgccttctggagaagagcagagatacacatgccatgtacagcatgagggctgccg aagcccctcaccctgagatggg

B*7805

(SEQ ID NO: 1648)
gctcccactccatgaggtatttctacaccgccatgtcccggcccggccgcggggagccccgcttcatcgcagtgggctac gtggacgacacccagttcgtgaggttcgacagcgacgccgcgagtccgaggaCggagccCcgggcgccatggatagagca ggaggggccggagtattgggacccgggaGacacagatctCcaagaccaacacacagactTaccgagagagcctgcggaacc tgcgcggctactacaaccagagcgaggccgggtctcacacttggcagaCgatgtaTggctgcgacgtggggccggacggg cgcctcctccgcgggcataaccagtacgcctacgacggcaaAgattacatcgccctgaacgaggacctgagctcctggac cgcggcggacaccgcggctcagatcacccagcgcaagtgggaggcggcccgtgaggcggagcagcTgagagcctacctgg agggccTgtgcgtggagtggctccgcagaCacctggagaacgggaaggagacgctgcagcgcgcgg

B*8101

(SEQ ID NO: 1649)
atgctggtcatggcgccccgaaccgtcctcctgctgctctgggggcagtggcccctgaccgagacctgggccggctccca ctccatgaggtatttctacacctccgtgtcccggcccggccgcggggagccccgcttcatctcagtgggctacgtggacg acacccagttcgtgaggttcgacagcgacgccgcgagtccgagagaggagccgcgggcgccgtggatagagcaggagggg ccggagtattgggaccggaacacacagatctacaaggcccaggcacagactgaccgagagagcctgcggaacctgcgcgg ctactacaaccagagcgaggccgggtctcacaccctccagagcatgtacggctgcgacgtggggccggacgggcgcctcc tccgcgggcataaccagtacgcctacgacggcaaggattacatcgccctgaacgaggacctgcgctcctggaccgccgcg gacacggcggctcagatctcccagcgcaagtggaggcggcccgtgtggcggagcagctgagagcctacctggagggcga gtgcgtggagtggctccgcagatacctggagaacgggaaggacaagctggagcgcgctgaccccccaaagacacacgtga cccaccacccatctctgaccatgaggccaccctgaggtgctgggccctgggtttctaccctgcggagatcacactgacc tggcagcgggatggcgaggaccaaactcaggacactgagcttgtggagaccagaccagcaggagatagaaccttccagaa gtggacagctgtggtggtgccttctggagaagagcagagatacacatgccatgtacagcatgaggggctgccgaagcccc tcaccctgagatgggagccgtcttcccagtccaccgtccccatcgtgggcattgttgctggcctggctgtccta...gca gttgtggtcatcggagctgtggtcgctgctgtgatgtgtaggaggaagagttcTggtgga

B*8201

(SEQ ID NO: 1650)
gctcccactccatgaggtatttctacaccgctatgtcccggcccggccgcggggagccccgcttcatctcagtgggctac gtggacgacacgcagttcgtgaggttcgacagcgacgccgcgagtccgagagaggagccgcgggcgccgtggatagagca ggaggggccggagtattgggaccggaacacacagatctacaaggcccaggcacagactgaccgagagagcctgcggaacc tgcgcggctactacaaccagagcgaggccgggtctcacaccctccagaggatgtttggctgcgacctggggcccgacggg cgcctcctccgcgggcataaccagttagcctacgacggcaaggattacatcgccctgaacgaggacctgagctcctggac -continued cgcggcggacaccgcggctcagatcacccagcgcaagtgggaggcggcccgtgtggcggagcaggacagagcctacctgg aggAcctgtgcgtggagtcgctccgcagatacctggagaacgggaaggagacgctgcagcgcgcgg

B*8202

(SEQ ID NO: 1651)

atgcgggtcacggcaccccgaaccctcctcctgctgctctgggggggcccctggccctgaccgagacctgggctggctccca ctccatgaggtatttctacaccgctatgtcccggcccggccgcggggagccccgcttcatctcagtgggctacgtggacg acacgcagttcgtgaggttcgacagcgacgccgcgagtccgagagaggagccgcgggcgccgtggatagagcaggagggg ccggagtattgggaccggaacacacagatctacaaggcccaggcacagactgaccgagagagcctgcggaacctgcgcgg ctactacaaccagagcgaggccgggtctcacaccctccagaggatgtttggctgcgacctggggcccgacgggcgcctcc tccgcgggcataaccagttagcctacgacggcaaggattacatcgccctgaacgaggacctgagctcctggaccgcggcg gacaccgcggctcagatcacccagcgcaagtgggaggcggcccgtgtggcggagcaggacagagcctacctggagggcct gtgcgtggagtcgctccgcagatacctggagaacgggaaggagacgctgcagcgcgcggaccccccaaagacacatgtga cccaccaccccatctctgaccatgaggccaccctgaggtgctgggccctgggcttctaccctgcggagatcacactgacc tggcagcgggatggcgaggaccaaactcaggacaccgagcttgtggagaccagaccagcaggagatagaaccttccagaa gtgggcagctgtggtggtgccttctggagaagagcagagatacacatgccatgtacagcatgaggggctgccgaagcccc tcaccctgagatgggagccatcttcccagtccaccatccccatcgtgggcattgttgctggcctggctgtccta...gca gttgtggtcatcggagctgtggtTgctactgtgatgtgtaggaggaagagctcaggtgga

B*8301

(SEQ ID NO: 1652)

atgcgggtcacggcgccccgaaccctcctcctgctgctctgggggggcaGtggccctgaccgagacctgggccggctccca ctccatgaggtatttctacaccgccAtgtcccggcccggccgcggggagccccgcttcatctcagtgggctacgtggacg acacccagttcgtgaggttcgacagcgacgccgcgagtccgagagaggagccgcgggcgccgtggatagagcaggagggg ccggagtattgggaccggaacacacagatctacaaggcccaggcacagactgaccgagagagcctgcggaacctgcgcgg ctactacaaccagagcgaggccgggtctcacatcAtccagaggatgtacggctgcgacgtggggccggacgggcgcctcc tccgcgggTatgaccagGacgcctacgacggcaaggattacatcgccctgaacgaggacctgagctcctggaccgcggcg gacaccgcggctcagatcacccagcgcaagtgggaggcggcccgtgtggcggagcaggaCagagcctacctggagggccT gtgcgtggagtCgctccgcagatacctggagaacgggaaggagacgctgcagcgcgcGg The following Tables 5-1 to 5-9 show Probe list B1, and Tables 6-1 to 6-8 show Probe list B2. The Allele-probe list is shown in Tables 7 and 8.

TABLE 5-1

| Probe No. | Base Sequence | |
|---|---|---|
| 0 | agg tat ttc tac acc tcc G | (SEQ ID No: 638) |
| 1 | ct cac acc ctc cag agC | (SEQ ID No: 639) |
| 2 | gc ctc ctc cgc ggg C | (SEQ ID No: 640) |
| 3 | c cgc ggg cat gac cag T | (SEQ ID No: 641) |
| 4 | gt gag gcg gag cag cG | (SEQ ID No: 642) |
| 5 | t gag gcg gag cag cgG | (SEQ ID No: 643) |
| 6 | gcc tac ctg gag ggc gA | (SEQ ID No: 644) |
| 7 | ggc gag tgc gtg gag tG | (SEQ ID No: 645) |
| 8 | c ggg aag gac aag ctg G | (SEQ ID No: 646) |
| 9 | g gag tgg ctc cgc agG | (SEQ ID No: 647) |

TABLE 5-1-continued

| Probe No. | Base Sequence | |
|---|---|---|
| 10 | gc tac gtg gac gac acG | (SEQ ID No: 648) |
| 11 | a cag atc tac aag acc aac A | (SEQ ID No: 649) |
| 12 | gt gag gcg gag cag gaC | (SEQ ID No: 650) |
| 13 | c ctc ctc cgc ggg cat A | (SEQ ID No: 651) |
| 14 | cg tct tcc cag tcc acc A | (SEQ ID No: 652) |
| 15 | ct cac acc ctc cag agG | (SEQ ID No: 653) |
| 16 | ac cgg aac aca cag atc tT | (SEQ ID No: 654) |
| 17 | a cag atc ttc aag acc aac A | (SEQ ID No: 655) |
| 18 | cgc ggg cat gac cag tC | (SEQ ID No: 656) |
| 19 | c cgg aac aca cag atc tG | (SEQ ID No: 657) |
| 20 | ca cag act gac cga gag aA | (SEQ ID No: 658) |
| 21 | g gcc ggg tct cac atc A | (SEQ ID No: 659) |

TABLE 5-1-continued

| Probe No. | Base Sequence | |
|---|---|---|
| 22 | ac atc atc cag agg atg taT | (SEQ ID No: 660) |
| 23 | gg atg tat ggc tgc gac C | (SEQ ID No: 661) |
| 24 | c tgc gac ctg ggg ccC | (SEQ ID No: 662) |
| 25 | ag aca cag aag tac aag cG | (SEQ ID No: 663) |
| 26 | c aag cgc cag gca cag G | (SEQ ID No: 664) |
| 27 | gca cag gct gac cga gT | (SEQ ID No: 665) |
| 28 | gag gcc ggg tct cac aT | (SEQ ID No: 666) |
| 29 | g tct cac atc atc cag agG | (SEQ ID No: 667) |
| 30 | cgc ctc ctc cgc ggg T | (SEQ ID No: 668) |

TABLE 5-2

| Probe No. | Base Sequence | |
|---|---|---|
| 31 | c aag gcc cag gca cag G | (SEQ ID No: 669) |
| 32 | c aag acc aac aca cag act T | (SEQ ID No: 670) |
| 33 | cgc ggg tat gac cag tC | (SEQ ID No: 671) |
| 34 | gcc tac ctg gag ggc aC | (SEQ ID No: 672) |
| 35 | ctg gag aac ggg aag gaG | (SEQ ID No: 673) |
| 36 | g acg ctg gag cgc gcG | (SEQ ID No: 674) |
| 37 | gcc tac ctg gag ggc cT | (SEQ ID No: 675) |
| 38 | ggc ctg tgc gtg gag tC | (SEQ ID No: 676) |
| 39 | c ggc cgc ggg gag cT | (SEQ ID No: 677) |
| 40 | tcc tgg acc gcc gcg A | (SEQ ID No: 678) |
| 41 | cgg aac ctg cgc ggc C | (SEQ ID No: 679) |
| 42 | gcc tac ctg gag ggc C | (SEQ ID No: 680) |
| 43 | gg gag gcg gcc cgt gT | (SEQ ID No: 681) |
| 44 | gt gtg gcg gag cag gaC | (SEQ ID No: 682) |
| 45 | cgt gag gcg gag cag cT | (SEQ ID No: 683) |
| 46 | c cgg aac aca cag atc tC | (SEQ ID No: 684) |
| 47 | ca cag act tac cga gag G | (SEQ ID No: 685) |
| 48 | ctg cgg acc ctg ctc C | (SEQ ID No: 686) |
| 49 | c cgc ggg tat gac cag G | (SEQ ID No: 687) |
| 50 | cac tcc atg agg tat ttc G | (SEQ ID No: 688) |
| 51 | gg tat ttc gac acc gcc A | (SEQ ID No: 689) |
| 52 | cg aga gag gag ccg cC | (SEQ ID No: 690) |
| 53 | a gcc tac ctg gag ggc A | (SEQ ID No: 691) |
| 54 | g atg tgt agg agg aag agC | (SEQ ID No: 692) |
| 55 | ctg cgc acc gcg ctc C | (SEQ ID No: 693) |
| 56 | c cga gag aac ctg cgg aT | (SEQ ID No: 694) |

TABLE 5-2-continued

| Probe No. | Base Sequence | |
|---|---|---|
| 57 | gag aac ctg cgg atc gC | (SEQ ID No: 695) |
| 58 | ctg cgg atc gcg ctc C | (SEQ ID No: 696) |
| 59 | c acg ctg gag cgc gcG | (SEQ ID No: 697) |
| 60 | g gac cgg aac aca cag aC | (SEQ ID No: 698) |

TABLE 5-3

| Probe No. | Base Sequence | |
|---|---|---|
| 61 | c act tgg cag acg atg taT | (SEQ ID No: 699) |
| 62 | g gag tat tgg gac cgg G | (SEQ ID No: 700) |
| 63 | c cgg gac aca cag atc tT | (SEQ ID No: 701) |
| 64 | cgt gtg gcg gag cag cT | (SEQ ID No: 702) |
| 65 | cgc ggg tac cac cag G | (SEQ ID No: 703) |
| 66 | c aca cag act gac cga gT | (SEQ ID No: 704) |
| 67 | ttc aag acc aac aca cag G | (SEQ ID No: 705) |
| 68 | c cgg gag aca cag atc tC | (SEQ ID No: 706) |
| 69 | g tgc tgg gcc ctg ggC | (SEQ ID No: 707) |
| 70 | g gct cag atc acc cag cT | (SEQ ID No: 708) |
| 71 | g tct cac act tgg cag aC | (SEQ ID No: 709) |
| 72 | cgc ggg cat aac cag ttA | (SEQ ID No: 710) |
| 73 | cg atg tat ggc tgc gac C | (SEQ ID No: 711) |
| 74 | tgg gag cca tct tcc caA | (SEQ ID No: 712) |
| 75 | gag cag ctg aga gcc tG | (SEQ ID No: 713) |
| 76 | gg tct cac acc ctc cag T | (SEQ ID No: 714) |
| 77 | cc aga cca gca gga gaC | (SEQ ID No: 715) |
| 78 | cc ctg aga tgg gag ccA | (SEQ ID No: 716) |
| 79 | c atg agg tat ttc tac acc G | (SEQ ID No: 717) |
| 80 | c tcc cac tcc atg agg C | (SEQ ID No: 718) |
| 81 | g cag gag ggg ccg gaA | (SEQ ID No: 719) |
| 82 | g gag tgg ctc cgc aga C | (SEQ ID No: 720) |
| 83 | g acg ctg cag cyc gcG | (SEQ ID No: 721) |
| 84 | c acc ctc cag agg atg taT | (SEQ ID No: 722) |
| 85 | tc ctg ctg ctc tcg ggA | (SEQ ID No: 723) |
| 86 | gcg ccc cgg gcg ccA | (SEQ ID No: 724) |
| 87 | gag tat tgg gac cgg gaG | (SEQ ID No: 725) |
| 88 | c cgt gag gcg gag cag T | (SEQ ID No: 726) |
| 89 | gac caa act cag gac acC | (SEQ ID No: 727) |
| 90 | cc gcc tac gac ggc aaA | (SEQ ID No: 728) |

TABLE 5-4

| Probe No. | Base Sequence | |
|---|---|---|
| 91 | g agc tcc tgg acc gcG | (SEQ ID No: 729) |
| 92 | g gat tac atc gcc ctg aaT | (SEQ ID No: 730) |
| 93 | c gac acg cag ttc gtg C | (SEQ ID No: 731) |
| 94 | cag atc tcc aag acc aac A | (SEQ ID No: 732) |
| 95 | c gga gct gtg gtc gct A | (SEQ ID No: 733) |
| 96 | c acc ctc cag agg atg tT | (SEQ ID No: 734) |
| 97 | tac gcc tac gac ggc aaA | (SEQ ID No: 735) |
| 98 | cag atc tgc aag acc aac A | (SEQ ID No: 736) |
| 99 | cg agt ccg agg atg gcT | (SEQ ID No: 737) |
| 100 | g ggc ctg tgc gtg gaC | (SEQ ID No: 738) |
| 101 | gg gcc ggc tcc cac tT | (SEQ ID No: 739) |
| 102 | ac atg aag gcc tcc gcG | (SEQ ID No: 740) |
| 103 | gca gct gtg gtg gtg cT | (SEQ ID No: 741) |
| 104 | gtg acc cac cac ccc G | (SEQ ID No: 742) |
| 105 | g tat tgg gac cgg gag aT | (SEQ ID No: 743) |
| 106 | gcg agt ccg agg atg gC | (SEQ ID No: 744) |
| 107 | c acc ctc cag agg atg tC | (SEQ ID No: 745) |
| 108 | gg acc gcc gcg gac aA | (SEQ ID No: 746) |
| 109 | g atg tac ggc tgc gac C | (SEQ ID No: 747) |
| 110 | g tct cac acc ctc cag aC | (SEQ ID No: 748) |
| 111 | ct cac acc ctc cag acG | (SEQ ID No: 749) |
| 112 | ac cga gag aac ctg cgC | (SEQ ID No: 750) |
| 113 | c ggg aag gag acg ctg C | (SEQ ID No: 751) |
| 114 | cc ctg aac gag gac ctg A | (SEQ ID No: 752) |
| 115 | g gag ccc cgc ttc atc G | (SEQ ID No: 753) |
| 116 | agg tat ttc tac acc gcc A | (SEQ ID No: 754) |
| 117 | t ccg agg atg gcg ccC | (SEQ ID No: 755) |
| 118 | g ttc gac agc gac gcc A | (SEQ ID No: 756) |
| 119 | gag ccg cgg gcg ccA | (SEQ ID No: 757) |
| 120 | g gcg gag cag ctg aga A | (SEQ ID No: 758) |

TABLE 5-5

| Probe No. | Base Sequence | |
|---|---|---|
| 121 | a acc tac ctg gag ggc C | (SEQ ID No: 759) |
| 122 | acc tac ctg gag ggc cT | (SEQ ID No: 760) |
| 123 | c tcc aag acc aac aca cG | (SEQ ID No: 761) |
| 124 | c tac gtg gac gac acg cT | (SEQ ID No: 762) |
| 125 | c cgg gag aca cag atc tT | (SEQ ID No: 763) |
| 126 | ac aca cag act tac cga gT | (SEQ ID No: 764) |
| 127 | ca cag act tac cga gtg aA | (SEQ ID No: 765) |
| 128 | c cgc ggg cat aac cag tT | (SEQ ID No: 766) |
| 129 | cc cag ttc gtg agg ttc A | (SEQ ID No: 767) |
| 130 | c cgg gag aca cag atc tG | (SEQ ID No: 768) |
| 131 | g gct cag atc acc cag cA | (SEQ ID No: 769) |
| 132 | acc tac ctg gag ggc aC | (SEQ ID No: 770) |
| 133 | cac tcc atg agg tat ttc C | (SEQ ID No: 771) |
| 134 | gac ccc cca aag aca caT | (SEQ ID No: 772) |
| 135 | gag aca cag atc tcc aag aT | (SEQ ID No: 773) |
| 136 | gg gag gcg gcc cgt C | (SEQ ID No: 774) |
| 137 | gcg ccg tgg ata gag caA | (SEQ ID No: 775) |
| 138 | g acc aac aca cag act tac A | (SEQ ID No: 776) |
| 139 | ac acc ctc cag aat atg taT | (SEQ ID No: 777) |
| 140 | g gag ccc cgc ttc att G | (SEQ ID No: 778) |
| 141 | g gat tac atc gcc ctg aaG | (SEQ ID No: 779) |
| 142 | c acc ctc cag agg atg tG | (SEQ ID No: 780) |
| 143 | gcg ccg tgg ata gag caA | (SEQ ID No: 781) |
| 144 | cga gag aac ctg cgc aC | (SEQ ID No: 782) |
| 145 | gag aac ctg cgc acc gC | (SEQ ID No: 783) |
| 146 | g tct cac acc ctc cag aaT | (SEQ ID No: 784) |
| 147 | cag gag ggg ccg gag C | (SEQ ID No: 785) |
| 148 | ctg ggc ttc tac cct gG | (SEQ ID No: 786) |
| 149 | ca cag act gac cga gag G | (SEQ ID No: 787) |
| 150 | c gcc gcg gac acg gcA | (SEQ ID No: 788) |

TABLE 5-6

| Probe No. | Base Sequence | |
|---|---|---|
| 151 | ctg ctc tgg ggg gca G | (SEQ ID No: 789) |
| 152 | c cag agc gag gcc ggT | (SEQ ID No: 790) |
| 153 | c tcc gtg tcc cgg ccT | (SEQ ID No: 791) |
| 154 | cgc ggg tac cac cag C | (SEQ ID No: 792) |
| 155 | tg acc gag acc tgg gcT | (SEQ ID No: 793) |
| 156 | cag gag ggg ccg gag tT | (SEQ ID No: 794) |
| 157 | cga gag agc ctg cgg aC | (SEQ ID No: 795) |
| 158 | c acg gcg gct cag atc T | (SEQ ID No: 796) |
| 159 | cg gag cag ctg aga gcT | (SEQ ID No: 797) |

TABLE 5-6-continued

| Probe No. | Base Sequence | |
|---|---|---|
| 160 | gg ccc gac ggg cgc T | (SEQ ID No: 798) |
| 161 | cgc ggg cat gac cag tT | (SEQ ID No: 799) |
| 162 | cc atg tcc cgg ccc gT | (SEQ ID No: 800) |
| 163 | g acc gcg gcg gac acC | (SEQ ID No: 801) |
| 164 | c tgc gac gtg ggg ccC | (SEQ ID No: 802) |
| 165 | t ccg agg acg gag ccC | (SEQ ID No: 803) |
| 166 | gag ccc cgg gcg ccA | (SEQ ID No: 804) |
| 167 | cc gcg agt ccg agg aC | (SEQ ID No: 805) |
| 168 | cac atc atc cag agg atg tT | (SEQ ID No: 806) |
| 169 | ca cag act tac cga gag aA | (SEQ ID No: 807) |
| 170 | c atg tac ggc tgc gac C | (SEQ ID No: 808) |
| 171 | ctg cgg aac ctg cgc gA | (SEQ ID No: 809) |
| 172 | cat gac cag tcc gcc tG | (SEQ ID No: 810) |
| 173 | c acc atc cag agg atg tC | (SEQ ID No: 811) |
| 174 | gac ctg agc tcc tgg acA | (SEQ ID No: 812) |
| 175 | cga gag agc ctg cgc aC | (SEQ ID No: 813) |
| 176 | g cag gag ggg ccg gG | (SEQ ID No: 814) |
| 177 | ga acc tac ctg gag ggc A | (SEQ ID No: 815) |
| 178 | a acc tac ctg gag ggc aT | (SEQ ID No: 816) |
| 179 | c tgg acc gcg gcg gaG | (SEQ ID No: 817) |
| 180 | ta gag cag gag ggg ccA | (SEQ ID No: 818) |

TABLE 5-7

| Probe No. | Base Sequence | |
|---|---|---|
| 181 | tct cac act tgg cag acG | (SEQ ID No: 819) |
| 182 | g gcg gag cag cgg aga A | (SEQ ID No: 820) |
| 183 | cgg ccc ggc cgc ggA | (SEQ ID No: 821) |
| 184 | gg tct cac acc ctc caC | (SEQ ID No: 822) |
| 185 | c cgc ggg tat aac cag ttA | (SEQ ID No: 823) |
| 186 | g gcg gag cag tgg aga A | (SEQ ID No: 824) |
| 187 | gaa tat tgg gac cgg gaG | (SEQ ID No: 825) |
| 188 | gcg gct cag atc acc cG | (SEQ ID No: 826) |
| 189 | cac acc ctc cag agc aC | (SEQ ID No: 827) |
| 190 | ag tgg gag gcg gcc cT | (SEQ ID No: 828) |
| 191 | g acc gag acc tgg gcG | (SEQ ID No: 829) |
| 192 | c gcc acg agt ccg agg A | (SEQ ID No: 830) |
| 193 | g atc tcc cag cgc aag tT | (SEQ ID No: 831) |
| 194 | tg gag gcg gcc cgt gT | (SEQ ID No: 832) |

TABLE 5-7-continued

| Probe No. | Base Sequence | |
|---|---|---|
| 195 | tg acc gag acc tgg gcl | (SEQ ID No: 833) |
| 196 | g cgc tcc tgg acc gcG | (SEQ ID No: 834) |
| 197 | ag ggc gag tgc gtg gaT | (SEQ ID No: 835) |
| 198 | gg tat ttc cac acc gcc A | (SEQ ID No: 836) |
| 199 | c cgc ggg cat aac cag A | (SEQ ID No: 837) |
| 200 | ccg gag tat tgg gac cC | (SEQ ID No: 838) |
| 201 | gg tct cac atc atc cag G | (SEQ ID No: 839) |
| 202 | c gcc tac gac ggc aag A | (SEQ ID No: 840) |
| 203 | cgc ggg cat aac cag tC | (SEQ ID No: 841) |
| 204 | cc ggg tct cac act tgG | (SEQ ID No: 842) |
| 205 | c act tgg cag agg atg taT | (SEQ ID No: 843) |
| 206 | ga gag agc ctg cgg aaG | (SEQ ID No: 844) |
| 207 | c ggg aag gac acg ctg C | (SEQ ID No: 845) |
| 208 | c acg ctg cag cgc gcG | (SEQ ID No: 846) |
| 209 | cc atc tct gac cat gag gT | (SEQ ID No: 847) |
| 210 | cgg gag aca cag atc tcG | (SEQ ID No: 848) |

TABLE 5-8

| Probe No. | Base Sequence | |
|---|---|---|
| 211 | g gag gcg gcc cgt gtC | (SEQ ID No: 849) |
| 212 | a gag aac ctg cgc acc G | (SEQ ID No: 850) |
| 213 | gg gag ccc cgc ttc atT | (SEQ ID No: 851) |
| 214 | ctg cgc acc ccg ctc C | (SEQ ID No: 852) |
| 215 | gg ccg gag tat tgg gaG | (SEQ ID No: 853) |
| 216 | c cgc ggg cat aac cag G | (SEQ ID No: 854) |
| 217 | ggc gag tgc gtg gag tC | (SEQ ID No: 855) |
| 218 | cgg gcg ccg tgg gtG | (SEQ ID No: 856) |
| 219 | ga gag aac ctg cgg atc G | (SEQ ID No: 857) |
| 220 | gtg gac gac acg ctg ttG | (SEQ ID No: 858) |
| 221 | tg gag ggc ctg tgc gC | (SEQ ID No: 859) |
| 222 | gac ggc aag gat tac atc A | (SEQ ID No: 860) |
| 223 | c cgc ggg tat aac cag tT | (SEQ ID No: 861) |
| 224 | ctc cgc ggg tat aac cG | (SEQ ID No: 862) |
| 225 | gcg gag cag gac aga gT | (SEQ ID No: 863) |
| 226 | gag aca cag aag tac aag C | (SEQ ID No: 864) |
| 227 | cgc cag gca cag act gG | (SEQ ID No: 865) |
| 228 | t gtg gtc gct gct gtg G | (SEQ ID No: 866) |

TABLE 5-8-continued

| Probe No. | Base Sequence | |
|---|---|---|
| 229 | c ctg cgg aac ctg ctc C | (SEQ ID No: 867) |
| 230 | aga acc ttc cag aag tgg A | (SEQ ID No: 868) |
| 231 | ag ccc cgc ttc atc tcC | (SEQ ID No: 869) |
| 232 | c cgc ggg tat aac cag ttA | (SEQ ID No: 870) |
| 233 | ggc ctg tgc gtg gag G | (SEQ ID No: 871) |
| 234 | cgg atc gcg ctc cgc G | (SEQ ID No: 872) |
| 235 | ttc gcc tac gac ggc aaA | (SEQ ID No: 873) |
| 236 | ctc ctc cgc ggg cat aaA | (SEQ ID No: 874) |
| 237 | g cgt ctc ctc cgc ggT | (SEQ ID No: 875) |
| 238 | c ggg cgc ctc ctc cC | (SEQ ID No: 876) |
| 239 | g agt ccg agg acg gag A | (SEQ ID No: 877) |
| 240 | ata gag cag gag ggg cG | (SEQ ID No: 878) |

TABLE 5-9

| Probe No. | Base Sequence | |
|---|---|---|
| 241 | cc aga cca gca gga gat G | (SEQ ID No: 879) |
| 242 | cag cat gag ggg ctg cT | (SEQ ID No: 880) |
| 243 | cag act tac cga gag aac T | (SEQ ID No: 881) |
| 244 | gc gac gcc gcg agt cA | (SEQ ID No: 882) |
| 245 | c cgc ggg gag ccc cC | (SEQ ID No: 883) |
| 246 | cga gag agc ctg cgg aT | (SEQ ID No: 884) |
| 247 | gag agc ctg cgg atc gC | (SEQ ID No: 885) |
| 248 | g gca cag act gac cga gT | (SEQ ID No: 886) |
| 249 | g acc gcc gcg gac acC | (SEQ ID No: 887) |
| 250 | g cag gag ggg ccg gC | (SEQ ID No: 888) |
| 251 | cc gcg agt ccg aga gG | (SEQ ID No: 889) |
| 252 | gg tct cac act tgg cag aT | (SEQ ID No: 890) |
| 253 | acg gca ccc cga acc C | (SEQ ID No: 891) |
| 254 | ctc ctc ctg ctg ctc tG | (SEQ ID No: 892) |
| 255 | ag aca cag aag tac aag gG | (SEQ ID No: 893) |
| 256 | gg tct cac atc atc cag gT | (SEQ ID No: 894) |
| 257 | gc ggg cat gac cag tcT | (SEQ ID No: 895) |
| 258 | g acc gcg gcg gac acA | (SEQ ID No: 896) |
| 259 | g ccg gag tat tgg gac G | (SEQ ID No: 897) |
| 260 | c ctc ctc cgc ggg tat A | (SEQ ID No: 898) |
| 261 | c acg gcg gct cag atc aT | (SEQ ID No: 899) |
| 262 | tg cgg atc gcg ctc cC | (SEQ ID No: 900) |
| 263 | g ccg gag tat tgg gac gA | (SEQ ID No: 901) |

TABLE 5-9-continued

| Probe No. | Base Sequence | |
|---|---|---|
| 264 | g gag gcg gcc cgt gC | (SEQ ID No: 902) |
| 265 | c gac gcc gcg agt ccA | (SEQ ID No: 903) |
| 266 | gtc acc gta gct gtg gtC | (SEQ ID No: 904) |
| 267 | g tgt agg agg aag agt tcT | (SEQ ID No: 905) |
| 268 | c aga gcc tac ctg gag gA | (SEQ ID No: 906) |
| 269 | gtc atc gga gct gtg gtT | (SEQ ID No: 907) |

TABLE 6-1

| Probe No. | Base Sequence | |
|---|---|---|
| 0 | c acc tcc Gtg tcc cgg | (SEQ ID No: 908) |
| 1 | c ctc cag agC atg tac gg | (SEQ ID No: 909) |
| 2 | c cgc ggg Cat gac cag | (SEQ ID No: 910) |
| 3 | cat gac cag Tac gcc tac | (SEQ ID No: 911) |
| 4 | g gag cag cGg aga gcc | (SEQ ID No: 912) |
| 5 | gag cag cgG aga gcc ta | (SEQ ID No: 913) |
| 6 | g gag ggc gAg tgc gtg | (SEQ ID No: 914) |
| 7 | c gtg gag tGg ctc cgc | (SEQ ID No: 915) |
| 8 | ac aag ctg Gag cgc gct | (SEQ ID No: 916) |
| 9 | ctc cgc agG tac ctg ga | (SEQ ID No: 917) |
| 10 | g gac gac acG cag ttc gt | (SEQ ID No: 918) |
| 11 | aag acc aac Aca cag act g | (SEQ ID No: 919) |
| 12 | g gag cag gaC aga gcc ta | (SEQ ID No: 920) |
| 13 | cgc ggg cat Aac cag tac | (SEQ ID No: 921) |
| 14 | cag tcc acc Atc ccc atc | (SEQ ID No: 922) |
| 15 | c ctc cag agG atg tac gg | (SEQ ID No: 923) |
| 16 | aca cag atc tTc aag acc aa | (SEQ ID No: 924) |
| 17 | t gac cag tCc gcc tac g | (SEQ ID No: 925) |
| 18 | ca cag atc tGc aag gcc C | (SEQ ID No: 926) |
| 19 | c cga gag aAc ctg cgg a | (SEQ ID No: 927) |
| 20 | tct cac atc Atc cag agg a | (SEQ ID No: 928) |
| 21 | g agg atg taT ggc tgc ga | (SEQ ID No: 929) |
| 22 | c tgc gac Ctg ggg ccc | (SEQ ID No: 930) |
| 23 | ctg ggg ccC gac ggg | (SEQ ID No: 931) |
| 24 | g tac aag cGc cag gca c | (SEQ ID No: 932) |
| 25 | ag gca cag Gct gac cga | (SEQ ID No: 933) |
| 26 | t gac cga gTg agc ctg c | (SEQ ID No: 934) |
| 27 | gg tct cac aTc atc cag ag | (SEQ ID No: 935) |

TABLE 6-1-continued

| Probe No. | Base Sequence | |
|---|---|---|
| 28 | c atc cag agG atg tac gg | (SEQ ID No: 936) |
| 29 | tc cgc ggg Tat gac cag | (SEQ ID No: 937) |
| 30 | aag acc aac Aca cag act ta | (SEQ ID No: 938) |

TABLE 6-2

| Probe No. | Base Sequence | |
|---|---|---|
| 31 | aca cag act Tac cga gag a | (SEQ ID No: 939) |
| 32 | g gag ggc aCg tgc gtg | (SEQ ID No: 940) |
| 33 | ggg aag gaG acg ctg ga | (SEQ ID No: 941) |
| 34 | g aag gag aCg ctg gag c | (SEQ ID No: 942) |
| 35 | g gag ggc cTg tgc gtg | (SEQ ID No: 943) |
| 36 | c gtg gag tCg ctc cgc | (SEQ ID No: 944) |
| 37 | c ggg gag cTc cgc ttc | (SEQ ID No: 945) |
| 38 | c gcc gcg Aac acg gcg | (SEQ ID No: 946) |
| 39 | tg cgc ggc Cac tac aac | (SEQ ID No: 947) |
| 40 | g gag ggc Ctg tgc gtg | (SEQ ID No: 948) |
| 41 | g gcc cgt gTg gcg gag | (SEQ ID No: 949) |
| 42 | g gag cag cTg aga gcc t | (SEQ ID No: 950) |
| 43 | ca cag atc tCc aag acc aa | (SEQ ID No: 951) |
| 44 | aca cag act Tac cga gag g | (SEQ ID No: 952) |
| 45 | c cga gag Gac ctg cgg | (SEQ ID No: 953) |
| 46 | cc ctg ctc Cgc tac tac | (SEQ ID No: 954) |
| 47 | tat gac cag Gac gcc tac | (SEQ ID No: 955) |
| 48 | agg tat ttc Gac acc gcc | (SEQ ID No: 956) |
| 49 | c acc gcc Atg tcc cgg | (SEQ ID No: 957) |
| 50 | gag ccg cCg gcg ccg | (SEQ ID No: 958) |
| 51 | g gag ggc Acg tgc gtg | (SEQ ID No: 959) |
| 52 | g agg aag agC tca ggt gg | (SEQ ID No: 960) |
| 53 | cc gcg ctc Cgc tac tac | (SEQ ID No: 961) |
| 54 | c ctg cgg aTc gcg ctc | (SEQ ID No: 962) |
| 55 | g cgg atc gCg ctc cgc | (SEQ ID No: 963) |
| 56 | tc gcg ctc Cgc tac tac | (SEQ ID No: 964) |
| 57 | g aag gac aCg ctg gag c | (SEQ ID No: 965) |
| 58 | ac aca cag aCc ttc aag ac | (SEQ ID No: 966) |
| 59 | g acg atg taT ggc tgc ga | (SEQ ID No: 967) |
| 60 | gg gac cgg Gac aca cag | (SEQ ID No: 968) |
| 61 | ac cac cag Gac gcc tac | (SEQ ID No: 969) |

TABLE 6-3

| Probe No. | Base Sequence | |
|---|---|---|
| 62 | aac aca cag Gct gac cga | (SEQ ID No: 970) |
| 63 | gcc ctg ggC ttc tac cc | (SEQ ID No: 971) |
| 64 | c acc cag cTc aag tgg g | (SEQ ID No: 972) |
| 65 | ct tgg cag aCg atg tat gg | (SEQ ID No: 973) |
| 66 | t aac cag ttA gcc tac gac | (SEQ ID No: 974) |
| 67 | c tgc gac Ctg ggg ccg | (SEQ ID No: 975) |
| 68 | a tct tcc caA tcc acc gtc | (SEQ ID No: 976) |
| 69 | g aga gcc tGc ctg gag g | (SEQ ID No: 977) |
| 70 | acc ctc cag Tgg atg tat g | (SEQ ID No: 978) |
| 71 | a gca gga gaG aga acc ttc | (SEQ ID No: 979) |
| 72 | a tgg gag ccA tct tcc ca | (SEQ ID No: 980) |
| 73 | tc tac acc Gcc gtg tcc | (SEQ ID No: 981) |
| 74 | tcc atg agg Cat ttc tac ac | (SEQ ID No: 982) |
| 75 | g ggg ccg gaA tat tgg ga | (SEQ ID No: 983) |
| 76 | tc cgc aga Cac ctg gag | (SEQ ID No: 984) |
| 77 | g acg ctg Cag cgc gcg | (SEQ ID No: 985) |
| 78 | ctc tcg ggA gcc ctg g | (SEQ ID No: 986) |
| 79 | cgg gcg ccA tgg ata ga | (SEQ ID No: 987) |
| 80 | g gac cgg gaG aca cag at | (SEQ ID No: 988) |
| 81 | cg gag cag Tgg aga gcc | (SEQ ID No: 989) |
| 82 | t cag gac acC gag ctt gt | (SEQ ID No: 990) |
| 83 | c gac ggc aaA gat tac atc | (SEQ ID No: 991) |
| 84 | tgg acc gcG gcg gac a | (SEQ ID No: 992) |
| 85 | c gcc ctg aaT gag gac ct | (SEQ ID No: 993) |
| 86 | cag ttc gtg Cgg ttc gac | (SEQ ID No: 994) |
| 87 | gtg gtc gct Act gtg atg | (SEQ ID No: 995) |
| 88 | ag agg atg tTt ggc tgc g | (SEQ ID No: 996) |
| 89 | ca cag atc tGc aag acc aa | (SEQ ID No: 997) |
| 90 | agg atg gcT ccc cgg g | (SEQ ID No: 998) |
| 91 | tgc gtg gaC ggg ctc c | (SEQ ID No: 999) |
| 92 | gc tcc cac tTc atg agg t | (SEQ ID No: 1000) |

TABLE 6-4

| Probe No. | Base Sequence | |
|---|---|---|
| 93 | gcc tcc gcG cag act ta | (SEQ ID No: 1001) |
| 94 | tg gtg gtg cTt tct gga g | (SEQ ID No: 1002) |
| 95 | ac cac ccc Gtc tct gac | (SEQ ID No: 1003) |
| 96 | ac cgg gag aTa cag atc tc | (SEQ ID No: 1004) |

TABLE 6-4-continued

| Probe No. | Base Sequence | |
|---|---|---|
| 97  | g agg atg gCg ccc cgg       | (SEQ ID No: 1005) |
| 98  | g agg atg tCt ggc tgc g     | (SEQ ID No: 1006) |
| 99  | c gcg gac aAg gcg gct       | (SEQ ID No: 1007) |
| 100 | cc ctc cag aCg atg tac g    | (SEQ ID No: 1008) |
| 101 | c ctc cag acG atg tac gg    | (SEQ ID No: 1009) |
| 102 | aac ctg cgC acc gcg c       | (SEQ ID No: 1010) |
| 103 | ag gac ctg Agc tcc tgg      | (SEQ ID No: 1011) |
| 104 | gc ttc atc Gca gtg ggc      | (SEQ ID No: 1012) |
| 105 | atg gcg ccC cgg gcg         | (SEQ ID No: 1013) |
| 106 | c gac gcc Acg agt ccg       | (SEQ ID No: 1014) |
| 107 | cag ctg aga Acc tac ctg     | (SEQ ID No: 1015) |
| 108 | cc aac aca cGg act tac c    | (SEQ ID No: 1016) |
| 109 | ggg aag gaG acg ctg ca      | (SEQ ID No: 1017) |
| 110 | ac gac acg cTg ttc gtg a    | (SEQ ID No: 1018) |
| 111 | ct tac cga gTg aac ctg c    | (SEQ ID No: 1019) |
| 112 | c cga gtg aAc ctg cgg a     | (SEQ ID No: 1020) |
| 113 | at aac cag tTc gcc tac ga   | (SEQ ID No: 1021) |
| 114 | gtg agg ttc Aac agc gac     | (SEQ ID No: 1022) |
| 115 | c acc cag cAc aag tgg g     | (SEQ ID No: 1023) |
| 116 | cg gag cag cig aga acc t    | (SEQ ID No: 1024) |
| 117 | agg tat ttc Cac acc tcc g   | (SEQ ID No: 1025) |
| 118 | a aag aca caT gtg acc cac   | (SEQ ID No: 1026) |
| 119 | atc tcc aag aTc aac aca ca  | (SEQ ID No: 1027) |
| 120 | g gcc cgt Cag gcg gag       | (SEQ ID No: 1028) |
| 121 | g ata gag caA gag ggg cc    | (SEQ ID No: 1029) |
| 122 | cag act tac Aga gag agc c   | (SEQ ID No: 1030) |
| 123 | g aat atg taT ggc tgc gac   | (SEQ ID No: 1031) |

TABLE 6-5

| Probe No. | Base Sequence | |
|---|---|---|
| 124 | cgc ttc att Gca gtg ggc     | (SEQ ID No: 1032) |
| 125 | gcc ctg aaG gag gac ct      | (SEQ ID No: 1033) |
| 126 | ct tac cga gTg agc ctg c    | (SEQ ID No: 1034) |
| 127 | g agg atg tGc ggc tgc g     | (SEQ ID No: 1035) |
| 128 | g ata gag caA gag ggg cc    | (SEQ ID No: 1036) |
| 129 | ca cag atc tGc aag gcc a    | (SEQ ID No: 1037) |
| 130 | c ctg cgc aCc gcg ctc       | (SEQ ID No: 1038) |

TABLE 6-5-continued

| Probe No. | Base Sequence | |
|---|---|---|
| 131 | cgc acc gCg ctc cgc         | (SEQ ID No: 1039) |
| 132 | c ctc cag aaT atg tat ggc   | (SEQ ID No: 1040) |
| 133 | gg ccg gag Cat tgg gac      | (SEQ ID No: 1041) |
| 134 | tc tac cct gGg gag atc a    | (SEQ ID No: 1042) |
| 135 | g gac acg gcA gct cag at    | (SEQ ID No: 1043) |
| 136 | g ggg gca Gtg gcc ctg       | (SEQ ID No: 1044) |
| 137 | gag gcc ggT tct cac ac      | (SEQ ID No: 1045) |
| 138 | tcc cgg ccT ggc cgc         | (SEQ ID No: 1046) |
| 139 | ac cac cag Cac gcc tac      | (SEQ ID No: 1047) |
| 140 | acc tgg gcT ggc tcc c       | (SEQ ID No: 1048) |
| 141 | g gtc acg gAg ccc cga       | (SEQ ID No: 1049) |
| 142 | g ccg gag tTt tgg gac c     | (SEQ ID No: 1050) |
| 143 | c ctc cag aaT atg tac ggc   | (SEQ ID No: 1051) |
| 144 | C ctg cgg aCc ctg ctc       | (SEQ ID No: 1052) |
| 145 | ct cag atc Tcc cag cgc      | (SEQ ID No: 1053) |
| 146 | g ctg aga gcT tac ctg ga    | (SEQ ID No: 1054) |
| 147 | c ggg cgc Ttc ctc cgc       | (SEQ ID No: 1055) |
| 148 | at gac cag tTc gcc tac g    | (SEQ ID No: 1056) |
| 149 | cgc ggg cat Aac cag ttc     | (SEQ ID No: 1057) |
| 150 | cgg ccc gTc cgc ggg         | (SEQ ID No: 1058) |
| 151 | gcg gac acC gcg gct c       | (SEQ ID No: 1059) |
| 152 | tct cac atc Atc cag agc a   | (SEQ ID No: 1060) |
| 153 | gtg ggg ccC gac ggg         | (SEQ ID No: 1061) |
| 154 | acg gag ccC cgg gcg         | (SEQ ID No: 1062) |

TABLE 6-6

| Probe No. | Base Sequence | |
|---|---|---|
| 155 | t ccg agg aCg gag ccc       | (SEQ ID No: 1063) |
| 156 | ac ctg cgc gAc tac tac a    | (SEQ ID No: 1064) |
| 157 | g tcc gcc tGc gac ggc       | (SEQ ID No: 1065) |
| 158 | tcc tgg acA gcg gcg g       | (SEQ ID No: 1066) |
| 159 | c cga gag aAc ctg cgc a     | (SEQ ID No: 1067) |
| 160 | g ggg ccg gGa tat tgg g     | (SEQ ID No: 1068) |
| 161 | tg gag ggc Atg tgc gtg      | (SEQ ID No: 1069) |
| 162 | g gag ggc aTg tgc gtg g     | (SEQ ID No: 1070) |
| 163 | gcg gcg gaG acc gcg         | (SEQ ID No: 1071) |
| 164 | g gag ggg ccA gaa tat tg    | (SEQ ID No: 1072) |
| 165 | ct tgg cag aCg atg tac g    | (SEQ ID No: 1073) |

TABLE 6-6-continued

| Probe No. | Base Sequence | |
|---|---|---|
| 166 | t tgg cag acG atg tac gg | (SEQ ID No: 1074) |
| 167 | cag cgg aga Acc tac ctg | (SEQ ID No: 1075) |
| 168 | ggc cgc ggA gag ccc | (SEQ ID No: 1076) |
| 169 | c acc ctc caC agg atg ta | (SEQ ID No: 1077) |
| 170 | cg gag cag Tgg aga acc | (SEQ ID No: 1078) |
| 171 | cag tgg aga Acc tac ctg | (SEQ ID No: 1079) |
| 172 | g atc acc cGg cgc aag t | (SEQ ID No: 1080) |
| 173 | c cag agc aCg tac ggc t | (SEQ ID No: 1081) |
| 174 | g gcg gcc cTt gtg gcg | (SEQ ID No: 1082) |
| 175 | acc tgg gcG ggc tcc c | (SEQ ID No: 1083) |
| 176 | gtc acg gcA ccc cga ac | (SEQ ID No: 1084) |
| 177 | agg tat ttc Cac acc gcc | (SEQ ID No: 1085) |
| 178 | gt ccg agg Aag gag ccg | (SEQ ID No: 1086) |
| 179 | g cgc aag tTg gag gcg g | (SEQ ID No: 1087) |
| 180 | acc tgg gcT ggc tcc c | (SEQ ID No: 1088) |
| 181 | tgc gtg gaT tgg ctc cg | (SEQ ID No: 1089) |
| 182 | cat aac cag Aac gcc tac g | (SEQ ID No: 1090) |
| 183 | t tgg gac cCg gag aca c | (SEQ ID No: 1091) |
| 184 | atc atc cag Gtg atg tat gg | (SEQ ID No: 1092) |
| 185 | gac ggc aag Aat tac atc g | (SEQ ID No: 1093) |

TABLE 6-7

| Probe No. | Base Sequence | |
|---|---|---|
| 186 | at aac cag tCc gcc tac g | (SEQ ID NO: 1094) |
| 187 | ctg cgg aaG ctg cgc g | (SEQ ID No: 1095) |
| 188 | t cac act tgG cag agg atg | (SEQ ID No: 1096) |
| 189 | c acg ctg Cag cgc gcg | (SEQ ID No: 1097) |
| 190 | ac cat gag gTc acc ctg a | (SEQ ID No: 1098) |
| 191 | a cag atc tcG aag acc aac | (SEQ ID No: 1099) |
| 192 | gcc cgt gtC gcg gag c | (SEQ ID No. 1100) |
| 193 | g cgc acc Gcg ctc cg | (SEQ ID No: 1101) |
| 194 | c cgc ttc atT gca gtg gg | (SEQ ID No: 1102) |
| 195 | c ctg cgc aCc ccg ctc | (SEQ ID No: 1103) |
| 196 | cc ccg ctc Cgc tac tac | (SEQ ID No: 1104) |
| 197 | g tat tgg gaG cgg gag ac | (SEQ ID No: 1105) |
| 198 | gc ggg cat Aac cag gac | (SEQ ID No: 1106) |
| 199 | cat aac cag Gac gcc tac | (SEQ ID No: 1107) |

TABLE 6-7-continued

| Probe No. | Base Sequence | |
|---|---|---|
| 200 | ctc cgc ggg Tat aac cag | (SEQ ID No: 1108) |
| 201 | ccg tgg gtG gag cag g | (SEQ ID No: 1109) |
| 202 | g cgg atc Gcg ctc cgc | (SEQ ID No: 1110) |
| 203 | c acg ctg ttG gtg agg tt | (SEQ ID No: 1111) |
| 204 | c ctg tgc gCg gag tcg | (SEQ ID No: 1112) |
| 205 | gat tac atc Acc ctg aac g | (SEQ ID No: 1113) |
| 206 | gg tat aac cGg tta gcc ta | (SEQ ID No: 1114) |
| 207 | ag gac aga gTc tac ctg g | (SEQ ID No: 1115) |
| 208 | aag tac aag Cgc cag gca | (SEQ ID No: 1116) |
| 209 | ca cag act gGc cga gtg a | (SEQ ID No: 1117) |
| 210 | gct gct gtg Gtg tgt agg | (SEQ ID No: 1118) |
| 211 | aac ctg ctc Cgc tac tac | (SEQ ID No: 1119) |
| 212 | cag aag tgg Aca gct gtg | (SEQ ID No: 1120) |
| 213 | cag cgc gcG gac ccc | (SEQ ID No: 1121) |
| 214 | c ttc atc tcC gtg ggc ta | (SEQ ID No: 1122) |
| 215 | c gtg gag Ggg ctc cgc | (SEQ ID No: 1123) |
| 216 | cg ctc cgc Gac tac aac | (SEQ ID No: 1124) |

TABLE 6-8

| Probe No. | Base Sequence | |
|---|---|---|
| 217 | c ggg cat aaA cag tac gc | (SEQ ID No: 1125) |
| 218 | c ctc cgc ggT tat aac ca | (SEQ ID No: 1126) |
| 219 | c ctc ctc cCc ggg cat | (SEQ ID No: 1127) |
| 220 | g acg gag Acc cgg gcg | (SEQ ID No: 1128) |
| 221 | g gag ggg cGg gag tat t | (SEQ ID No: 1129) |
| 222 | gca gga gat Gga acc ttc | (SEQ ID No: 1130) |
| 223 | g ggg ctg cTg aag ccc | (SEQ ID No: 1131) |
| 224 | cgg gtc aCg gcg ccc | (SEQ ID No: 1132) |
| 225 | t ccg agg aCg gag ccg | (SEQ ID No: 1133) |
| 226 | cga gag aac Ttg cgg atc | (SEQ ID No: 1134) |
| 227 | c gcg agt cAg agg acg g | (SEQ ID No: 1135) |
| 228 | g gag ccc cCc ttc atc g | (SEQ ID No: 1136) |
| 229 | g ggg ccg gCg tat tgg | (SEQ ID No: 1137) |
| 230 | t ccg aga gGg gag ccg | (SEQ ID No: 1138) |
| 231 | ct tgg cag aTg atg tat gg | (SEQ ID No: 1139) |
| 232 | g tac aag gGc cag gca c | (SEQ ID No: 1140) |
| 233 | tc atc cag gTg atg tat gg | (SEQ ID No: 1141) |
| 234 | t gac cag tcT gcc tac ga | (SEQ ID No: 1142) |

TABLE 6-8-continued

| Probe No. | Base Sequence | |
|---|---|---|
| 235 | gcg gac acA gcg gct c | (SEQ ID No: 1143) |
| 236 | tat tgg gac Ggg gag aca | (SEQ ID No: 1144) |
| 237 | cgc ggg tat Aac cag tac | (SEQ ID No: 1145) |
| 238 | ct cag atc aTc cag cgc a | (SEQ ID No: 1146) |
| 239 | c gcg ctc cCc tac tac a | (SEQ ID No: 1147) |
| 240 | at tgg gac gAg gag aca c | (SEQ ID No: 1148) |
| 241 | gcc cgt gCg gcg gag | (SEQ ID No: 1149) |
| 242 | g aag gag aCg ctg cag c | (SEQ ID No: 1150) |
| 243 | gcg agt ccA aga ggg ga | (SEQ ID No: 1151) |
| 244 | gct gtg gtC gct gtg gt | (SEQ ID No: 1152) |
| 245 | c ctg gag gAc ctg tgc g | (SEQ ID No: 1153) |
| 246 | a gct gtg gtT gct act gtg | (SEQ ID No: 1154) |

TABLE 7

Allele-Probe List 1

| Allele | 0 | 1 | 2 | 3 | 4 | 5 | 6 | 7 | 8 |
|---|---|---|---|---|---|---|---|---|---|
| B*070201 | 0 | 1 | 2 | 3 | 4 | 5 | 6 | 7 | 8 |
| B*070202 | 9 | | | | | | | | |
| B*070203 | 10 | | | | | | | | |
| B*0703 | 11 | | | | | | | | |
| B*0704 | 12 | | | | | | | | |
| B*0705 | 13 | 14 | | | | | | | |
| B*0706 | 13 | | | | | | | | |
| B*0707 | 15 | | | | | | | | |
| B*0708 | 16 | 17 | | | | | | | |
| B*0709 | 18 | | | | | | | | |
| B*0710 | 19 | | | | | | | | |
| B*0711 | 20 | 18 | | | | | | | |
| B*0712 | 21 | 22 | 23 | 24 | | | | | |
| B*0713 | 25 | 26 | 27 | | | | | | |
| B*0714 | 28 | 21 | 29 | 30 | | | | | |
| B*0715 | 31 | 27 | | | | | | | |
| B*0716 | 11 | 32 | | | | | | | |
| B*0717 | 30 | 33 | | | | | | | |
| B*0718 | 28 | 22 | | | | | | | |
| B*0719 | 12 | 34 | 35 | 36 | | | | | |
| B*0720 | 37 | 38 | | | | | | | |
| B*0721 | 39 | | | | | | | | |
| B*0722 | 40 | | | | | | | | |
| B*0723 | 41 | | | | | | | | |
| B*0724 | 42 | | | | | | | | |
| B*0725 | 43 | 44 | | | | | | | |
| B*0726 | 45 | | | | | | | | |
| B*0727 | 46 | 32 | 47 | 48 | | | | | |
| B*0728 | 30 | 49 | | | | | | | |
| B*0729 | 50 | 51 | | | | | | | |
| B*0730 | 52 | | | | | | | | |
| B*0731 | 53 | 34 | | | | | | | |
| B*0801 | 50 | 54 | | | | | | | |
| B*0802 | 50 | 55 | 54 | | | | | | |
| B*0803 | 56 | 57 | 58 | 13 | 43 | 44 | 53 | 34 | 59 |
| B*0804 | 50 | 46 | 13 | 44 | 53 | 59 | | | |
| B*0805 | 60 | | | | | | | | |
| B*0806 | 50 | 16 | 20 | 13 | 53 | 59 | | | |
| B*0807 | 50 | 16 | 44 | 53 | 59 | | | | |
| B*0809 | 50 | 61 | 13 | 44 | 53 | 59 | | | |
| B*0810 | 50 | 62 | 63 | 13 | 44 | 53 | 59 | | |
| B*0811 | 50 | 16 | 13 | 44 | 59 | | | | |
| B*0812 | 50 | 15 | 13 | 44 | 53 | 59 | | | |
| B*0813 | 50 | 16 | 64 | 53 | 59 | | | | |
| B*0814 | 50 | 65 | 44 | 53 | 59 | | | | |
| B*0815 | 66 | 44 | 34 | 59 | | | | | |
| B*0816 | 67 | 44 | 59 | | | | | | |
| B*0817 | 50 | 68 | 20 | 69 | | | | | |
| B*1301 | 21 | 70 | 54 | | | | | | |
| B*1302 | 71 | 70 | 54 | | | | | | |
| B*1303 | 55 | 61 | 72 | 43 | 64 | 37 | 54 | | |
| B*1304 | 73 | 18 | 64 | 74 | | | | | |
| B*1306 | 70 | 34 | | | | | | | |
| B*1308 | 75 | | | | | | | | |
| B*1309 | 71 | 61 | 72 | 70 | | | | | |
| B*1310 | 33 | 70 | | | | | | | |
| B*1311 | 70 | 69 | | | | | | | |

TABLE 7-continued

Allele-Probe List 1

| Allele | | | | | | | | | | | | | | |
|---|---|---|---|---|---|---|---|---|---|---|---|---|---|---|
| B*1401 | 76 | 77 | 78 | | | | | | | | | | | |
| B*1402 | 79 | 76 | 77 | 78 | | | | | | | | | | |
| B*1403 | 79 | 76 | 77 | | | | | | | | | | | |
| B*1404 | 80 | | | | | | | | | | | | | |
| B*1405 | 79 | 81 | 45 | 82 | 83 | | | | | | | | | |
| B*140601 | 79 | 81 | 15 | 45 | 82 | 83 | | | | | | | | |
| B*140602 | 79 | 81 | 84 | 45 | 82 | 83 | | | | | | | | |
| B*15010101 | 85 | 86 | 87 | 68 | 32 | 88 | 89 | 54 | | | | | | |
| B*150102 | 90 | 91 | 88 | 37 | 83 | | | | | | | | | |
| B*150103 | 92 | | | | | | | | | | | | | |
| B*150104 | 93 | 37 | | | | | | | | | | | | |
| B*1502 | 85 | 46 | 22 | 30 | 33 | 45 | 89 | 54 | | | | | | |
| B*1503 | 85 | 10 | 87 | 68 | 94 | 15 | 18 | 45 | 89 | 54 | | | | |
| B*1504 | 85 | 61 | 88 | 89 | 54 | | | | | | | | | |
| B*1505 | 15 | 43 | 64 | 37 | 89 | 95 | | | | | | | | |
| B*1506 | 96 | 45 | 95 | 54 | | | | | | | | | | |
| B*1507 | 86 | 87 | 68 | 32 | 88 | 54 | | | | | | | | |
| B*1508 | 85 | 16 | 32 | 88 | 89 | 54 | | | | | | | | |
| B*1509 | 85 | 97 | 45 | 89 | 54 | | | | | | | | | |
| B*1510 | 85 | 10 | 19 | 98 | 15 | 45 | 89 | 54 | | | | | | |
| B*151101 | 85 | 86 | 32 | 88 | 89 | 54 | | | | | | | | |
| B*151102 | 99 | | | | | | | | | | | | | |
| B*1512 | 100 | | | | | | | | | | | | | |
| B*1513 | 85 | 58 | 22 | 30 | 33 | 45 | 89 | 54 | | | | | | |
| B*1514 | 85 | 38 | 89 | 54 | | | | | | | | | | |
| B*1515 | 85 | 86 | 46 | 32 | 88 | 89 | 54 | | | | | | | |
| B*1516 | 101 | 54 | | | | | | | | | | | | |
| B*151701 | 102 | 65 | 89 | 95 | 54 | | | | | | | | | |
| B*1518 | 85 | 10 | 19 | 98 | 15 | 18 | 45 | 89 | 54 | | | | | |
| B*1519 | 103 | | | | | | | | | | | | | |
| B*1520 | 85 | 104 | 54 | | | | | | | | | | | |
| B*1521 | 85 | 19 | 22 | 30 | 33 | 45 | 89 | 54 | | | | | | |
| B*1523 | 85 | 19 | 98 | 58 | 15 | 18 | 45 | 89 | 54 | | | | | |
| B*1524 | 57 | 58 | 15 | 18 | 91 | 88 | 37 | 83 | | | | | | |
| B*1525 | 85 | 87 | 68 | 22 | 30 | 33 | 45 | 89 | 54 | | | | | |
| B*1527 | 96 | 88 | 37 | | | | | | | | | | | |
| B*1528 | 105 | | | | | | | | | | | | | |
| B*1529 | 85 | 16 | 17 | 15 | 18 | 45 | 89 | | | | | | | |
| B*1530 | 68 | 13 | 91 | 88 | 37 | | | | | | | | | |
| B*1531 | 106 | 15 | 30 | 33 | 43 | 64 | 37 | 83 | | | | | | |
| B*1532 | 107 | 88 | 37 | | | | | | | | | | | |
| B*1533 | 108 | | | | | | | | | | | | | |
| B*1534 | 68 | 109 | 18 | 91 | 88 | 37 | 83 | | | | | | | |
| B*1535 | 110 | 111 | 18 | 91 | 88 | 37 | 83 | | | | | | | |
| B*1536 | 112 | 30 | 33 | 45 | 42 | 37 | 113 | 83 | | | | | | |
| B*1537 | 10 | 19 | 32 | 114 | 45 | 37 | 82 | | | | | | | |
| B*1538 | 88 | 82 | 83 | | | | | | | | | | | |
| B*1539 | 115 | 106 | 87 | 68 | 94 | 15 | 18 | 45 | 37 | 83 | | | | |
| B*1540 | 115 | 106 | 87 | 68 | 94 | 15 | 18 | 45 | 83 | | | | | |
| B*1542 | 68 | 32 | 71 | 61 | 73 | 72 | 34 | 83 | | | | | | |
| B*1543 | 47 | 88 | 37 | 83 | | | | | | | | | | |
| B*1544 | 19 | 33 | 91 | 45 | 34 | 83 | | | | | | | | |
| B*1545 | 116 | 117 | 86 | 87 | 68 | 32 | 91 | 88 | 37 | 83 | | | | |
| B*1546 | 85 | 115 | 118 | 119 | 87 | 68 | 32 | 18 | 88 | 37 | 83 | | | |
| B*1547 | 10 | 87 | 68 | 94 | 32 | 15 | 18 | 114 | 91 | 83 | | | | |
| B*1548 | 68 | 13 | 120 | 121 | 122 | 83 | | | | | | | | |
| B*1549 | 123 | | | | | | | | | | | | | |
| B*1550 | 18 | 88 | 34 | 83 | | | | | | | | | | |
| B*1551 | 19 | 18 | 43 | 44 | 37 | 35 | 113 | 83 | | | | | | |
| B*1552 | 85 | 19 | 15 | 43 | 64 | 83 | | | | | | | | |
| B*1553 | 85 | 124 | 118 | 119 | 87 | 68 | 32 | 18 | 88 | 37 | 83 | | | |
| B*1554 | 85 | 10 | 87 | 68 | 32 | 88 | 89 | 54 | | | | | | |
| B*1555 | 85 | 43 | 64 | 89 | 54 | | | | | | | | | |
| B*1556 | 87 | 125 | 32 | 15 | 18 | 91 | 88 | 37 | 83 | | | | | |
| B*1557 | 126 | 127 | 37 | 113 | 83 | | | | | | | | | |
| B*1558 | 85 | 128 | 88 | 37 | 83 | | | | | | | | | |
| B*1560 | 129 | | | | | | | | | | | | | |
| B*1561 | 10 | 87 | 68 | 94 | 15 | 18 | 114 | 45 | 37 | 83 | | | | |
| B*1562 | 10 | 87 | 68 | 94 | 32 | 21 | 22 | 23 | 24 | 18 | 114 | 91 | 45 | 37 | 113 | 83 |
| B*1563 | 116 | 117 | 86 | 87 | 68 | 32 | 15 | 91 | 88 | 37 | 83 | | | |
| B*1564 | 10 | 46 | 94 | 32 | 15 | 18 | 114 | 45 | 37 | 83 | | | | |
| B*1565 | 116 | 115 | 106 | 87 | 68 | 94 | 32 | 15 | 18 | 91 | 37 | 83 | | |
| B*1566 | 85 | 130 | 32 | 88 | 89 | 54 | | | | | | | | |
| B*1567 | 131 | | | | | | | | | | | | | |
| B*1568 | 87 | 68 | 32 | 88 | 89 | | | | | | | | | |
| B*1569 | 68 | 18 | 45 | 120 | 132 | 83 | | | | | | | | |
| B*1570 | 116 | 117 | 86 | 87 | 68 | 94 | 15 | 18 | 91 | 88 | 37 | 83 | | |
| B*1571 | 133 | 86 | 87 | 68 | 32 | 15 | 88 | 89 | | | | | | |

TABLE 7-continued

Allele-Probe List 1

| Allele | | | | | | | | | | | | | | | |
|---|---|---|---|---|---|---|---|---|---|---|---|---|---|---|---|
| B*1572 | 10 | 19 | 18 | 45 | 37 | 134 | 89 | | | | | | | | |
| B*1573 | 72 | 88 | 37 | 83 | | | | | | | | | | | |
| B*1574 | 135 | | | | | | | | | | | | | | |
| B*1575 | 136 | | | | | | | | | | | | | | |
| B*180101 | 137 | 32 | 15 | 54 | | | | | | | | | | | |
| B*180102 | 138 | | | | | | | | | | | | | | |
| B*1802 | 137 | 139 | 54 | | | | | | | | | | | | |
| B*1803 | 137 | 15 | 54 | | | | | | | | | | | | |
| B*1804 | 140 | 137 | 46 | 32 | 15 | 43 | 64 | 82 | | | | | | | |
| B*1805 | 141 | | | | | | | | | | | | | | |
| B*1806 | 126 | 82 | 95 | 54 | | | | | | | | | | | |
| B*1807 | 137 | 16 | 32 | 15 | 43 | 64 | 82 | | | | | | | | |
| B*1808 | 142 | | | | | | | | | | | | | | |
| B*1809 | 137 | 55 | 15 | 43 | 64 | 82 | | | | | | | | | |
| B*1810 | 133 | 137 | 46 | 32 | 15 | 43 | 64 | | | | | | | | |
| B*1811 | 133 | 137 | 46 | 32 | 15 | 43 | 64 | 34 | | | | | | | |
| B*1812 | 137 | 87 | 68 | 32 | 15 | 43 | 64 | 82 | | | | | | | |
| B*1813 | 133 | 137 | 46 | 32 | 15 | 43 | 82 | | | | | | | | |
| B*1814 | 133 | 137 | 46 | 32 | 43 | 64 | 82 | | | | | | | | |
| B*1815 | 133 | 137 | 46 | 32 | 15 | 45 | 82 | | | | | | | | |
| B*1818 | 107 | 64 | 82 | | | | | | | | | | | | |
| B*2701 | 130 | 144 | 145 | 55 | 146 | 65 | 43 | 64 | 83 | | | | | | |
| B*2702 | 57 | 58 | 146 | 65 | 43 | 54 | | | | | | | | | |
| B*2703 | 147 | | | | | | | | | | | | | | |
| B*2704 | 65 | 148 | | | | | | | | | | | | | |
| B*270502 | 130 | 149 | 146 | 65 | 114 | 64 | 54 | | | | | | | | |
| B*270503 | 150 | | | | | | | | | | | | | | |
| B*270504 | 151 | 130 | 149 | 146 | 139 | 65 | 114 | 43 | 64 | 83 | | | | | |
| B*270505 | 152 | | | | | | | | | | | | | | |
| B*270506 | 153 | 114 | | | | | | | | | | | | | |
| B*2706 | 148 | | | | | | | | | | | | | | |
| B*2707 | 149 | 48 | 13 | 64 | 54 | | | | | | | | | | |
| B*2708 | 130 | 146 | 65 | 43 | 54 | | | | | | | | | | |
| B*2709 | 154 | | | | | | | | | | | | | | |
| B*2710 | 130 | 149 | 146 | 139 | 65 | 114 | 45 | 83 | | | | | | | |
| B*2711 | 155 | 48 | 13 | 43 | 64 | 54 | | | | | | | | | |
| B*2712 | 130 | 98 | 146 | 65 | 43 | 54 | | | | | | | | | |
| B*2713 | 130 | 149 | 146 | 65 | 114 | 64 | 54 | | | | | | | | |
| B*2714 | 149 | 73 | 65 | 114 | 43 | 64 | 83 | | | | | | | | |
| B*2715 | 146 | 65 | 34 | 83 | | | | | | | | | | | |
| B*2716 | 130 | 98 | 149 | 146 | 139 | 65 | 114 | 43 | 64 | 83 | | | | | |
| B*2717 | 156 | | | | | | | | | | | | | | |
| B*2718 | 133 | 124 | 68 | 94 | 32 | 146 | 65 | 114 | 45 | 83 | | | | | |
| B*2719 | 149 | 21 | 29 | 65 | 114 | 43 | 64 | 83 | | | | | | | |
| B*2720 | 146 | 13 | 45 | 83 | | | | | | | | | | | |
| B*2721 | 130 | 48 | 15 | 30 | 114 | 45 | 83 | | | | | | | | |
| B*2723 | 16 | 17 | 32 | 157 | 48 | 146 | 65 | 43 | 64 | 83 | | | | | |
| B*2724 | 48 | 158 | 83 | | | | | | | | | | | | |
| B*2725 | 146 | 37 | 83 | | | | | | | | | | | | |
| B*350101 | 16 | 17 | 21 | 22 | 18 | 114 | 43 | 64 | 37 | 104 | 54 | | | | |
| B*350102 | 159 | | | | | | | | | | | | | | |
| B*3502 | 160 | | | | | | | | | | | | | | |
| B*3503 | 161 | 114 | 43 | 64 | 37 | 104 | 54 | | | | | | | | |
| B*3504 | 24 | 13 | 114 | 43 | 64 | 37 | 104 | 54 | | | | | | | |
| B*3505 | 16 | 17 | 18 | 114 | 43 | 64 | 37 | 104 | 54 | | | | | | |
| B*3506 | 13 | 128 | 114 | 43 | 64 | 37 | 104 | 54 | | | | | | | |
| B*3507 | 162 | | | | | | | | | | | | | | |
| B*3508 | 16 | 17 | 21 | 22 | 18 | 114 | 43 | 37 | 104 | 54 | | | | | |
| B*350901 | 24 | 13 | 43 | 64 | 37 | 104 | 54 | | | | | | | | |
| B*350902 | 16 | 24 | 13 | 43 | 64 | 37 | 113 | 83 | | | | | | | |
| B*3510 | 87 | 125 | 17 | 32 | 21 | 22 | 23 | 24 | 18 | 114 | 163 | 43 | 64 | 37 | |
| B*3511 | 16 | 17 | 21 | 22 | 18 | 114 | 45 | 37 | 104 | 54 | | | | | |
| B*3512 | 13 | 114 | 43 | 64 | 37 | 104 | 54 | | | | | | | | |
| B*3513 | 87 | 125 | 32 | 24 | 161 | 114 | 163 | 43 | 64 | 37 | 113 | 83 | | | |
| B*3514 | 163 | 88 | 37 | 83 | | | | | | | | | | | |
| B*3515 | 16 | 17 | 21 | 22 | 18 | 114 | 43 | 64 | 104 | 54 | | | | | |
| B*3516 | 87 | 125 | 17 | 32 | 21 | 164 | 18 | 114 | 163 | 43 | 64 | 37 | 113 | 83 | |
| B*3517 | 165 | 166 | 16 | 17 | 32 | 21 | 164 | 18 | 114 | 163 | 43 | 64 | 37 | 113 | 83 |
| B*3518 | 16 | 17 | 21 | 24 | 13 | 43 | 37 | 113 | 83 | | | | | | |
| B*3519 | 119 | 16 | 17 | 32 | 21 | 22 | 23 | 24 | 18 | 114 | 163 | 43 | 64 | 37 | 113 | 83 |
| B*3520 | 167 | 166 | 46 | 94 | 32 | 21 | 22 | 23 | 24 | 18 | 114 | 163 | 43 | 64 | 37 | 113 | 83 |
| B*3521 | 18 | 114 | 163 | 45 | 37 | 82 | | | | | | | | | |
| B*3522 | 167 | 16 | 13 | 114 | 163 | 43 | 64 | 37 | 83 | | | | | | |
| B*3523 | 168 | 18 | 43 | 64 | 37 | 83 | | | | | | | | | |
| B*3524 | 18 | 43 | 64 | 37 | 82 | | | | | | | | | | |
| B*3525 | 10 | 16 | 17 | 32 | 21 | 22 | 23 | 24 | 18 | 114 | 163 | 43 | 64 | 37 | 113 | 83 |
| B*3526 | 81 | 42 | 37 | 83 | | | | | | | | | | | |
| B*3527 | 16 | 17 | 169 | 21 | 22 | 23 | 24 | 18 | 114 | 163 | 43 | 64 | 37 | 113 | 83 |

TABLE 7-continued

Allele-Probe List 1

| Allele | | | | | | | | | | | | | | | | |
|---|---|---|---|---|---|---|---|---|---|---|---|---|---|---|---|---|
| B*3528 | 167 | 166 | 87 | 68 | 94 | 32 | 21 | 22 | 23 | 24 | 18 | 114 | 163 | 43 | 64 | 37 | 113 |
| | 83 | | | | | | | | | | | | | | | |
| B*3529 | 165 | 166 | 16 | 17 | 21 | 22 | 23 | 24 | 18 | 114 | 163 | 43 | 64 | 37 | 113 | 83 |
| B*3530 | 165 | 166 | 16 | 17 | 32 | 21 | 170 | 24 | 18 | 114 | 163 | 43 | 64 | 37 | 113 | 83 |
| B*3531 | 151 | 165 | 16 | 17 | 32 | 13 | 43 | 64 | 54 | | | | | | | |
| B*3532 | 165 | 166 | 16 | 17 | 32 | 15 | 164 | 18 | 114 | 163 | 43 | 64 | 37 | 113 | 83 | |
| B*3533 | 16 | 32 | 24 | 161 | 114 | 163 | 43 | 64 | 113 | 83 | | | | | | |
| B*3534 | 165 | 166 | 16 | 17 | 32 | 21 | 22 | 23 | 24 | 114 | 163 | 43 | 64 | 37 | 113 | 83 |
| B*3535 | 18 | 43 | 64 | 120 | 132 | 83 | | | | | | | | | | |
| B*3536 | 171 | | | | | | | | | | | | | | | |
| B*3537 | 71 | 61 | 73 | 24 | 18 | 114 | 163 | 43 | 64 | 37 | 113 | 83 | | | | |
| B*3538 | 21 | 161 | 163 | 43 | 44 | 37 | 35 | 113 | 83 | | | | | | | |
| B*3539 | 165 | 166 | 16 | 17 | 32 | 28 | 29 | 114 | 163 | 43 | 64 | 37 | 83 | | | |
| B*3541 | 172 | | | | | | | | | | | | | | | |
| B*3542 | 155 | 104 | 95 | 54 | | | | | | | | | | | | |
| B*3543 | 167 | 16 | 32 | 15 | 88 | 54 | | | | | | | | | | |
| B*3544 | 16 | 13 | 91 | 88 | 37 | 83 | | | | | | | | | | |
| B*3545 | 21 | 24 | 18 | 163 | 43 | 37 | 38 | 83 | | | | | | | | |
| B*3701 | 173 | 54 | | | | | | | | | | | | | | |
| B*3702 | 32 | 47 | 146 | 65 | 114 | 64 | 54 | | | | | | | | | |
| B*3704 | 173 | 82 | 54 | | | | | | | | | | | | | |
| B*3705 | 173 | 44 | 34 | | | | | | | | | | | | | |
| B*3801 | 56 | 58 | 15 | 64 | 120 | 77 | 78 | | | | | | | | | |
| B*380201 | 144 | 55 | 15 | 64 | 120 | 77 | 78 | | | | | | | | | |
| B*380202 | 174 | | | | | | | | | | | | | | | |
| B*3803 | 81 | 68 | 175 | 55 | 15 | 13 | 128 | 64 | 120 | 132 | 83 | | | | | |
| B*3804 | 87 | 169 | 144 | 55 | 15 | 13 | 128 | 43 | 64 | 120 | 132 | 83 | | | | |
| B*3805 | 79 | 56 | 58 | 15 | 64 | 120 | 77 | | | | | | | | | |
| B*3806 | 16 | 56 | 58 | 15 | 13 | 128 | 43 | 64 | 120 | 132 | 83 | | | | | |
| B*3807 | 176 | | | | | | | | | | | | | | | |
| B*3808 | 81 | 177 | 178 | 83 | | | | | | | | | | | | |
| B*3809 | 179 | | | | | | | | | | | | | | | |
| B*390101 | 19 | 98 | 15 | 64 | 120 | 77 | 78 | | | | | | | | | |
| B*390103 | 19 | 77 | 54 | | | | | | | | | | | | | |
| B*390104 | 180 | | | | | | | | | | | | | | | |
| B*390201 | 68 | 77 | 54 | | | | | | | | | | | | | |
| B*390202 | 68 | 94 | 15 | 64 | 120 | 77 | 78 | | | | | | | | | |
| B*3903 | 19 | 98 | 64 | 120 | 77 | 78 | | | | | | | | | | |
| B*3904 | 116 | 19 | 98 | 15 | 64 | 120 | 77 | 78 | | | | | | | | |
| B*3905 | 32 | 15 | 64 | 120 | 77 | 78 | | | | | | | | | | |
| B*390601 | 71 | 181 | 64 | 120 | 77 | 78 | | | | | | | | | | |
| B*390602 | 71 | 61 | 64 | 120 | 77 | 78 | | | | | | | | | | |
| B*3907 | 81 | 18 | 64 | 120 | 132 | | | | | | | | | | | |
| B*3908 | 68 | 32 | 15 | 182 | 77 | 78 | | | | | | | | | | |
| B*3909 | 107 | 77 | 78 | | | | | | | | | | | | | |
| B*3910 | 11 | 15 | 64 | 120 | 77 | 78 | | | | | | | | | | |
| B*3911 | 81 | 19 | 32 | 15 | 182 | 89 | | | | | | | | | | |
| B*3912 | 183 | 113 | | | | | | | | | | | | | | |
| B*3913 | 68 | 32 | 15 | 13 | 128 | 43 | 64 | 120 | 132 | 83 | | | | | | |
| B*3914 | 81 | 19 | 98 | 13 | 64 | 120 | 132 | 83 | | | | | | | | |
| B*3915 | 81 | 19 | 98 | 15 | 161 | 64 | 120 | 132 | 83 | | | | | | | |
| B*3916 | 184 | | | | | | | | | | | | | | | |
| B*3917 | 185 | 120 | 132 | 83 | | | | | | | | | | | | |
| B*3918 | 81 | 88 | 186 | 132 | 83 | | | | | | | | | | | |
| B*3919 | 166 | 19 | 98 | 15 | 13 | 128 | 43 | 64 | 120 | 132 | 83 | | | | | |
| B*3920 | 169 | 15 | 13 | 128 | 43 | 64 | 120 | 132 | 83 | | | | | | | |
| B*3922 | 81 | 187 | 130 | 98 | 15 | 13 | 128 | 64 | 120 | 132 | 83 | | | | | |
| B*3923 | 188 | | | | | | | | | | | | | | | |
| B*3924 | 189 | | | | | | | | | | | | | | | |
| B*3926 | 190 | | | | | | | | | | | | | | | |
| B*3927 | 98 | 66 | 120 | 132 | 113 | 83 | | | | | | | | | | |
| B*400101 | 191 | | | | | | | | | | | | | | | |
| B*400102 | 133 | 124 | 118 | 192 | 119 | 87 | 68 | 32 | 15 | 13 | 193 | 194 | | | | |
| B*400103 | 133 | 124 | 118 | 192 | 87 | 68 | 32 | 15 | 13 | 193 | 194 | | | | | |
| B*4002 | 155 | 68 | 32 | 13 | 43 | 64 | 54 | | | | | | | | | |
| B*4003 | 155 | 87 | 68 | 32 | 18 | 43 | 64 | 54 | | | | | | | | |
| B*4004 | 155 | 23 | 13 | 43 | 64 | 54 | | | | | | | | | | |
| B*4005 | 155 | 13 | 45 | 37 | 54 | | | | | | | | | | | |
| B*400601 | 155 | 71 | 61 | 13 | 43 | 64 | 54 | | | | | | | | | |
| B*4007 | 125 | 32 | 15 | 13 | 193 | 194 | | | | | | | | | | |
| B*4008 | 155 | 16 | 32 | 13 | 43 | 64 | 54 | | | | | | | | | |
| B*4009 | 133 | 124 | 118 | 30 | 43 | 64 | 35 | 113 | 83 | | | | | | | |
| B*4010 | 115 | 118 | 192 | 119 | 87 | 68 | 32 | 15 | 13 | 193 | 194 | | | | | |
| B*4011 | 133 | 124 | 118 | 15 | 13 | 43 | 64 | 35 | 113 | 83 | | | | | | |
| B*4012 | 85 | 10 | 119 | 87 | 68 | 32 | 15 | 13 | 193 | 194 | | | | | | |
| B*4013 | 155 | 57 | 58 | 13 | 43 | 64 | | | | | | | | | | |
| B*401401 | 133 | 124 | 118 | 13 | 163 | 43 | 64 | | | | | | | | | |
| B*401402 | 133 | 124 | 118 | 13 | 196 | 43 | 64 | | | | | | | | | |

TABLE 7-continued

Allele-Probe List 1

| | | | | | | | | | | | | | |
|---|---|---|---|---|---|---|---|---|---|---|---|---|---|
| B*4015 | 197 | | | | | | | | | | | | |
| B*4016 | 133 | 198 | 124 | 118 | 119 | 87 | 68 | 32 | 13 | | | | |
| B*4018 | 133 | 124 | 118 | 68 | 43 | 64 | 35 | 113 | 83 | | | | |
| B*4019 | 118 | 68 | 94 | 56 | 13 | 43 | 64 | 113 | | | | | |
| B*4020 | 155 | 87 | 68 | 32 | 15 | 18 | 43 | 64 | | | | | |
| B*4021 | 117 | 86 | 87 | 68 | 32 | 15 | 13 | 193 | 194 | | | | |
| B*4023 | 133 | 124 | 118 | 192 | 119 | 87 | 68 | 32 | 15 | 13 | 158 | | |
| B*4024 | 133 | 118 | 119 | 87 | 68 | 94 | 32 | 170 | 24 | 43 | 64 | 113 | 83 |
| B*4025 | 133 | 124 | 118 | 192 | 119 | 46 | 32 | 15 | 13 | 193 | 194 | | |
| B*4026 | 118 | 87 | 68 | 32 | 97 | 45 | 37 | | | | | | |
| B*4027 | 199 | | | | | | | | | | | | |
| B*4028 | 23 | 97 | 45 | 37 | 82 | | | | | | | | |
| B*4029 | 200 | 13 | | | | | | | | | | | |
| B*4030 | 201 | 193 | 64 | | | | | | | | | | |
| B*4031 | 133 | 124 | 118 | 192 | 119 | 87 | 68 | 32 | 193 | 194 | | | |
| B*4032 | 133 | 198 | 124 | 118 | 119 | 87 | 68 | 32 | | | | | |
| B*4033 | 133 | 124 | 118 | 192 | 119 | 87 | 68 | 32 | 15 | 193 | 194 | | |
| B*4034 | 202 | | | | | | | | | | | | |
| B*4035 | 133 | 124 | 118 | 13 | 114 | 43 | 64 | 35 | 113 | 83 | | | |
| B*4036 | 15 | 128 | 193 | 194 | | | | | | | | | |
| B*4037 | 133 | 124 | 118 | 68 | 169 | 13 | 43 | 64 | 35 | 113 | 83 | | |
| B*4038 | 203 | 193 | 194 | | | | | | | | | | |
| B*4039 | 155 | 13 | 64 | 34 | 69 | | | | | | | | |
| B*4040 | 124 | 118 | 68 | 13 | 43 | 64 | 35 | 113 | 83 | | | | |
| B*4042 | 30 | 193 | 194 | | | | | | | | | | |
| B*4043 | 133 | 124 | 118 | 192 | 119 | 87 | 68 | 15 | 13 | 193 | 194 | | |
| B*4044 | 124 | 118 | 68 | 32 | 71 | 61 | 43 | 64 | 113 | | | | |
| B*4101 | 204 | 205 | 44 | 34 | 54 | | | | | | | | |
| B*4102 | 119 | 32 | 44 | 34 | 54 | | | | | | | | |
| B*4103 | 183 | 44 | | | | | | | | | | | |
| B*4104 | 24 | 43 | 44 | 53 | 34 | 59 | | | | | | | |
| B*4105 | 206 | | | | | | | | | | | | |
| B*4106 | 204 | 44 | 34 | 207 | 208 | | | | | | | | |
| B*4201 | 44 | 34 | 54 | | | | | | | | | | |
| B*4202 | 133 | 13 | 43 | 44 | 53 | 34 | 59 | | | | | | |
| B*4204 | 71 | 61 | 13 | 43 | 44 | 53 | 34 | 59 | | | | | |
| B*440201 | 118 | 55 | 44 | 37 | 209 | 54 | | | | | | | |
| B*440202 | 210 | 55 | 44 | 37 | 209 | | | | | | | | |
| B*440203 | 211 | | | | | | | | | | | | |
| B*440301 | 118 | 64 | 37 | 209 | 54 | | | | | | | | |
| B*440302 | 118 | 22 | 64 | 37 | 209 | 54 | | | | | | | |
| B*4404 | 34 | 209 | 54 | | | | | | | | | | |
| B*4405 | 87 | 144 | 212 | 55 | 21 | 30 | 44 | 37 | 38 | 83 | | | |
| B*4406 | 213 | 44 | 38 | | | | | | | | | | |
| B*4407 | 22 | 64 | 37 | 209 | 54 | | | | | | | | |
| B*4408 | 117 | 55 | 44 | 37 | 209 | 54 | | | | | | | |
| B*4409 | 118 | 44 | 37 | 209 | 54 | | | | | | | | |
| B*4410 | 168 | 64 | 38 | 83 | | | | | | | | | |
| B*4411 | 116 | 118 | 119 | 87 | 144 | 214 | 21 | 30 | 49 | 44 | 37 | 38 | 83 |
| B*4412 | 116 | 118 | 119 | 144 | 212 | 55 | 21 | 30 | 49 | 44 | 37 | 38 | 83 |
| B*4413 | 215 | | | | | | | | | | | | |
| B*4414 | 13 | 216 | 44 | 37 | 38 | 83 | | | | | | | |
| B*4415 | 175 | 55 | 30 | 185 | 44 | 38 | 83 | | | | | | |
| B*4416 | 116 | 118 | 119 | 87 | 112 | 212 | 21 | 30 | 49 | 44 | 113 | 83 | |
| B*4417 | 18 | 44 | 37 | 38 | 83 | | | | | | | | |
| B*4418 | 56 | 58 | 30 | 185 | 44 | 38 | 83 | | | | | | |
| B*4420 | 61 | 30 | 49 | 44 | 37 | 38 | 83 | | | | | | |
| B*4421 | 116 | 118 | 119 | 87 | 144 | 212 | 55 | 21 | 30 | 49 | 44 | 217 | 83 |
| B*4422 | 118 | 119 | 87 | 144 | 212 | 55 | 21 | 30 | 49 | 44 | 37 | 38 | 83 |
| B*4424 | 218 | 38 | 83 | | | | | | | | | | |
| B*4425 | 68 | 56 | 219 | 58 | 21 | 30 | 44 | 37 | 38 | 83 | | | |
| B*4426 | 220 | | | | | | | | | | | | |
| B*4427 | 118 | 55 | 49 | 44 | 37 | 38 | 89 | | | | | | |
| B*4428 | 118 | 21 | 22 | 30 | 49 | 163 | 43 | 37 | 38 | 83 | | | |
| B*4429 | 120 | 38 | 83 | | | | | | | | | | |
| B*4430 | 221 | | | | | | | | | | | | |
| B*4431 | 193 | 217 | | | | | | | | | | | |
| B*4432 | 200 | 38 | | | | | | | | | | | |
| B*4433 | 222 | | | | | | | | | | | | |
| B*4501 | 30 | 185 | 44 | 38 | 89 | 95 | 54 | | | | | | |
| B*4502 | 32 | 30 | 223 | 44 | 37 | 38 | 83 | | | | | | |
| B*4503 | 224 | | | | | | | | | | | | |
| B*4504 | 30 | 185 | 44 | 89 | 95 | 54 | | | | | | | |
| B*4505 | 225 | | | | | | | | | | | | |
| B*4506 | 30 | 185 | 44 | 38 | 83 | | | | | | | | |
| B*4601 | 226 | 54 | | | | | | | | | | | |
| B*4602 | 227 | | | | | | | | | | | | |
| B*470101 | 228 | | | | | | | | | | | | |

TABLE 7-continued

Allele-Probe List 1

| Allele | | | | | | | | | | | | | | |
|---|---|---|---|---|---|---|---|---|---|---|---|---|---|---|
| B*4702 | 96 | 43 | 64 | 69 | | | | | | | | | | |
| B*4703 | 229 | 96 | 65 | 43 | 64 | 83 | | | | | | | | |
| B*4704 | 94 | 144 | 145 | 55 | 146 | 65 | 43 | 64 | 83 | | | | | |
| B*4801 | 32 | 230 | | | | | | | | | | | | |
| B*4802 | 68 | 94 | 21 | 22 | 18 | 114 | 43 | 64 | 37 | 104 | 54 | | | |
| B*4803 | 87 | 68 | 32 | 15 | 13 | 193 | 194 | | | | | | | |
| B*4804 | 83 | 230 | | | | | | | | | | | | |
| B*4805 | 231 | 87 | 68 | 32 | 13 | | | | | | | | | |
| B*4806 | 16 | 32 | 13 | 193 | 194 | | | | | | | | | |
| B*4807 | 128 | 193 | 194 | | | | | | | | | | | |
| B*4901 | 58 | 185 | 45 | 89 | 95 | 54 | | | | | | | | |
| B*4902 | 144 | 55 | 185 | 45 | 89 | | | | | | | | | |
| B*4903 | 165 | 56 | 58 | 23 | 30 | 185 | 45 | 37 | 83 | | | | | |
| B*5001 | 185 | 45 | 89 | 95 | 54 | | | | | | | | | |
| B*5002 | 185 | 45 | 38 | 89 | 95 | 54 | | | | | | | | |
| B*5004 | 118 | 30 | 185 | 45 | 37 | 83 | | | | | | | | |
| B*510101 | 213 | 16 | 58 | 71 | 45 | 82 | 104 | 54 | | | | | | |
| B*510102 | 16 | 58 | 71 | 45 | 82 | 104 | 54 | | | | | | | |
| B*510103 | 213 | 16 | 58 | 71 | 61 | 97 | 114 | 45 | 37 | 82 | | | | |
| B*510104 | 213 | 166 | 16 | 58 | 71 | 61 | 13 | 114 | 45 | 37 | 82 | | | |
| B*510105 | 134 | 104 | 54 | | | | | | | | | | | |
| B*510201 | 213 | 16 | 58 | 71 | 97 | 114 | 45 | 37 | 104 | 54 | | | | |
| B*510202 | 16 | 58 | 71 | 97 | 114 | 45 | 37 | 104 | 54 | | | | | |
| B*5103 | 233 | 104 | | | | | | | | | | | | |
| B*5104 | 21 | 45 | 82 | 104 | 54 | | | | | | | | | |
| B*5105 | 58 | 97 | 114 | 43 | 37 | 104 | | | | | | | | |
| B*5106 | 213 | 166 | 16 | 58 | 97 | 114 | 45 | 37 | 82 | | | | | |
| B*5107 | 213 | 167 | 46 | 58 | 71 | 61 | 97 | 114 | 45 | 37 | 82 | | | |
| B*5108 | 44 | 82 | 104 | 54 | | | | | | | | | | |
| B*5109 | 213 | 43 | 64 | 37 | 82 | | | | | | | | | |
| B*5110 | 58 | 71 | 61 | 13 | 43 | 64 | 104 | | | | | | | |
| B*5112 | 234 | | | | | | | | | | | | | |
| B*511301 | 213 | 128 | 114 | 45 | 37 | 82 | | | | | | | | |
| B*511302 | 213 | 128 | 235 | 114 | 45 | 37 | 82 | | | | | | | |
| B*5114 | 236 | | | | | | | | | | | | | |
| B*5115 | 56 | 58 | 71 | 61 | 73 | 72 | 43 | 64 | 37 | 83 | | | | |
| B*5116 | 213 | 166 | 16 | 58 | 71 | 61 | 97 | 114 | 45 | 82 | | | | |
| B*5117 | 237 | | | | | | | | | | | | | |
| B*5118 | 238 | | | | | | | | | | | | | |
| B*5119 | 213 | 120 | 122 | 82 | | | | | | | | | | |
| B*5120 | 213 | 44 | 37 | 82 | | | | | | | | | | |
| B*5121 | 213 | 97 | 34 | 82 | | | | | | | | | | |
| B*5122 | 213 | 19 | 58 | 71 | 61 | 97 | 114 | 45 | 37 | 82 | | | | |
| B*5123 | 213 | 45 | 38 | | | | | | | | | | | |
| B*5124 | 213 | 166 | 16 | 58 | 71 | 61 | 13 | 45 | 37 | 82 | | | | |
| B*5126 | 239 | | | | | | | | | | | | | |
| B*5128 | 240 | | | | | | | | | | | | | |
| B*5129 | 213 | 16 | 58 | 71 | 82 | 104 | | | | | | | | |
| B*5130 | 104 | 241 | | | | | | | | | | | | |
| B*5131 | 213 | 97 | 43 | 64 | 82 | | | | | | | | | |
| B*5132 | 242 | | | | | | | | | | | | | |
| B*5133 | 213 | 166 | 16 | 58 | 71 | 61 | 97 | 114 | 45 | 37 | 82 | | | |
| B*5134 | 213 | 166 | 16 | 58 | 71 | 61 | 97 | 114 | 163 | 45 | | | | |
| B*520101 | 68 | 58 | 71 | 45 | 82 | 104 | 54 | | | | | | | |
| B*520102 | 213 | 68 | 58 | 71 | 45 | 82 | 104 | 54 | | | | | | |
| B*520103 | 167 | 87 | 68 | 58 | 71 | 61 | 97 | 45 | 37 | 82 | | | | |
| B*520104 | 243 | | | | | | | | | | | | | |
| B*5202 | 213 | 106 | 87 | 68 | 58 | 71 | 61 | 97 | 114 | 45 | 37 | 82 | | |
| B*5203 | 213 | 68 | 43 | 64 | 37 | | | | | | | | | |
| B*5204 | 244 | | | | | | | | | | | | | |
| B*5205 | 245 | | | | | | | | | | | | | |
| B*5301 | 17 | 58 | 21 | 22 | 18 | 114 | 43 | 64 | 37 | 104 | 54 | | | |
| B*5302 | 58 | 18 | 43 | 64 | 37 | 82 | | | | | | | | |
| B*5303 | 47 | 64 | 37 | 83 | | | | | | | | | | |
| B*5304 | 56 | 58 | 24 | 161 | 114 | 163 | 43 | 64 | 37 | 113 | 83 | | | |
| B*5305 | 17 | 246 | 247 | 58 | 21 | 22 | 23 | 24 | 18 | 114 | 163 | 43 | 64 | 37 | 113 | 83 |
| B*5306 | 213 | 18 | 114 | 45 | 37 | 82 | | | | | | | | |
| B*5307 | 173 | 64 | 37 | | | | | | | | | | | |
| B*5308 | 17 | 169 | 56 | 57 | 58 | 21 | 22 | 23 | 24 | 18 | 114 | 163 | 45 | 37 | 113 | 83 |
| B*5309 | 112 | 18 | 163 | 43 | 64 | 42 | 37 | 113 | 83 | | | | | |
| B*5401 | 93 | 54 | | | | | | | | | | | | |
| B*5402 | 133 | 93 | 34 | | | | | | | | | | | |
| B*5501 | 72 | 34 | 95 | 54 | | | | | | | | | | |
| B*5502 | 72 | 43 | 34 | 95 | 54 | | | | | | | | | |
| B*5503 | 248 | 72 | 34 | 113 | 83 | | | | | | | | | |
| B*5504 | 116 | 115 | 10 | 13 | 249 | 43 | 64 | 34 | 35 | 113 | 83 | | | |
| B*5505 | 250 | | | | | | | | | | | | | |
| B*5507 | 116 | 251 | 72 | 83 | | | | | | | | | | |

TABLE 7-continued

Allele-Probe List 1

| | | | | | | | | | | | | | |
|---|---|---|---|---|---|---|---|---|---|---|---|---|---|
| B*5508 | 115 | 10 | 15 | 13 | 249 | 43 | 64 | 37 | 83 | | | | |
| B*5509 | 116 | 115 | 10 | 71 | 61 | 73 | 72 | 163 | 83 | | | | |
| B*5510 | 71 | 61 | 73 | 72 | 43 | 34 | 83 | | | | | | |
| B*5511 | 252 | 34 | 83 | | | | | | | | | | |
| B*5512 | 20 | 72 | 43 | 34 | 95 | 54 | | | | | | | |
| B*5601 | 61 | 72 | 43 | 64 | 37 | 95 | 54 | | | | | | |
| B*5602 | 72 | 43 | 64 | 37 | 95 | 54 | | | | | | | |
| B*5603 | 253 | 254 | 115 | 15 | 88 | 54 | | | | | | | |
| B*5604 | 115 | 10 | 72 | 43 | 64 | 37 | 83 | | | | | | |
| B*5605 | 213 | 10 | 71 | 61 | 97 | 114 | 45 | 37 | 82 | | | | |
| B*5606 | 213 | 167 | 166 | 71 | 61 | 97 | 114 | 45 | 37 | 82 | | | |
| B*5607 | 10 | 144 | 55 | 71 | 61 | 73 | 72 | 43 | 64 | 37 | 83 | | |
| B*5608 | 255 | 64 | 37 | 83 | | | | | | | | | |
| B*5609 | 115 | 10 | 21 | 22 | 23 | 24 | 18 | 114 | 163 | 43 | 64 | 37 | 113 | 83 |
| B*5610 | 116 | 115 | 10 | 109 | 72 | 43 | 34 | 83 | | | | | |
| B*5611 | 253 | 24 | 161 | 163 | 43 | 64 | 37 | 69 | | | | | |
| B*570101 | 256 | 18 | 64 | 74 | | | | | | | | | |
| B*570102 | 257 | | | | | | | | | | | | |
| B*5702 | 13 | 74 | | | | | | | | | | | |
| B*570301 | 13 | 64 | 74 | | | | | | | | | | |
| B*570302 | 258 | | | | | | | | | | | | |
| B*5704 | 201 | 49 | 43 | 83 | | | | | | | | | |
| B*5705 | 259 | 30 | 260 | 43 | 37 | | | | | | | | |
| B*5706 | 261 | | | | | | | | | | | | |
| B*5707 | 201 | 38 | 83 | | | | | | | | | | |
| B*5708 | 262 | | | | | | | | | | | | |
| B*5709 | 201 | 12 | 83 | | | | | | | | | | |
| B*5801 | 259 | 21 | 95 | 54 | | | | | | | | | |
| B*5802 | 76 | 54 | | | | | | | | | | | |
| B*5804 | 263 | | | | | | | | | | | | |
| B*5805 | 264 | | | | | | | | | | | | |
| B*5806 | 76 | 37 | | | | | | | | | | | |
| B*5807 | 76 | 38 | | | | | | | | | | | |
| B*5901 | 58 | 72 | 43 | 34 | 95 | 54 | | | | | | | |
| B*670101 | 81 | 15 | 64 | 120 | 77 | 78 | | | | | | | |
| B*670102 | 15 | 13 | 128 | 43 | 64 | 120 | 132 | 113 | | | | | |
| B*6702 | 265 | | | | | | | | | | | | |
| B*7301 | 266 | | | | | | | | | | | | |
| B*7801 | 213 | 16 | 71 | 45 | 82 | 104 | 54 | | | | | | |
| B*780201 | 16 | 32 | 71 | 45 | 82 | 104 | 54 | | | | | | |
| B*780202 | 213 | 166 | 16 | 32 | 71 | 61 | 97 | 114 | 45 | 37 | 82 | | |
| B*7803 | 213 | 19 | 98 | 71 | 61 | 97 | 114 | 45 | 37 | 82 | | | |
| B*7804 | 97 | 114 | 43 | 64 | 37 | 104 | | | | | | | |
| B*7805 | 167 | 165 | 87 | 68 | 32 | 71 | 61 | 97 | 45 | 37 | 82 | | |
| B*8101 | 267 | | | | | | | | | | | | |
| B*8201 | 268 | | | | | | | | | | | | |
| B*8202 | 269 | | | | | | | | | | | | |
| B*8301 | 151 | 116 | 21 | 30 | 49 | 44 | 37 | 38 | 83 | | | | |

TABLE 8

Allele-Probe List 2

B*070201 0 1 2 3 4 5 6 7 8
B*070202 9
B*070203 10
B*0703 11
B*0704 12
B*0705 13 14
B*0706 13
B*0707 15
B*0708 16 11
B*0709 17
B*0710 18
B*0711 19 17
B*0712 20 21 22 23
B*0713 24 25 26
B*0714 27 20 28 29
B*0715 25 26
B*0716 30 31
B*0717 29 17
B*0718 27 21
B*0719 12 32 33 34
B*0720 35 36
B*0721 37
B*0722 38
B*0723 39
B*0724 40
B*0725 41 12
B*0726 42
B*0727 43 44 45 46
B*0728 29 47
B*0729 48 49
B*0730 50
B*0731 51 32
B*0801 48 52
B*0802 48 53 52
B*0803 54 55 56 13 41 12 51 32 57
B*0804 48 43 13 12 51 57
B*0805 58
B*0806 48 16 19 13 51 57
B*0807 48 16 12 51 57
B*0809 48 59 13 12 51 57
B*0810 48 60 16 13 12 51 57
B*0811 48 16 13 12 51 57
B*0812 48 15 13 12 51 57
B*0813 48 16 42 51 57

TABLE 8-continued

Allele-Probe List 2

B*0814 48 61 12 51 57
B*0815 26 12 32 57
B*0816 62 12 57
B*0817 48 43 19 63
B*1301 20 64 52
B*1302 65 64 52
B*1303 53 59 66 41 42 35 52
B*1304 67 17 42 68
B*1306 64 32
B*1308 69
B*1309 65 59 66 64
B*1310 17 64
B*1311 64 63
B*1401 70 71 72
B*1402 73 70 71 72
B*1403 73 70 71
B*1404 74
B*1405 73 75 42 76 77
B*140601 73 75 15 42 76 77
B*140602 73 75 21 42 76 77
B*15010101 78 79 80 43 31 81 82 52
B*150102 83 84 81 35
B*150103 85
B*150104 86 35
B*1502 78 43 21 29 17 42 82 52
B*1503 78 10 80 43 30 15 17 42 82 52
B*1504 78 59 81 82 52
B*1505 15 41 42 35 82 87
B*1506 88 42 87 52
B*1507 79 80 43 31 81 52
B*1508 78 16 31 81 82 52
B*1509 78 83 42 82 52
B*1510 78 10 89 30 15 42 82 52
B*151101 78 79 31 81 82 52
B*151102 90
B*1512 91
B*1513 78 56 21 29 17 42 82 52
B*1514 78 36 82 52
B*1515 78 79 43 31 81 82 52
B*1516 92 52
B*151701 93 61 82 87 52
B*1518 78 10 89 30 15 17 42 82 52
B*1519 94
B*1520 78 95 52
B*1521 78 89 21 29 17 42 82 52
B*1523 78 89 30 56 15 17 42 82 52
B*1524 55 56 15 17 84 81 35
B*1525 78 80 43 21 29 17 42 82 52
B*1527 88 81 35
B*1528 96
B*1529 78 16 30 15 17 42 82
B*1530 43 13 84 81 35
B*1531 97 15 29 17 41 42 35 77
B*1532 98 81 35
B*1533 99
B*1534 43 67 17 84 81 35
B*1535 100 101 17 84 81 35
B*1536 102 29 17 42 40 35 77
B*1537 10 89 31 103 42 35 76
B*1538 81 76
B*1539 104 97 80 43 30 15 17 42 35 77
B*1540 104 97 80 43 30 15 17 42 77
B*1542 43 31 65 59 67 66 32
B*1543 45 81 35 77
B*1544 89 17 84 42 32 77
B*1545 49 105 79 80 43 31 84 81 35
B*1546 78 104 106 79 80 43 31 17 81 35 77
B*1547 10 80 43 30 31 15 17 103 84 77
B*1548 43 13 107 40 35 77
B*1549 108
B*1550 17 81 32
B*1551 89 17 41 12 35 109 77
B*1552 78 89 15 41 42 77
B*1553 78 110 106 79 80 43 31 17 81 35 77
B*1554 78 10 80 43 31 81 82 52
B*1555 78 41 42 82 52
B*1556 80 16 31 15 17 84 81 35
B*1557 111 112 35 77
B*1558 78 113 81 35 77
B*1560 114
B*1561 10 80 43 11 15 17 103 42 35 77
B*1562 10 80 43 30 31 20 21 22 23 17 103 84 42 35 1
B*1563 49 105 79 80 43 31 15 84 81 35
B*1564 10 43 30 31 15 17 103 42 35 77
B*1565 49 104 97 80 43 30 31 15 17 84 35 77
B*1566 78 89 31 81 82 52
B*1567 115
B*1568 80 43 31 81 82
B*1569 43 17 116 107 32 77
B*1570 49 105 79 80 43 11 15 17 84 81 35
B*1571 117 79 80 43 31 15 81 82
B*1572 10 89 17 42 35 118 82
B*1573 66 81 35
B*1574 119
B*1575 120
B*180101 121 31 15 52
B*180102 122
B*1802 121 123 52
B*1803 121 15 52
B*1804 124 121 43 31 15 41 42 76
B*1805 125
B*1806 126 76 87 52
B*1807 121 16 31 15 41 42 76
B*1808 127
B*1809 121 53 15 41 42 76
B*1810 117 121 43 31 15 41 42
B*1811 117 121 43 31 15 41 42 32
B*1812 121 80 43 31 15 41 42 76
B*1813 117 121 43 31 41 76
B*1814 117 121 43 31 41 42 76
B*1815 117 121 43 31 15 42 76
B*1818 98 42 76
B*2701 129 130 131 53 132 61 41 42 77
B*2702 55 56 132 61 41 52
B*2703 133
B*2704 61 134
B*270502 129 45 132 61 103 42 52
B*270503 135
B*270504 136 129 45 132 123 61 103 41 42 77
B*270505 137
B*270506 138 103
B*2706 134
B*2707 45 46 13 42 52
B*2708 129 132 61 41 52
B*2709 139
B*2710 129 45 132 123 61 103 42 77
B*2711 140 46 13 41 42 52
B*2712 89 11 132 61 41 52
B*2713 141
B*2714 45 67 61 103 41 42 77
B*2715 132 61 32 77
B*2716 89 11 45 132 123 61 103 41 42 77
B*2717 142
B*2718 117 110 43 30 31 132 61 103 42 77
B*2719 45 20 28 61 103 41 42 77
B*2720 143 13 42 77
B*2721 129 46 15 29 103 42 77
B*2723 16 30 31 144 46 132 61 41 42 77
B*2724 46 145 77
B*2725 132 35 77
B*350101 16 30 20 21 17 103 41 42 35 95 52
B*350102 146
B*3502 147
B*3503 148 103 41 42 35 95 52
B*3504 23 13 103 41 42 35 95 52
B*3505 16 30 17 103 41 42 35 95 52
B*3506 149 113 103 41 42 35 95 52
B*3507 150
B*3508 16 30 20 21 17 103 41 35 95 52
B*350901 23 13 41 42 35 95 52
B*350902 16 23 13 41 42 35 77
B*3510 80 16 30 31 20 21 22 23 17 103 151 41 42 35
B*3511 16 30 20 21 17 103 42 35 95 52
B*3512 13 103 41 42 35 95 52
B*3513 80 16 31 23 148 103 151 41 42 35 77
B*3514 151 81 35

TABLE 8-continued

Allele-Probe List 2

B*3515 16 30 20 21 17 103 41 42 95 52
B*3516 80 16 30 31 152 153 17 103 151 41 42 35 77
B*3517 154 79 16 30 31 152 153 17 103 151 41 42 35 77
B*3518 16 30 20 23 13 41 35 77
B*3519 79 16 30 31 20 21 22 23 17 103 151 41 42 35 77
B*3520 155 79 43 30 31 20 21 22 23 17 103 151 41 42 35 77
B*3521 17 103 151 42 35 76
B*3522 155 16 13 103 151 41 42 35 77
B*3523 88 17 41 42 35
B*3524 17 41 42 35 76
B*3525 10 16 30 31 20 21 22 23 17 103 151 41 42 35 77
B*3526 75 40 35 77
B*3527 16 30 19 20 21 22 23 17 103 151 41 42 35 77
B*3528 155 79 80 43 30 31 20 21 22 23 17 103 151 41 42 35 77
B*3529 154 79 16 11 20 21 22 23 17 103 151 41 42 35 77
B*3530 154 79 16 30 31 152 22 23 17 103 151 41 42 35 77
B*3531 136 154 16 30 31 13 41 42 52
B*3532 154 79 16 30 31 15 153 17 103 151 41 42 35 77
B*3533 16 31 23 148 103 151 41 42 77
B*3534 154 79 16 30 31 20 21 22 23 103 151 41 42 35 77
B*3535 17 41 116 107 32 77
B*3536 156
B*3537 65 59 22 23 17 103 151 41 42 35 77
B*3538 20 148 151 41 12 35 109 77
B*3539 154 79 16 30 31 27 28 103 151 41 42 35 77
B*3541 157
B*3542 140 95 87
B*3543 155 16 31 15 81 52
B*3544 16 13 84 81 35
B*3545 20 23 17 151 41 35 36 77
B*3701 98 52
B*3702 44 45 132 61 103 42 52
B*3704 98 76 52
B*3705 98 12 32
B*3801 54 56 15 116 107 71 72
B*380201 130 53 15 116 107 71 72
B*380202 158
B*3803 75 43 130 53 15 149 113 116 107 32 77
B*3804 80 159 130 53 15 149 113 41 116 107 32 77
B*3805 73 54 56 15 116 107 71
B*3806 16 54 56 15 149 113 41 116 107 32 77
B*3807 160
B*3808 75 161 162 77
B*3809 163
B*390101 89 11 15 116 107 71 72
B*390103 89 71 52
B*390104 164
B*390201 43 71 52
B*390202 43 11 15 116 107 71 72
B*3903 89 11 116 107 71 72
B*3904 49 89 11 15 116 107 71 72
B*3905 31 15 116 107 71 72
B*390601 165 166 116 107 71 72
B*390602 65 59 116 107 71 72
B*3907 75 17 116 107 32
B*3908 43 31 15 167 71 72
B*3909 98 71 72
B*3910 11 15 116 107 71 72
B*3911 75 89 31 15 167 82
B*3912 168 77
B*3913 43 31 15 149 113 41 116 107 32 77
B*3914 75 89 11 13 116 107 32 77
B*3915 75 89 11 15 148 116 107 32 77
B*3916 169
B*3917 66 107 32
B*3918 75 170 171 32 77
B*3919 79 89 11 15 149 113 41 116 107 32 77
B*3920 19 15 149 113 41 116 107 32 77
B*3922 75 80 89 11 15 149 113 116 107 32 77
B*3923 172
B*3924 173
B*3926 174
B*3927 11 26 107 32 77
B*400101 175
B*400102 176 177 110 106 178 79 80 43 31 15 13 179 41
B*400103 177 110 106 178 80 43 31 15 13 179 41
B*4002 140 43 31 13 41 42 52
B*4003 140 80 43 31 17 41 42 52
B*4004 140 67 13 41 42 52
B*4005 140 13 42 35 52
B*400601 140 65 59 13 41 42 52
B*4007 16 31 15 13 179 41
B*4008 140 16 31 13 41 42 52
B*4009 117 110 106 29 41 42 109 77
B*4010 104 106 178 79 80 43 31 15 13 179 41
B*4011 117 110 106 15 13 41 42 109 77
B*4012 78 10 79 80 43 31 15 13 179 41
B*4013 140 55 56 13 41 42
B*401401 177 110 106 13 151 41 42
B*401402 177 110 106 13 84 41 42
B*4015 181
B*4016 176 43 30 31 13
B*4018 117 110 106 43 41 42 109 77
B*4019 106 43 30 54 13 41 42 77
B*4020 140 80 43 31 15 17 41 42
B*4021 105 79 80 43 31 15 13 179 41
B*4023 176 177 110 106 178 79 80 43 31 15 13 145
B*4024 117 106 79 80 43 30 31 22 23 41 42 77
B*4025 177 110 106 178 79 43 31 15 13 179 41
B*4026 106 80 43 31 83 42 35
B*4027 182
B*4028 67 83 42 35 76
B*4029 183 13
B*4030 184 179 42
B*4031 177 110 106 178 79 80 43 31 179 41
B*4032 177 49 110 106 79 80 43 31
B*4033 177 110 106 178 79 80 43 31 15 179 41
B*4034 185
B*4035 117 110 106 13 103 41 42 109 77
B*4036 15 113 179 41
B*4037 117 110 106 43 19 13 41 42 109 77
B*4038 186 179 41
B*4039 140 13 42 32 63
B*4040 110 106 43 13 41 42 109 77
B*4042 29 179 41
B*4043 177 110 106 178 79 80 43 15 13 179 41
B*4044 110 106 43 31 65 59 41 42 77
B*4101 176 21 12 32 52
B*4102 176 12 32 52
B*4103 168 12
B*4104 23 41 12 51 32 57
B*4105 187
B*4106 188 12 32 189
B*4201 12 32 52
B*4202 117 13 41 12 51 32 57
B*4204 65 59 13 41 12 51 32 57
B*440201 106 53 12 35 190 52
B*440202 191 53 12 35 190
B*440203 192
B*440301 106 42 35 190 52
B*440302 106 21 42 35 190 52
B*4404 32 190 52
B*4405 80 130 193 53 20 29 12 35 36 77
B*4406 194 12 36
B*4407 21 42 35 190 52
B*4408 105 53 12 35 190 52
B*4409 106 12 35 190 52
B*4410 88 42 36
B*4411 49 106 79 80 195 196 20 29 47 12 35 36 77
B*4412 49 106 79 130 193 53 20 29 47 12 35 36 77
B*4413 197
B*4414 198 199 12 35 36 77
B*4415 130 53 200 66 12 36
B*4416 49 106 79 80 102 193 20 29 47 12 77
B*4417 17 12 35 36 77
B*4418 176 56 200 12 36 77
B*4420 59 29 47 12 35 36 77
B*4421 49 106 79 80 130 193 53 20 29 47 12 36 77
B*4422 106 79 80 130 193 53 20 29 47 12 35 36 77
B*4424 201 36 77
B*4425 43 54 202 56 20 29 12 35 36 77
B*4426 203
B*4427 106 53 47 12 35 36 82
B*4428 106 20 21 29 47 151 41 35 36 77
B*4429 107 36 77
B*4430 204

TABLE 8-continued

Allele-Probe List 2

B*4431 179 36
B*4432 183 36
B*4433 205
B*4501 176 200 12 36 82 87 52
B*4502 31 200 113 12 35 36 77
B*4503 206
B*4504 176 200 12 82 87 52
B*4505 207
B*4506 200 66 12 36
B*4601 208 52
B*4602 209
B*470101 210
B*4702 88 41 42 63
B*4703 211 88 61 41 42
B*4704 30 130 131 53 132 61 41 42 77
B*4801 31 212
B*4802 43 30 20 21 17 103 41 42 35 95 52
B*4803 80 43 31 15 13 179 41
B*4804 213 212
B*4805 214 80 43 31 13
B*4806 16 31 13 179 41
B*4807 113 179 41
B*4901 176 56 42 82 87 52
B*4902 130 53 66 42 82
B*4903 154 54 56 22 200 66 42 35
B*5001 176 42 82 87 52
B*5002 176 42 36 82 87 52
B*5004 106 200 66 42 35
B*510101 194 16 56 65 42 76 95 52
B*510102 16 56 65 42 76 95 52
B*510103 194 16 56 65 59 83 103 42 35 76
B*510104 194 79 16 56 65 59 13 103 42 35 76
B*510105 118 95 87
B*510201 194 16 56 65 83 103 42 35 95 52
B*510202 16 56 65 83 103 42 35 95 52
B*5103 215 95
B*5104 20 42 76 95 52
B*5105 56 83 103 41 35 95
B*5106 194 79 16 56 83 103 42 35 76
B*5107 194 155 43 56 65 59 83 103 42 35 76
B*5108 12 76 95 52
B*5109 194 41 42 35 76
B*5110 56 65 59 13 41 42 95
B*5112 216
B*511301 194 113 103 42 35 76
B*511302 194 113 83 103 42 35 76
B*5114 217
B*5115 54 56 65 59 67 66 41 42 35
B*5116 194 79 16 56 65 59 83 103 42 76
B*5117 218
B*5118 219
B*5119 194 107 35 76
B*5120 194 12 35 76
B*5121 194 83 32 76
B*5122 194 89 56 65 59 83 103 42 35 76
B*5123 194 42 36
B*5124 194 79 16 56 65 59 13 42 35 76
B*5126 220
B*5128 221
B*5129 194 16 56 65 76 95
B*5130 95 222
B*5131 194 83 41 42 76
B*5132 223
B*5133 92 76
B*5134 194 79 16 56 65 59 83 103 151 42
B*520101 224 43 56 65 42 76 95 52
B*520102 194 43 56 65 42 76 95 52
B*520103 225 80 43 56 65 59 83 42 35 76
B*520104 226
B*5202 194 97 80 43 56 65 59 83 103 42 35 76
B*5203 194 43 41 42 35
B*5204 227
B*5205 228
B*5301 30 56 20 21 17 103 41 42 35 95 52
B*5302 56 17 41 42 35 76
B*5303 45 42 35 77
B*5304 54 56 23 148 103 151 41 42 35 77
B*5305 30 54 55 56 20 21 22 23 17 103 151 41 42 35 77
B*5306 194 17 103 42 35 76
B*5307 98 42 35
B*5308 30 19 54 55 56 20 21 22 23 17 103 151 42 35 77
B*5309 102 17 151 41 42 40 35 77
B*5401 86 52
B*5402 117 86 32
B*5501 176 32 87 52
B*5502 176 41 32 87 52
B*5503 26 66 32 77
B*5504 49 104 10 13 151 41 42 32 109 77
B*5505 229
B*5507 49 230 66 77
B*5508 104 10 15 13 151 41 42 35 77
B*5509 49 104 10 65 59 67 66 151
B*5510 65 59 67 66 41 32
B*5511 231 32 77
B*5512 176 19 41 32 87 52
B*5601 176 59 41 42 35 87 52
B*5602 176 41 42 35 87 52
B*5603 176 81 82 87 52
B*5604 104 10 66 41 42 35
B*5605 194 10 65 59 83 103 42 35 76
B*5606 194 155 79 65 59 83 103 42 35 76
B*5607 10 130 53 65 59 67 66 41 42 35
B*5608 232 42 35 77
B*5609 104 10 20 21 22 23 17 103 151 41 42 35 77
B*5610 49 104 10 67 66 41 32
B*5611 176 23 151 41 42 35 77 63
B*570101 233 17 42 68
B*570102 234
B*5702 13 68
B*570301 13 42 68
B*570302 235
B*5704 184 47 41 77
B*5705 236 200 237 41 35
B*5706 238
B*5707 184 36 77
B*5708 239
B*5709 184 12 77
B*5801 236 20 87 52
B*5802 70 52
B*5804 240
B*5805 241
B*5806 70 35
B*5807 70 36
B*5901 176 56 41 32 87 52
B*670101 75 15 116 107 71 72
B*670102 15 149 113 41 116 107 32 242
B*6702 243
B*7301 244
B*7801 194 16 65 42 76 95 52
B*780201 16 31 65 42 76 95 52
B*780202 194 79 16 31 65 59 83 103 42 35 76
B*7803 194 89 11 65 59 83 103 42 35 76
B*7804 83 103 41 42 35 95
B*7805 155 154 80 43 31 65 59 83 42 35 76
B*8101 136 212
B*8201 245
B*8202 246
B*8301 136 49 20 29 47 12 35 36 77

Example 5

Probes for Identification of HLA-C Allele

Extraction of DNA from 1 ml of human blood was performed using GFX Genomic Blood DNA Purification Kit from Amersham Biosciences in the same manner as in Example 1.

Next, quantitative PCR was carried out in the same manner as in Example 1 except that probes in the probe list in Tables 9-1 to 9-4 were used respectively, and 3 μl of the mixed primers consisting of 1 μl each of the respective solutions of the following primers (10 pmol/μl) was used:

```
AAACACGGTCACCTCAGGGGGAT        (SEQ ID NO: 1992)

GGCCTGAGTGTGGTTGGAACG          (SEQ ID NO: 1993)

CCAGCTCGTAGTTGTGTCTGCA.        (SEQ ID NO: 1994)
```

After PCR amplification, the sample was identified being Cw*120202, referring to Amp Plot and Dissociation curves on a display of 5700 software and the allele-probe list in Tables 11-1 to 11-4.

Example 6

Extraction of DNA from 1 ml of human blood was performed in the same manner as in Example 1. PCR of human HLA-C was then performed in the same manner as in Example 2 except that 6 µl of the mixed primer consisting of 1 µl each of the solutions containing the following sequences at 10 pmol/µl respectively and 9 µl of ultra pure water was used.

```
AAACACGGTCACCTCAGGGGGAT        (SEQ ID NO: 1992)

GGCCTGAGTGTGGTTGGAACG          (SEQ ID NO: 1993)

CCAGCTCGTAGTTGTGTCTGCA         (SEQ ID NO: 1994)

CCATGTGTCAACTTATGCC            (SEQ ID NO: 1995)

AGAATTACCTTTTCCAG              (SEQ ID NO: 1996)

AGAATTACGTTTTCCAG              (SEQ ID NO: 1997)
```

At the same time, a DNA microarray was prepared to identify the allele in the specimen in the same manner as in Example 2. Probes in Tables 10-1 to 10-4 were used for the probe spots respectively.

Then, hybridization and fluorescence determination was performed using the above-prepared sample and the DNA microarray in the same manner as in Example 2 and the sample was identified as Cw*120202 referring to the probe-allele list in Tables 12-1 to 12-4.

```
Allele list
Cw*0102:
                                                        (SEQ ID NO: 1653)
atgcgggtcatggcgccccgaaccctcatcctgctgctctcgggagccctggccctgaccgagacctgggcctgct cccactccatgaagtatttcttcacatccgtgtcccggcctggccgcggagagccccgcttcatctcagtgggcta cgtggacgacacgcagttcgtgcggttcgacagcgacgccgcgagtccgagaggggagccgcgggcgccgtgggtg gagcaggaggggccggagtattgggaccgggagacacagaagtacaagcgccaggcacagactgaccgagtgagcc tgcggaacctgcgcggctactacaaccagagcgaggccgggtctcacaccctccagtggatgtGtggctgcgacct ggggcccgacgggcgcctcctccgcgggtatgaccagtAcgcctacgacggcaaggattacatcgccctgaacgag gacctgcgctcctggaccgccgcggacacCgcggctcagatcacccagcgcaagtgggaggcggcccgtgaggcgg agcagcggagagcctacctggagggcacgtgcgtggagtggctccgcagatacctggagaacgggaaggagacgct gcagcgcgcggaacacccaaagacacacgtgacccaccatcccgtctctgaccatgaggccaccctgaggtgctgg gccctgggcttctaccctgcggagatcacactgacctggcagtgggatggggaggaccaaactcaggacaccgagc ttgtggagaccaggccagcaggagatggaaccttccagaagtgggcagctgtgAtggtgccttctggagaagagca gagatacacgtgccatgtgcagcacgaggggctgccggagcccctcaccctgagatgggagccgtcttcccagccc accatccccatcgtgggcatcgttgctggcctggctgtcctggctgtcctagctgtcctaggagctgtggtggctg ttgtgatgtgtaggaggaagagctcaggtggaaaaggaggggagctgctctcaggctgcgtccagcaacagtgccca gggctctgatgagtctctcatcgcttgtaa;

Cw*0103:
                                                        (SEQ ID NO: 1654)
atgcgggtcatggcgccccgaaccctcatcctgctgctctcgggagccctggccctgaccgagacctgggcctgct cccactccatgaagtatttcttcacatccgtgtcccggcctggccgcggagagccccgcttcatctcagtgggcta cgtggacgacacgcagttcgtgcggttcgacagcgacgccgcgagtccgagaggggagccgcgggcgccgtgggtg gagcaggaggggccggagtattgggaccgggagacacagaagtacaagcgccaggcacagactgaccgagtgagcc tgcggaacctgcgcggctactacaaccagagcgaggccgggtctcacaccctccagtggatgtgtggctgcgacct ggggcccgacgggcgcctcctccgcgggtatAaccagttcgcctacgacggcaaggattacatcgccctgaacgag gacctgcgctcctggaccgccgcggacaccgcggctcagatcacccagcgcaagtgggaggcggcccgtgaggcgg agcagcggagagcctacctggagggcacgtgcgtggagtggctccgcagatacctggagaacgggaaggagacgct gcagcgcgcggaacacccaaagacacacgtgacccaccatcccgtctctgaccatgaggccaccctgaggtgctgg gccctgggcttctaccctgcggagatcacactgacctggcagtgggatggggaggaccaaactcaggacaccgagc ttgtggagaccaggccagcaggagatggaaccttccagaagtgggcagctgtgatggtgccttctggagaagagca
``` gagatacacgtgccatgtgcagcacgaggggctgccggagcccctcaccctgagatgggagccgtcttcccagccc accatccccatcgtgggcatcgttgctggcctggctgtcctggctgtcctagctgtcctaggagctgtggtggctg ttgtgatgtgtaggaggaagagctcaggtggaaaaggagggagctgctctcaggctgcgtccagcaacagtgccca gggctctgatgagtctctcatcgcttgtaa;

Cw*0104:

(SEQ ID NO: 1655)
atgcgggtcatggcgccccgaaccctcatcctgctgctctcgggagccctggccctgaccgagacctgggcctgct cccactccatgaagtatttcttcacatccgtgtcccggcctggccgcggagagccccgcttcatctcagtgggcta cgtggacgacacgcagttcgtgcggttcgacagcgacgccgcgagtccgagaggggagccgcgggcgccgtgggtg gagcaggaggggccggagtattgggaccgggagacacagaagtacaagcgccaggcacagactgaccgagtgagcc tgcggaacctgcgcggctactacaaccagagcgaggccgggtctcacaccctccagtggatgtgtggctgcgacct ggggcccgacgggcgcctcctccgcgggtatgaccagtccgcctacgacggcaaggattacatcgccctgaacgag gacctgcgctcctggaccgcTgcggacacggcggctcagatcacccagcgcaagtgggaggcggcccgtgaggcgg agcagtggagagcctacctggagggcacgtgcgtggagtggctccgcagatacctggagaacgggaaggagacgct gcagcgcgcggaacacccaaagacacacgtgacccaccatcccgtctctgaccatgaggccaccctgaggtgctgg gccctgggcttctaccctgcggagatcacactgacctggcagcgggatggcgaggaccaaactcaggacaccgagc ttgtggagaccaggccagcaggagatggaaccttccagaagtgggcagctgtggtggtgccttctggagaagagca gagatacacgtgccatgtgcagcacgaggggctgccAgagcccctcaccctgagatgggagccatcttcccagccc accatccccatcgtgggcatcgttgctggcctggctgtcctggctgtcctagctgtcctaggagctgtgAtggctg ttgtgatgtgtaggaggaagagctcaggtggaaaaggagggagctgctctcaggctgcgtccagcaacagtgccca gggctctgatgagtctctcatcgcttgtaa;

Cw*0105:

(SEQ ID NO: 1656)
gctcccactccatgaagtatttcttcacatccgtgtcccggcctggccgcggagagccccgcttcatctcagtggg ctacgtggacgacacgcagttcgtgcggttcgacagcgacgccgcgagtccgagaggggagccgcgggcgccgtgg gtggagcaggaggggccggagtattgggaccgggagacacagaagtacaagcgccaggcacagactgaccgagtga gcctgcggaacctgcgcggctactacaaccagagcgaggccgggtctcacaccctccagaggatgtCtggctgcga cctggggcccgacgggcgcctcctccgcgggtatgaccagtacgcctacgacggcaaggattacatcgccctgaac gaggacctgcgctcctggaccgccgcggacaccgcggctcagatcacccagcgcaagtgggaggcggcccgtgagg cggagcagcggagagcctacctggagggcacgtgcgtggagtggctccgcagatacctggagaacgggaaggagac gctgcagcgcgcgcgg;

Cw*0106:

(SEQ ID NO: 1657)
gctcccactccatgaagtatttcttcacatccgtgtcccggcctggccgcggagagccccgcttcatctcagtggg ctacgtggacgacacgcagttcgtgcggttcgacagcgacgccgcgagtccgagaggggagccgcgggcgccgtgg gtggagcaggaggggccggagtattgggaccgggagacacagaagtacaagcgccaggcacagactgaccgagtga gcctgcggaacctgcgcggctactacaaccagagcgaggccgggtctcacaccctccagtggatgtgtggctgcga cctggggcccgacgggcgcctcctccgcgggtatgaccagtacgcctacgacggcaaggattacatcgccctgaac gaggacctgcgctcctggaccgccgcggacaccgcggctcagatcacccagcgcaagtgggaggcggcccgtgTgg cggagcagcggagagcctacctggagggcacgtgcgtggagtggctccgcagatacctggagaacgggaaggagac gctgcagcgcgcgcgg;

Cw*0107:
(SEQ ID NO: 1658)
gctcccactccatgaagtatttcttcacatccgtgtcccggcctggccgcggagagccccgcttcatctcagtggg ctacgtggacgacacgcagttcgtgcggttcgacagcgacgccgcgagtccgagaggggagccgcgggcgccgtgg gtggagcaggaggggccggagtattgggaccgggagacacagaagtacaagcgccaggcacagactgaccgagtga gcctgcggaacctgcgcggctactacaaccagagcgaggccgggtctcacaccctccagtggatgtgtggctgcga cctgggcccgacgggcgcctcctccgcAggtatgaccagtacgcctacgacggcaaggattacatcgccctgaac gaggacctgcgctcctggaccgccgcggacaccgcggctcagatcacccagcgcaagtgggaggcggcccgtgagg cggagcagcggagagcctacctggagggcacgtgcgtggagtggctccgcagatacctggagaacgggaaggagac gctgcagcgcgcgg;

Cw*0108:
(SEQ ID NO: 1659)
gctcccactccatgaagtatttcttcacatccgtgtcccggcctggccgcggagagccccgcttcatctcagtggg ctacgtggacgacacgcagttcgtgcggttcgacagcgacgccgcgagtccgagaggggagccgcgggcgccgtgg gtggagcaggaggggccggagtattgggaccgggagacacagaagtacaagcgccaggcacagactgaccgagtga gcctgcggaacctgcgcggctactacaaccagagcgaggccgggtctcacaccctccagtggatgtgtggctgcga cctgggcccgacgggcgcctcctccgcgggtatgaccagtacgcctacgacggcaaggattacatcgccctgaac gaggacctgcgctcctggaccgccgcggacaccgcggctcagatcacccagcgcaagtgggaggcggccTgtgagg cggagcagcggagagcctacctggagggcacgtgcgtggagtggctccgcagatacctggagaacgggaaggagac gctgcagcgcgcgg;

Cw*0109:
(SEQ ID NO: 1660)
gctcccactccatgaagtatttcttcacatccgtgtcccggcctggccgcggagagccccgcttcatctcagtggg ctacgtggacgacacgcagttcgtgcggttcgacagcgacgccgcgagtccgagaggggagccgcgggcgccgtgg gtggagcaggaggggccggagtattgggaccgggagacacagaagtacaagcgccaggcacagactgaccgagtga gcctgcggaacctgcgcggctactacaaccagagcgaggccgggtctcacaccctccagtggatgtgtggctgcga cctgggcccgacgggcgcctcctccgcgggtatgaccagtacgcctacgacggcaaggattacatcgccctgaac gaggacctgcgctcctggaccgccgcggacaccgcggctcagatcacccagcgcaagtgggaggcggcccgtgagg cggagcagTggagagcctacctggagggcacgtgcgtggagtggctccgcagatacctggagaacgggaaggagac gctgcagcgcgcgg;

Cw*020201:
(SEQ ID NO: 1661)
atgcgggtcatggcgccccgaaccctcctcctgctgctctcgggagccctggccctgaccgagacctgggcctgct cccactccatgaggtatttctacaccgctgtgtcccggcccagccgcggagagccccacttcatcgcagtgggcta cgtggacgacacgcagttcgtgcggttcgacagcgacgccgcgagtccaagaggggagccgcgggcgccgtgggtg gagcaggaggggccggagtattgggaccgggagacacagaagtacaagcgccaggcacagactgaccgagtgaacc tgcggaaactAcgcggctactacaaccagagcgaggccgggtctcacaccctccagaggatgtacggctgcgacct ggggcccgacgggcgcctcctccgcgggtatgaccagtccgcctacgacggcaaggattacatcgccctgaacgag gacctgcgctcctggaccgccgcggacacagcggctcagatcacccagcgcaagtgggaggcggcccgtgaggcgg agcagtggagagcctacctggagggcgagtgcgtggagtggctccgcagatacctggagaacgggaaggagacgct gcagcgcgcggaacaccccaaagacacacgtgacccaccatcccgtctctgaccatgaggccaccctgaggtgctgg gccctgggcttctaccctacggagatcacactgacctggcagcgggatggcgaggaccaaactcaggacaccgagc ttgtggagaccaggccagcaggagatggaaccttccagaagtgggcagctgtggtggtgccttctggagaagagca gagatacacgtgccatgtgcagcacgaggggctgccggagcccctcaccctgagatgggagccatcttcccagccc -continued accatccccatcgtgggcatcgttgctggcctggctgtcctggctgtcctagctgtcctaggagctgtggtggctg ttgtgatgtgtaggaggaagagctcaggtggaaaaggagggagctgctctcaggctgcgtccagcaacagtgccca gggctctgatgagtctctcatcgcttgtaa;

Cw*020202:

(SEQ ID NO: 1662)
atgcgggtcatggcgccccgaaccctcctcctgctgctctcggggagccctggccctgaccgagacctgggcctgct cccactccatgaggtatttctacaccgctgtgtcccggcccagccgcggagagccccacttcatcgcagtgggcta cgtggacgacacgcagttcgtgcggttcgacagcgacgccgcgagtccaagaggggagccgcgggcgccgtgggtg gagcaggaggggccggagtattgggaccgggagacacagaagtacaagcgccaggcacagactgaccgagtgaacc tgcggaaactgcgcggctactacaaccagagcgaggccgggtctcacaccctccagaggatgtacggctgcgacct ggggcccgacgggcgcctcctccgcgggtatgaccagtccgcctacgacggcaaggattacatcgccctgaacgag gacctgcgctcctggaccgccgcggacacagcggctcagatcacccagcgcaagtgggaggcggcccgtgaggcgg agcagtggagagcctacctggagggcgagtgcgtggagtggctccgcagatacctggagaacgggaaggagacgct gcagcgcgcggaacacccaaagacacacgtgacccaccatcccgtctctgaccatgaggccaccctgaggtgctgg gccctgggcttctaccctAcggagatcacactgacctggcagcgggatggcgaggaccaaactcaggacaccgagc ttgtggagaccaggccagcaggagatggaaccttccagaagtgggcagctgtggtggtgccttctggagaagagca gagatacacgtgccatgtgcagcacgaggggctgccggagcccctcaccctgagatgggagccatcttcccagccc accatccccatcgtgggcatcgttgctggcctggctgtcctggctgtcctagctgtcctaggagctgtggtggctg ttgtgatgtgtaggaggaagagctcaggtggaaaaggagggagctgctctcaggctgcgtccagcaacagtgccca gggctctgatgagtctctcatcgcttgtaa;

Cw*020203:

(SEQ ID NO: 1663)
gctcccactccatgaggtatttctacaccgctgtgtcccggcccagccgcggagagccccacttcatcgcagtggg ctacgtggacgacacgcagttcgtgcggttcgacagcgacgccgcgagtccaagaggggagccgcgggcgccgtgg gtggagcaggaggggccggagtattgggaccgggagacacagaagtacaagcgccaggcacagactgaccgagtga acctgcggaaactgcgcggctactacaaccagagcgaggccgggtctcacaccctccagaggatgtatggctgcga cctggggcccgacgggcgcctcctccgcgggtatgaccagtccgcctacgacggcaaggattacatcgccctgaac gaggacctgcgctcctggaccgccgcggacacAgcggctcagatcacccagcgcaagtgggaggcggcccgtgagg cggagcagTggagagcctacctggagggcgagtgcgtggagtggctccgcagatacctggagaacgggaaggagac gctgcagcgcgcgcgg;

Cw*020204:

(SEQ ID NO: 1664)
atgcgggtcatggcgccccgaaccctcctcctgctgctctcggggagccctggccctgaccgagacctgggcctgct cccactccatgaggtatttctacaccgctgtgtcccggcccAgccgcggagagccccacttcatcgcagtgggcta cgtggacgacacgcagttcgtgcggttcgacagcgacgccgcgagtccaagaggggagccgcgggcgccgtgggtg gagcaggaggggccggagtattgggaccgggagacacagaagtacaagcgccaggcacagactgaccgagtgaacc tgcggaaactgcgcggctactacaaccagagcgaggccgggtctcacaccctccagaggatgtacggctgcgacct ggggcccgacgggcgcctcctccgcgggtatgaccagtccgcctacgacggcaaggattacatcgccctgaacgag gacctgcgctcctggaccgccgcggacacGgcggctcagatcacccagcgcaagtgggaggcggcccgtgaggcgg agcagtggagagcctacctggagggcgagtgcgtggagtggctccgcagatacctggagaacgggaaggagacgct gcagcgcgcggaacacccaaagacacacgtgacccaccatcccgtctctgaccatgaggccaccctgaggtgctgg gccctgggcttctaccctgcggagatcacactgacctggcagcgggatggcgaggaccaaactcaggacaccgagc ttgtggagaccaggccagcaggagatggaaccttccagaagtgggcagctgtggtggtgccttctggagaagagca gagatacacgtgccatgtgcagcacgaggggctgccggagcccctcaccctgagatgggagccAtcttcccagccc accatccccatcgtgggcatcgttgctggcctggctgtcctggctgtcctagctgtcctaggagctgtggtggctg
ttgtgatgtgtaggaggaagagctcag;

Cw*020205:
(SEQ ID NO: 1665)
gctcccactccatgaggtatttctacaccgctgtgtcccggcccAgccgcggagagcccacttcatcgcagtggg
ctacgtggacgacacgcagttcgtgcggttcgacagcgacgccgcgagtccaagaggggagccgcgggcgccgtgg
gtggagcaggaggggccggagtattgggaccgggagacacagaagtacaagcgccaggcacagactgaccgagtga
acctgcggaaactgcgcggctactacaaccagagcgaggccgggtctcacaccctccagAggatgtatggctgcga
cctggggcccgacgggcgcctcctccgcgggtatgaccagtCcgcctacgacggcaaggattacatcgccctgaac
gaggacctgcgctcctggaccgccgcggacacGgcggctcagatcacccagcgcaagtgggaggcggcccgtgagg
cggagcagTggagagcctacctggagggcgAgtgcgtggagtggctccgcagatacctggagaacgggaaggagac
gctgcagcgcgcgg;

Cw*0203:
(SEQ ID NO: 1666)
gctcccactccatgaggtatttctacaccgctgtgtcccggcccagccgcggagagcccacttcatcgcagtggg
ctacgtggacgacacgcagttcgtgcggttcgacagcgacgccgcgagtccaagaggggagccgcgggcgccgtgg
gtggagcaggaggggccggagtattgggaccgggagacacagaagtacaagcgccaggcacagactgaccgagtga
acctgcggaaactgcgcggctactacaaccagagcgaggccgggtctcacaccctccagaggatgtacggctgcga
cctggggcccgacgggcgcctcctccgcgggtatgaccagtccgcctacgacggcaaggattacatcgccctgaac
gaggacctgcgctcctggaccgccgcggacacagcggctcagatcacccagcgcaagtgggaggcggcccgtgTgg
cggagcagctgagagcctacctggagggcgAgtgcgtggagtggctccgcagatacctggagaacgggaaggagac
gctgcagcgcgcgg;

Cw*0204:
(SEQ ID NO: 1667)
gctcccactccatgaggtGtttctacaccgctgtgtcccggcccagccgcggagagcccacttcatcgcagtggg
ctacgtggacgacacgcagttcgtgcggttcgacagcgacgccgcgagtccaagaggggagccgcgggcgccgtgg
gtggagcaggaggggccggagtattgggaccgggagacacagaagtacaagcgccaggcacagactgaccgagtga
acctgcggaaactgcgcggctactacaaccagagcgaggccgggtctcacaccctccagaggatgtacggctgcga
cctggggcccgacgggcgcctcctccgcgggtatgaccagtccgcctacgacggcaaggattacatcgccctgaac
gaggacctgcgctcctggaccgccgcggacacagcggctcagatcacccagcgcaagtgggaggcggcccgtgagg
cggagcagtggagagcctacctggagggcgagtgcgtggagtggctccgcagatacctggagaacgggaaggagac
gctgcagcgcgcgg;

Cw*0205:
(SEQ ID NO: 1668)
gctcccactccatgaggtatttctacaccgctgtgtcccggcccAgccgcggagagcccacttcatcgcagtggg
ctacgtggacgacacgcagttcgtgcggttcgacagcgacgccgcgagtccaagaggggagccgcgggcgccgtgg
gtggagcaggaggggccggagtattgggaccgggagacacagaagtacaagcgccaggcacagactgaccgagtga
acctgcggaaactgcgcggctactacaaccagagcgaggccgggtctcacaccctccagtggatgtatggctgcga
cctggggcccgacgggcgcctcctccgcgggtatgaccagtCcgcctacgacggcaaggattacatcgccctgaac
gaggacctgcgctcctggaccgccgcggacacGgcggctcagatcacccagcgcaagtgggaggcggcccgtgagg
cggagcagTggagagcctacctggagggcgAgtgcgtggagtggctccgcagatacctggagaacgggaaggagac
gctgcagcgcgcgg;

Cw*0206:
(SEQ ID NO: 1669)
gctcccactccatgaggtatttctacaccgctgtgtcccggcccagccgcggagagccccacttcatcgcagtggg ctacgtggacgacacgcagttcgtgcggttcgacagcgacgccgcgagtccaagaggggagccgcgggcgccgtgg gtggagcaggaggggccggagtattgggaccgggagacacagaagtacaagcgccaggcacagactgaccgagtga acctgcggaaactgcgcggctactacaaccagagcgaggccgggtctcacaccctccagaggatgtacggctgcga cctggggcccgacgggcgcctcctccgcgggcatgaccagttAgcctacgacggcaaggattacatcgccctgaac gaggacctgcgctcctggaccgccgcggacacggcggctcagatcacccagcgcaagtgggaggcggcccgtgagg cggagcagtggagagcctacctggagggcgAgtgcgtggagtggctccgcagatacctggagaacgggaaggagac gctgcagcgcgcgcgg;

Cw*030201:
(SEQ ID NO: 1670)
atgcgggtcatggcgccccgaaccctcatcctgctgctctcgggagccctggccctgaccgagacctgggccggct cccactccatgaggtatttctacaccgctgtgtcccggcccggccgcggggagccccacttcatcgcagtgggcta cgtggacgacacgcagttcgtgcggttcgacagcgacgccgcgagtccgagaggggagccgcgggcgccgtgggtg gagcaggaggggccggagtattgggaccgggagacacagaagtacaagcgccaggcacagactgaccgagtgagcc tgcggaacctgcgcggctactacaaccagagcgaggccgggtctcacatcctccagaggatgtatggctgcgacgt ggggcccgacgggcgcctcctccgcgggtatgaccagtccgcctacgacggcaaggattacatcgccctgaacgag gatctgcgctcctggaccgccgcggacacggcggctcagatcacccagcgcaagtgggaggcggcccgtgaggcgg agcagctgagagcctacctggagggcctgtgcgtggagtggctccgcagatacctgaagaatgggaaggagacgct gcagcgcgcggaacacccaaagacacacgtgacccaccatcccgtctctgaccatgaggccaccctgaggtgctgg gccctgggcttctaccctgcggagatcacactgacctggcagtgggatgggaggaccaaactcaggacacTgagc ttgtggagaccaggccagcaggagatggaaccttccagaagtgggcagctgtggtggtgccttctggagaagagca gagatacacgtgccatgtgcagcacgaggggctgccggagccccteacccctgagatgggagccAtcttcccagccc accatccccatcgtgggcatcgttgctggcctggctgtcctggctgtcctagctgtcctaggagctgtggtggctg ttgtgatgtgtaggaggaagagctcaggtggaaaaggagggagctgctctcaggctgcgtccagcaacagtgccca gggctctgatgagtctctcatcgcttgtaa;

Cw*030202:
(SEQ ID NO: 1671)
atgcgggtcatggcgccccgaaccctcatcctgctgctctcgggagccctggccctgaccgagacctgggccggct cccactccatgaggtatttctacaccgctgtgtcccggcccggccgcggggagccccacttcatcgcagtgggcta cgtggacgacacgcagttcgtgcggttcgacagcgacgccgcgagtccgagaggggagccgcgggcgccgtgggtg gagcaggaggggccggagtattgggaccgggagacacagaagtacaagcgccaggcacagactgaccgagtgagcc tgcggaacctgcgcggctactacaaccagagcgaggccgggtctcacatcctccagaggatgtatggctgcgacgt ggggcccgacgggcgcctcctccgcgggtatgaccagtCcgcctacgacggcaaggattacatcgccctgaacgag gatctgcgctcctggaccgccgcggacacggcggctcagatcacccagcgcaagtgggaggcggcccgtgaggcgg agcagctgagagcctacctggagggcctgtgcgtggagtggctccgcagatacctgaagaatgggaaggagacgct gcagcgcgcggaacacccaaagacacacgtgacccaccatcccgtctctgaccatgaggccaccctgaggtgctgg gccctgggcttctaccctgcggagatcacactgacctggcagtgggatgggaggaccaaactcaggacacTgagc ttgtggagaccaggccagcaggagatggaaccttccagaagtgggcagctgtggtggtgccttctggagaagagca gagatacacgtgccatgtgcagcacgaggggctgccggagccccteacccctgagatgggagccgtcttcccagccc accatccccatcgtgggcatcgttgctggcctggctgtcctggctgtcctagctgtcctaggagctgtggtggctg ttgtgatgtgtaggaggaagagctcaggtggaaaaggagggagctgctctcaggctgcgtccagcaacagtgccca gggctctgatgagtctctcatcgcttgtaa;

Cw*030301:

(SEQ ID NO: 1672)

atgcgggtcatggcgccccgaaccctcatcctgctgctctcggggagccctggccctgaccgagacctgggccggct cccactccatgaggtatttctacaccgctgtgtcccggcccggccgcggggagccccacttcatcgcagtgggcta cgtggacgacacgcagttcgtgcggttcgacagcgacgccgcgagtccgagaggggagccgcgggcgccgtgggtg gagcaggaggggccggagtattgggaccgggagacacagaagtacaagcgccaggcacagactgaccgagtgagcc tgcggaacctgcgcggctactacaaccagagcgaggccAggtctcacatcAtccagaggatgtatggctgcgacgt ggggcccgacgggcgcctcctccgcgggtatgaccagtacgcctacgacggcaaggattacatcgccctgaacgag gatctgcgctcctggaccgccgcggacacggcggctcagatcacccagcgcaagtgggaggcggcccgtgaggcgg agcagctgagagcctacctggagggcctgtgcgtggagtggctccgcagatacctgaagaatgggaaggagacgct gcagcgcgcggaacacccaaagacacacgtgacccaccatcccgtctctgaccatgaggccaccctgaggtgctgg gccctgggcttctaccctgcggagatcacactgacctggcagtgggatggggaggaccaaactcaggacactgagc ttgtggagaccaggccagcaggagatggaaccttccagaagtgggcagctgtgGtggtgccttctggagaagagca gagatacacgtgccatgtgcagcacgaggggctgccggagcccctcaccctgagatgggagccgtcttcccagccc accatccccatcgtgggcatcgttgctggcctggctgtcctggctgtcctagctgtcctaggagctgtggtggctg ttgtgatgtgtaggaggaagagctcaggtggaaaaggagggagctgctctcaggctgcgtccagcaacagtgccca gggctctgatgagtctctcatcgcttgtaa;

Cw*030302:

(SEQ ID NO: 1673)

atgcgggtcatggcgccccgaaccctcatcctgctgctctcggggagccctggccctgaccgagacctgggccggct cccactccatgaggtatttctacaccgctgtgtcccggcccggccgcggggagccccacttcatcgcagtgggcta cgtggacgacacgcagttcgtgcggttcgacagcgacgccgcgagtccgagaggggagccgcgggcgccgtgggtg gagcaggaggggccggagtattgggaccgggagacacagaagtacaagcgccaggcacagactgaccgagtgagcc tgcggaacctgcgcggctactacaaccagagcgaggccaggtctcacatcatccagaggatgtatggctgcgacgt ggggcccgacgggcgcctcctccgcgggtatgaccagtacgcctacgacggcaaggattacatcgccctgaacgag gatctgcgctcctggaccgccgcggacacggcggcCcagatcacccagcgcaagtgggaggcggcccgtgaggcgg agcagctgagagcctacctggagggcctgtgcgtggagtggctccgcagatacctgaagaatgggaaggagacgct gcagcgcgcggaacacccaaagacacacgtgacccaccatcccgtctctgaccatgaggccaccctgaggtgctgg gccctgggcttctaccctgcggagatcacactgacctggcagtgggatggggaggaccaaactcaggacactgagc ttgtggagaccaggccagcaggagatggaaccttccagaagtgggcagctgtggtggtgccttctggagaagagca gagatacacgtgccatgtgcagcacgaggggctgccggagcccctcaccctgagatgggagccgtcttcccagccc accatccccatcgtgggcatcgttgctggcctggctgtcctggctgtcctagctgtcctaggagctgtggtggctg ttgtgatgtgtaggaggaagagctcaggtggaaaaggagggagctgctctcaggctgcgtccagcaacagtgccca gggctctgatgagtctctcatcgcttgtaa;

Cw*030303:

(SEQ ID NO: 1674)

gctcccactccatgaggtatttctacaccgctgtgtcccggcccggccgcggggagccccacttcatcgcagtggg ctacgtggacgacacgcagttcgtgcggttcgacagcgacgccgcgagtccgagaggggagccgcgggcgccgtgg gtggagcaggaggggccggagtattgggaccgggagacacagaagtacaagcgccaggcacagactgaccgagtga gcctgcggaacctgcgcggctactacaaccagagcgaggccaggtctcacatcatccagaggatgtatggctgcga cgtgggAcccgacgggcgcctcctccgcgggtatgaccagtacgcctacgacggcaaggattacatcgccctgaac -continued gaggatctgcgctcctggaccgccgcggacacggcggctcagatcacccagcgcaagtgggaggcggcccgtgagg cggagcagctgagagcctacctggagggcctgtgcgtggagtggctccgcagatacctgaagaatgggaaggagac gctgcagcgcgcgg;

Cw*030401:
(SEQ ID NO: 1675)
atgcgggtcatggcgcccgaaccctcatcctgctgctctcgggagccctggccctgaccgagacctgggccggct cccactccatgaggtatttctacaccgctgtgtcccggcccggccgcggggagccccacttcatcgcagtgggcta cgtggacgacacgcagttcgtgcggttcgacagcgacgccgcgagtccgagaggggagccgcgggcgccgtgggtg gagcaggaggggccggagtattgggaccgggagacacagaagtacaagcgccaggcacagactgaccgagtgagcc tgcggaacctgcgcggctactacaaccagagcgaggccgggtctcacatcAtccagaggatgtatggctgcgacgt ggggcccgacgggcgcctcctccgcgggtatgaccagtacgcctacgacggcaaggattacatcgccctgaacgag gatctgcgctcctggaccgccgcggacacggcggctcagatcacccagcgcaagtgggaggcggcccgtgaggcgg agcagctgagagcctacctggagggcctgtgcgtggagtggctccgcagatacctgaagaatgggaaggagacgct gcagcgcgcggaacacccaaagacacacgtgacccaccatcccgtctctgaccatgaggccaccctgaggtgctgg gccctgggcttctaccctgcggagatcacactgacctggcagtgggatggggaggaccaaactcaggacacTgagc ttgtggagaccaggccagcaggagatggaaccttccagaagtgggcagctgtggtggtgccttctggagaagagca gagatacacgtgccatgtgcagcacgaggggctgccggagcccctcaccctgagatgggagccgtcttcccagccc accatccccatcgtgggcatcgttgctggcctggctgtcctggctgtcctagctgtcctaggagctgtggtggctg ttgtgatgtgtaggaggaagagctcaggtggaaaaggagggagctgctctcaggctgcgtccagcaacagtgccca gggctctgatgagtctctcatcgcttgtaa;

Cw*030402:
(SEQ ID NO: 1676)
gctcccactccatgaggtatttctacaccgctgtgtcccggcccggccgcggggagccccacttcatcgcagtggg ctacgtggacgacacgcagttcgtgcggttcgacagcgacgccgcgagtccgagaggggagccgcgggcgccgtgg gtggagcaggaggggccggagtattgggaccgggagacacagaagtacaagcgccaggcacagactgaccgagtga gcctgcggaacctgcgcggctactacaaccagagcgaggccgggtctcacatcAtccagaggatgtaCggctgcga cgtggggcccgacgggcgcctcctccgcgggtatgaccagtacgcctacgacggcaaggattacatcgccctgaac gaggatctgcgctcctggaccgccgcggacacggcggctcagatcacccagcgcaagtgggaggcggcccgtgagg cggagcagctgagagcctacctggagggcctgtgcgtggagtggctccgcagatacctgaagaaTgggaaggagac gctgcagcgcgcgg;

Cw*0305:
(SEQ ID NO: 1677)
gctcccactccatgaggtatttctacaccgctgtgtcccggcccggccgcggggagccccacttcatcgcagtggg ctacgtggacgacacgcagttcgtgcggttcgacagcgacgccgcgagtccgagaggggagccgcgggcgccgtgg gtggagcaggaggggccggagtattgggaccgggagacacagaagtacaagcgccaggcacagactgaccgagtga gcctgcggaacctgcgcggctactacaaccagagcgaggccgggtctcacaccctccagagCatgtacggctgcga cgtggggcccgacgggcgcctcctccgcgggtatgaccagtacgcctacgacggcaaggattacatcgccctgaac gaggatctgcgctcctggaccgccgcggacacggcggctcagatcacccagcgcaagtgggaggcggcccgtgagg cggagcagctgagagcctacctggagggcctgtgcgtggagtggctccgcagatacctgaagaaTgggaaggagac gctgcagcgcgcgg;

Cw*0306:
(SEQ ID NO: 1678)
gctcccactccatgaggtatttctacaccgctgtgtcccggcccggccgcggggagccccacttcatcgcagtggg ctacgtggacgacacgcagttcgtgcggttcgacagcgacgccgcgagtccgagaggggagccgcgggcgccgtgg gtggagcaggaggggccggagtattgggaccgggagacacagaagtacaagcgccaggcacagactgaccgagtga gcctgcggaacctgcgcggctactacaaccagagcgaggccgggtctcacatcatccagaggatgtatggctgcga cgtggggcccgacgggcgcctcctccgcgggtatgTccagtacgcctacgacggcaaggattacatcgccctgaac gaggatctgcgctcctggaccgccgcggacacggcggctcagatcacccagcgcaagtgggaggcggcccgtgagg cggagcagctgagagcctacctggagggcctgtgcgtggagtggctccgcagatacctgaagaatgggaaggagac gctgcagcgcgcgg;

Cw*0307: (SEQ ID NO: 1679)

gctcccactccatgaggtatttctacaccgctgtgtcccggcccggccgcggggagccccacttcatcgcagtggg ctacgtggacgacacgcagttcgtgcggttcgacagcgacgccgcgagtccgagaggggagccgcgggcgccgtgg gtggagcaggaggggccggagtattgggaccgggagacacagaagtacaagcgccaggcacagactgaccgagtga AcctgcggaaActgcgcggctactacaaccagagcgaggccgggtctcacatcAtccagaggatgtatggctgcga cGtggggcccgacgggcgcctcctccgcgggtatgaccagtacgcctacgacggcaaggattacatcgccctgaac gaggatctgcgctcctggaccgccgcggacacggcggctcagatcacccagcgcaagtgggaggcggcccgtgagg cggagcagctgagagcctacctggagggcCTgtgcgtggagtggctccgcagatacctgaagaaTgggaaggagac gctgcagcgcgcgg;

Cw*0308: (SEQ ID NO: 1680)

atgcgggtcatggcgccccgaaccctcatcctgctgctctcggggagccctggccctgaccgagacctgggccggct cccactccatgaggtatttctacaccgctgtgtcccggcccggccgcggggagccccacttcatcgcagtgggcta cgtggacgacacgcagttcgtgcggttcgacagcgacgccgcgagtccgagaggggagccgcgggcgccgtgggtg gagcaggaggggccggagtattgggaccgggagacacagaaCtacaagcgccaggcacagactgaccgagtgagcc tgcggaacctgcgcggctactacaaccagagcgaggccgggtctcacatcAtccagaggatgtatggctgcgacgt ggggcccgacgggcgcctcctccgcgggtatgaccagtacgcctacgacggcaaggattacatcgccctgaacgag gatctgcgctcctggaccgccgcggacacggcggctcagatcacccagcgcaagtgggaggcggcccgtgaggcgg agcagctgagagcctacctggagggcctgtgcgtggagtggctccgcagatacctgaagaatgggaaggagacgct gcagcgcgcggaacacccaaagacacacgtgacccaccatcccgtctctgaccatgaggccaccctgaggtgctgg gccctgggcttctaccctgcggagatcacactgacctggcagtgggatggggaggaccaaactcaggacacTgagc ttgtggagaccaggccagcaggagatggaaccttccagaagtgggcagctgtggtggtgccttctggagaagagca gagatacacgtgccatgtgcagcacgaggggctgccggagcccctcaccctgagatgggagccgtcttcccagccc accatccccatcgtgggcatcgttgctggcctggctgtcctggctgtcctagctgtcctaggagctgtggtggctg ttgtgatgtgtaggaggaagagctcag;

Cw*0309: (SEQ ID NO: 1681)

gctcccactccatgaggtatttctacaccgctgtgtcccggcccggccgcggggagccccacttcatcGcagtggg ctacgtggacgacacgcagttcgtgcggttcgacagcgacgccgcgagtccgagaggggagccgcgggcgccgtgg gtggagcaggaggggccggagtattgggaccgggagacacagaagtacaagcgccaggcacagactgaccgagtga gcctgcggaacctgcgcggctactacaaccagagcgaggccgggtctcacatcAtccagaggatgtatggctgcga cctggggcccgacgggcgcctcctccgcgggtatgaccagtacgcctacgacggcaaggattacatcgccctgaac gaggatctgcgctcctggaccgccgcggacacggcggctcagatcacccagcgcaagtgggaggcggcccgtgagg cggagcagctgagagcctacctggagggcCTgtgcgtggagtggctccgcagatacctgaagaaTgggaaggagac gctgcagcgcgcgg;

Cw*0310:
(SEQ ID NO: 1682)
gctcccactccatgaggtatttctacaccgctgtgtcccggcccggccgcggggagccccacttcatcgcagtggg ctacgtggacgacacgcagttcgtgcggttcgacagcgacgccgcgagtccgagaggggagccgcgggcgccgtgg gtggagcaggaggggccggagtattgggaccgggagacacagaagtacaagcgccaggcacagactgaccgagtga gcctgcggaaActgcgcggctactacaaccagagcgaggccgggtctcacatcAtccagaggatgtatggctgcga cGtggggcccgacgggcgcctcctccgcgggtatgaccagtacgcctacgacggcaaggattacatcgccctgaac gaggatctgcgctcctggaccgccgcggacacggcggctcagatcacccagcgcaagtgggaggcggcccgtgagg cggagcagctgagagcctacctggagggccTgtgcgtggagtggctccgcagatacctgaagaaTgggaaggagac gctgcagcgcgcgg;

Cw*0311:
(SEQ ID NO: 1683)
gctcccactccatgaggtatttctacaccgctgtgtcccggcccggccgcggagagccccgcttcatctcagtggg ctacgtggacgacacgcagttcgtgcggttcgacagcgacgccgcgagtccgagaggggagccgcgggcgccgtgg gtggagcaggaggggccggagtattgggaccgggagacacagaagtacaagcgccaggcacagactgaccgagtga gcctgcggaacctgcgcggctactacaaccagagcgaggccAggtctcacatcAtccagaggatgtatggctgcga cgtggggcccgacgggcgcctcctccgcgggtatgaccagtacgcctacgacggcaaggattacatcgccctgaac gaggatctgcgctcctggaccgccgcggacacggcggctcagatcacccagcgcaagtgggaggcggcccgtgagg cggagcagctgagagcctacctggagggcctgtgcgtggagtggctccgcagatacctgaagaatgggaaggagac gctgcagcgcgcgg;

Cw*0312:
(SEQ ID NO: 1684)
gctcccactccatgaggtatttctacaccgctgtgtcccggcccggccgcggggagccccacttcatcgcagtggg ctacgtggacgacacgcagttcgtgcggttcgacagcgacgccgcgagtccgagaggggagccgcgggcgccgtgg gtggagcaggaggggccggagtattgggaccgggagacacagaagtacaagcgccaggcacagactgaccgagtga gcctgcggaacctgcgcggctactacaaccagagcgaggccAggtctcacatcatccagaggatgtatggctgcga cgtggggcccgacgggcgcctcctccgcgggtatgaccagttAgcctacgacggcaaggattacatcgccctgaac gaggatctgcgctcctggaccgccgcggacacggcggctcagatcacccagcgcaagtgggaggcggcccgtgagg cggagcagctgagagcctacctggagggcctgtgcgtggagtggctccgcagatacctgaagaatgggaaggagac gctgcagcgcgcgg;

Cw*0313:
(SEQ ID NO: 1685)
atgcgggtcatggcgccccgaaccctcatcctgctgctctcgggagccctggccctgaccgagacctgggccggct cccactccatgaggtatttctacaccgctgtgtcccggcccggccgcggggagccccacttcatcgcagtgggcta cgtggacgacacgcagttcgtgcggttcgacagcgacgccgcgagtccgagaggggagccgcgggcgccgtgggtg gagcaggaggggccggagtattgggaccgggagacacagaagtacaagcgccaggcacagactgaccgagtgagcc tgcggaacctgcgcggctactacaaccagagcgaggccAggtctcacaccctccagaggatgtatggctgcgacgt ggggcccgacgggcgcctcctccgcgggtatgaccagtacgcctacgacggcaaggattacatcgccctgaacgag gatctgcgctcctggaccgccgcggacacggcggctcagatcacccagcgcaagtgggaggcggcccgtgaggcgg agcagctgagagcctacctggagggcctgtgcgtggagtggctccgcagatacctgaagaatgggaaggagacgct gcagcgcgcggaacaccccaaagacacacgtgacccaccatcccgtctctgaccatgaggccaccctgaggtgctgg gccctgggcttctaccctgcggagatcacactgacctggcagtgggatggggaggaccaaactcaggacactgagc ttgtggagaccaggccagcaggagatggaaccttccagaagtgggcagctgtgGtggtgccttctgagaagagca gagatacacgtgccatgtgcagcacgaggggctgccggagcccctcaccctgagatgggagccgtcttcccagccc -continued accatcccatcgtgggcatcgttgctggcctggctgtcctggctgtcctagctgtcctaggagctgtggtggctg ttgtgatgtgtaggaggaagagctcaggtggaaaaggagggagctgctctcaggctgcgtccagcaacagtgccca gggctctgatgagtctctcatcgcttgtaa;

Cw*0314:
(SEQ ID NO: 1686)
gctcccactccatgaggtatttctacaccgctgtgtcccggcccggccgcggggagccccacttcatcgcagtggg ctacgtggacgacacgcagttcgtgcggttcgacagcgacgccgcgagtccgagaggggagccgcgggcgccgtgg gtggagcaggaggggccggagtattgggaccgggagacacagaagtacaagcgccaggcacagactgaccgagtga gcctgcggaacctgcgcggctactacaaccagagcgaggccgggtctcacatcatccagaggatgtatggctgcga cgtggggcccgacgggcgcctcctccgcgggtatgaccagtccgcctacgacggcaaggattacatcgccctgaac gaggacctgcgctcctggaccgccgcggacaccgcggctcagatcacccagcgcaagttggaggcggcccgtgCgg cggagcagctgagagcctacctggagggcacgtgcgtggagtggctccgcagatacctgaagaaTgggaaggagac gctgcagcgcgcgg;

Cw*0315:
(SEQ ID NO: 1687)
gctcccactccatgaggtatttctacaccgctgtgtcccggcccggccgcggggagccccacttcatcgcagtggg ctacgtggacgacacgcagttcgtgcggttcgacagcgacgccgcgagtccgagaggggagccgcgggcgccgtgg gtggagcaggaggggccggagtattgggaccgggagacacagaagtacaagcgccaggcacaggctgaccgagtga acctgcggaaactgcgcggctactacaaccagagcgaggAcgggtctcacatcctccagaggatgtatggctgcga cgtggggcccgacgggcgcctcctccgcgggtatgaccagtCcgcctacgacggcaaggattacatcgccctgaac gaggatctgcgctcctggaccgccgcggacacggcggctcagatcacccagcgcaagtgggaggcggcccgtgagg cggagcagctgagagcctacctggagggccTgtgcgtggagtggctccgcagatacctgaagaaTgggaaggagac gctgcagcgcgcgg;

Cw*0316:
(SEQ ID NO: 1688)
gctcccactccatgaggtatttctacaccgctgtgtcccggcccggccgcggggagccccacttcatcgcagtggg ctacgtggacgacacgcagttcgtgcggttcgacagcgacgccgcgagtccgagaggggagccgcgggcgccgtgg gtggagcaggaggggccggagtattgggaccgggagacacagaagtacaagcgccaggcacagactgaccgagtga gcctgcggaacctgcgcggctactacaaccagagcgaggccgggtctcacatcctccagaggatgtatggctgcga cGtggggcccgacgggcgcctcctccgcgggtatgaccagtCcgcctacgacggcaaggattacatcgccctgaac gaggatctgcgctcctggaccgccgcggacacGgcggctcagatcacccagcgcaagtgggaggcggcccgtgagg cggagcagcTgagagcctacctggagggcacgtgcgtggagtggctccgcagatacctggagaacgggaaggagac gctgcagcgcgcgg;

Cw*040101:
(SEQ ID NO: 1689)
atgcgggtcatggcgccccgaaccctcatcctgctgctctcgggagccctggccctgaccgagacctgggccggct cccactccatgaggtatttctccacatccgtgtcctggcccggccgcggggagccccgcttcatcgcagtgggcta cgtggacgacacgcagttcgtgcggttcgacagcgacgccgcgagtccaagaggggagccgcgggagccgtgggtg gagcaggaggggccggagtattgggaccgggagacacagaagtacaagcgccaggcacaggctgaccgagtgaacc tgcggaaactgcgcggctactacaaccagagcgaggacgggtctcacaccctccagaggatgtttggctgcgacct ggggccggacgggcgcctcctccgcgggtataaccagttcgcctacgacggcaaggattacatcgccctgaacgag gatctgcgctcctggaccgccgcggacacggcggctcagatcacccagcgcaagtgggaggcggcccgtgaggcgg agcagcggagagcctacctggagggcacgtgcgtggagtggctccgcagatacctggagaacgggaaggagacgct gcagcgcgcggaacacccaaagacacacgtgacccaccatcccgtctctgaccatgaggccacccctgaggtgctgg gccctgggcttctaccctgcggagatcacactgacctggcagtgggatggggaggaccaaactcaggacaccgagc ttgtggagaccaggccagcaggagatggaaccttccagaagtgggcagctgtggtggtgccttctggagaagagca gagatacacgtgccatgttcagcacgaggggctgccggaccccctcaccctgagatggaagccgtcttcccagccc accatccccatcgtgggcatcgttgctggcctggctgtcctggctgtcctagctgtcctaggagctAtggtggctg ttgtgatgtgtaggaggaagagctcaggtggaaaaggagggagctgctctcaggctgcgtccagcaacagtgccca gggctctgatgagtctctcatcgcttgtaa;

Cw*040102:
(SEQ ID NO: 1690)
gctcccactccatgaggtatttctccacatccgtgtcctggcccggccgcggggagccccgcttcatcgcagtggg ctacgtggacgacacAcagttcgtgcggttcgacagcgacgccgcgagtccaagaggggagccgcgggagccgtgg gtggagcaggaggggccggagtattgggaccgggagacacagaagtacaagcgccaggcacaggctgaccgagtga acctgcggaaactgcgcggctactacaaccagagcgaggacgggtctcacaccctccagaggatgtttggctgcga cctggggccggacgggcgcctcctccgcgggtataaccagttcgcctacgacggcaaggattacatcgccctgaac gaggatctgcgctcctggaccgccgcggacacggcggctcagatcacccagcgcaagtgggaggcggcccgtgagg cggagcagcggagagcctacctggagggcacgtgcgtggagtggctccgcagatacctggagaacgggaaggagac gctgcagcgcgcgg;

Cw*0403:
(SEQ ID NO: 1691)
atgcgggtcatggcgccccgaaccctcatcctgctgctctcgggagccctggccctgaccgagacctgggccggct cccactccatgaggtatttctacaccgctgtgtcccggcccagccgcgggagagccccActtcatcgcagtgggcta cgtggacgacacgcagttcgtgcggttcgacagcgacgccgcgagtccaagaggggagccgcgggcgccgtgggtg gagcaggaggggccggagtattgggaccgggagacacagaagtacaagcgccaggcacaggctgaccgagtgaacc tgcggaaactgcgcggctactacaaccagagcgaggacgggtctcacaccctccagaggatgtttggctgcgacct ggggccggacgggcgcctcctccgcgggtataaccagttcgcctacgacggcaaggattacatcgccctgaacgag gatctgcgctcctggaccgccgcggacacggcggctcagatcacccagcgcaagtgggaggcggcccgtgaggcgg agcagcggagagcctacctggagggcacgtgcgtggagtggctccgcagatacctggagaacgggaaggagacgct gcagcgcgcggaacacccaaagacacacgtgacccaccatcccgtctctgaccatgaggccaccctgaggtgctgg gccctgggcttctaccctgcggagatcacactgacctggcagtgggatggggaggaccaaaactcaggacaccgagc ttgtggagaccaggccagcaggagatggaaccttccagaagtgggcagctgtggtggtgccttctggagaagagca gagatacacgtgccatgtTcagcacgaggggctgccggaccccctcaccctgagatggaagccgtcttcccagccc accatccccatcgtgggcatcgttgctggcctggctgtcctggctgtcctagctgtcctaggagctgtggtggctg ttgtgatgtgtaggaggaagagctcaggtggaaaaggagggagctgctctcaggctgcgtccagcaacagtgccca gggctctgatgagtctctcatcgcttgtaa;

Cw*0404:
(SEQ ID NO: 1692)
gctcccactccatgaggtatttctccacatccgtgtcctggcccggccgcggggagccccgcttcatcgcagtggg ctacgtggacgacacgcagttcgtgcggttcgacagcgacgccgcgagtccaagaggggagccgcgggAgccgtgg gtggagcaggaggggccggagtattgggaccgggagacacagaagtacaagcgccaggcacaggctgaccgagtga acctgcggaaactgcgcggctactacaaccagagcgaggacgggtctcacaccctccagaggatgtttggctgcga cctggggccggacgggcgcctcctccgcgggtataaccagttcgcctacgacggcaaggattacatcgccctgaac gaggatctgcgctcctggaccgccgcggacacggcggctcagatcacccagcgcaagtgggaggcggcccgtgagg cggagcagcTgagagcctacctggagggcacgtgcgtggagtggctccgcagatacctggagaacgggaaggagac gctgcagcgcgcgg;

Cw*0405:
(SEQ ID NO: 1693)
gctcccactccatgaggtatttctccacatccgtgtcctggcccggccgcggggagccccgcttcatcgcagtggg ctacCtggacgacacgcagttcgtgcggttcgacagcgacgccgcgagtccaagaggggagccgcgggagccgtgg gtggagcaggaggggccggagtattgggaccgggagacacagaagtacaagcgccaggcacaggctgaccgagtga acctgcggaaactgcgcggctactacaaccagagcgaggacgggtctcacaccctccagaggatgtttggctgcga cctggggccggacgggcgcctcctccgcgggtataaccagttcgcctacgacggcaaggattacatcgccctgaac gaggatctgcgctcctggaccgccgcggacacggcggctcagatcacccagcgcaagtgggaggcggcccgtgagg cggagcagcggagagcctacctggagggcacgtgcgtggagtggctccgcagatacctggagaacgggaaggagac gctgcagcgcgcgg;

Cw*0406:
(SEQ ID NO: 1694)
gctcccactccatgaggtatttctacaccgctgtgtcccggcccagccgcgggagagccccActtcatcgcagtggg ctacgtggacgacacgcagttcgtgcggttcgacagcgacgccgcgagtccaagaggggagccgcgggcgccgtgg gtggagcaggaggggccggagtattgggaccgggagacacagaagtacaagcgccaggcacaggctgaccgagtga acctgcggaaactgcgcggctactacaaccagagcgaggacgggtctcacaccctccagaggatgtttggctgcga cctggggccGgacgggcgcctcctccgcgggtataaccagttcgcctacgacggcaaggattacatcgccctgaac gaggatctgcgctcctggaccgccgcggacacggcggctcagatcacccagcgcaagtgggaggcggcccgtgagg cggagcagcTgagagcctacctggagggcacgtgcgtggagtggctccgcagatacctggagaacgggaaggagac gctgcagcgcgcgg;

Cw*0407:
(SEQ ID NO: 1695)
gctcccactccatgaggtatttctccacatccgtgtccTggcccggccgcggggagccccgcttcatcgcagtggg ctacgtggacgacacgcagttcgtgcggttcgacagcgacgccgcgagtccaagaggggagccgcgggcgccgtgg gtggagcaggaggggccggagtattgggaccgggagacacagaagtacaagcgccaggcacagGctgaccgagtga acctgcggaaactgcgcggctactacaaccagagcgaggacgggtctcacaccctccagaggatgtttggctgcga cctggggccggacgggcgcctcctccgcgggtataaccagttcgcctacgacggcaaggattacatcgccctgaac gaggatctgcgctcctggaccgccgcggacacggcggctcagatcacccagcgcaagtgggaggcggcccgtgagg cggagcagcggagagcctacctggagggcacgtgcgtggagtggctccgcagatacctggagaacgggaaggagac gctgcagcgcgcgg;

Cw*0408:
(SEQ ID NO: 1696)
gctcccactccatgaggtatttctccacatccgtgtcctggcccggccgcggggagccccgcttcatcgcagtggg ctacgtggacgacacgcagttcgtgcggttcgacagcgacgccgcgagtccaagaggggagccgcgggAgccgtgg gtggagcaggaggggccggagtattgggaccgggagacacagaagtacaagcgccaggcacaggctgaccgagtga acctgcggaaactgcgcggctactacaaccagagcgaggacgggtctcacaccctccagaggatgtttggctgcga cctggggccggacgggcgcctcctccgcgggtataaccagttcgcctacgacggcaaggattacatcgccctgaac gaggatctgcgctcctggaccgccgcggacacggcggctcagatcacccagcgcaagtgggaggcggcccgtgagg cggagcagcggagagcctacctggagggccTgtgcgtggagtggctccgcagatacctggagaacgggaaggagac gctgcagcgcgcgg;

Cw*0410:
(SEQ ID NO: 1697)
gctcccactccatgaggtatttctccacatccgtgtcctggcccggccgcggggagccccgcttcatcgcagtggg ctacgtggacgacacgcagttcgtgcggttcgacagcgacgccgcgagtccaagaggggagccgcgggAgccgtgg gtggagcaggaggggccggagtattgggaccgggagacacagaagtacaagcgccaggcacagactgaccgagtga -continued

```
acctgcggaaactgcgcggctactacaaccagagcgaggacgggtctcacaccctccagaggatgtttggctgcga
cctggggccggacgggcgcctcctccgcgggtataaccagttcgcctacgacggcaaggattacatcgccctgaac
gaggatctgcgctcctggaccgccgcggacacggcggctcagatcacccagcgcaagtgggaggcggcccgtgagg
cggagcagcggagagcctacctggagggcacgtgcgtggagtggctccgcagatacctggagaacgggaaggagac
gctgcagcgcgcgg;
```

Cw*0501:
(SEQ ID NO: 1698)
```
atgcgggtcatggcgccccgaaccctcatcctgctgctctcggagccctggccctgaccgagacctgggcctgct
cccactccatgaggtatttctacaccgccgtgtcccggcccggccgcggagagccccgcttcatcgcagtgggcta
cgtggacgacacgcagttcgtgcagttcgacagcgacgccgcgagtccaagaggggagccgcgggcgccgtgggtg
gagcaggaggggccggagtattgggaccgggagacacagaagtacaagcgccaggcacagactgaccgagtgaacc
tgcggaaActgcgcggctactacaaccagagcgaggccgggtctcacaccctccagaggatgtatggctgcgacct
ggggcccgacgggcgcctcctccgcgggtataaccagttcgcctacgacggcaaggattacatcgccctgaatgag
gacctgcgctcctggaccgccgcggacaAggcggctcagatcacccagcgcaagtgggaggcggcccgtgaggcgg
agcagcggagagcctacctggagggcacgtgcgtggagtggctccgcagatacctggagaacgggaagaagacgct
gcagcgcgcggaacacccaaagacacacgtgacccaccatcccgtctctgaccatgaggccaccctgaggtgctgg
gccctgggcttctaccctgcggagatcacactgacctggcagcgggatggcgaggaccaaactcaggacaccgagc
ttgtggagaccaggccagcaggagatggaaccttccagaagtgggcagctgtggtggtgccttctggagaagagca
gagatacacgtgccatgtgcagcacgaggggctgccagagcccctcaccctgagatgggGgccatcttcccagccc
accatccccatcgtgggcatcgttgctggcctggctgtcctggctgtcctagctgtcctaggagctgtgatggctg
ttgtgatgtgtaggaggaagagctcaggtggaaaaggagggagctgctctcaggctgcgtccagcaacagtgccca
gggctctgatgagtctctcatcgcttgtaa;
```

Cw*0502:
(SEQ ID NO: 1699)
```
gctcccactccatgaggtatttctacaccgccgtgtcccggcccggccgcggagagccccgcttcatcgcagtggg
ctacgtggacgacacgcagttcgtgcagttcgacagcgacgccgcgagtccaagaggggagccgcgggcgccgtgg
gtggagcaggaggggccggagtattgggaccgggagacacagaagtacaagcgccaggcacagactgaccgagtga
acctgcggaaactgcgcggctactacaaccagagcgaggccgggtctcacaccctccagaggatgtatggctgcga
cctggggcccgacgggcgcctcctccgcgggtataaccagttcgcctacgacggcaaggattacatcgccctgaat
gaggacctgcgctcctggaccgccgcggacaaggcggctcagatcacccagcgcaagtgggaggcggcccgtgagg
cggagcagcggagagcctacctggagggcatgtgcgtggagtggctGcgcagatacctggagaacgggaaggagac
gctgcagcgcgcgg;
```

Cw*0503:
(SEQ ID NO: 1700)
```
atgcgggtcatggcgccccgaaccctcatcctgctgctctcggagccctggccctgaccgagacctgggcctgct
cccactccatgaggtatttctacaccgccgtgtcccggcccggccgcggagagccccgcttcatcgcagtgggcta
cgtggacgacacgcagttcgtgcagttcgacagcgacgccgcgagtccaagaggggagccgcgggcgccgtgggtg
gagcaggaggggccggagtattgggaccgggagacacagaagtacaagcgccaggcacagactgaccgagtgaacc
tgcggaaactgcgcggctactacaaccagagcgaggccgggtctcacaccctccagaggatgtatggctgcgacct
ggggcccgacgggcgcctcctccgcgggtataaccagttcgcctacgacggcaaggattacatcgccctgaatgag
gacctgcgctcctggaccgccgcggacaaggcggctcagatcacccagcgcaagtgggaggcggcccgtgaggcgg
agcagcggagagcctacctggagggcacgtgcgtggagtggctccgcagatacctggagaacgggaagaagacgct
gcagcgcgcggacccccaaagacacatgtgacccaccaccccatctctgaccatgaggTcaccctgaggtgctgg
gccctgggcttctaccctgcggagatcacactgacctggcagcgggatggcgaggaccaaactcaggacaccgagc
```

-continued ttgtggagaccaggccagcaggagatggaaccttccagaagtgggcagctgtggtggtgccttctggagaagagca gagatacacgtgccatgtgcagcacgaggggctgccagagcccctcaccctgagatgggggccatcttcccagccc accatcccatcgtgggcatcgttgctggcctggctgtcctggctgtcctagctgtcctaggagctgtgatggctg ttgtgatgtgtaggaggaagagctcaggtggaaaaggagggagctgctctcaggctgcgtccagcaacagtgccca gggctctgatgagtctctcatcgcttgtaa;

Cw*0504:
(SEQ ID NO: 1701)
gctcccactccatgaggtatttctacaccgccgtgtcccggcccggccgcggagagccccgcttcatcgcagtggg ctacgtggacgacacgcagttcgtgcagttcgacagcgacgccgcgagtccaagaggggagccgcgggcgccgtgg gtggagcaggaggggccggagtattgggaccgggagacacagaagtacaagcgccaggcacagactgaccgagtga acctgcggaaactgcgcggctactacaaccagagcgaggcccgggtctcacaccctccagaggatgtatggctgcga cctggggcccgacgggcgcctcctccgcgggtatgaccagtCcgcctacgacggcaaggattacatcgccctgaat gaggacctgcgctcctggaccgccgcggacaAggcggctcagatcacccagcgcaagtgggaggcggcccgtgagg cggagcagcggagagcctacctggagggcacgtgcgtggagtggctccgcagatacctggagaacgggaagAagac gctgcagcgcgcgg;

Cw*0505:
(SEQ ID NO: 1702)
gctcccactccatgaggtatttctacaccgccgtgtcccggcccggccgcggagagccccgcttcatcgcagtggg ctacgtggacgacacgcagttcgtgcagttcgacagcgacgccgcgagtccaagaggggagccgcgggcgccgtgg gtggagcaggaggggccggagtattgggaccgggagacacagaagtacaagcgccaggcacagactgaccgagtga acctgcggaaactgcgcggctactacaaccagagcgaggcccgggtctcacaccctccagaggatgtatggctgcga cGtggggcccgacgggcgcctcctccgcgggtataaccagtTcgcctacgacggcaaggattacatcgccctgaat gaggacctgcgctcctggaccgccgcggacaAggcggctcagatcacccagcgcaagtgggaggcggcccgtgagg cggagcagcggagagcctacctggagggcacgtgcgtggagtggctccgcagatacctggagaacgggaagAagac gctgcagcgcgcgg;

Cw*0506:
(SEQ ID NO: 1703)
gctcccactccatgaggtatttctacaccgccgtgtcccggcccggccgcggagagccccgcttcatcgcagtggg ctacgtggacgacacgcagttcgtgcagttcgacagcgacgccgcgagtccaagaggggagccgcgggcgcGgtgg gtggagcaggaggggccggagtattgggaccgggagacacagaagtacaagcgccaggcacagactgaccgagtga acctgcggaaactgcgcggctactacaaccagagcgaggcccgggtctcacaccctccagaggatgtatggctgcga cctggggcccgacgggcgcctcctccgcgggtataaccagttcgcctacgacggcaaggattacatcgccctgaat gaggacctgcgctcctggaccgccgcggacaaggcggctcagatcacccagcgcaagtgggaggcggcccgtgagg cggagcagcggagagcctacctggagggcacgtgcgtggagtggctccgcagatacctggagaacgggaagaagac gctgcagcgcgcgg;

Cw*0602:
(SEQ ID NO: 1704)
atgcgggtcatggcgccccgaaccctcatcctgctgctctcgggagccctggccctgaccgagacctgggcctgct cccactccatgaggtatttcgacaccgccgtgtcccggcccggccgcggagagccccgcttcatctcagtgggcta cgtggacgacacgcagttcgtgcggttcgacagcgacgccgcgagtccgagaggggagccCgggcgccgtgggtg gagcaggaggggccggagtattgggaccgggagacacagaagtacaagcgccaggcacaggctgaccgagtgaacc tgcggaaactgcgcggctactacaaccagagcgaggacgggtctcacaccctccagtggatgtatggctgcgacct ggggcccgacgggcgcctcctccgcgggtatgaccagtccgcctacgacggcaaggattacatcgccctgaacgag gacctgcgctcctggaccgccgcggacacggcggctcagatcacccagcgcaagtgggaggcggcccgtgaggcgg -continued agcagTggagagcctacctggagggcacgtgcgtggagtggctccgcagatacctggagaacgggaaggagacgct gcagcgcgcggaacacccaaagacacacgtgacccaccatcccgtctctgaccatgaggccaccctgaggtgctgg gccctgggcttctaccctgcggagatcacactgacctggcagcgggatggcgaggaccaaactcaggacaccgagc ttgtggagaccaggccagcaggagatggaaccttccagaagtgggcagctgtggtggtgccttctggagaagagca gagatacacgtgccatgtgcagcacgaggggctgccagagcccctcaccctgagatgggagccatcttcccagccc accatcccatcgtgggcatcgttgctggcctggctgtcctggctgtcctagctgtcctaggagctgtgAtggctg ttgtgatgtgtaggaggaagagctcaggtggaaaaggagggagctgctctcaggctgcgtccagcaacagtgccca gggctctgatgagtctctcatcgcttgtaa;

Cw*0603:

(SEQ ID NO: 1705)
gctcccactccatgaggtatttctacaccgcTgtgtcccggcccggccgcggagagccccgcttcatctcagtggg ctacgtggacgacacgcagttcgtgcggttcgacagcgacgccgcgagtccgagaggggagccCcgggcgccgtgg gtggagcaggaggggccggagtattgggaccgggagacacagaagtacaagcgccaggcacaggctgaccgagtga acctgcggaaactgcgcggctactacaaccagagcgaggacgggtctcacaccctccagtggatgtatggctgcga cctggggcccgacgggcgcctcctccgcgggtatgaccagtCcgcctacgacggcaaggattacatcgccctgaac gaggacctgcgctcctggaccgccgcggacacggcggctcagatcacccagcgcaagtgggaggcggcccgtgagg cggagcagTggagagcctacctggagggcacgtgcgtggagtggctccgcagatacctggagaacgggaaggagac gctgcagcgcgcgg;

Cw*0604:

(SEQ ID NO: 1706)
gctcccactccatgaggtatttcgacaccgccgtgtcccggcccggccgcggagagccccgcttcatctcagtggg ctacgtggacgacacgcagttcgtgcggttcgacagcgacgccgcgagtccgagaggggagccCcgggcgccgtgg gtggagcaggaggggccggagtattgggaccgggagacacagaagtacaagcgccaggcacaggctgaccgagtga acctgcggaaactgcgcggctactacaaccagagcgaggacgggtctcacaccctccagtggatgtatggctgcga cctggggcccgacgggcgcctcctccgcgggtatgaccagtccgcctacgacggcaaggattacatcgccctgaac gaggacctgcgctcctggaccgccgcggacacggcggctcagatcacccagcgcaagtgggaggcggcccgtgagg cggagcagcTgagagcctacctggagggcacgtgcgtggagtggctccgcagatacctggagaacgggaaggagac gctgcagcgcgcgg;

Cw*0605:

(SEQ ID NO: 1707)
gctcccactccatgaggtatttcgacaccgccgtgtcccggcccggccgcggagagccccgcttcatctcagtggg ctacgtggacgacacgcagttcgtgcagttcgacagcgacgccgcgagtccAagaggggagccCcgggcgccgtgg gtggagcaggaggggccggagtattgggaccgggagacacagaagtacaagcgccaggcacagactgaccgagtga acctgcggaaactgcgcggctactacaaccagagcgaggacgggtctcacaccctccagtggatgtatggctgcga cctggggcccgacgggcgcctcctccgcgggtatgaccagtCcgcctacgacggcaaggattacatcgccctgaac gaggacctgcgctcctggaccgccgcggacacGgcggctcagatcacccagcgcaagtgggaggcggcccgtgagg cggagcagcggagagcctacctggagggcacgtgcgtggagtggctccgcagatacctggagaacgggaaggagac gctgcagcgcgcgg;

Cw*0606:

(SEQ ID NO: 1708)
gctcccactccatgaggtatttcgacaccgccgtgtcccggcccggccgcggagagccccgcttcatctcagtggg ctacgtggacgacacgcagttcgtgcggttcgacagcgacgccgcgagtccgagaggggagccCcgggcgccgtgg gtggagcaggaggggccggagtattgggaccgggagacacagaagtacaagcgccaggcacaggctgaccgagtga acctgcggaaactgcgcggctactacaaccagagcgaggacgggtctcacaccctccagtggatgtatggctgcga cctggggcccgacgggcgcctcctccgcgggtatgaccagtccgcctacgacggcaaggattacatcgccctgaac gaggacctgcgctcctggaccgccgcggacacggcggctcagatcacccagcgcaagtgggaggcggcccgtgagg cggagcagcggagagcctacctggagggcacgtgcgtggagtggctccgcagatacctggagaacgggaaggagac gctgcagcgcgcggaacacccaaagacacacgtgacccaccatcccgtctctgaccatgaggccaccctgaggtgc tgggccctgggcttctaccctgcggagatcacactgacctggcagcgggatggcgaggaccaaactcaggacaccg agcttgtggagaccaggccagcaggagatggaaccttccagaagtgggcagctgtggtggtgccttctggagaaga gcagagatacacgtgccatgtgcagcacgaggggctgccagagcccctcaccctgagatgggagccatcttcccag cccaccatcccatcgtgggcatcgttgctggcctggctgtcctggctgtcctagctgtcctaggagctgtgAtgg ctgttgtgatgtgtaggaggaagagctcag;

Cw*0607:
(SEQ ID NO: 1709)
gctcccactccatgaggtatttcgacaccgccgtgtcccggcccggccgcggagagccccgcttcatctcagtggg ctacgtggacgacacgcagttcgtgcggttcgacagcgacgccgcgagtccgagaggggagcccggcgccgtgg gtggagAaggagggccggagtattgggaccgggagacacagaagtacaagcgccaggcacaggctgaccgagtga acctgcggaaactgcgcggctactacaaccagagcgaggacgggtctcacaccctccagtggatgtatggctgcga cctggggcccgacgggcgcctcctccgcgggtatgaccagtccgcctacgacggcaaggattacatcgccctgaac gaggacctgcgctcctggaccgccgcggacacggcggctcagatcacccagcgcaagtgggaggcggcccgtgagg cggagcagtggagagcctacctggagggcacgtgcgtggagtggctccgcagatacctggagaacgggaaggagac gctgcagcgcgcgg;

Cw*0608:
(SEQ ID NO: 1710)
gctcccactccatgaggtatttcgacaccgccgtgtcccggcccggccgcggagagccccgcttcatctcagtggg ctacgtggacgacacgcagttcgtgcggttcgacagcgacgccgcgagtccgagaggggagcccgggcgccgtgg gtggagcaggaggggccggagtattgggaccgggagacacagaagtacaagcgccaggcacaggctgaccgagtga acctgcggaaactgcgcggctactacaaccagagcgaggAcgggtctcacaccctccagtggatgtatggctgcga cctggggcccgacgggcgcctcctccgcgggtatgaccagtCcgcctacgacggcaaggattacatcgccctgaac gaggacctgcgctcctggaccgccgcggacacGgcggctcagatcacccagcgcaagtgggaggcggcccgtgagg cggagcagTggagagcctacctggagggcgAgtgcgtggagtggctccgcagatacctggagaacgggaaggagac gctgcagcgcgcgg;

Cw*0609:
(SEQ ID NO: 1711)
gctcccactccatgaggtatttcgacaccgccgtgtcccggcccggccgcggagagccccgcttcatctcagtggg ctacgtggacgacacgcagttcgtgcggttcgacagcgacgccgcgagtccgagaggggagccCcgggcgccgtgg gtggagcaggaggggccggagtattgggaccgggagacacagaagtacaagcgccaggcacaggctgaccgagtga acctgcggaaactgcgcggctactacaaccagagcgaggacgggtctcacaccctccagtggatgtatggctgcga cctggggcccgacgggcgcctcctccgcgggtataaccagtTcgcctacgacggcaaggattacatcgccctgaac gaggacctgcgctcctggaccgccgcggacacggcggctcagatcacccagcgcaagtgggaggcggcccgtgagg cggagcagTggagagcctacctggagggcacgtgcgtggagtggctccgcagatacctggagaacgggaaggagac gctgcagcgcgcgg;

Cw*070101:
(SEQ ID NO: 1712)
atgcgggtcatggcgccccgagccctcctcctgctgctctcggaggcctggcccctgaccgagacctggcctgct cccactccatgaggtatttcgacaccgccgtgtcccggcccggccgcggagagccccgcttcatctcagtgggcta cgtggacgacacgcagttcgtgcggttcgacagcgacgccgcgagtccgagaggggagccgcgggcgccgtgggtg gagcaggaggggccggagtattgggaccgggagacacagaactacaagcgccaggcacaggctgaccgagtgagcc -continued tgcggaacctgcgcggctactacaaccagagcgaggacgggtctcacaccctccagaggatgtAtggctgcgacct ggggcccgacgggcgcctcctccgcgggtatgaccagtccgcctacgacggcaaggattacatcgccctgaacgag gacctgcgctcctggaccgccgcggacaccgcggctcagatcacccagcgcaagtTggaggcggcccgtgcggcgg agcagctgagagcctacctggagggcacgtgcgtggagtggctccgcagatacctggagaacgggaaggagacgct gcagcgcgcAgaaccccaaagacacacgtgacccaccacccctctctgaccatgaggccaccctgaggtgctgg gccctgggcttctaccctgcggagatcacactgacctggcagcgggatggggaggaccagacccaggacaccgagc ttgtggagaccaggccagcaggagatggaaccttccagaagtgggcagctgtggtggtgccttctggacaagagca gagatacacgtgccatatgcagcacgaggggctgcaagagcccctcaccctgagctgggagccatcttcccagccc accatccccatcatgggcatcgttgctggcctggctgtcctggttgtcctagctgtccttggagctgtggtcaccg ctatgatgtgtaggaggaagagctcaggtggaaaaggagggagctgctctcaggctgcgtgcagcaacagtgccca gggctctgatgagtctctcatcActtgtaa;

Cw*070102:

(SEQ ID NO: 1713)

atgcgggtcatggcgccccgagccctcctcctgctgctctcggggaggcctggccctgaccgagacctgggcctgct cccactccatgaggtatttcgacaccgccgtgtcccggcccggccgcggagagccccgcttcatctcagtgggcta cgtggacgacacgcagttcgtgcggttcgacagcgacgccgagtccgagaggggagccgcgggcgccgtgggtg gagcaggaggggccggagtatgggaccgggagacacagaactacaagcgccaggcacaggctgaccgagtgagcc tgcggaacctgcgcggctactacaaccagagcgaggacgggtctcacaccctccagaggatgtatggctgcgacct ggggcccgacgggcgcctcctccgcgggtatgaccagtccgcctacgacggcaaggattacatcgccctgaacgag gacctgcgctcctggaccgccgcggacaccgcggctcagatcacccagcgcaagttggaggcggcccgtgcggcgg agcagctgagagcctacctggagggcacgtgcgtggagtggctccgcagatacctggagaacgggaaggagacgct gcagcgcgcagaaccccaaagacacacgtgacccaccacccctctctgaccatgaggccaccctgaggtgctgg gccctgggcttctaccctgcggagatcacactgacctggcagcgggatggggaggaccagacccaggacaccgagc ttgtggagaccaggccagcaggagatggaaccttccagaagtgggcagctgtggtggtgccttctggacaagagca gagatacacgtgccatatgcagcacgaggggctgcaagagcccctcaccctgagctgggagccatcttcccagccT accatccccatcatgggcatcgttgctggcctggctgtcctggttgtcctagctgtccttggagctgtggtcaccg ctatgatgtgtaggaggaagagctcaggtggaaaaggagggagctgctctcaggctgcgtgcagcaacagtgccca gggctctgatgagtctctcatcacttgtaa;

Cw*070201:

(SEQ ID NO: 1714)

atgcgggtcatggcgccccgagccctcctcctgctgctctcggggaggcctggccctgaccgagacctgggcctgct cccactccatgaggtatttcgacaccgccgtgtcccggcccggccgcggagagccccgcttcatctcagtgggcta cgtggacgacacgcagttcgtgcggttcgacagcgacgccgagtccgagaggggagccgcgggcgccgtgggtg gagcaggaggggccggagtatgggaccgggagacacagaagtacaagcgccaggcacaggctgaccgagtgagcc tgcggaacctgcgcggctactacaaccagagcgaggacgggtctcacaccctccagaggatgtCtggctgcgacct ggggcccgacgggcgcctcctccgcgggtatgaccagtccgcctacgacggcaaggattacatcgccctgaacgag gacctgcgctcctggaccgccgcggacaccgcggctcagatcacccagcgcaagtTggaggcggcccgtgcggcgg agcagctgagagcctacctggagggcacgtgcgtggagtggctccgcagatacctggagaacgggaaggagacgct gcagcgcgcagaaccccaaagacacacgtgacccaccacccctctctgaccatgaggccaccctgaggtgctgg gccctgggcttctaccctgcggagatcacactgacctggcagcgggatggggaggaccagacccaggacaccgagc ttgtggagaccaggccagcaggagatggaaccttccagaagtgggcagctgtggtggtgccttctggacaagagca gagatacacgtgccatatgcagcacgaggggctgcaagagcccctcaccctgagctgggagccatcttcccagccc accatccccatcatgggcatcgttgctggcctggctgtcctggttgtcctagctgtccttggagctgtggtcaccg ctatgatgtgtaggaggaagagctcaggtggaaaaggagggagctgctctcaggctgcgtgcagcaacagtgccca gggctctgatgagtctctcatcActtgtaa;

Cw*0703:

(SEQ ID NO: 1715)
tgctcccactccatgaggtatttcgacaccgccgtgtcccggcccggcgccggagagccccgcttcatctcagtgg gctacgtggacgacacgcagttcgtgcggttcgacagcgacgccgcgagtccgagaggggagccgcgggcgccgtg ggtggagcaggaggggccggagtattgggaccgggagacacagaagtacaagcgccaggcacaggctgaccgagtg agcctgcggaacctgcgcggctactacaaccagagcgaggacgggtctcacaccctccagaggatgtctggctgcg acctggggcccgacgggcgcctcctccgcgggtatgaccagtccgcctacgacggcaaggattacatcgccctgaa cgaggacctgcgctcctggaccgcggcggacaccgcggctcagatcacccagcgcaagtgggaggcggcccgtgcg gcggagcagctgagagcctacctggagggActgtgcgtggagtggctccgcagatacctggagaacgggaaggaga cgctgcagcgcgcagaaccccaaagacacacgtgacccaccacccctctctgaccatgaggccaccctgaggtg ctgggccctgggcttctaccctgcggagatcacactgacctggcagcgggatggggaggaccagacccaggacacc gagcttgtggagaccaggccagcaggagatggaaccttccagaagtgggcagctgtggtggtgccttctggacaag agcagagatacacgtgccatatgcagcacgaggggctgcaagagcccctcaccctgagctgggagccatcttccca gcccaccatccccatcatgggcatcgttgctggcctggctgtcctggttgtcctagctgtccttggagctgtggtc accgctatgatgtgtaggaggaagagctcaggtggaaaaggagggagctgctctcaggctgcgtgcagcaacagtg cccagggctctgatgagtctctcatcacttgtaa;

Cw*070401:

(SEQ ID NO: 1716)
atgcgggtcatggcgccccgagccctcctcctgctgctctcggggaggcctggccctgaccgagacctgggcctgct cccactccatgaggtatttcgacaccgccgtgtcccggcccggccgcggagagccccgcttcatctcagtgggcta cgtggacgacacgcagttcgtgcggttcgacagcgacgccgcgagtccgagaggggagccccgggcgccgtgggtg gagcaggaggggccggagtattgggaccgggagacacagaagtacaagcgccaggcacaggctgaccgagtgagcc tgcggaacctgcgcggctactacaaccagagcgaggacgggtctcacaccttccagaggatgtatggctgcgacct gggggcccgacgggcgcctcctccgcgggtatgaccagttcgcctacgacggcaaggattacatcgccctgaacgag gacctgcgctcctggaccgccgcggacaccgcggctcagatcacccagcgcaagttggaggcggcccgtgcggcgg agcaggaCagagcctacctggagggcacgtgcgtggagtggctccgcagatacctggagaacgggaagaagacgct gcagcgcgcggaaccccaaagacacacgtgacccaccaccccctctctgaccatgaggccaccctgaggtgctgg gccctgggcttctaccctgcggagatcacactgacctggcagcgggatggggaggaccagacccaggacaccgagc ttgtggagaccaggccagcaggagatggaaccttccagaagtgggcagctgtggtggtgccttctggacaagagca gagatacacgtgccatatgcagcacgaggggctgcaagagcccctcaccctgagctgggagccatcttcccagccc accatccccatcatgggcatcgttgctggcctggctgtcctggttgtcctagctgtccttggagctgtggtcaccg ctatgatgtgtaggaggaagagctcaggtggaaaaggagggagctgctctcaggctgcgtgcagcaacagtgccca gggctctgatgagtctctcatcActtgtaa;

Cw*070402:

(SEQ ID NO: 1717)
atgcgggtcatggcgccccgagccctcctcctgctgctctcggggaggcctggccctgaccgagacctgggcctgct cccactccatgaggtatttcgacaccgccgtgtcccggcccggccgcggagagccccgcttcatctcagtgggcta cgtggacgacacgcagttcgtgcggttcgacagcgacgccgcgagtccgagaggggagccccgggcgccgtgggtg gagcaggaggggccggagtattgggaccgggagacacagaagtacaagcgccaggcacaggctgaccgagtgagcc tgcggaacctgcgcggctactaTaaccagagcgaggacgggtctcacaccttccagaggatgtatggctgcgacct gggggcccgacgggcgcctcctccgcgggtatgaccagttcgcctacgacggcaaggattacatcgccctgaacgag -continued gacctgcgctcctggaccgccgcggacaccgcggctcagatcacccagcgcaagttggaggcggcccgtgcggcgg agcaggacagagcctacctggagggcacgtgcgtggagtggctccgcagatacctggagaacgggaagaagacgct gcagcgcgcggaaccccaaagacacacgtgacccaccacccctctctgaccatgaggccaccctgaggtgctgg gccctgggcttctaccctgcggagatcacactgacctggcagcgggatggggaggaccagacccaggacaccgagc ttgtggagaccaggccagcaggagatggaaccttccagaagtgggcagctgtggtggtgccttctggacaagagca gagatacacgtgccatatgcagcacgaggggctgcaagagcccctcccctgagctgggagccatcttcccagccc accatccccatcatgggcatcgttgctggcctggctgtcctggttgtcctagctgtccttggagctgtggtcaccg ctatgatgtgtaggaggaagagctcaggtggaaaaggagggagctgctctcaggctgcgtgcagcaacagtgccca gggctctgatgagtctctcatcacttgtaa;

Cw*0705:

(SEQ ID NO: 1718)
gctcccactccatgaggtatttcgacaccgccgtgtcccggcccggccgcggagagcccccgcttcatctcagtggg ctacgtggacgacacgcagttcgtgcggttcgacagcgacgccgcgagtccgagaggggagccgcgggcgccgtgg gtggagcaggaggggccggagtattgggaccgggagacacagaagtacaagcgccaggcacaggctgaccgagtga gcctgcggaacctgcgcggctactacaaccagagcgaggacgggtctcacaccctccagaaTatgtatggctgcga cctggggcccgacgggcgcctcctccgcgggtatgaccagtccgcctacgacggcaaggattacatcgccctgaac gaggacctgcgctcctggaccgccgcggacaccgcggctcagatcacccagcgcaagttggaggcggcccgtgcgg cggagcagctgagagcctacctggagggcacgtgcgtggagtggctccgcagatacctggagaacgggaaggagac gctgcagcgcgcag;

Cw*0706:

(SEQ ID NO: 1719)
atgcgggtcatggcgccccgagccctcctcctgctgctctcggggaggcctggccctgaccgagacctgggcctgct cccactccatgaggtatttcgacaccgccgtgtcccggcccggccgcggagagcccgcttcatctcagtgggcta cgtggacgacacgcagttcgtgcggttcgacagcgacgccgcgagtccgagaggggagccgcgggcgccgtgggtg gagcaggaggggccggagtattgggaccgggagacacagaactacaagcgccaggcacaggctgaccgagtgagcc tgcggaacctgcgcggctactacaaccagagcgaggacgggtctcacaccctccagaggatgtatggctgcgacct ggggcccgacgggcgcctcctccgcgggtatgaccagtccgcctacgacggcaaggattacatcgccctgaacgag gacctgcgctcctggaccgccgcggacaccgcggctcagatcacccagcgcaagttggaggcggcccgtgcggcgg agcagctgagagcctacctggagggcacgtgcgtggagtggctccgcagatacctggagaacgggaaggagacgct gcagcgcgcagaaccccaaagacacacgtgacccaccacccctctctgaccatgaggccaccctgaggtgctgg gccctgggcttctaccctgcggagatcacactgacctggcagcgggatggggaggaccagacccaggacaccgagc ttgtggagaccaggccagcaggagatggaaccttccagaagtgggcagctgtggtggtgccttctggacaagagca gagatacacgtgccatatgcagcacgaggggctgcaagagcccctcccctgagctgggagccatcttcccagccc accatccccatcatgggcatcgttgctggcctggctgtcctggttgtcctagctgtccttggagctgtggtcaccg ctaAgatgtgtaggaggaagagctcaggtggaaaaggagggagctgctctcaggttgcgtgcagcaacagtgccca gggctctgatgagtctctcatcacttgtaa;

Cw*0707:

(SEQ ID NO: 1720)
gctcccactccatgaggtatttcgacaccgccgtgtcccggcccggccgcggagagcccccgcttcatctcagtggg ctacgtggacgacacgcagttcgtgcggttcgacagcgacgccgcgagtccgagaggggagccgcgggcgccgtgg gtggagcaggaggggccggagtattgggaccgggagacacagaactacaagcgccaggcacaggctgaccgagtga acctgcggaaActgcgcggctactacaaccagagcgaggccgggtctcacaccctccagaggatgtAtggctgcga cctggggcccgacgggcgcctcctccgcgggtatgaccagtCcgcctacgacggcaaggattacatcgccctgaac gaggacctgcgctcctggaccgccgcggacaccgcggctcagatcacccagcgcaagtTggaggcggcccgtgcgg -continued cggagcagctgagagcctacctggagggcacgtgcgtggagtggctccgcagatacctggagaacgggaaggagac gctgcagcgcgcAg;

Cw*0708:

(SEQ ID NO: 1721)

gctcccactccatgaggtatttcgacaccgccgtgtcccggcccggccgcggagagccccgcttcatctcagtggg ctacgtggacgacacgcagttcgtgcggttcgacagcgacgccgcgagtccgagaggggagccgcgggcgccgtgg gtggagcaggaggggccggagtattgggaccgggagacacagaagtacaagcgccaggcacaggctgaccgagtga gcctgcggaacctgcgcggctactacaaccagagcgaggacgggtctcacaccctccagaggatgtTtggctgcga cctggggcccgacgggcgcctcctccgcgggtatgaccagtCcgcctacgacggcaaggattacatcgccctgaac gaggacctgcgctcctggaccgccgcggacaccgcggctcagatcacccagcgcaagtTggaggcggcccgtgcgg cggagcagctgagagcctacctggagggcacgtgcgtggagtggctccgcagatacctggagaacgggaaggagac gctgcagcgcgcAg;

Cw*0709:

(SEQ ID NO: 1722)

gctcccactccatgaggtatttcgacaccgccgtgtcccggcccggccgcggagagccccgcttcatctcagtggg ctacgtggacgacacgcagttcgtgcggttcgacagcgacgccgcgagtccgagaggggagccgcgggcgccgtgg gtggagcaggaggggccggagtattgggaccgggagacacagaactacaagcgccaggcacaggctgaccgagtga acctgcggaaActgcgcggctactacaaccagagcgaggAcgggtctcacaccctccagaggatgtAtggctgcga cctggggcccgacgggcgcctcctccgcgggtatgaccagtCcgcctacgacggcaaggattacatcgccctgaac gaggacctgcgctcctggaccgccgcggacaccgcggctcagatcacccagcgcaagtTggaggcggcccgtgcgg cggagcagctgagagcctacctggagggcacgtgcgtggagtggctccgcagatacctggagaacgggaaggagac gctgcagcgcgcAg;

Cw*0710:

(SEQ ID NO: 1723)

gctcccactccatgaggtatttcgacaccgccgtgtcccggcccggccgcggagagccccgcttcatctcagtggg ctacgtggacgacacgcagttcgtgcggttcgacagcgacgccgcgagtccgagaggggagccgcgggcgccgtgg gtggagcaggaggggccggagtattgggaccgggagacacagaagtacaagcgccaggcacaggctgaccgagtga gcctgcggaacctgcgcggctactacaaccagagcgaggacgggtctcacatcAtccagaggatgtCtggctgcga cctggggcccgacgggcgcctcctccgcgggtatgaccagtCcgcctacgacggcaaggattacatcgccctgaac gaggacctgcgctcctggaccgccgcggacaccgcggctcagatcacccagcgcaagtTggaggcggcccgtgcgg cggagcagctgagagcctacctggagggcacgtgcgtggagtggctccgcagatacctggagaacgggaaggagac gctgcagcgcgcAg;

Cw*0711:

(SEQ ID NO: 1724)

atgcgggtcatggcgccccgagccctcctcctgctgctctcggggaggcctggccctgaccgagacctgggcctgct cccactccatgaggtatttcgacaccgccgtgtcccggcccggccgcggagagccccgcttcatctcagtgggcta cgtggacgacacgcagttcgtgcggttcgacagcgacgccgcgagtccgagaggggagcccgggcgccgtgggtg gagcaggaggggccggagtattgggaccgggagacacagaagtacaagcgccaggcacaggctgaccgagtgagcc tgcggaacctgcgcggctactacaaccagagcgaggacgggtctcacaccttccagaggatgtatggctgcgacct ggggcccgacgggcgcctcctccgcgggtatgaccagttcgcctacgacggcaaggattacatcgccctgaacgag gacctgcgctcctggaccgccgcggacaccgcggctcagatcacccagcgcaagttggaggcggcccgtgcggcgg agcaggaCagagcctacctggagggcacgtgcgtggagtggctccgcagatacctggagaacgggaagaagacgct gcagcgcgcggaaccccaaagacacacgtgacccaccacccccctctctgaccatgaggccaccctgaggtgctgg gccctgggcttctaccctgcggagatcacactgacctggcagcgggatggggaggaccagacccaggacaccgagc -continued ttgtggagaccaggccagcaggagatggaaccttccagaagtgggcagctgtggtggtgccttctggacaagagca gagatacacgtgccatatgcagcacgaggggctgcaagagcccctcaccctgagctgggagccatcttcccagccc accatccccatcatgggcatcgttgctggcctggctgtcctggttgtcctagctgtccttggagctgtggtcaccg ctatgatgtgtaggaggaagagctcaggtggaaaaggagggagctgctctcaggctgcgtGcagcaacagtgccca gggctctgatgagtctctcatcgcttgtaa;

Cw*0712:
(SEQ ID NO: 1725)
gctcccactccatgaggtatttcgacaccgccgtgtcccggcccggccgcggagagccccgcttcatctcagtggg ctacgtggacgacacgcagttcgtgcggttcgacagcgacgccgcgagtccgagaggggagcccgggcgccgtgg gtggagcaggaggggccggagtattgggaccgggagacacagaagtacaagcgccaggcacaggctgaccgagtga gcctgcggaacctgcgcggctactacaaccagagcgaggacgggtctcacaccttccagaggatgtatggctgcga cctggggcccgacgggcgcctcctccgcgggtatgaccagttcgcctacgacggcaaggattacatcgccctgaac gaggacctgcgctcctggaccgccgcggacaccgcggctcagatcacccagcgcaagtggaggcggcccgtgcgg cggagcaggaCagagcctacctggagggcacgtgcgtggagtggctccgcagatacctggagaacgggaagaagac gctgcagcgcgcgg;

Cw*0713:
(SEQ ID NO: 1726)
gctcccactccatgaggtatttcgacaccgccgtgtcccggcccggccgcggagagccccgcttcatctcagtggg ctacgtggacgacacgcagttcgtgcggttcgacagcgacgccgcgagtccgagaggggagccgcgggcgccgtgg gtggagcaggaggggccggagtattgggaccgggagacacagaagtacaagcgccaggcacaggctgaccgagtga gcctgcggaacctgcgcggctactacaaccagagcgaggacgggtctcacaccctccagaggatgtCtggctgcga cctggggcccgacgggcgcctcctccgcgggtatgaccagtTcgcctacgacggcaaggattacatcgccctgaac gaggacctgcgctcctggaccgccgcggacaccgcggctcagatcacccagcgcaagtTggaggcggcccgtgcgg cggagcagctgagagcctacctggagggcacgtgcgtggagtggctccgcagatacctggagaacgggaaggagac gctgcagcgcgcAg;

Cw*0714:
(SEQ ID NO: 1727)
gctcccactccatgaggtatttcgacaccgccgtgtcccggcccggccgcggagagccccgcttcatctcagtggg ctacgtggacgacacgcagttcgtgcggttcgacagcgacgccgcgagtccgagaggggagccgcgggcgccgtgg gtggagcaggaggggccggagtattgggaccgggagacacagaagtacaagcgccaggcacaggctgaccgagtga gcctgcggaacctgcgcggctactacaaccagagcgaggacgggtctcacaccctccagaggatgtacggctgcga cctggggcccgacgggcgcctcctccgcgggtatgaccagtccgcctacgacggcaaggattacatcgccctgaac gaggacctgcgctcctggaccgccgcggacaccgcggctcagatcacccagcgcaagttggaggcggcccgtgcgg cggagcagctgagagcctacctggagggcacgtgcgtggagtggctccgcagatacctggagaacgggaaggagac gctgcagcgcAcag;

Cw*0715:
(SEQ ID NO: 1728)
gctcccactccatgaggtatttcgacaccgccgtgtcccggcccggccgcggagagccccgcttcatctcagtggg ctacgtggacgacacgcagttcgtgcggttcgacagcgacgccgcgagtccgagaggggagccgcgggcgccgtgg gtggagcaggaggggccggagtattgggaccgggagacacagaagtacaagcgccaggcacaggctgaccgagtga gcctgcggaacctgcgcggctactacaaccagagcgaggacgggtctcacaccctccagaggatgtCtggctgcga cctggggcccgacgggcgcctcctccgcgggtatgaccagtccgcctacgacggcaaggattacatcgccctgaac gaggacctgcgctcctggaccgccgcggacaccgcggctcagatcacccagcgcaagttggaggcggcccgtgcgg cggagcagctgagagcctacctggagggcgAgtgcgtggagtggctccgcagatacctggagaacgggaaggagac gctgcagcgcgcAg;

Cw*0716:

(SEQ ID NO: 1729)

gctcccactccatgaggtatttcgacaccgccgtgtcccggcccggccgcggagagccccgcttcatctcagtggg ctacgtggacgacacgcagttcgtgcggttcgacagcgacgccgcgagtccgagaggggagccgcgggcgccgtgg gtggagcaggaggggccggagtattgggaccgggagacacagaaCtacaagcgccaggcacaggctgaccgagtga gcctgcggaacctgcgcggctactacaaccagagcgaggccgggtctcacaccctccagaggatgtAtggctgcga cctggggcccgacgggcgcctcctccgcgggtatgaccagtCcgcctacgacggcaaggattacatcgccctgaac gaggacctgcgctcctggaccgccgcggacaccgcggctcagatcacccagcgcaagtTggaggcggcccgtgcgg cggagcagctgagagcctacctggagggcacgtgcgtggagtggctccgcagatacctggagaacgggaaggagac gctgcagcgcgcAg;

Cw*0717:

(SEQ ID NO: 1730)

gctcccactccatgaggtatttcgacaccgccgtgtcccggcccggccgcggagagccccgcttcatctcagtggg ctacgtggacgacacgcagttcgtgcggttcgacagcgacgccgcgagtccgagaggggagccgcgggcgccgtgg gtggagcaggaggggccggagtattgggaccgggagacacagaagtacaagcgccaggcacaggctgaccgagtga gcctgcggaacctgcgcggctactacaaccagagcgaggacgggtctcacaccctccagaggatgtCtggctgcga cctggggcccgacgggcgcctcctccgcgggtatgaccagtccgcctacgacggcaaggattacatcgccctgaac gaggacctgcgctcctggaccgccgcggacaccgcggctcagatcacccagcgcaagtgggaggcggcccgtgcgg cggagcagctgagagcctacctggagggcacgtgcgtggagtggctccgcagatacctggagaacgggaaggagac gctgcagcgcgcagaacccccaaagacacacgtgacccaccacccctctctgaccatgaggccaccctgaggtgc tgggccctgggcttctaccctgcggagatcacactgacctggcagcgggatggggaggaccagacccaggacaccg agcttgtggagaccaggccagcaggagatggaaccttccagaagtgggcagctgtggtggtgccttctggacaaga gcagagatacacgtgccatatgcagcacgaggggctgcaagagcccctcaccctgagCtggg;

Cw*0718:

(SEQ ID NO: 1731)

atgcgggtcatggcgccccgagccctcctcctgctgctctcggggaggcctggccctgaccgagacctgggcctgct cccactccatgaggtatttcgacaccgccgtgtcccggcccggccgcggagagccccgcttcatctcagtgggcta cgtggacgacacgcagttcgtgcggttcgacagcgacgccgcgagtccgagaggggagccgcgggcgccgtgggtg gagcaggaggggccggagtattgggaccgggagacacagaactacaagcgccaggcacaggctgaccgagtgagcc tgcggaacctgcgcggctactacaaccagagcgaggacgggtctcacaccctccagaggatgtatggctgcgacct ggggcccgacgggcgcctcctccgcgggtatgaccagtccgcctacgacggcaaggattacatcgccctgaacgag gacctgcgctcctggaccgccgcggacaccgcggctcagatcacccagcgcaagttggaggcggcccgtgcggcgg agcagctgagagcctacctggagggcacgtgcgtggagtggctccgcagatacctggagaacgggaaggagacgct gcagcgcgcagaacccccaaagacacacgtgacccaccacccctctctgaccatgaggccaccctgaggtgctgg gccctgggcttctaccctgcggagatcacactgacctggcagcgggatggggaggaccagacccaggacaccgagc ttgtggagaccaggccagcaggagatggaaccttccagaagtgggcagctgtggtggtgccttctggacaagagca gagatacacgtgccatatgcagcacgaggggctgcaagagcccctcaccctgagctgggagccatcttcccagccc accatcccatcatgggcatcgttgctggcctggctgtcctggttgtcctagctgtccttggagctgtggtcaccg ctatgatgtgtaggaggaagagctcaggtggaaaaggagggagctgctctcaggTtgcgtgcagcaacagtgccca gggctctgatgagtctctcatcacttgtaa;

Cw*080101:

(SEQ ID NO: 1732)

atgcgggtcatggcgccccgaaccctcatcctgctgctctcgggagccctggccctgaccgagacctgggcctgct cccactccatgaggtatttctacaccgccgtgtcccggcccggccgcggagagccccgcttcatcgcagtgggcta -continued cgtggacgacacgcagttcgtgcagttcgacagcgacgccgcgagtccaagaggggagccgcgggcgccgtgggtg
gagcaggaggggccggagtattgggaccgggagacacagaagtacaagcgccaggcacagactgaccgagtgagcc
tgcggaacctgcgcggctactacaaccagagcgaggccgggtctcacaccctccagaggatgtatggctgcgacct
ggggcccgacgggcgcctcctccgcgggtataaccagttcgcctacgacggcaaggattacatcgccctgaatgag
gacctgcgctcctggaccgccgcggacacggcggctcagatcacccagcgcaagtgggaggcggcccgtacggcgg
agcagcTgagagcctacctggagggcacgtgcgtggagtggctccgcagatacctggagaacgggaagaagacgct
gcagcgcgcggaacacccaaagacacacgtgacccaccatcccgtctctgaccatgaggccaccctgaggtgctgg
gccctgggcttctaccctgcggagatcacactgacctggcagcgggatggcgaggaccaaactcaggacaccgagc
ttgtggagaccaggccagcaggagatggaaccttccagaagtgggcagctgtggtggtgccttctggagaagagca
gagatacacgtgccatgtgcagcacgaggggctgccagagcccctcaccctgagatgggGccatcttcccagccc
accatccccatcgtgggcatcgttgctggcctggctgtcctggctgtcctagctgtcctaggagctgtgatggctg
ttgtgatgtgtaggaggaagagctcaggtggaaaaggagggagctgctctcaggctgcgtccagcaacagtgccca
gggctctgatgagtctctcatcgcttgtaa;

Cw*080102:
(SEQ ID NO: 1733)
gctcccactccatgaggtatttctacaccgccgtgtcccggcccggccgcggagagccccgcttcatcgcagtggg
ctacgtggacgacacgcagttcgtgcagttcgacagcgacgccgcgagtccaagaggggagccgcgggcgccgtgg
gtggagcaggaggggccggagtattgggaccgggagacacagaagtacaagcgccaggcacagactgaccgagtga
gcctgcggaacctgcgcggctactacaaccagagcgaggccgggtctcacaccctccagaggatgtaCggctgcga
cctggggcccgacgggcgcctcctccgcgggtataaccagtTcgcctacgacggcaaggattacatcgccctgaat
gaggacctgcgctcctggaccgccgcggacacggcggctcagatcacccagcgcaagtgggaggcggcccgtAcgg
cggagcagctgagagcctacctggagggcacgtgcgtggagtggctccgcagatacctggagaacgggaagaagac
gctgcagcgcgcgcgg;

Cw*0802:
(SEQ ID NO: 1734)
atgcgggtcatggcgccccgaaccctcatcctgctgctctcgggagccctggccctgaccgagacctgggcctgct
cccactccatgaggtatttctacaccgccgtgtcccggcccggccgcggagagccccgcttcatcgcagtgggcta
cgtggacgacacgcagttcgtgcagttcgacagcgacgccgcgagtccaagaggggagccgcgggcgccgtgggtg
gagcaggaggggccggagtattgggaccgggagacacagaagtacaagcgccaggcacagactgaccgagtgagcc
tgcggaacctgcgcggctactacaaccagagcgaggccgggtctcacaccctccagaggatgtatggctgcgacct
ggggcccgacgggcgcctcctccgcgggtataaccagttcgcctacgacggcaaggattacatcgccctgaatgag
gacctgcgctcctggaccgccgcggacaAggcggctcagatcacccagcgcaagtgggaggcggcccgtgaggcgg
agcagcggagagcctacctggagggcacgtgcgtggagtggctccgcagatacctggagaacgggaagaagacgct
gcagcgcgcggaacacccaaagacacacgtgacccaccatcccgtctctgaccatgaggccaccctgaggtgctgg
gccctgggcttctaccctgcggagatcacactgacctggcagcgggatggcgaggaccaaactcaggacaccgagc
ttgtggagaccaggccagcaggagatggaaccttccagaagtgggcagctgtggtggtgccttctggagaagagca
gagatacacgtgccatgtgcagcacgaggggctgccagagcccctcaccctgagatgggGccatcttcccagccc
accatccccatcgtgggcatcgttgctggcctggctgtcctggctgtcctagctgtcctaggagctgtgatggctg
ttgtgatgtgtaggaggaagagctcaggtggaaaaggagggagctgctctcaggctgcgtccagcaacagtgccca
gggctctgatgagtctctcatcgcttgtaa;

Cw*0803:
(SEQ ID NO: 1735)
atgcgggtcatggcgccccgaaccctcatcctgctgctctcgggagccctggccctgaccgagacctgggcctgct
cccactccatgaggtatttctacaccgccgtgtcccggcccggccgcggagagccccgcttcatcgcagtgggcta -continued cgtggacgacacgcagttcgtgcagttcgacagcgacgccgcgagtccaagaggggagccgcgggcgccgtgggtg gagcaggaggggccggagtattgggaccgggagacacagaagtacaagcgccaggcacagactgaccgagtgagcc tgcggaacctgcgcggctactacaaccagagcgaggccgggtctcacaccctccagaggatgtatggctgcgacct ggggcccgacgggcgcctcctccgcgggtataaccagttcgcctacgacggcaaggattacatcgccctgaatgag gacctgcgctcctggaccgccgcggacacggcggctcagatcacccagcgcaagtgggaggcggcccgtacggcgg agcagctgagagcctacctggagggcacgtgcgtggagtggctccgcagatacctggagaacAggaagaagacgct gcagcgcgcggaacacccaaagacacacgtgacccaccatcccgtctctgaccatgaggccaccctgaggtgctgg gccctgggcttctaccctgcggagatcacactgacctggcagcgggatggcgaggaccaaactcaggacaccgagc ttgtggagaccaggccagcaggagatggaaccttccagaagtgggcagctgtggtggtgccttctggagaagagca gagatacacgtgccatgtgcagcacgaggggctgccagagcccctcaccctgagatgggggccatcttcccagccc accatccccatcgtgggcatcgttgctggcctggctgtcctggctgtcctagctgtcctaggagctgtgAtggctg ttgtgatgtgtaggaggaagagctcaggtggaaaaggagggagctgctctcaggctgcgtccagcaacagtgccca gggctctgatgagtctctcatcgcttgtaa;

Cw*0804:

(SEQ ID NO: 1736)
gctcccactccatgaggtatttctacaccgccgtgtcccggcccggccgcggagagccccgcttcatcgcagtggg ctacgtggacgacacgcagttcgtgcagttcgacagcgacgccgcgagtccaagaggggagccgcgggcgccgtgg gtggagcaggaggggccggagtattgggaccgggagacacagaagtacaagcgccaggcacagactgaccgagtga gcctgcggaacctgcgcggctactacaaccagagcgaggccgggtctcacaccctccagaggatgtatggctgcga cctggggcccgacgggcgcctcctccgcgggtataaccagttcgcctacgacggcaaggattacatcgccctgaat gaggacctgcgctcctggaccgccgcggacaAggcggctcagatcacccagcgcaagtgggaggcggcccgtgagg cggagcagcTgagagcctacctggagggcacgtgcgtggagtggctccgcagatacctggagaacgggaagAagac gctgcagcgcgcgg;

Cw*0805:

(SEQ ID NO: 1737)
gctcccactccatgaggtatttctacaccgccgtgtcccggcccggccgcggagagccccgcttcatcgcagtggg ctacgtggacgacacgcagttcgtgcagttcgacagcgacgccgcgagtccaagaggggagccgcgggcgccgtgg gtggagcaggaggggccggagtattgggaccgggagacacagaagtacaagcgccaggcacagGctgaccgagtga gcctgcggaacctgcgcggctactacaaccagagcgaggccgggtctcacaccctccagaggatgtatggctgcga cctggggcccgacgggcgcctcctccgcgggtataaccagtTcgcctacgacggcaaggattacatcgccctgaat gaggacctgcgctcctggaccgccgcggacaAggcggctcagatcacccagcgcaagtgggaggcggcccgtgagg cggagcagcggagagcctacctggagggcacgtgcgtggagtggctccgcagatacctggagaacgggaagAagac gctgcagcgcgcgg;

Cw*0806:

(SEQ ID NO: 1738)
gctcccactccatgaggtatttctacaccgccgtgtcccggcccggccgcggagagccccgcttcatcgcagtggg ctacgtggacgacacgcagttcgtgcagttcgacagcgacgccgcgagtccaagaggggagccgcgggcgccgtgg gtggagcaggaggggccggagtattgggaccgggagacacagaagtacaagcgccaggcacagactgaccgagtga gcctgcggaacctgcgcggctactacaaccagagcgaggccgggtctcacaccctccagaggatgtatggctgcga cctggggcccgacgggcgcctcctccgcgggtataaccagttcgcctacgacggcaaggattacatcgccctgaat gaggacctgcgctcctggaccgccgcggacacggcggctcagatcacccagcgcaagtgggaggcggcccgtacgg cggagcagctgagagcctacctggagggcGcgtgcgtggagtggctccgcagatacctggagaacAggaagaagac gctgcagcgcgcgg;

-continued

Cw*0807:

(SEQ ID NO: 1739)
gctcccactccatgaggtatttctacaccgccgtgtcccggcccggccgcggagagccccgcttcatcgcagtggg ctacgtggacgacacgcagttcgtgcagttcgacagcgacgccgcgagtccaagaggggagccgcgggcgccgtgg gtggagcaggaggggccggagtattgggaccgggagacacagaagtacaagcgccaggcacagactgaccgagtga gcctgcggaacctgcgcggctactacaaccagagcgaggcccgggtctcacaccctccagaggatgtatggctgcga cctggggcccgacgggcgcctcctccgcgggtataaccagttcgcctacgacggcaaggattacatcgccctgaat gaggacctgcgctcctggaccgccgcggacaAggcggctcagatcacccagcgcaagtTggaggcggcccgtgagg cggagcagcggagagcctacctggagggcacgtgcgtggagtggctccgcagatacctggagaacgggaagAagac gctgcagcgcgcgg;

Cw*0808:

(SEQ ID NO: 1740)
gctcccactccatgaggtatttctacaccgccgtgtcccggcccggccgcggagagccccgcttcatcgcagtggg ctacgtggacgacacgcagttcgtgcagttcgacagcgacgccgcgagtccaagaggggagccgcgggcgccgtgg gtggagcaggaggggccggagtattgggaccgggagacacagaagtacaagcgccaggcacagactgaccgagtga gcctgcggaacctgcgcggctactacaaccagagcgaggcccgggtctcacaccctccagagCatgtatggctgcga cctggggcccgacgggcgcctcctccgcgggtataaccagttcgcctacgacggcaaggattacatcgccctgaat gaggacctgcgctcctggaccgccgcggacacggcggctcagatcacccagcgcaagtgggaggcggcccgtacgg cggagcagctgagagcctacctggagggcacgtgcgtggagtggctccgcagatacctggagaacgggaagAagac gctgcagcgcgcgg;

Cw*0809:

(SEQ ID NO: 1741)
atgcgggtcatggcgccccgaaccctcaccctgctgctctcggggagccctggccctgaccgagacctgggcctgct cccactccatgaggtatttctacaccgccgtgtcccggcccggccgcggagagccccgcttcatcgcagtgggcta cgtggacgacacgcagttcgtgcagttcgacagcgacgccgcgagtccaagaggggagccgcgggcgccgtgggtg gagcaggaggggccggagtattgggaccgggagacacagaagtacaagcgccaggcacagactgaccgagtgagcc tgcggaacctgcgcggctactacaaccagagcgaggcccgggtctcacaccctccagaggatgtatggctgcgacct ggggcccgacgggcgcctcctccgcgggtatgaccagtccgcctacgacggcaaggattacatcgccctgaatgag gacctgcgctcctggaccgccgcggacacggcggctcagatcacccagcgcaagtgggaggcggcccgtacggcgg agcagctgagagcctacctggagggcacgtgcgtggagtggctccgcagatacctggagaacgggGagaagacgct gcagcgcgcggaacacccaaagacacacgtgacccaccatcccgtctctgaccatgaggccaccctgaggtgctgg gcc;

Cw*120201:

(SEQ ID NO: 1742)
atgcgggtcatggcgccccgaaccctcatcctgctgctctcggggagccctggccctgaccgagacctgggcctgct cccactccatgaggtatttctacaccgccgtgtcccggcccggccgcggagagccccgcttcatcgcagtgggcta cgtggacgacacgcagttcgtgcggttcgacagcgacgccgcgagtccaagaggggagccgcgggcgccgtgggtg gagcaggaggggccggagtattgggaccgggagacacagaagtacaagcgccaggcacaggctgaccgagtgagcc tgcggaacctgcgcggctactacaaccagagcgaggcccgggtctcacaccctccagaggatgtaCggctgcgacct ggggcccgacgggcgcctcctccgcgggtatgaccagtccgcctacgacggcaaggattacatcgccctgaacgag gacctgcgctcctggaccgcTgcggacacggcggctcagatcacccagcgcaagtgggaggcggcccgtgaggcgg agcagtggagagcctacctggagggcacgtgcgtggagtggctccgcagatacctggagaacgggaaggagacgct gcagcgcgcggaacacccaaagacacacgtgacccaccatcccgtctctgaccatgaggccaccctgaggtgctgg gccctgggcttctaccctgcggagatcacactgacctggcagcgggatggcgaggaccaaaactcaggacaccgagc ttgtggagaccaggccagcaggagatggaaccttccagaagtgggcagctgtggtggtgccttctggagaagagca -continued gagatacacgtgccatgtgcagcacgaggggctgccggagcccctcaccctgagatgggagccatcttcccagccc accatccccatcgtgggcatcgttgctggcctggctgtcctggctgtcctagctgtcctaggagctgtgAtggctg ttgtgatgtgtaggaggaagagctcaggtggaaaaggagggagctgctctcaggctgcgtccagcaacagtgccca gggctctgatgagtctctcatcgcttgtaa;

Cw*120202:

(SEQ ID NO: 1743)
atgcgggtcatggcgccccgaaccctcatcctgctgctctcgggagccctggccctgaccgagacctgggcctgct cccactccatgaggtatttctacaccgccgtgtcccggcccggccgcggagagccccgcttcatcgcagtgggcta cgtggacgacacgcagttcgtgcggttcgacagcgacgccgcgagtccaagaggggagccgcgggcgccgtgggtg gagcaggaggggccggagtattgggaccgggagacacagaagtacaagcgccaggcacaggctgaccgagtgagcc tgcggaacctgcgcggctactacaaccagagcgaggccgggtctcacaccctccagaggatgtaCggctgcgacct ggggcccgacgggcgcctcctccgcgggtatgaccagtccgcctacgacggcaaggattacatcgccctgaacgag gacctgcgctcctggaccgcTgcggacacggcggctcagatcacccagcgcaagtgggaggcggcccgtgaggcgg agcagtggagagcctacctggagggcacgtgcgtggagtggctccgcagatacctggagaacgggaaggagacgct gcagcgcgcggaacacccaaagacacacgtgacccaccatcccgtctctgaccatgaggccaccctgaggtgctgg gccctgggcttctaccctgcggagatcacactgacctggcagcgggatggcgaggaccaaactcaggacaccgagc ttgtggagaccaggccagcaggagatggaaccttccagaagtgggcagctgtggtggtgccttctggagaagagca gagatacacgtgccatgtgcagcacgaggggctgccAgagcccctcaccctgagatgggagccatcttcccagccc accatccccatcgtgggcatcgttgctggcctggctgtcctggctgtcctagctgtcctaggagctgtgAtggctg ttgtgatgtgtaggaggaagagctcaggtggaaaaggagggagctgctctcaggctgcgtccagcaacagtgccca gggctctgatgagtctctcatcgcttgtaa;

Cw*120203:

(SEQ ID NO: 1744)
gctcccactccatgaggtatttctacaccgccgtgtcccggcccggccgcggagagccccgcttcatcgcagtggg ctacgtggacgacacgcagttcgtgcggttcgacagcgacgccgcgagtccaagaggggagccgcgggcgccgtgg gtggagcaggaggggccggagtattgggaccgggagacacagaagtacaagcgccaggcacaggctgaccgagtga gcctgcggaacctgcgcggctactacaaccagagcgaggccgggtctcacaccctccagaggatgtAtggctgcga cctggggcccgacgggcgcctcctccgcgggtatgaccagtccgcctacgacggcaaggattacatcgccctgaac gaggacctgcgctcctggaccgcTgcggacacggcggctcagatcacccagcgcaagtgggaggcggcccgtgagg cggagcagtggagagcctacctggagggcacgtgcgtggagtggctccgcagatacctggagaacgggaaggagac gctgcagcgcgcgg;

Cw*120301:

(SEQ ID NO: 1745)
atgcgggtcatggcgccccgaaccctcatcctgctgctctcgggagccctggccctgaccgagacctgggcctgct cccactccatgaggtatttctacaccgccgtgtcccggcccggccgcggagagccccgcttcatcgcagtgggcta cgtggacgacacgcagttcgtgcggttcgacagcgacgccgcgagtccaagaggggagccgcgggcgccgtgggtg gagcaggaggggccggagtattgggaccgggagacacagaagtacaagcgccaggcacagGctgaccgagtgagcc tgcggaacctgcgcggctactacaaccagagcgaggccgggtctcacaccctccagtggatgtatggctgcgacct ggggcccgacgggcgcctcctccgcgggtatgaccagtccgcctacgacggcaaggattacatcgccctgaacgag gacctgcgctcctggacTgccgcggacacggcggctcagatcacccagcgcaagtgggaggcggcccgtgaggcgg agcagtggagagcctacctggagggcacgtgcgtggagtggctccgcagatacctggagaacgggaaggagacgct gcagcgcgcggaacacccaaagacacacgtgacccaccatcccgtctctgaccatgaggccaccctgaggtgctgg gccctgggcttctaccctgcggagatcacactgacctggcagcgggatggcgaggaccaaactcaggacaccgagc -continued ttgtggagaccaggccagcaggagatggaaccttccagaagtgggcagctgtggtggtgccttctggagaagagca gagatacacgtgccatgtgcagcacgaggggctgccagagcccctcaccctgagatgggagccatcttcccagccc accatccccatcgtgggcatcgttgctggcctggctgtcctggctgtcctagctgtcctaggagctgtgAtggctg ttgtgatgtgtaggaggaagagctcaggtggaaaaggagggagctgctctcaggctgcgtccagcaacagtgccca gggctctgatgagtctctcatcgcttgtaa;

Cw*120302:

(SEQ ID NO: 1746)

gctcccactccatgaggtatttctacaccgccgtgtcccggcccggccgcggagagccccgcttcatcgcagtggg ctacgtggacgacacgcagttcgtgcggttcgacagcgacgccgcgagtccaagaggggagccgcgggcgccgtgg gtggagcaggaggggccggagtatttgggaccgggagacacagaagtacaagcgccaggcacaggctgaccgagtga gcctgcggaacctgcgcggctactacaaccagagcgaggccgggtctcacaccctccagtggatgtatggctgcga cctggggcccgacgggcgcctcctccgcgggtatgaccagtccgcctacgacggcaaggattacatcgccctgaac gaggacctgcgctcctggaccgcGgcggacacggcggctcagatcacccagcgcaagtgggaggcggcccgtgagg cggagcagTggagagcctacctggagggcacgtgcgtggagtggctccgcagatacctggagaacgggaaggagac gctgcagcgcgcgg;

Cw*120401:

(SEQ ID NO: 1747)

atgcgggtcatggcgccccgaaccctcatcctgctgctctcggggagccctggccctgaccgagacctgggcctgct cccactccatgaggtatttctacaccgccgtgtcccggcccggccgcggagagccccgcttcatcGcagtgggcta cgtggacgacacgcagttcgtgcggttcgacagcgacgccgcgagtccgagaggggagccgcgggcgccgtgggtg gagcaggaggggccggagtatttgggaccgggagacacagaagtacaagcgccaggcacagGctgaccgagtgaacc tgcggaaActgcgcggctactacaaccagagcgaggccgggtctcacaccctccagtggatgtAtggctgcgacct ggggcccgacgggcgcctcctccgcgggtatgaccagtCcgcctacgacggcaaggattacatcgccctgaacgag gacctgcgctcctggaccgccgcggacacGgcggctcagatcacccagcgcaagtgggaggcggcccgtgaggcgg agcagTggagagcctacctggagggcacgtgcgtggagtggctccgcagatacctggagaacgggaaggagacgct gcagcgcgcggaacacccaaagacacacgtgacccaccatcccgtctctgaccatgaggccaccctgaggtgc;

Cw*120402:

(SEQ ID NO: 1748)

atgcgggtcatggcgccccgaaccctcatcctgctgctctcggggagccctggccctgaccgagacctgggcctgct cccactccatgaggtatttctacaccgccgtgtcccggcccggccgcggagagccccgcttcatcgcagtgggcta cgtggacgacacgcagttcgtgcggttcgacagcgacgccgcgagtccaagaggggagccgcgggcgccgtgggtg gagcaggaggggccggagtatttgggaccgggagacacagaagtacaagcgccaggcacagGctgaccgagtgaacc tgcggaaActgcgcggctactacaaccagagcgaggccgggtctcacaccctccagtggatgtatggctgcgacct ggggcccgacgggcgcctcctccgcgggtatgaccagtccgcctacgacggcaaggattacatcgccctgaacgag gacctgcgctcctggacTgccgcggacacggcggctcagatcacccagcgcaagtgggaggcggcccgtgaggcgg agcagtggagagcctacctggagggcacgtgcgtggagtggctccgcagatacctggagaacgggaaggagacgct gcagcgcgcggaacacccaaagacacacgtgacccaccatcccgtctctgaccatgaggccaccctgaggtgctgg gccctgggcttctaccctgcggagatcacactgacctggcagcgggatggcgaggaccaaactcaggacaccgagc ttgtggagaccaggccagcaggagatggaaccttccagaagtgggcagctgtggtggtgccttctggagaagagca gagatacacgtgccatgtgcagcacgaggggctgccagagcccctcaccctgagatgggagccatcttcccagccc accatccccatcgtgggcatcgttgctggcctggctgtcctggctgtcctagctgtcctaggagctgtgAtggctg ttgtgatgtgtaggaggaagagctcaggtggaaaaggagggagctgctctcaggctgcgtccagcaacagtgccca gggctctgatgagtctctcatcgcttgtaa;

Cw*1205:

(SEQ ID NO: 1749)
atgcgggtcatggcgccccgaaccctcatcctgctgctctcgggagccctggccctgaccgagacctgggcctgct cccactccatgaggtatttctacaccgccgtgtcccggcccggccgcggagagccccgcttcatcgcagtgggcta cgtggacgacacgcagttcgtgcggttcgacagcgacgccgcgagtccaagaggggagccgcgggcgccgtgggtg gagcaggaggggccggagtattgggaccgggagacacagaagtacaagcgccaggcacagactgaccgagtgaacc tgcggaaActgcgcggctactacaaccagagcgaggccgggtctcacaccctccagtggatgtatggctgcgacct ggggcccgacgggcgcctcctccgcgggtatgaccagtccgcctacgacggcaaggattacatcgccctgaacgag gacctgcgctcctggacTgccgcggacacggcggctcagatcacccagcgcaagtgggaggcggcccgtgaggcgg agcagtggagagcctacctggagggcacgtgcgtggagtggctccgcagatacctggagaacgggaaggagacgct gcagcgcgcggaacacccaaagacacacgtgacccaccatcccgtctctgaccatgaggccaccctgagtgctgg gccctgggcttctaccctgcggagatcacactgacctggcagcgggatggcgaggaccaaactcaggacaccgagc ttgtggagaccaggccagcaggagatggaaccttccagaagtgggcagctgtggtggtgccttctggagaagagca gagatacacgtgccatgtgcagcacgaggggctgccagagcccctcaccctgagatgggagccatcttcccagccc accatccccatcgtgggcatcgttgctggcctggctgtcctggctgtcctagctgtcctaggagctgtgAtggctg ttgtgatgtgtaggaggaagagctcaggtggaaaaggagggagctgctctcaggctgcgtccagcaacagtgccca gggctctgatgagtctctcatcgcttgtaa;

Cw*1206:

(SEQ ID NO: 1750)
gctcccactccatgaggtatttctacaccgccgtgtcccggcccggccgcggagagccccgcttcatcgcagtggg ctacgtggacgacacgcagttcgtgcggttcgacagcgacgccgcgagtccaagaggggagccgcgggcgccgtgg gtggagcaggaggggccggagtattgggaccgggagacacagaagtacaagcgccaggcacaggctgaccgagtga gcctgcggaacctgcgcggctactacaaccagagcgaggccgggtctcacaccctccagtggatgtatggctgcga cctggggcccgacgggcgcctcctccgcgggtatgaccagtccgcctacgacgTcaaggattacatcgccctgaac gaggacctgcgctcctggactgccgcggacacggcggctcagatcacccagcgcaagtgggaggcggcccgtgagg cggagcagtggagagcctacctggagggcacgtgcgtggagtggctccgcagatacctggagaacgggaaggagac gctgcagcgcgcgg;

Cw*1207:

(SEQ ID NO: 1751)
gctcccactccatgaggtatttctacaccgccgtgtcccggcccggccgcggagagccccgcttcatcgcagtggg ctacgtggacgacacgcagttcgtgcggttcgacagcgacgccgcgagtccaagaggggagccgcgggcgccgtgg gtggagcaggaggggccggagtattgggaccgggagacacagaagtacaagcgccaggcacaggctgaccgagtgG gcctgcggaacctgcgcggctactacaaccagagcgaggccgggtctcacaccctccagtggatgtatggctgcga cctggggcccgacgggcgcctcctccgcgggtatgaccagtccgcctacgacggcaaggattacatcgccctgaac gaggacctgcgctcctggactgccgcggacacggcggctcagatcacccagcgcaagtgggaggcggcccgtgagg cggagcagtggagagcctacctggagggcacgtgcgtggagtggctccgcagatacctggagaacgggaaggagac gctgcagcgcgcgg;

Cw*1208:

(SEQ ID NO: 1752)
atgcgggtcatggcgccccgaaccctcatcctgctgctctcgggagccctggccctgaccgagacctgggcctgct cccactccatgaggtatttctacaccgccgtgtcccggcccggccgcggagagccccgcttcatcgcagtgggcta cgtggacgacacgcagttcgtgcggttcgacagcgacgccgcgagtccaagaggggagccgcgggcgccgtgggtg gagcaggaggggccggagtattgggaccgggagacacagaaCtacaagcgccaggcacaggctgaccgagtgagcc tgcggaacctgcgcggctactacaaccagagcgaggccgggtctcacaccctccagaggatgtaCggctgcgacct -continued ggggcccgacgggcgcctcctccgcgggtatgaccagtccgcctacgacggcaaggattacatcgccctgaacgag gacctgcgctcctggaccgcTgcggacacggcggctcagatcacccagcgcaagtgggaggcggcccgtgaggcgg agcagtggagagcctacctggagggcacgtgcgtggagtggctccgcagatacctggagaacgggaaggagacgct gcagcgcgcggaacacccaaagacacacgtgacccaccatcccgtctctgaccatgaggccaccctgaggtgctgg gccctgggcttctaccctgcggagatcacactgacctggcagcgggatggcgaggaccaaactcaggacaccgagc ttgtggagaccaggccagcaggagatggaaccttccagaagtgggcagctgtggtggtgccttctggagaagagca gagatacacgtgccatgtgcagcacgaggggctgccAgagcccctcaccctgagatgggagccatcttcccagccc accatccccatcgtgggcatcgttgctggcctggctgtcctggctgtcctagctgtcctaggagctgtgAtggctg ttgtgatgtgtaggaggaagagctcaggtggaaaaggagggagctgctctcaggctgcgtccagcaacagtgccca gggctctgatgagtctctcatcgcttgtaa;

Cw*140201:

(SEQ ID NO: 1753)

atgcgggtcatggcgccccgaaccctcatcctgctgctctcgggagccctggccctgaccgagacctgggcctgct cccactccatgaggtatttctCcacatccgtgtcccggcccggccgcggggagccccgcttcatcgcagtgggcta cgtggacgacacgcagttcgtgcggttcgacagcgacgccgcgagtccgagaggggagccgcgggcgccgtggtg gagcaggaggggccggagtattgggaccgggagacacagaagtacaagcgccaggcacagactgaccgagtgagcc tgcggaacctgcgcggctactacaaccagagcgaggccgggtctcacaccctccagtggatgtttggctgcgacct ggggcccgacgggcgcctcctccgcgggtatgaccagtCcgcctacgacggcaaggattacatcgccctgaacgag gatctgcgctcctggaccgccgcggacacggcggctcagatcacccagcgcaagtgggaggcggcccgtgaggcgg agcagcggagagcctacctggagggcacgtgcgtggagtggctccgcagatacctggagaacgggaaggagacgct gcagcgcgcggaacacccaaagacacacgtgacccaccatcccgtctctgaccatgaggccaccctgaggtgctgg gccctgggcttctaccctgcggagatcacactgacctggcagtgggatggggaggaccaaactcaggacaccgagc ttgtggagaccaggccagcaggagatggaaccttccagaagtgggcagctgtgGtggtgccttctggagaagagca gagatacacgtgccatgtgcagcacgaggggctgccggagcccctcaccctgagatgggagccgtcttcccagccc accatccccatcgtgggcatcgttgctggcctggctgtcctggctgtcctagctgtcctaggagctgtggtggctg ttgtgatgtgtaggaggaagagctcaggtggaaaaggagggagctgctctcaggctgcgtccagcaacagtgccca gggctctgatgagtctctcatcgcttgtaa;

Cw*140202:

(SEQ ID NO: 1754)

gctcccactccatgaggtatttctCcacatccgtgtcccggcccggccgcggggagccccgcttcatcgcagtggg ctacgtggacgacacgcagttcgtgcggttcgacagcgacgccgcgagtccgagaggggagccgcgggcgccgtgg gtggagcaggaggggccggagtattgggaccgggagacacagaagtacaagcgccaggcacagactgaccgagtga gcctgcggaacctgcgcggctactacaaccagagcgaggccgggtctcacaccctccagtggatgtTtggctgcga cctggggcccgacgggcgcctcctccgcgggtatgaccagtCcgcctacgacggcaaggattacatcgccctgaac gaggacctgcgctcctggaccgccgcggacacggcggctcagatcacccagcgcaagtgggaggcggcccgtgagg cggagcagcggagagcctacctggagggcacgtgcgtggagtggctccgcagatacctggagaacgggaaggagac gctgcagcgcgcgg;

Cw*1403:

(SEQ ID NO: 1755)

atgcgggtcatggcgccccgaaccctcatcctgctgctctcgggagccctggccctgaccgagacctgggcctgct cccactccatgaggtatttctCcacatccgtgtcccggcccggccgcggggagccccacttcatcgcagtgggcta cgtggacgacacgcagttcgtgcggttcgacagcgacgccgcgagtcAagaggggagccgcgggcgccgtggtg gagcaggaggggccggagtattgggaccgggagacacagaagtacaagcgccaggcacagactgaccgagtgagcc tgcggaacctgcgcggctactacaaccagagcgaggccgggtctcacaccctccagtggatgtttggctgcgacct ggggcccgacgggcgcctcctccgcgggtatgaccagtCcgcctacgacggcaaggattacatcgccctgaacgag gatctgcgctcctggaccgccgcggacacggcggctcagatcacccagcgcaagtgggaggcggcccgtgaggcgg agcagcggagagcctacctggagggcacgtgcgtggagtggctccgcagatacctggagaacgggaaggagacgct gcagcgcgcggaacacccaaagacacacgtgacccaccatcccgtctctgaccatgaggccaccctgaggtgctgg gccctgggcttctaccctgcggagatcacactgacctggcagtgggatggggaggaccaaactcaggacaccgagc ttgtggagaccaggccagcaggagatggaaccttccagaagtgggcagctgtgGtggtgccttctggagaagagca gagatacacgtgccatgtgcagcacgaggggctgccggagcccctcaccctgagatgggagccgtcttcccagccc accatcccatcgtgggcatcgttgctggcctggctgtcctggctgtcctagctgtcctaggagctgtggtggctg ttgtgatgtgtaggaggaagagctcaggtggaaaaggagggagctgctctcaggctgcgtccagcaacagtgccca gggctctgatgagtctctcatcgcttgtaa;

Cw*1404:

(SEQ ID NO: 1756)

gctcccactccatgaggtatttctCcacatccgtgtcccggcccggccgcggggagccccgcttcatcgcagtggg ctacgtggacgacacgcagttcgtgcggttcgacagcgacgccgcgagtccgagaggggagccgcgggcgccgtgg gtggagcaggaggggccggagtattgggaccgggagacacagaagtacaagcgccaggcacaggctgaccgagtga AcctgcggaacctgcgcggctactacaaccagagcgaggccgggtctcacaccctccagtggatgtTtggctgcga cctggggcccgacgggcgcctcctccgcgggtatgaccagtCcgcctacgacggcaaggattacatcgccctgaac gaggaTctgcgctcctggaccgccgcggacacggcggctcagatcacccagcgcaagtgggaggcggcccgtgagg cggagcagcggagagcctacctggagggcacgtgcgtggagtggctccgcagatacctggagaacgggaaggagac gctgcagcgcgcgg;

Cw*1405:

(SEQ ID NO: 1757)

gctcccactccatgaggtatttctCcacatccgtgtcccggcccggccgcggggagccccgcttcatcgcagtggg ctacgtggacgacacgcagttcgtgcggttcgacagcgacgccgcgagtccgagaggggagccgcgggcgccgtgg gtggagcaggaggggccggagtattgggaccgggagacacagaagtacaagcgccaggcacagactgaccgagtga gcctgcggaacctgcgcggctactacaaccagagcgaggccgggtctcacaccctccagtggatgtAtggctgcga cctggggcccgacgggcgcctcctccgcgggtatgaccagtCcgcctacgacggcaaggattacatcgccctgaac gaggaTctgcgctcctggaccgccgcggacacggcggctcagatcacccagcgcaagtgggaggcggcccgtgagg cggagcagcggagagcctacctggagggcacgtgcgtggagtggctccgcagatacctggagaacgggaaggagac gctgcagcgcgcgg;

Cw*150201:

(SEQ ID NO: 1758)

atgcgggtcatggcgccccgaaccctcctcctgctgctctcgggagccctggccctgaccgagacctgggcctgct cccactccatgaggtatttctacaccgctgtgtcccggcccggccgcgggagagccccacttcatcgcagtgggcta cgtggacgacacgcagttcgtgcggttcgacagcgacgccgcgagtccaagaggggagccgcgggcgccgtgggtg gagcaggaggggccggagtattgggaccgggagacacagaactacaagcgccaggcacagactgaccgagtgaacc tgcggaaactgcgcggctactacaaccagagcgaggccgggtctcacatcatccagaggatgtatggctgcgacct ggggcccgacgggcgcctcctccgcgggcatgaccagttAgcctacgacggcaaggattacatcgccctgaacgag gacctgcgctcctggaccgccgcggacacggcggctcagatcacccagcgcaagtgggaggcggcccgtgaggcgg agcagctgagagcctacctggagggcacgtgcgtggagtggctccgcagatacctggagaacgggaaggagacgct gcagcgcgcggaacacccaaagacacacgtgacccaccatcccgtctctgaccatgaggccaccctgaggtgctgg gccctgggcttctaccctgcggagatcacactgacctggcagcgggatggcgaggaccaaactcaggacaccgagc ttgtggagaccaggccagcaggagatggaaccttccagaagtgggcagctgtggtggtgccttctggagaagagca

```
gagatacacgtgccatgtgcagcacgaggggctgccggagcccctcaccctgagatgggagccatcttcccagccc accatcccatcgtgggcatcgttgctggcctggctgtcctggctgtcctagctgtcctaggagctgtgAtggctg ttgtgatgtgtaggaggaagagctcaggtggaaaaggagggagctgctctcaggctgcgtccagcaacagtgccca gggctctgatgagtctctcatcgcttgtaa;
```

Cw*150202:

(SEQ ID NO: 1759)
```
gctcccattccatgaggtatttctacaccgctgtgtcccggcccggccgcggagagccccActtcatcgcagtggg ctacgtggacgacacgcagttcgtgcggttcgacagcgacgccgcgagtccaagaggggagccgcgggcgccgtgg gtggagcaggaggggccggagtatttgggaccgggagacacagaaCtacaagcgccaggcacagactgaccgagtga acctgcggaaActgcgcggctactacaaccagagcgaggccgggtctcacatcatccagaggatgtatggctgcga cctggggcccgacgggcgcctcctccgcgggCatgaccagttAgcctacgacggcaaggattacatcgccctgaac gaggacctgcgctcctggaccgccgcggacacggcggctcagatcacccagcgcaagtgggaggcggcccgtgagg cggagcagcTgagagcctacctggagggcacgtgcgtggagtggctccgcagatacctggagaacgggaaggagac gctgcagcgcgcgcgg;
```

Cw*1503:

(SEQ ID NO: 1760)
```
atgcgggtcatggcgccccgaaccctcctcctgctgctctcggggagccctggccctgaccgagacctgggcctgct cccactccatgaggtatttctacaccgctgtgtcccggcccggccgcggagagccccacttcatcgcagtgggcta cgtggacgacacgcagttcgtgcggttcgacagcgacgccgcgagtccaagaggggagccgcgggcgccgtgggtg gagcaggaggggccggagtatttgggaccgggagacacagaactacaagcgccaggcacagGctgaccgagtgaacc tgcggaaactgcgcggctactacaaccagagcgaggccgggtctcacatcatccagaggatgtatggctgcgacct ggggcccgacgggcgcctcctccgcgggcatgaccagttAgcctacgacggcaaggattacatcgccctgaacgag gacctgcgctcctggaccgccgcggacacggcggctcagatcacccagcgcaagtgggaggcggcccgtgaggcgg agcagctgagagcctacctggagggcacgtgcgtggagtggctccgcagatacctggagaacgggaaggagacgct gcagcgcgcggaacacccaaagacacacgtgacccaccatcccgtctctgaccatgaggccaccctgaggtgctgg gccctgggcttctaccctgcggagatcacactgacctggcagcgggatggcgaggaccaaactcaggacaccgagc ttgtggagaccaggccagcaggagatggaaccttccagaagtgggcagctgtggtggtgccttctggagaagagca gagatacacgtgccatgtgcagcacgaggggctgccggagcccctcaccctgagatgggagccatcttcccagccc accatcccatcgtgggcatcgttgctggcctggctgtcctggctgtcctagctgtcctaggagctgtgAtggctg ttgtgatgtgtaggaggaagagctcaggtggaaaaggagggagctgctctcaggctgcgtccagcaacagtgccca gggctctgatgagtctctcatcgcttgtaa;
```

Cw*1504:

(SEQ ID NO: 1761)
```
atgcgggtcatggcgccccgaaccctcctcctgctgctctcggggagccctggccctgaccgagacctgggcctgct cccactccatgaggtatttctacaccgctgtgtcccggcccggccgcggagagccccacttcatcgcagtgggcta cgtggacgacacgcagttcgtgcggttcgacagcgacgccgcgagtccaagaggggagccgcgggcgccgtgggtg gagcaggaggggccggagtatttgggaccgggagacacagaactacaagcgccaggcacagactgaccgagtgaacc tgcggaaactgcgcggctactacaaccagagcgaggccgggtctcacatcatccagaggatgtatggctgcgacct ggggcccgacgggcgcctcctccgcgggtatgaccagtCcgcctacgacggcaaggattacatcgccctgaacgag gacctgcgctcctggaccgccgcggacacggcggctcagatcacccagcgcaagtgggaggcggcccgtgaggcgg agcagcTgagagcctacctggagggcacgtgcgtggagtggctccgcagatacctggagaacgggaaggagacgct gcagcgcgcggaacacccaaagacacacgtgacccaccatcccgtctctgaccatgaggccaccctgaggtgctgg gccctgggcttctaccctgcggagatcacactgacctggcagcgggatggcgaggaccaaactcaggacaccgagc ttgtggagaccaggccagcaggagatggaaccttccagaagtgggcagctgtggtggtgccttctggagaagagca
``` gagatacacgtgccatgtgcagcacgaggggctgccggagcccctcaccctgagatgggagccatcttcccagccc accatcccatcgtgggcatcgttgctggcctggctgtcctggctgtcctagctgtcctaggagctgtgAtggctg ttgtgatgtgtaggaggaagagctcaggtggaaaaggagggagctgctctcaggctgcgtccagcaacagtgccca gggctctgatgagtctctcatcgcttgtaa;

Cw*150501:

(SEQ ID NO: 1762)

atgcgggtcatggcgccccgaacTctcctcctgctgctctcgggagccctggccctgaccgagacctgggcctgct cccactccatgaggtatttctacaccgctgtgtcccggcccggccgcggagagccccacttcatcgcagtgggcta cgtggacgacacgcagttcgtgcggttcgacagcgacgccgcgagtccaagaggggagccgcgggcgccgtgggtg gagcaggaggggccggagtattgggaccgggagacacagaactacaagcgccaggcacagactgaccgagtgaacc tgcggaaactgcgcggctactacaaccagagcgaggcccgggtctcacatcatccagaggatgtatggctgcgacct ggggcccgacgggcgcctcctccgcgggcatgaccagttcgcctacgacggcaaggattacatcgccctgaacgag gacctgcgctcctggaccgccgcggacacggcggctcagatcacccagcgcaagtgggaggcggcccgtgaggcgg agcagctgagagcctacctggagggcacgtgcgtggagtggctccgcagatacctggagaacgggaaggagacgct gcagcgcgcggaacacccaaagacacacgtgacccaccatcccgtctctgaccatgaggccaccctgagtgctgg gccctgggcttctaccctgcggagatcacactgacctggcagcgggatggcgaggaccaaactcaggacaccgagc ttgtggagaccaggccagcaggagatggaaccttccagaagtgggcagctgtggtggtgccttctggagaagagca gagatacacgtgccatgtgcagcacgaggggctgccggagcccctcaccctgagatgggagccatcttcccagccc accatcccatcgtgggcatcgttgctggcctggctgtcctggctgtcctagctgtcctaggagctgtgatggctg ttgtgatgtgtaggaggaagagctcaggtggaaaaggagggagctgctctcaggctgcgtccagcaacagtgccca gggctctgatgagtctctcatcgcttgtaa;

Cw*150502:

(SEQ ID NO: 1763)

atgcgggtcatggcgccccgaaccctcctcctgctgctctcgggagccctggccctgaccgagacctgggcctgct cccactccatgaggtatttctacaccgctgtgtcccggcccggccgcggagagccccacttcatcgcagtgggcta cgtggacgacacgcagttcgtgcggttcgacagcgacgccgcgagtccaagaggggagccgcgggcgccgtgggtg gagcaggaggggccggagtattgggaccgggagacacagaactacaagcgccaggcacagactgaccgagtgaacc tgcggaaactgcgcggctactacaaccagagcgaggcccgggtctcacatcatccagaggatgtatggctgcgacct ggggcccgacgggcgcctcctccgcgggCatgaccagtTcgcctacgacggcaaggattacatcgccctgaacgag gacctgcgctcctggaccgccgcggacacggcggctcagatcacccagcgcaagtgggaggcggcccgtgaggcgg agcagctgagagcctacctggagggcacgtgcgtggagtggctccgcagatacctggagaacgggaaggagacgct gcagcgcgcggaacacccaaagacacacgtgacccaccatcccgtctctgaccatgaggccaccctgagtgctgg gccctgggcttctaccctgcggagatcacactgacctggcagcgggatggcgaggaccaaactcaggacaccgagc ttgtggagaccaggccagcaggagatggaaccttccagaagtgggcagctgtggtggtgccttctggagaagagca gagatacacgtgccatgtgcagcacgaggggctgccggagcccctcaccctgagatgggagccatcttcccagccc accatcccatcgtgggcatcgttgctggcctggctgtcctggctgtcctagctgtcctaggagctgtgAtggctg ttgtgatgtgtaggaggaagagctcaggtggaaaaggagggagctgctctcaggctgcgtccagcaacagtgccca gggctctgatgagtctctcatcgcttgtaa;

Cw*1506:

(SEQ ID NO: 1764)

atgcgggtcatggcgccccgaaccctcctcctgctgctctcgggagccctggccctgaccgagacctgggcctgct cccactccatgaggtatttctacaccgctgtgtcccggcccggccgcggagagccccacttcatcgcagtgggcta cgtggacgacacgcagttcgtgcggttcgacagcgacgccgcgagtccaagaggggagccgcgggcgccgtgggtg

```
gagcaggaggggccggagtattgggaccgggagacacagaactacaagcgccaggcacagactgaccgagtgaacc tgcggaaactgcgcggctactacaaccagagcgaggccgggtctcacatcatccagaggatgtatggctgcgacct ggggcccgacgggcgcctcctccgcgggCatgaccagtacgcctacgacggcaaggattacatcgccctgaacgag gacctgcgctcctggaccgccgcggacacggcggctcagatcacccagcgcaagtgggaggcggcccgtgaggcgg agcagctgagagcctacctggagggcacgtgcgtggagtggctccgcagatacctggagaacgggaaggagacgct gcagcgcgcggaacacccaaagacacacgtgacccaccatcccgtctctgaccatgaggccaccctgaggtgctgg gccctgggcttctaccctgcggagatcacactgacctggcagcgggatggcgaggaccaaactcaggacaccgagc ttgtggagaccaggccagcaggagatggaaccttccagaagtgggcagctgtggtggtgccttctggagaagagca gagatacacgtgccatgtgcagcacgaggggctgccggagcccctcaccctgagatgggagccatcttcccagccc accatccccatcgtgggcatcgttgctggcctggctgtcctggctgtcctagctgtcctaggagctgtgAtggctg ttgtgatgtgtaggaggaagagctcag;

Cw*1507:
                                                            (SEQ ID NO: 1765)
gctcccactccatgaggtatttctacaccgctgtgtcccggcccggccgcggagagccccActtcatcgcagtggg ctacgtggacgacacgcagttcgtgcggttcgacagcgacgccgcgagtccaagaggggagccgcgggcgccgtgg gtggagcaggaggggccggagtattgggaccgggagacacagaaCtacaagcgccaggcacagactgaccgagtga gcctgcggaacctgcgcggctactacaaccagagcgaggccgggtctcacatcatccagaggatgtatggctgcga cctggggcccgacgggcgcctcctccgcgggCatgaccagttAgcctacgacggcaaggattacatcgccctgaac gaggacctgcgctcctggaccgccgcggacacggcggctcagatcacccagcgcaagtgggaggcggcccgtgagg cggagcagcTgagagcctacctggagggcacgtgcgtggagtggctccgcagatacctggagaacgggaaggagac gctgcagcgcgcgcgg;

Cw*1508:
                                                            (SEQ ID NO: 1766)
gctcccactccatgaggtatttctacaccgctgtgtcccggcccggccgcggagagccccActtcatcgcagtggg ctacgtggacgacacgcagttcgtgcggttcgacagcgacgccgcgagtccaagaggggagccgcgggcgccgtgg gtggagcaggaggggccggagtattgggaccgggagacacagaaCtacaagcgccaggcacagactgaccgagtga acctgcggaaActgcgcggctactacaaccagagcgaggccgggtctcacatcAtccagaggatgtatggctgcga cctggggcccgacgggcgcctcctccgcgggCatgaccagttAgcctacgacggcaaggattacatcgccctgaac gaggacctgcgctcctggaccgccgcggacacggcggctcagatcacccagcgcaagtgggaggcggcccgtgagg cggagcagcggagagcctacctggagggcacgtgcgtggagtggctccgcagatacctggagaacgggaaggagac gctgcagcgcgcgcgg;

Cw*1509:
                                                            (SEQ ID NO: 1767)
gctcccactccatgaggtatttctacaccgctgtgtcccggcccggccgcggagagccccacttcatcgcagtggg ctacgtggacgacacgcagttcgtgcggttcgacagcgacgccgcgagtccaagaggggagccgcgggcgccgtgg gtggagcaggaggggccggagtattgggaccgggagacacagaactacaagcgccaggcacagactgaccgagtga acctgcggaaactgcgcggctactacaaccagagcgaggccgggtctcacatcatccagaggatgtatggctgcga cctggggcccgacgggcgcctcctccgcgggCatgaccagtCcgcctacgacggcaaggattacatcgccctgaac gaggacctgcgctcctggaccgccgcggacacggcggctcagatcacccagcgcaagtgggaggcggcccgtgagg cggagcagcTgagagcctacctggagggcacgtgcgtggagtggctccgcagatacctggagaacgggaaggagac gctgcagcgcgcgcgg;

Cw*1510:
                                                            (SEQ ID NO: 1768)
gctcccactccatgaggtatttctacaccgccgtgtcccggcccggccgcggagagccccgcttcatcgcagtggg ctacgtggacgacacgcagttcgtgcggttcgacagcgacgccgcgagtccaagaggggagccgcgggcgccgtgg
```

-continued gtggagcaggaggggccggagtattgggaccgggagacacagaaCtacaagcgccaggcacagactgaccgagtga acctgcggaaActgcgcggctactacaaccagagcgaggccgggtctcacatcatccagaggatgtatggctgcga cctggggcccgacgggcgcctcctccgcgggCatgaccagttAgcctacgacggcaaggattacatcgccctgaac gaggacctgcgctcctggaccgccgcggacacggcggctcagatcacccagcgcaagtgggaggcggcccgtgagg cggagcagcTgagagcctacctggagggcacgtgcgtggagtggctccgcagatacctggagaacgggaaggagac gctgcagcgcgcgg;

Cw*1511:

(SEQ ID NO: 1769)

gctcccactccatgaggtatttctacaccgctgtgtcccggcccAgccgcggagagcccActtcatcgcagtggg ctacgtggacgacacgcagttcgtgcggttcgacagcgacgccgcgagtccaagaggggagccgcgggcgccgtgg gtggagcaggaggggccggagtattgggaccgggagacacagaagtacaagcgccaggcacagactgaccgagtga acctgcggaaActgcgcggctactacaaccagagcgaggccgggtctcacatcatccagaggatgtatggctgcga cctggggcccgacgggcgcctcctccgcgggCatgaccagttAgcctacgacggcaaggattacatcgccctgaac gaggacctgcgctcctggaccgccgcggacacggcggctcagatcacccagcgcaagtgggaggcggcccgtgagg cggagcagcTgagagcctacctggagggcacgtgcgtggagtggctccgcagatacctggagaacgggaaggagac gctgcagcgcgcgg;

Cw*1601:

(SEQ ID NO: 1770)

atgcgggtcatggcgccccgaaccctcatcctgctgctctcgggagccctggccctgaccgagacctgggcctgct cccactccatgaggtatttctacaccgccgtgtcccggcccggccgcggagagcccgcttcatcgcagtgggcta cgtggacgacacgcagttcgtgcggttcgacagcgacgccgcgagtccaagaggggagccgcgggcgccgtgggtg gagcaggaggggccggagtattgggaccgggagacacagaagtacaagcgccaggcacagactgaccgagtgagcc tgcggaacctgcgcggctactacaaccagagcgaggccgggtctcacaccctccagtggatgtatggctgcgacct ggggcccgacgggcgcctcctccgcgggtatgaccagtccgcctacgacggcaaggattacatcgccctgaacgag gacctgcgctcctggaccgccgcggacacggcggctcagatcacccagcgcaagtgggaggcggcccgtgcggcgg agcagcAgagagcctacctggagggcacgtgcgtggagtggctccgcagatacctggagaacgggaaggagacgct gcagcgcgcggaacacccaaagacacacgtgacccaccatctcgtctctgaccatgaggccaccctgagggtgctgg gccctgggcttctaccctgcggagatcacactgacctggcagcgggatggcgaggaccaaactcaggacaccgagc ttgtggagaccaggccagcaggagatggaaccttccagaagtgggcagctgtggtggtgcctctggagaagagca gagatacacgtgccatgtgcagcacgaggggctgccggagcccctcaccctgagatgggagccatcttcccagccc accatccccatcgtgggcatcgttgctggcctggctgtcctggctgtcctagctgtcctaggagctgtggtggctg ttgtTatgtgtaggaggaagagctcaggtggaaaaggagggagctgctctcaggctgcgtccagcaacagtgccca gggctctgatgagtctctcatcgcttgtaa;

Cw*1602:

(SEQ ID NO: 1771)

atgcgggtcatggcgccccgaaccctcatcctgctgctctcgggagccctggccctgaccgagacctgggcctgct cccactccatgaggtatttctacaccgccgtgtcccggcccggccgcggagagcccgcttcatcgcagtgggcta cgtggacgacacgcagttcgtgcggttcgacagcgacgccgcgagtccaagaggggagccgcgggcgccgtgggtg gagcaggaggggccggagtattgggaccgggagacacagaagtacaagcgccaggcacagactgaccgagtgaacc tgcggaaActgcgcggctactacaaccagagcgaggccgggtctcacaccctccagtggatgtatggctgcgacct ggggcccgacgggcgcctcctccgcgggtatgaccagtccgcctacgacggcaaggattacatcgccctgaacgag gacctgcgctcctggaccgccgcggacacggcggctcagatcacccagcgcaagtgggaggcggcccgtgcggcgg agcagcAgagagcctacctggagggcacgtgcgtggagtggctccgcagatacctggagaacgggaaggagacgct -continued gcagcgcgcggaacacccaaagacacacgtgacccaccatctcgtctctgaccatgaggccaccctgaggtgctgg gccctgggcttctaccctgcggagatcacactgacctggcagcgggatggcgaggaccaaactcaggacaccgagc ttgtggagaccaggccagcaggagatggaaccttccagaagtgggcagctgtggtggtgccttctggagaagagca gagatacacgtgccatgtgcagcacgaggggctgccggagcccctcaccctgagatgggagccatcttcccagccc accatccccatcgtgggcatcgttgctggcctggctgtcctggctgtcctagctgtcctaggagctgtggtggctg ttgtTatgtgtaggaggaagagctcaggtggaaaaggagggagctgctctcaggctgcgtccagcaacagtgccca gggctctgatgagtctctcatcgcttgtaa;

Cw*160401:

(SEQ ID NO: 1772)
atgcgggtcatggcgccccgaaccctcatcctgctgctctcgggagccctggccctgaccgagacctgggcctgct cccactccatgaggtatttctacaccgccgtgtcccggcccggccgcggagagccccgcttcatcgcagtgggcta cgtggacgacacgcagttcgtgcggttcgacagcgacgccgcgagtccaagaggggagccgcgggcgccgtgggtg gagcaggaggggccggagtattgggaccgggagacacagaagtacaagcgccaggcacagactgaccgagtgagcc tgcggaacctgcgcggctactacaaccagagcgaggccgggtctcacaccctccagtggatgtatggctgcgacct ggggcccgacgggcgcctcctccgcgggtatgaccagtccgcctacgacggcaaggattacatcgccctgaacgag gacctgcgctcctggaccgccgcggacacggcggctcagatcacccagcgcaagtgggaggcggcccgtgcggcgg agcagTggagagcctacctggagggcacgtgcgtggagtggctccgcagatacctggagaacgggaaggagacgct gcagcgcgcggaacacccaaagacacacgtgacccaccatctcgtctctgaccatgaggccaccctgaggtgctgg gccctgggcttctaccctgcggagatcacactgacctggcagcgggatggcgaggaccaaactcaggacaccgagc ttgtggagaccaggccagcaggagatggaaccttccagaagtgggcagctgtggtggtgccttctggagaagagca gagatacacgtgccatgtgcagcacgaggggctgccggagcccctcaccctgagatgggagccatcttcccagccc accatccccatcgtgggcatcgttgctggcctggctgtcctggctgtcctagctgtcctaggagctgtggtggctg ttgtTatgtgtaggaggaagagctcag;

Cw*1701:

(SEQ ID NO: 1773)
atgcgggtcatggcgccccaagccctcctcctgctgctctcgggagccctggccctgatcgagacctgggccggct cccactccatgaggtatttctacaccgccgtgtcccggcccggccgcggagagccccgcttcatcgcagtgggcta cgtggacgacacgcagttcgtgcggttcgacagcgacgccgcgagtccgagaggggagccgcgggcgccgtgggtg gagcaggaggggccggagtattgggaccgggagacacagaagtacaagcgccaggcacaggctgaccgagtgaacc tgcggaaactgcgcggctactacaaccagagcgaggccggttctcacaccatcagaggatgtatggctgcgacct ggggcccgacgggcgcctcctccgcgggtataaccagttcgcctacgacggcaaggattacatcgccctgaacgag gacctgcgctcctggaccgcggcggacacggcggctcagatctcccagcgcaagttggaggcggcccgtgaggcgg agcagctgagagcctacctggagggcgagtgcgtggagtggctccgcggatacctggagaacgggaaggagacgct gcagcgcgcggaacgcccaaagacacacgtgacccaccatcccgtctctgaccatgaggccaccctgaggtgctgg gccctgggcttctaccctgcggagatcacactgacctggcagcgggatgggaggaccaaactcaggacaccgagc ttgtggagaccaggccagcaggagatggaaccttccagaagtgggcagctgtggtggtgccttctggacaagaaca gagatacacgtgccatgtgcagcacgaggggctgcaggagccctgcaccctgagatggaagccgtcttcccagccc accatccccaacttgggcatcgtttctggcccagctgtcctggctgtcctggctgtcctggctgtcctagctgtcc taggagctgtggtcgctgctgtgataC;

Cw*1702:

(SEQ ID NO: 1774)
atgcgggtcatggcgccccgaaccctcatcctgctgctctcgggagccctggccctgatcgagacctgggccggct cccactccatgaggtatttctacaccgccgtgtcccggcccggccgcggagagccccgcttcatcgcagtgggcta cgtggacgacacgcagttcgtgcggttcgacagcgacgccgcgagtccgagaggggagccgcgggcgccgtgggtg -continued gagcaggagggccggagtattgggaccgggagacacagaagtacaagcgccaggcacaggctgaccgagtgaacc tgcggaaactgcgcggctactacaaccagagcgaggccggttctcacaccatccagaggatgtatggctgcgacct ggggcccgacgggcgcctcctccgcgggtataaccagttcgcctacgacggcaaggattacatcgccctgaacgag gacctgcgctcctggaccgcggcggacacggcggctcagatctcccagcgcaagttggaggcggcccgtgaggcgg agcagctgagagcctacctggagggcgagtgcgtggagtggctccgcggatacctggagaacgggaaggagacgct gcagcgcgcggaacgcccaaagacacacgtgacccaccatcccgtctctgaccatgaggccaccctgaggtgctgg gccctgggcttctaccctgcggagatcacactgacctggcagcgggatggggaggaccaaactcaggacaccgagc ttgtggagaccaggccagcaggagatggaaccttccagaagtgggcagctgtggtggtgccttctggacaagaaca gagatacacgtgccatgtgcagcacgaggggctgcaggagccctGcaccctgagatgga;

Cw*1703: (SEQ ID NO: 1775)
atgcgggtcatggcgccccaagccctcctcctgctgctctcgggagccctggccctgatcgagacctggAccggct cccactccatgaggtatttctacaccgccgtgtcccggcccggccgcggagagccccgcttcatcgcagtgggcta cgtggacgacacgcagttcgtgcggttcgacagcgacgccgcgagtccgagaggggagccgcgggcgccgtgggtg gagcaggaggggccggagtattgggaccgggagacacagaagtacaagcgccaggcacaggctgaccgagtgaacc tgcggaaactgcgcggctactacaaccagagcgaggccggttctcacaccatccagaggatgtatggctgcgacct ggggcccgacgggcgcctcctccgcgggtataaccagttcgcctacgacggcaaggattacatcgccctgaacgag gacctgcgctcctggaccgcggcggacacggcggctcagatctcccagcgcaagttggaggcggcccgtgaggcgg agcagctgagagcctacctggagggcgagtgcgtggagtggctccgcggatacctggagaacgggaaggagacgct gcagcgcgcggaacgcccaaagacacacgtgacccaccatcccgtctctgaccatgaggccaccctgaggtgctgg gccctgggcttctaccctgcggagatcacactgacctggcagcgggatggggaggaccaaactcaggacaccgagc ttgtggagaccaggccagcaggagatggaaccttccagaagtgggcagctgtggtggtgccttctggacaagaaca gagatacacgtgccatgtgcagcacgaggggctgcaggagccctgcaccctgagatggaagccgtcttcccagccc accatccccaacttgggcatcgtttctggcccagctgtcctggctgtcctggctgtcctggctgtcctagctgtcc taggagctgtggtcgctgctgtgatac;

Cw*1801: (SEQ ID NO: 1776)
atgcgggtcatggcgccccgagccctcctcctgctgctctcgggaggcctggccctgaccgagacctgggcctgct cccactccatgaggtatttcgacaccgccgtgtcccggcccggccgcggagagccccgcttcatctcagtgggcta cgtggacgacacgcagttcgtgcggttcgacagcgacgccgcgagtccgagaggggagccccgggcgccgtgggtg gagcaggaggggccggagtattgggaccgggagacacagaagtacaagcgccaggcacaggctgaccgagtgaacc tgcggaaactgcgcggctactacaaccagagcgaggacgggtctcacaccctccagaggatgtttggctgcgacct ggggcccgacgggcgcctcctccgcgggtataaccagttcgcctacgacggcaaggattacatcgccctgaacgag gatctgcgctcctggaccgccgcggacacggcggctcagatcacccagcgcaagtgggaggcggcccgtgaggcgg agcagcggagagcctacctggaggcacgtgcgtggagtggctccgcagatacctggagaacgggaaggagacgct gcagcgcgcggaacacccaaagacacacgtgacccaccatcccgtctctgaccatgaggccaccctgaggtgctgg gccctgggcttctaccctgcggagatcacactgacctggcagtgggatggggaggaccaaactcaggacaccgagc ttgtggagaccaggccagcaggagatggaaccttccagaagtgggcagctgtggtggtgccttctggagaagagca gagatacacgtgccatgtgcagcacgaggggctgccggagccccctcaccctgagatggAagccgtcttcccagccc accatccccatcgtgggcatcgttgctggcctggctgtcctggTtgtcctagctgtcctaggagctgtggtggctg ttgtgatgtgtaggaggaagagctcaggtggaaaaggagggagctgctctcaggctgcgtccagcaacagtgccca gggctctgatgagtctctcatcgcttgtaa;

-continued

Cw*1802:

(SEQ ID NO: 1777)

```
atgcgggtcatggcgccccgagccctcctcctgctgctctcggggaggcctggccctgaccgagacctgggcctgct
cccactccatgaggtatttcgacaccgccgtgtcccggcccggccgcggagagccccgcttcatctcagtgggcta
cgtggacgacacgcagttcgtgcggttcgacagcgacgccgcgagtccgagaggggagccCcgggcgccgtgggtg
gagcaggaggggccggagtattgggaccgggagacacagaagtacaagcgccaggcacaggctgaccgagtgaacc
tgcgaaactgcgcggctactacaaccagagcgaggacgggtctcacaccctccagaggatgtttggctgcgacct
ggggccggacgggcgcctcctccgcgggtataaccagttcgcctacgacggcaaggattacatcgccctgaacgag
gaTctgcgctcctggaccgccgcggacacggcggctcagatcacccagcgcaagtgggaggcggcccgtgaggcgg
agcagcggagagcctacctggagggcacgtgcgtggagtggctccgcagatacctggagaacgggaaggagacgct
gcagcgcgcggaacacccaaagacacacgtgacccaccatcccgtctctgaccatgaggccaccctgaggtgctgg
gccctgggcttctaccctgcggagatcacactgacctggcagtgggatggggaggaccaaactcaggacaccgagc
ttgtggagaccaggccagcaggagatggaaccttccagaagtgggcagctgtggtggtgccttctggagaagagca
gagatacacgtgccatgtgcagcacgaggggctgccggagcccctcaccctgagatggAagccgtcttcccagccc
accatccccatcgtgggcatcgttgctggcctggctgtcctggctgtcctagctgtcctaggagctgtggtggctg
ttgtgatgtgtaggaggaagagctcaggtggaaaaggagggagctgctctcaggctgcgtccagcaacagtgccca
gggctctgatgagtctctcatcgcttgtaa;
```

In the following, Probe Lists C1 and C2 are shown In Tables 9-1 to 9-4 and Tables 10-1 to 10-4 respectively.

TABLE 9-1

| Probe No. | Base Sequence | |
|---|---|---|
| 0 | c acc ctc cag tgg atg tG | (SEQ ID NO: 1778) |
| 1 | c cgc ggg tat gac cag tA | (SEQ ID No: 1779) |
| 2 | g acc gcc gcg gac acC | (SEQ ID No: 1780) |
| 3 | ag aag tgg gca gct gtg A | (SEQ ID No: 1781) |
| 4 | c ctc ctc cgc ggg tat A | (SEQ ID No: 1782) |
| 5 | g cgc tcc tgg acc gcT | (SEQ ID No: 1783) |
| 6 | g cac gag ggg ctg ccA | (SEQ ID No: 1784) |
| 7 | ct gtc cta gga gct gtg A | (SEQ ID No: 1785) |
| 8 | c acc ctc cag agg atg tC | (SEQ ID No: 1786) |
| 9 | gg gag gcg gcc cgt gT | (SEQ ID No: 1787) |
| 10 | ggg cgc ctc ctc cgc A | (SEQ ID No: 1788) |
| 11 | c aag tgg gag gcg gcc T | (SEQ ID No: 1789) |
| 12 | c cgt gag gcg gag cag T | (SEQ ID No: 1790) |
| 13 | a gtg aac ctg cgg aaa ctA | (SEQ ID No: 1791) |
| 14 | cc ctg ggc ttc tac cct A | (SEQ ID No: 1792) |
| 15 | g acc gcc gcg gac acA | (SEQ ID No: 1793) |
| 16 | gct gtg tcc cgg ccc A | (SEQ ID No: 1794) |
| 17 | g acc gcc gcg gac acG | (SEQ ID No: 1795) |
| 18 | cc ctg aga tgg gag ccA | (SEQ ID No: 1796) |
| 19 | gg tct cac acc ctc cag A | (SEQ ID No: 1797) |

TABLE 9-1-continued

| Probe No. | Base Sequence | |
|---|---|---|
| 20 | cgc ggg tat gac cag tC | (SEQ ID No: 1798) |
| 21 | gcc tac ctg gag ggc gA | (SEQ ID No: 1799) |
| 22 | c tcc cac tcc atg agg tG | (SEQ ID No: 1800) |
| 23 | cgc ggg cat gac cag ttA | (SEQ ID No: 1801) |
| 24 | g gac caa act cag gac acT | (SEQ ID No: 1802) |
| 25 | c aac cag agc gag gcc A | (SEQ ID No: 1803) |
| 26 | ag gcc agg tct cac atc A | (SEQ ID No: 1804) |
| 27 | g aag tgg gca gct gtg G | (SEQ ID No: 1805) |
| 28 | gcg gac acg gcg gcC | (SEQ ID No: 1806) |
| 29 | at ggc tgc gac gtg ggA | (SEQ ID No: 1807) |
| 30 | g gcc ggg tct cac atc A | (SEQ ID No: 1808) |

TABLE 9-2

| Probe No. | Base Sequence | |
|---|---|---|
| 31 | c atc atc cag agg atg taC | (SEQ ID No: 1809) |
| 32 | c cgc aga tac ctg aag aaT | (SEQ ID No: 1810) |
| 33 | ct cac acc ctc cag agC | (SEQ ID No: 1811) |
| 34 | ctc ctc cgc ggg tat gT | (SEQ ID No: 1812) |
| 35 | ca cag act gac cga gtg aA | (SEQ ID No: 1813) |
| 36 | cga gtg aac ctg cgg aaA | (SEQ ID No: 1814) |

TABLE 9-2-continued

| Probe No. | Base Sequence | |
|---|---|---|
| 37 | gg atg tat ggc tgc gac G | (SEQ ID No: 1815) |
| 38 | gcc tac ctg gag ggc cT | (SEQ ID No: 1816) |
| 39 | gac cgg gag aca cag aaC | (SEQ ID No: 1817) |
| 40 | g gag ccc cac ttc atc G | (SEQ ID No: 1818) |
| 41 | cga gtg agc ctg cgg aaA | (SEQ ID No: 1819) |
| 42 | cgc ggg tat gac tag ttA | (SEQ ID No: 1820) |
| 43 | g gag gcg gcc cgt gC | (SEQ ID No: 1821) |
| 44 | c tac aac cag agc gag gA | (SEQ ID No: 1822) |
| 45 | cgt gag gcg gag cag cT | (SEQ ID No: 1823) |
| 46 | cta gct gtc cta gga gct A | (SEQ ID No: 1824) |
| 47 | ggc tac gtg gac gac acA | (SEQ ID No: 1825) |
| 48 | gc cgc gga gag ccc cA | (SEQ ID No: 1826) |
| 49 | g aga tac acg tgc cat gtT | (SEQ ID No: 1827) |
| 50 | ga ggg gag ccg cgg gA | (SEQ ID No: 1828) |
| 51 | c atc gca gtg ggc tac C | (SEQ ID No: 1829) |
| 52 | c tgc gac ctg ggg ccG | (SEQ ID No: 1830) |
| 53 | tc tcc aca tcc gtg tcc T | (SEQ ID No: 1831) |
| 54 | c aag cgc cag gca cag G | (SEQ ID No: 1832) |
| 55 | gg acc gcc gcg gac aA | (SEQ ID No: 1833) |
| 56 | ctc act ctg aga tgg gG | (SEQ ID No: 1834) |
| 57 | tg tgc gtg gag tgg ctG | (SEQ ID No: 1835) |
| 58 | cc atc tct gac cat gag gT | (SEQ ID No: 1836) |
| 59 | ac ctg gag aac ggg aag A | (SEQ ID No: 1837) |
| 60 | c cgc ggg tat aac cag tT | (SEQ ID No: 1838) |

TABLE 9-3

| Probe No. | Base Sequence | |
|---|---|---|
| 61 | g gag ccg cgg gcg cG | (SEQ ID No: 1839) |
| 62 | t ccg aga ggg gag ccC | (SEQ ID No: 1840) |
| 63 | g agg tat ttc tac acc gcT | (SEQ ID No: 1841) |
| 64 | c gac gcc gcg agt ccA | (SEQ ID No: 1842) |
| 65 | gt cca aga ggg gag ccC | (SEQ ID No: 1843) |
| 66 | gcg ccg tgg gtg gag A | (SEQ ID No: 1844) |
| 67 | c acc ctc cag agg atg tA | (SEQ ID No: 1845) |
| 68 | g atc acc cag cgc aag tT | (SEQ ID No: 1846) |
| 69 | g acg ctg cag cgc gcA | (SEQ ID No: 1847) |
| 70 | c tct gat gag tct ctc atc A | (SEQ ID No: 1848) |

TABLE 9-3-continued

| Probe No. | Base Sequence | |
|---|---|---|
| 71 | gag cca tct tcc cag ccT | (SEQ ID No: 1849) |
| 72 | ga gcc tac ctg gag ggA | (SEQ ID No: 1850) |
| 73 | t gcg gcg gag cag gaC | (SEQ ID No: 1851) |
| 74 | aac ctg cgc ggc tac taT | (SEQ ID No: 1852) |
| 75 | g tct cac acc ctc cag aaT | (SEQ ID No: 1853) |
| 76 | a gct gtg gtc acc gct aA | (SEQ ID No: 1854) |
| 77 | c acc ctc cag agg atg tT | (SEQ ID No: 1855) |
| 78 | ag gac ggg tct cac atc A | (SEQ ID No: 1856) |
| 79 | ac atc atc cag agg atg tC | (SEQ ID No: 1857) |
| 80 | tgc tct cag gct gcg tG | (SEQ ID No: 1858) |
| 81 | c cgc ggg tat gac cag tT | (SEQ ID No: 1859) |
| 82 | g gag acg ctg cag cgc A | (SEQ ID No: 1860) |
| 83 | g ccc ctc acc ctg agC | (SEQ ID No: 1861) |
| 84 | ggg agc tgc tct cag gT | (SEQ ID No: 1862) |
| 85 | cgt acg gcg gag cag cT | (SEQ ID No: 1863) |
| 86 | acc ctc cag agg atg taC | (SEQ ID No: 1864) |
| 87 | tgg gag gcg gcc cgt A | (SEQ ID No: 1865) |
| 88 | cgc aga tac ctg gag aac A | (SEQ ID No: 1866) |
| 89 | gcc tac ctg gag ggc G | (SEQ ID No: 1867) |
| 90 | ga tac ctg gag aac ggg G | (SEQ ID No: 1868) |

TABLE 9-4

| Probe No. | Base Sequence | |
|---|---|---|
| 91 | ac ctg cgc tcc tgg acT | (SEQ ID No: 1869) |
| 92 | g cgc tcc tgg acc gcG | (SEQ ID No: 1870) |
| 93 | a gag ccc cgc ttc atc G | (SEQ ID No: 1871) |
| 94 | c acc ctc cag tgg atg tA | (SEQ ID No: 1872) |
| 95 | cag tcc gcc tac gac gT | (SEQ ID No: 1873) |
| 96 | a cag gct gac cga gtg G | (SEQ ID No: 1874) |
| 97 | cac tcc atg agg tat ttc tC | (SEQ ID No: 1875) |
| 98 | c acc ctc cag tgg atg tT | (SEQ ID No: 1876) |
| 99 | a cag gct gac cga gtg aA | (SEQ ID No: 1877) |
| 100 | atc gcc ctg aac gag gaT | (SEQ ID No: 1878) |
| 101 | gc ctc ctc cgc ggg C | (SEQ ID No: 1879) |
| 102 | tc atg gcg ccc cga acT | (SEQ ID No: 1880) |
| 103 | cgc ggg cat gac cag tT | (SEQ ID No: 1881) |
| 104 | cgc ggg cat gac cag tC | (SEQ ID No: 1882) |
| 105 | gt gcg gcg gag cag cA | (SEQ ID No: 1883) |

TABLE 9-4-continued

| Probe No. | Base Sequence | |
|---|---|---|
| 106 | gct gtg gtg gct gtt gtT | (SEQ ID No: 1884) |
| 107 | cgt gcg gcg gag cag T | (SEQ ID No: 1885) |
| 108 | tg gtc gct gct gtg ata C | (SEQ ID No: 1886) |
| 109 | gg ctg cag gag ccc tG | (SEQ ID No: 1887) |
| 110 | cc ctg atc gag acc tca A | (SEQ ID No: 1888) |
| 111 | cc ctc acc ctg aga tgg A | (SEQ ID No: 1889) |
| 112 | Ggc ctg gct gtc ctg gT | (SEQ ID No: 1890) |

TABLE 10-1

| Probe No. | Base Sequence | |
|---|---|---|
| 0 | g tgg atg tGt ggc tgc g | (SEQ ID No: 1891) |
| 1 | at gac cag tAc gcc tac g | (SEQ ID No: 1892) |
| 2 | gcg gac acC gcg gct c | (SEQ ID No: 1893) |
| 3 | gca gct gtg Atg gtg cct | (SEQ ID No: 1894) |
| 4 | cgc ggg tat Aac cag ttc | (SEQ ID No: 1895) |
| 5 | tgg acc gcT gcg gac ac | (SEQ ID No: 1896) |
| 6 | ggg ctg ccA gag ccc c | (SEQ ID No: 1897) |
| 7 | gga gct gtg Atg gct gtt | (SEQ ID No: 1898) |
| 8 | g agg atg tCt ggc tgc g | (SEQ ID No: 1899) |
| 9 | g gcc cgt gTg gcg gag | (SEQ ID No: 1900) |
| 10 | ctc ctc cgc Agg tat gac | (SEQ ID No: 1901) |
| 11 | g gcg gcc Tgt gag gcg | (SEQ ID No: 1902) |
| 12 | cg gag cag Tgg aga gcc | (SEQ ID No: 1903) |
| 13 | g cgg aaa ctA cgc ggc ta | (SEQ ID No: 1904) |
| 14 | ttc tat cct Acg gag atc a | (SEQ ID No: 1905) |
| 15 | gcg gac acA gcg gct c | (SEQ ID No: 1906) |
| 16 | c cgg ccc Agc cgc gg | (SEQ ID No: 1907) |
| 17 | gcg gac acG gcg gct c | (SEQ ID No: 1908) |
| 18 | a tgg gag ccA tct tcc ca | (SEQ ID No: 1909) |
| 19 | acc ctc cag Agg atg tat g | (SEQ ID No: 1910) |
| 20 | t gac cag tCc gcc tat g | (SEQ ID No: 1911) |
| 21 | g gag ggc gAg tgc gtg | (SEQ ID No: 1912) |
| 22 | cc atg agg tGt ttc tac ac | (SEQ ID No: 1913) |
| 23 | t gac cag ttA gcc tac gac | (SEQ ID No: 1914) |
| 24 | t tag gac acT gag ctt gtg | (SEQ ID No: 1915) |
| 25 | gc gag gcc Agg tct cac | (SEQ ID No: 1916) |
| 26 | tct cac atc Atc cag agg a | (SEQ ID No: 1917) |

TABLE 10-1-continued

| Probe No. | Base Sequence | |
|---|---|---|
| 27 | ca gct gtg Gtg gtg cct | (SEQ ID No: 1918) |
| 28 | acg gcg gcC cag atc ac | (SEQ ID No: 1919) |
| 29 | gac gtg ggA ccc gac g | (SEQ ID No: 1920) |
| 30 | g agg atg taC ggc tgc ga | (SEQ ID No: 1921) |

TABLE 10-2

| Probe No. | Base Sequence | |
|---|---|---|
| 31 | c ctg aag aaT ggg aag gag | (SEQ ID No: 1922) |
| 32 | c ctc cag agC atg tac gg | (SEQ ID No: 1923) |
| 33 | gc ggg tat gTc cag tac g | (SEQ ID No: 1924) |
| 34 | c cga gtg aAc ctg cgg a | (SEQ ID No: 1925) |
| 35 | ctg cgg aaA ctg cgc gg | (SEQ ID No: 1926) |
| 36 | c tgc gac Gtg ggg ccc | (SEQ ID No: 1927) |
| 37 | g gag ggc cTg tgc gtg | (SEQ ID No: 1928) |
| 38 | g aca cag aaC tac aag cgc | (SEQ ID No: 1929) |
| 39 | cac ttc atc Gca gtg ggc | (SEQ ID No: 1930) |
| 40 | gcc cgt gCg gcg gag | (SEQ ID No: 1931) |
| 41 | g agc gag gAc ggg tct c | (SEQ ID No: 1932) |
| 42 | g gag cag cTg aga gcc t | (SEQ ID No: 1933) |
| 43 | cta gga gct Atg gtg gct | (SEQ ID No: 1934) |
| 44 | g gac gac acA cag ttc gt | (SEQ ID No: 1935) |
| 45 | ga gag ccc cAc ttc atc g | (SEQ ID No: 1936) |
| 46 | g tgc cat gtT cag cac ga | (SEQ ID No; 1937) |
| 47 | ccg cgg gAg ccg tgg | (SEQ ID No: 1938) |
| 48 | tg ggc tac Ctg gac gac | (SEQ ID No: 1939) |
| 49 | ctg ggg ccG gac ggg | (SEQ ID No: 1940) |
| 50 | c gtg tcc Tgg ccc ggc | (SEQ ID No: 1941) |
| 51 | ag gca cag Gct gac cga | (SEQ ID No: 1942) |
| 52 | c gcg gac aAg gcg gct | (SEQ ID No: 1943) |
| 53 | tg aga tgg gGg cca tct t | (SEQ ID No: 1944) |
| 54 | g gag tgg ctG cgc aga ta | (SEQ ID No: 1945) |
| 55 | ac cat gag gTc acc ctg a | (SEQ ID No: 1946) |
| 56 | aac ggg aag Aag acg ctg | (SEQ ID No: 1947) |
| 57 | at aac cag tTc gcc tac ga | (SEQ ID No: 1948) |
| 58 | cgg gcg cGg tgg gtg | (SEQ ID No: 1949) |
| 59 | ggg gag ccC cgg gcg | (SEQ ID No: 1950) |
| 60 | tac acc gcT gtg tcc cg | (SEQ ID No: 1951) |

TABLE 10-3

| Probe No. | Base Sequence | |
|---|---|---|
| 61 | gcg agt ccA aga ggg ga | (SEQ ID No: 1952) |
| 62 | gg gtg gag Aag gag ggg | (SEQ ID No: 1953) |
| 63 | ag agg atg tAt ggc tgc g | (SEQ ID No: 1954) |
| 64 | g cgc aag tTg gag gcg g | (SEQ ID No: 1955) |
| 65 | cag cgc gcA gaa ccc c | (SEQ ID No: 1956) |
| 66 | g gct gcg tGc agc aac a | (SEQ ID No: 1957) |
| 67 | tcc cag ccT acc atc cc | (SEQ ID No: 1958) |
| 68 | ctg gag ggA ctg tgc gt | (SEQ ID No: 1959) |
| 69 | g gag cag gaC aga gcc ta | (SEQ ID No: 1960) |
| 70 | c ggc tac taT aac tag agc | (SEQ ID No: 1961) |
| 71 | c ctc cag aaT atg tat ggc | (SEQ ID No: 1962) |
| 72 | tc acc gct aAg atg tgt ag | (SEQ ID No: 1963) |
| 73 | ag agg atg tTt ggc tgc g | (SEQ ID No: 1964) |
| 74 | at gac cag tTc gcc tac g | (SEQ ID No: 1965) |
| 75 | ggg ctg caA gag ccc c | (SEQ ID No: 1966) |
| 76 | gc tct cag gTt gcg tgc a | (SEQ ID No: 1967) |
| 77 | g gcc cgt Acg gcg gag | (SEQ ID No: 1968) |
| 78 | ctg gag aac Agg aag aag a | (SEQ ID No: 1969) |
| 79 | g gag ggc Gcg tgc gtg | (SEQ ID No: 1970) |
| 80 | c ctc cag agC atg tat gg | (SEQ ID No: 1971) |
| 81 | gag aac ggg Gag aag acg | (SEQ ID No: 1972) |
| 82 | tcc tgg acT gcc gcg g | (SEQ ID No: 1973) |
| 83 | tgg acc gcG gcg gac a | (SEQ ID No: 1974) |
| 84 | gc ttc atc Gca gtg ggc | (SEQ ID No: 1975) |
| 85 | ag tgg atg tAt ggc tgc g | (SEQ ID No: 1976) |
| 86 | cc tac gac gTc aag gat ta | (SEQ ID No: 1977) |
| 87 | c cga gtg Ggc ctg cgg | (SEQ ID No: 1978) |
| 88 | gg tat ttc tCc aca tcc gt | (SEQ ID No: 1979) |
| 89 | ag tgg atg tTt ggc tgc g | (SEQ ID No: 1980) |
| 90 | g aac gag gaT ctg cgc tc | (SEQ ID No: 1981) |

TABLE 10-4

| Probe No. | Base Sequence | |
|---|---|---|
| 91 | c cgc ggg Cat gac cag | (SEQ ID No: 1982) |
| 92 | ccc cga acT ctc ctc ct | (SEQ ID No: 1983) |
| 93 | c cgc ggg Cat gac cag | (SEQ ID No: 1984) |
| 94 | g gag cag cAg aga gcc t | (SEQ ID No: 1985) |
| 95 | g gct gtt gtT atg tgt agg | (SEQ ID No: 1986) |
| 96 | t gtg gtc gcT gct gtg at | (SEQ ID No: 1987) |
| 97 | g gag ccc tGc acc ctg | (SEQ ID No: 1988) |
| 98 | g acc tgg Acc ggc tcc | (SEQ ID No: 1989) |
| 99 | ctg aga tgg Aag ccg tct | (SEQ ID No: 1990) |
| 100 | ct gtc ctg gTt gtc cta g | (SEQ ID No: 1991) |

TABLE 11-1

| Allele Number | Probe Number for Detection | | | | |
|---|---|---|---|---|---|
| Cw*0102 | 0 | 1 | 2 | 3 | |
| Cw*0103 | 4 | | | | |
| Cw*0104 | 5 | 6 | 7 | | |
| Cw*0105 | 8 | | | | |
| Cw*0106 | 9 | | | | |
| Cw*0107 | 10 | | | | |
| Cw*0108 | 11 | | | | |
| Cw*0109 | 12 | | | | |
| Cw*020201 | 13 | | | | |
| Cw*020202 | 14 | | | | |
| Cw*020203 | 15 | 12 | | | |
| Cw*020204 | 16 | 17 | 18 | | |
| Cw*020205 | 16 | 19 | 20 | 17 | 12 | 21 |
| Cw*0203 | 9 | 21 | | | |
| Cw*0204 | 22 | | | | |
| Cw*0205 | 16 | 20 | 17 | 12 | 21 |
| Cw*0206 | 23 | 21 | | | |
| Cw*030201 | 24 | 18 | | | |
| Cw*030202 | 20 | 24 | | | |
| Cw*030301 | 25 | 26 | 27 | | |
| Cw*030302 | 28 | | | | |
| Cw*030303 | 29 | | | | |
| Cw*030401 | 30 | 24 | | | |
| Cw*030402 | 30 | 31 | 32 | | |
| Cw*0305 | 33 | 32 | | | |
| Cw*0306 | 34 | | | | |
| Cw*0307 | 35 | 36 | 30 | 37 | 38 | 32 |
| Cw*0308 | 39 | 30 | 24 | | |
| Cw*0309 | 40 | 30 | 38 | 32 | |
| Cw*0310 | 41 | 30 | 37 | 38 | 32 |
| Cw*0311 | 25 | 26 | | | |

TABLE 11-2

| Allele Number | Probe Number for Detection | | | |
|---|---|---|---|---|
| Cw*0312 | 25 | 42 | | |
| Cw*0313 | 25 | 27 | | |
| Cw*0314 | 43 | 32 | | |
| Cw*0315 | 44 | 20 | 38 | 32 |
| Cw*0316 | 37 | 20 | 17 | 45 |
| Cw*040101 | 46 | | | |
| Cw*040102 | 47 | | | |
| Cw*0403 | 48 | 49 | | |
| Cw*0404 | 50 | 45 | | |
| Cw*0405 | 51 | | | |
| Cw*0406 | 48 | 52 | 45 | |
| Cw*0407 | 53 | 54 | | |
| Cw*0408 | 50 | 38 | | |
| Cw*0410 | 50 | | | |
| Cw*0501 | 36 | 55 | 56 | |
| Cw*0502 | 57 | | | |
| Cw*0503 | 58 | | | |
| Cw*0504 | 20 | 55 | 59 | |
| Cw*0505 | 37 | 60 | 55 | 59 |
| Cw*0506 | 61 | | | |

TABLE 11-2-continued

| Allele Number | Probe Number for Detection | | | | |
|---|---|---|---|---|---|
| Cw*0602 | 62 | 12 | 7 | | |
| Cw*0603 | 63 | 62 | 20 | 12 | |
| Cw*0604 | 62 | 45 | | | |
| Cw*0605 | 64 | 65 | 20 | 17 | |
| Cw*0606 | 62 | 7 | | | |
| Cw*0607 | 66 | | | | |
| Cw*0608 | 44 | 20 | 17 | 12 | 21 |
| Cw*0609 | 62 | 60 | 12 | | |
| Cw*070101 | 67 | 68 | 69 | 70 | |
| Cw*070102 | 71 | | | | |

TABLE 11-3

| Allele Number | Probe Number for Detection | | | | |
|---|---|---|---|---|---|
| Cw*070201 | 8 | 68 | 70 | | |
| Cw*0703 | 72 | | | | |
| Cw*070401 | 73 | 70 | | | |
| Cw*070402 | 74 | | | | |
| Cw*0705 | 75 | | | | |
| Cw*0706 | 76 | | | | |
| Cw*0707 | 36 | 67 | 20 | 68 | 69 |
| Cw*0708 | 77 | 20 | 68 | 69 | |
| Cw*0709 | 36 | 44 | 67 | 20 | 68 | 69 |
| Cw*0710 | 78 | 79 | 20 | 68 | 69 |
| Cw*0711 | 73 | 80 | | | |
| Cw*0712 | 73 | | | | |
| Cw*0713 | 8 | 81 | 68 | 69 | |
| Cw*0714 | 82 | | | | |
| Cw*0715 | 8 | 21 | 69 | | |
| Cw*0716 | 39 | 67 | 20 | 68 | 69 |
| Cw*0717 | 8 | 83 | | | |
| Cw*0718 | 84 | | | | |
| Cw*080101 | 85 | 56 | | | |
| Cw*080102 | 86 | 60 | 87 | | |
| Cw*0802 | 55 | 56 | | | |
| Cw*0803 | 88 | 7 | | | |
| Cw*0804 | 55 | 45 | 59 | | |
| Cw*0805 | 54 | 60 | 55 | 59 | |
| Cw*0806 | 89 | 88 | | | |
| Cw*0807 | 55 | 68 | 59 | | |
| Cw*0808 | 33 | 59 | | | |
| Cw*0809 | 90 | | | | |
| Cw*120201 | 86 | 5 | 7 | | |
| Cw*120202 | 86 | 5 | 6 | 7 | |
| Cw*120203 | 67 | 5 | | | |
| Cw*120301 | 54 | 91 | 7 | | |

TABLE 11-4

| Allele Number | Probe Number for Detection | | | | | |
|---|---|---|---|---|---|---|
| Cw*120302 | 92 | 12 | | | | |
| Cw*120401 | 93 | 54 | 36 | 94 | 20 | 17 | 12 |
| Cw*120402 | 54 | 36 | 91 | 7 | | |
| Cw*1205 | 36 | 91 | 7 | | | |
| Cw*1206 | 95 | | | | | |
| Cw*1207 | 96 | | | | | |
| Cw*1208 | 39 | 86 | 5 | 6 | 7 | |
| Cw*140201 | 97 | 20 | 27 | | | |
| Cw*140202 | 97 | 98 | 20 | | | |
| Cw*1403 | 97 | 64 | 20 | 27 | | |
| Cw*1404 | 97 | 99 | 98 | 20 | 100 | |
| Cw*1405 | 97 | 94 | 20 | 100 | | |
| Cw*150201 | 23 | 7 | | | | |
| Cw*150202 | 48 | 39 | 36 | 101 | 23 | 45 |
| Cw*1503 | 54 | 23 | 7 | | | |
| Cw*1504 | 20 | 45 | 7 | | | |
| Cw*150501 | 102 | | | | | |
| Cw*150502 | 101 | 103 | 7 | | | |
| Cw*1506 | 101 | 7 | | | | |
| Cw*1507 | 48 | 39 | 101 | 23 | 45 | |

TABLE 11-4-continued

| Allele Number | Probe Number for Detection | | | | | |
|---|---|---|---|---|---|---|
| Cw*1508 | 48 | 39 | 36 | 30 | 101 | 23 |
| Cw*1509 | 101 | 104 | 45 | | | |
| Cw*1510 | 39 | 36 | 101 | 23 | 45 | |
| Cw*1511 | 16 | 48 | 36 | 101 | 23 | 45 |
| Cw*1601 | 105 | 106 | | | | |
| Cw*1602 | 36 | 105 | 106 | | | |
| Cw*160401 | 107 | 106 | | | | |
| Cw*1701 | 108 | | | | | |
| Cw*1702 | 109 | | | | | |
| Cw*1703 | 110 | | | | | |
| Cw*1801 | 111 | 112 | | | | |
| Cw*1802 | 62 | 100 | 111 | | | |

TABLE 12-1

| Allele Number | Probe Number for Detection | | | | | |
|---|---|---|---|---|---|---|
| Cw*0102 | 0 | 1 | 2 | 3 | | |
| Cw*0103 | 4 | | | | | |
| Cw*0104 | 5 | 6 | 7 | | | |
| Cw*0105 | 8 | | | | | |
| Cw*0106 | 9 | | | | | |
| Cw*0107 | 10 | | | | | |
| Cw*0108 | 11 | | | | | |
| Cw*0109 | 12 | | | | | |
| Cw*020201 | 13 | | | | | |
| Cw*020202 | 14 | | | | | |
| Cw*020203 | 15 | 12 | | | | |
| Cw*020204 | 16 | 17 | 18 | | | |
| Cw*020205 | 16 | 19 | 20 | 17 | 12 | 21 |
| Cw*0203 | 9 | 21 | | | | |
| Cw*0204 | 22 | | | | | |
| Cw*0205 | 16 | 20 | 17 | 12 | 21 | |
| Cw*0206 | 23 | 21 | | | | |
| Cw*030201 | 24 | 18 | | | | |
| Cw*030202 | 20 | 24 | | | | |
| Cw*030301 | 25 | 26 | 27 | | | |
| Cw*030302 | 28 | | | | | |
| Cw*030303 | 29 | | | | | |
| Cw*030401 | 26 | 24 | | | | |
| Cw*030402 | 26 | 30 | 31 | | | |
| Cw*0305 | 32 | 31 | | | | |
| Cw*0306 | 33 | | | | | |
| Cw*0307 | 34 | 35 | 26 | 36 | 37 | 31 |
| Cw*0308 | 38 | 26 | 24 | | | |
| Cw*0309 | 39 | 26 | 37 | 31 | | |
| Cw*0310 | 35 | 26 | 36 | 37 | 31 | |
| Cw*0311 | 25 | 26 | | | | |

TABLE 12-2

| Allele Number | Probe Number for Detection | | | |
|---|---|---|---|---|
| Cw*0312 | 25 | 23 | | |
| Cw*0313 | 25 | 27 | | |
| Cw*0314 | 40 | 31 | | |
| Cw*0315 | 41 | 20 | 37 | 31 |
| Cw*0316 | 36 | 20 | 17 | 42 |
| Cw*040101 | 43 | | | |
| Cw*040102 | 44 | | | |
| Cw*0403 | 45 | 46 | | |
| Cw*0404 | 47 | 42 | | |
| Cw*0405 | 48 | | | |
| Cw*0406 | 45 | 49 | 42 | |
| Cw*0407 | 50 | 51 | | |
| Cw*0408 | 47 | 37 | | |
| Cw*0410 | 47 | | | |
| Cw*0501 | 35 | 52 | 53 | |
| Cw*0502 | 54 | | | |
| Cw*0503 | 55 | | | |
| Cw*0504 | 20 | 52 | 56 | |
| Cw*0505 | 36 | 57 | 52 | 56 |

TABLE 12-2-continued

| Allele Number | Probe Number for Detection | | | | |
|---|---|---|---|---|---|
| Cw*0506 | 58 | | | | |
| Cw*0602 | 59 | 12 | 7 | | |
| Cw*0603 | 60 | 59 | 20 | 12 | |
| Cw*0604 | 59 | 42 | | | |
| Cw*0605 | 61 | 59 | 20 | 17 | |
| Cw*0606 | 59 | 7 | | | |
| Cw*0607 | 62 | | | | |
| Cw*0608 | 41 | 20 | 17 | 12 | 21 |
| Cw*0609 | 59 | 57 | 12 | | |
| Cw*070101 | 63 | 64 | 65 | 66 | |
| Cw*070102 | 67 | | | | |
| Cw*070201 | 8 | 64 | 66 | | |

TABLE 12-3

| Allele Number | Probe Number for Detection | | | | |
|---|---|---|---|---|---|
| Cw*0703 | 68 | | | | |
| Cw*070401 | 69 | 66 | | | |
| Cw*070402 | 70 | | | | |
| Cw*0705 | 71 | | | | |
| Cw*0706 | 72 | | | | |
| Cw*0707 | 38 | 35 | 40 | 42 | |
| Cw*0708 | 73 | 40 | 42 | | |
| Cw*0709 | 38 | 35 | 41 | 40 | 42 |
| Cw*0710 | 26 | 8 | 20 | 64 | 42 |
| Cw*0711 | 69 | 66 | | | |
| Cw*0712 | 69 | | | | |
| Cw*0713 | 8 | 74 | 64 | 42 | |
| Cw*0714 | 30 | 64 | 40 | 42 | |
| Cw*0715 | 8 | 21 | | | |
| Cw*0716 | 38 | 40 | 42 | | |
| Cw*0717 | 8 | 75 | | | |
| Cw*0718 | 76 | | | | |
| Cw*080101 | 42 | 53 | | | |
| Cw*080102 | 30 | 57 | 77 | | |
| Cw*0802 | 52 | 53 | | | |
| Cw*0803 | 78 | 7 | | | |
| Cw*0804 | 52 | 42 | 56 | | |
| Cw*0805 | 51 | 57 | 52 | 56 | |
| Cw*0806 | 79 | 78 | | | |
| Cw*0807 | 52 | 64 | 56 | | |
| Cw*0808 | 80 | 56 | | | |
| Cw*0809 | 81 | | | | |
| Cw*120201 | 30 | 5 | 7 | | |
| Cw*120202 | 30 | 5 | 6 | 7 | |
| Cw*120203 | 63 | 5 | | | |
| Cw*120301 | 51 | 82 | 7 | | |

TABLE 12-4

| Allele Number | Probe Number for Detection | | | | | |
|---|---|---|---|---|---|---|
| Cw*120302 | 83 | 12 | | | | |
| Cw*120401 | 84 | 51 | 35 | 85 | 20 | 17 | 12 |
| Cw*120402 | 51 | 35 | 82 | 7 | | |
| Cw*1205 | 35 | 82 | 7 | | | |
| Cw*1206 | 86 | | | | | |
| Cw*1207 | 87 | | | | | |
| Cw*1208 | 38 | 30 | 5 | 6 | 7 | |
| Cw*140201 | 88 | 20 | 27 | | | |
| Cw*140202 | 88 | 89 | 20 | | | |
| Cw*1403 | 88 | 61 | 20 | 27 | | |
| Cw*1404 | 88 | 34 | 89 | 20 | 90 | |
| Cw*1405 | 88 | 85 | 20 | 90 | | |
| Cw*150201 | 23 | 7 | | | | |
| Cw*150202 | 45 | 38 | 35 | 91 | 23 | 42 |
| Cw*1503 | 51 | 23 | 7 | | | |
| Cw*1504 | 20 | 42 | 7 | | | |
| Cw*150501 | 92 | | | | | |
| Cw*150502 | 91 | 74 | 7 | | | |

TABLE 12-4-continued

| Allele Number | Probe Number for Detection | | | | | |
|---|---|---|---|---|---|---|
| Cw*1506 | 91 | 7 | | | | |
| Cw*1507 | 45 | 38 | 91 | 23 | 42 | |
| Cw*1508 | 45 | 38 | 35 | 26 | 91 | 23 |
| Cw*1509 | 91 | 20 | 42 | | | |
| Cw*1510 | 38 | 35 | 91 | 23 | 42 | |
| Cw*1511 | 16 | 45 | 35 | 91 | 23 | 42 |
| Cw*1601 | 94 | 95 | | | | |
| Cw*1602 | 35 | 94 | 95 | | | |
| Cw*160401 | 12 | 95 | | | | |
| Cw*1701 | 96 | | | | | |
| Cw*1702 | 97 | | | | | |
| Cw*1703 | 98 | | | | | |
| Cw*1801 | 99 | 100 | | | | |
| Cw*1802 | 59 | 90 | 99 | | | |

Example 7

Probes for Identification of HLA-DP Allele

Extraction of DNA from 1 ml of human blood was performed using GFX Genomic Blood DNA Purification Kit from Amersham Biosciences in the same manner as in Example 1.

Next, quantitative PCR was carried out in the same manner as in Example 1 except that probes in the probe list 1 in Tables 13-1 to 13-3 or 14-1 to 14-3 were used and 3 μl of the mixed primers contains 1 μl of respective solutions of the following primers (10 pmol/μl):

```
AAACACGGTCACCTCAGGGGAT    (SEQ ID NO: 2242)

GGCCTGAGTGTGGTTGGAACG     (SEQ ID NO: 2243)

CCAGCTCGTAGTTGTGTCTGCA    (SEQ ID NO: 2244)
```

After PCR amplification, referring to Amp Plot and Dissociation curves on a display of 5700 software, and to the list in Table 15-1 for the probes in Table 13-1, or to the list in Tables 15-2 to 15-5 for the probes in Tables 13-2 to 13-3, it was identified as DPA1*010301 and DPB1*0901.

Example 8

Extraction of DNA from 1 ml of human blood was performed in the same way as in Example 1. PCR of human HLA-DP was then performed in the same manner as in Example 2 except that 6 μl of the mixed primer consisting of 1 μl each of the solutions containing the following sequences at 10 pmol/μl respectively and 9 μl of ultra pure water.

```
AAACACGGTCACCTCAGGGGAT    (SEQ ID NO: 2242)

GGCCTGAGTGTGGTTGGAACG     (SEQ ID NO: 2243)

CCAGCTCGTAGTTGTGTCTGCA    (SEQ ID NO: 2244)

CCATGTGTCAACTTATGCC       (SEQ ID NO: 2245)

AGAATTACCTTTTCCAG         (SEQ ID NO: 2247)

AGAATTACGTTTTCCAG         (SEQ ID NO: 2248)
```

At the same time, a DNA microarray was prepared to identify the allele in the specimen described above in the same manner as in Example 2, except that probes in Tables 14-1 and 14-2 were used to form the probe spots respectively.

Then, hybridization was performed using the above specimen and the prepared DNA microarray in the same manner as in Example 2. Fluorometry measurement was conducted with GenePix4000B (Axon). Referring to the list in Table 16-1 when the probes in Table 14-1 were used, or to the list in Tables 16-2 to 16-5 when the probes in Table 14-2 were used, the sample was identified as DPA1*010301 and DPB1*0901.

```
Allele list
DPA1*010301:
                                                       (SEQ ID NO: 1998)
ccatgtgtcaacttatgccgcgtttgtacagacgcatagaccaacaggGgagtttatgtttgaatttgatgaAgat gagatgttctatgtggatctggacaagaaggagaccgtctggcatctggaggagtttggccAagccttttcctttg aggctcagggcgggctggctaacattgctatattgaacaacaacttgataccttgatccagcgttccaaccacac tcaggccaccaac;

DPA1*010302:
                                                       (SEQ ID NO: 1999)
gcgtttgtacagacgcatagaccaacaggAgagtttatgtttgaatttgatgaagatgagatgttctatgtggatc tggacaagaaggagaccgtctggcatctggaggagtttggccaagccttttcctttgaggctcagggcgggctggc taacattgctatattgaacaacaacttgataccttgatccagcgttccaaccacactcaggccaccaac;

DPA1*0104:
                                                       (SEQ ID NO: 2000)
gccgcgtttgtacagacgcatagaccaacaggggagtttatgtttgaatttgatgaCgatgagatgttctatgtgg atctggacaagaaggagaccgtctggcatctggaggagtttggccaagccttttcctttgaggctcagggcgggct ggctaacattgctatattgaacaacaacttgataccttgatccagcgttccaaccacactcaggccaccaac;

DPA1*0105:
                                                       (SEQ ID NO: 2001)
gccgcgtttgtacagacgcatagaccaacaggggagtttatgtttgaatttgatgaagatgagatgttctatgtgg atctggacaagaaggagaccgtctggcatctggaggagtttggccaagccttttcctttgaggctcagggcgggct ggctaacattgctatattgaacaacaacttgataccttgatccagcgttccaaccacactcaggccgccaaT;

DPA1*0106:
                                                       (SEQ ID NO: 2002)
ccatgtgtcaacttatgccgcgtttgtacagacgcatagaccaacaggggagtttatgtttgaatttgatgaagat gagcagttctatgtggatctggataaAaaggagaccgtctggcatctggaggagtttggccaagccttttcctttg aggctcagggcgggctggctaacattgctatattgaacaacaacttgataccttgatccagcgttccaaccacac tcaggccaccaac;

DPA1*0107:
                                                       (SEQ ID NO: 2003)
catgtgtcaacttatgccgcgtttgtacagacgcatagaccaacaggggagtttatgtttgaatttgatgaagatg agatgttctatgtggatctggacaagaaggagaccgtctggcatctggaggagtttggccaaAccttttcctttga ggctcagggcgggctggctaacattgctatattgaacaacaacttgataccttgatccagcgttccaaccacact caggccaccaac;

DPA1*0108:
                                                       (SEQ ID NO: 2004)
ccatgtgtcaacttatgccgcgtttgtacagacgcatagaccaacaggggagtttatgtttgaatttgatgaCgat gagatgttctatgtggatctggacaagaaggagaccgtctggcatctggaggagtttggccGagccttttcctttg aggctcagggcgggctggctaacattgctatattgaacaacaacttgataccttgatccagcgttccaaccacac tcaggccaccaac;

DPA1*020101:
                                                       (SEQ ID NO: 2005)
ccatgtgtcaacttatgccgcgtttgtacagacCcatagaccaacaggggagtttatgtttgaatttgatgaagat gagcagttctatgtggatctggataaAaaggagaccgtctggcatctggaggagtttggccgagccttttcctttg
```

DPA1*020102:
(SEQ ID NO: 2006)
ccatgtgtcaacttatgccgcgtttgtacagacgcatagaccaacaggggagtttatgtttgaatttgatgaagat gagcagttctatgtggatctggataaAaaggagaccgtctggcatctggaggagtttggccgagccttttcctttg aggctcagggcgggctggctaacattgctatattgaacaacaacttgaataccttgatccagcgttccaaccacac tcaggccgccaaT;

DPA1*020103:
(SEQ ID NO: 2007)
ccatgtgtcaacttatgccgcgtttgtacagacgcatagaccaacaggggagtttatgtttgaatttgatgaagat gagcAgttctatgtggatctggacaagaaggagaccgtctggcatctggaggagtttggccgagccttttcctttg aggctcagggcgggctggctaacattgctatattgaacaacaacttgaataccttgatccagcgttccaaccacac tcaggccgccaaT;

DPA1*020104:
(SEQ ID NO: 2008)
gcgtttgtacaaacccatagaccaacaggggagtttatgtttgaatttgatgaagatgagcagttctatgtggatc tggataaAaaggagaccgtctggcatctggaggagtttggccgagccttttcctttgaggctcagggcgggctggc taacattgctatattgaacaacaacttgaataccttgatccagcgttccaaccacactcaggccgccaaT;

DPA1*020105:
(SEQ ID NO: 2009)
ccatgtgtcaacttatgccgcgtttgtacagacgcatagaccaacaggAgagtttatgtttgaatttgatgaagat gagcAgttctatgtggatctggacaagaaggagaccgtctggcatctggaggagtttggccgagccttttcctttg aggctcagggcgggctggctaacattgctatattgaacaacaacttgaataccttgatccagcgttccaaccacac tcaggccgccaaT;

DPA1*020106:
(SEQ ID NO: 2010)
ccatgtgtcaacttatgccgcgtttgtacagacCcatagaccaacaggggagtttatgtttgaatttgatgaagat gagcagttctatgtggatctggaTaagaaggagaccgtctggcatctggaggagtttggccgagccttttcctttg aggctcagggcgggctggctaacattgctatattgaacaacaacttgaataccttgatccagcgttccaaccacac tcaggccgccaaT;

DPA1*020201:
(SEQ ID NO: 2011)
aacttatgccatgtttgtacagacccatagaccaacaggAgagtttatgtttgaatttgatgaagatgagcagttc tatgtggatctggaTaagaaggagaccgtctggcatctggaggagtttggccgagccttttcctttgaggctcagg gcgggctggctaacattgctatattgaacaacaacttgaataccttgatccagcgttccaaccacactcaggccgc caaT;

DPA1*020202:
(SEQ ID NO: 2012)
ccatgtgtcaacttatgccatgtttgtacagacCcatagaccaacaggAgagtttatgtttgaatttgatgaagat gagcAgttctatgtggatctggacaagaaggagaccgtctggcatctggaggagtttggccgagccttttcctttg aggctcagggcgggctggctaacattgctatattgaacaacaacttgaataccttgatccagcgttccaaccacac tcaggccgccaaT;

DPA1*020203:
(SEQ ID NO: 2013)
atgtgtcaacttatgccaTgtttgtacagacccatagaccaacaggggagtttatgtttgaatttgatgaagatga gcagttctatgtggatctggacaagaaggagaccgtctggcatctggaggagtttggccgagccttttcctttgag -continued gctcagggcgggctggctaacattgctatattgaacaacaacttgaataccttgatccagcgttccaaccacactc
aggccgccaaT;

DPA1*0203:
(SEQ ID NO: 2014)
ccatgtgtcaacttatgccgcgtttgtacagacCcatagaccaacaggggagtttatgtttgaatttgatgaagat
gagatgttctatgtggatctggacaagaaggagaccgtctggcatctggaggagtttggccgagccttttcctttg
aggctcagggcgggctggctaacattgctatattgaacaacaacttgaataccttgatccagcgttccaaccacac
tcaggccgccaaT;

DPA1*0301:
(SEQ ID NO: 2015)
gccatgtttgtacagacccatagaccaacaggggagtttatgtttgaatttgatgaagatgagatgttctatgtgg
atctggacaagaaggagaccgtctggcatctggaggagtttggccaagccttttcctttgaggctcagggcgggct
ggctaacattgctatatCgaacaacaacttgaataccttgatccagcgttccaaccacactcaggccaccaac;

DPA1*0302:
(SEQ ID NO: 2016)
ccatgtgtcaacttatgccaTgtttgtacagacccatagaccaacaggggagtttatgtttgaatttgatgaagat
gagatgttctatgtggatctggacaagaaggagaccgtctggcatctggaggagtttggccaagccttttcctttg
aggctcagggcgggctggctaacattgctatattgaacaacaacttgaataccttgatccagcgttccaaccacac
tcaggccaccaac;

DPA1*0401:
(SEQ ID NO: 2017)
gccgcgtttgtacagacgcatagaacaacaggagagtttatgtttgagtttgatgatgatgagatgttctatgtgg
atctggacaagaaggagaccgtctggcatctggaggagtttggccgagccttttcctttgaggctcagggcgggct
ggctaacattgctatattgaacaacaacttgaatatcgcTatccagcgttccaaccacactcaggccgccaat;

DPB1*010101:
(SEQ ID NO: 2018)
agaattacgtgtaccagggacggcaggaatgctacgcgtttaatgggacacagcgcttcctggagagatacatcta
caaccgggaggagtacgcgcgcttcgacagcgacgtgggggagttccgggcggtgacggagctggggcggcctgct
gcggagtactggaacagccagaaggacatcctggaggagaagcgggcagtgccggacaggGtAtgcagacacaact
acgagctggacgaggccgtgaccctgcagcgccgagtcc;

DPB1*010102:
(SEQ ID NO: 2019)
aattacgtgtaccagggacggcaggaatgctacgcgtttaatgggacacagcgcttcctggagagatacatctaca
accgggaggagtacgcgcgcttcgacagcgacgtgggAgagttccgggcggtgacggagctggggcggcctgctgc
ggagtactggaacagccagaaggacatcctggaggagaagcgggcagtgccggacagggtatgcagacacaactac
gagctggacgaggccgtgaccctgcagcgccga;

DPB1*020102 (SEQ ID NO: 2020):
(SEQ ID NO: 2021)
agaattaccttttccagggacggcaggaatgctacgcgtttaatgggacacagcgcttcctggagagatacatcta
caaccgggaggagttcgTgcgcttcgacagcgacgtgggggagttccgggcggtgacggagctggggcggcctgat
gAggagtactggaacagccagaaggacatcctggaggagGagcgggcagtgccggacaggatGtgcagacacaact
acgagctggGcgggcccatgaccctgcagcgccgagtcc;

DPB1*020103:
(SEQ ID NO: 2022)
agaattaccttttccagggacggcaggaatgctacgcgtttaatgggacacagcgcttcctggagagatacatcta
caaccgggaggagttcgtgcgcttcgacagcgacgtgggggagttccgggcggtgacggagctggggcggcctgaC
gaggagtactggaacagccagaaggacatcctggaggaggagcgggcagtgccggacaggatgtgcagacacaact
acgagctgggcgggcccatgaccctgcagcgccgag;

-continued

DPB1*020104:
(SEQ ID NO: 2023)
agaattaccttttccagggacggcaggaatgctacgcgtttaatgggacacagcgcttcctggagagatacatcta
caaccgggaggagttcgtgcgcttcgacagcgacgtgggggagttccgggcggtgacggagctggggcggcctgat
gaggagtactggaacagccagaaggacatcctggaggaggagcgggcagtTccggacaggatgtgcagacacaact
acgagctgggcgggcccatgaccctgcagcgccga;

DPB1*020105:
(SEQ ID NO: 2024)
agaattaccttttccagggacggcaggaatgctacgcgtttaatgggacacagcgcttcctggagagatacatcta
caaccgggaAgagttcgtgcgcttcgacagcgacgtgggggagttccgggcggtgacggagctggggcggcctgat
gaggagtactggaacagccagaaggacatcctggaggaggagcgggcagtgccggacaggatgtgcagacacaact
acgagctgggcgggcccatgaccctgcagcgccgag;

DPB1*020106:
(SEQ ID NO: 2025)
agaattaccttttccagggacggcaggaatgctacgcgtttaatgggacacagcgcttcctggagagatacatcta
caaccgggaggagttTgtgcgcttcgacagcgacgtgggggagttccgggcggtgacggagctggggcggcctgat
gaggagtactggaacagccagaaggacatcctggaggaggagcgggcagtgccggacaggatgtgcagacacaact
acgagctgggcgggcccatgaccctgcagcgccgag;

DPB1*0202:
(SEQ ID NO: 2026)
agaattaccttttccagggacggcaggaatgctacgcgtttaatgggacacagcgcttcctggagagatacatcta
caaccgggaggagCtcgtgcgcttcgacagcgacgtgggggagttccgggcggtgacggagctggggcggcctgaG
gcggagtactggaacagccagaaggacatcctggaggagGagcgggcagtgccggacaggatgtgcagacacaact
acgagctgggcgggcccAtgaccctgcagcgccgag;

DPB1*030101:
(SEQ ID NO: 2027)
agaattacgtgtaccagtTacggcaggaatgctacgcgtttaatgggacacagcgcttcctggagagatacatcta
caaccgggaggagttcgTgcgcttcgacagcgacgtgggggagttccgggcggtgacggagctggggcggcctgat
gaggaCtactggaacagccagaaggacCtcctggaggagaagcgggcagtgccggacagggtatgcagacacaact
acgagctggacgaggccgtgaccctgcagcgccgagtcc;

DPB1*030102:
(SEQ ID NO: 2028)
agaattacgtgtaccagttacggcaggaatgctacgcgtttaatgggacacagcgcttcctggagagatacatcta
caaccgggaggagttcgtgcgcttcgacagcgacgtgggggagttccgggcggtgacggagctggggcggcctgat
gaggactactggaacagccagaaggacctcctggaggagaagcgggcagtgccggacagggtatgcagacacaact
acgagctggacgaggccgtgaccctAcagcgccgag;

DPB1*0401:
(SEQ ID NO: 2029)
agaattaccttttccagggacggcaggaatgctacgcgtttaatgggacacagcgcttcctggagagatacatcta
caaccgggaggagtTcgcgcgcttcgacagcgacgtgggggagttccgggcggtgacggagctggggcggcctgct
gcggagtactggaacagccagaaggacatcctggaggagaagcgggcagtgccggacaggatGtgcagacacaact
acgagctggGcgggcccatgaccctgcagcgccgagtcc;

DPB1*0402:
(SEQ ID NO: 2030)
agaattaccttttccagggacggcaggaatgctacgcgtttaatgggacacagcgcttcctggagagatacatcta
caaccgggaggagttcgTgcgcttcgacagcgacgtgggggagttccgggcggtgacggagctggggcggcctgat
gAggagtactggaacagccagaaggacatcctggaggagaagcgggcagtgccggacaggatGtgcagacacaact
acgagctggGcgggcccatgaccctgcagcgccgagtcc;

DPB1*0501:
(SEQ ID NO: 2031)
agaattacctttccagggacggcaggaatgctacgcgtttaatgggacacagcgcttcctggagagatacatcta caaccgggaggagCtcgTgcgcttcgacagcgacgtgggggagttccgggcggtgacggagctggggcggcctgaG gcggagtactggaacagccagaaggacatcctggaggagaagcgggcagtgccggacaggatGtgcagacacaact acgagctggacgaggccgtgaccctgcagcgccgag;

DPB1*0601:
(SEQ ID NO: 2032)
agaattacgtgtaccagttacggcaggaatgctacgcgtttaatgggacacagcgcttcctggagagatacatcta caaccgggaggagttcgtgcgcttcgacagcgacgtgggggagttccgggcggtgacggagctggggcggcctgat gaggaCtactggaacagccagaaggacCtcctggaggagGagcgggcagtgccggacaggatGtgcagacacaact acgagctggacgaggccgtgaccctgcag;

DPB1*0801:
(SEQ ID NO: 2033)
cttttccagggacggcaggaatgctacgcgtttaatgggacacagcgcttcctggagagatacatctacaaccggg aggagttcgTgcgcttcgacagcgacgtgggggagttccgggcggtgacggagctggggcggcctgatgAggagta ctggaacagccagaaggacatcctggaggagGagcgggcagtgccggacagggtatgcagacacaactacgagctg gacgaggccgtgaccctgcag;

DPB1*0901:
(SEQ ID NO: 2034)
agaattacgtgcaccagtTacggcaggaatgctacgcgtttaatgggacacagcgcttcctggagagatacatcta caaccgggaggagttcgtgcgcttcgacagcgacgtgggggagttccgggcggtgacggagctggggcggcctgat gaggaCtactggaacagccagaaggacatcctggaggagGagcgggcagtgccggacagggtatgcagacacaact acgagctggacgaggccgtgaccctgcagcgccgag;

DPB1*1001:
(SEQ ID NO: 2035)
agaattacgtgcaccagtTacggcaggaatgctacgcgtttaatgggacacagcgcttcctggagagatacatcta caaccgggaggagttcgTgcgcttcgacagcgacgtgggggagttccgggcggtgacggagctggggcggcctgat gAggagtactggaacagccagaaggacatcctggaggagGagcgggcagtgccggacagggtatgcagacacaact acgagctggacgaggccgtgaccctgcagcgccgag;

DPB1*110101:
(SEQ ID NO: 2036)
gtgtaccagttacggcaggaatgctacgcgtttaatgggacacagcgcttcctggagagatacatctacaaccggC aggagtacgcgcgcttcgacagcgacgtgggagagttccgggcggtgacggagctggggcggcctgctgcggagta ctggaacagccagaaggacctcctggaggagaggcgggcagtgccggacaggatgtgcagacacaactacgagctg gacgaggccgtgaccctgcag;

DPB1*110102:
(SEQ ID NO: 2037)
agaattacgtgtaccagttacggcaggaatgctacgcgtttaatgggacacagcgcttcctggagagatacatcta caacAggcaggagtacgcgcgcttcgacagcgacgtgggagagttccgggcggtgacggagctggggcggcctgct gcggagtactggaacagccagaaggacctcctggaggagaggcgggcagtgccggacaggatgtgcagacacaact acgagctggacgaggccgtgaccctgcag;

DPB1*1301:
(SEQ ID NO: 2038)
agaattacgtgtaccagtTacggcaggaatgctacgcgtttaatgggacacagcgcttcctggagagatacatcta caaccgggaggagtacgcgcgcttcgacagcgacgtggggagttccgggcggtgacggagctggggcggcctgct gcggagtactggaacagccagaaggacatcctggaggagGagcgggcagtgccggacaggAtatgcagacacaact acgagctggacgaggccgtgaccctgcag;

-continued

DPB1*1401:

(SEQ ID NO: 2039)

agaattacgtgcaccagtTacggcaggaatgctacgcgtttaatgggacacagcgcttcctggagagatacatcta caaccgggaggagttcgTgcgcttcgacagcgacgtgggggagttccgggcggtgacggagctggggcggcctgat gaggaCtactggaacagccagaaggacCtcctggaggagaagcgggcagtgccggacagggtatgcagacacaact acgagctggacgaggccgtgaccctgcag;

DPB1*1501:

(SEQ ID NO: 2040)

agaattacgtgtaccagggacggcaggaatgctacgcgtttaatgggacacagcgcttcctggagagatacatcta caaccggCaggagtacgcgcgcttcgacagcgacgtgggagagttccgggcggtgacggagctggggcggcctgct gcggagtactggaacagccagaaggacctcctggaggagaggcgggcagtgccggacaggatgtgcagacacaact acgagctggtcgggcccAtgaccctgcagcgccgag;

DPB1*1601:

(SEQ ID NO: 2041)

agaattaccttttccagggacggcaggaatgctacgcgtttaatgggacacagcgcttcctggagagatacatcta caaccgggaggagttcgTgcgcttcgacagcgacgtgggggagttccgggcggtgacggagctggggcggcctgat gAggagtactggaacagccagaaggacatcctggaggagGagcgggcagtgccggacaggatGtgcagacacaact acgagctggacgaggccgtgaccctgcagcgccgag;

DPB1*1701:

(SEQ ID NO: 2042)

agaattacgtgcaccagtTacggcaggaatgctacgcgtttaatgggacacagcgcttcctggagagatacatcta caaccgggaggagttcgtgcgcttcgacagcgacgtgggggagttccgggcggtgacggagctggggcggcctgat gaggaCtactggaacagccagaaggacatcctggaggagGagcgggcagtgccggacaggatGtgcagacacaact acgagctggacgaggccgtgaccctgcagcgccgag;

DPB1*1801:

(SEQ ID NO: 2043)

gtgtaccagggacggcaggaatgctacgcgtttaatgggacacagcgcttcctggagagatacatctacaaccggg aggagttcgTgcgcttcgacagcgacgtgggggagttccgggcggtgacggagctggggcggcctgatgAggagta ctggaacagccagaaggacatcctggaggagaagcgggcagtgccggacaggatgtgcagacacaactacgagctg gTcgggcccatgaccctgcag;

DPB1*1901:

(SEQ ID NO: 2044)

agaattaccttttccagggacggcaggaatgctacgcgtttaatgggacacagcgcttcctggagagatacatcta caaccgggaggagttcgtgcgcttcgacagcgacgtgggggagttccgggcggtgacggagctggggcggcctgaG gcggagtactggaacagccagaaggacatcctggaggagGagcgggcagtgccggacaggAtatgcagacacaact acgagctggacgaggccgtgaccctgcagcgccgag;

DPB1*200101:

(SEQ ID NO: 2045)

agaattacgtgtaccagttacggcaggaatgctacgcgtttaatgggacacagcgcttcctggagagatacatcta caaccgggaggagttcgtgcgcttcgacagcgacgtgggggagttccgggcggtgacggagctggggcggcctgat gaggaCtactggaacagccagaaggacCtcctggaggagaagcgggcagtgccggacaggatGtgcagacacaact acgagctggacgaggccgtgaccctgcagcgccgag;

DPB1*200102:

(SEQ ID NO: 2046)

agaattacgtgtaccagttacggcaggaatgctacgcgtttaatgggacacagcgcttcctggagagatacatcta caaccgggaggagttcgtgcgcttcgacagcgacgtgggggagttccgggcggtgacggagctggggcggcctgat gaggactactggaacagccagaaggacctcctggaggagaagcgggcagtgccggacaggatgtgcagacacaact acgagctggacgaggccgtgaccctgcagcgTcga;

DPB1*2101:
(SEQ ID NO: 2047)
agaattacgtgtaccagtTacggcaggaatgctacgcgtttaatgggacacagcgcttcctggagagatacatcta caaccgggaggagCtcgtgcgcttcgacagcgacgtgggggagttccgggcggtgacggagctggggcggcctgaG gcggagtactggaacagccagaaggacatcctggaggagGagcgggcagtgccggacaggatGtgcagacacaact acgagctggacgaggccgtgaccctgcagcgccgag;

DPB1*2201:
(SEQ ID NO: 2048)
agaattaccttttccagggacggcaggaatgctacgcgtttaatgggacacagcgcttcctggagagatacatcta caaccgggaggagCtcgtgcgcttcgacagcgacgtgggggagttccgggcggtgacggagctggggcggcctgaG gcggagtactggaacagccagaaggacatcctggaggagGagcgggcagtgccggacaggatGtgcagacacaact acgagctggacgaggccgtgaccctgcagcgccgag;

DPB1*2301:
(SEQ ID NO: 2049)
agaattaccttttccagggacggcaggaatgctacgcgtttaatgggacacagcgcttcctggagagatacatcta caaccgggaggagttcgTgcgcttcgacagcgacgtgggggagttccgggcggtgacggagctggggcggcctgct gcggagtactggaacagccagaaggacatcctggaggagaagcgggcagtgccggacaggatGtgcagacacaact acgagctggGcgggcccatgaccctgcagcgccgag;

DPB1*2401:
(SEQ ID NO: 2050)
agaattaccttttccagggacggcaggaatgctacgcgtttaatgggacacagcgcttcctggagagatacatcta caaccgggaggagttcgcgcgcttcgacagcgacgtgggggagttccgggcggtgacggagctggggcggcctgaG gcggagtactggaacagccagaaggacatcctggaggagaagcgggcagtgccggacaggatgtgcagacacaact acgagctgggcgggcccAtgaccctgcagcgccgag;

DPB1*2501:
(SEQ ID NO: 2051)
agaattacgtgtaccagtTacggcaggaatgctacgcgtttaatgggacacagcgcttcctggagagatacatcta caaccgggaggagttcgTgcgcttcgacagcgacgtgggggagttccgggcggtgacggagctggggcggcctgat gAggagtactggaacagccagaaggacCtcctggaggagaagcgggcagtgccggacagggtatgcagacacaact acgagctggacgaggccgtgaccctgcagcgccgag;

DPB1*260101:
(SEQ ID NO: 2052)
gtgtaccagttacggcaggaatgctacgcgtttaatgggacacagcgcttcctggagagatacatctacaaccggg aggagtacgcgcgcttcgacagcgacgtgggagagttccgggcggtgacggagctggggcggcctgctgcggagta ctggaacagccagaaggacatcctggaggagaagcgggcagtgccggacagAgtatgcagacacaactacgagctg gacgaggccgtgaccctgcagcgccgag;

DPB1*260102:
(SEQ ID NO: 2053)
gtgtaccagttacggcaggaatgctacgcgtttaatgggacacagcgcttcctggagagatacatctacaaccggg aggagtacgcgcgcttcgacagcgacgtgggggagttccgggcggtgacggagctggggcggcctgctgcggagta ctggaacagccagaaggacatcctggaggagaagcgggcagtgccggacagggtatgcagacacaactacgagctg gacgaggccgtgaccctgcagcgccga;

DPB1*2701:
(SEQ ID NO: 2054)
agaattacgtgtaccagtTacggcaggaatgctacgcgtttaatgggacacagcgcttcctggagagatacatcta caaccgggaggagtacgcgcgcttcgacagcgacgtgggggagttccgggcggtgacggagctggggcggcctgct gcggagtactggaacagccagaaggacatcctggaggagaagcgggcagtgccggacaggatGtgcagacacaact acgagctggacgaggccgtgaccctgcagcgccgag;

-continued

DPB1*2801:

(SEQ ID NO: 2055)
agaattaccttttccagggacggcaggaatgctacgcgtttaatgggacacagcgcttcctggagagatacatcta caaccgggaggagttcgcgcgcttcgacagcgacgtgggggagttccgggcggtgacggagctggggcggcctgat gAggagtactggaacagccagaaggacCtcctggaggagaagcgggcagtgccggacaggatgtgcagacacaact acgagctggTcgggcccatgaccctgcagcgccgag;

DPB1*2901:

(SEQ ID NO: 2056)
agaattacgtgtaccagttacggcaggaatgctacgcgtttaatgggacacagcgcttcctggagagatacatcta caaccgggaggagttcgtgcgcttcgacagcgacgtgggggagttccgggcggtgacggagctggggcggcctgat gaggaCtactggaacagccagaaggacCtcctggaggagGagcgggcagtgccggacagggtatgcagacacaact acgagctggacgaggccgtgaccctgcagcgccgag;

DPB1*3001:

(SEQ ID NO: 2057)
agaattacgtgcaccagtTacggcaggaatgctacgcgtttaatgggacacagcgcttcctggagagatacatcta caaccgggaggagttcgtgcgcttcgacagcgacgtgggggagttccgggcggtgacggagctggggcggcctgaG gcggagtactggaacagccagaaggacatcctggaggagGagcgggcagtgccggacaggatGtgcagacacaact acgagctggacgaggccgtgaccctgcag;

DPB1*3101:

(SEQ ID NO: 2058)
agaattaccttttccagggacggcaggaatgctacgcgtttaatgggacacagcgcttcctggagagatacatcta caaccgggaggagttcgcgcgcttcgacagcgacgtgggggagttccgggcggtgacggagctggggcggcctgct gcggagtactggaacagccagaaggacctcctggaggagaagcgggcaTtgccggacaggatgtgcagacacaact acgagctggacgaggccgtgaccctgcagcgccgag;

DPB1*3201:

(SEQ ID NO: 2059)
agaattaccttttccagggacggcaggaatgctacgcgtttaatgggacacagcgcttcctggagagatacatcta caaccgggaggagttcgtgcgcttcgacagcgacgtgggggagttccgggcggtgacggagctggggcggcctgat gaggTgtactggaacagccagaaggacatcctggaggaggagcgggcagtgccggacaggatgtgcagacacaact acgagctgggcgggcccatgaccctgcagcgccgag;

DPB1*3301:

(SEQ ID NO: 2060)
agaattaccttttccagggacggcaggaatgctacgcgtttaatgggacacagcgcttcctggagagatacatcta caaccgggaggagttcgcgcgcttcgacagcgacgtgggggagttccgggcggtgacggagctggggcggcctgct gcggagtactggaacagccagaaggacatcctggaggagGagcgggcagtgccggacaggatGtgcagacacaact acgagctggGcgggcccatgaccctgcag;

DPB1*3401:

(SEQ ID NO: 2061)
agaattaccttttccagggacggcaggaatgctacgcgtttaatgggacacagcgcttcctggagagatacatcta caaccgggaggagctcgtgcgcttcgacagcgacgtgggggagttccgggcggtgacggagctggggcggcctgct gcggagtactggaacagccagaaggacctcctggaggagaagcgggcaTtgccggacaggatgtgcagacacaact acgagctggtcgggcccAtgaccctgcag;

DPB1*3501:

(SEQ ID NO: 2062)
agaattacgtgcaccagtTacggcaggaatgctacgcgtttaatgggacacagcgcttcctggagagatacatcta caaccgggaggagttcgTgcgcttcgacagcgacgtgggggagttccgggcggtgacggagctggggcggcctgat gaggaCtactggaacagccagaaggacatcctggaggagaagcgggcagtgccggacagggtatgcagacacaact acgagctggacgaggccgtgaccctgcag;

DPB1*3601:
(SEQ ID NO: 2063)
agaattacgtgtaccagtTacggcaggaatgctacgcgtttaatgggacacagcgcttcctggagagatacatcta caaccgggaggagCtcgTgcgcttcgacagcgacgtgggggagttccgggcggtgacggagctggggcggcctgaG gcggagtactggaacagccagaaggacatcctggaggagaagcgggcagtgccggacaggatGtgcagacacaact acgagctggacgaggccgtgaccctgcagcgccgag;

DPB1*3701:
(SEQ ID NO: 2064)
gtgtaccagttacggcaggaatgctacgcgtttaatgggacacagcgcttcctggagagatacatctacaaccggg aggagttcgTgcgcttcgacagcgacgtgggggagttccgggcggtgacggagctggggcggcctgatgAggagta ctggaacagccagaaggacatcctggaggagGagcgggcagtgccggacagggtatgcagacacaactacgagctg gacgaggccgtgaccctgcagcgccgag;

DPB1*3801:
(SEQ ID NO: 2065)
cttttccagggacggcaggaatgctacCcgtttaatgggacacagcgcttcctggagagatacatctacaaccggg aggagctcgtgcgcttcgacagcgacgtgggggagttccgggcggtgacggagctggggcggcctgaggcggagta ctggaacagccagaaggacatcctggaggagaagcgggcagtgccggacaggatgtgcagacacaactacgagctg gacgaggccgtgaccctgcag;

DPB1*3901:
(SEQ ID NO: 2066)
agaattacctttccagggacggcaggaatgctacgcgtttaatgggacacagcgcttcctggagagatacatcta caaccgggaggagtacgcgcgcttcgacagcgacgtgggggagttccgggcggtgacggagctggggcggcctgct gcggagtactggaacagccagaaggacatcctggaggagaagcgggcagtgccggacaggatGtgcagacacaact acgagctggGcgggcccatgaccctgcagcgccga;

DPB1*4001:
(SEQ ID NO: 2067)
agaattacctttccagggacggcaggaatgctacgcgtttaatgggacacagcgcttcctggagagatacatcta caaccgggaggagtacgcgcgcttcgacagcgacgtgggggagttccgggcggtgacggagctggggcggcctgct gcggagtactggaacagccagaaggacatcctggaggagaagcgggcagtgccggacaggatgtgcagacacaact acgagctggTcgggcccatgaccctgcagcgccga;

DPB1*4101:
(SEQ ID NO: 2068)
aattaccttttccagggacggcaggaatgctacgcgtttaatgggacacagcgcttcctggagagatacatctaca accgggaggagttcgtgcgcttcgacagcgacgtgggggagttccgggcggtgacggagctggggcggcctgatga ggagtactggaacagccagaaggacTtcctggaggagGagcgggcagtgccggacaggatgtgcagacacaactac gagctgggcgggcccatgaccctgcagcgccga;

DPB1*4401:
(SEQ ID NO: 2069)
agaattacgtgtaccagttacggcaggaatgctacgcgtttaatgggacacagcgcttcctggagagatacatcta caaccgggaggagCtcgtgcgcttcgacagcgacgtgggggagttccgggcggtgacggagctggggcggcctgat gaggactactggaacagccagaaggacCtcctggaggagGagcgggcagtgccggacagggtatgcagacacaact acgagctggacgaggccgtgaccctgcagcgccgag;

DPB1*4501:
(SEQ ID NO: 2070)
gtgcaccagttacggcaggaatgctacgcgtttaatgggacacagcgcttcctggagagatacatctacaaccggg aggagttcgTgcgcttcgacagcgacgtgggggagttccgggcggtgacggagctggggcggcctgatgAggagta ctggaacagccagaaggacCtcctggaggagaagcgggcagtgccggacagggtatgcagacacaactacgagctg gacgaggccgtgaccctgcag;

DPB1*4601:

(SEQ ID NO: 2071)

agaattaccttttccagggacggcaggaatgctacgcgtttaatgggacacagcgcttcctggagagatacatcta caaccgggaggagttcgtgcgcttcgacagcgacgtgggggagttccgggcggtgacggagctggggcggcctgat gaggaCtactggaacagccagaaggacatcctggaggagGagcgggcagtgccggacaggatgtgcagacacaact acgagctgggcgggcccAtgaccctgcagcgccgag;

DPB1*4701:

(SEQ ID NO: 2072)

agaattaccttttccagggacggcaggaatgctacgcgtttaatgggacacagcgcttcctggagagatacatcta caaccgggaggagttcgtgcgcttcgacagcgacgtgggggagttccgggcggtgacggagctggggcggcctgaG gcggagtactggaacagccagaaggacatcctggaggagGagcgggcagtgccggacaggatgtgcagacacaact acgagctgggcgggcccAtgaccctgcagcgccgag;

DPB1*4801:

(SEQ ID NO: 2073)

aattaccttttccagggacggcaggaatgctacgcgtttaatgggacacagcgcttcctggagagatacatctaca accgggaggagCtcgtgcgcttcgacagcgacgtgggggagttccgggcggtgacggagctggggcggcctgatgA ggagtactggaacagccagaaggacatcctggaggaggagcgggcagtgccggacaggatgtgcagacacaactac gagctggGcgggcccAtgaccctgcag;

DPB1*4901:

(SEQ ID NO: 2074)

aattaccttttccagggacggcaggaatgctacgcgtttaatgggacacagcgcttcctggagagatacatctaca accgggaggagtacgcgcgcttcgacagcgacgtgggggagttccgggcggtgacggagctggggcggcctgatgA ggagtactggaacagccagaaggacatcctggaggagaagcgggcagtgccggacaggatGtgcagacacaactac gagctggGcgggcccatgaccctgcag;

DPB1*5001:

(SEQ ID NO: 2075)

aattacgtgtaccagggacggcaggaatgctacgcgtttaatgggacacagcgcttcctggagagatacatctaca accgggaggagttcgTgcgcttcgacagcgacgtgggggagttccgggcggtgacggagctggggcggcctgatga ggaCtactggaacagccagaaggacCtcctggaggagaagcgggcagtgccggacagggtatgcagacacaactac gagctggacgaggccgtgaccctgcag;

DPB1*5101:

(SEQ ID NO: 2076)

agaattaccttttccagggacggcaggaatgctacgcgtttaatgggacacagcgcttcctggagagatacatcta caaccgggaggagtTcgcgcgcttcgacagcgacgtgggggagttccgggcggtgacggagctggggcggcctgat gAggagtactggaacagccagaaggacatcctggaggagaagcgggcagtgccggacaggatGtgcagacacaact acgagctggGcgggcccatgaccctgcagcgccgag;

DPB1*5201:

(SEQ ID NO: 2077)

agaattacgtgtaccagtTacggcaggaatgctacgcgtttaatgggacacagcgcttcctggagagatacatcta caaccgggaggagttcgTgcgcttcgacagcgacgtgggggagttccgggcggtgacggagctggggcggcctgct gcggagtactggaacagccagaaggacCtcctggaggagaagcgggcagtgccggacagggtatgcagacacaact acgagctggacgaggccgtgaccctgcag;

DPB1*5301:

(SEQ ID NO: 2078)

agaattaccttttccagggacggcaggaatgctacgcgtttaatgggacacagcgcttcctggagagatacatcta caaccgggaggagtacgcgcgcttcgacagcgacgtgggggagttccgggcggtgacggagctggggcggcctgat gAggagtactggaacagccagaaggacatcctggaggagaagcgggcagtgccggacaggatgtgcagacacaact acgagctggTcgggcccatgaccctgcag;

DPB1*5401:
(SEQ ID NO: 2079)
agaattacgtgcaccagtTacggcaggaatgctacgcgtttaatgggacacagcgcttcctggagagatacatcta caaccgggaggagttcgtgcgcttcgacagcgacgtgggggagttccgggcggtgacggagctggggcggcctgaG gcggagtactggaacagccagaaggacatcctggaggagGagcgggcagtgccggacagggtatgcagacacaact acgagctggacgaggccgtgaccctgcag;

DPB1*5501:
(SEQ ID NO: 2080)
agaattacgtgcaccagtTacggcaggaatgctacgcgtttaatgggacacagcgcttcctggagagatacatcta caaccgggaggagttcgTgcgcttcgacagcgacgtgggggagttccgggcggtgacggagctggggcggcctgct gcggagtactggaacagccagaaggacatcctggaggagGagcgggcagtgccggacaggatGtgcagacacaact acgagctggacgaggccgtgaccctgcag;

DPB1*5601:
(SEQ ID NO: 2081)
gtgtaccagttacggcaggaatgctacgcgtttaatgggacacagcgcttcctggagagatacatctacaaccggg aggagtTcgcgcgcttcgacagcgacgtgggggagttccgggcggtgacggagctggggcggcctgctgcggagta ctggaacagccagaaggacCtcctggaggagaagcgggcagtgccggacagggtatgcagacacaactacgagctg gacgaggccgtgaccctgcag;

DPB1*5701:
(SEQ ID NO: 2082)
cttttccagggacggcaggaatgctacgcgtttaatgggacacagcgcttcctggagagatacatctacaaccggg aggagttcgTgcgcttcgacagcgacgtgggggagttccgggcggtgacggagctggggcggcctgatgaggaCta ctggaacagccagaaggacCtcctggaggagaagcgggcagtgccggacagggtatgcagacacaactacgagctg gacgaggccg;

DPB1*5801:
(SEQ ID NO: 2083)
aattacgtgcaccagttacggcaggaatgctacgcgtttaatgggacacagcgcttcctggagagatacatctaca accgggaggagCtcgtgcgcttcgacagcgacgtgggggagttccgggcggtgacggagctggggcggcctgctgc ggagtactggaacagccagaaggacatcctggaggagGagcgggcagtgccggacaggatGtgcagacacaactac gagctggacgaggccgtgaccctgcag;

DPB1*5901:
(SEQ ID NO: 2084)
agaattacctttccagggacggcaggaatgctacgcgtttaatgggacacagcgcttcctggagagatacatcta caaccgggaggagttcgtgcgcttcgacagcgacgtgggggagttccgggcggtgacggagctggggcggcctgat gAggagtactggaacagccagaaggacCtcctggaggagaagcgggcagtgccggacaggatGtgcagacacaact acgagctggGcgggcccatgaccctgcag;

DPB1*6001:
(SEQ ID NO: 2085)
agaattacctttccagggacggcaggaatgctacgcgtttaatgggacacagcgcttcctggagagatacatcta caaccgggaggagttcgtgcgcttcgacagcgacgtgggggagttccgggcggtgacggagctggggcggcctgat gaggagtactggaacagccagaaggacaAcctggaggagaagcgggcagtgccggacaggatgtgcagacacaact acgagctgggcgggcccatgaccctgcag;

DPB1*6101N:
(SEQ ID NO: 2086)
agaattacgtgtaccagttacggcaggaatgctacgcgtttaatgggacacagcgcttcctggagagatacatcta caaccgggaggagttcgtgcgcttcgacagcgacgtgggggagttccgggcggtgacggagctggggcggcctgat gaggactactggaacagccagaaggacctcctgTaggagaagcgggcagtgccggacagggtatgcagacacaact acgagctggacgaggccgtgaccctgcagcgc;

-continued

DPB1*6201:

(SEQ ID NO: 2087)

agaattacctttccagggacggcaggaatgctacgcgtttaatgggacacagcgcttcctggagagatacatcta caaccgggaggagCtcgTgcgcttcgacagcgacgtgggggagttccgggcggtgacggagctggggcggcctgct gcggagtactggaacagccagaaggacatcctggaggagaagcgggcagtgccggacaggatgtgcagacacaact acgagctggTcgggcccatgaccctgcag;

DPB1*6301:

(SEQ ID NO: 2088)

aattacctttccagggacggcaggaatgctacgcgtttaatgggacacagcgcttcctggagagatacatctaca accgggaggagCtcgtgcgcttcgacagcgacgtgggggagttccgggcggtgacggagctggggcggcctgctgc ggagtactggaacagccagaaggacatcctggaggagaagcgggcagtgccggacaggatGtgcagacacaactac gagctggacgaggccgtgaccctgcag;

DPB1*6401N:

(SEQ ID NO: 2089)

aattaagtgtaccagttacggcaggaatgctacgcgtttaatgggacacagcgcttcctggagagatacatctaca accgggaggagttcgtgcgcttcgacagcgacgtgggggagttccgggcggtgacggagctggggcggcctgatga ggaCtactggaacagccagaaggacCtcctggaggagGagcgggcagtgccggacaggatGtgcagacacaactac gagctggacgaggccgtgaccctgcag;

DPB1*6501:

(SEQ ID NO: 2090)

agaattacctttccagggacggcaggaatgctacgcgtttaatgggacacagcgcttcctggagagatacatcta caaccgggaggagtacgcgcgcttcgacagcgacgtgggggagttccgggcggtgacggagctggggcggcctgct gcggagtactggaacagccagaaggacatcctggaggagaagcgggcagtgccggacagggtatgcagacacaact acgagctggacgaggccgtgaccctgcagcgccgag;

DPB1*6601:

(SEQ ID NO: 2091)

agaattacgtgcaccagtTacggcaggaatgctacgcgtttaatgggacacagcgcttcctggagagatacatcta caaccgggaggagtTcgcgcgcttcgacagcgacgtgggggagttccgggcggtgacggagctggggcggcctgct gcggagtactggaacagccagaaggacatcctggaggagaagcgggcagtgccggacaggatGtgcagacacaact acgagctggGcgggcccatgaccctgcagcgccgag;

DPB1*6701:

(SEQ ID NO: 2092)

agaattacgtgcaccagtTacggcaggaatgctacgcgtttaatgggacacagcgcttcctggagagatacatcta caaccgggaggagttcgTgcgcttcgacagcgacgtgggggagttccgggcggtgacggagctggggcggcctgct gcggagtactggaacagccagaaggacCtcctggaggagaagcgggcagtgccggacagggtatgcagacacaact acgagctggacgaggccgtgaccctgcagcgccgag;

DPB1*6801:

(SEQ ID NO: 2093)

agaattacctttccagggacggcaggaatgctacgcgtttaatgggacacagcgcttcctggagagatacatcta caaccgggaggagttcgTgcgcttcgacagcgacgtgggggagttccgggcggtgacggagctggggcggcctgat gAggagtactggaacagccagaaggacatcctggaggagaagcgggcagtgccggacagggtatgcagacacaact acgagctggacgaggccgtgaccctgcagcgccga;

DPB1*6901:

(SEQ ID NO: 2094)

agaattacgtgtaccagttacggcaggaatgctacgcgtttaatgggacacagcgcttcctggagagatacatcta caaccgggaggagttcgtgcgcttcgacagcgacgtgggggagttccgggcggtgacggagctggggcggcctgat gaggaCtactggaacagccagaaggacctcctggaggagaGgcgggcagtgccggacaggatgtgcagacacaact acgagctggacgaggccgtgacc;

DPB1*7001:
(SEQ ID NO: 2095)
aattacgtggaccagttacggcaggaatgctacgcgtttaatgggacacagcgcttcctggagagatacatctaca accgggaggagttcgTgcgcttcgacagcgacgtgggggagttccgggcggtgacggagctggggcggcctgatga ggaCtactggaacagccagaaggacCtcctggaggagaagcgggcagtgccggacagggtatgcagacacaactac gagctggacgaggccgtgaccctgcag;

DPB1*7101:
(SEQ ID NO: 2096)
aattacctttccagggacggcaggaatgctacgcgtttaatgggacacagcgcttcctggagagatacatctaca accgggaggagttcgTgcgcttcgacagcgacgtgggggagttccgggcggtgacggagctggggcggcctgctgc ggagtactggaacagccagaaggacatcctggaggagGagcgggcagtgccggacaggatGtgcagacacaactac gagctggGcgggcccatgaccctgcag;

DPB1*7201:
(SEQ ID NO: 2097)
aattacctttccagggacggcaggaatgctacgcgtttaatgggacacagcgcttcctggagagatacatctaca accgggaggagttcgcgcgcttcgacagcgacgtgggggagttccgggcggtgacggagctggggcggcctgctgc ggagtactggaacagccagaaggacCtcctggaggagaagcgggcagtgccggacaggatGtgcagacacaactac gagctggGcgggcccatgaccctgcag;

DPB1*7301:
(SEQ ID NO: 2098)
aattacctttccagggacggcaggaatgctacgcgtttaatgggacacagcgcttcctggagagatacatctaca accgggaggagttcgtgcgcttcgacagcgacgtgggggagttccgggcggtgacggagctggggcggcctgatgA ggagtactggaacagccagaaggacCtcctggaggagaagcgggcagtgccggacagggtatgcagacacaactac gagctggGcgggcccatgaccctgcag;

DPB1*7401:
(SEQ ID NO: 2099)
gtgtaccagttacggcaggaatgctacgcgtttaatgggacacagcgcttcctggagagatacatctacaaccggC aggagtacgcgcgcttcgacagcgacgtgggagagttccgggcggtgacggagctggggcggcctgctgcgcgagta ctggaacagccagaaggacctcctggaggagaggcgggcagtgccggacaggatgtgcagacacaactacgagctg gtcgggcccAtgaccctgcag;

DPB1*7501:
(SEQ ID NO: 2100)
cttttccagggacggcaggaatgctacgcgtttaatgggacacagcgcttcctggagagatacatctacaaccggg aggagttcgTgcgcttcgacagcgacgtgggggagttccgggcggtgacggagctggggcggcctgatgAggagta ctggaacagccagaaggacatcctggaggagaagcgggcagtgccggacagggtatgcagacacaactacgagctg gGcgggcccatgaccctgcag;

DPB1*7601:
(SEQ ID NO: 2101)
agaattacgtgcaccagtTacggcaggaatgctacgcgtttaatgggacacagcgcttcctggagagatacatcta caaccgggaggagttcgcgcgcttcgacagcgacgtgggggagttccgggcggtgacggagctggggcggcctgat gaggaCtactggaacagccagaaggacCtcctggaggagaagcgggcagtgccggacagggtatgcagacacaact acgagctggacgaggccgtgaccctgcag;

DPB1*7701:
(SEQ ID NO: 2102)
agaattacctttccagggacTgcaggaatgctacgcgtttaatgggacacagcgcttcctggagagatacatcta caaccgggaggagttcgtgcgcttcgacagcgacgtgggggagttccgggcggtgacggagctggggcggcctgat gaggagtactggaacagccagaaggacatcctggaggagaagcgggcagtgccggacaggatgtgcagacacaact acgagctgggcgggcccatgaccctgcagcgccgag;

-continued

DPB1*7801:
(SEQ ID NO: 2103)
agaattacgtgtaccagttacggcaggaatgctacgcgtttaatgggacacagcgcttcctggagagatacatcta caaccgggaggagttcgtgcgcttcgacagcgacgtgggggagttccgggcggtgacggagctggggcggcctgat gaggactactggaacagccagaaggacctcctggaggagaagcgggcagtgcTggacagggtatgcagacacaact acgagctggacgaggccgtgaccctgcagcgccgag;

DPB1*7901:
(SEQ ID NO: 2104)
agaattacgtgtaccagtTacggcaggaatgctacgcgtttaatgggacacagcgcttcctggagagatacatcta caaccgggaggagttcgTgcgcttcgacagcgacgtgggggagttccgggcggtgacggagctggggcggcctgat gAggagtactggaacagccagaaggacatcctggaggagaagcgggcagtgccggacagggtatgcagacacaact acgagctggacgaggccgtgaccctgcagcgccgag;

DPB1*8001:
(SEQ ID NO: 2105)
agaattaccttttccagggacggcaggaatgctacgcgtttaatgggacacagcgcttcctggagagatacatcta caaccgggaggagttcgtgcgcttcgacagcgacgtgggggagttccgggcggtgacggagctggggcggcctgat gaggaCtactggaacagccagaaggacatcctggaggagaagcgggcagtgccggacaggatgtgcagacacaact acgagctgggcgggcccAtgacc;

DPB1*8101:
(SEQ ID NO: 2106)
agaattaccttttccagggacggcaggaatgctacgcgtttaatgggacacagcgcttcctggagagatacatcta caaccgggaggagttcgcgcgcttcgacagcgacgtgggggagttccgggcggtgacggagctggggcggcctgat gAggagtactggaacagccagaaggacatcctggaggagGagcgggcagtgccggacaggatGtgcagacacaact acgagctggGcgggcccatgaccctgcagcgccgag;

DPB1*8201:
(SEQ ID NO: 2107)
agaattaccttttccagggacggcaggaatgctacgcgtttaatgggacacagcgcttcctggagagatacatcta caaccgggaggagttcgtgcgcttcgacagcgacgtgggggagttccgggcggtgacggagctggggcggcctgat gaggagtactggaacagccagaaggacatcctggaggagaagcgggcagtgccggacaggatgtgcagacacaact acgagctgggcgggcccAtgaccctgcagcAccgag;

DPB1*8301:
(SEQ ID NO: 2108)
agaattaccttttccagggacggcaggaatgctacgcgtttaatgggacacagcgcttcctggagagatacatcta caaccgggaggagttcgtgcgcttcgacagcgacgtgggggagttccgggcggtgacggagctggggcggcctgat gaggagtactggaacagccagaaggacTtcctggaggagaagcgggcagtgccggacaggatgtgcagacacaact acgagctgggcgggcccatgaccctgcagcgccgag;

DPB1*8401:
(SEQ ID NO: 2109)
agaattaccttttccagggacggcaggaatgctacgcgtttaatgggacacagcgcttcctggagagatacatcta caaccgggaggagttcgtgcgcttcgacagcgacgtgggggagttccgggcggtgacggagctggggcggcctgaG gAggagtactggaacagccagaaggacatcctggaggagaagcgggcagtgccggacagggtatgcagacacaact acgagctggacgaggccgtgaccctgcagcgccga;

DPB1*8501:
(SEQ ID NO: 2110)
agaattacgtgtaccagtTacggcaggaatgctacgcgtttaatgggacacagcgcttcctggagagatacatcta caaccgggaggagtacgcgcgcttcgacagcgacgtgggggagttccgggcggtgacggagctggggcggcctgct gcggagtactggaacagccagaaggacatcctggaggagaagcgggcagtgccggacaggatgtgcagacacaact acgagctggacgaggccgtgaccctgcagcAccgag;

DPB1*8601:
(SEQ ID NO: 2111)
gaattacgtgcaccagtTacggcaggaatgctacgcgtttaatgggacacagcgcttcctggagagatacatctac aaccgggaggagttcgtgcgcttcgacagcgacgtgggggagttccgggcggtgacggagctggggcggcctgatg aggaCtactggaacagccagaaggacatcctggaggagGagcgggcagtgccggacaggatgtgcagacacaacta cgagctgggcgggcccAtgaccctgcagcgccga;

DPB1*8701:
(SEQ ID NO: 2112)
agaattacgtgtaccagtTacggcaggaatgctacgcgtttaatgggacacagcgcttcctggagagatacatcta caaccgggaggagttcgTgcgcttcgacagcgacgtgggggagttccgggcggtgacggagctggggcggcctgct gcggagtactggaacagccagaaggacCtcctggaggagaagcgggcagtgccggacaggatGtgcagacacaact acgagctggacgaggccgtgaccctgcagcgccgag;

DPB1*8801:
(SEQ ID NO: 2113)
agaattacgtgtaccagtTacggcaggaatgctacgcgtttaatgggacacagcgcttcctggagagatacatcta caaccgggaggagttcgtgcgcttcgacagcgacgtgggggagttccgggcggtgacggagctggggcggcctgat gaggaCtactggaacagccagaaggacatcctggaggagGagcgggcagtgccggacagggtatgcagacacaact acgagctggacgaggccgtgaccctgcagcgccgag;

DPB1*8901:
(SEQ ID NO: 2114)
agaattacgtgtaccagggacggcaggaatgctacgcgtttaatgggacacagcgcttcctggagagatacatcta caaccgggaggagtacgcgcgcttcgacagcgacgtgggggagttccgggcggtgacggagctggggcggcctgct gcggagtactggaacagccagaaggacatcctggaggagaagcgggcagtgccggacaggatGtgcagacacaact acgagctggacgaggccgtgaccctgcagcgccgag;

DPB1*9001:
(SEQ ID NO: 2115)
agaattacgtgtaccagggacggcaggaatgctacgcgtttaatgggacacagcgcttcctggagagatacatcta caaccgggaggagtTcgcgcgcttcgacagcgacgtgggggagttccgggcggtgacggagctggggcggcctgct gcggagtactggaacagccagaaggacatcctggaggagaagcgggcagtgccggacagggtatgcagacacaact acgagctggacgaggccgtgaccctgcagcgccgag;

DPB1*9101:
(SEQ ID NO: 2116)
agaattacgtgcaccagttacggcaggaatgctacgcgtttaatgggacacagcgcttcctggagagatacatcta caaccgggaggagttcgtgcgcttcgacagcgacgtgggggagttccgggcggtgacggagctggggcggcctgat gaggaCtactggaacagccagaaggacCtcctggaggagaagcgggcagtgccggacaggatGtgcagacacaact acgagctggacgaggccgtgaccctgcagcgccgag;

DPB1*9201:
(SEQ ID NO: 2117)
agaattacgtgtaccagtTacggcaggaatgctacgcgtttaatgggacacagcgcttcctggagagatacatcta caaccgggaggagttcgcgcgcttcgacagcgacgtgggggagttccgggcggtgacggagctggggcggcctgat gaggaCtactggaacagccagaaggacCtcctggaggagaagcgggcagtgccggacagggtatgcagacacaact acgagctggacgaggccgtgaccctgcagcgccgag;

DPB1*9301:
(SEQ ID NO: 2118)
agaattacgtgtaccagtTacggcaggaatgctacgcgtttaatgggacacagcgcttcctggagagatacatcta caaccgggaggagttcgTgcgcttcgacagcgacgtgggggagttccgggcggtgacggagctggggcggcctgat gAggagtactggaacagccagaaggacatcctggaggagGagcgggcagtgccggacaggatGtgcagacacaact acgagctggacgaggccgtgaccctgcagcgccgag;

DPB1*9601:
(SEQ ID NO: 2119)
agaattaccttttccagggacggcaggaatgctacgcgtttaatgggacacagcgcttcctggagagatacatcta caaccgggaggagtacgcgcgcttcgacagcgacgtgggggagttccgggcggtgacggagctggggcggcctgct gcggagtactggaacagccagaagCacatcctggaggagaagcgggcagtgccggacaggatgtgcagacacaact acgagctgggcgggcccatgaccctgcagcgccgag;

In the following, Probe lists DP1-DP4 are shown in Tables 13-1 to 13-3 and Tables 14-1 to 14-3 respectively. Probe-Allele Lists DP1-4 are shown in Tables 15-1 to 15-5 and Tables 16-1 to 16-5.

TABLE 13-1

| Probe No. | Base Sequence | |
|---|---|---|
| 0 | acg cat aga cca aca ggG | (SEQ ID No: 2120) |
| 1 | ag ttt atg ttt gaa ttt gat gaA | (SEQ ID No: 2121) |
| 2 | t ctg gag gag ttt ggc cA | (SEQ ID No: 2122) |
| 3 | g acg cat aga cca aca ggA | (SEQ ID No: 2123) |
| 4 | g ttt atg ttt gaa ttt gat gaC | (SEQ ID No: 2124) |
| 5 | cac act cag gcc gcc aaT | (SEQ ID No: 2125) |
| 6 | ttc tat gtg gat ctg gat aaA | (SEQ ID No: 2126) |
| 7 | ctg gag gag ttt ggc caa A | (SEQ ID No: 2127) |
| 8 | ctg gag gag ttt ggc cG | (SEQ ID No: 2128) |
| 9 | gcc gcg ttt gta cag acC | (SEQ ID No: 2129) |
| 10 | t gaa ttt gat gaa gat gag cA | (SEQ ID No: 2130) |
| 11 | ag ttc tat gtg gat ctg gaT | (SEQ ID No: 2131) |
| 12 | g acc cat aga cca aca ggA | (SEQ ID No: 2132) |
| 13 | t gcc atg ttt gta cag acC | (SEQ ID No: 2133) |
| 14 | at gtg tca act tat gcc aT | (SEQ ID NO: 2134) |
| 15 | ctg gct aac att gct ata tC | (SEQ ID No: 2135) |
| 16 | cat gtg tca act tat gcc aT | (SEQ ID No: 2136) |
| 17 | aac aac aac tta aat atc gct | (SEQ ID No: 2137) |

TABLE 13-2

| Probe No. | Base Sequence | |
|---|---|---|
| 0 | gca gtg ccg gac agg G | (SEQ ID No: 2138) |
| 1 | ca gtg ccg gac agg gtA | (SEQ ID No: 2139) |
| 2 | tc gac agc gac gtg ggA | (SEQ ID No: 2140) |
| 3 | c aac cgg gag gag ttc gT | (SEQ ID No: 2141) |
| 4 | ctg ggg cgg cct gat gA | (SEQ ID No: 2142) |

TABLE 13-2-continued

| Probe No. | Base Sequence | |
|---|---|---|
| 5 | g gac atc ctg gag gag G | (SEQ ID No: 2143) |
| 6 | ca gtg ccg gac agg atG | (SEQ ID No: 2144) |
| 7 | a cac aac tac gag ctg gG | (SEQ ID No: 2145) |
| 8 | g ctg ggg cgg cct gaC | (SEQ ID No: 2146) |
| 9 | ag gag gag cgg gca gtT | (SEQ ID No: 2147) |
| 10 | ga tac atc tac aac cgg gaA | (SEQ ID No: 2148) |
| 11 | c tac aac cgg gag gag ttT | (SEQ ID No: 2149) |
| 12 | c tac aac cgg gag gag C | (SEQ ID No: 2150) |
| 13 | g ctg ggg cgg cct gaG | (SEQ ID No: 2151) |
| 14 | gag ctg ggc ggg ccc A | (SEQ ID No: 2152) |
| 15 | ag aat tac gtg tac cag tT | (SEQ ID No: 2153) |
| 16 | gg cgg cct gat gag gaC | (SEQ ID No: 2154) |
| 17 | gg aac agc cag aag gac C | (SEQ ID No: 2155) |
| 18 | ac gag gcc gtg acc ctA | (SEQ ID No: 2156) |
| 19 | c tac aac cgg gag gag tT | (SEQ ID No: 2157) |
| 20 | aac cgg gag gag ctc gT | (SEQ ID No: 2158) |
| 21 | g gac ctc ctg gag gag G | (SEQ ID No: 2159) |
| 22 | ag aat tac gtg cac cag tT | (SEQ ID No: 2160) |
| 23 | aga tac atc tac aac cgg C | (SEQ ID No: 2161) |
| 24 | g gag aga tac atc tac aac A | (SEQ ID No: 2162) |
| 25 | g gca gtg ccg gac agg A | (SEQ ID No: 2163) |
| 26 | gag ctg gtc ggg ccc A | (SEQ ID No: 2164) |
| 27 | ga cac aac tac gag ctg gT | (SEQ ID No: 2165) |
| 28 | cc gtg acc ctg cag cgT | (SEQ ID No: 2166) |
| 29 | gg gca gtg ccg gac agA | (SEQ ID No: 2167) |
| 30 | g gag gag aag cgg gca T | (SEQ ID No: 2168) |

TABLE 13-3

| Probe No. | Base Sequence | |
|---|---|---|
| 31 | ggg cgg cct gat gag gT | (SEQ ID No: 2169) |
| 32 | ga cgg cag gaa tgc tac C | (SEQ ID No: 2170) |

TABLE 13-3-continued

| Probe No. | Base Sequence | |
|---|---|---|
| 33 | gg aac agc cag aag gac T | (SEQ ID No: 2171) |
| 34 | g gac ttc ctg gag gag G | (SEQ ID No: 2172) |
| 35 | gg aac agc cag aag gac aA | (SEQ ID No: 2173) |
| 36 | gc cag aag gac ctc ctg T | (SEQ ID No: 2174) |
| 37 | gac ctc ctg gag gag aG | (SEQ ID No: 2175) |
| 38 | aat tac ctt ttc cag gga cT | (SEQ ID No: 2176) |
| 39 | gag aag cgg gca gtg cT | (SEQ ID No: 2177) |
| 40 | ccc atg acc ctg cag cA | (SEQ ID No: 2178) |
| 41 | tg ggg cgg cct gag gA | (SEQ ID No: 2179) |
| 42 | gcc gtg acc ctg cag cA | (SEQ ID No: 2180) |
| 43 | g aat tac gtg cac cag tT | (SEQ ID No: 2181) |
| 44 | ac tgg aac agc cag aag C | (SEQ ID No: 2182) |

TABLE 14-1

| Probe No. | Base Sequence | |
|---|---|---|
| 0 | a cca aca ggG gag ttt atg | (SEQ ID No: 2183) |
| 1 | gaa ttt gat gaA gat gag atg | (SEQ ID No: 2184) |
| 2 | ag ttt ggc cAa gcc ttt tc | (SEQ ID No: 2185) |
| 3 | ga cca aca ggA gag ttt atg | (SEQ ID No: 2186) |
| 4 | gaa ttt gat gaC gat gag atg | (SEQ ID No: 2187) |
| 5 | at ctg gat aaA aag gag acc | (SEQ ID No: 2188) |
| 6 | ttt ggc caa Acc ttt tcc tt | (SEQ ID No: 2189) |
| 7 | ag ttt ggc cGa gcc ttt tc | (SEQ ID No: 2190) |
| 8 | t gta cag acC cat aga cca | (SEQ ID No: 2191) |
| 9 | gaa gat gag cAg ttc tat gt | (SEQ ID No: 2192) |
| 10 | cg ttt gta caA acc cat aga | (SEQ ID No: 2193) |
| 11 | g gat ctg gaT aag aag gag | (SEQ ID No: 2194) |
| 12 | act tat gcc aTg ttt gta cag | (SEQ ID No: 2195) |
| 13 | att gct ata tCg aac aac aac | (SEQ ID No: 2196) |
| 14 | g aat atc gcT atc cag cgt | (SEQ ID No: 2197) |

TABLE 14-2

| Probe No. | Base Sequence | |
|---|---|---|
| 0 | tAc cag gga cgg cag ga | (SEQ ID No: 2198) |
| 1 | ccg gac agg Gta tgc aga | (SEQ ID No: 2199) |
| 2 | g gac agg gtA tgc aga ca | (SEQ ID No: 2200) |
| 3 | gac gtg ggA gag ttc cg | (SEQ ID No: 2201) |
| 4 | at tac ctt tTc cag gga cg | (SEQ ID No: 2202) |
| 5 | g gag ttc gTg cgc ttc g | (SEQ ID No: 2203) |
| 6 | gg cct gat gAg gag tac t | (SEQ ID No: 2204) |
| 7 | g gag gag Gag cgg gca | (SEQ ID No: 2205) |
| 8 | g gac agg atG tgc aga ca | (SEQ ID No: 2206) |
| 9 | gag ctg gGc ggg ccc | (SEQ ID No: 2207) |
| 10 | cgg cct gaC gag gag ta | (SEQ ID No: 2208) |
| 11 | cgg gca gtT ccg gac ag | (SEQ ID No: 2209) |
| 12 | c aac cgg gaA gag ttc gt | (SEQ ID No: 2210) |
| 13 | g gag gag ttT gtg cgc tt | (SEQ ID No: 2211) |
| 14 | g gag gag Ctc gtg cgc | (SEQ ID No: 2212) |
| 15 | cgg cct gaG gcg gag t | (SEQ ID No: 2213) |
| 16 | c ggg ccc Atg acc ctg | (SEQ ID No: 2214) |
| 17 | tg tac cag tTa cgg cag g | (SEQ ID No: 2215) |
| 18 | t gat gag gaC tac tgg aac | (SEQ ID No: 2216) |
| 19 | cag aag gac Ctc ctg gag | (SEQ ID No: 2217) |
| 20 | gtg acc ctA cag cgc cg | (SEQ ID No: 2218) |
| 21 | g gag gag tTc gcg cgc | (SEQ ID No: 2219) |
| 22 | g gag ctc gTg cgc ttc g | (SEQ ID No: 2220) |
| 23 | aat tac gtg Cac cag tta cg | (SEQ ID No: 2221) |
| 24 | tac aac cgg Cag gag tac | (SEQ ID No: 2222) |
| 25 | atc tac aac Agg cag gag t | (SEQ ID No: 2223) |
| 26 | ccg gac agg Ata tgc aga | (SEQ ID No: 2224) |
| 27 | c gag ctg gTc ggg ccc | (SEQ ID No: 2225) |
| 28 | g ccg gac agA gta tgc ag | (SEQ ID No: 2226) |
| 29 | g cac cag tTa cgg cag g | (SEQ ID No: 2227) |
| 30 | g cgg gca Ttg ccg gac | (SEQ ID No: 2228) |

TABLE 14-3

| Probe No. | Base Sequence | |
|---|---|---|
| 31 | ct gat gag gTg tac tgg aa | (SEQ ID No: 2229) |
| 32 | gaa tgc tac Ccg ttt aat gg | (SEQ ID No: 2230) |
| 33 | cag aag gac Ttc ctg gag | (SEQ ID No: 2231) |
| 34 | ag aag gac aAc ctg gag g | (SEQ ID No: 2232) |
| 35 | gac ctc ctg Tag gag aag | (SEQ ID No: 2233) |
| 36 | g gag gag aGg cgg gca | (SEQ ID No: 2234) |

TABLE 14-3-continued

| Probe No. | Base Sequence | |
|---|---|---|
| 37 | g gac cag tTa cgg cag g | (SEQ ID No: 2235) |
| 38 | tc cag gga cTg cag gaa t | (SEQ ID No: 2236) |
| 39 | g gca gtg cTg gac agg g | (SEQ ID No: 2237) |
| 40 | g ctg ggc gGg ccc atg | (SEQ ID No: 2238) |
| 41 | cgg cct gaG gag gag ta | (SEQ ID No: 2239) |
| 42 | gg cct gag gAg gag tac t | (SEQ ID No: 2240) |
| 43 | agc cag aag Cac atc ctg | (SEQ ID No: 2241) |

TABLE 15-1

| Allele Number | Probe Number for Detection | | | |
|---|---|---|---|---|
| DPA1*010301 | 0 | 1 | 2 | |
| DPA1*010302 | 3 | | | |
| DPA1*0104 | 4 | | | |
| DPA1*0105 | 5 | | | |
| DPA1*0106 | 6 | | | |
| DPA1*0107 | 7 | | | |
| DPA1*0108 | 4 | 8 | | |
| DPA1*020101 | 9 | 6 | 5 | |
| DPA1*020102 | 6 | 5 | | |
| DPA1*020103 | 10 | 5 | | |
| DPA1*020104 | 6 | 5 | | |
| DPA1*020105 | 3 | 10 | 5 | |
| DPA1*020106 | 9 | 11 | 5 | |
| DPA1*020201 | 12 | 11 | 5 | |
| DPA1*020202 | 13 | 12 | 10 | 5 |
| DPA1*020203 | 14 | 5 | | |
| DPA1*0203 | 9 | 5 | | |
| DPA1*0301 | 15 | | | |
| DPA1*0302 | 16 | | | |
| DPA1*0401 | 17 | | | |

TABLE 15-2

| Allele Number | Probe Number for Detection | | | |
|---|---|---|---|---|
| DPB1*010101 | 0 | 1 | | |
| DPB1*010102 | 2 | | | |
| DPB1*020102 | 3 | 4 | 5 | 6 | 7 |
| DPB1*020103 | 8 | | | |
| DPB1*020104 | 9 | | | |
| DPB1*020105 | 10 | | | |
| DPB1*020106 | 11 | | | |
| DPB1*0202 | 12 | 13 | 5 | 14 |
| DPB1*030101 | 15 | 3 | 16 | 17 |
| DPB1*030102 | 18 | | | |
| DPB1*0401 | 19 | 6 | 7 | |
| DPB1*0402 | 3 | 4 | 6 | 7 |
| DPB1*0501 | 12 | 20 | 13 | 6 |
| DPB1*0601 | 16 | 17 | 21 | 6 |
| DPB1*0801 | 3 | 4 | 5 | |
| DPB1*0901 | 22 | 16 | 5 | |
| DPB1*1001 | 22 | 3 | 4 | 5 |
| DPB1*110101 | 23 | | | |
| DPB1*110102 | 24 | | | |
| DPB1*1301 | 15 | 5 | 25 | |
| DPB1*1401 | 22 | 3 | 16 | 17 |
| DPB1*1501 | 23 | 26 | | |
| DPB1*1601 | 3 | 4 | 5 | 6 |
| DPB1*1701 | 22 | 16 | 5 | 6 |
| DPB1*1801 | 3 | 4 | 27 | |
| DPB1*1901 | 13 | 5 | 25 | |

TABLE 15-2-continued

| Allele Number | Probe Number for Detection | | | |
|---|---|---|---|---|
| DPB1*200101 | 16 | 17 | 6 | |
| DPB1*200102 | 28 | | | |
| DPB1*2101 | 15 | 12 | 13 | 5 | 6 |
| DPB1*2201 | 12 | 13 | 5 | 6 |

TABLE 15-3

| Allele Number | Probe Number for Detection | | | |
|---|---|---|---|---|
| DPB1*2301 | 3 | 6 | 7 | |
| DPB1*2401 | 13 | 14 | | |
| DPB1*2501 | 15 | 3 | 4 | 17 |
| DPB1*260101 | 29 | | | |
| DPB1*2701 | 15 | 6 | | |
| DPB1*2801 | 4 | 17 | 27 | |
| DPB1*2901 | 16 | 17 | 21 | |
| DPB1*3001 | 22 | 13 | 5 | 6 |
| DPB1*3101 | 30 | | | |
| DPB1*3201 | 31 | | | |
| DPB1*3301 | 5 | 6 | 7 | |
| DPB1*3401 | 30 | 26 | | |
| DPB1*3501 | 22 | 3 | 16 | |
| DPB1*3601 | 15 | 12 | 20 | 13 | 6 |
| DPB1*3701 | 3 | 4 | 5 | |
| DPB1*3801 | 32 | | | |
| DPB1*3901 | 6 | 7 | | |
| DPB1*4001 | 27 | | | |
| DPB1*4101 | 33 | 34 | | |
| DPB1*4401 | 12 | 17 | 21 | |
| DPB1*4501 | 3 | 4 | 17 | |
| DPB1*4601 | 16 | 5 | 14 | |
| DPB1*4701 | 13 | 5 | 14 | |
| DPB1*4801 | 12 | 4 | 7 | 14 |
| DPB1*4901 | 4 | 6 | 7 | |
| DPB1*5001 | 3 | 16 | 17 | |
| DPB1*5101 | 19 | 4 | 6 | 7 |
| DPB1*5201 | 15 | 3 | 17 | |
| DPB1*5301 | 4 | 27 | | |
| DPB1*5401 | 22 | 13 | 5 | |

TABLE 15-4

| Allele Number | Probe Number for Detection | | | |
|---|---|---|---|---|
| DPB1*5501 | 22 | 3 | 5 | 6 |
| DPB1*5601 | 19 | 17 | | |
| DPB1*5701 | 3 | 16 | 17 | |
| DPB1*5801 | 12 | 5 | 6 | |
| DPB1*5901 | 4 | 17 | 6 | 7 |
| DPB1*6001 | 35 | | | |
| DPB1*6101N | 36 | | | |
| DPB1*6201 | 12 | 20 | 27 | |
| DPB1*6301 | 12 | 6 | | |
| DPB1*6401N | 16 | 17 | 21 | 6 |
| DPB1*6601 | 22 | 19 | 6 | 7 |
| DPB1*6701 | 22 | 3 | 17 | |
| DPB1*6801 | 3 | 4 | | |
| DPB1*6901 | 16 | 37 | | |
| DPB1*7001 | 3 | 16 | 17 | |
| DPB1*7101 | 3 | 5 | 6 | 7 |
| DPB1*7201 | 17 | 6 | 7 | |
| DPB1*7301 | 4 | 17 | 7 | |
| DPB1*7401 | 23 | 26 | | |
| DPB1*7501 | 3 | 4 | 7 | |
| DPB1*7601 | 22 | 16 | 17 | |
| DPB1*7701 | 38 | | | |
| DPB1*7801 | 39 | | | |
| DPB1*7901 | 15 | 3 | 4 | |
| DPB1*8001 | 16 | 14 | | |
| DPB1*8101 | 4 | 5 | 6 | 7 |

TABLE 15-4-continued

| Allele Number | Probe Number for Detection | | | |
|---|---|---|---|---|
| DPB1*8201 | 14 | 40 | | |
| DPB1*8301 | 33 | | | |
| DPB1*8401 | 13 | 41 | | |
| DPB1*8501 | 15 | 42 | | |

TABLE 15-5

| Allele Number | Probe Number for Detection | | | |
|---|---|---|---|---|
| DPB1*8601 | 43 | 16 | 5 | 14 |
| DPB1*8701 | 15 | 3 | 17 | 6 |
| DPB1*8801 | 15 | 16 | 5 | |
| DPB1*8901 | 6 | | | |
| DPB1*9001 | 19 | | | |
| DPB1*9101 | 16 | 17 | 6 | |
| DPB1*9201 | 15 | 16 | 17 | |
| DPB1*9301 | 15 | 3 | 4 | 5 | 6 |
| DPB1*9601 | 44 | | | |

TABLE 16-1

| Allele Number | Probe Number for Detection | | | |
|---|---|---|---|---|
| DPA1*010301 | 0 | 1 | 2 | |
| DPA1*010302 | 3 | | | |
| DPA1*0104 | 4 | | | |
| DPA1*0106 | 5 | | | |
| DPA1*0107 | 6 | | | |
| DPA1*0108 | 4 | 7 | | |
| DPA1*020101 | 8 | 5 | 7 | |
| DPA1*020102 | 5 | 7 | | |
| DPA1*020103 | 9 | 7 | | |
| DPA1*020104 | 10 | | | |
| DPA1*020105 | 3 | 9 | 7 | |
| DPA1*020106 | 8 | 11 | 7 | |
| DPA1*020201 | 3 | 11 | 7 | |
| DPA1*020202 | 8 | 3 | 9 | 7 |
| DPA1*020203 | 12 | 7 | | |
| DPA1*0203 | 8 | 7 | | |
| DPA1*0301 | 13 | | | |
| DPA1*0302 | 12 | | | |
| DPA1*0401 | 14 | | | |

TABLE 16-2

| Allele Number | Probe Number for Detection | | | | |
|---|---|---|---|---|---|
| DPB1*010101 | 0 | 1 | 2 | | |
| DPB1*010102 | 3 | | | | |
| DPB1*020102 | 4 | 5 | 6 | 7 | 8 | 9 |
| DPB1*020103 | 10 | | | | |
| DPB1*020104 | 11 | | | | |
| DPB1*020105 | 12 | | | | |
| DPB1*020106 | 13 | | | | |
| DPB1*0202 | 14 | 15 | 7 | 16 | |
| DPB1*030101 | 17 | 5 | 18 | 19 | |
| DPB1*030102 | 20 | | | | |
| DPB1*0401 | 4 | 21 | 8 | 9 | |
| DPB1*0402 | 4 | 5 | 6 | 8 | 9 |
| DPB1*0501 | 4 | 14 | 22 | 15 | 8 |
| DPB1*0601 | 18 | 19 | 7 | 8 | |
| DPB1*0801 | 5 | 6 | 7 | | |
| DPB1*0901 | 23 | 18 | 7 | | |
| DPB1*1001 | 23 | 6 | 7 | | |
| DPB1*110101 | 17 | 24 | | | |
| DPB1*110102 | 25 | | | | |
| DPB1*1301 | 17 | 7 | 26 | | |
| DPB1*1401 | 23 | 5 | 18 | 19 | |

TABLE 16-2-continued

| Allele Number | Probe Number for Detection | | | | |
|---|---|---|---|---|---|
| DPB1*1501 | 24 | 16 | | | |
| DPB1*1601 | 4 | 5 | 6 | 7 | 8 |
| DPB1*1701 | 23 | 18 | 7 | 8 | |
| DPB1*1801 | 5 | 6 | 27 | | |
| DPB1*1901 | 4 | 15 | 7 | 26 | |
| DPB1*200101 | 18 | 19 | 8 | | |
| DPB1*200102 | 18 | 19 | 8 | | |

TABLE 16-3

| Allele Number | Probe Number for Detection | | | | |
|---|---|---|---|---|---|
| DPB1*2101 | 17 | 14 | 15 | 7 | 8 |
| DPB1*2201 | 4 | 14 | 15 | 7 | 8 |
| DPB1*2301 | 4 | 5 | 8 | 9 | |
| DPB1*2401 | 15 | 16 | | | |
| DPB1*2501 | 17 | 5 | 6 | 19 | |
| DPB1*260101 | 28 | | | | |
| DPB1*260102 | 17 | | | | |
| DPB1*2701 | 17 | 8 | | | |
| DPB1*2801 | 6 | 19 | 27 | | |
| DPB1*2901 | 18 | 19 | 7 | | |
| DPB1*3001 | 23 | 29 | 15 | 7 | 8 |
| DPB1*3101 | 30 | | | | |
| DPB1*3201 | 31 | | | | |
| DPB1*3301 | 4 | 7 | 8 | 9 | |
| DPB1*3401 | 30 | 16 | | | |
| DPB1*3501 | 23 | 5 | 18 | | |
| DPB1*3601 | 17 | 14 | 22 | 15 | 8 |
| DPB1*3701 | 17 | 5 | 6 | 7 | |
| DPB1*3801 | 32 | | | | |
| DPB1*3901 | 4 | 8 | 9 | | |
| DPB1*4001 | 4 | 27 | | | |
| DPB1*4101 | 33 | 7 | | | |
| DPB1*4401 | 14 | 19 | 7 | | |
| DPB1*4501 | 29 | 5 | 6 | 19 | |
| DPB1*4601 | 4 | 18 | 7 | 16 | |
| DPB1*4701 | 15 | 7 | 16 | | |
| DPB1*4801 | 14 | 6 | 9 | 16 | |
| DPB1*4901 | 6 | 8 | 9 | | |
| DPB1*5001 | 5 | 18 | 19 | | |
| DPB1*5101 | 4 | 21 | 6 | 8 | 9 |

TABLE 16-4

| Allele Number | Probe Number for Detection | | | |
|---|---|---|---|---|
| DPB1*5201 | 17 | 5 | 19 | |
| DPB1*5301 | 4 | 6 | 27 | |
| DPB1*5401 | 23 | 29 | 15 | 7 |
| DPB1*5501 | 23 | 7 | 8 | |
| DPB1*5601 | 17 | 21 | 19 | |
| DPB1*5701 | 5 | 18 | 19 | |
| DPB1*5801 | 29 | 14 | 7 | 8 |
| DPB1*5901 | 6 | 19 | 8 | 9 |
| DPB1*6001 | 34 | | | |
| DPB1*6101N | 35 | | | |
| DPB1*6201 | 14 | 22 | 27 | |
| DPB1*6301 | 14 | 8 | | |
| DPB1*6401N | 18 | 19 | 7 | 8 |
| DPB1*6501 | 4 | | | |
| DPB1*6601 | 23 | 16 | | |
| DPB1*6701 | 23 | 5 | 19 | |
| DPB1*6801 | 4 | 5 | 6 | |
| DPB1*6901 | 18 | 36 | | |
| DPB1*7001 | 37 | 5 | 18 | 19 |
| DPB1*7101 | 5 | 7 | 8 | 9 |
| DPB1*7201 | 19 | 8 | 9 | |
| DPB1*7301 | 6 | 19 | 9 | |
| DPB1*7401 | 17 | 24 | 16 | |
| DPB1*7501 | 5 | 6 | 9 | |

TABLE 16-4-continued

| Allele Number | Probe Number for Detection | | | | |
|---|---|---|---|---|---|
| DPB1*7601 | 23 | 18 | 19 | | |
| DPB1*7701 | 38 | | | | |
| DPB1*7801 | 39 | | | | |
| DPB1*7901 | 17 | 5 | 6 | | |
| DPB1*8001 | 4 | 18 | 40 | | |
| DPB1*8101 | 4 | 6 | 7 | 8 | 9 |

TABLE 16-5

| Allele Number | Probe Number for Detection | | | | |
|---|---|---|---|---|---|
| DPB1*8201 | 4 | 5 | 6 | 8 | 9 |
| DPB1*8301 | 33 | | | | |
| DPB1*8401 | 41 | 42 | | | |
| DPB1*8501 | 17 | 8 | | | |
| DPB1*8601 | 23 | 7 | 16 | | |
| DPB1*8701 | 17 | 5 | 19 | 8 | |
| DPB1*8801 | 17 | 18 | 7 | | |
| DPB1*8901 | 8 | | | | |
| DPB1*9001 | 21 | | | | |
| DPB1*9101 | 23 | 19 | 8 | | |
| DPB1*9201 | 17 | 18 | 19 | | |
| DPB1*9301 | 17 | 5 | 6 | 7 | 8 |
| DPB1*9601 | 43 | | | | |

Example 9

Probes for Identification of HLA-DQ Allele

Extraction of DNA from 1 ml of human blood was performed using GFX Genomic Blood DNA Purification Kit from Amersham Biosciences in the same manner as in Example 1.

Next, quantitative PCR was carried out in the same manner as in Example 1 except that probes in the probe lists DQ1A and DQ1B were used and 2 μl of the mixed primers consisting of 1 μl each of respective solutions of the following primers (10 pmol/μl) and 6 μl of ultra pure water were used:

```
GGTGAGGTAACTGATCTTG        (SEQ ID NO: 2413)

TCCTTCTGGCTGTTCCAGTACTC.   (SEQ ID NO: 2414)
```

After PCR amplification, referring to Amp Plot and Dissociation curves on a display of 5700 software, and to the allele-probe list (Table 19A, 19B-1 and 19B-2), it was identified as DQA1*0103 and DQB1*060101.

Example 10

Extraction of DNA from 1 ml of human blood was performed in the same way as in Example 3. PCR of human HLA-DQ was then performed in the same manner as in Example 2 except that 3 μl of the mixed primer consisting of 1 μl each of the solutions containing the following sequences at 10 pmol/μl respectively, and 12 μl of ultra pure water were used:

```
GGTGAGGTAACTGATCTTG        (SEQ ID NO: 2413)

ATGATCCTAAACAAAGCTCTG      (SEQ ID NO: 2415)

TGTGCTACTTCACCAACGGGACG.   (SEQ ID NO: 2416)
```

At the same time, a DNA microarray was prepared to identify the allele in the specimen described above in the same manner as in Example 2, except that probes in the probe list of Tables 18A, 18B-1 and 18B-2 were used to form the probe spots respectively.

Then, hybridization was performed using the above specimen and the prepared DNA microarray in the same manner as in Example 2. Fluorometry measurement was conducted with GenePix4000B (Axon). Referring to the allele-probe list (Tables 20A, 20B-1 and 20B-2), it was identified as DQA1*0103 and DQB1*060101.

Allele list
DQA1*010101

(SEQ ID NO: 2417)

atgatcctaaacaaagctctgctgctgggggccctcgctctgaccaccgtgatgagcccctgtggaggtgaagaca ttgtggctgaccacgttgcctcttgtggtgtaaacttgtaccagttttacggtccctctggccagtacacccatga atttgatggagatgagGagttctacgtggacctggagaggaaggagactgcctggcggtggcctgagttcagcaaa tttggaggttttgacccgcagggtgcactgagaaacatggctgtggcaaaacacaacttgaacatcatgattaaac gctacaactctaccgctgctaccaatgaggttcctgaggtcacagtgttttccaagtctcccgtgacactgggtca gcccaacaccctcatttgtcttgtggacaacatctttcctcctgtggtcaacatcacatggctgagcaatgggcag tcagtcacagaaggtgtttctgagaccagcttcctctccaagagtgatcattccttcttcaagatcagttacctca ccttcctcccttctgctgatgagatttatgactgcaaggtggagcactggggcctggaccagcctcttctgaaaca ctgggagcctgagattccagcccctatgtcagagctcacagagactgtggtctgcgccctgggggttgtctgtgggc ctcgtgggcattgtggtgggcactgtcttcatcatccaaggcctgcgttcagttggtgcttccagacaccaagggc cattgtga

DQA1*010102

(SEQ ID NO: 2418)

atgatcctaaacaaagctctgctgctgggggccctcgctctgaccaccgtgatgagcccctgtggaggtgaagaca ttgtggctgaccacgttgcctcttgtggtgtaaacttgtaccagttttacggtccctctggccagtacacccatga -continued atttgatggagatgaggagttctacgtggacctggagaggaaggagactgcctggcggtggcctgagttcagcaaa
tttggaggttttgacccgcagggtgcactgagaaacatggctgtggcaaaacacaacttgaacatcatgattaaac
gctacaactctaccgctgctaccaatgaggttcctgaggtcacagtgttttccaagtctcccgtgacactgggtca
gcccaacaccctcatttgtcttgtggacaacatctttcctcctgtggtcaacatcacatggctgagcaatgggcag
tcagtcacagaaggtgtttctgagaccagcttcctctccaagagtgatcattccttcttcaagatcagttacctca
ccttcctcccttctgctgatgagatttatgactgcaaggtggagcactggggcctggaccagcctcttctgaaaca
ctgggagcctgagattccagcccctatgtcagagctcacagagactgtggtctgcgccctggggttgtctgtgggc
ctcgtgggcattgtggtgggcactgtcttcatcatccaaggcctgcgttcagttggtgcttccagacaccaGgggc
cattgtga DQA1*010201 (SEQ ID NO: 2419)
atgatcctaaacaaagctctgctgctgggggcctcgctctgaccaccgtgatgagcccctgtggaggtgaagaca
ttgtggctgaccacgttgcctcttgtggtgtaaacttgtaccagttttacggtccctctggccagtacacccatga
atttgatggagatgagcagttctacgtggacctggagaggaaggagactgcctggcggtggcctgagttcagcaaa
tttggaggttttgacccgcagggtgcactgagaaacatggctgtggcaaaacacaacttgaacatcatgattaaac
gctacaactctaccgctgctaccaatgaggttcctgaggtcacagtgttttccaagtctcccgtgacactgggtca
gcccaacaccctcatttgtcttgtggacaacatctttcctcctgtggtcaacatcacatggctgagcaatgggcag
tcagtcacagaaggtgtttctgagaccagcttcctctccaagagtgatcattccttcttcaagatcagttacctca
ccttcctcccttctgctgatgagatttatgactgcaaggtggagcactggggcctggaccagcctcttctgaaaca
ctgggagcctgagattccagcccctatgtcagagctcacagagactgtggtctgcccctggggttgtctgtgggc
ctcAtgggcattgtggtgggcactgtcttcatcatccaaggcctgcgttcagttggtgcttccagacaccaagggc
cattgtga DQA1*010202 (SEQ ID NO: 2420)
atgatcctaaacaaagctctgctgctgggggcctcgctctgaccaccgtgatgagcccctgtggaggtgaagaca
ttgtggctgaccacgttgcctcttgtggtgtaaacttgtaccagttttacggtccctctggccagtacacccatga
atttgatggagatgagcagttctacgtggacctggagaggaaggagactgcctggcggtggcctgagttcagcaaa
tttggaggttttgacccgcagggtgcactgagaaacatggctgtggcaaaacacaacttgaacatcatgattaaac
gctacaactctaccgctgctaccaatgaggttcctgaggtcacagtgttttccaagtctcccgtgacactgggtca
gcccaacaccctcatCtgtcttgtggacaacatctttcctcctgtggtcaacatcacatggctgagcaatgggcag
tcagtcacagaaggtgtttctgagaccagcttcctctccaagagtgatcattccttcttcaagatcagttacctca
ccttcctcccttctgctgatgagatttatgactgcaaggtggagcactggggcctggaccagcctcttctgaaaca
ctgggagcctgagattccagcccctatgtcagagctcacagagactgtggtctgcccctggggttgtctgtgggc
ctcAtgggcattgtggtgggcactgtcttcatcatccaaggcctgcgttcagttggtgcttccagacaccaagggc
cattgtga DQA1*0103 (SEQ ID NO: 2421)
atgatcctaaacaaagctctgctgctgggggcctcgctctgaccaccgtgatgagcccctgtggaggtgaagaca
ttgtggctgaccatgttgcctcttgtggtgtaaacttgtaccagttttacggtccctctggccagttcacccatga
atttgatggagatgagcagttctacgtggacctggagaagaaggagactgcctggcggtggcctgagttcagcaaa
tttggaggttttgacccgcagggtgcactgagaaacatggctgtggcaaaacacaacttgaacatcatgattaaac
gctacaactctaccgctgctaccaatgaggttcctgaggtcacagtgttttccaagtctcccgtgacactgggtca
gcccaacaccctcatctgtcttgtggacaacatctttcctcctgtggtcaacatcacatggctgagcaatgggcac
Gcagtcacagaaggtgtttctgagaccagcttcctctccaagagtgatcattccttcttcaagatcagttacctca ccttcctcccttctgctgatgagatttatgactgcaaggtggagcactggggcctggaccagcctcttctgaaaca ctgggagcctgagattccagcccctatgtcagagctcacagagactgtggtctgtgccctggggttgtctgtgggc ctcgtgggcattgtggtgggcactgtcttcatcatccaaggcctgcgttcagttggtgcttccagacaccaagggc ccttgtga

DQA1*010401 (SEQ ID NO: 2422)

atgatcctaaacaaagctctgctgctgggggccctcgctctgaccaccatgatgagcccttgtggaggtgaaggca ttgtggctgaccacgttgcctcttgtggtgtaaacttgtaccagttttacggtccctctggccagtacacccatga atttgatggagatgaggagttctacgtggacctggagaggaaggagactgcctggcggtggcctgagttcagcaaa tttggaggttttgacccgcagggtgcactgagaaacatggctgtggcaaaacacaacttgaacatcatgattaaac gctacaactctaccgctgctaccaatgaggttcctgaggtcacagtgttttccaagtctcccgtgacactgggtca gcccaacaccctcatttgtcttgtggacaacatctttcctcctgtggtcaacatcacatggctgagcaatgggcag tcagtcacagaaggtgtttctgagaccagcttcctctccaagagtgatcattccttcttcaagatcagttacctca ccttcctcccttctgctgatgagatttatgactgcaaggtggagcactggggcctggaccagcctcttctgaaaca ctgggagcctgagattccagcccctatgtcagagctcacagagactgtggtctgcAccctggggttgtctgtgggc ctcgtgggcattgtggtgggcactgtcttcatcatccaaggcctgcgttcagttggtgcttccagacaccaagggc cattgtga

DQA1*010402 (SEQ ID NO: 2423)

atgatcctaaacaaagctctgctgctgggggccctcgctctgaccaccatgatgagcccttgtggaggtgaagGca ttgtggctgaccacgttgcctcttgtggtgtaaacttgtaccagttttacggtccctctggccagtacacccatga atttgatggagatgaggagttctacgtggacctggagaggaaggagactgcctggcggtggcctgagttcagcaaa tttggaggttttgacccgcagggtgcactgagaaacatggctgtggcaaaacacaacttgaacatcatgattaaac gctacaactctaccgctgctaccaatgaggttcctgaggtcacagtgttttccaagtctcccgtgacactgggtca gcccaacaccctcatttgtcttgtggacaacatctttcctcctgtggtcaacatcacCtggctgagcaatgggcag tcagtcacagaaggtgtttctgagaccagcttcctctccaagagtgatcattccttcttcaagatcagttacctca ccttcctcccttctgctgatgagatttatgactgcaaggtggagcactggggcctggaccagcctcttctgaaaca ctggg

DQA1*0105 (SEQ ID NO: 2424)

atgatcctaaacaaagctctgctgctgggggccctcgctctgaccaccatgatgagcccttgtggaggtgaagGca ttgtggctgaccacgttgcctcttgtggtgtaaacttgtaccagttttacggtccctctggccagtacacccatga atttgatggagatgaggagttctacgtggacctggagaggaaggagactgcctggcggtggcctgagttcagcaaa tttggaggttttgacccgcagggtgcactgagaaacatggctgtggcaaaacacaacttgaacatcatgattaaac gctacaactctaccgctgctaccaatgaggttcctgaggtcacagtgttttccaagtctcccgtgacactgggtca gcccaacaccctcatttgtcttgtggacaacatctttcctcctgtggtcaacatcacatggctgagcaatgggcag tcagtcacagaaggtgtttctgagaccagcttcctctccaagagtgatcattccttcttcaagatcagttacctca ccttcctcccttctgctgatgagatttatgactgcaaggtggagcactggggcctggaccagcctcttctgaaaca ctgggagcctgagattccagcccctatgtcagagctcacagagactgtggtctgcgccctggggttgtctgtgggc ctcgtgggcattgtggtgggcactgtcttcatcatccaaggcctgcgttcagttggtgcttccaga

DQA1*0106 (SEQ ID NO: 2425)

ctgaccacgttgcctcttgtggtgtaaacttgtaccagttttacggtccctctggccagtacacccatgaatttga tggagatgagcagttctacgtggacctggagaggaaggagGctgcctggcggtggcctgagttcagcaaatttgga -continued ggttttgacccgcagggtgcactgagaaacatggctgtggcaaaacacaacttgaacatcatgattaaacgctaca actctaccgctgctaccaatg

DQA1*0201

(SEQ ID NO: 2426)

atgatcctaaacaaagctctgatgctgggggccctcgccctgaccaccgtgatgagcccttgtggaggtgaagaca ttgtggctgaccacgttgcctcttacggtgtaaacttgtaccagtcttacggtccctctggccagttcacccatga atttgatggagacgaggagttctatgtggacctggagaggaaggagactgtctggaagttgcctctgttccacaga Cttaga...tttgacccgcaatttgcactgacaaacatcgctgtgctaaaacataacttgaacatcctgattaaac gctccaactctaccgctgctaccaatgaggttcctgaggtcacagtgttttccaagtctcccgtgacactgggtca gcccaacaccctcatctgtcttgtggacaacatctttcctcctgtggtcaacatcacctggctgagcaatgggcac tcagtcacagaaggtgtttctgagaccagcttcctctccaagagtgatcattccttcttcaagatcagttacctca ccttcctccctcgctgatgagatttatgactgcaaggtggagcactggggcctggatgagcctcttctgaaaca ctgggagcctgagattccagcacctatgtcagagctcacagagactgtggtctgtgccctggggttgtctgtgggc ctcgtgggcattgtggtggggaccgtcttgatcatccgaggcctgcgttcagttggtgcttccagacaccaagggc ccttgtga

DQA1*030101

(SEQ ID NO: 2427)

atgatcctaaacaaagctctgatgctgggggccctcgccctgaccaccgtgatgagcccttgtggaggtgaagaca ttgtggctgaccatgttgcctcttacggtgtaaacttgtaccagtcttatggtccctctgggcagtacagccatga atttgatggagacgaggagttctatgtggacctggagaggaaggagactgtctggcagttgcctctgttccgcaga tttagaagatttgaccgcaatttgcactgacaaacatcgctgtgctaaaacataacttgaacatcgtgattaaac gctccaactctaccgctgctaccaatgaggttcctgaggtcacagtgttttccaagtctcccgtgacactgggtca gcccaacaccctcatctgtcttgtggacaacatctttcctcctgtggtcaacatcacctggctgagcaatgggcac tcagtcacagaaggtgtttctgagaccagcttcctctccaagagtgatcattccttcttcaagatcagttacctca ccttcctccctcgctgatgagatttatgactgcaaggtggagcactggggcctggatgagcctcttctgaaaca ctgggagcctgagattccaAcacctatgtcagagctcacagagactgtggtctgcgccctggggttgtctgtgggc ctcgtgggcattgtggtggggaccgtcttgatcatccgaggcctgcgttcagttggtgcttccagacaccaagggc ccttgtga

DQA1*0302

(SEQ ID NO: 2428)

atgatcctaaacaaagctctgatgctgggggccctcgccctgaccaccgtgaCgagcccttgtggaggtgaagaca ttgtggctgaccatgttgcctcttacggtgtaaacttgtaccagtcttatggtccctctgggcagtacagccatga atttgatggagacgaggagttctatgtggacctggagaggaaggagactgtctggcagttgcctctgttccgcaga tttagaagatttgaccgcaatttgcactgacaaacatcgctgtgctaaaacataacttgaacatcgtgattaaac gctccaactctaccgctgctaccaatgaggttcctgaggtcacagtgttttccaagtctcccgtgacactgggtca gcccaacaccctcatctgtcttgtggacaacatctttcctcctgtggtcaacatcacctggctgagcaatgggcac tcagtcacagaaggtgtttctgagaccagcttcctctccaagagtgatcattccttcttcaagatcagttacctca ccttcctccctcgtgatgatgagatttatgactgcaaggtggagcactggggcctggatgagcctcttctgaaaca ctgggagcctgagattccaacacctatgtcagagctcacagagactgtggtctgcgccctggggttgtctgtgggc ctcgtgggcattgtggtggggaccgtcttgatcatccgaggcctgcgttcagttggtgcttccagacaccaagggc ccttgtga

DQA1*0303

(SEQ ID NO: 2429)

atgatcctaaacaaagctctgatgctgggggccctcgccctgaccaccgtgatgagcccttgtggaggtgaagaca ttgtggctgaccatgttgcctcttacggtgtaaacttgtaccagtcttatggtccctctgggcagtacagccatga -continued atttgatggagacgaggagttctatgtggacctggagaggaaggagactgtctggcagttgcctctgttccgcaga tttagaagatttgacccgcaatttgcactgacaaacatcgctgtgctaaaacataacttgaacatcgtgattaaac gctccaactctaccgctgctaccaatgaggttcctgaggtcacagtgttttccaagtctcccgtgacactgggtca gcccaacaccctcatctgtcttgtggacaacatctttcctcctgtggtcaacatcacctggctgagcaatgggcac tcagtcacagaaggtgtttctgagaccagcttcctctccaagagtgatcattccttcttcaagatcagttacctca ccttcctcccttctgAtgatgagatttatgactgcaaggtggagcactggggcctggatgagcctcttctgaaaca ctgggagcctgagattccaacacctatgtcagagctcacagagactgtggtctgcgccctggggttgtctgtgggc ctcgtgggcattgtggtggggaccgtcttgatcatccgaggcctgcgttcagttggtgcttccagacaccaagggc ccttgtga DQA1*040101
(SEQ ID NO: 2430)
atgatcctaaacaaagctctgctgctgggggcccttgccctgaccaccgtgatgagccctgtggaggtgaagaca ttgtggctgaccatgttgcctcttatggtgtaaacttgtaccagtcttacggtccctctggccagtacacccatga atttgatggagacgagcagttctacgtggacctggggaggaaggagactgtctggtgtttgcctgttctcagacaa tttaga...tttgacccgcaatttgcactgacaaacatcgctgtgacaaaacacaacttgaacatcctgattaaac gctccaactctacTgctgctaccaatgaggttcctgaggtcacagtgttttccaagtctcccgtgacgctgggtca gcccaacaccctcatctgtcttgtggacaacatctttcctcctgtggtcaacatcacatggctgagcaatgggcac tcagtcacagaaggtgtttctgagaccagcttcctctccaagagtgatcattccttcttcaagatcagttacctca ccttcctcccttctgctgatgagatttatgactgcaaggtggagcactggggcctggacgagcctcttctgaaaca ctgggagcctgagattccagcccctatgtcagagctcacagagactgtggtctgcgccctgggattgtctgtgggc ctcgtgggcattgtggtgggcactgtcttcatcatccgaggcctgcgttcagttggtgcttccagacaccaagggc cCttgtga DQA1*040102
(SEQ ID NO: 2431)
ctgaccatgttgcctcttatggtgtaaacttgtaccagtcttacggtccctctggccagtacacccatgaatttga tggagacgagcagttctacgtggacctggggaggaaggagactgtctggtgtttgcctgttctcagacaatttaga ...tttgacccgcaatttgcactgacaaacatcgctgtgacaaaacacaacttgaacatcctgattaaacgctcca actctactgctgctaccaatgaggttcctgaggtcacagtgttttccaagtctccTgtgacgctgggtcagcccaa caccctcatctgtcttgtggacaacatctttcctcctgtggtcaacatcacatggctgagcaatgggcactcagtc acagaaggtgtttctgagaccagcttcctctccaagagtgatcattccttcttcaagatcagttacctcaccttcc tcccttctgctgatgagatttatgactgcaaggtggagcactggggcctggacgagcctcttctgaaacactggg DQA1*050101
(SEQ ID NO: 2432)
atgatcctaaacaaagctctgatgctgggggcccttgccctgaccaccgtgatgagccctgtggaggtgaagaca ttgtggctgaccacgtcgcctcttatggtgtaaacttgtaccagtcttacggtccctctggccagtacacccatga atttgatggagatgagcagttctacgtggacctggggaggaaggagactgtctggtgtttgcctgttctcagacaa tttaga...tttgacccgcaatttgcactgacaaacatcgctgtcctaaaacataacttgaacagtctgattaaac gctccaactctaccgctgctaccaatgaggttcctgaggtcacagtgttttccaagtctcccgtgacactgggtca gcccaacatcctcatctgtcttgtggacaacatctttcctcctgtggtcaacatcacatggctgagcaatgggcac tcagtcacagaaggtgtttctgagaccagcttcctctccaagagtgatcattccttcttcaagatcagttacctca ccctcctcccttctgctgaggagagttatgactgcaaggtggagcactggggcctggacAagcctcttctgaaaca ctgggagcctgagattccagcccctatgtcagagctcacagagactgtggtctgcgccctgggAttgtctgtgggc ctcgtgggcattgtggtgggcactgtcttcatcatccgaggcctgcgttcagttggtgcttccagacaccaagggc ccttgtga

DQA1*050102

(SEQ ID NO: 2433)

gaagacattgtggctgaccacgttgcctcttAtggtgtaaacttgtaccagtcttacggtccctctggccagtaca cccatgaatttgatggagatgagcagttctacgtggacctggggaggaaggagactgtctggtgtttgcctgttct cagacaatttaga...tttgacccgcaatttgcactgacaaacatcgctgtcctaaaacataacttgaacagTctg attaaacgctccaactctaccgctgctaccaat

DQA1*0502

(SEQ ID NO: 2434)

ggtgtaaacttgtaccagtcttacggtccctctggccagtacacccatgaatttgatggagatgagcagttctacg tggacctggggaggaaggagactgtctggtgtttgcctgttctcagacaatttaga...tttgaccGgcaatttgc actgacaaacatcgctgtcctaaaacataacttgaacagtctgattaaacgctccaactctaccgctgctacc

DQA1*0503

(SEQ ID NO: 2435)

atgatcctaaacaaagctctgatgctgggggcccttgccctgaccacgtgatgagcccctgtggaggtgaagaca ttgtggctgaccacgtcgcctcttatggtgtaaacttgtaccagtcttacggtccctctggccagtacacccatga atttgatggagatgagcagttctacgtggacctggggaggaaggagactgtctggtgtttgcctgttctcagacaa tttaga...tttgacccgcaatttgcactgacaaacatcgctgtcctaaaacataacttgaacagtctgattaaac gctccaactctaccgctgctaccaatgaggttcctgaggtcacagtgttttccaagtctcccgtgacactgggtca gcccaacatcctcatctgtcttgtggacaacatctttcctcctgtggtcaacatcacatggctgagcaatgggcac tcagtcacagaaggtgtttctgagaccagcttcctctccaagagtgatcattccttcttcaagatcagttacctca ccctcctcccttctTctgaggagagttatgactgcaaggtggagcactggggcctggacaagcctcttctgaaaca ctgggagcctgagattccagcccctatgtcagagctcacagagactgtggtctgcgccctgggattgtctgtgggc ctcgtgggcattgtggtgggcactgtcttcatcatccgaggcctgcgttcagttggtgcttccagacaccaagggc ccttgtga

DQA1*0504

(SEQ ID NO: 2436)

ctgaccacgtcgcctcttatggtgtaaacttgtaccagtcttacggtcTctctggccagtacacccatgaatttga tggagatgagcagttctacgtggacctggggaggaaggagactgtctggtgtttgcctgttctcagacaatttaga ...tttgacccgcaatttgcactgacaaacatcgctgtcctaaaacataacttgaacagtctgattaaacgctcca actctaccgctgctaccaatg

DQA1*0505

(SEQ ID NO: 2437)

atgatcctaaacaaagctctgatgctggggacccttgccctgaccacgtgatgagcccctgtggaggtgaagaca ttgtggctgaccacgtcgcctcttatggtgtaaacttgtaccagtcttacggtccctctggccagtacacccatga atttgatggagatgagcagttctacgtggacctggggaggaaggagactgtctggtgtttgcctgttctcagacaa tttaga...tttgacccgcaatttgcactgacaaacatcgctgtcctaaaacataacttgaacagtctgattaaac gctccaactctaccgctgctaccaatgaggttcctgaggtcacagtgttttccaagtctcccgtgacactgggtca gcccaacatcctcatctgtcttgtggacaacatctttcctcctgtggtcaacatcacatggctgagcaatgggcac tcagtcacagaaggtgtttctgagaccagcttcctctccaagagtgatcattccttcttcaagatcagttacctca ccctcctcccttctgctgaggagagttatgactgcaaggtggagcactggggActggacaagcctcttctgaaaca ctgggagcctgagattccagcccctatgtcagagctcacagagactgtggtctgcgccctggggttgtctgtgggc ctcgtgggcattgtggtgggcactgtcttcatcatccgaggcctgcgttcagttggtgcttccagacaccaagggc ccttgtga -continued DQA1*060101
(SEQ ID NO: 2438)
atgatcctaaacaaagctctgctgctgggggcccttgccctgaccaccgtgatgagccctgtggaggtgaagaca ttgtggctgaccatgttgcctcttatggtgtaaacttgtaccagtcttacggtccctctggccagtTcacccatga atttgatggagacgagcagttctacgtggacctggggaggaaggagactgtctggtgtttgcctgttctcagacaa tttaga...tttgacccgcaatttgcactgacaaacatcgctgtgacaaaacacaacttgaacatcctgattaaac gctccaactctaccgctgctaccaatgaggttcctgaggtcacagtgttttccaagtctcccgtgacGctgggtca gcccaacaccctcatctgtcttgtggacaacatctttcctcctgtggtcaacatcacatggctgagcaatgggcac tcagtcacagaaggtgtttctgagaccagcttcctctccaagagtgatcattccttcttcaagatcagttacctca ccttcctcccttctgctgatgagatttatgactgcaaggtggagcactggggcctggacgagcctcttctgaaaca ctgggagcctgagattccagcccctatgtcagagctcacagagactgtggtctgcgccctgggattgtctgtgggc ctcgtgggcattgtggtgggcactgtcttcatcatccgaggcctgcgttcagttggtgcttccagacaccaagggc cCttgtga DQA1*060102
(SEQ ID NO: 2439)
ggtgtaaacttgtaccagtcttacggtccctctggccagttcacccatgaatttgatggagacgagcagttctacg tggacctggggaggaaggagactgtctggtgtttgcctgttctcagacaatttaga...tttgacccgcaatttgc actgacaaacatcgcCgtgacaaaacacaacttgaacatcctgattaaacgctccaactctaccgctgctaccaat ga DQB1*050101
(SEQ ID NO: 2440)
gggcctgtgctacttcaccaacgggacggagcgcgtgcggggtgtgaccagacacatctataaccgagaggagtac gtgcgcttcgacagcgacgtggggggtgtaccgggcAgtgacgccgcaggggcggcctgTtgccgagtactggaaca gccagaaggaagtcctggagggggcccgggcgTcggtggacaGggtgtgcagacacaactacgaggtggcgtaccg cgggatcctgcagaggagagtggagcccacagtgaccatctccccatccaggacagaggccctcaaccaccacaac ctgctgatctgctcggtgacagatttctatccaagccagatcaaagtccggtggtttcggaatgatcaggaggaga cagccggcgttgtgtccaccccctcattaggaacggtgactggaccttccagatcctggtgatgctggaaatgac tccccagcgtggagatgtctacacctgccacgtggagcaccccagcctccagagcccatcaccgtggagtgg DQB1*050102
(SEQ ID NO: 2441)
gggcctgtgctacttcaccaacgggacggagcgcgtgcggggtgtgaccagacacatctataaccgagaggagtac gtgcgcttcgacagcgacgtggggggtgtaccgggcggtgacgccgcaggggcggcctgttgccgagtactggaaca gccagaaggaagtcctggagggggcccgggcgtcggtggacagAgtgtgcagacacaactacgaggtggcgtaccg cgggatcctgcagagg DQB1*050201
(SEQ ID NO: 2442)
gggcctgtgctacttcaccaacgggacggagcgcgtgcggggtgtgaccagacacatctataaccgagaggagtac gtgcgcttcgacagcgacgtggggggtgtaccgggcggtgacgccgcaggggcggcctagcgccgagtactggaaca gccagaaggaagtcctggagggggcccgggcgtcggtggacagagtgtgcagacacaactacgaggtggcgtaccg cgggatcctgcagaggagagtggagcccacagtgaccatctccccatccaggacagaggccctcaaccaccacaac ctgctgatctgctcggtgacagatttctatccaagccaCatcaaagtccggtggtttcggaatgatcaggaggaga cagccggcgttgtgtccaccccctcattaggaacggtgactggaccttccagatcctggtgatgctggaaatgac tccccagcgtggagatgtctacacctgccacgtggagcaccccagcctccagagcccatcaccgtggagtgg

DQB1*050202

(SEQ ID NO: 2443)

gggcctgtgctacttcaccaacgggacggagcgcgtgcggggtgtgaccagacacatctataaccgagaggagtac gtgcgcttcgacagcgacgtgggggtgtaTcgggcggtgacgccgcaggggcggcctaGCgccgagtactggaaca gccagaaggaagtcctggagggggcccgggcgtcggtggacagAgtgtgcagacacaactacgaggtggcgtaccg cgggatcctgcagagga

DQB1*050301

(SEQ ID NO: 2444)

gggcctgtgctacttcaccaacgggacggagcgcgtgcggggtgtgaccagacacatctataaccgagaggagtac gtgcgcttcgacagcgacgtgggggtgtatcgggcggtgacgccgcaggggcggcctgACgccgagtactggaaca gccagaaggaagtcctggagggggcccgggcgtcggtggacagAgtgtgcagacacaactacgaggtggcgtaccg cgggatcctgcagaggagagtggagcccacagtgaccatctccccatccaggacagaggccctcaaccaccacaac ctgctgatctgctcggtgacagatttctatccaagccagatcaaagtccggtggtttcggaatgatcaggaggaga cagccggcgttgtgtccaccccccctcattaggaacggtgactggaccttccagatcctggtgatgctggaaatgac tccccagcgtggagatgtctacacctgccacgtggagcacccagcctccagagcccatcaccgtggagtgg

DQB1*050302

(SEQ ID NO: 2445)

gacggagcgcgtgcggggtgtgaccagacacatctataaccgagaggagtacgtgcgcttcgacagcgacgtgggg gtgtaTcgggcggtgacgccgcaggggcggcctgAtgccgagtactggaacagccagaaggaagtcctggag

DQB1*0504

(SEQ ID NO: 2446)

gggcctgtgctacttcaccaacgggacggagcgcgtgcggggtgtgaccagatacatctataaccgagaagagtac gtgcgcttcgacagcgacgtgggggtgtaccggcggtgacgccgcaggggcggcctaGcgccgagtactggaaca gccagaaggacatcctggaggAggaccgggcgtcggtggacagggtgtgcagacacaact

DQB1*0201

(SEQ ID NO: 2447)

gggcatgtgctacttcaccaacgggacagagcgcgtgcgtcttgtgagcagaagcatctataaccgagaagagatc gtgcgcttcgacagcgacgtgggggagttccggcggtgacgctgctggggctgcctgccgccgagtactggaaca gccagaaggacatcctggagaggaaAcgggcggcggtggacagggtgtgcagacacaactaccagttggagctccg cacgaccttgcagcggcgagtggagcccacagtgaccatctccccatccaggacagaggccctcaaccaccacaac ctgctggtctgctcggtgacagatttctatccagcccagatcaaagtccggtggtttcggaatgaccaggaggaga cagctggcgttgtgtccaccccccttattaggaatggtgactggaccttccagatcctggtgatgctggaaatgac tccccagcgtggagaCgtctacacctgccacgtggagcacccagcctccagagcccatcaccgtggagtgg

DQB1*0202

(SEQ ID NO: 2448)

gggcatgtgctacttcaccaacgggacagagcgcgtgcgtcttgtgagcagaagcatctataaccgagaagagatc gtgcgcttcgacagcgacgtgggggagttccggcggtgacgctgctggggctgcctgccgccgagtactggaaca gccagaaggacatcctggagaggaaacgggcggcggtggacagggtgtgcagacacaactaccagttggagctccg cacgaccttgcagcggcgagtggagcccacagtgaccatctccccatccaggacagaggccctcaaccaccacaac ctgctggtctgctcggtgacagatttctatccagcccagatcaaagtccggtggtttcggaatgGccaggaggaga cagctggcgttgtgtccaccccccttattaggaatggtgactggaccttccagatcctggtgatgctggaaatgac tccccagcgtggagaCgtctacacctgccacgtggagcacccagcctccagagcccatcaccgtggagtgg

DQB1*0203

(SEQ ID NO: 2449)

gggcatgtgctacttcaccaacgggacagagcgcgtgcgtcttgtgagcagaagcatctataaccgagaagagatc gtgcgcttcgacagcgacgtgggggagttccggcggtgacgctgctggggctgcctgAcgccgagtactggaaca gccagaaggacatcctggagaggaaacgggcggcggtggacagggtgtgcagacacaactaccagttggagctccg -continued cacgaccttgcagcggcgaccccatccaggacagaggccctcaaccaccacaacctgctggtctgctcggtgacag atttctatccagcccagatcaaagtccggtggtttcggaatgGccaggaggagacagctggcgttgtgtccacccc ccttattaggaatggtgactggaccttccagatcctggtgatgctggaaatgactccccagcgtggaga

DQB1*030101

(SEQ ID NO: 2450)
ggccatgtgctacttcaccaacgggacggagcgcgtgcgttatgtgaccagatacatctataaccgagaggagtac gcacgcttcgacagcgacgtggAggtgtaccgggcggtgacgccgctggggccgcctgAcgccgagtactggaaca gccagaaggaagtcctggagaggacccgggcggagttggacacggtgtgcagacacaactaccagttggagctccg cacgaccttgcagcggcgagtggagcccacagtgaccatctccccatccaggacagaggccctcaaccaccacaac ctgctggtctgctcagtgacagatttctatccagcccagatcaaagtccggtggtttcggaatgaccaggaggaga caaccggcgttgtgtccaccccccttattaggaacggtgactggaccttccagatcctggtgatgctggaaatgac tccccagcatggagaCgtctacacctgccacgtggagcaccccagcctccagaAcccatcaccgtggagtgg

DQB1*030102

(SEQ ID NO: 2451)
ggccatgtgctacttcaccaacgggacggagcgcgtgcgttatgtgaccagatacatctataaccgagaggagtac gcgcgcttcgacagcgacgtggAggtgtaccgggcggtgacgccgctggggccgcctgAcgccgagtactggaaca gccagaaggaagtcctggagaggacccgggcggagttggacacggtgtgcagacacaactaccagttggagctccg cacgaccttgcagcggcgag

DQB1*0302

(SEQ ID NO: 2452)
gggcatgtgctacttcaccaacgggacggagcgcgtgcgtcttgtgaccagatacatctataaccgagaggagtac gcAcgcttcgacagcgacgtggggtgtatcgggcggtgacgccgctggggccgcctgCcgccgagtactggaaca gccagaaggaagtcctggagaggacccgggcggagTtggacacggtgtgcagacacaactaccagttggagctccg cacgaccttgcagcggcgagtggagcccacagtgaccatctccccatccaggacagaggccctcaaccaccacaac ctgctggtctgctcagtgacagatttctatccagcccagatcaaagtccggtggtttcggaatgaccaggaggaga caactggcgttgtgtccaccccccttattaggaacggtgactggaccttccagatcctggtgatgctggaaatgac tccccagcgtggagacgtctacacctgccacgtggagcaccccagcctccagaacccatcaTcgtggagtgg

DQB1*030302

(SEQ ID NO: 2453)
gggcatgtgctacttcaccaacgggacggagcgcgtgcgtcttgtgaccagatacatctataaccgagaggagtac gcacgcttcgacagcgacgtggggtgtatcgggcggtgacgccgctggggccgcctgAcgccgagtactggaaca gccagaaggaagtcctggagaggacccgggcggagTtggacacggtgtgcagacacaactaccagttggagctccg cacgaccttgcagcggcgagtggagcccacagtgaccatctccccatccaggacagaggccctcaaccaccacaac ctgctggtctgctcagtgacagatttctatccagcccagatcaaagtccggtggtttcggaatgaccaggaggaga caactggcgttgtgtccaccccccttattaggaacggtgactggaccttccagatcctggtgatgctggaaatgac tccccagcgtggagacgtctacacctgccacgtggagcaccccagcctccagaacccatcaTcgtggagtgg

DQB1*030303

(SEQ ID NO: 2454)
gggcatgtgctacttcaccaacgggacggagcgcgtgcgtcTtgtgaccagatacatctataaccgagaggagtac gcgcgcttcgacagcgacgtggggtgtaTcgggcggtgacgccgctggggcCgcctgAcgccgagtactggaaca gccagaaggaagtcctggagAggacccgggcggagTtggacacggtgtgcagacacaactaccagttggagctccg cacgaccttgcagcggcgag

DQB1*0304

(SEQ ID NO: 2455)
ggccatgtgctacttcaccaacgggacggagcgcgtgcgttatgtgaccagatacatctataaccgagaggagtac gcacgcttcgacagcgacgtggAggtgtaccgggcggtgacgccgctggggccgcctgCcgccgagtactggaaca gccagaaggaagtcctggagaggacccgggcggagttggacacggtgtgcagacacaactaccagttggagctccg cacgaccttgcagcggcgagtggagcccacagtgaccatctccccatccaggacagaggccctcaaccaccacaac ctgctggtctgctcagtgacagatttctatccagcccagatcaaagtccggtggtttcggaatgaccaggaggaga caaccggcgttgtgtccaccccccttattaggaacggtgactggaccttccagatcctggtgatgctggaaatgac tccccagcatggagaCgtctacacctgccacgtggagcaccccagcctccagaAccccatcaccgtggagtgg

DQB1*030501 (SEQ ID NO: 2456)

gggcatgtgctacttcaccaacgggacCgagcgcgtgcggggtgtgaccagatacatctataaccgagaggagtac gcgcgcttcgacagcgacgtgggggtgtatcgggcggtgacgccgctggggccgcctgccgccgagtactggaaca gccagaaggaagtcctggagaggacccgggcggagTtggacacggtgtgcagacacaactaccagttggagctccg cacgaccttgcagcggcgagtggagcccacagtgaccatctccccatccaggacagaggccctcaaccaccacaac ctgctggtctgctcagtgacagatttctatccagcccagatcaaagtccggtggtttcggaatgaccaggaggaga caactggcgttgtgtccaccccccttattaggaacggtgactggaccttccagatcctggtgatgctggaaatgac tccccagcgtggagacgtctacacctgccacgtggagcaccccagcctccagaacccatcatcgtggagtgg

DQB1*030502 (SEQ ID NO: 2457)

gggcatgtgctacttcaccaacgggacggagcgcgtgcggggtgtgaccagatacatctataaccgagaggagtac gcgcgcttcgacagcgacgtgggggtgtaTcgggcggtgacgccgctggggccgcctgCcgccgagtactggaaca gccagaaggaagtcctggagAggacccgggcggagttggacaCggtgtgcagacacaactaccagttggagctccg cacgaccttgcagcggcgag

DQB1*0306 (SEQ ID NO: 2458)

gggcatgtgctacttcaccaacgggacggagcgcgtgcgtcttgtgaccagatacatctataaccgagaggagtac gcacgcttcgacagcgacgtgggggtgtatcgggcggtgacgccgctggggcCgcctgacgccgagtactggaata gccagaaggacatcctggaggaggaccgggcgtcggtggacaccgtAtgcagacacaactaccagttggagctccg cacgaccttgcagcggcgag

DQB1*0307 (SEQ ID NO: 2459)

gggcatgtgctacttcaccaacgggacggagcgcgtgcgtcttgtgaccagatacatctataaccgagaggagtac gcgcgcttcgacagcgacgtgggggtgtatcgggTggtgacgccgctggggccgcctgccgccgagtactggaaca gccagaaggaagtcctggagaggacccgggcggagttggacacggtgtgcagacacaactaccagttggagctccg cacgaccttgcagcggcga

DQB1*0308 (SEQ ID NO: 2460)

gggcatgtgctacttcaccaacgggacggagcgcgtgcgtcttgtgaccagatacatctataaccgagaggagtac gcAcgcttcgacagcgacgtgggggtgtaTcgggcggtgacgccgctggggccgcctgCcgccgagtactggaaca gccagaaggaagtcctggagggacccgggcggagttggacaCggtgtgcagacacaactaccagttggagctccg cacgaccttgcagcggcgag

DQB1*0309 (SEQ ID NO: 2461)

ggccatgtgctacttcaccaacgggacggagcgcgtgcgttatgtgaccagatacatctataaccgagaggagtac gcacgcttcgacagcgacgtggaggtgtaccggcggtgacgccgctggggccgcctgacgccgagtactggaaca gccagaaggaagtcctggagaggacccgggcggagttggacacggtgtgcagacacaactaccagttggagctccg cacgaccttgcagcggcgagtggagcccacagtgaccatctccccatccaggacagaggccctcaaccaccacaac ctgctggtctgctcagtgacagatttctatccagcccagatcaaagtccggtggtttcggaatgaccaggaggaga caaccggcgttgtgtccaccccccttattaggaacggtgactggaccttccagatcctggtgatgctggaaatgac tccccagcatgcC...gtctacacctgccacgtggagcaccccagcctccagaacccatcaccgtggagtgg DQB1*0310
(SEQ ID NO: 2462)
ggccatgtgctacttcaccaacgggacggagcgcgtgcgttatgtgaccagatacatctataaccgagaggagtac gcacgcttcgacagcgacgtgggggtgtaTcgggcggtgacgccgctggggccgcctgAcgccgagtactggaaca gccagaaggaagtcctggagaggacccgggcggagttggacacggtgtgcagacacaactaccagttggagctccg cacgaccttgcagcggcgagtggagcccacagtgaccatctccccatccaggacagaggccctcaaccaccacaac ctgctggtctgctcagtgacagatttctatccagcccagatcaaagtccggtggtttcggaatgaccaggaggaga caaccggcgttgtgtccaccccccttattaggaacggtgactggaccttccagatcctggtgatgctggaaatgac tccccagcAtggagaCgtctacacctgccacgtggagcaccccagcctccagaAccccatcaccgtggagtgg DQB1*0311
(SEQ ID NO: 2463)
gggcctgtgctacttcaccaacgggacggagcgcgtgcgtcttgtgaccagatacatctataaccgagaggagtac gcAcgcttcgacagcgacgtgggggtgtaTcgggcggtgacgccgctggggccgcctgCcgccgagtactggaaca gccagaaggaagtcctggagAggacccgggcggagttggacaCggtgtgcagacacaactaccagttggagctccg cacgaccttgcagcggcgag DQB1*0312
(SEQ ID NO: 2464)
ggccatgtgctacttcaccaacgggacggagcgcgtgcgtcTtgtgaccagatacatctataaccgagaggagtac gcAcgcttcgacagcgacgtgggggtgtaTcgggcggtgacgccgctggggccgcctgAcgccgagtactggaaca gccagaaggaagtcctggagAggacccgggcggagTtggacacggtgtgcagacacaactaccagttggagctccg cacgaccttgcagcggcgag DQB1*0313
(SEQ ID NO: 2465)
ggccatgtgctacttcaccaacgggacggagcgcgtgcgttatgtgaccagatacatctataaccgagaggagtac gcacgcttcgacagcgacgtggaggtgtaccgggcggtgacgccgctggggccgcctgacgccgagtactggaaca gccagaaggaagAcctggagaggacccgggcggagttggacacggtgtgcagacacaactaccagttggagctccg cacgaccttgcagcggcgag DQB1*0401
(SEQ ID NO: 2466)
gggcatgtgctacttcaccaacgggaccgagcTcgtgcggggtgtgaccagatacatctataaccgagaggagtac gcgcgcttcgacagcgacgtgggggtgtatcgggcggtgacgccgctggggcggcttgacgccgagtactggaata gccagaaggacatcctggaggaggaccgggcgtcggtggacaccgtatgcagacacaactaccagttggagctccg cacgaccttgcagcggcgagtggagcccacagtgaccatctccccatccaggacagaggccctcaaccaccacaac ctgctggtctgctcagtgacagatttctatccagcccagatcaaagtccggtggtttcggaatgaccaggaggaga caactggcgttgtgtccaccccccttattaggaacggtgactggaccttccagatcctggtgatgctggaaatgac tccccagcgtggagacgtctacacctgccacgtggagcaccccagcctccagaaccccatcatcgtggagtgg DQB1*0402
(SEQ ID NO: 2467)
gggcatgtgctacttcaccaacgggaccgagcgcgtgcggggtgtgaccagatacatctataaccgagaggagtac gcgcgcttcgacagcgacgtgggggtgtatcgggcggtgacgccgctggggcggcTtgacgccgagtactggaata gccagaaggacatcctggaggaggaccgggcgtcggtggacaccgtatgcagacacaactaccagttggagctccg cacgaccttgcagcggcgagtggagcccacagtgaccatctccccatccaggacagaggccctcaaccaccacaac ctgctggtctgctcagtgacagatttctatccagcccagatcaaagtccggtggtttcggaatgaccaggaggaga caactggcgttgtgtccaccccccttattaggaacggtgactggaccttccagatcctggtgatgctggaaatgac tccccagcgtggagacgtctacacctgccacgtggagcaccccagcctccagaaccccatcatcgtggagtgg

DQB1*060101

(SEQ ID NO: 2468)

ggccatgtgctacttcaccaaTgggacggagcgcgtgcgttatgtgaccagatacatctataaccgagaggaggac gtgcgcttcgacagcgacgtgggggtgtatcgggcggtgacgccgcaggggcggcctgacgccgagtactggaaca gccagaaggacatcctggagaggacccgagcggagttggacacggtgtgcagacacaactacgaggtggcgttccg cgggatcttgcagaggagagtggagcccacagtgaccatctccccatccaggacagaggccctcaaccaccacaac ctgctggtctgctcggtgacagatttctatccaggccagatcaaagtccggtggtttcggaatgaccaggaggaga cagctggcgttgtgtccacccccttattaggaacggtgactggaccttccagatcctggtgatgctggaaatgac tccccagcatggagacgtctacacctgccacgtggagcaccccagcctccagagcccatcaccgtggagtgg

DQB1*060102

(SEQ ID NO: 2469)

gccatgtgctacttcaccaacgggacggagcgcgtgcgttatgtgaccagatacatctataaccgagaggaggacg tgcgcttcgacagcgacgtgggggtgtatcgggcggtgacCccgcaggggcggcctgacgccgagtactggaacag ccagaaggacatcctggagaggacccgagcggagttggacacggtgtgcaga

DQB1*060103

(SEQ ID NO: 2470)

ggccatgtgctacttcaccaatgggacggagcgcgtgcgttatgtgaccagatacatctataaccgagaggaggac gtgcgcttcgacagcgacgtgggggtgtatcgggcggtgacgccgcaggggcggcctgacgccgagtactggaaca gccagaaggacatcctggagaggacccgagcggagttggacacggtgtgcagacacaactacgaggtggcgttccg cgggatcttgcagaggagagtggagcccacagtgaccatctccccatccaggacagaggccctcaaccaccacaac ctgctggtctgctcggtgacagatttctatccaggccagatcaaagtccggtggtttcggaatgaccaggaAgaga cagctggcgttgtgtccacccccttattaggaacggtgactggaccttccagatcctggtgatgctggaaatgac tccccagcatggagacgtctacacctgccacgtggagcaccccagcctccagagcccatcaccgtggagtgg

DQB1*0602

(SEQ ID NO: 2471)

gggcatgtgctacttcaccaacgggacggagcgcgtgcgtcttgtgaccagaTacatctataaccgagaggagtac gcgcgcttcgacagcgacgtgggggtgtaccgcgcggtgacgccgcaggggcggcctgatgccgagtactggaaca gccagaaggaagtcctggagggacccgggcggagttggacacggtgtgcagacacaactacgaggtggcgttccg cgggatcTtgcagaggagagtggagcccacagtgaccatctccccatccaggacagaggccctcaaccaccacaac ctgctggtctgctcggtgacagatttctatccaggccagatcaaagtccggtggtttcggaatgatcaggaggaga cagccggcgttgtgtccacccccttattaggaatggtgactggacTttccagatcctggtgatgctggaaatgac tccccagcgtggagatgtctacacctgccacgtggagcaccccagcctccagagcccatcaccgtggagtgg

DQB1*0603

(SEQ ID NO: 2472)

gggcatgtgctacttcaccaacgggacggagcgcgtgcgtcttgtAaccagacacatctataaccgagaggagtac gcgcgcttcgacagcgacgtgggggtgtaccgcgcggtgacgccgcaggggcggcctgatgccgagtactggaaca gccagaaggaagtcctggagggacccgggcggagttggacacggtgtgcagacacaactacgaggtggcgttccg cgggatcTtgcagaggagagtggagcccacagtgaccatctccccatccaggacagaggccctcaaccaccacaac ctgctggtctgctcggtgacagatttctatccaggccagatcaaagtccggtggtttcggaatgatcaggaggaga cagccggcgttgtgtccacccccttattaggaatggtgactggacTttccagatcctggtgatgctggaaatgac tccccagcgtggagatgtctacacctgccacgtggagcaccccagcctccagagcccatcaccgtggagtgg

DQB1*060401

(SEQ ID NO: 2473)

gggcatgtgctacttcaccaacgggacggagcgcgtgcgtcttgtaaccagacacatctataaccgagaggagtac gcgcgcttcgacagcgacgtgggggtgtaccgggcggtgacgccgcaggggcggcctgttgccgagtactggaaca gccagaaggaagtcctggagAggacccgggcggagttggacacggtgtgcagacacaactacgaggtggggtaccg

```
cgggatcctgcagaggagagtggagcccacagtgaccatctccccatccaggacagaggccctcaaccaccacaac ctgctggtctgctcggtgacagatttctatccaggccagatcaaagtccAgtggtttcggaatgatcaggaggaga cagccggcgttgtgtccaccccccttattaggaatggtgactggactttccagatcctggtgatgctggaaatgac tccccagcgtggagatgtctacacctgccacgtggagcaccccagcctccagagcccatcaccgtggagtgg
```

DQB1*060402
(SEQ ID NO: 2474)
```
gggcatgtgctacttcaccaacgggacggagcgcgtgcgtcttgtAaccagacacatctataaccgagaggagtac gcgcgcttcgacagcgacgtgggggtgtaccgCgcggtgacgccgcaggggcggcctgttgccgagtactggaaca gccagaaggaagtcctggagAggAcccgggcggagttggacacggtgtgcagacacaactacgaggtggGgtaccg cgggatcctgcagaggagagtggagcccacagtgaccatctccccatccaggacagaggcc
```

DQB1*060501
(SEQ ID NO: 2475)
```
gggcctgtgctacttcaccaacgggacggagcgcgtgcgtcttgtAaccagaTacatctataaccgagaggagtac gcgcgcttcgacagcgacgtgggggtgtaccgggcggtgacgccgcaggggcggcctgttgccgagtactggaaca gccagaaggaagtcctggagAggAcccgggcggagttggacacggtgtgcagacacaactacgaggtggGgtaccg cgggatcctgcagaggagagtggagcccacagtgaccatctccccatccaggacagaggcc
```

DQB1*060502
(SEQ ID NO: 2476)
```
ggacggagcgcgtgcgtcttgtAaccagatacatctataaccgagaggagtacgcgcgcttcgacagcgacgtggg ggtgtaccgggcggtgacgccgcaggggcggcctgtCgccgagtactggaacagccagaaggaagtcctggagAgg AcccgggcggagttggacaCg
```

DQB1*0606
(SEQ ID NO: 2477)
```
ggacggagcgcgtgcgtcttgtAaccagaTacatctataaccgagaggagtacgcgcgcttcgacagcgacgtggg ggtgtaccgggcggtgacgccgcaggggcggcctgttgccgagtactggaacagccagaaggaagtcctggagAgg AcccgggcggcggtggacagggtG
```

DQB1*0607
(SEQ ID NO: 2478)
```
gggcatgtgctacttcaccaacgggacggagcgcgtgcgtcttgtAaccagacacatctataaccgagaggagtac gcgcgcttcgacagcgacgtgggggtgtaccgcgcggtgacgccgcaggggcggcctgAtgccgagtactggaaca gccagaaggaagtcctggagAggAcccgggcggagttggacacggtgtgcagacacaactacgaggtggGgtaccg cgggatcc
```

DQB1*0608
(SEQ ID NO: 2479)
```
gggcatgtgctacttcaccaacgggacggagcgcgtgcgtcttgtAaccagacacatctataaccgagaggagtac gcgcgcttcgacagcgacgtgggggtgtaccgCgcggtgacgccgcaggggcggcctgttgccgagtactggaaca gccagaaggaagtcctggaggggacccgggcggagttggacacggtgtgcagacacaactacgaggtggcgttccg cgggatcT
```

DQB1*0609
(SEQ ID NO: 2480)
```
gggcatgtgctacttcaccaacgggacggagcgcgtgcgtcttgtaaccagaTacatctataaccgagaggagtac gcgcgcttcgacagcgacgtgggggtgtaccgggcggtgacgccgcaggggcggcctgttgccgagtactggaaca gccagaaggaagtcctggagAggacccgggcggagttggacacggtgtgcagacacaactacgaggtggggtaccg cgggatcctgcagaggagagtggagcccacagtgaccatctccccatccaggacagaggccctcaaccaccacaac ctgctggtctgctcggtgacagatttctatccaggccagatcaaagtccAgtggtttcggaatgatcaggaggaga cagccggcgttgtgtccaccccccttattaggaatggtgactggactttccagatcctggtgatgctggaaatgac tccccagcgtggagatgtctacacctgccacgtggagcaccccagcctccagagcccatcaccgtggagtgg
```

DQB1*0610
(SEQ ID NO: 2481)
gggcatgtgctacttcaccaacgggacggagcgcgtgcgtcttgtgaccagatacatctataaccgagaggagtac
gcgcgcttcgacagcgacgtgggggtgtaccgcgcggtgacgccgcaggggcggcctaGcgccgagtactggaaca
gccagaaggaagtcctggaggggacccgggcggagttggacacggtgtgcagacacaactacgaggtggcgttccg
cgggatcTtgcagaggagag DQB1*061101
(SEQ ID NO: 2482)
gggcatgtgctacttcaccaacgggacggagcgcgtgcgtcttgtgaccagaTacatctataaccgagaggagtac
gcgcgcttcgacagcgacgtgggggtgtaccgCgcggtgacgccgcaggggcggcctgAtgccgagtactggaaca
gccagaaggaagtcctggaggggacccgggcggagttggacacggtgtgcagacacaactacgaggtggcgttccg
cgggatcTtgcagagg DQB1*061102
(SEQ ID NO: 2483)
gggcatgtgctacttcaccaacgggacggagcgcgtgcgtcttgtAaccagaTacatctataaccgagaggagtac
gcgcgcttcgacagcgacgtgggggtgtaccgCgcggtgacgccgcaggggcggcctgAtgccgagtactggaaca
gccagaaggaagtcctggaggggacccgggcggagttggacacggtgtgcagacacaactacgaggtggcgttccg
cgggatcTtgcagaggagag DQB1*0612
(SEQ ID NO: 2484)
gggcatgtgctacttcaccaacgggacggagcgcgtgcgtcttgtaaccagaTacatctataaccgagaggagtac
gcgcgcttcgacagcgacgtgggggtgtaccgggcggtgacgccgcaggggcggcctgttgccgagtactggaaca
gccagaaggaagtcctggaggggacccgggcggagttggacacggtgtgcagacacaactacgaggtggggtaccg
cgggatcctgcagaggagagtggagcccacagtgaccatctccccatccaggacagaggccctcaaccaccacaac
ctgctggtctgctcggtgacagatttctatccaggccagatcaaagtccAgtggtttcggaatgatcaggaggaga
cagccggcgttgtgtccaccccccttattaggaatggtgactggactttccagatcctggtgatgctggaaatgac
tccccagcgtggagatgtctacacctgccacgtggagcaccccagcctccagagccccatcaccgtggagtgg DQB1*0613
(SEQ ID NO: 2485)
gggcatgtgctacttcaccaacgggacggagcgcgtgcgtcttgtgaccagaTacatctataaccgagaggagtac
gcgcgcttcgacagcgacgtgggggtgtaccgCgcggtgacgccgcaggggcggcctgttgccgagtactggaaca
gccagaaggaagtcctggaggggacccgggcggagttggacacggtgtgcagacacaactacgaggtggcgtTccg
cgggat DQB1*0614
(SEQ ID NO: 2486)
gggcatgtgctacttcaccaacgggacggagcgcgtgcgtcttgtAaccagacacatctataaccgagaggagtac
gcgcgcttcgacagcgacgtgggggtgtaccgCgcggtgacgccgcaggggcggcctgAtgccgagtactggaaca
gccagaaggaagtcctggaggggacccgggcggagttggacacggtgtgcagacacaactacgaggtggcgttccg
cgggatcTtgcagaggagag DQB1*0615
(SEQ ID NO: 2487)
gggcatgtgctacttcaccaacgggacggagcgcgtgcgtcttgtgaccagaTacatctataaccgagaggagtac
gcgcgcttcgacagcgacgtgggggtgtaccgcgcggtgacgccgcaggggcggcctgAtgccgagtactggaaca
gccagaaggaagtcctggagAggAcccgggcggagttggacacggtgtgcagacacaactacgaggtggGgtaccg
cgggatcctgcagaggagag DQB1*0616
(SEQ ID NO: 2488)
gggcatgtgctacttcaccaacgggacggagcgcgtgcgtcttgtgaccagatacatctataaccgagaggagtac
gcgcgcttcgacagcgacgtgggggtgtaccgcgcggtgacgccgcaggggcggcctgatgccgagAactggaaca

```
-continued
gccagaaggaagtcctggaggggacccgggcggagttggacacggtgtgcagacacaactacgaggtggcgttccg cgggatcttgcagaggagag DQB1*0617
                                                          (SEQ ID NO: 2489)
gggcatgtgctacttcaccaacgggacggagcgcgtgcgtcttgtAaccagacacatctataaccgagaggagtac gcgcgcttcgacagcgacgtgggggtgtaccgggcggtgacgccgcaggggcggcctgttgccgagtactggaaca gccagaaggaagtcctggaggggcccgggcggagttggacacggtgtgcagacacaactacgaggtggGgtaccgc DQB1*0618
                                                          (SEQ ID NO: 2490)
gggcatgtgctacttcaccaacgggacggagcgcgtgcgtcttgtAaccagatacatctataaccgagaggagtac gcgcgcttcgacagcgacgtgggggtgtaccgggcggtgacgccgcaggggcggcctgttgccgagtactggaaca gccagaaggaagtcctggagAggacccgggcggagttggacacggtgtgcagacacaactacgaggtggcgttccg cgggatcTtgcagaggag DQB1*0619
                                                          (SEQ ID NO: 2491)
gggcatgtgctacttcaccaacgggacggagcgcgtgcgtcTtgtgaccagatacatctataaccgagaggagtac gcgcgcttcgacagcgacgtgggggtgtaTcgggcggtgacgccgcTggggcggcctgAtgccgagtactggaaca gccagaaggaagtcctggaggggacccgggcggagTtggacacggtgtgcagacacaactacgaggtggcgttccg cgggatcTtgcagaggagag DQB1*0620
                                                          (SEQ ID NO: 2492)
gggcctgtgctacttcaccaacgggacggagcgcgtgcgtcttgtgaccagaTacatctataaccgagaggagtac gcgcgcttcgacagcgacgtgggggtgtaccgCgcggtgacgccgcaggggcggcctgAtgccgagtactggaaca gccagaaggaagtcctggaggggacccgggcggagttggacacggtgtgcagacacaactacgaggtggcgtTccgc
```

In the following, Probe Lists DQ1 and DQ2 are shown in Tables 17A, 17B-1 and 17B-2 and tables 18A, 18B-1 and 18B-2 respectively. Tables 19A, 19B-1 and 19B-2 and Tables 20A, 20B-1 and 20B-2 show Allele-Prove Lists.

TABLE 17A

| Probe No. | Base Sequence | |
|---|---|---|
| 0 | t gaa ttt gat gga gat gag G | (SEQ ID No: 2249) |
| 1 | ggt gct tcc aga cac caG | (SEQ ID No: 2250) |
| 2 | gg ttg tct gtg ggc ctc A | (SEQ ID No: 2251) |
| 3 | cag ccc aac acc ctc atC | (SEQ ID No: 2252) |
| 4 | g ctg agc aat ggg cac G | (SEQ ID No: 2253) |
| 5 | ca gag act gtg gtc tgc A | (SEQ ID No: 2254) |
| 6 | c cct tgt gga ggt gaa gG | (SEQ ID No: 2255) |
| 7 | cct gtg gtc aac atc acC | (SEQ ID No: 2256) |
| 8 | ccc tgt gga ggt gaa gG | (SEQ ID No: 2257) |
| 9 | c ctg gag agg aag gag G | (SEQ ID No: 2258) |
| 10 | tg cct ctg ttc cac aga C | (SEQ ID No: 2259) |
| 11 | x ag cct gag att cca A | (SEQ ID No: 2260) |
| 12 | gcc ctg acc acc gtg aC | (SEQ ID No: 2261) |
| 13 | c acc ttc ctc cct tct gA | (SEQ ID No: 2262) |

TABLE 17A-continued

| Probe No. | Base Sequence | |
|---|---|---|
| 14 | tt aaa cgc tcc aac tct acT | (SEQ ID No: 2263) |
| 15 | cc aga cac caa ggg ccC | (SEQ ID No: 2264) |
| 16 | ca gtg ttt tcc aag tct ccT | (SEQ ID No: 2265) |
| 17 | g cac tgg ggc ctg gac A | (SEQ ID No: 2266) |
| 18 | g gtc tgc gcc ctg ggA | (SEQ ID No: 2267) |
| 19 | ct gac cac gtt gcc tct tA | (SEQ ID No: 2268) |
| 20 | c cta aaa cat aac ttg aac agT | (SEQ ID No: 2269) |
| 21 | c aga caa ttt aga ttt gac cG | (SEQ ID No: 2270) |
| 22 | tc acc ctc ctc cct tct T | (SEQ ID No: 2271) |
| 23 | tg tac cag tct tac ggt cT | (SEQ ID No: 2272) |
| 24 | ag gtg gag cac tgg ggA | (SEQ ID No: 2273) |
| 25 | ggt ccc tct ggc cag tT | (SEQ ID No: 2274) |
| 26 | cc aag tct ccc gtg acG | (SEQ ID No: 2275) |
| 27 | gca ctg aca aac atc gcC | (SEQ ID No: 2276) |

TABLE 17B-1

| Probe No. | Base Sequence | |
|---|---|---|
| 0 | g ggg gtg tac cgg gcA | (SEQ ID No: 2277) |
| 1 | cg cag ggg cgg cct gT | (SEQ ID No: 2278) |
| 2 | ag ggg gcc cgg gcg T | (SEQ ID No: 2279) |
| 3 | gg gcg tcg gtg gac aG | (SEQ ID No: 2280) |
| 4 | gg gcg tcg gtg gac agA | (SEQ ID No: 2281) |
| 5 | ca gat ttc tat cca agc caC | (SEQ ID No: 2282) |
| 6 | gc gac gtg ggg gtg taT | (SEQ ID No: 2283) |
| 7 | cg cag ggg cgg cct aG | (SEQ ID No: 2284) |
| 8 | g cag ggg cgg cct agC | (SEQ ID No: 2285) |
| 9 | cg cag ggg cgg cct gA | (SEQ ID No: 2286) |
| 10 | g cag ggg cgg cct gaC | (SEQ ID No: 2287) |
| 11 | g aag gac atc ctg gag gA | (SEQ ID No: 2288) |
| 12 | g gac atc ctg gag agg aaA | (SEQ ID No: 2289) |
| 13 | ct ccc cag cgt gga gaC | (SEQ ID No: 2290) |
| 14 | c cgg tgg ttt cgg aat gG | (SEQ ID No: 2291) |
| 15 | ctg ctg ggg ctg cct gA | (SEQ ID No: 2292) |
| 16 | c ttc gac agc gac gtg gA | (SEQ ID No: 2293) |
| 17 | cg ctg ggg ccg cct gA | (SEQ ID No: 2294) |
| 18 | ct ccc cag cat gga gaC | (SEQ ID No: 2295) |
| 19 | cac ccc agc ctc cag aA | (SEQ ID No: 2296) |
| 20 | aac cga gag gag tac gcA | (SEQ ID No: 2297) |
| 21 | g ctg ggg ccg cct gC | (SEQ ID No: 2298) |
| 22 | agg acc cgg gcg gag T | (SEQ ID No: 2299) |
| 23 | c ctc cag aac ccc atc aT | (SEQ ID No: 2300) |
| 24 | cg gag cgc gtg cgt cT | (SEQ ID No: 2301) |
| 25 | g acg ccg ctg ggg cC | (SEQ ID No: 2302) |
| 26 | cag aag gaa gtc ctg gag A | (SEQ ID No: 2303) |
| 27 | tac ttc acc aac ggg acC | (SEQ ID No: 2304) |

TABLE 17B-2

| Probe No. | Base Sequence | |
|---|---|---|
| 28 | cgg gcg gag ttg gac aC | (SEQ ID No: 2305) |
| 29 | cg tcg gtg gac acc gtA | (SEQ ID No: 2306) |
| 30 | gtg ggg gtg tat cgg gT | (SEQ ID No: 2307) |
| 31 | tg act ccc cag cat gcC | (SEQ ID No: 2308) |
| 32 | g gaa atg act ccc cag cA | (SEQ ID No: 2309) |
| 33 | gg aac agc cag aag gaa gA | (SEQ ID No: 2310) |
| 34 | acc aac ggg acc gag cT | (SEQ ID No: 2311) |

TABLE 17B-2-continued

| Probe No. | Base Sequence | |
|---|---|---|
| 35 | g ccg ctg ggg cgg cT | (SEQ ID No: 2312) |
| 36 | cc atg tgc tac ttc acc aaT | (SEQ ID No: 2313) |
| 37 | tg tat cgg gcg gtg acC | (SEQ ID No: 2314) |
| 38 | g ttt cgg aat gac cag gaA | (SEQ ID No: 2315) |
| 39 | gtg cgt ctt gtg acc aga T | (SEQ ID No: 2316) |
| 40 | g gcg ttc cgc ggg atc T | (SEQ ID No: 2317) |
| 41 | t agg aat ggt gac tgg acT | (SEQ ID No: 2318) |
| 42 | gag cgc gtg cgt ctt gtA | (SEQ ID No: 2319) |
| 43 | ca ggc cag atc aaa gtc cA | (SEQ ID No: 2320) |
| 44 | c gtg ggg gtg tac cgC | (SEQ ID No: 2321) |
| 45 | ag gaa gtc ctg gag agg A | (SEQ ID No: 2322) |
| 46 | a cac aac tac gag gtg gG | (SEQ ID No: 2323) |
| 47 | gtg cgt ctt gta acc aga T | (SEQ ID No: 2324) |
| 48 | g cag ggg cgg cct gtC | (SEQ ID No: 2325) |
| 49 | c aac tac gag gtg gcg tT | (SEQ ID No: 2326) |
| 50 | g cgg cct gat gcc gag A | (SEQ ID No: 2327) |
| 51 | gg gcg gtg acg ccg cT | (SEQ ID No: 2328) |
| 52 | cg ctg ggg cgg cct gA | (SEQ ID No: 2329) |
| 53 | ggg acc cgg gcg gag T | (SEQ ID No: 2330) |

TABLE 18A

| Probe No. | Base Sequence | |
|---|---|---|
| 0 | gga gat gag Gag ttc tac g | (SEQ ID No: 2331) |
| 1 | c aga cac caG ggg cca tt | (SEQ ID No: 2332) |
| 2 | gtg ggc ctc Atg ggc att | (SEQ ID No: 2333) |
| 3 | c acc ctc atC tgt ctt gtg | (SEQ ID No: 2334) |
| 4 | aat ggg cac Gca gtc aca | (SEQ ID No: 2335) |
| 5 | g gtc tgc Acc ctg ggg | (SEQ ID No: 2336) |
| 6 | ga ggt gaa gGc att gtg g | (SEQ ID No: 2337) |
| 7 | c aac atc acC tgg ctg ag | (SEQ ID No: 2338) |
| 8 | gg aag gag Gct gcc tgg | (SEQ ID No: 2339) |
| 9 | ctg ttc cac aga Ctt aga c c ttt | (SEQ ID No: 2340) |
| 10 | gag att cca Aca cct atg tc | (SEQ ID No: 2341) |
| 11 | c acc gtg aCg agc cct t | (SEQ ID No: 2342) |
| 12 | ctc cct tct gAt gat gag at | (SEQ ID No: 2343) |
| 13 | c aac tct acT gct gct acc | (SEQ ID No: 2344) |
| 14 | c atc atc cGa ggc ctg c | (SEQ ID No: 2345) |

TABLE 18A-continued

| Probe No. | Base Sequence | |
|---|---|---|
| 15 | c aag tct ccT gtg acg ct | (SEQ ID No: 2346) |
| 16 | ggc ctg gac Aag cct ctt | (SEQ ID No: 2347) |
| 17 | c gcc ctg ggA ttg tct gt | (SEQ ID No: 2348) |
| 18 | gtt gcc tct tAt ggt gta aa | (SEQ ID No: 2349) |
| 19 | aac ttg aac agT ctg att aaa c | (SEQ ID No: 2350) |
| 20 | a cg ttt gac cGg caa ttt gca c | (SEQ ID No: 2351) |
| 21 | ctc cct tct Tct gag gag | (SEQ ID No: 2352) |
| 22 | ct tac ggt cTc tct ggc c | (SEQ ID No: 2353) |
| 23 | g cac tgg ggA ctg gac aa | (SEQ ID No: 2354) |
| 24 | ct ggc cag tTc acc cat g | (SEQ ID No: 2355) |
| 25 | ccc gtg acG ctg ggt c | (SEQ ID No: 2356) |
| 26 | ca aac atc gcC gtg aca aaa | (SEQ ID No: 2357) |

TABLE 18B-1

| Probe No. | Base Sequence | |
|---|---|---|
| 0 | tac cgg gcA gtg acg cc | (SEQ ID No: 2358) |
| 1 | g cgg cct gTt gcc gag | (SEQ ID No: 2359) |
| 2 | c cgg gcg Tcg gtg gac | (SEQ ID No: 2360) |
| 3 | g gtg gac aGg gtg tgc a | (SEQ ID No: 2361) |
| 4 | g gtg gac agA gtg tgc ag | (SEQ ID No: 2362) |
| 5 | t cca agc caC atc aaa gtc | (SEQ ID No: 2363) |
| 6 | ggg gtg taT cgg gcg g | (SEQ ID No: 2364) |
| 7 | g cgg cct aGc gcc gag | (SEQ ID No: 2365) |
| 8 | cgg cct agC gcc gag t | (SEQ ID No: 2366) |
| 9 | g cgg cct gAc gcc gag | (SEQ ID No: 2367) |
| 10 | cgg cct gaC gcc gag t | (SEQ ID No: 2368) |
| 11 | g cgg cct gAt gcc gag | (SEQ ID No: 2369) |
| 12 | c ctg gag gAg gac cgg | (SEQ ID No: 2370) |
| 13 | gag agg aaA cgg gcg gc | (SEQ ID No: 2371) |
| 14 | g cgt gga gaC gtc tac ac | (SEQ ID No: 2372) |
| 15 | t cgg aat gGc cag gag g | (SEQ ID No: 2373) |
| 16 | g ctg cct gAc gcc gag | (SEQ ID No: 2374) |
| 17 | c gac gtg gAg gtg tac c | (SEQ ID No: 2375) |
| 18 | g ccg cct gAc gcc gag | (SEQ ID No: 2376) |
| 19 | g cat gga gaC gtc tac ac | (SEQ ID No: 2377) |
| 20 | gc ctc cag aAc ccc atc a | (SEQ ID No: 2378) |

TABLE 18B-1-continued

| Probe No. | Base Sequence | |
|---|---|---|
| 21 | g gag tac gcA cgc ttc ga | (SEQ ID No: 2379) |
| 22 | ccg cct gCc gcc gag | (SEQ ID No: 2380) |
| 23 | gg gcg gag Ttg gac acg | (SEQ ID No: 2381) |
| 24 | ac ccc atc aTc gtg gag t | (SEQ ID No: 2382) |
| 25 | gc gtg cgt cTt gtg acc a | (SEQ ID No: 2383) |
| 26 | g ctg ggc cCg cct gac | (SEQ ID No: 2384) |
| 27 | c ctg gag Agg acc cgg | (SEQ ID No: 2385) |

TABLE 18B-2

| Probe No. | Base Sequence | |
|---|---|---|
| 28 | aac ggg acC gag cgc g | (SEQ ID No: 2386) |
| 29 | ag ttg gac aCg gtg tgc a | (SEQ ID No: 2387) |
| 30 | g gac acc gtA tgc aga ca | (SEQ ID No: 2388) |
| 31 | g tat cgg gTg gtg acg c | (SEQ ID No: 2389) |
| 32 | cc cag cat gcC g t gtc tac | (SEQ ID No: 2390) |
| 33 | t ccc cag cAt gga gac g | (SEQ ID No: 2391) |
| 34 | ag aag gaa gAc ctg gag ag | (SEQ ID No: 2392) |
| 35 | g acc gag cTc gtg cgg | (SEQ ID No: 2393) |
| 36 | g ggg cgg cTt gac gcc | (SEQ ID No: 2394) |
| 37 | c ttc acc aaT ggg acg ga | (SEQ ID No: 2395) |
| 38 | gcg gtg acC ccg cag g | (SEQ ID No: 2396) |
| 39 | t gac cag gaA gag aca gc | (SEQ ID No: 2397) |
| 40 | t gtg acc aga Tac atc tat aa | (SEQ ID No: 2398) |
| 41 | gc ggg atc Ttg cag agg | (SEQ ID No: 2399) |
| 42 | t gac tgg acT ttc cag atc | (SEQ ID No: 2400) |
| 43 | g cgt ctt gtA acc aga cac | (SEQ ID No: 2401) |
| 44 | tc aaa gtc cAg tgg ttt cg | (SEQ ID No: 2402) |
| 45 | gtg tac cgC gcg gtg ac | (SEQ ID No: 2403) |
| 46 | g gag agg Acc cgg gcg | (SEQ ID No: 2404) |
| 47 | c gag gtg gGg tac cgc | (SEQ ID No: 2405) |
| 48 | g cgt ctt gtA acc aga tac | (SEQ ID No: 2406) |
| 49 | t gta acc aga Tac atc tat aac | (SEQ ID No: 2407) |
| 50 | cgg cct gtC gcc gag t | (SEQ ID No: 2408) |
| 51 | c cgg gcg gAg ttg gac | (SEQ ID No: 2409) |
| 52 | g gtg gcg tTc cgc ggg | (SEQ ID No: 2410) |
| 53 | gat gcc gag Aac tgg aac | (SEQ ID No: 2411) |
| 54 | acg ccg cTg ggg cgg | (SEQ ID No: 2412) |

TABLE 19A

| Allele Number | Probe Number for Detection | | |
|---|---|---|---|
| DQA1*010101 | 0 | | |
| DQA1*010102 | 1 | | |
| DQA1*010201 | 2 | | |
| DQA1*010202 | 3 | 2 | |
| DQA1*0103 | 4 | | |
| DOA1*010401 | 5 | | |
| DQA1*010402 | 6 | 7 | |
| DQA1*0105 | 8 | | |
| DQA1*0106 | 9 | | |
| DQA1*0201 | 10 | | |
| DQA1*030101 | 11 | | |
| DQA1*0302 | 12 | | |
| DQA1*0303 | 13 | | |
| DQA1*040101 | 14 | 15 | |
| DQA1*040102 | 16 | | |
| DQA1*050101 | 17 | 18 | |
| DQA1*050102 | 19 | 20 | |
| DQA1*0502 | 21 | | |
| DQA1*0503 | 22 | | |
| DQA1*0504 | 23 | | |
| DQA1*0505 | 24 | | |
| DQA1*060101 | 25 | 26 | 15 |
| DQA1*060102 | 27 | | |

TABLE 19B-1

| Allele Number | Probe Number for Detection | | | | | |
|---|---|---|---|---|---|---|
| DQB1*050101 | 0 | 1 | 2 | 3 | | |
| DQB1*050102 | 4 | | | | | |
| DQB1*050201 | 5 | | | | | |
| DQB1*050202 | 6 | 7 | 8 | 4 | | |
| DQB1*050301 | 9 | 10 | 4 | | | |
| DQB1*050302 | 6 | 11 | | | | |
| DQB1*0504 | 7 | 12 | | | | |
| DQB1*0201 | 13 | 14 | | | | |
| DQB1*0202 | 15 | 14 | | | | |
| DQB1*0203 | 16 | 15 | | | | |
| DQB1*030101 | 17 | 18 | 19 | 20 | | |
| DQB1*030102 | 17 | 18 | | | | |
| DQB1*0302 | 21 | 22 | 23 | 24 | | |
| DQB1*030302 | 18 | 23 | 24 | | | |
| DQB1*030303 | 25 | 6 | 26 | 18 | 27 | 23 |
| DQB1*0304 | 17 | 22 | 19 | 20 | | |
| DQB1*030501 | 28 | 23 | | | | |
| DQB1*030502 | 6 | 22 | 27 | 29 | | |
| DQB1*0306 | 26 | 30 | | | | |
| DQB1*0307 | 31 | | | | | |
| DQB1*0308 | 21 | 6 | 22 | 29 | | |
| DQB1*0309 | 32 | | | | | |
| DQB1*0310 | 6 | 18 | 33 | 19 | 20 | |
| DQB1*0311 | 21 | 6 | 22 | 27 | 29 | |
| DQB1*0312 | 25 | 21 | 6 | 18 | 27 | 23 |
| DQB1*0313 | 34 | | | | | |
| DQB1*0401 | 35 | | | | | |
| DQB1*0402 | 36 | | | | | |
| DQB1*060101 | 37 | | | | | |
| DQB1*060102 | 38 | | | | | |
| DQB1*060103 | 39 | | | | | |
| DQB1*0602 | 40 | 41 | 42 | | | |
| DQB1*0603 | 43 | 41 | 42 | | | |

TABLE 19B-2

| Allele Number | Probe Number for Detection | | | | |
|---|---|---|---|---|---|
| DQB1*060401 | 27 | 44 | | | |
| DQB1*060402 | 43 | 45 | 27 | 46 | 47 |
| DQB1*060501 | 48 | 49 | 27 | 46 | 47 |
| DQB1*060502 | 48 | 50 | 27 | 46 | 51 |
| DQB1*0606 | 48 | 49 | 27 | 46 | |
| DQB1*0607 | 43 | 11 | 27 | 46 | 47 |

TABLE 19B-2-continued

| Allele Number | Probe Number for Detection | | | | |
|---|---|---|---|---|---|
| DQB1*0608 | 43 | 45 | 52 | | |
| DQB1*0609 | 49 | 27 | 44 | | |
| DQB1*0610 | 7 | 41 | | | |
| DQB1*061101 | 40 | 45 | 11 | 52 | |
| DQB1*061102 | 48 | 49 | 45 | 11 | 41 |
| DQB1*0612 | 49 | 44 | | | |
| DQB1*0613 | 40 | 45 | 52 | | |
| DQB1*0614 | 43 | 45 | 11 | 41 | |
| DQB1*0615 | 40 | 11 | 27 | 46 | 47 |
| DQB1*0616 | 53 | | | | |
| DQB1*0617 | 43 | 29 | | | |
| DQB1*0618 | 48 | 27 | 41 | | |
| DQB1*0619 | 25 | 6 | 54 | 11 | 23 | 41 |
| DQB1*0620 | 40 | 45 | 11 | | |

TABLE 20A

| Allele Number | Probe Number for Detection | | |
|---|---|---|---|
| DQA1*010101 | 0 | | |
| DQA1*010102 | 1 | | |
| DQA1*010201 | 2 | | |
| DQA1*010202 | 3 | 2 | |
| DQA1*0103 | 4 | | |
| DQA1*010401 | 5 | | |
| DQA1*010402 | 6 | 7 | |
| DQA1*0105 | 6 | | |
| DQA1*0106 | 8 | | |
| DQA1*0201 | 9 | | |
| DQA1*030101 | 10 | | |
| DQA1*0302 | 11 | | |
| DQA1*0303 | 12 | | |
| DQA1*040101 | 13 | 14 | |
| DQA1*040102 | 15 | | |
| DQA1*050101 | 16 | 17 | |
| DQA1*050102 | 18 | 19 | |
| DQA1*0502 | 20 | | |
| DQA1*0503 | 21 | | |
| DQA1*0504 | 22 | | |
| DQA1*0505 | 23 | | |
| DQA1*060101 | 24 | 25 | 14 |
| DQA1*060102 | 26 | | |

TABLE 20B-1

| Allele Number | Probe Number for Detection | | | | | |
|---|---|---|---|---|---|---|
| DQB1*050101 | 0 | 1 | 2 | 3 | | |
| DQB1*050102 | 4 | | | | | |
| DQB1*050201 | 5 | | | | | |
| DQB1*050202 | 6 | 7 | 8 | 4 | | |
| DQB1*050301 | 9 | 10 | 4 | | | |
| DQB1*050302 | 6 | 11 | | | | |
| DQB1*0504 | 7 | 12 | | | | |
| DQB1*0201 | 13 | 14 | | | | |
| DQB1*0202 | 15 | 14 | | | | |
| DQB1*0203 | 16 | 15 | | | | |
| DQB1*030101 | 17 | 18 | 19 | 20 | | |
| DQB1*030102 | 17 | 18 | | | | |
| DQB1*0302 | 21 | 22 | 23 | 24 | | |
| DQB1*030302 | 18 | 23 | 24 | | | |
| DQB1*030303 | 25 | 6 | 26 | 18 | 27 | 23 |
| DQB1*0304 | 17 | 22 | 19 | 20 | | |
| DQB1*030501 | 28 | 23 | | | | |
| DQB1*030502 | 6 | 22 | 27 | 29 | | |
| DQB1*0306 | 26 | 30 | | | | |
| DQB1*0307 | 31 | | | | | |
| DQB1*0308 | 21 | 6 | 22 | 29 | | |
| DQB1*0309 | 32 | | | | | |
| DQB1*0310 | 6 | 18 | 33 | 19 | 20 | |
| DQB1*0311 | 21 | 6 | 22 | 27 | 29 | |
| DQB1*0312 | 25 | 21 | 6 | 18 | 27 | 23 |

TABLE 20B-1-continued

| Allele Number | Probe Number for Detection | | |
|---|---|---|---|
| DQB1*0313 | 34 | | |
| DQB1*0401 | 35 | | |
| DQB1*0402 | 36 | | |
| DQB1*060101 | 37 | | |
| DQB1*060102 | 38 | | |
| DQB1*060103 | 39 | | |
| DQB1*0602 | 40 | 41 | 42 |
| DQB1*0603 | 43 | 41 | 42 |

TABLE 20B-2

| Allele Number | Probe Number for Detection | | | | |
|---|---|---|---|---|---|
| DQB1*060401 | 27 | 44 | | | |
| DQB1*060402 | 43 | 45 | 27 | 46 | 47 |
| DQB1*060501 | 48 | 49 | 27 | 46 | 47 |
| DQB1*060502 | 48 | 50 | 27 | 46 | 51 |
| DQB1*0606 | 48 | 49 | 27 | 46 | |
| DQB1*0607 | 43 | 11 | 27 | 46 | 47 |
| DQB1*0608 | 43 | 45 | 52 | | |
| DQB1*0609 | 49 | 27 | 44 | | |
| DQB1*0610 | 7 | 41 | | | |
| DQB1*061101 | 40 | 45 | 11 | 52 | |
| DQB1*061102 | 48 | 49 | 45 | 11 | 41 |
| DQB1*0612 | 49 | 44 | | | |
| DQB1*0613 | 40 | 45 | 52 | | |
| DQB1*0614 | 43 | 45 | 11 | 41 | |
| DQB1*0615 | 40 | 11 | 27 | 46 | 47 |
| DQB1*0616 | 53 | | | | |
| DQB1*0617 | 43 | 29 | | | |
| DQB1*0618 | 48 | 27 | 41 | | |
| DQB1*0619 | 25 | 6 | 54 | 11 | 23 | 41 |
| DQB1*0620 | 40 | 45 | 11 | | |

Example 11

Probes for Identification of HLA-DR Allele

Extraction of DNA from 1 ml of human blood was performed using GFX Genomic Blood DNA Purification Kit from Amersham Biosciences in the same manner as in Example 1.

Next, quantitative PCR was carried out in the same manner as in Example 1 except that probes in the probe list 1 in Tables 21-1 and 21-2 were used and 4 µl of the mixed primers consisting of 1 µl each of respective solutions of the following primers (10 pmol/µl) and 4 µl of ultra pure water were used:

```
AGAGTACTCCAAGAAACGTG    (SEQ ID NO: 3314)

CCGCTGCACCGTGAAGCT      (SEQ ID NO: 3315)

TCGCTGCACTGTGAAGCT      (SEQ ID NO: 3316)

CCTCTGCACTGTGAAGCT.     (SEQ ID NO: 3317)
```

Referring to Amp Plot and Dissociation curves on a display of 5700 software, it was found that probes 62, 12, and 152 were amplified. Therefore, it was identified as DRB1*040502 and DRB1*130202 referring to the allele-probe list 1 (Tables 23-1 to 23-13).

Example 12

Extraction of DNA from 1 ml of human blood was performed in the same way as in Example 3. PCR of human HLA-DRB exon 2 was then performed in the same manner as in Example 2 except that 6 µl of the mixed primer consisting of 1 µl each of the solutions containing the following sequences at 10 pmol/µl respectively, and 9 µl of ultra pure water were used:

```
CCGGATCCTTCGTGTCCCCACAGCACG  (SEQ ID NO: 3318)

AACCCCGTAGTTGTGTCTGCA        (SEQ ID NO: 3319)

AGAGTACTCCAAGAAACGTG         (SEQ ID NO: 3314)

CCGCTGCACCGTGAAGCT           (SEQ ID NO: 3315)

TCGCTGCACTGTGAAGCT           (SEQ ID NO: 3316)

CCTCTGCACTGTGAAGCT.          (SEQ ID NO: 3317)
```

At the same time, a DNA microarray was prepared to identify the allele in the specimen described above in the same manner as in Example 2, except that probes in the probe list of Tables 22-1 to 22-7 were used to form the probe spots respectively.

Then, hybridization was performed using the above specimen and the prepared DNA microarray in the same manner as in Example 2. The fluorometry measurement was conducted with GenePix4000B (Axon).

As a result it was found that probes 59, 133, and 134 were amplified. Therefore, it was identified as DRB1*040502 and DRB1*130202 referring to the allele-probe list 1 (Tables 24-1 to 24-13).

```
Allele list
DRB1*010101:
                                                         (SEQ ID NO: 2493)
atggtgtgtctgaagctccctggaggctcctgcatgacagcgctgacagtgacactgatggtgctgagctcccac tggctttggctggggacacccgaccacgtttcttgtggcagcttaagtttgaatgtcatttcttcaatgggacgga gcgggtgcggttgctggaAagaTgcatctataaccaagaggagtCcgtgcgcttcgacagcgacgtgggggagtac cgggcggtgacggagctggggcggcctgaTgcCgagtactggaacagccagaaggacctcctggagcagaggcggg ccgcggtggacacctactgcagacacaactacggggttgGtgagagcttcacagtgcagcggcgag;

DRB1*010102:
                                                         (SEQ ID NO: 2494)
cacgtttcttgtggcagcttaagtttgaatgtcatttcttcaatgggacggagcgggtgcggttgctggaaagatg catctataaccaagaggaAtccgtgcgcttcgacagcgacgtgggggagtaccgggcggtgacggagctggggcgg
``` cctgatgccgagtactggaacagccagaaggacctcctggagcagaggcgggccgcggtggacacctactgcagac acaactacggggttggtgagagcttcacagtgcagcggcgag;

DRB1*010201:

(SEQ ID NO: 2495)

ggggacacccgaccacgtttcttgtggcagcttaagtttgaatgtcatttcttcaatgggacggagcgggtgcggt tgctggaaagatgcatctataaccaagaggagtccgtgcgcttcgacagcgacgtgggggagtaccgggcggtgac ggagctggggcggcctgatgccgagtactggaacagccagaaggacctcctggagcagaggcgggccgcggtggac acctaTtgcagacacaactacggggCtgtggagagcttcacagtgcagcggcgag;

DRB1*010202:

(SEQ ID NO: 2496)

cacgtttcttgtggcagcttaagtttgaatgtcatttcttcaatgggacggagcgggtgcggttgctggaaagatg catctataaccaagaggagtccgtgcgcttcgacagcgacgtgggggagtaccgggcggtgacggagctggggcgg cctgatgccgagtactggaacagccagaaggacctcctggagcagaggcgggccgcCgtggacacctattgcagac acaactacggggctgtgg;

DRB1*0103:

(SEQ ID NO: 2497)

atggtgtgtctgaagctccctggaggctcctgcatgacagcgctgacagtgacactgatggtgctgagctccccac tggctttggctggggacacccgaccacgtttcttgtggcagcttaagtttgaatgtcatttcttcaatgggacgga gcgggtgcggttgctggaaagatgcatctataaccaagaggagtccgtgcgcttcgacagcgacgtgggggagtac cgggcggtgacggagctggggcggcctgatgccgagtactggaacagccagaaggacAtcctggaagacGAgcggg ccgcggtggacacctactgcagacacaactacggggttggtgagagcttcacagtgcagcggcgag;

DRB1*0104:

(SEQ ID NO: 2498)

ggggacacccgaccacgtttcttgtggcagcttaagtttgaatgtcatttcttcaatgggacggagcgggtgcggt tgctggaaagatgcatctataaccaagaggagtccgtgcgcttcgacagcgacgtgggggagtaccgggcggtgac ggagctggggcggcctgatgccgagtactggaacagccagaaggacctcctggagcagaggcgggccgcggtggac aaTtactgcagacacaactacggggttgtGgagagcttcacagtgcagcggcgag;

DRB1*0105:

(SEQ ID NO: 2499)

cacgtttcttgtggcagcttaagtttgaatgtcatttcttcaatgggacggagcgggtgcggttgctggaaagatg catctataaccaagaggagtccgtgcgcttcgacagcgacgtgAgggagtaccgggcggtgacggagctggggcgg cctgatgccgagtactggaacagccagaaggacctcctggagcagaggcgggccgcggtggacacctactgcagac acaactacggggttggtgagagcttcacagtgcagcggcgag;

DRB1*0106:

(SEQ ID NO: 2500)

cacgtttcttgtggcagcttaagtttgaatgtcatttcttcaatgggacggagcgggtgcggttgctggaaagatg catctataaccaagaggagtccgtgcgcttcgacagcgacgtgggggagtaccgggcggtgacggagctggggcgg cctgatgccgagtactggaacagccagaaggacctcctggagcaggCgcgggccgcggtggacacctactgcagac acaactacggggttgtGgagagcttcacagtgcagcggcgag;

DRB1*0107:

(SEQ ID NO: 2501)

cacgtttcttgtggGagcttaagtttgaatgtcatttcttcaatgggacggagcgggtgcggttgctggaaagatg catctataaccaagaggagtccgtgcgcttcgacagcgacgtgggggagtaccgggcggtgacggagctggggcgg cctgatgccgagtactggaacagccagaaggacctcctggagcagaggcgggccgcggtggacacctactgcagac acaactacggggttggtgagagcttcacagtgcagcggcgag;

DRB1*0108:
(SEQ ID NO: 2502)
cacgtttcttgtggcagcttaagtttgaatgtcatttcttcaatgggacggagcgggtgcggttgctggaaagatg catctataaccaagaggagtAcgtgcgcttcgacagcgacgtgggggagtaccgggcggtgacggagctggggcgg cctgatgccgagtactggaacagccagaaggacctcctggagcagaggcgggccgcggtggacacctactgcagac acaactacggggttggtgagagcttcacagtgcagcggcgag;

DRB1*0109:
(SEQ ID NO: 2503)
cacgtttcttgtggcagcttaagtttgaatgtcatttcttcaatgggacggagcgggtgcggttgctggaaagatg catctataaccaagaggagtccgtgcgcttcgacagcgacgtgggggagtaccgggcggtgacggagctggggcgg cctgatgccgagtactggaacagccagaaggacctcctggagcagGCgcgggccgcggtggacacctactgcagac acaactacggggttggtgagagcttcacagtgcagcggcgag;

DRB1*0110:
(SEQ ID NO: 2504)
cacgtttcttgtggcagcttaagtttgaatgtcatttcttcaatgggacggagcgggtgcggttgctggaaagatg catctataaccaagaggagtccgtgcgcttcgacagcgacgtgggggagtaccgggcggtgacggagctggggcgg cctgatgccgagtactggaacagccagaaggacctcctggagcagaAgcgggccgcggtggacacctactgcagac acaactacggggttggtgagagcttcacagtgcagcggcgag;

DRB1*030101:
(SEQ ID NO: 2505)
ggggacaccagaccacgtttcttggagtactctacgtctgagtgtcatttcttcaatgggacggagcgggtgcggt AcctggacagatacttcCataaccaggaggagAAcgtgcgcttcgacagcgacgtgggggagtTccgggcggtgac ggagctggggcggcctgatgccgagtactggaacagccagaaggacctcctggagcagaagcggggccGggtggac aActactgcagacacaactacggggttgtGgagagcttcacagtgcagcggcgag;

DRB1*030102:
(SEQ ID NO: 2506)
cacgtttcttggagtactctacgtctgagtgtcatttcttcaatgggacggagcgggtgcggtacctggacagata cttccataaccaggaggagaacgtgcgcttcgacagcgacgtgggggagttccgggcggtgacggagctggggcgg cctgatgccgagtactggaacagccagaaggacctcctggagcagaagcggggccGgtggacaaTtactgcagac acaactacggggttgtGgagagcttcacagtgcagcg;

DRB1*030201:
(SEQ ID NO: 2507)
ggggacaccagaccacgtttcttggAgtactctacgtctgagtgtcatttcttcaatgggacggagcgggtgcggt tcctggaGagatacttcCataaccaggaggagAAcgtgcgcttcgacagcgacgtgggggagtaccgggcggtgac ggagctggggcggcctgatgccgagtactggaacagccagaaggacctcctggagcagaagcggggccGgtggac aActactgcagacacaactacggggttggtgagagcttcacagtgcagcggcgag;

DRB1*030202:
(SEQ ID NO: 2508)
ggggacaccagaccacgtttcttggagtactctacgtctgagtgtcatttcttcaatgggacggagcgggtgcggt tcctggaGagatacttccataaccaggaggagAAcgtgcgcttcgacagcgacgtgggggagtaccgggcggtgac ggagctggggcggcctgatgccgagtactggaacagccagaaggacctcctggagcagaagcggggccGgtggac aaTtactgcagacacaactacggggttggtgagagcttcacagtgcagcggcgag;

DRB1*0303:
(SEQ ID NO: 2509)
tactctacgtctgagtgtcatttcttcaatgggacggagcgggtgcggttcctggaGagatacttcCataaccagg aggagAAcgtgcgcttcgacagcgacgtgggggagtaccgggcggtgacggagctggggcggcctgatgccgagta ctggaacagccagaaggacctcctggagcagaagcggggccGgtggacaActactgcagacacaactacggggtt gtGgagagcttcacagtgcagcggcga;

-continued

DRB1*0304:
(SEQ ID NO: 2510)
cacgtttcttggagtactctacgtctgagtgtcatttcttcaatgggacggagcgggtgcggtAcctggacagata cttcCataaccaGgaggagtccgtgcgcttcgacagcgacgtgggggagtTccgggcggtgacggagctggggcgg cctgatgccgagtactggaacagccagaaggacctcctggagcagaagcggggccGgtggacaActactgcagac acaactacggggttgtGgagagcttcacagtgcagcggcgag;

DRB1*030501:
(SEQ ID NO: 2511)
cacgtttcttggagtactctacgtctgagtgtcatttcttcaatgggacggagcgggtgcggtAcctggacagata cttcCataaccaggaggagAAcgtgcgcttcgacagcgacgtgggggagtTccgggcggtgacggagctggggcgg cctgatgccgagtactggaacagccagaaggacctcctggagcagaagcggggccGgtggacaActactgcagac acaactacggggttggtgagagcttcacagtgcagcggcgag;

DRB1*030502:
(SEQ ID NO: 2512)
cacgtttcttggagtactctacgtctgagtgtcatttcttcaatgggacggagcgggtgcggtacctggacagata cttccataaccaggaggagaacgtgcgcttcgacagcgacgtgggggagttccgggcggtgacggagctggggcgg cctgatgccgagtactggaacagccagaaggacctcctggagcagaagcggggccgggtggacaActactgcagac acaactacggggttggtgagagcttcacGgtgcagcggcgag;

DRB1*0306:
(SEQ ID NO: 2513)
ttcttggagtactctacgtctgagtgtcatttcttcaatgggacggagcgggtgcggtAcctggaCagatacttcC ataaccaggaggagAAcgtgcgcttcgacagcgacgtgggggagtaccgggcggtgacggagctggggcggcctga tgccgagtactggaacagccagaaggacctcctggagcagaagcggggccGgtggacaActactgcagacacaac tacggggttgtGgagagcttcacagtgcag;

DRB1*0307:
(SEQ ID NO: 2514)
ggggacaccagaccacgtttcttggagtactctacgtctgagtgtcatttcttcaatgggacggagcgggtgcggt tcctggacagatacttcCataaccaggaggagAAcgtgcgcttcgacagcgacgtgggggagtTccgggcggtgac ggagctggggcggcctgatgccgagtactggaacagccagaaggacctcctggagcagaagcggggccGgtggac aActactgcagacacaactacggggttgtGgagagcttcacagtgcagcggcgag;

DRB1*0308:
(SEQ ID NO: 2515)
ggggacaccagaccacgtttcttggagtactctacgtctgagtgtcatttcttcaatgggacggagcgggtgcggt acctggacagatacttccataaccaggaggagAacgtgcgcttcgacagcgacgtgggggagttccgggcggtgac ggagctggggcggcctgatgAGgagtactggaacagccagaaggacctcctggagcagaagcggggccGgtggac aActactgcagacacaactacggggttgtGgagagcttcacagtgcagcggcgag;

DRB1*0309:
(SEQ ID NO: 2516)
ttggagtactctacgtctgagtgtcatttcttcaatgggacggagcgggtgcggtacctggacagatacttccata accGgaggagaacgtgcgcttcgacagcgacgtgggggagttccgggcggtgacggagctggggcggcctgatgc cgagtactggaacagccagaaggacctcctggagcagaagcggggccgggtggacaactactgcagacacaactac ggggttggtgagagcttcacagtgcagcgg;

DRB1*0310:
(SEQ ID NO: 2517)
ggggacaccagaccacgtttcttggagtactctacgtctgagtgtcatttcttcaatgggacggagcgggtgcggt acctggacagatacttccataaccaggaggagaacgtgcgcttcgacagcgacgtgggggagttccgggcggtgac ggagctggggcggcctgCtgcggagcactggaacagccagaaggacctcctggagcagaagcggggccGgtggac aActactgcagacacaactacggggttgtGgagagcttcacagtgcagcggcgag;

DRB1*0311:
(SEQ ID NO: 2518)
cacgtttcttggagtactctacgtctgagtgtcatttcttcaatgggacggagcgggtgcggtAcctggacagata cttccataaccaggaggagaacgtgcgcttcgacagcgacgtgggggagttccgggcggtgacggagctggggcgg cctgatgccgagtactggaacagccagaaggacctcctggagcagaagcggggcCAggtggacaActactgcagac acaactacggggttgtGgagagcttcacagtgcagcggcga;

DRB1*0312:
(SEQ ID NO: 2519)
ttggagtactctacgtctgagtgtcatttcttcaatgggacggagcgggtgcggtacctggacagatacttccata accaggaggagaacgtgcgcttcgacagcgacgtgggggagttccgggcggtgacggagctggggcggcctagCgc cgagtactggaacagccagaaggacctcctggagcagaagcggggccGgtggacaActactgcagacacaactac ggggttgtGgag;

DRB1*0313:
(SEQ ID NO: 2520)
cacgtttcttggagtactctacgtctgagtgtcatttcttcaatgggacggagcgggtgcggtacctggacagata cttccataaccaggaggagaacgtgcgcttcgacagcgacgtgggggagttccgggcggtgacggagctggggcgg cctgatgccgagtCctggaacagccagaaggacctcctggagcagaagcggggccGgtggacaActactgcagac acaactacggggttgtGgagagcttcacagtgcagcggcgag;

DRB1*0314:
(SEQ ID NO: 2521)
cacgtttcttggagtactctacgtctgagtgtcatttcttcaatgggacggagcgggtgcggtAcctggacagata cttcCataaccaggaggagAAcgtgcgcttcgacagcgacgtgggggagtTccggcggtgacggagctggggcgg cctgatgccgagtactggaacagccagaaggacctcctggagcagaagcggggccGgtggacacctactgcagac acaactacggggttggtgagagcttcacagtgcagcggcgag;

DRB1*0315:
(SEQ ID NO: 2522)
cacgtttcttggagtactctacgtctgagtgtcatttcttcaatgggacggagcgggtgcggtAcctggacagata cttcCataaccaggaggagAAcgtgcgcttcgacagcgacgtgggggagtTccggcggtgacggagctggggcgg cctgatgccgagtactggaacagccagaaggacctcctggagcagaagcggggccGgtggacacctactgcagac acaactacggggttgtGgagagcttcacagtgcagcggcga;

DRB1*0316:
(SEQ ID NO: 2523)
cacgtttcttggagtactctacgtctgagtgtcatttcttcaatgggacggagcgggtgcggtacctggacagata cttccataaccaggaggagaacgtgcgcttcgacagcgacgtgggggagttcTgggcggtgacggagctggggcgg cctgatgccgagtactggaacagccagaaggacctcctggagcagaagcggggccgggtggacaactactgcagac acaactacggggttgtg;

DRB1*0317:
(SEQ ID NO: 2524)
cacgtttcttggagtactctaCgtctgagtgtcatttcttcaatgggacggagcgggtgcggttcctggaCagata cttctataaccaagaggagtAcgtgcgcttcgacagcgacgtgggggagtaccggcggtgaGggagctggggcgg cctgatgccgagtactggaacagccagaaggacctcctggagcagaagcggggccaggtggacaaTtactgcagac acaactacggggttggtgagagcttcacagtgcagcggcgag;

DRB1*0318:
(SEQ ID NO: 2525)
cacgtttcttggagtactctacgtctgagtgtcatttcttcaatgggacggagcgggtgcggtacctggacagata cttccataaccaggaggagaacgtgcgcttcgacagcgacgtgCgggagttccgggcggtgacggagctggggcgg cctgatgccgagtactggaacagccagaaggacctcctggagcagaagcggggccgggtggacaactactgcagac acaactacggggttgtGgagagcttcacagtgcagcggcgag;

```
DRB1*0319:
                                                         (SEQ ID NO: 2526)
cacgtttcttggagtactctacgtctgagtgtcatttcttcaatgggacggagcgggtgcggtacctggacagata cttccataaccaggaggagaacgtgcgcttcgacagcgacgtgggggagttccgggcggtgacggagctggggcgg cctgatgccgagtactggaacagccagaaggacAtcctggagcagaagcggggccGggtggacaActactgcagac acaactacggggttgtGgagagcttcacagtgcagcggcgag;

DRB1*0320:
                                                         (SEQ ID NO: 2527)
cacgtttcttggagtactctacgtctgagtgtcatttcttcaatgggacggagcgggtgcggtacctggacagata cttccataaccaggaggagaacgtgcgcttcgacagcgacgtgggggagttccgggcggtgacggagctggggcgg cctgatgccgagtactggaacagccagaaggacctcctggagcagaagcggggccgggtggacaActactgcagac acaactacggggCtgtggagagcttcacagtgcagcgg;

DRB1*0321:
                                                         (SEQ ID NO: 2528)
cgtttcttggagtactctacgtctgagtgtcatttcttcaatgggacggagcgggtgcggttcctggacagatact tccataaccaggaggagtTcgtgcgcttcgacagcgacgtgggggagtTccgggcggtgacggagctggggcggcc tgatgccgagtactggaacagccagaaggacctcctggagcagaagcggggccGgtggacaActactgcagacac aactacggggttgtGgagagcttcacagtgcagcggcga DRB1*0322:
                                                         (SEQ ID NO: 2529)
tttcttggagtactctacgtctgagtgtcatttcttcaatgggacggagcgggtgcggtacctggacagatacttc Gataaccaggaggagaacgtgcgcttcgacagcgacgtgggggagttccgggcggtgacggagctggggcggcctg atgccgagtactggaacagccagaaggacctcctggagcagaagcggggccgggtggacaactactgcagacacaa ctacggggttgtggagagcttcacagtgcagcggcgag;

DRB1*0323:
                                                         (SEQ ID NO: 2530)
cacgtttcttggagtactctacgtctgagtgtcatttcttcaatgggacggagcgggtgcggtacctggacagata cttccataaccGggaggagaacgtgcgcttcgacagcgacgtgggggagttccgggcggtgacggagctggggcgg cctgatgccgagtactggaacagccagaaggacctcctggagcagaagcggggccgggtggacaactactgcagac acaactacggggttgtGgagagcttcacagtgcagcggcgag;

DRB1*0324:
                                                         (SEQ ID NO: 2531)
cacgtttcttggagtactctacgtctgagtgtcatttcttcaatgggacggagcgggtgcggttcctggacagata cttccataaccaggaggagaacgtgcgcttcgacagcgacgtgggggagtTccgggcggtgacggagctggggcgg cctgatgccgagtactggaacagccagaaggacctcctggagcagaagcggggcCAggtggacaaTtactgcagac acaactacggggttgtGgagagcttcacagtgcagcggcgag;

DRB1*0325:
                                                         (SEQ ID NO: 2532)
cacgtttcttggagtactctacgtctgagtgtcatttcttcaatgggacggagcgggtgcggtAcctggacagata cttcCataaccaGgaggagtAcgtgcgcttcgacagcgacgtgggggagtTccgggcggtgacggagctggggcgg cctgatgccgagtactggaacagccagaaggacctcctggagcagaagcggggccGggtggacaActactgcagac acaactacggggttgtGgagagcttcacagtgcagcggcgag;

DRB1*040101:
                                                         (SEQ ID NO: 2533)
atggtgtgtctgaagTtccctggaggctcctgcatggcagctctgacagtgacactgatggtgctgagctccccac tggctttggctggggacacccgaccacgtttcttggagcaggttaaacatgagtgtcatttcttcaacgggacgga gcgggtgcggttcctggacagatacttctatcaccaagaggagtacgtgcgcttcgacagcgacgtgggggagtac cgggcggtgacggagctggggcggcctgatgccgagtactggaacagccagaaggacctcctggagcagaAgcggg ccgcggtggacacctactgcagacacaactacggggttggtgagagcttcacagtgcagcggcgag;
```

DRB1*040102:
(SEQ ID NO: 2534)
cacgtttcttggagcaggttaaacatgagtgtcatttcttcaacgggacggagcgggtgcggttcctggacagata cttctatcaccaagaAgagtacgtgcgcttcgacagcgacgtggggagtaccgggcggtgacggagctggggcgg cctgatgccgagtactggaacagccagaaggacctcctggagcagaagcgggccgcggtggacacctactgcagac acaactacggggttggtgagagcttcacagtgcagcggcgag;

DRB1*0402:
(SEQ ID NO: 2535)
atggtgtgtctgaagTtccctggaggctcctgcatggcagctctgacagtgacactgatggtgctgagctccccac tggctttggctggggacacccgaccacgtttcttggagcaggttaaacatgagtgtcatttcttcaacgggacgga gcgggtgcggttcctggacagatacttctatcaccaagaggagtacgtgcgcttcgacagcgacgtggggagtac cgggcggtgacggagctggggcggcctgatgccgagtactggaacagccagaaggacatcctggaagacgAgcggg ccgcggtggacacctactgcagacacaactacggggttgtGgagagcttcacagtgcagcggcgag;

DRB1*040301:
(SEQ ID NO: 2536)
ggggacacccgaccacgtttcttggagcaggttaaaCatgagtgtcatttcttcaacgggacggagcgggtgcggt tcctggacagatacttctatcaccaagaggagtAcgtgcgcttcgacagcgacgtggggagtaccgggcggtgac ggagctggggcggcctgatgccgagtactggaacagccagaaggacctcctggagcagaggcgggccgAggtggac acctactgcagacacaactacggggttgtGgagagcttcacagtgcagcggcgag;

DRB1*040302:
(SEQ ID NO: 2537)
cacgtttcttggagcaggttaaaCatgagtgtcatttcttcaacgggacggagcgggtgcggttcctggacagata cttctatcaccaagaggagtacgtgcgcttcgacagcgacgtggggagtaccgggcggtgacggagctggggcgg cctgacgcTgagtactggaacagccagaaggacctcctggagcagaggcgggccgAggtggacacctactgcagac acaactacggggttgtGgagagcttcacagtgcagcggcgag;

DRB1*0404:
(SEQ ID NO: 2538)
atggtgtgtctgaagTtccctggaggctcctgcatggcagctctgacagtgacactgatggtgctgagctccccac tggctttggctggggacacccgaccacgtttcttggagcaggttaaacatgagtgtcatttcttcaacgggacgga gcgggtgcggttcctggacagatacttctatcaccaagaggagtacgtgcgcttcgacagcgacgtggggagtac cgggcggtgacggagctggggcggcctgatgccgagtactggaacagccagaaggacctcctggagcagaggcggg ccgcggtggacacctactgcagacacaactacggggttgtGgagagcttcacagtgcagcggcgag;

DRB1*040501:
(SEQ ID NO: 2539)
ggggacacccgaccacgtttcttggagcaggttaaaCAtgagtgtcatttcttcaacgggacggagcgggtgcggt tcctggacagatacttctatCaccaagaggagtAcgtgcgcttcgacagcgacgtggggagtaccgggcggtgac ggagctggggcggcctaGcgccgagtactggaacagccagaaggacctcctggagcagaggcgggccgcggtggac acctactgcagacacaactacggggttggtgagagcttcacagtgcagcggcga;

DRB1*040502:
(SEQ ID NO: 2540)
cacgtttcttggagcaggttaaacatgagtgtcatttcttcaacgggacggagcgggtgcggttcctggacagata cttctatcaccaagaggagtacgtgcgGttcgacagcgacgtggggagtaccgggcggtgacggagctggggcgg cctagcgccgagtactggaacagccagaaggacctcctggagcagaggcgggccgcggtggacacctactgcagac acaactacggggttggtgagagcttcacagtgcagcggcgag;

DRB1*040503:
(SEQ ID NO: 2541)
cacgtttcttggagcaggttaaacatgagtgtcatttcttcaacgggacggagcgggtgcggttcctggacagata cttctatcaccaagaggagtacgtgcgcttcgacagcgacgtggggagtaccgggcggtgacggagctggggcgg -continued cctagcgccgagtactggaacagccagaaggacctcctggagcagaggcgggccgcggtggacacctactgcagac acaactacggggttggtgagagcttcacagtgcagcgAcgag;

DRB1*040504:

(SEQ ID NO: 2542)

cacgtttcttggagcaggttaaacatgagtgtcatttcttcaacgggacggagcgggtgcggttcctggacagata cttctatCaccaagaggagtacgtgcgcttcgacagcgacgtgggggagtaccgggcggtgacggagctggggcgg cctagCgccgagtactggaacagccagaaggacctcctggagcagaggcgggccgcggtggacacctactgcagac acaactacggggttggtgagagcttcacGgtgcagcggcgag;

DRB1*0406:

(SEQ ID NO: 2543)

ggggacacccgaccacgtttcttggagcaggttaaaCatgagtgtcatttcttcaacgggacggagcgggtgcggt tcctggacagatacttctatCaccaagaggagtccgtgcgcttcgacagcgacgtgggggagtaccgggcggtgac ggagctggggcggcctgatgccgagtactggaacagccagaaggacctcctggagcagaggcgggccgAggtggac acctactgcagacacaactacggggttgtGgagagcttcacagtgcagcggcgag;

DRB1*040701:

(SEQ ID NO: 2544)

ggggacacccgaccacgtttcttggagcaggttaaaCatgagtgtcatttcttcaacgggacggagcgggtgcggt tcctggacagatacttctatcaccaagaggagtAcgtgcgcttcgacagcgacgtgggggagtaccgggcggtgac ggagctggggcggcctgatgccgagtactggaacagccagaaggacctcctggagcagaggcgggccgAggtggac acctactgcagacacaactacggggttggtgagagcttcacagtgcagcggcga;

DRB1*040702:

(SEQ ID NO: 2545)

cacgtttcttggagcaggttaaacatgagtgtcatttcttcaacgggacggagcgggtgcggttcctggacagata cttctatcaccaagaggagtacgtgcgcttcgacagcgacgtgggggagtaccgggcggtgacggagctggggcgg cctgatgccgagtactggaacagccagaaggacctcctggagcagagAcgggccgaggtggacacctactgcagac acaactacggggttggtgagagcttcacagtgcagcgg;

DRB1*0408:

(SEQ ID NO: 2546)

tttcttggagcaggttaaACatgagtgtcatttcttcaacgggacggagcgggtgcggttcctggacagatacttc tatCaccaagaggagtAcgtgcgcttcgacagcgacgtgggggagtaccgggcggtgacggagctggggcggcctg atgccgagtactggaacagccagaaggacctcctggagcagaggcgggccgcggtggacacctactgcagacacaa ctacggggttggtgagagcttcacagtgcagcggcgag;

DRB1*0409:

(SEQ ID NO: 2547)

tgagtgtcatttcttcaacgggacggagcgggtgcggttcctggacagatacttctatCaccaagaggagtacgtg cgcttcgacagcgacgtgggggagtaccgggcggtgacggagctggggcggcctaGcgccgagtactggaacagcc agaaggacctcctggagcagaAgcgggccgcggtggacacctactgcagacacaactacggggttggtgagag;

DRB1*0410:

(SEQ ID NO: 2548)

tttcttggagcaggttaaacatgagtgtcatttcttcaacgggacggagcgggtgcggttcctggacagatacttc tatCaccaagaggagtAcgtgcgcttcgacagcgacgtgggggagtaccgggcggtgacggagctggggcggccta Gcgccgagtactggaacagccagaaggacctcctggagcagaggcgggccgcggtggacacctactgcagacacaa ctacggggttgtGgagagcttcacagtgcagcggcgag;

DRB1*0411:

(SEQ ID NO: 2549)

atggtgtgtctgaagTtccctggaggctcctgcatggcagctctgacagtgacactgatggtgctgagctccccac tggctttggctggggacacccgaccacgtttcttggagcaggttaaacatgagtgtcatttcttcaacgggacgga gcgggtgcggttcctggacagatacttctatcaccaagaggagtacgtgcgcttcgacagcgacgtgggggagtac cgggcggtgacggagctggggcggcctagcgccgagtactggaacagccagaaggacctcctggagcagaggcggg ccgAggtggacacctactgcagacacaactacggggttgtGgagagcttcacagtgcagcggcgag;

DRB1*0412:

(SEQ ID NO: 2550)
ttcttggagcaggttaaacatgagtgtcatttcttcaacgggacggagcgggtgcggttcctggacagatacttct atCaccaagaggagtacgtgcgcttcgacagcgacgtgggggagtaccgggcggtgacggagctggggcggcctaG cgccgagtactggaacagccagaaggacAtcctggaagacaggcgggcccTggtggacacctactgcagacacaac tacggggttgtGgagagcttcacagtgcagcgg;

DRB1*0413:

(SEQ ID NO: 2551)
catgagtgtcatttcttcaacgggacggagcgggtgcggttcctggacagatacttctatCaccaagaggagtacg tgcgcttcgacagcgacgtgggggagtaccgggcggtgacggagctggggcggcctgatgccgagtactggaacag ccagaaggacctcctggagcagaAgcgggccgcggtggacacctactgcagacacaactacggggttgtGgagagc ttcaca;

DRB1*0414:

(SEQ ID NO: 2552)
tgagtgtcatttcttcaacgggacggagcgggtgcggttcctggacagatacttctatCaccaagaggagtacgtg cgcttcgacagcgacgtgggggagtaccgggcggtgacggagctggggcggcctgatgccgagtactggaacagcc agaaggacAtcctggaagacGAgcgggccgcggtggacacctactgcagacacaactacggggttggtgagag;

DRB1*0415:

(SEQ ID NO: 2553)
cacgtttcttggagcaggttaaaCatgagtgtcatttcttcaacgggacggagcgggtgcggttcctggacagata cttctatcaccaagaggagtacgtgcgcttcgacagcgacgtgggggagtaccgggcggtgacggagctggggcgg cctgatgaGgagtactggaacagccagaaggacTtcctggaagaCaggcgggccgcggtggacacctactgcagac acaactacggggttgtGgagag;

DRB1*0416:

(SEQ ID NO: 2554)
atgagtgtcatttcttcaacgggacggagcgggtgcggttcctggacagatacttctatcaccaagaggagtacgt gcgcttcgacagcgacgtgggggagtaccgggcggtgacggagctggggcggcctgatgccCagtactggaacagc cagaaggacctcctggagcagaagcgggccgcggtggacacctactgcagacacaactacggggttggtg;

DRB1*0417:

(SEQ ID NO: 2555)
atgagtgtcatttcttcaacgggacggagcgggtgcggttcctggacagatacttctatCaccaagaggagtacgt gcgcttcgacagcgacgtgggggagtaccgggcggtgacggagctggggcggcctaGcgccgagtactggaacagc cagaaggacctcctggagcagaggcgggccgAggtggacacctactgcagacacaactacggggttggt;

DRB1*0418:

(SEQ ID NO: 2556)
atgagtgtcatttcttcaacgggacggagcgggtgcggttcctggacagatacttctatCaccaagaggagtacgt gcgcttcgacagcgacgtgggggagtaccgggcggtgacggagctggggcggcctgatgccgagtactggaacagc cagaaggacAtcctggaagacaggcgggcccTggtggacacctactgcagacacaactacggggttgtGgagagct tcacagtgca;

DRB1*0419:

(SEQ ID NO: 2557)
tttcttggagcaggttaaACatgagtgtcatttcttcaacgggacggagcgggtgcggttcctggacagatacttc tatCaccaagaggagtccgtgcgcttcgacagcgacgtgggggagtaccgggcggtgacggagctggggcggcctg atgccgagtactggaacagccagaaggacctcctggagcagaggcgggccgcggtggacacctactgcagacacaa ctacggggttggtgagagcttcacagtgcagcggcgag;

DRB1*0420:
(SEQ ID NO: 2558)
atgagtgtcatttcttcaacgggacggagcgggtgcggttcctggacagatacttctatCaccaagaggagtccgt gcgcttcgacagcgacgtgggggagtaccgggcggtgacggagctggggcggcctgatgccgagtactggaacagc cagaaggacctcctggagcagaggcgggccgAggtggacacctactgcagacacaactacggggttggtg;

DRB1*0421:
(SEQ ID NO: 2559)
gagcaggttaaacatgagtgtcatttcttcaacgggacggagcgggtgcggttcctggacagatacttctatCacc aagaggagtccgtgcgcttcgacagcgacgtgggggagtaccgggcggtgacggagctggggcggcctgatgccga gtactggaacagccagaaggacctcctggagcagaAgcgggccgcggtggacacctactgcagacacaactacggg gttggtgagagcttcacagtg;

DRB1*0422:
(SEQ ID NO: 2560)
gagcaggttaaacatgagtgtcatttcttcaacgggacggagcgggtgcggttcctggacagatacttctatCacc aagaggagtAcgtgcgcttcgacagcgacgtgggggagtaccgggcggtgacggagctggggcggcctgatgccga gtactggaacagccagaaggacctcctggagcagaagcggggccGgtggacaActactgcagacacaactacggg gttgtGgagagcttcaca;

DRB1*0423:
(SEQ ID NO: 2561)
cacgtttcttggagcaggttaaacatgagtgtcatttcttcaacgggacggagcgggtgcggttcctggacagata cttctatcaccaagaggagtacgtgcgcttcgacagcgacgtgggggagtaccgggcggtgacggagctggggcgg cctgatgccgagtactggaacagccagaaggacctcctggagcagaggcgggccgcggtggacacctactgcagac acaactacggggttgtggagagAttcacagtgcagcggcgag;

DRB1*0424:
(SEQ ID NO: 2562)
cacgtttcttggagcaggttaaacatgagtgtcatttcttcaacgggacggagcgggtgcggttcctggacagata cttctatcaccaagaggagtacgtgcgcttcgacagcgacgtgggggagtaccgggcggtgacggagctggggcgg cctaGCgccgagtactggaacagccagaaggacctcctggagcGgaggcgggccgcggtggacacctactgcagac acaactacggggttggtgagagcttcacagtgcagcggcgag;

DRB1*0425:
(SEQ ID NO: 2563)
ttggagcaggttaaacatgagtgtcatttcttcaacgggacggagcgggtgcggttcctggacagatacttctatC accaagaggagtAcgtgcgcttcgacagcgacgtgggggagtaccgggcggtgacggagctggggcggcctgatgc cgagtactggaacagccagaaggacTtcctggaagacaggcgggcccTggtggacacctactgcagacacaactac ggggttgtGgagag;

DRB1*0426:
(SEQ ID NO: 2564)
cacgtttcttggagcaggttaaacatgagtgtcatttcttcaacgggacggagcgggtgcggttcctggacagata cttctatcaccaagaggagtacgtgcgcttcgacagcgacgtgggggagtaccgggcggtgacggagctggggcgg cctgatAccgagtactggaacagccagaaggacctcctggagcagaagcgggccgcggtggacacctactgcagac acaactacggggttggtg;

DRB1*0427:
(SEQ ID NO: 2565)
cacgtttcttggagcaggttaaacatgagtgtcatttcttcaacgggacggagcgggtgcggttcctggacagata cttctatcaccaagaggagtAcgtgcgcttcgacagcgacgtgggggagtaccgggcggtgacggagctggggcgg cctgatgccgagtactggaacagccagaaggacctcctggagcagaggcgggccgAggtggacacctactgcagac acaactacggggCtgtggagagcttcacagtg;

DRB1*0428:

(SEQ ID NO: 2566)
cacgtttcttggagcaggttaaacatgagtgtcatttcttcaacgggacggagcgggtgcggttcctggacagata cttctatCaccaagaggagtAcgtgcgcttcgacagcgacgtgggggagtTccgggcggtgacggagctggggcgg cctaGcgccgagtactggaacagccagaaggacctcctggagcagaggcgggccgcggtggacacctactgcagac acaactacggggttggtgagagcttcacagtgcagcggcgag;

DRB1*0429:

(SEQ ID NO: 2567)
cacgtttcttggagcaggttaaacatgagtgtcatttcttcaacgggacggagcgggtgcggttcctggacagata cttctatcaccaagaggagtacgtgcgcttcgacagcgacgtgggggagtaccgggcggtgaTggagctggggcgg cctagcgccgagtactggaacagccagaaggacctcctggagcagaggcgggccgcggtggacacctactgcagac acaactacggggttggtgagagcttcacagtgcagcggcgag;

DRB1*0430:

(SEQ ID NO: 2568)
cacgtttcttggagcaggttaaacatgagtgtcatttcttcaacgggacggagcgggtgcggttcctggacagata cttctatcaccaagaggagtacgtgcgcttcgacagcgacgtgggggagtaccgggTggtgacggagctggggcgg cctagcgccgagtactggaacagccagaaggacctcctggagcagaggcgggccgcggtggacacctactgcagac acaactacggggttggtgagagcttcacagtgcagcggcgag;

DRB1*0431:

(SEQ ID NO: 2569)
cacgtttcttggagcaggttaaaCatgagtgtcatttcttcaacgggacggagcgggtgcggttcctggacagata cttctatCaccaagaggagtAcgtgcgcttcgacagcgacgtgggggagtaccgggcggtgacggagctggggcgg cctgatgccgagtactggaacagccagaaggacctcctggagcagaggcgggccCTggtggacacctactgcagac acaactacggggttggtgagagcttcacagtgcagcggcgag;

DRB1*0432:

(SEQ ID NO: 2570)
ttggagcaggttaaacatgagtgtcatttcttcaacgggacggagcgggtgcggttcctggacagatacttctatc accaagaggagtacgtgcgcttcgacagcgacgtgggggagtaccgggcggtgacggagctggggcggcctgatgc cgagtactggaacagccagaaggacctcctggagcagaggcAggccgcggtggacacctactgcagacacaactac ggggttgtggag;

DRB1*0433:

(SEQ ID NO: 2571)
cacgtttcttggagcaggttaaacatgagtgtcatttcttcaacgggacggagcgggtgcggttcctggacagata cttctatcaccaagaggagtacgtgcActtcgacagcgacgtgggggagtaccgggcggtgacggagctggggcgg cctgatgccgagtactggaacagccagaaggacctcctggagcagaagcgggccgcggtggacacctactgcagac acaactacggggttggtgagagcttcacagtgcagcggcgag;

DRB1*0434:

(SEQ ID NO: 2572)
tttcttggagcaggttaaaCCtgagtgtcatttcttcaacgggacggagcgggtgcggttcctggacagatacttc tatcaccaagaggagtAcgtgcgcttcgacagcgacgtgggggagtaccgggcggtgacggagctggggcggcctg atgccgagtactggaacagccagaaggacctcctggagcagaAgcgggccgcggtggacacctactgcagacacaa ctacggggttggtga;

DRB1*0435:

(SEQ ID NO: 2573)
cacgtttcttggagcaggttaaaCatgagtgtcatttcttcaacgggacggagcgggtgcggttcctggacagata cttctatcaccaagaggagtacgtgcgcttcgacagcgacgtgggggagtTccggcggtgacggagctggggcgg cctgatgccgagtactggaacagccagaaggacctcctggagcagaAgcgggccgcggtggacacctactgcagac acaactacggggttggtgagagcttcacagtg;

-continued

DRB1*0436:
(SEQ ID NO: 2574)
cacgtttcttggagcaggttaaaCatgagtgtcatttcttcaacgggacggagcgggtgcggttcctggacagata cttctatcaccaagaggagtacgtgcgcttcgacagcgacgtggggagtaccgggcggtgacggagctggggcgg cctgatgccgagtactggaacagccagaaggacTtcctggaagaCaggcgggccgcggtggacacctactgcagac acaactacggggttgtGgagagcttcacagtgcagcggcgag;

DRB1*0437:
(SEQ ID NO: 2575)
cacgtttcttggagcaggttaaaCatgagtgtcatttcttcaacgggacggagcgggtgcggttcctggacagata cttctatcaccaagaggagtacgtgcgcttcgacagcgacgtggggagtaccgggcggtgacggagctggggcgg cctgatgccgagtactggaacagccagaaggacctcctggaagacGAgcgggccgcggtggacacctactgcagac acaactacggggttgtGgagagcttcacagtgcagcggcgag;

DRB1*0438:
(SEQ ID NO: 2576)
cacgtttcttggagcaggttaaaCatgagtgtcatttcttcaacgggacggagcgggtgcggttcctggacagata cttctatcaccaagaggagtacgtgcgcttcgacagcgacgtggggagtaccgggcggtgacggagctggggcgg cctgatgccgagtactggaacagccagaaggacAtcctggagcagaAgcgggccgcggtggacacctactgcagac acaactacggggttggtgagagcttcacagtgcagcggcgag;

DRB1*0439:
(SEQ ID NO: 2577)
cacgtttcttggagcaggttaaacatgagtgtcatttcttcaacgggacggagcgggtgcggttcctggacagata cttctatcaccaagaggagtacgtgcgcttcgacagcgacgtgggggaCtaccgggcggtgacggagctggggcgg cctgatgccgagtactggaacagccagaaggacctcctggagcagaggcgggccgaggtggacacctactgcagac acaactacggggttgtggagagcttcacagtgcagcgg;

DRB1*0440:
(SEQ ID NO: 2578)
cacgtttcttggagcaggttaaacatgagtgtcatttcttcaacgggacggagcgggtgcggttcctggacagata cttctatcaccaagaggagtacgtgcgcttcgacagcgacgtggggagtaccgggcggtgacggagctggggcgg cctgatgGcgagtactggaacagccagaaggacctcctggagcagaggcgggccgcggtggacacctactgcagac acaactacggggttgtggagagcttcacagtgcagcgg;

DRB1*0441:
(SEQ ID NO: 2579)
cacgtttcttggagcaggttaaaCatgagtgtcatttcttcaacgggacggagcgggtgcggttcctggacagata cttctatcaccaagaggagAAcgtgcgcttcgacagcgacgtggggagtaccgggcggtgacggagctggggcgg cctgatgccgagtactggaacagccagaaggacctcctggagcagaggcgggccgAggtggacacctactgcagac acaactacggggttgtGgagagcttcacagtgcagcgg;

DRB1*0442:
(SEQ ID NO: 2580)
cacgtttcttggagcaggttaaaCatgagtgtcatttcttcaacgggacggagcgggtgcggttcctggacagata cttctatcaccaagaggagtacgtgcgcttcgacagcgacgtggggagtTccgggcggtgacggagctggggcgg cctgatgccgagtactggaacagccagaaggacctcctggagcagaggcgggccgcggtggacacctactgcagac acaactacggggttgtGgagagcttcacagtgcagcggcgag;

DRB1*0443;
(SEQ ID NO: 2581)
cacgtttcttggagcaggttaaaCatgagtgtcatttcttcaacgggacggagcgggtgcggttcctggacagata cttctatCaccaagaggagtacgtgcgcttcgacagcgacgtggggagtTccgggcggtgacggagctggggcgg cctgatgccgagtactggaacagccagaaggacctcctggagcagaggcgggccgcggtggacacctactgcagac acaactacggggttggtgagagcttcacagtgcagcgg;

DRB1*0444:
(SEQ ID NO: 2582)
cacgtttcttggagcaggttaaacatgagtgtcatttcttcaacgggacggagcgggtgcggttcctggacagata cttctatCaccaagaggagtAcgtgcgcttcgacagcgacgtgggggagtaccgggcggtgacggagctggggcgg cctgatgccgagtactggaacagccagaaggacctcctggagcagaggcgggccgcggtggacaaTtactgcagac acaactacggggttgtGgagagcttcacagtgcagc;

DRB1*070101:
(SEQ ID NO: 2583)
atggtgtgtctgaagctccctggaggctcctgcatggcagctctgacagtgacactgatggtgctgagctccccac tggctttggctggggacacccAaccacgtttcctgtggcagggtaagtataagtgtcatttcttcaacgggacgga gcgggtgcagttcctggaaagactcttctataaccaggaggagttcgtgcgcttcgacagcgacgtgggggagtac cgggcggtgacggagctagggcggcctgtcgccgagtcctggaacagccagaaggacatcctggaggacaggcggg gcCaggtggacaccgtGtgcagacacaactacggggttggtgagagcttcacagtgcagcggcgag;

DRB1*070102:
(SEQ ID NO: 2584)
cacgtttcctgtggcagggtaaAtataagtgtcatttcttcaacgggacggagcgggtgcagttcctggaaagact cttctataaccaggaggagttcgtgcgcttcgacagcgacgtgggggagtaccgggcggtgacggagctAgggcgg cctgtcgccgagtCctggaacagccagaaggacatcctggaggacaggcggggccaggtggacaccgtGtgcagac acaactacggggttggtg;

DRB1*0703:
(SEQ ID NO: 2585)
cacgtttcctgtggcagggtaagtataagtgtcatttcttcaacgggacggagcgggtgcagttcctggaaagTct cttctataaccaggaggagttcgtgcgcttcgacagcgacgtgggggagtaccgggcggtgacggagctagggcgg cctgtcgccgagtcctggaacagccagaaggacatcctggaggacaggcggggccaggtggacaccgtgtgcagac acaactacggggttggtg;

DRB1*0704:
(SEQ ID NO: 2586)
tttcctgtggcagggtaagtataagtgtcatttcttcaacgggacggagcgggtgcagttcctggaaagactcttc tataaccaggaggagttcgtgcgcttcgacagcgacgtgggggagtaccgggcggtgacggagctAgggcggcctg tcgccgagtcctggaacagccagaaggacatcctggaggacaggcggggccaggtggacaaTtactgcagacacaa ctacggggttggtgagagc;

DRB1*0705:
(SEQ ID NO: 2587)
cacgtttcctgtggcagggtaagtataagtgtcatttcttcaacgggacggagcgggtgcagttcctggaaagact cttctataaccaggaggagttcgtgcgcttcgacagcgacgtgggggagtaccgggcggtgacggagctagggcgg cctgtcgccgagtcctggaacagccGgaaggacatcctggaggacaggcggggccaggtggacaccgtgtgcagac acaactacggggttggtgagagcttcacag;

DRB1*0706:
(SEQ ID NO: 2588)
cacgtttcctgtggcagggtaagtataagtgtcatttcttcaacgggacggagcgggtgcagttcctggaaagact cttctataaccaggaggagttcgtgcgcttcgacagcgacgtgggggagtaccgggcggtgacggagctAgggcgg cctgctgcGgagtactggaacagccagaaggacatcctggaggacaggcggggccaggtggacaccgtGtgcagac acaactacggggttggtgagagcttcacagtgcagcggcgag;

DRB1*0707:
(SEQ ID NO: 2589)
cacgtttcctgtggcagggtaagtataagtgtcatttcttcaacgggacggagcgggtgcagttcctggaaagact cttctataaccaggaggagttcgtgcgcttcgacagcgacgtgggggagtaccgggcggtgacggagctagggTgg cctgtcgccgagtcctggaacagccagaaggacatcctggaggacaggcggggccaggtggacaccgtgtgcagac acaactacggggttggtgagagcttcacagtg;

DRB1*080101:
(SEQ ID NO: 2590)
ggggacaccegaccacgtttcttggagtactctacgggtgagtgtTatttcttcaatgggacggagcgggtgcggt tcctggacagatacttctataaccaagaggagtacgtgcgcttcgacagcgacgtgggggagtaccgggcggtgac ggagctggggcggcctagCgccgagtactggaacagccagaaggacTtcctggaagacaggcgggcccTggtggac acctactgcagacacaactacggggttggtgagagcttcacGgtgcagcggcgag;

DRB1*080102:
(SEQ ID NO: 2591)
cacgtttcttggagtactctacgggtgagtgttatttcttcaatgggacggagcgggtgcggttcctggacagata Tttctataaccaagaggagtacgtgcgcttcgacagcgacgtgggggagtaccgggcggtgacggagctggggcgg cctagcgccgagtactggaacagccagaaggacttcctggaagacaggcgggccctggtggacacctactgcagac acaactacggggttggtgagagcttcacggtgcagcggcgag;

DRB1*080201:
(SEQ ID NO: 2592)
atggtgtgtctgaggctccctggaggctcctgcatggcagTtctgacagtgacactgatggtgctgagctccccac tggctttggctggggacaccagaccacgtttcttggagtactctacgggtgagtgttatttcttcaatgggacgga gcgggtgcggttcctggacagatacttctataaccaagaggagtacgtgcgcttcgacagcgacgtgggggagtac cgggcggtgacggagctggggcggcctgatgccgagtactggaacagccagaaggacttcctggaagacaggcggg ccctggtggacacctactgcagacacaactacggggttggtgagagcttcacGgtgcagcggcgag;

DRB1*080202:
(SEQ ID NO: 2593)
cacgtttcttggagtactctacgggtgagtgtTatttcttcaatgggacggagcgggtgcggttcctggacagata cttctataaccaagaggagtAcgtgcgcttcgacagcgacgtgggggagtaccgggcggtgacggagctggggcgg cctgatgccgagtactggaacagccagaaggacTtcctggaagacaggcgggcccTggtggacacctactgcagac acaactacggggttggtgagagcttcacagtgcagcggcgag;

DRB1*080203:
(SEQ ID NO: 2594)
cgtttcttggagtactctacgggtgagtgttatttcttcaatgggacggagcgggtgcggttcctggacagatact tctataaccaagaggagtacgtgcgcttcgacagcgacgtgggggagtaccgggcggtgacAgagctggggcggcc tgatgccgagtactggaacagccagaaggacttcctggaagacaggcgggccctggtggacacctactgcagacac aactacggggttggtgagagcttcacggtg;

DRB1*080302:
(SEQ ID NO: 2595)
ggggacaccagaccacgtttcttggagtactctaCgggtgagtgtTatttcttcaatgggacggagcgggtgcggt tcctggacagatacttctataaccaagaggagtacgtgcgcttcgacagcgacgtgggggagtaccgggcggtgac ggagctggggcggcctaGcgccgagtactggaacagccagaaggacAtcctggaagacaggcgggcccTggtggac acctactgcagacacaactacggggttggtgagagcttcacagtgcagcggcgag;

DRB1*080401:
(SEQ ID NO: 2596)
ggggacaccagaccacgtttcttggagtactctacgggtgagtgtTatttcttcaatgggacggagcgggtgcggt tcctggacagatacttctataaccaagaggagtAcgtgcgcttcgacagcgacgtgggggagtaccgggcggtgac ggagctggggcggcctgatgccgagtactggaacagccagaaggacTtcctggaagacaggcgggcccTggtggac acctactgcagacacaactacggggttgtGgagagcttcacagtgcagcggcgag;

DRB1*080402:
(SEQ ID NO: 2597)
ttcaatgggacggagcgggtgcggttcctggacagatacttctataaccaagaggagtAcgtgcgcttcgacagcg acgtgggggagtaccgggcggtgacggagctggggcggcctgatgccgagtactggaacagccagaaggacTtcct ggaagacaggcgggcccTggtggacacctactgcagacacaactacggggttgTtgagagcttcacagtgcagcgg;

DRB1*080403:
(SEQ ID NO: 2598)
cacgtttcttggagtactctacgggtgagtgttatttcttcaatgggacggagcgggtgcggttcctggacagata cttctataaccaagaggagtacgtgcgcttcgacagcgacgtgggggagtaccgggcggtgacggagctggggcgg cctgatgccgagtactggaacagccagaaggacttcctggaagacaggcgggcccTggtggacacctactgcagac acaactacggggttgTtgagagcttcacGgtgcagcggcga;

DRB1*080404:
(SEQ ID NO: 2599)
cacgtttcttggagtactctacgggtgagtgttatttcttcaatgggacggagcgggtgcggttcctggacagata cttctataaccaagaggagtacgtgcgcttcgacagcgacgtgggggagtaccgggcggtgacggagctggggcgg cctgatgccgagtactggaacagccagaaggacttcctggaagacaggcgggcccTggtggacacctactgcagac acaactacggggttgtGgagagcttcacGgtgcagcggcgag;

DRB1*0805:
(SEQ ID NO: 2600)
cacgtttcttggagtactctacgggtgagtgtTatttcttcaatgggacggagcgggtgcggttcctggacagata cttctataaccaagaggagtacgtgcgcttcgacagcgacgtgggggagtaccgggcggtgacggagctggggcgg cctaGcgccgagtactggaacagccagaaggacTtcctggaagaCaggcgggccgcggtggacacctactgcagac acaactacggggttggt;

DRB1*0806:
(SEQ ID NO: 2601)
ccacgtttcttggagtactctacgggtgagtgttatttcttcaatgggacggagcgggtgcggttcctggacagat acttctataaccaagaggagtacgtgcgcttcgacagcgacgtgggggagtaccgggcggtgacggagctggggcg gcctaGcgccgagtactggaacagccagaaggacTtcctggaagacaggcgggcccTggtggacacctactgcaga cacaactacggggttgtGgagagcttcacagtgcagcggcgag;

DRB1*0807:
(SEQ ID NO: 2602)
cacgtttcttggagtactctacgggtgagtgttatttcttcaatgggacggagcgggtgcggttcctggacagata cttctataaccaagaggagtacgtgcgcttcgacagcgacgtgggggagtaccgggcggtgacggagctggggcgg cctgTtgccgagtactggaacagccagaaggacTtcctggaagacaggcgggcccTggtggacacctactgcagac acaactacggggttggtgagagcttcacGgtgcagcggcgag;

DRB1*0808:
(SEQ ID NO: 2603)
ttggagtactctacgggtgagtgttatttcttcaatgggacggagcgggtgcggttcctggacagatacttctata accaagaggagtacgtgcgcttcgacagcgacgtgggggagtaccgggcggtgacggagctggggcggcctgCtgc ggagCactggaacagccagaaggacttcctggaagacaggcgggcccTggtggacacctactgcagacacaactac ggggttggtgag;

DRB1*0809:
(SEQ ID NO: 2604)
cacgtttcttggagtactctaCgggtgagtgttatttcttcaatgggacggagcgggtgcggttcctggacagata cttccataaccaggaggagtTcgtgcgcttcgacagcgacgtgggggagtaccgggcggtgacggagctggggcgg cctgatgccgagtactggaacagccagaaggacTtcctggaagacaggcgggcccTggtggacacctactgcagac acaactacggggttggtgagagcttcacGgtgcagcggcgag;

DRB1*0810:
(SEQ ID NO: 2605)
cacgtttcttggagtactctacgggtgagtgtTatttcttcaatgggacggagcgggtgcggttcctggacagata cttctataaccaagaggagtacgtgcgcttcgacagcgacgtgggggagtaccgggcggtgacggagctggggcgg cctaGcgccgagtactggaacagccagaaggacAtcctggaagacaggcgggcccTggtggacacctactgcagac acaactacggggttgtGgagagcttcacagtgcagcggcgag;

DRB1*0811:
(SEQ ID NO: 2606)
cacgtttcttggagtactctacgggtgagtgttatttcttcaatgggacggagcgggtgcggttcctggacagata cttctataaccaagaggagtacgtgcgcttcgacagcgacgtgggggagtaccgggcggtgacggagctggggcgg cctgCtgccgagtactggaacagccagaaggacttcctggaagacaggcgggcccTggtggacacctactgcagac acaactacggggttggtgagagcttcacGgtg;

DRB1*0812:
(SEQ ID NO: 2607)
cacgtttcttggagtactctacgggtgagtgttatttcttcaatgggacggagcgggtgcggttcctggacagata cttctataaccaagaggagtacgtgcgcttcgacagcgacgtgggggagtaccgggcggtgacggagctggggcgg cctagcgccgagtactggaacagccagaaggacAtcctggaagacaggcgggcccTggtggacacctactgcagac acaactacggggCtgtggagagcttcacagtgcagcggcgag;

DRB1*0813:
(SEQ ID NO: 116 2608)
tcttggagtactctacgggtgagtgtTatttcttcaatgggacggagcgggtgcggttcctggacagatacttcta taaccaagaggagtAcgtgcgcttcgacagcgacgtgggggagtaccgggcggtgacggagctggggcggcctgat gccgagtactggaacagccagaaggacctcctggaagacaggcgggcccTggtggacacctactgcagacacaact acggggttggtgagagcttcacGgtg;

DRB1*0814:
(SEQ ID NO: 2609)
cacgtttcttggagtactctaGggtgagtgttatttcttcaatgggacggagcgggtgcggttcctggacagata cttctataaccaagaggagtacgtgcgcttcgacagcgacgtgggggagtaccgggcggtgacggagctggggcgg cctagcgccgagtactggaacagccagaaggacatcctggaagacaggcgggcccTggtggacacctactgcagac acaactacggggttggtgagagcttcacagtg;

DRB1*0815:
(SEQ ID NO: 2610)
tttcttggagtactctacgggtgagtgttatttcttcaatgggacggagcgggtgcggttcctggacagatacttc tataaccaagaggagtacgtgcgcttcgacagcgacgtgggggagtaccgggcggtgacggagctggggcggcctg atgcggagCactggaacagccagaaggacAtcctggaagacaggcgggcccTggtggacacctactgcagacacaa ctacggggttggtg;

DRB1*0816:
(SEQ ID NO: 2611)
cacgtttcttggagtactctacgggtgagtgttatttcttcaatgggacggagcgggtgcggttcctggacagata cttctataaccaagaggagGacgtgcgcttcgacagcgacgtgggggagtaccgggcggtgacggagctggggcgg cctagcgccgagtactggaacagccagaaggacttcctggaagacaggcgggcccTggtggacacctactgcagac acaactacggggttggtgagagcttcacGgtgcagcggcgag;

DRB1*0817:
(SEQ ID NO: 2612)
cacgtttcttggagtactctacgggtgagtgttatttcttcaatgggacggagcgggtgcggttcctggacagata cttctataaccaagaggagtacgtgcgcttcgacagcgacgtgggggagtTccgggcggtgacggagctggggcgg cctaGcgccgagtactggaacagccagaaggacTtcctggaagacaggcgggcccTggtggacacctactgcagac acaactacggggttggtg;

-continued

DRB1*0818:
(SEQ ID NO: 2613)
cacgtttcttggagtactctaCgggtgagtgtTatttcttcaatgggacggagcgggtgcggttcctggacagata cttctataaccaagaggagtacgtgcgcttcgacagcgacgtgggggagtaccgggcggtgacggagctggggcgg cctaGcgccgagtactggaacagccagaaggacAtcctggaagaCaggcgggccgcggtggacacctactgcagac acaactacggggttggtgagagcttcacagtgcagcggcgag;

DRB1*0819:
(SEQ ID NO: 2614)
tttcttggagtactctacgggtgagtgttatttcttcaatgggacggagcgggtgcggttcctggacagatacttc tataaccaagaggagtacgtgcgcttcgacagcgacgtgggggagtaccgggcggtgacggagctggggcggccta TcgccgagtactggaacagccagaaggacAtcctggaagacaggcgggcccTggtggacacctactgcagacacaa ctacggggttggtgagagcttcacagtgc;

DRB1*0820:
(SEQ ID NO: 2615)
cacgtttcttggagtactctacgtCtgagtgtcatttcttcaatgggacggagcgggtgcggttcctggacagata cttctataaccaagaggagtAcgtgcgcttcgacagcgacgtgggggagtaccgggcggtgacggagctggggcgg cctgatgccgagtactggaacagccagaaggacTtcctggaagacaggcgggcccTggtggacacctactgcagac acaactacggggttgtGgagagcttcacagtgcagcggcga;

DRB1*0821:
(SEQ ID NO: 2616)
cacgtttcttggagtactctaTgggtgagtgttatttcttcaatgggacggagcgggtgcggttcctggacagata cttccataaccaggaggagttcgtgcgcttcgacagcgacgtgggggagtaccgggcggtgacggagctggggcgg cctgatgccgagtactggaacagccagaaggacttcctggaagacaggcgggccctggtggacacctactgcagac acaactacggggttggtgagagcttcacggtgcagcggcga;

DRB1*0822:
(SEQ ID NO: 2617)
cacgtttcttggagtactctacgggtgagtgttatttcttcaatgggacggagcgggtgcggttcctggacagata cttctataaccaagaggagtacgtgcgcttcgacagcgacgtgggggagtaccgggcggtgacggagctggggcgg cctagcgccgagtactggaacagccagaaggacttcctggaagacaggcgggccctggtggacacctactgcagac acaactacggggCtgtGgagagcttcacGgtgcagcggcgag;

DRB1*0823:
(SEQ ID NO: 2618)
cacgtttcttggagtactctacgggtgagtgttatttcttcaatgggacggagcgggtgcggttcctggacagata cttctataaccaagaggagtacgtgcgcttcgacagcgacgtgAgggagtaccgggcggtgacggagctggggcgg cctagcgccgagtactggaacagccagaaggacatcctggaagacaggcgggcccTggtggacacctactgcagac acaactacggggttggtgagagcttcacagtgcagcggcgag;

DRB1*0824:
(SEQ ID NO: 2619)
cacgtttcttggagtactctacgggtgagtgtTatttcttcaatgggacggagcgggtgcggttcctggacagata cttctataaccaagaggagtAcgtgcgcttcgacagcgacgtgggggagtaccgggcggtgacggagctggggcgg cctgatgccgagtactggaacagccagaaggacTtcctggaagaCaggcgggccgcggtggacacctactgcagac acaactacggggttggtgagagcttcacagtgcagcgg;

DRB1*090102:
(SEQ ID NO: 2620)
ggggacacccaaccacgtttcttgaagcaggataagtttgagtgtcatttcttcaacgggacggagcgggtgcggt atctgcacagaggcatctataaccaagaggagaacgtgcgcttcgacagcgacgtgggggagtaccgggcggtgac ggagctggggcggcctgtcgccgagtCctggaacagccagaaggacttcctggagcggaggcgggccgaggtggac accgtgtgcagacacaactacggggttggtgagagcttcacagtgcagAggcgag;

DRB1*0902:
(SEQ ID NO: 2621)
cacgtttcttgaagcaggataagtttgagtgtcatttcttcaacgggacggagcgggtgcggtatctgcacagagg catctataaccaagaggagaacgtgcgcttcgacagcgacgtgggggagtaccgggcggtgacggagctggggcgg cctgacgcTgagtactggaacagccagaaggacttcctggagcggaggcgggccgaggtggacaccgtgtgcagac acaactacggggttggtgagagcttcacagtgcagAggcgag;

DRB1*100101:
(SEQ ID NO: 2622)
atggtgtgtctgaggctccctggaggctcctgcatggcagttctgacagtgacactgatggtgctgagctccccac tggctttggctggggacaccagaccacgtttcttggaggaggttaagtttgagtgtcatttcttcaacgggacgga gcgggtgcggttgctggaaagacgcgtccataaccaagaggagtacgcgcgctacgacagcgacgtgggggagtac cgggcggtgacggagctggggcggcctgatgccgagtactggaacagccagaaggacctcctggagcggaggcgTg ccgcggtggacacctactgcagacacaactacggggttggtgagagcttcacagtgcagcggcgag;

DRB1*100102:
(SEQ ID NO: 2623)
cacgtttcttggaggaggttaagtttgagtgtcatttcttcaacgggacggagcgggtgcggttgctggaaagacg cGtccataaccaagaggagtacgcgcgctacgacagcgacgtgggggagtaccgggcggtgacggagctggggcgg cctgatgccgagtactggaacagccagaaggacctcctggagcggaggcgCgccgcggtggacacctactgcagac acaactacggggttggtgagagcttcacagtgcagcggcgag;

DRB1*110101:
(SEQ ID NO: 2624)
atggtgtgtctgaggctccctggaggctcctgcatggcagTtctgacagtgacactgatggtgctgagctccccac tggctttggctggggacaccagaccacgtttcttggagtactctacgtctgagtgtcatttcttcaatgggacgga gcgggtgcggttcctggacagatacttctataaccaagaggagtacgtgcgcttcgacagcgacgtgggggagttc cgggcggtgacggagctggggcggcctgatgaGgagtactggaacagccagaaggacTtcctggaagaCaggcggg ccgcggtggacacctactgcagacacaactacggggttggtgagagcttcacagtgcagcggcgag;

DRB1*110102:
(SEQ ID NO: 2625)
ggggacaccagaccacgtttcttggagtactctacgtctgagtgtcatttcttcaatgggacggagcgggtgcggt tcctggacagatacttctataaccaagaggagtacgtgcgcttcgacagcgacgtgggggagttccgggcggtgac ggagctggggcggcctgatgaGgagtactggaacagccagaaggacTtcctggaagaCaggcgggccgcggtggac acctactgcagacacaactacggggttggtgagagcttcacGgtgcagcggcgag;

DRB1*110103:
(SEQ ID NO: 2626)
cacgtttcttggagtactctacgtctgagtgtcatttcttcaatgggacggagcgggtgcggttcctggacagata cttctataaccaagaggagtacgtgcgcttcgacagcgacgtgggggagttccgggcggtgacggagctggggcgg cctgatgaGgagtactggaacagccagaaggacTtcctggaaGaCaggcgCgccgcggtggacacctactgcagac acaactacggggttggtgagagcttcacagtgcagcggcgag;

DRB1*110104:
(SEQ ID NO: 2627)
cgtttcttggagtactctacgtctgagtgtcatttcttcaaCgggacggagcgggtgcggttcctggacagatact tctataaccaagaggagtAcgtgcgcttcgacagcgacgtgggggagtTccgggcggtgacggagctggggcggcc tgatgAggagtactggaacagccagaaggacTtcctggaagaCaggcgggccgcggtggacacctactgcagacac aactacggggttggtgagagcttcacagtgcagcggcgag;

DRB1*1102:
(SEQ ID NO: 2628)
ggggacaccagaccacgtttcttggagtactctacgtctgagtgtcatttcttcaatgggacggagcgggtgcggt tcctggacagatacttctataaccaagaggagtacgtgcgcttcgacagcgacgtgggggagttccgggcggtgac -continued ggagctggggcggcctgatgAggagtactggaacagccagaaggacAtcctggaagacGAgcgggccgcggtggac acctactgcagacacaactacggggttgtGgagagcttcacagtgcagcggcgag;

DRB1*1103:

(SEQ ID NO: 2629)

atggtgtgtctgaggctccctggaggctcctgcatggcagTtctgacagtgacactgatggtgctgagctccccac tggctttggctggggacaccagaccacgtttcttggagtactctacgtctgagtgtcatttcttcaatgggacgga gcgggtgcggttcctggacagatacttctataaccaagaggagtacgtgcgcttcgacagcgacgtgggggagttc cgggcggtgacggagctggggcggcctgatgaggagtactggaacagccagaaggacttcctggaagacgAgcggg ccgcggtggacacctactgcagacacaactacggggttgtGgagagcttcacagtgcagcggcgag;

DRB1*110401:

(SEQ ID NO: 2630)

atggtgtgtctgaggctccctggaggctcctgcatggcagTtctgacagtgacactgatggtgctgagctccccac tggctttggctggggacaccagaccacgtttcttggagtactctacgtctgagtgtcatttcttcaatgggacgga gcgggtgcggttcctggacagatacttctataaccaagaggagtacgtgcgcttcgacagcgacgtgggggagttc cgggcggtgacggagctggggcggcctgatgaggagtactggaacagccagaaggacTtcctggaagaCaggcggg ccgcggtggacacctactgcagacacaactacggggttgtGgagagcttcacagtgcagcggcgag;

DRB1*110402:

(SEQ ID NO: 2631)

ggggacaccagaccacgtttcttggagtactctacgtctgagtgtcatttcttcaatgggacggagcgggtgcggt tcctggacagatacttctataaccaagaggagtacgtgcgcttcgacagcgacgtgggggagttccgggcggtgac ggagctggggcggcctgatgaGgagtactggaacagccagaaggacttcctggaagacaggcgggccgcggtggac acctactgcagacacaactacggggttgtGgagagcttcacGgtgcagcggcgag;

DRB1*1105:

(SEQ ID NO: 2632)

ccacgtttcttggagtactctacgGgtgagtgtcatttcttcaatgggacggagcgggtgcggttcctggacagat acttctataaccaagaggagtacgtgcgcttcgacagcgacgtgggggagttccgggcggtgacggagctggggcg gcctgatgAGgagtactggaacagccagaaggacTtcctggaagaCaggcgggccgcggtggacacctactgcaga cacaactacggggttggtgagagcttcacagtgcagcggcga;

DRB1*110601:

(SEQ ID NO: 2633)

cgtttcttggagtactctacgtctgagtgtcatttcttcaatgggacggagcgggtgcggttcctggacagatact tctataaccaagaggagtacgtgcgcttcgacagcgacgtgggggagttccgggcggtgacggagctggggcggcc tgatgaGgagtactggaacagccagaaggacTtcctggaagaCaggcgggccgcggtggacacctactgcagacac aactacggggCtgtggagagcttcacagtgcagcggcgag;

DRB1*110602:

(SEQ ID NO: 2634)

tttcttggagtactctacgtctgagtgtcatttcttcaatgggacggagcgggtgcggttcctggacagatacttc tataaccaagaggagtacgtgcgcttcgacagcgacgtgggggagttccgggcggtgacggagctggggcggcctg atgaGgagtactggaacagccagaaggacTtcctggaagaCaggcgggccgcggtggacacctaTtgcagacacaa ctacggggCtgtggagagcttcacagtgcagcggcgag;

DRB1*1107:

(SEQ ID NO: 2635)

ttggagtactctacgtctgagtgtcatttcttcaatgggacggagcgggtgcggttcctggacagatacttctata accaagaggagtacgtgcgcttcgacagcgacgtgggggagttccgggcggtgacggagctggggcggcctgatgA GgagtactggaacagccagaaggacctcctggagcagaagcggggccGggtggacaActactgcagacacaactac ggggttgtGgagagcttcacagtgcagcggcgag;

DRB1*110801:

(SEQ ID NO: 2636)
gtctgagtgtcatttcttcaatgggacggagcgggtgcggttcctggacagatacttctataaccaagaggagtAc gtgcgcttcgacagcgacgtgggggagtTccggcggtgacggagctggggcggcctgatgAggagtactggaaca gccagaaggacctcctggaagaCaggcgggccgcggtggacacctactgcagacacaactacggggttggtgagag cttcacagtg;

DRB1*110802:

(SEQ ID NO: 2637)
gtctgagtgtcatttcttcaatgggacggagcgggtgcggttcctggacagatacttctataaccaagaggagtac gtgcgcttcgacagcgacgtgggggagttccggcggtgacggagctggggcggcctgatgaGgagtactggaaca gccagaaggacctcctggaagaCaggcgggccgcggtggacacctactgcagacacaactacggggttggtgagag cttcacGgtg;

DRB1*1109:

(SEQ ID NO: 2638)
catttcttcaatgggacggagcgggtgcggttcctggacagatacttccataaccaGgaggagAAcgtgcgcttcg acagcgacgtgggggagtTccggcggtgacggagctggggcggcctgatgAggagtactggaacagccagaagga cTtcctggaagaCaggcgggccgcggtggacacctactgcagacacaactacggggttggtgagagcttcacagtg cag;

DRB1*1110:

(SEQ ID NO: 2639)
gagtgtcatttcttcaatgggacggagcgggtgcggttcctggacagatacttcCataaccaGgaggagtTcgtgc gcttcgacagcgacgtgggggagtTccggcggtgacggagctggggcggcctgatgAggagtactggaacagcca gaaggacTtcctggaagaCaggcgggccgcggtggacacctactgcagacacaactacggggttggt;

DRB1*1111:

(SEQ ID NO: 2640)
tttcttggagtactctacgtctgagtgtcatttcttcaatgggacggagcgggtgcggttcctggacagatacttc tataaccaagaggagtacgtgcgcttcgacagcgacgtgggggagtTccggcggtgacggagctggggcggcctg atgAggagtactggaacagccagaaggacTtcctggaagacGAgcgggccgcggtggacacctactgcagacacaa ctacggggttggtgagagcttcacagtgcagcggcgag;

DRB1*111201:

(SEQ ID NO: 2641)
gagtgtcatttcttcaatgggacggagcgggtgcggttcctggacagatacttctataaccaagaggagtTcgtgc gcttcgacagcgacgtgggggagtTccggcggtgacggagctggggcggcctgatgAggagtactggaacagcca gaaggacTtcctggaagaCaggcgggccgcggtggacacctactgcagacacaactacggggttggt;

DRB1*111202:

(SEQ ID NO: 2642)
cacgtttcttggagtactctacgtCtgagtgtcatttcttcaatgggacggagcgggtgcggttcctggacagata cttctataaccaGgaggagtTcgtgcgcttcgacagcgacgtgggggagtTccggcggtgacggagctggggcgg cctgatgAggagtactggaacagccagaaggacTtcctggaagaCaggcgggccgcggtggacacctactgcagac acaactacggggttggtgagagcttcacagtgcagcggcgag;

DRB1*1113:

(SEQ ID NO: 2643)
ggggacaccagaccacgtttcttggagtactctacgtctgagtgtcatttcttcaatgggacggagcgggtgcggt tcctggacagatacttccataaccaggaggagttcgtgcgcttcgacagcgacgtgggggagtTccggcggtgac ggagctggggcggcctgatgAGgagtactggaacagccagaaggacctcctggagcGgaggcgggccgcggtggac acctaTtgcagacacaactacggggttgtGgagagcttcacagtgcagcggcga;

DRB1*1114:
(SEQ ID NO: 2644)
ggggacaccagaccacgtttcttggagtactctacgtctgagtgtcatttcttcaatgggacggagcgggtgcggt tcctggacagatacttctataaccaagaggagtacgtgcgcttcgacagcgacgtggggagttccgggcggtgac ggagctggggcggcctgatgAggagtactggaacagccagaaggacAtcctggaagacGAgcgggccgcggtggac acctactgcagacacaactacggggttggtgagagcttcacagtgcagcggcgag;

DRB1*1115:
(SEQ ID NO: 2645)
ggggacaccagaccacgtttcttggagtactctacgtctgagtgtcatttcttcaatgggacggagcgggtgcggt tcctggacagatacttctataaccaagaggaggacTtgcgcttcgacagcgacgtggggagttccgggcggtgac ggagctggggcggcctgatgaGgagtactggaacagccagaaggacTtcctggaaGaCaggcgggccgcggtggac acctactgcagacacaactacggggttggtgagagcttcacagtgcagcggcgag;

DRB1*1116:
(SEQ ID NO: 2646)
cacgtttcttggagtactctacgtctgagtgtcatttcttcaatgggacggagcgggtgcggttcctggacagata cttccataaccaggaggagAacgtgcgcttcgacagcgacgtggggagttccgggcggtgacggagctggggcgg cctgatgAggagtactggaacagccagaaggacAtcctggaagacGAgcgggccgcggtggacacctactgcagac acaactacggggttgtGgagagcttcacagtgcagcggcgag;

DRB1*1117:
(SEQ ID NO: 2647)
ggggacaccagaccacgtttcttggagtactctacgtCtgagtgtcatttcttcaatgggacggagcgggtgcggt tcctggacagatacttccataaccaggaggagttcgtgcgcttcgacagcgacgtggggagtaccgggcggtgac ggagctggggcggcctgatgAGgagtactggaacagccagaaggacctcctggagcggaggcgggccgAggtggac acctaTtgcagacacaactacggggttgtGgagagcttcacagtgcagcggcgag;

DRB1*1118:
(SEQ ID NO: 2648)
tttcttggagtactctacgtctgagtgtcatttcttcaatgggacggagcgggtgcggttcctggacagatacttc tataaccaagaggagtAcgtgcgcttcgacagcgacgtggggagttccgggcggtgacggagctggggcggcctg atgAggagtactggaacagccagaaggacAtcctggaagaCaggcgggccgcggtggacacctactgcagacacaa ctacggggttgtGgagagcttcacagtgcagcggcgag;

DRB1*1119:
(SEQ ID NO: 2649)
tttcttggagtactctacgtctgagtgtcatttcttcaatgggacggagcgggtgcggttcctggacagatacttc tataaccaagaggagtAcgtgcgcttcgacagcgacgtggggagttccgggcggtgacggagctggggcggcctg atgAggagtactggaacagccagaaggacAtcctggaagaCaggcgggccgcggtggacacctactgcagacacaa ctacggggttggtgagagcttcacagtgcagcggcgag;

DRB1*1120:
(SEQ ID NO: 2650)
ttggagtactctacgtctgagtgtcatttcttcaatgggacggagcgggtgcggttcctggacagatacttccata accaggaggagAacgtgcgcttcgacagcgacgtggggagttccgggcggtgacggagctggggcggcctgatgA ggagtactggaacagccagaaggacAtcctggaagacGAgcgggccgcggtggacacctactgcagacacaactac ggggttggtgagagcttcacagtgcagc;

DRB1*1121:
(SEQ ID NO: 2651)
ttggagtactctacgtctgagtgtcatttcttcaatgggacggagcgggtgcggttcctggacagatacttctata accaagaggagtacgtgcgcttcgacagcgacgtggggagttccgggcggtgacggagctggggcggcctgatga ggagtactggaacagccagaaggacatcctggaagacGAgcgggccgcggtggacacctactgcagacacaactac ggggCtgtggaga;

-continued

DRB1*1122:
(SEQ ID NO: 2652)
cacgtttcttggagcaggttaaaCatgagtgtcatttcttcaatgggacggagcgggtgcggttcctggacagata
cttctataaccaggaggagtacgtgcgcttcgacagcgacgtgggggagtTccgggcggtgacggagctggggcgg
cctgatgaGgagtactggaacagccagaaggacTtcctggaagaCaggcgggccgcggtggacacctactgcagac
acaactacggggttggtgagag;

DRB1*1123:
(SEQ ID NO: 2653)
ccacgtttcttggagtactctacgtctgagtgtcatttcttcaatgggacggagcgggtgcggttcctggacagat
acttctataaccaagaggagtacgtgcgcttcgacagcgacgtgggggagttccgggcggtgacggagctggggcg
gcctgatgAGgagtactggaacagccagaaggacTtcctggaagaCaggcgggccCTggtggacacctactgcaga
cacaactacggggttggtg;

DRB1*1124:
(SEQ ID NO: 2654)
ttcttggagtactctacgtctgagtgtcatttcttcaatgggacggagcgggtgcggttcctggacagatacttct
ataaccaagaggagGacgtgcgcttcgacagcgacgtgggggagttccgggcggtgacggagctggggcggcctga
tgaGgagtactggaacagccagaaggacTtcctggaaGaCaggcgggccgcggtggacacctactgcagacacaac
tacggggttggtgagagcttcac;

DRB1*1125:
(SEQ ID NO: 2655)
cacgtttcttggagtactctacgtctgagtgtcatttcttcaatgggacggagcgggtgcggttcctggacagata
cttctataaccaagaggagtacgtgcgcttcgacagcgacgtgggggagttccgggcggtgacggagctggggcgg
cctgatgaGgagtactggaacagccagaaggacTtcctggaagacaggcgggcccTggtggacacctactgcagac
acaactacggggttgtGgagagcttcacagtgcagcggcgag;

DRB1*1126:
(SEQ ID NO: 2656)
ttggagtactctacgtCtgaGtgtcatttcttcaatgggacggagcgggtgcggttcctggacagatacttctata
accaagaggagtAcgtgcgcttcgacagcgacgtgggggagtTccgggcggtgacggagctggggcggcctgatgA
ggagtactggaacagccagaaggacctcctggagcagaggcgggccgcggtggacacctactgcagacacaactac
ggggttggtgag;

DRB1*112701:
(SEQ ID NO: 2657)
tttcttggagtactctacgtctgagtgtcatttcttcaatgggacggagcgggtgcggttcctggacagatacttc
tataaccaagaggagtacgtgcgcttcgacagcgacgtgggggagttccgggcggtgacggagctggggcggcctg
atgaggagtactggaacagccagaaggacttcctggaAgaCaggcgggccgcggtggacaaTtactgcagacacaa
ctacggggttggtgagag;

DRB1*112702:
(SEQ ID NO: 2658)
cacgtttcttggagtactctacgtctgagtgtcatttcttcaatgggacggagcgggtgcggttcctggacagata
cttctataaccaagaggagtacgtgcgcttcgacagcgacgtgggggagttccgggcggtgacggagctggggcgg
cctgatgAggagtactggaacagccagaaggacttcctggaagaCaggcgggccgcggtggacaActactgcagac
acaactacggggttggtgagagcttcacagtgcagcggcgag;

DRB1*1128:
(SEQ ID NO: 2659)
cacgtttcttggagtactctacgtctgaGtgtcatttcttcaatgggacggagcgggtgcggttcctggacagata
cttctataaccaagaggagAAcgtgcgcttcgacagcgacgtgggggagtTccggcggtgacggagctggggcgg
cctgatgAggagtactggaacagccagaaggacTtcctggaagaCaggcgggccgcggtggacacctactgcagac
acaactacggggttggtgagagcttcacagtgcagcggcgag;

DRB1*1129:
(SEQ ID NO: 2660)
cacgtttcttggagtactctaCgtCtgaGtgtcatttcttcaatgggacggagcgggtgcggttcctggacagata cttctataaccaagaggagtccgtgcgcttcgacagcgacgtgggggagtTccgggcggtgacggagctggggcgg cctgatgAggagtactggaacagccagaaggacTtcctggaagaCaggcgggccgcggtggacacctactgcagac acaactacggggttggtgagagcttcacagtgcagcggcgag;

DRB1*1130:
(SEQ ID NO: 2661)
cacgtttcttggagcTgcttaagtctgagtgtcatttcttcaatgggacggagcgggtgcggttcctggacagata cttctataaccaagaggagtacgtgcgcttcgacagcgacgtgggggagttccgggcggtgacggagctggggcgg cctgatgaggagtactggaacagccagaaggacttcctggaagaCaggcgggccgcggtggacacctactgcagac acaactacggggttggtgagagcttcacagtgcagcggcga;

DRB1*1131:
(SEQ ID NO: 2662)
ggggacaccagaccacgtttcttggagtactctacgtctgagtgtcatttcttcaatgggacggagcgggtgcggt tcctggacagatacttctataaccaagaggagtacgtgcgcttcgacagcgacgtgggggagttccgggcggtgac ggagctggggcggcctgatgAggagCactggaacagccagaaggacAtcctggaagaCaggcgggccgcggtggac acctactgcagacacaactacggggttggtgagagcttcacagtgcagcggcgag;

DRB1*1132:
(SEQ ID NO: 2663)
cacgtttcttggagtactctacgtctgagtgtcatttcttcaatgggacggagcgggtgcggttcctggacagata cttctataaccaagaggagtacgtgcgcttcgacagcgacgtgggggagttccgggcggtgacggagctggggcgg cctgatgAGgagtactggaacagccagaaggacTtcctggaagaCaggcgggccgTggtggacacctactgcagac acaactacggggttggtgagagcttcacagtgcagcggcgag;

DRB1*1133:
(SEQ ID NO: 2664)
ttggagtactctacgtctgagtgtcatttcttcaatgggacggagcgggtgcggttcctggacagatacttctata accaagaggagtacgtgcgcttcgacagcgacgtgggggagttccgggcggtgacggagctggggcggcctgatga ggaCtactggaacagccagaaggacttcctggaagacaggcgggccgcggtggacacctactgcagacacaactac ggggttggtgagagcttcacagtgcagcggc;

DRB1*1134:
(SEQ ID NO: 2665)
cacgtttcttggagtactctacgtctgagtgtcatttcttcaatgggacggagcgggtgcggttcctggacagata cttctataaccaagaggagtAcgtgcgcttcgacagcgacgtgggggagtTccgggcggtgacggagctggggcgg cctgatgAggagtactggaacagccagaaggacctcctggagcagaggcgggccgcggtggacacctactgcagac acaactacggggttgtGgagagcttcacagtgcagcggcga;

DRB1*1135:
(SEQ ID NO: 2666)
ttggagtactctacgtctgagtgtcatttcttcaatgggacggagcgggtgcggttcctggacagatacttctata accaagaggagtacgtgcgcttcgacagcgacgtgggggagttccgggcggtgacggagctggggcggcctgatga ggaCtactggaacagccagaaggacttcctggaagacaggcgggccgcggtggacacctactgcagacacaactac ggggttgtGgagagcttcacagtgcagcggc;

DRB1*1136:
(SEQ ID NO: 2667)
cgtttcttggagtactctacgtctgagtgtcatttcttcaatgggacggagcgggtgcggttcctggacagatact tctataaccaagaggagtacgtgcgcttcgacagcgacgtgggggagtTccgggcggtgacggagctggggcggcc tgatgAggagtactggaacagccagaaggacctcctggaagacGAgcgggccgcggtggacacctactgcagacac aactacggggttgtGgagagcttcacagtgcagcggcga;

```
DRB1*1137:
                                                         (SEQ ID NO: 2668)
cacgtttcttggagtactctaCgtCtgaGtgtcatttcttcaatgggacggagcgggtgcggttcctggacagata cttctataaccaagaggagtAcgtgcgcttcgacagcgacgtgggggagtaccgggcggtgacggagctggggcgg cctgatgAggagtactggaacagccagaaggacTtcctggaagaCaggcgggccgcggtggacacctactgcagac acaactacggggttggtgagagcttcacagtgcagcggcgag;

DRB1*1138:
                                                         (SEQ ID NO: 2669)
cacgtttcttggagtactctacgtctgagtgtcatttcttcaatgggacggagcgggtgcggttcctggacagata cttctataaccaagaggagtacgtgcgcttcgacagcgacgtgggggagttccgggcggtgacggagctggggcgg cctgatgaggGgtactggaacagccagaaggacttcctggaagacaggcgggccgcggtggacacctactgcagac acaactacggggttgtggagagcttcacagtgcagcggcgag;

DRB1*1139:
                                                         (SEQ ID NO: 2670)
cacgtttcttggagtactctacgtctgagtgtcatttcttcaatgggacggagcgggtgcggttcctggacagata cttctataaccaagaggagtacgtgcgcttcgacagcgacgtgggggagttccgggcggtgaGggagctggggcgg cctgatgaggagtactggaacagccagaaggacttcctggaagaCaggcgggccgcggtggacacctactgcagac acaactacggggttggtgagagcttcacagtgcagcggcgag;

DRB1*1140:
                                                         (SEQ ID NO: 2671)
cacgtttcttggagtactctacgtctgagtgtcatttcttcaatgggacggagcgggtgcggttcctggacagata cttccataaccaggaggagAacgtgcgcttcgacagcgacgtgggggagtTccgggcggtgacggagctggggcgg cctgatgAggagtactggaacagccagaaggacTtcctggaagacGAgcgggccgcggtggacacctactgcagac acaactacggggttgtGg;

DRB1*1141:
                                                         (SEQ ID NO: 2672)
tttcttggagtactctacgtctgagtgtcatttcttcaatgggacggagcgggtgcggttcctggacagatacttc tataaccaagaggagtacgtgcgcttcgacagcgacgtgggggagtaccgggcggtgacggagctggggcggcctg atgAggagtactggaacagccagaaggacTtcctggaagacGAgcgggccgcggtggacacctactgcagacacaa ctacggggttgtGgagagcttcacagtgcagcggcgag;

DRB1*1142:
                                                         (SEQ ID NO: 2673)
cacgtttcttggagtactctacgtctgagtgtcatttcttcaatgggacggagcgggtgcggttcctggacagata cttctataaccaagaggagtAcgtgcgcttcgacagcgacgtgggggagtTccgggcggtgacggagctggggcgg cctgatgAggagtactggaacagccagaaggacctcctggaagaCaggcgggccgcggtggacacctactgcagac acaactacggggttgtGgagagcttcacagtgcagcggcgag;

DRB1*1143:
                                                         (SEQ ID NO: 2674)
cacgtttcttggagtactctacgtctgagtgtcatttcttcaatgggacggagcgggtgcggttcctggacagata cttctataaccaagaggagtacgtgcgcttcgacagcgacgtgggggagttccgggcggtgaGggagctggggcgg cctgatgaggagtactggaacagccagaaggacttcctggaagaCaggcgggccgcggtggacacctactgcagac acaactacggggttgtGgagagcttcacagtgcagcggcgag;

DRB1*120101:
                                                         (SEQ ID NO: 2675)
atggtgtgtctgaggctccctggaggctcctgcatggcagtTctgacagtgacactgatggtgctgagctccccac tggctttggctggggacaccAgaccacgtttcttggagtactctacggtgagtgttatttcttcaatgggacgga gcgggtgcggttActggagagacacttccataaccaggaggagCtcctgcgcttcgacagcgacgtgggggagttc cgggcggtgacggagctggggcggcctgtcgccgagtCctgaacagccagaaggacAtcctggaagacaggcgcg ccgcggtggacacctaTtgcagacacaactacggggCtgtggagagcttcacagtgcagcggcgag;
```

DRB1*120102:

(SEQ ID NO: 2676)
atggtgtgtctgaggctccctggaggctcctgcatggcagtTctgacagtgacactgatggtgctgagctccccac tggctttggctggggacaccAgaccacgtttcttggagtactctacgggtgagtgttatttcttcaatgggacgga gcgggtgcggttActggagagacacttccataaccaggaggagCtcctgcgcttcgacagcgacgtgggggagttc cgggcggtgacggagctggggcggcctgtcgccgagtCctggaacagccagaaggacAtcctggaagacaggcggg ccgcggtggacacctactgcagacacaactacggggCtgtggagagcttcacagtgcagcggcgag;

DRB1*120201:

(SEQ ID NO: 2677)
cacgtttcttggagtactctacggtgagtgttatttcttcaatgggacggagcgggtgcggttactggagagaca cttccataaccaggaggagCtcctgcgcttcgacagcgacgtgggggagttccgggcggtgacggagctggggcgg cctgtcgccgagtcctggaacagccagaaggacTtcctggaagacaggcgcgccgcggtggacacctaTtgcagac acaactacggggCtgtggagagcttcacagtgcagcggcgag;

DRB1*120202:

(SEQ ID NO: 2678)
ttcttggagtactctacggtgagtgttatttcttcaatgggacggagcgggtgcggttactggagagacacttcc ataaccaggaggagCtcctgcgcttcgacagcgacgtgggggagttccgggcggtgacggagctggggcggcctgt cgccgagtcctggaacagccagaaggacTtcctggaagacaggcgCgccgcggtggacacctactgcagacacaac tacggggCtgtggag;

DRB1*120302:

(SEQ ID NO: 2679)
cacgtttcttggagtactctacggtgagtgttatttcttcaatgggacggagcgggtgcggttActggagagaca cttccataaccaggaggagCtcctgcgcttcgacagcgacgtgggggagttccgggcggtgacggagctggggcgg cctgtcgccgagtCctggaacagccagaaggacAtcctggaagacaggcgCgccgcggtggacacctactgcagac acaactacggggttgtggagagcttcacagtgcagcgg;

DRB1*1204:

(SEQ ID NO: 2680)
gagtactctacggtgagtgttatttcttcaatgggacggagcgggtgcggttactggagagacacttccataacc aggaggagCtcctgcgcttcgacagcgacgtgggggagttccgggcggtgacggagctggggcggcctgatgaGga gtactggaacagccagaaggacAtcctggaagacaggcgcgccgcggtggacacctaTtgcagacacaactacggg gCtgtgg;

DRB1*1205:

(SEQ ID NO: 2681)
cacgtttcttggagtactctacggtgagtgttatttcttcaatgggacggagcgggtgcggttActggagagaca cttccataaccaggaggagttcctgcgcttcgacagcgacgtgggggagttccgggcggtgacggagctggggcgg cctgtcgccgagtCctggaacagccagaaggacAtcctggaagacaggcgcgccgcggtggacacctaTtgcagac acaactacggggCtgtggagagcttcacagtgcagcggcgag;

DRB1*1206:

(SEQ ID NO: 2682)
ggggacaccagaccacgtttcttggagtactctacggtgagtgttatttcttcaatgggacggagcgggtgcggt tActggagagacacttccataaccaggaggagCtcctgcgcttcgacagcgacgtgggggagttccgggcggtgac ggagctggggcggcctgtcgccgagtCctggaacagccagaaggacAtcctggaagacaggcgcgccgcggtggac acctaTtgcagacacaactacggggCtgtggagagcttcacagtgcagcggcgag;

DRB1*1207:

(SEQ ID NO: 2683)
cacgtttcttggagtactctacggtgagtgttatttcttcaatgggacggagcgggtgcggttactggagagaca cttccataaccaggaggagctcctgcgcttcgacagcgacgtgggggagttccgggcggtgacggagctggggcgg cctgtcgccgagtcctggaacagccagaaggacatcctggGagacaggcgcgccgcggtggacacctattgcagac acaactacggggctgtggagagcttcacagtgcagcggcgag;

DRB1*1208:
(SEQ ID NO: 2684)
cacgtttcttggagtactctacgggtgagtgttatttcttcaatgggacggagcgggtgcggttCctggagagaca cttccataaccaggaggagCtcctgcgcttcgacagcgacgtgggggagttccgggcggtgacggagctggggcgg cctgtcgccgagtCctggaacagccagaaggacAtcctggaagacaggcgcgccgcggtggacacctaTtgcagac acaactacggggCtgtggagagcttcacagtgcagcggcgag;

DRB1*130101:
(SEQ ID NO: 2685)
ggggacaccagaccacgtttcttggagtactctacgtctgagtgtcatttcttcaatgggacggagcgggtgcggt tcctggaCagatacttccataaccaggaggagAAcgtgcgcttcgacagcgacgtgggggagtTccgggcggtgac ggagctggggcggcctgatgccgagtactggaacagccagaaggacAtcctggaagacGAgcgggccgcggtggac acctactgcagacacaactacggggttgtGgagagcttcacagtgcagcggcgag;

DRB1*130102:
(SEQ ID NO: 2686)
cacgtttcttggagtactctacgtctgagtgtcatttcttcaatgggacggagcgggtgcggttcctggacagata cttccataaccaggaggagaacgtgcgcttcgacagcgacgtgggggagttccgggcggtgacggagctggggcgg cctgatgccgagtactggaacagccagaaggacatcctggaagacgagcgggCgcggtggacacctactgcagac acaactacggggttgtggagagcttcacagtgcagcggcgag;

DRB1*130103:
(SEQ ID NO: 2687)
cacgtttcttggagtactctacgtctgagtgtcatttcttcaatgggacggagcgggtgcggttcctggacagata cttccataaccaggaggagaacgtgcgcttcgacagcgacgtgggggagttccgggcggtgacggagctggggcgg cctgatgccgagtactggaacagccagaaggacatcctggaagacgAgcgggccgcggtggacacctaTtgcagac acaactacggggttgtGgagagcttcacagtgcagcggcgag;

DRB1*130201:
(SEQ ID NO: 2688)
ggggacaccagaccacgtttcttggagtactctacgtctgagtgtcatttcttcaatgggacggagcgggtgcggt tcctggaCagatacttccataaccaggaggagAAcgtgcgcttcgacagcgacgtgggggagtTccgggcggtgac ggagctggggcggcctgatgccgagtactggaacagccagaaggacAtcctggaagacGAgcgggccgcggtggac acctactgcagacacaactacggggttggtgagagcttcacagtgcagcggcgag;

DRB1*130202:
(SEQ ID NO: 2689)
cacgtttcttggagtactctacgtctgagtgtcatttcttcaatgggacggagcgggtgcggttcctggacagata cttccataaccaggaggagaacgtgcgcttcgacagcgacgtgggggagttccgggcggtgacggagctggggcgg cctgatgccgagtactggaacagccagaaggacatcctggaagacgAgcCgccgcggtggacacctactgcagac acaactacggggttggtgagagcttcacagtgcagcgg;

DRB1*130301:
(SEQ ID NO: 2690)
ggggacaccagaccacgtttcttggagtactctacgtctgagtgtcatttcttcaatgggacggagcgggtgcggt tcctggacagatacttctataaccaagaggagtacgtgcgcttcgacagcgacgtgggggagtaccgggcggtgac ggagctggggcggcctagCgccgagtactggaacagccagaaggacatcctggaagaCaAgcgggccgcggtggac acctactgcagacacaactacggggttggtgagagcttcacGgtgcagcggcgag;

DRB1*130302:
(SEQ ID NO: 2691)
ttggagtactctacgtctgagtgtcatttcttcaatgggacggagcgggtgcggttcctggacagatacttctata accaagaggagtacgtgcgcttcgacagcgacgtgggggagtaccgggcggtgacggagctggggcggcctaGcgc -continued cgagtactggaacagccagaaggacatcctggaagaCaAgcgggccgcggtggacacctactgcagacacaactac ggggttggtgagagcttcacagtgcagcggcgag;

DRB1*1304:
(SEQ ID NO: 2692)
ggggacaccagaccacgtttcttggagtactctacgtctgagtgtcatttcttcaatgggacggagcgggtgcggt tcctggacagatacttctataaccaagaggagtacgtgcgcttcgacagcgacgtggggggagtTccggcggtgac ggagctggggcggcctaGcgccgagtactggaacagccagaaggacatcctggaagacGAgcgggccgcggtggac acctactgcagacacaactacggggttgtGgagagcttcacagtgcagcggcgag;

DRB1*1305:
(SEQ ID NO: 2693)
cgtttcttggagtactctacgtctgaGtgtcatttcttcaatgggacggagcgggtgcggttcctggacagatact tccataaccaGgaggagAacgtgcgcttcgacagcgacgtggggggagtTccgggcggtgacggagctggggcggcc tgatgccgagtactggaacagccagaaggacTtcctggaagaCaggcgggccgcggtggacacctactgcagacac aactacggggttggtgagagcttcacagtgcagcggcgag;

DRB1*1306:
(SEQ ID NO: 2694)
tgtcatttcttcaatgggacggagcgggtgcggttcctggaCagatacttccataaccaggaggagAacgtgcgct tcgacagcgacgtgggggagtTccgggcggtgacggagctggggcggcctgatgccgagtactggaacagccagaa ggacAtcctggaagaCaggcgggccgcggtggacacctactgcagacacaactacggggttgtGgagagcttcaca;

DRB1*130701:
(SEQ ID NO: 2695)
cacgtttcttggagtactCtaCgtCtgaGtgtcatttcttcaatgggacggagcgggtgcggttcctggaCagata cTtctataaccaagaggagtAcgtgcgcttcgacagcgacgtgggggagtaccgggcggtgacggagctggggcgg cctgatgccgagtactggaacagccagaaggacTtcctggaaGaCaggcgggccgcggtggacacctactgcagac acaactacggggttggtgagagcttcacagtgcagcggcgag;

DRB1*130702:
(SEQ ID NO: 2696)
cacgtttcttggagtactctacgtCtgagtgtcatttcttcaatgggacggagcgggtgcggttcctggaCagata cTtctataaccaagaggagtAcgtgcgcttcgacagcgacgtgggggagtaccgggcggtgacggagctggggcgg cctgacgcTgagtactggaacagccagaaggacTtcctggaaGaCaggcgggccgcggtggacacctactgcagac acaactacggggttggtgagagcttcacagtgcagcggcg;

DRB1*1308:
(SEQ ID NO: 2697)
ttcttggagtactctacgtctgagtgtcatttcttcaatgggacggagcgggtgcggttcctggaCagatacttcc ataaccaggaggagtTcgtgcgcttcgacagcgacgtgggggagtaccgggcggtgacggagctggggcggcctga tgccgagtactggaacagccagaaggacatcctggaagacGAgcgggccgcggtggacacctactgcagacacaac tacggggttgtGgagagcttcacagtg;

DRB1*1309:
(SEQ ID NO: 2698)
tttcttggagtactctacgtctgagtgtcatttcttcaatgggacggagcgggtgcggttcctggacagatacttc cataaccaggaggagaAcgtgcgcttcgacagcgacgtgggggagtTccgggcggtgacggagctggggcggcctg atgccgagtactggaacagccagaaggacAtcctggagcaggCgcgggccgcggtggacacctactgcagacacaa ctacggggttgtGgagagcttcacagtg;

DRB1*1310:
(SEQ ID NO: 2699)
cacgtttcttggagtactctacgtctgagtgtcatttcttcaatgggacggagcgggtgcggttcctggaCagata cttccataaccaggaggagAacgtgcgcttcgacagcgacgtgggggagtTccgggcggtgacggagctggggcgg cctgatgccgagtactggaacagccagaaggacAtcctggaagaCaAgcgggccgcggtggacacctactgcagac acaactacggggttgtGgagagcttcacagtgcagcggcgag;

DRB1*1311:
(SEQ ID NO: 2700)
cacgtttcttggagtactctacgtctgagtgtcatttcttcaatgggacggagcgggtgcggttcctggacagata cttctataaccaagaggagtAcgtgcgcttcgacagcgacgtgggggagtTccgggcggtgacggagctggggcgg cctgatgccgagtactggaacagccagaaggacTtcctggaagaCaggcgggccgcggtggacacctactgcagac acaactacggggttgtGgagagcttcacagtgcagcggcgag;

DRB1*1312:
(SEQ ID NO: 2701)
cacgtttcttggagtactctacgtCtgagtgtcatttcttcaatgggacggagcgggtgcggttcctggacagata cttctataaccaagaggagtacgtgcgcttcgacagcgacgtgggggagtaccgggcggtgacggagctggggcgg cctaGcgccgagtactggaacagccagaaggacAtcctggaagaCaggcgggccgcggtggacacctactgcagac acaactacggggttggtgagagcttcacagtgcagcggcgag;

DRB1*1313:
(SEQ ID NO: 2702)
cacgtttcttggagtactctacgtCtgagtgtcatttcttcaatgggacggagcgggtgcggttcctggacagata cttctataaccaagaggagtacgtgcgcttcgacagcgacgtgggggagtaccgggcggtgacggagctggggcgg cctaGcgccgagtactggaacagccagaaggacAtcctggaagacaggcgggcccTggtggacacctactgcagac acaactacggggttggtgagagcttcacagtgca;

DRB1*131401:
(SEQ ID NO: 2703)
tacgtctgagtgtcatttcttcaatgggacggagcgggtgcggttcctggacagatacttctataaccaagaggag tAcgtgcgcttcgacagcgacgtgggggagtTccgggcggtgacggagctggggcggcctgatgccgagtactgga acagccagaaggacTtcctggaaGaCaggcgggccgcggtggacacctactgcagacacaactacggggttggtg;

DRB1*131402:
(SEQ ID NO: 2704)
cacgtttcttggagtactctacgtctgagtgtcatttcttcaatgggacggagcgggtgcggttcctggacagata cttctataaccaagaggagtacgtgcgcttcgacagcgacgtgggggagtTccgggcggtgacggagctggggcgg cctgacgcTgagtactggaacagccagaaggacTtcctggaaGaCaggcgggccgcggtggacacctactgcagac acaactacggggttggtgagagcttcacagtgcagcggcgag;

DRB1*1315:
(SEQ ID NO: 2705)
tttcttggagtactctacgtctgagtgtcatttcttcaatgggacggagcgggtgcggttcctggaGagatacttc cataaccaggaggagaacgtgcgcttcgacagcgacgtgggggagtTccgggcggtgacggagctggggcggcctg atgccgagtactggaacagccagaaggacatcctggaagacGAgcgggccgcggtggacacctactgcagacacaa ctacggggttgtGgagagcttcacagtgcagcggcgag;

DRB1*1316:
(SEQ ID NO: 2706)
ggagtactctacgtctgagtgtcatttcttcaatgggacggagcgggtgcggttcctggacagatacttccataac caggaggagaacgtgcgcttcgacagcgacgtgggggagttccgggcggtgacggagctggggcggcctgatgccg agtactggaacagccagaaggacatcctggaagacgagcgggccgcggtggacacctactgcagacacaactacgg ggttgAtgagagcttcaca;

DRB1*1317:
(SEQ ID NO: 2707)
ggggacaccagaccacgtttcttggagtactctacgggtgagtgtTatttcttcaatgggacggagcgggtgcggt tcctggacagatacttctataaccaagaggagtacgtgcgcttcgacagcgacgtgggggagttccgggcggtgac ggagctggggcggcctgatgccgagtactggaacagccagaaggacatcctggaagacgAgcgggccgcggtggac acctactgcagacacaactacggggttgtGgagagcttcacagtgcagcggcgag;

DRB1*1318:
(SEQ ID NO: 2708)
cacgtttcttggagtactctacgtctgagtgtcatttcttcaatgggacggagcgggtgcggttcctggacagata cttccataaccaggaggagAacgtgcgcttcgacagcgacgtgggggagtTccggcggtgacggagctggggcgg cctgatgccgagtactggaacagccagaaggacTtcctggaagacaggcgggcccTggtggacacctactgcagac acaactacggggttgtGgagagcttcacagtgcagcggcgag;

DRB1*1319:
(SEQ ID NO: 2709)
ggggacaccagaccacgtttcttggagtactctacgtctgagtgtcatttcttcaatgggacggagcgggtgcggt tcctggaGagatacttccataaccaggaggagtTcgtgcgcttcgacagcgacgtgggggagtaccgggcggtgac ggagctggggcggcctgatgccgagtactggaacagccagaaggacatcctggaagacGAgcgggccgcggtggac acctactgcagacacaactacggggttgtGgagagcttcacagtgcagcggcgag;

DRB1*1320:
(SEQ ID NO: 2710)
cacgtttcttggagtactctacgtctgagtgtcatttcttcaatgggacggagcgggtgcggttcctggaCagata cttccataaccaggaggagAAcgtgcgcttcgacagcgacgtgggggagtTccggcggtgacggagctggggcgg cctgatgccgagtactggaacagccagaaggacctcctggaagacGAgcgggccgcggtggacacctactgcagac acaactacggggttgtGgagagcttcacagtgcagcgg;

DRB1*1321:
(SEQ ID NO: 2711)
ggggacaccagaccacgtttcttggagtactctacgtCtgagtgtcatttcttcaatgggacggagcgggtgcggt tcctggacagatacttctataaccaagaggagtacgtgcgcttcgacagcgacgtgggggagtTccgggcggtgac ggagctggggcggcctaGcgccgagtactggaacagccagaaggacTtcctggaagaCaggcgggccgcggtggac acctactgcagacacaactacggggttggtgagagcttcacagtgcagcggcgag;

DRB1*1322:
(SEQ ID NO: 2712)
gaccacgtttcttggagtactctacgtCtgagtgtcatttcttcaatgggacggagcgggtgcggttcctggaCag atacttctataaccaagaggagtAcgtgcgcttcgacagcgacgtgggggagtTccggcggtgacggagctgggg cggcctgatgccgagtactggaacagccagaaggacAtcctggaagacGAgcgggccgcggtggacacctactgca gacacaactacggggttgtGgagagcttcacagtgcagcggcgag;

DRB1*1323:
(SEQ ID NO: 2713)
cgtttcttggagtactctacgtctgagtgtcatttcttcaatgggacggagcgggtgcggttcctggacagatact tctataaccaagaggagtacgtgcgcttcgacagcgacgtgggggagttccgggcggtgacggagctggggcggcc tgatgccgagtactggaacagccagaaggacatcctggaagacGAgcgggccgcggtggacacctactgcagacac aactacggggttggtgagagcttcacGgtgcagcggc;

DRB1*1324:
(SEQ ID NO: 2714)
cgtttcttggagtactctacgtctgagtgtcatttcttcaatgggacggagcgggtgcggttcctggacagatact tctataaccaagaggagtacgtgcgcttcgacagcgacgtgggggagtTccggcggtgacggagctggggcggcc tgatgccgagtactggaacagccagaaggacTtcctggaagacGAgcgggccgcggtggacacctactgcagacac aactacggggttgtGgagagcttcacagtgcagcggc;

DRB1*1325:
(SEQ ID NO: 2715)
cacgtttcttggagtactCtaCgtCtgaGtgtcatttcttcaatgggacggagcgggtgcggttcctggaCagata cttctataaccaagaggagtAcgtgcgcttcgacagcgacgtgggggagtTccggcggtgacggagctggggcgg cctgatgccgagtactggaacagccagaaggacctcctggaagaCaggcgggccgcggtggacacctactgcagac acaactacggggttggtgaga;

-continued

DRB1*1326:
(SEQ ID NO: 2716)
cacgtttcttggagtactctacgtctgagtgtcatttcttcaatgggacggagcgggtgcggttcctggagagata cttcCataaccaGgaggagAAcgtgcgcttcgacagcgacgtgggggagtaccggccggtgacggagctggggcgg cctgacgcTgagtactggaacagccagaaggacTtcctggaaGaCaggcgCgccgcggtggacacctactgcagac acaactacggggttggtgagagcttcacagtgcagcggcgag;

DRB1*1327:
(SEQ ID NO: 2717)
cacgtttcttggagtactctacgtctgagtgtcatttcttcaatgggacggagcgggtgcggtAcctggacagata cttccataaccaggaggagaacgtgcgcttcgacagcgacgtgggggagttccggccggtgacggagctggggcgg cctgatgccgagtactggaacagccagaaggacatcctggaagacGAgcgggccgcggtggacacctactgcagac acaactacggggttgtGgagagcttcacagtgcagcggcgag;

DRB1*1328:
(SEQ ID NO: 2718)
ttggagtactctacgtctgagtgtcatttcttcaatgggacggagcgggtgcggttcctggacagatacttccata accaggaggagaacgtgcgcttcgacagcgacgtgggggagttccggccggtgacggagctggggcggcctgatgc cgagtactggaacagccagaaggacatcctggaagacgagcgggccgcggtggacacctactgcagacacaactac

Cgggttgtggagagcttcac;

DRB1*1329:
(SEQ ID NO: 2719)
cacgtttcttggagtactctacgtctgagtgtcatttcttcaatgggacggagcgggtgcggttcctggaCagata cttccataaccaggaggagAAcgtgcgcttcgacagcgacgtgggggagtTccggccggtgacggagctggggcgg cctgatgccgagtactggaacagccagaaggacctcctggaagacGAgcgggccgcggtggacacctactgcagac acaactacggggttggtgagagcttcacagtgcagcggcgag;

DRB1*1330:
(SEQ ID NO: 2720)
tttcttggagtactctacgtctgagtgtcatttcttcaatgggacggagcgggtgcggttcctggacagatacttc tataaccaagaggagtacgtgcgcttcgacagcgacgtgggggagtTccggccggtgacggagctggggcggccta GcgccgagtactggaacagccagaaggacAtcctggaagaCaggcgggccgcggtggacacctactgcagacacaa ctacggggttggtgagagcttcaca;

DRB1*1331:
(SEQ ID NO: 2721)
cacgtttcttggagtactctacgtctgagtgtcatttcttcaatgggacggagcgggtgcggttcctggacagata cttccataaccaggaggagaacgtgcgcttcgacagcgacgtgggggagttccggccggtgacggagctggggcgg cctgTcgccgagtactggaacagccagaaggacAtcctggaagacGAgcgggccgcggtggacacctactgcagac acaactacggggttggtgagagcttcacagtgcagcggcga;

DRB1*1332:
(SEQ ID NO: 2722)
cacgtttcttggagtactctacgtctgagtgtcatttcttcaatgggacggagcgggtgcggttcctggacagata cttccataaccaggaggagAacgtgcgcttcgacagcgacgtgggggagtaccggccggtgacggagctggggcgg cctaGcgccgagtactggaacagccagaaggacatcctggaagacGAgcgggccgcggtggacacctactgcagac acaactacggggttgtGgagagcttcacagtgcagcggcgag;

DRB1*1333:
(SEQ ID NO: 2723)
cacgtttcttggagtactctacgtctgagtgtcatttcttcaatgggacggagcgggtgcggttcctggacagata cttctataaccaagaggagtacgtgcgcttcgacagcgacgtgggggagtaccggccggtgacggagctggggcgg cctaGcgccgagtactggaacagccagaaggacatcctggaagaCaagcgggccgcggtggacaActactgcagac acaactacggggttggtg;

DRB1*1334:
(SEQ ID NO: 2724)
cacgtttcttggagtactctacgtctgagtgtcatttcttcaatgggacggagcgggtgcggttcctggacagata cttccataaccaggaggagaacCtgcgcttcgacagcgacgtgggggagttccgggcggtgacggagctggggcgg cctgatgccgagtactggaacagccagaaggacatcctggaagacGAgcgggccgcggtggacacctactgcagac acaactacggggttggtgagagcttcacagtgcagcggcgag;

DRB1*1335:
(SEQ ID NO: 2725)
cacgtttcttggagtactctacgtctgagtgtcatttcttcaatgggacggagcgggtgcggttcctggacagata cttccataaccaggaggagaacgtgcgcttcgacagcgacgtgggggagttccTggcggtgacggagctggggcgg cctgatgccgagtactggaacagccagaaggacatcctggaagacgagcgggccgcggtggacacctactgcagac acaactacggggttgtggagagcttcacagtgcagcgg;

DRB1*1336:
(SEQ ID NO: 2726)
cacgtttcttggagtactctacgtctgagtgtcatttcttcaatgggacggagcgggtgcggttcctggaCagata cttccataaccaggaggagAAcgtgcgcttcgacagcgacgtgggggagtaccgggcggtgacggagctggggcgg cctgatgccgagtactggaacagccagaaggacAtcctggaagacGAgcgggccgcggtggacacctactgcagac acaactacggggttggtgagagcttcacagtgcagcggcgag;

DRB1*1337:
(SEQ ID NO: 2727)
cacgtttcttggagtactctacgtctgagtgtcatttcttcaatgggacggagcgggtgcggttcctggacagata cttctataaccaagaggagtacgtgcgcttcgacagcgacgtgggggagtaccgggcggtgacggagctggggcgg cctgatgccgagtactggaacagccagaaggacatcctggaagaCaAgcgggccgcggtggacacctactgcagac acaactacggggttggtgagagcttcacGgtgcagcggcga;

DRB1*1338:
(SEQ ID NO: 2728)
cacgtttcttggagtactctacgtctgagtgtcatttcttcaatgggacggagcgggtgcggttcctggacagata cttctataaccaagaggagtacgtgcgcttcgacagcgacgtgggggagtaccgggcggtgacggagctggggcgg cctaGcgccgagtactggaacagccagaaggacatcctggaagacGAgcgggccgcggtggacacctactgcagac acaactacggggttggt;

DRB1*1339:
(SEQ ID NO: 2729)
cacgtttcttggagtactctacgtctgagtgtcatttcttcaatgggacggagcgggtgcggttcctggacagata cttccataaccaggaggagaacgtgcgcttcgacagcgacgtgggggagttccgggcggtgacggagctggggcgg cctgatgccgagtCctggaacagccagaaggacAtcctggaagacGAgcgggccgcggtggacacctactgcagac acaactacggggttggtgagagcttcacagtgcagcggcgag;

DRB1*1340:
(SEQ ID NO: 2730)
ttggagtactctacgtctgagtgtcatttcttcaatgggacggagcgggtgcggttcctggaCagatacttccata accaggaggagAAcgtgcgcttcgacagcgacgtgggggagtaccgggcggtgacggagctggggcggcctgatgc cgagtactggaacagccagaaggacAtcctggaagacGAgcgggccgcggtggacacctactgcagacacaactac ggggttgtGgagagcttcacagtgcagcggcg;

DRB1*1341:
(SEQ ID NO: 2731)
cacgtttcttggagtactctacgtctgagtgtcatttcttcaatgggacggagcgggtgcggtAcctggacagata cttccataaccaggaggagaacgtgcgcttcgacagcgacgtgggggagttccgggcggtgacggagctggggcgg cctgatgccgagtactggaacagccagaaggacatcctggaagacGAgcgggccgcggtggacacctactgcagac acaactacggggttggtgagagcttcacagtgcagcggcgag;

-continued

DRB1*1342:
(SEQ ID NO: 2732)
cacgtttcttggagtactctacgtctgagtgtcatttcttcaatgggacggagcgggtgcggttcctggacagata
cttccataaccaggaggagAacgtgcgcttcgacagcgacgtgggggagttccgggcggtgacggagctggggcgg
cctgatgccgagtactggaacagccagaaggacTtcctggaagaCaggcgggccgcggtggacacctactgcagac
acaactacggggttgtGgagagcttcacagtgcagcggcgag;

DRB1*1343:
(SEQ ID NO: 2733)
cacgtttcttggagtactctacgtctgagtgtcatttcttcaatgggacggagcgggtgcggttcctggacagata
cttccataaccaggaggagaacgtgcgcttcgacagcgacgtgggggagtTccgggcggtgacggagctggggcgg
cctgCtgcggagcactggaacagccagaaggacctcctggaagacGAgcgggccgcggtggacacctactgcagac
acaactacggggttgtGgagagcttcacagtgcagcggcga;

DRB1*1344:
(SEQ ID NO: 2734)
cacgtttcttggagtactctacgtCtgaGtgtcatttcttcaatgggacggagcgggtgcggttcctggaCagata
cttctataaccaagaggagtAcgtgcgcttcgacagcgacgtgggggagtTccgggcggtgacggagctggggcgg
cctgatgccgagtactggaacagccagaaggacctcctggagcagaggcgggccgcggtggacacctactgcagac
acaactacggggttgtGgagagcttcacagtgcagcggcgag;

DRB1*1345:
(SEQ ID NO: 2735)
ttggagtactctacgtctgagtgtcatttcttcaatgggacggagcgggtgcggttcctggacagatacttctata
accaagaggagtacgtgcgcttcgacagcgacgtgggggagtTccgggcggtgacggagctggggcggcctgCtgc
ggagcactggaacagccagaaggacAtcctggaagacGAgcgggccgcggtggacacctactgcagacacaactac
ggggttggtgagag;

DRB1*1346:
(SEQ ID NO: 2736)
cacgtttcttggagtactctacgtctgagtgtcatttcttcaatgggacggagcgggtgcggttcctggacagata
cttctataaccaagaggagtAcgtgcgcttcgacagcgacgtgggggagttccgggcggtgacggagctggggcgg
cctgTCgccgagtactggaacagccagaaggacTtcctggaAgaCaggcgggccgcggtggacacctactgcagac
acaactacggggttggtgagagcttcacagtgcagcggcgag;

DRB1*1347:
(SEQ ID NO: 2737)
cacgtttcttggagtactctacgtCtgagtgtcatttcttcaatgggacggagcgggtgcggttcctggacagata
cttctataaccaagaggagtAcgtgcgcttcgacagcgacgtgggggagtaccgggcggtgacggagctggggcgg
cctgatgccgagtactggaacagccagaaggacTtcctggaagacaggcgggcccTgGtggacacctactgcagac
acaactacggggttggtgagagcttcacGgtgcagcggcgag;

DRB1*1348:
(SEQ ID NO: 2738)
cacgtttcttggagtactctacgtctgagtgtcatttcttcaatgggacggagcgggtgcggttcctggacagata
cttctataaccaagaggagtacgtgcgcttcgacagcgacgtgggggagtaccgggcggtgacggagctggggcgg
cctaGcgccgagtactggaacagccagaaggacatcctggaagacGAgcgggccgcggtggacacctactgcagac
acaactacggggttgtGgagagcttcacagtgcagcggcgag;

DRB1*1349:
(SEQ ID NO: 2739)
cacgtttcttggagtactctacgtCtgagtgtcatttcttcaatgggacggagcgggtgcggttcctggacagata
cttctataaccaagaggagtacgtgcgcttcgacagcgacgtgggggagtaccgggcggtgacggagctggggcgg
cctaGcgccgagtactggaacagccagaaggacTtcctggaagaCaggcgggccgcggtggacacctactgcagac
acaactacggggttggtgagagcttcacagtgcagcgg;

DRB1*1350:
(SEQ ID NO: 2740)
cacgtttcttggagtactctacgtctgaGtgtcatttcttcaatgggacggagcgggtgcggttcctggacagata cttctataaccaagaggagAacgtgcgcttcgacagcgacgtgggggagtTccgggcggtgacggagctggggcgg cctgatgccgagtactggaacagccagaaggacTtcctggaagaCaggcgggccgcggtggacacctactgcagac acaactacggggttggtgagagcttcacagtgcagcggcgag;

DRB1*1351:
(SEQ ID NO: 2741)
cacgtttcttggagtactctacgtctgagtgtcatttcttcaatgggacggagcgggtgcggttcctggacagata cttccataaccaggaggagaacgtgcgcttcgacagcgacgtgggggagttccgggcgTtgacggagctggggcgg cctgatgccgagtactggaacagccagaaggacatcctggaagacgagcgggccgcggtggacacctactgcagac acaactacggggttgtggagagcttcacagtgcagcggcgag;

DRB1*1352:
(SEQ ID NO: 2742)
cacgtttcttggagtactctacgtctgagtgtcatttcttcaatgggacggagcgggtgcggttcctggaCagata cttccataaccaGgaggagtAcgtgcgcttcgacagcgacgtgggggagtTccgggcggtgacggagctggggcgg cctgatgccgagtactggaacagccagaaggacAtcctggaagacGAgcgggccgcggtggacacctactgcagac acaactacggggttgtGgagagcttcacagtg;

DRB1*1353:
(SEQ ID NO: 2743)
cacgtttcttggagtactctacgtctgagtgtcatttcttcaatgggacggagcgggtgcggttcctggaGagata cttccataaccaggaggagaAcgtgcgcttcgacagcgacgtgggggagtaccgggcggtgacggagctggggcgg cctgatgccgagtactggaacagccagaaggacatcctggaagacGAgcgggccgcggtggacacctactgcagac acaactacggggttgtGgagagcttcacagtgcagcggcga;

DRB1*1354:
(SEQ ID NO: 2744)
cacgtttcttggagtactctacgtctgagtgtcatttcttcaatgggacggagcgggtgcggttcctggacagata cttctataaccaagaggagtacgtgcgcttcgacagcgacgtgggggagttccgggcggtgacggagctggggcgg cctgtcgccgagtCctggaacagccagaaggacttcctggaagacGAgcgggccgcggtggacacctactgcagac acaactacggggttgtGgagagcttcacagtgcagcggcgag;

DRB1*1355:
(SEQ ID NO: 2745)
tttcttggagtactctacgtCtgagtgtcatttcttcaatgggacggagcgggtgcggttcctggacagatacttc tataaccaagaggagtacgtgcgcttcgacagcgacgtgggggagtaccgggcggtgacggagctggggcggccta gCgccgagtactggaacagccagaaggacTtcctggaagacaggcgggcccTggtggacacctactgcagacacaa ctacggggttggtgagagcttcacGgtgcagcggcgag;

DRB1*140101:
(SEQ ID NO: 2746)
atggtgtgtctgaggctccctggaggctcctgcatggcagTtctgacagtgacactgatggtgctgagctccccac tggctttggctggggacaccagaccacgtttcttggagtactctacgtCtgagtgtcatttcttcaatgggacgga gcgggtgcggttcctggacagatacttccataaccaggaggagttcgtgcgcttcgacagcgacgtgggggagtac cgggcggtgacggagctggggcggcctgctgcggagcactggaacagccagaaggacctcctggagcggaggcggg ccgAggtggacacctaTtgcagacacaactacggggttgtGgagagcttcacagtgcagcggcgag;

DRB1*140102:
(SEQ ID NO: 2747)
cacgtttcttggagtacTctacgtCtgagtgtcatttcttcaatgggacggagcgggtgcggttcctggacagata cttccataaccaggaggagttcgtgcgcttcgacagcgacgtgggggagtaccgggcggtgacggagctggggcgg cctgCtgcggagcactggaacagccagaaggacctcctggagcggaggcgggccgAggtggacacctactgcagac acaactacggggttgtGg;

DRB1*1402:

(SEQ ID NO: 2748)

atggtgtgtctgaggctccctggaggctcctgcatggcagTtctgacagtgacactgatggtgctgagctccccac tggctttggctggggacaccagaccacgtttcttggagtactctacgtctgagtgtcatttcttcaatgggacgga gcgggtgcggttcctggagagatacttccataaccaGgaggagAAcgtgcgcttcgacagcgacgtgggggagtac cgggcggtgacggagctggggcggcctgatgccgagtactggaacagccagaaggacctcctggagcagaggcggg ccgcggtggacacctactgcagacacaactacggggttggtgagagcttcacagtgcagcggcgag;

DRB1*1403:

(SEQ ID NO: 2749)

atggtgtgtctgaggctccctggaggctcctgcatggcagTtctgacagtgacactgatggtgctgagctccccac tggctttggctggggacaccagaccacgtttcttggagtactctacgtctgagtgtcatttcttcaatgggacgga gcgggtgcggttcctggagagatacttccataaccaggaggagAacgtgcgcttcgacagcgacgtgggggagtac cgggcggtgacggagctggggcggcctgatgccgagtactggaacagccagaaggacctcctggaagacaggcggg cccTggtggacacctactgcagacacaactacggggttggtgagagcttcacagtgcagcggcgag;

DRB1*1404:

(SEQ ID NO: 2750)

atggtgtgtctgaggctccctggaggctcctgcatggcagTtctgacagtgacactgatggtgctgagctccccac tggctttggctggggacaccagaccacgtttcttggagtactctacgggtgagtgtTatttcttcaatgggacgga gcgggtgcggttcctggacagatacttccataaccaggaggagttcgtgcgcttcgacagcgacgtgggggagtac cgggcggtgacggagctggggcggcctgctgcggagcactggaacagccagaaggacctcctggagcggaggcggg ccgAggtggacacctaTtgcagacacaactacggggttgtGgagagcttcacagtgcagcggcgag;

DRB1*140501:

(SEQ ID NO: 2751)

cacgtttcttggagtactctacgtctgagtgtcaAttcttcaatgggacggagcgggtgcggttcctggacagata cttccataaccaggaggagttcgtgcgcttcgacagcgacgtgggggagtaccgggcggtgacggagctggggcgg cctgatgcTgagtactggaacagccagaaggacctcctggagcggaggcgggccgaggtggacacctaTtgcagac acaactacggggttgtGgagagcttcacagtgcagcggcgag;

DRB1*140502:

(SEQ ID NO: 2752)

cacgtttcttggagtactctacgtctgagtgtcaAttcttcaatgggacggagcgggtgcggttcctggacagata cttccataaccaggaggagttcgtgcgcttcgacagcgacgtgggggagtaccgggcggtgacggagctggggcgg cctgatgccgagtactggaacagccagaaggacctcctggagcggaggcgggccgaggtggacacctaTtgcagac acaactacggggttgtGgagagcttcacagtgcagcggcgag;

DRB1*1406:

(SEQ ID NO: 2753)

cacgtttcttggagtactctaCgtctgagtgtcatttcttcaatgggacggagcgggtgcggttcctggaGagata cttccataaccaggaggagAAcgtgcgcttcgacagcgacgtgggggagtaccgggcggtgacggagctggggcgg cctgatgccgagtactggaacagccagaaggacctcctggagcagaggcgggccgcggtggacacctactgcagac acaactacggggttgtGgagagcttcacagtgcagcggcgag;

DRB1*140701:

(SEQ ID NO: 2754)

cacgtttcttggagtacTctacgtCtgagtgtcatttcttcaatgggacggagcgggtgcggttcctggacagata cttccataaccaggaggagttcgtgcgcttcgacagcgacgtgggggagtaccgggcggtgacggagctggggcgg cctgCtgcggagcactggaacagccagaaggacctcctggagcggaggcgggccgAggtggacacctaTtgcagac acaactacggggttggtgagagcttcacagtgcagcggcga;

-continued

DRB1*140702:
(SEQ ID NO: 2755)
cacgtttcttggagtactctacgtctgagtgtcatttcttcaatgggacggagcgggtgcggttcctggacagata cttccataaccaggaggagttcgtgcgcttcgacagcgacgtgggggagtaccgggcggtgacggagctggggcgg cctgCtgcggagcactggaacagccagaaggacctcctggagcggaggcgggccgaggtggacacctaTtgcagac acaactacggggttggtgagagcttcacGgtgcagcggcgag;

DRB1*1408:
(SEQ ID NO: 2756)
cacgtttcttggagtacTctacgtCtgagtgtcatttcttcaatgggacggagcgggtgcggttcctggacagata cttccataaccaggaggagttcgtgcgcttcgacagcgacgtgggggagtaccgggcggtgacggagctggggcgg cctgatgcggagCactggaacagccagaaggacctcctggagcggaggcgggccgAggtggacacctaTtgcagac acaactacggggttgtGgagagcttcacagtgcagcggcga;

DRB1*1409:
(SEQ ID NO: 2757)
tttcttggagtactctaCgtctgaGtgtcatttcttcaatgggacggagcgggtgcggttcctggaCagatacttc CataaccaGgaggagAacgtgcgcttcgacagcgacgtgggggagtaccgggcggtgacggagctggggcggcctg atgccgagtactggaacagccagaaggacctcctggagcagaggcgggccgcggtggacacctactgcagacacaa ctacggggttggtgagagcttcacagtgcagcggcgag;

DRB1*1410:
(SEQ ID NO: 2758)
ttcttggagcaggttaaacAtgagtgtcatttcttcaatgggacggagcgggtgcggttcctggacagatacttcc ataaccaggaggagttcgtgcgcttcgacagcgacgtgggggagtaccgggcggtgacggagctggggcggcctgC tgcggagcactggaacagccagaaggacctcctggagcggaggcgggccgAggtggacacctaTtgcagacacaac tacggggttgtGgagagcttcacagtgcagcgg;

DRB1*1411:
(SEQ ID NO: 2759)
gagtactctacggGtgagtgtTatttcttcaatgggacggagcgggtgcggttcctggacagatacttccataacc aggaggagttcgtgcgcttcgacagcgacgtgggggagtaccgggcggtgacggagctggggcggcctgatgAGga gtactggaacagccagaaggacctcctggagcggaggcgggccgAggtggacacctaTtgcagacacaactacggg gttgtGg;

DRB1*1412:
(SEQ ID NO: 2760)
gtctgagtgtcatttcttcaatgggacggagcgggtgcggttcctggaGagatacttccataaccaggaggagAAc gtgcgcttcgacagcgacgtgggggagtaccgggcggtgacggagctggggcggcctgatgccgagtactggaaca gccagaaggacctcctggaagacaggcgggcccTggtggacacctactgcagacacaactacggggttgtGg;

DRB1*1413:
(SEQ ID NO: 2761)
gagtactctacgtctgagtgtcatttcttcaatgggacggagcgggtgcggttcctggaGagatacttccataacc aggaggagAAcgtgcgcttcgacagcgacgtgggggagtaccgggcggtgacggagctggggcggcctaGcgccga gtactggaacagccagaaggacctcctggagcagaggcgggccgcggtggacacctactgcagacacaactacggg gttggtg;

DRB1*1414:
(SEQ ID NO: 2762)
ttcttggagtactctacgtCtgagtgtcatttcttcaatgggacggagcgggtgcggttcctggacagatacttcc ataaccaggaggagtTcgtgcgcttcgacagcgacgtgggggagtaccgggcggtgacggagctggggcggcctga tgccgagtactggaacagccagaaggacctcctggagcggaggcgggccgAggtggacacctaTtgcagacacaac tacggggttggtgagagcttcacagtg;

DRB1*1415:
(SEQ ID NO: 2763)
ctctacgggtgagtgtTatttcttcaatgggacggagcgggtgcggttcctggacagatacttccataaccaggag gagtTcgtgcgcttcgacagcgacgtgggggagtaccgggcggtgacggagctgggcggcctgatgccgagtact ggaacagccagaaggacTtcctggaagacaggcgggcccTggtggacacctactgcagacacaactacggggttgt

Ggagagcttcacagtgcag;

DRB1*1416:
(SEQ ID NO: 2764)
ttggagtactctacgtctgagtgtcatttcttcaatgggacggagcgggtgcggttcctggacagatacttccata accaggaggagttcgtgcgcttcgacagcgacgtgggggagtaccgggcggtgacggagctgggcggcctgCtgc ggagcactggaacagccagaaggacAtcctggaagacGAgcgggccgcggtggacacctactgcagacacaactac ggggttgtGgag;

DRB1*1417:
(SEQ ID NO: 2765)
cacgtttcttggagtactctacgtctgaGtgtcatttcttcaatgggacggagcgggtgcggttcctggaCagata cttcCataaccaggaggagAacgtgcgcttcgacagcgacgtgggggagtTccgggcggtgacggagctgggcgg cctgatgccgagtactggaacagccagaaggacctcctggagcagaggcgggccgcggtggacacctactgcagac acaactacggggttgtGgagagcttcacagtgcagcgg;

DRB1*1418:
(SEQ ID NO: 2766)
gagtactctacgtctgagtgtcatttcttcaatgggacggagcgggtgcggttcctggagagatacttccataacc aggaggagAAcgtgcgcttcgacagcgacgtgggggagtaccgggcggtgacggagctgggcggcctgatgcTga gtactggaacagccagaaggacctcctggagcggaggcgggccgAggtggacacctaTtgcagacacaactacggg gttgtGgagagcttcacagtgcagcggcga;

DRB1*1419:
(SEQ ID NO: 2767)
ggggacaccagaccacgtttcttggAgtactctaCgtctgagtgtcatttcttcaatgggacggagcgggtgcggt tcctggaGagatacttccataaccaggaggagAAcgtgcgcttcgacagcgacgtgggggagtaccgggcggtgac ggagctgggcggcctgatgccgagtactggaacagccagaaggacctcctggagcagaAgcgggccgcggtggac acctactgcagacacaactacggggttggtgagagcttcaca;

DRB1*1420:
(SEQ ID NO: 2768)
ttggagtactctacgtCtgagtgtcatttcttcaatgggacggagcgggtgcggttCctggaGagatacttccata accaggaggagtTcgtgcgcttcgacagcgacgtgggggagtaccgggcggtgacggagctgggcggcctgatgc cgagtactggaacagccagaaggacctcctggagcagaggcgggccgcggtggacacctactgcagacacaactac ggggttgtGgaga;

DRB1*1421:
(SEQ ID NO: 2769)
ttggagtactctacgtctgagtgtcatttcttcaatgggacggagcgggtgcggttcctggaCagatacttcCata accaggaggagAacgtgcgcttcgacagcgacgtgggggagtTccgggcggtgacggagctgggcggcctgatgc cgagtactggaacagccagaaggacctcctggagcagaAgcgggccgcggtggacacctactgcagacacaactac ggggttgtGgaga;

DRB1*1422:
(SEQ ID NO: 2770)
cacgtttcttggagtactctacgtctgagtgtcatttcttcaatgggacggagcgggtgcggttcctggacagata cttccataaccaggaggagtTcgtgcgcttcgacagcgacgtgggggagtaccgggcggtgacggagctgggcgg cctgCtgcggagCactggaacagccagaaggacTtcctggaAgaCaggcgggccgcggtggacacctactgcagac acaactacggggttggtgagagcttcacagtgcagcggcgag;

-continued

DRB1*1423:
(SEQ ID NO: 2771)
cacgtttcttggagtacTctacgtCtgagtgtcatttcttcaatgggacggagcgggtgcggttcctggacagata cttccataaccaggaggagtTcgtgcgcttcgacagcgacgtgggggagtaccgggcggtgacggagctggggcgg cctgatgccgagtactggaacagccagaaggacctcctggagcggaggcgggccgAggtggacacctaTtgcagac acaactacggggttgtGgagagcttcacagtgcagcggcgag;

DRB1*1424:
(SEQ ID NO: 2772)
ttcttggagtactctacgtctgagtgtcatttcttcaatgggacggagcgggtgcggttcctggaGagatacttcc ataaccaGgaggagAAcgtgcgcttcgacagcgacgtgggggagtaccgggcggtgacggagctggggcggcctga tgccgagtactggaacagccagaaggacAtcctggagcagGCgcgggccgcggtggacacctactgcagacacaac tacggggttggtgagagcttcacagtgcagcggcgag;

DRB1*1425:
(SEQ ID NO: 2773)
tttcttggagtactctacgtCtgagtgtcatttcttcaatgggacggagcgggtgcggttcctggacagatacttc tataaccaagaggagtAcgtgcgcttcgacagcgacgtgggggagtaccgggcggtgacggagctggggcggcctg CtgcggagCactggaacagccagaaggacTtcctggaAgaCaggcgggccgcggtggacacctactgcagacacaa ctacggggttggtgagagcttcacagtgcagcggcgag;

DRB1*1426:
(SEQ ID NO: 2774)
cacgtttcttggagtactctacgtctgagtgtcatttcttcaatgggacggagcgggtgcAgttcctggacagata cttccataaccaggaggagttcgtgcgcttcgacagcgacgtgggggagtaccgggcggtgacggagctggggcgg cctgctgcggagcactggaacagccagaaggacctcctggagcggaggcgggccgaggtggacacctattgcagac acaactacggggttgtGgagagcttcacagtgcagcggcgag;

DRB1*1427:
(SEQ ID NO: 2775)
cacgtttcttggagtactctacgtctgagtgtcatttcttcaatgggacggagcgggtgcggttcctggaGagata cttccataaccaggaggagAAcgtgcgcttcgacagcgacgtgggggagtaccgggcggtgacggagctggggcgg cctgatgccgagtactggaacagccagaaggacTtcctggaagaCaggcgggccCTggtggacacctactgcagac acaactacggggttggtgagagcttcacagtgcagcggcgag;

DRB1*1428:
(SEQ ID NO: 2776)
cacgtttcttggagtactctacgggtgagtgttatttcttcaatgggacggagcgggtgcggttcctggacagata cttccataaccaggaggagttcgtgcgcttcgacagcgacgtgggggagtaccgggcggtgacggagctggggcgg cctgCtgcggagcactggaacagccagaaggacctcctggagcggaggcgggccgaggtggacacctattgcagac acaactacggggCtgtGgagagcttcaca;

DRB1*1429:
(SEQ ID NO: 2777)
cacgtttcttggagtactctacgtctgagtgtcatttcttcaatgggacggagcgggtgcggttcctggaGagata cttccataaccaGgaggagAAcgtgcgcttcgacagcgacgtgggggagtaccgggcggtgacggagctggggcgg cctgatgccgagtactggaacagccagaaggacctcctggagcagaggcgggccgcggtggacacctactgcagac acaactacggggCtgtggagagcttcacagtgcagcggcgag;

DRB1*1430:
(SEQ ID NO: 2778)
tttcttggagtactctacgtctgaGtgtcatttcttcaatgggacggagcgggtgcggttcctggaCagatacttc CataaccaGgaggagAacgtgcgcttcgacagcgacgtgggggagtTccgggcggtgacggagctggggcggcctg atgccgagtactggaacagccagaaggacctcctggagcagaggcgggccgcggtggacacctactgcagacacaa ctacggggttggtgagagcttcaca;

DRB1*1431:
(SEQ ID NO: 2779)
tttcttggagtactctacgggtgagtgtTatttcttcaatgggacggagcgggtgcggttcctggacagatacttc cataaccaggaggagttcgtgcgcttcgacagcgacgtgggggagtaccgggcggtgacggagctggggcggcctg CtgcggagcactggaacagccagaaggacctcctggagcggaggcgggccgcggtggacacctaTtgcagacacaa ctacggggttgtGgagagcttcaca;

DRB1*1432:
(SEQ ID NO: 2780)
cacgtttcttggagtacTctacgtCtgagtgtcatttcttcaatgggacggagcgggtgcggttcctggacagata cttccataaccaggaggagttcgtgcgcttcgacagcgacgtgggggagtaccgggcggtgacggagctggggcgg cctgCtgcggagcactggaacagccagaaggacctcctggagcGgaggcgggccgcggtggacacctactgcagac acaactacggggttgtGgagagcttcacagtgcagcggcgag;

DRB1*1433:
(SEQ ID NO: 2781)
ttggagtactctacgtctgagtgtcatttcttcaatgggacggagcgggtgcggttcctggacagatacttccata accaggaggagaAcgtgcgcttcgacagcgacgtgggggagtTccgggcggtgacggagctggggcggcctgatgc cgagtactggaacagccagaaggacctcctggagcagaggcgggccgAggtggacacctactgcagacacaactac ggggttgtGgagagcttcacagtgcagcggc;

DRB1*1434:
(SEQ ID NO: 2782)
cacgtttcttggagtacTctacgtCtgagtgtcatttcttcaatgggacggagcgggtgcggttcctggacagata cttccataaccaggaggagttcgtgcgcttcgacagcgacgtgggggagtaccgggcggtgacggagctggggcgg cctgatgcggagCactggaacagccagaaggacctcctggagcggaggcgggccgcggtggacacctaTtgcagac acaactacggggttgtGgagagcttcacagtgcagcggcgag;

DRB1*1435:
(SEQ ID NO: 2783)
cacgtttcttggagtactctacgtctgagtgtcatttcttcaatgggacggagcgggtgcggttcctggacagata cttccataaccaggaggagttcgtgcgcttcgacagcgacgtgggggagtTccgggcggtgacggagctggggcgg cctgCtgcggagcactggaacagccagaaggacctcctggagcggaggcgggccgAggtggacacctaTtgcagac acaactacggggttgtGgagagcttcacagtgcagcgg;

DRB1*1436:
(SEQ ID NO: 2784)
cacgtttcttggagtactctacgtctgagtgtcatttcttcaatgggacggagcgggtgcggttcctggacagata cttccataaccaggaggagttcgtgcgcttcgacagcgacgtgCgggagtaccgggcggtgacggagctggggcgg cctgatgccgagtactggaacagccagaaggacctcctggagcggaggcgggccgaggtggacacctaTtgcagac acaactacggggttggtgagagcttcacagtgcagcggcgag;

DRB1*1437:
(SEQ ID NO: 2785)
cacgtttcttggagtactctacgtctgagtgtcaAttcttcaatgggacggagcgggtgcggttcctggacagata cttccataaccaggaggagttcgtgcgcttcgacagcgacgtgggggagtaccgggcggtgacggagctggggcgg cctgatgctgagtactggaacagccagaaggacatcctggagcaggCgcgggccgcggtggacacctactgcagac acaactacggggttgtGgagagcttcacagtgcagcggcgag;

DRB1*1438:
(SEQ ID NO: 2786)
cacgtttcttggagtactctacgtctgagtgtcatttcttcaatgggacggagcgggtgcggttcctggacagata cttccataaccaggaggagttcgtgcgcttcgacagcgacgtgggggagtaccgggcggtgacggagctggggcgg cctgCtgcggagcactggaacagccagaaggacctcctggagcggaggcgggccgaggtggacaaTtactgcagac acaactacggggttgtGgagagcttcacagtgcagcggcgag;

-continued

DRB1*1439:

(SEQ ID NO: 2787)
cacgtttcttggagtaccctacgtCtgagtgtcatttcttcaatgggacggagcgggtgcggttcctggacagata cttccataaccaggaggagttcgtgcgcttcgacagcgacgtgggggagtaccgggcggtgacggagctggggcgg cctgCtgcggagcactggaacagccagaaggacctcctggagcggaggcgggccgAggtggacacctaTtgcagac acaactacggggttgtGgagagcttcacagtgcagcggcgag;

DRB1*1440:

(SEQ ID NO: 2788)
cacgtttcttggagtactctacgtctgagtgtcatttcttcaatgggacggagcgggtgcggttcctggaGagata cttccataaccaggaggagtTcgtgcgcttcgacagcgacgtgggggagtaccgggcggtgacggagctggggcgg cctgatgccgagtactggaacagccagaaggacctcctggaagaCaggcgggccCTggtggacacctactgcagac acaactacggggttggtgagagcttcacagtgcagcggcgag;

DRB1*1441:

(SEQ ID NO: 2789)
cacgtttcttggagtactctaCgtCtgagtgtcatttcttcaatgggacggagcgggtgcggttCctggaGagata cttccataaccaggaggagtTcCtgcgcttcgacagcgacgtgggggagtaccgggcggtgacggagctggggcgg cctgatgccgagtactggaacagccagaaggacctcctggagcagaggcgggccgcggtggacacctactgcagac acaactacggggttggtgagagcttcacagtgcagcggcga;

DRB1*1442:

(SEQ ID NO: 2790)
cacgtttcttggagtactctacgtctgagtgtcatttcttcaatgggacggagcgggtgcggttcctggacagata cttctataaccaagaggagtAcgtgcgcttcgacagcgacgtgggggagtTccgggcggtgacggagctggggcgg cctgatgccgagtactggaacagccagaaggacctcctggagcggaggcgggccgAggtggacacctaTtgcagac acaactacggggttggtgagagcttcacagtgcagcggcgag;

DRB1*1443:

(SEQ ID NO: 2791)
cacgtttcttggagtactctacgtctgagtgtcaattcttcaatgggacggagcgggtgcggttcctggacagata cttccataaccaggaggagttcgtgcgcttcgacagcgacgtgggggagtaccgggcggtgacggagctggggcgg cctgatgctgagtactggaacagccagaaggacctcctggagcggaggcgggccgaggtggacGcctattgcagac acaactacggggttgtggagagcttcacagtgcagcggcgag;

DRB1*1444:

(SEQ ID NO: 2792)
cacgtttcttggagtactctacgtctgagtgtcaAttcttcaatgggacggagcgggtgcggttcctggacagata cttccataaccaggaggagttcgtgcgcttcgacagcgacgtgggggagtaccgggcggtgacggagctggggcgg cctgatgcTgagtactggaacagccagaaggacctcctggagcggaggcgggccgaggtggacacctaTtgcagac acaactacggggttggtgagagcttcacagtgcagcggcgag;

DRB1*1445:

(SEQ ID NO: 2793)
cacgtttcttggagtactctacgtctgagtgtcaAttcttcaatgggacggagcgggtgcggttcctggacagata cttccataaccaggaggagttcgtgcgcttcgacagcgacgtgggggagtaccgggcggtgacggagctggggcgg cctgatgctgagtactggaacagccagaaggacAtcctggagcggaggcgggccgaggtggacacctaTtgcagac acaactacggggttgtGgagagcttcacagtgcagcggcgag;

DRB1*150101:

(SEQ ID NO: 2794)
atggtgtgtctgaagctccctggaggctcctgcatgacagcgctgacagtgacactgatggtgctgagctccccac tggctttgTctggggacacccgaccacgtttcctgtggcagcctaagagggagtgtcatttcttcaatgggacgga gcgggtgcggttcctggacagatacttctataaccaggaggagtccgtgcgcttcgacagcgacgtgggggagttc cgggcggtgacggagctggggcggcctgacgctgagtactggaacagccagaaggacatcctggagcaggcgcggg ccgcggtggacacctactgcagacacaactacggggttgtggagagcttcacagtgcagcggcgag;

-continued

DRB1*150102:
(SEQ ID NO: 2795)
cacgtttcctgtggcagcctaagagggagtgtcatttcttcaatgggacggagcgggtgcggttcctggacagata
cttctataaccaggaggagtccgtgcgcttcgacagcgacgtgggggagttccgggcggtgacggagctggggcgg
cctgacgctgagtactggaacagccagaaggacatcctggagcaggcgcgggccgcggtggacacctactgcagac
acaactacggAgttgtGgagagcttcacagtgcagcgg;

DRB1*150103:
(SEQ ID NO: 2796)
cacgtttcctgtggcagcctaagagGgagtgtcatttcttcaatgggacggagcgggtgcggttcctggacagata
cttctataaccaggaggagtccgtgcgcttcgacagcgacgtgggggagttccgggcggtgacggagctggggcgg
cctgacgctgagtactggaacagccagaaggacatcctggagcaggcgcgggccgcggtggacacctaTtgcagac
acaactacggggttgtGgagagcttcacagtgcagcgg;

DRB1*150104:
(SEQ ID NO: 2797)
cacgtttcctgtggcagcctaagagGgagtgtcatttcttcaatgggacggagcgggtgcggttcctggacagata
cttctataaccaggaggagtccgtgcgcttcgacagcgacgtgggggagtTccgggcggtgacggagctggggcgg
cctgatgccgagtactggaacagccagaaggacAtcctggagcaggCgcgggccgcggtggacacctactgcagac
acaactacggggttgtGgagagcttcacagtgcagcggcgag;

DRB1*150201:
(SEQ ID NO: 2798)
ggggacacccgaccacgtttcctgtggcagcctaagagGgagtgtcatttcttcaatgggacggagcgggtgcggt
tcctggacagatacttctataaccaggaggagtccgtgcgcttcgacagcgacgtgggggagtTccgggcggtgac
ggagctggggcggcctgacgcTgagtactggaacagccagaaggacAtcctggagcaggCgcgggccgcggtggac
acctactgcagacacaactacggggttggtgagagcttcacagtgcagcggcgag;

DRB1*150202:
(SEQ ID NO: 2799)
gagtgtcatttcttcaatgggacggagcgggtgcggttcctggacagatacttctataaccaggaggagtccgtgc
gcttcgacagcgacgtgggggagtTccgggcggtgacggagctggggcggcctgatgccgagtactggaacagcca
gaaggacAtcctggagcagGCgcgggccgcggtggacacctactgcagacacaactacggggttggtg;

DRB1*150203:
(SEQ ID NO: 2800)
cacgtttcctgtggcagcctaagagggagtgtcatttcttcaatgggacggagcgggtgcggttcctggacagata
cttctataaTcaggaggagtccgtgcgcttcgacagcgacgtgggggagttccgggcggtgacggagctggggcgg
cctgacgctgagtactggaacagccagaaggacatcctggagcaggcgcgggccgcggtggacacctactgcagac
acaactacggggttggtg;

DRB1*1503:
(SEQ ID NO: 2801)
ggggacacccgaccacgtttcctgtggcagcctaagagGgagtgtcatttcttcaatgggacggagcgggtgcggt
tcctggacagaCacttctataaccaggaggagtccgtgcgcttcgacagcgacgtgggggagtTccgggcggtgac
ggagctggggcggcctgacgcTgagtactggaacagccagaaggacAtcctggagcaggCgcgggccgcggtggac
acctactgcagacacaactacggggttgtGgagagcttcacagtgcagcggcgag;

DRB1*1504:
(SEQ ID NO: 2802)
ttcctgtggcagcctaagagGgagtgtcatttcttcaatgggacggagcgggtgcggttcctggacagatacttct
ataaccaggaggagtccgtgcgcttcgacagcgacgtgggggagttccgggcggtgacggagctggggcggcctga
cgctgagtactggaacagccagaaggacTtcctggagcaggCgcgggccgcggtggacacctactgcagacacaac
tacggggttgtGgagagcttcacagtg;

DRB1*1505:

(SEQ ID NO: 2803)
ttcctgtggcagcctaagagGgagtgtcatttcttcaatgggacggagcgggtgcggttcctggacagatacttct ataaccaggaggagtccgtgcgcttcgacagcgacgtgggggagtTccgggcggtgacggagctggggcggcctga cgcTgagtactggaacagccagaaggacctcctggagcaggCgcgggccgcggtggacacctactgcagacacaac tacggggttgtGgagagcttcacagtgcagcgg;

DRB1*1506:

(SEQ ID NO: 2804)
ctgtggcagcctaagagggagtgtcatttcttcaatgggacggagcgggtgcggttcctggacagatacttctata accaggaggagtccgtgcgcttcgacagcgacgtgggggagttccgggcggCgacggagctggggcggcctgacgc tgagtactggaacagccagaaggacatcctggagcaggcgcgggccgcggtggacacctactgcagacacaactac ggggttgtggagagcttcacagtgcagcggcgag;

DRB1*1507:

(SEQ ID NO: 2805)
tttcctgtggcagcctaagagGgagtgtcatttcttcaatgggacggagcgggtgcggttcctggacagatacttc tataaccaggaggagtccgtgcgcttcgacagcgacgtgggggagtaccgggcggtgacggagctggggcggcctg acgcTgagtactggaacagccagaaggacAtcctggagcaggCgcgggccgcggtggacacctactgcagacacaa ctacggggttgtGgagagc;

DRB1*1508:

(SEQ ID NO: 2806)
cacgtttcctgtggcagcctaagagggagtgtcatttcttcaatgggacggagcgggtgcggttcctggacagata cttctataaccaggaggagtccgtgcgcttcgacagcgacgtgggggagttccgggcggtgacggagctggggcgg cctgacgctgagtactggaacagccagaagAacatcctggagcaggcgcgggccgcggtggacacctactgcagac acaactacggggttggtgagagcttcacagtgcagcggcgag;

DRB1*1509:

(SEQ ID NO: 2807)
cacgtttcctgtggcagcctaagagggagtgtcatttcttcaatgggacggagcgggtgcggttcctggacagata cttctataaccaggaggagtccgtgcgcttcgacagcgacgtgggggagttccAggcggtgacggagctggggcgg cctgacgctgagtactggaacagccagaaggacatcctggagcaggCgcgggccgcggtggacacctactgcagac acaactacggggttgtggagagcttcacagtgcagcggcgag;

DRB1*1510:

(SEQ ID NO: 2808)
gtttcctgtggcagcctaagagGgagtgtcatttcttcaatgggacggagcgggtgcggttcctggacagatactt ctataaccaggaggagtccgtgcgcttcgacagcgacgtgggggagttccgggcggtgacggagctggggcggcct gacgctgagtactggaacagccagaaggacatcctggaagacgAgcgggccgcggtggacacctactgcagacaca actacggggttgtGgagagc;

DRB1*1511:

(SEQ ID NO: 2809)
cacgtttcctgtggcagcctaagagGgagtgtcatttcttcaatgggacggagcgggtgcggttcctggacagata cttctataaccaggaggagtccgtgcgcttcgacagcgacgtgggggagtaccgggcggtgacggagctggggcgg cctgacgcTgagtactggaacagccagaaggacAtcctggagcaggCgcgggccgcggtggacacctactgcagac acaactacggggttggtgagagcttcacagtgcagcggcgag;

DRB1*1512:

(SEQ ID NO: 2810)
gcacgtttcctgtggcagcctaagagGgagtgtcatttcttcaatgggacggagcgggtgcggttcctggacagat acttctataaccaggaggagtccgtgcgcttcgacagcgacgtgggggagttccgggcggtgacggagctggggcg gcctaGCgccgagtactggaacagccagaaggacAtcctggagcaggCgcgggccgcggtggacacctactgcaga cacaactacggggttgtGgagagcttcacagtgcagcggcgag;

DRB1*1513:
(SEQ ID NO: 2811)
cacgtttcctgtggcagcctaagagGgagtgtcatttcttcaatgggacggagcgggtgcggttcctggacagata cttctataaccaggaggagtccgtgcgcttcgacagcgacgtgggggagtTccggcggtgacggagctggggcgg cctgacgcTgagtactggaacagcca...ggacAtcctggagcaggCgcgggccgcggtggacacctactgcagac acaactacggggttgtGgagagcttcacagtgcagcgg;

DRB1*160101:
(SEQ ID NO: 2812)
atggtgtgtctgaagctccctggaggctcctgcatgacagcgctgacagtgacactgatggtgctgagctccccac tggctttggctggggacacccgaccacgtttcctgtggcagcctaagagGgagtgtcatttcttcaatgggacgga gcgggtgcggttcctggacagatacttctataaccaggaggagtccgtgcgcttcgacagcgacgtgggggagtac cgggcggtgacggagctggggcggcctgacgctgagtactggaacagccagaaggacTtcctggaagacaggcgCg ccgcggtggacacctactgcagacacaactacggggttggtgagagcttcacagtgcagcggcgag;

DRB1*160102:
(SEQ ID NO: 2813)
cgtttcctgtggcagcctaagagGgagtgtcatttcttcaatgggacggagcgggtgcggttcctggacagatact tctataaccaggaggagtccgtgcgcttcgacagcgacgtgggggagtaccgggcggtgacggagctggggcggcc tgacgctgagtactggaacagccagaaggacTtcctggaagaCaggcgggccgcggtggacacctactgcagacac aactacggggttggtgagagcttcaca;

DRB1*160201;
(SEQ ID NO: 2814)
atggtgtgtctgaagctccctggaggctcctgcatgacagcgctgacagtgacactgatggtgctgagctccccac tggctttggctggggacacccgaccacgtttcctgtggcagcctaagagGgagtgtcatttcttcaatgggacgga gcgggtgcggttcctggacagatacttctataaccaggaggagtccgtgcgcttcgacagcgacgtgggggagtac cgggcggtgacggagctggggcggcctgacgctgagtactggaacagccagaaggacctcctggaagacaggcgCg ccgcggtggacacctactgcagacacaactacggggttggtgagagcttcacagtgcagcggcgag;

DRB1*160202:
(SEQ ID NO: 2815)
tttcctgtggcagcctaagagGgagtgtcatttcttcaatgggacggagcgggtgcggttcctggacagatacttc tataaccaggaggagtccgtgcgcttcgacagcgacgtgggggagtaccgggcggtgacggagctggggcggcctg acgctgagtactggaacagccagaaggacctcctggaagaCaggcgggccgcggtggacacctactgcagacacaa ctacggggttggtg;

DRB1*1603:
(SEQ ID NO: 2816)
atggtgtgtctgaagctccctggaggctcctgcatgacagcgctgacagtgacactgatggtgctgagctccccac tggctttggctggggacacccgaccacgtttcctgtggcagcctaagagggagtgtcatttcttcaatgggacgga gcgggtgcggttcctggacagatacttctataaccaggaggagtccgtgcgcttcgacagcgacgtgggggagtac cgggcggtgacggagctggggcggcctgacgctgagtactggaacagccagaaggacttcctggaagacagggCcg ccgcggtggacacctactgcagacacaactacggggttggtgagagcttcacagtgcagcggcgag;

DRB1*1604:
(SEQ ID NO: 2817)
tggcagcctaagagggagtgtcatttcttcaatgggacggagcgggtgcggttcctggacagatacttctataacc aGgaggagtccgtgcgcttcgacagcgacgtgggggagtaccgggcggtgacggagctggggcggcctgacgcTga gtactggaacagccagaaggacTtcctggaagaCaggcgggccCTggtggacacctactgcagacacaactacggg gttggtg;

DRB1*1605:
(SEQ ID NO: 2818)
ctgtggcagcctaagagGgagtgtcatttcttcaatgggacggagcgggtgcggttcctggacagatacttctata accaggaggagtccgtgcgcttcgacagcgacgtgggggagtaccgggcggtgacggagctggggcggcctgacgc tgagtactggaacagccagaaggacAtcctggaagacaggcgCgccgcggtggacacctactgcagacacaactac ggggttggtgag;

DRB1*1607:

(SEQ ID NO: 2819)

cacgtttcctgtggcagcctaagagggagtgtcatttcttcaatgggacggagcgggtgcggttccCggacagata cttctataaccaggaggagtccgtgcgcttcgacagcgacgtgggggagtaccgggcggtgacggagctggggcgg cctgacgctgagtactggaacagccagaaggacatcctggaagacaggcgcgccgcggtggacacctactgcagac acaactacggggttggtgagagcttcacagtgca;

DRB1*1608:

(SEQ ID NO: 2820)

cacgtttcctgtggcagcctaagagGgagtgtcatttcttcaatgggacggagcgggtgcggttcctggacagata cttctataaccaggaggagaAcgtgcgcttcgacagcgacgtgggggagtaccgggcggtgacggagctggggcgg cctgacgctgagtactggaacagccagaaggacTtcctggaagacaggcgCgccgcggtggacacctactgcagac acaactacggggttggtgagagcttcacagtgcagcggcgag;

DRB3*010101:

(SEQ ID NO: 2821)

ggggacacccgaccacgtttcttggagctgcGtaagtctgagtgtcatttcttcaatgggacggagcgggtgcggt acctggaCagatacttccataaccaggaggagttcCtgcgcttcgacagcgacgtgggggagtaccgggcggtgac ggagctggggcggcctgtCgccgagtcctggaacagccagaaggacctcctggagcagaagcggggccGgtggac aaTtactgcagacacaactacggggttggtgagagcttcacagtgcagcggcgag;

DRB3*01010201:

(SEQ ID NO: 2822)

atggtgtgtctgaagctccctggaggctccagcttggcagcgttgacagtgacactgatggtgctgagctcccgac tggcttttCgctggggacacccgaccacgtttcttggagctgcgtaagtctgagtgtcatttcttcaatgggacgga gcgggtgcggtacctggacagatacttccataaccaggaggagttcctgcgcttcgacagcgacgtgggggagtac cgggcggtgacggagctggggcggcctgtcgccgagtcctggaacagccagaaggacctcctggagcagaagcggg gccGggtggacaattactgcagacacaactacggggttggtgagagcttcacagtgcagcggcgag;

DRB3*010103:

(SEQ ID NO: 2823)

ggggacacccgaccacgtttcttggagctgcGtaagtctgagtgtcatttcttcaatgggacggagcgggtgcggt acctggaCagatacttccataaccaggaggagttcCtgcgcttcgacagcgacgtgggggagtaccgggcggtgac ggagctggggcggcctgttgccgagtcctggaacagccagaaggacctcctggagcagaagcggggccGgtggac aaTtactgcagacacaactacggggttggtgagagc;

DRB3*010104:

(SEQ ID NO: 2824)

cacgtttcttggagctgcgtaagtctgagtgtcatttcttcaatgggacggagcgggtgcggtacctggacagata cttccataaccaggaggagttcctgcgcttcgacagcgacgtgggggagtaccgggcggtgacggagctggggcgg cctgtcgccgagtcctggaacagccagaaggacctcctggagcagaagcggggccgggtggacaaTtactgcagac acaactacggAgttggtg;

DRB3*0102:

(SEQ ID NO: 2825)

ggggacacccgaccacgtttcttggagctgTGtaagtctgagtgtcatttcttcaatgggacggagcgggtgcggt acctggaCagatacttccataaccaggaggagttcCtgcgcttcgacagcgacgtggggagtaccgggcggtgac ggagctggggcggcctgtCgccgagtcctggaacagccagaaggacctcctggagcagaagcggggccGgtggac aaTtactgcagacacaactacggggttggtgagagc;

DRB3*0103:
(SEQ ID NO: 2826)
cacgtttcttggagctgcGtaagtctgagtgtcatttcttcaatgggacggagcgggtgcggtacctggaGagata cttccataaccaggaggagttcCtgcgcttcgacagcgacgtgggggagtaccgggcggtgacggagctggggcgg cctgtCgccgagtcctggaacagccagaaggacctcctggagcagaagcggggccGgGgtggacaaTtactgcagac acaactacggggttggtgagagc;

DRB3*0104:
(SEQ ID NO: 2827)
cacgtttctcggagctgcGtaagtctgagtgtcatttcttcaatgggacggagcgggtgcggtacctggaCagata cttccataaccaggaggagttcCtgcgcttcgacagcgacgtgggggagtaccgggcggtgacggagctggggcgg cctgtCgccgagtcctggaacagccagaaggacctcctggagcagaagcggggccGgtggacaaTtactgcagac acaactacggggttggtgagagcttcaca;

DRB3*0105:
(SEQ ID NO: 2828)
cacgtttcttggagctgcgtaagtctgagtgtcatttcttcaatgggacggagcgggtgcggtacctgAacagata cttccataaccaggaggagttcctgcgcttcgacagcgacgtgggggagtaccgggcggtgacggagctggggcgg cctgtcgccgagtcctggaacagccagaaggacctcctggagcagaagcggggccgggtggacaaTtactgcagac acaactacggggttggtgagagcttcacagtgcagcggcg;

DRB3*0106:
(SEQ ID NO: 2829)
cacgtttcttggagctgcGtaagtctgagtgtcatttcttcaatgggacggagcgggtgcggtacctggaCagata cttccataaccaggaggagtTcgtgcgcttcgacagcgacgtgggggagtaccgggcggtgacggagctggggcgg cctgtCgccgagtcctggaacagccagaaggacctcctggagcagaagcggggccGgtggacaaTtactgcagac acaactacggggttggtg;

DRB3*0107:
(SEQ ID NO: 2830)
cacgtttcttggagctgcGtaagtctgagtgtcatttcttcaatgggacggagcgggtgcggtacctggacagata cttccataaccaggaggagtacgcgcgcttcgacagcgacgtgggggagtaccgggcggtgagggagctggggcgg cctgatgccgagtactggaacagccagaaggacctcctggagcagaAgcggggccAgtggacaaTtactgcagac acaactacggggttggtg;

DRB3*0108:
(SEQ ID NO: 2831)
cacgtttcttggagctgcGtaagtctgagtgtcatttcttcaatgggacggagcgggtgcggtacctggacagata cttccataaccaggaggagAAcgtgcgcttcgacagcgacgtgggggagtaccgggcggtgacggagctggggcgg cctgtCgccgagtcctggaacagccagaaggacctcctggagcagaagcggggccGgtggacaaTtactgcagac acaactacggggttggtgagagcttcacagtgcagcgg;

DRB3*0109:
(SEQ ID NO: 2832)
cacgtttcttggagctgcGtaagtctgagtgtcatttcttcaatgggacggagcgggtgcggttcctggagagaca cttccataaccaggaggagtacgCgcgcttcgacagcgacgtgggggagtaccgggcggtgacggagctggggcgg cctgtCgccgagtcctggaacagccagaaggacctcctggagcagaagcggggccGgtggacaaTtactgcagac acaactacggggttggtgagagcttcacagtgcagcgg;

DRB3*0110:
(SEQ ID NO: 2833)
cacgtttcttggagctgcgtaagtctgagtgtcatttcttcaatgggacggagcgggtgcggtacctggacagata cttccataaccaggaggagttcctgAgcttcgacagcgacgtgggggagtaccgggcggtgacggagctggggcgg cctgtcgccgagtcctggaacagccagaaggacctcctggagcagaagcggggccgggtggacaattactgcagac acaactacggggttggtg;

DRB3*0201:
(SEQ ID NO: 2834)
atggtgtgtctgaagctccctggaggctccagcttggcagcgttgacagtgacactgatggtgctgagctcccgac tggcttTCgctggggacacccgaccacgtttcttggagctgcttaagtctgagtgtcatttcttcaatgggacgga gcgggtgcggttcctggagagacacttccataaccaggaggagtacgcgcgcttcgacagcgacgtgggggagtac cgggcggtgaggagctggggcggcctgatgccgagtactggaacagccagaaggacctcctggagcagaagcggg gccaggtggacaattactgcagacacaactacggggttgtGgagagcttcacagtgcagcggcgag;

DRB3*020201:
(SEQ ID NO: 2835)
ggggacacccgaccacgtttcttgGagctgcttaagtctgagtgtcatttcttcaatgggacggagcgggtgcggt tcctggagagaCacttccataaccaggaggagtacgCgcgcttcgacagcgacgtgggggagtaccgggcggtgaG ggagctggggcggcctgatgccgagtactggaacagccagaaggacctcctggagcagaagcggggccaggtggac aaTtactgcagacacaactacggggttggtgagagcttcacagtgcagcggcgag;

DRB3*020202:
(SEQ ID NO: 2836)
cacgtttcttggagctgcttaagtctgagtgtcatttcttcaatgggacggagcgggtgcggttcctggagagaCa cttccataaccaggaggagtacgCgcgcttcgacagcgacgtgggggagtaccgggcggtgaGggagctggggcgg cctgatgccgagtactggaacagccagaaggacctcctggagcagaagcggggccAggtggacaActactgcagac acaactacggggttggtg;

DRB3*020203:
(SEQ ID NO: 2837)
cacgtttcttggagctgcttaagtctgagtgtcatttcttcaatgggacggagcgggtgcggttcctggagagaca cttccataaccaggaggagtacgcgcgcttcgacagcgacgtgggggagtaccgggcggtgagggagctggggcgg cctgatgccgagtactggaacagccagaaggacctcctggagcagaagcggggccaggtggacaattactgcagGc acaactacggggttggtgagagcttcacagtgcagcggcgag;

DRB3*020204:
(SEQ ID NO: 2838)
cacgtttcttggagctgcttaagtctgagtgtcatttcttcaatgggacggagcgggtgcggttcctggagagaca cttccataaccaggaggagtacgcgcgcttcgacagcgacgtgggggagtaccgggcggtgaGggagctggggcgg cctgatgcGgagtactggaacagccagaaggacctcctggagcagaagcggggccaggtggacaaTtactgcagac acaactacggggttggtgagagcttcacagtgcagcggcgag;

DRB3*0203:
(SEQ ID NO: 2839)
ttggagctgcttaagtctgagtgtcatttcttcaatgggacggagcgggtgcggttcctggagagaCacttccata accaGgaggagtccgtgcgcttcgacagcgacgtgggggagtaccgggcggtgaGggagctggggcggcctgatgc cgagtactggaacagccagaaggacctcctggagcagaagcggggccaggtggacaaTtactgcagacacaactac ggggttggtgaga;

DRB3*0204:
(SEQ ID NO: 2840)
cacgtttcttggagctgcttaagtctgagtgtcatttcttcaatgggacggagcgggtgcggttcctggagagaca cttccataaccaggaggagtacgcgcgcttcgacagcgacgtgggggagtaccgggcggtgaGggagctggggcgg cctgatgccgagtactggaacagccagaaggacctcctggagcagaagcggggccGgtggacaActactgcagac acaactacggggttgtGgagagcttcacagtgcagcggcgag;

DRB3*0205:
(SEQ ID NO: 2841)
cgtttcttggagctgcttaagtctgagtgtcatttcttcaatgggacggagcgggtgcggttcctggaGagatact tccataaccaggaggagtacgCgcgcttcgacagcgacgtgggggagtaccgggcggtgaGggagctggggcggcc tgatgccgagtactggaacagccagaaggacctcctggagcagaagcggggccaggtggacaaTtactgcagacac aactacggggttggtgagagcttcacagtgcag;

DRB3*0206:
(SEQ ID NO: 2842)
cacgtttcttggagctgcttaagtctgagtgtcatttcttcaatgggacggagcgggtgcggttcctggagagaca cttccataaccaggaggagAacgCgcgcttcgacagcgacgtgggggagtaccgggcggtgaGggagctggggcgg cctgatgccgagtactggaacagccagaaggacctcctggagcagaagcggggccaggtggacaaTtactgcagac acaactacggggttggtg;

DRB3*0207:
(SEQ ID NO: 2843)
ttggagctgcttaagtctgagtgtcatttcttcaatgggacggagcgggtgcggttcctggagagacacttccata accaggaggagtacgcgcgcttcgacagcgacgtgggggagtaccgggcggtgaGggagctgggcggcctgTCgc cgagtactggaacagccagaaggacctcctggagcagaagcggggccaggtggacaaTtactgcagacacaactac ggggttggtgagag;

DRB3*0208:
(SEQ ID NO: 2844)
cacgtttcttggagctgcttaagtctgagtgtcatttcttcaatgggacggagcgggtgcggttcctggagagaca cttccataaccaggaggagtacgcgcgcttcgacagcgacgtgggggagtaccgggcggtgaGggagctggggcgg cctaGCgccgagtactggaacagccagaaggacctcctggagcagaagcggggccaggtggacaaTtactgcagac acaactacggggttggtg;

DRB3*0209:
(SEQ ID NO: 2845)
cacgtttcttggagctgcttaagtctgagtgtcatttcttcaatgggacggagcgggtgcggttcctggagagaca cttccataaccaggaggagtacGcgcgcttcgacagcgacgtgggggagtaccgggcggtgacggagctggggcgg cctgtcgccgagtCctggaacagccagaaggacctcctggagcagaagcggggccAggtggacaaTtactgcagac acaactacggggttggtgagagcttcaca;

DRB3*0210:
(SEQ ID NO: 2846)
ggggacacccgaccacgtttcttgGagctgcttaagtctgagtgtcatttcttcaatgggacggagcgggtgcggt tcctggagagaCacttccataaccaggaggagtacGcgcgcttcgacagcgacgtgggggagtaccgggcggtgac ggagctggggcggcctgatgccgagtactggaacagccagaaggacctcctggagcagaagcggggccAggtggac aaTtactgcagacacaactacggggttggtgagagcttcacagtgcagcggcgag;

DRB3*0211:
(SEQ ID NO: 2847)
ggggacacccgaccacgtttcttggagctgcttaagtctgagtgtcatttcttcaatgggacggagcgggtgcggt tcctggagagacacttccataaccaggaggagtacgcgcgcttcgacagcgacgtgggggagtaccgggcggtgaG ggagctgggcggcctgatgccgagtactggaacagccagaaggacAtcctggagcagaagcggggccaggtggac aaTtactgcagacacaactacggggttggtgagagcttcacagtgcagcggcgag;

DRB3*0212:
(SEQ ID NO: 2848)
cacgtttcttgcagctgcttaagtctgagtgtcatttcttcaatgggacggagcgggtgcggttcctggagagaCa cttccataaccaggaggagtacGcgcgcttcgacagcgacgtgggggagtaccgggcggtgaGggagctggggcgg cctgatgccgagtactggaacagccagaaggacctcctggagcagaagcggggccaggtggacaaTtactgcagac acaactacggggttggtgagagcttcacagtgcagcggcgag;

DRB3*0213:
(SEQ ID NO: 2849)
cacgtttcttggagctgcttaagtctgagtgtcatttcttcaatgggacggagcgggtgcggCtcctggagagaca cttccataaccaggaggagtacgcgcgcttcgacagcgacgtgggggagtaccgggcggtgagggagctggggcgg cctgatgccgagtactggaacagccagaaggacctcctggagcagaagcggggccaggtggacaattactgcagac acaactacggggttggtgagagcttcacagtgcagcggcgag;

-continued

DRB3*0214:
(SEQ ID NO: 2850)
cacgtttcttggagctgcttaagtctgagtgtcatttcttcaatgggacggagcgggtgcggttcctggagagaca cttccataaccaggaggagtacgcgcgcttcgacagcgacgtgggggagtaccgggcggtgagggagctggggcgg cctgatgccgagtactggaacagccagaaggacctcctggagcagaagcggggccaggtggacaattactgcagac acaactacggggttgCtgagagcttcacagtgcagcggcgag;

DRB3*0215:
(SEQ ID NO: 2851)
cacgtttcttggagctgcttaagtctgagtgtcatttcttcaatgggacggagcgggtgcggttcctggagagaCa cttccataaccaggaggagtacgCgcgcttcgacagcgacgtgggggagtaccgggcggtgaGggagctggggcgg cctgatgccgagtactggaacagccagaaggacctcctggagcagaagcggggccAggtggacacctactgcagac acaactacggggttggtgagagcttcacagtgcagcggcgag;

DRB3*0216:
(SEQ ID NO: 2852)
cacgtttcttggagctgcttaagtctgagtgtcatttcttcaatgggacggagcgggtgcggttcctggagagaca cttccataaccaggaggagtacgcgcgcttcgacagcgacgtgggggagtaccgggcggtgaGggagctggggcgg cctgctgcggagCactggaacagccagaaggacctcctggagcagaagcggggccaggtggacaaTtactgcagac acaactacggggttggtgagagcttcacagtgcagcggcgag;

DRB3*0217:
(SEQ ID NO: 2853)
cacgtttcttggagctgcttaagtctgagtgtcatttcttcaatgggacggagcgggtgcggttcctggagagaca cttccataaccaggaggagtacgcgcgcttcgacagcgacgtgggggagtaccgggcggtgaGggagctggggcgg cctgatgccgagtactggaacagccagaaggaTtcctggagcagaagcggggccaggtggacaaTtactgcagac acaactacggggttggtgagagcttcacagtgcagcggcgag;

DRB3*030101:
(SEQ ID NO: 2854)
ggggacacccgaccacgtttcttggagctgcttaagtctgagtgtcatttcttcaatgggacggagcgggtgcggt tcctggagagatacttccataaccaggaggagttcgtgcgcttcgacagcgacgtgggggagtaccgggcggtgac ggagctggggcggcctgtcgccgagtCctggaacagccagaaggacctcctggagcagaagcggggccaggtggac aaTtactgcagacacaactacggggttgtGgagagcttcacagtgcagcggcgag;

DRB3*030102:
(SEQ ID NO: 2855)
cacgtttcttggagctgcttaagtctgagtgtcatttcttcaatgggacggagcgggtgcggttcctggagagata cttccataaccaggaggagttcgtgcgcttcgacagcgacgtgggggagtaccgggcggtgacggagctggggcgg cctgtcgccgagtcctggaacagccagaaggacctcctggagcagaagcggggccaggtggacaattactgcagac acaactacggCgttgtggagagcttcacagtgcagcggcgag;

DRB3*0302:
(SEQ ID NO: 2856)
cacgtttcttggagctgcttaagtctgagtgtcatttcttcaatgggacggagcgggtgcggttcctggagagaCa cttccataaccaggaggagttcgtgcgcttcgacagcgacgtgggggagtaccgggcggtgacggagctggggcgg cctgtcgccgagtCctggaacagccagaaggacctcctggagcagaagcggggccaggtggacaaTtactgcagac acaactacggggttgtGg;

DRB3*0303:
(SEQ ID NO: 2857)
tttcttggagctgcttaagtctgagtgtcatttcttcaatgggacggagcgggtgcggttcctggaGagatacttc cataaccaggaggagtTcgtgcgcttcgacagcgacgtgggggagtaccgggcggtgacggagctggggcggcctg tCgccgagtCctggaacagccagaaggacctcctggagcagaagcggggccGgtggacaaTtactgcagacacaa ctacggggttggtgagagcttcaca;

DRB4*010101:

(SEQ ID NO: 2858)
atggtgtgtctgaagctccctggaggctcctgtatggcagcgctgacagtgacattgaCggtgctgagctccccac tggctttggctggggacacccaaccacgtttcttggagcaggctaagtgtgagtgtcatttcctcaatgggacgga gcgagtgtggaacctgatcagatacatctataaccaagaggagtacgcgcgctacaacagtgacctgggggagtac caggcggtgacggagctggggcggcctgacgctgagtactggaacagccagaaggacctcctggagcggaggcggg ccgaggtggacacctactgcagatacaactacggggttgtggagagcttcacagtgcagcggcgag;

DRB4*0102:

(SEQ ID NO: 2959)
gagcgagtgtggaacctgatcagatacatctataaccaagaggagtacgcgcgctacaacagtgacctgggggagt accaggcggtgacggagctggggcggcctgacgctgagtactggaacagccagaaggacctcctggagcggaggcg ggccgaggtggGcacctactgcagatacaactacggggttgtggagagcttcacagtgcagcggcgag;

DRB4*010302:

(SEQ ID NO: 2860)
ggggacacccaaccacgtttcttggagcaggctaagtgtgagtgtcatttcCtcaatgggacggagcgagtgtgga aCctgatcagatacatctataaccaagaggagtacgcgcgctacaacagtgacctgggggagtaccaggcggtgac ggagctggggcggcctgacgctgagtactggaacagccagaaggacctcctggagcggaggcgggccgaggtggac acctactgcagaTacaactacggggttgtggagagcttcacagtgcagcggcgag;

DRB4*010303:

(SEQ ID NO: 2861)
atggtgtgtctgaagctccctggaggctcctgtatggcagcgctgacagtgacattgaCggtgctgagctccccac tggctttggctggggacacccaaccacgtttcttggagcaggctaagtgtgagtgtcatttcctcaatgggacgga gcgagtgtggaacctgatcagatacatctataaccaagaggagtacgcgcgctacaacagtgacctgggggagtac caggcggtgacggagctggggcggcctgacgctgagtactggaacagccagaaggacctcctggagcggaggcggg ccgaggtggacacctaTtgcagatacaactacggggttgtggagagcttcacagtgcagcggcgag;

DRB4*010304:

(SEQ ID NO: 2862)
cacgtttcttggagcaggctaagtgtgagtgtcatttcctcaatgggacggagcgagtgtggaacctgatcagata catctataaccaagaggagtacgcgcgctacaacagtgaTctgggggagtaccaggcggtgacggagctggggcgg cctgacgctgagtactggaacagccagaaggacctcctggagcggaggcgggccgaggtggacacctactgcagat acaactacggggttgtggagagcttcacagtgcagcggcgag;

DRB4*0104:

(SEQ ID NO: 2863)
cacgtttcttggagcaggctaagtgtgagtgtcatttcctcaatgggacggagcgagtgtggaacctgatcagata catctataaccaagaggagtacgcgcgctacaacagtgacctgggggagtaccaggcggtgacggagctggggcgg cctgacgctgagtactggaacagccagaaggacctcctggagcggaggcgggccgaggtggacaActactgcagaT acaactacggggttgtggagagcttcacagtgcagcggcgag;

DRB4*0105:

(SEQ ID NO: 2864)
ttggagcaggctaagtgtgagtgtcatttcCtcaatgggacggagcgagtgtggAacctgatcagatacatctata accaagaggagtacgcgcgctacaacagtgacctgggggagtaccaggcggtgacggagctggggcggcctgacgc tgagtactggaacagccagaaggacctcctggagcggaggcgggccgaggtggacacctactgcagacacaactac ggggttgtggagag;

DRB4*0106:

(SEQ ID NO: 2865)
cacgtttcttggagcaggctaagtgtgagtgtcatttcCtcaatgggacggagcgagtgtggaaCctgatcagata catctataaccaagaggagtacgcgcgctacaacagtgacctgggggagtaccaggcggtgacggagctggggcgg cctgacgctgagtactggaacagccagaaggacctcctggagcggaggcgggccgaggtggacacctactgcagaT acaactacggggttgtggagagcttcacagtgcagcggcgag;

DRB4*0201N:

(SEQ ID NO: 2866)
ggtgctgagctccccactggctttggctggggacacccAaccacgtttcttggagcaggctaagtgtgagtgtcat ttcctcaatgggacggagcctgatcagatacatctataaccaagaggagtacgcgcgctacaacagtgacctgggg gagtaccaggcggtgacggagctggggcggcctgacgctgagtactggaacagccagaaggacctcctggagcgga ggcgggccgaggtggacacctactgcagatacaactacggggttgtGgagagcttcacagtgcagcggcgag;

DRB5*010101:

(SEQ ID NO: 2867)
atggtgtgtctgaagctccctggaggttcctacatggcaaAgctgacagtgacactgatggtgctgagctccccac tggctttggctggggacacccgaccacgtttcttgcagcaggataagtatgagtgtcatttcttcaacgggacgga gcgggtgcggttcctgcacagagacatctataaccaagaggaggacttgcgcttcgacagcgacgtgggggagtac cggcggtgacggagctggggcggcctgacgctgagtactggaacagccagaaggacttcctggaagacaggcgcg ccgcggtggacacctactgcagacacaactacggggttggtgagagcttcacagtgcagcggcgag;

DRB5*010102:

(SEQ ID NO: 2868)
cacgtttcttgcagcaggataagtatgagtgtcatttcttcaacgggacggagcgggtgcggttcctgcacagaga catctataaccaagaggaggacTtgcgcttcgacagcgacgtgggggagtaccggcggtgacggagctggggcgg cctgacgcTgagtactggaacagccagaaggacTtcctggaaGaCaggcgggccgcggtggacacctactgcagac acaactacggggttggtgagagcttcaca;

DRB5*0102:

(SEQ ID NO: 2869)
ggggacacccgaccacgtttcttgCagcaggataagtatgagtgtcatttcttcaacgggacggagcgggtgcggt tcctgcacagaggcatctataaccaagaggagAacgtgcgcttcgacagcgacgtgggggagtaccggcggtgac ggagctggggcggcctgacgctgagtactggaacagccagaaggacTtcctggaaGacaggcgCgccgcggtggac acctactgcagacacaactacggggttggtgagagcttcacagtgcagcggcgag;

DRB5*0103;

(SEQ ID NO: 2870)
ttgcagcaggataagtatgagtgtcatttcttcaacgggacggagcgggtgcggttcctgcacagaGgcatctata accaagaggagaacgtgcgcttcgacagcgacgtgggggagtaccggcggtgacggagctggggcggcctgacgc tgagtactggaacagccagaaggacttcctggaagacaCgcgCgccgcggtggacacctactgcagacacaactac ggggttggtgagagcttcacag;

DRB5*0104:

(SEQ ID NO: 2871)
ggggacacccgaccacgtttcttgcagcaggataagtatgagtgtcatttcttcaacgggacggagcgggtgcggt tcctgcacagagacatctataaccaagaggaggacTtgcgcttcgacagcgacgtgggggagtaccggcggtgac ggagctggggcggcctgacgctgagtactggaacagccagaaggacttcctggaagacaggcgggcccTggtggac acctactgcagacacaactacggggttggtgagagcttcacagtgcagcggcgag;

DRB5*0105:

(SEQ ID NO: 2872)
ccacgtttcttgcagcaggataagtatgagtgtcatttcttcaacgggacggagcgggtgcggttcctgcacagag acatctataaccaagaggagGacgtgcgcttcgacagcgacgtgggggagtaccggcggtgacggagctggggcg gcctgacgctgagtactggaacagccagaaggacTtcctggaaGacaggcgCgccgcggtggacacctactgcaga cacaactacggggttggtgagagcttcacagtgcagcgg;

-continued

DRB5*0106:
(SEQ ID NO: 2873)
cacgtttcttgcagcaggataagtatgagtgtcatttcttcaacgggacggagcgggtgcggttcctgcacagaga catctataaccaagaggaggacTtgcgcttcgacagcgacgtgggggagtaccgggcggtgacggagctggggcgg cctgacgctgagtactggaacagccagaaggacatcctggagcaggcgcgggccgcggtggacacctactgcagac acaactacggggctgtGgagagcttcacagtgcagcggcga;

DRB5*0107:
(SEQ ID NO: 2874)
cacgtttcttgcagcaggataagtatgagtgtcatttcttcaacgggacggagcgggtgcggttcctgcacagaga catctataaccaagaggaggacTtgcgcttcgacagcgacgtgggggagtaccgggcggtgacggagctggggcgg cctgacgctgagtactggaacagccagaaggacAtcctggaaGacaggcgCgccgcggtggacacctactgcagac acaactacggggttggtg;

DRB5*0109:
(SEQ ID NO: 2875)
cacgtttcttgcagcaggataagtatgagtgtcatttcttcaacgggacggagcgggtgcggttcctgcacagaga catctataaccaagaggaggacttgcgcttcgacagcgacgtgggggagtaccgggcggtgacggagctggggcgg cctgacgctgagtactggaacagccagaaggacttcctggaaAacaggcgcgccgcggtggacacctactgcagac acaactacggggttggtg;

DRB5*0110N:
(SEQ ID NO: 2876)
cacgtttcttgcagcaggataagtatgagtgtcatttcttcaacgggacggagcgggtgcggttcctgcacagaGg catctataaccaagaggagAacgtgcgcttcgacagcgacgtgggggagtaccgggcggtgacggagctggggcgg cctgacgctgagtactggaacagccagaaggacTtcctggaaGacaggcgCgccgcggtggacacctactgca..c acaactacggggttggtgagagcttcacagtgcagcggcgag;

DRB5*0111:
(SEQ ID NO: 2877)
cacgtttcttgcagcaggataagtatgagtgtcatttcttcaacgggacggagcgggtgcggttcctgcacagaga catctataaccaagaggaggacTtgcgcttcgacagcgacgtgggggagtaccgggcggtgacggagctggggcgg cctgacgctgagtactggaacagccagaaggacatcctggagcaggCgcgggccgcggtggacacctactgcagac acaactacggggttggtgagagcttcacagtgcagcggcgag;

DRB5*0112:
(SEQ ID NO: 2878)
cacgtttcttgcagcaggataagtatgagtgtcatttcttcaacgggacggagcgggtgcggttcctgcacagaga catctataaccaagaggaggacTtgcgcttcgacagcgacgtgggggagtaccgggcggtgacggagctggggcgg cctgacgccgagtCctggaacagccagaaggacttcctggagcGgaggcgggccgaggtggacaccgtGtgcagac acaactacggggttggtgagagcttcacagtgcagcggcgag;

DRB5*0202:
(SEQ ID NO: 2879)
atggtgtgtctgaagctccctggaggttcctAcatggcagtgctgacagtgacactgatggtgctgagctccccac tggctttggctggggacaccccgaccatgtttcttgcagcaggataagtatgagtgtcatttcttcaacgggacgga gcgggtgcggttcctgcacagaggcatctataaccaagaggagaacgtgcgcttcgacagcgacgtgggggagtac cgggcggtgacggagctggggcggcctgacgctgagtactggaacagccagaaggacatcctggagcaggcgcggg ccgcggtggacacctactgcagacacaactacggggctgtGgagagcttcacagtgcagcggcgag;

DRB5*0203:
(SEQ ID NO: 2880)
tttcttgcagcaggataagtatgagtgtcatttcttcaacgggacggagcgggtgcggttcctgcacagaGgcatc tataaccaagaggagAacgtgcgcttcgacagcgacgtgggggagtaccgggcggtgacggagctggggcggcctg -continued acgctgagtactggaacagccagaaggacAtcctggagcagGCgcgggccgcggtggacacctactgcagacacaa ctacggggttggtgagagcttcacagtgcagcgg;

DRB5*0204:
(SEQ ID NO: 2881)
catgtttcttgcagcaggataagtatgagtgtcatttcttcaacgggacggagcgggtgcggttcctgcacagaGg catctataaccaagaggagaacgtgcgcttcgacagcgacgtgggggagtaccgggcggtgacggagctggggcgg cctgacgctgagtactggaacagccagaaggacTtcctggagcaggCgcgggccgcggtggacacctactgcagac acaactacggggctgtGgagagcttcaca;

DRB5*0205:
(SEQ ID NO: 2882)
catgtttcttgcagcaggataagtatgagtgtcatttcttcaacgggacggagcgggtgcggttcctgcacagaGg catctataaccaagaggagAacgtgcgcttcgacagcgacgtgggggagtaccgggcggtgacggagctggggcgg cctgacgctgagtactggaacagccagaaggacctcctggagcagaggcgggccgcggtggacacctactgcagac acaactacggggctgtGgagagcttcacagtgcagcggcgag In the following, Probe List DR1 and 2 are shown in Tables 21-1 to 21-8 and Tables 22-1 to 22-7 respectively. Allele-Probe Lists 1 and 2 are shown in Tables 23-1 to 23-13 and Tables 24-1 to 24-13 respectively.

TABLE 21-1

| Probe No. | Base Sequence | |
|---|---|---|
| 0 | g gtg cgg ttg Ctg gaA | (SEQ ID No: 2883) |
| 1 | g Cgg ttg ctg gaa aga T | (SEQ ID No: 2884) |
| 2 | c tat aac caa gag gag tC | (SEQ ID No: 2885) |
| 3 | ctg ggg cgg cct gaT | (SEQ ID No: 2886) |
| 4 | ggg cgg cct gat gcC | (SEQ ID No: 2887) |
| 5 | cac aac tac ggg gtt gG | (SEQ ID No: 2888) |
| 6 | c atc tat aac caa gag gaA | (SEQ ID No: 2889) |
| 7 | c gcg gtg gac acc taT | (SEQ ID No: 2890) |
| 8 | ga cac aac tac ggg gC | (SEQ ID No: 2891) |
| 9 | ag agg cgg gcc gcC | (SEQ ID No: 2892) |
| 10 | g aac agc cag aag gac A | (SEQ ID No: 2893) |
| 11 | g gac atc ctg gaa gac G | (SEQ ID No: 2894) |
| 12 | gac atc ctg gaa gac gA | (SEQ ID No: 2895) |
| 13 | g gcc gcg gtg gac aaT | (SEQ ID No: 2896) |
| 14 | ac aac tac ggg gtt gtG | (SEQ ID No: 2897) |
| 15 | c ttc gac agc gac gtg A | (SEQ ID No: 2898) |
| 16 | c ctc ctg gag cag gC | (SEQ ID No: 2899) |
| 17 | ca cgt ttc ttg tgg G | (SEQ ID No: 2900) |
| 18 | tc tat aac caa gag gag tA | (SEQ ID No: 2901) |
| 19 | gac ctc ctg gag cag G | (SEQ ID No: 2902) |
| 20 | gac ctc ctg gag cag aA | (SEQ ID No: 2903) |
| 21 | g gag cgg gtg cgg tA | (SEQ ID No: 2904) |

TABLE 21-1-continued

| Probe No. | Base Sequence | |
|---|---|---|
| 22 | c ctg gac aga tac ttc C | (SEQ ID No: 2905) |
| 23 | c cat aac cag gag gag A | (SEQ ID No: 2906) |
| 24 | c cat aac cag gag gag aA | (SEQ ID No: 2907) |
| 25 | gc gac gtg ggg gag tT | (SEQ ID No: 2908) |
| 26 | G cag aag cgg ggc cG | (SEQ ID No: 2909) |
| 27 | G ggc cgg gtg gac aA | (SEQ ID No: 2910) |
| 28 | g ggc cgg gtg gac aaT | (SEQ ID No: 2911) |
| 29 | ca cgt ttc ttg gA | (SEQ ID No: 2912) |
| 30 | g gtg cgg ttc ctg gaG | (SEQ ID No: 2913) |

TABLE 21-2

| Probe No. | Base Sequence | |
|---|---|---|
| 31 | c ctg gag aga tac ttc C | (SEQ ID No: 2914) |
| 32 | c aga tac ttc cat aac caG | (SEQ ID No: 2915) |
| 33 | tt ggt gag agc ttc acG | (SEQ ID No: 2916) |
| 34 | g gtg cgg tac ctg gaC | (SEQ ID No: 2917) |
| 35 | g ggg cgg cct gat gA | (SEQ ID No: 2918) |
| 36 | ggg cgg cct gat gaG | (SEQ ID No: 2919) |
| 37 | c aga tac ttc cat aac cG | (SEQ ID No: 2920) |
| 38 | ctg ggg cgg cct gC | (SEQ ID No: 2921) |
| 39 | ag cag aag cgg ggc C | (SEQ ID No: 2922) |
| 40 | g cag aag cgg ggc cA | (SEQ ID No: 2923) |
| 41 | gg ggc cag gtg gac aA | (SEQ ID No: 2924) |
| 42 | ctg ggg cgg cct agC | (SEQ ID No: 2925) |

TABLE 21-2-continued

| Probe No. | Base Sequence | |
|---|---|---|
| 43 | gg cct gat gcc gag tC | (SEQ ID No: 2926) |
| 44 | gac gtg ggg gag ttc T | (SEQ ID No: 2927) |
| 45 | gt ttc ttg gag tac tct aC | (SEQ ID No: 2928) |
| 46 | g gtg cgg ttc ctg gaC | (SEQ ID No: 2929) |
| 47 | g tac cgg gcg gtg aG | (SEQ ID No: 2930) |
| 48 | g ggc cag gtg gac aaT | (SEQ ID No: 2931) |
| 49 | ttc gac agc gac gtg C | (SEQ ID No: 2932) |
| 50 | c cat aac cag gag gag tT | (SEQ ID No: 2933) |
| 51 | c ctg gac aga tac ttc G | (SEQ ID No: 2934) |
| 52 | c cat aac cag gag gag tA | (SEQ ID No: 2935) |
| 53 | atg gtg tgt ctg aag T | (SEQ ID No: 2936) |
| 54 | ga tac ttc tat cac caa gaA | (SEQ ID No: 2937) |
| 55 | tc ttg gag cag gtt aaa C | (SEQ ID No: 2938) |
| 56 | c tat cac caa gag gag tA | (SEQ ID No: 2939) |
| 57 | g cag agg cgg gcc gA | (SEQ ID No: 2940) |
| 58 | ggg cgg cct gac gcT | (SEQ ID No: 2941) |
| 59 | c ttg gag cag gtt aaa cA | (SEQ ID No: 2942) |
| 60 | ctg gac aga tac ttc tat C | (SEQ ID No: 2943) |

TABLE 21-3

| Probe No. | Base Sequence | |
|---|---|---|
| 61 | g ctg ggg cgg cct aG | (SEQ ID No: 2944) |
| 62 | a gag gag tac gtg cgG | (SEQ ID No: 2945) |
| 63 | gc ttc aca gtg cag cgA | (SEQ ID No: 2946) |
| 64 | c ctc ctg gag cag agA | (SEQ ID No: 2947) |
| 65 | t ttc ttg gag cag gtt aaA | (SEQ ID No: 2948) |
| 66 | a gac agg cgg gcc cT | (SEQ ID No: 2949) |
| 67 | g aac agc cag aag gac T | (SEQ ID No: 2950) |
| 68 | ag gac ttc ctg gaa gaC | (SEQ ID No: 2951) |
| 69 | gg cgg cct gat gcc C | (SEQ ID No: 2952) |
| 70 | c ggg gtt gtg gag agA | (SEQ ID No: 2953) |
| 71 | g gac ctc ctg gag cG | (SEQ ID No: 2954) |
| 72 | ctg ggg cgg cct gat A | (SEQ ID No: 2955) |
| 73 | ag tac cgg gcg gtg aT | (SEQ ID No: 2956) |
| 74 | g ggg gag tac cgg gT | (SEQ ID No: 2957) |
| 75 | g cag agg cgg gcc C | (SEQ ID No: 2958) |
| 76 | g cag agg cgg gcc cT | (SEQ ID No: 2959) |

TABLE 21-3-continued

| Probe No. | Base Sequence | |
|---|---|---|
| 77 | tc ctg gag cag agg cA | (SEQ ID No: 2960) |
| 78 | caa gag gag tac gtg cA | (SEQ ID No: 2961) |
| 79 | c ttg gag cag gtt aaa cC | (SEQ ID No: 2962) |
| 80 | gac ctc ctg gaa gac G | (SEQ ID No: 2963) |
| 81 | gac ctc ctg gaa gac gA | (SEQ ID No: 2964) |
| 82 | gac atc ctg gag cag aA | (SEQ ID No: 2965) |
| 83 | agc gac gtg gaC | (SEQ ID No: 2966) |
| 84 | g ggg cgg cct gat gG | (SEQ ID No: 2967) |
| 85 | tc tat cac caa gag gag A | (SEQ ID No: 2968) |
| 86 | c tat cac caa gag gag aA | (SEQ ID No: 2969) |
| 87 | g gct ggg gac acc cA | (SEQ ID No: 2970) |
| 88 | g gac agg cgg ggc C | (SEQ ID No: 2971) |
| 89 | c cag gtg gac acc gtG | (SEQ ID No: 2972) |
| 90 | tc ctg tgg cag ggt aaA | (SEQ ID No: 2973) |

TABLE 21-4

| Probe No. | Base Sequence | |
|---|---|---|
| 91 | g gcg gtg acg gag ctA | (SEQ ID No: 2974) |
| 92 | g cct gtc gcc gag tC | (SEQ ID No: 2975) |
| 93 | gtg cag ttc ctg gaa agT | (SEQ ID No: 2976) |
| 94 | ag tcc tgg aac agc cG | (SEQ ID No: 2977) |
| 95 | gg cgg cct gct gcG | (SEQ ID No: 2978) |
| 96 | gtg acg gag cta ggg T | (SEQ ID No: 2979) |
| 97 | c tct acg ggt gag tgt T | (SEQ ID No: 2980) |
| 98 | cgg ttc ctg gac aga taT | (SEQ ID No: 2981) |
| 99 | gc tcc tgc atg gca gT | (SEQ ID No: 2982) |
| 100 | g tac cgg gcg gtg acA | (SEQ ID No: 2983) |
| 101 | cac aac tac ggg gtt gT | (SEQ ID No: 2984) |
| 102 | gtt gtt gag agc ttc acG | (SEQ ID No: 2985) |
| 103 | tt gtg gag agc ttc acG | (SEQ ID No: 2986) |
| 104 | g ctg ggg cgg cct gT | (SEQ ID No: 2987) |
| 105 | gg cct gct gcg gag C | (SEQ ID No: 2988) |
| 106 | gt ttc ttg gag tac tct aG | (SEQ ID No: 2989) |
| 107 | gg cct gat gcg gag C | (SEQ ID No: 2990) |
| 108 | tc tat aac caa gag gag G | (SEQ ID No: 2991) |
| 109 | ag gac atc ctg gaa gaC | (SEQ ID No: 2992) |
| 110 | g ctg ggg cgg cct aT | (SEQ ID No: 2993) |
| 111 | c ttg gag tac tct acg tC | (SEQ ID No: 2994) |

TABLE 21-4-continued

| Probe No. | Base Sequence | |
|---|---|---|
| 112 | gt ttc ttg gag tac tct aT | (SEQ ID No: 2995) |
| 113 | c aac tac ggg gct gtG | (SEQ ID No: 2996) |
| 114 | ct gtg gag agc ttc acG | (SEQ ID No: 2997) |
| 115 | g agc ttc aca gtg cag A | (SEQ ID No: 2998) |
| 116 | ctg gag cgg agg cgT A | (SEQ ID No: 2999) |
| 117 | g ttg ctg gaa aga cgc G | (SEQ ID No: 3000) |
| 118 | ctg gag cgg agg cgC | (SEQ ID No: 3001) |
| 119 | g aag gac ttc ctg gaa G | (SEQ ID No: 3002) |
| 120 | g ctg gaa gac agg cgC | (SEQ ID No: 3003) |

TABLE 21-5

| Probe No. | Base Sequence | |
|---|---|---|
| 121 | t gag tgt cat ttc ttc aaC | (SEQ ID No: 3004) |
| 122 | gac ttc ctg gaa gac gA | (SEQ ID No: 3005) |
| 123 | c ttg gag tac tct acg G | (SEQ ID No: 3006) |
| 124 | g gac ctc ctg gaa gaC | (SEQ ID No: 3007) |
| 125 | g gac ttc ctg gaa gac G | (SEQ ID No: 3008) |
| 126 | tc tat aac caa gag gag tT | (SEQ ID No: 3009) |
| 127 | c aga tac ttc tat aac caG | (SEQ ID No: 3010) |
| 128 | c tat aac cag gag gag tT | (SEQ ID No: 3011) |
| 129 | at aac caa gag gag gac T | (SEQ ID No: 3012) |
| 130 | cgg agg cgg gcc gA | (SEQ ID No: 3013) |
| 131 | cc gag gtg gac acc taT | (SEQ ID No: 3014) |
| 132 | aa gac agg cgg gcc C | (SEQ ID No: 3015) |
| 133 | ttg gag tac tct acg tC | (SEQ ID No: 3016) |
| 134 | gag tac tct acg tct gaG | (SEQ ID No: 3017) |
| 135 | cag aag gac ttc ctg gaA | (SEQ ID No: 3018) |
| 136 | g gcc gcg gtg gac aA | (SEQ ID No: 3019) |
| 137 | ttc tat aat caa gag gag A | (SEQ ID No: 3020) |
| 138 | tc tat aac caa gag gag aA | (SEQ ID No: 3021) |
| 139 | ca cgt ttc ttg gag cT | (SEQ ID No: 3022) |
| 140 | cgg cct gat gag gag C | (SEQ ID No: 3023) |
| 141 | a gac agg cgg gcc gT | (SEQ ID No: 3024) |
| 142 | g cgg cct gat gag gaC | (SEQ ID No: 3025) |
| 143 | g cgg cct gat gag gG | (SEQ ID No: 3026) |
| 144 | g ttc cgg gcg gtg aG | (SEQ ID No: 3027) |
| 145 | gc tcc tgc atg gca gtT | (SEQ ID No: 3028) |
| 146 | ttg gct ggg gac acc A | (SEQ ID No: 3029) |

TABLE 21-5-continued

| Probe No. | Base Sequence | |
|---|---|---|
| 147 | g gag cgg gtg cgg ttA | (SEQ ID No: 3030) |
| 148 | c cat aac cag gag gag C | (SEQ ID No: 3031) |
| 149 | cag aag gac atc ctg gG | (SEQ ID No: 3032) |
| 150 | gag cgg gtg cgg ttC | (SEQ ID No: 3033) |

TABLE 21-6

| Probe No. | Base Sequence | |
|---|---|---|
| 151 | g gaa gac gag cgg gcT | (SEQ ID No: 3034) |
| 152 | c ctg gaa gac gag cGc | (SEQ ID No: 3035) |
| 153 | g gac atc ctg gaa gac aA | (SEQ ID No: 3036) |
| 154 | a cgt ttc ttg gag tac tC | (SEQ ID No: 3037) |
| 155 | gg ttc ctg gac aga tac T | (SEQ ID No: 3038) |
| 156 | at atc ctg gag cag gC | (SEQ ID No: 3039) |
| 157 | cac aac tat ggg gtt gA | (SEQ ID No: 3040) |
| 158 | g aga tac ttc cat aat caG | (SEQ ID No: 3041) |
| 159 | c tgc aga cac aac tac C | (SEQ ID No: 3042) |
| 160 | t aac cag gag gag aac C | (SEQ ID No: 3043) |
| 161 | ac gtg ggg gag ttc cT | (SEQ ID No: 3044) |
| 162 | ctg ggg cgg cct gtC | (SEQ ID No: 3045) |
| 163 | gg gag ttc cgg gcg T | (SEQ ID No: 3046) |
| 164 | ca cgt ttc ttg gag tac T | (SEQ ID No: 3047) |
| 165 | tct acg tct gag tgt caA | (SEQ ID No: 3048) |
| 166 | ggg cgg cct gat gcT | (SEQ ID No: 3049) |
| 167 | t ttc ttg gag tac tct aC | (SEQ ID No: 3050) |
| 168 | gac atc ctg gag cag G | (SEQ ID No: 3051) |
| 169 | g acg gag cgg gtg CA | (SEQ ID No: 3052) |
| 170 | g gcc gag gtg gac aaT | (SEQ ID No: 3053) |
| 171 | ttg gag tac cct acg tC | (SEQ ID No: 3054) |
| 172 | t aac cag gag gag ttc C | (SEQ ID No: 3055) |
| 173 | gg gcc gag gtg gac G | (SEQ ID No: 3056) |
| 174 | c tcc cca ctg gct ttg T | (SEQ ID No: 3057) |
| 175 | gc aga cac aac tat ggA | (SEQ ID No: 3058) |
| 176 | cac aac tac gga gtt gtG | (SEQ ID No: 3059) |
| 177 | g tgg cag cct aag agG | (SEQ ID No: 3060) |
| 178 | tg gac aga tac ttc tat aaT | (SEQ ID No: 3061) |
| 179 | cgg ttc ctg gac aga C | (SEQ ID No: 3062) |
| 180 | ac ttc ctg gag cag gC | (SEQ ID No: 3063) |

TABLE 21-7

| Probe No. | Base Sequence | |
|---|---|---|
| 181 | g gag ttc cgg gcg gC | (SEQ ID No: 3064) |
| 182 | c tgg aac agc tag aag A | (SEQ ID No: 3065) |
| 183 | ac gtg ggg gag ttc cA | (SEQ ID No: 3066) |
| 184 | c tgg aac agc ca ggg gac A | (SEQ ID No: 3067) |
| 185 | tc ctg gaa gac agg gC | (SEQ ID No: 3068) |
| 186 | g cgg gtg cgg ttc cC | (SEQ ID No: 3069) |
| 187 | c tat aac cag gag gag aA | (SEQ ID No: 3070) |
| 188 | cgt ttc ttg gag ctg cG | (SEQ ID No: 3071) |
| 189 | c tcc cga ctg gct ttC | (SEQ ID No: 3072) |
| 190 | ca cgt ttc ttg gag ctg T | (SEQ ID No: 3073) |
| 191 | cgt ttc ttg gag ctg tG | (SEQ ID No: 3074) |
| 192 | g gtg cgg tac ctg gaG | (SEQ ID No: 3075) |
| 193 | gt ttc tcg gag ctg cG | (SEQ ID No: 3076) |
| 194 | cgg gtg cgg tat ctg A | (SEQ ID No: 3077) |
| 195 | ac cag gag gag tac gC | (SEQ ID No: 3078) |
| 196 | c cag gag gag ttc ctg A | (SEQ ID No: 3079) |
| 197 | ca cgt ttc ttg G | (SEQ ID No: 3080) |
| 198 | cgg ttc ctg gag aga C | (SEQ ID No: 3081) |
| 199 | gtg gac aat tac tgc agG | (SEQ ID No: 3082) |
| 200 | ggg cgg cct gat gcG | (SEQ ID No: 3083) |
| 201 | aga cac ttc cat aac caG | (SEQ ID No: 3084) |
| 202 | ac cag gag gag aac gC | (SEQ ID No: 3085) |
| 203 | g gag cgg gtg cgg C | (SEQ ID No: 3086) |
| 204 | cac aac tac ggg gtt gC | (SEQ ID No: 3087) |
| 205 | gc aga cac aac tac ggC | (SEQ ID No: 3088) |
| 206 | g ctg aca gtg aca ttg aC | (SEQ ID No: 3089) |
| 207 | cgg gcc gag gtg gG | (SEQ ID No: 3090) |
| 208 | ag tgt gag tgt cat ttc C | (SEQ ID No: 3091) |
| 209 | g gag cga gtg tgg aaC | (SEQ ID No: 3092) |
| 210 | g gac acc tac tgc aga T | (SEQ ID No: 3093) |

TABLE 21-8

| Probe No. | Base Sequence | |
|---|---|---|
| 211 | cg cgc tac aac agt gaT | (SEQ ID No: 3094) |
| 212 | gg gcc gag gtg gac aA | (SEQ ID No: 3095) |
| 213 | tg gac aac tac tgc aga T | (SEQ ID No: 3096) |
| 214 | acg gag cga gtg tgg A | (SEQ ID No: 3097) |
| 215 | a ggt tcc tac atg gca aA | (SEQ ID No: 3098) |

TABLE 21-8-continued

| Probe No. | Base Sequence | |
|---|---|---|
| 216 | ca cgt ttc ttg C | (SEQ ID No: 3099) |
| 217 | atc tat aac caa gag gag A | (SEQ ID No: 3100) |
| 218 | cgg ttc ctg cac aga G | (SEQ ID No: 3101) |
| 219 | gac ttc ctg gaa gac aC | (SEQ ID No: 3102) |
| 220 | c ctg gaa gac acg cgC | (SEQ ID No: 3103) |
| 221 | g aag gac atc ctg gaa G | (SEQ ID No: 3104) |
| 222 | ag aag gac ttc ctg gaa A | (SEQ ID No: 3105) |
| 223 | g cct gac gcc gag tC | (SEQ ID No: 3106) |
| 224 | ag gac ttc ctg gag cG | (SEQ ID No: 3107) |
| 225 | c gag gtg gac acc gtG | (SEQ ID No: 3108) |
| 226 | ctc cct gga ggt tcc tA | (SEQ ID No: 3109) |

TABLE 22-1

| Probe No. | Base Sequence | |
|---|---|---|
| 0 | g ttg ctg gaA aga tgc at | (SEQ ID No: 3110) |
| 1 | ctg gaa aga Tgc atc tat a | (SEQ ID No: 3111) |
| 2 | gag gag tCc gtg cgc | (SEQ ID No: 3112) |
| 3 | cgg cct gaT gcc gag | (SEQ ID No: 3113) |
| 4 | cct gat gcC gag tac tg | (SEQ ID No: 3114) |
| 5 | c ggg gtt gGt gag agc | (SEQ ID No: 3115) |
| 6 | caa gag gaA tcc gtg cg | (SEQ ID No: 3116) |
| 7 | g gac acc taT tgc aga ca | (5EQ ID No: 3117) |
| 8 | c tac ggg gCt gtg gag | (SEQ ID No: 3118) |
| 9 | gg gcc gcC gtg gac | (SEQ ID No: 3119) |
| 10 | cag aag gac Atc ctg gaa | (SEQ ID No: 3120) |
| 11 | g gaa gac Gag cgg gc | (SEQ ID No: 3121) |
| 12 | gaa gac gAg cgg gcc | (SEQ ID No: 3122) |
| 13 | g gtg gac aaT tac tgc ag | (SEQ ID No: 3123) |
| 14 | ggg gtt gtG gag agc t | (SEQ ID No: 3124) |
| 15 | c gac gtg Agg gag tac | (SEQ ID No: 3125) |
| 16 | gag cag gCg cgg gc | (SEQ ID No: 3126) |
| 17 | ttc ttg tgg Gag ctt aag | (SEQ ID No: 3127) |
| 18 | a gag gag tAc gtg cgc | (SEQ ID No: 3128) |
| 19 | gag cag Gcg cgg gc | (SEQ ID No: 3129) |
| 20 | gag cag aAg cgg gcc | (SEQ ID No: 3130) |
| 21 | xc acc Aga c | (SEQ ID No: 3131) |
| 22 | g gtg cgg tAc ctg gac | (SEQ ID No: 3132) |

TABLE 22-1-continued

| Probe No. | Base Sequence | |
|---|---|---|
| 23 | g gtg gac aAc tac tgc a | (SEQ ID No: 3133) |
| 24 | cgg ggc cGg gtg ga | (SEQ ID No: 3134) |
| 25 | g ttc ctg gaG aga tac tt | (SEQ ID No: 3135) |
| 26 | aga tac ttc Cat aac cag g | (SEQ ID No: 3136) |
| 27 | g gag gag Aac gtg cgc | (SEQ ID No: 3137) |
| 28 | g gag gag aAc gtg cgc | (SEQ ID No: 3138) |
| 29 | cat aac caG gag gag tc | (SEQ ID No: 3139) |
| 30 | ggg gag tTc cgg gcg | (SEQ ID No: 3140) |

TABLE 22-2

| Probe No. | Base Sequence | |
|---|---|---|
| 31 | agc ttc acG gtg cag c | (SEQ ID No: 3141) |
| 32 | g tac ctg gaC aga tac tt | (SEQ ID No: 3142) |
| 33 | g cct gat gAg gag tac t | (SEQ ID No: 3143) |
| 34 | cct gat gaG gag tac tg | (SEQ ID No: 3144) |
| 35 | c cat aac cGg gag gag | (SEQ ID No: 3145) |
| 36 | cgg cct gCt gcg gag | (SEQ ID No: 3146) |
| 37 | g cgg ggc Cag cta ga | (SEQ ID No: 3147) |
| 38 | cgg ggc cAg gtg gac | (SEQ ID No: 3148) |
| 39 | cgg cct aGc gcc gag | (SEQ ID No: 3149) |
| 40 | cgg cct agC gcc gag | (SEQ ID No: 3150) |
| 41 | t gcc gag tCc tgg aac | (SEQ ID No: 3151) |
| 42 | g gag ttc Tgg gcg gtg | (SEQ ID No: 3152) |
| 43 | ag tac tct aCg tct gag t | (SEQ ID No: 3153) |
| 44 | g ttc ctg gaC aga tac tt | (SEQ ID No: 3154) |
| 45 | gcg gtg aGg gag ctg | (SEQ ID No: 3155) |
| 46 | c gac gtg Cgg gag ttc | (SEQ ID No: 3156) |
| 47 | ag aag gac Atc ctg gag | (SEQ ID No: 3157) |
| 48 | g gag gag tTc gtg cgc | (SEQ ID No: 3158) |
| 49 | aga tac ttc Gat aac cag g | (SEQ ID No: 3159) |
| 50 | c cat aac caG gag gag ta | (SEQ ID No: 3160) |
| 51 | g gag gag tAc gtg cgc | (SEQ ID No: 3161) |
| 52 | gt ctg aag Ttc cct gga | (SEQ ID No: 3162) |
| 53 | t cac caa gaA gag tac gt | (SEQ ID No: 3163) |
| 54 | cag gtt aaa Cat gag tgt c | (SEQ ID No: 3164) |
| 55 | cgg gcc gAg gtg gac | (SEQ ID No: 3165) |
| 56 | cct gac gcT gag tac tg | (SEQ ID No: 3166) |
| 57 | ag gtt aaa cAt gag tgt ca | (SEQ ID No: 3167) |

TABLE 22-2-continued

| Probe No. | Base Sequence | |
|---|---|---|
| 58 | tac ttc tat Cac caa gag g | (SEQ ID No: 3168) |
| 59 | tac gtg cgG ttc gac ag | (SEQ ID No: 3169) |
| 60 | gg cag agA cgg gcc | (SEQ ID No: 3170) |

TABLE 22-3

| Probe No. | Base Sequence | |
|---|---|---|
| 61 | g cag gtt aaA cat gag tg | (SEQ ID No: 3171) |
| 62 | cgg gcc cTg gtg gac | (SEQ ID No: 3172) |
| 63 | cag aag gac Ttc ctg gaa | (SEQ ID No: 3173) |
| 64 | ctg gaa gaC agg cgg g | (SEQ ID No: 3174) |
| 65 | ct gat gcc Cag tac tgg | (SEQ ID No: 3175) |
| 66 | t gtg gag agA ttc aca gt | (SEQ ID No: 3176) |
| 67 | ctg gag cGg agg cgg | (SEQ ID No: 3177) |
| 68 | g cgg gcc Ctg gtg ga | (SEQ ID No: 3178) |
| 69 | gg cct gat Acc gag tac | (SEQ ID No: 3179) |
| 70 | g gcg gtg aTg gag ctg | (SEQ ID No: 3180) |
| 71 | g tac cgg gTg gtg acg | (SEQ ID No: 3181) |
| 72 | cag agg cAg gcc gcg | (SEQ ID No: 3182) |
| 73 | g tac gtg cAc ttc gac a | (SEQ ID No: 3183) |
| 74 | cag gtt aaa Cct gag tgt | (SEQ ID No: 3184) |
| 75 | ag gtt aaa cCt gag tgt c | (SEQ ID No: 3185) |
| 76 | gtg ggg gaC tac cgg | (SEQ ID No: 3186) |
| 77 | g cct gat gGc gag tac | (SEQ ID No: 3187) |
| 78 | a gag gag Aac gtg cgc | (SEQ ID No: 3188) |
| 79 | a gag gag aAc gtg cgc | (SEQ ID No: 3189) |
| 80 | xacc cAa c | (SEQ ID No: 3190) |
| 81 | gac acc gtG tgc aga c | (SEQ ID No: 3191) |
| 82 | g cag ggt aaA tat aag tgt | (SEQ ID No: 3192) |
| 83 | acg gag ctA ggg cgg | (SEQ ID No: 3193) |
| 84 | c gcc gag tCc tgg aac | (SEQ ID No: 3194) |
| 85 | c ctg gaa agT ctc ttc ta | (SEQ ID No: 3195) |
| 86 | g aac agc cGg aag gac | (SEQ ID No: 3196) |
| 87 | cct gct gcG gag tac t | (SEQ ID No: 3197) |
| 88 | g cta ggg Tgg cct gtc | (SEQ ID No: 3198) |
| 89 | ggt gag tgt Tat ttc ttc a | (SEQ ID No: 3199) |
| 90 | tg gac aga taT ttc tat aac | (SEQ ID No: 3200) |

TABLE 22-4

| Probe No. | Base Sequence | |
|---|---|---|
| 91 | g tgt ctg aGg ctc cct | (SEQ ID No: 3201) |
| 92 | gcg gtg acA gag ctg g | (SEQ ID No: 3202) |
| 93 | c ggg gtt gTt gag agc | (SEQ ID No: 3203) |
| 94 | cgg cct gTt gcc gag | (SEQ ID No: 3204) |
| 95 | t gcg gag Cac tgg aac | (SEQ ID No: 3205) |
| 96 | g tac tct aCg ggt gag t | (SEQ ID No: 3206) |
| 97 | cgg cct gCt gcc gag | (SEQ ID No: 3207) |
| 98 | g tac tct aGg ggt gag t | (SEQ ID No: 3208) |
| 99 | a gag gag Gac gtg cgc | (SEQ ID No: 3209) |
| 100 | cgg cct aTc gcc gag | (SEQ ID No: 3210) |
| 101 | c tct acg tCt gag tgt c | (SEQ ID No: 3211) |
| 102 | ag tac tct aTg ggt gag t | (SEQ ID No: 3212) |
| 103 | ggg gct gtG gag agc | (SEQ ID No: 3213) |
| 104 | gtg cgg taT ctg cac ag | (SEQ ID No: 3214) |
| 105 | gg agg cgT gcc gcg | (SEQ ID No: 3215) |
| 106 | gaa aga cgc Gtc cat aac | (SEQ ID No: 3216) |
| 107 | gg agg cgC gcc gcg | (SEQ ID No: 3217) |
| 108 | c ctg gaa Gac agg cgc | (SEQ ID No: 3218) |
| 109 | ctg gaa gaC agg cgc g | (SEQ ID No: 3219) |
| 110 | ac agg cgC gcc gcg | (SEQ ID No: 3220) |
| 111 | ttc ttc aaC ggg acg ga | (SEQ ID No: 3221) |
| 112 | ac tct acg Ggt gag tgt | (SEQ ID No: 3222) |
| 113 | c cat aac caG gag gag aa | (SEQ ID No: 3223) |
| 114 | c cat aac caG gag gag tt | (SEQ ID No: 3224) |
| 115 | a gag gag tTc gtg cgc | (SEQ ID No: 3225) |
| 116 | c tat aac caG gag gag tt | (SEQ ID No: 3226) |
| 117 | g gag gac Ttg cgc ttc | (SEQ ID No: 3227) |
| 118 | c ctg gaa Gac agg cgg | (SEQ ID No: 3228) |
| 119 | t acg tct gaG tgt cat ttc | (SEQ ID No: 3229) |
| 120 | ttc ctg gaA gac agg cg | (SEQ ID No: 3230) |

TABLE 22-5

| Probe No. | Base Sequence | |
|---|---|---|
| 121 | tc ttg gag cTg ctt aag t | (SEQ ID No: 3231) |
| 122 | g cct gat gAg gag cac | (SEQ ID No: 3232) |
| 123 | at gag gag Cac tgg aac | (SEQ ID No: 3233) |
| 124 | cgg gcc gTg gtg gac | (SEQ ID No: 3234) |
| 125 | t gat gag gaC tac tgg aa | (SEQ ID No: 3235) |
| 126 | t gat gag gGg tat tgg a | (SEQ ID No: 3236) |
| 127 | c atg gca gtT ctg aca gt | (SEQ ID No: 3237) |
| 128 | gtg cgg ttA ctg gag ag | (SEQ ID No: 3238) |
| 129 | g gag gag Ctc ctg cg | (SEQ ID No: 3239) |
| 130 | c atc ctg gGa gac agg | (SEQ ID No: 3240) |
| 131 | gtg cgg ttC ctg gag a | (SEQ ID No: 3241) |
| 132 | gag cgg gcT gcg gtg | (SEQ ID No: 3242) |
| 133 | gaa gac gAg cgc gcc | (SEQ ID No: 3243) |
| 134 | ac gag cgC gcc gcg | (SEQ ID No: 3244) |
| 135 | ctg gaa gaC aag cgg g | (SEQ ID No: 3245) |
| 136 | g gaa gac aAg cgg gcc | (SEQ ID No: 3246) |
| 137 | g gag tac tCt acg tct g | (SEQ ID No: 3247) |
| 138 | gac aga tac Ttc tat aac c | (SEQ ID No: 3248) |
| 139 | c ggg gtt gAt gag agc | (SEQ ID No: 3249) |
| 140 | ac aac tac Cgg gtt gtg | (SEQ ID No: 3250) |
| 141 | cgg cct gTc gcc gag | (SEQ ID No: 3251) |
| 142 | g gag aac Ctg cgc ttc | (SEQ ID No: 3252) |
| 143 | g gag ttc cTg gcg gtg | (SEQ ID No: 3253) |
| 144 | cgg cct gtC gcc gag | (SEQ ID No: 3254) |
| 145 | c cgg gcg Ttg acg ga | (SEQ ID No: 3255) |
| 146 | ttg gag tac Tct acg tct | (SEQ ID No: 3256) |
| 147 | ct gag tgt caA ttc ttc aat | (SEQ ID No: 3257) |
| 148 | cct gat gcT gag tac tg | (SEQ ID No: 3258) |
| 149 | gt ttc ttg gAg tac tct ac | (SEQ ID No: 3259) |
| 150 | g cgg gtg cAg ttc ctg | (SEQ ID No: 3260) |

TABLE 22-6

| Probe No. | Base Sequence | |
|---|---|---|
| 151 | c gac gtg Cgg gag tac | (SEQ ID No: 3261) |
| 152 | c cct acg tCt gag tgt c | (SEQ ID No: 3262) |
| 153 | g gag gag tTc ctg cgc | (SEQ ID No: 3263) |
| 154 | g gag ttc Ctg cgc ttc | (SEQ ID No: 3264) |
| 155 | g gtg gac Gcc tat tgc | (SEQ ID No: 3265) |
| 156 | g gct ttg Tct ggg gac | (SEQ ID No: 3266) |
| 157 | c aac tac ggA gtt gtg ga | (SEQ ID No: 3267) |
| 158 | gga gtt gtG gag agc tt | (SEQ ID No: 3268) |
| 159 | cct aag agG gag tgt ca | (SEQ ID No: 3269) |

TABLE 22-6-continued

| Probe No. | Base Sequence | |
|---|---|---|
| 160 | c ttc tat aaT cag gag gag | (SEQ ID No: 3270) |
| 161 | ctg gac aga Cac ttc tat | (SEQ ID No: 3271) |
| 162 | ag aag gac Ttc ctg gag | (SEQ ID No: 3272) |
| 163 | cgg gcg gCg acg ga | (SEQ ID No: 3273) |
| 164 | gc cag aag Aac atc ctg | (SEQ ID No: 3274) |
| 165 | g gag ttc cAg gcg gtg | (SEQ ID No: 3275) |
| 166 | caa gg gac Atc ctg gag c | (SEQ ID No: 3276) |
| 167 | gac agg gCc gcc gc | (SEQ ID No: 3277) |
| 168 | g cgg ttc cCg gac aga | (SEQ ID No: 3278) |
| 169 | g gag ctg cGt aag tct g | (SEQ ID No: 3279) |
| 170 | ctg gct ttC gct ggg g | (SEQ ID No: 3280) |
| 171 | ttg gag ctg Tgt aag tct | (SEQ ID No: 3281) |
| 172 | g gag ctg tGt aag tct g | (SEQ ID No: 3282) |
| 173 | g tac ctg gaG aga tac tt | (SEQ ID No: 3283) |
| 174 | cgg tac ctg Aac aga tac | (SEQ ID No: 3284) |
| 175 | gag cag aAg cgg ggc | (SEQ ID No: 3285) |
| 176 | g gag tac gCg cgc ttc | (SEQ ID No: 3286) |
| 177 | ag ttc ctg Agc ttc gac | (SEQ ID No: 3287) |
| 178 | cgt ttc ttg Gag ctg ctt | (SEQ ID No: 3288) |
| 179 | ctg gag aga Cac ttc cat | (SEQ ID No: 3289) |
| 180 | t tac tgc agG cac aac ta | (SEQ ID No: 3290) |

TABLE 22-7

| Probe No. | Base Sequence | |
|---|---|---|
| 181 | cct gat gcG gag tac tg | (SEQ ID No: 3291) |
| 182 | g gag gag Aac gcg cg | (SEQ ID No: 3292) |
| 183 | g gag aac gCg cgc ttc | (SEQ ID No: 3293) |
| 184 | cgt ttc ttg Cag ctg ctt | (SEQ ID No: 3294) |
| 185 | g gtg cgg Ctc ctg ga | (SEQ ID No: 3295) |
| 186 | c ggg gtt gCt gag agc | (SEQ ID No: 3296) |
| 187 | aac tac ggC gtt gtg ga | (SEQ ID No: 3297) |
| 188 | g aca ttg aCg gtg ctg a | (SEQ ID No: 3298) |
| 189 | c gag gtg gGc acc tac | (SEQ ID No: 3299) |
| 190 | gtg tgg aaC ctg atc ag | (SEQ ID No: 3300) |
| 191 | g gac acc taT tgc aga ta | (SEQ ID No: 3301) |
| 192 | aac agt gaT ctg ggg ga | (SEQ ID No: 3302) |
| 193 | tac tgc aga Tac aac tac g | (SEQ ID No: 3303) |
| 194 | tgt cat ttc Ctc aat ggg | (SEQ ID No: 3304) |

TABLE 22-7-continued

| Probe No. | Base Sequence | |
|---|---|---|
| 195 | ga gtg tgg Aac ctg atc | (SEQ ID No: 3305) |
| 196 | c atg gca aAg ctg aca g | (SEQ ID No: 3306) |
| 197 | cgt ttc ttg Cag cag gat | (SEQ ID No: 3307) |
| 198 | ctg cac aga Ggc atc tat | (8EQ ID No: 3308) |
| 199 | gaa gac aCg cgc gcc | (SEQ ID No: 3309) |
| 200 | ac acg cgC gcc gcg | (SEQ ID No: 3310) |
| 201 | c ctg gaa Aac agg cgc | (SEQ ID No: 3311) |
| 202 | a ggt tcc tAc atg gca g | (SEQ ID No: 3312) |
| 203 | tgt ttc ttg Cag cag gat | (SEQ ID No: 3313) |

TABLE 23-1

| Allele Number | Probe Number for Detection | | | | | | |
|---|---|---|---|---|---|---|---|
| DRB1*010101 | 0 | 2 | 3 | 4 | 5 | | |
| DRB1*010102 | 6 | | | | | | |
| DRB1*010201 | 7 | 8 | | | | | |
| DRB1*010202 | 9 | | | | | | |
| DRB1*0103 | 10 | 11 | 12 | | | | |
| DRB1*0104 | 13 | 14 | | | | | |
| DRB1*0105 | 15 | | | | | | |
| DRB1*0106 | 16 | 14 | | | | | |
| DRB1*0107 | 17 | | | | | | |
| DRB1*0108 | 18 | | | | | | |
| DRB1*0109 | 19 | 16 | | | | | |
| DRB1*0110 | 20 | | | | | | |
| DRB1*030101 | 21 | 22 | 23 | 24 | 25 | 26 | 27 | 14 |
| DRB1*030102 | 26 | 28 | 14 | | | | |
| DRB1*030201 | 29 | 30 | 31 | 23 | 24 | 26 | 27 |
| DRB1*030202 | 30 | 23 | 24 | 26 | 28 | | |
| DRB1*0303 | 30 | 31 | 23 | 24 | 26 | 27 | 14 |
| DRB1*0304 | 21 | 22 | 32 | 25 | 26 | 27 | 14 |
| DRB1*030501 | 21 | 22 | 23 | 24 | 25 | 26 | 27 |
| DRB1*030502 | 27 | 33 | | | | | |
| DRB1*0306 | 21 | 34 | 22 | 23 | 24 | 26 | 27 | 14 |
| DRB1*0307 | 22 | 23 | 24 | 25 | 26 | 27 | 14 |
| DRB1*0308 | 23 | 35 | 36 | 26 | 27 | 14 | |
| DRB1*0309 | 37 | | | | | | |
| DRB1*0310 | 38 | 26 | 27 | 14 | | | |
| DRB1*0311 | 21 | 39 | 40 | 41 | 14 | | |
| DRB1*0312 | 42 | 26 | 27 | 14 | | | |
| DRB1*0313 | 43 | 26 | 27 | 14 | | | |
| DRB1*0314 | 21 | 22 | 23 | 24 | 25 | 26 | |
| DRB1*0315 | 21 | 22 | 23 | 24 | 25 | 26 | 14 |

TABLE 23-2

| Allele Number | Probe Number for Detection | | | | | | |
|---|---|---|---|---|---|---|---|
| DRB1*0316 | 44 | | | | | | |
| DRB1*0317 | 45 | 46 | 18 | 47 | 48 | | |
| DRB1*0318 | 49 | 14 | | | | | |
| DRB1*0319 | 10 | 26 | 27 | 14 | | | |
| DRB1*0320 | 27 | 8 | | | | | |
| DRB1*0321 | 50 | 25 | 26 | 27 | 14 | | |
| DRB1*0322 | 51 | | | | | | |
| DRB1*0323 | 37 | 14 | | | | | |
| DRB1*0324 | 25 | 39 | 40 | 48 | 14 | | |
| DRB1*0325 | 21 | 22 | 32 | 52 | 25 | 26 | 27 | 14 |
| DRB1*040101 | 53 | 20 | | | | | |
| DRB1*040102 | 54 | | | | | | |
| DRB1*0402 | 53 | 12 | 14 | | | | |
| DRB1*040301 | 55 | 56 | 57 | 14 | | | |

TABLE 23-2-continued

| Allele Number | Probe Number for Detection | | | | |
|---|---|---|---|---|---|
| DRB1*040302 | 55 | 58 | 57 | 14 | |
| DRB1*0404 | 53 | 14 | | | |
| DRB1*040501 | 55 | 59 | 60 | 56 | 61 |
| DRB1*040502 | 62 | | | | |
| DRB1*040503 | 63 | | | | |
| DRB1*040504 | 60 | 42 | 33 | | |
| DRB1*0406 | 55 | 60 | 57 | 14 | |
| DRB1*040701 | 55 | 56 | 57 | | |
| DRB1*040702 | 64 | | | | |
| DRB1*0408 | 65 | 55 | 59 | 60 | 56 |
| DRB1*0409 | 60 | 61 | 20 | | |
| DRB1*0410 | 60 | 56 | 61 | 14 | |
| DRB1*0411 | 53 | 57 | 14 | | |
| DRB1*0412 | 60 | 61 | 10 | 66 | 14 |
| DRB1*0413 | 60 | 20 | 14 | | |
| DRB1*0414 | 60 | 10 | 11 | 12 | |

TABLE 23-3

| Allele Number | Probe Number for Detection | | | | |
|---|---|---|---|---|---|
| DRB1*0415 | 55 | 36 | 67 | 68 | 14 |
| DRB1*0416 | 69 | | | | |
| DRB1*0417 | 60 | 61 | 57 | | |
| DRB1*0418 | 60 | 10 | 66 | 14 | |
| DRB1*0419 | 65 | 55 | 59 | 60 | |
| DRB1*0420 | 60 | 57 | | | |
| DRB1*0421 | 60 | 20 | | | |
| DRB1*0422 | 60 | 56 | 26 | 27 | 14 |
| DRB1*0423 | 70 | | | | |
| DRB1*0424 | 61 | 42 | 71 | | |
| DRB1*0425 | 60 | 56 | 67 | 66 | 14 |
| DRB1*0426 | 72 | | | | |
| DRB1*0427 | 56 | 57 | 8 | | |
| DRB1*0428 | 60 | 56 | 25 | 61 | |
| DRB1*0429 | 73 | | | | |
| DRB1*0430 | 74 | | | | |
| DRB1*0431 | 55 | 60 | 56 | 75 | 76 |
| DRB1*0432 | 77 | | | | |
| DRB1*0433 | 78 | | | | |
| DRB1*0434 | 55 | 79 | 56 | 20 | |
| DRB1*0435 | 55 | 25 | 20 | | |
| DRB1*0436 | 55 | 67 | 68 | 14 | |
| DRB1*0437 | 55 | 80 | 81 | 14 | |
| DRB1*0438 | 55 | 10 | 82 | | |
| DRB1*0439 | 83 | | | | |
| DRB1*0440 | 84 | | | | |
| DRB1*0441 | 55 | 85 | 86 | 57 | 14 |
| DRB1*0442 | 55 | 25 | 14 | | |
| DRB1*0443 | 55 | 60 | 25 | | |
| DRB1*0444 | 60 | 56 | 13 | 14 | |

TABLE 23-4

| Allele Number | Probe Number for Detection | | | | |
|---|---|---|---|---|---|
| DRB1*070101 | 87 | 88 | 89 | | |
| DRB1*070102 | 90 | 91 | 92 | 89 | |
| DRB1*0703 | 93 | | | | |
| DRB1*0704 | 91 | 48 | | | |
| DRB1*0705 | 94 | | | | |
| DRB1*0706 | 91 | 95 | 89 | | |
| DRB1*0707 | 96 | | | | |
| DRB1*080101 | 97 | 42 | 67 | 66 | 33 |
| DRB1*080102 | 98 | | | | |
| DRB1*080201 | 99 | 33 | | | |
| DRB1*080202 | 97 | 18 | 67 | 66 | |
| DRB1*080203 | 100 | | | | |
| DRB1*080302 | 45 | 97 | 61 | 10 | 66 |
| DRB1*080401 | 97 | 18 | 67 | 66 | 14 |
| DRB1*080402 | 18 | 67 | 66 | 101 | |
| DRB1*080403 | 66 | 101 | 102 | | |

TABLE 23-4-continued

| Allele Number | Probe Number for Detection | | | | |
|---|---|---|---|---|---|
| DRB1*080404 | 66 | 14 | 103 | | |
| DRB1*0805 | 97 | 61 | 67 | 68 | |
| DRB1*0806 | 61 | 67 | 66 | 14 | |
| DRB1*0807 | 104 | 67 | 66 | 33 | |
| DRB1*0808 | 38 | 105 | 66 | | |
| DRB1*0809 | 45 | 50 | 67 | 66 | 33 |
| DRB1*0810 | 97 | 61 | 10 | 66 | 14 |
| DRB1*0811 | 38 | 66 | 33 | | |
| DRB1*0812 | 10 | 66 | 8 | | |
| DRB1*0813 | 97 | 18 | 66 | 33 | |
| DRB1*0814 | 106 | | | | |
| DRB1*0815 | 107 | 10 | 66 | | |
| DRB1*0816 | 108 | 33 | | | |
| DRB1*0817 | 25 | 61 | 67 | 66 | |

TABLE 23-5

| Allele Number | Probe Number for Detection | | | | |
|---|---|---|---|---|---|
| DRB1*0818 | 45 | 97 | 61 | 10 | 109 |
| DRB1*0819 | 110 | 10 | 66 | | |
| DRB1*0820 | 111 | 18 | 67 | 66 | 14 |
| DRB1*0821 | 112 | | | | |
| DRB1*0822 | 8 | 113 | 114 | | |
| DRB1*0823 | 15 | 66 | | | |
| DRB1*0824 | 97 | 18 | 67 | 68 | |
| DRB1*090102 | 92 | 115 | | | |
| DRB1*0902 | 58 | 115 | | | |
| DRB1*100101 | 116 | | | | |
| DRB1*100102 | 117 | 118 | | | |
| DRB1*110101 | 99 | 36 | 67 | 68 | |
| DRB1*110102 | 36 | 67 | 68 | 33 | |
| DRB1*110103 | 36 | 67 | 119 | 68 | 120 |
| DRB1*110104 | 121 | 18 | 25 | 35 | 67 | 68 |
| DRB1*1102 | 35 | 10 | 11 | 12 | 14 |
| DRB1*1103 | 99 | 122 | 14 | | |
| DRB1*110401 | 99 | 67 | 68 | 14 | |
| DRB1*110402 | 36 | 14 | 103 | | |
| DRB1*1105 | 123 | 35 | 36 | 67 | 68 |
| DRB1*110601 | 36 | 67 | 68 | 8 | |
| DRB1*110602 | 36 | 67 | 68 | 7 | 8 |
| DRB1*1107 | 35 | 36 | 26 | 27 | 14 |
| DRB1*110801 | 18 | 25 | 35 | 124 | |
| DRB1*110802 | 36 | 124 | 33 | | |
| DRB1*1109 | 32 | 23 | 24 | 25 | 35 | 67 | 68 |
| DRB1*1110 | 22 | 32 | 50 | 25 | 35 | 67 | 68 |
| DRB1*1111 | 25 | 35 | 67 | 125 | 122 |
| DRB1*111201 | 126 | 25 | 35 | 67 | 68 |
| DRB1*111202 | 111 | 127 | 128 | 25 | 35 | 67 | 68 |

TABLE 23-6

| Allele Number | Probe Number for Detection | | | | |
|---|---|---|---|---|---|
| DRB1*1113 | 25 | 35 | 36 | 71 | 7 | 14 |
| DRB1*1114 | 35 | 10 | 11 | 12 | |
| DRB1*1115 | 129 | 36 | 67 | 119 | 68 |
| DRB1*1116 | 23 | 35 | 10 | 11 | 12 | 14 |
| DRB1*1117 | 111 | 35 | 36 | 130 | 131 | 14 |
| DRB1*1118 | 18 | 35 | 10 | 109 | 14 |
| DRB1*1119 | 18 | 35 | 10 | 109 | |
| DRB1*1120 | 23 | 35 | 10 | 11 | 12 |
| DRB1*1121 | 11 | 12 | 8 | | |
| DRB1*1122 | 55 | 25 | 36 | 67 | 68 |
| DRB1*1123 | 35 | 36 | 67 | 68 | 132 | 66 |
| DRB1*1124 | 108 | 36 | 67 | 119 | 68 |
| DRB1*1125 | 36 | 67 | 66 | 14 | |
| DRB1*1126 | 133 | 134 | 18 | 25 | 35 |
| DRB1*112701 | 135 | 68 | 13 | | |
| DRB1*112702 | 35 | 68 | 136 | | |
| DRB1*1128 | 134 | 137 | 138 | 25 | 35 | 67 | 68 |
| DRB1*1129 | 45 | 111 | 134 | 25 | 35 | 67 | 68 |
| DRB1*1130 | 139 | 68 | | | |

TABLE 23-6-continued

| Allele Number | Probe Number for Detection | | | | | |
|---|---|---|---|---|---|---|
| DRB1*1131 | 35 | 140 | 10 | 109 | | |
| DRB1*1132 | 35 | 36 | 67 | 68 | 141 | |
| DRB1*1133 | 142 | | | | | |
| DRB1*1134 | 18 | 25 | 35 | 14 | | |
| DRB1*1135 | 142 | 14 | | | | |
| DRB1*1136 | 25 | 35 | 80 | 81 | 14 | |
| DRB1*1137 | 45 | 111 | 134 | 18 | 35 | 67 | 68 |
| DRB1*1138 | 143 | | | | | |
| DRB1*1139 | 144 | 68 | | | | |
| DRB1*1140 | 23 | 25 | 35 | 67 | 125 | 122 | 14 |
| DRB1*1141 | 35 | 67 | 125 | 122 | 14 | |

TABLE 23-7

| Allele Number | Probe Number for Detection | | | | | | | |
|---|---|---|---|---|---|---|---|---|
| DRB1*1142 | 18 | 25 | 35 | 124 | 14 | | | |
| DRB1*1143 | 144 | 68 | 14 | | | | | |
| DRB1*120101 | 145 | 146 | 147 | 148 | 92 | 10 | 7 | 8 |
| DRB1*120102 | 145 | 146 | 147 | 148 | 92 | 10 | 8 | |
| DRB1*120201 | 148 | 67 | 7 | 8 | | | | |
| DRB1*120202 | 148 | 67 | 120 | 8 | | | | |
| DRB1*120302 | 147 | 148 | 92 | 10 | 120 | | | |
| DRB1*1204 | 148 | 36 | 10 | 7 | 8 | | | |
| DRB1*1205 | 147 | 92 | 10 | 7 | 8 | | | |
| DRB1*1206 | 147 | 148 | 92 | 10 | 7 | 8 | | |
| DRB1*1207 | 149 | | | | | | | |
| DRB1*1208 | 150 | 148 | 92 | 10 | 7 | 8 | | |
| DRB1*130101 | 46 | 23 | 24 | 25 | 10 | 11 | 12 | 14 |
| DRB1*130102 | 151 | | | | | | | |
| DRB1*130103 | 12 | 7 | 14 | | | | | |
| DRB1*130201 | 46 | 23 | 24 | 25 | 10 | 11 | 12 | |
| DRB1*130202 | 12 | 152 | | | | | | |
| DRB1*130301 | 42 | 109 | 153 | 33 | | | | |
| DRB1*130302 | 61 | 109 | 153 | | | | | |
| DRB1*1304 | 25 | 61 | 11 | 12 | 14 | | | |
| DRB1*1305 | 134 | 32 | 23 | 25 | 67 | 68 | | |
| DRB1*1306 | 46 | 23 | 25 | 10 | 109 | 14 | | |
| DRB1*130701 | 154 | 45 | 111 | 134 | 46 | 155 | 18 | 67 | 119 | 68 |
| DRB1*130702 | 111 | 46 | 155 | 18 | 58 | 67 | 119 | 68 |
| DRB1*1308 | 46 | 50 | 11 | 12 | 14 | | | |
| DRB1*1309 | 24 | 25 | 10 | 156 | 14 | | | |
| DRB1*1310 | 46 | 23 | 25 | 10 | 109 | 153 | 14 | |
| DRB1*1311 | 18 | 25 | 67 | 68 | 14 | | | |
| DRB1*1312 | 111 | 61 | 10 | 109 | | | | |

TABLE 23-8

| Allele Number | Probe Number for Detection | | | | | | | |
|---|---|---|---|---|---|---|---|---|
| DRB1*1313 | 111 | 61 | 10 | 66 | | | | |
| DRB1*131401 | 18 | 25 | 67 | 119 | 68 | | | |
| DRB1*131402 | 25 | 58 | 67 | 119 | 68 | | | |
| DRB1*1315 | 30 | 25 | 11 | 12 | 14 | | | |
| DRB1*1316 | 157 | | | | | | | |
| DRB1*1317 | 97 | 12 | 14 | | | | | |
| DRB1*1318 | 23 | 25 | 67 | 66 | 14 | | | |
| DRB1*1319 | 30 | 50 | 11 | 12 | 14 | | | |
| DRB1*1320 | 46 | 23 | 24 | 25 | 80 | 81 | 14 | |
| DRB1*1321 | 111 | 25 | 61 | 67 | 68 | | | |
| DRB1*1322 | 111 | 46 | 18 | 25 | 10 | 11 | 12 | 14 |
| DRB1*1323 | 11 | 12 | 33 | | | | | |
| DRB1*1324 | 25 | 67 | 125 | 122 | 14 | | | |
| DRB1*1325 | 154 | 45 | 111 | 134 | 46 | 18 | 25 | 124 |
| DRB1*1326 | 31 | 158 | 23 | 24 | 58 | 67 | 119 | 68 | 120 |
| DRB1*1327 | 21 | 11 | 12 | 14 | | | | |
| DRB1*1328 | 159 | | | | | | | |
| DRB1*1329 | 46 | 23 | 24 | 25 | 80 | 81 | | |
| DRB1*1330 | 25 | 61 | 10 | 109 | | | | |
| DRB1*1331 | 104 | 10 | 11 | 12 | | | | |
| DRB1*1332 | 23 | 61 | 11 | 12 | 14 | | | |
| DRB1*1333 | 61 | 109 | 136 | | | | | |
| DRB1*1334 | 160 | 11 | 12 | | | | | |

TABLE 23-8-continued

| Allele Number | Probe Number for Detection | | | | | |
|---|---|---|---|---|---|---|
| DRB1*1335 | 161 | | | | | |
| DRB1*1336 | 46 | 23 | 24 | 10 | 11 | 12 |
| DRB1*1337 | 109 | 153 | 33 | | | |
| DRB1*1338 | 61 | 11 | 12 | | | |
| DRB1*1339 | 43 | 10 | 11 | 12 | | |
| DRB1*1340 | 46 | 23 | 24 | 10 | 11 | 12 | 14 |

TABLE 23-9

| Allele Number | Probe Number for Detection | | | | | | | |
|---|---|---|---|---|---|---|---|---|
| DRB1*1341 | 21 | 11 | 12 | | | | | |
| DRB1*1342 | 23 | 67 | 68 | 14 | | | | |
| DRB1*1343 | 25 | 38 | 80 | 81 | 14 | | | |
| DRB1*1344 | 111 | 134 | 46 | 18 | 25 | 14 | | |
| DRB1*1345 | 25 | 38 | 10 | 11 | 12 | | | |
| DRB1*1346 | 18 | 104 | 162 | 67 | 135 | 68 | | |
| DRB1*1347 | 111 | 18 | 67 | 66 | 33 | | | |
| DRB1*1348 | 61 | 11 | 12 | 14 | | | | |
| DRB1*1349 | 111 | 61 | 67 | 68 | | | | |
| DRB1*1350 | 134 | 137 | 25 | 67 | 68 | | | |
| DRB1*1351 | 163 | | | | | | | |
| DRB1*1352 | 46 | 32 | 52 | 25 | 10 | 11 | 12 | 14 |
| DRB1*1353 | 30 | 24 | 11 | 12 | 14 | | | |
| DRB1*1354 | 92 | 125 | 122 | 14 | | | | |
| DRB1*1355 | 111 | 42 | 67 | 66 | 33 | | | |
| DRB1*140101 | 99 | 111 | 130 | 131 | 14 | | | |
| DRB1*140102 | 164 | 111 | 38 | 130 | 14 | | | |
| DRB1*1402 | 99 | 158 | 23 | 24 | | | | |
| DRB1*1403 | 99 | 23 | 66 | | | | | |
| DRB1*1404 | 99 | 97 | 130 | 131 | 14 | | | |
| DRB1*140501 | 165 | 166 | 131 | 14 | | | | |
| DRB1*140502 | 165 | 131 | 14 | | | | | |
| DRB1*1406 | 45 | 30 | 23 | 24 | 14 | | | |

TABLE 23-9-continued

| Allele Number | Probe Number for Detection | | | | |
|---|---|---|---|---|---|
| DRB1*140701 | 164 | 111 | 38 | 130 | 131 |
| DRB1*140702 | 38 | 131 | 33 | | |
| DRB1*1408 | 164 | 111 | 107 | 130 | 131 | 14 |
| DRB1*1409 | 167 | 134 | 46 | 22 | 32 | 23 |
| DRB1*1410 | 59 | 38 | 130 | 131 | 14 |
| DRB1*1411 | 97 | 35 | 36 | 130 | 131 | 14 |
| DRB1*1412 | 30 | 23 | 24 | 66 | 14 |

TABLE 23-10

| Allele Number | Probe Number for Detection | | | | | |
|---|---|---|---|---|---|---|
| DRB1*1413 | 30 | 23 | 24 | 61 | | |
| DRB1*1414 | 111 | 50 | 130 | 131 | | |
| DRB1*1415 | 97 | 50 | 67 | 66 | 14 | |
| DRB1*1416 | 38 | 10 | 11 | 12 | 14 | |
| DRB1*1417 | 134 | 46 | 22 | 23 | 25 | 14 |
| DRB1*1418 | 23 | 24 | 166 | 130 | 131 | 14 |
| DRB1*1419 | 29 | 45 | 30 | 23 | 24 | 20 |
| DRB1*1420 | 133 | 150 | 30 | 50 | 14 | |
| DRB1*1421 | 46 | 22 | 23 | 25 | 20 | 14 |
| DRB1*1422 | 50 | 38 | 105 | 67 | 135 | 68 |
| DRB1*1423 | 164 | 111 | 50 | 130 | 131 | 14 |
| DRB1*1424 | 30 | 158 | 23 | 24 | 10 | 168 | 156 |
| DRB1*1425 | 111 | 18 | 38 | 105 | 67 | 135 | 68 |
| DRB1*1426 | 169 | 14 | | | | |
| DRB1*1427 | 30 | 23 | 24 | 67 | 68 | 132 | 66 |
| DRB1*1428 | 38 | 8 | 113 | | | |
| DRB1*1429 | 30 | 158 | 23 | 24 | 8 | |
| DRB1*1430 | 134 | 46 | 22 | 32 | 23 | 25 |
| DRB1*1431 | 97 | 38 | 7 | 14 | | |
| DRB1*1432 | 164 | 111 | 38 | 71 | 14 | |
| DRB1*1433 | 24 | 25 | 57 | 14 | | |
| DRB1*1434 | 164 | 111 | 107 | 7 | 14 | |
| DRB1*1435 | 25 | 38 | 130 | 131 | 14 | |
| DRB1*1436 | 49 | 131 | | | | |
| DRB1*1437 | 165 | 156 | 14 | | | |
| DRB1*1438 | 38 | 170 | 14 | | | |
| DRB1*1439 | 171 | 38 | 130 | 131 | 14 | |
| DRB1*1440 | 30 | 50 | 124 | 132 | 66 | |
| DRB1*1441 | 45 | 111 | 150 | 30 | 50 | 172 |
| DRB1*1442 | 18 | 25 | 130 | 131 | | |

TABLE 23-11

| Allele Number | Probe Number for Detection | | | | | |
|---|---|---|---|---|---|---|
| DRB1*1443 | 173 | | | | | |
| DRB1*1444 | 165 | 166 | 131 | | | |
| DRB1*1445 | 165 | 10 | 131 | 14 | | |
| DRB1*50101 | 174 | | | | | |
| DRB1*150102 | 175 | 176 | | | | |
| DRB1*150103 | 177 | 7 | 14 | | | |
| DRB1*150104 | 177 | 25 | 10 | 156 | 14 | |
| DRB1*150201 | 177 | 25 | 58 | 10 | 156 | |
| DRB1*150202 | 25 | 10 | 168 | 156 | | |
| DRB1*150203 | 178 | | | | | |
| DRB1*1503 | 177 | 179 | 25 | 58 | 10 | 156 | 14 |
| DRB1*1504 | 177 | 67 | 180 | 14 | | |
| DRB1*1505 | 177 | 25 | 58 | 16 | 14 | |
| DRB1*1506 | 181 | | | | | |
| DRB1*1507 | 177 | 58 | 10 | 156 | 14 | |
| DRB1*1508 | 182 | | | | | |
| DRB1*1509 | 183 | 156 | | | | |
| DRB1*1510 | 177 | 12 | 14 | | | |
| DRB1*1511 | 177 | 58 | 10 | 156 | | |
| DRB1*1512 | 177 | 61 | 42 | 10 | 156 | 14 |
| DRB1*1513 | 177 | 25 | 58 | 184 | 156 | 14 |
| DRB1*160101 | 177 | 67 | 120 | | | |
| DRB1*160102 | 177 | 67 | 68 | | | |
| DRB1*160201 | 177 | 120 | | | | |
| DRB1*160202 | 177 | 124 | | | | |
| DRB1*1603 | 185 | | | | | |

TABLE 23-11-continued

| Allele Number | Probe Number for Detection | | | | | |
|---|---|---|---|---|---|---|
| DRB1*1604 | 127 | 58 | 67 | 68 | 132 | 66 |
| DRB1*1605 | 177 | 10 | 120 | | | |
| DRB1*1607 | 186 | | | | | |
| DRB1*1608 | 177 | 187 | 67 | 120 | | |

TABLE 23-12

| Allele Number | Probe Number for Detection | | | | | |
|---|---|---|---|---|---|---|
| DRB3*010101 | 188 | 34 | 172 | 162 | 26 | 28 |
| DRB3*01010201 | 189 | 26 | | | | |
| DRB3*010103 | 188 | 34 | 172 | 26 | 28 | |
| DRB3*010104 | 28 | 175 | | | | |
| DRB3*0102 | 190 | 191 | 34 | 172 | 162 | 26 | 28 |
| DRB3*0103 | 188 | 192 | 172 | 162 | 26 | 28 |
| DRB3*0104 | 193 | 34 | 172 | 162 | 26 | 28 |
| DRB3*0105 | 194 | 28 | | | | |
| DRB3*0106 | 188 | 34 | 50 | 162 | 26 | 28 |
| DRB3*0107 | 188 | 20 | 40 | 48 | | |
| DRB3*0108 | 188 | 23 | 24 | 162 | 26 | 28 |
| DRB3*0109 | 188 | 195 | 162 | 26 | 28 | |
| DRB3*0110 | 196 | | | | | |
| DRB3*0201 | 189 | 14 | | | | |
| DRB3*020201 | 197 | 198 | 195 | 47 | 48 | |
| DRB3*020202 | 198 | 195 | 47 | 40 | 41 | |
| DRB3*020203 | 199 | | | | | |
| DRB3*020204 | 47 | 200 | 48 | | | |
| DRB3*0203 | 198 | 201 | 47 | 48 | | |
| DRB3*0204 | 47 | 26 | 27 | 14 | | |
| DRB3*0205 | 30 | 195 | 47 | 48 | | |
| DRB3*0206 | 23 | 202 | 47 | 48 | | |
| DRB3*0207 | 47 | 104 | 162 | 48 | | |
| DRB3*0208 | 47 | 61 | 42 | 48 | | |
| DRB3*0209 | 195 | 92 | 40 | 48 | | |
| DRB3*0210 | 197 | 198 | 195 | 40 | 48 | |
| DRB3*0211 | 47 | 10 | 48 | | | |
| DRB3*0212 | 198 | 195 | 47 | 48 | | |
| DRB3*0213 | 203 | | | | | |
| DRB3*0214 | 204 | | | | | |

TABLE 23-13

| Allele Number | Probe Number for Detection | | | | | |
|---|---|---|---|---|---|---|
| DRB3*0215 | 198 | 195 | 47 | 40 | | |
| DRB3*0216 | 47 | 105 | 48 | | | |
| DRB3*0217 | 47 | 67 | 48 | | | |
| DRB3*030101 | 92 | 48 | 14 | | | |
| DRB3*030102 | 205 | | | | | |
| DRB3*0302 | 198 | 92 | 48 | 14 | | |
| DRB3*0303 | 30 | 50 | 162 | 92 | 26 | 28 |
| DRB4*010101 | 206 | | | | | |
| DRB4*0102 | 207 | | | | | |
| DRB4*010302 | 208 | 209 | 210 | | | |
| DRB4*010303 | 206 | 131 | | | | |
| DRB4*010304 | 211 | | | | | |
| DRB4*0104 | 212 | 213 | | | | |
| DRB4*0105 | 208 | 214 | | | | |
| DRB4*0106 | 208 | 209 | 210 | | | |
| DRB4*0201N | 87 | 14 | | | | |
| DRB5*010101 | 215 | | | | | |
| DRB5*010102 | 129 | 58 | 67 | 119 | 68 | |
| DRB5*0102 | 2 | 216 | 217 | 67 | 119 | 120 |
| DRB5*0103 | 218 | 219 | 220 | | | |
| DRB5*0104 | 129 | 66 | | | | |
| DRB5*0105 | 108 | 67 | 119 | 120 | | |
| DR85*0106 | 129 | 113 | | | | |
| DRB5*0107 | 129 | 10 | 221 | 120 | | |
| DRB5*0109 | 222 | | | | | |
| DRB5*0110N | 218 | 217 | 67 | 119 | 120 | |
| DRB5*0111 | 129 | 156 | | | | |
| DRB5*0112 | 129 | 223 | 224 | 225 | | |
| DRB5*0202 | 226 | 113 | | | | |

TABLE 23-13-continued

| Allele Number | Probe Number for Detection | | | | |
|---|---|---|---|---|---|
| DRB5*0203 | 218 | 217 | 10 | 168 | 156 |
| DRB5*0204 | 218 | 67 | 180 | 113 | |
| DRB5*0205 | 218 | 217 | 113 | | |

TABLE 24-1

| Allele Number | Probe Number for Detection | | | | | |
|---|---|---|---|---|---|---|
| DRB1*010101 | 0 | 1 | 2 | 3 | 4 | 5 |
| DRB1*010102 | 6 | | | | | |
| DRB1*010201 | 7 | 8 | | | | |
| DRB1*010202 | 9 | | | | | |
| DRB1*0103 | 10 | 11 | 12 | | | |
| DRB1*0104 | 13 | 14 | | | | |
| DRB1*0105 | 15 | | | | | |
| DRB1*0106 | 16 | 14 | | | | |
| DRB1*0107 | 17 | | | | | |
| DRB1*0108 | 18 | | | | | |
| DRB1*0109 | 19 | 16 | | | | |
| DRB1*0110 | 20 | | | | | |
| DRB1*030101 | 21 | 22 | 23 | 14 | | |
| DRB1*030102 | 24 | 13 | 14 | | | |
| DRB1*030201 | 21 | 25 | 23 | | | |
| DRB1*030202 | 21 | 13 | | | | |
| DRB1*0303 | 25 | 26 | 27 | 28 | 24 | 23 | 14 |
| DRB1*0304 | 22 | 26 | 29 | 30 | 24 | 23 | 14 |
| DRB1*030501 | 22 | 26 | 27 | 28 | 30 | 24 | 23 |
| DRB1*030502 | 23 | 31 | | | | |
| DRB1*0306 | 22 | 32 | 26 | 27 | 28 | 24 | 23 | 14 |
| DRB1*0307 | 21 | 23 | 14 | | | |
| DRB1*0308 | 21 | 33 | 34 | 23 | 14 | |
| DRB1*0309 | 35 | | | | | |
| DRB1*0310 | 36 | 24 | 23 | 14 | | |
| DRB1*0311 | 22 | 37 | 38 | 23 | 14 | |
| DRB1*0312 | 39 | 40 | 24 | 23 | | |
| DRB1*0313 | 41 | 24 | 23 | 14 | | |
| DRB1*0314 | 22 | 26 | 27 | 28 | 30 | 24 |

TABLE 24-2

| Allele Number | Probe Number for Detection | | | | | | |
|---|---|---|---|---|---|---|---|
| DRB1*0315 | 22 | 26 | 27 | 28 | 30 | 24 | 14 |
| DRB1*0316 | 42 | | | | | | |
| DRB1*0317 | 43 | 44 | 18 | 45 | 13 | | |
| DRB1*0318 | 46 | 14 | | | | | |
| DRB1*0319 | 47 | 24 | 23 | 14 | | | |
| DRB1*0320 | 23 | 8 | | | | | |
| DRB1*0321 | 48 | 30 | 24 | 23 | 14 | | |
| DRB1*0322 | 49 | | | | | | |
| DRB1*0323 | 35 | 14 | | | | | |
| DRB1*0324 | 30 | 37 | 38 | 13 | 14 | | |
| DRB1*0325 | 22 | 26 | 50 | 51 | 30 | 24 | 23 | 14 |
| DRB1*040101 | 52 | 20 | | | | | |
| DRB1*040102 | 53 | | | | | | |
| DRB1*0402 | 52 | 12 | 14 | | | | |
| DRB1*040301 | 54 | 18 | 55 | 14 | | | |
| DRB1*040302 | 54 | 56 | 55 | 14 | | | |
| DRB1*0404 | 52 | 14 | | | | | |
| DRB1*040501 | 54 | 57 | 58 | 18 | 39 | | |
| DRB1*040502 | 59 | | | | | | |
| DRB1*040503 | 54 | 57 | 58 | 18 | 39 | | |
| DRB1*040504 | 58 | 40 | 31 | | | | |
| DRB1*0406 | 54 | 58 | 55 | 14 | | | |
| DRB1*040701 | 54 | 18 | 55 | | | | |
| DRB1*040702 | 60 | | | | | | |
| DRB1*0408 | 61 | 54 | 57 | 58 | 18 | | |
| DRB1*0409 | 58 | 39 | 20 | | | | |
| DRB1*0410 | 58 | 18 | 39 | 14 | | | |
| DRB1*0411 | 52 | 55 | 14 | | | | |
| DRB1*0412 | 58 | 39 | 10 | 62 | 14 | | |
| DRB1*0413 | 58 | 20 | 14 | | | | |

TABLE 24-3

| Allele Number | Probe Number for Detection | | | | |
|---|---|---|---|---|---|
| DRB1*0414 | 58 | 10 | 11 | 12 | |
| DRB1*0415 | 54 | 58 | 34 | 63 | 64 |
| DRB1*0416 | 65 | | | | |
| DRB1*0417 | 58 | 39 | 55 | | |
| DRB1*0418 | 58 | 10 | 62 | 14 | |
| DRB1*0419 | 61 | 54 | 57 | 58 | |
| DRB1*0420 | 58 | 55 | | | |
| DRB1*0421 | 61 | 54 | 57 | 20 | |
| DRB1*0422 | 58 | 18 | 24 | 23 | 14 |
| DRB1*0423 | 66 | | | | |
| DRB1*0424 | 39 | 40 | 67 | | |
| DRB1*0425 | 58 | 18 | 63 | 64 | 68 | 62 |
| DRB1*0426 | 69 | | | | |
| DRB1*0427 | 18 | 55 | 8 | | |
| DRB1*0428 | 58 | 18 | 30 | 39 | |
| DRB1*0429 | 70 | | | | |
| DRB1*0430 | 71 | | | | |
| DRB1*0431 | 54 | 58 | 18 | 68 | 62 |
| DRB1*0432 | 72 | | | | |
| DRB1*0433 | 73 | | | | |
| DRB1*0434 | 74 | 75 | 18 | 20 | |
| DRB1*0435 | 54 | 30 | 20 | | |
| DRB1*0436 | 54 | 63 | 64 | 14 | |
| DRB1*0437 | 54 | 11 | 12 | 14 | |
| DRB1*0438 | 54 | 47 | 20 | | |
| DRB1*0439 | 76 | | | | |
| DRB1*0440 | 77 | | | | |
| DRB1*0441 | 54 | 78 | 79 | 55 | 14 |
| DRB1*0442 | 54 | 30 | 14 | | |
| DRB1*0443 | 54 | 58 | 30 | | |

TABLE 24-4

| Allele Number | Probe Number for Detection | | | | |
|---|---|---|---|---|---|
| DRB1*0444 | 58 | 18 | 13 | 14 | |
| DRB1*070101 | 80 | 37 | 81 | | |
| DRB1*070102 | 82 | 83 | 84 | 81 | |
| DRB1*0703 | 85 | | | | |
| DRB1*0704 | 83 | 13 | | | |
| DRB1*0705 | 86 | | | | |
| DRB1*0706 | 83 | 87 | 81 | | |
| DRB1*0707 | 88 | | | | |
| DRB1*080101 | 89 | 40 | 63 | 62 | 31 |
| DRB1*080102 | 90 | | | | |
| DRB1*080201 | 91 | 31 | | | |
| DRB1*080202 | 89 | 18 | 63 | 62 | |
| DRB1*080203 | 92 | | | | |
| DRB1*080302 | 21 | 10 | 62 | | |
| DRB1*080401 | 21 | 62 | 14 | | |
| DRB1*080402 | 18 | 63 | 62 | 93 | |
| DRB1*080403 | 62 | 93 | 31 | | |
| DRB1*080404 | 62 | 14 | 31 | | |
| DRB1*0805 | 89 | 39 | 63 | 64 | |
| DRB1*0806 | 39 | 63 | 62 | 14 | |
| DRB1*0807 | 94 | 63 | 62 | 31 | |
| DRB1*0808 | 36 | 95 | 62 | | |
| DRB1*0809 | 96 | 48 | 63 | 62 | 31 |
| DRB1*0810 | 89 | 39 | 10 | 62 | 14 |
| DRB1*0811 | 97 | 62 | | | |
| DRB1*0812 | 10 | 62 | 8 | | |
| DRB1*0813 | 96 | 89 | 18 | 62 | |
| DRB1*0814 | 98 | | | | |
| DRB1*0815 | 95 | 10 | 62 | | |
| DRB1*0816 | 99 | 31 | | | |

TABLE 24-5

| Allele Number | Probe Number for Detection | | | | |
|---|---|---|---|---|---|
| DRB1*0817 | 30 | 39 | 63 | 62 | |
| DRB1*0818 | 96 | 89 | 39 | 10 | 64 |

TABLE 24-5-continued

| Allele Number | Probe Number for Detection | | | | | |
|---|---|---|---|---|---|---|
| DRB1*0819 | 100 | 10 | 62 | | | |
| DRB1*0820 | 101 | 18 | 63 | 62 | 14 | |
| DRB1*0821 | 102 | | | | | |
| DRB1*0822 | 8 | 103 | 31 | | | |
| DRB1*0823 | 15 | 62 | | | | |
| DRB1*0824 | 89 | 18 | 63 | 64 | | |
| DRB1*090102 | 104 | 84 | | | | |
| DRB1*0902 | 104 | 56 | | | | |
| DRB1*100101 | 105 | | | | | |
| DRB1*100102 | 106 | 107 | | | | |
| DRB1*110101 | 91 | 34 | 63 | 64 | | |
| DRB1*110102 | 34 | 63 | 64 | 31 | | |
| DRB1*110103 | 34 | 63 | 108 | 109 | 110 | |
| DRB1*110104 | 111 | 18 | 30 | 33 | 63 | 64 |
| DRB1*1102 | 21 | 34 | 10 | 11 | 12 | 14 |
| DRB1*1103 | 91 | 12 | 14 | | | |
| DRB1*110401 | 91 | 63 | 64 | 14 | | |
| DRB1*110402 | 34 | 14 | 31 | | | |
| DRB1*1105 | 112 | 33 | 34 | 63 | 64 | |
| DRB1*110601 | 34 | 63 | 64 | 8 | | |
| DRB1*110602 | 34 | 63 | 64 | 7 | 8 | |
| DRB1*1107 | 33 | 34 | 24 | 23 | 14 | |
| DRB1*110801 | 18 | 30 | 33 | 64 | | |
| DRB1*110802 | 18 | 30 | 33 | 64 | | |
| DRB1*1109 | 113 | 27 | 28 | 30 | 33 | 63 | 64 |
| DRB1*1110 | 26 | 114 | 48 | 30 | 33 | 63 | 64 |
| DRB1*1111 | 30 | 33 | 63 | 11 | 12 | |
| DRB1*11201 | 115 | 30 | 33 | 63 | 64 | |

TABLE 24-6

| Allele Number | Probe Number for Detection | | | | | |
|---|---|---|---|---|---|---|
| DRB1*111202 | 101 | 116 | 48 | 30 | 33 | 63 | 64 |
| DRB1*1113 | 21 | 30 | 33 | 67 | 7 | 14 |
| DRB1*1114 | 21 | 34 | 10 | 11 | 12 | |
| DRB1*1115 | 117 | 34 | 63 | 118 | 64 | |
| DRB1*1116 | 27 | 33 | 10 | 11 | 12 | 14 |
| DRB1*1117 | 21 | 33 | 55 | 7 | 14 | |
| DRB1*1118 | 18 | 33 | 10 | 64 | 14 | |
| DRB1*1119 | 18 | 33 | 10 | 64 | | |
| DRB1*1120 | 27 | 33 | 10 | 11 | 12 | |
| DRB1*1121 | 33 | 10 | 11 | 12 | | |
| DRB1*1122 | 54 | 30 | 34 | 63 | 64 | |
| DRB1*1123 | 33 | 34 | 63 | 64 | 68 | 62 |
| DRB1*1124 | 99 | 34 | 63 | 118 | 64 | |
| DRB1*1125 | 34 | 63 | 62 | 14 | | |
| DRB1*1126 | 43 | 101 | 119 | 18 | 30 | 33 |
| DRB1*112701 | 120 | 64 | 13 | | | |
| DRB1*112702 | 33 | 64 | 23 | | | |
| DRB1*1128 | 119 | 78 | 79 | 30 | 33 | 63 | 64 |
| DRB1*1129 | 43 | 101 | 119 | 30 | 33 | 63 | 64 |
| DRB1*1130 | 121 | 64 | | | | |
| DRB1*1131 | 122 | 123 | 10 | 64 | | |
| DRB1*1132 | 33 | 34 | 63 | 64 | 124 | |
| DRB1*1133 | 125 | | | | | |
| DRB1*1134 | 18 | 30 | 33 | 14 | | |
| DRB1*1135 | 125 | 14 | | | | |
| DRB1*1136 | 30 | 33 | 11 | 12 | 14 | |
| DRB1*1137 | 43 | 101 | 119 | 18 | 33 | 63 | 64 |
| DRB1*1138 | 126 | | | | | |
| DRB1*1139 | 45 | 64 | | | | |
| DRB1*1140 | 27 | 30 | 33 | 63 | 11 | 12 |

TABLE 24-7

| Allele Number | Probe Number for Detection | | | | | | | |
|---|---|---|---|---|---|---|---|---|
| DRB1*1141 | 33 | 63 | 11 | 12 | 14 | | | |
| DRB1*1142 | 18 | 30 | 33 | 64 | 14 | | | |
| DRB1*1143 | 45 | 64 | 14 | | | | | |
| DRB1*120101 | 127 | 21 | 128 | 129 | 84 | 10 | 7 | 8 |
| DRB1*120102 | 127 | 21 | 128 | 129 | 84 | 10 | 8 | |
| DRB1*120201 | 129 | 63 | 7 | 8 | | | | |
| DRB1*120202 | 129 | 63 | 110 | | | | | |
| DRB1*120302 | 128 | 129 | 84 | 10 | 110 | | | |
| DRB1*1204 | 129 | 34 | 10 | 7 | | | | |
| DRB1*1205 | 128 | 84 | 10 | 7 | 8 | | | |
| DRB1*1206 | 21 | 128 | 129 | 84 | 10 | 7 | 8 | |
| DRB1*1207 | 130 | | | | | | | |
| DRB1*1208 | 131 | 129 | 84 | 10 | 7 | 8 | | |
| DRB1*130101 | 21 | 27 | 30 | 10 | 11 | 12 | 14 | |
| DRB1*130102 | 132 | | | | | | | |
| DRB1*130103 | 12 | 7 | 14 | | | | | |
| DRB1*130201 | 21 | 27 | 30 | 10 | 11 | 12 | | |
| DRB1*130202 | 133 | 134 | | | | | | |
| DRB1*130301 | 40 | 135 | 136 | 31 | | | | |
| DRB1*130302 | 39 | 135 | 136 | | | | | |
| DRB1*1304 | 21 | 40 | 10 | 11 | 12 | 14 | | |
| DRB1*1305 | 119 | 113 | 27 | 30 | 63 | 64 | | |
| DRB1*1306 | 44 | 27 | 30 | 10 | 64 | 14 | | |
| DRB1*130701 | 137 | 43 | 101 | 119 | 44 | 138 | 18 | 63 | 118 | 64 |
| DRB1*130702 | 101 | 44 | 138 | 18 | 56 | 63 | 118 | 64 |
| DRB1*1308 | 44 | 48 | 11 | 12 | 14 | | | |
| DRB1*1309 | 28 | 30 | 47 | 16 | 14 | | | |
| DRB1*1310 | 44 | 27 | 30 | 10 | 135 | 136 | 14 | |
| DRB1*1311 | 18 | 30 | 63 | 64 | 14 | | | |

TABLE 24-8

| Allele Number | Probe Number for Detection | | | | | | |
|---|---|---|---|---|---|---|---|
| DRB1*1312 | 101 | 39 | 10 | 64 | | | |
| DRB1*1313 | 101 | 39 | 10 | 62 | | | |
| DRB1*131401 | 18 | 30 | 63 | 118 | 64 | | |
| DRB1*131402 | 30 | 56 | 63 | 118 | 64 | | |
| DRB1*1315 | 25 | 30 | 11 | 12 | 14 | | |
| DRB1*1316 | 139 | | | | | | |
| DRB1*1317 | 21 | 89 | 30 | 10 | 11 | 12 | 14 |
| DRB1*1318 | 27 | 30 | 63 | 62 | 14 | | |
| DRB1*1319 | 21 | 48 | 10 | 11 | 12 | 14 | |
| DRB1*1320 | 44 | 27 | 28 | 30 | 11 | 12 | 14 |
| DRB1*1321 | 21 | 40 | 63 | 64 | | | |
| DRB1*1322 | 101 | 44 | 18 | 30 | 10 | 11 | 12 | 14 |
| DRB1*1323 | 11 | 12 | 31 | | | | |
| DRB1*1324 | 30 | 63 | 11 | 12 | 14 | | |
| DRB1*1325 | 137 | 43 | 101 | 119 | 44 | 18 | 30 | 64 |
| DRB1*1326 | 26 | 113 | 27 | 28 | 56 | 63 | 108 | 109 | 110 |
| DRB1*1327 | 22 | 11 | 12 | 14 | | | |
| DRB1*1328 | 140 | | | | | | |
| DRB1*1329 | 44 | 27 | 28 | 30 | 11 | 12 | |
| DRB1*1330 | 30 | 39 | 10 | 64 | | | |
| DRB1*1331 | 141 | 10 | 11 | 12 | | | |
| DRB1*1332 | 27 | 39 | 11 | 12 | 14 | | |
| DRB1*1333 | 39 | 135 | 23 | | | | |
| DRB1*1334 | 142 | 11 | 12 | | | | |
| DRB1*1335 | 143 | | | | | | |
| DRB1*1336 | 44 | 27 | 28 | 10 | 11 | 12 | |
| DRB1*1337 | 135 | 136 | 31 | | | | |
| DRB1*1338 | 39 | 11 | 12 | | | | |
| DRB1*1339 | 41 | 10 | 11 | 12 | | | |

TABLE 24-9

| Allele Number | Probe Number for Detection | | | | | | |
|---|---|---|---|---|---|---|---|
| DRB1*1340 | 44 | 27 | 28 | 10 | 11 | 12 | 14 |
| DRB1*1341 | 22 | 11 | 12 | | | | |
| DRB1*1342 | 27 | 63 | 64 | 14 | | | |
| DRB1*1343 | 30 | 36 | 11 | 12 | 14 | | |
| DRB1*1344 | 101 | 119 | 44 | 18 | 30 | 14 | |
| DRB1*1345 | 30 | 36 | 10 | 11 | 12 | | |
| DRB1*1346 | 18 | 141 | 144 | 63 | 120 | 64 | |
| DRB1*1347 | 101 | 18 | 63 | 62 | 31 | | |
| DRB1*1348 | 39 | 11 | 12 | 14 | | | |
| DRB1*1349 | 101 | 39 | 63 | 64 | | | |
| DRB1*1350 | 119 | 78 | 30 | 63 | 64 | | |
| DRB1*1351 | 145 | | | | | | |
| DRB1*1352 | 44 | 50 | 51 | 30 | 10 | 11 | 12 | 14 |
| DRB1*1353 | 25 | 28 | 11 | 12 | 14 | | |
| DRB1*1354 | 84 | 11 | 12 | 14 | | | |
| DRB1*1355 | 101 | 40 | 63 | 62 | 31 | | |
| DRB1*140101 | 91 | 101 | 55 | 7 | 14 | | |
| DRB1*140102 | 146 | 101 | 36 | 67 | 55 | | |
| DRB1*1402 | 91 | 27 | 28 | | | | |
| DRB1*1403 | 91 | 27 | 62 | | | | |
| DRB1*1404 | 91 | 89 | 55 | 7 | 14 | | |
| DRB1*140501 | 147 | 148 | 7 | 14 | | | |
| DRB1*140502 | 147 | 7 | 14 | | | | |
| DRB1*1406 | 149 | 43 | 25 | 27 | 28 | 14 | |
| DRB1*140701 | 146 | 101 | 36 | 55 | 7 | | |
| DRB1*140702 | 36 | 7 | 31 | | | | |
| DRB1*1408 | 146 | 101 | 95 | 55 | 7 | 14 | |
| DRB1*1409 | 43 | 119 | 44 | 26 | 113 | 27 | |
| DRB1*1410 | 57 | 36 | 55 | 7 | 14 | | |
| DRB1*1411 | 89 | 33 | 34 | 55 | 7 | | |
| DRB1*1412 | 25 | 27 | 28 | 64 | 68 | 62 | |

TABLE 24-10

| Allele Number | Probe Number for Detection | | | | | |
|---|---|---|---|---|---|---|
| DRB1*1413 | 25 | 27 | 28 | 39 | | |
| DRB1*1414 | 146 | 101 | 48 | 55 | 7 | |
| DRB1*1415 | 89 | 48 | 63 | 62 | 14 | |

TABLE 24-10-continued

| Allele Number | Probe Number for Detection | | | | | |
|---|---|---|---|---|---|---|
| DRB1*1416 | 48 | 36 | 10 | 11 | 12 | |
| DRB1*1417 | 119 | 44 | 26 | 27 | 30 | 14 |
| DRB1*1418 | 27 | 28 | 148 | 55 | 7 | 14 |
| DRB1*1419 | 21 | 25 | 27 | 28 | 20 | |
| DRB1*1420 | 43 | 101 | 131 | 25 | 48 | |
| DRB1*1421 | 44 | 26 | 27 | 30 | 20 | |
| DRB1*1422 | 48 | 36 | 95 | 63 | 120 | 64 |
| DRB1*1423 | 146 | 101 | 48 | 55 | 7 | 14 |
| DRB1*1424 | 25 | 113 | 27 | 28 | 47 | 19 | 16 |
| DRB1*1425 | 101 | 18 | 36 | 95 | 63 | 120 | 64 |
| DRB1*1426 | 150 | 14 | | | | |
| DRB1*1427 | 25 | 27 | 28 | 63 | 64 | 68 | 62 |
| DRB1*1428 | 36 | 8 | 103 | | | |
| DRB1*1429 | 25 | 113 | 27 | 28 | 8 | |
| DRB1*1430 | 119 | 44 | 26 | 113 | 27 | 30 |
| DRB1*1431 | 89 | 36 | 7 | 14 | | |
| DRB1*1432 | 146 | 101 | 36 | 67 | 14 | |
| DRB1*1433 | 28 | 30 | 55 | 14 | | |
| DRB1*1434 | 146 | 101 | 95 | 7 | 14 | |
| DRB1*1435 | 30 | 36 | 55 | 7 | 14 | |
| DRB1*1436 | 151 | 7 | | | | |
| DRB1*1437 | 147 | 16 | 14 | | | |
| DRB1*1438 | 36 | 13 | 14 | | | |
| DRB1*1439 | 152 | 36 | 55 | 7 | 14 | |
| DRB1*1440 | 25 | 48 | 64 | 68 | 62 | |
| DRB1*1441 | 43 | 101 | 131 | 25 | 153 | 154 |
| DRB1*1442 | 18 | 30 | 55 | 7 | | |
| DRB1*1443 | 155 | | | | | |

TABLE 24-11

| Allele Number | Probe Number for Detection | | | | | |
|---|---|---|---|---|---|---|
| DRB1*1444 | 147 | 148 | 7 | | | |
| DRB1*1445 | 147 | 47 | 7 | 14 | | |
| DRB1*150101 | 156 | | | | | |
| DRB1*150102 | 157 | 158 | | | | |
| DRB1*150103 | 159 | 7 | 14 | | | |
| DRB1*150104 | 159 | 30 | 47 | 16 | 14 | |
| DRB1*150201 | 159 | 30 | 56 | 47 | 16 | |
| DRB1*150202 | 30 | 47 | 19 | 16 | | |
| DRB1*150203 | 160 | | | | | |
| DRB1*1503 | 159 | 161 | 30 | 56 | 47 | 16 | 14 |
| DRB1*1504 | 159 | 162 | 16 | 14 | | |
| DRB1*1505 | 159 | 30 | 56 | 16 | 14 | |
| DRB1*1506 | 163 | | | | | |
| DRB1*1507 | 159 | 56 | 47 | 16 | | |
| DRB1*1508 | 164 | | | | | |
| DRB1*1509 | 165 | 16 | | | | |
| DRB1*1510 | 159 | 12 | | | | |
| DRB1*1511 | 159 | 56 | 47 | 16 | | |
| DRB1*1512 | 159 | 39 | 40 | 47 | 16 | 14 |
| DRB1*1513 | 159 | 30 | 56 | 166 | 16 | 14 |
| DRB1*160101 | 159 | 63 | 110 | | | |
| DRB1*160102 | 159 | 63 | 64 | | | |
| DRB1*160201 | 159 | 110 | | | | |
| DRB1*160202 | 159 | 64 | | | | |
| DRB1*1603 | 167 | | | | | |
| DRB1*1604 | 159 | 62 | | | | |
| DRB1*1605 | 159 | 10 | 110 | | | |
| DRB1*1607 | 168 | | | | | |
| DRB1*1608 | 159 | 28 | 63 | 110 | | |
| DRB3*010101 | 169 | 32 | 154 | 144 | 24 | 13 |
| DRB3*01010201 | 170 | 24 | | | | |

TABLE 24-12

| Allele Number | Probe Number for Detection | | | | | |
|---|---|---|---|---|---|---|
| DRB3*010103 | 169 | 32 | 154 | 24 | 13 | |
| DRB3*010104 | 169 | 32 | 154 | 144 | 24 | 13 |
| DRB3*0102 | 171 | 172 | 32 | 154 | 144 | 24 | 13 |
| DRB3*0103 | 169 | 173 | 154 | 144 | 24 | 13 |

TABLE 24-12-continued

| Allele Number | Probe Number for Detection | | | | |
|---|---|---|---|---|---|
| DRB3*0104 | 169 | 32 | 154 | 144 | 24 | 13 |
| DRB3*0105 | 174 | 13 | | | | |
| DRB3*0106 | 169 | 32 | 48 | 144 | 24 | 13 |
| DRB3*0107 | 169 | 175 | 38 | 13 | | |
| DRB3*0108 | 169 | 27 | 28 | 144 | 24 | 13 |
| DRB3*0109 | 169 | 176 | 144 | 24 | 13 | |
| DRB3*0110 | 177 | | | | | |
| DRB3*0201 | 170 | 14 | | | | |
| DRB3*020201 | 178 | 179 | 176 | 45 | 13 | |
| DRB3*020202 | 178 | 179 | 176 | 45 | 38 | 23 |
| DRB3*020203 | 180 | | | | | |
| DRB3*020204 | 45 | 181 | 13 | | | |
| DRB3*0203 | 179 | 29 | 45 | 13 | | |
| DRB3*0204 | 45 | 24 | 23 | 14 | | |
| DRB3*0205 | 178 | 25 | 176 | 45 | 13 | |
| DRB3*0206 | 182 | 183 | 45 | 13 | | |
| DRB3*0207 | 45 | 141 | 144 | 13 | | |
| DRB3*0208 | 45 | 39 | 40 | 13 | | |
| DRB3*0209 | 176 | 84 | 38 | 13 | | |
| DRB3*0210 | 178 | 179 | 176 | 38 | 13 | |
| DRB3*0211 | 45 | 47 | 13 | | | |
| DRB3*0212 | 184 | 13 | | | | |
| DRB3*0213 | 185 | | | | | |
| DRB3*0214 | 186 | | | | | |
| DRB3*0215 | 178 | 179 | 176 | 45 | 38 | |
| DRB3*0216 | 45 | 95 | 13 | | | |
| DRB3*0217 | 45 | 162 | 13 | | | |

TABLE 24-13

| Allele Number | Probe Number for Detection | | | | |
|---|---|---|---|---|---|
| DRB3*030101 | 84 | 13 | 14 | | | |
| DRB3*030102 | 187 | | | | | |
| DRB3*0302 | 179 | 48 | 84 | 175 | 38 | 13 |
| DRB3*0303 | 25 | 48 | 144 | 84 | 24 | 13 |
| DRB4*010101 | 188 | | | | | |
| DRB4*0102 | 189 | | | | | |
| DRB4*010302 | 80 | 190 | 14 | | | |
| DRB4*010303 | 188 | 191 | | | | |
| DRB4*010304 | 192 | | | | | |
| DRB4*0104 | 23 | 193 | | | | |
| DRB4*0105 | 194 | 195 | | | | |
| DRB4*0106 | 194 | 190 | 193 | | | |
| DRB4*0201N | 80 | 14 | | | | |
| DRB5*010101 | 196 | | | | | |
| DRB5*010102 | 117 | 56 | 63 | 118 | 64 | |
| DRB5*0102 | 197 | 78 | 63 | 108 | 110 | |
| DRB5*0103 | 198 | 199 | 200 | | | |
| DRB5*0104 | 117 | 62 | | | | |
| DRB5*0105 | 99 | 63 | 108 | 110 | | |
| DRB5*0106 | 117 | 103 | | | | |
| DRB5*0107 | 117 | 10 | 108 | 110 | | |
| DRB5*0109 | 201 | | | | | |
| DRB5*0110N | 197 | 78 | 63 | 108 | 110 | |
| DRB5*0111 | 117 | 16 | | | | |
| DRB5*0112 | 117 | 84 | 67 | 81 | | |
| DRB5*0202 | 202 | 103 | | | | |
| DRB5*0203 | 198 | 78 | 47 | 19 | 1 | |

TABLE 24-13-continued

| Allele Number | Probe Number for Detection | | | |
|---|---|---|---|---|
| DRB5*0204 | 203 | 162 | 16 | 103 |
| DRB5*0205 | 203 | 78 | 103 | |

Example 13

Probes for Identification of HLA-MICA Allele

Extraction of DNA from 1 ml of human blood was performed using GFX Genomic Blood DNA Purification Kit from Amersham Biosciences in the same manner as in Example 1.

Next, quantitative PCR was carried out in the same manner as in Example 1 except that probes in Tables 25-1 and 25-2 were used and 2 μl of the mixed primers consisting of 1 μl each of respective solutions of the following primers (10 pmol/μl) and 6 μl of ultra pure water:

```
AGTGGAGCCAGTGGACCCAAGA    (SEQ ID NO: 3423)

TGATGTTTTCTTCTTACAACAAC   (SEQ ID NO: 3424)
```

After PCR amplification, referring to Amp Plot and Dissociation curves on a display of 5700 software, and to the allele-probe list 1 (Tables 27-1 and 27-2), it was identified as MICA*00201.

Example 14

Extraction of DNA from 1 ml of human blood was performed in the same way as in Example 3. PCR of human HLA-MICA was then performed in the same manner as in Example 2 except that 3 μl of the mixed primer consisting of 1 μl each of the solutions containing the following sequences at 10 pmol/μl respectively, and 12 μl of ultra pure water were used:

```
GTCTTCGTTATAACCTCACGGT    (SEQ ID NO: 3425)

GCTCGTGAGCCTGCAGGTCCTG    (SEQ ID NO: 3426)

AGTGGAGCCAGTGGACCCAAGA    (SEQ ID NO: 3427)
```

At the same time, a DNA microarray was prepared to identify the allele in the specimen described above in the same manner as in Example 2, except that probes in the probe list of Table 26-1 were used to form the probe spots respectively.

Then, hybridization was performed using the above specimen and the prepared DNA microarray in the same manner as in Example 2. The DNA microarray was air-dried and the fluorometry measurement was conducted with GenePix4000B (Axon). Referring to the allele-probe correspondence list 2 (Tables 28-1 and 28-2), it was identified as MICA*00201.

Allele list
MICA*001

(SEQ ID NO: 3428)

cttcgttataacctcacggtgctgtcctgggatggatctgtgcagtcagggtttctcactgaggtacatctgga tggtcagcccttcctgcgctgtgacaggcagaaatgcagggcaaagccccagggacagtgggcagaagatgtcctg ggaaataagacatgggacagagagaccagAgacttgacagggaacggaaaggacctcaggatgaccctggctcata tcaaggaccagaaagaaggcttgcattccctccaggagattagggtctgtgagatccatgaagacaacagcaccag gagctcccagcatttctactacgatggggagctcttcctctcccaaaacctggagactAaggaatggacaatgccc cagtcctccagagctcagaccttggccatgaacgtcaggaatttcttgaaggaagatgccatgaagaccaagacac actatcacgctatgcatgcagactgcctgcaggaactacggcgatatctaAaatccGgcgtagtcctgaggagaac agtgcccccatggtgaatgtcacccgcagcgaggcctcagagggcaacattaccgtgacatgcagggcttctggc ttctatccctggaatatcacactgaGctggcgtcaggatggggtatctttgagccacgacacccagcagtgggggg atgtcctgcctgatgggaatggaacctaccagacctgggtggccaccaggatttgccaaggagaggagcagaggtt cacctgctacatggaacacagcgggaatcacagcactcaccctgtgccctctgggaaagtgctggtgcttcagagt cattggcagacattccatgtttctgctgttgctgctNNNgctgctNNNNNNNNNNNNNNNNNNNNNattttgttatta ttattttctatgtccgttgttgtaagaagaaaacatcagctgcagagggtccagagctcgtgagcctgcaggtcct ggatcaacacccagttgggacgagtgaccacagggatgccacacagctcggatttcagcctctgatgtcagatctt gggtccactggctccact

MICA*00201

(SEQ ID NO: 3429)

gtcttcgttataacctcacggtgctgtccggggatggatctgtgcagtcagggtttctcgctgaggtacatctgga tggtcagcccttcctgcgctgtgacaggcagaaatgcagggcaaagccccagggacagtgggcagaagatgtcctg ggaaataagacatgggacagagagaccagggacttgacagggaacggaaaggacctcaggatgaccctggctcata tcaaggaccagaaagaaggcttgcattccctccaggagattagggtctgtgagatccatgaagacaacagcaccag gagctcccagcatttctactacgatggggagctcttcctctcccaaaacctggagactgaggaatggacaatgccc cagtcctccagagctcagaccttggccatgaacgtcaggaatttcttgaaggaagatgccatgaagaccaagacac actatcacgctatgcatgcagactgcctgcaggaactacggcgatatctaaaatccggcgtagtcctgaggagaac agtgcccccatggtgaatgtcacccgcagcgaggcctcagagggcaacattaccgtgacatgcagggcttctggc ttctatccctggaatatcacactgagctggcgtcaggatggggtatctttgagccacgacacccagcagtgggggg atgtcctgcctgatgggaatggaacctaccagacctgggtggccaccaggatttgccaaggagaggagcagaggtt cacctgctacatggaacacagcgggaatcacagcactcaccctgtgccctctgggaaagtgctggtgcttcagagt cattggcagacattccatgtttctgctgttgctgctgctgctgctgctgctgcttttgttattattattt tctaCgtctgttgttgtaagaagaaaacatcagctgcagagggtccagagctcgtgagcctgcaggtcctggatca acacccagttgggacgagtgaccacagggatgccacacagctcggatttcagcctctgatgtcagatcttgggtcc actggctccact

MICA*00202

(SEQ ID NO: 3430)

gtcttcgttataacctcacggtgctgtccGgggatggatctgtgcagtcagggtttctcgctgaggtacatctgga tggtcagcccttcctgcgctgtgacaggcagaaatgcagggcaaagccccagggacagtgggcagaagatgtcctg ggaaataagacatgggacagagagaccagggacttgacagggaacggaaaggacctcaggatgaccctggctcata tcaaggaccagaaagaaggcttgcattccctccaggagattagggtctgtgagatccatgaagacaacagcaccag gagctcccagcatttctactacgatggggagctcttcctctcccaaaacctggagactgaggaatggacaatgccc cagtcctccagagctcagaccttggccatgaacgtcaggaatttcttgaaggaagatgccatgaagaccaagacac actatcacgctatgcatgcagactgcctgcaggaactacggcgatatctaaaatccggcgtagtcctgaggagaac -continued agtgcccccatggtgaatgtcacccgcagTgaggcctcagagggcaacattaccgtgacatgcagggcttctggc ttctatccctggaatatcacactgagctggcgtcaggatggggtatctttgagccacgacacccagcagtgggggg atgtcctgcctgatgggaatggaacctaccagacctgggtggccaccaggatttgccaaggagaggagcagaggtt cacctgctacatggaacacagcgggaatcacagcactcaccctgtgccctctg

MICA*004 (SEQ ID NO: 3431)

gtcttcgttataaacctcacggtgctgtcctgggatggatctgtgcagtcagggtttcttgctgaggtacatctgga tggtcagcccttcctgcgctatgacaggcagaaatgcagggcaaagcccagggacagtgggcagaagatgtcctg ggaaataagacatgggacagagagaccagggacttgacagggaacggaaaggacctcaggatgaccctggctcata tcaaggaccagaaagaaggcttgcattccctccaggagattagggtctgtgagatccatgaagacaacagcaccag gagctcccagcatttctactacgatggggagctcttcctctcccaaaacgtggagactgaggaatggacagtgccc cagtcctccagagctcagaccttggccatgaacgtcaggaatttcttgaaggaagatgccatgaagaccaagacac actatcacgctatgcatgcagactgcctgcaggaactacggcgatatctagaatccagcgtagtcctgaggagaaG agtgcccccatggtgaatgtcacccgcagcgaggcctcagagggcaacatcaccgtgacatgcagggcttccagc ttctatccccggaatatcacactgacctggcgtcaggatggggtatctttgagccacgacacccagcagtgggggg atgtcctgcctgatgggaatggaacctaccagacctgggtggccaccaggatttgccaaggagaggagcagaggtt cacctgctacatggaacacagcgggaatcacagcactcaccctgtgccctctgggaaagtgctggtgcttcagagt cattggcagacattccatgttctgctgttgctgctgctgctgctgctatttttgttattattattttctatgtcc gttgttgtaagaagaaaacatcagctgcagagggtccagagctcgtgagcctgcaggtcctggatcaacacccagt tgggacgagtgaccacagggatgccacacagctcggatttcagcctctgatgtcagCtcttgggtccactggctcc act

MICA*005 (SEQ ID NO: 3432)

gtcttcgttataaacctcacggtgctgtcctgggatggatctgtgcagtcagggtttcttgctgaggtacatctgga tggtcagcccttcctgcgctAtgacaggcagaaatgcagggcaaagcccagggacagtgggcagaagatgtcctg ggaaataagacatgggacagagagaccagggacttgacagggaacggaaaggacctcaggatgaccctggctcata tcaaggaccagaaagaaggcttgcattccctccaggagattagggtctgtgagatccatgaagacaacagcaccag gagctcccagcatttctactacgatggggagctcttcctctcccaaaacctggagactgaggaatggacaGtgccc cagtcctccagagctcagaccttggccatgaacgtcaggaatttcttgaaggaagatgccatgaagaccaagacac actatcacgctatgcatgcagactgcctgcaggaactacggcgatatctaaaatccggcgtagtcctgaggagaac agtgcccccatggtgaatgtcacccgcagcgaggcctcagagggcaacattaccgtgacatgcagggcttccagc ttctatccccggaatatcacactgaCctggcgtcaggatggggtatctttgagccacgacacccagcagtgggggg atgtcctgcctgatgggaatggaacctaccagacctgggtggccaccaggatttgccGaggagaggagcagaggtt cacctgctacatggaacacagcgggaatcacagcactcaccctgtgccctct

MICA*006 (SEQ ID NO: 3433)

gtcttcgttataaacctcacggtgctgtcctgggatggatctgtgcagtcagggtttcttgctgaggtacatctgga tggtcagcccttcctgcgctatgacaggcagaaatgcagggcaaagcccagggacagtgggcagaagatgtcctg ggaaataagacatgggacagagagaccagggacttgacagggaacggaaaggacctcaggatgaccctggctcata tcaaggaccagaaagaaggcttgcattccctccaggagattagggtctgtgagatccatgaagacaacagcaccag gagctcccagcatttctactacgatggggagctcttcctctcccaaaacgtggagactgaggaatggacagtgccc cagtcctccagagctcagaccttggccatgaacgtcaggaatttcttgaaggaagatgccatgaagaccaagacac actatcacgctatgcatgcagactgcctgcaggaactacggcgatatctagaatccagcAtagtcctgaggagaac agtgcccccatggtgaatgtcacccgcagcgaggcctcagagggcaacatcaccgtgacatgcagggcttccagc

```
ttctatccccggaatatcacactgacctggcgtcaggatggggtatctttgagccacgacacccagcagtgggggg atgtcctgcctgatgggaatggaacctaccagacctgggtggccaccaggatttgccaaggagaggagcagaggtt cacctgctacatggaacacagcgggaatcacagcactcaccctgtgccctctgggaaagtgctggtgcttcagagt cattggcagacattccatgtttctgctgttgctgctgctgctgctattttttgttattattattttctatgtcc gttgttgtaagaagaaaacatcagctgcagagggtccagagctcgtgagcctgcaggtcctggatcaacacccagt tgggacgagtgaccacaggatgccacacagctcggatttcagcctctgatgtcagctcttgggtccactggctcc act
```

MICA*00701 (SEQ ID NO: 3434)

```
gtcttcgttataaacctcacggtgctgtcctgggatggatctgtgcagtcagggtttctcgctgaggtacatctgga tggtcagcccttcctgcgctgtgacaggcagaaatgcagggcaaagcccagggacagtgggcagaagatgtcctg ggaaataagacatgggacagagagaccagggacttgacagggaacggaaaggacctcaggatgaccctggctcata tcaaggaccagaaagaaggcttgcattccctccaggagattagggtctgtgagatccatgaagacaacagcaccag gagctcccagcatttctactacgatggggagctcttcctctcccaaaacctggagactgaggaatggacaatgccc cagtcctccagagctcagaccttggccatgaacgtcaggaatttcttgaaggaagatgccatgaagaccaagacac actatcacgctatgcatgcagactgcctgcaggaactacggcgatatctaaaatccggcgtagtcctgaggagaac agtgcccccatggtgaatgtcacccgcagTgaggcctcagagggcaacattaccgtgacatgcagggcttctggc ttctatccctggaatatcacactgagctggcgtcaggatggggtatctttgagccacgacacccagcagtgggggg atgtcctgcctgatgggaatggaacctaccagacctgggtggccaccaggatttgccaaggagaggagcagaggtt cacctgctacatggaacacagcgggaatcacagcactcaccctgtgccctctgggaaagtgctggtgcttcagagt cattggcagacattccatgtttctgctgttgctgctgctgctattttttgttattattattttctatgtccgttgtt gtaagaagaaaacatcagctgcagagggtccag
```

MICA*00702 (SEQ ID NO: 3435)

```
gtcttcgttataaacctcacggtgctgtcctgggatggatctgtgcagtcagggtttctcgctgaggtacatctgga tggtcagcccttcctgcgctgtgacaggcagaaatgcagggcaaagcccagggacagtgggcagaagatgtcctg ggaaataagacatgggacagagagaccagGgacttgacagggaacggaaaggacctcaggatgaccctggctcata tcaaggaccagaaagaaggcttgcattccctccaggagattagggtctgtgagatccatgaagacaacagcaccag gagctcccagcatttctactacgatggggagctcttcctctcccaaaacctggagactGaggaatggacaatgccc cagtcctccagagctcagaccttggccatgaacgtcaggaatttcttgaaggaagatgccatgaagaccaagacac actatcacgctatgcatgcagactgcctgcaggaactacggcgatatctaaaatccggcgtagtcctgaggagaac agtgcccccatggtgaatgtcacccgcagcgaggcctcagagggcaacattaccgtgacatgcagggcttctggc ttctatccctggaatatcacactgagctggcgtcaggatggggtatctttgagccacgacacccagcagtgggggg atgtcctgcctgatgggaatggaacctaccagacctgggtggccaccaggatttgccaaggagaggagcagaggtt cacctgctacatggaacacagcgggaatcacagcactcaccctgtgccctctg
```

MICA*00801 (SEQ ID NO: 3436)

```
gtcttcgttataaacctcacggtgctgtcctgggatggatctgtgcagtcagggtttcttgctgaggtacatctgga tggtcagcccttcctgcgctatgacaggcagaaatgcagggcaaagcccagggacagtgggcagaagatgtcctg ggaaataagacatgggacagagagaccagggacttgacagggaacggaaaggacctcaggatgaccctggctcata tcaaggaccagaaagaaggcttgcattccctccaggagattagggtctgtgagatccatgaagacaacagcaccag gagctcccagcatttctactacgatggggagctcttcctctcccaaaacctggagactgaggaatggacagtgccc cagtcctccagagctcagaccttggccatgaacgtcaggaatttcttgaaggaagatgccatgaagaccaagacac
```

MICA*00802

(SEQ ID NO: 3437)

gtcttcgttataacctcacggtgctgtcctgggatggatctgtgcagtcagggtttcttgctgaggtacatctgga tggtcagcccttcctgcgctatgacaggcagaaatgcagggcaaagcccagggacagtgggcagaagatgtcctg ggaaataagacatgggacagagagaccagggacttgacagggaacggaaaggacctcaggatgaccctggctcata tcaaggaccagaaagaaggcttgcattccctccaggagattagggtctgtgagatccatgaagacaacagcaccag gagctcccagcatttctactacgatggggagctcttcctctcccaaaacctggagactgaggaatggacagtgccc cagtcctccagagctcagaccttggccatgaacgtcaggaatttcttgaaggaagatgccatgaagaccaagacac actatcacgctatgcatgcagactgcctgcaggaactacggcgatatctagaatccggcgtagtcctgaggagaac agtgcccccatggtgaatgtcacccgcagcgaggcctcagagggcaacatcaccgtgacatgcagggcttccagc ttctatccccggaatatcatactgacctggcgtcaggatggggtatctttgagccacgacacccagcagtgggggg atgtcctgcctgatgggaatggaacctaccagacctgggtggccacTaggatttgccgaggagaggagcagaggtt cacctgctacatggaacacagcgggaatcacagcactcaccctgtgccctctgggaaagtgctggtgcttcagagt cattggcagacattccatgtttctgctgttgctgctggctgctgcTattttgttattattattttctatgtccgt tgttgtaagaagaaaacatcagctgcagagggtccag

MICA*00803

(SEQ ID NO: 3438)

gtcttcgttataacctcacggtgctgtcctgggatggatctgtgcagtcagggtttcttgctgaggtacatctgga tggtcagcccttcctgcgctatgacaggcagaaatgcagggcaaagcccagggacagtgggcagaagatgtcctg ggaaataagacatgggacagagagaccagggacttgacagggaacggaaaggacctcaggatgaccctggctcata tcaaggaccagaaagaaggcttgcattccctccaggagattagggtctgtgagatccatgaagacaacagcaccag gagctcccagcatttctactacgatggggagctcttcctctcccaaaacctggagactgaggaatggacagtgccc cagtcctccagagctcagaccttggccatgaacgtcaggaatttcttgaaggaagatgccatgaagaccaagacac actatcacgctatgcatgcagactgcctgcaggaactacggcgatatctagaatccggcgtagtcctgaggagaac agtgcccccatggtgaatgtcacccgcagcgaggcAtcagagggcaacatcaccgtgacatgcagggcttccagc ttctatccccggaatatcatactgacctggcgtcaggatggggtatctttgagccacgacacccagcagtgggggg atgtcctgcctgatgggaatggaacctaccagacctgggtggccaccaggatttgccgaggagaggagcagaggtt cacctgctacatggaacacagcgggaatcacagcactcaccctgtgccctctg

MICA*00901

(SEQ ID NO: 3439)

gtcttcgttataacctcacggtgctgtcctgggatggatctgtgcagtcagggtttcttgctgaggtacatctgga tggtcagcccttcctgcgctatgacaggcagaaatgcagggcaaagcccagggacagtgggcagaagatgtcctg ggaaataagacatgggacagagagaccagggacttgacagggaacggaaaggacctcaggatgaccctggctcata tcaaggaccagaaagaaggcttgcattccctccaggagattagggtctgtgagatccatgaagacaacagcaccag gagctcccagcatttctactacgatggggagctcttcctctcccaaaacGtggagactgaggaatggacagtgccc cagtcctccagagctcagaccttggccatgaacgtcaggaatttcttgaaggaagatgccatgaagaccaagacac -continued

```
actatcacgctatgcatgcagactgcctgcaggaactacggcgatatctagaatccagcgtagtcctgaggagaac agtgcccccatggtgaatgtcacccgcagcgaggcctcagagggcaacatcaccgtgacatgcagggcttccagc ttctatccccggaatatcacactgacctggcgtcaggatggggtatctttgagccacgacacccagcagtgggggg atgtcctgcctgatgggaatggaacctaccagacctgggtggccaccaggatttgccaaggagaggagcagaggtt cacctgctacatggaacacagcgggaatcacagcactcaccctgtgccctctgggaaagtgctggtgcttcagagt cattggcagacattccatgtttctgctgttgctgctgctgctgctatttttgttattattattttctatgtcc gttgttgtaagaagaaaacatcagctgcagagggtccagagctcgtgagcctgcaggtcctggatcaacacccagt tgggacgagtgaccacagggatgccacacagctcggatttcagcctctgatgtcagCtcttgggtccactggctcc act
```

MICA*00902

(SEQ ID NO: 3440)

```
gtcttcgttataaacctcacggtgctgtcctgggatggatctgtgcagtcagggtttcttgctgaggtacatctgga tggtcagcccttcctgcgctatgacaggcagaaatgcagggcaaagcccagggacagtgggcagaagatgtcctg ggaaataagacatgggacagagagaccagggacttgacagggaacggaaaggacctcaggatgaccctggctcata tcaaggaccagaaagaaggcttgcattccctccaggagattagggtctgtgagatccatgaagcaacagcaccag gagctcccagcatttctactaTgatggggagctcttcctctcccaaaacgtggagactgaggaatggacagtgccc cagtcctccagagctcagaccttggccatgaacgtcaggaatttcttgaaggaagatgccatgaagaccaagacac actatcacgctatgcatgcagactgcctgcaggaactacggcgatatctagaatccagcgtagtcctgaggagaac agtgcccccatggtgaatgtcacccgcagcgaggcctcagagggcaacatcaccgtgacatgcagggcttccagc ttctatccccggaatatcacactgacctggcgtcaggatggggtatctttgagccacgacacccagcagtgggggg atgtcctgcctgatgggaatggaacctaccagacctgggtggccaccaggatttgccaaggagaggagcagaggtt cacctgctacatggaacacagcgggaatcacagcactcaccctgtgccctctgggaaagtgctggtgcttcagagt cattggcagacattccatgtttctgctgttgctgctgctgctgctatttttgttattattattttctatgtcc gttgttgtaagaagaaaacatcagctgcagagggtccagagctcgtgagcctgcaggtcctggatcaacacccagt tgggacgagtgaccacagggatgccacacagctcggatttcagcctctgatgtcagctcttgggtccactggctcc act
```

MICA*010

(SEQ ID NO: 3441)

```
gtcttccttataaacctcacggtgctgtcctgggatggatctgtgcagtcagggtttcttgctgaggtacatctgga tggtcagcccttcctgcgctatgacaggcagaaatgcagggcaaagcccagggacagtgggcagaagatgtcctg ggaaataagacatgggacagagagaccagggacttgacagggaacggaaaggacctcaggatgaccctggctcata tcaaggaccagaaagaaggcttgcattccctccaggagattagggtctgtgagatccatgaagcaacagcaccag gagctcccagcatttctactacgatggggagctcttcctctcccaaaacctggagactgaggaatggacagtgccc cagtcctccagagctcagaccttggccatgaacgtcaggaatttcttgaaggaagatgccatgaagaccaagacac actatcacgctatgcatgcagactgcctgcaggaactacggcgatatctagaatccAgcgtagtcctgaggagaac agtgcccccatggtgaatgtcacccgcagcgaggcctcagagggcaacatcaccgtgacatgcagggcttccagc ttctatccccggaatatcatactgacctggcgtcaggatggggtatctttgagccacgacacccagcagtgggggg atgtcctgcctgatgggaatggaacctaccagacctgggtggccaccaggatttgccGaggagaggagcagaggtt cacctgctacatggaacacagcgggaatcacagcactcaccctgtgccctctgggaaagtgctggtgcttcagagt cattggcagacattccatgtttctgctgttgctgctgctgctgctatttttgttattattattttctatgtccgtt gttgtaagaagaaaacatcagctgcagagggtccagagctcgtgagcctgcaggtcctggatcaacacccagttgg gacgagtgaccacagggatgccacacagctcggatttcagcctctgatgtcagCtcttgggtccactggctccact
```

MICA*011

(SEQ ID NO: 3442)

gtcttcgttataaacctcacggtgctgtccggggatggatctgtgcagtcagggtttctcgctgaggtacatctgga
tggtcagcccttcctgcgctgtgacaggcagaaatgcagggcaaagccccagggacagtgggcagaagatgtcctg
ggaaataagacatgggacagagagaccagggacttgacagggaacggaaaggacctcaggatgaccctggctcata
tcaaggaccagaaagaaggcttgcattccctccaggagattagggtctgtgagatccatgaagacaacagcaccag
gagctcccagcatttctactacgatggggagctcttcctctcccaaaacctggagactgaggaatggacaatgccc
cagtcctccagagctcagaccttggccatgaacgtcaggaatttcttgaaggaagatgccgtgaagaccaagacac
actatcacgctatgcatgcagactgcctgcaggaactacggcgatatctaaaatccggcgtagtcctgaggagaac
agtgcccccatggtgaatgtcacccgcagcgaggcctcagagggcaacattaccgtgacatgcagggcttctggc
ttctatccctggaatatcacactgagctggcgtcaggatggggtatctttgagccacgacacccagcagtgggggg
atgtcctgcctgatgggaatggaacctaccagacctgggtggccaccaggatttgccaaggagaggagcagaggtt
cacctgctacatggaacacagcgggaatcacagcactcacgctgtgccctctgggaaagtgctggtgcttcagagt
cattggcagacattccatgtttctgctgttgctgctgctgctgctgctatttttgttattattattttctatgtct
gttgttgtaagaagaaaacatcagctgcagagggtccagagctcgtgagcctgcaggtcctggatcaacacccagt
tgggacgagtgaccacagggatgccacacagctcggatttcagcctctgatgtcagctcttgggtccGctggctcc
act

MICA*01201

(SEQ ID NO: 3443)

gtcttcgttataaacctcacggtgctgtcctgggatggatctgtgcagtcagggtttctcactgaggtacatctgga
tggtcagcccttcctgcgctgtgacaggcagaaatgcagggcaaagccccagggacagtgggcagaagatgtcctg
ggaaataagacatgggacagagagaccagagacttgacagggaacggaaaggacctcaggatgaccctggctcata
tcaaggaccagaaagaaggcttgcattccctccaggagattagggtctgtgagatccatgaagacaacagcaccag
gagctcccagcatttctactacgatggggagctcttcctctcccaaaacctggagactgaggaatggacaatgccc
cagtcctccagagctcagaccttggccatgaacgtcaggaatttcttgaaggaagatgccatgaagaccaagacac
Tctatcacgctatgcatgcagactgcctgcaggaactacggcgatatctaaaatccggcgtagtcctgaggagaac
agtgcccccatggtgaatgtcacccgcagcgaggcctcagagggcaacattaccgtgacatgcagggcttctggc
ttctatccctggaatatcacactgagctggcgtcaggatggggtatctttgagccacgacacccagcagtgggggg
atgtcctgcctgatgggaatggaacctaccagacctgggtggccaccaggatttgccaaggagaggagcagaggtt
cacctgctacatggaacacagcgggaatcacagcactcaccctgtgccctctgggaaagtgctggtgcttcagagt
cattggcagacattccatgtttctgctgttgctgctgctgctatttttgttattattattttctatgtccgttgtt
gtaagaagaaaacatcagctgcagagggtccagagctcgtgagcctgcaggtcctggatcaacacccagttgggac
gagtgaccacagggatgccacacagctcggatttcagcctctgatgtcagatcttgggtccactggctccact

MICA*01202

(SEQ ID NO: 3444)

gtcttcgttataaacctcacggtgctgtcctgggatggatctgtgcagtcagggtttctcactgaggtacatctgga
tggtcagcccttcctgcgctgtgacaggcagaaatgcagggcaaagccccagggacagtgggcagaagatgtcctg
ggaaataagacatgggacagagagaccagagacttgacagggaacggaaaggacctcaggatgaccctggctcata
tcaaggaccagaaagaaggcttgcattccctccaggagattagggtctgtgagatccatgaagacaacagcaccag
gagctcccagcatttctactacgatggggagctcttcctctcccaaaacctggagactgaggaatggacaatgccc
cagtcctccagagctcagaccttggccatgaacgtcaggaatttcttgaaggaagatgccatgaagaccaagacac
tctatcacgctatgcatgcagactgcctgcaggaactacggcgatatctaaaatccggcgtagtcctgaggagaac
agtgcccccatggtgaatgtcacccgcagcgaggcctcagagggcaacattaccgtgacatgcagggcttctggc
ttctatccctggaatatcacactgagctggcgtcaggatggggtatctttgagccacgacacccagcagtgggggg atgtcctgcctgatgggaatggaacctaccagacctgggtggccaccaggatttgccaaggagaggagcaAaggtt cacctgctacatggaacacagcgggaatcacagcactcaccctgtgccctctg

MICA*013

(SEQ ID NO: 3445)

gtcttcgttataaacctcacggtgctgtccGgggatggatctgtgcagtcagggtttctcgctgaggtacatctgga tggtcagcccttcctgcgctgtgacaggcagaaatgcagggcaaagcccagggacagtgggcagaagatgtcctg ggaaataagacatgggacagagagaccagggacttgacagggaacggaaaggacctcaggatgaccctggctcata tcaaggaccagaaagaaggcttgcattccctccaggagattagggtctgtgagatccatgaagacaacagcaccag gagctcccagcatttctactacgatggggagctcttcctctcccaaaacctggagactgaggaatggacagtgccc cagtcctccagagctcagaccttggccatgaacgtcaggaatttcttgaaggaagatgccatgaagaccaagacac actatcacgctatgcatgcagactgcctgcaggaactacggcgatatctaGaatccggcgtagtcctgaggagaac agtgcccccatggtgaatgtcacccgcagcgaggcctcagagggcaacattaccgtgacatgcagggcttctggc ttctatccctggaatatcacactgagctggcgtcaggatggggtatctttgagccacgacacccagcagtgggggg atgtcctgcctgatgggaatggaacctaccagacctgggtggccaccaggatttgccGaggagaggagcagaggtt cacctgctacatggaacacagcgggaatcacagcactcaccctgtgccctct

MICA*014

(SEQ ID NO: 3446)

gtcttcgttataaacctcacggtgctgtccggggatggatctgtgcagtcagggtttctcgctgaggtacatctgga tggtcagcccttcctgcgctgtgacaggcagaaatgcagggcaaagcccagggacagtgggcagaagatgtcctg ggaaataagacatgggacagagagaccagggacttgacagggaacggaaaggacctcaggatgaccctggctcata tcaaggaccagaaagaaggcttgcattccctccaggagattagggtctgtgagatccatgaagacaacagcaccag gagctcccagcatttctactacgatAgggagctcttcctctcccaaaacctggagactgaggaatggacaatgccc cagtcctccagagctcagaccttggccatgaacgtcaggaatttcttgaaggaagatgccatgaagaccaagacac actatcacgctatgcatgcagactgcctgcaggaactacggcgatatctagaatccggcgtagtcctgaggagaaG agtgcccccatggtgaatgtcacccgcagcgaggcctcagagggcaacattaccgtgacatgcagggcttctggc ttctatccctggaatatcacactgagctggcgtcaggatggggtatctttgagccacgacacccagcagtgggggg atgtcctgcctgatgggaatggaacctaccagacctgggtggccaccaggatttgccaaggagaggagcagaggtt cacctgctacatggaacacagcgggaatcacagcactcaccctgtgccctct

MICA*015

(SEQ ID NO: 3447)

gtcttcgttataaacctcacggtgctgtccggggatggatctgtgcagtcagggtttctcgctgaggtacatctgga tggtcagcccttcctgcgctgtgacaggcagaaatgcagggcaaagcccagggacagtgggcagaagatgtcctg ggaaataagacatgggacagagagaccagggacttgacagggaacggaaaggacctcaggatgaccctggctcata tcaaggaccagaaagaaggcttgcattccctccaggagattagggtctgtgagatccatgaagacaacagcaccag gagctcccagcatttctactacgatAgggagctcttcctctcccaaaacctggagactgaggaatggacaatgccc cagtcctccagagctcagaccttggccatgaacgtcaggaatttcttgaaggaagatgccatgaagaccaagacac actatcacgctatgcatgcagactgcctgcaggaactacggcgatatctaaaatccggcgtagtcctgaggagaac agtgcccccatggtgaatgtcacccgcagcgaggcctcagagggcaacattaccgtgacatgcagggcttctggc ttctatccctggaatatcacactgagctggcgtcaggatggggtatctttgagccacgacacccagcagtgggggg atgtcctgcctgatgggaatggaacctaccagacctgggtggccaccaggatttgccaaggagaggagcagaggtt cacctgctacatggaacacagcgggaatcacagcactcaccctgtgccctctggaaagtgctggtgcttcagagtc attggcagacattccatgtttctgctgttgctgctgctgctgctgctgctgctattttttgttattattatttt ctacgtctgttgttgtaagaagaaaacatcagctgcagagggtccagGgctcgtgag

MICA*016

(SEQ ID NO: 3448)

gtcttcgttataacctcacggtgctgtcctgggatggatctgtgcagtcagggtttcttgctgaggtacatctgga tggtcagcccttcctgcgctatgacaggcagaaatgcagggcaaagcccagggacagtgggcagaagatgtcctg ggaaataagacatgggacagagagaccagggacttgacagggaacggaaaggacctcaggatgaccctggctcata tcaaggaccagaaagaaggcttgcattccctccaggagattagggtctgtgagatccatgaagacaacagcaccag gagctcccagcatttctactacgatggggagctcttcctctcccaaaacctggagactgaggaatggacagtgccc cagtcctccagagctcagaccttggccatgaacgtcaggaatttcttgaaggaagatgccatgaagaccaagacac actatcacgctatgcatgcagactgcctgcaggaactacggcgatatctagaatccagcgtagtcctgaggagaac agtgcccccatggtgaatgtcacccgcagcgaggcctcagagggcaacatcaccgtgacatgcagggcttccagc ttctatccccggaatatcatactgacctggcgtcaggatgggCtatcttttgagccacgacacccagcagtgggggg atgtcctgcctgatgggaatggaacctaccagacctgggtggccaccaggatttgccgaggagaggagcagaggtt cacctgctacatggaacacagcgggaatcacagcactcaccctgtgccctctgggaaagtgctggtgcttcagagt cattggcagacattccatgtttctgctgttgctgctgctgctgctattttttgttattattattttctatgtccgtt gttgtaagaagaaaacatcagctgcagagggtccagagctcgtgagcctgcaggtcctggatcaacacccagttgg gacgagtgaccacagggatgccacacagctcggatttcagcctctgatgtcagCtcttgggtccactggctccact

MICA*017

(SEQ ID NO: 3449)

gtcttcgttataacctcacggtgctgtccggggatggatctgtgcagtcagggtttctcgctgaggtacatctgga tggtcagcccttcctgcgctgtgacaggcagaaatgcagggcaaagcccagggacagtgggcagaagatgtcctg ggaaataagacatgggacagagagaccagggacttgacagggaacggaaaggacctcaggatgaccctggctcata tcaaggaccagaaagaaggcttgcattccctccGggagattagggtctgtgagatccatgaagacaacagcaccag gagctcccagcatttctactacgatggggagctcttcctctcccaaaacctggagactgaggaatggacaatgccc cagtcctccagagctcagaccttggccatgaacgtcaggaatttcttgaaggaagatgccatgaagaccaagacac actatcacgctatgcatgcagactgcctgcaggaactacggcgatatctaaaatccggcgtagtcctgaggagaac agtgcccccatggtgaatgtcacccgcagcgaggcctcagagggcaacattaccgtgacatgcagggcttctggc ttctatccctggaatatcacactgagctggcgtcaggatggggtatcttttgagccacgacacccagcagtgggggg atgtcctgcctgatgggaatggaacctaccagacctgggtggccaccaggatttgccaaggagaggagcagaggtt cacctgctacatggaacacagcgggaatcacagcactcaccctgtgccctctgggaaagtgctggtgcttcagagtc attggcagacattccatgtttctgctgttgctgctgctgctgctgctgctgctattttttgttattattattttt ctacgtctgttgttgtaagaagaaaacatcagctgcagagggtccagggctcgtgag

MICA*018

(SEQ ID NO: 3450)

gtcttcgttataacctcacggtgctgtcctgggatggatctgtgcagtcagggtttctcactgaggtacatctgga tggtcagcccttcctgcgctgtgacaggcagaaatgcagggcaaagcccagggacagtgggcagaagatgtcctg ggaaataagacatgggacagagagaccagagacttgacagggaacggaaaggacctcaggatgaccctggctcata tcaaggaccagaaagaaggcttgcattccctccaggagattagggtctgtgagatccatgaagacaacagcaccag gagctcccagcatttctactacgatggggagctcttcctctcccaaaacctggagactGaggaatggacaatgccc cagtcctccagagctcagaccttggccatgaacgtcaggaatttcttgaaggaagatgccatgaagaccaagacac actatcacgctatgcatgcagactgcctgcaggaactacggcgatatctaaaatccggcgtagtcctgaggagaac agtgcccccatggtgaatgtcacccgcagcgaggcctcagagggcaacattaccgtgacatgcagggcttctggc ttctatccctggaatatcacactgagctggcgtcaggatggggtatcttttgagccacgacacccagcagtgggggg atgtcctgcctgatgggaatggaacctaccagacctgggtggccaccaggatttgccaaggagaggagcagaggtt cacctgctacatggaacacagcgggaatcacagcactcaccctgtgccctctgggaaagtgctggtgcttcagagt

```
cattggcagacattccatgtttctgctgttgctgctgctgctattttttgttattattattttctatgtccgttgtt gtaagaagaaaacatcagctgcagagggtccagagctcgtgagcctgcaggtcctggatcaacacccagttgggac gagtgaccacagggatgccacacagctcggatttcagcctctgatgtcagatcttgggtccactggctccact
```

MICA*019

(SEQ ID NO: 3451)
```
gtcttcgttataaccctcacggtgctgtcctgggatggatctgtgcagtcagggtttcttgctgaggtacatctgga tggtcagcccttcctgcgctatgacaggcagaaatgcagggcaaagcccagggacagtgggcagaagatgtcctg ggaaataagacatgggacagagagaccagggacttgacagggaacggaaaggacctcaggatgaccctggctcata tcaaggaccagaaagaaggcttgcattccctccaggagatagggtctgtgagatccatgaagacaacagcaccag gagctcccagcatttctactacgatggggagctcttcctctcccaaaacctggagactgaggaatggacagtgccc cagtcctccagagctcagaccttggccatgaacgtcaggaatttcttgaaggaagatgccatgaagaccaagacac actatcacgctatgcatgcagactgcctgcaggaactacggcgatatctagaatccagcgtagtcctgaggagaac agtgcccccatggtgaatgtcacccgcagcgaggcctcagagggcaacatcaccgtgacatgcagggcttccagc ttctatccccggaatatcatactgacctggcgtcaggatggggtatctttgagccacgacacccagcagtggggggg atgtcctgcctgatgggaatggaacctaccagacctgggtggccaccaggatttgccgaggagaggagcagaggtt cacctgctacatggaacacagcgggaatcacagcactcaccctgtgccctctgggaaagtgctggtgcttcagagt cattggcagacattccatgtttctgctgttgctgctgctgctgctattttttgttattattattttctatgtccgtt gttgtaagaagaaaacatcagctgcagagggtccagagctcgtgagcctgcaggtcctggatcaacacccagttgg gacgagtgT
```

MICA*020

(SEQ ID NO: 3452)
```
gtcttcgttataaccctcacggtgctgtccggggatggatctgtgcagtcagggtttctcgctgaggtacatctgga tggtcagcccttcctgcgctgtgacaggcagaaatgcagggcaaagcccagggacagtgggcagaagatgtcctg ggaaataagacatgggacagagagaccagggacttgacagggaacggaaaggacctcaggatgaccctggctcata tcaaggaccagaaagaaggcttgcattccctccaggagattagggtctgtgagatccatgaagacaacagcaccag gagctcccagcatttctactacgatggggagctcttcctctcccaaaacctggagactgaggaatggacaatgccc cagtcctccagagctcagaccttggccatgaacgtcaggaatttcttgaaggaagatgccatgaagaccaagacac actatcacgctatgcatgcagactgcctgcaggaactacggcgatatctaaaatccggcgtagtcctgaggagaac agtgcccccatggtgaatgtcacccgcagcgaggcctcagagggcaacattaccgtgacatgcagggcttctggc ttctatccctggaatatcacactgagctggcgtcaggatggggtatctttgagccacgacacccagcagtggggggg atgtcctgcctgatgggaatggaacctaccagacctgggtggccaccaggatttgccaaggagaggagcagaggtt cacctgctacatggaacacagcgggaatcacagcactcaccctgtgccctctgggaaagtgctggtgcttcagagt cattggcagacattccatgtttctgctgttgctgctgctgctgctgctgctgctgcTattttttgttattatta ttttctacgtctgttgttgtaagaagaaaacatcagctgcagagggtccag
```

MICA*021

(SEQ ID NO: 3453)
```
gtcttcgttataaccctcacggtgctgtcctgggatggatctgtgcagtcagggtttctcactgaggtacatctgga tggtcagcccttcctgcgctgtgacaggcagaaatgcagggcaaagcccagggacagtgggcagaagatgtcctg ggaaaCaagacatgggacagagagaccagagacttgacagggaacggaaaggacctcaggatgaccctggctcata tcaaggaccagaaagaaggcttgcattccctccaggagattagggtctgtgagatccatgaagacaacagcaccag gagctcccagcatttctactacgatggggagctcttcctctcccaaaacctggagactgaggaatggacaatgccc cagtcctccagagctcagaccttggccatgaacgtcaggaatttcttgaaggaagatgccatgaagaccaagacac tctatcacgctatgcatgcagactgcctgcaggaactacggcgatatctaaaatccggcgtagtcctgaggagaac
``` agtgcccccatggtgaatgtcacccgcagcgaggcctcagagggcaacattaccgtgacatgcagggcttctggc ttctatccctggaatatcacactgagctggcgtcaggatggggtatctttgagccacgacacccagcagtgggggg atgtcctgcctgatgggaatggaacctaccagacctgggtggccaccaggatttgccaaggagaggagcagaggtt cacctgctacatggaacacagcgggaatcacagcactcaccctgtgccctctg

MICA*022

(SEQ ID NO: 3454)

gtcttcgttataaacctcacggtgctgtccGgggatggatctgtgcagtcagggtttctcgctgaggtacatctgga tggtcagcccttcctgcgctgtgacaggcagaaatgcagggcaaagccccagggacagtgggcagaagatgtcctg ggaaataagacatgggacagagagaccagggacttgacagggaacggaaaggacctcaggatgaccctggctcata tcaaggaccagaaagaaggcttgcattccctccaggagattagggtctgtgagatccatgaagacaacagcaccag gagctcccagcatttctactacgatggggagctcttcctctcccaaaacctggagactgaggaatggacagtgccc cagtcctccagagctcagaccttggccatgaacgtcaggaatttcttgaaggaagatgccatgaagaccaagacac actatcacgctatgcatgcagactgcctgcaggaactacggcgatatctagaatccAgcgtagtcctgaggagaac agtgcccccatggtgaatgtcacccgcagcgaggcctcagagggcaacatcaccgtgacatgcagggcttccagc ttctatccccggaatatcatactgacctggcgtcaggatggggtatctttgagccacgacacccagcagtgggggg atgtcctgcctgatgggaatggaacctaccagacctgggtggccaccaggatttgccGaggagaggagcagaggtt cacctgctacatggaacacagcgggaatcacagcactcaccctgtgccctctg

MICA*023

(SEQ ID NO: 3455)

gtcttcgttataaacctcacggtgctgtccGgggatggatctgtgcagtcagggtttctcgctgaggtacatctgga tggtcagcccttcctgcgctgtgacaggcagaaatgcagggcaaagccccagggacagtgggcagaagatgtcctg ggaaataagacatgggacagagagaccagggacttgacagggaacggaaaggacctcaggatgaccctggctcata tcaaggaccagaaagaaggcttgcattccctccaggagattagggtctgtgagatccatgaagacaacagcaccag gagctcccagcatttctactacgatggggagctcttcctctcccaaaacctggagactgaggaatggacaatgccc cagtcctccagagctcagaccttggccatgaacgtcaggaatttcttgaaggaagatgccatgaagaccaagacac actatcacgctatgcatgcagactgcctgcaggaactacggcgatatctaaaatccggcgtagtcctgaggagaac agtgcccccatggtgaatgtcacccgcagcgaggcctcagagggcaacattaccgtgacatgcagggcttctggc ttctatccctggaatatcacactgagctggcgtcaggatggggtatctttgagccacgacacccagcagtgggggg atgtcctgcctgatgggaatggaacctaccagacctgggtggccaccaggatttgccaaggagaggagcagaggtt cacctgctacatggaacacagcgggaatcacagcactcaccctgtgccctctgggaaagtgctggtgcttcagagt cattggcagacattccatgttttctgctgttgctgctGgctgctgctattttttgttattattattttctatgtccgt tgttgtaa

MICA*024

(SEQ ID NO: 3456)

gtcttcgttataaacctcacggtgctgtcctgggatggatctgtgcagtcagggtttctTgctgaggtacatctgga tggtcagcccttcctgcgctAtgacaggcagaaatgcagggcaaagccccagggacagtgggcagaagatgtcctg ggaaataagacatgggacagagagaccagggacttgacagggaacggaaaggacctcaggatgaccctggctcata tcaaggaccagaaagaaggcttgcattccctccaggagattagggtctgtgagatccatgaagacaacagcaccag gagctcccagcatttctactacgatggggagctcttcctctcccaaaacctggagactgaggaatggacaGtgccc cagtcctccagagctcagaccttggccatgaacgtcaggaatttcttgaaggaagatgccatgaagaccaagacac actatcacgctatgcatgcagactgcctgcaggaactacggcgatatctagaatccggcgtagtcctgaggagaac agtgcccccatggtgaatgtcacccgcagcgaggcctcagagggcaacatCaccgtgacatgcagggcttccagc ttctatccccggaatatcacactgaCctggcgtcaggatggggtatctttgagccacgacacccagcagtgggggg atgtcctgcctgatgggaatggaacctaccagacctgggtggccaccaggatttgccaaggagaggagcagaggtt cacctgctacatggaacacagcgggaatcacagcactcaccctgtgccctctg

MICA*025

(SEQ ID NO: 3457)

gtcttccttataacctcacggtgctgtcctgggatggatctgtgcagtcagggtttctTgctgaggtacatctgga tggtcagcccttcctgcgctatgacaggcagaaatgcagggcaaagcccagggacagtgggcagaagatgtcctg ggaaataagacatgggacagagagaccagggacttgacagggaacggaaaggacctcaggatgaccctggctcata tcaaggaccagaaagaaggcttgcattccctccaggagattagggtctgtgagatccatgaagacaacagcaccag gagctcccagcatttctactacgatggggagctcttcctctcccaaaacctggagactGaggaatggacaatgccc cagtcctccagagctcagaccttggccatgaacgtcaggaatttcttgaaggaagatgccatgaagaccaagacac actatcacgctatgcatgcagactgcctgcaggaactacggcgatatctaaaatccggcgtagtcctgaggagaac agtgcccccatggtgaatgtcacccgcagcgaggcctcagagggcaacattaccgtgacatgcagggcttctggc ttctatccctggaatatcacactgagctggcgtcaggatggggtatctttgagccacgacacccagcagtgggggg atgtcctgcctgatgggaatggaacctaccagacctgggtggccaccaggatttgccaaggagaggagcagaggtt cacctgctacatggaacacagcgggaatcacagcactcaccctgtgccctctg

MICA*026

(SEQ ID NO: 3458)

gtcttcgttataacctcacggtgctgtcctgggatggatctgtgcagtcagggtttctcgctgaggtacatctgga tggtcagcccttcctgcgctgtgacaggcagaaatgcagggcaaagcccagggacagtgggcagaagatgtcctg ggaaataagacatgggacagagagaccagggacttgacagggaacggaaaggacctcaggatgaccctggctcata tcaaggaccagaaagaaggcttgcattccctccaggagattagggtctgtgagatccatgaagacaacagcaccag gagctcccagcatttctactacgatggggagctcttcctctcccaaaacctggagactgaggaatggacaatgccc cagtcctccagagctcagaccttggccatgaacgtcaggaatttcttgaaggaagatgccatgaagaccaagacac actatcacgctatgcatgcagactgcctgcaggaactacggcgatatctaaaatccggcgtagtcctgaggagaac agtgcccccatggtgaatgtcacccgcagTgaggcctcagagggcaacattaccgtgacatgcagggcttctggc ttctatccctggaatatcacactgagctggcgtcaggatggggtatctttgagccacgacacccagcagtgggggg atgtcctgcctgatgggaatggaacctaccagacctgggtggccaccaggatttgccaaggagaggagcagaggtt cacctgctacatggaacacagcgggaatcacagcactcaccctgtgccctctgggaaagtgctggtgcttcagagt cattggcagacattccatgtttctgctgttgctgctgctgctgctgcTattttttgttattattattttctatgtcc gttgttgtaagaagaaaacatcagctgcagagggtccag

MICA*027

(SEQ ID NO: 3459)

gtcttcgttataacctcacggtgctgtcctgggatggatctgtgcagtcagggtttcttgctgaggtacatctgga tggtcagcccttcctgcgctatgacaggcagaaatgcagggcaaagcccagggacagtgggcagaagatgtcctg ggaaataagacatgggacagagagaccagggacttgacagggaacggaaaggacctcaggatgaccctggctcata tcaaggaccagaaagaaggcttgcattccctccaggagattagggtctgtgagatccatgaagacaacagcaccag gagctcccagcatttctactacgatggggagctcttcctctcccaaaacctggagactgaggaatggacagtgccc cagtcctccagagctcagaccttggccatgaacgtcaggaatttcttgaaggaagatgccatgaagaccaagacac actatcacgctatgcatgcagactgcctgcaggaactacggcgatatctagaatccggcgtagtcctgaggagaac agtgcccccatggtgaatgtcacccgcagcgaggcctcagagggcaacatcaccgtgacatgcagggcttccagc ttctatccccggaatatcaTactgacctggcgtcaggatggggtatctttgagccacgacacccagcagtgggggg atgtcctgcctgatgggaatggaacctaccagacctgggtggccaccaggatttgccgaggagaggagcagaggtt cacctgctacatggaacacagcgggaatcacagcactcaccctgtgccctctgggaaagtgctggtgcttcagagt -continued cattggcagacattccatgtttctgctgttgctgctgctgctgcTattttgttattattattttctatgtccgtt gttgtaagaagaaaacatcagctgcagagggtccag MICA*028 (SEQ ID NO: 3460)
gtcttcgttataacctcacggtgctgtcctgggatggatctgtgcagtcagggtttcttgctgaggtacatctgga
tggtcagcccttcctgcgctatgacaggcagaaatgcagggcaaagccccagggacagtgggcagaagatgtcctg
ggaaataagacatgggacagagagaccagggacttgacagggaacggaaaggacctcaggatgaccctggctcata
tcaaggaccagaaagaaggcttgcattccctccaggagattagggtctgtgagatccatgaagacaacagccaccag
gagctcccagcatttctactacgatggggagctcttcctctcccaaaacctggagactgaggaatggacagtgccc
cagtcctccagagctcagaccttggccatgaacgtcaggaatttcttgaaggaagatgccatgaagaccaagacac
actatcacgctatgcatgcagactgcctgcaggaactacggcgatatctaGaatccggcgtagtcctgaggagaac
agtgcccccatggtgaatgtcacccgcagcgaggcctcagagggcaacattaccgtgacatgcagggcttctggc
ttctatccctggaatatcacactgagctggcgtcaggatggggtatctttgagccacgacacccagcagtggggggg
atgtcctgcctgatgggaatggaacctaccagacctgggtggccaccaggatttgccaaggagaggagcagaggtt
cacctgctacatggaacacagcgggaatcacagcactcaccctgtgccctctgggaaagtgctggtgcttcagagt
cattggcagacattccatgtttctgctgttgctgctGgctgctgctattttgttattattattttctatgtccgt
tgttgtaa MICA*029 (SEQ ID NO: 3461)
gtcttcgttataacctcacggtgctgtcctgggatggatctgtgcagtcagggtttctcgctgaggtacatctgga
tggtcagcccttcctgcgctgtgacaggcagaaatgcagggcaaagccccagggacagtgggcagaagatgtcctg
ggaaataagacatgggacagagagaccagggacttgacagggaacggaaaggacctcaggatgaccctggctcata
tcaaggaccagaaagaaggcttgcattccctccaggagattagggtctgtgagatccatgaagacaacagccaccag
gagctcccagcatttctactacgatggggagctcttcctctcccaaaacctggagactgaggaatggacaatgccc
cagtcctccagagctcagaccttggccatgaacAtcaggaatttcttgaaggaagatgccatgaagaccaagacac
actatcacgctatgcatgcagactgcctgcaggaactacggcgatatctaaaatccggcgtagtcctgaggagaac
agtgcccccatggtgaatgtcacccgcagcgaggcctcagagggcaacattaccgtgacatgcagggcttctggc
ttctatccctggaatatcacactgagctggcgtcaggatggggtatctttgagccacgacacccagcagtggggggg
atgtcctgcctgatgggaatggaacctaccagacctgggtggccaccaggatttgccaaggagaggagcagaggtt
cacctgctacatggaacacagcgggaatcacagcactcaccctgtgccctctgggaaagtgctggtgcttcagagt
cattggcagacattccatgtttctgctgttgctgctgctgctattttgttattattattttctatgtccgttgtt
gtaagaagaaaacatcagctgcagagggtccag MICA*030 (SEQ ID NO: 3462)
gtcttcgttataacctcacggtgctgtccggggatggatctgtgcagtcagggtttctcgctgaggtacatctgga
tggtcagcccttcctgcgctgtgacaggcagaaatgcagggcaaagccccagggacagtgggcagaagatgtcctg
ggaaataagacatgggacagagagaccagggacttgacagggaacggaaaggacctcaggatgaccctggctcata
tcaaggaccagaaagaaggcttgcattccctccaggagattagggtctgtgagatccatgaagacaacagccaccag
gagctcccagcatttctactacgatggggagctcttcctctcccaaaacctggagactgaggaatggacaatgccc
cagtcctccagagctcagaccttggccatgaacgtcaggaatttcttgaaggaagatgccatgaagaccaagacac
actatcacgctatgcatgcagactgcctgcaggaactacggcgatatctaaaatccggcgtagtcctgaggagaac
agtgcccccatggtgaatgtcacccgcagcgaggcctcagagggcaacattaccgtgacatgcagggcttctggc
ttctatccctggaatatcacactgagctggcgtcaggatggggtatctttgagccacgacacccagcagtgggggg

```
atgtcctgcctgatgggaatggaacctaccagacctgggtggccaccaggatttgccaaggagaggagcagaggtt
cacctgctacatggaacacagcgggaatcacagcactcacGctgtgccctctg
```

MICA*031

(SEQ ID NO: 3463)
```
gtcttcgttataaacctcacggtgctgtcctgggatggatctgtgcagtcagggtttctTgctgaggtacatctgga
tggtcagcccttcctgcgctatgacaggcagaaatgcagggcaaagcccagggacagtgggcagaagatgtcctg
ggaaataagacatgggacagagagaccagggacttgacagggaacggaaaggacctcaggatgaccctggctcata
tcaaggaccagaaagaaggcttgcattccctccaggagattagggtctgtgagatccatgaagacaacagcaccag
gagctcccagcatttctactacgatggggagctcttcctctcccaaaacctggagactaaggaatggacaatgccc
cagtcctccagagctcagaccttggccatgaacgtcaggaatttcttgaaggaagatgccatgaagaccaagacac
actatcacgctatgcatgcagactgcctgcaggaactacggcgatatctaaaatccggcgtagtcctgaggagaac
agtgcccccatggtgaatgtcacccgcagcgaggcctcagagggcaacattaccgtgacatgcagggcttctggc
ttctatccctggaatatcacactgagctggcgtcaggatggggtatctttgagccacgacacccagcagtgggggg
atgtcctgcctgatgggaatggaacctaccagacctgggtggccaccaggatttgccaaggagaggagcagaggtt
cacctgctacatggaacacagcgggaatcacagcactcaccctgtgccctctg
```

MICA*032

(SEQ ID NO: 3464)
```
gtcttcgttataaacctcacggtgctgtcctgggatggatctgtgcagtcagggtttcttgctgaggtacatctgga
tggtcagcccttcctgcgctatgacaggcagaaatgcagggcaaagcccagggacagtgggcagaagatgtcctg
ggaaataagacatgggacagagagaccagggacttgacagggaacggaaaggacctcaggatgaccctggctcata
tcaaggaccagaaagaaggcttgcattccctccaggagattagggtctgtgagatccatgaagacaacagcaccag
gagctcccagcatttctactacgatggggagctcttcctctcccaaaacctggagactgaggaatggacaatgccc
cagtcctccagagctcagaccttggccatgaacgtcaggaatttcttgaaggaagatgccatgaagaccaagacac
TctatcacgctatgcatgcagactgcctgcaggaactacggcgatatctaaaatccAgcgtagtcctgaggagaaG
agtgcccccatggtgaatgtcacccgcagcgaggcctcagagggcaacattaccgtgacatgcagggcttctggc
ttctatccctggaatatcacactgagctggcgtcaggatggggtatctttgagccacgacacccagcagtgggggg
atgtcctgcctgatgggaatggaacctaccagacctgggtggccaccaggatttgccaaggagaggagcagaggtt
cacctgctacatggaacacagcgggaatcacagcactcaccctgtgccctctg
```

MICA*033

(SEQ ID NO: 3465)
```
gtcttcgttataaacctcacggtgctgtcctgggatggatctgtgcagtcagggtttcttgctgaggtacatctgga
tggtcagcccttcctgcgctatgacaggcagaaatgcagggcaaagcccagggacagtgggcagaagatgtcctg
ggaaataagacatgggacagagagaccagggacttgacagggaacggaaaggacctcaggatgaccctggctcata
tcaaggaccagaaagaaggcttgcattccctccaggagattagggtctgtgagatccatgaagacaacagcaccag
gagctcccagcatttctactacgatggggagctcttcctctcccaaaacctggagTctgaggaatggacagtgccc
cagtcctccagagctcagaccttggccatgaacgtcaggaatttcttgaaggaagatgccatgaagaccaagacac
actatcacgctatgcatgcagactgcctgcaggaactacggcgatatctagaatccagcgtagtcctgaggagaac
agtgcccccatggtgaatgtcacccgcagcgaggcctcagagggcaacatcaccgtgacatgcagggcttccagc
ttctatccccggaatatcatactgacctggcgtcaggatggggtatctttgagccacgacacccagcagtgggggg
atgtcctgcctgatgggaatggaacctaccagacctgggtggccaccaggatttgccgaggagaggagcagaggtt
cacctgctacatggaacacagcgggaatcacagcactcaccctgtgccctctgggaaagtgctggtgcttcagagt
cattggcagacattccatgtttctgctgttgctgctgctgctgctatttttgttattattattttctatgtccgtt
gttgtaagaagaaaacatcagctgcagagggtccag
```

MICA*034

(SEQ ID NO: 3466)

gtcttcgttataacctcacggtgctgtccggggatggatctgtgcagtcagggtttctcgctgaggtacatctgga tggtcagcccttcctgcgctgtgacaggcagaaatgcagggcaaagccccagggacagtgggcagaagatgtcctg ggaaataagacatgggacagagagaccagggacttgacagggaacggaaaggacctcaggatgaccctggctcata tcaaggaccagaaagaaggcttgcattccctccaggagattagggtctgtgagatccatgaagacaacagcaccag gagctcccagcatttctactacgatggggagctcttcctctcccaaaacctggagactgaggaatggacaatgccc cagtcctccagagctcagaccttggccatgaacgtcaggaatttcttgaaggaagatgccGtgaagaccaagacac actatcacgctatgcatgcagactgcctgcaggaactacggcgatatctaaaatccggcgtagtcctgaggagaac agtgcccccatggtgaatgtcacccgcagcgaggcctcagagggcaacatcaccgtgacatgcagggcttccagc ttctatccccggaatatcacactgaCctggcgtcaggatggggtatctttgagccacgacacccagcagtgggggg atgtcctgcctgatgggaatggaacctaccagacctgggtggccaccaggatttgccaaggagaggagcagaggtt cacctgctacatggaacacagcgggaatcacagcactcaccctgtgccctctg

MICA*035

(SEQ ID NO: 3467)

gtcttcgttataacctcacggtgctgtccGgggatggatctgtgcagtcagggtttctcgctgaggtacatctgga tggtcagcccttcctgcgctgtgacaggcagaaatgcagggcaaagccccagggacagtgggcagaagatgtcctg ggaaataagacatgggacagagagaccagggacttgacagggaacggaaaggacctcaggatgaccctggctcata tcaaggaccagaaagaaggcttgcattccctccaggagattagggtctgtgagatccatgaagacaacagcaccag gagctcccagcatttctactacgatggggagctcttcctctcccaaaacctggagactgaggaatggacaatgccc cagtcctccagagctcagaccttggccatgaacgtcaggaatttcttgaaggaagatgccatgaagaccaagacac actatcacgctatgcatgcagactgcctgcaggaactacggcgatatctaaaatccggcgtagtcctgaggagaac agtgcccccatggtgaatgtcacccgcagcgaggcctcagagggcaacatcaccgtgacatgcagggcttccagc ttctatccccggaatatcaTactgacctggcgtcaggatggggtatctttgagccacgacacccagcagtgggggg atgtcctgcctgatgggaatggaacctaccagacctgggtggccaccaggatttgccgaggagaggagcagaggtt cacctgctacatggaacacagcgggaatcacagcactcaccctgtgccctctg

MICA*036

(SEQ ID NO: 3468)

gtcttcgttataacctcacggtgctgtccggggatggatctgtgcagtcagggtttctcgctgaggtacatctgga tggtcagcccttcctgcgctgtgacaggcagaaatgcagggcaaagccccagggacagtgggcagaagatgtcctg ggaaataagacatgggacagagagaccagggacttgacagggaacggaaaggacctcaggatgaccctggctcata tcaaggaccagaaagaaggcttgcattccctccaggagattagggtctgtgagatccatgaagacaacagcaccaA gagctcccagcatttctactacgatggggagctcttcctctcccaaaacctggagactgaggaatggacaatgccc cagtcctccagagctcagaccttggccatgaacgtcaggaatttcttgaaggaagatgccatgaagaccaagacac actatcacgctatgcatgcagactgcctgcaggaactacggcgatatctagaatccagcgtagtcctgaggagaac agtgcccccatggtgaatgtcacccgcagcgaggcctcagagggcaacattaccgtgacatgcagggcttctggc ttctatccctggaatatcacactgagctggcgtcaggatggggtatctttgagccacgacacccagcagtgggggg atgtcctgcctgatgggaatggaacctaccagacctgggtggccaccaggatttgccaaggagaggagcagaggtt cacctgctacatggaacacagcgggaatcacagcactcaccctgtgccctctg

MICA*037

(SEQ ID NO: 3469)

gtcttcgttataacctcacggtgctgtcctgggatggatctgtgcagtcagggtttctcgctgaggtacatctgga tggtcagcccttcctgcgctgtgacaggcagaaatgcagggcaaagccccagggacagtgggcagaagatgtcctg ggaaataagacatgggacagagagaccagggacttgacagggaacggaaaggacctcaggatgaccctggctcata -continued

```
tcaaggaccagaaagaaggcttgcattccctccaggagattagggtctgtgagatccatgaagacaacagcaccag gagctcccagcatttctactacgatggggagctcttcctctcccaaaacctggagactgaggaatggacaatgccc cagtcctccagagctcagaccttggccatgaacgtcaggaatttcttgaaggaagatgccatgaagaccaagacac actatcacgctatgcatgcagactgcctgcaggaactacggcgatatctaaaatccggcgtagtcctgaggagaac agtgcccccatggtgaatgtcacccgcagcgaggcctcagagggcaacatcaccgtgacatgcagggcttccagc ttctatccccggaatatcaTactgacctggcgtcaggatggggtatctttgagccacgacacccagcagtgggggg atgtcctgcctgatgggaatggaacctaccagacctgggtggccaccaggatttgccgaggagaggagcagaggtt cacctgctacatggaacacagcgggaatcacagcactcaccctgtgccctctg
```

MICA*038                                                              (SEQ ID NO: 3470)
```
gtcttcgttataaacctcacggtgctgtcctgggatggatctgtgcagtcagggtttctcgctgaggtacatctgga tggtcagcccttcctgcgctgtgacaggcagaaatgcagggcaaagcccagggacagtgggcagaagatgtcctg ggaaataagacatgggacagagagaccagggacttgacagggaacggaaaggacctcaggatgaccctggctcata tcaaggaccagaaagaaggcttgcattccctccaggagattagggtctgtgagatccatgaagacaacagcaccag gagctcccagcatttctactacgatggggagctcttcctctcccaaaacctggagactgaggaatggacaatgccc cagtcctccagagctcagaccttggccatgaacgtcaggaatttcttgaaggaagatgccatgaagaccaagacac actatcacgctatgcatgcagactgcctgcaggaactacggcgatatctaaaatccggcgtagtcctgaggagaac agtgcccccatggtgaatgtcacccgcagcgaggcctcagagggcaacatCaccgtgacatgcagggcttccagc ttctatccccggaatatcacactgacctggcgtcaggatggggtatctttgagccacgacacccagcagtgggggg atgtcctgcctgatgggaatggaacctaccagacctgggtggccaccaggatttgccaaggagaggagcagaggtt cacctgctacatggaacacagcgggaatcacagcactcaccctgtgccctctg
```

MICA*039                                                              (SEQ ID NO: 3471)
```
gtcttcgttataaacctcacggtgctgtcctgggatggatctgtgcagtcagggtttctcgctgaggtacatctgga tggtcagcccttcctgcgctgtgacaggcagaaatgcagggcaaagcccagggacagtgggcagaagatgtcctg ggaaataagacatgggacagagagaccagggacttgacagggaacggaaaggacctcaggatgaccctggctcata tcaaggaccagaaagaaggcttgcattccctccaggagattagggtctgtgagatccatgaagacaacagcaccag gagctcccagcatttctactacgatggggagctcttcctctcccaaaacctggagactgaggaatggacaatgccc cagtcctccagagctcagaccttggccatgaacgtcaggaatttcttgaaggaagatgccatgaagaccaagacac actatcacgctatgcatgcagactgcctgcaggaactacggcgatatctaaaatccggcgtagtcctgaggagaac agtgcccccatggtgaatgtcacccgcagcgaggcctcagagggcaacatcaccgtgacatgcagggcttccagc ttctatccccggaatatcatactgacctggcgtcaggatgggCtatctttgagccacgacacccagcagtgggggg atgtcctgcctgatgggaatggaacctaccagacctgggtggccaccaggatttgccgaggagaggagcagaggtt cacctgctacatggaacacagcgggaatcacagcactcaccctgtgccctctg
```

MICA*040                                                              (SEQ ID NO: 3472)
```
gtcttcgttataaacctcacggtgctgtcctgggatggatctgtgcagtcagggtttctcgctgaggtacatctgga tggtcagcccttcctgcgctgtgacaggcagaaatgcagggcaaagcccagggacagtgggcagaagatgtcctg ggaaataagacatgggacagagagaccagGgacttgacagggaacggaaaggacctcaggatgaccctGgctcata tcaaggaccagaaagaaggcttgcattccctccaggagattagggtctgtgagatccatgaagacaacagcaccag gagctcccagcatttctactacgatggggagctcttcctctcccaaaacctggagactaaggaatggacaatgccc cagtcctccagagctcagaccttggccatgaacgtcaggaatttcttgaaggaagatgccatgaagaccaagacac actatcacgctatgcatgcagactgcctgcaggaactacggcgatatctaaaatccggcgtagtcctgaggagaac agtgcccccatggtgaatgtcacccgcagcgaggcctcagagggcaacattaccgtgacatgcagggcttctggc
```

-continued ttctatccctggaatatcacactgagctggcgtcaggatggggtatctttgagccacgacacccagcagtgggggg atgtcctgcctgatgggaatggaacctaccagacctgggtggccaccaggatttgccaaggagaggagcagaggtt cacctgctacatggaacacagcgggaatcacagcactcaccctgtgccctctg

MICA*041

(SEQ ID NO: 3473)

gtcttcgttataaacctcacggtgctgtccggggatggatctgtgcagtcagggtttctcgctgaggGacatctgga tggtcagcccttcctgcgctgtgacaggcagaaatgcagggcaaagcccagggacagtgggcagaagatgtcctg ggaaataagacatgggacagagagaccagggacttgacagggaacggaaaggacctcaggatgaccctggctcata tcaaggaccagaaagaaggcttgcattccctccaggagattagggtctgtgagatccatgaagacaacagcaccag gagctcccagcatttctactacgatggggagctcttcctctcccaaaacctggagactgaggaatggacaatgccc cagtcctccagagctcagaccttggccatgaacgtcaggaatttcttgaaggaagatgccatgaagaccaagacac actatcacgctatgcatgcagactgcctgcaggaactacggcgatatctaaaatccggcgtagtcctgaggagaac agtgcccccatggtgaatgtcacccgcagcgaggcctcagagggcaacattaccgtgacatgcagggcttctggc ttctatccctggaatatcacactgagctggcgtcaggatggggtatctttgagccacgacacccagcagtgggggg atgtcctgcctgatgggaatggaacctaccagacctgggtggccaccaggatttgccaaggagaggagcagaggtt cacctgctacatggaacacagcgggaatcacagcactcaccctgtgccctctgggaaagtgctggtgcttcagagt cattggcagacattccatgtttctgctgttgctgctgctgctgctgctgctgctattttttgttattattattt tctaCgtctgttgttgtaagaagaaaacatcagctgcagagggtccag

MICA*042

(SEQ ID NO: 3474)

gtcttcgttataaacctcacggtgctgtcctgggatggatctgtgcagtcagggtttcttgctgaggtacatctgga tggtcagcccttcctgcgctatgacaggcagaaatgcagggcaaagcccagggacagtgggcagaagatgtcctg ggaaataagacatgggacagagagaccagggacttgacagggaacggaaaggacctcaggatgaccctggctcata tcaaggaccagaaagaaggcttgcattccctccaggagattagggtctgtgagatccatgaagacaacagcaccag gagctcccagcatttctactacgatggggagctcttcctctcccaaaacctggagactgaggaatggacaatgccc cagtcctccagagctcagaccttggccatgaacgtcaggaatttcttgaaggaagatgccatgaagaccaagacac actatcacgctatgcatgcagactgcctgcaggaactacggcgatatctaaaatccggcgtagtcctgaggagaac agtgcccccatggtgaatgtcacccgcagcgaggcctcagagggcaacatcaccgtgacatgcagggcttccagc ttctatccccggaatatcatactgacctggcgtcaggatggggtatctttgagccacgacacccagcagtgggggg atgtcctgcctgatgggaatggaacctaccagacctgggtggccacTaggatttgccgaggagaggagcagaggtt cacctgctacatggaacacagcgggaatcacagcactcaccctgtgccctctg

MICA*043

(SEQ ID NO: 3475)

gtcttcgttataaacctcacggtgctgtcctgggatggatctgtgcagtcagggtttctcgctgaggtacatctgga tggtcagcccttcctgcgctgtgacaggcagaaatgcagggcaaagcccagggacagtgggcagaagatgtcctg ggaaataagacatgggacagagagaccagggacttgacagggaacggaaaggacctcaggatgaccctggctcata tcaaggaccagaaagaaggcttgcattccctccaggagattagggtctgtgagatccatgaagacaacagcaccag gagctcccagcatttctactacgatggggagctcttcctctcccaaaacctggagactgaggaatggacaatgccc cagtcctccagagctcagaccttggccatgaacgtcaggaatttcttgaaggaagatgccatgaagaccaagacac gctatcacgctatgcatgcagactgcctgcaggaactacggcgatatctaaaatccggcgtagtcctgaggagaac agtgcccccatggtgaatgtcacccgcagcgaggcctcagagggcaacattaccgtgacatgcagggcttctggc ttctatccctggaatatcacactgagctggcgtcaggatggggtatctttgagccacgacacccagcagtgggggg atgtcctgcctgatgggaatggaacctaccagacctgggtggccaccaggatttgccaaggagaggagcagagTtt -continued cacctgctacatggaacacagcgggaatcacagcactcaccctgtgccctctgggaaagtgctggtgcttcagagt cattggcagacattccatgtttctgctgttgctgctgctgctattttttgttattattattttctatgtctgttgtt gtaagaagaaaacatcagctgcagagggtccag

MICA*044

(SEQ ID NO: 3476)

gtcttcgttataaccctcacggtgctgtccGgggatggatctgtgcagtcagggtttctcgctgaggtacatctgga tggtcagcccttcctgcgctatgacaggcagaaatgcagggcaaagcccagggacagtgggcagaagatgtcctg ggaaataagacatgggacagagagaccagggacttgacagggaacggaaaggacctcaggatgaccctggctcata tcaaggaccagaaagaaggcttgcattccctccaggagattagggtctgtgagatccatgaagcaacagcaccag gagctcccagcatttctactacgatggggagctcttcctctcccaaaacgtggagactgaggaatggacagtgccc cagtcctccagagctcagaccttggccatgaacgtcaggaatttcttgaaggaagatgccatgaagaccaagacac actatcacgctatgcatgcagactgcctgcaggaactacggcgatatctagaatccagcgtagtcctgaggagaaG agtgcccccatggtgaatgtcacccgcagcgaggcctcagagggcaacatcaccgtgacatgcagggcttccagc ttctatccccggaatatcacactgaCctggcgtcaggatggggtatctttgagccacgacacccagcagtgggggg atgtcctgcctgatgggaatggaacctaccagacctgggtggccaccaggatttgccaaggagaggagcagaggtt cacctgctacatggaacacagcgggaatcacagcactcaccctgtgccctctg

MICA*045

(SEQ ID NO: 3477)

gtcttcgttataaccctcacggtgctgtcctgggatggatctgtgcagtcagggtttctcgctgaggtacatctgga tggtcagcccttcctgcgctgtgacaggcagaaatgcagggcaaagcccagggacagtgggcagaagatgtcctg ggaaataagacatgggacagagagaccagggacttgacagggaacggaaaggacctcaggatgaccctggctcata tcaaggaccagaaagaaggcttgcattccctccaggagattagggtctgtgagatccatgaagacaacagcaccag gagctcccagcatttctactacgatggggagctcttcctctcccaaaacctggagactgaggaatggacaatgccc cagtcctccagagctcagaccttggccatgaacgtcaggaatttcttgaaggaagatgccatgaagaccaagacac actatcacgctatgcatgcagactgcctgcaggaactacggcgatatctaaaatccggcgtagtcctgaggagaac agtgcccccatggtgaatgtcacccgcagtgaggcctcagagggcaacattaccgtgacatgcagggcttctggc ttctatccctggaatatcacactgagctggcgtcaggatggggtatctttgagccacgacacccagcagtgggggg atgtcctgcctgatgggaatggaacctaccagacctgggtggccaccaggatttgcGaaggagaggagcagaggtt cacctgctacatggaacacagcgggaatcacagcactcaccctgtgccctctgggaaagtgctggtgcttcagagt cattggcagacattccatgtttctgctgttgctgctgctgctattttttgttattattattttctatgtccgttgtt gtaagaagaaaacatcagctgcagagggtccag

MICA*046

(SEQ ID NO: 3478)

gtcttcgttataaccctcacggtgctgtccggggatggatctgtgcagtcagggtttctcgctgaggtacatctgga tggtcagcccttcctgcgctgtgacaggcagaaatgcagggcaaagcccagggacagtgggcagaagatgtcctg ggaaataagacatgggacagagagaccagggacttgacagggaacggaaaggacctcaggatgaccctggctcata tcaaggaccagaaagaaggcttgcattccctccaggagattagggtctgtgagatccatgaagacaacagcaccag gagctcccagcatttctactacgatggggagctcttcctctcccaaaacctggagactgaggaatggacaatgccc cagtcctccagagctcagaccttggccatgaacgtcaggaatttcttgaaggaagatgccatgaagaccaagacac actatcacgctatgcatgcagactgcctgcaggaactacggcgatatctaaaatccggcgtagtcctgaggagaac agtgcccccatggtgaatgtcacccgcagcgaggcctcagagggcaacattaccgtgacatgcagggcttctggc ttctGtccctggaatatcacactgagctggcgtcaggatggggtatctttgagccacgacacccagcagtgggggg atgtcctgcctgatgggaatggaacctaccagacctgggtggccaccaggatttgccaaggagaggagcagaggtt cacctgctacatggaacacagcgggaatcacagcactcaccctgtgccctctgggaaagtgctggtgcttcagagt

MICA*047

(SEQ ID NO: 3479)

```
cattggcagacattccatgtttctgctgttgctgctgctgctgctgctgctgctattttgttattattattt
tctacgtctgttgttgtaagaagaaaacatcagctgcagagggtccag
```

MICA*047

(SEQ ID NO: 3479)

```
gtcttcgttataacctcacggtgctgtccggggatggatctgtgcagtcagggtttctcgctgaggGacatctgga
tggtcagcccttcctgcgctgtgacaggcagaaatgcagggcaaagccccagggacagtgggcagaagatgtcctg
ggaaataagacatgggacagagagaccagggacttgacagggaacggaaaggacctcaggatgaccctggctcata
tcaaggaccagaaagaaggcttgcattccctccaggagattagggtctgtgagatccatgaagacaacagcaccag
gagctcccagcatttctactacgatggggagctcttcctctcccaaaacctggagactgaggaatggacaatgccc
cagtcctccagagctcagaccttggccatgaacgtcaggaatttcttgaaggaagatgccatgaagaccaagacac
actatcacgctatgcatgcagactgcctgcaggaactacggcgatatctaaaatccggcgtagtcctgaggagaac
agtgcccccatggtgaatgtcacccgcagcgaggcctcagagggcaacattaccgtgacatgcagggcttctggc
ttctatccctggaatatcacactgagctggcgtcaggatggggtatctttgagccacgacacccagcagtgggggg
atgtcctgcctgatgggaatggaacctaccagacctgggtggccaccaggatttgccaaggagaggagcagaggtt
cacctgctacatggaacacagcgggaatcacagcactcacGctgtgccctctgggaaagtgctggtgcttcagagt
cattggcagacattccatgtttctgctgttgctgctgctgctgctgctattttgttattattatttcctatgtct
gttgttgtaagaagaaaacatcagctgcagagggtccag
```

MICA*048

(SEQ ID NO: 3480)

```
gtcttcgttataacctcacggtgctgtcctgggatggatctgtgcagtcagggtttcttgctgaggtacatctgga
tggtcagcccttcctgcgctatgacaggcagaaatgcagggcaaagccccagggacagtgggcagaagatgtcctg
ggaaataagacatgggacagagagaccagggacttgacagggaacggaaaggacctcaggatgaccctggctcata
tcaaggaccagaaagaaggcttgcattccctccaggagattagggtctgtgagatccatgaagacaacagcaccag
gagctcccagcatttctactacgatggggagctcttcctctcccaaaacctggagactgaggaatggacagtgccc
cagtcctccagagctcagaccttggccatgaacgtcaggaatttcttgaaggaagatgccatgaagaccaagacac
actatcacgctatgcatgcagactgcctgcaggaactacggcgatatctagaatccggcgtagtcctgaggagaac
agtgcccccatggtgaatgtcacccgcagcgaggcctcagagggcaacatcaccgtgacatgcagggcttccagc
ttctatccccggaatatcatactgacctggcgtcaggatggggtatctttgagccacgacacccagcagtgggggg
atgtcctgcctgatgggaatggaacctaccagacctgggtggccaccaggatttgccgaggagaggagcagaggtt
cacctgctacatggaacacagcgggaatcacagcactcaccctgtgccctctgggaaagtgctggtgcttcagagt
cattggcagacattccatgtttctgctgttgctgctgctgctgctattttgttattattattttctatgtccgtt
gttgtaagaagaaaacatcagctgcagaTggtccagagctcgtgagcctgcaggtcctggatcaacacccagttgg
gacgagtgaccacagggatgccacacagctcggatttcagcctctgatgtcagctcttgggtccactggctccact
```

MICA*049

(SEQ ID NO: 3481)

```
gtcttcgttataacctcacggtgctgtcctgggatggatctgtgcagtcagggtttcttgctgaggtacatctgga
tggtcagcccttcctgcgctatgacaggcagaaatgcagggcaaagccccagggacagtgggcagaagatgtcctg
ggaaataagacatgggacagagagaccagggacttgacagggaacggaaaggacctcaggatgaccctggctcata
tcaaggaccagaaagaaggcttgcattccctccaggagattagggtctgtgagatccatgaagacaacagcaccag
gagctcccagcatttctactacgatggggagctcttcctctcccaaaacgtggagactgaggaatggacagtgccc
cagtcctccagagctcagaccttggccatgaacgtcaggaatttcttgaaggaagatgccatgaagaccaagacac
actatcacgctatgcatgcagactgcctgcaggaactacggcgatatctagaatccagcgtagtcctgaggagaac
agtgcccccatggtgaatgtcacccgcagcgaggcctcagagggcaacatcaccgtgacatgcagggcttccagc
```

-continued

```
ttctatccccggaatatcacactgacctggcgtcaggatggggtatctttgagccacgacacccagcagtgggggg atgtcctgcctgatgggaatggaacctaccagacctgggtggccaccaggatttgccaaggagaggagcagaggtt cacctgctacatggaacacagcgggaatcacagcactcaccctgtgccctctgggaaagtgctggtgcttcagagt cattggcagacattccatgtttctgctgttgctgctgctgctgctattttttgttattattattttctatgtcc gttgttgtaagaagaaaacatcagctgcagagggtccagagctcgtgagcctgcaggtcctggatcaacacccagt tgggaTgagtgaccacagggatgccacacagctcggatttcagcctctgatgtcagctcttgggtccactggctcc act
```

In the following, Probe List M1 and M2 are shown in Tables 25-1 and 25-2 and Tables 26-1 and 26-2 and Tables 27-1 and 27-2 and Tables 28-1 and 28-2 respectively.

TABLE 25-1

| Probe No. | Base Sequence | |
|---|---|---|
| 0 | tgg gac aga gag acc agA | (SEQ ID No: 3320) |
| 1 | tcc caa aac ctg gag act A | (SEQ ID No: 3321) |
| 2 | g gaa cta cgg cga tat cta A | (SEQ ID No: 3322) |
| 3 | cgg cga tat cta aaa tcc G | (SEQ ID No: 3323) |
| 4 | cc tgg aat atc aca ctg aG | (SEQ ID No: 3324) |
| 5 | t att ttt gtt att att att ttc taC | (SEQ ID No: 3325) |
| 6 | c ctc acg gtg ctg tcc G | (SEQ ID No: 3326) |
| 7 | gtg aat gtc acc cgc agT | (SEQ ID No: 3327) |
| 8 | c gta gtc ctg agg aga aG | (SEQ ID No: 3328) |
| 9 | t cag cct ctg atg tca gC | (SEQ ID No: 3329) |
| 10 | cag ccc ttc ctg cgc tc | (SEQ ID No: 3330) |
| 11 | gag act gag gaa tgg aca G | (SEQ ID No: 3331) |
| 12 | cc cgg aat atc aca ctg aC | (SEQ ID No: 3332) |
| 13 | gcc acc agg att tgc cG | (SEQ ID No: 3333) |
| 14 | g cga tat cta gat tcc agc A | (SEQ ID No: 3334) |
| 15 | gg gac aga gag acc agG | (SEQ ID No: 3335) |
| 16 | cc caa aac ctg gag act G | (SEQ ID No: 3336) |
| 17 | gtt tct gct gtt gct gct G | (SEQ ID No: 3337) |
| 18 | ag acc tgg gtg gcc acT | (SEQ ID No: 3338) |
| 19 | t gct gct g gct gct gcT | (SEQ ID No: 3339) |
| 20 | c acc cgc agc gag gcA | (SEQ ID No: 3340) |
| 21 | ctc ttc ctc tcc caa aac G | (SEQ ID No: 3341) |
| 22 | gc tcc cag cat ttc tac taT | (SEQ ID No: 3342) |
| 23 | cgg cga tat cta gaa tcc A | (SEQ ID No: 3343) |
| 24 | g tca gct ctt ggg tcc G | (SEQ ID No: 3344) |
| 25 | cc atg aag acc aag aca cT | (SEQ ID No: 3345) |
| 26 | tgc caa gga gag gag caA | (SEQ ID No: 3346) |
| 27 | gaa cta cgg cga tat cta G | (SEQ ID No: 3347) |
| 28 | c cag cat ttc tac tac gat A | (SEQ ID No: 3348) |

TABLE 25-1-continued

| Probe No. | Base Sequence | |
|---|---|---|
| 29 | gct gca gag ggt cca gG | (SEQ ID No: 3349) |
| 30 | c tgg cgt cag gat ggg C | (SEQ ID No: 3350) |

TABLE 25-2

| Probe No. | Base Sequence | |
|---|---|---|
| 31 | ggc ttg cat tcc ctc cG | (SEQ ID No: 3351) |
| 32 | c cca gtt ggg acg agt gT | (SEQ ID No: 3352) |
| 33 | ct gct gct gct gct gcT | (SEQ ID No: 3353) |
| 34 | a gaa gat gtc ctg gga aaC | (SEQ ID No: 3354) |
| 35 | t gtg cag tca ggg ttt ctT | (SEQ ID No: 3355) |
| 36 | gcc tca gag ggc aac atC | (SEQ ID No: 3356) |
| 37 | ct gct gct gct gct gcT | (SEQ ID No: 3357) |
| 38 | ttc tat ccc cgg aat atc aT | (SEQ ID No: 3358) |
| 39 | gtt gct gct gct gct gcT | (SEQ ID No: 3359) |
| 40 | cag acc ttg gcc atg aac A | (SEQ ID No: 3360) |
| 41 | gg aat cac agc act cac G | (SEQ ID No: 3361) |
| 42 | a cgg cga tat cta aaa tcc A | (SEQ ID No: 3362) |
| 43 | ctc tcc caa aac ctg gag T | (SEQ ID No: 3363) |
| 44 | ttc ttg aag gaa gat gcc G | (SEQ ID No: 3364) |
| 45 | cat gaa gac aac agc acc aA | (SEQ ID No: 3365) |
| 46 | ggg ttt atc gct gag gG | (SEQ ID No: 3366) |
| 47 | caa gga gag gag cag agT | (SEQ ID No: 3367) |
| 48 | g gcc acc agg att tgc G | (SEQ ID No: 3368) |
| 49 | c agg gct tct ggc ttc tG | (SEQ ID No: 3369) |
| 50 | ag aaa aca tca gct gca gaT | (SEQ ID No: 3370) |
| 51 | at caa cac cca gtt ggg aT | (SEQ ID No: 3371) |

TABLE 26-1

| Probe No. | Base Sequence | |
|---|---|---|
| 0 | a gag acc agA gac ttg aca | (SEQ ID No: 3372) |
| 1 | ctg gag act Aag gaa tgg a | (SEQ ID No: 3373) |
| 2 | cga tat cta Aaa tcc ggc g | (SEQ ID No: 3374) |
| 3 | cta aaa tcc Ggc gta gtc c | (SEQ ID No: 3375) |
| 4 | c aca ctg aGc tgg cgt c | (SEQ ID No: 3376) |
| 5 | att att ttc taC gtc tgt tgt t | (SEQ ID No: 3377) |
| 6 | tg ctg tcc Ggg gat gga | (SEQ ID No: 3378) |

TABLE 26-1-continued

| Probe No. | Base Sequence | |
|---|---|---|
| 7 | acc cgc agT gag gcc tc | (SEQ ID No: 3379) |
| 8 | g agg aga aGa gtg ccc c | (SEQ ID No: 3380) |
| 9 | tg atg tca gCt ctt ggg tc | (SEQ ID No: 3381) |
| 10 | c ctg cgc tAt gac agg c | (SEQ ID No: 3382) |
| 11 | gaa tgg aca Gtg ccc cag | (SEQ ID No: 3383) |
| 12 | c aca ctg aCc tgg cgt c | (SEQ ID No: 3384) |
| 13 | gg att tgc cGa gga gag g | (SEQ ID No: 3385) |
| 14 | gaa tcc agc Ata gtc ctg a | (SEQ ID No: 3386) |
| 15 | a gag acc agG gac ttg ac | (SEQ ID No: 3387) |
| 16 | ctg gag act Gag gaa tgg | (SEQ ID No: 3388) |
| 17 | gtt gct gct G gct gct g | (SEQ ID No: 3389) |
| 18 | g gtg gcc acT agg att tg | (SEQ ID No: 3390) |
| 19 | gct gct g gct gct gcT a | (SEQ ID No: 3391) |
| 20 | agc gag gcA tca gag gg | (SEQ ID No: 3392) |
| 21 | tcc caa aac Gtg gag act g | (SEQ ID No: 3393) |
| 22 | at ttc tac taT gat ggg gag | (SEQ ID No: 3394) |
| 23 | cta gaa tcc Agc gta gtc c | (SEQ ID No: 3395) |
| 24 | t ggg tcc Gct ggc tcc | (SEQ ID No: 3396) |
| 25 | cc aag aca cTc tat cac gc | (SEQ ID No: 3397) |
| 26 | a gag gag caA agg ttc acc | (SEQ ID No: 3398) |
| 27 | cga tat cta Gaa tcc ggc g | (SEQ ID No: 3399) |
| 28 | tac tac gat Agg gag ctc t | (SEQ ID No: 3400) |
| 29 | g ggt cca gGg ctc gtg | (SEQ ID No: 3401) |
| 30 | cag gat ggg Cta tct ttg a | (SEQ ID No: 3402) |

TABLE 26-2

| Probe No. | Base Sequence | |
|---|---|---|
| 31 | at tcc ctc cGg gag att ag | (SEQ ID No: 3403) |
| 32 | t gct gct gct gct gcT at | (SEQ ID No: 3404) |
| 33 | ct gct gct gcT att ttt gtt | (SEQ ID No: 3405) |
| 34 | c ctg gga aaC aag aca tgg | (SEQ ID No: 3406) |
| 35 | a ggg ttt ctT gct gag gta | (SEQ ID No: 3407) |

TABLE 26-2-continued

| Probe No. | Base Sequence | |
|---|---|---|
| 36 | g ggc aac atC acc gtg ac | (SEQ ID No: 3408) |
| 37 | gct gct gct gct gcT att | (SEQ ID No: 3409) |
| 38 | cgg aat atc aTa ctg acc tg | (SEQ ID No: 3410) |
| 39 | gcc atg aac Atc agg aat tt | (SEQ ID No: 3411) |
| 40 | gc act cac Gct gtg ccc | (SEQ ID No: 3412) |
| 41 | cta aaa tcc Ag gta gtc c | (SEQ ID No: 3413) |
| 42 | aac ctg gag Tct gag gaa t | (SEQ ID No: 3414) |
| 43 | gaa gat gcc Tct gag gaa t | (SEQ ID No: 3415) |
| 44 | c agc acc aAg acg tcc c | (SEQ ID No: 3416) |
| 45 | c gct gag gGa cat ctg g | (SEQ ID No: 3417) |
| 46 | g gag cag agT ttc acc tg | (SEQ ID No: 3418) |
| 47 | agg att tgc Gaa gga gag g | (SEQ ID No: 3419) |
| 48 | ct ggc ttc tGt ccc tgg a | (SEQ ID No: 3420) |
| 49 | a gct gca gaT ggt cca ga | (SEQ ID No: 3421) |
| 50 | ca gtt ggg aTg agt gac c | (SEQ ID No: 3422) |

TABLE 27-1

| Allele Number | Probe Number for Detection | | | | |
|---|---|---|---|---|---|
| MICA*001 | 0 | 1 | 2 | 3 | 4 |
| MICA*00201 | 5 | | | | |
| MICA*00202 | 6 | 7 | | | |
| MICA*004 | 8 | 9 | | | |
| MICA*005 | 10 | 11 | 12 | 13 | |
| MICA*006 | 14 | | | | |
| MICA*00701 | 7 | | | | |
| MICA*00702 | 15 | 16 | | | |
| MICA*00801 | 17 | 9 | | | |
| MICA*00802 | 18 | 19 | | | |
| MICA*00803 | 20 | | | | |
| MICA*00901 | 21 | 9 | | | |
| MICA*00902 | 22 | | | | |
| MICA*010 | 23 | 13 | 9 | | |
| MICA*011 | 24 | | | | |
| MICA*01201 | 25 | | | | |
| MICA*01202 | 26 | | | | |
| MICA*013 | 6 | 27 | 13 | | |
| MICA*014 | 28 | 8 | | | |
| MICA*015 | 28 | 29 | | | |
| MICA*016 | 30 | 9 | | | |
| MICA*017 | 31 | | | | |
| MICA*018 | 16 | | | | |
| MICA*019 | 32 | | | | |
| MICA*020 | 33 | | | | |
| MICA*021 | 34 | | | | |
| MICA*022 | 6 | 23 | 13 | | |
| MICA*023 | 6 | 17 | | | |
| MICA*024 | 35 | 10 | 11 | 36 | 12 |
| MICA*025 | 35 | 16 | | | |

TABLE 27-2

| Allele Number | Probe Number for Detection | | | |
|---|---|---|---|---|
| MICA*026 | 7 | 37 | | |
| MICA*027 | 38 | 39 | | |
| MICA*028 | 27 | 17 | | |
| MICA*029 | 40 | | | |
| MICA*030 | 41 | | | |
| MICA*031 | 35 | | | |
| MICA*032 | 25 | 42 | 8 | |
| MICA*033 | 43 | | | |
| MICA*034 | 44 | 12 | | |
| MICA*035 | 6 | 38 | | |
| MICA*036 | 45 | | | |
| MICA*037 | 38 | | | |
| MICA*038 | 36 | | | |
| MICA*039 | 30 | | | |
| MICA*040 | 15 | | | |
| MICA*041 | 46 | 5 | | |
| MICA*042 | 18 | | | |
| MICA*043 | 47 | | | |
| MICA*044 | 6 | 8 | 12 | |
| MICA*045 | 48 | | | |
| MICA*046 | 49 | | | |
| MICA*047 | 46 | 41 | | |
| MICA*048 | 50 | | | |
| MICA*049 | 51 | | | |

TABLE 28-1

| Allele Number | Probe Number for Detection | | | | |
|---|---|---|---|---|---|
| MICA*001 | 0 | 1 | 2 | 3 | 4 |
| MICA*00201 | 5 | | | | |
| MICA*00202 | 6 | 7 | | | |
| MICA*004 | 8 | 9 | | | |
| MICA*005 | 10 | 11 | 12 | 13 | |
| MICA*006 | 14 | | | | |
| MICA*00701 | 7 | | | | |
| MICA*00702 | 15 | 16 | | | |
| MICA*00801 | 17 | 9 | | | |
| MICA*00802 | 18 | 19 | | | |
| MICA*00803 | 20 | | | | |
| MICA*00901 | 21 | 9 | | | |
| MICA*00902 | 22 | | | | |
| MICA*010 | 23 | 13 | 9 | | |
| MICA*011 | 24 | | | | |
| MICA*01201 | 25 | | | | |
| MICA*01202 | 26 | | | | |
| MICA*013 | 6 | 27 | 13 | | |
| MICA*014 | 28 | 8 | | | |
| MICA*015 | 28 | 29 | | | |
| MICA*016 | 30 | 9 | | | |
| MICA*017 | 31 | | | | |
| MICA*018 | 16 | | | | |
| MICA*019 | 23 | 13 | 32 | | |
| MICA*020 | 33 | | | | |

TABLE 28-2

| Allele Number | Probe Number for Detection | | | | |
|---|---|---|---|---|---|
| MICA*021 | 34 | | | | |
| MICA*022 | 6 | 23 | 13 | | |
| MICA*023 | 6 | 17 | | | |
| MICA*024 | 35 | 10 | 11 | 36 | 12 |
| MICA*025 | 35 | 16 | | | |
| MICA*026 | 7 | 37 | | | |
| MICA*027 | 38 | 32 | | | |
| MICA*028 | 27 | 17 | | | |
| MICA*029 | 39 | | | | |
| MICA*030 | 40 | | | | |
| MICA*031 | 35 | | | | |
| MICA*032 | 25 | 41 | 8 | | |

TABLE 28-2-continued

| Allele Number | Probe Number for Detection | | |
|---|---|---|---|
| MICA*033 | 42 | | |
| MICA*034 | 43 | 12 | |
| MICA*035 | 6 | 38 | |
| MICA*036 | 44 | | |
| MICA*037 | 38 | | |
| MICA*038 | 36 | | |
| MICA*039 | 30 | | |
| MICA*040 | 15 | | |
| MICA*041 | 45 | 5 | |
| MICA*042 | 18 | | |
| MICA*043 | 46 | | |
| MICA*044 | 6 | 8 | 12 |
| MICA*045 | 47 | | |
| MICA*046 | 48 | | |
| MICA*047 | 45 | 40 | |
| MICA*048 | 49 | | |
| MICA*049 | 50 | | |

The present invention is not limited to the above embodiments and various changes and modifications can be made within the spirit and scope of the present invention. Therefore, to apprise the public of the scope of the present invention, the following claims are made.

This application claims priority from Japanese Patent Application Nos. 2003-430553 filed on Dec. 25, 2003, 2003-430554 filed on Dec. 25, 2003, 2003-430555 filed on Dec. 25, 2003, 2003-430556 filed on Dec. 25, 2003, 2003-430557 filed on Dec. 25, 2003, 2003-430558 filed on Dec. 25, 2003 and 2003-430559 filed on Dec. 25, 2003, which are hereby incorporated by reference herein.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08624015B2). An electronic copy of the "Sequence Listing" will also be available from the USPTO upon request and payment of the fee set forth in 37 CFR 1.19(b)(3).

The invention claimed is:

1. A DNA microaray comprising: a probe set comprising multiple probes that are isolated and that can be used for identification of an HLA-MICA allele contained in a specimen; and a substrate on which the probe set is immobilized, wherein the multiple probes comprise SEQ ID NOs. 3320 to 3371 or SEQ ID NOs. 3372 to 3422 so that the alleles of SEQ ID NOs. 3428 to 3481 can be identified by conducting a set of polymerase chain reactions (PCRs) using different probes selected from the probe set.

* * * * *